US009725759B2

(12) United States Patent
Barany et al.

(10) Patent No.: US 9,725,759 B2
(45) Date of Patent: *Aug. 8, 2017

(54) METHOD OF DESIGNING ADDRESSABLE ARRAY SUITABLE FOR DETECTION OF NUCLEIC ACID SEQUENCE DIFFERENCES USING LIGASE DETECTION REACTION

(71) Applicant: Cornell Research Foundation, Inc., Ithaca, NY (US)

(72) Inventors: Francis Barany, New York, NY (US); Monib Zirvi, Monmouth Junction, NJ (US); Norman P. Gerry, Philadelphia, PA (US); Reyna Favis, Iselin, NJ (US); Richard Kliman, Iselin, NJ (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/096,446

(22) Filed: Apr. 12, 2016

(65) Prior Publication Data

US 2016/0215329 A1    Jul. 28, 2016

Related U.S. Application Data

(60) Continuation of application No. 13/947,777, filed on Jul. 22, 2013, now Pat. No. 9,340,834, which is a
(Continued)

(51) Int. Cl.
*C07H 21/00* (2006.01)
*C12Q 1/68* (2006.01)

(52) U.S. Cl.
CPC ......... *C12Q 1/6837* (2013.01); *C12Q 1/6827* (2013.01); *C12Q 1/6874* (2013.01); *C12Q 1/6886* (2013.01)

(58) Field of Classification Search
None
See application file for complete search history.

(56) References Cited

U.S. PATENT DOCUMENTS 4,683,202 A     7/1987   Mullis
4,883,750 A    11/1989   Whiteley et al.
(Continued)

FOREIGN PATENT DOCUMENTS

EP    0 357 011    8/1989
EP    0 387 696    3/1990
(Continued)

OTHER PUBLICATIONS

"Nucleic Acid Hybridization—General Aspects," in *Nonradioactive In Situ Hybridization Application Manual*, Indianapolis, Indiana: Boehringer Mannheim Corporation, Chapter III (1992).
(Continued)

*Primary Examiner* — Robert T Crow
(74) *Attorney, Agent, or Firm* — LeClairRyan, a Professional Corporation

(57) ABSTRACT

The present invention is directed to a method of designing a plurality of capture oligonucleotide probes for use on a support to which complementary oligonucleotide probes will hybridize with little mismatch, where the plural capture oligonucleotide probes have melting temperatures within a narrow range. The present invention further relates to an oligonucleotide array comprising of a support with the plurality of oligonucleotide probes immobilized on the support, a method of using the support to detect single-base changes, insertions, deletions, or translocations in a plurality of target nucleotide sequences, and a kit for such detection, which includes the support on which the oligonucleotides have been immobilized.

25 Claims, 253 Drawing Sheets

Related U.S. Application Data division of application No. 12/252,169, filed on Oct. 15, 2008, now Pat. No. 8,492,085, which is a division of application No. 10/257,158, filed as application No. PCT/US01/10958 on Apr. 4, 2001, now Pat. No. 7,455,965.

(60) Provisional application No. 60/197,271, filed on Apr. 14, 2000.

(56) References Cited

U.S. PATENT DOCUMENTS

| | | |
|---|---|---|
| 4,988,617 A | 1/1991 | Landegren et al. |
| 5,035,996 A | 7/1991 | Hartley |
| 5,104,792 A | 4/1992 | Silver et al. |
| 5,143,854 A | 9/1992 | Pirrung et al. |
| 5,202,231 A | 4/1993 | Drmanac et al. |
| 5,258,506 A | 11/1993 | Urdea et al. |
| 5,278,298 A | 1/1994 | Chakraborty et al. |
| 5,288,468 A | 2/1994 | Church et al. |
| 5,290,925 A | 3/1994 | Fino |
| 5,314,809 A | 5/1994 | Erlich et al. |
| 5,324,633 A | 6/1994 | Fodor et al. |
| 5,352,582 A | 10/1994 | Lichtenwalter et al. |
| 5,371,241 A | 12/1994 | Brush |
| 5,391,480 A | 2/1995 | Davis et al. |
| 5,405,783 A | 4/1995 | Pirrung et al. |
| 5,407,798 A | 4/1995 | Martinelli et al. |
| 5,412,087 A | 5/1995 | McGall et al. |
| 5,415,839 A | 5/1995 | Zaun et al. |
| 5,418,149 A | 5/1995 | Gelfand et al. |
| 5,424,186 A | 6/1995 | Fodor et al. |
| 5,429,807 A | 7/1995 | Matson et al. |
| 5,445,934 A | 8/1995 | Fodor et al. |
| 5,470,705 A | 11/1995 | Grossman et al. |
| 5,494,810 A | 2/1996 | Barany et al. |
| 5,496,699 A | 3/1996 | Sorenson |
| 5,506,137 A | 4/1996 | Mathur et al. |
| 5,510,270 A | 4/1996 | Fodor et al. |
| 5,512,441 A | 4/1996 | Ronai |
| 5,516,635 A | 5/1996 | Ekins et al. |
| 5,516,663 A | 5/1996 | Backman et al. |
| 5,525,464 A | 6/1996 | Drmanac et al. |
| 5,527,681 A | 6/1996 | Holmes |
| 5,536,649 A | 7/1996 | Fraiser et al. |
| 5,593,840 A | 1/1997 | Bhatnagar et al. |
| 5,594,121 A | 1/1997 | Froehler et al. |
| 5,648,213 A | 7/1997 | Reddy et al. |
| 5,667,974 A | 9/1997 | Birkenmeyer et al. |
| 5,695,934 A | 12/1997 | Brenner |
| 5,700,637 A | 12/1997 | Southern |
| 5,723,320 A | 3/1998 | Dehlinger |
| 5,728,526 A | 3/1998 | George, Jr. et al. |
| 5,731,171 A | 3/1998 | Bohlander |
| 5,744,305 A | 4/1998 | Fodor et al. |
| 5,800,984 A | 9/1998 | Vary |
| 5,834,181 A | 11/1998 | Shuber |
| 5,837,832 A | 11/1998 | Chee et al. |
| 5,858,659 A | 1/1999 | Sapolsky et al. |
| 5,868,136 A | 2/1999 | Fox et al. |
| 5,876,924 A | 3/1999 | Zhang et al. |
| 5,912,148 A | 6/1999 | Eggerding |
| 5,932,711 A | 8/1999 | Boles et al. |
| 5,942,391 A | 8/1999 | Zhang et al. |
| 5,981,176 A | 11/1999 | Wallace |
| 6,027,889 A | 2/2000 | Barany et al. |
| 6,054,564 A | 4/2000 | Barany et al. |
| 6,060,237 A * | 5/2000 | Nygren ............... B82Y 30/00 356/364 |
| 6,143,495 A | 11/2000 | Lizardi et al. |
| 6,156,501 A | 12/2000 | McGall et al. |
| 6,506,594 B1 | 1/2003 | Barany et al. |
| 6,569,647 B1 | 5/2003 | Zhang et al. |
| 6,852,487 B1 | 2/2005 | Barany et al. |
| 7,455,965 B2 | 11/2008 | Barany et al. |
| 8,492,085 B2 | 7/2013 | Barany et al. |
| 9,340,834 B2 * | 5/2016 | Barany ............... C12Q 1/6827 |
| 2003/0175750 A1 | 9/2003 | Barany et al. |

FOREIGN PATENT DOCUMENTS

| | | |
|---|---|---|
| EP | 0 487 104 A1 | 5/1992 |
| EP | 0 601 714 A1 | 6/1994 |
| EP | 0 624 643 A | 11/1994 |
| EP | 0 628 640 A1 | 12/1994 |
| EP | 0 630 973 A | 12/1994 |
| EP | 0 799 897 A | 10/1997 |
| JP | H08503091 A | 4/1996 |
| WO | WO 89/10977 | 11/1989 |
| WO | WO 90/11372 | 10/1990 |
| WO | WO 90/15070 | 12/1990 |
| WO | WO 92/10558 | 6/1992 |
| WO | WO 92/10566 | 6/1992 |
| WO | WO 92/10588 | 6/1992 |
| WO | WO 92/16655 | 10/1992 |
| WO | WO 93/04199 | 3/1993 |
| WO | WO 93/09250 | 5/1993 |
| WO | WO 93/17126 | 9/1993 |
| WO | WO 93/20227 | 10/1993 |
| WO | WO 93/20236 | 10/1993 |
| WO | WO 93/22680 | 11/1993 |
| WO | WO 93/25563 | 12/1993 |
| WO | WO 94/01446 | 1/1994 |
| WO | WO 94/09022 | 4/1994 |
| WO | WO 94/11530 | 5/1994 |
| WO | WO 94/11837 A1 | 5/1994 |
| WO | WO 94/17206 | 8/1994 |
| WO | WO 94/17210 | 8/1994 |
| WO | WO 91/17239 | 11/1994 |
| WO | WO 95/00533 | 1/1995 |
| WO | WO 95/35390 | 12/1995 |
| WO | WO 96/06190 | 2/1996 |
| WO | WO 96/15271 | 5/1996 |
| WO | WO 97/31256 | 8/1997 |
| WO | WO 97/45559 | 12/1997 |
| WO | WO 98/03673 | 1/1998 |
| WO | WO 00/47767 | 8/2000 |
| WO | WO 00/56927 | 9/2000 |
| WO | WO 01/79548 | 10/2001 |

OTHER PUBLICATIONS

Abravaya et al., "Detection of Point Mutations with a Modified Ligase Chain Reaction (Gap-LCR)," *Nucleic Acids Research* 23(4):675-682 (1995).

Ahrendt et al., "Rapid p53 Sequence Analysis in Primary Lung Cancer Using an Oligonucleotide Probe Array," *Proc. Natl. Acad. Sci. USA* 96:7382-7387 (1999).

Bains, "Mixed Hybridization and Conventional Strategies for DNA Sequencing," *GATA* 10(3-4):84-94 (1993).

Balles et al., "Facilitated Isolation of Rare Recombinants by Ligase Chain Reaction: Selection for Intragenic Crossover Events in the Drosophila Optomotor-Blind Gene," *Mol. Gen. Genet.* 245:734-740 (1994).

Barany, "Genetic Disease Detection and DNA Amplification Using Cloned Thermostable Ligase," *Proc. Natl. Acad. Sci. USA* 88:189-193 (1991).

Barany, "Ligase Chain Reaction (LCR)—Overview and Applications," *PCR Methods and Applications* 3(4): S51-S64 (1994).

Barany, "Cloning, Overexpression, and Nucleotide Sequence of a Thermostable DNA Ligase Gene," *Gene* 109:1-11 (1991).

Barany, "The Ligase Chain Reaction in a PCR World," *PCR Methods and Applications* 1:5-16 (1991).

Beattie et al., "Advances in Genosensor Research," *Clin. Chem.* 41(5):700-706 (1995).

Belgrader et al., "A Multiplex PCR-Ligase Detection Reaction Assay for Human Identity Testing," *Genome Science & Tech.* 1:77-87 (1996).

Berthelemy et al., "Identification of K-*ras* Mutations in Pancreatic Juice in the Early Diagnosis of Pancreatic Cancer," *Annals of Internal Medicine* 123(3):188-191 (1995).

(56) References Cited

OTHER PUBLICATIONS

Biancalana et al., "Moderate Instability of the Trinucleotide Repeat in Spine Bulbar Muscular Atrophy," *Hum. Mol. Genet.* 1(4):255-258 (1992).
Brennan et al., "Molecular Assessment of Histopathological Staging in Squamous-Cell Carcinoma of the Head and Neck," *The New England Journal of Medicine*, 332(7):429-435 (1995).
Bronner et al., "Mutation in the DNA Mismatch Repair Gene Homologue hMLH1 is Associated with Hereditary Non-Polyposis Colon Cancer," *Nature (London)* 368:258-261.
Buyse et al., "Rapid DNA Typing of Class II HLA Antigens Using the Polymerase Chain Reaction and Reverse Dot Blot Hybridization," *Tissue Antigens* 41:1-14 (1993).
Cairns et al., "Homozygous Deletions of 9p21 in Primary Human Bladder Tumors Detected by Comparative Multiple Polymerase Chain Reaction." *Cancer Res.* 54:1422-1424 (1994).
Cawkwell et al., "Frequency of Allele Loss of DCC, p53, RBI, WT1, NF1, NM23 and PC/MCC in Colorectal Cancer Assayed by Fluorescent Multiplex Polymerase Chain Reaction," *Br. J. Cancer* 70(5):813-818 (1994).
Celi et al., "A Rapid and Versatile Method to Synthesize Internal Standards for Competitive PCR," *Nucleic Acids Research* 21(4):1047 (1993).
Chamberlain et al., "Deletion Screening of the Duchenne Muscular Dystrophy Locus Via Multiplex DNA Amplification," *Nucleic Acids Research* 16(23):11141-11156 (1988).
Chan et al., "Polymeric Self-Assembled Monolayers. 3. Pattern Transfer by Use of Photolithography, Electrochemical, Methods and an Ultrathin, Self-Assembled Diacetylenic Resist," *J. Am. Chem. Soc.* 117:5875-5976 (1995).
Chee et al., "Accessing Genetic Information with High-Density DNA Arrays," *Science* 274:610-614 (1996).
Chehab et al., "Detection of Specific DNA Sequences by Fluorescence Amplification: A Color Complementation Assay," *Proc. Natl. Acad. Sci. USA* 86:9178-9182 (1989).
Cheng et al., "In Situ Attenuated Total Reflectance Fourier Transform Infrared Spectroscopy of Carboxylate-Bearing, Siloxane-Anchored, Self-Assembled Monolayers: A Study of Carboxylate Reactivity and Acid-Base Properties," *Langmuir* 11:1190-1195.
Chetverin et al., "Sequencing of Pools of Nucleic Acids on Oligonucleotide Arrays," *BioSystems* 30:215-231 (1993).
Chung et al., "Evidence for a Mechanism Predisposing to Intergenerational CAG Repeat Instability in Spinocerebeller Ataxia Type I," *Nat. Genet.* 5:254-258 (1993).
Cronin et al., "Cystic Fibrosis Mutation Detection by Hybridization to Light-Generated DNA Probe Arrays," *Human Mutation* 7:244-255 (1996).
Davis et al., "Quantitative Detection of Hepatitis C Virus RNA With a solid-Phase Signal Amplification Method: Definition of Optimal Conditions for Specimen Collection and Clinical Application in Interferon-Treated Patients," *Hepatology* 19(6):1337-1341.
Day et al., "Detection of Steroid 21-Hydroxylase Alleles Using Gene-Specific PCR and a Multiplexed Ligation Detection Reaction," *Genomics* 29:152-162 (1995).
Day et al., "Identification of Non-Amplifying CYP21 Genes When Using PCR-Based Diagnosis of 21-Hydroxylase Deficiency in Congenital Adrenal Hyperplasia (CAH) Affected Pedigrees," *Hum. Mol. Genet.* 5(12):2039-2048 (1996).
Deng et al., "An Improved Method of Competitive PCR for Quantitation of Gene Copy Number," *Nucleic Acids Research* 21(20):4848-4849 (1993).
Drobyshev et al., "Sequence Analysis by Hybridization with Oligonucleotide Microchip: Identification of β-Thalassemia Mutations," *Gene* 188:45-52 (1997).
Eggerding, "A One-Step Coupled Amplification and Oligonucleotide Ligation Procedure for Multiplex Genetic Typing," *PCR Methods and Applications* 4:337-345.
Favis et al., "Mutation Detection in K-ras, BRCA1, BRCA2, and p53 Using PCR/LDR and a Universal DNA Microarray," *Ann. NY Acad. Sci.* 906:39-43 (2000).
Favis et al., "Universal DNA Array Detection of Small Insertions and Deletions in BRCA1 and BRCA2," *Nat. Biotechnol.* 18(5):561-564 (2000).
Fishel et al., "The Human Mutator Gene Homolog MSH2 and its Associate with Hereditary Nonpolyposis Colon Cancer," *Cell* 75:1027-1038 (1993).
Fodor et al., "Multiplexed Biochemical Assays with Biological Chips," *Nature* 364:555-556 (1993).
Frenkel et al., "Specific, Sensitive and Rapid Assay for Human Immunodeficiency Virus Type 1 pol Mutations Associated with Resistance to Zidovudine and Didanosine," *J. Clin. Microbiol.* 33(2):342-347 (1995).
Friedhoff, et al., "Quantitative Polymerase Chain Reaction with Oligodeoxynucleotide Ligation Assay/Enzyme-Linked Immunosorbent Assay Detection," *Anal. Biochem.* 215:9-16 (1993).
Gerry et al., "Universal DNA Microarray Method for Multiplex Detection of Low Abundance Point Mutations," *J. Mol. Biol.* 292:251-262 (1999).
Gibbs et al., "Detection of Single DNA Base Differences by Competitive Oligonucleotide Priming," *Nucleic Acids Research* 17(7):2437-2448 (1989).
Gonzalez-Zulueta et al., "Microsatellite Instability in Bladder Cancer," *Cancer Res.* 53:5620-5623 (1993).
Graham et al., "Gene Probe Assays on a Fibre-Optic Evanescent Wave Biosensor," *Biosensors & Bioelectronics* 7:487-493 (1992).
Grossman et. al., "High-Density Multiplex Detection of Nucleic Acid Sequences: Oligonucleotide Ligation Assay and Sequence-Coded Separation," *Nucleic Acids Research* 22(21):4527-4534 (1994).
Guo et al., "Direct Fluorescence Analysis of Genetic Polymorphisms by Hybridization with Oligonucleotide Arrays on Glass Supports," *Nucleic Acids Research* 22:5456-5465.
Gyllensten et al., "PCR-Based HLA Class II Typing," *PCR Methods and Applications* 1:91-98 (1991).
Hacia et al., "Detection of Heterozygous Mutations in *BRCA1* Using High Density Oligonucleotide Arrays and Two-Colour Fluorescence Analysis," *Nature Genetics* 14:441-447 (1996).
Hacia, "Resequencing and Mutational Analysis Using Oligonucleotide Microarrays," *Nat. Genetics* (SUPPL.) 2:42-47 (1999).
Hames et al., eds., Nucleic Acid Hybridisation. A Practical Approach, Oxford, England IRL Press, pp. 5-7 (1985).
Han et al., "Genetic Instability in Pancreatic Cancer and Poorly Differentiated Type of Gastric Cancer," *Cancer Res.* 53:5087-5089 (1993).
Hayashi et al., "Genetic Diagnosis Identifies Occult Lymph Node Metastases Undetectable by the Histopathological Method," *Cancer Res.* 54:3853-3856 (1994).
Heller et al., "Discovery and Analysis of Inflammatory Disease-Related Genes Using cDNA Microarrays," *Proc. Nat'l. Acad. Sci. USA* 94:2150-2155 (1997).
Hollstein et al., "p53 Mutations in Human Cancers," *Science* 253:49-53 (1991).
Hsuih et al., "Novel, Ligation-Dependent PCR Assay for Detection of Hepatitis C Virus in Serum," *J. Clin. Microbiol.* 34(3):501-507 (1996).
Imbert et al., "Origin of the Expansion Mutation in Myotonic Dystrophy," *Nat. Genet.* 4:72-76 (1993).
Ionov et al., "Ubiquitous Somatic Mutations in Simple Repeated Sequences Reveal a New Mechanism for Colonic Carcinogenesis," *Nature (London)* 363:558-561 (1993).
Iovannisci et al., "Ligation Amplification and Fluorescence Detection of *Mycobacterium Tuberculosis* DNA," *Mol. Cell. Probes* 7(1):35-43 (1993).
Janssen et al., "Evaluation of the DNA Fingerprinting Method AFLP as a New Tool in Bacterial Taxonomy," *Microbiology* 142:1881-1893 (1996).
Jen et al., "Molecular Determinants of Dysplasia in Colorector Lesions," *Cancer Res.* 54:5523-5526(1994).
Jin et al., "Alternating Current Impedance Characterization of the Structure of Alkylsiloxane Self-Assembled Monolayers on Silicon," *Langmuir* 10:2662-2671 (1994).

(56) References Cited

OTHER PUBLICATIONS

Jou et al., "Deletion Detection in the Dystrophin Gene by Multiplex Gap Ligase Chain Reaction and Immunochromatographic Strip Technology," *Human Mutation* 5:86-93.
Khanna et al., "Ligase Detection Reaction for Identification of Low Abundance Mutations," *Clin. Biochem.* 32(4):287-290 (1999).
Khanna et al., "Multiplex PCR/LDR for Detection of K-*ras* Mutations in Primary Colon Tumors," *Oncogene* 18:27-38 (1999).
Khrapko et al., "A Method for DNA Sequencing by Hybridization with Oligonucleotide Matrix," *J. DNA Seq. Map* 1:375-388 (1991).
Kim et al., "Polymeric Self-Assembled Monolayers. 2. Synthesis and Characterization of Self-Assembled Polydiacetylene Mono- and Multilayers," *J. Am. Chem. Soc.* 117:3963-3967 (1995).
Koide et al., "Unstable Expansion of CAG Repeat in Hereditary Dentatorubral-Pallidoluysian Atrophy (DRPLA)," *Nat. Genet.* 6:9-13 (1994).
Kovach et al., "Mutation Detection by Highly Sensitive Methods Indicates that p53 Gene Mutations in Breast Cancer Can Have Important Prognostic Value," *Proc. Natl. Acad. Sci. USA* 93:1093-1096 (1996).
Kozal et al., "Extensive Polymorphisms Observed in HIV-1 Clade B Protease Gene Using High-Density Oligonucleotide Arrays," *Nature Medicine* 2:753-759 (1996).
Kreiner, "Rapid Genetic Sequence Analysis Using a DNA Probe Array System," *American Laboratory*, pp. 39-43 (1996).
Kremer et al., "Mapping of DNA Instability at the Fragile X to a Trinucleotide Repeat Sequence p(CCG)n," *Science* 252:1711-1714 (1991).
Kuppuswamy et al., "Single Nucleotide Primer Extension to Detect Genetic Diseases: Experimental Application to Hemophilia B (factor IX) and Cystic Fibrosis Genes," *Proc. Natl. Acad. Sci. USA* 88:1143-1147 (1991).
Kuznetsova et al., "DNA Sequencing by Hybridization with Oligonucleotides Immobilized in a Gel," *Mol. Biol. (Mosk) (Russia)* 28(2):290-299 (1994).
Landegren et al., "A Ligase-Mediated Gene Detection Technique," *Science* 241:1077-1080 (1988).
Lauer et al., "Cloning, Nucleotide Sequence, and Engineered Expression of *Thermus thermophilus* DNA Ligase, a Homolog of *Escherichia coli* DNA Ligase," *Journal of Bacteriology* 173(16):5047-5053 (1991).
Leach et al., "Mutations of a mutS Homolog in Hereditary Nonpolyposis Colorectal Cancer," *Cell* 75:1215-1225 (1993).
Lin et al., "Multiplex Genotype Determination at a Large Number of Gene Loci," *Proc. Natl. Acad. Sci. USA* 93:2582-2587 (1996).
Lipshutz et al., "Using Oligonucleotide Probe Arrays to Assess Genetic Diversity," *Biotechniques* 19:442-447 (1995).
Livak et al., "Detection of Single Base Differences Using Biotinylated Nucleotides With Very Long Linker Arms," *Nucleic Acids Research* 20:4831-4837 (1989).
Livshits et al., "Dissociation of Duplexes Formed by Hybridization of DNA with Gel-Immobilized Oligonucleotides," *Journal of Biomolecular Structure & Dynamics* 11(4):783-795 (1994).
Lu et al., "Quantitative Aspects of the Mutant Analysis by PCR anc Restriction Enzyme Cleavage (MAPREC)," *PCR Methods and Applications* 3:176-180 (1993).
Lysov et al., "DNA Sequencing by Hybridization to Oligonucleotide Matrix Calculation of Continuous Stacking Hybridization Efficiency," *Journal of Biomolecular Structure & Dynamics* 11(4):797-812 (1994).
Lysov et al., "Measurement of Distances Between DNA Segments Increases Efficiency of Sequencing by Hybridization with Oligonucleotide Matrix," *Molecular Biology* 28(3):433-436 (1994).
Mao et al., "Microsatellite Alteration as Clonal Markers for the Detection of Human Cancer," *Proc. Natl. Acad. Sci. USA* 91:9871-9875 (1994).
Mao et al., "Molecular Detection of Primary Bladder Cancer," *Science* 271:659-662 (1996).

Maskos et al., "A Novel Method for the Analysis of Multiple Sequence Variants by Hybridization to Oligonucleotides," *Nucleic Acids Research* 21:2267-2268 (1993).
Maskos et al., "A Study of Oligonucleotide Reassociation Using Large Arrays of Oligonucleotides Synthesized on a Glass Support," *Nucleic Acids Research* 21:4663-4669.
Merlo et al., "Frequent Microsatellite Instability in Primary Small Cell Lung Cancer," *Cancer Res.* 54:2098-2101 (1994).
Milner et al., "Selecting Effective Antisense Reagents on Combinatorial Oligonucleotide Arrays," *Nature Biotechnology* 15:537-541 (1997).
Mitsudomi et al., "Mutations of ras Genes Distinguish a Subset of Non-Small-Cell Lung Cancer Cell Lines from Small-Cell Lung Cancer Cell Lines," *Oncogene* 6:1353-1362 (1991).
Munkholm et al., "Polymer Modification of Fiber Optic Chemical Sensors as a Method of Enhancing Fluorescence Signal for pH Measurement," *Anal. Chem.* 58:1427-1430 (1986).
Nawroz et al., "Allelotype of Head and Neck Squamous Cell Carcinoma," *Cancer Res.* 54:1152-1155 (1994).
Newton et al., "The Production of PCR Products with 5" Single-Stranded Tails Using Primers that Incorporate Novel Phosphoram Phosphoramidite Intermediates," *Nucleic Acids Research* 21(5):115-162 (1993).
Nickerson et al., "Automated DNA Diagnostics Using an ELISA-Based Oligonucleotide Ligation Assay," *Proc. Natl. Acad. Sci. USA* 87:8923-8927 (1990).
Nikiforov et al., "Genetic Bit Analysis: A Solid Phase Method for Typing Single Nucleotide Polymorphisms," *Nucleic Acids Research* 22(20):4167-4175 (1994).
Nilsson et al., "Padlock Probes: Circularizing Oligonucleotides for Localized DNA Detection," *Science* 265:2085-2088 (1994).
Orr et al., "Expansion of an Unstable Trinucleotide CAG Repeat in Spinocerebeller Ataxia Type 1," *Nat. Genet.* 4:221-226 (1993).
Papadopoulos et al., "Mutation of mutl. Homolog in Hereditary Colon Cancer," *Science* 263:1625-1629 (1994).
Parinov et al., "DNA Sequencing by Hybridization to Microchip Octa- and Decanuleotides Extended by Stacked Pentanucleotides," *Nucleic Acids Research* 24:2998-3004 (1996).
Park et al., "Detection of HCV RNA Using Ligation-Dependent Polymerase Chain Reaction in Formalin-Fixed Paraffin-Embedded Liver Tissue," *American Journal of Pathology* 149(5):1485-1491 (1996).
Pease et al., "Light-Generated Oligonucleotide Arrays for Rapid DNA Sequence Analysis," *Proc. Natl. Acad. Sci. USA* 91:5022-5026 (1994).
Peinado et al., "Isolation and Characterization of Allelic Losses and Gains in Colorectal Tumors by Arbitrarily Primed Polymerase Chain Reaction," *Proc. Natl. Acad. Sci. USA* 89:10065-10069 (1992).
Peltomäki et al., "Microsatellite Instability is Associated with Tumors that Characterize the Hereditary Non-Polyposis Colorectal Carcinoma Syndrome," *Cancer Res.* 53:5853-5855 (1993).
Powell et al., "Molecular Diagnosis of Familial Adenomatous Polyposis," *The New England Journal of Medicine* 329(27):1982-1987 (1993).
Radford et al., "Allelotyping of Ductal Carcinoma in Situ of the Breast: Deletion of Loci on 8p, 13q, 16q, 17p and 171[1]," *Cancer Research* 55:3399-3405 (1995).
Redston et al., "Common Occurrence of APC and K-ras Gene Mutations in the Spectrum of Colitis-Associated Neoplasias," *Gastroenterology* 108:383-392 (1995).
Reed et al., "Chromosome-Specific Microsatellite Sets for Fluorescence-Based, Semi-Automated Genome Mapping," *Nature Genetics* 7:390-395 (1994).
Reyes et al., "Ligase Chain Reaction Assay for Human Mutations: The Sickle Cell by LCR Assay," *Clinical Chemistry* 43(1):40-44 (1997).
Reynolds et al., "Analysis of Genetic Markers in Forensic DNA Samples Using the Polymerase Chain Reaction," *Anal. Chem.* 63:2-15 (1991).
Risinger et al., "Genetic Instability of Microsatellites in Endometrial Carcinoma," *Cancer Res.* 53:5100-5103 (1993).

(56) References Cited

OTHER PUBLICATIONS

Ruppert et al., "Evidence for Two Bladder Cancer Suppressor Loci on Human Chromosome $9^1$," *Cancer Res.* 53:5093-5094 (1993).
Rust et al., "Mutagenically Separated PCR (MS-PCR): A Highly Specific One Step Procedure for Easy Mutation Detection," *Nucleic Acids Research* 21(16):3623-3629.
Saiki et al., "Enzymatic Amplification of β-Globin Genomic Sequences and Restriction Site Analysis for Diagnosis of Sickle Cell Anemia," *Science* 230:1350-1354 (1985).
Sambrook et al., *Molecular Cloning a Laboratory Manual*, $2^{nd}$ Ed., Cold Spring Laboratory Press (1989) (Index Only).
Schena et al., "Parallel Human Genome Analysis: Microarray-Based Expression Monitoring of 1000 Genes," *Proc. Natl. Acad. Sci. USA* 93:10614-10619 (1996).
Schena et al., "Quantitative Monitoring of Gene Expression Patterns with a Complementary DNA Microarray," *Science* 270:467-470 (1995).
Shalon et al., "A DNA Microarray System for Analyzing Complex DNA Samples Using Two-Color Fluorescent Probe Hybridization," *Genome Research* 6:639-645 (1996).
Sidransky et al., "Identification of ras Oncogene Mutations in the Stool of Patients with Curable Colorector Tumors," *Science* 256:102-105 (1992).
Southern et al., "Analyzing and Comparing Nucleic Acid Sequences by Hybridization to Arrays of Oligonucleotides: Evaluation Using Experimental Models," *Genomics* 13:1008-1017 (1992).
Southern, "DNA Chips: Analyzing Sequence by Hybridization to Oligonucleotides on a Large Scale," *Trends in Genet.* 12(3):110-115 (1996).
Suzuki et al., "Detection of ras Gene Mutations in Human Lung Cancers by Single-Strand Conformation Polymorphism Analysis of Polymerase Chain Reaction Products," *Oncogene* 5:1037-1043 (1990).
Syvänen et al., "Identification of Individuals by Analysis of Biallelic DNA Markers, Using PCR and Solid-Phase Minisequencing," *Am. J. Hum. Genet.* 52:46-59 (1993).
Tada et al., "Clinical Application of ras Gene Mutation for Diagnosis of Pancreatic Adenocarcinoma," *Gastroenterology* 100:233-238 (1991).
Tada et al., "Detection of ras Gene Mutations in Pancreatic Juice and Peripheral Blood of Patients with Pancreatic Adenocarcinoma," *Cancer Res.* 53:2472-2474 (1993).
Tavormina et al., "Thanatophoric Dysplasia (Types I and II) Caused by Distinct Mutations in Fibroblast Growth Factor Receptor 3," *Nature Genetics* 9:32128 (1995).
Telenti et al., "Competitive Polymerase Chain Reaction Using an Internal Standard: Application to the Quantitation of Viral DNA," *Journal of Virological Methods* 39:259-268 (1992).
The Huntington' s Disease Collaborative Research Group, "A Novel Gene Containing a Trinucleotide Repeat that is Expanded and Unstable on Huntington's Disease Chromosomes," *Cell* 72:971-983 (1993).
Thibodeau et al., "Microsatellite Instability in Cancer of the Proximal Colon," *Science* 260:816-819 (1993).
Timofeev et al., "Regioselective Immobilization of Short Oligonucleotides to Acrylic Copolymer Gels," *Nucleic Acids Research* 27(3):788-794 (1999).
Tong et al., "Biochemical Properties of High Fidelity DNA Ligase from Thermus species AK16D," *Nucleic Acids Research* 27(3):788-794 (1999).
Tsui, "Mutations and Sequence Variations Detected in the Cystic Fibrosis Transmembrane Conductance Regulator (CFTR) Gene: a Report from the Cystic Fibrosis Genetic Analysis Consortium," *Human Mutation* 1:197-203 (1992).
Urdea, "Synthesis and Characterization of Branched DNA (bDNA) for the Direct and Quantitative Detection of CMV, HBV, HCV, and HIV," *Clincal Chemistry* 39(4):725-726.
Van Der Riet et al., "Frequent Loss of Chromosome 9p21-22 Early in Head and Neck Cancer Progression," *Cancer Res.* 54:1156-1158 (1994).
Van Ness et al., "A Versatile Solid Support System for Oligodeoxynucleotide Probe-based Hybridization Assays," *Nucleic Acids Research* 19:3345-3350 (1991).
Wallace et al., "Ligase Chain Reaction for the Detection of Specific DNA Sequences and Point Mutations," in Pfeifer, ed., *Technologies for Detection of DNA Damage and Mutations*, New York, NY: Plenum, Press, pp. 307-322 (1996).
Wang et al., "Large-Scale Identification, Mapping, and Genotyping of Single-Nucleotide Polymorphisms in the Human Genome," *Science* 280:1077-1082 (1998).
Weber et al., "Abundant Class of Human DNA Polymorphisms Which Can Be Typed Using the Polymerase Chain Reaction," *Amer. J. Hum. Genet.* 44:388-396 (1989).
Weissenbach et al., "A Second-Generation Linkage Map of the Human Genome," *Nature (London)* 359:794-800 (1992).
Winn-Deen, et al., "Sensitive Fluorescence Method for Detecting DNA Ligation Amplification Products," *Clinical Chemistry* 37(9):1522-1523 (1991).
Wu et al., "The Ligation Amplification Reaction (LAR)-Amplification of Specific DNA Sequences Using Sequential Rounds of Template-Dependent Ligation," *Genomics* 4:560-569 (1989).
Yershov et al., "DNA Analysis and Diagnostics on Oligonucleotide Microchips," *Proc. Natl. Acad. Sci. USA* 93:4913-4918 (1996).
Zebala et al., "Characterization of Steady State, Single Turnover, and Binding Kinetics of the *Taq*I Restriction Endonuclease," *J. Biol. Chem.* 267(12):8097-8105 (1992).
Zebala et al., "Implications for the Ligase Chain Reaction in Gastroenterology," *Clin. Gastroenterol.* 17(2):171-175 (1993).
Zhang et al., "Single-base Mutational Analysis of Cancer and Genetic Disease Using Membrane Modified Oligonucleotides," *Nucleic Acids Research* 19:3929-3933 (1991).
Zirvi et al., "Improved Fidelity of Thermostable Ligases for Detection of Microsatellite Repeat Sequences Using Nucleoside Analogs," *Nucleic Acids Research* 27(24):e41 (1999).
Zirvi et al., "Ligase-based Detection of Mononucleotide Repeat Sequences," *Nucleic Acids Research* 27(24):e40 (1999).
"Acrylamide" *Wikipedia Encyclopedia*, Retrieved from the internet *at* http://en.wikipedia.org/wiki/Acrylamide on Sep. 15, 2005.
Notice of Reasons for Rejection for JP2016-097780 dated May 11, 2017 (english translation).

\* cited by examiner

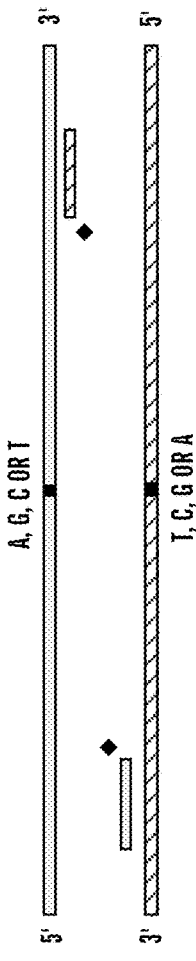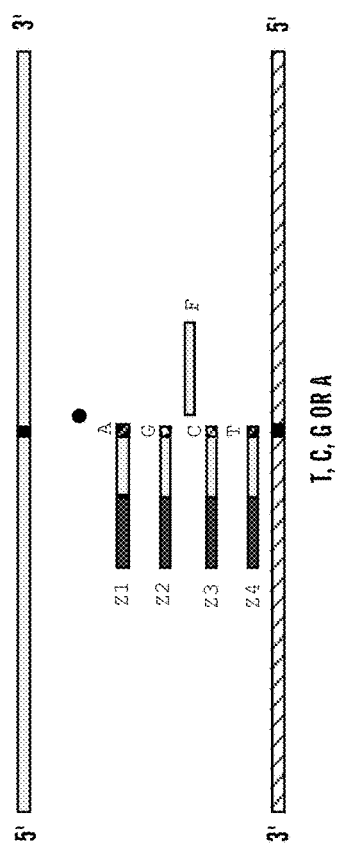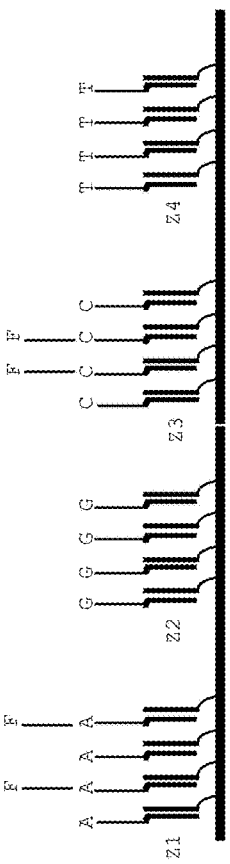

PCR/LDR, SCHEME 3

1. PCR AMPLIFY REGION(S) CONTAINING MUTATIONS USING PRIMERS, dNTPS AND Taq POLYMERASE. ◆

2. PERFORM LDR USING ALLELE-SPECIFIC LDR PRIMERS AND THERMOSTABLE LIGASE. ●
ALLELE SPECIFIC OLIGONUCLEOTIDES LIGATE TO COMMON OLIGONUCLEOTIDES ONLY WHEN THERE IS PERFECT COMPLEMENTARITY AT THE JUNCTION.

3. CAPTURE FLUORESCENT PRODUCTS ON ADDRESSABLE ARRAY AND QUANTIFY EACH ALLELE.

FIG. 5

PCR/ LDR, SCHEME 4

1. PCR AMPLIFY REGION(S) CONTAINING MUTATIONS USING PRIMERS, dNTPS AND Taq POLYMERASE. ◆

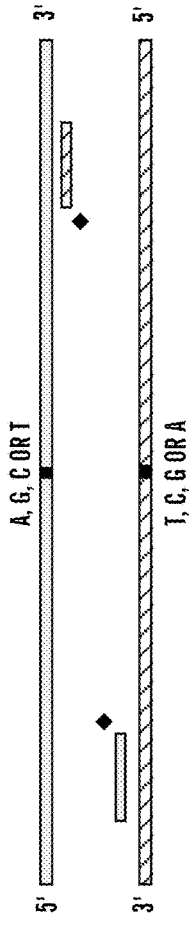

2. PERFORM LDR USING ALLELE-SPECIFIC LDR PRIMERS AND THERMOSTABLE LIGASE.● ALLELE SPECIFIC OLIGONUCLEOTIDES LIGATE TO COMMON OLIGONUCLEOTIDES ONLY WHEN THERE IS PERFECT COMPLEMENTARITY AT THE JUNCTION.

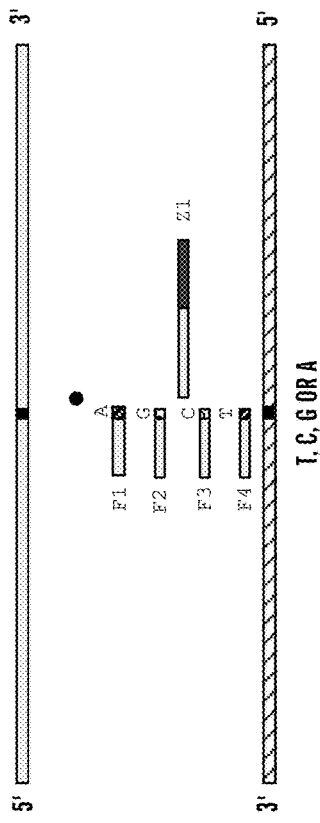

3. CAPTURE FLUORESCENT PRODUCTS ON ADDRESSABLE ARRAY AND QUANTIFY EACH ALLELE.

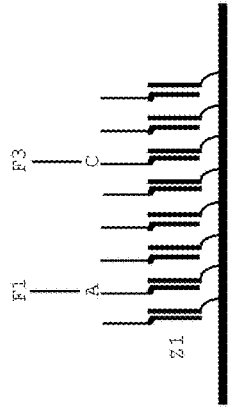

*FIG. 6*

PCR/LDR: NEARBY ALLELES, SCHEME 5

1.
PCR AMPLIFY REGION(S) CONTAINING MUTATIONS USING PRIMERS, dNTPs AND Taq POLYMERASE. ♦

A, G, C or T

T, C, G or A

2.
PERFORM LDR USING ALLELE-SPECIFIC LDR PRIMERS AND THERMOSTABLE LIGASE. ● ALLELE SPECIFIC OLIGONUCLEOTIDES LIGATE TO COMMON OLIGONUCLEOTIDES ONLY WHEN THERE IS PERFECT COMPLEMENTARITY AT THE JUNCTION.

Z1 — A
Z2 — G
Z3 — C — F
Z4 — T
Z5 — A
Z6 — G
Z7 — C — F
Z8 — T

T, C, G or A

3.
CAPTURE FLUORESCENT PRODUCTS ON ADDRESSABLE ARRAY AND QUANTIFY EACH ALLELE.

Z1 (A) Z2 (G) Z3 (C) Z4 (T)

HETEROZYGOUS: A AND C ALLELES.

Z5 (A) Z6 (G) Z7 (C) Z8 (T)

HETEROZYGOUS: G, C, AND T ALLELES.

*FIG. 7*

PCR/ LDR : ADJACENT ALLELES, CANCER DETECTION, SCHEME 10

1.
PCR AMPLIFY
REGION(S)
CONTAINING
MUTATIONS USING
PRIMERS, dNTPS AND
Taq POLYMERASE.◆

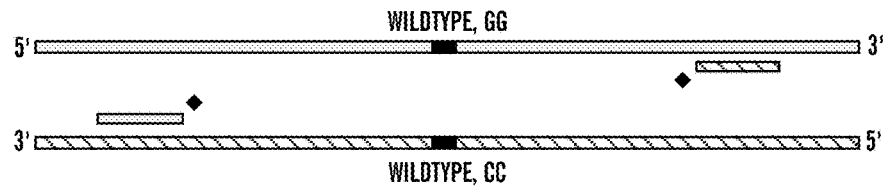

2.
PERFORM LDR USING
ALLELE-SPECIFIC LDR
PRIMERS AND
THERMOSTABLE LIGASE.●
ALLELE SPECIFIC
OLIGONUCLEOTIDES LIGATE
TO COMMON
OLIGONUCLEOTIDES ONLY
WHEN THERE IS PERFECT
COMPLEMENTARITY AT THE
JUNCTION.

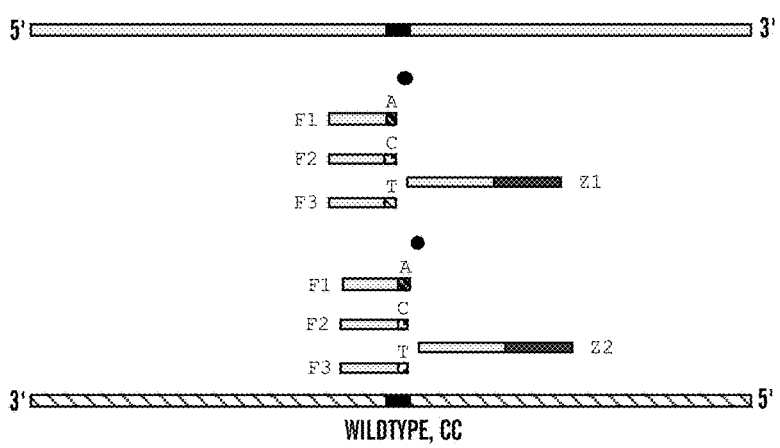

3.
CAPTURE FLUORESCENT PRODUCTS
ON ADDRESSABLE ARRAY AND
QUANTIFY EACH ALLELE.

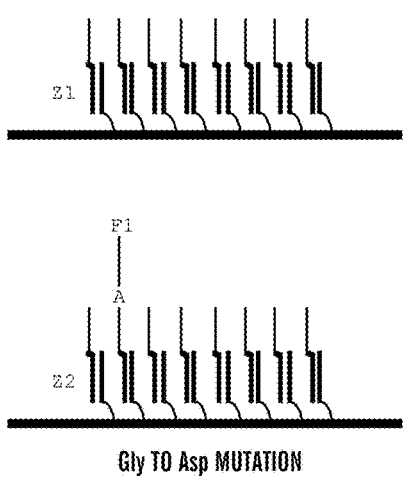

Gly TO Asp MUTATION

*FIG. 12*

PCR/ LDR : NEARBY ALLELES, SCHEME 11

1.
PCR AMPLIFY REGION(S) CONTAINING MUTATIONS USING PRIMERS, dNTPS AND Taq POLYMERASE. ◆

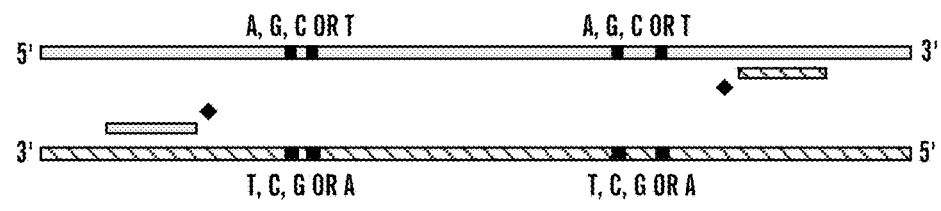

2.
PERFORM LDR USING ALLELE-SPECIFIC LDR PRIMERS AND THERMOSTABLE LIGASE. ● ALLELE SPECIFIC OLIGONUCLEOTIDES LIGATE TO COMMON OLIGONUCLEOTIDES ONLY WHEN THERE IS PERFECT COMPLEMENTARITY AT THE JUNCTION.

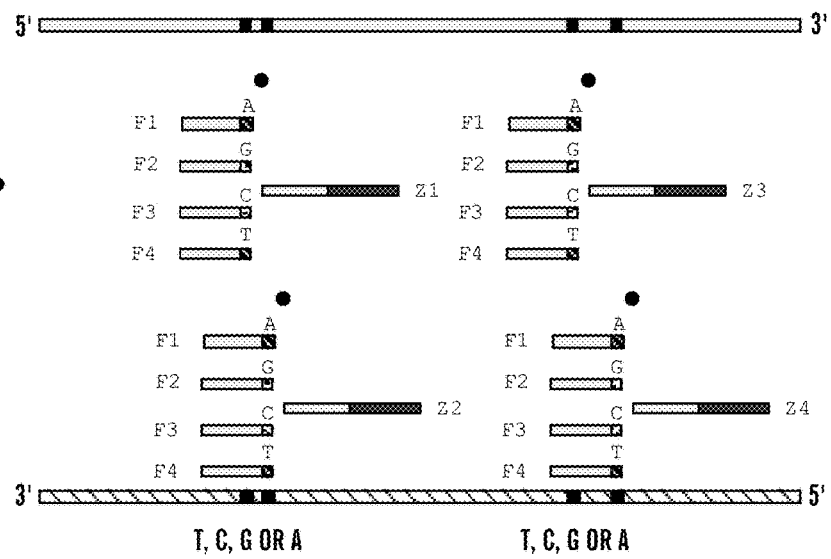

3.
CAPTURE FLUORESCENT PRODUCTS ON ADDRESSABLE ARRAY AND QUANTIFY EACH ALLELE.

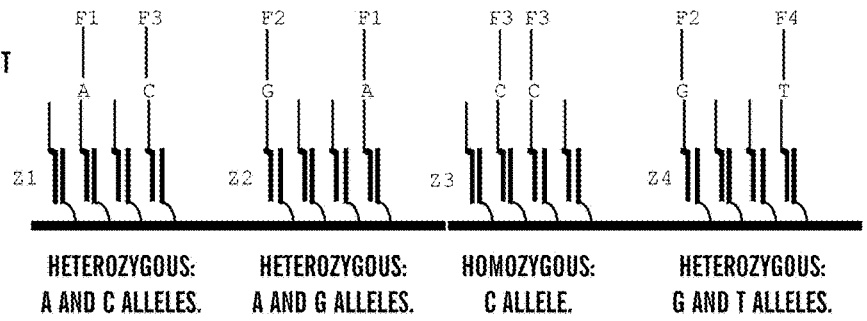

*FIG. 13*

PCR/LDR: ADJACENT AND NEARBY ALLELES, SCHEME 12

1. PCR AMPLIFY REGION(S) CONTAINING MUTATIONS USING PRIMERS, dNTPS AND Taq POLYMERASE. ◆

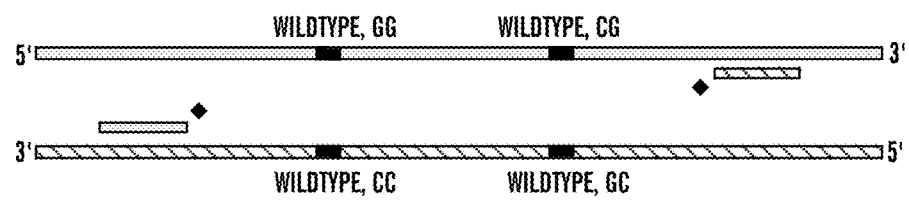

2. PERFORM LDR USING ALLELE-SPECIFIC LDR PRIMERS AND THERMOSTABLE LIGASE. ● ALLELE SPECIFIC OLIGONUCLEOTIDES LIGATE TO COMMON OLIGONUCLEOTIDES ONLY WHEN THERE IS PERFECT COMPLEMENTARITY AT THE JUNCTION.

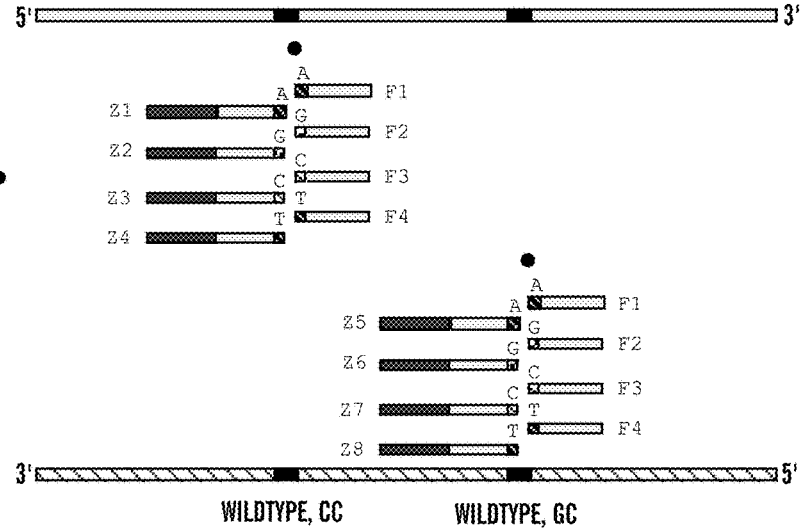

3. CAPTURE FLUORESCENT PRODUCTS ON ADDRESSABLE ARRAY AND QUANTIFY EACH ALLELE.

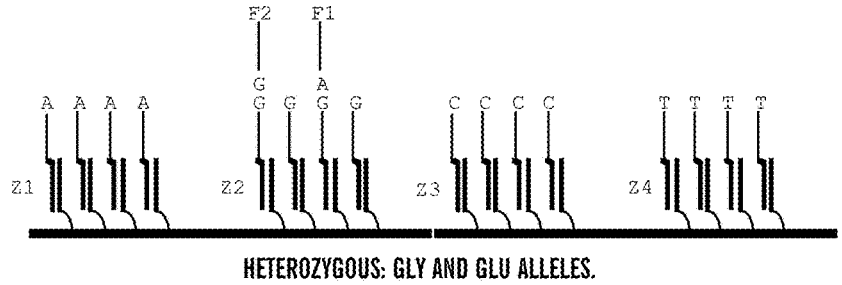

HETEROZYGOUS: GLY AND GLU ALLELES.

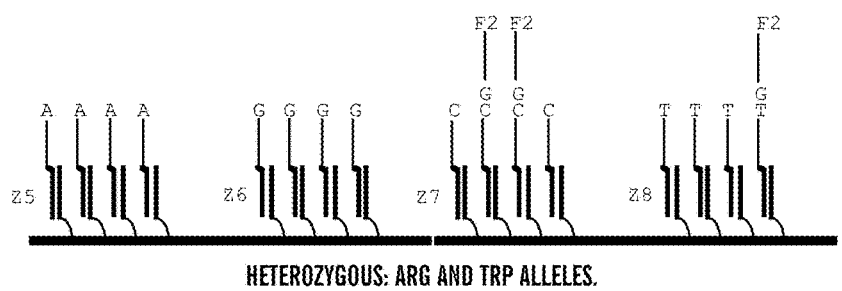

HETEROZYGOUS: ARG AND TRP ALLELES.

*FIG. 14*

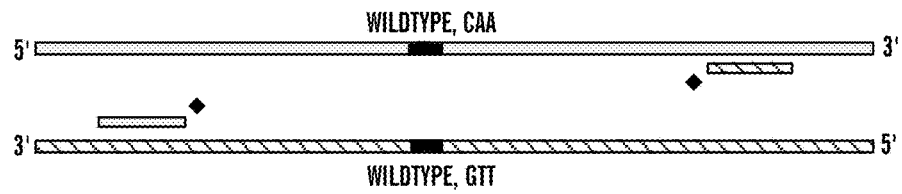
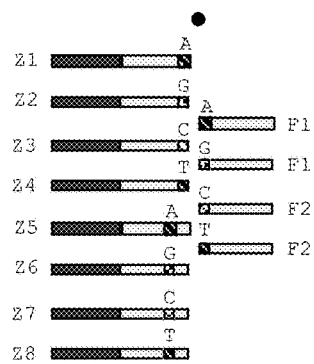
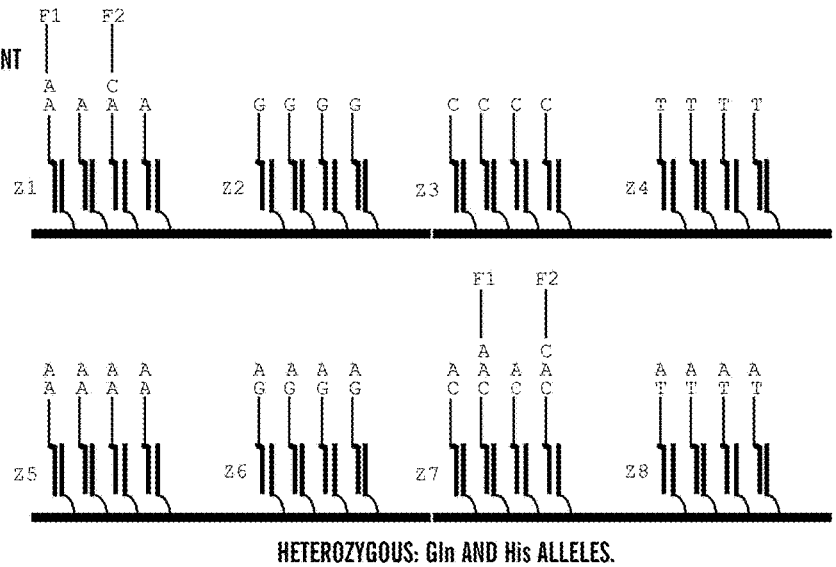
FIG. 15

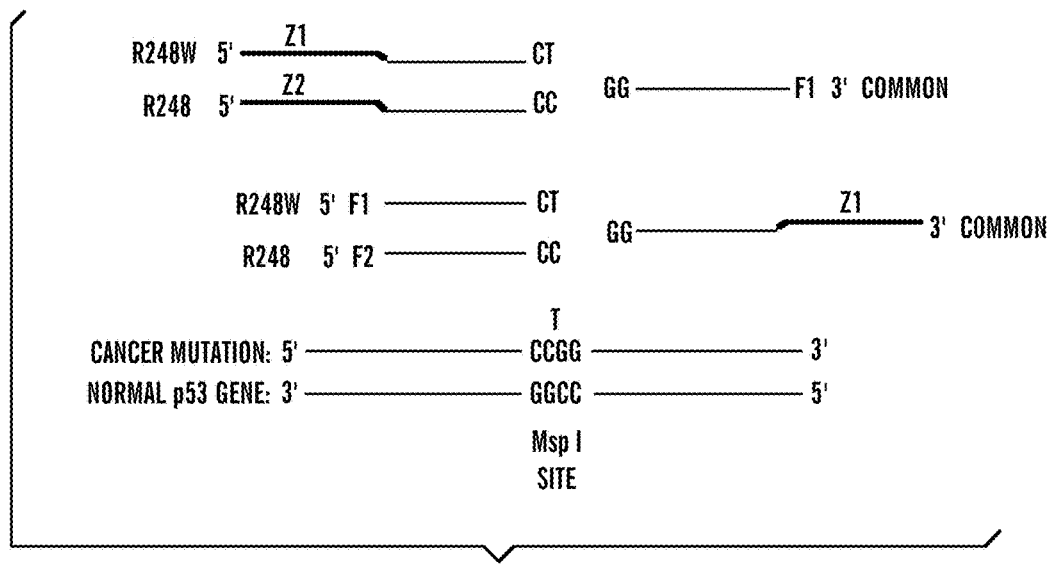
FIG. 17A
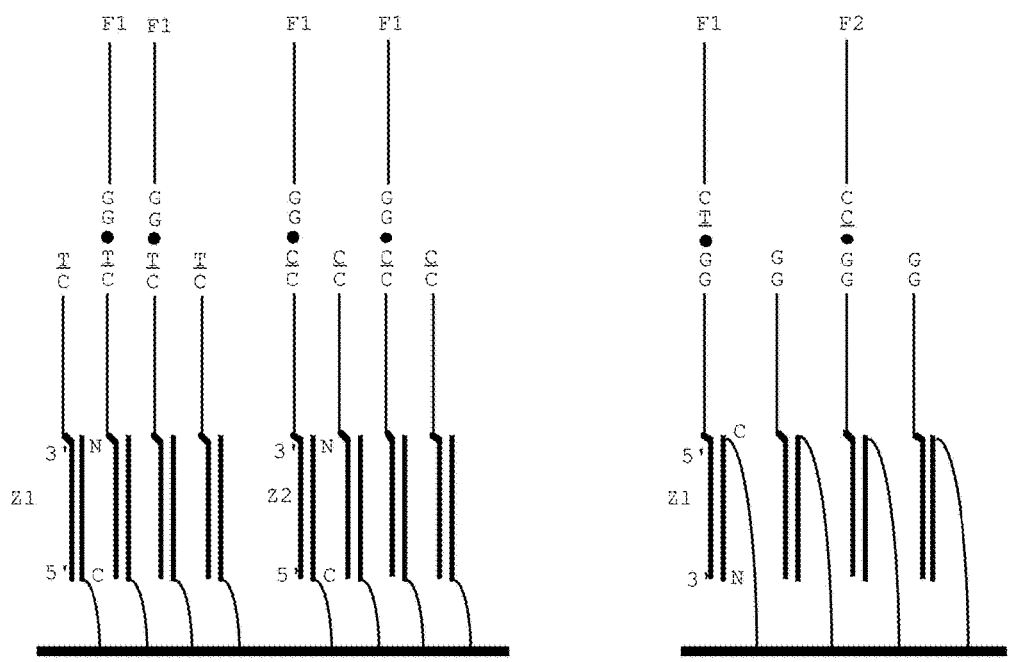
FIG. 17B  FIG. 17C

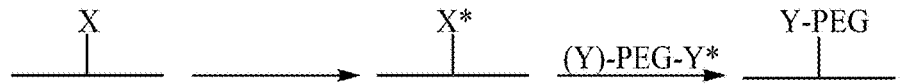
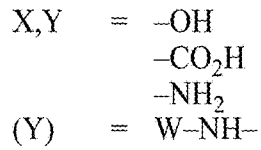
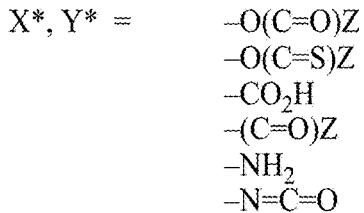
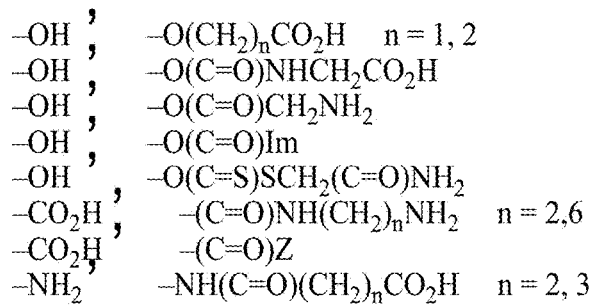
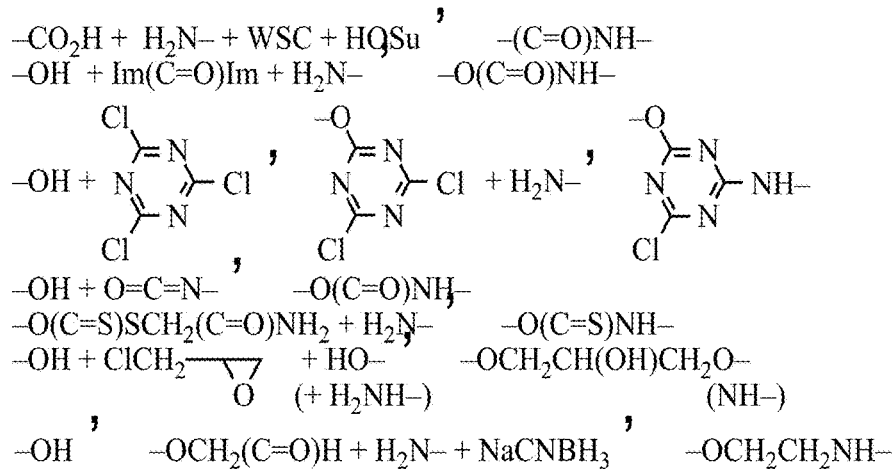
FIG. 18

*FIG. 19*

PCR/ PCR/ LDR

1.
PCR AMPLIFY REGIONS CONTAINING ALLELIC VARIATIONS USING GENE-SPECIFIC/UNIVERSAL PRIMERS, dNTPS AND Taq POLYMERASE. ◆

GENE-SPECIFIC =
UNIVERSAL =

BRCA1 Ex 1 — 185delAG ?
BRCA1 Ex 20 — 5328insC ?
BRCA2 Ex 11 — 6174delT ?

2.
PCR AMPLIFY ALL PRIMARY PRODUCTS USING UNIVERSAL PRIMERS, dNTPS AND Taq POLYMERASE.

3.
PERFORM LDR USING ALLELE-SPECIFIC LDR PRIMERS AND THERMOSTABLE LIGASE. ● ALLELE-SPECIFIC OLIGONUCLEOTIDES LIGATE TO COMMON OLIGONUCLEOTIDES ONLY WHEN THERE IS PERFECT COMPLEMENTARITY AT THE JUNCTION.

185delAG ?
5328insC ?
6174delT ?

4.
SEPARATE FLUORESCENT PRODUCTS ON A DNA SEQUENCER AND QUANTIFY EACH ALLELE.

HOMOZYGOUS WT | HETEROZYGOUS | HOMOZYGOUS WT

*FIG. 20*

PCR/PCR/ LDR/Array of BRCA1 Ex 20: 5382insC Mutant and Wild-type control

1. PCR amplify regions containing allelic variations using gene-specific/universal primers, dNTPs and polymerase.◆
   Gene-specific =
   Universal =

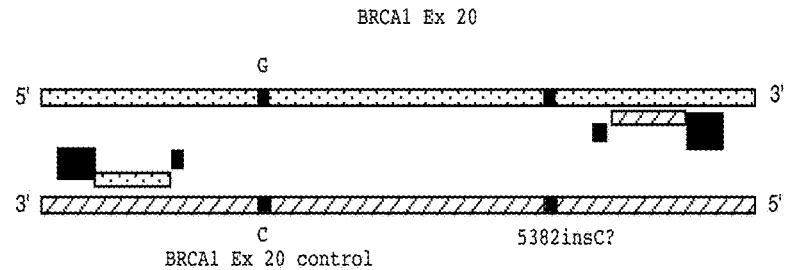

2. Perform LDR using allele-specific LDR primers and thermostable ligase.●
   Since mutant LDR products can be either Cy3 or Cy5 labeled, control product is labeled with both Cy3 and Cy5 so it is visible in both channels during array analysis.

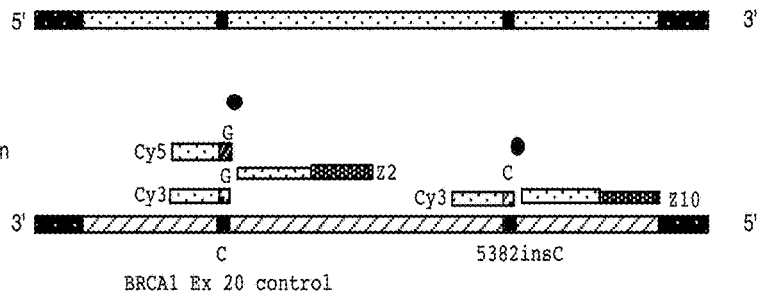

3. Capture fluorescent products on addressable array and quantify each allele.

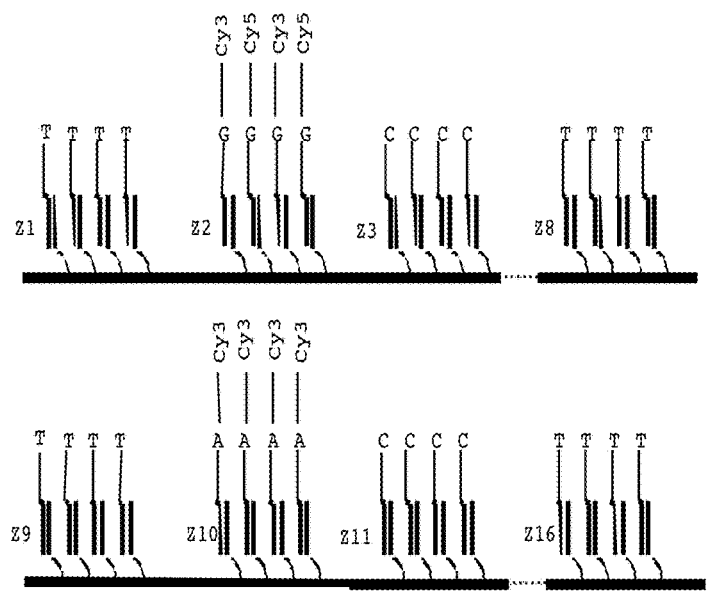

*FIG. 22*

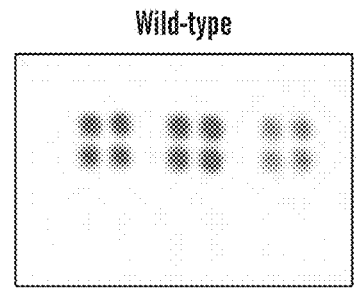
*FIG. 23A*
*FIG. 23B*
Individual samples
BRCA1 185delAG
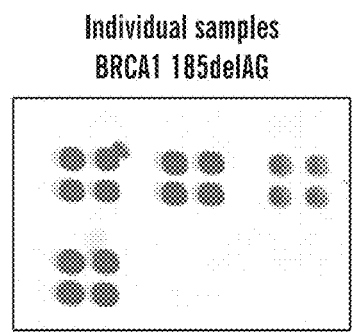
*FIG. 23C*
Pooled samples
BRCA1 185delAG
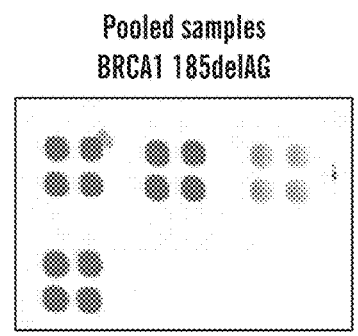
*FIG. 23D*
Individual samples
BRCA1 5382insC
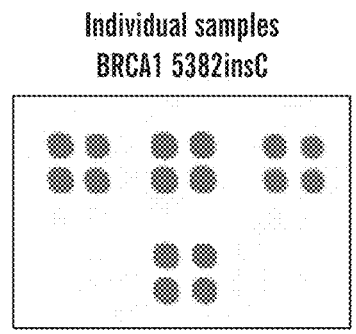
*FIG. 23E*
Pooled samples
BRCA1 5382insC
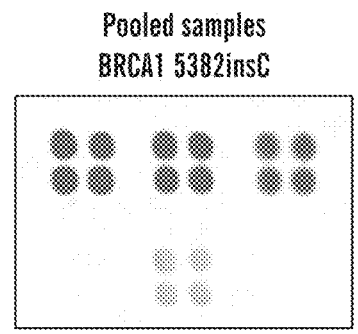
*FIG. 23F*
Individual samples
BRCA2 6174delT
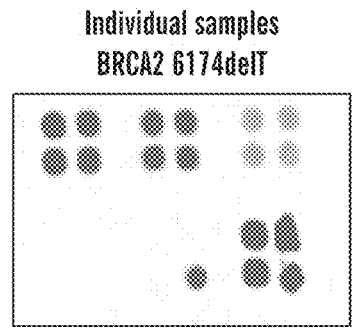
*FIG. 23G*
Pooled samples
BRCA2 6174delT
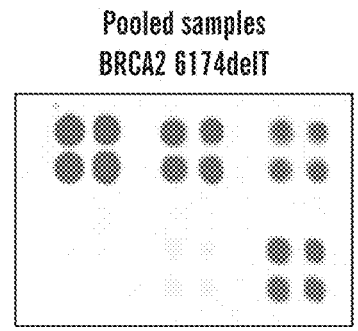
*FIG. 23H*

WT

ZIP 1
ZIP 2
ZIP 3
ZIP 4

Y220 A-G
ZIP 31

R175 G2-A
ZIP 21

R282 C-T
ZIP 50

R196 C-T
ZIP 26

R273 G-A
ZIP 47

R273 C-T
ZIP 46

Cy3
CHANNEL
BACKGROUND

FIG. 25A

| SEQ ID NO: | 4,633 ID# | HEX ID# | Tm | ZIPCODE (5'-3') | TETRAMER NUMBERS | | | | |
|---|---|---|---|---|---|---|---|---|---|
| 1 | 3 | 8 | 77.6 | TTGAAATCCAGCGCAAAATCTGCG | 1 | 4 | 31 | 21 | 4 | 29 |
| 2 | 5 | 15 | 77.2 | TTGAAAAGCCTACACGACGGCGAA | 1 | 6 | 26 | 30 | 35 | 16 |
| 3 | 7 | 22 | 76.5 | TTGATCTGCCATACGGGCTTACGG | 1 | 8 | 15 | 35 | 17 | 35 |
| 4 | 15 | 45 | 80.6 | TTGACTTGTCCCCAGCACGGCCAT | 1 | 11 | 28 | 31 | 35 | 15 |
| 5 | 17 | 56 | 80.4 | TTGACGTTGACCAGCCCGTTGCAA | 1 | 12 | 32 | 36 | 12 | 21 |
| 6 | 20 | 72 | 76.4 | TTGACGAAGCTTTCCCCATGATG | 1 | 16 | 17 | 28 | 15 | 27 |
| 7 | 24 | 90 | 81.2 | TTGAGCAAGGACGACCGCAAACGG | 1 | 21 | 34 | 32 | 21 | 35 |
| 8 | 30 | 126 | 82.4 | TTGAGATGACGACGGTGCGGCAA | 1 | 27 | 35 | 35 | 29 | 21 |
| 9 | 33 | 140 | 76.3 | TTGATCCCATCGAAAGGGACGATG | 1 | 28 | 24 | 6 | 34 | 27 |
| 10 | 36 | 150 | 80.1 | TTGATGCGTCTGGGACGTGCCTTG | 1 | 29 | 8 | 34 | 33 | 11 |
| 11 | 44 | 166 | 80.3 | TTGACACGTCGTCAGCTCCCGTGC | 1 | 30 | 10 | 31 | 28 | 33 |
| 12 | 48 | 180 | 80 | TTGACAGCCTGTTGCGGTGCGTCT | 1 | 31 | 14 | 29 | 33 | 19 |
| 13 | 52 | 202 | 76.5 | TTGAGTGCGGTACTTGCAGCGATG | 1 | 33 | 18 | 11 | 31 | 27 |
| 14 | 55 | 222 | 81.2 | TTGAACGGTCTGCACGTCCCAGCC | 1 | 35 | 8 | 30 | 28 | 36 |
| 15 | 67 | 269 | 82.2 | TGATTCTGGTGCGTGCCAGCCAGC | 2 | 8 | 33 | 33 | 31 | 31 |
| 16 | 69 | 274 | 76.8 | TGATTGTCGCTTTCTGACGGAGCC | 2 | 9 | 17 | 8 | 35 | 36 |
| 17 | 73 | 294 | 77.9 | TGATCGTTTGCGGGTATCCCTCGT | 2 | 12 | 29 | 18 | 28 | 10 |
| 18 | 75 | 310 | 77.9 | TGATCGAAAGGACAGCAGCCTCCC | 2 | 16 | 25 | 31 | 36 | 28 |
| 19 | 79 | 328 | 76.9 | TGATGCAAGCAACGAACACGCTGT | 2 | 21 | 21 | 16 | 30 | 14 |
| 20 | 92 | 372 | 79.5 | TGATTGCGAGTGGACCATCGCCAT | 2 | 29 | 22 | 32 | 24 | 15 |
| 21 | 94 | 379 | 80 | TGATCACGCTTGCCATGGACGGAC | 2 | 30 | 11 | 15 | 34 | 34 |
| 22 | 104 | 418 | 82 | TGATGTGCCTCAACGGGTGCAGCC | 2 | 33 | 13 | 35 | 33 | 36 |
| 23 | 111 | 431 | 75.6 | TGATGGACCGTTAGCCGATGTTGA | 2 | 34 | 12 | 36 | 27 | 1 |
| 24 | 118 | 444 | 79.5 | TGATACGGAGGAGGACTGCGTGCG | 2 | 35 | 25 | 34 | 29 | 29 |
| 25 | 129 | 555 | 79.9 | TTAGGATGAGCCAGCCTGCGAGCC | 3 | 27 | 36 | 36 | 29 | 36 |
| 26 | 151 | 690 | 77.7 | AATCTCGTCGTTTCCCCTCATGCG | 4 | 10 | 12 | 28 | 13 | 29 |
| 27 | 166 | 805 | 77.4 | AATCGCAACTGTCGTTCACGGTGC | 4 | 21 | 14 | 12 | 30 | 33 |
| 28 | 167 | 842 | 81.4 | AATCAGGACACGCAGCGACCTGCG | 4 | 25 | 30 | 31 | 32 | 29 |
| 29 | 183 | 926 | 76.7 | AATCGACCCTGTGTCTGCTTTGCG | 4 | 32 | 14 | 19 | 17 | 29 |
| 30 | 197 | 983 | 76.9 | AATCAGCCAAAGCGAAGTGCGATG | 4 | 36 | 6 | 16 | 33 | 27 |
| 31 | 216 | 1111 | 76.2 | ATACGACCTCGTGAGTTCCCGCAA | 5 | 32 | 10 | 20 | 28 | 21 |
| 32 | 226 | 1207 | 75.4 | AAAGCTTGACCTATCGAGCCGTGC | 6 | 11 | 23 | 24 | 36 | 33 |
| 33 | 268 | 1503 | 75.5 | AAAGAGCCGCTTGAGTCGAAATCG | 6 | 36 | 17 | 20 | 16 | 24 |
| 34 | 297 | 1649 | 75.7 | TCTGCTTGCTCACCTACCATTGCG | 8 | 11 | 13 | 26 | 15 | 29 |
| 35 | 332 | 1771 | 75 | TCTGATCGCCTAGGTAACGGGGAC | 8 | 24 | 26 | 18 | 35 | 34 |
| 36 | 358 | 1847 | 76.9 | TCTGCAGCGGTACTGTGGACCCAT | 8 | 31 | 18 | 14 | 34 | 15 |
| 37 | 375 | 1912 | 75.8 | TCTGAGCCACCTAATCTCCCACGG | 8 | 36 | 23 | 4 | 28 | 35 |
| 38 | 385 | 1941 | 77.4 | TGTCTCGTTCCCACCTCCATTCCC | 9 | 10 | 28 | 23 | 15 | 28 |
| 39 | 442 | 2093 | 81.4 | TGTCATCGCAGCGAGTCAGCCACG | 9 | 24 | 31 | 20 | 31 | 30 |
| 40 | 445 | 2103 | 77.7 | TGTCCCTAACCTGATGGTGCGCAA | 9 | 26 | 23 | 27 | 33 | 21 |
| 41 | 461 | 2143 | 77.3 | TGTCTGCGGTCTCCATATCGGTGC | 9 | 29 | 19 | 15 | 24 | 33 |
| 42 | 469 | 2154 | 76.2 | TGTCCACGCGTTACCTTGTCGATG | 9 | 30 | 12 | 23 | 9 | 27 |
| 43 | 487 | 2196 | 79.1 | TGTCGTGCTCTGACCTTGCGCTCA | 9 | 33 | 8 | 23 | 29 | 13 |
| 44 | 508 | 2231 | 81.7 | TGTCACGGAATCGTGCTGCGGCTT | 9 | 35 | 4 | 33 | 29 | 17 |
| 45 | 527 | 2307 | 77.4 | TCGTTCTGGCTTGGACGCTTCTCA | 10 | 8 | 17 | 34 | 17 | 13 |
| 46 | 602 | 2543 | 80 | TCGTTGCGTGTCGGACCTTGGATG | 10 | 29 | 9 | 34 | 11 | 27 |
| 47 | 686 | 2755 | 78.3 | CTTGCGTTGATGCGAATCGTCGAA | 11 | 12 | 27 | 16 | 10 | 16 |
| 48 | 973 | 3831 | 77.7 | CTGTCACGCTCAACCTTCCCCGTT | 14 | 30 | 13 | 23 | 28 | 12 |
| 49 | 987 | 3866 | 77.6 | CTGTGTGCCGTTTCGTGTGCAGTG | 14 | 33 | 12 | 10 | 33 | 22 |
| 50 | 1053 | 4127 | 77 | CCATGCAATCCCAGGATGTCGGTA | 15 | 21 | 28 | 25 | 9 | 18 |
| 51 | 1093 | 4232 | 78.7 | CCATCAGCTCTGGCAATGCGGAGT | 15 | 31 | 8 | 21 | 29 | 20 |

FIG. 25B

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 52 | 1142 | 4394 | 75.4 | CGAATCTGGGTAAGGAAGCCATCG | 16 | 8 | 18 | 25 | 36 | 24 |
| 53 | 1145 | 20638 | 77.7 | CGAATGTCCTGTCCATCGAATGCG | 16 | 9 | 14 | 15 | 16 | 29 |
| 54 | 1159 | 4453 | 75.2 | CGAACGTTTACATGCGTCGTAGCC | 16 | 12 | 7 | 29 | 10 | 36 |
| 55 | 1193 | 4568 | 78.3 | CGAAAGTGAGCCGCAACTTGGGAC | 16 | 22 | 36 | 21 | 11 | 34 |
| 56 | 1246 | 4751 | 78.9 | CGAAGGACAGTGAGTGTGCGCACG | 16 | 34 | 22 | 22 | 29 | 30 |
| 57 | 1560 | 6171 | 75.4 | GCAAAGCCATACCTTGGCTTGCTT | 21 | 36 | 5 | 11 | 17 | 17 |
| 58 | 1641 | 6531 | 75.7 | ACCTCTTGCCTACGAACAGCCGAA | 23 | 11 | 26 | 16 | 31 | 16 |
| 59 | 1655 | 6599 | 78.8 | ACCTGCAAGTGCCCATGTGCCCTA | 23 | 21 | 33 | 15 | 33 | 26 |
| 60 | 1919 | 7289 | 80.1 | AGGATCTGGACCGGACTCCCCGAA | 25 | 8 | 32 | 34 | 28 | 16 |
| 61 | 1982 | 7538 | 78 | AGGAACGGCAGCTACACACGAGCC | 25 | 35 | 31 | 7 | 30 | 36 |
| 62 | 2081 | 8056 | 78.1 | GATGGACCACCTCAGCGCTTGACC | 27 | 32 | 23 | 31 | 17 | 32 |
| 63 | 2105 | 8145 | 77.8 | TCCCTTAGGACCCAGCGTCTGTGC | 28 | 3 | 32 | 31 | 19 | 33 |
| 64 | 2623 | 8944 | 75.5 | TGCGCCATAAAGGACCTTAGCCAT | 29 | 15 | 6 | 32 | 3 | 15 |
| 65 | 2755 | 9114 | 75.8 | TGCGAGGACCATGGTAGGTAAGCC | 29 | 25 | 15 | 18 | 18 | 36 |
| 66 | 12 | 42 | 81.5 | TTGATCGTGGACACGGCACGCTCA | 1 | 10 | 34 | 35 | 30 | 13 |
| 67 | 26 | 94 | 78.2 | TTGAAGTGCAGCCACGAAAGCGAA | 1 | 22 | 31 | 30 | 6 | 16 |
| 68 | 29 | 112 | 79.3 | TTGAATCGGAGTTGCGCGTTGGAC | 1 | 24 | 20 | 29 | 12 | 34 |
| 69 | 82 | 346 | 80.9 | TGATGATGGCTTCAGCTGCGCGAA | 2 | 27 | 17 | 31 | 29 | 16 |
| 70 | 86 | 351 | 79.2 | TGATTCCCTTGAACGGTCCCGGAC | 2 | 28 | 1 | 35 | 28 | 34 |
| 71 | 124 | 521 | 78.3 | TTAGGCAATTGATCCCGACCGTGC | 3 | 21 | 1 | 28 | 32 | 33 |
| 72 | 132 | 567 | 78.2 | TTAGTCCCACGGGATGCGTTGACC | 3 | 28 | 35 | 27 | 12 | 32 |
| 73 | 191 | 962 | 77.5 | AATCGGACATCGAGTGTCCCCAGC | 4 | 34 | 24 | 22 | 28 | 31 |
| 74 | 210 | 1078 | 75.8 | ATACTGCGCGTTCTGTGAGTTGCG | 5 | 29 | 12 | 14 | 20 | 29 |
| 75 | 325 | 1744 | 78.5 | TCTGGTCTGCAATCGTCACGCAGC | 8 | 19 | 21 | 10 | 30 | 31 |
| 76 | 436 | 2073 | 79.4 | TGTCAGTGCACGGCTTCTGTTGCG | 9 | 22 | 30 | 17 | 14 | 29 |
| 77 | 551 | 2365 | 77.2 | TCGTCTCAGCTTGACCGCTTCAGC | 10 | 13 | 17 | 32 | 17 | 31 |
| 78 | 629 | 2593 | 76.7 | TCGTCAGCCCTAATCGACCTGTGC | 10 | 31 | 26 | 24 | 23 | 33 |
| 79 | 644 | 2624 | 75.5 | TCGTGTGCGCTTAATCACGGAATC | 10 | 33 | 17 | 4 | 35 | 4 |
| 80 | 804 | 3213 | 76.4 | CGTTCGAAGTCTCTTGACGGACGG | 12 | 16 | 19 | 11 | 35 | 35 |
| 81 | 836 | 3345 | 75.7 | CGTTTCCCAATCATCGGCAAGTCT | 12 | 28 | 4 | 24 | 21 | 19 |
| 82 | 872 | 3431 | 77.5 | CGTTGTGCTGATGCAAATCGGCTT | 12 | 33 | 2 | 21 | 24 | 17 |
| 83 | 949 | 3748 | 79.9 | CTGTCTTGGTGCGCAAAGGATGCG | 14 | 11 | 33 | 21 | 25 | 29 |
| 84 | 1148 | 4415 | 77.1 | CGAATCGTTTGAGCAAGACCCACG | 16 | 10 | 1 | 21 | 32 | 30 |
| 85 | 1235 | 4695 | 76.7 | CGAACAGCTGCGAATCGTCTAGCC | 16 | 31 | 29 | 4 | 19 | 36 |
| 86 | 1406 | 5575 | 75.8 | GAGTTCGTGCTTACGGCTTGAGCC | 20 | 10 | 17 | 35 | 11 | 36 |
| 87 | 1603 | 6332 | 75.6 | AGTGTCCCGAGTACCTGGACACGG | 22 | 28 | 20 | 23 | 34 | 35 |
| 88 | 2216 | 8362 | 76.3 | TCCCGCTTTGATTCTGTCGTTCGT | 28 | 17 | 2 | 8 | 10 | 10 |
| 89 | 2286 | 8468 | 75 | TCCCACCTGTCTACCTAGCCGACC | 28 | 23 | 19 | 23 | 36 | 32 |
| 90 | 2364 | 8591 | 77.1 | TCCCCACGATACACCTTTGATGCG | 28 | 30 | 5 | 23 | 1 | 29 |
| 91 | 2556 | 30603 | 76.3 | TGCGCTTGATACTGTCGCTTCGAA | 29 | 11 | 5 | 9 | 17 | 16 |
| 92 | 2587 | 8909 | 75.8 | TGCGCTCAATACAGCCTCGTATCG | 29 | 13 | 5 | 36 | 10 | 24 |
| 93 | 2741 | 9095 | 79.8 | TGCGATCGCGAAGCAATGATCGTT | 29 | 24 | 16 | 21 | 2 | 12 |
| 94 | 2793 | 9168 | 77.9 | TGCGTCCCTCTGTGATCACGAGGA | 29 | 28 | 8 | 2 | 30 | 25 |
| 95 | 2821 | 9200 | 80.5 | TGCGCACGAGGAATCGCTTGAGTG | 29 | 30 | 25 | 24 | 11 | 22 |
| 96 | 3120 | 9759 | 76.9 | CACGGTGCTACAGTGCAAAGCACG | 30 | 33 | 7 | 33 | 6 | 30 |
| 97 | 6 | 18 | 79.1 | TTGAAAAGGGACGTGCGCTTCGAA | 1 | 6 | 34 | 33 | 17 | 16 |
| 98 | 8 | 25 | 79.5 | TTGATCTGCACGCGTTGTGCGGTA | 1 | 8 | 30 | 12 | 33 | 18 |
| 99 | 9 | 29 | 80.3 | TTGATGTCCCATTCCCACGCGTT | 1 | 9 | 15 | 28 | 30 | 12 |
| 100 | 13 | 43 | 79.2 | TTGATCGTAGCCGGTATGCGACGG | 1 | 10 | 36 | 18 | 29 | 35 |
| 101 | 18 | 64 | 79.7 | TTGACCATGCTTCGAAACGGCGAA | 1 | 15 | 17 | 16 | 35 | 16 |
| 102 | 21 | 75 | 77.4 | TTGACGAAATCGGCAACCTATGCG | 1 | 16 | 24 | 21 | 26 | 29 |

FIG. 25C

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 103 | 32 | 12925 | 75.7 | TTGATCCCGGTATTAGAGCCCACG | 1 | 28 | 18 | 3 | 36 | 30 |
| 104 | 42 | 161 | 80.7 | TTGATGCGTGCGCTCAATCGAGGA | 1 | 29 | 29 | 13 | 24 | 25 |
| 105 | 43 | 165 | 80.1 | TTGATGCGAGCCGATGCCATCTTG | 1 | 29 | 36 | 27 | 15 | 11 |
| 106 | 49 | 186 | 79.1 | TTGACAGCACGGGACCCCTACACG | 1 | 31 | 35 | 32 | 26 | 30 |
| 107 | 53 | 208 | 80.3 | TTGAGTGCTCCCGCAACGTTGTGC | 1 | 33 | 28 | 21 | 12 | 33 |
| 108 | 58 | 230 | 76.8 | TTGAACGGGCAAACCTCTTGCTTG | 1 | 35 | 21 | 23 | 11 | 11 |
| 109 | 59 | 232 | 78.7 | TTGAACGGGATGGCAAGGACCTCA | 1 | 35 | 27 | 21 | 34 | 13 |
| 110 | 60 | 238 | 81.2 | TTGAAGCCTGTCCGTTTGCGACGG | 1 | 36 | 9 | 12 | 29 | 35 |
| 111 | 62 | 12961 | 75.5 | TTGAAGCCAGGATCCCAAAGCCTA | 1 | 36 | 25 | 28 | 6 | 26 |
| 112 | 68 | 270 | 78.4 | TGATTCTGACGGTCCCGCTTACGG | 2 | 8 | 35 | 28 | 17 | 35 |
| 113 | 70 | 275 | 82.6 | TGATTGTCCACGTGCGGGACACGG | 2 | 9 | 30 | 29 | 34 | 35 |
| 114 | 76 | 311 | 82.5 | TGATCGAAGTGCCACGCACGCGTT | 2 | 16 | 33 | 30 | 30 | 12 |
| 115 | 78 | 322 | 78.2 | TGATGGTAACGGCTCAAGCCGCTT | 2 | 18 | 35 | 13 | 36 | 17 |
| 116 | 81 | 335 | 80.5 | TGATGCAAAGCCGTGCAGCCTCTG | 2 | 21 | 36 | 33 | 36 | 8 |
| 117 | 84 | 349 | 80.6 | TGATGATGGTGCGCTTAGCCGCAA | 2 | 27 | 33 | 17 | 36 | 21 |
| 118 | 88 | 361 | 77.3 | TGATTCCCTCCCGGTATCGTACGG | 2 | 28 | 28 | 18 | 10 | 35 |
| 119 | 89 | 362 | 80.2 | TGATTCCCCACGGAGTGGACCAGC | 2 | 28 | 30 | 20 | 34 | 31 |
| 120 | 95 | 386 | 80.8 | TGATCACGATCGGGACGCAACACG | 2 | 30 | 24 | 34 | 21 | 30 |
| 121 | 96 | 388 | 77.8 | TGATCACGTCCCTTGAGACCGCAA | 2 | 30 | 28 | 1 | 32 | 21 |
| 122 | 98 | 404 | 80.2 | TGATCAGCCACGGGACAGCCAGTG | 2 | 31 | 30 | 34 | 36 | 22 |
| 123 | 99 | 405 | 76.7 | TGATCAGCGGACTTAGTCCCGTGC | 2 | 31 | 34 | 3 | 28 | 33 |
| 124 | 100 | 409 | 76.4 | TGATGACCCGAATGATTGTCGCAA | 2 | 32 | 16 | 2 | 9 | 21 |
| 125 | 101 | 411 | 79.7 | TGATGACCATCGAGCCCACGAGGA | 2 | 32 | 24 | 36 | 30 | 25 |
| 126 | 105 | 420 | 77.3 | TGATGTGCCGAAGAGTCACGGGAC | 2 | 33 | 16 | 20 | 30 | 34 |
| 127 | 106 | 421 | 80.4 | TGATGTGCGTCTACGGAGCCTGCG | 2 | 33 | 19 | 35 | 36 | 29 |
| 128 | 107 | 422 | 79.7 | TGATGTGCGAGTACGGACGGCGTT | 2 | 33 | 20 | 35 | 35 | 12 |
| 129 | 109 | 426 | 76.6 | TGATGTGCTGCGAAAGAGGATCCC | 2 | 33 | 29 | 6 | 25 | 28 |
| 130 | 112 | 435 | 78.3 | TGATGGACGACCCGAAGGACCTTG | 2 | 34 | 32 | 16 | 34 | 11 |
| 131 | 114 | 437 | 80.1 | TGATGGACAGCCGCTTGACCGATG | 2 | 34 | 36 | 17 | 32 | 27 |
| 132 | 125 | 532 | 76.8 | TTAGGCAATGCGCTGTCCTAACGG | 3 | 21 | 29 | 14 | 26 | 35 |
| 133 | 126 | 539 | 75.3 | TTAGATCGCACGTCTGCTTGCCAT | 3 | 24 | 30 | 8 | 11 | 15 |
| 134 | 135 | 599 | 75.7 | TTAGCAGCGCAATACAGGACCACG | 3 | 31 | 21 | 7 | 34 | 30 |
| 135 | 140 | 627 | 76.2 | TTAGGGACCTGTGTGCCTTGCGTT | 3 | 34 | 14 | 33 | 11 | 12 |
| 136 | 145 | 636 | 77.2 | TTAGGGACGGACAATCGATGCACG | 3 | 34 | 34 | 4 | 27 | 30 |
| 137 | 150 | 683 | 76.5 | AATCTCTGCGTTCCTATGCGCGAA | 4 | 8 | 12 | 26 | 29 | 16 |
| 138 | 153 | 714 | 76 | AATCCGTTTCCCATACGATGCGAA | 4 | 12 | 28 | 5 | 27 | 16 |
| 139 | 157 | 743 | 77.7 | AATCCGAATCTGTCCCTCCCGGAC | 4 | 16 | 8 | 28 | 28 | 34 |
| 140 | 159 | 748 | 76.5 | AATCCGAAGCAAACGGTGTCGATG | 4 | 16 | 21 | 35 | 9 | 27 |
| 141 | 161 | 756 | 78.2 | AATCCGAACACGGACCGGACAGTG | 4 | 16 | 30 | 32 | 34 | 22 |
| 142 | 162 | 762 | 76 | AATCGCTTTTAGGATGCAGCACGG | 4 | 17 | 3 | 27 | 31 | 35 |
| 143 | 163 | 768 | 75.4 | AATCGCTTCCATCGAAGACCGGTA | 4 | 17 | 15 | 16 | 32 | 18 |
| 144 | 165 | 793 | 79.6 | AATCGAGTCGAATGCGTCCCAGCC | 4 | 20 | 16 | 29 | 28 | 36 |
| 145 | 168 | 843 | 76.7 | AATCAGGAACGGCGTTCTTGGCTT | 4 | 25 | 35 | 12 | 11 | 17 |
| 146 | 171 | 877 | 76.6 | AATCTGCGTCGTTCTGTCCCGATG | 4 | 29 | 10 | 8 | 28 | 27 |
| 147 | 179 | 919 | 77.2 | AATCCAGCGATGGGACGAGTCGTT | 4 | 31 | 27 | 34 | 20 | 12 |
| 148 | 189 | 949 | 76.8 | AATCGTGCAGGACTCAGGACTGCG | 4 | 33 | 25 | 13 | 34 | 29 |
| 149 | 192 | 966 | 78.9 | AATCGGACTGCGCCATACCTGCAA | 4 | 34 | 29 | 15 | 23 | 21 |
| 150 | 201 | 993 | 78 | AATCAGCCATCGCTGTGCTTGCAA | 4 | 36 | 24 | 14 | 17 | 21 |
| 151 | 203 | 999 | 79.5 | AATCAGCCGTGCGGTAGACCGGAC | 4 | 36 | 33 | 18 | 32 | 34 |
| 152 | 205 | 1040 | 79 | ATACGCTTGGACGAGTTGCGGCAA | 5 | 17 | 34 | 20 | 29 | 21 |
| 153 | 206 | 1047 | 79.6 | ATACGCAAGACCATCGCACGGCAA | 5 | 21 | 32 | 24 | 30 | 21 |

FIG. 25D

| SEQ ID NO: | 4,633 ID# | HEX ID# | Tm | ZIPCODE (5'-3') | TETRAMER NUMBERS | | | | |
|---|---|---|---|---|---|---|---|---|---|
| 154 | 214 | 1104 | 77.1 | ATACCAGCCTCAAGCCCGAAGTGC | 5 | 31 | 13 | 36 | 16 | 33 |
| 155 | 218 | 1122 | 80.3 | ATACGTGCTCGTGCTTTGCGTGCG | 5 | 33 | 10 | 17 | 29 | 29 |
| 156 | 228 | 1217 | 76.3 | AAAGCGTTTGTCCTTGGATGCGAA | 6 | 12 | 9 | 11 | 27 | 16 |
| 157 | 231 | 1229 | 77.1 | AAAGCTCATCGTGGACCGAAAGCC | 6 | 13 | 10 | 34 | 16 | 36 |
| 158 | 234 | 1271 | 75.1 | AAAGCGAACTGTAGTGCAGCACGG | 6 | 16 | 14 | 22 | 31 | 35 |
| 159 | 242 | 1333 | 76.6 | AAAGATCGCTTGCTGTACGGCGAA | 6 | 24 | 11 | 14 | 35 | 16 |
| 160 | 243 | 1337 | 76.5 | AAAGATCGGGTATGCGCACGTGTC | 6 | 24 | 18 | 29 | 30 | 9 |
| 161 | 248 | 1393 | 76 | AAAGTGCGATCGAGGACTCAACGG | 6 | 29 | 24 | 25 | 13 | 35 |
| 162 | 255 | 1441 | 75.6 | AAAGGACCGCAACTGTTCGTGCTT | 6 | 32 | 21 | 14 | 10 | 17 |
| 163 | 264 | 1474 | 76.7 | AAAGGGACCGAAAGTGCCATGGAC | 6 | 34 | 16 | 22 | 15 | 34 |
| 164 | 271 | 1519 | 80.5 | TACACCATTCCCTCCCCAGCGCAA | 7 | 15 | 28 | 28 | 31 | 21 |
| 165 | 272 | 1533 | 81.8 | TACATCCCCTTGCGAATGCGTGCG | 7 | 28 | 11 | 16 | 29 | 29 |
| 166 | 281 | 1587 | 76.8 | TACAACGGCTGTTCGTTGTCGCAA | 7 | 35 | 14 | 10 | 9 | 21 |
| 167 | 282 | 1590 | 76.1 | TACAACGGGCTTTGTCCACGGAGT | 7 | 35 | 17 | 9 | 30 | 20 |
| 168 | 286 | 1602 | 78.6 | TACAACGGACGGCCATCCATGCTT | 7 | 35 | 35 | 15 | 15 | 17 |
| 169 | 289 | 1620 | 78.5 | TCTGTTGAAGCCCGTTCGAAACGG | 8 | 1 | 36 | 12 | 16 | 35 |
| 170 | 290 | 1621 | 78.2 | TCTGTGATTGCGCTTGGGACGATG | 8 | 2 | 29 | 11 | 34 | 27 |
| 171 | 291 | 1624 | 78.6 | TCTGAATCTGCGCGAATGTCTGCG | 8 | 4 | 29 | 16 | 9 | 29 |
| 172 | 292 | 1625 | 76.4 | TCTGAATCCACGTTAGTGCGCACG | 8 | 4 | 30 | 3 | 29 | 30 |
| 173 | 298 | 1650 | 76.5 | TCTGCTTGCTGTGCTTTCCCCCTA | 8 | 11 | 14 | 17 | 28 | 26 |
| 174 | 299 | 1651 | 75.1 | TCTGCTTGGCTTAGTGGCTTCACG | 8 | 11 | 17 | 22 | 17 | 30 |
| 175 | 300 | 1653 | 80.1 | TCTGCTTGGATGCCATACGGTGCG | 8 | 11 | 27 | 15 | 35 | 29 |
| 176 | 301 | 1656 | 79.8 | TCTGCTTGGACCCTGTCACGGCAA | 8 | 11 | 32 | 14 | 30 | 21 |
| 177 | 304 | 1670 | 78.8 | TCTGCGTTATCGCACGGAGTGCAA | 8 | 12 | 24 | 30 | 20 | 21 |
| 178 | 306 | 1678 | 79.5 | TCTGCGTTAGCCGGACCTGTCACG | 8 | 12 | 36 | 34 | 14 | 30 |
| 179 | 313 | 1698 | 80.3 | TCTGCCATGACCGACCTCCCCTTG | 8 | 15 | 32 | 32 | 28 | 11 |
| 180 | 317 | 1722 | 80.4 | TCTGGCTTTGTCCAGCGCAATCCC | 8 | 17 | 9 | 31 | 21 | 28 |
| 181 | 321 | 1733 | 80 | TCTGGCTTGTGCGTCTGTGCCGTT | 8 | 17 | 33 | 19 | 33 | 12 |
| 182 | 322 | 1735 | 76.9 | TCTGGGTACGTTCGAATCCCCCAT | 8 | 18 | 12 | 16 | 28 | 15 |
| 183 | 324 | 1740 | 76.5 | TCTGGGTAGTGCATCGCGAAGCTT | 8 | 18 | 33 | 24 | 16 | 17 |
| 184 | 331 | 1765 | 79.3 | TCTGACCTACGGGTGCCGTTGTGC | 8 | 23 | 35 | 33 | 12 | 33 |
| 185 | 333 | 1772 | 79.4 | TCTGATCGTGCGGTCTACGGGTGC | 8 | 24 | 29 | 19 | 35 | 33 |
| 186 | 335 | 1776 | 80.3 | TCTGATCGGGACCAGCATCGGACC | 8 | 24 | 34 | 31 | 24 | 32 |
| 187 | 340 | 1800 | 79.3 | TCTGTCCCCTGTGACCAGCCGATG | 8 | 28 | 14 | 32 | 36 | 27 |
| 188 | 346 | 1811 | 79.1 | TCTGTGCGAAAGGGACCAGCAGGA | 8 | 29 | 6 | 34 | 31 | 25 |
| 189 | 353 | 1833 | 77.3 | TCTGCACGACCTTTGATCCCGATG | 8 | 30 | 23 | 1 | 28 | 27 |
| 190 | 363 | 1865 | 82.1 | TCTGGTGCAATCGACCCACGCAGC | 8 | 33 | 4 | 32 | 30 | 31 |
| 191 | 376 | 1917 | 77.7 | TCTGAGCCGACCTCGTGATGCTTG | 8 | 36 | 32 | 10 | 27 | 11 |
| 192 | 387 | 1945 | 79.7 | TGTCTCGTGTGCTCGTGACCGCAA | 9 | 10 | 33 | 10 | 32 | 21 |
| 193 | 392 | 1960 | 77.2 | TGTCCGTTTTGAGGACGACCATCG | 9 | 12 | 1 | 34 | 32 | 24 |
| 194 | 393 | 1961 | 78.6 | TGTCCGTTTGATTCCCCTTGGCAA | 9 | 12 | 2 | 28 | 11 | 21 |
| 195 | 395 | 1974 | 79.8 | TGTCCGTTGTGCCGTTCAGCCTGT | 9 | 12 | 33 | 12 | 31 | 14 |
| 196 | 399 | 1983 | 77.6 | TGTCCCATTTGAAAAGCAGCTGCG | 9 | 15 | 1 | 6 | 31 | 29 |
| 197 | 418 | 2028 | 75.5 | TGTCGCTTACGGATACAGCCGATG | 9 | 17 | 35 | 5 | 36 | 27 |
| 198 | 422 | 2035 | 79 | TGTCGGTAGGACATCGGGACCACG | 9 | 18 | 34 | 24 | 34 | 30 |
| 199 | 425 | 2049 | 81.3 | TGTCGAGTGCTTGTGCGTGCGACC | 9 | 20 | 17 | 33 | 33 | 32 |
| 200 | 430 | 2057 | 79.5 | TGTCGCAACTTGCTTGGTGCTCCC | 9 | 21 | 11 | 11 | 33 | 28 |
| 201 | 431 | 2058 | 77.8 | TGTCGCAACCATCACGGTCTGCTT | 9 | 21 | 15 | 30 | 19 | 17 |
| 202 | 432 | 2061 | 76.6 | TGTCGCAAGGTAAATCTGCGTCCC | 9 | 21 | 18 | 4 | 29 | 28 |
| 203 | 443 | 2094 | 78.4 | TGTCATCGGACCAATCATCGCGAA | 9 | 24 | 32 | 4 | 24 | 16 |
| 204 | 444 | 2097 | 79.5 | TGTCAGGACGAATCCCATCGGCAA | 9 | 25 | 16 | 28 | 24 | 21 |

FIG. 25E

| SEQ ID NO: | 4,633 ID# | HEX ID# | Tm | ZIPCODE (5'-3') | TETRAMER NUMBERS | | | | |
|---|---|---|---|---|---|---|---|---|---|
| 205 | 448 | 2109 | 76.6 | TGTCGATGCTTGTACATCCCGCAA | 9 | 27 | 11 | 7 | 28 | 21 |
| 206 | 449 | 2114 | 81.9 | TGTCGATGGATGGACCTGCGACGG | 9 | 27 | 27 | 32 | 29 | 35 |
| 207 | 450 | 2115 | 78.3 | TGTCGATGTCCCTCGTGCTTGTGC | 9 | 27 | 28 | 10 | 17 | 33 |
| 208 | 451 | 2116 | 79.2 | TGTCGATGTGCGCCTACAGCATCG | 9 | 27 | 29 | 26 | 31 | 24 |
| 209 | 452 | 2117 | 76.1 | TGTCGATGCACGACCTTTAGCGAA | 9 | 27 | 30 | 23 | 3 | 16 |
| 210 | 464 | 2147 | 75.8 | TGTCTGCGCCTATGATCTTGCAGC | 9 | 29 | 26 | 2 | 11 | 31 |
| 211 | 472 | 2158 | 75.9 | TGTCCACGGCAAAAAGCCTAGACC | 9 | 30 | 21 | 6 | 26 | 32 |
| 212 | 473 | 2163 | 78.8 | TGTCCACGCAGCAATCAGCCTTGA | 9 | 30 | 31 | 4 | 36 | 1 |
| 213 | 476 | 2174 | 79.6 | TGTCCAGCATCGCCATGATGGCTT | 9 | 31 | 24 | 15 | 27 | 17 |
| 214 | 477 | 2176 | 79.2 | TGTCCAGCCAGCCTTGCGAACTGT | 9 | 31 | 31 | 11 | 16 | 14 |
| 215 | 480 | 2181 | 80.9 | TGTCGACCAAAGAGCCAGCCCGAA | 9 | 32 | 6 | 36 | 36 | 16 |
| 216 | 481 | 2185 | 76.4 | TGTCGACCGGTAAGCCGACCATAC | 9 | 32 | 18 | 36 | 32 | 5 |
| 217 | 482 | 2186 | 81.6 | TGTCGACCAGTGCAGCGATGGCAA | 9 | 32 | 22 | 31 | 27 | 21 |
| 218 | 484 | 2189 | 80.6 | TGTCGACCTCCCGACCTCGTCAGC | 9 | 32 | 28 | 32 | 10 | 31 |
| 219 | 485 | 2191 | 79 | TGTCGACCGTGCTGTCAATCCACG | 9 | 32 | 33 | 9 | 4 | 30 |
| 220 | 488 | 2197 | 78.1 | TGTCGTGCTGTCTCGTAGCCCGAA | 9 | 33 | 9 | 10 | 36 | 16 |
| 221 | 495 | 2208 | 77.1 | TGTCGTGCCCTATCTGTGCGGTCT | 9 | 33 | 26 | 8 | 29 | 19 |
| 222 | 497 | 2212 | 79.2 | TGTCGTGCCAGCCCATAGGAATCG | 9 | 33 | 31 | 15 | 25 | 24 |
| 223 | 498 | 2215 | 80.1 | TGTCGGACAAAGTGCGACGGATCG | 9 | 34 | 6 | 29 | 35 | 24 |
| 224 | 499 | 2217 | 77.4 | TGTCGGACCTCAATACGTGCCAGC | 9 | 34 | 13 | 5 | 33 | 31 |
| 225 | 501 | 2219 | 78.4 | TGTCGGACCCATGACCCTCACCAT | 9 | 34 | 15 | 32 | 13 | 15 |
| 226 | 510 | 2234 | 75.9 | TGTCACGGCGTTAAAGTGTCCGAA | 9 | 35 | 12 | 6 | 9 | 16 |
| 227 | 515 | 2247 | 77.9 | TGTCAGCCCTTGCAGCAAAGCTTG | 9 | 36 | 11 | 31 | 6 | 11 |
| 228 | 525 | 2301 | 76.3 | TCGTAAAGACGGTGTCGCAACACG | 10 | 6 | 35 | 9 | 21 | 30 |
| 229 | 537 | 2336 | 77.2 | TCGTCTTGCTTGCGTTATCGCCAT | 10 | 11 | 11 | 12 | 24 | 15 |
| 230 | 545 | 2353 | 76.4 | TCGTCGTTGCAACTCAGGTATGCG | 10 | 12 | 21 | 13 | 18 | 29 |
| 231 | 547 | 2355 | 76.3 | TCGTCGTTAGGAACCTACGGCGAA | 10 | 12 | 25 | 23 | 35 | 16 |
| 232 | 548 | 2359 | 77.1 | TCGTCGTTCACGTACATCGTTGCG | 10 | 12 | 30 | 7 | 10 | 29 |
| 233 | 554 | 2371 | 81 | TCGTCTGTTCGTGACCACGGTGCG | 10 | 14 | 10 | 32 | 35 | 29 |
| 234 | 557 | 2382 | 79.3 | TCGTCCATATCGCAGCCCATCAGC | 10 | 15 | 24 | 31 | 15 | 31 |
| 235 | 560 | 2390 | 78.4 | TCGTCCATGGACCGAAGCAAGACC | 10 | 15 | 34 | 16 | 21 | 32 |
| 236 | 581 | 2470 | 82 | TCGTACCTGTGCCAGCCACGGTGC | 10 | 23 | 33 | 31 | 30 | 33 |
| 237 | 582 | 2475 | 75.7 | TCGTATCGCTGTACCTCGTTTGCG | 10 | 24 | 14 | 23 | 12 | 29 |
| 238 | 588 | 2502 | 75.9 | TCGTCCTAACGGATCGTTGAAGCC | 10 | 26 | 35 | 24 | 1 | 36 |
| 239 | 589 | 2509 | 81.8 | TCGTGATGATCGGTGCACGGTCCC | 10 | 27 | 24 | 33 | 35 | 28 |
| 240 | 591 | 2523 | 77.1 | TCGTTCCCCTCAAGTGGACCACCT | 10 | 28 | 13 | 22 | 32 | 23 |
| 241 | 596 | 2531 | 79.5 | TCGTTCCCAGTGGATGGGACCCAT | 10 | 28 | 22 | 27 | 34 | 15 |
| 242 | 597 | 2534 | 77.9 | TCGTTCCCGATGAGGAACGGTGAT | 10 | 28 | 27 | 25 | 35 | 2 |
| 243 | 599 | 2536 | 80.5 | TCGTTCCCCAGCCGTTGTCTCAGC | 10 | 28 | 31 | 12 | 19 | 31 |
| 244 | 606 | 2549 | 80.7 | TCGTTGCGGCAATGATCCATCACG | 10 | 29 | 21 | 2 | 15 | 30 |
| 245 | 609 | 2555 | 81.8 | TCGTTGCGTCCCCTCAGTGCCTCA | 10 | 29 | 28 | 13 | 33 | 13 |
| 246 | 610 | 2557 | 80.5 | TCGTTGCGCACGTGATCGTTCCAT | 10 | 29 | 30 | 2 | 12 | 15 |
| 247 | 613 | 2560 | 80.9 | TCGTTGCGGTGCTGATGGACATCG | 10 | 29 | 33 | 2 | 34 | 24 |
| 248 | 638 | 2611 | 81.5 | TCGTGACCGACCGATGTCCCAGGA | 10 | 32 | 32 | 27 | 28 | 25 |
| 249 | 649 | 2631 | 80.4 | TCGTGTGCGATGGAGTGTGCCCAT | 10 | 33 | 27 | 20 | 33 | 15 |
| 250 | 650 | 2633 | 78.1 | TCGTGTGCGACCTGATATCGGTGC | 10 | 33 | 32 | 2 | 24 | 33 |
| 251 | 657 | 2649 | 77.5 | TCGTGGACAGGAGATGGCTTGTGC | 10 | 34 | 25 | 27 | 17 | 33 |
| 252 | 663 | 2659 | 81 | TCGTACGGTGATCACGCAGCACGG | 10 | 35 | 2 | 30 | 31 | 35 |
| 253 | 667 | 2674 | 76.2 | TCGTACGGGACAAAGCGTTGTCT | 10 | 35 | 34 | 6 | 12 | 19 |
| 254 | 678 | 2722 | 81.6 | CTTGTGTCGTGCACGGCTGTTGCG | 11 | 9 | 33 | 35 | 14 | 29 |
| 255 | 679 | 2725 | 75.8 | CTTGTCGTCCATAGCCTCCCGGTA | 11 | 10 | 15 | 36 | 28 | 18 |

FIG. 25F

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 256 | 692 | 2779 | 79 | CTTGCCATGTCTTGCGGCTTACGG | 11 | 15 | 19 | 29 | 17 | 35 |
| 257 | 695 | 2808 | 76.3 | CTTGGCTTTCGTCCATCTTGGTGC | 11 | 17 | 10 | 15 | 11 | 33 |
| 258 | 711 | 2878 | 79.6 | CTTGAGGAGCTTTGCGCCATGCAA | 11 | 25 | 17 | 29 | 15 | 21 |
| 259 | 721 | 2907 | 77.2 | CTTGTCCCAAAGGCTTGCAATCCC | 11 | 28 | 6 | 17 | 21 | 28 |
| 260 | 726 | 2928 | 75.6 | CTTGTGCGCTTGAAAGCGAATCTG | 11 | 29 | 11 | 6 | 16 | 8 |
| 261 | 727 | 2931 | 77.5 | CTTGTGCGGAGTTGTCAGCCGGTA | 11 | 29 | 20 | 9 | 36 | 18 |
| 262 | 731 | 2945 | 80.3 | CTTGCACGTGTCTCCCAGCCCAT | 11 | 30 | 9 | 28 | 36 | 15 |
| 263 | 733 | 2948 | 75.6 | CTTGCACGCTGTCGAATTAGCAGC | 11 | 30 | 14 | 16 | 3 | 31 |
| 264 | 749 | 3014 | 78.3 | CTTGGGACACCTCTGTGTGCGCAA | 11 | 34 | 23 | 14 | 33 | 21 |
| 265 | 753 | 3027 | 79.5 | CTTGACGGAGTGACGGCGAACGAA | 11 | 35 | 22 | 35 | 16 | 16 |
| 266 | 759 | 3038 | 78.5 | CTTGAGCCAATCTGCGGCAACCAT | 11 | 36 | 4 | 29 | 21 | 15 |
| 267 | 760 | 3045 | 75 | CTTGAGCCGTCTCCTAATCGAGCC | 11 | 36 | 19 | 26 | 24 | 36 |
| 268 | 762 | 3048 | 78.2 | CTTGAGCCAGTGAAAGTGCGCACG | 11 | 36 | 22 | 6 | 29 | 30 |
| 269 | 773 | 3108 | 80.7 | CGTTTCTGTCGTTCCCGTGCGGAC | 12 | 8 | 10 | 28 | 33 | 34 |
| 270 | 784 | 3142 | 78.7 | CGTTTCGTGTCTGGACCACGTCCC | 12 | 10 | 19 | 34 | 30 | 28 |
| 271 | 809 | 3232 | 79.6 | CGTTGCTTTGCGGATGTCGTACGG | 12 | 17 | 29 | 27 | 10 | 35 |
| 272 | 810 | 3238 | 75.4 | CGTTGGTAAAAGTCGTTCCCAGCC | 12 | 18 | 6 | 10 | 28 | 36 |
| 273 | 811 | 3245 | 80.4 | CGTTGGTACACGCCATCAGCCACG | 12 | 18 | 30 | 15 | 31 | 30 |
| 274 | 832 | 3321 | 78.9 | CGTTCCTACACGCTTGTGCGGACC | 12 | 26 | 30 | 11 | 29 | 32 |
| 275 | 837 | 3349 | 76.4 | CGTTTCCCCGTTGGTAAATCCCAT | 12 | 28 | 12 | 18 | 4 | 15 |
| 276 | 838 | 3351 | 77.5 | CGTTTCCCCCATTGTCGAGTCGTT | 12 | 28 | 15 | 9 | 20 | 12 |
| 277 | 843 | 3364 | 79.4 | CGTTTCCCGTGCTGCGAGTGTGAT | 12 | 28 | 33 | 29 | 22 | 2 |
| 278 | 844 | 3366 | 76.1 | CGTTTGCGTTAGAGTGCACGATCG | 12 | 29 | 3 | 22 | 30 | 24 |
| 279 | 857 | 3398 | 77.8 | CGTTCACGCACGTGTCAAAGTCCC | 12 | 30 | 30 | 9 | 6 | 28 |
| 280 | 867 | 3420 | 76.8 | CGTTGACCCTTGGCAATACAACGG | 12 | 32 | 11 | 21 | 7 | 35 |
| 281 | 878 | 3451 | 80.1 | CGTTGTGCACGGCTTGTGTCCGTT | 12 | 33 | 35 | 11 | 9 | 12 |
| 282 | 898 | 3516 | 76.1 | CTCAAAAGTGCGTCGTTGATTGCG | 13 | 6 | 29 | 10 | 2 | 29 |
| 283 | 899 | 3518 | 75.4 | CTCAAAAGGACCTCTGCAGCCGTT | 13 | 6 | 32 | 8 | 31 | 12 |
| 284 | 901 | 3530 | 78.5 | CTCATCGTGCAACGTTGACCACGG | 13 | 10 | 21 | 12 | 32 | 35 |
| 285 | 923 | 3620 | 77.7 | CTCATCCCGGACAGGAGTGCACCT | 13 | 28 | 34 | 25 | 33 | 23 |
| 286 | 961 | 3798 | 80 | CTGTGATGCAGCCGAAATCGCAGC | 14 | 27 | 31 | 16 | 24 | 31 |
| 287 | 965 | 3809 | 77.1 | CTGTTCCCTGCGTTGAGGTATGCG | 14 | 28 | 29 | 1 | 18 | 29 |
| 288 | 972 | 3829 | 79.1 | CTGTTGCGACGGGCAACCATTGAT | 14 | 29 | 35 | 21 | 15 | 2 |
| 289 | 982 | 3856 | 77.2 | CTGTGACCCCATCTTGATCGGCAA | 14 | 32 | 15 | 11 | 24 | 21 |
| 290 | 989 | 3872 | 80.5 | CTGTGTGCATCGGACCACCTTGCG | 14 | 33 | 24 | 32 | 23 | 29 |
| 291 | 991 | 3873 | 77.2 | CTGTGTGCCACGATACGGACCGTT | 14 | 33 | 30 | 5 | 34 | 12 |
| 292 | 993 | 3878 | 77 | CTGTGGACCCTACCATTCCCAGCC | 14 | 34 | 26 | 15 | 28 | 36 |
| 293 | 994 | 3882 | 81 | CTGTGGACCACGGTGCGATGCTCA | 14 | 34 | 30 | 33 | 27 | 13 |
| 294 | 1016 | 3987 | 76.6 | CCATTGTCCAGCTTGAACGGCTGT | 15 | 9 | 31 | 1 | 35 | 14 |
| 295 | 1018 | 3993 | 75.1 | CCATTCGTTCGTCGTTGCTTATCG | 15 | 10 | 10 | 12 | 17 | 24 |
| 296 | 1020 | 3999 | 80.8 | CCATTCGTGAGTCACGTGCGCAGC | 15 | 10 | 20 | 30 | 29 | 31 |
| 297 | 1074 | 4202 | 79.8 | CCATTGCGATACGGACATCGGCAA | 15 | 29 | 5 | 34 | 24 | 21 |
| 298 | 1077 | 4209 | 80 | CCATTGCGCGAAGATGCTCACAGC | 15 | 29 | 16 | 27 | 13 | 31 |
| 299 | 1085 | 4220 | 79.4 | CCATCACGAATCGCTTGTGCGCTT | 15 | 30 | 4 | 17 | 33 | 17 |
| 300 | 1099 | 4243 | 77.3 | CCATCAGCAGCCAAAGGTCTTCCC | 15 | 31 | 36 | 6 | 19 | 28 |
| 301 | 1126 | 14325 | 76.8 | CGAATTGATCCCAATCCGAATCCC | 16 | 1 | 28 | 4 | 16 | 28 |
| 302 | 1129 | 4341 | 77 | CGAATTAGCACGGGTACAGCACGG | 16 | 3 | 30 | 18 | 31 | 35 |
| 303 | 1147 | 30238 | 79.8 | CGAATGTCTCCCGTGCCCATAGCC | 16 | 9 | 28 | 33 | 15 | 36 |
| 304 | 1151 | 4428 | 75.9 | CGAATCGTACCTTGCGGTCTCGTT | 16 | 10 | 23 | 29 | 19 | 12 |
| 305 | 1152 | 14366 | 76.5 | CGAATCGTCCTAAGGATCCCAGCC | 16 | 10 | 26 | 25 | 28 | 36 |
| 306 | 1162 | 4467 | 80.7 | CGAACTCACGTTCACGCGTTTGCG | 16 | 13 | 12 | 30 | 12 | 29 |

FIG. 25G

| SEQ ID NO: | 4,633 ID# | HEX ID# | Tm | ZIPCODE (5'-3') | TETRAMER NUMBERS | | | | |
|---|---|---|---|---|---|---|---|---|---|
| 307 | 1167 | 4480 | 77.4 | CGAACCATTGATCTTGCACGCGTT | 16 | 15 | 2 | 11 | 30 | 12 |
| 308 | 1172 | 4490 | 78.2 | CGAACCATCAGCGACCGTCTAGCC | 16 | 15 | 31 | 32 | 19 | 36 |
| 309 | 1179 | 4518 | 78.4 | CGAAGCTTCTGTTCCCGTTTCCC | 16 | 17 | 14 | 28 | 12 | 28 |
| 310 | 1200 | 4598 | 76.4 | CGAAATCGACCTTCTGGATGCAGC | 16 | 24 | 23 | 8 | 27 | 31 |
| 311 | 1201 | 4604 | 79 | CGAAATCGACGGGAGTTGTCTGCG | 16 | 24 | 35 | 20 | 9 | 29 |
| 312 | 1221 | 4659 | 76.6 | CGAATGCGGCTTCGTTAAAGCTTG | 16 | 29 | 17 | 12 | 6 | 11 |
| 313 | 1222 | 4660 | 76.6 | CGAATGCGGGTAATACTGCGTCGT | 16 | 29 | 18 | 5 | 29 | 10 |
| 314 | 1249 | 4759 | 76.7 | CGAAGGACGTGCACCTCCTACGAA | 16 | 34 | 33 | 23 | 26 | 16 |
| 315 | 1251 | 4761 | 77.2 | CGAAACGGTTAGCTGTCAGCACGG | 16 | 35 | 3 | 14 | 31 | 35 |
| 316 | 1259 | 4782 | 79.8 | CGAAACGGAGCCGTCTCGTTGCTT | 16 | 35 | 36 | 19 | 12 | 17 |
| 317 | 1263 | 4793 | 79.1 | CGAAAGCCGCAAAGTGAATCGTGC | 16 | 36 | 21 | 22 | 4 | 33 |
| 318 | 1284 | 4872 | 76.1 | GCTTTCGTCGAAGTCTCACGCCAT | 17 | 10 | 16 | 19 | 30 | 15 |
| 319 | 1290 | 4896 | 76.5 | GCTTCTTGACGGAGCCTTGACACG | 17 | 11 | 35 | 36 | 1 | 30 |
| 320 | 1375 | 5432 | 77.1 | GTCTCTTGCGTTTGCGCCTAGCAA | 19 | 11 | 12 | 29 | 26 | 21 |
| 321 | 1398 | 5534 | 78.6 | GTCTGTGCGGACCCTAACGGCTCA | 19 | 33 | 34 | 26 | 35 | 13 |
| 322 | 1424 | 5680 | 79 | GAGTGACCCAGCTGTCGGACCACG | 20 | 32 | 31 | 9 | 34 | 30 |
| 323 | 1427 | 5684 | 79.5 | GAGTGTGCCTTGTGCGCGAACGTT | 20 | 33 | 11 | 29 | 16 | 12 |
| 324 | 1439 | 5787 | 80.7 | GCAATACATCCCGGACACGGGCAA | 21 | 7 | 28 | 34 | 35 | 21 |
| 325 | 1454 | 5821 | 78.8 | GCAATCGTGATGGTCTTGCGTCCC | 21 | 10 | 27 | 19 | 29 | 28 |
| 326 | 1462 | 5855 | 78 | GCAACGTTGGACCTTGCTGTTCCC | 21 | 12 | 34 | 11 | 14 | 28 |
| 327 | 1463 | 5859 | 75.3 | GCAACTCAACCTCCATTCGTTCCC | 21 | 13 | 23 | 15 | 10 | 28 |
| 328 | 1465 | 5862 | 89.8 | GCAACTCATGCGCACGTCTGGTGC | 21 | 13 | 29 | 30 | 8 | 33 |
| 329 | 1479 | 5941 | 77.6 | GCAAGCAATTAGCACGCCATCGAA | 21 | 21 | 3 | 30 | 15 | 16 |
| 330 | 1485 | 5962 | 76.9 | GCAAAGTGTCGTTTGATGCGGGAC | 21 | 22 | 10 | 1 | 29 | 34 |
| 331 | 1489 | 5980 | 77.9 | GCAAACCTCTCATGCGTGATTGCG | 21 | 23 | 13 | 29 | 2 | 29 |
| 332 | 1496 | 14968 | 78.2 | GCAAATCGATCGCGAACGAAGGAC | 21 | 24 | 24 | 16 | 16 | 34 |
| 333 | 1499 | 6008 | 75.1 | GCAAATCGAGCCAATCGGTAACCT | 21 | 24 | 36 | 4 | 18 | 23 |
| 334 | 1550 | 6148 | 77.1 | GCAAGGACGTCTTGTCCGTTCACG | 21 | 34 | 19 | 9 | 12 | 30 |
| 335 | 1561 | 6173 | 78.4 | GCAAAGCCCGTTCAGCACCTTCTG | 21 | 36 | 12 | 31 | 23 | 8 |
| 336 | 1580 | 6250 | 76.9 | AGTGCGAACTTGTCTGGGACTGCG | 22 | 16 | 11 | 8 | 34 | 29 |
| 337 | 1632 | 6471 | 75.2 | ACCTTTAGCGTTTGTCTGCGTCCC | 23 | 3 | 12 | 9 | 29 | 28 |
| 338 | 1647 | 6557 | 75.4 | ACCTCGAACCATTACATGCGGCTT | 23 | 16 | 15 | 7 | 29 | 17 |
| 339 | 1650 | 6572 | 76.2 | ACCTGCTTCGAAGTGCCTGTCAGC | 23 | 17 | 16 | 33 | 14 | 31 |
| 340 | 1675 | 6706 | 78.3 | ACCTGTGCTTGACACGATCGCACG | 23 | 33 | 1 | 30 | 24 | 30 |
| 341 | 1700 | 6802 | 76.1 | ATCGAAAGCTCAGTGCGCAAGCTT | 24 | 6 | 13 | 33 | 21 | 17 |
| 342 | 1710 | 6845 | 77.1 | ATCGCTTGTGTCTGCGAGCCTCTG | 24 | 11 | 9 | 29 | 36 | 8 |
| 343 | 1712 | 6850 | 75.7 | ATCGCTTGCGAAAAAGCTGTCCAT | 24 | 11 | 16 | 6 | 14 | 15 |
| 344 | 1724 | 6870 | 75.1 | ATCGCGTTGAGTAGGAGGACGGAC | 24 | 12 | 20 | 25 | 34 | 34 |
| 345 | 1736 | 6882 | 81.7 | ATCGCTCATCTGGTGCGGACGCAA | 24 | 13 | 8 | 33 | 34 | 21 |
| 346 | 1737 | 6903 | 80.1 | ATCGCTGTGATGCGTTACGGCACG | 24 | 14 | 27 | 12 | 35 | 30 |
| 347 | 1743 | 6911 | 77.2 | ATCGCCATAATCCAGCCAGCACCT | 24 | 15 | 4 | 31 | 31 | 23 |
| 348 | 1766 | 6956 | 75.7 | ATCGGCTTCAGCAAAGTCTGCCAT | 24 | 17 | 31 | 6 | 8 | 15 |
| 349 | 1781 | 6994 | 79.4 | ATCGGAGTGGACCACGCTTGGGAC | 24 | 20 | 34 | 30 | 11 | 34 |
| 350 | 1794 | 7018 | 76.4 | ATCGAGTGCTCAAGGAATCGGCAA | 24 | 22 | 13 | 25 | 24 | 21 |
| 351 | 1813 | 7068 | 76.9 | ATCGCCTAGATGTGCGAGGATCCC | 24 | 26 | 27 | 29 | 25 | 28 |
| 352 | 1831 | 7104 | 80.2 | ATCGTCCCAGCCCTGTGATGGTGC | 24 | 28 | 36 | 14 | 27 | 33 |
| 353 | 1877 | 7191 | 76.6 | ATCGGGACTACAATCGCAGCGATG | 24 | 34 | 7 | 24 | 31 | 27 |
| 354 | 1889 | 7213 | 79.4 | ATCGACGGTGTCCGAACCATGCAA | 24 | 35 | 9 | 16 | 15 | 21 |
| 355 | 1904 | 7235 | 76.7 | ATCGAGCCGAGTTTGACGAACACG | 24 | 36 | 20 | 1 | 16 | 30 |
| 356 | 1923 | 7302 | 78.5 | AGGATCGTGACCAGGACAGCACGG | 25 | 10 | 32 | 25 | 31 | 35 |
| 357 | 1940 | 7357 | 78.7 | AGGAGCTTGATGTCCCGCAATCCC | 25 | 17 | 27 | 28 | 21 | 28 |

FIG. 25H

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 358 | 1944 | 7388 | 76.7 | AGGAAGTGGGTAGCAATCCCCACG | 25 | 22 | 18 | 21 | 28 | 30 |
| 359 | 1975 | 7510 | 79.3 | AGGAGTGCGTGCCTTGGACCACCT | 25 | 33 | 33 | 11 | 32 | 23 |
| 360 | 2007 | 7750 | 78.7 | CCTACAGCAGGAGACCGACCGCAA | 26 | 31 | 25 | 32 | 32 | 21 |
| 361 | 2029 | 7882 | 77.9 | GATGCCATGCAACAGCAGGACAGC | 27 | 15 | 21 | 31 | 25 | 31 |
| 362 | 2083 | 8075 | 79.2 | GATGGGACCTTGCACGTCGTCGAA | 27 | 34 | 11 | 30 | 10 | 16 |
| 363 | 2098 | 8128 | 78.2 | TCCCTGATTCCCCGAACGTTGATG | 28 | 2 | 28 | 16 | 12 | 27 |
| 364 | 2128 | 15756 | 76.4 | TCCCTACATGCGTTAGGACCCACG | 28 | 7 | 29 | 3 | 32 | 30 |
| 365 | 2134 | 8207 | 79.3 | TCCCTCTGGATGCACGAATCGTGC | 28 | 8 | 27 | 30 | 4 | 33 |
| 366 | 2158 | 8259 | 79.9 | TCCCCTTGTGCGATCGCTGTCTCA | 28 | 11 | 29 | 24 | 14 | 13 |
| 367 | 2174 | 8284 | 78.8 | TCCCCGTTACGGAGTGGTCTGCAA | 28 | 12 | 35 | 22 | 19 | 21 |
| 368 | 2177 | 8289 | 79.4 | TCCCCTCATACAACGGCCATGCAA | 28 | 13 | 7 | 35 | 15 | 21 |
| 369 | 2179 | 8294 | 76.8 | TCCCCTCACTGTCCTATCCCAGCC | 28 | 13 | 14 | 26 | 28 | 36 |
| 370 | 2183 | 8299 | 75.3 | TCCCCTCACCTAATACACGGCGTT | 28 | 13 | 26 | 5 | 35 | 12 |
| 371 | 2197 | 8327 | 78.3 | TCCCCCATATACGCAACAGCAGCC | 28 | 15 | 5 | 21 | 31 | 36 |
| 372 | 2207 | 8344 | 76.9 | TCCCCGAATGATGCTTCGTTTTGA | 28 | 16 | 2 | 17 | 12 | 1 |
| 373 | 2237 | 8396 | 78.7 | TCCCGGTAGACCCCATGACCACCT | 28 | 18 | 32 | 15 | 32 | 23 |
| 374 | 2243 | 8403 | 78.1 | TCCCGTCTCTGTGATGAGCCCGTT | 28 | 19 | 14 | 27 | 36 | 12 |
| 375 | 2254 | 40508 | 82.8 | TCCCGAGTTGTCGACCCCATTGCG | 28 | 20 | 9 | 32 | 15 | 29 |
| 376 | 2271 | 8440 | 79.1 | TCCCGCAAAGGAGAGTGATGCGAA | 28 | 21 | 25 | 20 | 27 | 16 |
| 377 | 2293 | 8479 | 76.5 | TCCCATCGTGTCTGATAGCCAGCC | 28 | 24 | 9 | 2 | 36 | 36 |
| 378 | 2304 | 8502 | 77.7 | TCCCAGGACTGTTTGACACGGCAA | 28 | 25 | 14 | 1 | 30 | 21 |
| 379 | 2365 | 8592 | 76.3 | TCCCCACGTACAGGACAATCAGCC | 28 | 30 | 7 | 34 | 4 | 36 |
| 380 | 2369 | 8597 | 80 | TCCCCACGGCTTCTTGACCTCGAA | 28 | 30 | 17 | 11 | 23 | 16 |
| 381 | 2403 | 8640 | 80.9 | TCCCGACCGCTTGGTACCATGTGC | 28 | 32 | 17 | 18 | 15 | 33 |
| 382 | 2421 | 8665 | 77.3 | TCCCGGACTGATCGTTGATGCTTG | 28 | 34 | 2 | 12 | 27 | 11 |
| 383 | 2422 | 8666 | 76.9 | TCCCGGACTTAGCGAACTTGTCCC | 28 | 34 | 3 | 16 | 11 | 28 |
| 384 | 2440 | 8695 | 79.7 | TCCCACGGCGAATGTCCCTACGTT | 28 | 35 | 16 | 9 | 26 | 12 |
| 385 | 2444 | 8703 | 81.8 | TCCCACGGTCCCGAGTGGTAACGG | 28 | 35 | 28 | 20 | 18 | 35 |
| 386 | 2452 | 8710 | 77.1 | TCCCAGCCTACATGTCACGGGATG | 28 | 36 | 7 | 9 | 35 | 27 |
| 387 | 2461 | 8720 | 80.4 | TCCCAGCCGATGGATGATCGGGTA | 28 | 36 | 27 | 27 | 24 | 18 |
| 388 | 2468 | 8728 | 79.2 | TGCGTTGACTTGAGTGACGGCACG | 29 | 1 | 11 | 22 | 35 | 30 |
| 389 | 2471 | 15876 | 76.1 | TGCGTTGAACCTACGGGGACTGAT | 29 | 1 | 23 | 35 | 34 | 2 |
| 390 | 2477 | 40574 | 78.8 | TGCGTGATCGTTCTCACAGCCGAA | 29 | 2 | 12 | 13 | 31 | 16 |
| 391 | 2479 | 8749 | 79.4 | TGCGTGATGTCTCACGCGAACAGC | 29 | 2 | 19 | 30 | 16 | 31 |
| 392 | 2482 | 8752 | 77 | TGCGTGATGATGTGTCCGAAGTGC | 29 | 2 | 27 | 9 | 16 | 33 |
| 393 | 2497 | 8775 | 77.2 | TGCGAATCCTGTTGTCCAGCGTCT | 29 | 4 | 14 | 9 | 31 | 19 |
| 394 | 2503 | 8788 | 75.3 | TGCGATACGTCTGAGTAGCCCGAA | 29 | 5 | 19 | 20 | 36 | 16 |
| 395 | 2507 | 8796 | 76.1 | TGCGAAAGTGATAGCCAGTGGCAA | 29 | 6 | 2 | 36 | 22 | 21 |
| 396 | 2515 | 8808 | 77.9 | TGCGAAAGGTGCAGGAGAGTTCCC | 29 | 6 | 33 | 25 | 20 | 28 |
| 397 | 2517 | 15901 | 77.1 | TGCGTACATCGTACGGCTCACACG | 29 | 7 | 10 | 35 | 13 | 30 |
| 398 | 2530 | 8817 | 78.5 | TGCGTACAGGACTGCGAAAGTGCG | 29 | 7 | 34 | 29 | 6 | 29 |
| 399 | 2546 | 8864 | 75.1 | TGCGTCGTGGTACCTATGTCGCTT | 29 | 10 | 18 | 26 | 9 | 17 |
| 400 | 2578 | 8901 | 76.5 | TGCGCGTTCCTAAAAGCCATCTGT | 29 | 12 | 26 | 6 | 15 | 14 |
| 401 | 2592 | 15912 | 78.2 | TGCGCTCACTCAGACCAAAGGCAA | 29 | 13 | 13 | 32 | 6 | 21 |
| 402 | 2594 | 15913 | 78.7 | TGCGCTCACGAACCATCGTTTTGA | 29 | 13 | 16 | 15 | 12 | 1 |
| 403 | 2595 | 30609 | 77.9 | TGCGCTCAGAGTTTAGCACGACGG | 29 | 13 | 20 | 3 | 30 | 35 |
| 404 | 2599 | 8923 | 79.3 | TGCGCTCAAGCCAGGAGCTTGGTA | 29 | 13 | 36 | 25 | 17 | 18 |
| 405 | 2600 | 8924 | 76.6 | TGCGCTGTTTGAGTGCTCGTATCG | 29 | 14 | 1 | 33 | 10 | 24 |
| 406 | 2608 | 21521 | 76.7 | TGCGCTGTCGTTAGGATCTGTCCC | 29 | 14 | 12 | 25 | 8 | 28 |
| 407 | 2614 | 30613 | 77.9 | TGCGCTGTGAGTCTGTCGAAAGCC | 29 | 14 | 20 | 14 | 16 | 36 |
| 408 | 2624 | 40623 | 77.7 | TGCGCCATCTGTAGCCTGATCAGC | 29 | 15 | 14 | 36 | 2 | 31 |

FIG. 25I

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 409 | 2641 | 8968 | 79.5 | TGCGCGAAGACCACCTCTGTACGG | 29 | 16 | 32 | 23 | 14 | 35 |
| 410 | 2642 | 8970 | 80.4 | TGCGCGAAGGACGCAATTAGTCCC | 29 | 16 | 34 | 21 | 3 | 28 |
| 411 | 2643 | 8973 | 77.3 | TGCGGCTTAATCCTCAGCAACGAA | 29 | 17 | 4 | 13 | 21 | 16 |
| 412 | 2655 | 8991 | 79.4 | TGCGGGTATCTGCTGTGACCCAGC | 29 | 18 | 8 | 14 | 32 | 31 |
| 413 | 2663 | 9004 | 77.7 | TGCGGGTAGATGCCTAGACCGACC | 29 | 18 | 27 | 26 | 32 | 32 |
| 414 | 2687 | 21565 | 80.5 | TGCGGAGTGAGTGCTTCAGCACGG | 29 | 20 | 20 | 17 | 31 | 35 |
| 415 | 2690 | 9040 | 80.1 | TGCGGAGTTGCGAGTGCGAACTGT | 29 | 20 | 29 | 22 | 16 | 14 |
| 416 | 2691 | 30634 | 78.6 | TGCGGAGTCACGTCCCTACAAGCC | 29 | 20 | 30 | 28 | 7 | 36 |
| 417 | 2708 | 9054 | 82.1 | TGCGAGTGAATCGGACGGACGTGC | 29 | 22 | 4 | 34 | 34 | 33 |
| 418 | 2721 | 9070 | 76.7 | TGCGACCTTCTGTACAGTGCTGCG | 29 | 23 | 8 | 7 | 33 | 29 |
| 419 | 2748 | 9104 | 81.3 | TGCGATCGGTGCGAGTTTGAAGCC | 29 | 24 | 33 | 20 | 1 | 36 |
| 420 | 2762 | 40657 | 78.4 | TGCGCCTATTAGAGCCGTGCCTGT | 29 | 26 | 3 | 36 | 33 | 14 |
| 421 | 2763 | 9128 | 77.3 | TGCGCCTAAATCCTGTCTTGCGAA | 29 | 26 | 4 | 14 | 11 | 16 |
| 422 | 2770 | 9139 | 77.3 | TGCGCCTAAGTGCGAAACCTTTGA | 29 | 26 | 22 | 16 | 23 | 1 |
| 423 | 2784 | 9156 | 76.9 | TGCGGATGAGGATTGATCGTTCGT | 29 | 27 | 25 | 1 | 10 | 10 |
| 424 | 2791 | 30649 | 78.8 | TGCGTCCCATACTGATGTGCCACG | 29 | 28 | 5 | 2 | 33 | 30 |
| 425 | 2802 | 9177 | 78 | TGCGTCCCAGGAGTGCTTAGAGCC | 29 | 28 | 25 | 33 | 3 | 36 |
| 426 | 2843 | 9222 | 77.7 | TGCGGACCTTAGCTCACCATTCCC | 29 | 32 | 3 | 13 | 15 | 28 |
| 427 | 2861 | 9247 | 78.9 | TGCGGTGCAGTGGGTATCTGGCTT | 29 | 33 | 22 | 18 | 8 | 17 |
| 428 | 2876 | 9264 | 78.6 | TGCGGGACGGTAACGGTGATCCTA | 29 | 34 | 18 | 35 | 2 | 26 |
| 429 | 2886 | 9275 | 79.1 | TGCGACGGAAAGGGTATGTCACGG | 29 | 35 | 6 | 18 | 9 | 35 |
| 430 | 2904 | 9292 | 77.7 | TGCGAGCCCTGTTTAGGATGTCCC | 29 | 36 | 14 | 3 | 27 | 28 |
| 431 | 3018 | 9551 | 79.4 | CACGGAGTGATGAGCCCTTGCGAA | 30 | 20 | 27 | 36 | 11 | 16 |
| 432 | 3021 | 9556 | 75.2 | CACGGCAAATACTCTGGAGTTGCG | 30 | 21 | 5 | 8 | 20 | 29 |
| 433 | 3045 | 9608 | 77.8 | CACGATCGGCAAATCGTCGTCTTG | 30 | 24 | 21 | 24 | 10 | 11 |
| 434 | 3053 | 9626 | 80 | CACGAGGAAGTGGCAACACGCAGC | 30 | 25 | 22 | 21 | 30 | 31 |
| 435 | 3057 | 9633 | 79 | CACGAGGAGACCCTCACGAATGCG | 30 | 25 | 32 | 13 | 16 | 29 |
| 436 | 3103 | 9728 | 79.9 | CACGCAGCGCTTGCTTTCTGAGGA | 30 | 31 | 17 | 17 | 8 | 25 |
| 437 | 3153 | 9818 | 76.1 | CACGAGCCGGTACGTTGGTAGGAC | 30 | 36 | 18 | 12 | 18 | 34 |
| 438 | 3171 | 9864 | 77.6 | CAGCATACGTGCTCCCAGGAGCAA | 31 | 5 | 33 | 28 | 25 | 21 |
| 439 | 3256 | 10059 | 78.4 | CAGCGAGTCCATGGACAGTGCGAA | 31 | 20 | 15 | 34 | 22 | 16 |
| 440 | 3258 | 10060 | 76.6 | CAGCGAGTGGTAATCGTCCCCTCA | 31 | 20 | 18 | 24 | 28 | 13 |
| 441 | 3273 | 10091 | 80.3 | CAGCAGTGATCGCTTGAGCCTGCG | 31 | 22 | 24 | 11 | 36 | 29 |
| 442 | 3342 | 10220 | 76.4 | CAGCCAGCAAAGCCTAAGGAGCAA | 31 | 31 | 6 | 26 | 25 | 21 |
| 443 | 3343 | 10221 | 77 | CAGCCAGCTACAAGCCAGGACGAA | 31 | 31 | 7 | 36 | 25 | 16 |
| 444 | 3473 | 10530 | 76.7 | GACCGCAAACCTGTCTATCGCGAA | 32 | 21 | 23 | 19 | 24 | 16 |
| 445 | 3492 | 16297 | 76.5 | GACCGATGCGAATACAGACCCGAA | 32 | 27 | 16 | 7 | 32 | 16 |
| 446 | 3493 | 10589 | 78.5 | GACCGATGGAGTGATGGACCACGG | 32 | 27 | 20 | 27 | 32 | 35 |
| 447 | 3501 | 30792 | 79.6 | GACCTCCCGCAAGTCTGGACCGAA | 32 | 28 | 21 | 19 | 34 | 16 |
| 448 | 3653 | 10942 | 75.6 | GTGCGCTTCCTAACGGGATGAAAG | 33 | 17 | 26 | 35 | 27 | 6 |
| 449 | 3678 | 30832 | 77 | GTGCGCAACGTTGCTTTTAGCGTT | 33 | 21 | 12 | 17 | 3 | 12 |
| 450 | 3711 | 11060 | 78.1 | GTGCAGGACCTAAGCCATCGACGG | 33 | 25 | 26 | 36 | 24 | 35 |
| 451 | 3822 | 11330 | 76.4 | GGACCTTGAGGATGTCGATGGCAA | 34 | 11 | 25 | 9 | 27 | 21 |
| 452 | 3920 | 11597 | 77.6 | GGACCAGCCGTTTGAGATGCCAT | 34 | 31 | 12 | 1 | 27 | 15 |
| 453 | 3967 | 11693 | 79.2 | ACGGTTGATTGAATCGCGTTTGCG | 35 | 1 | 1 | 24 | 12 | 29 |
| 454 | 4057 | 41152 | 78.3 | ACGGCTCAGGACATACCCATTGCG | 35 | 13 | 34 | 5 | 15 | 29 |
| 455 | 4062 | 11897 | 75.6 | ACGGCTGTGGTACTCATCGTTCCC | 35 | 14 | 18 | 13 | 10 | 28 |
| 456 | 4145 | 12041 | 77.8 | ACGGAGTGGCTTGTCTGACCAGCC | 35 | 22 | 17 | 19 | 32 | 36 |
| 457 | 4162 | 30941 | 78 | ACGGATCGTCTGTCTGGACCCGAA | 35 | 24 | 8 | 8 | 32 | 16 |
| 458 | 4174 | 12091 | 75.6 | ACGGAGGATGATACCTCACGGTGC | 35 | 25 | 2 | 23 | 30 | 33 |
| 459 | 4317 | 16775 | 75.8 | AGCCTTAGCCATTCTGCGAACGAA | 36 | 3 | 15 | 8 | 16 | 16 |

FIG. 25J

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 460 | 4348 | 12389 | 75.5 | AGCCTGTCGCAAATACCGTTCGTT | 36 | 9 | 21 | 5 | 12 | 12 |
| 461 | 4352 | 12396 | 75 | AGCCTCGTTTAGTCGTTGCGGTCT | 36 | 10 | 3 | 10 | 29 | 19 |
| 462 | 4446 | 12578 | 76.8 | AGCCGTCTGGACTGATTCTGCACG | 36 | 19 | 34 | 2 | 8 | 30 |
| 463 | 4448 | 12580 | 76.2 | AGCCGAGTTTAGCCTACACGTGCG | 36 | 20 | 3 | 26 | 30 | 29 |
| 464 | 4545 | 12741 | 75.7 | AGCCTGCGTACACTGTCCATTCCC | 36 | 29 | 7 | 14 | 15 | 28 |
| 465 | 4586 | 12811 | 77.8 | AGCCGACCAGCCTTAGGGACGAGT | 36 | 32 | 36 | 3 | 34 | 20 |
| 466 | 1 | 20001 | 77.6 | TTGATTGAAGCCATCGGCTTTCCC | 1 | 1 | 36 | 24 | 17 | 28 |
| 467 | 2 | 12884 | 79.9 | TTGAAATCCACGTCCCCGAAACGG | 1 | 4 | 30 | 28 | 16 | 35 |
| 468 | 4 | 30001 | 77.3 | TTGAAAAGCGTTCTCATGCGCGTT | 1 | 6 | 12 | 13 | 29 | 12 |
| 469 | 10 | 39 | 82 | TTGATCGTCAGCCACGACGGACGG | 1 | 10 | 31 | 30 | 35 | 35 |
| 470 | 11 | 12889 | 81.8 | TTGATCGTGTGCACGGTGCGATCG | 1 | 10 | 33 | 35 | 29 | 24 |
| 471 | 14 | 40001 | 79.9 | TTGACTTGCGAAGTGCGTGCCGTT | 1 | 11 | 16 | 33 | 33 | 12 |
| 472 | 16 | 30002 | 78.8 | TTGACGTTTCCCCACGAGTGCGTT | 1 | 12 | 28 | 30 | 22 | 12 |
| 473 | 19 | 68 | 83 | TTGACCATGTGCACGGCACGCCAT | 1 | 15 | 33 | 35 | 30 | 15 |
| 474 | 22 | 40002 | 80.3 | TTGACGAAACGGCTCACAGCCACG | 1 | 16 | 35 | 13 | 31 | 30 |
| 475 | 23 | 40003 | 78.6 | TTGAGCTTTCCCGGTATCCCGGAC | 1 | 17 | 28 | 18 | 28 | 34 |
| 476 | 25 | 30003 | 77.1 | TTGAAGTGCGAAATCGGTGCACCT | 1 | 22 | 16 | 24 | 33 | 23 |
| 477 | 27 | 100 | 79.1 | TTGAACCTCAGCCACGAGCCAGGA | 1 | 23 | 31 | 30 | 36 | 25 |
| 478 | 28 | 12908 | 79.6 | TTGAACCTAGCCTGCGTCCCGACC | 1 | 23 | 36 | 29 | 28 | 32 |
| 479 | 31 | 12921 | 78.4 | TTGATCCCAAAGGCAAAGCCATCG | 1 | 28 | 6 | 21 | 36 | 24 |
| 480 | 34 | 40004 | 78.9 | TTGATCCCTCCCCTACACGCGTT | 1 | 28 | 28 | 26 | 30 | 12 |
| 481 | 35 | 40005 | 81.4 | TTGATGCGTTGACAGCGGACGCAA | 1 | 29 | 1 | 31 | 34 | 21 |
| 482 | 37 | 12931 | 78.4 | TTGATGCGCGAACCTAGATGCACG | 1 | 29 | 16 | 26 | 27 | 30 |
| 483 | 38 | 30005 | 76.4 | TTGATGCGGGTATTAGCACGGACC | 1 | 29 | 18 | 3 | 30 | 32 |
| 484 | 39 | 12933 | 81.2 | TTGATGCGAGTGACGGGTGCTCCC | 1 | 29 | 22 | 35 | 33 | 28 |
| 485 | 40 | 30006 | 77.6 | TTGATGCGCCTATCTGACGGCTTG | 1 | 29 | 26 | 8 | 35 | 11 |
| 486 | 41 | 12934 | 79.1 | TTGATGCGGATGCAGCTACATGCG | 1 | 29 | 27 | 31 | 7 | 29 |
| 487 | 45 | 12936 | 81.1 | TTGACACGCTTGCACGATCGGTGC | 1 | 30 | 11 | 30 | 24 | 33 |
| 488 | 46 | 12939 | 80.8 | TTGACACGGTGCCCATCTGTTGCG | 1 | 30 | 33 | 15 | 14 | 29 |
| 489 | 47 | 30007 | 77.4 | TTGACACGACGGAAAGGCAAATCG | 1 | 30 | 35 | 6 | 21 | 24 |
| 490 | 50 | 40008 | 79.5 | TTGACAGCAGCCAGTGGTGCTCCC | 1 | 31 | 36 | 22 | 33 | 28 |
| 491 | 51 | 12944 | 79.2 | TTGAGACCTGCGCAGCCGAAGGTA | 1 | 32 | 29 | 31 | 16 | 18 |
| 492 | 54 | 40009 | 79.4 | TTGAGGACACGGTCCCTGTCTGCG | 1 | 34 | 35 | 28 | 9 | 29 |
| 493 | 56 | 12951 | 77.5 | TTGAACGGCTTGCTTGCCATATCG | 1 | 35 | 11 | 11 | 15 | 24 |
| 494 | 57 | 30014 | 79.3 | TTGAACGGGAGTACGGCACGCTTG | 1 | 35 | 20 | 35 | 30 | 11 |
| 495 | 61 | 40010 | 77.2 | TTGAAGCCCTTGAGGAACGGGGTA | 1 | 36 | 11 | 25 | 35 | 18 |
| 496 | 63 | 12968 | 79 | TGATTTGAAGCCCTCAAGCCGCAA | 2 | 1 | 36 | 13 | 36 | 21 |
| 497 | 64 | 12969 | 79 | TGATTGATTGCGGCAACTTGCACG | 2 | 2 | 29 | 21 | 11 | 30 |
| 498 | 65 | 264 | 79.9 | TGATTCTGCCATGGACACGGGTGC | 2 | 8 | 15 | 34 | 35 | 33 |
| 499 | 66 | 12973 | 78.4 | TGATTCTGCAGCAGGACCATTGCG | 2 | 8 | 31 | 25 | 15 | 29 |
| 500 | 71 | 282 | 81.2 | TGATTCGTCAGCCAGCGTGCGATG | 2 | 10 | 31 | 31 | 33 | 27 |
| 501 | 72 | 286 | 80.2 | TGATCTTGCCATTCCCGGACCAGC | 2 | 11 | 15 | 28 | 34 | 31 |
| 502 | 74 | 308 | 76.1 | TGATCGAAGCTTAGCCCCTATGCG | 2 | 16 | 17 | 36 | 26 | 29 |
| 503 | 77 | 12989 | 77.1 | TGATGGTATGCGTCGTTCGTTCCC | 2 | 18 | 29 | 10 | 10 | 28 |
| 504 | 80 | 20049 | 77.2 | TGATGCAAGATGGATGTCCCAGCC | 2 | 21 | 27 | 27 | 28 | 36 |
| 505 | 83 | 12997 | 78.6 | TGATGATGGCAACAGCTCCCCCAT | 2 | 27 | 21 | 31 | 28 | 15 |
| 506 | 85 | 350 | 82.6 | TGATGATGACGGACCCACGTGCG | 2 | 27 | 35 | 32 | 30 | 29 |
| 507 | 87 | 40012 | 78 | TGATTCCCGAGTAGCCCACGTCGT | 2 | 28 | 20 | 36 | 30 | 10 |
| 508 | 90 | 13002 | 78 | TGATTCCCGTGCAAAGACGGACCT | 2 | 28 | 33 | 6 | 35 | 23 |
| 509 | 91 | 30016 | 78.4 | TGATTGCGGAGTCTTGACGGGAC | 2 | 29 | 20 | 11 | 35 | 34 |
| 510 | 93 | 30017 | 78.9 | TGATTGCGGATGAATCATCGTGCG | 2 | 29 | 27 | 4 | 24 | 29 |

*FIG. 25K*

| SEQ ID NO: | 4,633 ID# | HEX ID# | Tm | ZIPCODE (5'-3') | TETRAMER NUMBERS | | | | |
|---|---|---|---|---|---|---|---|---|---|
| 511 | 97 | 13012 | 80 | TGATCAGCATCGTCCCGCAAATCG | 2 | 31 | 24 | 28 | 21 | 24 |
| 512 | 102 | 413 | 83.1 | TGATGACCGATGCACGACGGGCAA | 2 | 32 | 27 | 30 | 35 | 21 |
| 513 | 103 | 13014 | 78.6 | TGATGACCGTGCAGCCGGTACTCA | 2 | 32 | 33 | 36 | 18 | 13 |
| 514 | 108 | 425 | 77.3 | TGATGTGCTCCCTACATCCCTGCG | 2 | 33 | 28 | 7 | 28 | 29 |
| 515 | 110 | 13017 | 80.4 | TGATGTGCGGACGATGAGCCGGTA | 2 | 33 | 34 | 27 | 36 | 18 |
| 516 | 113 | 40013 | 80.6 | TGATGGACGGACATCGGACCGCTT | 2 | 34 | 34 | 24 | 32 | 17 |
| 517 | 115 | 438 | 80.1 | TGATACGGTCGTCAGCCGTTTGCG | 2 | 35 | 10 | 31 | 12 | 29 |
| 518 | 116 | 439 | 79.8 | TGATACGGCTTGCACGACGGAGGA | 2 | 35 | 11 | 30 | 35 | 25 |
| 519 | 117 | 20065 | 78.3 | TGATACGGCGTTTTAGCACGTGCG | 2 | 35 | 12 | 3 | 30 | 29 |
| 520 | 119 | 30021 | 76.2 | TGATACGGCCTAGATGACGGCGTT | 2 | 35 | 26 | 27 | 35 | 12 |
| 521 | 120 | 40015 | 76.3 | TTAGCTTGGCAACTCACAGCGCAA | 3 | 11 | 21 | 13 | 31 | 21 |
| 522 | 121 | 30023 | 77.7 | TTAGCGTTAGCCTCTGCAGCGCAA | 3 | 12 | 36 | 8 | 31 | 21 |
| 523 | 122 | 40016 | 75.3 | TTAGCCATAGCCTTGAAGCCGGAC | 3 | 15 | 36 | 1 | 36 | 34 |
| 524 | 123 | 13046 | 75.1 | TTAGCGAAACCTAGCCAGCCCCTA | 3 | 16 | 23 | 36 | 36 | 26 |
| 525 | 127 | 544 | 77.3 | TTAGAGGATGCGCTCATCCCCGTT | 3 | 25 | 29 | 13 | 28 | 12 |
| 526 | 128 | 30025 | 78.1 | TTAGGATGCGAACACGGATGTGCG | 3 | 27 | 16 | 30 | 27 | 29 |
| 527 | 130 | 40017 | 76.3 | TTAGTCCCCGTTCGAAGATGCGAA | 3 | 28 | 12 | 16 | 27 | 16 |
| 528 | 131 | 13070 | 78.6 | TTAGTCCCATCGACGGTGCGGGTA | 3 | 28 | 24 | 35 | 29 | 18 |
| 529 | 133 | 30026 | 80.6 | TTAGTCCCAGCCCGAAAGCCCAGC | 3 | 28 | 36 | 16 | 36 | 31 |
| 530 | 134 | 40018 | 81.1 | TTAGTGCGCTTGTGCGGTGCATCG | 3 | 29 | 11 | 29 | 33 | 24 |
| 531 | 136 | 30028 | 76.2 | TTAGCAGCCCTATCTGCAGCGACC | 3 | 31 | 26 | 8 | 31 | 32 |
| 532 | 137 | 603 | 75.3 | TTAGCAGCACGGTACACACGGCTT | 3 | 31 | 35 | 7 | 30 | 17 |
| 533 | 138 | 13093 | 79.3 | TTAGGACCGATGGCTTCACGTGCG | 3 | 32 | 27 | 17 | 30 | 29 |
| 534 | 139 | 30030 | 78.8 | TTAGGTGCGACCGTGCCGTTTGAT | 3 | 33 | 32 | 33 | 12 | 2 |
| 535 | 141 | 13103 | 77.3 | TTAGGGACATCGCCTAAGCCCGAA | 3 | 34 | 24 | 26 | 36 | 16 |
| 536 | 142 | 13104 | 76.8 | TTAGGGACCCTATCCCCGAATCCC | 3 | 34 | 26 | 28 | 16 | 28 |
| 537 | 143 | 30031 | 77.1 | TTAGGGACTCCCTCTGACGGCAGC | 3 | 34 | 28 | 8 | 35 | 31 |
| 538 | 144 | 13105 | 75.8 | TTAGGGACCACGTCGTATCGAGCC | 3 | 34 | 30 | 10 | 24 | 36 |
| 539 | 146 | 13110 | 77.7 | TTAGACGGATCGATCGAGCCGGAC | 3 | 35 | 24 | 24 | 36 | 34 |
| 540 | 147 | 646 | 80.7 | TTAGACGGAGGAACGGCACGGCAA | 3 | 35 | 25 | 35 | 30 | 21 |
| 541 | 148 | 20075 | 77.8 | TTAGAGCCGCAAGAGTGTGCCACG | 3 | 36 | 21 | 20 | 33 | 30 |
| 542 | 149 | 13129 | 77 | AATCAAAGCGTTTCCCAGCCCTTG | 4 | 6 | 12 | 28 | 36 | 11 |
| 543 | 152 | 30036 | 76.6 | AATCCGTTGCAACTGTAGCCCACG | 4 | 12 | 21 | 14 | 36 | 30 |
| 544 | 154 | 721 | 75.4 | AATCCTCAACGGTCCCATACACGG | 4 | 13 | 35 | 28 | 5 | 35 |
| 545 | 155 | 741 | 79.2 | AATCCGAAAATCAGCCTGCGCGTT | 4 | 16 | 4 | 36 | 29 | 12 |
| 546 | 156 | 13151 | 77.6 | AATCCGAAAAAGGATGCGAATGCG | 4 | 16 | 6 | 27 | 16 | 29 |
| 547 | 158 | 745 | 77.7 | AATCCGAACTCAACGGGCAAGTGC | 4 | 16 | 13 | 35 | 21 | 33 |
| 548 | 160 | 749 | 81.1 | AATCCGAAAGTGCACGCACGGTGC | 4 | 16 | 22 | 30 | 30 | 33 |
| 549 | 164 | 779 | 75.5 | AATCGGTAGCAAAAAGGGACGCAA | 4 | 18 | 21 | 6 | 34 | 21 |
| 550 | 169 | 30039 | 75.3 | AATCCCTATGCGTGTCATCGGCTT | 4 | 26 | 29 | 9 | 24 | 17 |
| 551 | 170 | 867 | 76.6 | AATCTCCCGTCTCGAAGACCCGAA | 4 | 28 | 19 | 16 | 32 | 16 |
| 552 | 172 | 13204 | 75 | AATCTGCGGCTTTACAGGACGCTT | 4 | 29 | 17 | 7 | 34 | 17 |
| 553 | 173 | 40024 | 78.8 | AATCTGCGAGGAGACCTCCCACGG | 4 | 29 | 25 | 32 | 28 | 35 |
| 554 | 174 | 888 | 78.1 | AATCTGCGGACCGGTATCCCACCT | 4 | 29 | 32 | 18 | 28 | 23 |
| 555 | 175 | 40025 | 78.3 | AATCTGCGGTGCTCTGACGGTCGT | 4 | 29 | 33 | 8 | 35 | 10 |
| 556 | 176 | 20090 | 78.4 | AATCCACGTCGTACGGGCAACAGC | 4 | 30 | 10 | 35 | 21 | 31 |
| 557 | 177 | 13215 | 78.7 | AATCCAGCCTTGCTTGGGACGGAC | 4 | 31 | 11 | 11 | 34 | 34 |
| 558 | 178 | 13217 | 75.5 | AATCCAGCCCTAAGGAGGACAGCC | 4 | 31 | 26 | 25 | 34 | 36 |
| 559 | 180 | 20095 | 78.4 | AATCCAGCTGCGCGTTCGAACTGT | 4 | 31 | 29 | 12 | 16 | 14 |
| 560 | 181 | 921 | 77.7 | AATCCAGCACGGGTCTAGCCGATG | 4 | 31 | 35 | 19 | 36 | 27 |
| 561 | 182 | 923 | 78.8 | AATCGACCAATCGCTTGACCGCAA | 4 | 32 | 4 | 17 | 32 | 21 |

FIG. 25L

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 562 | 184 | 13219 | 76.4 | AATCGACCCCATCGTTAGTGTGCG | 4 | 32 | 15 | 12 | 22 | 29 |
| 563 | 185 | 30045 | 75.8 | AATCGACCCCTAACGGAAAGCGTT | 4 | 32 | 26 | 35 | 6 | 12 |
| 564 | 186 | 13223 | 78.7 | AATCGACCGATGCCATTCGTCGAA | 4 | 32 | 27 | 15 | 10 | 16 |
| 565 | 187 | 30046 | 78.3 | AATCGACCGGACAGGATGATTGCG | 4 | 32 | 34 | 25 | 2 | 29 |
| 566 | 188 | 13226 | 76.5 | AATCGTGCCTCAATACCAGCACGG | 4 | 33 | 13 | 5 | 31 | 35 |
| 567 | 190 | 40031 | 80.8 | AATCGTGCGATGCAGCGTCTGCAA | 4 | 33 | 27 | 31 | 19 | 21 |
| 568 | 193 | 20097 | 77.6 | AATCGGACAGCCAGGAATCGATCG | 4 | 34 | 36 | 25 | 24 | 24 |
| 569 | 194 | 973 | 76.1 | AATCACGGCTCACTCATCCCCTCA | 4 | 35 | 13 | 13 | 28 | 13 |
| 570 | 195 | 977 | 76.9 | AATCACGGACCTCTCAAGCCGACC | 4 | 35 | 23 | 13 | 36 | 32 |
| 571 | 196 | 978 | 78.4 | AATCACGGGATGCGAACGAAGTGC | 4 | 35 | 27 | 16 | 16 | 33 |
| 572 | 198 | 40034 | 75.8 | AATCAGCCCGTTAAAGTGCGGATG | 4 | 36 | 12 | 6 | 29 | 27 |
| 573 | 199 | 40035 | 79.8 | AATCAGCCCTCAATCGCAGCAGCC | 4 | 36 | 13 | 24 | 31 | 36 |
| 574 | 200 | 20100 | 77.7 | AATCAGCCGGTACCATAGCCTGCG | 4 | 36 | 18 | 15 | 36 | 29 |
| 575 | 202 | 20101 | 75.7 | AATCAGCCAGGATGTCCCTATGCG | 4 | 36 | 25 | 9 | 26 | 29 |
| 576 | 204 | 1022 | 77.8 | ATACCCATCGAAGGACTGCGCAGC | 5 | 15 | 16 | 34 | 29 | 31 |
| 577 | 207 | 40037 | 77.9 | ATACGCAAACGGCTCATCCCGGTA | 5 | 21 | 35 | 13 | 28 | 18 |
| 578 | 208 | 20103 | 77.6 | ATACCCTAACGGCAGCTGCGCTGT | 5 | 26 | 35 | 31 | 29 | 14 |
| 579 | 209 | 1063 | 80.7 | ATACGATGACGGCAGCTCCCGCAA | 5 | 27 | 35 | 31 | 28 | 21 |
| 580 | 211 | 13280 | 79.6 | ATACTGCGCTGTTCCCCACGAGCC | 5 | 29 | 14 | 28 | 30 | 36 |
| 581 | 212 | 20105 | 75.4 | ATACTGCGCGAATTAGGCAAAGCC | 5 | 29 | 16 | 3 | 21 | 36 |
| 582 | 213 | 1094 | 77.8 | ATACCACGATCGTCCCCGAACGAA | 5 | 30 | 24 | 28 | 16 | 16 |
| 583 | 215 | 40038 | 78 | ATACCAGCGGACCCTAAGCCAGCC | 5 | 31 | 34 | 26 | 36 | 36 |
| 584 | 217 | 1117 | 78.3 | ATACGACCGAGTTGCGTCCCGATG | 5 | 32 | 20 | 29 | 28 | 27 |
| 585 | 219 | 20108 | 76.3 | ATACGTGCTGCGGGTACCATGGAC | 5 | 33 | 29 | 18 | 15 | 34 |
| 586 | 220 | 30048 | 78.3 | ATACGTGCCACGATCGCTTGTCCC | 5 | 33 | 30 | 24 | 11 | 28 |
| 587 | 221 | 40039 | 78.8 | ATACGGACGACCTGTCGGACGCAA | 5 | 34 | 32 | 9 | 34 | 21 |
| 588 | 222 | 1148 | 75.2 | ATACACGGCCTAACGGTGTCCGTT | 5 | 35 | 26 | 35 | 9 | 12 |
| 589 | 223 | 30052 | 79.2 | ATACACGGTCCCCGTTGGACCAGC | 5 | 35 | 28 | 12 | 34 | 31 |
| 590 | 224 | 30053 | 76.7 | ATACAGCCCGAACAGCTCCCTCGT | 5 | 36 | 16 | 31 | 28 | 10 |
| 591 | 225 | 1200 | 78.8 | AAAGTCGTAGCCATCGCACGCAGC | 6 | 10 | 36 | 24 | 30 | 31 |
| 592 | 227 | 40040 | 76.2 | AAAGCGTTTTGACGTTAGCCTGCG | 6 | 12 | 1 | 12 | 36 | 29 |
| 593 | 229 | 13343 | 75.2 | AAAGCGTTATCGTCCCGACCTCTG | 6 | 12 | 24 | 28 | 32 | 8 |
| 594 | 230 | 40041 | 79.8 | AAAGCGTTGACCGATGACGGCCAT | 6 | 12 | 32 | 27 | 35 | 15 |
| 595 | 232 | 30054 | 76.2 | AAAGCCATGCTTTCCCTCCCAAAG | 6 | 15 | 17 | 28 | 28 | 6 |
| 596 | 233 | 40042 | 76.9 | AAAGCGAATCGTTCGTCTTGCACG | 6 | 16 | 10 | 10 | 11 | 30 |
| 597 | 235 | 30055 | 76.1 | AAAGCGAACGAAGATGCCATCAGC | 6 | 16 | 16 | 27 | 15 | 31 |
| 598 | 236 | 1277 | 77.2 | AAAGCGAACAGCGACCCCTACAGC | 6 | 16 | 31 | 32 | 26 | 31 |
| 599 | 237 | 13376 | 75.8 | AAAGGCTTATCGTGCGTCGTGCTT | 6 | 17 | 24 | 29 | 10 | 17 |
| 600 | 238 | 40043 | 75.2 | AAAGGCAAAAGTGTCCAGCGGAC | 6 | 21 | 6 | 9 | 31 | 34 |
| 601 | 239 | 30058 | 76.6 | AAAGGCAATCGTTGTCGGTATGCG | 6 | 21 | 10 | 9 | 18 | 29 |
| 602 | 240 | 13388 | 79 | AAAGGCAAAGTGCGAACACGGCAA | 6 | 21 | 22 | 16 | 30 | 21 |
| 603 | 241 | 30059 | 78.1 | AAAGGCAACAGCGCAAGCAAGGAC | 6 | 21 | 31 | 21 | 21 | 34 |
| 604 | 244 | 40044 | 76.5 | AAAGATCGGCAAAAGTCCCCGAA | 6 | 24 | 21 | 6 | 28 | 16 |
| 605 | 245 | 30060 | 79.6 | AAAGATCGCAGCGCTTGATGTGCG | 6 | 24 | 31 | 17 | 27 | 29 |
| 606 | 246 | 1355 | 79.7 | AAAGGATGCTCAAGCCCAGCACGG | 6 | 27 | 13 | 36 | 31 | 35 |
| 607 | 247 | 13417 | 76.1 | AAAGTCCCGAGTTGCGTGCGTTAG | 6 | 28 | 20 | 29 | 29 | 3 |
| 608 | 249 | 30063 | 77.8 | AAAGTGCGAGCCATCGACCTACGG | 6 | 29 | 36 | 24 | 23 | 35 |
| 609 | 250 | 40048 | 77.9 | AAAGCACGGCTTGGTAGTGCGACC | 6 | 30 | 17 | 18 | 33 | 32 |
| 610 | 251 | 40049 | 78.3 | AAAGCACGGCAATGATCACGGACC | 6 | 30 | 21 | 2 | 30 | 32 |
| 611 | 252 | 1413 | 79.4 | AAAGCACGAGTGGGACGTGCATCG | 6 | 30 | 22 | 34 | 33 | 24 |
| 612 | 253 | 13443 | 75.7 | AAAGCAGCGCTTGGTAATCGGGTA | 6 | 31 | 17 | 18 | 24 | 18 |

*FIG. 25M*

| SEQ ID NO: | 4,633 ID# | HEX ID# | Tm | ZIPCODE (5'-3') | TETRAMER NUMBERS | | | | |
|---|---|---|---|---|---|---|---|---|---|
| 613 | 254 | 30067 | 75 | AAAGGACCGGTAAAAGCGAAGCAA | 6 | 32 | 18 | 6 | 16 | 21 |
| 614 | 256 | 13456 | 76.6 | AAAGGTGCTCGTCAGCAGTGCGTT | 6 | 33 | 10 | 31 | 22 | 12 |
| 615 | 257 | 13457 | 78.1 | AAAGGTGCCTTGGTGCGATGCCTA | 6 | 33 | 11 | 33 | 27 | 26 |
| 616 | 258 | 30069 | 78.4 | AAAGGTGCCTCATGTCACGGGTGC | 6 | 33 | 13 | 9 | 35 | 33 |
| 617 | 259 | 30070 | 77.2 | AAAGGTGCCGAAATCGGGACTTGA | 6 | 33 | 16 | 24 | 34 | 1 |
| 618 | 260 | 40052 | 78.9 | AAAGGTGCCAGCGGTAGGACCAGC | 6 | 33 | 31 | 18 | 34 | 31 |
| 619 | 261 | 1467 | 77.4 | AAAGGGACTTGAACGGGCTTGCAA | 6 | 34 | 1 | 35 | 17 | 21 |
| 620 | 262 | 40053 | 77.6 | AAAGGGACCTCAGCAAAGCCCCAT | 6 | 34 | 13 | 21 | 36 | 15 |
| 621 | 263 | 30072 | 76.6 | AAAGGGACCCATGCTTCCATGACC | 6 | 34 | 15 | 17 | 15 | 32 |
| 622 | 265 | 1483 | 77 | AAAGACGGTCTGGCTTACGGGTGC | 6 | 35 | 8 | 17 | 35 | 33 |
| 623 | 266 | 30073 | 77.7 | AAAGACGGCGTTGTGCAAAGTCCC | 6 | 35 | 12 | 33 | 6 | 28 |
| 624 | 267 | 13472 | 78.3 | AAAGACGGATCGCACGCCTAGCAA | 6 | 35 | 24 | 30 | 26 | 21 |
| 625 | 269 | 40054 | 78.7 | AAAGAGCCGAGTGGACATCGTGCG | 6 | 36 | 20 | 34 | 24 | 29 |
| 626 | 270 | 20130 | 78.6 | AAAGAGCCAGTGACGGCCATCACG | 6 | 36 | 22 | 35 | 15 | 30 |
| 627 | 273 | 20134 | 77.6 | TACATCCCCGAAGGTAACGGCAGC | 7 | 28 | 16 | 18 | 35 | 31 |
| 628 | 274 | 1538 | 77.3 | TACATCCCATCGGAGTTCCCGACC | 7 | 28 | 24 | 20 | 28 | 32 |
| 629 | 275 | 1555 | 79.9 | TACATGCGGGACGAGTGACCCACG | 7 | 29 | 34 | 20 | 32 | 30 |
| 630 | 276 | 13501 | 76.8 | TACACAGCTGCGTACATGCGCCAT | 7 | 31 | 29 | 7 | 29 | 15 |
| 631 | 277 | 13503 | 77.8 | TACAGACCGCAACGAAAGCCTCCC | 7 | 32 | 21 | 16 | 36 | 28 |
| 632 | 278 | 13505 | 80.2 | TACAGTGCACGGGCAAGACCGTGC | 7 | 33 | 35 | 21 | 32 | 33 |
| 633 | 279 | 13506 | 75 | TACAACGGTCGTATCGCTTGCCAT | 7 | 35 | 10 | 24 | 11 | 15 |
| 634 | 280 | 1586 | 78.1 | TACAACGGCTTGCTCAGACCGCAA | 7 | 35 | 11 | 13 | 32 | 21 |
| 635 | 283 | 1593 | 79.9 | TACAACGGGAGTTGCGCAGCCTCA | 7 | 35 | 20 | 29 | 31 | 13 |
| 636 | 284 | 1595 | 78.7 | TACAACGGACCTGATGCAGCGCAA | 7 | 35 | 23 | 27 | 31 | 21 |
| 637 | 285 | 30077 | 75.6 | TACAACGGCACGTGCGACCTTTAG | 7 | 35 | 30 | 29 | 23 | 3 |
| 638 | 287 | 13515 | 76.2 | TACAAGCCGCAAGTCTTGCGTTGA | 7 | 36 | 21 | 19 | 29 | 1 |
| 639 | 288 | 13516 | 79.8 | TACAAGCCATCGCAGCCTTGGCAA | 7 | 36 | 24 | 31 | 11 | 21 |
| 640 | 293 | 1633 | 81.4 | TCTGTCTGCGTTTGCGGCAAAGCC | 8 | 8 | 12 | 29 | 21 | 36 |
| 641 | 294 | 13523 | 79.2 | TCTGTCTGCGAATGCGGACCGTCT | 8 | 8 | 16 | 29 | 32 | 19 |
| 642 | 295 | 20141 | 75.6 | TCTGTCGTGCTTGACCAGCCTGTC | 8 | 10 | 17 | 32 | 36 | 9 |
| 643 | 296 | 40058 | 77.3 | TCTGCTTGCGTTGCTTTGTCCGTT | 8 | 11 | 12 | 17 | 9 | 12 |
| 644 | 302 | 40059 | 79.7 | TCTGCGTTTTGAGTGCAGCCCAGC | 8 | 12 | 1 | 33 | 36 | 31 |
| 645 | 303 | 30080 | 76.6 | TCTGCGTTCGTTCTTGCGAAACCT | 8 | 12 | 12 | 11 | 16 | 23 |
| 646 | 305 | 13535 | 78.6 | TCTGCGTTGATGAGGACAGCTGCG | 8 | 12 | 27 | 25 | 31 | 29 |
| 647 | 307 | 1679 | 78.5 | TCTGCTCAGCAAACCTGTGCACGG | 8 | 13 | 21 | 23 | 33 | 35 |
| 648 | 308 | 1680 | 81.3 | TCTGCTCACAGCACGGGTGCGATG | 8 | 13 | 31 | 35 | 33 | 27 |
| 649 | 309 | 1688 | 80.9 | TCTGCTGTCACGGACCCAGCCGTT | 8 | 14 | 30 | 32 | 31 | 12 |
| 650 | 310 | 1693 | 77.5 | TCTGCCATCGAAAGTGGTGCCTTG | 8 | 15 | 16 | 22 | 33 | 11 |
| 651 | 311 | 13539 | 79.1 | TCTGCCATGGTACGTTTGCGGACC | 8 | 15 | 18 | 12 | 29 | 32 |
| 652 | 312 | 30083 | 80.1 | TCTGCCATTCCCATCGTCTGCACG | 8 | 15 | 28 | 24 | 8 | 30 |
| 653 | 314 | 1703 | 78.5 | TCTGCGAATCTGCGTTTGATTGCG | 8 | 16 | 8 | 12 | 2 | 29 |
| 654 | 315 | 13544 | 80.1 | TCTGCGAAAGTGACGGAGCCCGTT | 8 | 16 | 22 | 35 | 36 | 12 |
| 655 | 316 | 1718 | 78.7 | TCTGCGAAGTGCCTTGTCGTTCCC | 8 | 16 | 33 | 11 | 10 | 28 |
| 656 | 318 | 13550 | 75.4 | TCTGGCTTAGGAACGGGCTTCTTG | 8 | 17 | 25 | 35 | 17 | 11 |
| 657 | 319 | 40061 | 77.6 | TCTGGCTTTGCGAATCCTTGGCTT | 8 | 17 | 29 | 4 | 11 | 17 |
| 658 | 320 | 1732 | 78.5 | TCTGGCTTGACCGACCCGAAGATG | 8 | 17 | 32 | 32 | 16 | 27 |
| 659 | 323 | 1739 | 78.1 | TCTGGGTATCCCCGAATGTCCACG | 8 | 18 | 28 | 16 | 9 | 30 |
| 660 | 326 | 1750 | 78.1 | TCTGGCAATGATATCGCACGGTGC | 8 | 21 | 2 | 24 | 30 | 33 |
| 661 | 327 | 1751 | 77.1 | TCTGGCAAAAGGCTTTCCCCTTG | 8 | 21 | 6 | 17 | 28 | 11 |
| 662 | 328 | 1752 | 78.3 | TCTGGCAACTGTCAGCGCTTCGAA | 8 | 21 | 14 | 31 | 17 | 16 |
| 663 | 329 | 13554 | 76.9 | TCTGGCAAGGTATCTGCAGCCAGC | 8 | 21 | 18 | 8 | 31 | 31 |

FIG. 25N

| SEQ ID NO: | 4,633 ID# | HEX ID# | Tm | ZIPCODE (5'-3') | TETRAMER NUMBERS | | | | |
|---|---|---|---|---|---|---|---|---|---|
| 664 | 330 | 1763 | 80.5 | TCTGAGTGGCAATCCCTCCCTGCG | 8 | 22 | 21 | 28 | 28 | 29 |
| 665 | 334 | 30086 | 80.4 | TCTGATCGGTGCTGCGAATCGTGC | 8 | 24 | 33 | 29 | 4 | 33 |
| 666 | 336 | 1788 | 79.3 | TCTGCCTACAGCCGAATCCCGCTT | 8 | 26 | 31 | 16 | 28 | 17 |
| 667 | 337 | 40062 | 80.1 | TCTGGATGCCATGTGCCGAACAGC | 8 | 27 | 15 | 33 | 16 | 31 |
| 668 | 338 | 30087 | 77.3 | TCTGGATGCGAAAAAGTGCGCCTA | 8 | 27 | 16 | 6 | 29 | 26 |
| 669 | 339 | 1797 | 79.2 | TCTGGATGGGACGGTATGCGCTTG | 8 | 27 | 34 | 18 | 29 | 11 |
| 670 | 341 | 40063 | 79 | TCTGTCCCCATTCGTGATGGTGC | 8 | 28 | 15 | 10 | 27 | 33 |
| 671 | 342 | 40064 | 79.4 | TCTGTCCCGCTTTCTGGATGTGCG | 8 | 28 | 17 | 8 | 27 | 29 |
| 672 | 343 | 40065 | 76.8 | TCTGTCCCGGTACCATATCGCGAA | 8 | 28 | 18 | 15 | 24 | 16 |
| 673 | 344 | 13566 | 78.8 | TCTGTCCCGAGTGGACGCAACCAT | 8 | 28 | 20 | 34 | 21 | 15 |
| 674 | 345 | 13568 | 78.2 | TCTGTCCCAGCCCCTATCCCACCT | 8 | 28 | 36 | 26 | 28 | 23 |
| 675 | 347 | 1812 | 79.9 | TCTGTGCGTCTGTCCCCGAAGCAA | 8 | 29 | 8 | 28 | 16 | 21 |
| 676 | 348 | 1822 | 80.1 | TCTGTGCGTGCGGATGACCTACGG | 8 | 29 | 29 | 27 | 23 | 35 |
| 677 | 349 | 1823 | 78.3 | TCTGTGCGGACCTCGTTGATCACG | 8 | 29 | 32 | 10 | 2 | 30 |
| 678 | 350 | 1828 | 75.6 | TCTGCACGCTTGTTAGCAGCACCT | 8 | 30 | 11 | 3 | 31 | 23 |
| 679 | 351 | 1831 | 79.4 | TCTGCACGCCATGTGCCGTTTACA | 8 | 30 | 15 | 33 | 12 | 7 |
| 680 | 352 | 40067 | 80.3 | TCTGCACGGAGTTGTCGGACGTGC | 8 | 30 | 20 | 9 | 34 | 33 |
| 681 | 354 | 30090 | 78.7 | TCTGCACGCCTAAGCCCTGTGACC | 8 | 30 | 26 | 36 | 14 | 32 |
| 682 | 355 | 40068 | 79.8 | TCTGCACGGATGACGGACCTCGAA | 8 | 30 | 27 | 35 | 23 | 16 |
| 683 | 356 | 1845 | 78 | TCTGCAGCCTGTGGTACACGCGTT | 8 | 31 | 14 | 18 | 30 | 12 |
| 684 | 357 | 20165 | 81.5 | TCTGCAGCCGAAGCTTGCAAACGG | 8 | 31 | 16 | 17 | 21 | 35 |
| 685 | 359 | 13579 | 81 | TCTGCAGCGTGCGCAAAGCCTACA | 8 | 31 | 33 | 21 | 36 | 7 |
| 686 | 360 | 1860 | 80 | TCTGGACCTGCGCCATCTCAGCAA | 8 | 32 | 29 | 15 | 13 | 21 |
| 687 | 361 | 1861 | 80.4 | TCTGGACCCACGGACCTGTCCAGC | 8 | 32 | 30 | 32 | 9 | 31 |
| 688 | 362 | 13581 | 78.8 | TCTGGACCGACCAGTGCGTTCCAT | 8 | 32 | 32 | 22 | 12 | 15 |
| 689 | 364 | 1867 | 79.3 | TCTGGTGCTCGTCTGTGTGCACGG | 8 | 33 | 10 | 14 | 33 | 35 |
| 690 | 365 | 30091 | 77.5 | TCTGGTGCCGGTACAGCCTCAATCG | 8 | 33 | 18 | 31 | 13 | 24 |
| 691 | 366 | 40071 | 81.9 | TCTGGTGCATCGGGACATCGGTGC | 8 | 33 | 24 | 34 | 24 | 33 |
| 692 | 367 | 40072 | 77.3 | TCTGGGACCGTTGTCTAGCCCGTT | 8 | 34 | 12 | 19 | 36 | 12 |
| 693 | 368 | 40073 | 79 | TCTGGGACCCTAATCGACGGCGTT | 8 | 34 | 26 | 24 | 35 | 12 |
| 694 | 369 | 1898 | 79.3 | TCTGACGGGAGTGCAACACGGACC | 8 | 35 | 20 | 21 | 30 | 32 |
| 695 | 370 | 13593 | 78 | TCTGACGGGCAACTTGATCGCTCA | 8 | 35 | 21 | 11 | 24 | 13 |
| 696 | 371 | 1902 | 76.5 | TCTGACGGGATGACCTAGCCGATG | 8 | 35 | 27 | 23 | 36 | 27 |
| 697 | 372 | 1904 | 79.5 | TCTGACGGACGGGCTTAGTGTGCG | 8 | 35 | 35 | 17 | 22 | 29 |
| 698 | 373 | 1906 | 78.1 | TCTGAGCCAAAGGTGCCCATCGTT | 8 | 36 | 6 | 33 | 15 | 12 |
| 699 | 374 | 40076 | 77.5 | TCTGAGCCGCAAGGTAACGGACCT | 8 | 36 | 21 | 18 | 35 | 23 |
| 700 | 377 | 1921 | 78.9 | TGTCTTGAAGCCCATTGCGCCTA | 9 | 1 | 36 | 15 | 29 | 26 |
| 701 | 378 | 1924 | 83.9 | TGTCAATCCAGCGTGCTGCGTGCG | 9 | 4 | 31 | 33 | 29 | 29 |
| 702 | 379 | 1926 | 81 | TGTCAATCACGGAGCCCACGGGAC | 9 | 4 | 35 | 36 | 30 | 34 |
| 703 | 380 | 1927 | 80.5 | TGTCAATCAGCCAGCCCAGCTCCC | 9 | 4 | 36 | 36 | 31 | 28 |
| 704 | 381 | 1928 | 78.2 | TGTCAAAGCCATACGGCAGCGATG | 9 | 6 | 15 | 35 | 31 | 27 |
| 705 | 382 | 1933 | 79.2 | TGTCAAAGCAGCCACGTGATTGCG | 9 | 6 | 31 | 30 | 2 | 29 |
| 706 | 383 | 1936 | 77.8 | TGTCTGTCCGAAGGACCAGCTCCC | 9 | 9 | 16 | 34 | 31 | 28 |
| 707 | 384 | 13599 | 76.7 | TGTCTGTCGCAAAGCCAAAGTCCC | 9 | 9 | 21 | 36 | 6 | 28 |
| 708 | 386 | 1943 | 83.1 | TGTCTCGTCACGTGCGGACCTGCG | 9 | 10 | 30 | 29 | 32 | 29 |
| 709 | 388 | 1946 | 78.3 | TGTCTCGTACGGCGTTTTGATGCG | 9 | 10 | 35 | 12 | 1 | 29 |
| 710 | 389 | 1947 | 80.3 | TGTCCTTGCTCAATCGGTGCGTGC | 9 | 11 | 13 | 24 | 33 | 33 |
| 711 | 390 | 30093 | 76.9 | TGTCCTTGCACGTTAGGACCCGAA | 9 | 11 | 30 | 3 | 32 | 16 |
| 712 | 391 | 1957 | 78 | TGTCCTTGGACCCGAAGTGCCCTA | 9 | 11 | 32 | 16 | 33 | 26 |
| 713 | 394 | 1969 | 79.3 | TGTCCGTTACCTTCCCGACCGACC | 9 | 12 | 23 | 28 | 32 | 32 |
| 714 | 396 | 1978 | 77.5 | TGTCCTCAGCAATGTCGGACAGCC | 9 | 13 | 21 | 9 | 34 | 36 |

FIG. 25O

| SEQ ID NO: | 4,633 ID# | HEX ID# | Tm | ZIPCODE (5'-3') | TETRAMER NUMBERS | | | | |
|---|---|---|---|---|---|---|---|---|---|
| 715 | 397 | 20181 | 78.4 | TGTCCTCATCCCACCTCACGAGCC | 9 | 13 | 28 | 23 | 30 36 |
| 716 | 398 | 20184 | 76.5 | TGTCCTGTACGGAATCAGCCGACC | 9 | 14 | 35 | 4 | 36 32 |
| 717 | 400 | 1984 | 81 | TGTCCCATCTTGGACCCAGCACGG | 9 | 15 | 11 | 32 | 31 35 |
| 718 | 401 | 1987 | 75.8 | TGTCCCATCGAAATCCGAACCAT | 9 | 15 | 16 | 4 | 16 15 |
| 719 | 402 | 13609 | 77 | TGTCCCATGCAAAGGAAGGAGCAA | 9 | 15 | 21 | 25 | 25 21 |
| 720 | 403 | 1992 | 78.5 | TGTCCCATCCTACGTTGTGCGCAA | 9 | 15 | 26 | 12 | 33 21 |
| 721 | 404 | 1993 | 80 | TGTCCCATGATGGCAAGTGCCAGC | 9 | 15 | 27 | 21 | 33 31 |
| 722 | 405 | 13610 | 79.6 | TGTCCCATCAGCACGGGATGAGGA | 9 | 15 | 31 | 35 | 27 25 |
| 723 | 406 | 13612 | 77.3 | TGTCCCATAGCCATACTGCGGTGC | 9 | 15 | 36 | 5 | 29 33 |
| 724 | 407 | 30095 | 78.2 | TGTCCGAACGTTGCTTGGACGATG | 9 | 16 | 12 | 17 | 34 27 |
| 725 | 408 | 30096 | 76.3 | TGTCCGAAGCTTCTTGGGACGGTA | 9 | 16 | 17 | 11 | 34 18 |
| 726 | 409 | 13616 | 77.5 | TGTCCGAAACCTCGAATGCGAGTG | 9 | 16 | 23 | 16 | 29 22 |
| 727 | 410 | 40078 | 78.2 | TGTCCGAAAGGAAGGAGGACGCAA | 9 | 16 | 25 | 25 | 34 21 |
| 728 | 411 | 2007 | 76.3 | TGTCCGAACCTACTCATCCCCACG | 9 | 16 | 26 | 13 | 28 30 |
| 729 | 412 | 2011 | 78.7 | TGTCCGAACAGCGGACAAAGAGCC | 9 | 16 | 31 | 34 | 6 36 |
| 730 | 413 | 40080 | 77.9 | TGTCGCTTCGTTCGTTATCGGCAA | 9 | 17 | 12 | 12 | 24 21 |
| 731 | 414 | 13620 | 78.1 | TGTCGCTTCCATCGTTGATGACGG | 9 | 17 | 15 | 12 | 27 35 |
| 732 | 415 | 40081 | 77.3 | TGTCGCTTGCTTCCATTGTCGCTT | 9 | 17 | 17 | 15 | 9 17 |
| 733 | 416 | 30098 | 76.9 | TGTCGCTTATCGACCTAGCCGTGC | 9 | 17 | 24 | 23 | 36 33 |
| 734 | 417 | 13621 | 78.8 | TGTCGCTTAGGAAGCCACGGCTTG | 9 | 17 | 25 | 36 | 35 11 |
| 735 | 419 | 2029 | 80.1 | TGTCGGTATCGTTCCCTCCCGTGC | 9 | 18 | 10 | 28 | 28 33 |
| 736 | 420 | 2031 | 76.8 | TGTCGGTAGCAAACCTACGGCAGC | 9 | 18 | 21 | 23 | 35 31 |
| 737 | 421 | 2034 | 79.3 | TGTCGGTACAGCCAGCGCAAGCTT | 9 | 18 | 31 | 31 | 21 17 |
| 738 | 423 | 2037 | 78.3 | TGTCGTCTTCGTGGACCGTTTCCC | 9 | 19 | 10 | 34 | 12 28 |
| 739 | 424 | 2039 | 81.1 | TGTCGTCTCGAATCCCGACCACGG | 9 | 19 | 16 | 28 | 32 35 |
| 740 | 426 | 2050 | 79 | TGTCGAGTCAGCAGCCCGAACCAT | 9 | 20 | 31 | 36 | 16 15 |
| 741 | 427 | 30099 | 77.2 | TGTCGCAATTGACCATAGCCGACC | 9 | 21 | 1 | 15 | 36 32 |
| 742 | 428 | 2054 | 77.1 | TGTCGCAAAATCTCGTGATGTGCG | 9 | 21 | 4 | 10 | 27 29 |
| 743 | 429 | 40082 | 78.6 | TGTCGCAATCGTGCTTGATGCCAT | 9 | 21 | 10 | 17 | 27 15 |
| 744 | 433 | 2062 | 81.3 | TGTCGCAAGAGTTGCGCACGATCG | 9 | 21 | 20 | 29 | 30 24 |
| 745 | 434 | 2063 | 78.7 | TGTCGCAAAGTGGTCTGTGCCGAA | 9 | 21 | 22 | 19 | 33 16 |
| 746 | 435 | 13629 | 80.5 | TGTCGCAATGCGGACCCCTATCGT | 9 | 21 | 29 | 32 | 26 10 |
| 747 | 437 | 2074 | 83.3 | TGTCAGTGCAGCAGCCGGACTGCG | 9 | 22 | 31 | 36 | 34 29 |
| 748 | 438 | 2079 | 81.6 | TGTCACCTCACGCGAAACGGCGTT | 9 | 23 | 30 | 16 | 35 12 |
| 749 | 439 | 2082 | 80.4 | TGTCATCGTCGTCAGCGCAAAGCC | 9 | 24 | 10 | 31 | 21 36 |
| 750 | 440 | 2090 | 81.7 | TGTCATCGGATGGCAAACGGGTGC | 9 | 24 | 27 | 21 | 35 33 |
| 751 | 441 | 30100 | 82 | TGTCATCGTGCGCAGCGTGCAATC | 9 | 24 | 29 | 31 | 33 4 |
| 752 | 446 | 2107 | 81.4 | TGTCCCTACAGCAGCCCAGCGTGC | 9 | 26 | 31 | 36 | 31 33 |
| 753 | 447 | 40083 | 79.1 | TGTCCCTAACGGGACCTGCGGTCT | 9 | 26 | 35 | 32 | 29 19 |
| 754 | 453 | 2119 | 79.4 | TGTCGATGGTGCCCATCTTGCCAT | 9 | 27 | 33 | 15 | 11 15 |
| 755 | 454 | 40084 | 80.9 | TGTCGATGGACGATGCGTTTCCC | 9 | 27 | 34 | 27 | 12 28 |
| 756 | 455 | 40085 | 76.5 | TGTCTCCCCGTTAGGATTGATGCG | 9 | 28 | 12 | 25 | 1 29 |
| 757 | 456 | 13642 | 79.3 | TGTCTCCCAGGAGGACGACCGCTT | 9 | 28 | 25 | 34 | 32 17 |
| 758 | 457 | 2135 | 78.8 | TGTCTGCGTTGAACGGGACCACCT | 9 | 29 | 1 | 35 | 32 23 |
| 759 | 458 | 2136 | 80.7 | TGTCTGCGAATCGACCCAGCCCAT | 9 | 29 | 4 | 32 | 31 15 |
| 760 | 459 | 2137 | 78.6 | TGTCTGCGAAAGCAGCCTTGGCTT | 9 | 29 | 6 | 31 | 11 17 |
| 761 | 460 | 40087 | 76.6 | TGTCTGCGGGTACGAACCTAACGG | 9 | 29 | 18 | 16 | 26 35 |
| 762 | 462 | 2145 | 83.4 | TGTCTGCGAGTGGCAATGCGGCAA | 9 | 29 | 22 | 21 | 29 21 |
| 763 | 463 | 2146 | 77.2 | TGTCTGCGAGGACGAAACACGACCT | 9 | 29 | 25 | 16 | 30 23 |
| 764 | 465 | 2149 | 79.7 | TGTCTGCGTGCGGTGCCCTATGAT | 9 | 29 | 29 | 33 | 26 2 |
| 765 | 466 | 30103 | 82.4 | TGTCTGCGGTGCCAGCTCTGGTGC | 9 | 29 | 33 | 31 | 8 33 |

FIG. 25P

| SEQ ID NO: | 4,633 ID# | HEX ID# | Tm | ZIPCODE (5'-3') | TETRAMER NUMBERS | | | | |
|---|---|---|---|---|---|---|---|---|---|
| 766 | 467 | 13646 | 79.5 | TGTCCACGTCGTGACCCTTGCCAT | 9 | 30 | 10 | 32 | 11 | 15 |
| 767 | 468 | 2153 | 80.4 | TGTCCACGCTTGGACCCACGTTGA | 9 | 30 | 11 | 32 | 30 | 1 |
| 768 | 470 | 30104 | 77.2 | TGTCCACGGCTTCCTAGCAACGAA | 9 | 30 | 17 | 26 | 21 | 16 |
| 769 | 471 | 40088 | 78 | TGTCCACGGGTACTGTCACGACGG | 9 | 30 | 18 | 14 | 30 | 35 |
| 770 | 474 | 2164 | 77.7 | TGTCCACGGACCTCGTGCTTGGTA | 9 | 30 | 32 | 10 | 17 | 18 |
| 771 | 475 | 40090 | 78.4 | TGTCCAGCACCTTCGTACGGTCCC | 9 | 31 | 23 | 10 | 35 | 28 |
| 772 | 478 | 40091 | 78.7 | TGTCCAGCGACCTTGAGGACCAGC | 9 | 31 | 32 | 1 | 34 | 31 |
| 773 | 479 | 2180 | 79.2 | TGTCGACCAATCTCCCGTGCCTTG | 9 | 32 | 4 | 28 | 33 | 11 |
| 774 | 483 | 30110 | 80.6 | TGTCGACCAGGACTCATGCGGCAA | 9 | 32 | 25 | 13 | 29 | 21 |
| 775 | 486 | 13654 | 78.3 | TGTCGTGCAATCAATCCACGCCAT | 9 | 33 | 4 | 4 | 30 | 15 |
| 776 | 489 | 2198 | 78.1 | TGTCGTGCTCGTGCAAGACCGTCT | 9 | 33 | 10 | 21 | 32 | 19 |
| 777 | 490 | 30111 | 82.1 | TGTCGTGCCTTGCTGTCACGCACG | 9 | 33 | 11 | 14 | 30 | 30 |
| 778 | 491 | 30112 | 77.8 | TGTCGTGCGGTATCTGGCAAAGGA | 9 | 33 | 18 | 8 | 21 | 25 |
| 779 | 492 | 40092 | 79.4 | TGTCGTGCGTCTTCTGGGACGGAC | 9 | 33 | 19 | 8 | 34 | 34 |
| 780 | 493 | 2205 | 76.6 | TGTCGTGCACCTACCTGTGCGGTA | 9 | 33 | 23 | 23 | 33 | 18 |
| 781 | 494 | 40093 | 78.3 | TGTCGTGCAGGACTGTCGAAACGG | 9 | 33 | 25 | 14 | 16 | 35 |
| 782 | 496 | 2210 | 78 | TGTCGTGCTCCCCGAAAATCCTGT | 9 | 33 | 28 | 16 | 4 | 14 |
| 783 | 500 | 2218 | 76.7 | TGTCGGACCTGTGCTTAGCCCTTG | 9 | 34 | 14 | 17 | 36 | 11 |
| 784 | 502 | 40094 | 78.3 | TGTCGGACGTCTGGTAAGCCGCTT | 9 | 34 | 19 | 18 | 36 | 17 |
| 785 | 503 | 13659 | 77.4 | TGTCGGACACCTCGTTACGGCTTG | 9 | 34 | 23 | 12 | 35 | 11 |
| 786 | 504 | 13660 | 75.5 | TGTCGGACCCTAAATCGCTTCGTT | 9 | 34 | 26 | 4 | 17 | 12 |
| 787 | 505 | 13661 | 76.7 | TGTCGGACGATGAGTGCCTAAGCC | 9 | 34 | 27 | 22 | 26 | 36 |
| 788 | 506 | 2226 | 81.2 | TGTCGGACTCCCGACCAGTGGTGC | 9 | 34 | 28 | 32 | 22 | 33 |
| 789 | 507 | 2230 | 78.6 | TGTCACGGTTGATCCCACGGACCT | 9 | 35 | 1 | 28 | 35 | 23 |
| 790 | 509 | 2233 | 79.2 | TGTCACGGCTTGCGTTGCAAAGTG | 9 | 35 | 11 | 12 | 21 | 22 |
| 791 | 511 | 40096 | 76.8 | TGTCACGGGCTTACCTGATGCCAT | 9 | 35 | 17 | 23 | 27 | 15 |
| 792 | 512 | 30115 | 77.4 | TGTCACGGGAGTAGGACGTTTGCG | 9 | 35 | 20 | 25 | 12 | 29 |
| 793 | 513 | 30116 | 76.8 | TGTCACGGGCAAAAAGCGAAAAAG | 9 | 35 | 21 | 6 | 16 | 6 |
| 794 | 514 | 13665 | 80.5 | TGTCACGGTCCCCTTGGGACAGGA | 9 | 35 | 28 | 11 | 34 | 25 |
| 795 | 516 | 13667 | 75.4 | TGTCAGCCCTGTATACCGAATGCG | 9 | 36 | 14 | 5 | 16 | 29 |
| 796 | 517 | 2249 | 77.2 | TGTCAGCCGCTTTTGACGTTTCGT | 9 | 36 | 17 | 1 | 12 | 10 |
| 797 | 518 | 2252 | 77.2 | TGTCAGCCACCTGCAAGATGGCTT | 9 | 36 | 23 | 21 | 27 | 17 |
| 798 | 519 | 40097 | 77.7 | TGTCAGCCATCGTTAGCAGCCAGC | 9 | 36 | 24 | 3 | 31 | 31 |
| 799 | 520 | 13669 | 79.6 | TGTCAGCCGACCGCTTTCGTTCTG | 9 | 36 | 32 | 17 | 10 | 8 |
| 800 | 521 | 13672 | 77.3 | TCGTTGATGCTTCTTGGTGCGCTT | 10 | 2 | 17 | 11 | 33 | 17 |
| 801 | 522 | 2282 | 80.3 | TCGTTTAGGGACAGCCAGCCACGG | 10 | 3 | 34 | 36 | 36 | 35 |
| 802 | 523 | 2287 | 77.2 | TCGTAATCCACGCGTTGGTAACGG | 10 | 4 | 30 | 12 | 18 | 35 |
| 803 | 524 | 2300 | 77.7 | TCGTAAAGGGACAGGATCCCTGCG | 10 | 6 | 34 | 25 | 28 | 29 |
| 804 | 526 | 13686 | 76.5 | TCGTAAAGAGCCAAAGCACGCCAT | 10 | 6 | 36 | 6 | 30 | 15 |
| 805 | 528 | 2310 | 79.1 | TCGTTCTGTGCGCGAAGTGCTTGA | 10 | 8 | 29 | 16 | 33 | 1 |
| 806 | 529 | 30120 | 77.2 | TCGTTCTGCACGATACGACCGCTT | 10 | 8 | 30 | 5 | 32 | 17 |
| 807 | 530 | 2316 | 77.9 | TCGTTGTCCGTTGAGTTGCGAGGA | 10 | 9 | 12 | 20 | 29 | 25 |
| 808 | 531 | 2317 | 80.8 | TCGTTGTCCTCAACGGTGCGGCTT | 10 | 9 | 13 | 35 | 29 | 17 |
| 809 | 532 | 2321 | 79.5 | TCGTTGTCGAGTTGCGCTTGGACC | 10 | 9 | 20 | 29 | 11 | 32 |
| 810 | 533 | 30121 | 78 | TCGTTGTCCACGAGCCCGTTACCT | 10 | 9 | 30 | 36 | 12 | 23 |
| 811 | 534 | 30122 | 78.6 | TCGTTGTCACGGTCGTGCAAGGA | 10 | 9 | 35 | 10 | 21 | 25 |
| 812 | 535 | 13693 | 77.4 | TCGTTCGTGGTATGCGCCCTAATCG | 10 | 10 | 18 | 29 | 26 | 24 |
| 813 | 536 | 13694 | 79 | TCGTTCGTTGCGATCGTACATGCG | 10 | 10 | 29 | 24 | 7 | 29 |
| 814 | 538 | 30123 | 78 | TCGTCTTGCGTTCTTGCTTGCAGC | 10 | 11 | 12 | 11 | 11 | 31 |
| 815 | 539 | 2340 | 79.2 | TCGTCTTGTCCCGGACTCCCGAGT | 10 | 11 | 28 | 34 | 28 | 20 |
| 816 | 540 | 13698 | 78.5 | TCGTCTTGGACCAGCCACCTGACC | 10 | 11 | 32 | 36 | 23 | 32 |

FIG. 25Q

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 817 | 541 | 2345 | 77.5 | TCGTCTTGAGCCAGCCATACACGG | 10 | 11 | 36 | 36 | 5 | 35 |
| 818 | 542 | 2346 | 79.2 | TCGTCGTTTGATGCAACAGCGTGC | 10 | 12 | 2 | 21 | 31 | 33 |
| 819 | 543 | 2347 | 79.1 | TCGTCGTTTGTCAATCGTGCGTGC | 10 | 12 | 9 | 4 | 33 | 33 |
| 820 | 544 | 40099 | 77.6 | TCGTCGTTCGAAGGTAGCAATGCG | 10 | 12 | 16 | 18 | 21 | 29 |
| 821 | 546 | 2354 | 77.5 | TCGTCGTTACCTCGTTCGAATGCG | 10 | 12 | 23 | 12 | 16 | 29 |
| 822 | 549 | 13701 | 81 | TCGTCGTTGACCCACGCACGAGTG | 10 | 12 | 32 | 30 | 30 | 22 |
| 823 | 550 | 2363 | 76.3 | TCGTCGTTAGCCAGCCTTGACCAT | 10 | 12 | 36 | 36 | 1 | 15 |
| 824 | 552 | 2367 | 80 | TCGTCTCACAGCGTGCCGTTCGTT | 10 | 13 | 31 | 33 | 12 | 12 |
| 825 | 553 | 13703 | 76.9 | TCGTCTCAAGCCTTAGGTGCCACG | 10 | 13 | 36 | 3 | 33 | 30 |
| 826 | 555 | 2375 | 80.4 | TCGTCTGTAGCCCAGCTGCGGCTT | 10 | 14 | 36 | 31 | 29 | 17 |
| 827 | 556 | 2379 | 79.6 | TCGTCCATCTCAAGCCCCATGCAA | 10 | 15 | 13 | 36 | 15 | 21 |
| 828 | 558 | 13705 | 80.1 | TCGTCCATCAGCGGTAACGGGACC | 10 | 15 | 31 | 18 | 35 | 32 |
| 829 | 559 | 13706 | 80.1 | TCGTCCATGACCCACGCTTGCTTG | 10 | 15 | 32 | 30 | 11 | 11 |
| 830 | 561 | 2393 | 77.1 | TCGTCGAAAATCACGGTGTCGCTT | 10 | 16 | 4 | 35 | 9 | 17 |
| 831 | 562 | 2394 | 78.1 | TCGTCGAAAAAGGACCACGGAGGA | 10 | 16 | 6 | 32 | 35 | 25 |
| 832 | 563 | 2395 | 82 | TCGTCGAATCTGTGCGGGACCACG | 10 | 16 | 8 | 29 | 34 | 30 |
| 833 | 564 | 40100 | 79.1 | TCGTCGAAACCTTCCCGGACCTGT | 10 | 16 | 23 | 28 | 34 | 14 |
| 834 | 565 | 13712 | 76.4 | TCGTCGAAAGGAATCGGATGGATG | 10 | 16 | 25 | 24 | 27 | 27 |
| 835 | 566 | 2407 | 80.2 | TCGTCGAAGTGCGCAATCCCAGTG | 10 | 16 | 33 | 21 | 28 | 22 |
| 836 | 567 | 2413 | 77.5 | TCGTCGCTTCTCAGACCTGCGAGGA | 10 | 17 | 13 | 32 | 29 | 25 |
| 837 | 568 | 2429 | 78.6 | TCGTGGTAAGCCCACGGAGTCAGC | 10 | 18 | 36 | 30 | 20 | 31 |
| 838 | 569 | 2431 | 80.4 | TCGTGTCTCGTTTCCCACGGAGCC | 10 | 19 | 12 | 28 | 35 | 36 |
| 839 | 570 | 13723 | 82.3 | TCGTGTCTGCAAAGCCAGCCGTGC | 10 | 19 | 21 | 36 | 36 | 33 |
| 840 | 571 | 2435 | 81.1 | TCGTGTCTGTGCATCGTGCGGGAC | 10 | 19 | 33 | 24 | 29 | 34 |
| 841 | 572 | 2436 | 79.5 | TCGTGAGTTCGTCAGCGGACGACC | 10 | 20 | 10 | 31 | 34 | 32 |
| 842 | 573 | 20241 | 78.4 | TCGTGAGTCCATTGCGGTCTTCCC | 10 | 20 | 15 | 29 | 19 | 28 |
| 843 | 574 | 40102 | 77.8 | TCGTGCAATTGATGTCGTGCATCG | 10 | 21 | 1 | 9 | 33 | 24 |
| 844 | 575 | 2447 | 76.7 | TCGTGCAAGCTTCTTGGATGGACC | 10 | 21 | 17 | 11 | 27 | 32 |
| 845 | 576 | 2452 | 81.2 | TCGTGCAATGCGGTGCTCGTTCTG | 10 | 21 | 29 | 33 | 10 | 8 |
| 846 | 577 | 2454 | 77.2 | TCGTGCAAGGACAGCCTCGTTGAT | 10 | 21 | 34 | 36 | 10 | 2 |
| 847 | 578 | 2457 | 79.1 | TCGTAGTGTGCGGGTAACGGGTGC | 10 | 22 | 29 | 18 | 35 | 33 |
| 848 | 579 | 2459 | 81 | TCGTAGTGGTGCGATGGTGCGTGC | 10 | 22 | 33 | 27 | 33 | 33 |
| 849 | 580 | 2469 | 80.3 | TCGTACCTCAGCACGGACGGGGAC | 10 | 23 | 31 | 35 | 35 | 34 |
| 850 | 583 | 13733 | 75.5 | TCGTATCGGCTTATCGCACGTGTC | 10 | 24 | 17 | 24 | 30 | 9 |
| 851 | 584 | 2485 | 79.8 | TCGTATCGGGACGACCTCCCAGGA | 10 | 24 | 34 | 32 | 28 | 25 |
| 852 | 585 | 20255 | 75.4 | TCGTAGGAGACCTCTGAGCCAGCC | 10 | 25 | 32 | 8 | 36 | 36 |
| 853 | 586 | 2491 | 78.3 | TCGTAGGAAGCCCCATCCATGTGC | 10 | 25 | 36 | 15 | 15 | 33 |
| 854 | 587 | 20256 | 78.8 | TCGTCCTAAAAGTGCGTGCGAGCC | 10 | 26 | 6 | 29 | 29 | 36 |
| 855 | 590 | 2516 | 80.8 | TCGTGATGAGCCGCAACAGCCTCA | 10 | 27 | 36 | 21 | 31 | 13 |
| 856 | 592 | 13744 | 75.6 | TCGTTCCCCTGTTTAGCGAAAGGA | 10 | 28 | 14 | 3 | 16 | 25 |
| 857 | 593 | 40104 | 77 | TCGTTCCCCCATAAAGGTGCACCT | 10 | 28 | 15 | 6 | 33 | 23 |
| 858 | 594 | 2528 | 77.2 | TCGTTCCCGTCTGCAACCTAGCAA | 10 | 28 | 19 | 21 | 26 | 21 |
| 859 | 595 | 40106 | 78.8 | TCGTTCCCGAGTCCATCTTGGCAA | 10 | 28 | 20 | 15 | 11 | 21 |
| 860 | 598 | 13745 | 79.4 | TCGTTCCCTGCGTCGTACGGTCTG | 10 | 28 | 29 | 10 | 35 | 8 |
| 861 | 600 | 30130 | 80.8 | TCGTTCCCGGACTGTCGTGCCTGT | 10 | 28 | 34 | 9 | 33 | 14 |
| 862 | 601 | 13747 | 77.7 | TCGTTGCGAATCAATCGCAACCAT | 10 | 29 | 4 | 4 | 21 | 15 |
| 863 | 603 | 30132 | 78.4 | TCGTTGCGTCGTAGTGGAGTTGCG | 10 | 29 | 10 | 22 | 20 | 29 |
| 864 | 604 | 13748 | 78.3 | TCGTTGCGCTCATTGATGCGAATC | 10 | 29 | 13 | 1 | 29 | 4 |
| 865 | 605 | 30133 | 79.3 | TCGTTGCGGAGTGGTAGACCCACG | 10 | 29 | 20 | 18 | 32 | 30 |
| 866 | 607 | 2550 | 76.2 | TCGTTGCGAGTGAAAGCGAATTGA | 10 | 29 | 22 | 6 | 16 | 1 |
| 867 | 608 | 30134 | 80.2 | TCGTTGCGGATGGGTAGGACAGCC | 10 | 29 | 27 | 18 | 34 | 36 |

FIG. 25R

| SEQ ID NO: | 4,633 ID# | HEX ID# | Tm | ZIPCODE (5'-3') | TETRAMER NUMBERS | | | | |
|---|---|---|---|---|---|---|---|---|---|
| 868 | 611 | 2558 | 81.4 | TCGTTGCGCAGCTGTCCACGTCTG | 10 | 29 | 31 | 9 | 30 | 8 |
| 869 | 612 | 2559 | 80.1 | TCGTTGCGGACCAAAGGTGCAGTG | 10 | 29 | 32 | 6 | 33 | 22 |
| 870 | 614 | 2561 | 78.8 | TCGTTGCGAGCCAATCTCGTAGCC | 10 | 29 | 36 | 4 | 10 | 36 |
| 871 | 615 | 20265 | 75.6 | TCGTCACGAAAGATACACGGCAGC | 10 | 30 | 6 | 5 | 35 | 31 |
| 872 | 616 | 2564 | 81.5 | TCGTCACGTCTGTCCCTGCGAGCC | 10 | 30 | 8 | 28 | 29 | 36 |
| 873 | 617 | 2565 | 79.7 | TCGTCACGCTTGCTCACAGCTCCC | 10 | 30 | 11 | 13 | 31 | 28 |
| 874 | 618 | 13749 | 77.9 | TCGTCACGCGTTTCTGGGTAGCAA | 10 | 30 | 12 | 8 | 18 | 21 |
| 875 | 619 | 30135 | 76 | TCGTCACGCTGTAGCCCCTAGGAC | 10 | 30 | 14 | 36 | 26 | 34 |
| 876 | 620 | 2569 | 78.9 | TCGTCACGCCATGATGGATGCTTG | 10 | 30 | 15 | 27 | 27 | 11 |
| 877 | 621 | 2574 | 77.3 | TCGTCACGGCAATACAGACCGGAC | 10 | 30 | 21 | 7 | 32 | 34 |
| 878 | 622 | 20267 | 75.7 | TCGTCACGAGTGAAAGGCTTGTGC | 10 | 30 | 22 | 6 | 17 | 33 |
| 879 | 623 | 13751 | 77.9 | TCGTCACGATCGTCTGACGGCCTA | 10 | 30 | 24 | 8 | 35 | 26 |
| 880 | 624 | 2580 | 81.5 | TCGTCACGACGGGATGACGGTCGT | 10 | 30 | 35 | 27 | 35 | 10 |
| 881 | 625 | 2585 | 77.3 | TCGTCAGCCTCATGTCAGCCGTCT | 10 | 31 | 13 | 9 | 36 | 19 |
| 882 | 626 | 2587 | 79.4 | TCGTCAGCCCATGACCTGTCAGCC | 10 | 31 | 15 | 32 | 9 | 36 |
| 883 | 627 | 40109 | 76.2 | TCGTCAGCGGGTATTGAGGACCGTT | 10 | 31 | 18 | 1 | 34 | 12 |
| 884 | 628 | 30137 | 78.8 | TCGTCAGCGAGTAGTGCAGCGTGC | 10 | 31 | 20 | 22 | 31 | 33 |
| 885 | 630 | 13756 | 80.5 | TCGTCAGCGACCGAGTTCGTTCCC | 10 | 31 | 32 | 20 | 10 | 28 |
| 886 | 631 | 2601 | 80 | TCGTGACCAATCCGTTGGACTGCG | 10 | 32 | 4 | 12 | 34 | 29 |
| 887 | 632 | 2602 | 79.6 | TCGTGACCAAAGCTTGAGCCGTGC | 10 | 32 | 6 | 11 | 36 | 33 |
| 888 | 633 | 40110 | 76.5 | TCGTGACCCGTTACCTTCTGACGG | 10 | 32 | 12 | 23 | 8 | 35 |
| 889 | 634 | 40111 | 78.3 | TCGTGACCCTGTTTGAAGCCGCTT | 10 | 32 | 14 | 1 | 36 | 17 |
| 890 | 635 | 30138 | 78.4 | TCGTGACCGCTTCCATGAGTTCCC | 10 | 32 | 17 | 15 | 20 | 28 |
| 891 | 636 | 30139 | 82.1 | TCGTGACCGTCTGGACGTGCGACC | 10 | 32 | 19 | 34 | 33 | 32 |
| 892 | 637 | 40112 | 78.1 | TCGTGACCATCGTCGTAGGATGCG | 10 | 32 | 24 | 10 | 25 | 29 |
| 893 | 639 | 2614 | 76.4 | TCGTGTGCAATCTCTGCCATCAGC | 10 | 33 | 4 | 8 | 15 | 31 |
| 894 | 640 | 2615 | 80.8 | TCGTGTGCTCTGCCATAGCCGCAA | 10 | 33 | 8 | 15 | 36 | 21 |
| 895 | 641 | 2616 | 80.9 | TCGTGTGCTGTCGCAATCCCGATG | 10 | 33 | 9 | 21 | 28 | 27 |
| 896 | 642 | 30141 | 78.3 | TCGTGTGCCTTGATACCACGCAGC | 10 | 33 | 11 | 5 | 30 | 31 |
| 897 | 643 | 20269 | 76.2 | TCGTGTGCCTGTGCTTCCATATCG | 10 | 33 | 14 | 17 | 15 | 24 |
| 898 | 645 | 20270 | 79.1 | TCGTGTGCGGTAACCTACGGACGG | 10 | 33 | 18 | 23 | 35 | 35 |
| 899 | 646 | 2626 | 78.8 | TCGTGTGCGTCTGGACAGTGCGTT | 10 | 33 | 19 | 34 | 22 | 12 |
| 900 | 647 | 2627 | 78.6 | TCGTGTGCGAGTCACGAGGAGTGC | 10 | 33 | 20 | 30 | 25 | 33 |
| 901 | 648 | 2628 | 77.9 | TCGTGTGCGCAAAAAGAGCCTCTG | 10 | 33 | 21 | 6 | 36 | 8 |
| 902 | 651 | 2637 | 80.8 | TCGTGGACTTGATCCCTGCGCGTT | 10 | 34 | 1 | 28 | 29 | 12 |
| 903 | 652 | 2638 | 80.6 | TCGTGGACAATCCAGCGACCCGTT | 10 | 34 | 4 | 31 | 32 | 12 |
| 904 | 653 | 2639 | 79.8 | TCGTGGACAAAGGCAAGTGCCGAA | 10 | 34 | 6 | 21 | 33 | 16 |
| 905 | 654 | 20272 | 78.4 | TCGTGGACCTTGGACCGTCTACGG | 10 | 34 | 11 | 32 | 19 | 35 |
| 906 | 655 | 40114 | 76.8 | TCGTGGACCTGTTGCGCCTAAAAG | 10 | 34 | 14 | 29 | 26 | 6 |
| 907 | 656 | 40115 | 79.4 | TCGTGGACGAGTTCTGGTGCGACC | 10 | 34 | 20 | 8 | 33 | 32 |
| 908 | 658 | 13764 | 78.8 | TCGTGGACGATGCCTACAGCCCAT | 10 | 34 | 27 | 26 | 31 | 15 |
| 909 | 659 | 13765 | 77.5 | TCGTGGACTCCCTCCCATACAGCC | 10 | 34 | 28 | 28 | 5 | 36 |
| 910 | 660 | 2653 | 81.4 | TCGTGGACTGCGGTGCCTCAGACC | 10 | 34 | 29 | 33 | 13 | 32 |
| 911 | 661 | 40117 | 77.7 | TCGTGGACCACGTTAGATCGGCAA | 10 | 34 | 30 | 3 | 24 | 21 |
| 912 | 662 | 2658 | 79.7 | TCGTGGACAGCCCCATAGTGCGAA | 10 | 34 | 36 | 15 | 22 | 16 |
| 913 | 664 | 30143 | 77.1 | TCGTACGGTCGTTCTGATCGCGTT | 10 | 35 | 10 | 8 | 24 | 12 |
| 914 | 665 | 13771 | 78.3 | TCGTACGGCCATGGTATCGTGCAA | 10 | 35 | 15 | 18 | 10 | 21 |
| 915 | 666 | 40118 | 76.7 | TCGTACGGCCTAATCGCTCAATCG | 10 | 35 | 26 | 24 | 13 | 24 |
| 916 | 668 | 2677 | 75.5 | TCGTAGCCCTTGACAGCGCAACCTA | 10 | 36 | 1 | 31 | 21 | 26 |
| 917 | 669 | 2681 | 78.8 | TCGTAGCCTGTCGGTAAGCCTGCG | 10 | 36 | 9 | 18 | 36 | 29 |
| 918 | 670 | 13779 | 75 | TCGTAGCCTCGTAGGACTGTTGCG | 10 | 36 | 10 | 25 | 14 | 29 |

FIG. 25S

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 919 | 671 | 13780 | 77.5 | TCGTAGCCCGTTTCTGTTGATGCG | 10 | 36 | 12 | 8 | 1 | 29 |
| 920 | 672 | 13781 | 77.8 | TCGTAGCCCCATGAGTGACCCCAT | 10 | 36 | 15 | 20 | 32 | 15 |
| 921 | 673 | 30148 | 78.6 | TCGTAGCCTGCGATACTCCCCACG | 10 | 36 | 29 | 5 | 28 | 30 |
| 922 | 674 | 2696 | 78 | CTTGTTGAAGCCGACCGGTAACGG | 11 | 1 | 36 | 32 | 18 | 35 |
| 923 | 675 | 2703 | 81.4 | CTTGAATCGACCACGGGTGCACGG | 11 | 4 | 32 | 35 | 33 | 35 |
| 924 | 676 | 2709 | 79.9 | CTTGAAAGTCCCGGACCGAATGCG | 11 | 6 | 28 | 34 | 16 | 29 |
| 925 | 677 | 2719 | 78.9 | CTTGTCTGCACGGACCCCTATGCG | 11 | 8 | 30 | 32 | 26 | 29 |
| 926 | 680 | 20288 | 75.6 | CTTGCTTGACCTGCAAACGGTTGA | 11 | 11 | 23 | 21 | 35 | 1 |
| 927 | 681 | 2735 | 75.4 | CTTGCTTGATCGTTAGTGCGACGG | 11 | 11 | 24 | 3 | 29 | 35 |
| 928 | 682 | 40122 | 77.8 | CTTGCTTGCCTACTTGCACGGCAA | 11 | 11 | 26 | 11 | 30 | 21 |
| 929 | 683 | 2737 | 79.3 | CTTGCTTGGATGGACATCGCGAA | 11 | 11 | 27 | 34 | 24 | 16 |
| 930 | 684 | 30149 | 78.1 | CTTGCGTTTGAAGCCGGTAACGG | 11 | 12 | 1 | 36 | 18 | 35 |
| 931 | 685 | 13804 | 77.7 | CTTGCGTTACCTTGCGGACCACCT | 11 | 12 | 23 | 29 | 32 | 23 |
| 932 | 687 | 2767 | 78.3 | CTTGCTCACACGGGACAGGAAGCC | 11 | 13 | 30 | 34 | 25 | 36 |
| 933 | 688 | 2769 | 81.9 | CTTGCTCAGTGCCAGCGACCACGG | 11 | 13 | 33 | 31 | 32 | 35 |
| 934 | 689 | 40125 | 78 | CTTGCTGTGCAAGTGCCGTTACGG | 11 | 14 | 21 | 33 | 12 | 35 |
| 935 | 690 | 30151 | 79 | CTTGCCATCCATCACGGCAACCAT | 11 | 15 | 15 | 30 | 21 | 15 |
| 936 | 691 | 30152 | 77.2 | CTTGCCATGCTTAGTGGTGCAGCC | 11 | 15 | 17 | 22 | 33 | 36 |
| 937 | 693 | 30153 | 76.6 | CTTGCGAATTGAATCGGTGCCCTA | 11 | 16 | 1 | 24 | 33 | 26 |
| 938 | 694 | 40127 | 75 | CTTGCGAAGCTTCCTAGGACGCTT | 11 | 16 | 17 | 26 | 34 | 17 |
| 939 | 696 | 2811 | 76.9 | CTTGGCTTCCATCACGTCCCAGTG | 11 | 17 | 15 | 30 | 28 | 22 |
| 940 | 697 | 2813 | 79.2 | CTTGGCTTGTCTTCCCGACCGGAC | 11 | 17 | 19 | 28 | 32 | 34 |
| 941 | 698 | 40128 | 79.3 | CTTGGCTTCAGCGGACCTGTTCCC | 11 | 17 | 31 | 34 | 14 | 28 |
| 942 | 699 | 30155 | 78.1 | CTTGGGCTTGTGCCTTGCTTGGCTT | 11 | 17 | 33 | 11 | 11 | 17 |
| 943 | 700 | 40129 | 77.9 | CTTGGGCTTACGGCGTTAGCCAGGA | 11 | 17 | 35 | 12 | 36 | 25 |
| 944 | 701 | 2828 | 75.3 | CTTGGTCTTCGTCCTATCCCACGG | 11 | 19 | 10 | 26 | 28 | 35 |
| 945 | 702 | 20300 | 78.3 | CTTGGTCTCACGGCAAGACCCAGC | 11 | 19 | 30 | 21 | 32 | 31 |
| 946 | 703 | 40132 | 76.8 | CTTGGCAAGCTTTGATTCCCCCAT | 11 | 21 | 17 | 2 | 28 | 15 |
| 947 | 704 | 2847 | 77.2 | CTTGGCAAGAGTGGACAGGATGCG | 11 | 21 | 20 | 34 | 25 | 29 |
| 948 | 705 | 30156 | 76.1 | CTTGGCAAACCTTTAGCACGCGTT | 11 | 21 | 23 | 3 | 30 | 12 |
| 949 | 706 | 30157 | 75.2 | CTTGGCAAATCGAAAGGATGGCTT | 11 | 21 | 24 | 6 | 27 | 17 |
| 950 | 707 | 40133 | 77.1 | CTTGGCAAAGGAAGCCCTGTTCGT | 11 | 21 | 25 | 36 | 14 | 10 |
| 951 | 708 | 30158 | 82.7 | CTTGGCAAGACCAGCCGTGCGACC | 11 | 21 | 32 | 36 | 33 | 32 |
| 952 | 709 | 2858 | 77.2 | CTTGAGTGCGAAGACCATCGACGG | 11 | 22 | 16 | 32 | 24 | 35 |
| 953 | 710 | 2866 | 81.3 | CTTGACCTGTGCGGACAGCCCGAA | 11 | 23 | 33 | 34 | 36 | 16 |
| 954 | 712 | 30159 | 78.4 | CTTGAGGATGCGACCTCAGCGGAC | 11 | 25 | 29 | 23 | 31 | 34 |
| 955 | 713 | 2881 | 80.6 | CTTGAGGACACGAGCCCAGCCGAA | 11 | 25 | 30 | 36 | 31 | 16 |
| 956 | 714 | 13849 | 75.2 | CTTGCCTAATCGAGGATGCGGTCT | 11 | 26 | 24 | 25 | 29 | 19 |
| 957 | 715 | 13852 | 75.7 | CTTGCCTAACGGTCCCAATCCTCA | 11 | 26 | 35 | 28 | 4 | 13 |
| 958 | 716 | 20309 | 75 | CTTGGATGTCGTGACCAGCCTCTG | 11 | 27 | 10 | 32 | 36 | 8 |
| 959 | 717 | 13853 | 78.8 | CTTGGATGCTTGCAGCAGCCCTA | 11 | 27 | 11 | 31 | 36 | 26 |
| 960 | 718 | 2898 | 76.7 | CTTGGATGCGTTGCTTGACCGAGT | 11 | 27 | 12 | 17 | 32 | 20 |
| 961 | 719 | 2899 | 77.6 | CTTGGATGCTGTTCGTCAGCCGAA | 11 | 27 | 14 | 10 | 31 | 16 |
| 962 | 720 | 30160 | 77.9 | CTTGGATGGCAAAGCCGAGTGCTT | 11 | 27 | 21 | 36 | 20 | 17 |
| 963 | 722 | 2910 | 76.8 | CTTGTCCCCTGTCTTGAGCCCAT | 11 | 28 | 14 | 11 | 36 | 15 |
| 964 | 723 | 2921 | 78.6 | CTTGTCCCACGGGCAATTGAATCG | 11 | 28 | 35 | 21 | 1 | 24 |
| 965 | 724 | 2926 | 81.8 | CTTGTGCGTGTCCAGCGTGCTCCC | 11 | 29 | 9 | 31 | 33 | 28 |
| 966 | 725 | 13864 | 78.1 | CTTGTGCGTCGTTTGACAGCCAGC | 11 | 29 | 10 | 1 | 31 | 31 |
| 967 | 728 | 2938 | 80.4 | CTTGTGCGTGCGCCATTCTGCTGT | 11 | 29 | 29 | 15 | 8 | 14 |
| 968 | 729 | 2940 | 79 | CTTGTGCGCAGCAGTGCACGAATC | 11 | 29 | 31 | 22 | 30 | 4 |
| 969 | 730 | 13871 | 77.2 | CTTGCACGAATCTCTGGACCGTGC | 11 | 30 | 4 | 8 | 32 | 33 |

FIG. 25T

| SEQ ID NO: | 4,633 ID# | HEX ID# | Tm | ZIPCODE (5'-3') | TETRAMER NUMBERS | | | | |
|---|---|---|---|---|---|---|---|---|---|
| 970 | 732 | 2947 | 75.8 | CTTGCACGCTTGTTGAGCAATCGT | 11 | 30 | 11 | 1 | 21 | 10 |
| 971 | 734 | 2951 | 79.1 | CTTGCACGAGTGGCAAAGCCCTTG | 11 | 30 | 22 | 21 | 36 | 11 |
| 972 | 735 | 40137 | 76.6 | CTTGCACGAGGACCTACACGCCAT | 11 | 30 | 25 | 26 | 30 | 15 |
| 973 | 736 | 2959 | 76.4 | CTTGCAGCTGATACGGGCAAGGAC | 11 | 31 | 2 | 35 | 21 | 34 |
| 974 | 737 | 2960 | 80 | CTTGCAGCAATCGTGCATCGAGCC | 11 | 31 | 4 | 33 | 24 | 36 |
| 975 | 738 | 30162 | 76.8 | CTTGCAGCCTCAGGTATCCCCCAT | 11 | 31 | 13 | 18 | 28 | 15 |
| 976 | 739 | 13879 | 78 | CTTGCAGCGGTAATCGTGCGTGTC | 11 | 31 | 18 | 24 | 29 | 9 |
| 977 | 740 | 13880 | 75.3 | CTTGCAGCGTCTAAAGACGGCTCA | 11 | 31 | 19 | 6 | 35 | 13 |
| 978 | 741 | 13883 | 77.4 | CTTGCAGCGACCTACAGTGCCAGC | 11 | 31 | 32 | 7 | 33 | 31 |
| 979 | 742 | 2979 | 78.4 | CTTGGACCTTGAGACCACGGGCAA | 11 | 32 | 1 | 32 | 35 | 21 |
| 980 | 743 | 40139 | 77.2 | CTTGGACCAGGACCTAACGGACGG | 11 | 32 | 25 | 26 | 35 | 35 |
| 981 | 744 | 20324 | 76.7 | CTTGGACCGGACCCTAGATGCCAT | 11 | 32 | 34 | 26 | 27 | 15 |
| 982 | 745 | 30163 | 76.3 | CTTGGTGCGGTACTCAAGCCCTTG | 11 | 33 | 18 | 13 | 36 | 11 |
| 983 | 746 | 40140 | 80.3 | CTTGGTGCGTCTTCGTGTGCCGAA | 11 | 33 | 19 | 10 | 33 | 16 |
| 984 | 747 | 13893 | 75.8 | CTTGGTGCGAGTAATCGACCCGTT | 11 | 33 | 20 | 4 | 32 | 12 |
| 985 | 748 | 20327 | 78.4 | CTTGGTGCGGACTCTGTGCGTTGA | 11 | 33 | 34 | 8 | 29 | 1 |
| 986 | 750 | 30165 | 76.8 | CTTGGGACATCGAGGAGCTTGCAA | 11 | 34 | 24 | 25 | 17 | 21 |
| 987 | 751 | 3019 | 78.6 | CTTGGGACGACCCGTTGCTTCTCA | 11 | 34 | 32 | 12 | 17 | 13 |
| 988 | 752 | 40142 | 77.6 | CTTGACGGGAGTAGCCACGGGGTA | 11 | 35 | 20 | 36 | 35 | 18 |
| 989 | 754 | 13905 | 77.6 | CTTGACGGACCTCACGGACCCTGT | 11 | 35 | 23 | 30 | 32 | 14 |
| 990 | 755 | 30166 | 77.4 | CTTGACGGAGGATCGTAGCCGGAC | 11 | 35 | 25 | 10 | 36 | 34 |
| 991 | 756 | 13906 | 77.9 | CTTGACGGGATGGGTAAGGATGCG | 11 | 35 | 27 | 18 | 25 | 29 |
| 992 | 757 | 3036 | 76.8 | CTTGAGCCTTGACTCATCCCGCAA | 11 | 36 | 1 | 13 | 28 | 21 |
| 993 | 758 | 3037 | 78.5 | CTTGAGCCTGATAGCCTGCGACGG | 11 | 36 | 2 | 36 | 29 | 35 |
| 994 | 761 | 13910 | 78.2 | CTTGAGCCGAGTGTGCTGATTGCG | 11 | 36 | 20 | 33 | 2 | 29 |
| 995 | 763 | 3053 | 75.4 | CTTGAGCCTCCCTGATCCATACGG | 11 | 36 | 28 | 2 | 15 | 35 |
| 996 | 764 | 13912 | 79.1 | CTTGAGCCCAGCGGACTACATGCG | 11 | 36 | 31 | 34 | 7 | 29 |
| 997 | 765 | 20336 | 77.6 | CTTGAGCCGGACGAGTTCGTAGCC | 11 | 36 | 34 | 20 | 10 | 36 |
| 998 | 766 | 30168 | 79.2 | CGTTTTGAATCGGGACGTGCAGGA | 12 | 1 | 24 | 34 | 33 | 25 |
| 999 | 767 | 13918 | 80.8 | CGTTTGATCACGCTCATGCGCAGC | 12 | 2 | 30 | 13 | 29 | 31 |
| 1000 | 768 | 13920 | 75 | CGTTTAGGCAAGATGGGACCGTT | 12 | 3 | 21 | 27 | 34 | 12 |
| 1001 | 769 | 40145 | 75.4 | CGTTAATCGCAAGCTTTGTCGTGC | 12 | 4 | 21 | 17 | 9 | 33 |
| 1002 | 770 | 3086 | 79.7 | CGTTAATCTCCCCACGTCCCGTGC | 12 | 4 | 28 | 30 | 28 | 33 |
| 1003 | 771 | 40146 | 78.2 | CGTTAATCCACGCTCAAGCCAGCC | 12 | 4 | 30 | 13 | 36 | 36 |
| 1004 | 772 | 30172 | 76.3 | CGTTAAAGCCATTCCCAAAGCACG | 12 | 6 | 15 | 28 | 6 | 30 |
| 1005 | 774 | 3109 | 75 | CGTTTCTGCGTTGGTAAGGAGCAA | 12 | 8 | 12 | 18 | 25 | 21 |
| 1006 | 775 | 13938 | 75.1 | CGTTTCTGGCAATTAGCTTGCAA | 12 | 8 | 21 | 3 | 11 | 16 |
| 1007 | 776 | 30174 | 77.9 | CGTTTCTGGGACAATCGCAATCCC | 12 | 8 | 34 | 4 | 21 | 28 |
| 1008 | 777 | 3121 | 78.4 | CGTTTCTGAGCCGGACAGCCAAAG | 12 | 8 | 36 | 34 | 36 | 6 |
| 1009 | 778 | 40147 | 78.5 | CGTTTGTCCCATCACGTGTCTGCG | 12 | 9 | 15 | 30 | 9 | 29 |
| 1010 | 779 | 3127 | 79.6 | CGTTTGTCGTCTTGCGGGTATGCG | 12 | 9 | 19 | 29 | 18 | 29 |
| 1011 | 780 | 3129 | 79.6 | CGTTTGTCATCGCGTTCACGTCCC | 12 | 9 | 24 | 12 | 30 | 28 |
| 1012 | 781 | 3131 | 77.7 | CGTTTGTCGATGCCATACCTTGCG | 12 | 9 | 27 | 15 | 23 | 29 |
| 1013 | 782 | 20344 | 76.1 | CGTTTCGTAAAGCGAATGCGACCT | 12 | 10 | 6 | 16 | 29 | 23 |
| 1014 | 783 | 30177 | 76.9 | CGTTTCGTGGTAACGGCGTTATCG | 12 | 10 | 18 | 35 | 12 | 24 |
| 1015 | 785 | 40148 | 76 | CGTTTCGTACGGAAAGCTTGCCAT | 12 | 10 | 35 | 6 | 11 | 15 |
| 1016 | 786 | 40149 | 80.2 | CGTTCTTGCAGCCGTTCCATGCAA | 12 | 11 | 31 | 12 | 15 | 21 |
| 1017 | 787 | 30179 | 76.9 | CGTTCGTTTTGAGCAATCCCATCG | 12 | 12 | 1 | 21 | 28 | 24 |
| 1018 | 788 | 3159 | 78 | CGTTCGTTAAAGACGGTCCCGTGC | 12 | 12 | 6 | 35 | 28 | 33 |
| 1019 | 789 | 40151 | 76.4 | CGTTCGTTCGAAAAAGAGGATGCG | 12 | 12 | 16 | 6 | 25 | 29 |
| 1020 | 790 | 3165 | 80.4 | CGTTCGTTGTCTTGCGTGCGCTGT | 12 | 12 | 19 | 29 | 29 | 14 |

FIG. 25U

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 1021 | 791 | 13963 | 81.1 | CGTTCTCAATCGGACCCACGCGAA | 12 | 13 | 24 | 32 | 30 | 16 |
| 1022 | 792 | 3182 | 78 | CGTTCTCAACGGGACCCTTGATCG | 12 | 13 | 35 | 32 | 11 | 24 |
| 1023 | 793 | 3183 | 76.2 | CGTTCTGTTCGTAGGAACGGACGG | 12 | 14 | 10 | 25 | 35 | 35 |
| 1024 | 794 | 3190 | 80.7 | CGTTCCATTGTCGACCAGCCCAGC | 12 | 15 | 9 | 32 | 36 | 31 |
| 1025 | 795 | 13969 | 77.7 | CGTTCCATCCATCGAACTGTTGCG | 12 | 15 | 15 | 16 | 14 | 29 |
| 1026 | 796 | 13970 | 79.3 | CGTTCCATATCGCCATTGCGGATG | 12 | 15 | 24 | 15 | 29 | 27 |
| 1027 | 797 | 3201 | 77 | CGTTCCATGATGTGATCAGCGCAA | 12 | 15 | 27 | 2 | 31 | 21 |
| 1028 | 798 | 3202 | 78 | CGTTCCATGACCAATCGATGCGAA | 12 | 15 | 32 | 4 | 27 | 16 |
| 1029 | 799 | 3203 | 78.3 | CGTTCCATGGACGCAAACCTCGTT | 12 | 15 | 34 | 21 | 23 | 12 |
| 1030 | 800 | 20357 | 75.9 | CGTTCCATACGGAGCCTCTGAGGA | 12 | 15 | 35 | 36 | 8 | 25 |
| 1031 | 801 | 30185 | 76.8 | CGTTCGAATCGTAGCCGATGCTGT | 12 | 16 | 10 | 36 | 27 | 14 |
| 1032 | 802 | 13972 | 79 | CGTTCGAACTTGCACGGCTTGACC | 12 | 16 | 11 | 30 | 17 | 32 |
| 1033 | 803 | 3210 | 77 | CGTTCGAACTCAGATGTCCCGTGC | 12 | 16 | 13 | 27 | 28 | 33 |
| 1034 | 805 | 20361 | 75.5 | CGTTCGAAGAGTTGCGGCTTACCT | 12 | 16 | 20 | 29 | 17 | 23 |
| 1035 | 806 | 40152 | 76.2 | CGTTCGAAATCGTACAACGGAGCC | 12 | 16 | 24 | 7 | 35 | 36 |
| 1036 | 807 | 13977 | 80.1 | CGTTCGAAGACCGACCCACGGGTA | 12 | 16 | 32 | 32 | 30 | 18 |
| 1037 | 808 | 20363 | 78 | CGTTGCTTGTCTACGGGGACGACC | 12 | 17 | 19 | 35 | 34 | 32 |
| 1038 | 812 | 3249 | 75.2 | CGTTGTCTCGTTATCGGTCTTGCG | 12 | 19 | 12 | 24 | 19 | 29 |
| 1039 | 813 | 3257 | 80.1 | CGTTGAGTTCGTGCAAACGGGCAA | 12 | 20 | 10 | 21 | 35 | 21 |
| 1040 | 814 | 3260 | 78.1 | CGTTGAGTCAGCCGAACGTTTCCC | 12 | 20 | 31 | 16 | 12 | 28 |
| 1041 | 815 | 20369 | 75.9 | CGTTGAGTGGACGATGCAGCAATC | 12 | 20 | 34 | 27 | 31 | 4 |
| 1042 | 816 | 13992 | 77.5 | CGTTGCAATGATGCTTTGCGGTCT | 12 | 21 | 2 | 17 | 29 | 19 |
| 1043 | 817 | 40155 | 77 | CGTTGCAACGAACGAAAATCGACC | 12 | 21 | 16 | 16 | 4 | 32 |
| 1044 | 818 | 30191 | 78.2 | CGTTGCAAGGTAGACCTGCGGACC | 12 | 21 | 18 | 32 | 29 | 32 |
| 1045 | 819 | 13994 | 75.2 | CGTTGCAAGAGTAAAGTGCGCGTT | 12 | 21 | 20 | 6 | 29 | 12 |
| 1046 | 820 | 30192 | 76.4 | CGTTGCAAACCTCCTAGCAAACGG | 12 | 21 | 23 | 26 | 21 | 35 |
| 1047 | 821 | 20374 | 75.3 | CGTTGCAACAGCACCTCTGTAGCC | 12 | 21 | 31 | 23 | 14 | 36 |
| 1048 | 822 | 3277 | 77.8 | CGTTGCAAAGCCGCTTTACAGCAA | 12 | 21 | 36 | 17 | 7 | 21 |
| 1049 | 823 | 3281 | 77.9 | CGTTAGTGCACGGGACACCTTCCC | 12 | 22 | 30 | 34 | 23 | 28 |
| 1050 | 824 | 14003 | 80.7 | CGTTAGTGCAGCCAGCGGACGCTT | 12 | 22 | 31 | 31 | 34 | 17 |
| 1051 | 825 | 14004 | 80.9 | CGTTAGTGGTGCCACGGACCCGAA | 12 | 22 | 33 | 30 | 32 | 16 |
| 1052 | 826 | 3291 | 80.2 | CGTTACCTGACCTGCGCGTTGCAA | 12 | 23 | 32 | 29 | 12 | 21 |
| 1053 | 827 | 14013 | 79.3 | CGTTATCGCTGTCAGCGTGCCCAT | 12 | 24 | 14 | 31 | 33 | 15 |
| 1054 | 828 | 30193 | 76.3 | CGTTATCGGGTATCGTGACCCGAA | 12 | 24 | 18 | 10 | 32 | 16 |
| 1055 | 829 | 40156 | 77 | CGTTATCGGACCTCTGGGACGCTT | 12 | 24 | 32 | 8 | 34 | 17 |
| 1056 | 830 | 3309 | 76 | CGTTAGGATGCGTACAGTGCGTGC | 12 | 25 | 29 | 7 | 33 | 33 |
| 1057 | 831 | 14021 | 77.5 | CGTTAGGAAGCCGGTAGGACTGCG | 12 | 25 | 36 | 18 | 34 | 29 |
| 1058 | 833 | 30194 | 76.1 | CGTTGATGCGTTAATCGGACTCCC | 12 | 27 | 12 | 4 | 34 | 28 |
| 1059 | 834 | 14032 | 79.2 | CGTTGATGGACCGTGCCCTAGCAA | 12 | 27 | 32 | 33 | 26 | 21 |
| 1060 | 835 | 40157 | 81 | CGTTGATGGGACGACCCACGAGGA | 12 | 27 | 34 | 32 | 30 | 25 |
| 1061 | 839 | 3356 | 78.6 | CGTTTCCAGTGGGTACACGGTGC | 12 | 28 | 22 | 18 | 30 | 33 |
| 1062 | 840 | 40160 | 76.3 | CGTTTCCCCCTAAATCCCATCAGC | 12 | 28 | 26 | 4 | 15 | 31 |
| 1063 | 841 | 3361 | 77.3 | CGTTTCCCTCCCTCGTCGAAGATG | 12 | 28 | 28 | 10 | 16 | 27 |
| 1064 | 842 | 14040 | 80.9 | CGTTTCCCTGCGCCATGGTACGAA | 12 | 28 | 29 | 15 | 18 | 16 |
| 1065 | 845 | 40162 | 78.5 | CGTTTGCGATACAGCCTCCCCTCA | 12 | 29 | 5 | 36 | 28 | 13 |
| 1066 | 846 | 40164 | 79.9 | CGTTTGCGCGAATGCGTTAGCTTG | 12 | 29 | 16 | 29 | 3 | 11 |
| 1067 | 847 | 20392 | 80.7 | CGTTTGCGGCTTGTGCCCTCAGCTT | 12 | 29 | 17 | 33 | 13 | 17 |
| 1068 | 848 | 40165 | 78.3 | CGTTTGCGGTCTTACACACGCGAA | 12 | 29 | 19 | 7 | 30 | 16 |
| 1069 | 849 | 14044 | 76.9 | CGTTTGCGAGGAATCGTTAGCGAA | 12 | 29 | 25 | 24 | 3 | 16 |
| 1070 | 850 | 3381 | 79.3 | CGTTTGCGGATGCCATGCTTGAGT | 12 | 29 | 27 | 15 | 17 | 20 |
| 1071 | 851 | 14045 | 78.5 | CGTTTGCGTCCCTTGAGCTTCAGC | 12 | 29 | 28 | 1 | 17 | 31 |

FIG. 25V

| SEQ ID NO: | 4,633 ID# | REX ID# | Tm | ZIPCODE (5'-3') | TETRAMER NUMBERS | | | | |
|---|---|---|---|---|---|---|---|---|---|
| 1072 | 852 | 14046 | 82 | CGTTTGCGCACGCGTTGCTTTGAT | 12 | 29 | 30 | 12 | 17 | 2 |
| 1073 | 853 | 40166 | 78.2 | CGTTCACGTCGTTGTCCAGCGGTA | 12 | 30 | 10 | 9 | 31 | 18 |
| 1074 | 854 | 20396 | 76.2 | CGTTCACGCTGTGATCCATCGAA | 12 | 30 | 11 | 2 | 15 | 16 |
| 1075 | 855 | 40167 | 78.3 | CGTTCACGCTGTCTTGTGCGGGTA | 12 | 30 | 14 | 11 | 29 | 18 |
| 1076 | 856 | 40171 | 76.1 | CGTTCACGGATGTTAGCGAATCCC | 12 | 30 | 27 | 3 | 16 | 28 |
| 1077 | 858 | 14053 | 81 | CGTTCACGCAGCGCAATCGTGGTA | 12 | 30 | 31 | 21 | 10 | 18 |
| 1078 | 859 | 20400 | 75.2 | CGTTCACGGACCAAAGTTAGTGCG | 12 | 30 | 32 | 6 | 3 | 29 |
| 1079 | 860 | 3401 | 78.7 | CGTTCACGACGGGTCTGCAAGCTT | 12 | 30 | 35 | 19 | 21 | 17 |
| 1080 | 861 | 20402 | 79.6 | CGTTCACGAGCCTCGTCACGCCTA | 12 | 30 | 36 | 10 | 30 | 26 |
| 1081 | 862 | 20403 | 75 | CGTTCAGCTCTGGACCAAAGCTCA | 12 | 31 | 8 | 32 | 6 | 13 |
| 1082 | 863 | 30197 | 77.1 | CGTTCAGCGCTTCGTTTCTGCCTA | 12 | 31 | 17 | 12 | 8 | 26 |
| 1083 | 864 | 3411 | 80.5 | CGTTCAGCCACGCAGCAGGACTCA | 12 | 31 | 30 | 31 | 25 | 13 |
| 1084 | 865 | 14060 | 78.1 | CGTTCAGCGTGCTTGAAATCGTGC | 12 | 31 | 33 | 1 | 4 | 33 |
| 1085 | 866 | 3418 | 77.8 | CGTTGACCTCTGTCCCCAGCGAGT | 12 | 32 | 8 | 28 | 31 | 20 |
| 1086 | 868 | 40173 | 77.9 | CGTTGACCCTGTCGAACGAATCCC | 12 | 32 | 14 | 16 | 16 | 28 |
| 1087 | 869 | 3424 | 75.6 | CGTTGACCATCGTTAGCACGCCTA | 12 | 32 | 24 | 3 | 30 | 26 |
| 1088 | 870 | 3426 | 78.4 | CGTTGACCTGCGCTCAGGTAAGCC | 12 | 32 | 29 | 13 | 18 | 36 |
| 1089 | 871 | 40175 | 77.8 | CGTTGACCCAGCTCCCGTCTAGGA | 12 | 32 | 31 | 28 | 19 | 25 |
| 1090 | 873 | 3435 | 81 | CGTTGTGCTGTCCTTGCAGCTGCG | 12 | 33 | 9 | 11 | 31 | 29 |
| 1091 | 874 | 20413 | 75.9 | CGTTGTGCCTTGTACACAGCGACC | 12 | 33 | 11 | 7 | 31 | 32 |
| 1092 | 875 | 30199 | 78.1 | CGTTGTGCCTCAAAAGTCCCCAGC | 12 | 33 | 13 | 6 | 28 | 31 |
| 1093 | 876 | 40177 | 78.9 | CGTTGTGCGATGTGTCGCTTCAGC | 12 | 33 | 27 | 9 | 17 | 31 |
| 1094 | 877 | 3450 | 80.6 | CGTTGTGCGACCGTCTATCGTGCG | 12 | 33 | 32 | 19 | 24 | 29 |
| 1095 | 879 | 30200 | 78.1 | CGTTGGACCGTTGGACCGAATGAT | 12 | 34 | 12 | 34 | 16 | 2 |
| 1096 | 880 | 30202 | 77.1 | CGTTGGACGGTACGAAGCTTCACG | 12 | 34 | 18 | 16 | 17 | 30 |
| 1097 | 881 | 40178 | 79.7 | CGTTGGACAGGATGTCACGGCAGC | 12 | 34 | 25 | 9 | 35 | 31 |
| 1098 | 882 | 14078 | 77.9 | CGTTGGACGGACTTGAAGTGTGCG | 12 | 34 | 34 | 1 | 22 | 29 |
| 1099 | 883 | 3463 | 80.8 | CGTTGGACACGGCCATCTGTGCAA | 12 | 34 | 35 | 15 | 14 | 21 |
| 1100 | 884 | 14079 | 76.9 | CGTTACGGTTGAACCTGGACGTGC | 12 | 35 | 1 | 23 | 34 | 33 |
| 1101 | 885 | 3465 | 77.5 | CGTTACGGAATCCTTGCACGCTCA | 12 | 35 | 4 | 11 | 30 | 13 |
| 1102 | 886 | 14080 | 77.9 | CGTTACGGAAAGGACCGACCATCG | 12 | 35 | 6 | 32 | 32 | 24 |
| 1103 | 887 | 3468 | 78 | CGTTACGGTCTGGACCGCAAGGAC | 12 | 35 | 8 | 32 | 21 | 34 |
| 1104 | 888 | 30203 | 78 | CGTTACGGCTGTCTTGTCCCGACC | 12 | 35 | 14 | 11 | 28 | 32 |
| 1105 | 889 | 3472 | 75 | CGTTACGGGAGTTTGATTGATGCG | 12 | 35 | 20 | 1 | 1 | 29 |
| 1106 | 890 | 30204 | 80.2 | CGTTACGGGATGCAGCAGTGCGAA | 12 | 35 | 27 | 31 | 22 | 16 |
| 1107 | 891 | 30205 | 77.3 | CGTTAGCCTTGAGTGCCTTGCACG | 12 | 36 | 1 | 33 | 11 | 30 |
| 1108 | 892 | 14087 | 79.2 | CGTTAGCCTGATTGCGCAGCCTTG | 12 | 36 | 2 | 29 | 31 | 11 |
| 1109 | 893 | 14097 | 77.2 | CGTTAGCCGACCTGTCATCGCTTG | 12 | 36 | 32 | 9 | 24 | 11 |
| 1110 | 894 | 3498 | 78.1 | CGTTAGCCACGGCTCAAATCGACC | 12 | 36 | 35 | 13 | 4 | 32 |
| 1111 | 895 | 3502 | 77.2 | CTCATTGAAGCCTCGTACGGTGCG | 13 | 1 | 36 | 10 | 35 | 29 |
| 1112 | 896 | 14102 | 79.4 | CTCAAATCGCTTCAGCAGCCTGCG | 13 | 4 | 17 | 31 | 36 | 29 |
| 1113 | 897 | 14106 | 79.2 | CTCAAAAGCGTTGTGCCAGCAGCC | 13 | 6 | 12 | 33 | 31 | 36 |
| 1114 | 900 | 3525 | 79.9 | CTCATGTCTGCGCAGCTGCGGTCT | 13 | 9 | 29 | 31 | 29 | 19 |
| 1115 | 902 | 3532 | 82.1 | CTCATCGTCACGGGACTGCGGCAA | 13 | 10 | 30 | 34 | 29 | 21 |
| 1116 | 903 | 20437 | 76.8 | CTCATCGTAGCCAGGAGTGCCGAA | 13 | 10 | 36 | 25 | 33 | 16 |
| 1117 | 904 | 20439 | 76.2 | CTCACTTGAGTGCGTTCGTTTGCG | 13 | 11 | 22 | 12 | 12 | 29 |
| 1118 | 905 | 20441 | 76 | CTCACGTTTCGTGACCTGTCTGCG | 13 | 12 | 10 | 32 | 9 | 29 |
| 1119 | 906 | 14112 | 78.1 | CTCACGTTACGGCGAAAGGAACGG | 13 | 12 | 35 | 16 | 25 | 35 |
| 1120 | 907 | 3546 | 81.2 | CTCACTCAACGGCGAATGCGCCAT | 13 | 13 | 35 | 16 | 29 | 15 |
| 1121 | 908 | 3547 | 79.6 | CTCACCATGCTTGGACGGACACGG | 13 | 15 | 17 | 34 | 34 | 35 |
| 1122 | 909 | 3548 | 75.7 | CTCACCATTGCGAAAGGACCCTGT | 13 | 15 | 29 | 6 | 32 | 14 |

FIG. 25W

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 1123 | 910 | 14114 | 80.1 | CTCACGAAATCGATCGCAGCTGCG | 13 | 16 | 24 | 24 | 31 | 29 |
| 1124 | 911 | 3557 | 78 | CTCACGAACACGAGGAACGGTCCC | 13 | 16 | 30 | 25 | 35 | 28 |
| 1125 | 912 | 3558 | 82.6 | CTCACGAACAGCACGGCACGGTGC | 13 | 16 | 31 | 35 | 30 | 33 |
| 1126 | 913 | 30207 | 77.4 | CTCAGCAAACGGACGGAAAGGGAC | 13 | 21 | 35 | 35 | 6 | 34 |
| 1127 | 914 | 3582 | 80.1 | CTCAAGTGGTGCCGAAGTGCTGCG | 13 | 22 | 33 | 16 | 33 | 29 |
| 1128 | 915 | 3585 | 80.7 | CTCAACCTACGGTGCGGACCGTGC | 13 | 23 | 35 | 29 | 32 | 33 |
| 1129 | 916 | 20457 | 77.2 | CTCAATCGCTTGGCAAACGGTCTG | 13 | 24 | 11 | 21 | 35 | 8 |
| 1130 | 917 | 30208 | 77.4 | CTCAATCGCCATCACGCGTTTGAT | 13 | 24 | 15 | 30 | 12 | 2 |
| 1131 | 918 | 3591 | 76.5 | CTCAATCGGGTAGCTTCAGCGTGC | 13 | 24 | 18 | 17 | 31 | 33 |
| 1132 | 919 | 14129 | 78.8 | CTCAATCGACGGGTCTGGACACGG | 13 | 24 | 35 | 19 | 34 | 35 |
| 1133 | 920 | 3600 | 78.2 | CTCAAGGAGCTTCAGCCAGCCGAA | 13 | 25 | 17 | 31 | 31 | 16 |
| 1134 | 921 | 3601 | 81.6 | CTCAAGGACACGGTGCCACGACGG | 13 | 25 | 30 | 33 | 30 | 35 |
| 1135 | 922 | 14132 | 78.8 | CTCATCCCGCTTGCAACCATGACC | 13 | 28 | 17 | 21 | 15 | 32 |
| 1136 | 924 | 3624 | 80.7 | CTCATGCGAATCATCGCAGCCACG | 13 | 29 | 4 | 24 | 31 | 30 |
| 1137 | 925 | 3625 | 79 | CTCATGCGTCTGAGCCTGCGGTCT | 13 | 29 | 8 | 36 | 29 | 19 |
| 1138 | 926 | 3629 | 76.7 | CTCATGCGCTCAGGACCGTTTGAT | 13 | 29 | 13 | 34 | 12 | 2 |
| 1139 | 927 | 14135 | 76 | CTCATGCGGTCTAGCCCTTGTCGT | 13 | 29 | 19 | 36 | 11 | 10 |
| 1140 | 928 | 3637 | 77.2 | CTCATGCGTCCCCCTACCTAACGG | 13 | 29 | 28 | 26 | 26 | 35 |
| 1141 | 929 | 40180 | 80.5 | CTCATGCGGACCGCTTGACCTCGT | 13 | 29 | 32 | 17 | 32 | 10 |
| 1142 | 930 | 14139 | 79.2 | CTCACACGCCTAGGACACGGCAGC | 13 | 30 | 26 | 34 | 35 | 31 |
| 1143 | 931 | 3649 | 81.8 | CTCACACGCAGCGTGCCTCACACG | 13 | 30 | 31 | 33 | 13 | 30 |
| 1144 | 932 | 3650 | 80.6 | CTCACACGGACCGTCTGCAATGCG | 13 | 30 | 32 | 19 | 21 | 29 |
| 1145 | 933 | 3658 | 82.3 | CTCACAGCATCGAGCCACGGCGAA | 13 | 31 | 24 | 36 | 35 | 16 |
| 1146 | 934 | 14144 | 79.7 | CTCACAGCTGCGGGACAGGAGCAA | 13 | 31 | 29 | 34 | 25 | 21 |
| 1147 | 935 | 20484 | 77 | CTCAGACCGATGGTCTCCATTGCG | 13 | 32 | 27 | 19 | 15 | 29 |
| 1148 | 936 | 3672 | 79.4 | CTCAGACCGTGCGAGTAGCCTGCG | 13 | 32 | 33 | 20 | 36 | 29 |
| 1149 | 937 | 3691 | 80.8 | CTCAGGACGATGCACGTCCCGGAC | 13 | 34 | 27 | 30 | 28 | 34 |
| 1150 | 938 | 14153 | 78.5 | CTCAGGACGGACCCATAGCCCCAT | 13 | 34 | 34 | 15 | 36 | 15 |
| 1151 | 939 | 30211 | 75.5 | CTCAACGGCCATAAAGGCAAGACC | 13 | 35 | 15 | 6 | 21 | 32 |
| 1152 | 940 | 3701 | 75.4 | CTCAACGGGTCTCCATTTGAAGCC | 13 | 35 | 19 | 15 | 1 | 36 |
| 1153 | 941 | 3703 | 78.8 | CTCAACGGATCGGACCTGTCCACG | 13 | 35 | 24 | 32 | 9 | 30 |
| 1154 | 942 | 40182 | 78.7 | CTCAACGGAGGAAAAGTGCGGCAA | 13 | 35 | 25 | 6 | 29 | 21 |
| 1155 | 943 | 20493 | 78 | CTCAACGGCCTAGGACGTGCGTCT | 13 | 35 | 26 | 34 | 33 | 19 |
| 1156 | 944 | 3708 | 76 | CTCAAGCCTTGAAATCACGGCGTT | 13 | 36 | 1 | 4 | 35 | 12 |
| 1157 | 945 | 3711 | 77.1 | CTCAAGCCTCTGAGCCCGTTCCAT | 13 | 36 | 8 | 36 | 12 | 15 |
| 1158 | 946 | 30212 | 77.4 | CTCAAGCCCGTTGGACTCCCAAAG | 13 | 36 | 12 | 34 | 28 | 6 |
| 1159 | 947 | 30213 | 75.5 | CTCAAGCCGGTACGAACCATAGCC | 13 | 36 | 18 | 16 | 15 | 36 |
| 1160 | 948 | 30214 | 76.4 | CTCAAGCCGATGTCCCTGCGTTAG | 13 | 36 | 27 | 28 | 29 | 3 |
| 1161 | 950 | 3749 | 79 | CTGTCGTTCGTTACGGCAGCGGAC | 14 | 12 | 12 | 35 | 31 | 34 |
| 1162 | 951 | 3750 | 79.8 | CTGTCGTTCCATTCCCTGCGGGAC | 14 | 12 | 15 | 28 | 29 | 34 |
| 1163 | 952 | 3757 | 79.2 | CTGTCGTTCAGCCCTATGCGCAGC | 14 | 12 | 31 | 26 | 29 | 31 |
| 1164 | 953 | 3765 | 78.1 | CTGTCGAACGTTTGCGCAGCAATC | 14 | 16 | 12 | 29 | 31 | 4 |
| 1165 | 954 | 20509 | 77.6 | CTGTCGAATCCCCGTTGACCGAGT | 14 | 16 | 28 | 12 | 32 | 20 |
| 1166 | 955 | 20511 | 76.8 | CTGTGCTTGTGCGAGTCCATCACG | 14 | 17 | 33 | 20 | 15 | 30 |
| 1167 | 956 | 3781 | 80.1 | CTGTGCAACCATAGCCGGACGCAA | 14 | 21 | 15 | 36 | 34 | 21 |
| 1168 | 957 | 3782 | 78.6 | CTGTGCAACGAATGTCAGCCACGG | 14 | 21 | 16 | 9 | 36 | 35 |
| 1169 | 958 | 14170 | 76.3 | CTGTGCAAGCAATCTGCAGCCTTG | 14 | 21 | 21 | 8 | 31 | 11 |
| 1170 | 959 | 3786 | 80.7 | CTGTGCAAGACCGCAAATCGTGCG | 14 | 21 | 32 | 21 | 24 | 29 |
| 1171 | 960 | 14173 | 79.1 | CTGTGATGTGCGAATCGGACGCAA | 14 | 27 | 29 | 4 | 34 | 21 |
| 1172 | 962 | 3800 | 76 | CTGTTCCCCTTGAGGACCATCACG | 14 | 28 | 11 | 25 | 15 | 30 |
| 1173 | 963 | 30215 | 77.5 | CTGTTCCCGCTTCCTAGTGCGACC | 14 | 28 | 17 | 26 | 33 | 32 |

FIG. 25X

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 1174 | 964 | 3805 | 79.8 | CTGTTCCCAGTGCGAATCCCGGAC | 14 | 28 | 22 | 16 | 28 | 34 |
| 1175 | 966 | 3817 | 80.6 | CTGTTGCGTGTCCACGCCTATGCG | 14 | 29 | 9 | 30 | 26 | 29 |
| 1176 | 967 | 14180 | 78.3 | CTGTTGCGCGAACTTGCCATGGTA | 14 | 29 | 16 | 11 | 15 | 18 |
| 1177 | 968 | 40184 | 77.7 | CTGTTGCGGCTTTCGTGCTTTTGA | 14 | 29 | 17 | 10 | 17 | 1 |
| 1178 | 969 | 40185 | 78.8 | CTGTTGCGGAGTCCATCAGCGCTT | 14 | 29 | 20 | 15 | 31 | 17 |
| 1179 | 970 | 40186 | 77.4 | CTGTTGCGAGGAAAAGCTGTTGCG | 14 | 29 | 25 | 6 | 14 | 29 |
| 1180 | 971 | 14181 | 77.2 | CTGTTGCGCAGCACGGCCTAATAC | 14 | 29 | 31 | 35 | 26 | 5 |
| 1181 | 974 | 3832 | 79.4 | CTGTCACGCTGTTCCCGACCAGGA | 14 | 30 | 14 | 28 | 32 | 25 |
| 1182 | 975 | 20528 | 78.5 | CTGTCACGCCATAATCGTGCCACG | 14 | 30 | 15 | 4 | 33 | 30 |
| 1183 | 976 | 14182 | 76.4 | CTGTCACGCGAAATACGCAACGAA | 14 | 30 | 16 | 5 | 21 | 16 |
| 1184 | 977 | 3836 | 79.3 | CTGTCACGGGTAACGGCGAAGCAA | 14 | 30 | 18 | 35 | 16 | 21 |
| 1185 | 978 | 3837 | 79.7 | CTGTCACGGATGGGACGCAACAGC | 14 | 30 | 27 | 34 | 21 | 31 |
| 1186 | 979 | 3847 | 81.6 | CTGTCAGCATCGCGTTGCAATGCG | 14 | 31 | 24 | 12 | 21 | 29 |
| 1187 | 980 | 3849 | 82 | CTGTCAGCGATGTGCGGTGCCCAT | 14 | 31 | 27 | 29 | 33 | 15 |
| 1188 | 981 | 40187 | 80.4 | CTGTCAGCTGCGAGTGAGCCGTGC | 14 | 31 | 29 | 22 | 36 | 33 |
| 1189 | 983 | 40188 | 77.7 | CTGTGACCGCAAATACGACCGTGC | 14 | 32 | 21 | 5 | 32 | 33 |
| 1190 | 984 | 14187 | 80.6 | CTGTGACCTCCCCAGCTGCGTCGT | 14 | 32 | 28 | 31 | 29 | 19 |
| 1191 | 985 | 14188 | 80.7 | CTGTGACCTGCGCACGCCATTGTC | 14 | 32 | 29 | 30 | 15 | 9 |
| 1192 | 986 | 20536 | 77 | CTGTGACCCACGACCTACGGCTTG | 14 | 32 | 30 | 23 | 35 | 11 |
| 1193 | 988 | 3869 | 77 | CTGTGTGCGCTTCCATCTTGGGAC | 14 | 33 | 17 | 15 | 11 | 34 |
| 1194 | 990 | 40189 | 81 | CTGTGTGCTGCGGATGATCGGCAA | 14 | 33 | 29 | 27 | 24 | 21 |
| 1195 | 992 | 14190 | 79.6 | CTGTGTGCGGACTGATCACGTGCG | 14 | 33 | 34 | 2 | 30 | 29 |
| 1196 | 995 | 3884 | 76.5 | CTGTGGACGGACATACGGACGCTT | 14 | 34 | 34 | 5 | 34 | 17 |
| 1197 | 996 | 14193 | 80.7 | CTGTGGACAGCCCTCACACGTGCG | 14 | 34 | 36 | 13 | 30 | 29 |
| 1198 | 997 | 3886 | 79.7 | CTGTACGGCTTGGACCGTGCGATG | 14 | 35 | 11 | 32 | 33 | 27 |
| 1199 | 998 | 3891 | 77.8 | CTGTACGGACCTACGGGACCACGG | 14 | 35 | 23 | 35 | 32 | 35 |
| 1200 | 999 | 3900 | 77.9 | CTGTAGCCTCGTGCTTCACGCGAA | 14 | 36 | 10 | 17 | 30 | 16 |
| 1201 | 1000 | 30218 | 75.5 | CTGTAGCCGCTTATCGTGTCTGCG | 14 | 36 | 17 | 24 | 9 | 29 |
| 1202 | 1001 | 3905 | 80.9 | CTGTAGCCGTCTTGCGGGACGTGC | 14 | 36 | 19 | 29 | 34 | 33 |
| 1203 | 1002 | 3912 | 75.7 | CTGTAGCCTCCCAAAGCTCAACGG | 14 | 36 | 28 | 6 | 13 | 35 |
| 1204 | 1003 | 3915 | 76.8 | CTGTAGCCGACCTCTGCTTGCAGC | 14 | 36 | 32 | 8 | 11 | 31 |
| 1205 | 1004 | 3923 | 78.7 | CCATTTGAGGACCGAACACGACGG | 15 | 1 | 34 | 16 | 30 | 35 |
| 1206 | 1005 | 3927 | 81.6 | CCATTGATGACCGGACCACGGCAA | 15 | 2 | 32 | 34 | 30 | 21 |
| 1207 | 1006 | 20546 | 76.1 | CCATTTAGGACCAAAGCCATTGCG | 15 | 3 | 32 | 6 | 15 | 29 |
| 1208 | 1007 | 20548 | 76.3 | CCATAATCCGTTGCTTGTGCCCAT | 15 | 4 | 12 | 17 | 33 | 15 |
| 1209 | 1008 | 3942 | 78.1 | CCATAATCTCCCCATCACGCGAA | 15 | 4 | 28 | 15 | 30 | 16 |
| 1210 | 1009 | 14213 | 78 | CCATAATCAGCCCGAATCCCTCCC | 15 | 4 | 36 | 16 | 28 | 28 |
| 1211 | 1010 | 3948 | 77.6 | CCATAAAGCTTGCAGCATCGGCAA | 15 | 6 | 11 | 31 | 24 | 21 |
| 1212 | 1011 | 14216 | 76.9 | CCATAAAGACGGCGAAGACCCGTT | 15 | 6 | 35 | 16 | 32 | 12 |
| 1213 | 1012 | 3965 | 79.8 | CCATTCTGAGGATGCGGGACGGAC | 15 | 8 | 25 | 29 | 34 | 34 |
| 1214 | 1013 | 14222 | 77.6 | CCATTCTGAGCCTGTCATCGCGAA | 15 | 8 | 36 | 9 | 24 | 16 |
| 1215 | 1014 | 3982 | 80.2 | CCATTGTCATCGCCATGACCGTGC | 15 | 9 | 24 | 15 | 32 | 33 |
| 1216 | 1015 | 3985 | 79.6 | CCATTGTCTGCGCCATCGTTGGAC | 15 | 9 | 29 | 15 | 12 | 34 |
| 1217 | 1017 | 3990 | 79.2 | CCATTGTCACGGCCATGATGGACC | 15 | 9 | 35 | 15 | 27 | 32 |
| 1218 | 1019 | 30219 | 77 | CCATTCGTGCTTTACAAGCCACGG | 15 | 10 | 17 | 7 | 36 | 35 |
| 1219 | 1021 | 14233 | 75.4 | CCATCTTGCGAATTAGGTGCTCCC | 15 | 11 | 16 | 3 | 33 | 28 |
| 1220 | 1022 | 4021 | 81.6 | CCATCGTTCTCATCCCTGCGTGCG | 15 | 12 | 13 | 28 | 29 | 29 |
| 1221 | 1023 | 4025 | 76.5 | CCATCGTTGCAAATACATCGTGCG | 15 | 12 | 21 | 5 | 24 | 29 |
| 1222 | 1024 | 4026 | 76.2 | CCATCGTTACCTAGCCACCTTGCG | 15 | 12 | 23 | 36 | 23 | 29 |
| 1223 | 1025 | 4027 | 75.6 | CCATCGTTATCGTGCGAAAGCTCA | 15 | 12 | 24 | 29 | 6 | 13 |
| 1224 | 1026 | 4033 | 78.8 | CCATCGTTGACCGCTTAGGATGCG | 15 | 12 | 32 | 17 | 25 | 29 |

FIG. 25Y

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 1225 | 1027 | 4034 | 77.9 | CCATCGTTGTGCCCTAGGACGGAC | 15 | 12 | 33 | 26 | 34 | 34 |
| 1226 | 1028 | 4040 | 78.6 | CCATCTCAACGGCACGAGCCTGAT | 15 | 13 | 35 | 30 | 36 | 2 |
| 1227 | 1029 | 4042 | 78.6 | CCATCTGTTCGTGCAATCGTTGCG | 15 | 14 | 10 | 21 | 10 | 29 |
| 1228 | 1030 | 4045 | 77.7 | CCATCTGTTCCCGGTACACGTCCC | 15 | 14 | 28 | 18 | 30 | 28 |
| 1229 | 1031 | 4046 | 82.3 | CCATCTGTGTGCGTGCGATGTGCG | 15 | 14 | 33 | 33 | 27 | 29 |
| 1230 | 1032 | 4052 | 79.1 | CCATCCATCCTACAGCTGCGCAGC | 15 | 15 | 26 | 31 | 29 | 31 |
| 1231 | 1033 | 14242 | 80.2 | CCATCCATGGACGACCTGCGACCT | 15 | 15 | 34 | 32 | 29 | 23 |
| 1232 | 1034 | 14243 | 78 | CCATCGAATCGTCGTTGATGGCAA | 15 | 16 | 10 | 12 | 27 | 21 |
| 1233 | 1035 | 14244 | 78 | CCATCGAACGTTCACGAGTGCAGC | 15 | 16 | 12 | 30 | 22 | 31 |
| 1234 | 1036 | 40192 | 76.9 | CCATCGAACGAACCTACGAATGCG | 15 | 16 | 16 | 26 | 16 | 29 |
| 1235 | 1037 | 40193 | 78.7 | CCATCGAAACCTTGTCGACCACGG | 15 | 16 | 23 | 9 | 32 | 35 |
| 1236 | 1038 | 30222 | 79.5 | CCATCGAACAGCCCATTCGTCACG | 15 | 16 | 31 | 15 | 10 | 30 |
| 1237 | 1039 | 4076 | 79.9 | CCATGCTTCTCAACGGCAGCATCG | 15 | 17 | 13 | 35 | 31 | 24 |
| 1238 | 1040 | 14253 | 75.2 | CCATGCTTAGGAAGGAATCGCGTT | 15 | 17 | 25 | 25 | 24 | 12 |
| 1239 | 1041 | 14255 | 77 | CCATGCTTCAGCTACATCCCGTGC | 15 | 17 | 31 | 7 | 28 | 33 |
| 1240 | 1042 | 4087 | 78.3 | CCATGCTTGACCCGAAGCTTCAGC | 15 | 17 | 32 | 16 | 17 | 31 |
| 1241 | 1043 | 4088 | 80.1 | CCATGCTTGTGCGACCGACCTTGA | 15 | 17 | 33 | 32 | 32 | 1 |
| 1242 | 1044 | 4093 | 77.5 | CCATGGTAGCTTGCAAATCGCGAA | 15 | 18 | 17 | 21 | 24 | 16 |
| 1243 | 1045 | 4099 | 79.1 | CCATGGTACAGCTGCGACGGGGTA | 15 | 18 | 31 | 29 | 35 | 18 |
| 1244 | 1046 | 4100 | 81.5 | CCATGGTAGTGCACGGAGCCGTGC | 15 | 18 | 33 | 35 | 36 | 33 |
| 1245 | 1047 | 4104 | 79.7 | CCATGTCTCACGTGCGCTTGTCCC | 15 | 19 | 30 | 29 | 11 | 28 |
| 1246 | 1048 | 14264 | 78.1 | CCATGCAATCGTGCAAATCGAGGA | 15 | 21 | 10 | 21 | 24 | 25 |
| 1247 | 1049 | 40195 | 76.2 | CCATGCAACGAATCCCAATCCCTA | 15 | 21 | 16 | 28 | 4 | 26 |
| 1248 | 1050 | 4121 | 79.9 | CCATGCAAGTCTTCCCAGCCGGAC | 15 | 21 | 19 | 28 | 36 | 34 |
| 1249 | 1051 | 4122 | 80.7 | CCATGCAAGAGTTCCCCAGCCACG | 15 | 21 | 20 | 28 | 31 | 30 |
| 1250 | 1052 | 40196 | 76.8 | CCATGCAAATCGTTAGGGACGTGC | 15 | 21 | 24 | 3 | 34 | 33 |
| 1251 | 1054 | 14269 | 78.3 | CCATGCAACACGATCGATCGGATG | 15 | 21 | 30 | 24 | 24 | 27 |
| 1252 | 1055 | 14270 | 77.6 | CCATGCAAGACCCGTTAGCCCCTA | 15 | 21 | 32 | 12 | 36 | 26 |
| 1253 | 1056 | 20576 | 76.2 | CCATGCAAGGACGAGTTCCCTCTG | 15 | 21 | 34 | 20 | 28 | 8 |
| 1254 | 1057 | 4132 | 79.1 | CCATGCAAAGCCCTCAGCAAGTGC | 15 | 21 | 36 | 13 | 21 | 33 |
| 1255 | 1058 | 20578 | 77 | CCATAGTGGACCCTTGCTGTTGCG | 15 | 22 | 32 | 11 | 14 | 29 |
| 1256 | 1059 | 4140 | 76.1 | CCATACCTTCCCATACCAGCTGCG | 15 | 23 | 28 | 5 | 31 | 29 |
| 1257 | 1060 | 4147 | 75.7 | CCATATCGGGTATCTGGACCACGG | 15 | 24 | 18 | 8 | 32 | 35 |
| 1258 | 1061 | 20580 | 76.6 | CCATATCGGAGTGATGTGCGGGAC | 15 | 24 | 20 | 27 | 29 | 34 |
| 1259 | 1062 | 4150 | 78.2 | CCATATCGTCCCGTTCACGAGGA | 15 | 24 | 28 | 12 | 30 | 25 |
| 1260 | 1063 | 4158 | 79.6 | CCATAGGAAGGATCCCACGCACG | 15 | 25 | 25 | 28 | 30 | 30 |
| 1261 | 1064 | 14279 | 77.2 | CCATGATGCGTTCAGCGTCTAGCC | 15 | 27 | 12 | 31 | 19 | 36 |
| 1262 | 1065 | 4178 | 80.1 | CCATGATGATCGGATGGTGCACGG | 15 | 27 | 24 | 27 | 33 | 35 |
| 1263 | 1066 | 4179 | 76 | CCATGATGCCTAGGACGACCCTTG | 15 | 27 | 26 | 34 | 32 | 11 |
| 1264 | 1067 | 4181 | 79.5 | CCATGATGTCCCGATGCGAACAGC | 15 | 27 | 28 | 27 | 16 | 31 |
| 1265 | 1068 | 4182 | 80 | CCATGATGCAGCCACGCCATCTGT | 15 | 27 | 31 | 30 | 15 | 14 |
| 1266 | 1069 | 14281 | 76.8 | CCATTCCCTTAGCGTTCAGCCCAT | 15 | 28 | 3 | 12 | 31 | 15 |
| 1267 | 1070 | 14283 | 77.7 | CCATTCCCCTCAACGGGATGTCTG | 15 | 28 | 13 | 35 | 27 | 8 |
| 1268 | 1071 | 20589 | 78.2 | CCATTCCCACCTAGTGCACGCCAT | 15 | 28 | 23 | 22 | 30 | 15 |
| 1269 | 1072 | 40200 | 75.3 | CCATTGCGTGATAATCCTTGGCAA | 15 | 29 | 2 | 4 | 11 | 21 |
| 1270 | 1073 | 40201 | 78.3 | CCATTGCGTTAGCGTTTCCCGGTA | 15 | 29 | 3 | 12 | 28 | 18 |
| 1271 | 1075 | 14287 | 77.7 | CCATTGCGTGTCGGTAAAAGTGCG | 15 | 29 | 9 | 18 | 6 | 29 |
| 1272 | 1076 | 40202 | 76.8 | CCATTGCGTCGTAAAGTCCCATCG | 15 | 29 | 10 | 6 | 28 | 24 |
| 1273 | 1078 | 40203 | 79.7 | CCATTGCGAGGACACGGAGTGTGC | 15 | 29 | 25 | 30 | 20 | 33 |
| 1274 | 1079 | 4213 | 80.6 | CCATTGCGTGCGAATCCAGCAGTG | 15 | 29 | 29 | 4 | 31 | 22 |
| 1275 | 1080 | 4214 | 82.1 | CCATTGCGCACGGCAAGAGTCGAA | 15 | 29 | 30 | 21 | 20 | 16 |

FIG. 25Z

| SEQ ID NO: | 4,633 ID# | HEX ID# | Tm | ZIPCODE (5'-3') | TETRAMER NUMBERS | | | | |
|---|---|---|---|---|---|---|---|---|---|
| 1276 | 1081 | 4215 | 81.3 | CCATTGCGGACCCACGTCTGGATG | 15 | 29 | 32 | 30 | 8 | 27 |
| 1277 | 1082 | 4216 | 81.3 | CCATTGCGGTGCGGACCGTTAGTG | 15 | 29 | 33 | 34 | 12 | 22 |
| 1278 | 1083 | 4217 | 80.1 | CCATTGCGACGGCCATATCGACCT | 15 | 29 | 35 | 15 | 24 | 23 |
| 1279 | 1084 | 4218 | 80.4 | CCATCACGTTGAAGCCTGCGGCTT | 15 | 30 | 1 | 36 | 29 | 17 |
| 1280 | 1086 | 4221 | 80.6 | CCATCACGTCTGGCAATCCCAGCC | 15 | 30 | 8 | 21 | 28 | 36 |
| 1281 | 1087 | 4224 | 77.3 | CCATCACGAGTGACCTTCCCCCAT | 15 | 30 | 22 | 23 | 28 | 15 |
| 1282 | 1088 | 40204 | 79.6 | CCATCACGATCGGCTTTTGATGCG | 15 | 30 | 24 | 17 | 1 | 29 |
| 1283 | 1089 | 40205 | 79 | CCATCACGTGCGAAAGATCGAGCC | 15 | 30 | 29 | 6 | 24 | 36 |
| 1284 | 1090 | 40206 | 81.6 | CCATCACGGACCGAGTGCTTTGCG | 15 | 30 | 32 | 20 | 17 | 29 |
| 1285 | 1091 | 4230 | 80.6 | CCATCACGAGCCGATGAGTGCACG | 15 | 30 | 36 | 27 | 22 | 30 |
| 1286 | 1092 | 4231 | 77.9 | CCATCAGCTTGATCCCCATCAGC | 15 | 31 | 1 | 28 | 15 | 31 |
| 1287 | 1094 | 4233 | 78.4 | CCATCAGCCTTGGGACCGTTCTCA | 15 | 31 | 11 | 34 | 12 | 13 |
| 1288 | 1095 | 20601 | 76.6 | CCATCAGCCGTTTTAGTCCCCCAT | 15 | 31 | 12 | 3 | 28 | 15 |
| 1289 | 1096 | 4236 | 80 | CCATCAGCAGTGGCAAGTGCAGCC | 15 | 31 | 22 | 21 | 33 | 36 |
| 1290 | 1097 | 4237 | 76.2 | CCATCAGCACCTTTAGTGCGGACC | 15 | 31 | 23 | 3 | 29 | 32 |
| 1291 | 1098 | 4238 | 76.9 | CCATCAGCTCCCAGGAGACCCCTA | 15 | 31 | 28 | 25 | 32 | 26 |
| 1292 | 1100 | 30226 | 78.8 | CCATGACCGAGTAGGAACGGTGCG | 15 | 32 | 20 | 25 | 35 | 29 |
| 1293 | 1101 | 4253 | 77 | CCATGACCAGGAAATCTCCCGACC | 15 | 32 | 25 | 4 | 28 | 32 |
| 1294 | 1102 | 40209 | 79.3 | CCATGACCGATGCTTGGCTTCGAA | 15 | 32 | 27 | 11 | 17 | 16 |
| 1295 | 1103 | 4256 | 78 | CCATGACCTCCCGGTAGTCTTGCG | 15 | 32 | 28 | 18 | 19 | 29 |
| 1296 | 1104 | 14299 | 80.6 | CCATGACCAGCCGAGTGCAATCCC | 15 | 32 | 36 | 20 | 21 | 28 |
| 1297 | 1105 | 4261 | 77 | CCATGTGCTGATACCTGTGCGCAA | 15 | 33 | 2 | 23 | 33 | 21 |
| 1298 | 1106 | 4262 | 81.4 | CCATGTGCAATCTGCGACGGGACC | 15 | 33 | 4 | 29 | 35 | 32 |
| 1299 | 1107 | 4264 | 79.5 | CCATGTGCTCTGCGTTGGACGCTT | 15 | 33 | 8 | 12 | 34 | 17 |
| 1300 | 1108 | 4268 | 78.4 | CCATGTGCCTGTCGTTTGTCACGG | 15 | 33 | 14 | 12 | 9 | 35 |
| 1301 | 1109 | 14301 | 76.4 | CCATGTGCGCTTCGTTAATCCCAT | 15 | 33 | 17 | 12 | 4 | 15 |
| 1302 | 1110 | 4273 | 77.6 | CCATGTGCATCGGGTAACCTTCCC | 15 | 33 | 24 | 18 | 23 | 28 |
| 1303 | 1111 | 4274 | 75.5 | CCATGTGCAGGAATACTCCCCGTT | 15 | 33 | 25 | 5 | 28 | 12 |
| 1304 | 1112 | 4275 | 80.8 | CCATGTGCTGCGGGACTCTGGACC | 15 | 33 | 29 | 34 | 8 | 32 |
| 1305 | 1113 | 14305 | 78.6 | CCATGTGCGACCCCTACCTATGCG | 15 | 33 | 32 | 26 | 26 | 29 |
| 1306 | 1114 | 4278 | 80.2 | CCATGTGCAGCCCACGAAAGCTCA | 15 | 33 | 36 | 30 | 6 | 13 |
| 1307 | 1115 | 40211 | 77.6 | CCATGGACGGTACTCATGCGATCG | 15 | 34 | 18 | 13 | 29 | 24 |
| 1308 | 1116 | 4288 | 77.2 | CCATGGACAGGACACGAGGACGAA | 15 | 34 | 25 | 30 | 25 | 16 |
| 1309 | 1117 | 4292 | 80.5 | CCATGGACCACGGTCTCACGGGAC | 15 | 34 | 30 | 19 | 30 | 34 |
| 1310 | 1118 | 14310 | 80.2 | CCATGGACGTGCCAGCTTGAGCAA | 15 | 34 | 33 | 31 | 1 | 21 |
| 1311 | 1119 | 4297 | 80.5 | CCATACGGAATCGCAATGCGAGCC | 15 | 35 | 4 | 21 | 29 | 36 |
| 1312 | 1120 | 4298 | 81 | CCATACGGTCTGGCAAAGCCGCAA | 15 | 35 | 8 | 21 | 36 | 21 |
| 1313 | 1121 | 40213 | 77.5 | CCATACGGCTTGCCTATCCCGGTA | 15 | 35 | 11 | 26 | 28 | 18 |
| 1314 | 1122 | 4304 | 77.7 | CCATACGGGCAATCTGAGTGCACG | 15 | 35 | 21 | 8 | 22 | 30 |
| 1315 | 1123 | 4309 | 77.4 | CCATACGGGACCCTGTAGCCGGTA | 15 | 35 | 32 | 14 | 36 | 18 |
| 1316 | 1124 | 30227 | 78.2 | CCATACGGGTGCTCGTCCATCGTT | 15 | 35 | 33 | 10 | 15 | 12 |
| 1317 | 1125 | 14321 | 79.7 | CCATAGCCGTGCGCAACGAACTTG | 15 | 36 | 33 | 21 | 16 | 11 |
| 1318 | 1127 | 4335 | 78.8 | CGAATGATTGCGCCATTGATGCAA | 16 | 2 | 29 | 15 | 2 | 21 |
| 1319 | 1128 | 20626 | 78.1 | CGAATGATCACGCTGTACGGGCAA | 16 | 2 | 30 | 14 | 35 | 21 |
| 1320 | 1130 | 40217 | 77.6 | CGAAAATCCACGACGGTTGACACG | 16 | 4 | 30 | 35 | 1 | 30 |
| 1321 | 1131 | 30232 | 78.6 | CGAAAATCGTGCCTGTTGCGGTCT | 16 | 4 | 33 | 14 | 29 | 19 |
| 1322 | 1132 | 40218 | 77.2 | CGAAAATCGGACTTGATGCGCTTG | 16 | 4 | 34 | 1 | 29 | 11 |
| 1323 | 1133 | 20631 | 80.6 | CGAAATACGCTTTCCCGCAATGCG | 16 | 5 | 17 | 28 | 21 | 29 |
| 1324 | 1134 | 30233 | 77.2 | CGAAAAGCGAAATCGTTGATGCAA | 16 | 6 | 16 | 24 | 1 | 29 |
| 1325 | 1135 | 30234 | 76 | CGAAAAGTCCCTGCGGAGTTTGA | 16 | 6 | 28 | 29 | 20 | 1 |
| 1326 | 1136 | 30235 | 75.8 | CGAAAAGCACGAAAGCCATAGCC | 16 | 6 | 30 | 6 | 15 | 36 |

FIG. 25AA

| SEQ ID NO: | 4,633 ID# | HEX ID# | Tm | ZIPCODE (5'-3') | TETRAMER NUMBERS | | | | |
|---|---|---|---|---|---|---|---|---|---|
| 1327 | 1137 | 4381 | 78 | CGAAAAAGCAGCGGACCTCAAGGA | 16 | 6 | 31 | 34 | 13 | 25 |
| 1328 | 1138 | 14350 | 79.1 | CGAAAAAGGTGCCACGCAGCTGTC | 16 | 6 | 33 | 30 | 31 | 9 |
| 1329 | 1139 | 4385 | 78.5 | CGAAAAAGAGCCGTGCCTCAGTGC | 16 | 6 | 36 | 33 | 13 | 33 |
| 1330 | 1140 | 4388 | 80.9 | CGAATCTGTCGTTGCGCGAAAGCC | 16 | 8 | 10 | 29 | 16 | 36 |
| 1331 | 1141 | 30236 | 76.1 | CGAATCTGCCATAGGAGACCACGG | 16 | 8 | 15 | 25 | 32 | 35 |
| 1332 | 1143 | 4399 | 76.8 | CGAATCTGCACGTACACAGCCACG | 16 | 8 | 30 | 7 | 31 | 30 |
| 1333 | 1144 | 4403 | 80.2 | CGAATGTCCTCAAGCCGTGCCCAT | 16 | 9 | 13 | 36 | 33 | 15 |
| 1334 | 1146 | 20640 | 77.3 | CGAATGTCGTCTCTGTTGCGAGCC | 16 | 9 | 19 | 14 | 29 | 36 |
| 1335 | 1149 | 4421 | 78.2 | CGAATCGTCTGTCAGCGCAACAGC | 16 | 10 | 14 | 31 | 21 | 31 |
| 1336 | 1150 | 14364 | 77 | CGAATCGTGCTTCCATAGCCATCG | 16 | 10 | 17 | 15 | 36 | 24 |
| 1337 | 1153 | 4437 | 79.7 | CGAACTTGTCGTGACCCAGCCACG | 16 | 11 | 10 | 32 | 31 | 30 |
| 1338 | 1154 | 40222 | 78.9 | CGAACTTGGCTTGACCCACGATCG | 16 | 11 | 17 | 32 | 30 | 24 |
| 1339 | 1155 | 30240 | 78.5 | CGAACTTGCAGCAGTGGATGCGAA | 16 | 11 | 31 | 22 | 27 | 16 |
| 1340 | 1156 | 4448 | 78.6 | CGAACTTGGACCCTTGTGCGCTGT | 16 | 11 | 32 | 11 | 29 | 14 |
| 1341 | 1157 | 14373 | 79.7 | CGAACTTGGTGCCAGCCGTTGATG | 16 | 11 | 33 | 31 | 12 | 27 |
| 1342 | 1158 | 20649 | 77.2 | CGAACTTGAGCCGATGGAGTCACG | 16 | 11 | 36 | 27 | 20 | 30 |
| 1343 | 1160 | 20650 | 75.9 | CGAACGTTGAGTCGAACACGATCG | 16 | 12 | 20 | 16 | 30 | 24 |
| 1344 | 1161 | 4464 | 76.8 | CGAACGTTGTGCTCTGCAGCTTGA | 16 | 12 | 33 | 8 | 31 | 1 |
| 1345 | 1163 | 4468 | 79.2 | CGAACTCACCATGCAAACGGCGTT | 16 | 13 | 15 | 21 | 35 | 12 |
| 1346 | 1164 | 4469 | 79.3 | CGAACTCAGCTTTGCGAGGATGCG | 16 | 13 | 17 | 29 | 25 | 29 |
| 1347 | 1165 | 4471 | 75.5 | CGAACTCATCCCATACGCAAGCAA | 16 | 13 | 28 | 5 | 21 | 21 |
| 1348 | 1166 | 4473 | 80.2 | CGAACTCACAGCCAGCGCTTGTGC | 16 | 13 | 31 | 31 | 17 | 33 |
| 1349 | 1168 | 40224 | 78.5 | CGAACCATCGAACCATGACCGGAC | 16 | 15 | 10 | 15 | 32 | 34 |
| 1350 | 1169 | 4487 | 77 | CGAACCATATCGAGTGCAGCGGAC | 16 | 15 | 24 | 22 | 31 | 34 |
| 1351 | 1170 | 14385 | 76.1 | CGAACCATCCTAAATCCGTTTGCG | 16 | 15 | 26 | 4 | 12 | 29 |
| 1352 | 1171 | 20658 | 75.6 | CGAACCATCACGTTAGGCAAGCAA | 16 | 15 | 30 | 3 | 21 | 21 |
| 1353 | 1173 | 4493 | 78.8 | CGAACCATGGACCTCATCCCTCCC | 16 | 15 | 34 | 13 | 28 | 28 |
| 1354 | 1174 | 30244 | 78.6 | CGAACGAAAAAGACCTTGCGGCAA | 16 | 16 | 6 | 23 | 29 | 21 |
| 1355 | 1175 | 14389 | 75.7 | CGAACGAATCGTTTAGCGTTGCAA | 16 | 16 | 10 | 3 | 12 | 21 |
| 1356 | 1176 | 14395 | 77.2 | CGAAGCTTTGATCACGCGTTGACC | 16 | 17 | 2 | 30 | 12 | 32 |
| 1357 | 1177 | 4513 | 76.1 | CGAAGCTTTACATGCGTTGATGCG | 16 | 17 | 7 | 29 | 1 | 29 |
| 1358 | 1178 | 4517 | 76.2 | CGAAGCTTCGTTCGAAGGACAGGA | 16 | 17 | 12 | 16 | 34 | 25 |
| 1359 | 1180 | 30245 | 76.7 | CGAAGCTTCGAATCGTGCAACCAT | 16 | 17 | 16 | 10 | 21 | 15 |
| 1360 | 1181 | 20663 | 75.8 | CGAAGCTTGTGCGGACAAAGTTGA | 16 | 17 | 33 | 34 | 6 | 1 |
| 1361 | 1182 | 20668 | 77.2 | CGAAGAGTCCATACGGTCCCAGCC | 16 | 20 | 15 | 35 | 28 | 36 |
| 1362 | 1183 | 20670 | 78.1 | CGAAGCAATTGAACCTTGCGGGAC | 16 | 21 | 1 | 23 | 29 | 34 |
| 1363 | 1184 | 4548 | 76.3 | CGAAGCAAATCAGCCACCTACGG | 16 | 21 | 4 | 36 | 23 | 35 |
| 1364 | 1185 | 40225 | 79 | CGAAGCAAAAGCCATCGTTTGCG | 16 | 21 | 6 | 15 | 12 | 29 |
| 1365 | 1186 | 30248 | 75.2 | CGAAGCAACCATACGGCGTTAGTG | 16 | 21 | 15 | 35 | 12 | 22 |
| 1366 | 1187 | 20673 | 77.3 | CGAAGCAAGATGAGCCTGTCCACG | 16 | 21 | 27 | 36 | 9 | 30 |
| 1367 | 1188 | 4557 | 78 | CGAAAGTGCTTGGCAACGTTCACG | 16 | 22 | 11 | 21 | 12 | 30 |
| 1368 | 1189 | 20675 | 79.9 | CGAAAGTGCGTTTGCGTCTGGTGC | 16 | 22 | 12 | 29 | 8 | 33 |
| 1369 | 1190 | 4558 | 76.5 | CGAAAGTGCGAATGTCAGTGCGAA | 16 | 22 | 16 | 9 | 22 | 16 |
| 1370 | 1191 | 14414 | 77.4 | CGAAAGTGGCTTGGACTCGTTCCC | 16 | 22 | 17 | 34 | 10 | 28 |
| 1371 | 1192 | 14416 | 80.8 | CGAAAGTGGATGGACCCAGCTGCG | 16 | 22 | 27 | 32 | 31 | 29 |
| 1372 | 1194 | 4578 | 78.6 | CGAAACCTGAGTACGGTGCGCGTT | 16 | 23 | 20 | 35 | 29 | 12 |
| 1373 | 1195 | 4579 | 75.9 | CGAAACCTGCAACTGTGGTATGCG | 16 | 23 | 21 | 14 | 18 | 29 |
| 1374 | 1196 | 4584 | 77.7 | CGAAACCTTGCGGGTAACCTCGAA | 16 | 23 | 29 | 18 | 23 | 16 |
| 1375 | 1197 | 30249 | 79.1 | CGAAACCTGACCTTGATGCGCAGC | 16 | 23 | 32 | 1 | 29 | 31 |
| 1376 | 1198 | 4585 | 78.9 | CGAAACCTGTGCGTCTGACCGGAC | 16 | 23 | 33 | 19 | 32 | 34 |
| 1377 | 1199 | 30250 | 78.9 | CGAAATCGGAGTTCTGCCATTGCG | 16 | 24 | 20 | 8 | 15 | 29 |

FIG. 25BB

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 1378 | 1202 | 14431 | 78.2 | CGAAAGGAAGTGCACGGATGAGCC | 16 | 25 | 22 | 30 | 27 | 36 |
| 1379 | 1203 | 4616 | 78.2 | CGAAAGGATCCCGGTAGGACGACC | 16 | 25 | 28 | 18 | 34 | 32 |
| 1380 | 1204 | 40232 | 78.3 | CGAAAGGAAGCCAGCCTGTCGATG | 16 | 25 | 36 | 36 | 9 | 27 |
| 1381 | 1205 | 14434 | 75.8 | CGAACCTAGCAATGTCGCAAGCAA | 16 | 26 | 21 | 9 | 21 | 21 |
| 1382 | 1206 | 14435 | 76.2 | CGAACCTAGTGCAATCAGCCGCTT | 16 | 26 | 33 | 4 | 36 | 17 |
| 1383 | 1207 | 4628 | 80.7 | CGAAGATGTCGTTGCGACGGTCCC | 16 | 27 | 10 | 29 | 35 | 28 |
| 1384 | 1208 | 20694 | 75.9 | CGAAGATGGTCTATCGAGCCCGAA | 16 | 27 | 19 | 24 | 36 | 16 |
| 1385 | 1209 | 4633 | 78.1 | CGAAGATGTCCCCTCAAGCCATCG | 16 | 27 | 28 | 13 | 36 | 24 |
| 1386 | 1210 | 4634 | 78.4 | CGAAGATGCACGCTGTGCAACGTT | 16 | 27 | 30 | 14 | 21 | 12 |
| 1387 | 1211 | 40233 | 79.2 | CGAAGATGGGACTCCCACGGGGTA | 16 | 27 | 34 | 28 | 35 | 18 |
| 1388 | 1212 | 30252 | 78.5 | CGAAGATGAGCCTGATGTGCGCAA | 16 | 27 | 36 | 2 | 33 | 21 |
| 1389 | 1213 | 4640 | 77.8 | CGAATCCCTGTCCAGCAATCGCTT | 16 | 28 | 9 | 31 | 4 | 17 |
| 1390 | 1214 | 30254 | 77.7 | CGAATCCCGATGATACGACCGGAC | 16 | 28 | 27 | 5 | 32 | 34 |
| 1391 | 1215 | 4649 | 79.5 | CGAATCCCCACGAATCAGTGTGCG | 16 | 28 | 30 | 4 | 22 | 29 |
| 1392 | 1216 | 4650 | 81.2 | CGAATCCCCAGCGTGCTGATCGAA | 16 | 28 | 31 | 33 | 2 | 16 |
| 1393 | 1217 | 4652 | 79 | CGAATCCCACGGATCGTCGTGGTA | 16 | 28 | 35 | 24 | 10 | 18 |
| 1394 | 1218 | 14444 | 76.9 | CGAATGCGTGATCAGCAAAGGCTT | 16 | 29 | 2 | 31 | 6 | 17 |
| 1395 | 1219 | 40235 | 80.7 | CGAATGCGTACACAGCGTGCCAGC | 16 | 29 | 7 | 31 | 33 | 31 |
| 1396 | 1220 | 4658 | 79.4 | CGAATGCGCGAACAGCAGGATGAT | 16 | 29 | 16 | 31 | 25 | 2 |
| 1397 | 1223 | 4665 | 79.9 | CGAATGCGCAGCTACAGACCCACG | 16 | 29 | 31 | 7 | 32 | 30 |
| 1398 | 1224 | 4668 | 78.3 | CGAACACGTCTGTCTGGTGCCGAA | 16 | 30 | 8 | 8 | 33 | 16 |
| 1399 | 1225 | 20704 | 79.8 | CGAACACGCCATTCCCAATCCCAT | 16 | 30 | 15 | 28 | 4 | 15 |
| 1400 | 1226 | 4671 | 76.3 | CGAACACGGAGTTTAGTCCCTGCG | 16 | 30 | 20 | 3 | 28 | 29 |
| 1401 | 1227 | 4674 | 80.9 | CGAACACGTGCGGATGGTCTGCAA | 16 | 30 | 29 | 27 | 19 | 21 |
| 1402 | 1228 | 14449 | 79.9 | CGAACACGCACGCACGTTAGAGCC | 16 | 30 | 30 | 30 | 3 | 36 |
| 1403 | 1229 | 14453 | 79.7 | CGAACAGCAATCACGGACGGATCG | 16 | 31 | 4 | 35 | 35 | 24 |
| 1404 | 1230 | 30255 | 76.4 | CGAACAGCTCGTAGTGCTGTTGCG | 16 | 31 | 10 | 22 | 14 | 29 |
| 1405 | 1231 | 40236 | 80.3 | CGAACAGCCTTGCCATGCAAGCAA | 16 | 31 | 11 | 15 | 21 | 21 |
| 1406 | 1232 | 4689 | 75.8 | CGAACAGCGAGTTTGATCCCACCT | 16 | 31 | 20 | 1 | 28 | 23 |
| 1407 | 1233 | 4690 | 75.6 | CGAACAGCAGTGTTAGCAGCAGCC | 16 | 31 | 22 | 3 | 31 | 36 |
| 1408 | 1234 | 40238 | 77.9 | CGAACAGCGATGAAAGGTGCGATG | 16 | 31 | 27 | 6 | 33 | 27 |
| 1409 | 1236 | 4696 | 79.5 | CGAACAGCCAGCGACCGGTACTCA | 16 | 31 | 31 | 32 | 18 | 13 |
| 1410 | 1237 | 4704 | 77.3 | CGAAGACCCTGTCTCAGTGCGTGC | 16 | 32 | 14 | 13 | 33 | 33 |
| 1411 | 1238 | 14466 | 75 | CGAAGACCGTCTAGGATCCCCTCA | 16 | 32 | 19 | 25 | 28 | 13 |
| 1412 | 1239 | 4713 | 76.2 | CGAAGACCTCCCCCTAATCGCTGT | 16 | 32 | 28 | 26 | 24 | 14 |
| 1413 | 1240 | 14470 | 75.9 | CGAAGACCTGCGTTAGCTCAAGCC | 16 | 32 | 29 | 3 | 13 | 36 |
| 1414 | 1241 | 40239 | 77.2 | CGAAGTGCGGTAAATCTCGTTGCG | 16 | 33 | 18 | 4 | 10 | 29 |
| 1415 | 1242 | 14481 | 77 | CGAAGTGCAGGAAGCCTCGTCTCA | 16 | 33 | 25 | 36 | 10 | 13 |
| 1416 | 1243 | 4734 | 77.9 | CGAAGTGCTCCCCCTAGATGCGAA | 16 | 33 | 28 | 26 | 27 | 16 |
| 1417 | 1244 | 14485 | 80.5 | CGAAGTGCAGCCGATGGGACTCGT | 16 | 33 | 36 | 27 | 34 | 10 |
| 1418 | 1245 | 4747 | 77.6 | CGAAGGACGCTTGACCTGATGCAA | 16 | 34 | 17 | 32 | 2 | 21 |
| 1419 | 1247 | 14491 | 78 | CGAAGGACACCTTCTGTCCCACGG | 16 | 34 | 23 | 8 | 28 | 35 |
| 1420 | 1248 | 4755 | 77 | CGAAGGACGATGGAGTACGGGCTT | 16 | 34 | 27 | 20 | 35 | 17 |
| 1421 | 1250 | 30260 | 77.9 | CGAAACGGTGATTCCCTGTCGACC | 16 | 35 | 2 | 28 | 9 | 32 |
| 1422 | 1252 | 14498 | 78.3 | CGAAACGGTCTGCAGCAAAGTCCC | 16 | 35 | 8 | 31 | 6 | 28 |
| 1423 | 1253 | 30262 | 77.5 | CGAAACGGGAGTGGACGGTATCGT | 16 | 35 | 20 | 34 | 18 | 10 |
| 1424 | 1254 | 20723 | 75.1 | CGAAACGGACCTAGGACGTTTCGT | 16 | 35 | 23 | 25 | 12 | 10 |
| 1425 | 1255 | 40241 | 77.5 | CGAAACGGAGGACTTGATCGAGCC | 16 | 35 | 25 | 11 | 24 | 36 |
| 1426 | 1256 | 4775 | 76 | CGAAACGGCCTATCGTGCAAGAGT | 16 | 35 | 26 | 10 | 21 | 20 |
| 1427 | 1257 | 4778 | 81.2 | CGAAACGGTGCGCTGTTCGTCGTT | 16 | 35 | 29 | 14 | 10 | 12 |
| 1428 | 1258 | 4781 | 81 | CGAAACGGACGGCACGATCGTGAT | 16 | 35 | 35 | 30 | 24 | 2 |

FIG. 25CC

| SEQ ID NO: | 4,633 ID# | HEX ID# | Tm | ZIPCODE (5'-3') | TETRAMER NUMBERS | | | | |
|---|---|---|---|---|---|---|---|---|---|
| 1429 | 1260 | 30263 | 76.5 | CGAAAGCCTGATCCTATCCCGGAC | 16 | 36 | 2 | 26 | 28 | 34 |
| 1430 | 1261 | 4786 | 77.6 | CGAAAGCCTCTGGCAACGAAGGAC | 16 | 36 | 8 | 21 | 16 | 34 |
| 1431 | 1262 | 40243 | 77.2 | CGAAAGCCCTCAAATCGATGGGAC | 16 | 36 | 13 | 4 | 27 | 34 |
| 1432 | 1264 | 14508 | 75.6 | CGAAAGCCACCTTTAGCAGCTCGT | 16 | 36 | 23 | 3 | 31 | 10 |
| 1433 | 1265 | 4795 | 79.4 | CGAAAGCCATCGGTCTGATGCGAA | 16 | 36 | 24 | 19 | 27 | 16 |
| 1434 | 1266 | 30266 | 77.1 | CGAAAGCCAGGAAGTGGATGGCTT | 16 | 36 | 25 | 22 | 27 | 17 |
| 1435 | 1267 | 14510 | 78.2 | CGAAAGCCGATGCGAATGATAGCC | 16 | 36 | 27 | 16 | 2 | 36 |
| 1436 | 1268 | 14511 | 82.2 | CGAAAGCCGTGCGATGGGACGTCT | 16 | 36 | 33 | 27 | 34 | 19 |
| 1437 | 1269 | 20732 | 75.4 | GCTTTGATATCGCTTGACGGGACC | 17 | 2 | 24 | 11 | 35 | 32 |
| 1438 | 1270 | 4811 | 80.2 | GCTTTGATCAGCTCCCGACCTGCG | 17 | 2 | 31 | 28 | 32 | 29 |
| 1439 | 1271 | 4812 | 78.8 | GCTTTGATGACCCCATTCCCGACC | 17 | 2 | 32 | 15 | 28 | 32 |
| 1440 | 1272 | 4829 | 77.1 | GCTTAATCCAGCGGTATCCCCACG | 17 | 4 | 31 | 18 | 28 | 30 |
| 1441 | 1273 | 30268 | 79.1 | GCTTAAAGCGTTTGCGCCATGTGC | 17 | 6 | 12 | 29 | 15 | 33 |
| 1442 | 1274 | 30269 | 77.5 | GCTTAAAGCAGCGACCGCTTCGTT | 17 | 6 | 31 | 32 | 17 | 12 |
| 1443 | 1275 | 14530 | 78.9 | GCTTTCTGCTTGACGGCTTGGCAA | 17 | 8 | 11 | 35 | 11 | 21 |
| 1444 | 1276 | 14532 | 75.6 | GCTTTCTGCTCAGGACGCTTTCGT | 17 | 8 | 13 | 34 | 17 | 10 |
| 1445 | 1277 | 4845 | 78 | GCTTTCTGCTGTTCCCCAGCCTCA | 17 | 8 | 14 | 28 | 31 | 13 |
| 1446 | 1278 | 14535 | 75.8 | GCTTTCTGCCTAAGGATGCGATCG | 17 | 8 | 26 | 25 | 29 | 24 |
| 1447 | 1279 | 14536 | 77.9 | GCTTTCTGGGACGCAAATCGCCTA | 17 | 8 | 34 | 21 | 24 | 26 |
| 1448 | 1280 | 20744 | 76.5 | GCTTTGTCGAGTGTCTTCCCTGCG | 17 | 9 | 20 | 19 | 28 | 29 |
| 1449 | 1281 | 14544 | 78.9 | GCTTTGTCGACCGCTTCGAAGCAA | 17 | 9 | 32 | 17 | 16 | 21 |
| 1450 | 1282 | 4867 | 80.6 | GCTTTCGTTGTCGTGCTGCGCTCA | 17 | 10 | 9 | 33 | 29 | 13 |
| 1451 | 1283 | 14548 | 77.7 | GCTTTCGTCGTTGTGCAGGAGCAA | 17 | 10 | 12 | 33 | 25 | 21 |
| 1452 | 1285 | 14552 | 78.2 | GCTTTCGTGATGCCTATCCCTGCG | 17 | 10 | 27 | 26 | 28 | 29 |
| 1453 | 1286 | 30272 | 75.5 | GCTTTCGTAGCCTTAGTCCCGCAA | 17 | 10 | 36 | 3 | 28 | 21 |
| 1454 | 1287 | 30273 | 77.1 | GCTTCTTGCCATCTTGGATGTGCG | 17 | 11 | 15 | 11 | 27 | 29 |
| 1455 | 1288 | 30274 | 76.5 | GCTTCTTGGCAAAGTGCGTTACGG | 17 | 11 | 21 | 22 | 12 | 35 |
| 1456 | 1289 | 4887 | 79.9 | GCTTCTTGATCGACGGTCCCACGG | 17 | 11 | 24 | 35 | 28 | 35 |
| 1457 | 1291 | 4907 | 78.7 | GCTTCGTTCAGCCGTTGACCAGGA | 17 | 12 | 31 | 12 | 32 | 25 |
| 1458 | 1292 | 30275 | 79 | GCTTCGTTGTGCAGCCCGAATGTC | 17 | 12 | 33 | 36 | 16 | 9 |
| 1459 | 1293 | 4917 | 80.9 | GCTTCTCAGTGCGCTTTGCGCGTT | 17 | 13 | 33 | 17 | 29 | 12 |
| 1460 | 1294 | 14568 | 80.1 | GCTTCTGTACGGGACCGACCTGCG | 17 | 14 | 35 | 32 | 32 | 29 |
| 1461 | 1295 | 30276 | 79.9 | GCTTCCATTCCCGATGTCCCTCCC | 17 | 15 | 28 | 27 | 28 | 28 |
| 1462 | 1296 | 14575 | 80 | GCTTCGAACTTGGCAATCCCGTGC | 17 | 16 | 11 | 21 | 28 | 33 |
| 1463 | 1297 | 4950 | 78.5 | GCTTCGAACTGTGCAAAGCCCAGC | 17 | 16 | 14 | 21 | 36 | 31 |
| 1464 | 1298 | 4953 | 78.1 | GCTTCGAAAGTGGCAAACGGGATG | 17 | 16 | 22 | 21 | 35 | 27 |
| 1465 | 1299 | 30277 | 77.3 | GCTTCGAAAGGATGCGCTGTGATG | 17 | 16 | 25 | 29 | 14 | 27 |
| 1466 | 1300 | 20755 | 75.2 | GCTTGCTTCTTGATACAGCCGCAA | 17 | 17 | 11 | 5 | 36 | 21 |
| 1467 | 1301 | 40247 | 76.7 | GCTTGCTTTCCCTCTGAGCCGAGT | 17 | 17 | 28 | 8 | 36 | 20 |
| 1468 | 1302 | 4982 | 76.1 | GCTTGGTAGCAAGTGCGGACGAGT | 17 | 18 | 21 | 33 | 34 | 20 |
| 1469 | 1303 | 4991 | 79.3 | GCTTGAGTCGTTTCCCGACCAGCC | 17 | 20 | 12 | 28 | 32 | 36 |
| 1470 | 1304 | 4994 | 81.1 | GCTTGAGTGTGCTGCGCTTGCACG | 17 | 20 | 33 | 29 | 11 | 30 |
| 1471 | 1305 | 14589 | 77.5 | GCTTGCAAAAAGCACGCGAAAGTG | 17 | 21 | 5 | 30 | 16 | 22 |
| 1472 | 1306 | 30279 | 78.2 | GCTTGCAATCGTCTCAGCAATGCG | 17 | 21 | 10 | 13 | 21 | 29 |
| 1473 | 1307 | 30280 | 78 | GCTTGCAACGAAGTCTCAGCGCAA | 17 | 21 | 16 | 19 | 31 | 21 |
| 1474 | 1308 | 30281 | 76.7 | GCTTGCAAACCTCACGCCATCCTA | 17 | 21 | 23 | 30 | 15 | 26 |
| 1475 | 1309 | 5005 | 78 | GCTTGCAAGATGCAGCTCCCCCTA | 17 | 21 | 27 | 31 | 28 | 26 |
| 1476 | 1310 | 5022 | 78.8 | GCTTACCTCAGCTCCCAGCCAGCC | 17 | 23 | 31 | 28 | 36 | 36 |
| 1477 | 1311 | 40248 | 75.7 | GCTTATCGCTTGTCTGGTGCTCCC | 17 | 24 | 11 | 8 | 33 | 28 |
| 1478 | 1312 | 30283 | 75.3 | GCTTATCGCCTATTGAACGGCGTT | 17 | 24 | 26 | 1 | 35 | 12 |
| 1479 | 1313 | 14603 | 78.7 | GCTTATCGGACCGACCCTTGCGTT | 17 | 24 | 32 | 32 | 11 | 12 |

FIG. 25DD

| SEQ ID NO: | 4,633 ID# | HEX ID# | Tm | ZIPCODE (5'-3') | TETRAMER NUMBERS | | | | |
|---|---|---|---|---|---|---|---|---|---|
| 1480 | 1314 | 5045 | 78.9 | GCTTCCTACGTTTGCGCTTGCGAA | 17 | 26 | 12 | 29 | 11 | 16 |
| 1481 | 1315 | 30284 | 78.9 | GCTTGATGGCAAAGGACACGACGG | 17 | 27 | 21 | 25 | 30 | 35 |
| 1482 | 1316 | 30285 | 77 | GCTTGATGCACGAAAGCGTTGCTT | 17 | 27 | 30 | 6 | 12 | 17 |
| 1483 | 1317 | 20770 | 76 | GCTTGATGGTGCATACCGTTTCCC | 17 | 27 | 33 | 5 | 12 | 28 |
| 1484 | 1318 | 5072 | 78.3 | GCTTTCCCATCGGTCTGACCTCCC | 17 | 28 | 24 | 19 | 32 | 28 |
| 1485 | 1319 | 14622 | 80.2 | GCTTTCCCGACCGGTATGTCGCAA | 17 | 28 | 32 | 18 | 9 | 21 |
| 1486 | 1320 | 30289 | 79.7 | GCTTTGCGTACAACGGGCAATCCC | 17 | 29 | 7 | 35 | 21 | 28 |
| 1487 | 1321 | 14629 | 78.8 | GCTTTGCGCGAAGAGTATCGGCAA | 17 | 29 | 16 | 20 | 24 | 21 |
| 1488 | 1322 | 5087 | 75.6 | GCTTTGCGGGTAAATCGAGTACGG | 17 | 29 | 18 | 4 | 20 | 35 |
| 1489 | 1323 | 30290 | 79.4 | GCTTTGCGAGTGGGACCTTGAGCC | 17 | 29 | 22 | 34 | 11 | 36 |
| 1490 | 1324 | 14631 | 77.5 | GCTTTGCGATCGGCAATCCCTTAG | 17 | 29 | 24 | 21 | 28 | 3 |
| 1491 | 1325 | 14632 | 79.4 | GCTTTGCGACGGTGTCAAAGGCAA | 17 | 29 | 35 | 9 | 6 | 21 |
| 1492 | 1326 | 5097 | 81.5 | GCTTCACGTGTCCACGTCCCCACG | 17 | 30 | 9 | 30 | 28 | 30 |
| 1493 | 1327 | 40252 | 76.5 | GCTTCACGCTTGAAAGCAGCGAGT | 17 | 30 | 11 | 6 | 31 | 20 |
| 1494 | 1328 | 5100 | 75.7 | GCTTCACGCTGTTACAATCGGCAA | 17 | 30 | 14 | 7 | 24 | 21 |
| 1495 | 1329 | 14636 | 79.9 | GCTTCACGTCCCGATGCTTGGACC | 17 | 30 | 28 | 27 | 11 | 32 |
| 1496 | 1330 | 30293 | 80.4 | GCTTCACGGACCCACGGAGTCGAA | 17 | 30 | 32 | 30 | 20 | 16 |
| 1497 | 1331 | 5108 | 78.6 | GCTTCAGCAATCTCCCCGAAAGCC | 17 | 31 | 4 | 28 | 16 | 36 |
| 1498 | 1332 | 5109 | 79.6 | GCTTCAGCTCTGAGCCTCCCCACG | 17 | 31 | 8 | 36 | 28 | 30 |
| 1499 | 1333 | 30294 | 75 | GCTTCAGCTCGTAATCTCCCCAGC | 17 | 31 | 10 | 4 | 28 | 31 |
| 1500 | 1334 | 5117 | 75.8 | GCTTCAGCGCAAAAAGAATCGACC | 17 | 31 | 21 | 6 | 4 | 32 |
| 1501 | 1335 | 40256 | 78.3 | GCTTCAGCACCTGGTAAGCCACGG | 17 | 31 | 23 | 18 | 36 | 35 |
| 1502 | 1336 | 5123 | 79.7 | GCTTCAGCCACGGCAACTCAGCAA | 17 | 31 | 30 | 21 | 13 | 21 |
| 1503 | 1337 | 5128 | 80.8 | GCTTGACCAATCCACGTGCGAGCC | 17 | 32 | 4 | 30 | 29 | 36 |
| 1504 | 1338 | 30296 | 77.5 | GCTTGACCCCATGCTTGCTTAGCC | 17 | 32 | 15 | 17 | 17 | 36 |
| 1505 | 1339 | 40258 | 79.7 | GCTTGACCCCTAAGCCCACGCTCA | 17 | 32 | 26 | 36 | 30 | 13 |
| 1506 | 1340 | 14653 | 81.1 | GCTTGACCCAGCGACCGTGCTCTG | 17 | 32 | 31 | 32 | 33 | 8 |
| 1507 | 1341 | 14656 | 78.6 | GCTTGTGCATCGGTGCCTTGACCT | 17 | 33 | 24 | 33 | 11 | 23 |
| 1508 | 1342 | 5148 | 77.6 | GCTTGTGCTCCCAATCTGCGTTGA | 17 | 33 | 28 | 4 | 29 | 1 |
| 1509 | 1343 | 20786 | 79.4 | GCTTGGACCGTTTCTGGTGCCCAT | 17 | 34 | 12 | 8 | 33 | 15 |
| 1510 | 1344 | 5158 | 76.1 | GCTTGGACCGAATCTGGCAATGTC | 17 | 34 | 16 | 8 | 21 | 9 |
| 1511 | 1345 | 5161 | 78.6 | GCTTGGACTCCCCTTGTGTCGCAA | 17 | 34 | 28 | 11 | 9 | 21 |
| 1512 | 1346 | 40259 | 77.9 | GCTTGGACCACGTACATCCCAGCC | 17 | 34 | 30 | 7 | 28 | 36 |
| 1513 | 1347 | 14668 | 78.6 | GCTTACGGTCTGACGGTGCGTCGT | 17 | 35 | 8 | 35 | 29 | 10 |
| 1514 | 1348 | 30301 | 75.9 | GCTTAGCCCTGTAATCACGGGCAA | 17 | 36 | 14 | 4 | 35 | 21 |
| 1515 | 1349 | 5192 | 76.4 | GCTTAGCCATCGCTCAAAAGCGAA | 17 | 36 | 24 | 13 | 6 | 16 |
| 1516 | 1350 | 5216 | 76.9 | GGTATCTGGTGCAGGACGAATGCG | 18 | 8 | 33 | 25 | 16 | 29 |
| 1517 | 1351 | 5219 | 80.1 | GGTATGTCGCTTTGCGCAGCTCCC | 18 | 9 | 17 | 29 | 31 | 28 |
| 1518 | 1352 | 5252 | 78.6 | GGTACGAACAGCGGTAAGCCGCAA | 18 | 16 | 31 | 18 | 36 | 21 |
| 1519 | 1353 | 30304 | 75.2 | GGTACGAAAGCCTACAAGCCCGAA | 18 | 16 | 36 | 7 | 36 | 16 |
| 1520 | 1354 | 5266 | 80.2 | GGTAGCAACAGCGACCCAGCCAGC | 18 | 21 | 31 | 32 | 31 | 31 |
| 1521 | 1355 | 5268 | 77.3 | GGTAGCAAGGACTGCGTCTGTGCG | 18 | 21 | 34 | 29 | 8 | 29 |
| 1522 | 1356 | 5277 | 79.8 | GGTAACCTCACGTGCGCTGTTGCG | 18 | 23 | 30 | 29 | 14 | 29 |
| 1523 | 1357 | 40264 | 76.1 | GGTAATCGGCAACGTTCTTGACGG | 18 | 24 | 21 | 12 | 11 | 35 |
| 1524 | 1358 | 5296 | 76.5 | GGTAGATGGCTTCGTTTCCCCAGC | 18 | 27 | 17 | 12 | 28 | 31 |
| 1525 | 1359 | 14728 | 76.9 | GGTATGCGGCAACTGTATCGGTGC | 18 | 29 | 21 | 14 | 24 | 33 |
| 1526 | 1360 | 5328 | 77 | GGTATGCGAGTGGTGCGGTAGTGC | 18 | 29 | 22 | 33 | 18 | 33 |
| 1527 | 1361 | 30306 | 76.3 | GGTACACGGCAACGTTCCATTCGT | 18 | 30 | 21 | 12 | 15 | 10 |
| 1528 | 1362 | 5341 | 78.7 | GGTACACGATCGGACCAGGATGCG | 18 | 30 | 24 | 32 | 25 | 29 |
| 1529 | 1363 | 5344 | 78.1 | GGTACACGAGCCGAGTCAGCGCTT | 18 | 30 | 36 | 20 | 31 | 17 |
| 1530 | 1364 | 30307 | 75.7 | GGTACAGCGCTTAGGAGGACGTGC | 18 | 31 | 17 | 25 | 34 | 33 |

FIG. 25EE

| SEQ ID NO: | 4,633 ID# | HEX ID# | Tm | ZIPCODE (5'-3') | TETRAMER NUMBERS | | | | |
|---|---|---|---|---|---|---|---|---|---|
| 1531 | 1365 | 5355 | 78.2 | GGTACAGCGACCCTGTTCCCTCCC | 18 | 31 | 32 | 14 | 28 | 28 |
| 1532 | 1366 | 5360 | 76.6 | GGTAGACCGGTACAGCATCGCGAA | 18 | 32 | 18 | 31 | 24 | 16 |
| 1533 | 1367 | 5362 | 79.8 | GGTAGACCATCGCAGCGTGCATCG | 18 | 32 | 24 | 31 | 33 | 24 |
| 1534 | 1368 | 40267 | 80.4 | GGTAGACCGTGCCCATCCATTGCG | 18 | 32 | 33 | 15 | 15 | 29 |
| 1535 | 1369 | 5368 | 75.5 | GGTAGACCACGGTTAGTGCGAGCC | 18 | 32 | 35 | 3 | 29 | 36 |
| 1536 | 1370 | 30308 | 76.2 | GGTAACGGTCGTTTAGACGGTGCG | 18 | 35 | 10 | 3 | 35 | 29 |
| 1537 | 1371 | 30309 | 77.6 | GGTAACGGCTGTGTGCGATGGATG | 18 | 35 | 14 | 33 | 27 | 27 |
| 1538 | 1372 | 30310 | 75.4 | GGTAAGCCGAGTACCTTGCGCTGT | 18 | 36 | 20 | 23 | 29 | 14 |
| 1539 | 1373 | 5420 | 77.3 | GTCTTTGATGCGCGTTTGCGAAAG | 19 | 1 | 29 | 12 | 29 | 6 |
| 1540 | 1374 | 5425 | 79 | GTCTTCTGCAGCTGCGCTTGCCAT | 19 | 8 | 31 | 29 | 11 | 15 |
| 1541 | 1376 | 5437 | 81.1 | GTCTCTTGCAGCACGGTCCCTGCG | 19 | 11 | 31 | 35 | 28 | 29 |
| 1542 | 1377 | 5440 | 78.2 | GTCTCGTTCGAACAGCAGCCGCTT | 19 | 12 | 16 | 31 | 36 | 17 |
| 1543 | 1378 | 5444 | 80.7 | GTCTCGTTGTGCCACGTCGTTGCG | 19 | 12 | 33 | 30 | 10 | 29 |
| 1544 | 1379 | 5449 | 77.2 | GTCTCCATTCCCACGGCTGTAGCC | 19 | 15 | 28 | 35 | 14 | 36 |
| 1545 | 1380 | 5450 | 78.1 | GTCTCGAACGAACAGCGCAACACG | 19 | 16 | 16 | 31 | 21 | 30 |
| 1546 | 1381 | 5453 | 79.1 | GTCTCGAAATCGCGAAACGGGACC | 19 | 16 | 24 | 16 | 35 | 32 |
| 1547 | 1382 | 20836 | 75 | GTCTGCAAATCGAATCTCCCCGTT | 19 | 21 | 24 | 4 | 28 | 12 |
| 1548 | 1383 | 5481 | 81.2 | GTCTGATGCAGCATCGTGCGGCAA | 19 | 27 | 31 | 24 | 29 | 21 |
| 1549 | 1384 | 30311 | 80.3 | GTCTTCCCCTTGACGGCGTTGCAA | 19 | 28 | 11 | 35 | 12 | 21 |
| 1550 | 1385 | 30312 | 76.5 | GTCTTCCCCCATTCTGACGGGGTA | 19 | 28 | 15 | 8 | 35 | 18 |
| 1551 | 1386 | 40269 | 78.8 | GTCTTCCCACGGAGTGCCATGTGC | 19 | 28 | 35 | 22 | 15 | 33 |
| 1552 | 1387 | 5498 | 78.5 | GTCTTGCGAGTGATCGAGCCAGCC | 19 | 29 | 22 | 24 | 36 | 36 |
| 1553 | 1388 | 30313 | 77.3 | GTCTTGCGGACCTCCCTACAACGG | 19 | 29 | 32 | 28 | 7 | 35 |
| 1554 | 1389 | 5507 | 78.7 | GTCTCACGCTCAACGGCTTGCCAT | 19 | 30 | 13 | 35 | 11 | 15 |
| 1555 | 1390 | 30314 | 79.2 | GTCTCACGGCTTTGTCAGCCGTGC | 19 | 30 | 17 | 9 | 36 | 33 |
| 1556 | 1391 | 5509 | 78.8 | GTCTCACGCCTAGACCTGCGGCAA | 19 | 30 | 26 | 32 | 29 | 21 |
| 1557 | 1392 | 5510 | 79.1 | GTCTCACGTCCCCTGTGCTTTGCG | 19 | 30 | 28 | 14 | 17 | 29 |
| 1558 | 1393 | 14801 | 79.9 | GTCTCACGACGGCGTTCGTTGTGC | 19 | 30 | 35 | 12 | 12 | 33 |
| 1559 | 1394 | 5519 | 77.1 | GTCTCAGCCAGCTCGTTCGTCGAA | 19 | 31 | 31 | 10 | 10 | 16 |
| 1560 | 1395 | 5520 | 79.6 | GTCTCAGCGGACGGACGGACCCTA | 19 | 31 | 34 | 34 | 34 | 26 |
| 1561 | 1396 | 40271 | 78.9 | GTCTGTGCGCTTCACGTTGATGCG | 19 | 33 | 17 | 30 | 1 | 29 |
| 1562 | 1397 | 40272 | 78.5 | GTCTGTGCGCAAGGACCGTTCCAT | 19 | 33 | 21 | 34 | 12 | 15 |
| 1563 | 1399 | 40273 | 80.6 | GTCTGTGCAGCCGCTTTCCCAGGA | 19 | 33 | 36 | 17 | 28 | 25 |
| 1564 | 1400 | 30315 | 75.8 | GTCTGGACGCTTACGGCGAAAAAG | 19 | 34 | 17 | 35 | 16 | 6 |
| 1565 | 1401 | 5540 | 81.7 | GTCTGGACTCCCGCAACACGTGCG | 19 | 34 | 28 | 21 | 30 | 29 |
| 1566 | 1402 | 5545 | 79.8 | GTCTGGACAGCCATCGATCGTGCG | 19 | 34 | 36 | 24 | 24 | 29 |
| 1567 | 1403 | 14814 | 75.6 | GTCTAGCCGGTACAGCTCCCATCG | 19 | 36 | 18 | 31 | 28 | 24 |
| 1568 | 1404 | 5568 | 83.1 | GAGTTCTGTGCGCACGCACGGCAA | 20 | 8 | 29 | 30 | 30 | 21 |
| 1569 | 1405 | 5569 | 80.9 | GAGTTCTGCACGACGGCACGTCCC | 20 | 8 | 30 | 35 | 30 | 28 |
| 1570 | 1407 | 5577 | 79 | GAGTCTTGCACGCCATAGCCCACG | 20 | 11 | 30 | 15 | 36 | 30 |
| 1571 | 1408 | 5580 | 77.2 | GAGTCGTTCGTTAGCCATCGTGCG | 20 | 12 | 12 | 36 | 24 | 29 |
| 1572 | 1409 | 20857 | 77.9 | GAGTCTGTCACGCAGCAGCCAGGA | 20 | 14 | 30 | 31 | 36 | 25 |
| 1573 | 1410 | 30317 | 77.9 | GAGTCGAAAGCCTGCGTCGTCCAT | 20 | 16 | 36 | 29 | 10 | 15 |
| 1574 | 1411 | 5597 | 77.7 | GAGTGCTTGCAACACGCACGACCT | 20 | 17 | 21 | 30 | 30 | 23 |
| 1575 | 1412 | 5599 | 81.9 | GAGTGCTTCACGGTGCGTGCAGCC | 20 | 17 | 30 | 33 | 33 | 36 |
| 1576 | 1413 | 5612 | 76.5 | GAGTATCGTGCGATCGGACCCTCA | 20 | 24 | 29 | 24 | 32 | 13 |
| 1577 | 1414 | 20866 | 77.7 | GAGTCCTACAGCTCCCGCTTTGCG | 20 | 26 | 31 | 28 | 17 | 29 |
| 1578 | 1415 | 5633 | 78 | GAGTTCCCGTGCCCTATCGTGTGC | 20 | 28 | 33 | 26 | 10 | 33 |
| 1579 | 1416 | 14828 | 80.9 | GAGTTGCGAAAGCACGGGACGTGC | 20 | 29 | 6 | 30 | 34 | 33 |
| 1580 | 1417 | 5645 | 76.4 | GAGTTGCGCCATTACATCCCGGTA | 20 | 29 | 15 | 7 | 28 | 18 |
| 1581 | 1418 | 40276 | 77.2 | GAGTTGCGGGTAGCAATCTGCACG | 20 | 29 | 18 | 21 | 8 | 30 |

FIG. 25FF

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 1582 | 1419 | 40277 | 79.5 | GAGTTGCGACCTAGCCTCCCTGCG | 20 | 29 | 23 | 36 | 28 | 29 |
| 1583 | 1420 | 5671 | 81.7 | GAGTCAGCGATGGTGCGGACACGG | 20 | 31 | 27 | 33 | 34 | 35 |
| 1584 | 1421 | 20874 | 76.3 | GAGTCAGCTCCCTCTGGACCCGTT | 20 | 31 | 28 | 8 | 32 | 12 |
| 1585 | 1422 | 5673 | 79.3 | GAGTCAGCGGACAGCCGAGTCACG | 20 | 31 | 34 | 36 | 20 | 30 |
| 1586 | 1423 | 5676 | 76.7 | GAGTGACCCGTTTCCCCGAACTGT | 20 | 32 | 12 | 28 | 16 | 14 |
| 1587 | 1425 | 14843 | 80.9 | GAGTGACCGTGCGACCAGCCCTTG | 20 | 32 | 33 | 32 | 36 | 11 |
| 1588 | 1426 | 20876 | 76.4 | GAGTGTGCTTGAGGACTCCCGTGC | 20 | 33 | 1 | 34 | 28 | 33 |
| 1589 | 1428 | 5693 | 77.8 | GAGTGGACCCATTGTCGGACGGAC | 20 | 34 | 15 | 9 | 34 | 34 |
| 1590 | 1429 | 5699 | 77.8 | GAGTGGACGGACTGTCATCGCACG | 20 | 34 | 34 | 9 | 24 | 30 |
| 1591 | 1430 | 14849 | 75.3 | GAGTACGGCCATTTAGTGCGGCTT | 20 | 35 | 15 | 3 | 29 | 17 |
| 1592 | 1431 | 5716 | 79.9 | GAGTAGCCATCGGACCAGCCCACG | 20 | 36 | 24 | 32 | 36 | 30 |
| 1593 | 1432 | 5730 | 79 | GCAATTGAGTGCGGACCGAACAGC | 21 | 1 | 33 | 34 | 16 | 31 |
| 1594 | 1433 | 5732 | 78.7 | GCAATGATTCGTTCCCCTTGCACG | 21 | 2 | 10 | 28 | 11 | 30 |
| 1595 | 1434 | 5737 | 80.1 | GCAATGATCAGCGCTTTCCCAGCC | 21 | 2 | 31 | 17 | 28 | 36 |
| 1596 | 1435 | 5752 | 77.6 | GCAAAATCATCGGTGCCGAAACCT | 21 | 4 | 24 | 33 | 16 | 23 |
| 1597 | 1436 | 40281 | 77.2 | GCAAAATCTCCCATCGCTCATCCC | 21 | 4 | 28 | 24 | 13 | 28 |
| 1598 | 1437 | 14874 | 78.9 | GCAAAATCCACGCAGCCTGTGACC | 21 | 4 | 30 | 31 | 14 | 32 |
| 1599 | 1438 | 5778 | 75.5 | GCAAAAAGACCTAGGAAGCCGCAA | 21 | 6 | 23 | 25 | 36 | 21 |
| 1600 | 1440 | 30319 | 76.2 | GCAATCTGCGTTTAGGGACACGG | 21 | 8 | 12 | 3 | 34 | 35 |
| 1601 | 1441 | 30320 | 76.7 | GCAATCTGGCAACGTTATCGCGTT | 21 | 8 | 21 | 12 | 24 | 12 |
| 1602 | 1442 | 5792 | 78.2 | GCAATCTGTCCCGCAACTCAAGCC | 21 | 8 | 28 | 21 | 13 | 36 |
| 1603 | 1443 | 5793 | 80.8 | GCAATCTGTGCGCTGTGGACGTGC | 21 | 8 | 29 | 14 | 34 | 33 |
| 1604 | 1444 | 30321 | 77.4 | GCAATCTGGACCAATCAGCCCCAT | 21 | 8 | 32 | 4 | 36 | 15 |
| 1605 | 1445 | 40284 | 82.7 | GCAATCTGGGACAGCCGTGCCAGC | 21 | 8 | 34 | 36 | 33 | 31 |
| 1606 | 1446 | 5796 | 80.4 | GCAATGTCTCGTGACCTGCGCGAA | 21 | 9 | 10 | 32 | 29 | 16 |
| 1607 | 1447 | 30323 | 78.4 | GCAATGTCGCTTTCGTGTGCCTCA | 21 | 9 | 17 | 10 | 33 | 13 |
| 1608 | 1448 | 20893 | 77 | GCAATGTCGGTAGACCTCCCGCTT | 21 | 9 | 18 | 32 | 28 | 17 |
| 1609 | 1449 | 14901 | 80.5 | GCAATGTCATCGTCCCTCCCCACG | 21 | 9 | 24 | 28 | 28 | 30 |
| 1610 | 1450 | 5804 | 79 | GCAATGTCTGCGGATGCGAAGGAC | 21 | 9 | 29 | 27 | 16 | 34 |
| 1611 | 1451 | 14902 | 79.2 | GCAATGTCCACGCGAAATCGTCGT | 21 | 9 | 30 | 16 | 24 | 10 |
| 1612 | 1452 | 5812 | 77.5 | GCAATCGTCTGTTGCGAATCCGAA | 21 | 10 | 14 | 29 | 4 | 16 |
| 1613 | 1453 | 5818 | 77.5 | GCAATCGTACCTGCTTGTGCCGAA | 21 | 10 | 23 | 17 | 33 | 16 |
| 1614 | 1455 | 30324 | 77.3 | GCAATCGTAGCCTGATTCCCAGC | 21 | 10 | 36 | 2 | 28 | 31 |
| 1615 | 1456 | 5835 | 81.2 | GCAACTTGGATGAGCCCACGCGAA | 21 | 11 | 27 | 36 | 30 | 16 |
| 1616 | 1457 | 14911 | 79.4 | GCAACTTGCAGCCGAAGCAAGTGC | 21 | 11 | 31 | 16 | 21 | 33 |
| 1617 | 1458 | 40286 | 77.1 | GCAACGTTTTGATCGTCACGAGCC | 21 | 12 | 1 | 10 | 30 | 36 |
| 1618 | 1459 | 5842 | 80.2 | GCAACGTTTACAACGGCAGCGCAA | 21 | 12 | 7 | 35 | 31 | 21 |
| 1619 | 1460 | 14919 | 81.6 | GCAACGTTGATGGTGCTCCCTGCG | 21 | 12 | 27 | 33 | 28 | 29 |
| 1620 | 1461 | 30326 | 77.3 | GCAACGTTTCCCACCTTTGAAGCC | 21 | 12 | 28 | 23 | 1 | 36 |
| 1621 | 1464 | 5860 | 78.6 | GCAACTCAATCGCGAAGTGCCCAT | 21 | 13 | 24 | 16 | 33 | 15 |
| 1622 | 1466 | 5863 | 80.2 | GCAACTCACACGACGGGTGCAGGA | 21 | 13 | 30 | 35 | 33 | 25 |
| 1623 | 1467 | 5864 | 78.6 | GCAACTCAACGGGCTTGGACAGGA | 21 | 13 | 35 | 17 | 34 | 25 |
| 1624 | 1468 | 30327 | 78.7 | GCAACTGTTGCGGCAAGCAAACCT | 21 | 14 | 29 | 21 | 21 | 23 |
| 1625 | 1469 | 5875 | 79.5 | GCAACCATCTCAGGACCAGCGCAA | 21 | 15 | 13 | 34 | 31 | 21 |
| 1626 | 1470 | 20911 | 77.5 | GCAACCATCGAATGTCACGGATCG | 21 | 15 | 16 | 9 | 35 | 24 |
| 1627 | 1471 | 5881 | 79 | GCAACCATGATGACGGTCCCAGGA | 21 | 15 | 27 | 35 | 28 | 25 |
| 1628 | 1472 | 5882 | 75.8 | GCAACCATTGCGTCCCTTAGTCGT | 21 | 15 | 29 | 28 | 3 | 10 |
| 1629 | 1473 | 5885 | 79.7 | GCAACCATGGACGATGCGAAGTGC | 21 | 15 | 34 | 27 | 16 | 33 |
| 1630 | 1474 | 20915 | 76.2 | GCAACGAAGCTTGACCTGTCGCTT | 21 | 16 | 17 | 32 | 9 | 17 |
| 1631 | 1475 | 40288 | 77 | GCAAGCTTGCTTTGTCCTTGGCAA | 21 | 17 | 17 | 9 | 11 | 21 |
| 1632 | 1476 | 5912 | 78.2 | GCAAGCTTCACGGCTTCAGCCTGT | 21 | 17 | 30 | 17 | 31 | 14 |

FIG. 25GG

| SEQ ID NO: | 4,633 ID# | HEX ID# | Tm | ZIPCODE (5'-3') | TETRAMER NUMBERS | | | | |
|---|---|---|---|---|---|---|---|---|---|
| 1633 | 1477 | 5914 | 78.8 | GCAAGCTTAGCCGATGGTGCCTCA | 21 | 17 | 36 | 27 | 33 | 13 |
| 1634 | 1478 | 5924 | 75 | GCAAGTCTGCTTAATCGACCGCAA | 21 | 19 | 17 | 4 | 32 | 21 |
| 1635 | 1480 | 14946 | 78.1 | GCAAGCAAAATCGCAATCGTTCCC | 21 | 21 | 4 | 21 | 10 | 28 |
| 1636 | 1481 | 5946 | 79.3 | GCAAGCAACTTGCTCATGCGAGCC | 21 | 21 | 11 | 13 | 29 | 36 |
| 1637 | 1482 | 5948 | 76.7 | GCAAGCAACTCAGACCCACGTCGT | 21 | 21 | 13 | 32 | 30 | 10 |
| 1638 | 1483 | 5952 | 75.6 | GCAAGCAAGCTTTCCCGATGAATC | 21 | 21 | 17 | 28 | 27 | 4 |
| 1639 | 1484 | 40290 | 78.4 | GCAAGCAACAGCATACGACCGCAA | 21 | 21 | 31 | 5 | 32 | 21 |
| 1640 | 1486 | 14955 | 77.4 | GCAAAGTGGGTACCATTGCGCTCA | 21 | 22 | 18 | 15 | 29 | 13 |
| 1641 | 1487 | 20929 | 78.4 | GCAAACCTTCTGAGCCCTTGCACG | 21 | 23 | 8 | 36 | 11 | 30 |
| 1642 | 1488 | 5978 | 79.2 | GCAAACCTTGTCCAGCTCCCGGAC | 21 | 23 | 9 | 31 | 28 | 34 |
| 1643 | 1490 | 20930 | 77.9 | GCAAACCTCCATTGCGGGACAATC | 21 | 23 | 15 | 29 | 34 | 4 |
| 1644 | 1491 | 30333 | 76.8 | GCAAACCTGCAAGACCCTCAGCAA | 21 | 23 | 21 | 32 | 13 | 21 |
| 1645 | 1492 | 40294 | 80.3 | GCAAACCTGACCGCAAAGCCGGTA | 21 | 23 | 32 | 21 | 36 | 18 |
| 1646 | 1493 | 14961 | 80 | GCAAACCTGGACGCAAGACCGACC | 21 | 23 | 34 | 21 | 32 | 32 |
| 1647 | 1494 | 40295 | 75.4 | GCAAATCGCTCACCTAAGCCGTCT | 21 | 24 | 13 | 26 | 36 | 19 |
| 1648 | 1495 | 30334 | 78.2 | GCAAATCGGAGTTGTCCAGCAGCC | 21 | 24 | 20 | 9 | 31 | 36 |
| 1649 | 1497 | 40297 | 79.4 | GCAAATCGTCCCCAGCTGTCCCAT | 21 | 24 | 28 | 31 | 9 | 15 |
| 1650 | 1498 | 6006 | 77.2 | GCAAATCGGACCATACGTGCAGGA | 21 | 24 | 32 | 5 | 33 | 25 |
| 1651 | 1500 | 6010 | 78.9 | GCAAAGGATCTGTGCGGCAAATCG | 21 | 25 | 8 | 29 | 21 | 24 |
| 1652 | 1501 | 14971 | 80.7 | GCAAAGGACTTGGGACACGGTGCG | 21 | 25 | 11 | 34 | 35 | 29 |
| 1653 | 1502 | 6012 | 79.7 | GCAAAGGACTCAGTGCAGCCGCAA | 21 | 25 | 13 | 33 | 36 | 21 |
| 1654 | 1503 | 40298 | 75.1 | GCAAAGGAACCTATCGGATGCGTT | 21 | 25 | 23 | 24 | 27 | 12 |
| 1655 | 1504 | 14972 | 78.4 | GCAAAGGAATCGCACGGGTACGAA | 21 | 25 | 24 | 30 | 18 | 16 |
| 1656 | 1505 | 6024 | 79.1 | GCAACCTAGACCGCTTTCCCACGG | 21 | 26 | 32 | 17 | 28 | 35 |
| 1657 | 1506 | 14975 | 76.5 | GCAACCTAAGCCAGGATCGTTCCC | 21 | 26 | 36 | 25 | 10 | 28 |
| 1658 | 1507 | 30336 | 76.3 | GCAAGATGCGTTAGTGGGACAGCC | 21 | 27 | 12 | 22 | 34 | 36 |
| 1659 | 1508 | 14978 | 78.3 | GCAAGATGCCTACACGCGAAAGCC | 21 | 27 | 26 | 30 | 16 | 36 |
| 1660 | 1509 | 6038 | 77.2 | GCAAGATGTGCGTTGAGACCCAGC | 21 | 27 | 29 | 1 | 32 | 31 |
| 1661 | 1510 | 14982 | 77.1 | GCAATCCCAATCACGGCGAATACA | 21 | 28 | 4 | 35 | 16 | 7 |
| 1662 | 1511 | 14983 | 78.2 | GCAATCCCTCTGCAGCGAGTGCTT | 21 | 28 | 8 | 31 | 20 | 17 |
| 1663 | 1512 | 30342 | 82.2 | GCAATCCCACGGGGACAAATCGTGC | 21 | 28 | 35 | 34 | 4 | 33 |
| 1664 | 1513 | 40304 | 79.6 | GCAATGCGTTAGGATGCCATTGCG | 21 | 29 | 3 | 27 | 15 | 29 |
| 1665 | 1514 | 40305 | 79.3 | GCAATGCGAAAGGATGCGTTCGAA | 21 | 29 | 6 | 27 | 12 | 16 |
| 1666 | 1515 | 6065 | 78.4 | GCAATGCGTCGTCGAATCGTCTCA | 21 | 29 | 10 | 16 | 10 | 13 |
| 1667 | 1516 | 6067 | 80.9 | GCAATGCGCGTTGTGCCTGTGGTA | 21 | 29 | 12 | 33 | 14 | 18 |
| 1668 | 1517 | 30344 | 79.9 | GCAATGCGCTCAACCTCGTTGTGC | 21 | 29 | 13 | 23 | 12 | 33 |
| 1669 | 1518 | 6069 | 79.7 | GCAATGCGCGAATCTGGATGATCG | 21 | 29 | 16 | 8 | 27 | 24 |
| 1670 | 1519 | 6071 | 81.9 | GCAATGCGCAGCGCTTTCTGATCG | 21 | 29 | 31 | 17 | 8 | 24 |
| 1671 | 1520 | 6072 | 76.5 | GCAATGCGGGACTTAGACCTTCCC | 21 | 29 | 34 | 3 | 23 | 28 |
| 1672 | 1521 | 6075 | 79.8 | GCAACACGAATCGATGCAGCGGAC | 21 | 30 | 4 | 27 | 31 | 34 |
| 1673 | 1522 | 6077 | 79.3 | GCAACACGTCTGCCTATGCGCCAT | 21 | 30 | 8 | 26 | 29 | 15 |
| 1674 | 1523 | 14994 | 77.8 | GCAACACGCGTTCTGTGGTAACGG | 21 | 30 | 12 | 14 | 18 | 35 |
| 1675 | 1524 | 40306 | 77 | GCAACACGCTCAGCAAAAAGCGTT | 21 | 30 | 13 | 21 | 6 | 12 |
| 1676 | 1525 | 6091 | 79.4 | GCAACACGTCCCGTCTTCCCCTGT | 21 | 30 | 28 | 19 | 28 | 14 |
| 1677 | 1526 | 15001 | 80.2 | GCAACACGGGACCACGATCGGAGT | 21 | 30 | 34 | 30 | 24 | 20 |
| 1678 | 1527 | 15002 | 80.7 | GCAACAGCTTGATGCGCCATCACG | 21 | 31 | 1 | 29 | 15 | 30 |
| 1679 | 1528 | 40308 | 75.4 | GCAACAGCTCGTAGGAATCGGCTT | 21 | 31 | 10 | 25 | 24 | 17 |
| 1680 | 1529 | 20970 | 77.8 | GCAACAGCCCATAGTGATCGCACG | 21 | 31 | 15 | 22 | 24 | 30 |
| 1681 | 1530 | 30346 | 75.9 | GCAACAGCGGTAAAAGGCTTCAGC | 21 | 31 | 18 | 6 | 17 | 31 |
| 1682 | 1531 | 30347 | 77.3 | GCAACAGCGAGTAGGAGTGCCACG | 21 | 31 | 20 | 25 | 33 | 30 |
| 1683 | 1532 | 15007 | 75.1 | GCAACAGCCCTAATACAGCCCGTT | 21 | 31 | 26 | 5 | 36 | 12 |

FIG. 25HH

| SEQ ID NO: | 4,633 ID# | HEX ID# | Tm | ZIPCODE (5'-3') | TETRAMER NUMBERS | | | | |
|---|---|---|---|---|---|---|---|---|---|
| 1684 | 1533 | 15008 | 80.3 | GCAACAGCCACGCTTGCAGCTCTG | 21 | 31 | 30 | 11 | 31 | 8 |
| 1685 | 1534 | 40312 | 77.6 | GCAAGACCCCATTCGTCGTTTCGT | 21 | 32 | 15 | 10 | 12 | 10 |
| 1686 | 1535 | 30348 | 76.1 | GCAAGACCACCTAATCGGACACGG | 21 | 32 | 23 | 4 | 34 | 35 |
| 1687 | 1536 | 40313 | 79.9 | GCAAGACCGGACGGACCACGAAAG | 21 | 32 | 34 | 34 | 30 | 6 |
| 1688 | 1537 | 30349 | 78.2 | GCAAGTGCCTTGAATCTGCGGGAC | 21 | 33 | 11 | 4 | 29 | 34 |
| 1689 | 1538 | 30350 | 78.9 | GCAAGTGCCTGTCTGTTCCCACGG | 21 | 33 | 14 | 14 | 28 | 35 |
| 1690 | 1539 | 20980 | 76.9 | GCAAGTGCGGTATCCCGAGTGATG | 21 | 33 | 18 | 28 | 20 | 27 |
| 1691 | 1540 | 40314 | 78.1 | GCAAGTGCGCAATTAGATCGTGCG | 21 | 33 | 21 | 3 | 24 | 29 |
| 1692 | 1541 | 40315 | 80.8 | GCAAGTGCACCTGACCTCCCACG | 21 | 33 | 23 | 32 | 28 | 30 |
| 1693 | 1542 | 6133 | 78.4 | GCAAGTGCATCGCCTAGTGCTCCC | 21 | 33 | 24 | 26 | 33 | 28 |
| 1694 | 1543 | 15018 | 78.1 | GCAAGTGCCCTAGTGCGTGCAGTG | 21 | 33 | 26 | 33 | 33 | 22 |
| 1695 | 1544 | 6137 | 80.4 | GCAAGTGCTCCCGTCTGTGCCCAT | 21 | 33 | 28 | 19 | 33 | 15 |
| 1696 | 1545 | 15020 | 77.7 | GCAAGTGCGTGCAAAGGCTTTTGA | 21 | 33 | 33 | 6 | 17 | 1 |
| 1697 | 1546 | 15021 | 78.5 | GCAAGTGCACGGACCTTCGTCCAT | 21 | 33 | 35 | 23 | 10 | 15 |
| 1698 | 1547 | 6142 | 81 | GCAAGGACAATCCGAATGCGGCAA | 21 | 34 | 4 | 16 | 29 | 21 |
| 1699 | 1548 | 40316 | 81.8 | GCAAGGACTCGTGGACGTGCGTGC | 21 | 34 | 10 | 34 | 33 | 33 |
| 1700 | 1549 | 30351 | 78.1 | GCAAGGACCTGTTCTGGCAAACGG | 21 | 34 | 14 | 8 | 21 | 35 |
| 1701 | 1551 | 6151 | 78 | GCAAGGACATCGCCATTCCCTGTC | 21 | 34 | 24 | 15 | 28 | 9 |
| 1702 | 1552 | 40317 | 77.6 | GCAAGGACCAGCTTAGGGACTGCG | 21 | 34 | 31 | 3 | 34 | 29 |
| 1703 | 1553 | 6156 | 77.5 | GCAAGGACGGACAGGAGCTTGACC | 21 | 34 | 34 | 25 | 17 | 32 |
| 1704 | 1554 | 6159 | 78.3 | GCAAACGGCTGTCACGTGATCGAA | 21 | 35 | 14 | 30 | 2 | 16 |
| 1705 | 1555 | 6160 | 78.1 | GCAAACGGGCTTGTGCCCTAAGTG | 21 | 35 | 17 | 33 | 26 | 22 |
| 1706 | 1556 | 40318 | 79.9 | GCAAACGGGTCTGAGTCACGCACG | 21 | 35 | 19 | 20 | 30 | 30 |
| 1707 | 1557 | 15029 | 78.7 | GCAAACGGAGTGCTCACAGCCGTT | 21 | 35 | 22 | 13 | 31 | 12 |
| 1708 | 1558 | 6164 | 81.8 | GCAAACGGTGCGCGAAGTCTGTGC | 21 | 35 | 29 | 16 | 19 | 33 |
| 1709 | 1559 | 6167 | 81.1 | GCAAACGGGACGATGTCTGCGAA | 21 | 35 | 34 | 27 | 8 | 16 |
| 1710 | 1562 | 6175 | 77.9 | GCAAAGCCGTCTGTCTGCAAGCAA | 21 | 36 | 19 | 19 | 21 | 21 |
| 1711 | 1563 | 6176 | 75.9 | GCAAAGCCACCTCCATCGAACCTA | 21 | 36 | 23 | 15 | 16 | 26 |
| 1712 | 1564 | 20998 | 75.3 | GCAAAGCCAGGAACCTAAAGGCAA | 21 | 36 | 25 | 23 | 6 | 21 |
| 1713 | 1565 | 30357 | 76.5 | GCAAAGCCCCTAGTGCCGAAGTCT | 21 | 36 | 26 | 33 | 16 | 19 |
| 1714 | 1566 | 6178 | 78.4 | GCAAAGCCTCCCCTGTGGTAAGCC | 21 | 36 | 28 | 14 | 18 | 36 |
| 1715 | 1567 | 6183 | 76.1 | AGTGAATCCGAAAGGAGTGCTGCG | 22 | 4 | 16 | 25 | 33 | 29 |
| 1716 | 1568 | 6187 | 81.3 | AGTGAATCACGGCAGCAGCCACGG | 22 | 4 | 35 | 31 | 36 | 35 |
| 1717 | 1569 | 6195 | 81.4 | AGTGTCTGCACGCAGCCACGGACC | 22 | 8 | 30 | 31 | 30 | 32 |
| 1718 | 1570 | 6200 | 79.4 | AGTGTCGTACGGACCTTGCGTGCG | 22 | 10 | 35 | 23 | 29 | 29 |
| 1719 | 1571 | 40320 | 77.5 | AGTGCTTGCCATAGCCAGCCCTGT | 22 | 11 | 15 | 36 | 36 | 14 |
| 1720 | 1572 | 6205 | 76.6 | AGTGCTTGGGTAGGACGTGCGATG | 22 | 11 | 18 | 34 | 33 | 27 |
| 1721 | 1573 | 15037 | 75.6 | AGTGCTTGCCTACCATAGCCCGAA | 22 | 11 | 26 | 15 | 36 | 16 |
| 1722 | 1574 | 30358 | 77 | AGTGCTTGGGACTGCGGGTAGACC | 22 | 11 | 34 | 29 | 18 | 32 |
| 1723 | 1575 | 30359 | 76.8 | AGTGCGTTTCGTAGTGGGACTGCG | 22 | 12 | 10 | 22 | 34 | 29 |
| 1724 | 1576 | 6219 | 78.4 | AGTGCGTTGTCTGATGCGTTTGCG | 22 | 12 | 19 | 27 | 12 | 29 |
| 1725 | 1577 | 6230 | 78.7 | AGTGCTCATCCCCGAAGGACGACC | 22 | 13 | 28 | 16 | 34 | 32 |
| 1726 | 1578 | 30360 | 80.4 | AGTGCTGTTCCCATCGGTGCCAGC | 22 | 14 | 28 | 24 | 33 | 31 |
| 1727 | 1579 | 6238 | 78.6 | AGTGCCATCTTGACGGCTCAACGG | 22 | 15 | 11 | 35 | 13 | 35 |
| 1728 | 1581 | 6258 | 76.1 | AGTGCGAATGCGAAAGTTGAAGCC | 22 | 16 | 29 | 6 | 1 | 36 |
| 1729 | 1582 | 40323 | 77.8 | AGTGGCTTCGTTCTTGCACGTCCC | 22 | 17 | 12 | 11 | 30 | 28 |
| 1730 | 1583 | 40324 | 78.6 | AGTGGCTTTCCCGGACCCTACACG | 22 | 17 | 28 | 34 | 26 | 30 |
| 1731 | 1584 | 6269 | 76.9 | AGTGGCTTTGCGCCTAGATGGCTT | 22 | 17 | 29 | 26 | 27 | 17 |
| 1732 | 1585 | 6270 | 77.9 | AGTGGCTTGACCCTGTACGGCAGC | 22 | 17 | 32 | 14 | 35 | 31 |
| 1733 | 1586 | 30364 | 77.9 | AGTGGCTTAGCCTCGTGACCCACG | 22 | 17 | 36 | 10 | 32 | 30 |
| 1734 | 1587 | 6273 | 76.9 | AGTGGGTACGTTACGGGTGCCCAT | 22 | 18 | 12 | 35 | 33 | 15 |

FIG. 25II

| SEQ ID NO: | 4,633 ID# | HEX ID# | Tm | ZIPCODE (5'-3') | TETRAMER NUMBERS | | | | |
|---|---|---|---|---|---|---|---|---|---|
| 1735 | 1588 | 6278 | 78 | AGTGGGTATGCGGCTTGACCCTCA | 22 | 18 | 29 | 17 | 32 | 13 |
| 1736 | 1589 | 6283 | 75.1 | AGTGGCAAAAGTCTGCTGTTGCG | 22 | 21 | 6 | 8 | 14 | 29 |
| 1737 | 1590 | 6290 | 80.9 | AGTGGCAAAGTGAGCCTGCGCAGC | 22 | 21 | 22 | 36 | 29 | 31 |
| 1738 | 1591 | 40325 | 79.6 | AGTGGCAAGACCTCGTGTGCGTGC | 22 | 21 | 32 | 10 | 33 | 33 |
| 1739 | 1592 | 6309 | 78.2 | AGTGATCGCTCAACGGAGCCGGTA | 22 | 24 | 13 | 35 | 36 | 18 |
| 1740 | 1593 | 15068 | 77.4 | AGTGATCGTGCGACCTTGTCACGG | 22 | 24 | 29 | 23 | 9 | 35 |
| 1741 | 1594 | 15069 | 78.4 | AGTGATCGCAGCACCTTGCGGAGT | 22 | 24 | 31 | 23 | 29 | 20 |
| 1742 | 1595 | 40327 | 79.8 | AGTGATCGGTGCATCGGCTTGCAA | 22 | 24 | 33 | 24 | 17 | 21 |
| 1743 | 1596 | 15071 | 79.1 | AGTGATCGACGGGTATCCCACGG | 22 | 24 | 35 | 18 | 28 | 35 |
| 1744 | 1597 | 6313 | 75.8 | AGTGCCTATCCCCTTGGCTTCGTT | 22 | 26 | 28 | 11 | 17 | 12 |
| 1745 | 1598 | 6316 | 82.2 | AGTGCCTACAGCGCAATGCGCACG | 22 | 26 | 31 | 21 | 29 | 30 |
| 1746 | 1599 | 21014 | 78.4 | AGTGCCTAGTGCGCTTACGGGCAA | 22 | 26 | 33 | 17 | 35 | 21 |
| 1747 | 1600 | 6325 | 79.9 | AGTGGATGAGCCGGACACGGCCTA | 22 | 27 | 36 | 34 | 35 | 26 |
| 1748 | 1601 | 15080 | 77.5 | AGTGTCCCTCGTAGCCAGCCAGGA | 22 | 28 | 10 | 36 | 36 | 25 |
| 1749 | 1602 | 6329 | 79.5 | AGTGTCCCCTGTTCCCGATGCAGC | 22 | 28 | 14 | 28 | 27 | 31 |
| 1750 | 1604 | 6337 | 76.4 | AGTGTCCCGTGCATACCGAAATCG | 22 | 28 | 33 | 5 | 16 | 24 |
| 1751 | 1605 | 6341 | 80.2 | AGTGTGCGAATCTGCGCAGCAGGA | 22 | 29 | 4 | 29 | 31 | 25 |
| 1752 | 1606 | 6343 | 79.4 | AGTGTGCGCTTGGTCTGACCACGG | 22 | 29 | 11 | 19 | 32 | 35 |
| 1753 | 1607 | 6347 | 77.9 | AGTGTGCGCGAACTGTGATGCCAT | 22 | 29 | 16 | 14 | 27 | 15 |
| 1754 | 1608 | 30366 | 75.3 | AGTGTGCGCCTAGAGTAGCCGCTT | 22 | 29 | 26 | 20 | 36 | 17 |
| 1755 | 1609 | 15086 | 78.6 | AGTGTGCGTGCGTACACACGCCAT | 22 | 29 | 29 | 7 | 30 | 15 |
| 1756 | 1610 | 40331 | 75.8 | AGTGCACGCGTTAAAGAGCCACCT | 22 | 30 | 12 | 6 | 36 | 23 |
| 1757 | 1611 | 15088 | 78.3 | AGTGCACGCGAATACACAGCACGG | 22 | 30 | 16 | 7 | 31 | 35 |
| 1758 | 1612 | 40332 | 79.5 | AGTGCACGTGCGCGTTTACAAGCC | 22 | 30 | 29 | 12 | 7 | 36 |
| 1759 | 1613 | 30369 | 76.5 | AGTGCACGGACCTTAGAGCCCCAT | 22 | 30 | 32 | 3 | 36 | 15 |
| 1760 | 1614 | 15093 | 75.6 | AGTGCAGCGCTTCCTAAAAGGTGC | 22 | 31 | 17 | 26 | 6 | 33 |
| 1761 | 1615 | 6392 | 76.6 | AGTGGACCGCAACCTAGTGCATCG | 22 | 32 | 21 | 26 | 33 | 24 |
| 1762 | 1616 | 40333 | 78.7 | AGTGGACCGGACTCTGTCCCGACC | 22 | 32 | 34 | 8 | 28 | 32 |
| 1763 | 1617 | 21032 | 75.8 | AGTGGTGCAATCCTCAGTGCTCCC | 22 | 33 | 4 | 13 | 33 | 28 |
| 1764 | 1618 | 30374 | 77.7 | AGTGGTGCCCATCGAAGCTTGGAC | 22 | 33 | 15 | 16 | 17 | 34 |
| 1765 | 1619 | 15105 | 75 | AGTGGTGCGTCTATACTGCGCAGC | 22 | 33 | 19 | 5 | 29 | 31 |
| 1766 | 1620 | 40334 | 77.7 | AGTGGTGCGAGTCCTATGCGGACC | 22 | 33 | 20 | 26 | 29 | 32 |
| 1767 | 1621 | 6416 | 76.7 | AGTGGGACTCGTCTTGATCGTGCG | 22 | 34 | 10 | 11 | 24 | 29 |
| 1768 | 1622 | 40335 | 75.5 | AGTGGGACCCATAATCCTTGTGCG | 22 | 34 | 15 | 4 | 11 | 29 |
| 1769 | 1623 | 30377 | 81.1 | AGTGACGGCTCAGTGCTGCGCCAT | 22 | 35 | 13 | 33 | 29 | 15 |
| 1770 | 1624 | 30378 | 77.5 | AGTGACGGGTACTTGGGACGTGC | 22 | 35 | 18 | 11 | 34 | 33 |
| 1771 | 1625 | 30379 | 76.9 | AGTGACGGGATGTGATTCCCCGTT | 22 | 35 | 27 | 2 | 28 | 12 |
| 1772 | 1626 | 6444 | 79.1 | AGTGACGGGACGTCTTCCCAGGA | 22 | 35 | 34 | 19 | 28 | 25 |
| 1773 | 1627 | 15116 | 76.4 | AGTGAGCCCTTGATACCAGCGCAA | 22 | 36 | 11 | 5 | 31 | 21 |
| 1774 | 1628 | 15118 | 76.5 | AGTGAGCCATCGAAAGCGTTCGAA | 22 | 36 | 24 | 6 | 12 | 16 |
| 1775 | 1629 | 15120 | 79.8 | AGTGAGCCGGACGTCTAGCCACGG | 22 | 36 | 34 | 19 | 36 | 35 |
| 1776 | 1630 | 6461 | 78.1 | ACCTTTGACGAATGCGACGGTCGT | 23 | 1 | 16 | 29 | 35 | 10 |
| 1777 | 1631 | 30380 | 76.3 | ACCTTGATTGCGTGCGGTCTCCTA | 23 | 2 | 29 | 29 | 19 | 26 |
| 1778 | 1633 | 6493 | 76.2 | ACCTTCTGCTTGTGCGGCTTATCG | 23 | 8 | 11 | 29 | 17 | 24 |
| 1779 | 1634 | 40339 | 79.9 | ACCTTCTGTGCGCAGCGTCTTCCC | 23 | 8 | 29 | 31 | 19 | 28 |
| 1780 | 1635 | 6505 | 78.9 | ACCTTGTCCCATGTGCCCATCACG | 23 | 9 | 15 | 33 | 15 | 30 |
| 1781 | 1636 | 30382 | 77.8 | ACCTTCGTTCGTATCGTGCGAGCC | 23 | 10 | 10 | 24 | 29 | 36 |
| 1782 | 1637 | 40340 | 77.5 | ACCTTCGTCGTTACGGCCATACGG | 23 | 10 | 12 | 35 | 15 | 35 |
| 1783 | 1638 | 6521 | 75 | ACCTTCGTTCCCTTAGGATGTGCG | 23 | 10 | 28 | 3 | 27 | 29 |
| 1784 | 1639 | 40341 | 81.9 | ACCTTCGTCAGCACGGTGCGCTCA | 23 | 10 | 31 | 35 | 29 | 13 |
| 1785 | 1640 | 30383 | 77.9 | ACCTCTTGGCTTCCTATGCGTGCG | 23 | 11 | 17 | 26 | 29 | 29 |

FIG. 25JJ

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 1786 | 1642 | 6539 | 78.1 | ACCTCGTTCTTGCCATACGGCGAA | 23 | 12 | 11 | 15 | 35 | 16 |
| 1787 | 1643 | 6540 | 75.7 | ACCTCGTTCCATAGCCCTGTGTGC | 23 | 12 | 15 | 36 | 14 | 33 |
| 1788 | 1644 | 6549 | 78.6 | ACCTCCATCACGGCTTGAGTTGCG | 23 | 15 | 30 | 17 | 20 | 29 |
| 1789 | 1645 | 6551 | 77.9 | ACCTCCATACGGGATGCACGCCTA | 23 | 15 | 35 | 27 | 30 | 26 |
| 1790 | 1646 | 30384 | 76.8 | ACCTCGAACGTTAGCCCAGCGAGT | 23 | 16 | 12 | 36 | 31 | 20 |
| 1791 | 1648 | 6558 | 78.7 | ACCTCGAAGGTATGCGCTCATGCG | 23 | 16 | 18 | 29 | 13 | 29 |
| 1792 | 1649 | 6569 | 77.4 | ACCTGCTTCTTGTCCCCACGAGGA | 23 | 17 | 11 | 28 | 30 | 25 |
| 1793 | 1651 | 6575 | 77.5 | ACCTGCTTTGCGGAGTCGAACGTT | 23 | 17 | 29 | 20 | 16 | 12 |
| 1794 | 1652 | 40344 | 81.5 | ACCTGCTTCAGCCTTGCACGTGCG | 23 | 17 | 31 | 11 | 30 | 29 |
| 1795 | 1653 | 6589 | 80.9 | ACCTGCAATGATGCAATGCGTGCG | 23 | 21 | 2 | 21 | 29 | 29 |
| 1796 | 1654 | 21067 | 76.1 | ACCTGCAAGAGTCTTGGTGCAGCC | 23 | 21 | 20 | 11 | 33 | 36 |
| 1797 | 1656 | 6602 | 75.8 | ACCTAGTGCCATTCTGCAGCGCTT | 23 | 22 | 15 | 8 | 31 | 17 |
| 1798 | 1657 | 6638 | 78.2 | ACCTTCCAATCGATGGTGCATCG | 23 | 28 | 4 | 27 | 33 | 24 |
| 1799 | 1658 | 40349 | 77.6 | ACCTTCCCAAAGTGATTGCGGTGC | 23 | 28 | 6 | 2 | 29 | 33 |
| 1800 | 1659 | 30387 | 76.6 | ACCTTCCCCTGTCAGCGAGTTCGT | 23 | 28 | 14 | 31 | 20 | 10 |
| 1801 | 1660 | 30388 | 77.3 | ACCTTCCCACCTCGAACACGCCTA | 23 | 28 | 23 | 16 | 30 | 26 |
| 1802 | 1661 | 15180 | 77.9 | ACCTTCCCATCGTCGTCACGTCGT | 23 | 28 | 24 | 10 | 30 | 10 |
| 1803 | 1662 | 21077 | 76.5 | ACCTTCCCCTAAGCCTCCCTCTG | 23 | 28 | 26 | 36 | 28 | 8 |
| 1804 | 1663 | 6652 | 79.5 | ACCTTCCCACGGCTCAGATGACGG | 23 | 28 | 35 | 13 | 27 | 35 |
| 1805 | 1664 | 30389 | 77 | ACCTTGCGTTGATGATTGCGTCGT | 23 | 29 | 1 | 2 | 29 | 10 |
| 1806 | 1665 | 6665 | 77.5 | ACCTTGCGCGAAAAAGTCGTCGTT | 23 | 29 | 16 | 6 | 10 | 12 |
| 1807 | 1666 | 6666 | 78.5 | ACCTTGCGGCTTGCTTTCGTCTCA | 23 | 29 | 17 | 17 | 10 | 13 |
| 1808 | 1667 | 6671 | 81.1 | ACCTTGCGACGGCAGCACCTCTCA | 23 | 29 | 35 | 31 | 23 | 13 |
| 1809 | 1668 | 6672 | 79.5 | ACCTCACGAAAGTCCCAGCCACGG | 23 | 30 | 6 | 28 | 36 | 35 |
| 1810 | 1669 | 15189 | 77.9 | ACCTCACGGTCTTCCCCGAAGACC | 23 | 30 | 19 | 28 | 16 | 32 |
| 1811 | 1670 | 6678 | 76.6 | ACCTCACGGAGTCTGTACGGTGCG | 23 | 30 | 20 | 14 | 35 | 29 |
| 1812 | 1671 | 15190 | 79.7 | ACCTCACGTCCCCATACGGCTCA | 23 | 30 | 28 | 15 | 35 | 13 |
| 1813 | 1672 | 40354 | 77.6 | ACCTGACCCGAACTGTGGACCAGC | 23 | 32 | 16 | 14 | 34 | 31 |
| 1814 | 1673 | 30390 | 77.2 | ACCTGACCCACGAAAGGCAACGTT | 23 | 32 | 30 | 6 | 21 | 12 |
| 1815 | 1674 | 21097 | 77.2 | ACCTGACCACGGTTGATGCGTGTC | 23 | 32 | 35 | 1 | 29 | 9 |
| 1816 | 1676 | 6711 | 76.7 | ACCTGTGCCTCAGCAAGATGACGG | 23 | 33 | 13 | 21 | 27 | 35 |
| 1817 | 1677 | 30391 | 80.4 | ACCTGTGCGAGTCGAAACGGGTGC | 23 | 33 | 20 | 16 | 35 | 33 |
| 1818 | 1678 | 15203 | 79.7 | ACCTGTGCACCTCAGCGATGCAGC | 23 | 33 | 23 | 31 | 27 | 31 |
| 1819 | 1679 | 15205 | 78.3 | ACCTGTGCAGGATCCCACGGTGTC | 23 | 33 | 25 | 28 | 35 | 9 |
| 1820 | 1680 | 30392 | 78.3 | ACCTGTGCCCTACACGGGACATCG | 23 | 33 | 26 | 30 | 34 | 24 |
| 1821 | 1681 | 15207 | 77.4 | ACCTGGACCTTGTGCGAATCGCTT | 23 | 34 | 11 | 29 | 4 | 17 |
| 1822 | 1682 | 15212 | 77.1 | ACCTGGACGATGTGCGCTGTAGGA | 23 | 34 | 27 | 29 | 14 | 25 |
| 1823 | 1683 | 15213 | 77.8 | ACCTGGACTCCCTCGTCAGCGATG | 23 | 34 | 28 | 10 | 31 | 27 |
| 1824 | 1684 | 30393 | 79.5 | ACCTGGACAGCCAATCCACGAGCC | 23 | 34 | 36 | 4 | 30 | 36 |
| 1825 | 1685 | 6736 | 76.7 | ACCTACGGTTGACGAAGCAATGCG | 23 | 35 | 1 | 16 | 21 | 29 |
| 1826 | 1686 | 30394 | 75.7 | ACCTACGGCGTTCGAAGCTTGGTA | 23 | 35 | 12 | 16 | 17 | 18 |
| 1827 | 1687 | 6766 | 80.8 | ATCGTTGACGAAAGCCAGCCGCAA | 24 | 1 | 16 | 36 | 36 | 21 |
| 1828 | 1688 | 6770 | 78.3 | ATCGTTGAAGGATGCGGACCATCG | 24 | 1 | 25 | 29 | 32 | 24 |
| 1829 | 1689 | 30398 | 77.3 | ATCGTTGAACGGTGCGTCTGGATG | 24 | 1 | 35 | 29 | 8 | 27 |
| 1830 | 1690 | 6773 | 82.3 | ATCGTGATCACGGTGCACGGCGAA | 24 | 2 | 30 | 33 | 35 | 16 |
| 1831 | 1691 | 6779 | 76.4 | ATCGTTAGGTGCACCTTGCGCCTA | 24 | 3 | 33 | 23 | 29 | 26 |
| 1832 | 1692 | 30399 | 76.4 | ATCGAATCCGTTACGGTGCGTGTC | 24 | 4 | 12 | 35 | 29 | 9 |
| 1833 | 1693 | 6781 | 76.5 | ATCGAATCCTCAATCGGCAACACG | 24 | 4 | 13 | 24 | 21 | 30 |
| 1834 | 1694 | 6783 | 80.1 | ATCGAATCATCGGGACAGCCACGG | 24 | 4 | 24 | 34 | 36 | 35 |
| 1835 | 1695 | 40358 | 80.2 | ATCGAATCGACCTGCGTCCCATCG | 24 | 4 | 32 | 29 | 28 | 24 |
| 1836 | 1696 | 6789 | 77.5 | ATCGAATCGGACCTTGATCGGTGC | 24 | 4 | 34 | 11 | 24 | 33 |

FIG. 25KK

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 1837 | 1697 | 6793 | 75 | ATCGATACGCTTTGCGCTGTATCG | 24 | 5 | 17 | 29 | 14 | 24 |
| 1838 | 1698 | 6796 | 80.4 | ATCGATACCAGCCCATTGCGGCAA | 24 | 5 | 31 | 15 | 29 | 21 |
| 1839 | 1699 | 6797 | 76.8 | ATCGATACACGGTTGAACGGCGAA | 24 | 5 | 35 | 1 | 35 | 16 |
| 1840 | 1701 | 40360 | 79.4 | ATCGTCTGCCATGCTTCACGACGG | 24 | 8 | 15 | 17 | 30 | 35 |
| 1841 | 1702 | 6814 | 77.8 | ATCGTCTGCCTAAGCCGATGACGG | 24 | 8 | 26 | 36 | 27 | 35 |
| 1842 | 1703 | 6815 | 80 | ATCGTCTGCAGCGGACAGTGGCAA | 24 | 8 | 31 | 34 | 22 | 21 |
| 1843 | 1704 | 6820 | 77.9 | ATCGTGTCCCATTCGTGCAACACG | 24 | 9 | 15 | 10 | 21 | 30 |
| 1844 | 1705 | 21109 | 82.8 | ATCGTGTCGTGCGATGACGGTGCG | 24 | 9 | 33 | 27 | 35 | 29 |
| 1845 | 1706 | 6828 | 79.6 | ATCGTCGTTTGACACGGGACGCAA | 24 | 10 | 1 | 30 | 34 | 21 |
| 1846 | 1707 | 6837 | 79.4 | ATCGTCGTGATGGGACGCTTTCCC | 24 | 10 | 27 | 34 | 17 | 28 |
| 1847 | 1708 | 21110 | 76.4 | ATCGTCGTGTGCTTGACTGTTGCG | 24 | 10 | 33 | 1 | 14 | 29 |
| 1848 | 1709 | 6841 | 78.5 | ATCGTCGTAGCCCAGCTCTGCAA | 24 | 10 | 36 | 31 | 8 | 16 |
| 1849 | 1711 | 15250 | 78 | ATCGCTTGCTTGCGAAGCAAGCTT | 24 | 11 | 11 | 16 | 21 | 17 |
| 1850 | 1713 | 30401 | 76.9 | ATCGCTTGGGTATCGTTGCGTTGA | 24 | 11 | 18 | 10 | 29 | 1 |
| 1851 | 1714 | 30402 | 77.1 | ATCGCTTGACCTTGTCGCTTTCCC | 24 | 11 | 23 | 9 | 17 | 28 |
| 1852 | 1715 | 40364 | 76.1 | ATCGCTTGCCTATGATCAGCAGCC | 24 | 11 | 26 | 2 | 31 | 36 |
| 1853 | 1716 | 15254 | 79.2 | ATCGCTTGCACGGAGTTCCCACCT | 24 | 11 | 30 | 20 | 28 | 23 |
| 1854 | 1717 | 30403 | 76.5 | ATCGCGTTTGATACGGTCTGGTGC | 24 | 12 | 2 | 35 | 8 | 33 |
| 1855 | 1718 | 30404 | 76.3 | ATCGCGTTTTAGGCTTAGCCGCTT | 24 | 12 | 3 | 17 | 36 | 17 |
| 1856 | 1719 | 6860 | 76.8 | ATCGCGTTAAAGCACGGTCTGTGC | 24 | 12 | 6 | 30 | 19 | 33 |
| 1857 | 1720 | 6865 | 76.6 | ATCGCGTTCTTGGGTAAGCCACCT | 24 | 12 | 11 | 18 | 36 | 23 |
| 1858 | 1721 | 30405 | 78.2 | ATCGCGTTCGTTCAGCATCGGAGT | 24 | 12 | 12 | 31 | 24 | 20 |
| 1859 | 1722 | 30406 | 77.3 | ATCGCGTTCTGTTCCCGAACCTA | 24 | 12 | 14 | 28 | 16 | 26 |
| 1860 | 1723 | 40366 | 76.2 | ATCGCGTTGGTATGTCCAGCGAGT | 24 | 12 | 18 | 9 | 31 | 20 |
| 1861 | 1725 | 6871 | 77.5 | ATCGCGTTAGTGTCTGACGGCACG | 24 | 12 | 22 | 8 | 35 | 30 |
| 1862 | 1726 | 6873 | 76.8 | ATCGCGTTATCGGCTTAGTGCACG | 24 | 12 | 24 | 17 | 22 | 30 |
| 1863 | 1727 | 6874 | 76.1 | ATCGCGTTGATGTACACCATTGCG | 24 | 12 | 27 | 7 | 15 | 29 |
| 1864 | 1728 | 6877 | 75.9 | ATCGCGTTGGACTACAAGCCCTTG | 24 | 12 | 34 | 7 | 36 | 11 |
| 1865 | 1729 | 6880 | 78.2 | ATCGCTCATGATACGGTCCCCACG | 24 | 13 | 2 | 35 | 28 | 30 |
| 1866 | 1731 | 30407 | 79.5 | ATCGCTCACGTTTGCGACCTGTGC | 24 | 13 | 12 | 29 | 23 | 33 |
| 1867 | 1732 | 6886 | 78.8 | ATCGCTCAGATGGCAAGACCTGCG | 24 | 13 | 27 | 21 | 32 | 29 |
| 1868 | 1733 | 6894 | 80.4 | ATCGCTGTTGATTCCCAGCCTGCG | 24 | 14 | 2 | 28 | 36 | 29 |
| 1869 | 1734 | 6895 | 81.1 | ATCGCTGTTGTCCACGCACGGGAC | 24 | 14 | 9 | 30 | 30 | 34 |
| 1870 | 1735 | 6896 | 81.4 | ATCGCTGTCTTGCCATTGCGCAGC | 24 | 14 | 11 | 15 | 29 | 31 |
| 1871 | 1736 | 15268 | 77.9 | ATCGCTGTGCAATGCGTGTCCTGT | 24 | 14 | 21 | 29 | 9 | 14 |
| 1872 | 1738 | 15270 | 79.5 | ATCGCTGTTGCGCGTTTGATCAGC | 24 | 14 | 29 | 12 | 2 | 31 |
| 1873 | 1739 | 30408 | 77.3 | ATCGCTGTCACGAATCTGCGCTGT | 24 | 14 | 30 | 4 | 29 | 14 |
| 1874 | 1740 | 30409 | 81.2 | ATCGCTGTGACCGACCCTCATGCG | 24 | 14 | 32 | 32 | 13 | 29 |
| 1875 | 1741 | 30410 | 77.6 | ATCGCCATTTGATGCGTGATCGAA | 24 | 15 | 1 | 29 | 2 | 16 |
| 1876 | 1742 | 15272 | 77 | ATCGCCATTGATCGAACTTGCGAA | 24 | 15 | 2 | 16 | 11 | 16 |
| 1877 | 1744 | 30411 | 75.3 | ATCGCCATTCGTAATCCGTTCGTT | 24 | 15 | 10 | 4 | 12 | 12 |
| 1878 | 1745 | 30412 | 75 | ATCGCCATCTTGAAAGCTTGGCTT | 24 | 15 | 11 | 6 | 11 | 17 |
| 1879 | 1746 | 30413 | 78.5 | ATCGCCATCTCACTTGCGAAACGG | 24 | 15 | 13 | 11 | 16 | 35 |
| 1880 | 1747 | 6918 | 77.2 | ATCGCCATGCTTCTGTGTGCTCGT | 24 | 15 | 17 | 14 | 33 | 10 |
| 1881 | 1748 | 30414 | 77.3 | ATCGCCATAGGAAGCCCGTTCTCA | 24 | 15 | 25 | 36 | 12 | 13 |
| 1882 | 1749 | 40369 | 76.4 | ATCGCCATCCTAAGGAACGGTCGT | 24 | 15 | 26 | 25 | 35 | 10 |
| 1883 | 1750 | 30415 | 76.6 | ATCGCCATGTGCTTAGGCAAATCG | 24 | 15 | 33 | 3 | 21 | 24 |
| 1884 | 1751 | 6929 | 77.4 | ATCGCGAAATACCTCATCCCACGG | 24 | 16 | 5 | 13 | 28 | 35 |
| 1885 | 1752 | 6932 | 76.9 | ATCGCGAATCTGCTCATGCGAAAG | 24 | 16 | 8 | 13 | 29 | 6 |
| 1886 | 1753 | 21122 | 76.5 | ATCGCGAATCGTGGTAAATCGTGC | 24 | 16 | 10 | 18 | 4 | 33 |
| 1887 | 1754 | 40370 | 78.8 | ATCGCGAACTGTCTTGCACGAGCC | 24 | 16 | 14 | 11 | 30 | 36 |

FIG. 25LL

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 1888 | 1755 | 6936 | 75.1 | ATCGCGAAGGTATTGAGACCAGCC | 24 | 16 | 18 | 1 | 32 | 36 |
| 1889 | 1756 | 6937 | 75.9 | ATCGCGAAGTCTCGAAGCAAAGGA | 24 | 16 | 19 | 16 | 21 | 25 |
| 1890 | 1757 | 30416 | 76.6 | ATCGCGAAACCTCCATGGTATCCC | 24 | 16 | 23 | 15 | 18 | 28 |
| 1891 | 1758 | 15285 | 75.4 | ATCGCGAACCTACAGCTCGTAGCC | 24 | 16 | 26 | 31 | 10 | 36 |
| 1892 | 1759 | 6943 | 79.8 | ATCGCGAATGCGTGTCGCAACTGT | 24 | 16 | 29 | 9 | 21 | 14 |
| 1893 | 1760 | 30417 | 78.3 | ATCGCGAAGACCATACCACGACGG | 24 | 16 | 32 | 5 | 30 | 35 |
| 1894 | 1761 | 21125 | 78 | ATCGGCTTTTAGCCATCAGCTGCG | 24 | 17 | 3 | 15 | 31 | 29 |
| 1895 | 1762 | 6947 | 76.4 | ATCGGCTTTACACCATGTGCGGAC | 24 | 17 | 7 | 15 | 33 | 34 |
| 1896 | 1763 | 40373 | 76 | ATCGGCTTTCTGTTGACAGCGACC | 24 | 17 | 8 | 1 | 31 | 32 |
| 1897 | 1764 | 6950 | 77.6 | ATCGGCTTCGTTGACCACCTGGAC | 24 | 17 | 12 | 32 | 23 | 34 |
| 1898 | 1765 | 30418 | 76.9 | ATCGGCTTCTGTATCGGACCCAGC | 24 | 17 | 14 | 24 | 32 | 31 |
| 1899 | 1767 | 6958 | 76.7 | ATCGGCTTGTGCTTAGCAGCCTCA | 24 | 17 | 33 | 3 | 31 | 13 |
| 1900 | 1768 | 40375 | 75.3 | ATCGGGTACGTTAGGACACGCGTT | 24 | 18 | 12 | 25 | 30 | 12 |
| 1901 | 1769 | 15292 | 76.1 | ATCGGGTAGCAAGTCTCAGCGTGC | 24 | 18 | 21 | 19 | 31 | 33 |
| 1902 | 1770 | 6968 | 75.5 | ATCGGGTAAGGAACCTGCAAGCAA | 24 | 18 | 25 | 23 | 21 | 21 |
| 1903 | 1771 | 15294 | 76.8 | ATCGGGTATCCCAGGACCATCGAA | 24 | 18 | 28 | 25 | 15 | 16 |
| 1904 | 1772 | 6974 | 75 | ATCGGGTAACGGTACAGCAAAGCC | 24 | 18 | 35 | 7 | 21 | 36 |
| 1905 | 1773 | 30421 | 76.1 | ATCGGGTAAGCCTGATACGGAGCC | 24 | 18 | 36 | 2 | 35 | 36 |
| 1906 | 1774 | 15298 | 76.3 | ATCGGTCTCGAAAATCGCAACGAA | 24 | 19 | 16 | 4 | 21 | 16 |
| 1907 | 1775 | 40376 | 76.4 | ATCGGTCTGCTTAGCCGGTAAGCC | 24 | 19 | 17 | 36 | 18 | 36 |
| 1908 | 1776 | 6981 | 79.5 | ATCGGTCTATCGCACGGGACCAGC | 24 | 19 | 24 | 30 | 34 | 31 |
| 1909 | 1777 | 6986 | 77.5 | ATCGGTCTACGGCCATGGACCTTG | 24 | 19 | 35 | 15 | 34 | 11 |
| 1910 | 1778 | 40377 | 77.8 | ATCGGAGTGCAAGCTTGACCGGAC | 24 | 20 | 21 | 17 | 32 | 34 |
| 1911 | 1779 | 6990 | 79.2 | ATCGGAGTATCGCTTGCAGCGCAA | 24 | 20 | 24 | 11 | 31 | 21 |
| 1912 | 1780 | 6992 | 76.1 | ATCGGAGTCAGCTTAGACGGCACG | 24 | 20 | 31 | 3 | 35 | 30 |
| 1913 | 1782 | 40378 | 78.3 | ATCGGCAATGATTGCGACCTGACC | 24 | 21 | 2 | 29 | 23 | 32 |
| 1914 | 1783 | 15303 | 75.8 | ATCGGCAATACAAATCGCAAAGCC | 24 | 21 | 7 | 4 | 21 | 36 |
| 1915 | 1784 | 30422 | 78.6 | ATCGGCAATGTCTCCCTCTGCACG | 24 | 21 | 9 | 28 | 8 | 30 |
| 1916 | 1785 | 40379 | 77.6 | ATCGGCAACTCAAAAGGGACCACG | 24 | 21 | 13 | 6 | 34 | 30 |
| 1917 | 1786 | 40380 | 76.1 | ATCGGCAACCATACCTTCTGGCAA | 24 | 21 | 15 | 23 | 8 | 21 |
| 1918 | 1787 | 40381 | 75.8 | ATCGGCAAGCTTTTAGATCGCGAA | 24 | 21 | 17 | 3 | 24 | 16 |
| 1919 | 1788 | 40382 | 76.1 | ATCGGCAAGAGTAGCCGTCTGTGC | 24 | 21 | 20 | 36 | 19 | 33 |
| 1920 | 1789 | 15309 | 77.1 | ATCGGCAAGCAATCGTAGTGGCAA | 24 | 21 | 21 | 10 | 22 | 21 |
| 1921 | 1790 | 7008 | 77.7 | ATCGGCAAAGTGCTTGATCGTCCC | 24 | 21 | 22 | 11 | 24 | 28 |
| 1922 | 1791 | 30423 | 77.4 | ATCGGCAAAGGAAGTGGTGCTCGT | 24 | 21 | 25 | 22 | 33 | 10 |
| 1923 | 1792 | 7013 | 78.5 | ATCGGCAACAGCAGTGCTGTGTGC | 24 | 21 | 31 | 22 | 14 | 33 |
| 1924 | 1793 | 7015 | 75.8 | ATCGGCAAGGACTGTCGGTAATCG | 24 | 21 | 34 | 9 | 18 | 24 |
| 1925 | 1795 | 7019 | 77.2 | ATCGAGTGCGAATGATGGACCACG | 24 | 22 | 16 | 2 | 34 | 30 |
| 1926 | 1796 | 7022 | 77 | ATCGAGTGCCTATGCGCTCACAGC | 24 | 22 | 26 | 29 | 13 | 31 |
| 1927 | 1797 | 30424 | 77.8 | ATCGAGTGGTGCTTGAACGGAGCC | 24 | 22 | 33 | 1 | 35 | 36 |
| 1928 | 1798 | 7026 | 79.3 | ATCGACCTGGTAACGGCACGGACC | 24 | 23 | 18 | 35 | 30 | 32 |
| 1929 | 1799 | 7027 | 75.8 | ATCGACCTGCAATCTGAGGAACGG | 24 | 23 | 21 | 8 | 25 | 35 |
| 1930 | 1800 | 7032 | 80.7 | ATCGACCTGGACCACGTGCGTCGT | 24 | 23 | 34 | 30 | 29 | 10 |
| 1931 | 1801 | 30425 | 79.1 | ATCGATCGCTGTATCGCAGCCGAA | 24 | 24 | 14 | 24 | 31 | 16 |
| 1932 | 1802 | 30426 | 75.8 | ATCGATCGGCTTAGGAGACCCGTT | 24 | 24 | 17 | 25 | 32 | 12 |
| 1933 | 1803 | 15317 | 76.9 | ATCGATCGAGGAAGCCGGACAATC | 24 | 24 | 25 | 36 | 34 | 4 |
| 1934 | 1804 | 30427 | 80.2 | ATCGATCGGTGCCGTTTGTCAGCC | 24 | 24 | 33 | 12 | 9 | 36 |
| 1935 | 1805 | 21139 | 77.1 | ATCGAGGAACCTGCTTAGCCCACG | 24 | 25 | 23 | 17 | 36 | 30 |
| 1936 | 1806 | 7049 | 78.9 | ATCGAGGAATCGGTGCCTGTGCAA | 24 | 25 | 24 | 33 | 14 | 21 |
| 1937 | 1807 | 7056 | 76.3 | ATCGCCTATGATACGGCAGCCTCA | 24 | 26 | 2 | 35 | 31 | 13 |
| 1938 | 1808 | 15323 | 77.2 | ATCGCCTAAAAGCTCAAGCCACGG | 24 | 26 | 6 | 13 | 36 | 35 |

FIG. 25MM

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 1939 | 1809 | 7059 | 79.4 | ATCGCCTATGTCCCATTGCGAGCC | 24 | 26 | 9 | 15 | 29 | 36 |
| 1940 | 1810 | 30428 | 76.7 | ATCGCCTACGTTTCGTCCATTCCC | 24 | 26 | 12 | 10 | 15 | 28 |
| 1941 | 1811 | 30429 | 75.9 | ATCGCCTAGCTTTCCCCTCATCGT | 24 | 26 | 17 | 28 | 13 | 10 |
| 1942 | 1812 | 30430 | 75.8 | ATCGCCTAAGGAATACACGGCACG | 24 | 26 | 25 | 5 | 35 | 30 |
| 1943 | 1814 | 21141 | 77.2 | ATCGCCTATGCGGGTATCGTTCGT | 24 | 26 | 29 | 18 | 10 | 10 |
| 1944 | 1815 | 15327 | 77.4 | ATCGCCTACACGGCTTCGTTTCGT | 24 | 26 | 30 | 17 | 12 | 10 |
| 1945 | 1816 | 7073 | 78.7 | ATCGGATGTTGAGCAAAGCCTGCG | 24 | 27 | 1 | 21 | 36 | 29 |
| 1946 | 1817 | 40389 | 80.2 | ATCGGATGTCGTGGACGACCAGCC | 24 | 27 | 10 | 34 | 32 | 36 |
| 1947 | 1818 | 30432 | 77.1 | ATCGGATGCTCAACGGAATCCGTT | 24 | 27 | 13 | 35 | 4 | 12 |
| 1948 | 1819 | 15330 | 76.5 | ATCGGATGCTGTCGTTACGGATCG | 24 | 27 | 14 | 12 | 35 | 24 |
| 1949 | 1820 | 15331 | 80.3 | ATCGGATGGTCTGTGCCAGCGGAC | 24 | 27 | 19 | 33 | 31 | 34 |
| 1950 | 1821 | 40390 | 78.5 | ATCGGATGATCGAGGAACGGGGAC | 24 | 27 | 24 | 25 | 35 | 34 |
| 1951 | 1822 | 30433 | 76.8 | ATCGGATGCCTAGTCTTCCCCACG | 24 | 27 | 26 | 19 | 28 | 30 |
| 1952 | 1823 | 7082 | 80.1 | ATCGGATGTGCGCTTGTGATTGCG | 24 | 27 | 29 | 11 | 2 | 29 |
| 1953 | 1824 | 30434 | 80.3 | ATCGGATGCACGCTTGGCTTGGAC | 24 | 27 | 30 | 11 | 17 | 34 |
| 1954 | 1825 | 7083 | 76.7 | ATCGGATGCAGCTTAGTGCGGATG | 24 | 27 | 31 | 3 | 29 | 27 |
| 1955 | 1826 | 30435 | 78.7 | ATCGGATGGGACAGCCTGATGCAA | 24 | 27 | 34 | 36 | 2 | 21 |
| 1956 | 1827 | 40391 | 80.1 | ATCGGATGACGGCTTGTCCCGATG | 24 | 27 | 35 | 11 | 28 | 27 |
| 1957 | 1828 | 15335 | 82.9 | ATCGTCCCTGTCCGAATGCGCACG | 24 | 28 | 9 | 16 | 29 | 30 |
| 1958 | 1829 | 30437 | 76.9 | ATCGTCCCAGGATCGTGCTTAGCC | 24 | 28 | 25 | 10 | 17 | 36 |
| 1959 | 1830 | 30438 | 78.5 | ATCGTCCCGATGCCTACGTTTCCC | 24 | 28 | 27 | 26 | 12 | 28 |
| 1960 | 1832 | 40393 | 76.5 | ATCGTGCGTTGATGTCCGTTAGCC | 24 | 29 | 1 | 9 | 12 | 36 |
| 1961 | 1833 | 15343 | 78.2 | ATCGTGCGTTAGTCCCTCCCCGTT | 24 | 29 | 3 | 28 | 28 | 12 |
| 1962 | 1834 | 7108 | 79.9 | ATCGTGCGCTTGCTTGCACGTGAT | 24 | 29 | 11 | 11 | 30 | 2 |
| 1963 | 1835 | 7109 | 76.7 | ATCGTGCGCTCATGTCTCCCAAAG | 24 | 29 | 13 | 9 | 28 | 6 |
| 1964 | 1836 | 30439 | 78.5 | ATCGTGCGCCATCCTAGCAAATCG | 24 | 29 | 15 | 26 | 21 | 24 |
| 1965 | 1837 | 7110 | 77.5 | ATCGTGCGGCTTCCATAATCGACC | 24 | 29 | 17 | 15 | 4 | 32 |
| 1966 | 1838 | 15345 | 78.6 | ATCGTGCGGAGTGCTTTCGTGACC | 24 | 29 | 20 | 17 | 10 | 32 |
| 1967 | 1839 | 7116 | 80 | ATCGTGCGTCCCCAGCAAAGAGGA | 24 | 29 | 28 | 31 | 6 | 25 |
| 1968 | 1840 | 7117 | 79 | ATCGTGCGCACGTACAAGCCACCT | 24 | 29 | 30 | 7 | 36 | 23 |
| 1969 | 1841 | 7119 | 80.5 | ATCGTGCGGTGCGGTACCATTCGT | 24 | 29 | 33 | 18 | 15 | 10 |
| 1970 | 1842 | 30440 | 78.5 | ATCGCACGAAAGGACCGCTTGATG | 24 | 30 | 6 | 32 | 17 | 27 |
| 1971 | 1843 | 30441 | 80.4 | ATCGCACGCTTGGTCTACGGACGG | 24 | 30 | 11 | 19 | 35 | 35 |
| 1972 | 1844 | 7127 | 79.2 | ATCGCACGCGAAGAGTCGTTCGAA | 24 | 30 | 16 | 20 | 12 | 16 |
| 1973 | 1845 | 40394 | 78 | ATCGCACGGCTTACCTCACGGGTA | 24 | 30 | 17 | 23 | 30 | 18 |
| 1974 | 1846 | 21150 | 77.3 | ATCGCACGAGTGTTAGTGCGCGTT | 24 | 30 | 22 | 3 | 29 | 12 |
| 1975 | 1847 | 40395 | 78.7 | ATCGCACGACCTGCAAAGGAGTGC | 24 | 30 | 23 | 21 | 25 | 33 |
| 1976 | 1848 | 7133 | 79.3 | ATCGCACGTCCCCTCACGAAGCTT | 24 | 30 | 28 | 13 | 16 | 17 |
| 1977 | 1849 | 7134 | 83.1 | ATCGCACGTGCGCTCAGTGCATCG | 24 | 30 | 29 | 13 | 33 | 24 |
| 1978 | 1850 | 7137 | 80.8 | ATCGCACGACGGCTGTGCAAACCT | 24 | 30 | 35 | 14 | 21 | 23 |
| 1979 | 1851 | 7138 | 79.2 | ATCGCACGAGCCATACGACCGATG | 24 | 30 | 36 | 5 | 32 | 27 |
| 1980 | 1852 | 7141 | 76.9 | ATCGCAGCTTAGCGAAGCAAGCAA | 24 | 31 | 3 | 16 | 21 | 21 |
| 1981 | 1853 | 15350 | 77.1 | ATCGCAGCTCTGTTGAGGACTGCG | 24 | 31 | 8 | 1 | 34 | 29 |
| 1982 | 1854 | 7146 | 81 | ATCGCAGCTGTCGAGTGTGCGCAA | 24 | 31 | 9 | 20 | 33 | 21 |
| 1983 | 1855 | 30443 | 78.1 | ATCGCAGCTCGTCCTACAGCGGAC | 24 | 31 | 10 | 26 | 31 | 34 |
| 1984 | 1856 | 30444 | 77.5 | ATCGCAGCGTCTCTTGGGACCCTA | 24 | 31 | 19 | 11 | 34 | 26 |
| 1985 | 1857 | 40397 | 77.1 | ATCGCAGCAGTGTGTCCGTTCGTT | 24 | 31 | 22 | 9 | 12 | 12 |
| 1986 | 1858 | 7153 | 77.1 | ATCGCAGCATCGATACGTGCACCT | 24 | 31 | 24 | 5 | 33 | 23 |
| 1987 | 1859 | 7155 | 79.1 | ATCGCAGCGGACATACTGCGAGGA | 24 | 31 | 34 | 5 | 29 | 25 |
| 1988 | 1860 | 7156 | 81.5 | ATCGCAGCACGGCTCACGAAGTGC | 24 | 31 | 35 | 13 | 16 | 33 |
| 1989 | 1861 | 7159 | 76.4 | ATCGGACCTACAAGCCGACCCTGT | 24 | 32 | 7 | 36 | 32 | 14 |

FIG. 25NN

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 1990 | 1862 | 30446 | 79.3 | ATCGGACCCGTTCCATTCTGGTGC | 24 | 32 | 12 | 15 | 8 | 33 |
| 1991 | 1863 | 7166 | 79.3 | ATCGGACCGCAAGATGTGTCGTGC | 24 | 32 | 21 | 27 | 9 | 33 |
| 1992 | 1864 | 30447 | 78.1 | ATCGGACCATCGAGTGGCTTCGAA | 24 | 32 | 24 | 22 | 17 | 16 |
| 1993 | 1865 | 7171 | 77.8 | ATCGGACCTGCGTGTCAATCCCAT | 24 | 32 | 29 | 9 | 4 | 15 |
| 1994 | 1866 | 21160 | 75.6 | ATCGGACCGGACTTGACGTTTGTC | 24 | 32 | 34 | 1 | 12 | 9 |
| 1995 | 1867 | 15358 | 79.8 | ATCGGACCACGGCCATAGGAGCAA | 24 | 32 | 35 | 15 | 25 | 21 |
| 1996 | 1868 | 40399 | 77 | ATCGGTGCTTGATGATCAGCCGAA | 24 | 33 | 1 | 2 | 31 | 16 |
| 1997 | 1869 | 40400 | 78.8 | ATCGGTGCTGTCACCTACGGGCAA | 24 | 33 | 9 | 23 | 35 | 21 |
| 1998 | 1870 | 15361 | 76.5 | ATCGGTGCCTCACGAACCTACACG | 24 | 33 | 13 | 16 | 26 | 30 |
| 1999 | 1871 | 7181 | 76.1 | ATCGGTGCGGTAGTCTGACCGGTA | 24 | 33 | 18 | 19 | 32 | 18 |
| 2000 | 1872 | 7185 | 76.6 | ATCGGTGCGATGTTAGGCAAGTGC | 24 | 33 | 27 | 3 | 21 | 33 |
| 2001 | 1873 | 30449 | 82.6 | ATCGGTGCCACGCTGTGGACGCTT | 24 | 33 | 30 | 14 | 34 | 17 |
| 2002 | 1874 | 21166 | 79.4 | ATCGGTGCGGACAGTGCACGAAAG | 24 | 33 | 34 | 22 | 30 | 6 |
| 2003 | 1875 | 7188 | 79.7 | ATCGGTGCAGCCGAGTCGTTAGCC | 24 | 33 | 36 | 20 | 12 | 36 |
| 2004 | 1876 | 40402 | 78.6 | ATCGGGACAAAGACGGCTGTTCCC | 24 | 34 | 6 | 35 | 14 | 28 |
| 2005 | 1878 | 7193 | 75.9 | ATCGGGACCGTTCCTATCCCTCTG | 24 | 34 | 12 | 26 | 28 | 8 |
| 2006 | 1879 | 15366 | 77.8 | ATCGGGACCGAAGAGTACGGGGAC | 24 | 34 | 16 | 20 | 35 | 34 |
| 2007 | 1880 | 7197 | 79.2 | ATCGGGACGCTTGATGTCGTCACG | 24 | 34 | 17 | 27 | 10 | 30 |
| 2008 | 1881 | 30450 | 75 | ATCGGGACGGTAGGTAAAAGCACG | 24 | 34 | 18 | 18 | 6 | 30 |
| 2009 | 1882 | 40404 | 76.7 | ATCGGGACGAGTAAAGTCCCCACG | 24 | 34 | 20 | 6 | 28 | 30 |
| 2010 | 1883 | 40405 | 77.9 | ATCGGGACACCTGGTATCCCCGTT | 24 | 34 | 23 | 18 | 28 | 12 |
| 2011 | 1884 | 7203 | 77.2 | ATCGGGACTCCCTTGACTTGGCAA | 24 | 34 | 28 | 1 | 11 | 21 |
| 2012 | 1885 | 7206 | 77.6 | ATCGGGACACGGAGGACGTTCTTG | 24 | 34 | 35 | 25 | 12 | 11 |
| 2013 | 1886 | 30452 | 79.4 | ATCGACGGTTGATCTGGTGCTGCG | 24 | 35 | 1 | 8 | 33 | 29 |
| 2014 | 1887 | 7210 | 80.6 | ATCGACGGATACACGGAGCCGCAA | 24 | 35 | 5 | 35 | 36 | 21 |
| 2015 | 1888 | 7211 | 79.2 | ATCGACGGTACAACGGGACCGGAC | 24 | 35 | 7 | 35 | 32 | 34 |
| 2016 | 1890 | 40406 | 76.9 | ATCGACGGCTTGTTAGCTTGCACG | 24 | 35 | 11 | 3 | 11 | 30 |
| 2017 | 1891 | 15370 | 77.8 | ATCGACGGCTGTTGATCGTTGCAA | 24 | 35 | 14 | 2 | 12 | 21 |
| 2018 | 1892 | 21169 | 76.4 | ATCGACGGCCATTACAGGTATGCG | 24 | 35 | 15 | 7 | 18 | 29 |
| 2019 | 1893 | 7219 | 76.3 | ATCGACGGATCGGGTACGAAACCT | 24 | 35 | 24 | 18 | 16 | 23 |
| 2020 | 1894 | 15371 | 75.8 | ATCGACGGAGGACGAACGAAAGTG | 24 | 35 | 25 | 16 | 16 | 22 |
| 2021 | 1895 | 30454 | 79.3 | ATCGACGGGATGAGTGTCCCGGAC | 24 | 35 | 27 | 22 | 28 | 34 |
| 2022 | 1896 | 21173 | 81.6 | ATCGACGGACGGAATCCAGCCGAA | 24 | 35 | 35 | 4 | 31 | 16 |
| 2023 | 1897 | 7225 | 79.4 | ATCGACGGAGCCCCATACCTCACG | 24 | 35 | 36 | 15 | 23 | 30 |
| 2024 | 1898 | 30455 | 76.5 | ATCGAGCCTGATGGTAAGCCCGTT | 24 | 36 | 2 | 18 | 36 | 12 |
| 2025 | 1899 | 7227 | 77.2 | ATCGAGCCTTAGGACCGCTTCACG | 24 | 36 | 3 | 32 | 17 | 30 |
| 2026 | 1900 | 15375 | 78.7 | ATCGAGCCTGTCTCCCATCGTCCC | 24 | 36 | 9 | 28 | 24 | 28 |
| 2027 | 1901 | 15376 | 76.6 | ATCGAGCCCTTGATCGACCTCGTT | 24 | 36 | 11 | 24 | 23 | 12 |
| 2028 | 1902 | 40407 | 77.4 | ATCGAGCCCTGTGTCTACGGCGTT | 24 | 36 | 14 | 19 | 35 | 12 |
| 2029 | 1903 | 40408 | 77 | ATCGAGCCGGTAACCTGCAAGGAC | 24 | 36 | 18 | 23 | 21 | 34 |
| 2030 | 1905 | 7236 | 79.4 | ATCGAGCCGCAATGTCCTGTCACG | 24 | 36 | 21 | 9 | 14 | 30 |
| 2031 | 1906 | 21178 | 75.6 | ATCGAGCCAGGAGGTATCTGCGAA | 24 | 36 | 25 | 18 | 8 | 16 |
| 2032 | 1907 | 40409 | 78.8 | ATCGAGCCTCCCCGTTTTAGTGCG | 24 | 36 | 28 | 12 | 3 | 29 |
| 2033 | 1908 | 7241 | 75.9 | ATCGAGCCGACCTTAGGACCGAGT | 24 | 36 | 32 | 3 | 32 | 20 |
| 2034 | 1909 | 7245 | 76.4 | AGGATGATCGAACCATTCCCGCTT | 25 | 2 | 16 | 15 | 28 | 17 |
| 2035 | 1910 | 15383 | 75 | AGGATTAGGCAATCCCGCAAGATG | 25 | 3 | 21 | 28 | 21 | 27 |
| 2036 | 1911 | 30457 | 76.6 | AGGAAATCGCAATCTGACGGGCTT | 25 | 4 | 21 | 8 | 35 | 17 |
| 2037 | 1912 | 30458 | 76.9 | AGGAAATCGGACTCGTCAGCGCTT | 25 | 4 | 34 | 10 | 31 | 17 |
| 2038 | 1913 | 7271 | 76.5 | AGGAAAAGCCATCCATGATGCACG | 25 | 6 | 15 | 15 | 27 | 30 |
| 2039 | 1914 | 15390 | 75.9 | AGGAAAAGGCTTTGCGCTTGTTGA | 25 | 6 | 17 | 29 | 11 | 1 |
| 2040 | 1915 | 21182 | 75.8 | AGGAAAAGTCCCTGATGTGCGTGC | 25 | 6 | 28 | 2 | 33 | 33 |

FIG. 25OO

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2041 | 1916 | 30459 | 75.7 | AGGAAAAGCACGATCGAAAGGCAA | 25 | 6 | 30 | 24 | 6 | 21 |
| 2042 | 1917 | 40411 | 76.9 | AGGATCTGCGTTCTGTCGTTTGCG | 25 | 8 | 12 | 14 | 12 | 29 |
| 2043 | 1918 | 21184 | 77.8 | AGGATCTGCGAAACCTCACGACGG | 25 | 8 | 16 | 23 | 30 | 35 |
| 2044 | 1920 | 15398 | 79.2 | AGGATCTGAGCCACGGCCATCGTT | 25 | 8 | 36 | 35 | 15 | 12 |
| 2045 | 1921 | 21188 | 81.4 | AGGATGTCCAGCTCGTTGCGTGCG | 25 | 9 | 31 | 10 | 29 | 29 |
| 2046 | 1922 | 30460 | 77.2 | AGGATCGTCGAAAGCCCTTGCTTG | 25 | 10 | 16 | 36 | 11 | 11 |
| 2047 | 1924 | 30461 | 80.3 | AGGATCGTACGGCAGCGACCGATG | 25 | 10 | 35 | 31 | 32 | 27 |
| 2048 | 1925 | 15408 | 75.3 | AGGACTTGGCTTAGCCGGACAGTG | 25 | 11 | 17 | 36 | 34 | 22 |
| 2049 | 1926 | 7309 | 75.2 | AGGACTTGGGTATGTCGTGCCGTT | 25 | 11 | 18 | 9 | 33 | 12 |
| 2050 | 1927 | 40412 | 76.7 | AGGACTTGGCAATGATTCCCGGAC | 25 | 11 | 21 | 2 | 28 | 34 |
| 2051 | 1928 | 7318 | 77.6 | AGGACGTTATCGATCGTCCCGTGC | 25 | 12 | 24 | 24 | 28 | 33 |
| 2052 | 1929 | 7321 | 78.5 | AGGACGTTCAGCGAGTTGCGCCTA | 25 | 12 | 31 | 20 | 29 | 26 |
| 2053 | 1930 | 40413 | 79.3 | AGGACGTTGTGCATCGCGTTGACC | 25 | 12 | 33 | 24 | 12 | 32 |
| 2054 | 1931 | 7324 | 80.6 | AGGACGTTGGACGTGCTCCCTCCC | 25 | 12 | 34 | 33 | 28 | 28 |
| 2055 | 1932 | 40414 | 78.3 | AGGACCATGCAATGTCAGCCGGAC | 25 | 15 | 21 | 9 | 36 | 34 |
| 2056 | 1933 | 21197 | 75.6 | AGGACCATAGTGGCAAGGACACGG | 25 | 15 | 22 | 21 | 34 | 35 |
| 2057 | 1934 | 7333 | 77 | AGGACCATCAGCAAAGCCATGCAA | 25 | 15 | 31 | 6 | 15 | 21 |
| 2058 | 1935 | 15417 | 81.6 | AGGACCATGTGCTCCCACGGCGTT | 25 | 15 | 33 | 28 | 35 | 12 |
| 2059 | 1936 | 7339 | 75.3 | AGGACGAACGTTTTAGCAGCGACC | 25 | 16 | 12 | 3 | 31 | 32 |
| 2060 | 1937 | 7343 | 76.3 | AGGACGAAACCTTCTGCCATGCAA | 25 | 16 | 23 | 8 | 15 | 21 |
| 2061 | 1938 | 15422 | 75.7 | AGGACGAAACGGGGTAAAAGCCAT | 25 | 16 | 35 | 18 | 6 | 15 |
| 2062 | 1939 | 7352 | 77.3 | AGGAGCTTTCTGAGCCCACGATCG | 25 | 17 | 8 | 36 | 30 | 24 |
| 2063 | 1941 | 15438 | 79.6 | AGGAGCAAGGACCGAACCATTGCG | 25 | 21 | 34 | 16 | 15 | 29 |
| 2064 | 1942 | 30463 | 77.5 | AGGAGCAAACGGACCTCAGCGGTA | 25 | 21 | 35 | 23 | 31 | 18 |
| 2065 | 1943 | 40415 | 77.5 | AGGAAGTGCCATCGTTTCCCATCG | 25 | 22 | 15 | 12 | 28 | 24 |
| 2066 | 1945 | 7390 | 78 | AGGAAGTGCCTACACGCACGAGCC | 25 | 22 | 26 | 30 | 30 | 36 |
| 2067 | 1946 | 7393 | 77.5 | AGGAAGTGCAGCATCGCTCAGCAA | 25 | 22 | 31 | 24 | 13 | 21 |
| 2068 | 1947 | 7396 | 78.1 | AGGAAGTGAGCCCCTAAGCCACGG | 25 | 22 | 36 | 26 | 36 | 35 |
| 2069 | 1948 | 15443 | 77.8 | AGGAACCTCAGCCCATAGCCGCTT | 25 | 23 | 31 | 15 | 36 | 17 |
| 2070 | 1949 | 7404 | 79.7 | AGGAACCTGACCGCTTGGACGTGC | 25 | 23 | 32 | 17 | 34 | 33 |
| 2071 | 1950 | 7408 | 76.4 | AGGAATCGCCATCTGTGCTTCGAA | 25 | 24 | 15 | 14 | 17 | 16 |
| 2072 | 1951 | 15446 | 80.2 | AGGAATCGACCTTCCCGTGCGCTT | 25 | 24 | 23 | 28 | 33 | 17 |
| 2073 | 1952 | 30465 | 79.2 | AGGAATCGCAGCGGTAGTGCCCAT | 25 | 24 | 31 | 18 | 33 | 15 |
| 2074 | 1953 | 40419 | 79.7 | AGGAAGGACACGATCGACGGCAGC | 25 | 25 | 30 | 24 | 35 | 31 |
| 2075 | 1954 | 40420 | 79.9 | AGGAGATGGCAAATCGCACGCCAT | 25 | 27 | 21 | 24 | 30 | 15 |
| 2076 | 1955 | 30466 | 78.4 | AGGATCCCCTTGGTCTAGCCGCAA | 25 | 28 | 11 | 19 | 36 | 21 |
| 2077 | 1956 | 15460 | 76.5 | AGGATCCCGAGTTCGTGATGGCTT | 25 | 28 | 20 | 10 | 27 | 17 |
| 2078 | 1957 | 7449 | 78.7 | AGGATGCGCGTTCTTGCTGTGGAC | 25 | 29 | 12 | 11 | 14 | 34 |
| 2079 | 1958 | 15467 | 80.3 | AGGATGCGAGTGCGTTGCAACACG | 25 | 29 | 22 | 12 | 21 | 30 |
| 2080 | 1959 | 7455 | 78.8 | AGGATGCGTGCGACGGTACACGTT | 25 | 29 | 29 | 35 | 7 | 12 |
| 2081 | 1960 | 15469 | 78.4 | AGGATGCGGTGCTACACAGCGCTT | 25 | 29 | 33 | 7 | 31 | 17 |
| 2082 | 1961 | 21221 | 77.6 | AGGACACGATACGATGCAGCTGCG | 25 | 30 | 5 | 27 | 31 | 29 |
| 2083 | 1962 | 21224 | 77.4 | AGGACACGGGTATTGAACGGACGG | 25 | 30 | 10 | 1 | 35 | 35 |
| 2084 | 1963 | 7463 | 76.1 | AGGACACGACCTAGCCTCTGTGCG | 25 | 30 | 23 | 36 | 8 | 29 |
| 2085 | 1964 | 30468 | 76 | AGGACACGCCTAAAAGGGACGCTT | 25 | 30 | 26 | 6 | 34 | 17 |
| 2086 | 1965 | 7470 | 80 | AGGACACGGGACGTCTTGCGTCGT | 25 | 30 | 34 | 19 | 29 | 10 |
| 2087 | 1966 | 7479 | 80.4 | AGGACAGCATCGGTGCAGTGCACG | 25 | 31 | 24 | 33 | 22 | 30 |
| 2088 | 1967 | 15479 | 79.5 | AGGACAGCAGGATGCGGATGTCCC | 25 | 31 | 25 | 29 | 27 | 28 |
| 2089 | 1968 | 40425 | 77.4 | AGGACAGCCCTATGTCCAGCCGAA | 25 | 31 | 26 | 9 | 31 | 16 |
| 2090 | 1969 | 30470 | 77.3 | AGGACAGCCACGTTAGTCCCCGAA | 25 | 31 | 30 | 3 | 28 | 16 |
| 2091 | 1970 | 21235 | 76.9 | AGGAGTGCATACGACCATCGGCAA | 25 | 33 | 5 | 32 | 24 | 21 |

FIG. 25PP

| SEQ ID NO: | 4,633 ID# | HEX ID# | Ta | ZIPCODE (5'-3') | TETRAMER NUMBERS | | | | |
|---|---|---|---|---|---|---|---|---|---|
| 2092 | 1971 | 7498 | 80.5 | AGGAGTGCAAAGTGCGGTGCGACC | 25 | 33 | 6 | 29 | 33 | 32 |
| 2093 | 1972 | 15487 | 76.4 | AGGAGTGCGTCTAAAGCAGCGTGC | 25 | 33 | 19 | 6 | 31 | 33 |
| 2094 | 1973 | 7506 | 76 | AGGAGTGCCCTACAGCAGTGGTGC | 25 | 33 | 26 | 31 | 22 | 33 |
| 2095 | 1974 | 15491 | 77.8 | AGGAGTGCGACCTCGTTGTCGGAC | 25 | 33 | 32 | 10 | 9 | 34 |
| 2096 | 1976 | 15493 | 80.5 | AGGAGGACCTTGTCCCGCAAACGG | 25 | 34 | 11 | 28 | 21 | 35 |
| 2097 | 1977 | 15495 | 78.2 | AGGAGGACCCATGGACTCCCCTCA | 25 | 34 | 15 | 34 | 28 | 13 |
| 2098 | 1978 | 7522 | 77.4 | AGGAGGACGATGACCTCACGCGTT | 25 | 34 | 27 | 23 | 30 | 12 |
| 2099 | 1979 | 7533 | 78 | AGGAACGGATCGCCTACCATGCAA | 25 | 35 | 24 | 26 | 15 | 21 |
| 2100 | 1980 | 15502 | 77.7 | AGGAACGGAGGACACGCTGTGACC | 25 | 35 | 25 | 30 | 14 | 32 |
| 2101 | 1981 | 7535 | 78 | AGGAACGGGATGGTCTCAGCTCCC | 25 | 35 | 27 | 19 | 31 | 28 |
| 2102 | 1983 | 7539 | 76.7 | AGGAAGCCAAAGGAGTTCCCCAT | 25 | 36 | 6 | 20 | 28 | 15 |
| 2103 | 1984 | 40427 | 76.4 | AGGAAGCCCTCAATACCACGCCAT | 25 | 36 | 13 | 5 | 30 | 15 |
| 2104 | 1985 | 15506 | 79.2 | AGGAAGCCAGTGCAGCCCATCCAT | 25 | 36 | 22 | 31 | 15 | 15 |
| 2105 | 1986 | 15508 | 79 | AGGAAGCCCACGGCTTTTGACAGC | 25 | 36 | 30 | 17 | 1 | 31 |
| 2106 | 1987 | 7553 | 79.5 | AGGAAGCCCAGCCACGCTGTGAGT | 25 | 36 | 31 | 30 | 14 | 20 |
| 2107 | 1988 | 7554 | 78.8 | AGGAAGCCGTGCTGTCCTCACACG | 25 | 36 | 33 | 9 | 13 | 30 |
| 2108 | 1989 | 7558 | 76.5 | CCTATTGATGCGGCAATCGTCGTT | 26 | 1 | 29 | 21 | 10 | 12 |
| 2109 | 1990 | 15522 | 77.5 | CCTATGTCGCAATGTCGTGCGCTT | 26 | 9 | 21 | 9 | 33 | 17 |
| 2110 | 1991 | 7587 | 81.3 | CCTATGTCACGGGACCGCAATGCG | 26 | 9 | 35 | 32 | 21 | 29 |
| 2111 | 1992 | 7589 | 78 | CCTATCGTTCGTTGTCTGCGCACG | 26 | 10 | 10 | 9 | 29 | 30 |
| 2112 | 1993 | 15526 | 81.7 | CCTATCGTCACGGTGCCAGCTGCG | 26 | 10 | 30 | 33 | 31 | 29 |
| 2113 | 1994 | 7611 | 80.7 | CCTACGTTGACCGACCGGACTGCG | 26 | 12 | 32 | 32 | 34 | 29 |
| 2114 | 1995 | 15536 | 80.7 | CCTACTGTTGCGCACGACGGGACC | 26 | 14 | 29 | 30 | 35 | 32 |
| 2115 | 1996 | 7640 | 80 | CCTAGCTTGACCTCCCGTGCCACG | 26 | 17 | 32 | 28 | 33 | 30 |
| 2116 | 1997 | 40430 | 75.4 | CCTAGCAAGCAACACGCCTACACG | 26 | 21 | 21 | 30 | 26 | 30 |
| 2117 | 1998 | 30474 | 76 | CCTAATCGCCATAGTGTCCCCACG | 26 | 24 | 15 | 22 | 28 | 30 |
| 2118 | 1999 | 7700 | 77 | CCTATCCCTTGAAGCCACGGCTGT | 26 | 28 | 1 | 36 | 35 | 14 |
| 2119 | 2000 | 30475 | 79.4 | CCTATCCCCTCAGACCACGGCGAA | 26 | 28 | 13 | 32 | 35 | 16 |
| 2120 | 2001 | 30476 | 75.6 | CCTATCCCCACGTGATAGCCGGTA | 26 | 28 | 30 | 2 | 36 | 18 |
| 2121 | 2002 | 7731 | 78.5 | CCTACACGTCGTAGCCCACGCGTT | 26 | 30 | 10 | 36 | 30 | 12 |
| 2122 | 2003 | 7733 | 78.8 | CCTACACGCTGTCGTTGTGCGTGC | 26 | 30 | 14 | 12 | 33 | 33 |
| 2123 | 2004 | 7740 | 77.7 | CCTACACGCAGCAGTGTGCGACCT | 26 | 30 | 31 | 22 | 29 | 23 |
| 2124 | 2005 | 21261 | 77.6 | CCTACAGCGTCTTCGTCAGCTGCG | 26 | 31 | 19 | 10 | 31 | 29 |
| 2125 | 2006 | 7747 | 78.4 | CCTACAGCGAGTCACGGCAAAGCC | 26 | 31 | 20 | 30 | 21 | 36 |
| 2126 | 2008 | 30477 | 75.1 | CCTAGACCCGAACCATCCATACGG | 26 | 32 | 16 | 15 | 15 | 35 |
| 2127 | 2009 | 21266 | 75.5 | CCTAGTGCGTCTCGTTACGGGACC | 26 | 33 | 19 | 12 | 35 | 32 |
| 2128 | 2010 | 7780 | 75.2 | CCTAGTGCACGGTTGAGCAAATCG | 26 | 33 | 35 | 1 | 21 | 24 |
| 2129 | 2011 | 15616 | 79.6 | CCTAGGACCACGCAGCTCGTGCAA | 26 | 34 | 30 | 31 | 10 | 21 |
| 2130 | 2012 | 40433 | 75.6 | CCTAAGCCGAGTAGTGGTGCGACC | 26 | 36 | 20 | 22 | 33 | 32 |
| 2131 | 2013 | 40434 | 77.5 | CCTAAGCCACCTCTTGTCCCTGCG | 26 | 36 | 23 | 11 | 28 | 29 |
| 2132 | 2014 | 7825 | 80.1 | GATGTTGAAGCCGTGCGTGCGGTA | 27 | 1 | 36 | 33 | 33 | 18 |
| 2133 | 2015 | 7831 | 80.5 | GATGAATCGTGCACGGCGTTTCCC | 27 | 4 | 33 | 35 | 12 | 28 |
| 2134 | 2016 | 7832 | 78.5 | GATGAATCACGGTCGTTCCCCACG | 27 | 4 | 35 | 10 | 28 | 30 |
| 2135 | 2017 | 7834 | 79 | GATGAAAGCCATCAGCGGACGTGC | 27 | 6 | 15 | 31 | 34 | 33 |
| 2136 | 2018 | 15632 | 76.9 | GATGAAAGCGAAAGCCCCATCGTT | 27 | 6 | 16 | 36 | 15 | 12 |
| 2137 | 2019 | 15633 | 82.8 | GATGAAAGCACGCAGCTGCGTGCG | 27 | 6 | 30 | 31 | 29 | 29 |
| 2138 | 2020 | 7845 | 77.4 | GATGCTTGCGTTCCATGTGCACCT | 27 | 11 | 12 | 15 | 33 | 23 |
| 2139 | 2021 | 7854 | 80.6 | GATGCGTTTGTCCGAAAGCCACGG | 27 | 12 | 9 | 16 | 36 | 35 |
| 2140 | 2022 | 15643 | 78.1 | GATGCGTTGGACAGCCCCTACAGC | 27 | 12 | 34 | 36 | 26 | 31 |
| 2141 | 2023 | 7867 | 80.7 | GATGCTCACACGCGAACACGGTGC | 27 | 13 | 30 | 16 | 30 | 33 |
| 2142 | 2024 | 7870 | 77 | GATGCTGTCGAACCTATGCGGTGC | 27 | 14 | 16 | 26 | 29 | 33 |

FIG. 25QQ

| SEQ ID NO: | 4,633 ID# | BEX ID# | Tm | ZIPCODE (5'-3') | TETRAMER NUMBERS | | | | | |
|---|---|---|---|---|---|---|---|---|---|---|
| 2143 | 2025 | 7873 | 80 | GATGCTGTCAGCCACGGCTTGTGC | 27 | 14 | 31 | 30 | 17 | 33 |
| 2144 | 2026 | 7875 | 79.7 | GATGCTGTAGCCACGGGCAACACG | 27 | 14 | 36 | 35 | 21 | 30 |
| 2145 | 2027 | 7879 | 76.9 | GATGCCATCGTTTCGTGCTTGGAC | 27 | 15 | 12 | 10 | 17 | 34 |
| 2146 | 2028 | 30489 | 77.5 | GATGCCATCCATCAGCCGAAACCT | 27 | 15 | 15 | 31 | 16 | 23 |
| 2147 | 2030 | 7883 | 77.6 | GATGCCATAGGAGGACCAGCCGAA | 27 | 15 | 25 | 34 | 31 | 16 |
| 2148 | 2031 | 7884 | 77.2 | GATGCCATCCTACGAAAGCCGACC | 27 | 15 | 26 | 16 | 36 | 32 |
| 2149 | 2032 | 15648 | 79.1 | GATGCCATTCCCGGTACAGCCCAT | 27 | 15 | 28 | 18 | 31 | 15 |
| 2150 | 2033 | 7895 | 79.9 | GATGCGAACTCATGCGGGACTCCC | 27 | 16 | 13 | 29 | 34 | 28 |
| 2151 | 2034 | 30483 | 78 | GATGCGAAATCGCCTACAGCGCTT | 27 | 16 | 24 | 26 | 31 | 17 |
| 2152 | 2035 | 7908 | 78.7 | GATGCGAAACGGGCAATGTCCTTG | 27 | 16 | 35 | 21 | 9 | 11 |
| 2153 | 2036 | 15657 | 79.2 | GATGCGAAAGCCGCTTGCAACTTG | 27 | 16 | 36 | 17 | 21 | 11 |
| 2154 | 2037 | 7913 | 80.8 | GATGGCTTCTTGCACGGACCGTGC | 27 | 17 | 11 | 30 | 32 | 33 |
| 2155 | 2038 | 30484 | 77.5 | GATGGCTTGCAAAGGATCGTGCAA | 27 | 17 | 21 | 25 | 10 | 21 |
| 2156 | 2039 | 7923 | 79.3 | GATGGCTTGACCGTCTCAGCTGCG | 27 | 17 | 32 | 19 | 31 | 29 |
| 2157 | 2040 | 15665 | 76.8 | GATGGGTATGCGATCGCACGAATC | 27 | 18 | 29 | 24 | 30 | 4 |
| 2158 | 2041 | 7931 | 82.3 | GATGGGTAGTGCCACGTGCGCACG | 27 | 18 | 33 | 30 | 29 | 30 |
| 2159 | 2042 | 7933 | 78.4 | GATGGAGTTCCCGGTAGTGCGCAA | 27 | 20 | 28 | 18 | 33 | 21 |
| 2160 | 2043 | 7938 | 79.8 | GATGGCAATCTGCGAATCCCAGCC | 27 | 21 | 8 | 16 | 28 | 36 |
| 2161 | 2044 | 40438 | 75.8 | GATGGCAACGTTATACGCAATGCG | 27 | 21 | 12 | 5 | 21 | 29 |
| 2162 | 2045 | 30485 | 75.8 | GATGGCAAGCTTCAGCCCTAGTGC | 27 | 21 | 17 | 31 | 26 | 33 |
| 2163 | 2046 | 30486 | 76 | GATGGCAAACCTAAAGCAGCCGAA | 27 | 21 | 23 | 6 | 31 | 16 |
| 2164 | 2047 | 7947 | 80.2 | GATGGCAAGATGGACCAGCCCGAA | 27 | 21 | 27 | 32 | 36 | 16 |
| 2165 | 2048 | 7954 | 76 | GATGAGTGGCAACGTTCGTTTCCC | 27 | 22 | 21 | 12 | 12 | 28 |
| 2166 | 2049 | 40439 | 78.7 | GATGACCTTGCGCGTTGCTTCGTT | 27 | 23 | 29 | 12 | 17 | 12 |
| 2167 | 2050 | 30487 | 76.9 | GATGATCGCGTTCCATGCTTACGG | 27 | 24 | 12 | 15 | 17 | 35 |
| 2168 | 2051 | 7959 | 78.1 | GATGATCGCCATTGTCCACGCTCA | 27 | 24 | 15 | 9 | 30 | 13 |
| 2169 | 2052 | 40440 | 78.8 | GATGATCGGCTTCCATGGACTGCG | 27 | 24 | 17 | 15 | 34 | 29 |
| 2170 | 2053 | 30488 | 80.5 | GATGATCGCACGGATGCGTTCACG | 27 | 24 | 30 | 27 | 12 | 30 |
| 2171 | 2054 | 7980 | 77.4 | GATGCCTAAGCCGGTAGTGCGGAC | 27 | 26 | 36 | 18 | 33 | 34 |
| 2172 | 2055 | 7981 | 76.5 | GATGGATGCTCAGACCCGTTCGAA | 27 | 27 | 13 | 32 | 12 | 16 |
| 2173 | 2056 | 7985 | 80.8 | GATGGATGCCTATGCGAGCCTGCG | 27 | 27 | 26 | 29 | 36 | 29 |
| 2174 | 2057 | 15679 | 78.1 | GATGGATGGTGCTGATCACGCGAA | 27 | 27 | 33 | 2 | 30 | 16 |
| 2175 | 2058 | 7988 | 77.2 | GATGGATGAGCCAATCCAGCTCCC | 27 | 27 | 36 | 4 | 31 | 28 |
| 2176 | 2059 | 30489 | 75.1 | GATGTCCCGCTTAATCCTTGCGTT | 27 | 28 | 17 | 4 | 11 | 12 |
| 2177 | 2060 | 7993 | 77.3 | GATGTCCCGTCTCGTTGACCCCAT | 27 | 28 | 19 | 12 | 32 | 15 |
| 2178 | 2061 | 15686 | 79.6 | GATGTCCCCAGCGCTTCACGGTCT | 27 | 28 | 31 | 17 | 30 | 19 |
| 2179 | 2062 | 15687 | 78.2 | GATGTCCCGACCATACTCCCGCAA | 27 | 28 | 32 | 5 | 28 | 21 |
| 2180 | 2063 | 21306 | 76 | GATGTGCGTTAGCAGCGATGATCG | 27 | 29 | 3 | 31 | 27 | 24 |
| 2181 | 2064 | 15692 | 76.8 | GATGTGCGGGTAATCGGCTTGATG | 27 | 29 | 18 | 24 | 17 | 27 |
| 2182 | 2065 | 15696 | 80.2 | GATGTGCGCACGCGAATCGTAGGA | 27 | 29 | 30 | 16 | 10 | 25 |
| 2183 | 2066 | 30492 | 81.3 | GATGTGCGCAGCGCAAATCGACCT | 27 | 29 | 31 | 21 | 24 | 23 |
| 2184 | 2067 | 8021 | 82.6 | GATGCACGTGTCGTGCAGCCGGAC | 27 | 30 | 9 | 33 | 36 | 34 |
| 2185 | 2068 | 8024 | 78.2 | GATGCACGCCATCGTTCGTTCTCA | 27 | 30 | 15 | 12 | 12 | 13 |
| 2186 | 2069 | 8028 | 79.7 | GATGCACGAGTGACGGATCGGTGC | 27 | 30 | 22 | 35 | 24 | 33 |
| 2187 | 2070 | 15699 | 81.7 | GATGCACGTGCGGTCTGACCCAGC | 27 | 30 | 29 | 19 | 32 | 31 |
| 2188 | 2071 | 15700 | 80.1 | GATGCACGCACGCTTGATCGGGTA | 27 | 30 | 30 | 11 | 24 | 18 |
| 2189 | 2072 | 30494 | 81.5 | GATGCACGAGCCGACCAATCACGG | 27 | 30 | 36 | 32 | 4 | 35 |
| 2190 | 2073 | 8036 | 79 | GATGCAGCTGATTGCGATCGGGAC | 27 | 31 | 2 | 29 | 24 | 34 |
| 2191 | 2074 | 30495 | 79.8 | GATGCAGCTCGTCACGTCCCATCG | 27 | 31 | 10 | 30 | 28 | 24 |
| 2192 | 2075 | 15704 | 77.7 | GATGCAGCCTTGATCGCGAACTCA | 27 | 31 | 11 | 24 | 16 | 13 |
| 2193 | 2076 | 40443 | 76.7 | GATGCAGCCTCATGATGACCGCTT | 27 | 31 | 13 | 2 | 32 | 17 |

FIG. 25RR

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2194 | 2077 | 30496 | 76.1 | GATGCAGCGGTAGGTAACGGGATG | 27 | 31 | 18 | 18 | 35 | 27 |
| 2195 | 2078 | 8048 | 81 | GATGCAGCGTGCGCTTGTCTCACG | 27 | 31 | 33 | 17 | 19 | 30 |
| 2196 | 2079 | 15708 | 79.7 | GATGCAGCAGCCCTCATCCCGAGT | 27 | 31 | 36 | 13 | 28 | 20 |
| 2197 | 2080 | 40444 | 78.3 | GATGGACCCGTTGGACAAAGCGAA | 27 | 32 | 12 | 34 | 6 | 16 |
| 2198 | 2082 | 15712 | 77.2 | GATGGACCCACGACGGGGTAGGTA | 27 | 32 | 30 | 35 | 18 | 18 |
| 2199 | 2084 | 8088 | 79.4 | GATGACGGTTGAGCTTTGCGGCAA | 27 | 35 | 1 | 17 | 29 | 21 |
| 2200 | 2085 | 30499 | 77.5 | GATGACGGGGTAGACCCGAAGCAA | 27 | 35 | 18 | 32 | 16 | 21 |
| 2201 | 2086 | 40447 | 78.5 | GATGAGCCCTCACTCAAGCCTGCG | 27 | 36 | 13 | 13 | 36 | 29 |
| 2202 | 2087 | 21328 | 76.4 | GATGAGCCGTCTACGGCAGCAATC | 27 | 36 | 19 | 35 | 31 | 4 |
| 2203 | 2088 | 15729 | 78.1 | GATGAGCCATCGTCGTCCATGCAA | 27 | 36 | 24 | 10 | 15 | 21 |
| 2204 | 2089 | 8108 | 76.6 | GATGAGCCCAGCATACGCAACGTT | 27 | 36 | 31 | 5 | 21 | 12 |
| 2205 | 2090 | 8112 | 79.2 | TCCCTTGAAATCTGCGAGCCCGTT | 28 | 1 | 4 | 29 | 36 | 12 |
| 2206 | 2091 | 21331 | 77.9 | TCCCTTGAAGGAAGCCCTTGTCCC | 28 | 1 | 25 | 36 | 11 | 28 |
| 2207 | 2092 | 30500 | 76.5 | TCCCTTGATGCGTTAGGGTATGCG | 28 | 1 | 29 | 3 | 18 | 29 |
| 2208 | 2093 | 8118 | 77.6 | TCCCTTGACAGCAAAGATCGCACG | 28 | 1 | 31 | 6 | 24 | 30 |
| 2209 | 2094 | 15734 | 81.1 | TCCCTTGAGGACCACGGATGCACG | 28 | 1 | 34 | 30 | 27 | 30 |
| 2210 | 2095 | 8122 | 79.6 | TCCCTGATTCTGGGACCAGCAGCC | 28 | 2 | 8 | 34 | 31 | 36 |
| 2211 | 2096 | 21332 | 77.2 | TCCCTGATTCGTAATCACGGCACG | 28 | 2 | 10 | 4 | 35 | 30 |
| 2212 | 2097 | 40453 | 77.7 | TCCCTGATCGAATTGAAGCCAGCC | 28 | 2 | 16 | 1 | 36 | 36 |
| 2213 | 2099 | 15737 | 76.7 | TCCCTGATTGCGAGGACCTATCCC | 28 | 2 | 29 | 25 | 26 | 28 |
| 2214 | 2100 | 8131 | 79.1 | TCCCTGATGACCTGTCACGGACGG | 28 | 2 | 32 | 9 | 35 | 35 |
| 2215 | 2101 | 8136 | 77.3 | TCCCTTAGCTGTATCGTGCGCGAA | 28 | 3 | 14 | 24 | 29 | 16 |
| 2216 | 2102 | 30501 | 75.4 | TCCCTTAGGCAAGCTTGCAAGGAC | 28 | 3 | 21 | 17 | 21 | 34 |
| 2217 | 2103 | 8140 | 76.1 | TCCCTTAGAGGAAATCTGCGTGCG | 28 | 3 | 25 | 4 | 29 | 29 |
| 2218 | 2104 | 8143 | 77 | TCCCTTAGCACGCTTGAGGATCCC | 28 | 3 | 30 | 11 | 25 | 28 |
| 2219 | 2106 | 30502 | 79 | TCCCAATCCTGTGGACTCCCGCTT | 28 | 4 | 14 | 34 | 28 | 17 |
| 2220 | 2107 | 30503 | 76.4 | TCCCAATCGCTTCCTAGACCCCAT | 28 | 4 | 17 | 26 | 32 | 15 |
| 2221 | 2108 | 8155 | 75.5 | TCCCAATCGAGTACCTGACCGACC | 28 | 4 | 20 | 23 | 32 | 32 |
| 2222 | 2109 | 8157 | 80.2 | TCCCAATCAGTGGACCGACCAGCC | 28 | 4 | 22 | 32 | 32 | 36 |
| 2223 | 2110 | 30504 | 77.2 | TCCCAATCACCTCTTGAGCCCGTT | 28 | 4 | 23 | 11 | 36 | 12 |
| 2224 | 2111 | 15748 | 78.9 | TCCCAATCTCCCAGTGTGCGAGGA | 28 | 4 | 28 | 22 | 29 | 25 |
| 2225 | 2112 | 8162 | 76.7 | TCCCAATCGACCTCTGCACGAAAG | 28 | 4 | 32 | 8 | 30 | 6 |
| 2226 | 2113 | 8164 | 78.8 | TCCCAATCAGCCGATGCGTTAGGA | 28 | 4 | 36 | 27 | 12 | 25 |
| 2227 | 2114 | 8166 | 78.8 | TCCCATACCTTGGTGCACGGGATG | 28 | 5 | 11 | 33 | 35 | 27 |
| 2228 | 2115 | 30506 | 78 | TCCCATACCCATCAGCCAGCGAGT | 28 | 5 | 15 | 31 | 31 | 20 |
| 2229 | 2116 | 30507 | 76.3 | TCCCATACCGAAATACGTGCGGAC | 28 | 5 | 16 | 5 | 33 | 34 |
| 2230 | 2117 | 15753 | 78.4 | TCCCATACGTGCCGAACTCAAGCC | 28 | 5 | 33 | 16 | 13 | 36 |
| 2231 | 2118 | 30510 | 78 | TCCCAAAGCGTTTCGTCGTTCCAT | 28 | 6 | 12 | 10 | 12 | 15 |
| 2232 | 2119 | 40458 | 76.3 | TCCCAAAGGGTACCATCGTTCACG | 28 | 6 | 18 | 15 | 12 | 30 |
| 2233 | 2120 | 40459 | 78.9 | TCCCAAAGGTCTCGTTCACGGCAA | 28 | 6 | 19 | 12 | 30 | 21 |
| 2234 | 2121 | 30511 | 78.1 | TCCCAAAGACCTCACGATCGCGTT | 28 | 6 | 23 | 30 | 24 | 12 |
| 2235 | 2122 | 8183 | 76.4 | TCCCAAAGATCGCGAATTAGCGAA | 28 | 6 | 24 | 16 | 3 | 16 |
| 2236 | 2123 | 8184 | 76.2 | TCCCAAAGGATGACCTCTTGCGAA | 28 | 6 | 27 | 23 | 11 | 16 |
| 2237 | 2124 | 8186 | 76.8 | TCCCAAAGTGCGTGATCCATTCGT | 28 | 6 | 29 | 2 | 15 | 10 |
| 2238 | 2125 | 8188 | 77.6 | TCCCAAAGCAGCAATCTGTCGTGC | 28 | 6 | 31 | 4 | 9 | 33 |
| 2239 | 2126 | 8189 | 75.4 | TCCCAAAGGACCTCGTTCGTAGGA | 28 | 6 | 32 | 10 | 10 | 25 |
| 2240 | 2127 | 30512 | 79.2 | TCCCAAAGAGCCCTTGACGGCCTA | 28 | 6 | 36 | 11 | 35 | 26 |
| 2241 | 2129 | 15757 | 77.9 | TCCCTCTGCGTTTCCCTCGTTCTG | 28 | 8 | 12 | 28 | 10 | 8 |
| 2242 | 2130 | 40460 | 77.5 | TCCCTCTGCTCACCTAACGGCGTT | 28 | 8 | 13 | 26 | 35 | 12 |
| 2243 | 2131 | 15759 | 78.6 | TCCCTCTGGTCTGACCCGAATCCC | 28 | 8 | 19 | 32 | 16 | 28 |
| 2244 | 2132 | 30515 | 80.7 | TCCCTCTGATCGCAGCGCAAGACC | 28 | 8 | 24 | 31 | 21 | 32 |

FIG. 25SS

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2245 | 2133 | 8206 | 76.8 | TCCCTCTGAGGACGTTCTGTTGCG | 28 | 8 | 25 | 12 | 14 | 29 |
| 2246 | 2135 | 8208 | 77 | TCCCTCTGTCCCTTGATGTCGCAA | 28 | 8 | 28 | 1 | 9 | 21 |
| 2247 | 2136 | 40461 | 78.4 | TCCCTCTGGGACTGTCGACCATCG | 28 | 8 | 34 | 9 | 32 | 24 |
| 2248 | 2137 | 8213 | 78.6 | TCCCTGTCCTTGCGTTTCTGACGG | 28 | 9 | 11 | 12 | 8 | 35 |
| 2249 | 2138 | 40462 | 79.2 | TCCCTGTCATCGAATCGTGCGGAC | 28 | 9 | 24 | 4 | 33 | 34 |
| 2250 | 2139 | 15761 | 79.4 | TCCCTGTCAGGATGTCGACCTGCG | 28 | 9 | 25 | 9 | 32 | 29 |
| 2251 | 2140 | 40463 | 77 | TCCCTGTCGGACTACATCCCCGTT | 28 | 9 | 34 | 7 | 28 | 12 |
| 2252 | 2141 | 15766 | 78.7 | TCCCTCGTTGTCACCTCAGCAGCC | 28 | 10 | 9 | 23 | 31 | 36 |
| 2253 | 2142 | 30518 | 79.5 | TCCCTCGTCTCAGACCCAGCGCTT | 28 | 10 | 13 | 32 | 31 | 17 |
| 2254 | 2143 | 40464 | 77.4 | TCCCTCGTGGTATACATGCGCAGC | 28 | 10 | 18 | 7 | 29 | 31 |
| 2255 | 2144 | 8234 | 77.8 | TCCCTCGTGTCTTGTCAGCCTCCC | 28 | 10 | 19 | 9 | 36 | 28 |
| 2256 | 2145 | 40465 | 79.8 | TCCCTCGTGCAAAGTGGTGCAGGA | 28 | 10 | 21 | 22 | 33 | 25 |
| 2257 | 2146 | 40466 | 76.1 | TCCCTCGTACCTCCTAGTGCTGCG | 28 | 10 | 23 | 26 | 33 | 29 |
| 2258 | 2147 | 8237 | 79.8 | TCCCTCGTGATGCACGATCGAGGA | 28 | 10 | 27 | 30 | 24 | 25 |
| 2259 | 2148 | 8238 | 79.3 | TCCCTCGTTGCGCCATAGGAGCTT | 28 | 10 | 29 | 15 | 25 | 17 |
| 2260 | 2149 | 8240 | 76.6 | TCCCTCGTGACCTCGTGCAAAATC | 28 | 10 | 32 | 10 | 21 | 4 |
| 2261 | 2150 | 15769 | 76.4 | TCCCTCGTGTGCTTAGCCATGCTT | 28 | 10 | 33 | 3 | 15 | 17 |
| 2262 | 2151 | 21356 | 79.1 | TCCCTCGTGGACGCTTAGTGCGAA | 28 | 10 | 34 | 17 | 22 | 16 |
| 2263 | 2152 | 30519 | 78 | TCCCCTTGTGATTCGTTGCGACCT | 28 | 11 | 2 | 10 | 29 | 23 |
| 2264 | 2153 | 21357 | 76.8 | TCCCCTTGAAAGGGTAACCTTGCG | 28 | 11 | 6 | 18 | 23 | 29 |
| 2265 | 2154 | 30520 | 77.3 | TCCCCTTGTCTGACCTAGCCCGAA | 28 | 11 | 8 | 23 | 36 | 16 |
| 2266 | 2155 | 40469 | 78.3 | TCCCCTTGCTCAGGACTCTGGCAA | 28 | 11 | 13 | 34 | 8 | 21 |
| 2267 | 2156 | 30521 | 78.2 | TCCCCTTGGGTAAGTGTGCGGATG | 28 | 11 | 18 | 22 | 29 | 27 |
| 2268 | 2157 | 40470 | 77.5 | TCCCCTTGATCGTCTGTCCCCTTG | 28 | 11 | 24 | 8 | 28 | 11 |
| 2269 | 2159 | 15779 | 78.5 | TCCCCTTGAGCCAGGATTGATCCC | 28 | 11 | 36 | 25 | 1 | 28 |
| 2270 | 2160 | 30522 | 75.3 | TCCCCGTTTGATATCGTGATTCCC | 28 | 12 | 2 | 24 | 2 | 28 |
| 2271 | 2161 | 8266 | 77.9 | TCCCCGTTATACGTGCGATGGCTT | 28 | 12 | 5 | 33 | 27 | 17 |
| 2272 | 2162 | 40473 | 76.6 | TCCCCGTTTACATTGACACGCCAT | 28 | 12 | 7 | 1 | 30 | 15 |
| 2273 | 2163 | 40474 | 78 | TCCCCGTTTGTCTGTCGACCGAGT | 28 | 12 | 9 | 9 | 32 | 20 |
| 2274 | 2164 | 8267 | 78.4 | TCCCCGTTTCGTCAGCATCGAATC | 28 | 12 | 10 | 31 | 24 | 4 |
| 2275 | 2165 | 8268 | 78.3 | TCCCCGTTCTTGGAGTGGTATGCG | 28 | 12 | 11 | 20 | 18 | 29 |
| 2276 | 2166 | 8270 | 77 | TCCCCGTTCTCAGGTACACGCTCA | 28 | 12 | 13 | 18 | 30 | 13 |
| 2277 | 2167 | 8272 | 79 | TCCCCGTTCCATCACGGATGAGTG | 28 | 12 | 15 | 30 | 27 | 22 |
| 2278 | 2168 | 8274 | 77.6 | TCCCCGTTGCTTTCCCCTGTAGTG | 28 | 12 | 17 | 28 | 14 | 22 |
| 2279 | 2169 | 8276 | 78.8 | TCCCCGTTGCAATCTGACCTCGAA | 28 | 12 | 21 | 8 | 23 | 16 |
| 2280 | 2170 | 30523 | 76.3 | TCCCCGTTACCTTGATACGGGCTT | 28 | 12 | 23 | 2 | 35 | 17 |
| 2281 | 2171 | 8277 | 77.4 | TCCCCGTTATCGCCTATCCCAGTG | 28 | 12 | 24 | 26 | 28 | 22 |
| 2282 | 2172 | 8281 | 80.3 | TCCCCGTTTGCGTCGTAGGACAGC | 28 | 12 | 29 | 10 | 25 | 31 |
| 2283 | 2173 | 8283 | 80.6 | TCCCCGTTGTGCAGTGCGTTCTCA | 28 | 12 | 33 | 22 | 12 | 13 |
| 2284 | 2175 | 15780 | 81.6 | TCCCCTCATGATTGCGACGGGCTT | 28 | 13 | 2 | 29 | 35 | 17 |
| 2285 | 2176 | 8287 | 78.2 | TCCCCTCATTAGCTTGTGCGCGTT | 28 | 13 | 3 | 11 | 29 | 12 |
| 2286 | 2178 | 8290 | 75.7 | TCCCCTCATCTGGCTTTTAGCGAA | 28 | 13 | 8 | 17 | 3 | 16 |
| 2287 | 2180 | 8295 | 75.7 | TCCCCTCACCATCCTAAGCCAGTG | 28 | 13 | 15 | 26 | 36 | 22 |
| 2288 | 2181 | 30525 | 75.3 | TCCCCTCAGCTTAGGACGAACAGC | 28 | 13 | 17 | 25 | 16 | 31 |
| 2289 | 2182 | 8298 | 76.7 | TCCCCTCAACCTCCTACACGTCCC | 28 | 13 | 23 | 26 | 30 | 28 |
| 2290 | 2184 | 8302 | 79.2 | TCCCCTCACACGATCGTCGTGACC | 28 | 13 | 30 | 24 | 10 | 32 |
| 2291 | 2185 | 8303 | 79.1 | TCCCCTCACAGCCTGTTCCCACCT | 28 | 13 | 31 | 14 | 28 | 23 |
| 2292 | 2186 | 30527 | 79.2 | TCCCCTGTTGATGCTTGACCGTGC | 28 | 14 | 2 | 17 | 32 | 33 |
| 2293 | 2187 | 8308 | 80 | TCCCCTGTTCTGCCATGATGTGCG | 28 | 14 | 8 | 15 | 27 | 29 |
| 2294 | 2188 | 40477 | 80 | TCCCCTGTTGTCGCAAGACCGCTT | 28 | 14 | 9 | 21 | 32 | 17 |
| 2295 | 2189 | 30528 | 75.4 | TCCCCTGTTCGTACCTATCGCGTT | 28 | 14 | 10 | 23 | 24 | 12 |

FIG. 25TT

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2296 | 2190 | 15784 | 75.6 | TCCCCTGTCGAAAAAGCGTTAGGA | 28 | 14 | 16 | 6 | 12 | 25 |
| 2297 | 2191 | 8315 | 78.8 | TCCCCTGTGCAAAGTGGACCCTCA | 28 | 14 | 21 | 22 | 32 | 13 |
| 2298 | 2192 | 30529 | 77 | TCCCCTGTAGGATCCCGCAATGAT | 28 | 14 | 25 | 28 | 21 | 2 |
| 2299 | 2193 | 40479 | 79.1 | TCCCCTGTCCTAAGCCTGCGGGTA | 28 | 14 | 26 | 36 | 29 | 18 |
| 2300 | 2194 | 30530 | 81.8 | TCCCCTGTGATGGGACACGGGACC | 28 | 14 | 27 | 34 | 35 | 32 |
| 2301 | 2195 | 8320 | 81.3 | TCCCCTGTTGCGCTTGTGTCAGCC | 28 | 14 | 29 | 11 | 9 | 36 |
| 2302 | 2196 | 8325 | 76 | TCCCCCATTTGATCGTAGTGCGTT | 28 | 15 | 1 | 10 | 22 | 12 |
| 2303 | 2198 | 8330 | 76.3 | TCCCCCATCTTGTGCGGATGTTAG | 28 | 15 | 11 | 29 | 27 | 3 |
| 2304 | 2199 | 8331 | 77.9 | TCCCCCATCGTTGTCTCGAACGTT | 28 | 15 | 12 | 19 | 16 | 12 |
| 2305 | 2200 | 30532 | 77.9 | TCCCCCATCTCAGACCATCGCCTA | 28 | 15 | 13 | 32 | 24 | 26 |
| 2306 | 2201 | 30533 | 78.1 | TCCCCCATGCTTCTTGCGAAGGTA | 28 | 15 | 17 | 11 | 16 | 18 |
| 2307 | 2202 | 40481 | 75.8 | TCCCCCATGGTATTGAAAAGGCAA | 28 | 15 | 18 | 1 | 6 | 21 |
| 2308 | 2203 | 8335 | 76.6 | TCCCCCATAGTGAGTGCGTTCAGC | 28 | 15 | 22 | 22 | 12 | 31 |
| 2309 | 2204 | 8336 | 80 | TCCCCCATTGCGAATCAGCCAATC | 28 | 15 | 29 | 4 | 36 | 4 |
| 2310 | 2205 | 15792 | 80.4 | TCCCCCATGTGCCAGCTTAGCAGC | 28 | 15 | 33 | 31 | 3 | 31 |
| 2311 | 2206 | 21375 | 75.3 | TCCCCCATGGACACCTATACAGCC | 28 | 15 | 34 | 23 | 5 | 36 |
| 2312 | 2208 | 40485 | 76.5 | TCCCCGAAATACAATCTCCCGGAC | 28 | 16 | 5 | 4 | 28 | 34 |
| 2313 | 2209 | 8346 | 77.6 | TCCCCGAAAAAGGCAAGGTACACG | 28 | 16 | 6 | 21 | 18 | 30 |
| 2314 | 2210 | 8347 | 77 | TCCCCGAATACAAGTGCAGCCTCA | 28 | 16 | 7 | 22 | 31 | 13 |
| 2315 | 2211 | 8350 | 78.5 | TCCCCGAACTTGGATGCAGCAAAG | 28 | 16 | 11 | 27 | 31 | 6 |
| 2316 | 2212 | 40486 | 78.5 | TCCCCGAAGCTTTTGACCATTCCC | 28 | 16 | 17 | 1 | 15 | 28 |
| 2317 | 2213 | 40487 | 78.7 | TCCCCGAAGTCTGGTAGTGCTGCG | 28 | 16 | 19 | 18 | 33 | 29 |
| 2318 | 2214 | 15795 | 79.5 | TCCCCGAAAGTGGGACGGACTCTG | 28 | 16 | 22 | 34 | 34 | 8 |
| 2319 | 2215 | 8359 | 79.3 | TCCCCGAATGCGATCGTTAGTCCC | 28 | 16 | 29 | 24 | 3 | 28 |
| 2320 | 2217 | 40490 | 78.4 | TCCCGCTTTTAGGACCGGACGTCT | 28 | 17 | 3 | 32 | 34 | 19 |
| 2321 | 2218 | 21380 | 75.7 | TCCCGCTTTACACTGTACGGGGAC | 28 | 17 | 7 | 14 | 35 | 34 |
| 2322 | 2219 | 8367 | 78.7 | TCCCGCTTCGAAATCGTCTGCTTG | 28 | 17 | 16 | 24 | 8 | 11 |
| 2323 | 2220 | 8368 | 78.4 | TCCCGCTTGCTTGTGCGGTAGAGT | 28 | 17 | 17 | 33 | 18 | 20 |
| 2324 | 2221 | 30536 | 76.2 | TCCCGCTTGTCTAGGACTTGCAGC | 28 | 17 | 19 | 25 | 11 | 31 |
| 2325 | 2222 | 40494 | 79.6 | TCCCGCTTAGTGCTTGGACCGACC | 28 | 17 | 22 | 11 | 32 | 32 |
| 2326 | 2223 | 8372 | 76.4 | TCCCGCTTATCGAGCCTTGATTGA | 28 | 17 | 24 | 36 | 1 | 1 |
| 2327 | 2224 | 8375 | 77.6 | TCCCGCTTCACGATCGCCTAGAGT | 28 | 17 | 30 | 24 | 26 | 20 |
| 2328 | 2225 | 8376 | 80.1 | TCCCGCTTCAGCCTCAGATGCCAT | 28 | 17 | 31 | 13 | 27 | 15 |
| 2329 | 2226 | 15801 | 77.7 | TCCCGCTTAGCCTCTGGCTTTTGA | 28 | 17 | 36 | 8 | 17 | 1 |
| 2330 | 2227 | 15802 | 77.2 | TCCCGGTATGATCGAAGATGTGCG | 28 | 18 | 2 | 16 | 27 | 29 |
| 2331 | 2228 | 30537 | 77.2 | TCCCGGTAAATCCACGGGTAATCG | 28 | 18 | 4 | 30 | 18 | 24 |
| 2332 | 2229 | 40498 | 80.2 | TCCCGGTATGTCCTTGGCTTTGCG | 28 | 18 | 9 | 11 | 17 | 29 |
| 2333 | 2230 | 40499 | 76.6 | TCCCGGTACTCAAATCTGCGATCG | 28 | 18 | 13 | 4 | 29 | 24 |
| 2334 | 2231 | 30539 | 78 | TCCCGGTACTGTAGGAACGGCGAA | 28 | 18 | 14 | 25 | 35 | 16 |
| 2335 | 2232 | 40500 | 76.2 | TCCCGGTAGGTACCTAGTGCGCAA | 28 | 18 | 18 | 26 | 33 | 21 |
| 2336 | 2233 | 8391 | 75.9 | TCCCGGTAAGGAGCTTCGTTGATG | 28 | 18 | 25 | 17 | 12 | 27 |
| 2337 | 2234 | 40503 | 76 | TCCCGGTACCTATTAGCAGCGTGC | 28 | 18 | 26 | 3 | 31 | 33 |
| 2338 | 2235 | 30541 | 76.5 | TCCCGGTAGATGTCGTTCTGACGG | 28 | 18 | 27 | 10 | 8 | 35 |
| 2339 | 2236 | 8393 | 78.8 | TCCCGGTATGCGGGTAAGGATCGT | 28 | 18 | 29 | 18 | 25 | 10 |
| 2340 | 2238 | 8398 | 79.7 | TCCCGGTAAGCCCATCTGTCGAA | 28 | 18 | 36 | 15 | 14 | 16 |
| 2341 | 2239 | 15810 | 75.9 | TCCCGTCTTTGAGCTTGACCCTTG | 28 | 19 | 1 | 17 | 32 | 11 |
| 2342 | 2240 | 30542 | 81.9 | TCCCGTCTTGTCACGGTGCGGATG | 28 | 19 | 9 | 35 | 29 | 27 |
| 2343 | 2241 | 40504 | 77.6 | TCCCGTCTTCGTAGTGCTTGCACG | 28 | 19 | 10 | 22 | 11 | 30 |
| 2344 | 2242 | 40505 | 79.6 | TCCCGTCTCTCAACCTTGCGTCCC | 28 | 19 | 13 | 23 | 29 | 28 |
| 2345 | 2244 | 8406 | 79.5 | TCCCGTCTAGTGTCCCAGCCGACC | 28 | 19 | 22 | 28 | 36 | 32 |
| 2346 | 2245 | 8407 | 75.6 | TCCCGTCTACCTCCTATGCGCTGT | 28 | 19 | 23 | 26 | 29 | 14 |

FIG. 25UU

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2347 | 2246 | 30544 | 79 | TCCCGTCTATCGCTCATGCGTCGT | 28 | 19 | 24 | 13 | 29 | 10 |
| 2348 | 2247 | 15812 | 75.6 | TCCCGTCTCCTAAGGAGACCCCAT | 28 | 19 | 26 | 25 | 32 | 15 |
| 2349 | 2248 | 8409 | 80.8 | TCCCGTCTTGCGCCATGAGTTCGT | 28 | 19 | 29 | 15 | 20 | 10 |
| 2350 | 2249 | 40506 | 79.3 | TCCCGTCTCACGACCTTGTCCACG | 28 | 19 | 30 | 23 | 9 | 30 |
| 2351 | 2250 | 40507 | 77.6 | TCCCGTCTGGACTCTGGCTTGCTT | 28 | 19 | 34 | 8 | 17 | 17 |
| 2352 | 2251 | 15814 | 78.5 | TCCCGTCTACGGCTTGAATCGTGC | 28 | 19 | 35 | 11 | 4 | 33 |
| 2353 | 2252 | 30545 | 80 | TCCCGTCTAGCCGAGTGACCCGAA | 28 | 19 | 36 | 20 | 32 | 16 |
| 2354 | 2253 | 8412 | 77.3 | TCCCGAGTTGATCCATCTTGCACG | 28 | 20 | 2 | 15 | 11 | 30 |
| 2355 | 2255 | 30546 | 77.6 | TCCCGAGTCTTGATCGGCTTGCTT | 28 | 20 | 11 | 24 | 17 | 17 |
| 2356 | 2256 | 15816 | 77.4 | TCCCGAGTCGAAGACCCTCAAGGA | 28 | 20 | 16 | 32 | 13 | 25 |
| 2357 | 2257 | 40510 | 77 | TCCCGAGTATCGTCTGATCGGCAA | 28 | 20 | 24 | 8 | 24 | 21 |
| 2358 | 2258 | 8420 | 81.4 | TCCCGAGTCAGCGACCACCTGTGC | 28 | 20 | 31 | 32 | 23 | 33 |
| 2359 | 2259 | 30548 | 77.5 | TCCCGAGTGACCACGGGCTTAATC | 28 | 20 | 32 | 35 | 17 | 4 |
| 2360 | 2260 | 40511 | 79.5 | TCCCGAGTGTGCTGTCGATGAGCC | 28 | 20 | 33 | 9 | 27 | 36 |
| 2361 | 2261 | 8424 | 77 | TCCCGAGTACGGGCAAAGGAAAAG | 28 | 20 | 35 | 21 | 25 | 6 |
| 2362 | 2262 | 40512 | 76.5 | TCCCGCAATTGACGTTAAAGGTGC | 28 | 21 | 1 | 12 | 6 | 33 |
| 2363 | 2263 | 40513 | 78.4 | TCCCGCAATTAGCCATCCTATGCG | 28 | 21 | 3 | 15 | 26 | 29 |
| 2364 | 2264 | 40514 | 79.8 | TCCCGCAAAATCGGACAATCGCTT | 28 | 21 | 4 | 34 | 4 | 17 |
| 2365 | 2265 | 8429 | 76.3 | TCCCGCAATACAATCGAGTGGACC | 28 | 21 | 7 | 24 | 22 | 32 |
| 2366 | 2266 | 8431 | 76.4 | TCCCGCAACTTGAAAGATCGCTGT | 28 | 21 | 11 | 6 | 24 | 14 |
| 2367 | 2267 | 8436 | 79 | TCCCGCAACGAAGTGCTGATTCGT | 28 | 21 | 16 | 33 | 2 | 10 |
| 2368 | 2268 | 8437 | 79.2 | TCCCGCAAGCTTTCTGGTGCTTGA | 28 | 21 | 17 | 8 | 33 | 1 |
| 2369 | 2269 | 30549 | 78.8 | TCCCGCAAGAGTCCATGCAACCAT | 28 | 21 | 20 | 15 | 21 | 15 |
| 2370 | 2270 | 40515 | 78.8 | TCCCGCAAAGTGAGTGGATGCCAT | 28 | 21 | 22 | 22 | 27 | 15 |
| 2371 | 2272 | 8442 | 80.4 | TCCCGCAACAGCGGACAGGAAAAG | 28 | 21 | 31 | 34 | 25 | 6 |
| 2372 | 2273 | 8444 | 79.5 | TCCCGCAAGGACCCTACTTGGTGC | 28 | 21 | 34 | 26 | 11 | 33 |
| 2373 | 2274 | 8445 | 82.2 | TCCCGCAAAGCCGGACATACCGAA | 28 | 21 | 36 | 34 | 5 | 16 |
| 2374 | 2275 | 8447 | 77.6 | TCCCAGTGCTCAGTGCCGAATCTG | 28 | 22 | 13 | 33 | 16 | 8 |
| 2375 | 2276 | 8448 | 76.7 | TCCCAGTGCTGTATCGCACGTTGA | 28 | 22 | 14 | 24 | 30 | 1 |
| 2376 | 2277 | 8449 | 75.7 | TCCCAGTGCCATTCCCGAGTTTAG | 28 | 22 | 15 | 28 | 20 | 3 |
| 2377 | 2278 | 40518 | 78.4 | TCCCAGTGGCAATCGTCGAAGGAC | 28 | 22 | 21 | 10 | 16 | 34 |
| 2378 | 2279 | 8454 | 75.6 | TCCCAGTGCCTAGGACGTCTGCTT | 28 | 22 | 26 | 34 | 19 | 17 |
| 2379 | 2280 | 40519 | 79.5 | TCCCAGTGTCCCCCTAGTGCCAGC | 28 | 22 | 28 | 26 | 33 | 31 |
| 2380 | 2281 | 8457 | 78.8 | TCCCAGTGCAGCGTCTCGTTAGCC | 28 | 22 | 31 | 19 | 12 | 36 |
| 2381 | 2282 | 15826 | 79.7 | TCCCAGTGGGACAGTGGCTTGCAA | 28 | 22 | 34 | 22 | 17 | 21 |
| 2382 | 2283 | 8459 | 78.6 | TCCCAGTGAGCCCGTTTCGTTCTG | 28 | 22 | 36 | 12 | 10 | 8 |
| 2383 | 2284 | 21397 | 77.7 | TCCCACCTTCTGAATCTCCCTGCG | 28 | 23 | 8 | 4 | 28 | 29 |
| 2384 | 2285 | 8463 | 77.2 | TCCCACCTTGTCATCGGTGCAAAG | 28 | 23 | 9 | 24 | 33 | 6 |
| 2385 | 2287 | 8470 | 78.1 | TCCCACCTGCAACACGTGTCCTTG | 28 | 23 | 21 | 30 | 9 | 11 |
| 2386 | 2288 | 8471 | 76.8 | TCCCACCTAGGACAGCTCTGCACG | 28 | 23 | 25 | 31 | 8 | 30 |
| 2387 | 2289 | 15831 | 80.1 | TCCCACCTGATGCTTGTCGTTGCG | 28 | 23 | 27 | 11 | 10 | 29 |
| 2388 | 2290 | 8474 | 80.2 | TCCCACCTTCCCCACGCTCATGTC | 28 | 23 | 28 | 30 | 13 | 9 |
| 2389 | 2291 | 21400 | 77.7 | TCCCACCTCAGCCTTGGAGTACGG | 28 | 23 | 31 | 11 | 20 | 35 |
| 2390 | 2292 | 8476 | 76.9 | TCCCACCTACGGTCGTCGAACTCA | 28 | 23 | 35 | 10 | 16 | 13 |
| 2391 | 2294 | 40523 | 78.9 | TCCCATCGCGTTGCTTAAAGGCAA | 28 | 24 | 12 | 17 | 6 | 21 |
| 2392 | 2295 | 8483 | 79.6 | TCCCATCGCCATCAGCCTCATTGA | 28 | 24 | 15 | 31 | 13 | 1 |
| 2393 | 2296 | 30553 | 76.5 | TCCCATCGGATGTTAGACCTTGCG | 28 | 24 | 27 | 3 | 23 | 29 |
| 2394 | 2297 | 8489 | 79.2 | TCCCATCGTGCGAGGAGGTACACG | 28 | 24 | 29 | 25 | 18 | 30 |
| 2395 | 2298 | 8490 | 79 | TCCCATCGCACGTCGTTCCCATAC | 28 | 24 | 30 | 10 | 28 | 5 |
| 2396 | 2299 | 8491 | 80.8 | TCCCATCGCAGCCAGCAATCCTGT | 28 | 24 | 31 | 31 | 4 | 14 |
| 2397 | 2300 | 15834 | 79.2 | TCCCATCGGACCTTGACAGCATCG | 28 | 24 | 32 | 1 | 31 | 24 |

FIG. 25VV

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2398 | 2301 | 8493 | 80 | TCCCATCGGGACCTCAATCGGATG | 28 | 24 | 34 | 13 | 24 | 27 |
| 2399 | 2302 | 30554 | 79.7 | TCCCATCGAGCCATCGCCATACCT | 28 | 24 | 36 | 24 | 15 | 23 |
| 2400 | 2303 | 40528 | 80.9 | TCCCAGGACTTGGTGCGTGCTCGT | 28 | 25 | 11 | 33 | 33 | 10 |
| 2401 | 2305 | 15836 | 75.1 | TCCCAGGAGCTTACGGAGCCATAC | 28 | 25 | 17 | 35 | 36 | 5 |
| 2402 | 2306 | 40529 | 76.6 | TCCCAGGAGGTATTAGTGCGTGCG | 28 | 25 | 18 | 3 | 29 | 29 |
| 2403 | 2307 | 8506 | 78.9 | TCCCAGGAGAGTGGACTCCCAGCC | 28 | 25 | 20 | 34 | 28 | 36 |
| 2404 | 2308 | 15837 | 75.5 | TCCCAGGAACCTCGAAGCAACCTA | 28 | 25 | 23 | 16 | 21 | 26 |
| 2405 | 2309 | 40531 | 82.2 | TCCCAGGAGATGTGCGTGCGCTTG | 28 | 25 | 27 | 29 | 29 | 11 |
| 2406 | 2310 | 8510 | 76.8 | TCCCAGGATCCCCCTAAGGAGCTT | 28 | 25 | 28 | 26 | 25 | 17 |
| 2407 | 2311 | 8511 | 76.6 | TCCCAGGATGCGAATCGCAATTAG | 28 | 25 | 29 | 4 | 21 | 3 |
| 2408 | 2312 | 30559 | 76.4 | TCCCCCTATGATCGAAAGCCCCTA | 28 | 26 | 2 | 16 | 36 | 26 |
| 2409 | 2313 | 30560 | 76.7 | TCCCCCTACGTTCCTAATCGGTGC | 28 | 26 | 12 | 26 | 24 | 33 |
| 2410 | 2314 | 40535 | 77.9 | TCCCCCTACTCAGTGCACGGGGTA | 28 | 26 | 13 | 33 | 35 | 18 |
| 2411 | 2315 | 30561 | 77.6 | TCCCCCTAGCTTCACGGGTACACG | 28 | 26 | 17 | 30 | 18 | 30 |
| 2412 | 2316 | 30562 | 77 | TCCCCCTAGGTAGAGTTGCGGTGC | 28 | 26 | 18 | 20 | 29 | 33 |
| 2413 | 2317 | 8528 | 81 | TCCCCCTATGCGGATGTGCGAGTG | 28 | 26 | 29 | 27 | 29 | 22 |
| 2414 | 2318 | 8531 | 75.6 | TCCCCCTAGACCATACACGGCTTG | 28 | 26 | 32 | 5 | 35 | 11 |
| 2415 | 2319 | 40538 | 77.5 | TCCCCCTAGGACAATCCTCATGCG | 28 | 26 | 34 | 4 | 13 | 29 |
| 2416 | 2320 | 8532 | 79.7 | TCCCCCTAACGGCTGTGGACGGTA | 28 | 26 | 35 | 14 | 34 | 18 |
| 2417 | 2321 | 30563 | 76.1 | TCCCGATGTTGATCCCCCTAACCT | 28 | 27 | 1 | 28 | 26 | 23 |
| 2418 | 2322 | 21415 | 76.9 | TCCCGATGTTAGCTGTAGCCTGCG | 28 | 27 | 3 | 14 | 36 | 29 |
| 2419 | 2323 | 15848 | 80 | TCCCGATGTGTCACGGTGTCAGCC | 28 | 27 | 9 | 35 | 9 | 36 |
| 2420 | 2324 | 8539 | 75.3 | TCCCGATGCTGTAAAGGGACCTGT | 28 | 27 | 14 | 6 | 34 | 14 |
| 2421 | 2325 | 8541 | 77.7 | TCCCGATGGGTAAGTGTCCCCTCA | 28 | 27 | 18 | 22 | 28 | 13 |
| 2422 | 2326 | 15849 | 78.3 | TCCCGATGGAGTTGTCCTTGACGG | 28 | 27 | 20 | 9 | 11 | 35 |
| 2423 | 2327 | 30564 | 79 | TCCCGATGGCAAGCAAAAAGCTCA | 28 | 27 | 21 | 21 | 6 | 13 |
| 2424 | 2328 | 8545 | 81 | TCCCGATGATCGGGACAGTGGTGC | 28 | 27 | 24 | 34 | 22 | 33 |
| 2425 | 2329 | 8548 | 78.2 | TCCCGATGTGCGATACCCATAGCC | 28 | 27 | 29 | 5 | 15 | 36 |
| 2426 | 2330 | 8549 | 81.4 | TCCCGATGCACGGGACCTTGTTGA | 28 | 27 | 30 | 34 | 11 | 1 |
| 2427 | 2331 | 15852 | 80.5 | TCCCGATGGACCGCAACGTTCCTA | 28 | 27 | 32 | 21 | 12 | 26 |
| 2428 | 2332 | 8552 | 79.8 | TCCCGATGGGACCCTACAGCCTCA | 28 | 27 | 34 | 26 | 31 | 13 |
| 2429 | 2333 | 8553 | 81.2 | TCCCGATGACGGCTCACTTGGTGC | 28 | 27 | 35 | 13 | 11 | 33 |
| 2430 | 2334 | 15853 | 77.5 | TCCCGATGAGCCTGCGTTAGACCT | 28 | 27 | 36 | 29 | 3 | 23 |
| 2431 | 2335 | 40540 | 77.8 | TCCCTCCCTGATACCTCAGCGTGC | 28 | 28 | 2 | 23 | 31 | 33 |
| 2432 | 2336 | 30565 | 80.3 | TCCCTCCCTACAGTGCGCAAACGG | 28 | 28 | 7 | 33 | 21 | 35 |
| 2433 | 2337 | 8558 | 76.8 | TCCCTCCCTGTCCCTACGAAATCG | 28 | 28 | 9 | 26 | 16 | 24 |
| 2434 | 2338 | 40541 | 77.2 | TCCCTCCCCTTGTTAGGGACCCAT | 28 | 28 | 11 | 3 | 34 | 15 |
| 2435 | 2339 | 8560 | 77.1 | TCCCTCCCCTCACGTTCCATGAGT | 28 | 28 | 13 | 12 | 15 | 20 |
| 2436 | 2340 | 8561 | 79 | TCCCTCCCCTGTGTGCGAGTCTCA | 28 | 28 | 14 | 33 | 20 | 13 |
| 2437 | 2341 | 30566 | 79.5 | TCCCTCCCCGAATTAGCTGTTGCG | 28 | 28 | 16 | 3 | 14 | 29 |
| 2438 | 2342 | 8566 | 78.2 | TCCCTCCCATCGCCTAATCGGAGT | 28 | 28 | 24 | 26 | 24 | 20 |
| 2439 | 2343 | 30567 | 78.2 | TCCCTCCCAGGATTGAACGGGTCT | 28 | 28 | 25 | 1 | 35 | 19 |
| 2440 | 2344 | 8568 | 76.6 | TCCCTCCCGATGAAAGACCTGCTT | 28 | 28 | 27 | 6 | 23 | 17 |
| 2441 | 2345 | 21423 | 79.5 | TCCCTCCCACGGAATCAGGACAGC | 28 | 28 | 35 | 4 | 25 | 31 |
| 2442 | 2346 | 40543 | 76.2 | TCCCTGCGTGATAGTGGCAAACCT | 28 | 29 | 2 | 22 | 21 | 23 |
| 2443 | 2347 | 30568 | 80.5 | TCCCTGCGATACGTGCAATCGCAA | 28 | 29 | 5 | 33 | 4 | 21 |
| 2444 | 2348 | 30569 | 78.2 | TCCCTGCGAAAGAGTGCGAACCAT | 28 | 29 | 6 | 22 | 16 | 15 |
| 2445 | 2349 | 40544 | 78 | TCCCTGCGTACACCATATCGTGCG | 28 | 29 | 7 | 15 | 24 | 29 |
| 2446 | 2350 | 40545 | 80.3 | TCCCTGCGTGTCAGTGCTTGGTGC | 28 | 29 | 9 | 22 | 11 | 33 |
| 2447 | 2351 | 8575 | 77.4 | TCCCTGCGCTTGAGGAATACCGTT | 28 | 29 | 11 | 25 | 5 | 12 |
| 2448 | 2352 | 8578 | 82.9 | TCCCTGCGCGAACACGTGATCACG | 28 | 29 | 16 | 30 | 2 | 30 |

FIG. 25WW

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2449 | 2353 | 8579 | 79.8 | TCCCTGCGGCTTTTGAAGTGAGCC | 28 | 29 | 17 | 1 | 22 | 36 |
| 2450 | 2354 | 8581 | 82.1 | TCCCTGCGGCAACGTTGTCTCACG | 28 | 29 | 21 | 12 | 19 | 30 |
| 2451 | 2355 | 8582 | 79.3 | TCCCTGCGACCTGCAAATCGTGTC | 28 | 29 | 23 | 21 | 24 | 9 |
| 2452 | 2356 | 40547 | 80.7 | TCCCTGCGAGGAGAGTGTGCGGAC | 28 | 29 | 25 | 20 | 33 | 34 |
| 2453 | 2357 | 15859 | 83.6 | TCCCTGCGTCCCGAGTGCAAGCAA | 28 | 29 | 28 | 20 | 21 | 21 |
| 2454 | 2358 | 8585 | 82.8 | TCCCTGCGCACGGGTACGTTGACC | 28 | 29 | 30 | 18 | 12 | 32 |
| 2455 | 2359 | 8586 | 81.6 | TCCCTGCGCAGCCTGTAGGAAGCC | 28 | 29 | 31 | 14 | 25 | 36 |
| 2456 | 2360 | 8587 | 82.8 | TCCCTGCGGACCCTGTCAGCCTCA | 28 | 29 | 32 | 14 | 31 | 13 |
| 2457 | 2361 | 8588 | 82.9 | TCCCTGCGGTGCGCTTGCAAGAGT | 28 | 29 | 33 | 17 | 21 | 20 |
| 2458 | 2362 | 30570 | 78.3 | TCCCCACGTTGACAGCTCCCAATC | 28 | 30 | 1 | 31 | 28 | 4 |
| 2459 | 2363 | 30571 | 77.1 | TCCCCACGTTAGTCGTCTTGCGAA | 28 | 30 | 3 | 10 | 11 | 16 |
| 2460 | 2366 | 8593 | 81 | TCCCCACGTCTGGGACACGGTGTC | 28 | 30 | 8 | 34 | 35 | 9 |
| 2461 | 2367 | 8594 | 79 | TCCCCACGTCGTGTGCATACTCCC | 28 | 30 | 10 | 33 | 5 | 28 |
| 2462 | 2368 | 8596 | 79.5 | TCCCCACGCTGTTCTGAGCCAGTG | 28 | 30 | 14 | 8 | 36 | 22 |
| 2463 | 2370 | 21430 | 80.3 | TCCCCACGGGTATCCCCTGTCCAT | 28 | 30 | 18 | 28 | 14 | 15 |
| 2464 | 2371 | 8598 | 79.4 | TCCCCACGGTCTCAGCATCGAGTG | 28 | 30 | 19 | 31 | 24 | 22 |
| 2465 | 2372 | 8599 | 81.1 | TCCCCACGGCAAAATCGTGCTCTG | 28 | 30 | 21 | 4 | 33 | 8 |
| 2466 | 2373 | 8600 | 76.9 | TCCCCACGACCTAATCGATGCTCA | 28 | 30 | 23 | 4 | 27 | 13 |
| 2467 | 2374 | 8601 | 80.4 | TCCCCACGATCGCGAATGATCCAT | 28 | 30 | 24 | 16 | 2 | 15 |
| 2468 | 2375 | 8602 | 78.4 | TCCCCACGCCTAGTGCAGCCATAC | 28 | 30 | 26 | 33 | 36 | 5 |
| 2469 | 2376 | 8604 | 81.4 | TCCCCACGTGCGTGATTCGTCGTT | 28 | 30 | 29 | 2 | 10 | 12 |
| 2470 | 2377 | 8605 | 81.8 | TCCCCACGCAGCCGTTCTTGACCT | 28 | 30 | 31 | 12 | 11 | 23 |
| 2471 | 2378 | 8606 | 80.3 | TCCCCACGGACCAGCCTACACAGC | 28 | 30 | 32 | 36 | 7 | 31 |
| 2472 | 2379 | 8607 | 81.6 | TCCCCACGGTGCTGTCTGCGTGAT | 28 | 30 | 33 | 9 | 29 | 2 |
| 2473 | 2380 | 8608 | 81.4 | TCCCCACGGGACCCATCGTTGAGT | 28 | 30 | 34 | 15 | 12 | 20 |
| 2474 | 2381 | 30572 | 77.3 | TCCCCAGCTTGAAAAGGACCCTCA | 28 | 31 | 1 | 6 | 32 | 13 |
| 2475 | 2382 | 8611 | 79.3 | TCCCCAGCAATCGGACGGTAGACC | 28 | 31 | 4 | 34 | 18 | 32 |
| 2476 | 2383 | 30573 | 76.3 | TCCCCAGCTACAGCAAAAAGCAGC | 28 | 31 | 7 | 21 | 6 | 31 |
| 2477 | 2384 | 8615 | 77.8 | TCCCCAGCTCTGATCGGTCTGGAC | 28 | 31 | 8 | 24 | 19 | 34 |
| 2478 | 2385 | 8616 | 78.2 | TCCCCAGCTCGTCTGTGATGGCTT | 28 | 31 | 10 | 14 | 27 | 17 |
| 2479 | 2386 | 8617 | 79.5 | TCCCCAGCCTTGCTGTATCGGGAC | 28 | 31 | 11 | 14 | 24 | 34 |
| 2480 | 2387 | 8619 | 80.5 | TCCCCAGCCGAAGTGCCTCACTTG | 28 | 31 | 16 | 33 | 13 | 11 |
| 2481 | 2388 | 8621 | 77.8 | TCCCCAGCGGTAAGGACAGCAAAG | 28 | 31 | 18 | 25 | 31 | 6 |
| 2482 | 2389 | 15863 | 77.1 | TCCCCAGCACCTAATCACGGGAGT | 28 | 31 | 23 | 4 | 35 | 20 |
| 2483 | 2390 | 8623 | 81.1 | TCCCCAGCATCGGATGCTTGATCG | 28 | 31 | 24 | 27 | 11 | 24 |
| 2484 | 2391 | 30574 | 78.4 | TCCCCAGCAGGAGAGTAGCCCCAT | 28 | 31 | 25 | 20 | 36 | 15 |
| 2485 | 2392 | 8627 | 81.4 | TCCCCAGCCAGCTCTGTGTCACGG | 28 | 31 | 31 | 8 | 9 | 35 |
| 2486 | 2393 | 21442 | 80.3 | TCCCCAGCGGACCGAATGTCTGTC | 28 | 31 | 34 | 16 | 9 | 9 |
| 2487 | 2394 | 8629 | 81 | TCCCCAGCAGCCGGTAGCTTCCAT | 28 | 31 | 36 | 18 | 17 | 15 |
| 2488 | 2395 | 8631 | 77.3 | TCCCGACCTGATTGATTGTCTGCG | 28 | 32 | 2 | 2 | 9 | 29 |
| 2489 | 2396 | 15865 | 75.4 | TCCCGACCTTAGAATCGTGCCCTA | 28 | 32 | 3 | 4 | 33 | 26 |
| 2490 | 2397 | 40549 | 78.4 | TCCCGACCAATCTTGAGACCGTGC | 28 | 32 | 4 | 1 | 32 | 33 |
| 2491 | 2398 | 8634 | 75.2 | TCCCGACCTACATTGAACGGACCT | 28 | 32 | 7 | 1 | 35 | 23 |
| 2492 | 2399 | 8635 | 75.1 | TCCCGACCTGTCTCCCGAGTAAAG | 28 | 32 | 9 | 28 | 20 | 6 |
| 2493 | 2400 | 40550 | 79 | TCCCGACCCGTTTTAGCGTTTCGT | 28 | 32 | 12 | 3 | 12 | 10 |
| 2494 | 2401 | 21445 | 78.5 | TCCCGACCCTCAGGTAGCAACACG | 28 | 32 | 13 | 18 | 21 | 30 |
| 2495 | 2402 | 15866 | 76.9 | TCCCGACCCTGTAGGACTTGAGCC | 28 | 32 | 14 | 25 | 11 | 36 |
| 2496 | 2404 | 40551 | 77.5 | TCCCGACCGTCTAAAGGACCGATG | 28 | 32 | 19 | 6 | 32 | 27 |
| 2497 | 2405 | 8641 | 79.5 | TCCCGACCGAGTGTCTTGCGTCTG | 28 | 32 | 20 | 19 | 29 | 8 |
| 2498 | 2406 | 8642 | 79.9 | TCCCGACCGCAAAGGAGATGCCTA | 28 | 32 | 21 | 25 | 27 | 26 |
| 2499 | 2407 | 8646 | 76.7 | TCCCGACCCCTAATACGATGAGCC | 28 | 32 | 26 | 5 | 27 | 36 |

FIG. 25XX

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2500 | 2408 | 15867 | 83.3 | TCCCGACCCACGGTGCAGCCTACA | 28 | 32 | 30 | 33 | 36 | 7 |
| 2501 | 2409 | 8648 | 77.7 | TCCCGTGCTTGATCTGAGTGCAGC | 28 | 33 | 1 | 8 | 22 | 31 |
| 2502 | 2410 | 40555 | 75.5 | TCCCGTGCTTAGTGATAGCCCGTT | 28 | 33 | 3 | 2 | 36 | 12 |
| 2503 | 2411 | 30576 | 80.5 | TCCCGTGCTGTCCCATCGTTCCAT | 28 | 33 | 9 | 15 | 12 | 15 |
| 2504 | 2412 | 8651 | 80.1 | TCCCGTGCCTCAAATCGTGCAGTG | 28 | 33 | 13 | 4 | 33 | 22 |
| 2505 | 2413 | 8652 | 79.9 | TCCCGTGCCGAACGAACTCAACCT | 28 | 33 | 16 | 16 | 13 | 23 |
| 2506 | 2414 | 40558 | 80.3 | TCCCGTGCGTCTCTGTACGGTCCC | 28 | 33 | 19 | 14 | 35 | 28 |
| 2507 | 2415 | 8655 | 80.5 | TCCCGTGCACCTGTCTGATGGCAA | 28 | 33 | 23 | 19 | 27 | 21 |
| 2508 | 2416 | 8659 | 83.3 | TCCCGTGCTCCCGCTTGTGCTCTG | 28 | 33 | 28 | 17 | 33 | 8 |
| 2509 | 2417 | 8661 | 80.3 | TCCCGTGCGACCTTGAAGTGGGAC | 28 | 33 | 32 | 1 | 22 | 34 |
| 2510 | 2418 | 15868 | 80.9 | TCCCGTGCGTGCTTAGGTGCGAGT | 28 | 33 | 33 | 3 | 33 | 20 |
| 2511 | 2419 | 8663 | 79.6 | TCCCGTGCACGGAAAGCCTAGGAC | 28 | 33 | 35 | 6 | 26 | 34 |
| 2512 | 2420 | 8664 | 80.3 | TCCCGTGCAGCCAGGATTAGACGG | 28 | 33 | 36 | 25 | 3 | 35 |
| 2513 | 2423 | 8667 | 77.5 | TCCCGGACAATCATCGAGGAGACC | 28 | 34 | 4 | 24 | 25 | 32 |
| 2514 | 2424 | 30577 | 79.2 | TCCCGGACATACTGTCGGACTGCG | 28 | 34 | 5 | 9 | 34 | 29 |
| 2515 | 2425 | 21453 | 76.8 | TCCCGGACAAAGTCCCTTAGACGG | 28 | 34 | 6 | 28 | 3 | 35 |
| 2516 | 2426 | 8669 | 75.3 | TCCCGGACTACACTTGACGGGTCT | 28 | 34 | 7 | 11 | 35 | 19 |
| 2517 | 2427 | 40559 | 79.3 | TCCCGGACTCGTCGAAGACCTCGT | 28 | 34 | 10 | 16 | 32 | 10 |
| 2518 | 2428 | 8672 | 80.2 | TCCCGGACCTTGCCATCTCAATCG | 28 | 34 | 11 | 15 | 13 | 24 |
| 2519 | 2429 | 8673 | 81.2 | TCCCGGACCGTTCACGCTCAGATG | 28 | 34 | 12 | 30 | 13 | 27 |
| 2520 | 2430 | 40561 | 77.1 | TCCCGGACGTCTATACTCCCCGAA | 28 | 34 | 19 | 5 | 28 | 16 |
| 2521 | 2431 | 8678 | 81.2 | TCCCGGACATCGGAGTCTCATGCG | 28 | 34 | 24 | 20 | 13 | 29 |
| 2522 | 2432 | 30578 | 80.9 | TCCCGGACGATGCCATATCGCTTG | 28 | 34 | 27 | 15 | 24 | 11 |
| 2523 | 2433 | 8682 | 79.8 | TCCCGGACTGCGAATCCCTACGAA | 28 | 34 | 29 | 4 | 26 | 16 |
| 2524 | 2434 | 8683 | 80.2 | TCCCGGACCACGTTGACGAAGACC | 28 | 34 | 30 | 1 | 16 | 32 |
| 2525 | 2435 | 8684 | 81.4 | TCCCGGACGACCGGACAAAGGGTA | 28 | 34 | 32 | 34 | 6 | 18 |
| 2526 | 2436 | 8685 | 81.2 | TCCCGGACGTGCAAAGTCTGACGG | 28 | 34 | 33 | 6 | 8 | 35 |
| 2527 | 2437 | 8686 | 82 | TCCCGGACGGACGCAAAGGATGTC | 28 | 34 | 34 | 21 | 25 | 9 |
| 2528 | 2438 | 8687 | 80.4 | TCCCGGACAGCCACCTAGCCAGTG | 28 | 34 | 36 | 23 | 36 | 22 |
| 2529 | 2439 | 15871 | 77.3 | TCCCACGGTTGACTGTAGGATGCG | 28 | 35 | 1 | 14 | 25 | 29 |
| 2530 | 2441 | 8696 | 80 | TCCCACGGGCTTTCTGCGTTGAGT | 28 | 35 | 17 | 8 | 12 | 20 |
| 2531 | 2442 | 8697 | 78.5 | TCCCACGGGTCTGGTAGCTTGTGC | 28 | 35 | 19 | 18 | 17 | 33 |
| 2532 | 2443 | 40565 | 78.3 | TCCCACGGCCTATCCCATACTCCC | 28 | 35 | 26 | 28 | 5 | 28 |
| 2533 | 2445 | 8704 | 81.3 | TCCCACGGTGCGCCTAATACGCAA | 28 | 35 | 29 | 26 | 5 | 21 |
| 2534 | 2446 | 21461 | 80.8 | TCCCACGGGACCATACCTGTTGCG | 28 | 35 | 32 | 5 | 14 | 29 |
| 2535 | 2447 | 8708 | 80.9 | TCCCACGGGTGCATCGTTAGACGG | 28 | 35 | 33 | 24 | 3 | 35 |
| 2536 | 2448 | 40566 | 77.4 | TCCCAGCCTTGATCTGATCGGCTT | 28 | 36 | 1 | 8 | 24 | 17 |
| 2537 | 2449 | 30579 | 80.7 | TCCCAGCCTGATGATGTGCGCTCA | 28 | 36 | 2 | 27 | 29 | 13 |
| 2538 | 2450 | 8709 | 75.1 | TCCCAGCCTTAGAGTGCTTGGCTT | 28 | 36 | 3 | 22 | 11 | 17 |
| 2539 | 2451 | 40567 | 79 | TCCCAGCCATACAATCACGGGTGC | 28 | 36 | 5 | 4 | 35 | 33 |
| 2540 | 2453 | 30580 | 78.7 | TCCCAGCCTCTGTTGAGTGCGACC | 28 | 36 | 8 | 1 | 33 | 32 |
| 2541 | 2454 | 8711 | 78.6 | TCCCAGCCTCGTGTCTACGGATCG | 28 | 36 | 10 | 19 | 35 | 24 |
| 2542 | 2455 | 15874 | 77.1 | TCCCAGCCCTCATTAGTCCCGGTA | 28 | 36 | 13 | 3 | 28 | 18 |
| 2543 | 2456 | 8716 | 78.5 | TCCCAGCCGCTTCCTAACCTTCGT | 28 | 36 | 17 | 26 | 23 | 10 |
| 2544 | 2457 | 30581 | 77.9 | TCCCAGCCGGTATTAGGACCCCAT | 28 | 36 | 18 | 3 | 32 | 15 |
| 2545 | 2458 | 30583 | 76.8 | TCCCAGCCAGTGTTAGCCTATGCG | 28 | 36 | 22 | 3 | 26 | 29 |
| 2546 | 2459 | 8718 | 75.4 | TCCCAGCCACCTATACTGCGGAGT | 28 | 36 | 23 | 5 | 29 | 20 |
| 2547 | 2460 | 8719 | 80.3 | TCCCAGCCATCGGTGCTGATAGCC | 28 | 36 | 24 | 33 | 2 | 36 |
| 2548 | 2462 | 8721 | 79.9 | TCCCAGCCTCCCACCTTGATCGAA | 28 | 36 | 28 | 23 | 2 | 16 |
| 2549 | 2463 | 8722 | 81.3 | TCCCAGCCCACGGGTAAGCCTCTG | 28 | 36 | 30 | 18 | 36 | 8 |
| 2550 | 2464 | 8723 | 82.1 | TCCCAGCCCAGCCTTGGATGATCG | 28 | 36 | 31 | 11 | 27 | 24 |

FIG. 25YY

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2551 | 2465 | 8724 | 81 | TCCCAGCCGTGCAAAGAGGAGCAA | 28 | 36 | 33 | 6 | 25 | 21 |
| 2552 | 2466 | 21468 | 75.2 | TGCGTTGATTGAGAGTACGGCGTT | 29 | 1 | 1 | 20 | 35 | 12 |
| 2553 | 2467 | 40569 | 79.8 | TGCGTTGAAAAGATCGTGCGCGTT | 29 | 1 | 6 | 24 | 29 | 12 |
| 2554 | 2469 | 8729 | 76.4 | TGCGTTGACGTTCTGTCCTATGCG | 29 | 1 | 12 | 14 | 26 | 29 |
| 2555 | 2470 | 40571 | 78.6 | TGCGTTGACCATTCGTATCGCGAA | 29 | 1 | 15 | 10 | 24 | 16 |
| 2556 | 2472 | 15879 | 79.5 | TGCGTTGACACGCGTTTTGACGAA | 29 | 1 | 30 | 12 | 1 | 16 |
| 2557 | 2473 | 15881 | 80.5 | TGCGTTGAGGACGATGTCCCCCAT | 29 | 1 | 34 | 27 | 28 | 15 |
| 2558 | 2474 | 8740 | 78.5 | TGCGTTGAAGCCAGTGCGAAGATG | 29 | 1 | 36 | 22 | 16 | 27 |
| 2559 | 2475 | 15882 | 80.1 | TGCGTGATTGTCCAGCCTTGGTGC | 29 | 2 | 9 | 31 | 11 | 33 |
| 2560 | 2476 | 15883 | 79.8 | TGCGTGATCTTGGGACTCCCCGTT | 29 | 2 | 11 | 34 | 28 | 12 |
| 2561 | 2478 | 30585 | 80.1 | TGCGTGATGCTTTCCCACCTGTGC | 29 | 2 | 17 | 28 | 23 | 33 |
| 2562 | 2480 | 8750 | 81.3 | TGCGTGATGAGTCAGCCAGCCACG | 29 | 2 | 20 | 31 | 31 | 30 |
| 2563 | 2481 | 40575 | 79.9 | TGCGTGATGCAACTGTCCATTGCG | 29 | 2 | 21 | 14 | 15 | 29 |
| 2564 | 2483 | 30586 | 79.5 | TGCGTGATTCCCACCTCTTGCAGC | 29 | 2 | 28 | 23 | 11 | 31 |
| 2565 | 2484 | 40576 | 80.6 | TGCGTGATGGACCCATATCGCACG | 29 | 2 | 34 | 15 | 24 | 30 |
| 2566 | 2485 | 40577 | 80.6 | TGCGTGATAGCCCAGCAATCGCAA | 29 | 2 | 36 | 31 | 4 | 21 |
| 2567 | 2486 | 21481 | 75 | TGCGTTAGTTGAGACCGCTTACGG | 29 | 3 | 1 | 32 | 17 | 35 |
| 2568 | 2487 | 8756 | 78.1 | TGCGTTAGAAAGGACCCACGCGTT | 29 | 3 | 6 | 32 | 30 | 12 |
| 2569 | 2488 | 8758 | 76.1 | TGCGTTAGCGAATGTCGGACTTGA | 29 | 3 | 16 | 9 | 34 | 1 |
| 2570 | 2489 | 40578 | 77.7 | TGCGTTAGGCTTTCCCAGTGGACC | 29 | 3 | 17 | 28 | 22 | 32 |
| 2571 | 2490 | 30588 | 78.5 | TGCGTTAGTGCGCGAAATACTGCG | 29 | 3 | 29 | 16 | 5 | 29 |
| 2572 | 2491 | 8765 | 75.9 | TGCGTTAGGTGCTTGAGCAACAGC | 29 | 3 | 33 | 1 | 21 | 31 |
| 2573 | 2492 | 30589 | 80 | TGCGTTAGACGGGATGTGCGGATG | 29 | 3 | 35 | 27 | 29 | 27 |
| 2574 | 2493 | 8768 | 78.9 | TGCGTTAGAGCCGCTTGATGAGCC | 29 | 3 | 36 | 17 | 27 | 36 |
| 2575 | 2494 | 30590 | 79.2 | TGCGAATCAAAGATCGTCCCCACG | 29 | 4 | 6 | 24 | 28 | 30 |
| 2576 | 2495 | 30591 | 79 | TGCGAATCTCGTTCGTCACGCTCA | 29 | 4 | 10 | 10 | 30 | 13 |
| 2577 | 2496 | 40581 | 78.7 | TGCGAATCCTCAGACCCGAACAGC | 29 | 4 | 13 | 32 | 16 | 31 |
| 2578 | 2498 | 30592 | 78.4 | TGCGAATCCCATTCCCGTCTCTTG | 29 | 4 | 15 | 28 | 19 | 11 |
| 2579 | 2499 | 40582 | 77.3 | TGCGAATCGAGTAGCCGTGCTGAT | 29 | 4 | 20 | 36 | 33 | 2 |
| 2580 | 2500 | 8780 | 78.7 | TGCGAATCAGTGCAGCTGCGAAAG | 29 | 4 | 22 | 31 | 29 | 6 |
| 2581 | 2501 | 8782 | 79.9 | TGCGAATCCACGCGAACTCAAGGA | 29 | 4 | 30 | 16 | 13 | 25 |
| 2582 | 2502 | 40583 | 75.9 | TGCGATACGGTATGATAGCCGCAA | 29 | 5 | 18 | 2 | 36 | 21 |
| 2583 | 2504 | 30593 | 78.1 | TGCGATACGCAACTGTGCAATCCC | 29 | 5 | 21 | 14 | 21 | 28 |
| 2584 | 2505 | 40584 | 78 | TGCGATACCCTAGCTTGTGCGCAA | 29 | 5 | 26 | 17 | 33 | 21 |
| 2585 | 2506 | 8794 | 76.6 | TGCGATACGATGGCTTTCCCAAAG | 29 | 5 | 27 | 17 | 28 | 6 |
| 2586 | 2508 | 30594 | 76.5 | TGCGAAAGAAAGTCCCGCTTTTGA | 29 | 6 | 6 | 28 | 17 | 1 |
| 2587 | 2509 | 40586 | 78.2 | TGCGAAAGTCGTCTTGTGCGAGGA | 29 | 6 | 10 | 11 | 29 | 25 |
| 2588 | 2510 | 15896 | 79 | TGCGAAAGCGTTGGACATCGGTCT | 29 | 6 | 12 | 34 | 24 | 19 |
| 2589 | 2511 | 40587 | 77.2 | TGCGAAAGGGTATCGTCACGGATG | 29 | 6 | 18 | 10 | 30 | 27 |
| 2590 | 2512 | 30595 | 77.8 | TGCGAAAGGAGTGATGCACGGGTA | 29 | 6 | 20 | 27 | 30 | 18 |
| 2591 | 2513 | 40588 | 75 | TGCGAAAGACCTTTAGACGGGCTT | 29 | 6 | 23 | 3 | 35 | 17 |
| 2592 | 2514 | 8806 | 78.3 | TGCGAAAGTCCCCGTTGAGTGCTT | 29 | 6 | 28 | 12 | 20 | 17 |
| 2593 | 2516 | 8809 | 77.4 | TGCGTACAAAAGTGCGCTTGGCTT | 29 | 7 | 6 | 29 | 11 | 17 |
| 2594 | 2518 | 8811 | 76 | TGCGTACAACCTACGGTCCCCTGT | 29 | 7 | 23 | 35 | 28 | 14 |
| 2595 | 2519 | 8816 | 79.5 | TGCGTACAGACCACGGACGGGGTA | 29 | 7 | 32 | 35 | 35 | 18 |
| 2596 | 2521 | 8819 | 78.3 | TGCGTCTGTTGATCCCGAGTCACG | 29 | 8 | 1 | 28 | 20 | 30 |
| 2597 | 2522 | 8820 | 80.7 | TGCGTCTGTGATGTGCACGGGCTT | 29 | 8 | 2 | 33 | 35 | 17 |
| 2598 | 2523 | 8824 | 78.9 | TGCGTCTGTGTCTGCGATCGTCGT | 29 | 8 | 9 | 29 | 24 | 10 |
| 2599 | 2524 | 40589 | 78.8 | TGCGTCTGTCGTCCTACACGGCAA | 29 | 8 | 10 | 26 | 30 | 21 |
| 2600 | 2525 | 40590 | 78.5 | TGCGTCTGCTTGAAAGGTGCATCG | 29 | 8 | 11 | 6 | 33 | 24 |
| 2601 | 2526 | 30597 | 80.1 | TGCGTCTGCTCAAGGATGCGAGGA | 29 | 8 | 13 | 25 | 29 | 25 |

FIG. 25ZZ

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2602 | 2527 | 8828 | 77.3 | TGCGTCTGGCTTCACGATACGCTT | 29 | 8 | 17 | 30 | 5 | 17 |
| 2603 | 2528 | 40591 | 78.4 | TGCGTCTGGTCTAGTGACGGTGCG | 29 | 8 | 19 | 22 | 35 | 29 |
| 2604 | 2529 | 8831 | 79.1 | TGCGTCTGGCAAATCGTTGACACG | 29 | 8 | 21 | 24 | 1 | 30 |
| 2605 | 2530 | 8832 | 81.1 | TGCGTCTGAGTGTCCCTGCGCTCA | 29 | 8 | 22 | 28 | 29 | 13 |
| 2606 | 2531 | 40594 | 78.3 | TGCGTCTGATCGAAAGCAGCCTCA | 29 | 8 | 24 | 6 | 31 | 13 |
| 2607 | 2532 | 40595 | 77.2 | TGCGTCTGCCTATTGACACGGCTT | 29 | 8 | 26 | 1 | 30 | 17 |
| 2608 | 2533 | 8837 | 76.1 | TGCGTCTGCAGCTTAGCGTTTCTG | 29 | 8 | 31 | 3 | 12 | 8 |
| 2609 | 2534 | 8841 | 82.8 | TGCGTGTCTGATTGCGTCCCCACG | 29 | 9 | 2 | 29 | 28 | 30 |
| 2610 | 2535 | 8843 | 81 | TGCGTGTCTCTGCACGGTGCTCGT | 29 | 9 | 8 | 30 | 33 | 10 |
| 2611 | 2536 | 8844 | 82.7 | TGCGTGTCTGTCGTGCGGACGCTT | 29 | 9 | 9 | 33 | 34 | 17 |
| 2612 | 2537 | 40596 | 77.6 | TGCGTGTCGCTTATACAGCCAGCC | 29 | 9 | 17 | 5 | 36 | 36 |
| 2613 | 2538 | 40597 | 79.3 | TGCGTGTCGAGTTCCCAGCCAATC | 29 | 9 | 20 | 28 | 36 | 4 |
| 2614 | 2539 | 8852 | 75.9 | TGCGTGTCACCTATCGATCGCCTA | 29 | 9 | 23 | 24 | 24 | 26 |
| 2615 | 2540 | 30599 | 76.8 | TGCGTGTCAGGAGGTATCCCGGTA | 29 | 9 | 25 | 18 | 28 | 18 |
| 2616 | 2541 | 8853 | 80 | TGCGTGTCGATGGACCCTGTGACC | 29 | 9 | 27 | 32 | 14 | 32 |
| 2617 | 2542 | 40599 | 80.6 | TGCGTGTCTCCCCGAATCGTCCAT | 29 | 9 | 28 | 16 | 10 | 15 |
| 2618 | 2543 | 8856 | 78.9 | TGCGTGTCGACCTCGTCGTTCTCA | 29 | 9 | 32 | 10 | 12 | 13 |
| 2619 | 2544 | 8862 | 77.3 | TGCGTCGTCTCAACCTTCGTGCTT | 29 | 10 | 13 | 23 | 10 | 17 |
| 2620 | 2545 | 15908 | 75.8 | TGCGTCGTCTGTTAGGTCTTGCG | 29 | 10 | 14 | 3 | 19 | 29 |
| 2621 | 2547 | 40601 | 78.4 | TGCGTCGTGTCTAGTGAGCCCACG | 29 | 10 | 19 | 22 | 36 | 30 |
| 2622 | 2548 | 30602 | 76.7 | TGCGTCGTCCTATGCGAGGAAATC | 29 | 10 | 26 | 29 | 25 | 4 |
| 2623 | 2549 | 8866 | 80.5 | TGCGTCGTGATGCGTTCTGTGCAA | 29 | 10 | 27 | 12 | 14 | 21 |
| 2624 | 2550 | 8867 | 78.4 | TGCGTCGTTCCCCTATTAGCACG | 29 | 10 | 28 | 26 | 3 | 30 |
| 2625 | 2551 | 8868 | 82 | TGCGTCGTTGCGGGACTCGTATCG | 29 | 10 | 29 | 34 | 10 | 24 |
| 2626 | 2552 | 8869 | 81.6 | TGCGTCGTCACGCACGCTGTTGAT | 29 | 10 | 30 | 30 | 14 | 2 |
| 2627 | 2553 | 8870 | 78.5 | TGCGTCGTCGACCCCTAGACCCTTG | 29 | 10 | 32 | 26 | 32 | 11 |
| 2628 | 2554 | 8872 | 79.6 | TGCGTCGTGGACTCGTCACGTTGA | 29 | 10 | 34 | 10 | 30 | 1 |
| 2629 | 2555 | 8873 | 75.2 | TGCGCTTGTTAGAGCCTTGAATCG | 29 | 11 | 3 | 36 | 1 | 24 |
| 2630 | 2557 | 8874 | 76.5 | TGCGCTTGTACAATACCAGCGTGC | 29 | 11 | 7 | 5 | 31 | 33 |
| 2631 | 2558 | 8875 | 78.2 | TGCGCTTGTCTGCGAACGTTAGGA | 29 | 11 | 8 | 16 | 12 | 25 |
| 2632 | 2559 | 8877 | 80.2 | TGCGCTTGCGTTTCGTTGATGACC | 29 | 11 | 12 | 10 | 2 | 32 |
| 2633 | 2560 | 8878 | 76.5 | TGCGCTTGCTCAATACCGAAACCT | 29 | 11 | 13 | 5 | 16 | 23 |
| 2634 | 2561 | 15909 | 78.5 | TGCGCTTGCTGTCGAACCATTCTG | 29 | 11 | 14 | 16 | 15 | 8 |
| 2635 | 2562 | 30604 | 76.1 | TGCGCTTGGAGTATCGAATCCCAT | 29 | 11 | 20 | 24 | 4 | 15 |
| 2636 | 2563 | 40604 | 77.1 | TGCGCTTGAGTGAATCCTTGCCAT | 29 | 11 | 22 | 4 | 11 | 15 |
| 2637 | 2564 | 8885 | 78.6 | TGCGCTTGATCGATCGAGTGCTTG | 29 | 11 | 24 | 24 | 22 | 11 |
| 2638 | 2565 | 8887 | 77.8 | TGCGCTTGGATGACGGGAGTTACA | 39 | 11 | 27 | 35 | 20 | 7 |
| 2639 | 2566 | 8888 | 82.4 | TGCGCTTGCAGCCACGGAGTCTTG | 29 | 11 | 31 | 30 | 20 | 11 |
| 2640 | 2567 | 40605 | 81.7 | TGCGCTTGGTGCACCTCGTTTCGT | 29 | 11 | 33 | 23 | 12 | 10 |
| 2641 | 2568 | 8890 | 81.3 | TGCGCTTGAGCCGACCACCTATCG | 29 | 11 | 36 | 32 | 23 | 24 |
| 2642 | 2569 | 21509 | 76.9 | TGCGCGTTAATCCCTACCATCGAA | 29 | 12 | 4 | 26 | 15 | 16 |
| 2643 | 2570 | 40607 | 75.8 | TGCGCGTTATACTCTGAGCCGATG | 29 | 12 | 5 | 8 | 36 | 27 |
| 2644 | 2571 | 30606 | 75.2 | TGCGCGTTAAAGAATCGCAAAAAG | 29 | 12 | 6 | 4 | 21 | 6 |
| 2645 | 2572 | 8893 | 80 | TGCGCGTTTCTGCTTGATCGTCGT | 29 | 12 | 8 | 11 | 24 | 10 |
| 2646 | 2573 | 8894 | 79.2 | TGCGCGTTTCGTCGAACGAAGTCT | 29 | 12 | 10 | 16 | 16 | 19 |
| 2647 | 2574 | 8895 | 79.1 | TGCGCGTTCGTTAGTGCTTGCTCA | 29 | 12 | 12 | 22 | 11 | 13 |
| 2648 | 2575 | 30607 | 77.8 | TGCGCGTTGGTACCATTTAGCGAA | 29 | 12 | 18 | 15 | 3 | 16 |
| 2649 | 2576 | 8899 | 77.5 | TGCGCGTTGTCTGGTAGACCCTTG | 29 | 12 | 19 | 18 | 32 | 11 |
| 2650 | 2577 | 21511 | 78.1 | TGCGCGTTATCGTGATTGAACGG | 29 | 12 | 24 | 1 | 1 | 35 |
| 2651 | 2579 | 8902 | 78.3 | TGCGCGTTGATGTCCCCTTGAAGTG | 29 | 12 | 27 | 28 | 1 | 22 |
| 2652 | 2580 | 8903 | 82.1 | TGCGCGTTTCCCGCTTACCTGGAC | 29 | 12 | 28 | 17 | 23 | 34 |

FIG. 25AAA

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2653 | 2581 | 8904 | 82.6 | TGCGCGTTCACGGAGTCACGCCTA | 29 | 12 | 30 | 20 | 30 | 26 |
| 2654 | 2582 | 40609 | 80 | TGCGCGTTCAGCTTAGAGCCTCCC | 29 | 12 | 31 | 3 | 36 | 28 |
| 2655 | 2583 | 8906 | 78.9 | TGCGCGTTGACCTCCCATACGAGT | 29 | 12 | 32 | 28 | 5 | 20 |
| 2656 | 2584 | 8908 | 80.9 | TGCGCGTTACGGGTAGATGGTGC | 29 | 12 | 35 | 18 | 27 | 33 |
| 2657 | 2585 | 40611 | 77.4 | TGCGCTCATGATAATCAGCCGGAC | 29 | 13 | 2 | 4 | 36 | 34 |
| 2658 | 2586 | 40612 | 80 | TGCGCTCATTAGCACGCACGGAGT | 29 | 13 | 3 | 30 | 30 | 20 |
| 2659 | 2588 | 40614 | 78.7 | TGCGCTCAAAAGCTCAATCGTCCC | 29 | 13 | 6 | 13 | 24 | 28 |
| 2660 | 2589 | 8910 | 75.7 | TGCGCTCATACATGCGGGTATGAT | 29 | 13 | 7 | 29 | 18 | 2 |
| 2661 | 2590 | 8911 | 77.9 | TGCGCTCATCTGATCGTGTCCGTT | 29 | 13 | 8 | 24 | 9 | 12 |
| 2662 | 2591 | 40615 | 78.1 | TGCGCTCACGTTATCGCTTGAGGA | 29 | 13 | 12 | 24 | 11 | 25 |
| 2663 | 2593 | 8915 | 78.4 | TGCGCTCACTGTTCCCGTCTGATG | 29 | 13 | 14 | 28 | 19 | 27 |
| 2664 | 2596 | 8918 | 79.3 | TGCGCTCAGCAAAGTGCTCAGCAA | 29 | 13 | 21 | 22 | 13 | 21 |
| 2665 | 2597 | 30610 | 76 | TGCGCTCACCTACGAAAAGGGAC | 29 | 13 | 26 | 16 | 6 | 34 |
| 2666 | 2598 | 8921 | 80.4 | TGCGCTCAGATGGTGCGAGTGGAC | 29 | 13 | 27 | 33 | 20 | 34 |
| 2667 | 2601 | 40617 | 77.5 | TGCGCTGTTGATAAAGTGCGGACC | 29 | 14 | 2 | 6 | 29 | 32 |
| 2668 | 2602 | 8925 | 78.6 | TGCGCTGTAATCGCTTGTCTTGCG | 29 | 14 | 4 | 17 | 19 | 29 |
| 2669 | 2603 | 8926 | 79.1 | TGCGCTGTATACGACCACGGTCCC | 29 | 14 | 5 | 32 | 35 | 28 |
| 2670 | 2604 | 8928 | 75.2 | TGCGCTGTTACACCTAACGGAGGA | 29 | 14 | 7 | 26 | 35 | 25 |
| 2671 | 2605 | 40618 | 78.5 | TGCGCTGTTCTGTGATAGCCGTGC | 29 | 14 | 8 | 2 | 36 | 33 |
| 2672 | 2606 | 8929 | 78.4 | TGCGCTGTTGTCAATCGCAAGACC | 29 | 14 | 9 | 4 | 21 | 32 |
| 2673 | 2607 | 8931 | 79.8 | TGCGCTGTCTTGGACCAGTGCCAT | 29 | 14 | 11 | 32 | 22 | 15 |
| 2674 | 2609 | 40619 | 78.1 | TGCGCTGTCTCACCATTCTGCGTT | 29 | 14 | 13 | 15 | 8 | 12 |
| 2675 | 2610 | 40620 | 78.6 | TGCGCTGTCTGTTCTGCGAAATCG | 29 | 14 | 14 | 8 | 16 | 24 |
| 2676 | 2611 | 30611 | 76.5 | TGCGCTGTCCATCCTAAAAGCGTT | 29 | 14 | 15 | 26 | 6 | 12 |
| 2677 | 2612 | 8933 | 77 | TGCGCTGTCGAAAATCCCATCCTA | 29 | 14 | 16 | 4 | 15 | 26 |
| 2678 | 2613 | 30612 | 78.6 | TGCGCTGTGGTAGAGTTCCCGGAC | 29 | 14 | 18 | 20 | 28 | 34 |
| 2679 | 2615 | 15915 | 79 | TGCGCTGTAGTGGGACCGTTGCTT | 29 | 14 | 22 | 34 | 12 | 17 |
| 2680 | 2616 | 30614 | 78.9 | TGCGCTGTCAGCTTAGCTCATGCG | 29 | 14 | 31 | 3 | 13 | 29 |
| 2681 | 2617 | 8938 | 80.6 | TGCGCTGTGACCGGACCCATACCT | 29 | 14 | 32 | 34 | 15 | 23 |
| 2682 | 2618 | 8940 | 81 | TGCGCTGTACGGGTGCTCTGCTCA | 29 | 14 | 35 | 33 | 8 | 13 |
| 2683 | 2619 | 8941 | 79.4 | TGCGCTGTAGCCGAGTCTTGCGTT | 29 | 14 | 36 | 20 | 11 | 12 |
| 2684 | 2620 | 40621 | 78.1 | TGCGCCATTTGAACCTATCGGCTT | 29 | 15 | 1 | 23 | 24 | 17 |
| 2685 | 2621 | 8943 | 76.5 | TGCGCCATTTAGGAGTCGTTGCTT | 29 | 15 | 3 | 20 | 12 | 17 |
| 2686 | 2622 | 40622 | 78.9 | TGCGCCATAATCTCTGTGCGCTCA | 29 | 15 | 4 | 8 | 29 | 13 |
| 2687 | 2625 | 8946 | 79.4 | TGCGCCATCGAAGTCTTTGAACGG | 29 | 15 | 16 | 19 | 1 | 35 |
| 2688 | 2626 | 8947 | 80.5 | TGCGCCATGTCTGATGGACCCTCA | 29 | 15 | 19 | 27 | 32 | 13 |
| 2689 | 2627 | 30616 | 80.9 | TGCGCCATATCGGTCTCAGCGCTT | 29 | 15 | 24 | 19 | 31 | 17 |
| 2690 | 2628 | 8951 | 80 | TGCGCCATTCCCTCGTTACATCCC | 29 | 15 | 28 | 10 | 7 | 28 |
| 2691 | 2629 | 8952 | 80.1 | TGCGCCATGACCTGATCTTGACGG | 29 | 15 | 32 | 2 | 11 | 35 |
| 2692 | 2630 | 8954 | 81.8 | TGCGCCATGGACCCATCGAAGATG | 29 | 15 | 34 | 15 | 16 | 27 |
| 2693 | 2631 | 8955 | 82.9 | TGCGCCATACGGCTGTCTCATGCG | 29 | 15 | 35 | 14 | 13 | 29 |
| 2694 | 2632 | 40624 | 79.3 | TGCGCGAATGATCGTTCTTGGGAC | 29 | 16 | 2 | 12 | 11 | 34 |
| 2695 | 2633 | 8956 | 77.8 | TGCGCGAAAATCAAAGCAGCTGTC | 29 | 16 | 4 | 6 | 31 | 9 |
| 2696 | 2634 | 21535 | 80.4 | TGCGCGAACTCAGACCAGGACACG | 29 | 16 | 13 | 32 | 25 | 30 |
| 2697 | 2635 | 8959 | 80.5 | TGCGCGAACCATCTGTTGTCCGAA | 29 | 16 | 15 | 14 | 9 | 16 |
| 2698 | 2636 | 8960 | 78.7 | TGCGCGAACGAAAGCCAAAGAATC | 29 | 16 | 16 | 36 | 6 | 4 |
| 2699 | 2637 | 8962 | 80.8 | TGCGCGAAGCAACTCACCATCGAA | 29 | 16 | 21 | 13 | 15 | 16 |
| 2700 | 2638 | 8963 | 80.2 | TGCGCGAAATCGTGATCCATCAGC | 29 | 16 | 24 | 2 | 15 | 31 |
| 2701 | 2639 | 30619 | 80.8 | TGCGCGAAAGGAGATGGTGCCCTA | 29 | 16 | 25 | 27 | 33 | 26 |
| 2702 | 2640 | 15917 | 82.1 | TGCGCGAATCCCCTACAGCCTTG | 29 | 16 | 28 | 26 | 31 | 11 |
| 2703 | 2644 | 40625 | 76.1 | TGCGGCTTATACAATCGCTTGCAA | 29 | 17 | 5 | 4 | 17 | 21 |

FIG. 25BBB

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2704 | 2645 | 30620 | 81.6 | TGCGGCTTTCTGCAGCTCGTGACC | 29 | 17 | 8 | 31 | 10 | 32 |
| 2705 | 2646 | 8975 | 80.4 | TGCGGCTTCTTGCTGTGACCGATG | 29 | 17 | 11 | 14 | 32 | 27 |
| 2706 | 2647 | 8976 | 78.3 | TGCGGCTTCTCAAGTGAGTGCGAA | 29 | 17 | 13 | 22 | 22 | 16 |
| 2707 | 2648 | 8978 | 79.4 | TGCGGCTTCGAATTGATCTGACGG | 29 | 17 | 16 | 1 | 8 | 35 |
| 2708 | 2649 | 8980 | 78.9 | TGCGGCTTGCAATCTGAAAGAGCC | 29 | 17 | 21 | 8 | 6 | 36 |
| 2709 | 2650 | 8984 | 80.3 | TGCGGCTTTCCCCAGCCCTAGAGT | 29 | 17 | 28 | 31 | 26 | 20 |
| 2710 | 2651 | 30622 | 83.5 | TGCGGCTTCACGGGACCGAACTCA | 29 | 17 | 30 | 34 | 16 | 13 |
| 2711 | 2652 | 8988 | 79.6 | TGCGGCTTAGCCGACCCGAATTAG | 29 | 17 | 36 | 32 | 16 | 3 |
| 2712 | 2653 | 30623 | 76.6 | TGCGGGTAAAAGAGGAGGACCGTT | 29 | 18 | 6 | 25 | 34 | 12 |
| 2713 | 2654 | 8990 | 75.1 | TGCGGGTATACACCATACGGATCG | 29 | 18 | 7 | 15 | 35 | 24 |
| 2714 | 2656 | 30624 | 80 | TGCGGGTATGTCCACGAAAGCACG | 29 | 18 | 9 | 30 | 6 | 30 |
| 2715 | 2657 | 30625 | 78.2 | TGCGGGTACGTTCAGCCTTGGTCT | 29 | 18 | 12 | 31 | 11 | 19 |
| 2716 | 2658 | 21547 | 77.1 | TGCGGGTACTCAGCAACGTTTCGT | 29 | 18 | 13 | 21 | 12 | 10 |
| 2717 | 2659 | 8994 | 77.3 | TGCGGGTACTGTGCAACTTGTCCC | 29 | 18 | 14 | 21 | 11 | 28 |
| 2718 | 2660 | 30626 | 75.9 | TGCGGGTAGCTTAGCCGAGTAGGA | 29 | 18 | 17 | 36 | 20 | 25 |
| 2719 | 2661 | 8998 | 76.3 | TGCGGGTAGAGTGGACCTTGCCTA | 29 | 18 | 20 | 34 | 11 | 26 |
| 2720 | 2662 | 9003 | 76 | TGCGGGTACCTAGACCCAGCTCTG | 29 | 18 | 26 | 32 | 31 | 8 |
| 2721 | 2664 | 9005 | 78.9 | TGCGGGTACACGTGTCACGGAGTG | 29 | 18 | 30 | 9 | 35 | 22 |
| 2722 | 2665 | 9008 | 77.3 | TGCGGGTAGTGCTGTCTGTCGCTT | 29 | 18 | 33 | 9 | 9 | 17 |
| 2723 | 2666 | 9009 | 77.8 | TGCGGGTAGGACCCTAGAGTTGCG | 29 | 18 | 34 | 26 | 20 | 29 |
| 2724 | 2667 | 9010 | 82 | TGCGGGTAAGCCGTCTGCAACACG | 29 | 18 | 36 | 19 | 21 | 30 |
| 2725 | 2668 | 30627 | 77.4 | TGCGGTCTTGATCGAATCGTACGG | 29 | 19 | 2 | 16 | 10 | 35 |
| 2726 | 2669 | 21553 | 77.8 | TGCGGTCTTTAGCTGTTCGTTGCG | 29 | 19 | 3 | 14 | 10 | 29 |
| 2727 | 2670 | 40630 | 78.4 | TGCGGTCTAAAGGATGCAGCGCTT | 29 | 19 | 6 | 27 | 31 | 17 |
| 2728 | 2671 | 40631 | 76.9 | TGCGGTCTTCTGTCCCTTAGTGCG | 29 | 19 | 8 | 28 | 3 | 29 |
| 2729 | 2672 | 9014 | 76.8 | TGCGGTCTTGTCCAGCCGTTAAAG | 29 | 19 | 9 | 31 | 12 | 6 |
| 2730 | 2673 | 40632 | 79.5 | TGCGGTCTCTTGGGTATCCCCAGC | 29 | 19 | 11 | 18 | 28 | 31 |
| 2731 | 2674 | 9017 | 77.5 | TGCGGTCTCTGTTTGAATCGACGG | 29 | 19 | 14 | 1 | 24 | 35 |
| 2732 | 2675 | 40634 | 78.4 | TGCGGTCTCGAAAGGAGCAAAGGA | 29 | 19 | 16 | 25 | 21 | 25 |
| 2733 | 2676 | 21556 | 81.3 | TGCGGTCTGGTATCCCGACCCCAT | 29 | 19 | 18 | 28 | 32 | 15 |
| 2734 | 2677 | 40635 | 77.5 | TGCGGTCTGAGTAGTGTGCGTCCC | 29 | 19 | 20 | 22 | 29 | 28 |
| 2735 | 2678 | 30629 | 77.2 | TGCGGTCTACCTGCAAAAGGCAA | 29 | 19 | 23 | 21 | 6 | 21 |
| 2736 | 2679 | 30630 | 78.8 | TGCGGTCTATCGGACCGATGCCTA | 29 | 19 | 24 | 32 | 27 | 26 |
| 2737 | 2680 | 30631 | 77.3 | TGCGGTCTAGGAAAAGGACCCGAA | 29 | 19 | 25 | 6 | 32 | 16 |
| 2738 | 2681 | 30632 | 78.5 | TGCGGTCTGATGAAAGCTTGTGCG | 29 | 19 | 27 | 6 | 11 | 29 |
| 2739 | 2682 | 9025 | 79.2 | TGCGGTCTCAGCCGAACTTGAGGA | 29 | 19 | 31 | 16 | 11 | 25 |
| 2740 | 2683 | 30633 | 75.1 | TGCGGAGTTGATAGCCTTAGCACG | 29 | 20 | 2 | 36 | 3 | 30 |
| 2741 | 2684 | 21559 | 77.3 | TGCGGAGTATACGTGCGGTAACGG | 29 | 20 | 5 | 33 | 18 | 35 |
| 2742 | 2685 | 21560 | 76.4 | TGCGGAGTTCTGATACGCAACACG | 29 | 20 | 8 | 5 | 21 | 30 |
| 2743 | 2686 | 40636 | 78.1 | TGCGGAGTTCGTTCTGGACCCCTA | 29 | 20 | 10 | 8 | 32 | 26 |
| 2744 | 2688 | 9036 | 77.8 | TGCGGAGTGCAAGACCCGAATACA | 29 | 20 | 21 | 32 | 16 | 7 |
| 2745 | 2689 | 9039 | 78.9 | TGCGGAGTTCCCTGTCGATGTCGT | 29 | 20 | 28 | 9 | 27 | 10 |
| 2746 | 2692 | 9041 | 81.3 | TGCGGAGTGTGCGTGCACCTTCTG | 29 | 20 | 33 | 33 | 23 | 8 |
| 2747 | 2693 | 40638 | 80.3 | TGCGGAGTGGACCGTTGAGTTCCC | 29 | 20 | 34 | 12 | 20 | 28 |
| 2748 | 2694 | 9042 | 77.8 | TGCGGCAATTGAGATGCGTTTGAT | 29 | 21 | 1 | 27 | 12 | 2 |
| 2749 | 2695 | 15926 | 76.5 | TGCGGCAATTAGCGTTACCTGCTT | 29 | 21 | 3 | 12 | 23 | 17 |
| 2750 | 2696 | 30635 | 77.3 | TGCGGCAAAATCTTAGCAGCGGTA | 29 | 21 | 4 | 3 | 31 | 18 |
| 2751 | 2697 | 30636 | 77.8 | TGCGGCAAAAGTTAGGGACCAGC | 29 | 21 | 6 | 3 | 34 | 31 |
| 2752 | 2698 | 9045 | 77.4 | TGCGGCAATCTGATACCTTGACGG | 29 | 21 | 8 | 5 | 11 | 35 |
| 2753 | 2699 | 9046 | 79.3 | TGCGGCAACGAATGATTCCCTCTG | 29 | 21 | 16 | 2 | 28 | 8 |
| 2754 | 2700 | 9047 | 76 | TGCGGCAAGCTTAAAGGAGTGCTT | 29 | 21 | 17 | 6 | 20 | 17 |

FIG. 25CCC

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2755 | 2701 | 21570 | 82.7 | TGCGGCAAGTCTGACCCACGCTCA | 29 | 21 | 19 | 32 | 30 | 13 |
| 2756 | 2702 | 9048 | 76.4 | TGCGGCAAGAGTATCGATCGGTCT | 29 | 21 | 20 | 24 | 24 | 19 |
| 2757 | 2703 | 40641 | 78.6 | TGCGGCAAGATGAGGAAAAGGTGC | 29 | 21 | 27 | 25 | 6 | 33 |
| 2758 | 2704 | 9049 | 80.5 | TGCGGCAATCCCGCTTATACCGAA | 29 | 21 | 28 | 17 | 5 | 16 |
| 2759 | 2705 | 9050 | 79.1 | TGCGGCAACAGCAAAGACCTCGTT | 29 | 21 | 31 | 6 | 23 | 12 |
| 2760 | 2706 | 9051 | 79.5 | TGCGGCAAGACCCCTAACCTGGAC | 29 | 21 | 32 | 26 | 23 | 34 |
| 2761 | 2707 | 15927 | 79.9 | TGCGGCAAGTGCAAAGCGAAGGTA | 29 | 21 | 33 | 6 | 16 | 18 |
| 2762 | 2709 | 9056 | 82.9 | TGCGAGTGTCTGAGCCCAGCGCAA | 29 | 22 | 8 | 36 | 31 | 21 |
| 2763 | 2710 | 40642 | 78.8 | TGCGAGTGTCGTTGCGAGGATTGA | 29 | 22 | 10 | 29 | 25 | 1 |
| 2764 | 2711 | 9058 | 78.6 | TGCGAGTGCTTGCAGCATACAGCC | 29 | 22 | 11 | 31 | 5 | 36 |
| 2765 | 2712 | 15928 | 76.7 | TGCGAGTGGCTTCCATTGATAGCC | 29 | 22 | 17 | 15 | 2 | 36 |
| 2766 | 2713 | 30637 | 77.9 | TGCGAGTGGGTACTTGTCCCCGTT | 29 | 22 | 18 | 11 | 28 | 12 |
| 2767 | 2714 | 40643 | 81.7 | TGCGAGTGACCTCGAATCCCGCAA | 29 | 22 | 23 | 16 | 28 | 21 |
| 2768 | 2715 | 9063 | 77.1 | TGCGAGTGAGGAGATGCGTTCCAT | 29 | 22 | 25 | 27 | 12 | 15 |
| 2769 | 2716 | 9066 | 81.3 | TGCGAGTGTGCGGTGCCTTGAGTG | 29 | 22 | 29 | 33 | 11 | 22 |
| 2770 | 2717 | 9067 | 79.5 | TGCGAGTGCAGCACCTAGTGTGCG | 29 | 22 | 31 | 23 | 22 | 29 |
| 2771 | 2718 | 30638 | 78.5 | TGCGACCTTGATCAGCGTGCAAAG | 29 | 23 | 2 | 31 | 33 | 6 |
| 2772 | 2719 | 30639 | 79.1 | TGCGACCTAAAGGTGCTGCGTCGT | 29 | 23 | 6 | 33 | 29 | 10 |
| 2773 | 2720 | 9069 | 76.6 | TGCGACCTTACAGGACAGGAACGG | 29 | 23 | 7 | 34 | 25 | 35 |
| 2774 | 2722 | 40645 | 80.4 | TGCGACCTTCGTGTCTGACCTGCG | 29 | 23 | 10 | 19 | 32 | 29 |
| 2775 | 2723 | 40646 | 80 | TGCGACCTCTTGCGTTTCCCCTGT | 29 | 23 | 11 | 12 | 28 | 14 |
| 2776 | 2724 | 9071 | 75.9 | TGCGACCTCTCATTAGGACCAGCC | 29 | 23 | 13 | 3 | 32 | 36 |
| 2777 | 2725 | 21582 | 80.3 | TGCGACCTCTGTCAGCCCATGTGC | 29 | 23 | 14 | 31 | 15 | 33 |
| 2778 | 2726 | 9072 | 77 | TGCGACCTCCATGCAACTTGGTCT | 29 | 23 | 15 | 21 | 11 | 19 |
| 2779 | 2727 | 30640 | 76.8 | TGCGACCTCGAAGCTTAAAGCGAA | 29 | 23 | 16 | 17 | 6 | 16 |
| 2780 | 2728 | 9074 | 75.9 | TGCGACCTGGTAAAAGCTTGTCCC | 29 | 23 | 18 | 6 | 11 | 28 |
| 2781 | 2729 | 9077 | 76.4 | TGCGACCTAGTGACCTTGCGACCT | 29 | 23 | 22 | 23 | 29 | 23 |
| 2782 | 2730 | 9078 | 75.4 | TGCGACCTACCTCCTAACGGGGTA | 29 | 23 | 23 | 26 | 35 | 18 |
| 2783 | 2731 | 9079 | 78.3 | TGCGACCTATCGCAGCATACACGG | 29 | 23 | 24 | 31 | 5 | 35 |
| 2784 | 2732 | 9081 | 80.2 | TGCGACCTTCCCCGAACACGAATC | 29 | 23 | 28 | 16 | 30 | 4 |
| 2785 | 2733 | 9082 | 82.5 | TGCGACCTTGCGGTGCAGGATTGA | 29 | 23 | 29 | 33 | 25 | 1 |
| 2786 | 2734 | 30642 | 80.1 | TGCGACCTCACGTTGACACGGACC | 29 | 23 | 30 | 1 | 30 | 32 |
| 2787 | 2735 | 9085 | 78.9 | TGCGACCTGGACCGTTCGAACCTA | 29 | 23 | 34 | 12 | 16 | 26 |
| 2788 | 2736 | 30643 | 76.7 | TGCGATCGTTGATCCCCAGCTTAG | 29 | 24 | 1 | 28 | 31 | 3 |
| 2789 | 2737 | 9087 | 75.6 | TGCGATCGTGATAATCGATGCCAT | 29 | 24 | 2 | 4 | 27 | 15 |
| 2790 | 2738 | 9091 | 80.8 | TGCGATCGTGTCGCTTCACGAGGA | 29 | 24 | 9 | 17 | 30 | 25 |
| 2791 | 2739 | 21588 | 79.2 | TGCGATCGCTTGTCGTGGACAGTG | 29 | 24 | 11 | 10 | 34 | 22 |
| 2792 | 2740 | 9094 | 80.5 | TGCGATCGCCATGGTACACGCTGT | 29 | 24 | 15 | 18 | 30 | 14 |
| 2793 | 2742 | 9097 | 77 | TGCGATCGGGTAAATCCTTGCTCA | 29 | 24 | 18 | 4 | 11 | 13 |
| 2794 | 2743 | 9099 | 79.5 | TGCGATCGAGTGGCAACCATCCAT | 29 | 24 | 22 | 21 | 15 | 15 |
| 2795 | 2744 | 40650 | 80.1 | TGCGATCGATCGTGTCCTTGGTGC | 29 | 24 | 24 | 9 | 11 | 33 |
| 2796 | 2745 | 9100 | 76.2 | TGCGATCGCCTACCTACGAACCAT | 29 | 24 | 26 | 26 | 16 | 15 |
| 2797 | 2746 | 9101 | 81 | TGCGATCGTCCCGTCTCCATACGG | 29 | 24 | 28 | 19 | 15 | 35 |
| 2798 | 2747 | 9103 | 80.5 | TGCGATCGCAGCAAAGTGTCAGCC | 29 | 24 | 31 | 6 | 9 | 36 |
| 2799 | 2749 | 9105 | 80.2 | TGCGATCGACGGACCTGCAAAGTG | 29 | 24 | 35 | 23 | 21 | 22 |
| 2800 | 2750 | 9106 | 79.1 | TGCGATCGAGCCATACAGCCGTCT | 29 | 24 | 36 | 5 | 36 | 19 |
| 2801 | 2751 | 9107 | 78.9 | TGCGAGGATTAGCACGATCGCCAT | 29 | 25 | 3 | 30 | 24 | 15 |
| 2802 | 2752 | 15931 | 77.6 | TGCGAGGATGTCTCCCTCCCAATC | 29 | 25 | 9 | 28 | 28 | 4 |
| 2803 | 2753 | 9111 | 79.2 | TGCGAGGACTTGCACGTACATGCG | 29 | 25 | 11 | 30 | 7 | 29 |
| 2804 | 2754 | 40652 | 79.3 | TGCGAGGACTGTAGCCCCATCACG | 29 | 25 | 14 | 36 | 15 | 30 |
| 2805 | 2756 | 15933 | 77.5 | TGCGAGGAGCAAAAAGGACCACCT | 29 | 25 | 21 | 6 | 32 | 23 |

FIG. 25DDD

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2806 | 2757 | 40654 | 79.4 | TGCGAGGAAGTGAGTGGGACCACG | 29 | 25 | 22 | 22 | 34 | 30 |
| 2807 | 2758 | 9119 | 76.5 | TGCGAGGAAGGATGCGTTAGAGGA | 29 | 25 | 25 | 29 | 3 | 25 |
| 2808 | 2759 | 9122 | 80.1 | TGCGAGGACAGCCGTTCAGCTTGA | 29 | 25 | 31 | 12 | 31 | 1 |
| 2809 | 2760 | 9125 | 81.4 | TGCGAGGAACGGGAGTCACGCTTG | 29 | 25 | 35 | 20 | 30 | 11 |
| 2810 | 2761 | 40656 | 77.2 | TGCGCCTATTGACGAATGTCGCTT | 29 | 26 | 1 | 16 | 9 | 17 |
| 2811 | 2764 | 30646 | 78.5 | TGCGCCTATACAAGCCGGACCTTG | 29 | 26 | 7 | 36 | 34 | 11 |
| 2812 | 2765 | 15936 | 76.7 | TGCGCCTATGTCAGGAAGCCAATC | 29 | 26 | 9 | 25 | 36 | 4 |
| 2813 | 2766 | 9133 | 75.7 | TGCGCCTACTTGTGCGTTGAAATC | 29 | 26 | 11 | 29 | 1 | 4 |
| 2814 | 2767 | 9136 | 76.4 | TGCGCCTACGAAATACCAGCACCT | 29 | 26 | 16 | 5 | 31 | 23 |
| 2815 | 2768 | 40661 | 75.3 | TGCGCCTAGGTAAATCCGTTAGCC | 29 | 26 | 18 | 4 | 12 | 36 |
| 2816 | 2769 | 9137 | 76.4 | TGCGCCTAGTCTCACGCAGCTACA | 29 | 26 | 19 | 30 | 31 | 7 |
| 2817 | 2771 | 9141 | 80.7 | TGCGCCTATCCCGCAATGTCGAGT | 29 | 26 | 28 | 21 | 9 | 20 |
| 2818 | 2772 | 9142 | 79.2 | TGCGCCTATGCGAGTGCCTAAGGA | 29 | 26 | 29 | 22 | 26 | 25 |
| 2819 | 2773 | 9143 | 79.3 | TGCGCCTACACGGATGAAAGACGG | 29 | 26 | 30 | 27 | 6 | 35 |
| 2820 | 2774 | 15937 | 78 | TGCGCCTAGGACACCTTGCGTACA | 29 | 26 | 34 | 23 | 29 | 7 |
| 2821 | 2775 | 9146 | 80.4 | TGCGCCTAACGGCCTAACCTGTGC | 29 | 26 | 35 | 26 | 23 | 33 |
| 2822 | 2776 | 9147 | 79.4 | TGCGCCTAAGCCCTCAAGGAAGGA | 29 | 26 | 36 | 13 | 25 | 25 |
| 2823 | 2777 | 40663 | 78.4 | TGCGGATGTTGAGTGCGCTTTGTC | 29 | 27 | 1 | 33 | 17 | 9 |
| 2824 | 2778 | 30647 | 77.8 | TGCGGATGTGATGCTTCCATGCTT | 29 | 27 | 2 | 17 | 15 | 17 |
| 2825 | 2779 | 40666 | 77.8 | TGCGGATGTGTCCGTTAAAGCGAA | 29 | 27 | 9 | 12 | 6 | 16 |
| 2826 | 2780 | 9150 | 81.3 | TGCGGATGCGTTGATGCAGCTCTG | 29 | 27 | 12 | 27 | 31 | 8 |
| 2827 | 2781 | 9151 | 76.6 | TGCGGATGCTCAATACGTCTTCCC | 29 | 27 | 13 | 5 | 19 | 28 |
| 2828 | 2782 | 9152 | 79.5 | TGCGGATGCTGTGATGGCAACTCA | 29 | 27 | 14 | 27 | 21 | 13 |
| 2829 | 2783 | 30648 | 82 | TGCGGATGGCAAAGTGAGGATGCG | 29 | 27 | 21 | 22 | 25 | 29 |
| 2830 | 2785 | 40667 | 79.2 | TGCGGATGCCTATCGTCGTTGGAC | 29 | 27 | 26 | 10 | 12 | 34 |
| 2831 | 2786 | 9158 | 83.7 | TGCGGATGCACGCGTTGGACAGTG | 29 | 27 | 30 | 12 | 34 | 22 |
| 2832 | 2787 | 9160 | 80.7 | TGCGGATGGTGCCGAACTTGACCT | 29 | 27 | 33 | 16 | 11 | 23 |
| 2833 | 2788 | 40668 | 80.6 | TGCGGATGGGACTTGACAGCCCAT | 29 | 27 | 34 | 1 | 31 | 15 |
| 2834 | 2789 | 15940 | 79.7 | TGCGGATGACGGTGTCAATCGCTT | 29 | 27 | 35 | 9 | 4 | 17 |
| 2835 | 2790 | 9165 | 77.6 | TGCGTCCCAATCTCTGACCTTCCC | 29 | 28 | 4 | 8 | 23 | 28 |
| 2836 | 2792 | 9167 | 79 | TGCGTCCCAAAGCTTGGCAACTGT | 29 | 28 | 6 | 11 | 21 | 14 |
| 2837 | 2794 | 9169 | 76.4 | TGCGTCCCTCGTAAAGGTCTCGAA | 29 | 28 | 10 | 6 | 19 | 16 |
| 2838 | 2795 | 9170 | 80.4 | TGCGTCCCCTTGCTTGAATCAGCC | 29 | 28 | 11 | 11 | 4 | 36 |
| 2839 | 2796 | 30650 | 82.8 | TGCGTCCCCGTTGATGGCTTGGAC | 29 | 28 | 12 | 27 | 17 | 34 |
| 2840 | 2797 | 9171 | 78.1 | TGCGTCCCCATAATCAATCCAGC | 29 | 28 | 15 | 4 | 4 | 31 |
| 2841 | 2798 | 9172 | 80.2 | TGCGTCCCGAACCATACCTCAGC | 29 | 28 | 16 | 15 | 23 | 31 |
| 2842 | 2799 | 21616 | 77.6 | TGCGTCCCGGTAATACAGGAAGCC | 29 | 28 | 18 | 5 | 25 | 36 |
| 2843 | 2800 | 9173 | 79.2 | TGCGTCCCGTCTGAGTTGTCGCTT | 29 | 28 | 19 | 20 | 9 | 17 |
| 2844 | 2801 | 40670 | 78.9 | TGCGTCCCACCTATCGCTGTCGTT | 29 | 28 | 23 | 24 | 14 | 12 |
| 2845 | 2803 | 40671 | 82.2 | TGCGTCCCTCCCTCCCAGTGATCG | 29 | 28 | 28 | 28 | 22 | 24 |
| 2846 | 2804 | 9178 | 83 | TGCGTCCCGGACCTCAAGTGACGG | 29 | 28 | 34 | 13 | 22 | 35 |
| 2847 | 2805 | 9179 | 79.7 | TGCGTCCCACGGAGGAAATCCCTA | 29 | 28 | 35 | 25 | 4 | 26 |
| 2848 | 2806 | 9181 | 76.4 | TGCGTGCGATACCTTGCCTAACCT | 29 | 29 | 5 | 11 | 26 | 23 |
| 2849 | 2807 | 40672 | 80.2 | TGCGTGCGTCTGATACGGACGGAC | 29 | 29 | 8 | 5 | 34 | 34 |
| 2850 | 2808 | 9183 | 80.8 | TGCGTGCGTGTCCTCACAGCCCTA | 29 | 29 | 9 | 13 | 31 | 26 |
| 2851 | 2809 | 9184 | 81.9 | TGCGTGCGTCGTCAGCTGTCAGGA | 29 | 29 | 10 | 31 | 9 | 25 |
| 2852 | 2810 | 30651 | 81.7 | TGCGTGCGGCTTAGTGGCAAAGGA | 29 | 29 | 17 | 22 | 21 | 25 |
| 2853 | 2811 | 9186 | 79.4 | TGCGTGCGGAGTCCTACGTTGGAC | 29 | 29 | 20 | 26 | 12 | 34 |
| 2854 | 2812 | 9187 | 82.5 | TGCGTGCGATCGCGTTTGTCCTGT | 29 | 29 | 24 | 12 | 9 | 14 |
| 2855 | 2813 | 9188 | 79.9 | TGCGTGCGCCTACCATCTTGCTGT | 29 | 29 | 26 | 15 | 11 | 14 |
| 2856 | 2814 | 9189 | 83.6 | TGCGTGCGTCCCGCTTTGTCTCGT | 29 | 29 | 28 | 17 | 9 | 10 |

FIG. 25EEE

| SEQ ID NO: | 4,633 ID# | HEX ID# | Tm | ZIPCODE (5'-3') | TETRAMER NUMBERS | | | | |
|---|---|---|---|---|---|---|---|---|---|
| 2857 | 2815 | 21629 | 78.8 | TGCGCACGTTGAAAAGAGGAAGCC | 29 | 30 | 1 | 6 | 25 | 36 |
| 2858 | 2816 | 9191 | 77.9 | TGCGCACGTTAGCGTTACGGTGAT | 29 | 30 | 3 | 12 | 35 | 2 |
| 2859 | 2817 | 40673 | 78.5 | TGCGCACGAAAGACCTAGCCGTCT | 29 | 30 | 6 | 23 | 36 | 19 |
| 2860 | 2818 | 9193 | 80.9 | TGCGCACGTCGTCACGGACCATAC | 29 | 30 | 10 | 30 | 32 | 5 |
| 2861 | 2819 | 40674 | 83.5 | TGCGCACGCTGTCCATCACGAGGA | 29 | 30 | 14 | 15 | 30 | 25 |
| 2862 | 2820 | 9198 | 78.4 | TGCGCACGGTCTAATCGTGCTGTC | 29 | 30 | 19 | 4 | 33 | 9 |
| 2863 | 2822 | 21632 | 76.2 | TGCGCACGCCTATTAGGAGTAGCC | 29 | 30 | 26 | 3 | 20 | 36 |
| 2864 | 2823 | 9201 | 83 | TGCGCACGGATGCTGTTCTGGTGC | 29 | 30 | 27 | 14 | 8 | 33 |
| 2865 | 2824 | 9202 | 82.8 | TGCGCACGTCCCACCTTCGTGATG | 29 | 30 | 28 | 23 | 10 | 27 |
| 2866 | 2825 | 9203 | 83.4 | TGCGCACGGACCAGTGTCGTCGAA | 29 | 30 | 32 | 22 | 10 | 16 |
| 2867 | 2826 | 9204 | 81.2 | TGCGCACGGGACTCGTGGTAGGAC | 29 | 30 | 34 | 10 | 18 | 34 |
| 2868 | 2827 | 9205 | 83.1 | TGCGCACGAGCCGTCTAGGAACGG | 29 | 30 | 36 | 19 | 25 | 35 |
| 2869 | 2828 | 40675 | 79.6 | TGCGCAGCTTGACAGCAGGAGCTT | 29 | 31 | 1 | 31 | 25 | 17 |
| 2870 | 2829 | 40676 | 76.9 | TGCGCAGCTGATTTAGCGAAGCTT | 29 | 31 | 2 | 3 | 16 | 17 |
| 2871 | 2830 | 40677 | 77.5 | TGCGCAGCTTAGGCTTAATCGCAA | 29 | 31 | 3 | 17 | 4 | 21 |
| 2872 | 2831 | 30652 | 79.2 | TGCGCAGCATACTCTGCAGCCTCA | 29 | 31 | 5 | 8 | 31 | 13 |
| 2873 | 2832 | 9210 | 80.3 | TGCGCAGCTCGTGTCTCAGCCCTA | 29 | 31 | 10 | 19 | 31 | 26 |
| 2874 | 2833 | 9211 | 78.6 | TGCGCAGCCCATTTAGGCTTATCG | 29 | 31 | 15 | 3 | 17 | 24 |
| 2875 | 2834 | 9212 | 80.4 | TGCGCAGCGGTACTCAACGGAGTG | 29 | 31 | 18 | 13 | 35 | 22 |
| 2876 | 2835 | 30653 | 81.1 | TGCGCAGCGAGTGCAAATACACGG | 29 | 31 | 20 | 21 | 5 | 35 |
| 2877 | 2836 | 9214 | 78.4 | TGCGCAGCATCGTTAGGGTATCCC | 29 | 31 | 24 | 3 | 18 | 28 |
| 2878 | 2837 | 9215 | 78.8 | TGCGCAGCCCTAGATGTCGTAGCC | 29 | 31 | 26 | 27 | 10 | 36 |
| 2879 | 2838 | 9216 | 80.7 | TGCGCAGCGATGATACCACGAGGA | 29 | 31 | 27 | 5 | 30 | 25 |
| 2880 | 2839 | 9217 | 83.8 | TGCGCAGCCAGCCAGCCCTACTCA | 29 | 31 | 31 | 31 | 26 | 13 |
| 2881 | 2840 | 15942 | 81.8 | TGCGCAGCGACCAAAGAAAGGCAA | 29 | 31 | 32 | 6 | 6 | 21 |
| 2882 | 2841 | 9219 | 82.1 | TGCGCAGCAGCCTCGTTCTGTCGT | 29 | 31 | 36 | 10 | 8 | 10 |
| 2883 | 2842 | 15943 | 77.7 | TGCGGACCTGATCGAATGTCGGTA | 29 | 32 | 2 | 16 | 9 | 18 |
| 2884 | 2844 | 9223 | 79.2 | TGCGGACCAATCAGGAGACCGATG | 29 | 32 | 4 | 25 | 32 | 27 |
| 2885 | 2845 | 9224 | 76.9 | TGCGGACCATACAATCTGCGGTCT | 29 | 32 | 5 | 4 | 29 | 19 |
| 2886 | 2846 | 21640 | 78.4 | TGCGGACCTACACTGTTCCCGGAC | 29 | 32 | 7 | 14 | 28 | 34 |
| 2887 | 2847 | 40680 | 78.3 | TGCGGACCTGTCTGATACGGGACC | 29 | 32 | 9 | 2 | 35 | 32 |
| 2888 | 2848 | 9226 | 80.1 | TGCGGACCCGTTGCAATTAGGGAC | 29 | 32 | 12 | 21 | 3 | 34 |
| 2889 | 2849 | 9229 | 79.9 | TGCGGACCCCATCTGTTCTGGCTT | 29 | 32 | 15 | 14 | 8 | 17 |
| 2890 | 2850 | 9230 | 81 | TGCGGACCCGAACTTGATCGGATG | 29 | 32 | 16 | 11 | 24 | 27 |
| 2891 | 2851 | 9231 | 80.2 | TGCGGACCGAGTCCATGTGCTGTC | 29 | 32 | 20 | 15 | 33 | 9 |
| 2892 | 2852 | 9232 | 77.4 | TGCGGACCAGGAAAAGGTCTTCGT | 29 | 32 | 25 | 6 | 19 | 10 |
| 2893 | 2853 | 9234 | 80.9 | TGCGGACCGATGTGTCAGTGACGG | 29 | 32 | 27 | 9 | 22 | 35 |
| 2894 | 2854 | 9235 | 81.1 | TGCGGACCCAGCTCGTCTTGCTGT | 29 | 32 | 31 | 10 | 11 | 14 |
| 2895 | 2855 | 9236 | 82.3 | TGCGGACCGACCGGTAGCAACCAT | 29 | 32 | 32 | 18 | 21 | 15 |
| 2896 | 2856 | 9237 | 80.7 | TGCGGACCACGGAAAGCCATGTCT | 29 | 32 | 35 | 6 | 15 | 19 |
| 2897 | 2857 | 30654 | 79 | TGCGGTGCAATCACGGCCTAGTCT | 29 | 33 | 4 | 35 | 26 | 19 |
| 2898 | 2858 | 9240 | 81.2 | TGCGGTGCAAAGCGTTCACGTCTG | 29 | 33 | 6 | 12 | 30 | 8 |
| 2899 | 2859 | 40685 | 79.9 | TGCGGTGCTGTCCCTATCCCGTCT | 29 | 33 | 9 | 26 | 28 | 19 |
| 2900 | 2860 | 21649 | 80.2 | TGCGGTGCCGTTATCGAAAGGACC | 29 | 33 | 12 | 24 | 6 | 32 |
| 2901 | 2862 | 9248 | 80 | TGCGGTGCACCTCCATCCATCTTG | 29 | 33 | 23 | 15 | 15 | 11 |
| 2902 | 2863 | 9251 | 82.6 | TGCGGTGCTCCCCTGTACGGAGGA | 29 | 33 | 28 | 14 | 35 | 25 |
| 2903 | 2864 | 9252 | 82.5 | TGCGGTGCAGCCCCTACCATGCTT | 29 | 33 | 36 | 26 | 15 | 17 |
| 2904 | 2865 | 9253 | 78 | TGCGGGACTTGAGTCTGTCGCGTA | 29 | 34 | 1 | 19 | 33 | 18 |
| 2905 | 2866 | 9254 | 77 | TGCGGGACTGATTTGACAGCCCTA | 29 | 34 | 2 | 1 | 31 | 26 |
| 2906 | 2867 | 40686 | 79 | TGCGGGACATACGCTTAGCCAGGA | 29 | 34 | 5 | 17 | 36 | 25 |
| 2907 | 2868 | 30655 | 77.5 | TGCGGGACAAAGTTAGCGTTGTGC | 29 | 34 | 6 | 3 | 12 | 33 |

FIG. 25FFF

| SEQ ID NO: | 4,633 ID# | HEX ID# | Tm | ZIPCODE (5'-3') | TETRAMER NUMBERS | | | | |
|---|---|---|---|---|---|---|---|---|---|
| 2908 | 2869 | 30656 | 78.3 | TGCGGGACTGTCTCTGAGCCCCTA | 29 | 34 | 9 | 8 | 36 | 26 |
| 2909 | 2870 | 30657 | 78.6 | TGCGGGACCTTGTTAGGAGTTGCG | 29 | 34 | 11 | 3 | 20 | 29 |
| 2910 | 2871 | 9259 | 79.8 | TGCGGGACCGTTGGTATCCCAATC | 29 | 34 | 12 | 18 | 28 | 4 |
| 2911 | 2872 | 40688 | 80.1 | TGCGGGACCTCAGACCACCTGCTT | 29 | 34 | 13 | 32 | 23 | 17 |
| 2912 | 2873 | 30658 | 78.4 | TGCGGGACCTGTAATCCGTTCAGC | 29 | 34 | 14 | 4 | 12 | 31 |
| 2913 | 2874 | 9262 | 81.3 | TGCGGGACCGAACGTTCTCAGTGC | 29 | 34 | 16 | 12 | 13 | 33 |
| 2914 | 2875 | 9263 | 79.5 | TGCGGGACGCTTGCTTATACTGCG | 29 | 34 | 17 | 17 | 5 | 29 |
| 2915 | 2877 | 9265 | 77.5 | TGCGGGACGTCTACCTGCTTGATG | 29 | 34 | 19 | 23 | 17 | 27 |
| 2916 | 2878 | 9266 | 78 | TGCGGGACAGTGACGGACCTACCT | 29 | 34 | 22 | 35 | 23 | 23 |
| 2917 | 2879 | 9267 | 82.5 | TGCGGGACATCGCTCATCGTCGAA | 29 | 34 | 24 | 13 | 10 | 16 |
| 2918 | 2880 | 15946 | 77.4 | TGCGGGACCCTATACAGCAATCCC | 29 | 34 | 26 | 7 | 21 | 28 |
| 2919 | 2881 | 9270 | 82.8 | TGCGGGACGATGGTGCGATGAGTG | 29 | 34 | 27 | 33 | 27 | 22 |
| 2920 | 2882 | 9271 | 82 | TGCGGGACTGCGTGTCCCATTCTG | 29 | 34 | 29 | 9 | 15 | 8 |
| 2921 | 2883 | 15947 | 80.8 | TGCGGGACAGCCATACGCAAGCTT | 29 | 34 | 36 | 5 | 21 | 17 |
| 2922 | 2884 | 30659 | 77.6 | TGCGACGGTTAGGCTTTCTGGCTT | 29 | 35 | 3 | 17 | 8 | 17 |
| 2923 | 2885 | 30660 | 79.9 | TGCGACGGAATCAATCATCGACGG | 29 | 35 | 4 | 4 | 24 | 35 |
| 2924 | 2887 | 40691 | 79.1 | TGCGACGGTCTGCGAATTAGCGTT | 29 | 35 | 8 | 16 | 3 | 12 |
| 2925 | 2888 | 9277 | 80.3 | TGCGACGGCTCATTGAAGTGGTGC | 29 | 35 | 13 | 1 | 22 | 33 |
| 2926 | 2889 | 9278 | 80.2 | TGCGACGGCTGTCCATACCTGTGC | 29 | 35 | 14 | 15 | 23 | 33 |
| 2927 | 2890 | 9279 | 77.9 | TGCGACGGGTCTCTTGGAGTAGCC | 29 | 35 | 19 | 11 | 20 | 36 |
| 2928 | 2891 | 30661 | 77.5 | TGCGACGGGAGTCGTTAAAGGCTT | 29 | 35 | 20 | 12 | 6 | 17 |
| 2929 | 2892 | 40692 | 79.9 | TGCGACGGAGTGACCTCACGCCTA | 29 | 35 | 22 | 23 | 30 | 26 |
| 2930 | 2893 | 40693 | 80.9 | TGCGACGGAGGATGTCGGACTCGT | 29 | 35 | 25 | 9 | 34 | 10 |
| 2931 | 2894 | 9282 | 82.8 | TGCGACGGGATGGTGCTGTCATCG | 29 | 35 | 27 | 33 | 9 | 24 |
| 2932 | 2895 | 9284 | 83 | TGCGACGGGTGCGGTAAGGAGTGC | 29 | 35 | 33 | 18 | 25 | 33 |
| 2933 | 2896 | 9285 | 81.8 | TGCGACGGGGACGCTTAGCCTGAT | 29 | 35 | 34 | 17 | 36 | 2 |
| 2934 | 2897 | 9286 | 78.6 | TGCGAGCCTTGATGTCTCTGTGCG | 29 | 36 | 1 | 9 | 8 | 29 |
| 2935 | 2898 | 40694 | 78.8 | TGCGAGCCTGATTCTGGCAAGACC | 29 | 36 | 2 | 8 | 21 | 32 |
| 2936 | 2899 | 9288 | 77.1 | TGCGAGCCTTAGGCAATCTGCTTG | 29 | 36 | 3 | 21 | 8 | 11 |
| 2937 | 2900 | 9289 | 78.5 | TGCGAGCCAAAGGGACATACCAGC | 29 | 36 | 6 | 34 | 5 | 31 |
| 2938 | 2901 | 40696 | 76.5 | TGCGAGCCTACAAAAGGTGCCTGT | 29 | 36 | 7 | 6 | 33 | 14 |
| 2939 | 2902 | 9290 | 79.5 | TGCGAGCCTGTCGACCTACAACGG | 29 | 36 | 9 | 32 | 7 | 35 |
| 2940 | 2903 | 40697 | 80.1 | TGCGAGCCCTCAGGTAGGACCGAA | 29 | 36 | 13 | 18 | 34 | 16 |
| 2941 | 2905 | 9293 | 80.2 | TGCGAGCCCATGGTAAGCCAATC | 29 | 36 | 15 | 18 | 36 | 4 |
| 2942 | 2906 | 21669 | 80.9 | TGCGAGCCGGTATGTCAGCCTCGT | 29 | 36 | 18 | 9 | 36 | 10 |
| 2943 | 2907 | 40701 | 80.7 | TGCGAGCCAGGAGATGCGAAGACC | 29 | 36 | 25 | 27 | 16 | 32 |
| 2944 | 2908 | 9296 | 78.4 | TGCGAGCCCCTATCTGAGCCTTGA | 29 | 36 | 26 | 8 | 36 | 1 |
| 2945 | 2909 | 9297 | 82.9 | TGCGAGCCTCCCGCTTGATGCTGT | 29 | 36 | 28 | 17 | 27 | 14 |
| 2946 | 2910 | 9298 | 81.9 | TGCGAGCCCACGTGTCGCTTCTGT | 29 | 36 | 30 | 9 | 17 | 14 |
| 2947 | 2911 | 15948 | 83.7 | TGCGAGCCCAGCCAGCGTCTTTGA | 29 | 36 | 31 | 31 | 19 | 1 |
| 2948 | 2912 | 9300 | 81.2 | TGCGAGCCGGACTCGTGCTTGAGT | 29 | 36 | 34 | 10 | 17 | 20 |
| 2949 | 2913 | 9301 | 83.7 | TGCGAGCCACGGCAGCTGATCGTT | 29 | 36 | 35 | 31 | 2 | 12 |
| 2950 | 2914 | 9302 | 83.7 | TGCGAGCCAGCCGATGGGTACACG | 29 | 36 | 36 | 27 | 18 | 30 |
| 2951 | 2915 | 9304 | 79.9 | CACGTTGACCATTGCGCCATTCGT | 30 | 1 | 15 | 29 | 15 | 10 |
| 2952 | 2916 | 9305 | 78 | CACGTTGAGCAAACGGAAAGTGCG | 30 | 1 | 21 | 35 | 6 | 29 |
| 2953 | 2917 | 9307 | 80 | CACGTTGAATCGCACGGACCCTCA | 30 | 1 | 24 | 30 | 32 | 13 |
| 2954 | 2918 | 9311 | 79 | CACGTTGATTCGTGTGCCGTTCGAA | 30 | 2 | 10 | 33 | 12 | 16 |
| 2955 | 2919 | 30662 | 78.1 | CACGTGATTCCCAATCGCAAGCAA | 30 | 2 | 28 | 4 | 21 | 21 |
| 2956 | 2920 | 9314 | 81.6 | CACGTGATGTGCCCATTCCCCGAA | 30 | 2 | 33 | 15 | 28 | 16 |
| 2957 | 2921 | 15953 | 76.8 | CACGTTAGCACGGCAAAGTGGCTT | 30 | 3 | 30 | 21 | 22 | 17 |
| 2958 | 2922 | 9332 | 79.5 | CACGAATCCACGGACCACGGAGTG | 30 | 4 | 30 | 32 | 35 | 22 |

FIG. 25GGG

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 2959 | 2923 | 30663 | 77.4 | CACGATACGCAAAAAGACGGGCAA | 30 | 5 | 21 | 6 | 35 | 21 |
| 2960 | 2924 | 40704 | 78.4 | CACGATACTGCGTCTGACGGCGAA | 30 | 5 | 29 | 8 | 35 | 16 |
| 2961 | 2925 | 15961 | 78 | CACGATACACGGACGGAGGAAGCC | 30 | 5 | 35 | 35 | 25 | 36 |
| 2962 | 2926 | 9345 | 77.2 | CACGAAAGCTGTGGACCGAAGTGC | 30 | 6 | 14 | 34 | 16 | 33 |
| 2963 | 2927 | 15965 | 77.1 | CACGAAAGGCTAATCGCTTGTGCG | 30 | 6 | 18 | 24 | 11 | 29 |
| 2964 | 2928 | 30664 | 77.5 | CACGAAAGCCTAAGTGCACGCAGC | 30 | 6 | 26 | 22 | 30 | 31 |
| 2965 | 2929 | 9354 | 76 | CACGAAAGTGCGATACACCTTGCG | 30 | 6 | 29 | 5 | 23 | 29 |
| 2966 | 2930 | 9355 | 76.8 | CACGAAAGGTGCAAAGAGCCCTCA | 30 | 6 | 33 | 6 | 36 | 13 |
| 2967 | 2931 | 30665 | 79.8 | CACGAAAGGGACACCTGTGCTGCG | 30 | 6 | 34 | 23 | 33 | 29 |
| 2968 | 2932 | 30666 | 75 | CACGTCTGCGTTATACTGCGGCTT | 30 | 8 | 12 | 5 | 29 | 17 |
| 2969 | 2933 | 15972 | 78.6 | CACGTCTGTGCGTGATACGGGTGC | 30 | 8 | 29 | 2 | 35 | 33 |
| 2970 | 2934 | 9366 | 78.1 | CACGTCTGCACGGCTTAAAGCACG | 30 | 8 | 30 | 17 | 6 | 30 |
| 2971 | 2935 | 9367 | 77.6 | CACGTCTGCAGCATCGACCTTCGT | 30 | 8 | 31 | 24 | 23 | 10 |
| 2972 | 2936 | 40705 | 80.8 | CACGTCTGGACCCTTGGACCTGCG | 30 | 8 | 32 | 11 | 32 | 29 |
| 2973 | 2937 | 30667 | 76.1 | CACGTGTCCGTTAGGAGCAATCCC | 30 | 9 | 12 | 25 | 21 | 28 |
| 2974 | 2938 | 9376 | 81.4 | CACGTGTCGACCGATGGACCGGAC | 30 | 9 | 32 | 27 | 32 | 34 |
| 2975 | 2939 | 9379 | 80.9 | CACGTGTCAGCCGATGGCAACGAA | 30 | 9 | 36 | 27 | 21 | 16 |
| 2976 | 2940 | 9382 | 79.7 | CACGTCGTTCTGCGTTACGGACGG | 30 | 10 | 8 | 12 | 35 | 35 |
| 2977 | 2941 | 15975 | 77.8 | CACGTCGTTCGTCCATCGAAGTGC | 30 | 10 | 10 | 15 | 16 | 33 |
| 2978 | 2942 | 40706 | 77 | CACGTCGTCCATAAAGAGCCCACG | 30 | 10 | 15 | 6 | 36 | 30 |
| 2979 | 2943 | 9387 | 77.2 | CACGTCGTACCTGTCTTGCGAGCC | 30 | 10 | 23 | 19 | 29 | 36 |
| 2980 | 2944 | 9394 | 81.5 | CACGTCGTGGACGCAAGATGCACG | 30 | 10 | 34 | 21 | 27 | 30 |
| 2981 | 2945 | 9397 | 81.5 | CACGCTTGTGTCGGACCGAAACGG | 30 | 11 | 9 | 34 | 16 | 35 |
| 2982 | 2946 | 9404 | 78 | CACGCTTGAGTGAGTGGTGCGGAC | 30 | 11 | 22 | 22 | 33 | 34 |
| 2983 | 2947 | 30668 | 77.7 | CACGCTTGACCTCGTTAGCCCCAT | 30 | 11 | 23 | 12 | 36 | 15 |
| 2984 | 2948 | 21698 | 78.3 | CACGCTTGTCCCTCGTTGATGCAA | 30 | 11 | 28 | 10 | 2 | 21 |
| 2985 | 2949 | 9409 | 77.9 | CACGCTTGAGCCTCTGACCTGCAA | 30 | 11 | 36 | 8 | 23 | 21 |
| 2986 | 2950 | 30669 | 78.7 | CACGCGTTTACAAGGACACGCACG | 30 | 12 | 7 | 25 | 30 | 30 |
| 2987 | 2951 | 9414 | 78 | CACGCGTTTGTCGCTTAATCGTGC | 30 | 12 | 9 | 17 | 4 | 33 |
| 2988 | 2952 | 15981 | 79 | CACGCGTTTCGTGATGCGAATTGA | 30 | 12 | 10 | 27 | 16 | 1 |
| 2989 | 2953 | 9416 | 77.5 | CACGCGTTCTTGCGTTCGTTTGAT | 30 | 12 | 11 | 12 | 12 | 2 |
| 2990 | 2954 | 9418 | 76.9 | CACGCGTTCGAAGTGCGTCTACCT | 30 | 12 | 16 | 33 | 19 | 23 |
| 2991 | 2955 | 9420 | 76.7 | CACGCGTTGTCTTTAGTGCGCTCA | 30 | 12 | 19 | 3 | 29 | 13 |
| 2992 | 2956 | 9421 | 79.2 | CACGCGTTGCAAGCAATGTCCTCA | 30 | 12 | 21 | 21 | 9 | 13 |
| 2993 | 2957 | 40710 | 76.9 | CACGCGTTCCTATGATGACCCAGC | 30 | 12 | 26 | 2 | 32 | 31 |
| 2994 | 2958 | 9425 | 78.9 | CACGCGTTGATGCTCAAGGATCCC | 30 | 12 | 27 | 13 | 25 | 28 |
| 2995 | 2959 | 15985 | 78.1 | CACGCGTTTCCCTGATAGCCCTTG | 30 | 12 | 28 | 2 | 36 | 11 |
| 2996 | 2960 | 30670 | 80.3 | CACGCGTTAGCCCACGTCCCTGAT | 30 | 12 | 36 | 30 | 28 | 2 |
| 2997 | 2961 | 21702 | 81.6 | CACGCTCAAATCAGCCCACGGTGC | 30 | 13 | 4 | 36 | 30 | 33 |
| 2998 | 2962 | 40712 | 78 | CACGCTCACGAAAAAGCCATGTGC | 30 | 13 | 16 | 6 | 15 | 33 |
| 2999 | 2963 | 9436 | 77.9 | CACGCTCAGGTAATCGATCGCACG | 30 | 13 | 18 | 24 | 24 | 30 |
| 3000 | 2964 | 9439 | 78 | CACGCTCATCCCCATCCATTGAT | 30 | 13 | 28 | 15 | 15 | 2 |
| 3001 | 2965 | 40714 | 77.3 | CACGCTGTATCGACCTCAGCCAGC | 30 | 14 | 24 | 23 | 31 | 31 |
| 3002 | 2966 | 9454 | 80.5 | CACGCTGTTGCGCTCAAGGACGAA | 30 | 14 | 29 | 13 | 25 | 16 |
| 3003 | 2967 | 30672 | 78 | CACGCCATTACAACCTCAGCTGCG | 30 | 15 | 7 | 23 | 31 | 29 |
| 3004 | 2968 | 30673 | 80.2 | CACGCCATTCTGCTTGGTGCAGGA | 30 | 15 | 8 | 11 | 33 | 25 |
| 3005 | 2969 | 9462 | 79.2 | CACGCCATTCGTTCTGGGACAGGA | 30 | 15 | 10 | 8 | 34 | 25 |
| 3006 | 2970 | 15993 | 77.4 | CACGCCATCTTGAATCCACGCCTA | 30 | 15 | 11 | 4 | 30 | 26 |
| 3007 | 2971 | 15994 | 77.1 | CACGCCATCCATCGTTGGTACGTT | 30 | 15 | 15 | 12 | 18 | 12 |
| 3008 | 2972 | 30674 | 77.5 | CACGCCATGGTAAGGAACGGACCT | 30 | 15 | 18 | 25 | 35 | 23 |
| 3009 | 2973 | 15996 | 79.3 | CACGCCATGTCTCAGCTGTCGCAA | 30 | 15 | 19 | 31 | 9 | 21 |

FIG. 25HHH

| SEQ ID NO: | 4,633 ID# | HEX ID# | Tm | ZIPCODE (5'-3') | TETRAMER NUMBERS | | | | |
|---|---|---|---|---|---|---|---|---|---|
| 3010 | 2974 | 9468 | 78.5 | CACGCCATGAGTGTGCGCTTCTGT | 30 | 15 | 20 | 33 | 17 | 14 |
| 3011 | 2975 | 9469 | 76.8 | CACGCCATAGTGTGTCTCCCGACC | 30 | 15 | 22 | 9 | 28 | 32 |
| 3012 | 2976 | 15997 | 76.5 | CACGCCATAGGACGTTACGGTCGT | 30 | 15 | 25 | 12 | 35 | 10 |
| 3013 | 2977 | 9473 | 81.8 | CACGCCATTGCGGCTTCAGCTGTC | 30 | 15 | 29 | 17 | 31 | 9 |
| 3014 | 2978 | 15999 | 80.9 | CACGCCATCACGCTCAGGACTCCC | 30 | 15 | 30 | 13 | 34 | 28 |
| 3015 | 2979 | 30675 | 78.1 | CACGCCATGACCTACATGCGCCTA | 30 | 15 | 32 | 7 | 29 | 26 |
| 3016 | 2980 | 9477 | 77.1 | CACGCCATACGGAGTGAGCCAAAG | 30 | 15 | 35 | 22 | 36 | 6 |
| 3017 | 2981 | 40717 | 78.1 | CACGCGAATTGACGTTGCTTCAGC | 30 | 16 | 1 | 12 | 17 | 31 |
| 3018 | 2982 | 16001 | 78.7 | CACGCGAAAATCGAGTCACGGCTT | 30 | 16 | 4 | 20 | 30 | 17 |
| 3019 | 2983 | 40720 | 77.3 | CACGCGAATCTGAATCCTTGCAGC | 30 | 16 | 8 | 4 | 11 | 31 |
| 3020 | 2984 | 40722 | 76.9 | CACGCGAACTTGTTGAGGACGCTT | 30 | 16 | 11 | 1 | 34 | 17 |
| 3021 | 2985 | 30677 | 78.1 | CACGCGAACTGTCAGCCCTATCCC | 30 | 16 | 14 | 31 | 26 | 28 |
| 3022 | 2986 | 9483 | 76.9 | CACGCGAAGCTTCCATTCGTCTGT | 30 | 16 | 17 | 15 | 10 | 14 |
| 3023 | 2987 | 9484 | 75.9 | CACGCGAAGGTACTCATCCCGTCT | 30 | 16 | 18 | 13 | 28 | 19 |
| 3024 | 2988 | 9485 | 77.2 | CACGCGAAGTCTTCCCGATGTCTG | 30 | 16 | 19 | 28 | 27 | 8 |
| 3025 | 2989 | 16003 | 76.6 | CACGCGAAGCAACGAAATACCCAT | 30 | 16 | 21 | 16 | 5 | 15 |
| 3026 | 2990 | 40723 | 76.4 | CACGCGAAGATGTTAGAGCCGACC | 30 | 16 | 27 | 3 | 36 | 32 |
| 3027 | 2991 | 9490 | 80.1 | CACGCGAATCCCGGTACGAACGTT | 30 | 16 | 28 | 18 | 16 | 12 |
| 3028 | 2992 | 9491 | 82.3 | CACGCGAATGCGGATGCTTGGATG | 30 | 16 | 29 | 27 | 11 | 27 |
| 3029 | 2993 | 9495 | 75.2 | CACGGCTTTTAGTGATGGACTGCG | 30 | 17 | 3 | 2 | 34 | 29 |
| 3030 | 2994 | 9498 | 78.1 | CACGGCTTTCGTGTCTGCTTCACG | 30 | 17 | 10 | 19 | 17 | 30 |
| 3031 | 2995 | 9503 | 78.9 | CACGGCTTGCAAGCAACTGTGTGC | 30 | 17 | 21 | 21 | 14 | 33 |
| 3032 | 2996 | 40725 | 79.1 | CACGGCTTATCGGTGCGCTTTCTG | 30 | 17 | 24 | 33 | 17 | 8 |
| 3033 | 2997 | 9510 | 80.8 | CACGGCTTTCCCGTGCCTGTCTTG | 30 | 17 | 28 | 33 | 14 | 11 |
| 3034 | 2998 | 9513 | 78.6 | CACGGCTTGGACCTGTTGTCGCTT | 30 | 17 | 34 | 14 | 9 | 17 |
| 3035 | 2999 | 40726 | 78.1 | CACGGCTTAGCCCCATAGGATCCC | 30 | 17 | 36 | 15 | 25 | 28 |
| 3036 | 3000 | 9516 | 78.5 | CACGGGTATGATCAGCGATGCACG | 30 | 18 | 2 | 31 | 27 | 30 |
| 3037 | 3001 | 40727 | 77.4 | CACGGGTATCGTGCTTCAGCGGTA | 30 | 18 | 10 | 17 | 31 | 18 |
| 3038 | 3002 | 16011 | 78.4 | CACGGGTACCATGTCTGTGCGTGC | 30 | 18 | 15 | 19 | 33 | 33 |
| 3039 | 3003 | 40728 | 75.5 | CACGGGTAGCTTAAAGTCCCGTGC | 30 | 18 | 17 | 6 | 28 | 33 |
| 3040 | 3004 | 9527 | 76.1 | CACGGGTAGCAAAGTGATCGTCCC | 30 | 18 | 21 | 22 | 24 | 28 |
| 3041 | 3005 | 30679 | 76.4 | CACGGGTAAGGACACGTCGTCGTT | 30 | 18 | 25 | 30 | 10 | 12 |
| 3042 | 3006 | 9530 | 81.5 | CACGGGTAGATGTGCGTCCCTGCG | 30 | 18 | 27 | 29 | 28 | 29 |
| 3043 | 3007 | 30680 | 80.3 | CACGGGTAGACCAGCCGCAATCGT | 30 | 18 | 32 | 36 | 21 | 10 |
| 3044 | 3008 | 9532 | 75.6 | CACGGGTAGGACAAAGGGACGGTA | 30 | 18 | 34 | 6 | 34 | 18 |
| 3045 | 3009 | 9533 | 77.8 | CACGGTCTTGATCACGGCAAGTGC | 30 | 19 | 2 | 30 | 21 | 33 |
| 3046 | 3010 | 9534 | 77.8 | CACGGTCTTCTGTGCGCCATTGTC | 30 | 19 | 8 | 29 | 15 | 9 |
| 3047 | 3011 | 30681 | 78 | CACGGTCTGCAAGGTATCCCAGCC | 30 | 19 | 21 | 18 | 28 | 36 |
| 3048 | 3012 | 9540 | 79.5 | CACGGTCTTGCGCACGACCTCCTA | 30 | 19 | 29 | 30 | 23 | 26 |
| 3049 | 3013 | 9542 | 75.8 | CACGGTCTACGGTTGAAGCCCTGT | 30 | 19 | 35 | 1 | 36 | 14 |
| 3050 | 3014 | 9545 | 80.4 | CACGGAGTTGATCAGCTGCGGCAA | 30 | 20 | 2 | 31 | 29 | 21 |
| 3051 | 3015 | 9546 | 75.9 | CACGGAGTTCGTTTAGCAGCCCAT | 30 | 20 | 10 | 3 | 31 | 15 |
| 3052 | 3016 | 9549 | 75.1 | CACGGAGTGCTTACGGCACGATAC | 30 | 20 | 17 | 35 | 30 | 5 |
| 3053 | 3017 | 9550 | 78 | CACGGAGTAGGAGACCGTGCGCTT | 30 | 20 | 25 | 32 | 33 | 17 |
| 3054 | 3019 | 21741 | 79.8 | CACGGAGTAGCCGGACCAGCGAGT | 30 | 20 | 36 | 34 | 31 | 20 |
| 3055 | 3020 | 9554 | 75.8 | CACGGCAATTGATCTGCCTACACG | 30 | 21 | 1 | 8 | 26 | 30 |
| 3056 | 3022 | 21742 | 77.3 | CACGGCAATGTCACGGAAAGTCGT | 30 | 21 | 9 | 35 | 6 | 10 |
| 3057 | 3023 | 16021 | 76.8 | CACGGCAACTTGAATCATCGGACC | 30 | 21 | 11 | 4 | 24 | 32 |
| 3058 | 3024 | 9561 | 75.4 | CACGGCAAGGTACTCAGACCTCCC | 30 | 21 | 18 | 13 | 32 | 28 |
| 3059 | 3025 | 30684 | 76.7 | CACGGCAACCTAAGGAATCGCTCA | 30 | 21 | 26 | 25 | 24 | 13 |
| 3060 | 3026 | 40732 | 77.4 | CACGGCAAGATGTTGAGACCCGAA | 30 | 21 | 27 | 1 | 32 | 16 |

FIG. 25III

| SEQ ID NO: | 4,633 ID# | HEX ID# | Tm | ZIPCODE (5'-3') | TETRAMER NUMBERS | | | | |
|---|---|---|---|---|---|---|---|---|---|
| 3061 | 3027 | 9568 | 78.5 | CACGGCAATCCCCCTACGAAACCT | 30 21 28 26 16 23 | | | | |
| 3062 | 3028 | 9569 | 81 | CACGGCAATGCGTCTGCACGTGAT | 30 21 29 8 30 2 | | | | |
| 3063 | 3029 | 9570 | 81.4 | CACGGCAACACGGTGCATCGTCTG | 30 21 30 33 24 8 | | | | |
| 3064 | 3030 | 30685 | 76.5 | CACGAGTGGCTTATCGCGTTAGCC | 30 22 17 24 12 36 | | | | |
| 3065 | 3031 | 9578 | 79.9 | CACGAGTGGATGAGGATGCGCAGC | 30 22 27 25 29 31 | | | | |
| 3066 | 3032 | 16024 | 80.5 | CACGAGTGTCCCGCAACCATTCCC | 30 22 28 21 15 28 | | | | |
| 3067 | 3033 | 40735 | 79.6 | CACGAGTGGACCAATCCAGCCACG | 30 22 32 4 31 30 | | | | |
| 3068 | 3034 | 9585 | 77.7 | CACGACCTTGATGGACCGAATCCC | 30 23 2 34 16 28 | | | | |
| 3069 | 3035 | 9586 | 81 | CACGACCTTCTGCGAAACGGCAGC | 30 23 8 16 35 31 | | | | |
| 3070 | 3036 | 9587 | 78 | CACGACCTTCGTGCAAAGCCAGTG | 30 23 10 21 36 22 | | | | |
| 3071 | 3037 | 30686 | 78.7 | CACGACCTCCATATCGGACCGTGC | 30 23 15 24 32 33 | | | | |
| 3072 | 3038 | 16026 | 81.5 | CACGACCTATCGTGCGTGCGGGAC | 30 23 24 29 29 34 | | | | |
| 3073 | 3039 | 9593 | 79.6 | CACGACCTGATGTGCGGACCCTTG | 30 23 27 29 32 11 | | | | |
| 3074 | 3040 | 9597 | 79.8 | CACGACCTGGACGGTACACGCAGC | 30 23 34 18 30 31 | | | | |
| 3075 | 3041 | 9600 | 78.3 | CACGATCGAATCACGGGACCGTCT | 30 24 4 35 32 19 | | | | |
| 3076 | 3042 | 9604 | 75.5 | CACGATCGCTGTAGTGATCGCCAT | 30 24 14 22 24 15 | | | | |
| 3077 | 3043 | 30687 | 75.7 | CACGATCGGGTATACAACGGTCCC | 30 24 18 7 35 28 | | | | |
| 3078 | 3044 | 40739 | 78.4 | CACGATCGGTCTCTTGTCCCCGAA | 30 24 19 11 28 16 | | | | |
| 3079 | 3046 | 9609 | 81.2 | CACGATCGAGTGCCATCAGCGCAA | 30 24 22 15 31 21 | | | | |
| 3080 | 3047 | 9610 | 76.9 | CACGATCGACCTCGAAACGGTGTC | 30 24 23 16 35 9 | | | | |
| 3081 | 3048 | 16031 | 80.5 | CACGATCGAGCCGATGAGCCACCT | 30 24 36 27 36 23 | | | | |
| 3082 | 3049 | 9619 | 76.9 | CACGAGGAAAAGGCAATCCCGAGT | 30 25 6 21 28 20 | | | | |
| 3083 | 3050 | 9620 | 76.7 | CACGAGGATCGTCTTGACGGCTGT | 30 25 10 11 35 14 | | | | |
| 3084 | 3051 | 9621 | 77.3 | CACGAGGACTTGTGCGCTCAGACC | 30 25 11 29 13 32 | | | | |
| 3085 | 3052 | 30688 | 81.6 | CACGAGGACCATTCCCCAGCGACC | 30 25 15 28 31 32 | | | | |
| 3086 | 3054 | 9627 | 76.1 | CACGAGGAACCTTGCGAAAGCTGT | 30 25 23 29 6 14 | | | | |
| 3087 | 3055 | 9631 | 78.4 | CACGAGGACACGGCTTCTCAAGCC | 30 25 30 17 13 36 | | | | |
| 3088 | 3056 | 16035 | 80.4 | CACGAGGACAGCGCTTCAGCTCCC | 30 25 31 17 31 28 | | | | |
| 3089 | 3058 | 9634 | 77.6 | CACGAGGAGGACAGTGGACCCGTT | 30 25 34 22 32 12 | | | | |
| 3090 | 3059 | 30689 | 77.8 | CACGAGGAAGCCTTGAACGGTCGT | 30 25 36 1 35 10 | | | | |
| 3091 | 3060 | 9640 | 78.7 | CACGCCTAAATCGACCATCGGTGC | 30 26 4 32 24 33 | | | | |
| 3092 | 3061 | 30691 | 75.6 | CACGCCTAGCTTCGTTAGCCTCGT | 30 26 17 12 36 10 | | | | |
| 3093 | 3062 | 30692 | 77.7 | CACGCCTAATCGTGCGTCTGCTGT | 30 26 24 29 8 14 | | | | |
| 3094 | 3063 | 9650 | 77.1 | CACGCCTAGATGGGTACAGCGTGC | 30 26 27 18 31 33 | | | | |
| 3095 | 3064 | 30693 | 78.5 | CACGGATGTCGTCTTGGGACGCTT | 30 27 10 11 34 17 | | | | |
| 3096 | 3065 | 40744 | 78.1 | CACGGATGCTTGTCCCCATTGAT | 30 27 11 28 15 2 | | | | |
| 3097 | 3066 | 9660 | 76.6 | CACGGATGCTCAGCTTTGTCCCAT | 30 27 13 17 9 15 | | | | |
| 3098 | 3067 | 9663 | 75.5 | CACGGATGGGTATCGTAGCCCTGT | 30 27 18 10 36 14 | | | | |
| 3099 | 3068 | 30694 | 77.4 | CACGGATGGAGTCAGCCCTAAGCC | 30 27 20 31 26 36 | | | | |
| 3100 | 3069 | 9671 | 81.6 | CACGGATGCAGCGACCAGTGGGAC | 30 27 31 32 22 34 | | | | |
| 3101 | 3070 | 9672 | 80.3 | CACGGATGGTGCCGTTCACGTGTC | 30 27 33 12 30 9 | | | | |
| 3102 | 3071 | 9676 | 80.4 | CACGTCCCAATCGTGCGCAATCTG | 30 28 4 33 21 8 | | | | |
| 3103 | 3072 | 16048 | 80.5 | CACGTCCCTCTGGTGCAGCCACCT | 30 28 8 33 36 23 | | | | |
| 3104 | 3073 | 21776 | 75.4 | CACGTCCCGCTTGGTAGGTAGACC | 30 28 17 18 18 32 | | | | |
| 3105 | 3074 | 30695 | 77.9 | CACGTCCCGGTAGCTTGATGGGAC | 30 28 18 17 27 34 | | | | |
| 3106 | 3075 | 9686 | 80.1 | CACGTCCCTGCGGGTACTTGCCAT | 30 28 29 18 11 15 | | | | |
| 3107 | 3076 | 21783 | 77.6 | CACGTCCCACGGTGATCTCAATCG | 30 28 35 2 13 24 | | | | |
| 3108 | 3077 | 21785 | 78.7 | CACGTGCGTTGAAGTGCGTTGACC | 30 29 1 22 12 32 | | | | |
| 3109 | 3078 | 16052 | 79.2 | CACGTGCGATACACGGGACGAGT | 30 29 5 35 34 20 | | | | |
| 3110 | 3079 | 30696 | 78.1 | CACGTGCGTACATCCCAGGACGAA | 30 29 7 28 25 16 | | | | |
| 3111 | 3080 | 30697 | 81 | CACGTGCGTCTGCGTTTCTGCAGC | 30 29 8 12 8 31 | | | | |

FIG. 25JJJ

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 3112 | 3081 | 21787 | 76.4 | CACGTGCGTGTCTCGTTCGTCCTA | 30 | 29 | 9 | 10 | 10 | 26 |
| 3113 | 3082 | 21789 | 79 | CACGTGCGGCTTCCTATCTGGTGC | 30 | 29 | 17 | 26 | 8 | 33 |
| 3114 | 3083 | 9697 | 78.7 | CACGTGCGGGTAAGTGCACGAGTG | 30 | 29 | 18 | 22 | 30 | 22 |
| 3115 | 3084 | 9699 | 78.8 | CACGTGCGGAGTCGTTGAGTCACG | 30 | 29 | 20 | 12 | 20 | 30 |
| 3116 | 3085 | 9700 | 79.8 | CACGTGCGGCAAGGTACAGCCTTG | 30 | 29 | 21 | 18 | 31 | 11 |
| 3117 | 3086 | 9701 | 80.5 | CACGTGCGAGTGCCATGACCCTTG | 30 | 29 | 22 | 15 | 32 | 11 |
| 3118 | 3087 | 30698 | 78.8 | CACGTGCGATCGAAAGAGCCTCGT | 30 | 29 | 24 | 6 | 36 | 10 |
| 3119 | 3088 | 40756 | 80.6 | CACGTGCGCCTACTGTGACCACGG | 30 | 29 | 26 | 14 | 32 | 35 |
| 3120 | 3089 | 30700 | 83.8 | CACGTGCGTGCGGCAATACATGCG | 30 | 29 | 29 | 21 | 7 | 29 |
| 3121 | 3090 | 9705 | 79.9 | CACGTGCGACGGCCTAAAAGTCCC | 30 | 29 | 35 | 26 | 6 | 28 |
| 3122 | 3091 | 9706 | 76.5 | CACGCACGTTGAAATCTCCCCTGT | 30 | 30 | 1 | 4 | 28 | 14 |
| 3123 | 3092 | 9709 | 79.8 | CACGCACGTCTGGCTTCAGCGTCT | 30 | 30 | 8 | 17 | 31 | 19 |
| 3124 | 3093 | 40757 | 80.4 | CACGCACGTCGTCTCATGCGGAGT | 30 | 30 | 10 | 13 | 29 | 20 |
| 3125 | 3094 | 9713 | 76.1 | CACGCACGCCATAAAGAAAGGCTT | 30 | 30 | 15 | 6 | 6 | 17 |
| 3126 | 3095 | 40759 | 78.7 | CACGCACGGTCTTACACGTTTGCG | 30 | 30 | 19 | 7 | 12 | 29 |
| 3127 | 3096 | 9716 | 81.2 | CACGCACGATCGCAGCAATCAGGA | 30 | 30 | 24 | 31 | 4 | 25 |
| 3128 | 3097 | 9718 | 82.1 | CACGCACGCAGCCGAAGAGTCAGC | 30 | 30 | 31 | 16 | 20 | 31 |
| 3129 | 3098 | 9719 | 82 | CACGCACGGACCGACCGTCTTTGA | 30 | 30 | 32 | 32 | 19 | 1 |
| 3130 | 3099 | 30701 | 81.8 | CACGCAGCTTAGCACGGTGCGACC | 30 | 31 | 3 | 30 | 33 | 32 |
| 3131 | 3100 | 16054 | 80.4 | CACGCAGCTCTGCAGCCCATGGTA | 30 | 31 | 8 | 31 | 15 | 18 |
| 3132 | 3101 | 9724 | 77.5 | CACGCAGCCTTGGGTAAAAGAGCC | 30 | 31 | 11 | 18 | 6 | 36 |
| 3133 | 3102 | 40763 | 78.9 | CACGCAGCCTCAACGGACGGATAC | 30 | 31 | 13 | 35 | 35 | 5 |
| 3134 | 3104 | 30702 | 78.4 | CACGCAGCGGTACGTTATCGCTCA | 30 | 31 | 18 | 12 | 24 | 13 |
| 3135 | 3105 | 9729 | 79.6 | CACGCAGCGTCTGAGTTCCCCTCA | 30 | 31 | 19 | 20 | 28 | 13 |
| 3136 | 3106 | 9732 | 77.9 | CACGCAGCACCTTTGATCGTACGG | 30 | 31 | 23 | 1 | 10 | 35 |
| 3137 | 3107 | 9733 | 78.7 | CACGCAGCATCGCCTAGACCCCTA | 30 | 31 | 24 | 26 | 32 | 26 |
| 3138 | 3108 | 9734 | 79.7 | CACGCAGCGATGGGTAGACCGATG | 30 | 31 | 27 | 18 | 32 | 27 |
| 3139 | 3109 | 9735 | 81.8 | CACGCAGCTCCCCTTGGTGCAGTG | 30 | 31 | 28 | 11 | 33 | 22 |
| 3140 | 3110 | 40766 | 78.8 | CACGGACCAATCTGCGACCTACGG | 30 | 32 | 4 | 29 | 23 | 35 |
| 3141 | 3111 | 16056 | 79.8 | CACGGACCTCTGCGTTCACGATCG | 30 | 32 | 8 | 12 | 30 | 24 |
| 3142 | 3112 | 30703 | 80.9 | CACGGACCCCATGATGGTGCGTCT | 30 | 32 | 15 | 27 | 33 | 19 |
| 3143 | 3113 | 9749 | 79.5 | CACGGACCGCAATCGTCTTGGATG | 30 | 32 | 21 | 10 | 11 | 27 |
| 3144 | 3114 | 9750 | 76.6 | CACGGACCATCGAATCCGAATGTC | 30 | 32 | 24 | 4 | 16 | 9 |
| 3145 | 3115 | 9751 | 76.9 | CACGGACCAGGAGGTATGTCTGCG | 30 | 32 | 25 | 18 | 9 | 29 |
| 3146 | 3116 | 40770 | 77.2 | CACGGACCGATGTTAGCCATCGAA | 30 | 32 | 27 | 3 | 15 | 16 |
| 3147 | 3117 | 16058 | 78.9 | CACGGTGCTTAGACGGGTGCCTTG | 30 | 33 | 3 | 35 | 33 | 11 |
| 3148 | 3118 | 9758 | 79.9 | CACGGTGCAATCCCATCACGCTGT | 30 | 33 | 4 | 15 | 30 | 14 |
| 3149 | 3119 | 40772 | 76.9 | CACGGTGCAAAGAAAGCAGCCCTA | 30 | 33 | 6 | 6 | 31 | 26 |
| 3150 | 3121 | 30704 | 79.5 | CACGGTGCTCTGCTTGCGAACCAT | 30 | 33 | 8 | 11 | 16 | 15 |
| 3151 | 3122 | 9760 | 80.7 | CACGGTGCCTTGCGAACTCACACG | 30 | 33 | 11 | 16 | 13 | 30 |
| 3152 | 3123 | 40773 | 78.9 | CACGGTGCCTCAACCTCTCAACGG | 30 | 33 | 13 | 23 | 13 | 35 |
| 3153 | 3124 | 9764 | 79.5 | CACGGTGCCGAAAGGAGACCACCT | 30 | 33 | 16 | 25 | 32 | 23 |
| 3154 | 3125 | 9766 | 77.3 | CACGGTGCGAGTGCAAAGCCTTAG | 30 | 33 | 20 | 21 | 36 | 3 |
| 3155 | 3126 | 40775 | 77.2 | CACGGTGCACCTAGGAGCAAGTGC | 30 | 33 | 23 | 25 | 21 | 33 |
| 3156 | 3127 | 9770 | 78.1 | CACGGTGCAGGAATCGAGGAGGAC | 30 | 33 | 25 | 24 | 25 | 34 |
| 3157 | 3128 | 9771 | 76.3 | CACGGTGCCCTAACCTCCTATCCC | 30 | 33 | 26 | 23 | 26 | 28 |
| 3158 | 3129 | 9772 | 81.6 | CACGGTGCTCCCCAGCCTGTGATG | 30 | 33 | 28 | 31 | 14 | 27 |
| 3159 | 3130 | 9773 | 82 | CACGGTGCTGCGTGATGTGCAGGA | 30 | 33 | 29 | 2 | 33 | 25 |
| 3160 | 3131 | 30705 | 83.9 | CACGGTGCGGACGTGCAGCCTGAT | 30 | 33 | 34 | 33 | 36 | 2 |
| 3161 | 3132 | 40776 | 79.1 | CACGGGACTTGAGCTTCGTTTGCG | 30 | 34 | 1 | 17 | 12 | 29 |
| 3162 | 3133 | 9778 | 75.8 | CACGGGACAATCTTGAAGCCGAGT | 30 | 34 | 4 | 1 | 36 | 20 |

FIG. 25KKK

| SEQ ID NO: | 4,633 ID# | HEX ID# | Tm | ZIPCODE (5'-3') | TETRAMER NUMBERS | | | | |
|---|---|---|---|---|---|---|---|---|---|
| 3163 | 3134 | 9779 | 77.8 | CACGGGACATACAGCCACCTTCCC | 30 | 34 | 5 | 36 | 23 | 28 |
| 3164 | 3135 | 21811 | 77.2 | CACGGGACCTCACTCAGCTTGTGC | 30 | 34 | 13 | 13 | 17 | 33 |
| 3165 | 3136 | 9783 | 77.9 | CACGGGACCTGTCTTGAGTGCACG | 30 | 34 | 14 | 11 | 22 | 30 |
| 3166 | 3137 | 9789 | 76.9 | CACGGGACGAGTTTGAATCGATCG | 30 | 34 | 20 | 1 | 24 | 24 |
| 3167 | 3138 | 30706 | 77.9 | CACGGGACCCTAGTGCGGACAATC | 30 | 34 | 26 | 33 | 34 | 4 |
| 3168 | 3139 | 9793 | 79.7 | CACGGGACGACCACGGTGATGGTA | 30 | 34 | 32 | 35 | 2 | 18 |
| 3169 | 3140 | 9796 | 76 | CACGACGGAATCTCGTTGATTCCC | 30 | 35 | 4 | 10 | 2 | 28 |
| 3170 | 3141 | 16062 | 77.5 | CACGACGGTACAAGCCCAGCTTGA | 30 | 35 | 7 | 36 | 31 | 1 |
| 3171 | 3142 | 9799 | 81.4 | CACGACGGTGTCGTGCGTGCAATC | 30 | 35 | 9 | 33 | 33 | 4 |
| 3172 | 3143 | 21817 | 78.8 | CACGACGGAGTGCTTGTTGATGCG | 30 | 35 | 22 | 11 | 1 | 29 |
| 3173 | 3144 | 16063 | 80.2 | CACGACGGATCGCGTTTCGTCTCA | 30 | 35 | 24 | 12 | 10 | 13 |
| 3174 | 3145 | 9806 | 79.8 | CACGACGGCAGCTCTGGCTTCTCA | 30 | 35 | 31 | 8 | 17 | 13 |
| 3175 | 3146 | 9807 | 77.9 | CACGACGGGACAGGAAATCCTTG | 30 | 35 | 34 | 25 | 4 | 11 |
| 3176 | 3147 | 9810 | 76.9 | CACGAGCCAAAGTGCGGAGTGTCT | 30 | 36 | 6 | 29 | 20 | 19 |
| 3177 | 3148 | 9811 | 77.2 | CACGAGCCTACAACGGTGCGAAAG | 30 | 36 | 7 | 35 | 29 | 6 |
| 3178 | 3149 | 9812 | 77.4 | CACGAGCCTCTGAATCGCTTCACG | 30 | 36 | 8 | 4 | 17 | 30 |
| 3179 | 3150 | 9813 | 76.7 | CACGAGCCTGTCAGCCCCTATTGA | 30 | 36 | 9 | 36 | 26 | 1 |
| 3180 | 3151 | 40781 | 78.6 | CACGAGCCCTCACGTTGGACGTCT | 30 | 36 | 13 | 12 | 34 | 19 |
| 3181 | 3152 | 9817 | 75.7 | CACGAGCCGCTTACCTAGGAATCG | 30 | 36 | 17 | 23 | 25 | 24 |
| 3182 | 3154 | 30707 | 79.1 | CACGAGCCAGTGCGTTAGCCCTTG | 30 | 36 | 22 | 12 | 36 | 11 |
| 3183 | 3155 | 30708 | 80.3 | CACGAGCCACCTCAGCAGTGCAGC | 30 | 36 | 23 | 31 | 22 | 31 |
| 3184 | 3156 | 16069 | 82.3 | CACGAGCCTGCGGACCGGACTGAT | 30 | 36 | 29 | 32 | 34 | 2 |
| 3185 | 3157 | 9827 | 81.9 | CACGAGCCCACGGCAACAGCTCTG | 30 | 36 | 30 | 21 | 31 | 8 |
| 3186 | 3158 | 9830 | 82.8 | CACGAGCCGTGCGAGTCTTGTGCG | 30 | 36 | 33 | 20 | 11 | 29 |
| 3187 | 3159 | 9831 | 81 | CACGAGCCGGACCTCATCGTCAGC | 30 | 36 | 34 | 13 | 10 | 31 |
| 3188 | 3160 | 9837 | 80.3 | CAGCTTGAGTGCCGAAAGCCGGAC | 31 | 1 | 33 | 16 | 36 | 34 |
| 3189 | 3161 | 9839 | 79.3 | CAGCTGATGCTTGGACAGCCCAGC | 31 | 2 | 17 | 34 | 36 | 31 |
| 3190 | 3162 | 16071 | 78.9 | CAGCTGATGCAACACGCTTGGTGC | 31 | 2 | 21 | 30 | 11 | 33 |
| 3191 | 3163 | 40784 | 79.8 | CAGCTGATTCCCAGTGCACGGTGC | 31 | 2 | 28 | 22 | 30 | 33 |
| 3192 | 3164 | 9848 | 79.5 | CAGCAATCTCGTACGGCACGCGTT | 31 | 4 | 10 | 35 | 30 | 12 |
| 3193 | 3165 | 9849 | 77.2 | CAGCAATCCTCACGTTAGCCGTGC | 31 | 4 | 13 | 12 | 36 | 33 |
| 3194 | 3166 | 9851 | 76.8 | CAGCAATCGGTAACGGCTTGCTGT | 31 | 4 | 18 | 35 | 11 | 14 |
| 3195 | 3167 | 9852 | 79.3 | CAGCAATCGTCTTCCCCAGCTCCC | 31 | 4 | 19 | 28 | 31 | 28 |
| 3196 | 3168 | 9854 | 76.2 | CAGCAATCATCGAAAGCACGCTTG | 31 | 4 | 24 | 6 | 30 | 11 |
| 3197 | 3169 | 9861 | 81.1 | CAGCATACTCCCACGGACGGCGAA | 31 | 5 | 28 | 35 | 35 | 16 |
| 3198 | 3170 | 40787 | 82.5 | CAGCATACTGCGCACGTGCGTCCC | 31 | 5 | 29 | 30 | 29 | 28 |
| 3199 | 3172 | 9874 | 78.5 | CAGCAAAGGTGCGTCTAGCCAGCC | 31 | 6 | 33 | 19 | 36 | 36 |
| 3200 | 3173 | 9875 | 79.3 | CAGCAAAGACGGCACGAGTGAGCC | 31 | 6 | 35 | 30 | 22 | 36 |
| 3201 | 3174 | 9880 | 81.9 | CAGCTCTGGATGAGCCACGGCACG | 31 | 8 | 27 | 36 | 35 | 30 |
| 3202 | 3175 | 9886 | 79.3 | CAGCTGTCCTTGTCCCGCTTTCCC | 31 | 9 | 11 | 28 | 17 | 28 |
| 3203 | 3176 | 9887 | 81.8 | CAGCTGTCCTCATGCGTGCGGACC | 31 | 9 | 13 | 29 | 29 | 32 |
| 3204 | 3177 | 9894 | 78.3 | CAGCTGTCGTGCCCATGCAACCTA | 31 | 9 | 33 | 15 | 21 | 26 |
| 3205 | 3178 | 9896 | 78.3 | CAGCTGTCAGCCCGAAACCTACGG | 31 | 9 | 36 | 16 | 23 | 35 |
| 3206 | 3179 | 9902 | 78.4 | CAGCTCGTTCCCGCTTGGACAAAG | 31 | 10 | 28 | 17 | 34 | 6 |
| 3207 | 3180 | 40795 | 78.5 | CAGCTCGTCAGCTCGTGAGTTGCG | 31 | 10 | 31 | 10 | 20 | 29 |
| 3208 | 3181 | 16096 | 77.8 | CAGCCTTGAAAGGCTTAGCCTGCG | 31 | 11 | 6 | 17 | 36 | 29 |
| 3209 | 3182 | 21838 | 77.8 | CAGCCTTGTCTGGACCAGCCCTGT | 31 | 11 | 8 | 32 | 36 | 14 |
| 3210 | 3183 | 9910 | 75.1 | CAGCCTTGTCGTATACGTGCGACC | 31 | 11 | 10 | 5 | 33 | 32 |
| 3211 | 3184 | 9915 | 78.6 | CAGCCTTGAGTGGACCTGCGGGTA | 31 | 11 | 32 | 32 | 29 | 18 |
| 3212 | 3185 | 40798 | 78.4 | CAGCCTTGAGGAGCAAGACCACGG | 31 | 11 | 25 | 21 | 32 | 35 |
| 3213 | 3186 | 16097 | 79.3 | CAGCCTTGTCCCCTCAATCGAGCC | 31 | 11 | 28 | 13 | 24 | 36 |

FIG. 25LLL

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 3214 | 3187 | 9921 | 78.8 | CAGCCTTGGACCCGTTCGTTGATG | 31 | 11 | 32 | 12 | 12 | 27 |
| 3215 | 3188 | 9922 | 78.8 | CAGCCTTGACGGGCAAGTCTCGAA | 31 | 11 | 35 | 21 | 19 | 16 |
| 3216 | 3189 | 16099 | 75.7 | CAGCCGTTTACATCTGTCCCCGTT | 31 | 12 | 7 | 8 | 28 | 12 |
| 3217 | 3190 | 30714 | 77.1 | CAGCCGTTTCTGAAAGCAGCAGGA | 31 | 12 | 8 | 6 | 31 | 25 |
| 3218 | 3191 | 30715 | 76.5 | CAGCCGTTGCTTAGCCCTCATCTG | 31 | 12 | 17 | 36 | 13 | 8 |
| 3219 | 3192 | 9931 | 76.5 | CAGCCGTTGGTAACCTGACCCTCA | 31 | 12 | 18 | 23 | 32 | 13 |
| 3220 | 3193 | 16101 | 78.4 | CAGCCGTTGCAAATCGGTCTCCAT | 31 | 12 | 21 | 24 | 19 | 15 |
| 3221 | 3194 | 9933 | 77.1 | CAGCCGTTATCGGATGACCTTCCC | 31 | 12 | 24 | 27 | 23 | 28 |
| 3222 | 3195 | 16102 | 76.1 | CAGCCGTTCCTAACGGATACCACG | 31 | 12 | 26 | 35 | 5 | 30 |
| 3223 | 3196 | 30717 | 77.6 | CAGCCGTTGTGCTCGTAAAGGCAA | 31 | 12 | 33 | 10 | 6 | 21 |
| 3224 | 3197 | 9939 | 79.7 | CAGCCGTTGGACGATGGCTTGATG | 31 | 12 | 34 | 27 | 17 | 27 |
| 3225 | 3198 | 16104 | 77.7 | CAGCCGTTAGCCGCTTAGCCAAAG | 31 | 12 | 36 | 17 | 36 | 6 |
| 3226 | 3199 | 30718 | 76.2 | CAGCCTCATCGTAAAGGTGCGCTT | 31 | 13 | 10 | 6 | 33 | 17 |
| 3227 | 3200 | 30719 | 79.7 | CAGCCTCACCATCAGCGTGCGAGT | 31 | 13 | 15 | 31 | 33 | 20 |
| 3228 | 3201 | 40805 | 76.6 | CAGCCTCACGAACGAACGTTCCAT | 31 | 13 | 16 | 16 | 12 | 15 |
| 3229 | 3202 | 40806 | 78.3 | CAGCCTCAGCTTTCGTGCAATCCC | 31 | 13 | 17 | 10 | 21 | 28 |
| 3230 | 3203 | 9945 | 77.4 | CAGCCTCAGCAAGACCGAGTCACG | 31 | 13 | 21 | 32 | 20 | 30 |
| 3231 | 3204 | 40807 | 75.3 | CAGCCTCAACCTAATCGACCGCTT | 31 | 13 | 23 | 4 | 32 | 17 |
| 3232 | 3205 | 9947 | 79 | CAGCCTCATCCCGACCAAAGTCCC | 31 | 13 | 28 | 32 | 6 | 28 |
| 3233 | 3206 | 9950 | 78.3 | CAGCCTCAGACCTGATTCCCTGCG | 31 | 13 | 32 | 2 | 28 | 29 |
| 3234 | 3207 | 9954 | 75.1 | CAGCCTGTTTGATCGTTTGAACGG | 31 | 14 | 1 | 10 | 1 | 35 |
| 3235 | 3208 | 9955 | 78.9 | CAGCCTGTTGATCGAATCCCGTGC | 31 | 14 | 2 | 16 | 28 | 33 |
| 3236 | 3209 | 9956 | 79.9 | CAGCCTGTTCTGCGTTGCAAACGG | 31 | 14 | 8 | 12 | 21 | 35 |
| 3237 | 3210 | 9959 | 80.2 | CAGCCTGTCTCAAGCCGGACGACC | 31 | 14 | 13 | 36 | 34 | 32 |
| 3238 | 3211 | 40810 | 78.7 | CAGCCTGTCCATCTCATGCGGCTT | 31 | 14 | 15 | 13 | 29 | 17 |
| 3239 | 3212 | 9961 | 77.1 | CAGCCTGTGCTTCTCATCCCGATG | 31 | 14 | 17 | 13 | 28 | 27 |
| 3240 | 3213 | 21844 | 76.1 | CAGCCTGTGTGCCGAAGCTTACCT | 31 | 14 | 33 | 16 | 17 | 23 |
| 3241 | 3214 | 16113 | 79.5 | CAGCCCATTACACACGCACGTCCC | 31 | 15 | 7 | 30 | 30 | 28 |
| 3242 | 3215 | 16114 | 78 | CAGCCCATTCTGCCATCCATAGCC | 31 | 15 | 8 | 15 | 15 | 36 |
| 3243 | 3216 | 30720 | 76.6 | CAGCCCATCTTGTGATCACGGCTT | 31 | 15 | 11 | 2 | 30 | 17 |
| 3244 | 3217 | 30721 | 78.3 | CAGCCCATCGTTGCTTCCATCCAT | 31 | 15 | 12 | 17 | 15 | 15 |
| 3245 | 3218 | 40813 | 79.5 | CAGCCCATGTCTCCATGACCACGG | 31 | 15 | 19 | 15 | 32 | 35 |
| 3246 | 3219 | 40814 | 79 | CAGCCCATGAGTGCTTAGCCACGG | 31 | 15 | 20 | 17 | 36 | 35 |
| 3247 | 3220 | 9977 | 78.7 | CAGCCCATGCAATCTGCTCACACG | 31 | 15 | 21 | 8 | 13 | 30 |
| 3248 | 3221 | 40815 | 76.7 | CAGCCCATCCTAACGGCCATACCT | 31 | 15 | 26 | 35 | 15 | 23 |
| 3249 | 3222 | 30722 | 78.1 | CAGCCCATCACGAAAGGCTTGACC | 31 | 15 | 30 | 6 | 17 | 32 |
| 3250 | 3223 | 9988 | 79.1 | CAGCCCATACGGGAGTGTGCGGTA | 31 | 15 | 35 | 20 | 33 | 18 |
| 3251 | 3224 | 40818 | 77.3 | CAGCCGAATCTGAAAGCGAACACG | 31 | 16 | 8 | 6 | 16 | 30 |
| 3252 | 3225 | 9994 | 78 | CAGCCGAATGTCCGTTCTTGTCCC | 31 | 16 | 9 | 12 | 11 | 28 |
| 3253 | 3226 | 16124 | 77.3 | CAGCCGAAGTCTTGCGAATCGATG | 31 | 16 | 19 | 29 | 4 | 27 |
| 3254 | 3227 | 40821 | 78.4 | CAGCCGAAAGTGATACGTGCGCAA | 31 | 16 | 22 | 5 | 33 | 21 |
| 3255 | 3228 | 40822 | 78.2 | CAGCCGAAAGGATGTCATCGAGCC | 31 | 16 | 25 | 9 | 24 | 36 |
| 3256 | 3229 | 10006 | 81.6 | CAGCCGAATGCGCTTGGCAATGTC | 31 | 16 | 29 | 11 | 21 | 9 |
| 3257 | 3230 | 16127 | 78.7 | CAGCCGAACACGGCTTGCTTTGAT | 31 | 16 | 30 | 17 | 17 | 2 |
| 3258 | 3231 | 10009 | 78.9 | CAGCCGAAGACCCACGATACGTGC | 31 | 16 | 32 | 30 | 5 | 33 |
| 3259 | 3232 | 10010 | 82.4 | CAGCCGAAACGGCACGTGTCATCG | 31 | 16 | 35 | 30 | 9 | 24 |
| 3260 | 3233 | 10011 | 79.6 | CAGCCGAAAGCCGGTAGATGCGTT | 31 | 16 | 36 | 18 | 27 | 12 |
| 3261 | 3234 | 30724 | 77 | CAGCGCTTAATCTGCGTCTGCCAT | 31 | 17 | 4 | 29 | 8 | 15 |
| 3262 | 3235 | 10015 | 75.4 | CAGCGCTTTACACGTTTGTCCAGC | 31 | 17 | 7 | 12 | 9 | 31 |
| 3263 | 3236 | 30725 | 78.3 | CAGCGCTTTGTCCGAAAAGACGG | 31 | 17 | 9 | 16 | 6 | 35 |
| 3264 | 3237 | 16128 | 77.3 | CAGCGCTTTCGTTCGTTTGAATCG | 31 | 17 | 10 | 10 | 1 | 24 |

FIG. 25MMM

| SEQ ID NO: | 4,633 ID# | HBX ID# | Tm | ZIPCODE (5'-3') | TETRAMER NUMBERS | | | | | |
|---|---|---|---|---|---|---|---|---|---|---|
| 3265 | 3238 | 10019 | 76 | CAGCGCTTCTCAGGACCCATCCTA | 31 | 17 | 13 | 34 | 15 | 26 |
| 3266 | 3239 | 21856 | 79.5 | CAGCGCTTCTGTCGAAGTGCCAGC | 31 | 17 | 14 | 16 | 33 | 31 |
| 3267 | 3240 | 10024 | 77 | CAGCGCTTATCGCAAAATCCTCA | 31 | 17 | 24 | 16 | 4 | 13 |
| 3268 | 3241 | 10026 | 80.8 | CAGCGCTTTGCGGCTTGAGTTCGT | 31 | 17 | 29 | 17 | 20 | 10 |
| 3269 | 3242 | 10029 | 76.7 | CAGCGCTTAGCCTTGACTTGGTGC | 31 | 17 | 36 | 1 | 11 | 33 |
| 3270 | 3243 | 30726 | 77 | CAGCGGTACCATCCATGACCGGTA | 31 | 18 | 15 | 15 | 32 | 18 |
| 3271 | 3244 | 10036 | 75.8 | CAGCGGTACGAACGAACTTGCTCA | 31 | 18 | 16 | 16 | 11 | 13 |
| 3272 | 3245 | 30727 | 78.5 | CAGCGGTACAGCACCTGCTTGCAA | 31 | 18 | 31 | 23 | 17 | 21 |
| 3273 | 3246 | 10046 | 79.2 | CAGCGTCTTGATGGACCAGCCAGC | 31 | 19 | 2 | 34 | 31 | 31 |
| 3274 | 3247 | 30728 | 78 | CAGCGTCTCCATCTCATCGTTGCG | 31 | 19 | 15 | 13 | 10 | 29 |
| 3275 | 3248 | 30729 | 77.9 | CAGCGTCTCGAATCGTTCCCTCGT | 31 | 19 | 16 | 10 | 28 | 10 |
| 3276 | 3249 | 21861 | 79 | CAGCGTCTGCTTATCGTCCCACGG | 31 | 19 | 17 | 24 | 28 | 35 |
| 3277 | 3250 | 10050 | 78.4 | CAGCGTCTTGCGAGGAGATGGACC | 31 | 19 | 29 | 25 | 27 | 32 |
| 3278 | 3251 | 30730 | 77.7 | CAGCGTCTGGACTTGAATCGCGAA | 31 | 19 | 34 | 1 | 24 | 16 |
| 3279 | 3252 | 40828 | 78 | CAGCGTCTACGGAATCACGGGGAC | 31 | 19 | 35 | 4 | 35 | 34 |
| 3280 | 3253 | 10056 | 79 | CAGCGAGTTCTGCAGCGATGGCTT | 31 | 20 | 8 | 31 | 27 | 17 |
| 3281 | 3254 | 10057 | 80.5 | CAGCGAGTCTTGGCAACACGCGAA | 31 | 20 | 11 | 21 | 30 | 16 |
| 3282 | 3255 | 10058 | 75.9 | CAGCGAGTCGTTATCGTGTCACGG | 31 | 20 | 12 | 24 | 9 | 35 |
| 3283 | 3257 | 30731 | 77.7 | CAGCGAGTCGAAAGGACGAAAGCC | 31 | 20 | 16 | 25 | 16 | 36 |
| 3284 | 3259 | 16142 | 80.5 | CAGCGAGTGTGCGACCTGCGTGAT | 31 | 20 | 33 | 32 | 29 | 2 |
| 3285 | 3260 | 40831 | 77.3 | CAGCGCAATGATCGAAATCGGGTA | 31 | 21 | 2 | 16 | 24 | 18 |
| 3286 | 3261 | 16143 | 77.1 | CAGCGCAAATACAATCCAGCGGAC | 31 | 21 | 5 | 4 | 31 | 34 |
| 3287 | 3262 | 16144 | 77.5 | CAGCGCAATCTGGCTTGATGGGTA | 31 | 21 | 8 | 17 | 27 | 18 |
| 3288 | 3263 | 10076 | 79.3 | CAGCGCAATGTCCGTTGGACCTGT | 31 | 21 | 9 | 12 | 34 | 14 |
| 3289 | 3264 | 10078 | 77.4 | CAGCGCAACCATGGTAATCGAGGA | 31 | 21 | 15 | 18 | 24 | 25 |
| 3290 | 3265 | 10079 | 77.7 | CAGCGCAACGAATCGTCTTGAGGA | 31 | 21 | 16 | 10 | 11 | 25 |
| 3291 | 3266 | 30732 | 76.9 | CAGCGCAAGGTAGCAAGACCGGTA | 31 | 21 | 18 | 21 | 32 | 18 |
| 3292 | 3267 | 10081 | 76.5 | CAGCGCAAGAGTCGTTCTTGGACC | 31 | 21 | 20 | 12 | 11 | 32 |
| 3293 | 3268 | 40833 | 76.6 | CAGCGCAAAGTGTGATTCCCCCTA | 31 | 21 | 22 | 2 | 28 | 26 |
| 3294 | 3269 | 10084 | 79 | CAGCGCAAGGACGATGGACCAAAG | 31 | 21 | 34 | 27 | 32 | 6 |
| 3295 | 3270 | 10085 | 79.8 | CAGCGCAAACGGTCGTCACGAATC | 31 | 21 | 35 | 10 | 30 | 4 |
| 3296 | 3271 | 10086 | 80.7 | CAGCAGTGTCGTGTGCTCCCCACG | 31 | 22 | 10 | 33 | 28 | 30 |
| 3297 | 3272 | 30733 | 79.1 | CAGCAGTGGCTTGTGCCTGTTCCC | 31 | 22 | 17 | 33 | 14 | 28 |
| 3298 | 3274 | 10093 | 77.8 | CAGCAGTGCCTAATCGCACGCTGT | 31 | 22 | 26 | 24 | 30 | 14 |
| 3299 | 3275 | 16147 | 78.5 | CAGCAGTGTCCCCTTGCCATTCGT | 31 | 22 | 28 | 11 | 15 | 10 |
| 3300 | 3276 | 10097 | 79.9 | CAGCAGTGGGACGTCTACGGTGCG | 31 | 22 | 34 | 19 | 35 | 29 |
| 3301 | 3277 | 16148 | 77.1 | CAGCACCTCGAAAATCTGCGGATG | 31 | 23 | 16 | 4 | 29 | 27 |
| 3302 | 3278 | 30734 | 78.7 | CAGCACCTCACGTCTGCGAAGCAA | 31 | 23 | 30 | 8 | 16 | 21 |
| 3303 | 3279 | 10108 | 80.3 | CAGCACCTGTGCGACCTGTCCGAA | 31 | 23 | 33 | 32 | 9 | 16 |
| 3304 | 3280 | 10109 | 80.4 | CAGCACCTGGACGCTTGTGCAGGA | 31 | 23 | 34 | 17 | 33 | 25 |
| 3305 | 3281 | 30735 | 77.9 | CAGCATCGGCTTACCTGTGCATCG | 31 | 24 | 17 | 23 | 33 | 24 |
| 3306 | 3282 | 30736 | 77.9 | CAGCATCGGGTAAGTGAGCCGCTT | 31 | 24 | 18 | 22 | 36 | 17 |
| 3307 | 3283 | 16154 | 79.8 | CAGCATCGATCGGCAATCTGGTGC | 31 | 24 | 24 | 21 | 8 | 33 |
| 3308 | 3284 | 10125 | 79.7 | CAGCATCGACGGCACGGGTAAGTG | 31 | 24 | 35 | 30 | 18 | 22 |
| 3309 | 3285 | 10128 | 79 | CAGCAGGAAATCACGGTCCCTCCC | 31 | 25 | 4 | 35 | 28 | 28 |
| 3310 | 3286 | 10130 | 78 | CAGCAGGATCGTGTCTCGAATGCG | 31 | 25 | 10 | 19 | 16 | 29 |
| 3311 | 3287 | 10131 | 79.6 | CAGCAGGACTTGACGGCACGCCTA | 31 | 25 | 11 | 35 | 30 | 26 |
| 3312 | 3288 | 30737 | 78.8 | CAGCAGGAGCAAATCGGTGCTCGT | 31 | 25 | 21 | 24 | 33 | 10 |
| 3313 | 3289 | 10133 | 79 | CAGCAGGAAGTGTGCGCTGTCACG | 31 | 25 | 22 | 29 | 14 | 30 |
| 3314 | 3290 | 16157 | 78.9 | CAGCAGGACACGGATGGCTTACGG | 31 | 25 | 30 | 27 | 17 | 35 |
| 3315 | 3291 | 10135 | 77.6 | CAGCAGGAGTGCTCTGGGACTCCC | 31 | 25 | 33 | 8 | 34 | 28 |

FIG. 25NNN

| SEQ ID NO: | 4,633 ID# | HEX ID# | Tm | ZIPCODE (5'-3') | TETRAMER NUMBERS | | | | |
|---|---|---|---|---|---|---|---|---|---|
| 3316 | 3292 | 10136 | 76.7 | CAGCAGGAAGCCATACGGACAGGA | 31 | 25 | 36 | 5 | 34 | 25 |
| 3317 | 3293 | 30738 | 77.6 | CAGCCCTATCGTGCTTTGTCGCAA | 31 | 26 | 10 | 17 | 9 | 21 |
| 3318 | 3294 | 30739 | 77.6 | CAGCCCTACGAATCTGCAGCTCCC | 31 | 26 | 16 | 8 | 31 | 28 |
| 3319 | 3295 | 30740 | 75.7 | CAGCCCTAGCAAATACTCCCTGCG | 31 | 26 | 21 | 5 | 28 | 29 |
| 3320 | 3296 | 16161 | 76.7 | CAGCCCTAAGTGAGCCGTCTTCCC | 31 | 26 | 22 | 36 | 19 | 28 |
| 3321 | 3297 | 40839 | 78.1 | CAGCCCTAACCTTCCCAGCCGAGT | 31 | 26 | 23 | 28 | 36 | 20 |
| 3322 | 3298 | 10148 | 77.5 | CAGCCCTAACGGTCGTCTGTGCAA | 31 | 26 | 35 | 10 | 14 | 21 |
| 3323 | 3299 | 10151 | 80.1 | CAGCGATGAATCCACGGGACCGTT | 31 | 27 | 4 | 30 | 34 | 12 |
| 3324 | 3300 | 21879 | 75.7 | CAGCGATGTCTGACCTATCGCGAA | 31 | 27 | 8 | 23 | 24 | 16 |
| 3325 | 3301 | 10152 | 80.6 | CAGCGATGTGTCCCATGCTTTGCG | 31 | 27 | 9 | 15 | 17 | 29 |
| 3326 | 3302 | 10154 | 77.9 | CAGCGATGCTTGCTGTCTTGCGTT | 31 | 27 | 11 | 14 | 11 | 12 |
| 3327 | 3303 | 16166 | 77.6 | CAGCGATGCTCAGTGCTCTGAGCC | 31 | 27 | 13 | 33 | 8 | 36 |
| 3328 | 3304 | 40841 | 79.3 | CAGCGATGGTCTTGATTCCCGCAA | 31 | 27 | 19 | 2 | 28 | 21 |
| 3329 | 3305 | 16169 | 77 | CAGCGATGAGGATCGTTCGTGACC | 31 | 27 | 25 | 10 | 10 | 32 |
| 3330 | 3306 | 30741 | 76.5 | CAGCGATGCCTAGCAACCTAACGG | 31 | 27 | 26 | 21 | 26 | 35 |
| 3331 | 3307 | 16170 | 77.7 | CAGCGATGTCCCCTTGCCTACGTT | 31 | 27 | 28 | 11 | 26 | 12 |
| 3332 | 3308 | 10164 | 79.4 | CAGCGATGGACCGATGAGTGCGTT | 31 | 27 | 32 | 27 | 22 | 12 |
| 3333 | 3309 | 10167 | 80.6 | CAGCGATGACGGGATGTCGTTCCC | 31 | 27 | 35 | 27 | 10 | 28 |
| 3334 | 3310 | 10168 | 79.5 | CAGCGATGAGCCCTGTGCAATCGT | 31 | 27 | 36 | 14 | 21 | 10 |
| 3335 | 3311 | 30742 | 76.6 | CAGCTCCCAAAGTCCCCTGTAGCC | 31 | 28 | 6 | 28 | 14 | 36 |
| 3336 | 3312 | 30743 | 76.5 | CAGCTCCCCGTTAAAGATCGGACC | 31 | 28 | 12 | 6 | 24 | 32 |
| 3337 | 3313 | 30744 | 76 | CAGCTCCCCTGTATCGCGTTCCTA | 31 | 28 | 14 | 24 | 12 | 26 |
| 3338 | 3314 | 10175 | 78.9 | CAGCTCCCCGAAATCGTGTCGATG | 31 | 28 | 16 | 24 | 9 | 27 |
| 3339 | 3315 | 30745 | 77.7 | CAGCTCCCGAGTGCTTTTGAAGCC | 31 | 28 | 20 | 17 | 1 | 36 |
| 3340 | 3316 | 10178 | 75.9 | CAGCTCCCAGTGTTAGACGGCCAT | 31 | 28 | 22 | 3 | 35 | 15 |
| 3341 | 3317 | 10179 | 75.1 | CAGCTCCCACCTACCTGGACGTCT | 31 | 28 | 23 | 23 | 34 | 19 |
| 3342 | 3318 | 10180 | 77.8 | CAGCTCCCGATGGTCTTCGTCGTT | 31 | 28 | 27 | 19 | 10 | 12 |
| 3343 | 3319 | 16176 | 80 | CAGCTCCCTCCGAGTTCCCGAGT | 31 | 28 | 28 | 20 | 28 | 20 |
| 3344 | 3320 | 10182 | 78.8 | CAGCTCCCTGCGAATCAGGACGAA | 31 | 28 | 29 | 4 | 25 | 16 |
| 3345 | 3321 | 10183 | 80.7 | CAGCTCCCCACGGATGATCGATCG | 31 | 28 | 30 | 27 | 24 | 24 |
| 3346 | 3322 | 10186 | 78.9 | CAGCTCCCACGGTCGTTGTCCTTG | 31 | 28 | 35 | 10 | 9 | 11 |
| 3347 | 3323 | 16177 | 77.8 | CAGCTGCGTTGAGTGCCGTTGTCT | 31 | 29 | 1 | 33 | 12 | 19 |
| 3348 | 3324 | 40843 | 76.9 | CAGCTGCGTTAGTCTGGGACCGAA | 31 | 29 | 3 | 8 | 34 | 16 |
| 3349 | 3325 | 16179 | 79.6 | CAGCTGCGATACCGAAAGCCCGTT | 31 | 29 | 5 | 16 | 36 | 12 |
| 3350 | 3326 | 16180 | 80.7 | CAGCTGCGTCTGGACCCAGCACCT | 31 | 29 | 8 | 32 | 31 | 23 |
| 3351 | 3327 | 30746 | 76.2 | CAGCTGCGACCTAATCAGCCTCGT | 31 | 29 | 23 | 4 | 36 | 10 |
| 3352 | 3328 | 40845 | 80.4 | CAGCTGCGATCGGCTTTGATGCAA | 31 | 29 | 24 | 17 | 2 | 21 |
| 3353 | 3329 | 10195 | 79.4 | CAGCTGCGGATGGCTTGAGTCAGC | 31 | 29 | 27 | 17 | 20 | 31 |
| 3354 | 3330 | 10196 | 80.3 | CAGCTGCGTCCCTGTCCACGTTGA | 31 | 29 | 28 | 9 | 30 | 1 |
| 3355 | 3331 | 10197 | 82.9 | CAGCTGCGCACGCTTGACGGTCTG | 31 | 29 | 30 | 11 | 35 | 8 |
| 3356 | 3332 | 40848 | 77.4 | CAGCCACGTTGATTAGGACCGCAA | 31 | 30 | 1 | 3 | 32 | 21 |
| 3357 | 3333 | 10203 | 78.7 | CAGCCACGAATCGAGTTGCGGAGT | 31 | 30 | 4 | 20 | 29 | 20 |
| 3358 | 3334 | 10204 | 78 | CAGCCACGATACCGAAGGACGGAC | 31 | 30 | 5 | 16 | 34 | 34 |
| 3359 | 3335 | 30747 | 79.8 | CAGCCACGTCTGTGTCTCCCACGG | 31 | 30 | 8 | 9 | 28 | 35 |
| 3360 | 3336 | 21894 | 76.2 | CAGCCACGTCGTGCAAGTCTTCTG | 31 | 30 | 10 | 21 | 19 | 8 |
| 3361 | 3337 | 10208 | 79.4 | CAGCCACGCGTTCGTTCCATCTGT | 31 | 30 | 12 | 12 | 15 | 14 |
| 3362 | 3338 | 10210 | 79.6 | CAGCCACGCGAAGTGCAATCGTCT | 31 | 30 | 16 | 33 | 4 | 19 |
| 3363 | 3339 | 40850 | 77.1 | CAGCCACGCCTATCCCCCTATGTC | 31 | 30 | 26 | 28 | 26 | 9 |
| 3364 | 3340 | 30748 | 77.4 | CAGCCAGCTTGAGGACGGTATCCC | 31 | 31 | 1 | 34 | 18 | 28 |
| 3365 | 3341 | 16183 | 79.4 | CAGCCAGCTTAGGACCGTGCTCCC | 31 | 31 | 3 | 32 | 33 | 28 |
| 3366 | 3344 | 16184 | 79.3 | CAGCCAGCTGTCACGGAGGAGTGC | 31 | 31 | 9 | 35 | 25 | 33 |

FIG. 25000

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 3367 | 3345 | 30749 | 77.1 | CAGCCAGCCTCAATACGGTATGCG | 31 | 31 | 13 | 5 | 18 | 29 |
| 3368 | 3346 | 16186 | 77 | CAGCCAGCCCATATCGATACTGCG | 31 | 31 | 15 | 24 | 5 | 29 |
| 3369 | 3347 | 10228 | 77.6 | CAGCCAGCAGGACGTTCGAATTGA | 31 | 31 | 25 | 12 | 16 | 1 |
| 3370 | 3348 | 10229 | 76 | CAGCCAGCGATGTTAGGGACGTCT | 31 | 31 | 27 | 3 | 34 | 19 |
| 3371 | 3349 | 10230 | 79.4 | CAGCCAGCTCCCGGTACTTGAGCC | 31 | 31 | 28 | 18 | 11 | 36 |
| 3372 | 3350 | 10233 | 81.5 | CAGCCAGCAGCCCTTGGATGCTCA | 31 | 31 | 36 | 11 | 27 | 13 |
| 3373 | 3351 | 30750 | 77.7 | CAGCGACCAATCATACAGCCCACG | 31 | 32 | 4 | 5 | 36 | 30 |
| 3374 | 3352 | 40857 | 76 | CAGCGACCTCGTAGGAGCAACCAT | 31 | 32 | 10 | 25 | 21 | 15 |
| 3375 | 3353 | 40858 | 80 | CAGCGACCCTTGCCTAGACCCACG | 31 | 32 | 11 | 26 | 32 | 30 |
| 3376 | 3354 | 10239 | 80 | CAGCGACCGCAACACGGTCTCTTG | 31 | 32 | 21 | 30 | 19 | 11 |
| 3377 | 3355 | 10241 | 77.3 | CAGCGACCATCGTACACAGCCCAT | 31 | 32 | 24 | 7 | 31 | 15 |
| 3378 | 3356 | 30751 | 79.6 | CAGCGACCTCCCAATCGGACGAGT | 31 | 32 | 28 | 4 | 34 | 20 |
| 3379 | 3357 | 10242 | 79.8 | CAGCGACCCACGGCTTTACATCCC | 31 | 32 | 30 | 17 | 7 | 28 |
| 3380 | 3358 | 10244 | 78.8 | CAGCGACCGACCTCGTCTGTCGTT | 31 | 32 | 32 | 10 | 14 | 12 |
| 3381 | 3359 | 30752 | 80.1 | CAGCGACCAGCCAGGAAATCCAGC | 31 | 32 | 36 | 25 | 4 | 31 |
| 3382 | 3360 | 10249 | 77.4 | CAGCGTGCATACTGCGAAAGAGCC | 31 | 33 | 5 | 29 | 6 | 36 |
| 3383 | 3361 | 10251 | 76.5 | CAGCGTGCTACAAGTGCACGGGTA | 31 | 33 | 7 | 22 | 30 | 18 |
| 3384 | 3362 | 30753 | 80.8 | CAGCGTGCTCTGGATGGCAATCCC | 31 | 33 | 8 | 27 | 21 | 28 |
| 3385 | 3363 | 30754 | 77.8 | CAGCGTGCTCGTAGTGACGGCCTA | 31 | 33 | 10 | 22 | 35 | 26 |
| 3386 | 3364 | 10253 | 76.1 | CAGCGTGCCTGTAATCTGCGTGTC | 31 | 33 | 14 | 4 | 29 | 9 |
| 3387 | 3365 | 10254 | 80.2 | CAGCGTGCCGAACTGTGCTTCAGC | 31 | 33 | 16 | 14 | 17 | 31 |
| 3388 | 3366 | 10256 | 78.9 | CAGCGTGCGTCTCTTGCTTGCTCA | 31 | 33 | 19 | 11 | 11 | 13 |
| 3389 | 3367 | 30755 | 79.6 | CAGCGTGCACCTTCGTCACGACCT | 31 | 33 | 23 | 10 | 30 | 23 |
| 3390 | 3368 | 10259 | 83.5 | CAGCGTGCCACGCTTGTCGTGTGC | 31 | 33 | 30 | 11 | 10 | 33 |
| 3391 | 3369 | 10260 | 82.8 | CAGCGTGCGACCCACGGATGTTGA | 31 | 33 | 32 | 30 | 27 | 1 |
| 3392 | 3370 | 10262 | 80.5 | CAGCGTGCGGACATCGTGATACGG | 31 | 33 | 34 | 24 | 2 | 35 |
| 3393 | 3371 | 10263 | 83.4 | CAGCGTGCACGGCAGCGAGTCTCA | 31 | 33 | 35 | 31 | 20 | 13 |
| 3394 | 3372 | 10264 | 81.9 | CAGCGTGCAGCCCTCAACGGTCTG | 31 | 33 | 36 | 13 | 35 | 8 |
| 3395 | 3373 | 40861 | 77.2 | CAGCGGACTGATAGCCAGGACACG | 31 | 34 | 2 | 36 | 25 | 30 |
| 3396 | 3374 | 10265 | 76.5 | CAGCGGACAATCAAAGGCAACCAT | 31 | 34 | 4 | 6 | 21 | 15 |
| 3397 | 3375 | 30757 | 78.2 | CAGCGGACTGTCAATCCGAAAGCC | 31 | 34 | 9 | 4 | 16 | 36 |
| 3398 | 3376 | 10273 | 76.3 | CAGCGGACGAGTCGAAGCTTAGGA | 31 | 34 | 20 | 16 | 17 | 25 |
| 3399 | 3377 | 40864 | 78.3 | CAGCGGACACCTTACAAGCCAGCC | 31 | 34 | 23 | 7 | 36 | 36 |
| 3400 | 3378 | 30758 | 81.2 | CAGCGGACGATGGGACACCTCGAA | 31 | 34 | 27 | 34 | 23 | 16 |
| 3401 | 3379 | 16192 | 82.8 | CAGCGGACTGCGGTCTGGACGACC | 31 | 34 | 29 | 19 | 34 | 32 |
| 3402 | 3380 | 10278 | 81.6 | CAGCGGACCACGCCATGCTTTGTC | 31 | 34 | 30 | 15 | 17 | 9 |
| 3403 | 3381 | 10279 | 80 | CAGCGGACCAGCCCTACCATCAGC | 31 | 34 | 31 | 26 | 15 | 31 |
| 3404 | 3382 | 10280 | 82.6 | CAGCGGACACGGCGAACTGTGTGC | 31 | 34 | 35 | 16 | 14 | 33 |
| 3405 | 3383 | 40866 | 76.1 | CAGCACGGTTGAAATCCCTAACGG | 31 | 35 | 1 | 4 | 26 | 35 |
| 3406 | 3384 | 10283 | 77.8 | CAGCACGGTGATGATGCGTTAGCC | 31 | 35 | 2 | 27 | 12 | 36 |
| 3407 | 3385 | 40867 | 77 | CAGCACGGAATCTCTGGGTATGCG | 31 | 35 | 4 | 8 | 18 | 29 |
| 3408 | 3386 | 10285 | 75.6 | CAGCACGGATACAAAGCACGTCGT | 31 | 35 | 5 | 6 | 30 | 10 |
| 3409 | 3387 | 21913 | 78.1 | CAGCACGGCTGTGACCGCTTAGTG | 31 | 35 | 14 | 32 | 17 | 22 |
| 3410 | 3388 | 10291 | 79.7 | CAGCACGGCGAAGCTTGATGAGGA | 31 | 35 | 16 | 17 | 27 | 25 |
| 3411 | 3389 | 10292 | 79.1 | CAGCACGGGCTTGTCTCCTATGCG | 31 | 35 | 17 | 19 | 26 | 29 |
| 3412 | 3390 | 10293 | 76.4 | CAGCACGGGTACGAATCCCTACA | 31 | 35 | 18 | 16 | 28 | 7 |
| 3413 | 3391 | 21915 | 76.4 | CAGCACGGGAGTATCGAGTGAGCC | 31 | 35 | 20 | 24 | 22 | 36 |
| 3414 | 3392 | 30759 | 78.6 | CAGCACGGACCTTCTGCGTTCCAT | 31 | 35 | 23 | 8 | 12 | 15 |
| 3415 | 3393 | 10295 | 78.5 | CAGCACGGATCGTCCCAGTGACCT | 31 | 35 | 24 | 28 | 22 | 23 |
| 3416 | 3394 | 10296 | 77.6 | CAGCACGGAGGAACCTGAGTGCAA | 31 | 35 | 25 | 23 | 20 | 21 |
| 3417 | 3395 | 16194 | 81.4 | CAGCACGGAGCCACCTGTGCCTGT | 31 | 35 | 36 | 23 | 33 | 14 |

FIG. 25PPP

| SEQ ID NO: | 4,633 ID# | HEX ID# | Tm | ZIPCODE (5'-3') | TETRAMER NUMBERS | | | | |
|---|---|---|---|---|---|---|---|---|---|
| 3418 | 3396 | 30760 | 76.5 | CAGCAGCCTGATAAAGAGCCACGG | 31 | 36 | 2 | 6 | 36 | 35 |
| 3419 | 3397 | 16195 | 79.4 | CAGCAGCCAATCCTTGGTGCCTCA | 31 | 36 | 4 | 11 | 33 | 13 |
| 3420 | 3398 | 30761 | 76.8 | CAGCAGCCTCTGTCGTGGACCCTA | 31 | 36 | 8 | 10 | 34 | 26 |
| 3421 | 3399 | 40870 | 82 | CAGCAGCCTGTCGTGCGCAAGACC | 31 | 36 | 9 | 33 | 21 | 32 |
| 3422 | 3400 | 10310 | 76.4 | CAGCAGCCCGTTCCTAAGGAACCT | 31 | 36 | 12 | 26 | 25 | 23 |
| 3423 | 3401 | 10315 | 78.1 | CAGCAGCCGTCTCTTGCTCAGCAA | 31 | 36 | 19 | 11 | 13 | 21 |
| 3424 | 3402 | 30762 | 79.8 | CAGCAGCCGAGTGAGTCACGCGTT | 31 | 36 | 20 | 20 | 30 | 12 |
| 3425 | 3403 | 10319 | 79.2 | CAGCAGCCACCTGATGTGTCGCAA | 31 | 36 | 23 | 27 | 9 | 21 |
| 3426 | 3404 | 30763 | 80.2 | CAGCAGCCGATGATCGCTCACAGC | 31 | 36 | 27 | 24 | 13 | 31 |
| 3427 | 3405 | 10322 | 77.8 | CAGCAGCCGACCTACATCCCGTCT | 31 | 36 | 32 | 7 | 28 | 19 |
| 3428 | 3406 | 16203 | 80.4 | GACCTTAGGCAAACGGCACGCGAA | 32 | 3 | 21 | 35 | 30 | 16 |
| 3429 | 3407 | 30764 | 77.9 | GACCAATCCGAACGAACGAAACGG | 32 | 4 | 16 | 16 | 16 | 35 |
| 3430 | 3408 | 10346 | 80.3 | GACCAATCGGACGTGCGGACTCGT | 32 | 4 | 34 | 33 | 34 | 10 |
| 3431 | 3409 | 30765 | 75.7 | GACCAAAGCGTTAGCCCTGTCAGC | 32 | 6 | 12 | 36 | 14 | 31 |
| 3432 | 3410 | 10356 | 79.9 | GACCAAAGATCGCGTTGTGCTGCG | 32 | 6 | 24 | 12 | 33 | 29 |
| 3433 | 3411 | 10357 | 80.7 | GACCAAAGGATGCACGGACCTGCG | 32 | 6 | 27 | 30 | 32 | 29 |
| 3434 | 3412 | 10360 | 78.9 | GACCAAAGGGACGACCAGGAACGG | 32 | 6 | 34 | 32 | 25 | 35 |
| 3435 | 3413 | 16210 | 80.2 | GACCTCTGGTGCCAGCGCTTGGAC | 32 | 8 | 33 | 31 | 17 | 34 |
| 3436 | 3414 | 10372 | 79.2 | GACCTCTGACGGCGTTTCGTTCCC | 32 | 8 | 35 | 12 | 10 | 28 |
| 3437 | 3415 | 10375 | 76.9 | GACCTGTCGTGCAAAGCCATGACC | 32 | 9 | 33 | 6 | 15 | 32 |
| 3438 | 3416 | 30766 | 79 | GACCTCGTCGAATGCGGTCTGTGC | 32 | 10 | 16 | 29 | 19 | 33 |
| 3439 | 3417 | 10378 | 77.6 | GACCTCGTGGTATCCCGTGCGAGT | 32 | 10 | 18 | 28 | 33 | 20 |
| 3440 | 3418 | 10379 | 77.9 | GACCTCGTCACGGCTTACGGCTGT | 32 | 10 | 30 | 17 | 35 | 14 |
| 3441 | 3419 | 30767 | 76.9 | GACCCTTGCGAATCGTTACATGCG | 32 | 11 | 16 | 10 | 7 | 29 |
| 3442 | 3420 | 30768 | 75.6 | GACCCTTGGGTACCATTCCCCCTA | 32 | 11 | 18 | 15 | 28 | 26 |
| 3443 | 3421 | 30769 | 79.4 | GACCCTTGCAGCCCTACAGCCAGC | 32 | 11 | 31 | 26 | 31 | 31 |
| 3444 | 3422 | 16219 | 75.7 | GACCCGTTTACAGTGCGGACCTGT | 32 | 12 | 7 | 33 | 34 | 14 |
| 3445 | 3423 | 10396 | 78 | GACCCGTTTCTGCACGGTCTGACC | 32 | 12 | 8 | 30 | 19 | 32 |
| 3446 | 3424 | 30770 | 76.3 | GACCCGTTCTCAGCTTTCCCGAGT | 32 | 12 | 13 | 17 | 28 | 20 |
| 3447 | 3425 | 30771 | 77 | GACCCGTTGGTACAGCAATCTGCG | 32 | 12 | 18 | 31 | 4 | 29 |
| 3448 | 3426 | 10402 | 77.7 | GACCCGTTAGTGTTGATGCGCACG | 32 | 12 | 22 | 1 | 29 | 30 |
| 3449 | 3427 | 30772 | 78.3 | GACCCGTTAGGATCCCCCATCGAA | 32 | 12 | 25 | 28 | 15 | 16 |
| 3450 | 3428 | 40880 | 78.4 | GACCCGTTGATGATCGCAGCCCTA | 32 | 12 | 27 | 24 | 31 | 26 |
| 3451 | 3429 | 10404 | 77.8 | GACCCGTTTGCGAATCTGTCGCTT | 32 | 12 | 29 | 4 | 9 | 17 |
| 3452 | 3430 | 21938 | 77.4 | GACCCGTTCACGTGATGCTTCGAA | 32 | 12 | 30 | 2 | 17 | 16 |
| 3453 | 3431 | 10405 | 78.9 | GACCCGTTCAGCGGTATCTGTGCG | 32 | 12 | 31 | 18 | 8 | 29 |
| 3454 | 3432 | 10406 | 89.8 | GACCCGTTGTGCGGACACCTCAGC | 32 | 12 | 33 | 34 | 23 | 31 |
| 3455 | 3433 | 10422 | 76.6 | GACCCTGTGCAAGGTATGCGAGGA | 32 | 14 | 21 | 18 | 29 | 25 |
| 3456 | 3434 | 40883 | 78 | GACCCATTTGAGCAAGTGCGACC | 32 | 15 | 1 | 21 | 33 | 32 |
| 3457 | 3435 | 40885 | 79.5 | GACCCATGGTACTTGTGCGCACG | 32 | 15 | 18 | 11 | 29 | 30 |
| 3458 | 3436 | 16237 | 80.7 | GACCCATCACGGAGTGACCTGCG | 32 | 15 | 30 | 20 | 32 | 29 |
| 3459 | 3437 | 16239 | 78.5 | GACCCATACGGGGTACACGGACC | 32 | 15 | 35 | 18 | 30 | 32 |
| 3460 | 3438 | 30773 | 77.6 | GACCCGAATTGAAGGATCCCCGTT | 32 | 16 | 1 | 25 | 28 | 12 |
| 3461 | 3439 | 40889 | 76.4 | GACCCGAAGGTACCATCGAAAGCC | 32 | 16 | 18 | 15 | 16 | 36 |
| 3462 | 3440 | 10453 | 76.9 | GACCCGAAATCGGCTTCTCACGTT | 32 | 16 | 24 | 17 | 13 | 12 |
| 3463 | 3441 | 16250 | 79 | GACCCGAAACGGGCTTAGGACACG | 32 | 16 | 35 | 17 | 25 | 30 |
| 3464 | 3442 | 10460 | 75.6 | GACCGCTTTGATGGTAATCGCCAT | 32 | 17 | 2 | 18 | 24 | 15 |
| 3465 | 3443 | 30775 | 82.7 | GACCGCTTTGTCGGACCAGCGTGC | 32 | 17 | 9 | 34 | 31 | 33 |
| 3466 | 3444 | 16254 | 77.2 | GACCGCTTCTGTCCATGAGTTGCG | 32 | 17 | 14 | 15 | 20 | 29 |
| 3467 | 3445 | 30776 | 75.6 | GACCGCTTGCTTACGGAAAGGATG | 32 | 17 | 17 | 35 | 6 | 27 |
| 3468 | 3446 | 40894 | 76.2 | GACCGCTTATCGAATCGGTATGCG | 32 | 17 | 24 | 4 | 18 | 29 |

FIG. 25QQQ

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 3469 | 3447 | 30777 | 75.7 | GACCGCTTCCTAAGGAAGCCGTCT | 32 | 17 | 26 | 25 | 36 | 19 |
| 3470 | 3448 | 30778 | 81.3 | GACCGCTTTGCGTCGTGTGCACCT | 32 | 17 | 29 | 10 | 33 | 23 |
| 3471 | 3449 | 16256 | 77.3 | GACCGCTTGTGCAATCCGTTGGTA | 32 | 17 | 33 | 4 | 12 | 18 |
| 3472 | 3450 | 10478 | 80.4 | GACCGGTATTGATGCGACGGACGG | 32 | 18 | 1 | 29 | 35 | 35 |
| 3473 | 3451 | 30779 | 78.7 | GACCGGTACGTTGGACCTCATGCG | 32 | 18 | 12 | 34 | 13 | 29 |
| 3474 | 3452 | 16261 | 76.9 | GACCGGTACGAAGACCGGACTCGT | 32 | 18 | 16 | 32 | 34 | 10 |
| 3475 | 3453 | 40896 | 76.7 | GACCGGTAGCTTCACGAATCGCAA | 32 | 18 | 17 | 30 | 4 | 21 |
| 3476 | 3454 | 10487 | 76.5 | GACCGGTAGGTAGCTTTCCCCACG | 32 | 18 | 18 | 17 | 28 | 30 |
| 3477 | 3455 | 30780 | 76.1 | GACCGGTAAGGAAGGAACGGCCTA | 32 | 18 | 25 | 25 | 35 | 26 |
| 3478 | 3456 | 10491 | 77.7 | GACCGGTATGCGTGCGTGATTCTG | 32 | 18 | 29 | 29 | 2 | 8 |
| 3479 | 3457 | 40898 | 78.7 | GACCGTCTTCGTTTGAAGCCGCAA | 32 | 19 | 10 | 1 | 36 | 21 |
| 3480 | 3458 | 10498 | 76.7 | GACCGTCTCGAACAGCATCGTCGT | 32 | 19 | 16 | 31 | 24 | 10 |
| 3481 | 3459 | 16265 | 76 | GACCGTCTGCTTTGATGGACGCTT | 32 | 19 | 17 | 2 | 34 | 17 |
| 3482 | 3460 | 10503 | 79.9 | GACCGTCTGACCGTGCCTTGTCCC | 32 | 19 | 32 | 33 | 11 | 28 |
| 3483 | 3461 | 10509 | 75.6 | GACCGAGTGGTAAAAGACGGCAGC | 32 | 20 | 18 | 6 | 35 | 31 |
| 3484 | 3462 | 10512 | 79.2 | GACCGAGTGTGCCGTTGCAACCAT | 32 | 20 | 33 | 12 | 21 | 15 |
| 3485 | 3463 | 10513 | 78.3 | GACCGAGTGGACACGGTCGTCCAT | 32 | 20 | 34 | 35 | 10 | 15 |
| 3486 | 3464 | 10514 | 79.1 | GACCGAGTAGCCGATGCAGCGATG | 32 | 20 | 36 | 27 | 31 | 27 |
| 3487 | 3465 | 30781 | 78.9 | GACCGCAATGATACGGCGAACAGC | 32 | 21 | 2 | 35 | 16 | 31 |
| 3488 | 3466 | 21954 | 77.1 | GACCGCAAAATCTGTCCTGTTGCG | 32 | 21 | 4 | 9 | 14 | 29 |
| 3489 | 3467 | 40904 | 76.3 | GACCGCAATCTGTGATTCCCGGTA | 32 | 21 | 8 | 2 | 28 | 18 |
| 3490 | 3468 | 30782 | 77.7 | GACCGCAACTTGTGATGTGCGACC | 32 | 21 | 11 | 2 | 33 | 32 |
| 3491 | 3469 | 30783 | 77.4 | GACCGCAAGCTTTTGATCCCCTTG | 32 | 21 | 17 | 1 | 28 | 11 |
| 3492 | 3470 | 30784 | 80 | GACCGCAAGTCTCACGCGTTCACG | 32 | 21 | 19 | 30 | 12 | 30 |
| 3493 | 3471 | 10528 | 76.9 | GACCGCAAGAGTTGATGGACACGG | 32 | 21 | 20 | 2 | 34 | 35 |
| 3494 | 3472 | 10529 | 78.3 | GACCGCAAAGTGGATGGATGCGTT | 32 | 21 | 22 | 27 | 27 | 12 |
| 3495 | 3474 | 30785 | 80.1 | GACCGCAATCCCCATTCCCTGAT | 32 | 21 | 28 | 15 | 28 | 2 |
| 3496 | 3475 | 10537 | 80.2 | GACCAGTGTGCGGAGTGACCGCAA | 32 | 22 | 29 | 20 | 32 | 21 |
| 3497 | 3476 | 10538 | 81.2 | GACCAGTGCACGCTCACACGGCAA | 32 | 22 | 30 | 13 | 30 | 21 |
| 3498 | 3477 | 16277 | 81.4 | GACCAGTGAGCCGACCGACCCGTT | 32 | 22 | 36 | 32 | 32 | 12 |
| 3499 | 3478 | 10545 | 79.5 | GACCACCTCACGGATGCCATCACG | 32 | 23 | 30 | 27 | 15 | 30 |
| 3500 | 3479 | 40906 | 78.7 | GACCACCTACGGGCTTAGCCCGAA | 32 | 23 | 35 | 17 | 36 | 16 |
| 3501 | 3480 | 10550 | 77.4 | GACCATCGCTCAAGCCCTCAGGAC | 32 | 24 | 13 | 36 | 13 | 34 |
| 3502 | 3481 | 30786 | 78.3 | GACCATCGCGAATCCCCTGTTTGA | 32 | 24 | 16 | 28 | 14 | 1 |
| 3503 | 3482 | 16287 | 75.3 | GACCAGGACCATACGGCCATTGAT | 32 | 25 | 15 | 35 | 15 | 2 |
| 3504 | 3483 | 10566 | 77.2 | GACCAGGAATCGCGAAGATGGACC | 32 | 25 | 24 | 16 | 27 | 32 |
| 3505 | 3484 | 16289 | 78.3 | GACCAGGATCCCGCTTGAGTTCCC | 32 | 25 | 28 | 17 | 20 | 28 |
| 3506 | 3485 | 10570 | 78.7 | GACCAGGAGTGCCTTGGCTTGCAA | 32 | 25 | 33 | 11 | 17 | 21 |
| 3507 | 3486 | 10573 | 77.9 | GACCCCTACTTGCCATCACGGTGC | 32 | 26 | 11 | 15 | 30 | 33 |
| 3508 | 3487 | 40909 | 75.5 | GACCCCTACGTTAGGAACGGGACC | 32 | 26 | 12 | 25 | 35 | 32 |
| 3509 | 3488 | 30787 | 75.8 | GACCCCTACGAAGGTAAGCCCAGC | 32 | 26 | 16 | 18 | 36 | 31 |
| 3510 | 3489 | 30788 | 79.2 | GACCCCTAGCAACACGACGGAGCC | 32 | 26 | 21 | 30 | 35 | 36 |
| 3511 | 3490 | 10581 | 76.3 | GACCCCTAGTGCTGTCAGGATGCG | 32 | 26 | 33 | 9 | 25 | 29 |
| 3512 | 3491 | 16294 | 78.6 | GACCCCTAGGACAGCCGCAACCAT | 32 | 26 | 34 | 36 | 21 | 15 |
| 3513 | 3494 | 40915 | 79 | GACCGATGATCGTGCGCCTAGTGC | 32 | 27 | 24 | 29 | 26 | 33 |
| 3514 | 3495 | 16299 | 77.8 | GACCGATGAGGAATCGGGACGATG | 32 | 27 | 25 | 24 | 34 | 27 |
| 3515 | 3496 | 10595 | 77.3 | GACCGATGTGCGTCGTATCGTCGT | 32 | 27 | 29 | 10 | 24 | 10 |
| 3516 | 3497 | 16302 | 78.9 | GACCGATGCAGCCCTACACGATCG | 32 | 27 | 31 | 26 | 30 | 24 |
| 3517 | 3498 | 16303 | 80.4 | GACCGATGGTGCCAGCAGGAAGGA | 32 | 27 | 33 | 31 | 25 | 25 |
| 3518 | 3499 | 30791 | 77.2 | GACCGATGAGCCTCTGGGTAACGG | 32 | 27 | 36 | 8 | 18 | 35 |
| 3519 | 3500 | 10602 | 77.1 | GACCTCCCAAAGCGAAGATGCGTT | 32 | 28 | 6 | 16 | 27 | 12 |

FIG. 25RRR

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 3520 | 3502 | 10611 | 79.7 | GACCTCCCAGTGGTGCGCTTTCGT | 32 | 28 | 22 | 33 | 17 | 10 |
| 3521 | 3503 | 10612 | 76.1 | GACCTCCCACCTTACACGAATGCG | 32 | 28 | 23 | 7 | 16 | 29 |
| 3522 | 3504 | 10619 | 77.3 | GACCTCCCGGACTCTGCGAATGTC | 32 | 28 | 34 | 8 | 16 | 9 |
| 3523 | 3505 | 10621 | 79.3 | GACCTCCCAGCCCGTTGCTTTCTG | 32 | 28 | 36 | 12 | 17 | 8 |
| 3524 | 3506 | 30793 | 76.9 | GACCTGCGTTGAGTCTACGGCGAA | 32 | 29 | 1 | 19 | 35 | 16 |
| 3525 | 3507 | 10626 | 76 | GACCTGCGTCGTACCTGATGGACC | 32 | 29 | 10 | 23 | 27 | 32 |
| 3526 | 3508 | 10629 | 76.3 | GACCTGCGGAGTCTGTATCGACGG | 32 | 29 | 20 | 14 | 24 | 35 |
| 3527 | 3509 | 10631 | 78.2 | GACCTGCGATCGGTCTACCTTGCG | 32 | 29 | 24 | 19 | 23 | 29 |
| 3528 | 3510 | 30794 | 76.2 | GACCTGCGCCTAAGGAAAAGAGCC | 32 | 29 | 26 | 25 | 6 | 36 |
| 3529 | 3511 | 10634 | 82.2 | GACCTGCGTGCGCGTTTGTCAGGA | 32 | 29 | 29 | 12 | 9 | 25 |
| 3530 | 3512 | 10637 | 81.2 | GACCTGCGGTGCCACGAGGATTGA | 32 | 29 | 33 | 30 | 25 | 1 |
| 3531 | 3513 | 10638 | 78.2 | GACCCACGTTAGGGACGATGGCAA | 32 | 30 | 3 | 34 | 27 | 21 |
| 3532 | 3514 | 10639 | 80.5 | GACCCACGTGTCCCATGACCCAGC | 32 | 30 | 9 | 15 | 32 | 31 |
| 3533 | 3515 | 10640 | 76.8 | GACCCACGCTGTCAGCGTCTCCTA | 32 | 30 | 14 | 31 | 19 | 26 |
| 3534 | 3516 | 10644 | 75.8 | GACCCACGCCTATCGTCTCAAGGA | 32 | 30 | 26 | 10 | 13 | 25 |
| 3535 | 3517 | 10651 | 80.9 | GACCCACGAGCCGCAAGACCAGTG | 32 | 30 | 36 | 21 | 32 | 22 |
| 3536 | 3518 | 40923 | 77.5 | GACCCAGCTTGATACATGCGCGAA | 32 | 31 | 1 | 7 | 29 | 16 |
| 3537 | 3519 | 10654 | 78.7 | GACCCAGCATACCTTGGCAATGCG | 32 | 31 | 5 | 11 | 21 | 29 |
| 3538 | 3520 | 10655 | 75.8 | GACCCAGCTACACTTGGTGCCGTT | 32 | 31 | 7 | 11 | 33 | 12 |
| 3539 | 3521 | 16324 | 75.9 | GACCCAGCGTAGCTTTGTCGGTA | 32 | 31 | 18 | 17 | 9 | 18 |
| 3540 | 3522 | 10662 | 78.6 | GACCCAGCAGTGGACCAAAGCGAA | 32 | 31 | 22 | 32 | 6 | 16 |
| 3541 | 3523 | 40926 | 80 | GACCCAGCGATGCCATTGTCCCAT | 32 | 31 | 27 | 15 | 9 | 15 |
| 3542 | 3524 | 30796 | 81.7 | GACCCAGCGTGCAGGATGTCGTGC | 32 | 31 | 33 | 25 | 9 | 33 |
| 3543 | 3525 | 10665 | 79.6 | GACCCAGCAGCCGCAAAATCACCT | 32 | 31 | 36 | 21 | 4 | 23 |
| 3544 | 3526 | 16328 | 75.2 | GACCGACCTGATAGCCCCATATCG | 32 | 32 | 2 | 36 | 15 | 24 |
| 3545 | 3527 | 10668 | 78.5 | GACCGACCAAAGGTCTGACCGCAA | 32 | 32 | 6 | 19 | 32 | 21 |
| 3546 | 3528 | 10670 | 78.5 | GACCGACCTCTGCGAAGGACTCCC | 32 | 32 | 8 | 16 | 34 | 28 |
| 3547 | 3529 | 16329 | 75.3 | GACCGACCCTGTAAAGCAGCGTCT | 32 | 32 | 14 | 6 | 31 | 19 |
| 3548 | 3530 | 30797 | 78.7 | GACCGACCACCTGCAACGTTACGG | 32 | 32 | 23 | 21 | 12 | 35 |
| 3549 | 3531 | 10680 | 81.7 | GACCGACCGTGCCTCATCTGCACG | 32 | 32 | 33 | 13 | 8 | 30 |
| 3550 | 3532 | 16333 | 77 | GACCGTGCTTAGGCTTACGGCCAT | 32 | 33 | 3 | 17 | 35 | 15 |
| 3551 | 3533 | 21989 | 75.3 | GACCGTGCATACTCGTCTTGCAGC | 32 | 33 | 5 | 10 | 11 | 31 |
| 3552 | 3534 | 10690 | 78 | GACCGTGCCGAAGGTAAGTGACGG | 32 | 33 | 16 | 18 | 22 | 35 |
| 3553 | 3535 | 10691 | 75.4 | GACCGTGCGTCTCTCAAAAGGCTT | 32 | 33 | 19 | 13 | 6 | 17 |
| 3554 | 3536 | 10693 | 80.7 | GACCGTGCGCAATCGTGTCTCACG | 32 | 33 | 21 | 10 | 19 | 30 |
| 3555 | 3537 | 40932 | 79.6 | GACCGTGCAGTGTCTGTGCGGCTT | 32 | 33 | 22 | 8 | 29 | 17 |
| 3556 | 3538 | 30798 | 78.3 | GACCGTGCACCTCTCACGAAAGCC | 32 | 33 | 23 | 13 | 16 | 36 |
| 3557 | 3539 | 30799 | 78.4 | GACCGTGCAGGACCATGGACGAGT | 32 | 33 | 25 | 15 | 34 | 20 |
| 3558 | 3540 | 10697 | 81.3 | GACCGTGCTGCGGTCTGCAACGTT | 32 | 33 | 29 | 19 | 21 | 12 |
| 3559 | 3541 | 10698 | 81.7 | GACCGTGCCACGCTCACTTGACGG | 32 | 33 | 30 | 13 | 11 | 35 |
| 3560 | 3542 | 10699 | 80.5 | GACCGTGCCAGCCTCATCTGCGTT | 32 | 33 | 31 | 13 | 8 | 12 |
| 3561 | 3543 | 21992 | 80 | GACCGTGCGTGCGCTTGAGTTGTC | 32 | 33 | 33 | 17 | 20 | 9 |
| 3562 | 3544 | 10706 | 78.9 | GACCGGACCGTTCAGCGATGAGTG | 32 | 34 | 12 | 31 | 27 | 22 |
| 3563 | 3545 | 40935 | 79.7 | GACCGGACCTGTGGACCGTTGACC | 32 | 34 | 14 | 34 | 12 | 32 |
| 3564 | 3546 | 10709 | 77.9 | GACCGGACCGAAAATCTGTCACGG | 32 | 34 | 16 | 4 | 9 | 35 |
| 3565 | 3547 | 30800 | 79.4 | GACCGGACGCAAGCAAGCAATTGA | 32 | 34 | 21 | 21 | 21 | 1 |
| 3566 | 3548 | 10713 | 77.5 | GACCGGACATCGATCGATCGACCT | 32 | 34 | 24 | 24 | 24 | 23 |
| 3567 | 3549 | 40937 | 82.2 | GACCGGACCAGCGTCTCAGCAGCC | 32 | 34 | 31 | 19 | 31 | 36 |
| 3568 | 3550 | 30801 | 81.4 | GACCGGACGACCCTCACACGGCTT | 32 | 34 | 32 | 13 | 30 | 17 |
| 3569 | 3551 | 10715 | 80.4 | GACCGGACGTGCCTCAATCGCTGT | 32 | 34 | 33 | 13 | 24 | 14 |
| 3570 | 3552 | 10716 | 79.5 | GACCGGACACGGGTCTGCTTCGTT | 32 | 34 | 35 | 19 | 17 | 12 |

FIG. 25SSS

| SEQ ID NO: | 4,633 ID# | HEX ID# | Tm | ZIPCODE (5'-3') | TETRAMER NUMBERS | | | | |
|---|---|---|---|---|---|---|---|---|---|
| 3571 | 3553 | 16341 | 75.8 | GACCACGGTCGTAATCGATGTCCC | 32 | 35 | 10 | 4 | 27 | 28 |
| 3572 | 3554 | 10722 | 76.6 | GACCACGGCTTGATCGTGATGCTT | 32 | 35 | 11 | 24 | 2 | 17 |
| 3573 | 3555 | 10723 | 79.3 | GACCACGGCGTTGTCTGTGCCCTA | 32 | 35 | 12 | 19 | 33 | 26 |
| 3574 | 3556 | 30802 | 77.6 | GACCACGGCTGTATACCACGTGCG | 32 | 35 | 14 | 5 | 30 | 29 |
| 3575 | 3557 | 16342 | 75.3 | GACCACGGGGTATTAGACGGCTTG | 32 | 35 | 18 | 3 | 35 | 11 |
| 3576 | 3558 | 10726 | 75 | GACCACGGGTCTAGGATGTCGCTT | 32 | 35 | 19 | 25 | 9 | 17 |
| 3577 | 3559 | 40939 | 76.1 | GACCACGGGAGTATACAGCCGTGC | 32 | 35 | 20 | 5 | 36 | 33 |
| 3578 | 3560 | 16343 | 77.6 | GACCACGGCAGCTCGTTTAGAGCC | 32 | 35 | 31 | 10 | 3 | 36 |
| 3579 | 3561 | 30804 | 80.1 | GACCACGGAGCCAGCCACCTTCTG | 32 | 35 | 36 | 36 | 23 | 8 |
| 3580 | 3562 | 10735 | 76.9 | GACCAGCCAATCACGGCTGTTGTC | 32 | 36 | 4 | 35 | 14 | 9 |
| 3581 | 3563 | 10736 | 77.2 | GACCAGCCAAAGCGTTGCAACTTG | 32 | 36 | 6 | 12 | 21 | 11 |
| 3582 | 3564 | 10738 | 76 | GACCAGCCTCGTCCATAATCACGG | 32 | 36 | 10 | 15 | 4 | 35 |
| 3583 | 3565 | 10741 | 78 | GACCAGCCCCATGCTTCGTTTGTC | 32 | 36 | 15 | 17 | 12 | 9 |
| 3584 | 3566 | 10742 | 78.5 | GACCAGCCGCTTCGAACTCAGTGC | 32 | 36 | 17 | 16 | 13 | 33 |
| 3585 | 3567 | 30805 | 81.5 | GACCAGCCAGTGAGCCAGCCCCAT | 32 | 36 | 22 | 36 | 36 | 15 |
| 3586 | 3568 | 30806 | 76.5 | GACCAGCCATCGTACAATCGCGTT | 32 | 36 | 24 | 7 | 24 | 12 |
| 3587 | 3569 | 30807 | 77.5 | GACCAGCCCCTAAATCTGCGCTTG | 32 | 36 | 26 | 4 | 29 | 11 |
| 3588 | 3570 | 10748 | 81.4 | GACCAGCCTCCCGGACAGTGCCAT | 32 | 36 | 28 | 34 | 22 | 15 |
| 3589 | 3571 | 10749 | 79.5 | GACCAGCCTGCGTGTCCGTTCTCA | 32 | 36 | 29 | 9 | 12 | 13 |
| 3590 | 3572 | 10750 | 81.3 | GACCAGCCGACCGATGCTCACGAA | 32 | 36 | 32 | 27 | 13 | 16 |
| 3591 | 3573 | 10753 | 77.3 | GTGCTTGAGCTTATCGGCAATGCG | 33 | 1 | 17 | 24 | 21 | 29 |
| 3592 | 3574 | 10758 | 83.3 | GTGCTTGAGTGCGTGCTGCGCGAA | 33 | 1 | 33 | 33 | 29 | 16 |
| 3593 | 3575 | 22007 | 77.7 | GTGCTGATCCATGTGCCTTGACGG | 33 | 2 | 15 | 33 | 11 | 35 |
| 3594 | 3576 | 10763 | 81.5 | GTGCTGATGTGCCGTTTGCGGGAC | 33 | 2 | 33 | 12 | 29 | 34 |
| 3595 | 3577 | 10775 | 76.5 | GTGCAATCCGAACGTTGGACTCGT | 33 | 4 | 16 | 12 | 34 | 10 |
| 3596 | 3578 | 10776 | 75 | GTGCAATCGGTATCGTCGAAATCG | 33 | 4 | 18 | 10 | 16 | 24 |
| 3597 | 3579 | 10780 | 77.5 | GTGCAATCGATGAGCCCCATGATG | 33 | 4 | 27 | 36 | 15 | 27 |
| 3598 | 3580 | 10781 | 77.1 | GTGCAATCTCCCGCAAATACTGCG | 33 | 4 | 28 | 21 | 5 | 29 |
| 3599 | 3581 | 22013 | 76.6 | GTGCAATCCACGGATGTCTGTCCC | 33 | 4 | 30 | 27 | 8 | 28 |
| 3600 | 3582 | 30809 | 79.8 | GTGCAATCCAGCAGCCCACGTCTG | 33 | 4 | 31 | 36 | 30 | 8 |
| 3601 | 3583 | 16358 | 78.5 | GTGCATACCACGGCAAATCGGGAC | 33 | 5 | 30 | 21 | 24 | 34 |
| 3602 | 3584 | 10792 | 81.4 | GTGCATACAGCCACGGTGCGTCCC | 33 | 5 | 36 | 35 | 29 | 28 |
| 3603 | 3585 | 10793 | 78.4 | GTGCAAAGTCGTCGAACACGCGAA | 33 | 6 | 10 | 16 | 30 | 16 |
| 3604 | 3586 | 10799 | 75.6 | GTGCAAAGCCTAATCGGCAAGACC | 33 | 6 | 26 | 24 | 21 | 32 |
| 3605 | 3587 | 16360 | 79.4 | GTGCAAAGCAGCCAGCAGTGAGCC | 33 | 6 | 31 | 31 | 22 | 36 |
| 3606 | 3588 | 30810 | 77.4 | GTGCAAAGGACCATCGGCTTAGCC | 33 | 6 | 32 | 24 | 17 | 36 |
| 3607 | 3589 | 10808 | 78.1 | GTGCTCTGGGTAATCGGGACTGCG | 33 | 8 | 18 | 24 | 34 | 29 |
| 3608 | 3590 | 10809 | 79.5 | GTGCTCTGCCTAGCTTTGCGCACG | 33 | 8 | 26 | 17 | 29 | 30 |
| 3609 | 3591 | 10810 | 78.7 | GTGCTCTGTGCGCGTTAGTGCGAA | 33 | 8 | 29 | 12 | 22 | 16 |
| 3610 | 3592 | 16367 | 77.5 | GTGCTGTCCGAAACGGCTGTTTGA | 33 | 9 | 16 | 35 | 14 | 1 |
| 3611 | 3593 | 16368 | 80.9 | GTGCTGTCCACGGGACACGGGGTA | 33 | 9 | 30 | 34 | 35 | 18 |
| 3612 | 3594 | 16369 | 81.4 | GTGCTGTCGACCGACCCAGCCTCA | 33 | 9 | 32 | 32 | 31 | 13 |
| 3613 | 3595 | 10823 | 79.9 | GTGCTGTCACGGGTCTTCCCGGAC | 33 | 9 | 35 | 19 | 28 | 34 |
| 3614 | 3596 | 10825 | 77.3 | GTGCTCGTTGATAGCCGCTTCACG | 33 | 10 | 2 | 36 | 17 | 30 |
| 3615 | 3597 | 10828 | 78.4 | GTGCTCGTCTTGTGTCACGGCGAA | 33 | 10 | 11 | 9 | 35 | 16 |
| 3616 | 3598 | 10834 | 76.9 | GTGCTCGTAGGAAATCAGCCGCAA | 33 | 10 | 25 | 4 | 36 | 21 |
| 3617 | 3599 | 10836 | 78.8 | GTGCTCGTTCCCCGTTTTGACACG | 33 | 10 | 28 | 12 | 1 | 30 |
| 3618 | 3600 | 16374 | 80.4 | GTGCTCGTGGACGGACGCTTCCAT | 33 | 10 | 34 | 34 | 17 | 15 |
| 3619 | 3601 | 22025 | 77.5 | GTGCTCGTAGCCTCTGACGGGGAC | 33 | 10 | 36 | 8 | 35 | 34 |
| 3620 | 3602 | 10843 | 80.1 | GTGCCTTGTTGATCCCGTGCCGTT | 33 | 11 | 1 | 28 | 33 | 12 |
| 3621 | 3603 | 10844 | 76.9 | GTGCCTTGAAAGGCAACTTGCGAA | 33 | 11 | 6 | 21 | 11 | 16 |

FIG. 25TTT

| SEQ ID NO: | 4,633 ID# | HEX ID# | Tm | ZIPCODE (5'-3') | TETRAMER NUMBERS | | | | |
|---|---|---|---|---|---|---|---|---|---|
| 3622 | 3604 | 30811 | 80.5 | GTGCCTTGGTCTGGACTGCGCGTT | 33 | 11 | 19 | 34 | 29 | 12 |
| 3623 | 3605 | 40950 | 78.2 | GTGCCTTGAGGAGTGCTCCCGATG | 33 | 11 | 25 | 33 | 28 | 27 |
| 3624 | 3606 | 10852 | 75.3 | GTGCCTTGCCTATCGTATCGTCCC | 33 | 11 | 26 | 10 | 24 | 28 |
| 3625 | 3607 | 10853 | 78.5 | GTGCCTTGGATGGCTTCGAACGAA | 33 | 11 | 27 | 17 | 16 | 16 |
| 3626 | 3608 | 10855 | 77.6 | GTGCCTTGCAGCTGTCAGTGCCAT | 33 | 11 | 31 | 9 | 22 | 15 |
| 3627 | 3609 | 30812 | 78.3 | GTGCCGTTTGAAGGAGACCTGCG | 33 | 12 | 1 | 25 | 32 | 29 |
| 3628 | 3610 | 30813 | 76.6 | GTGCCGTTTAGATCGGATGCGAA | 33 | 12 | 3 | 24 | 27 | 16 |
| 3629 | 3611 | 30814 | 76.8 | GTGCCGTTTCTGTGCGATACGCTT | 33 | 12 | 8 | 29 | 5 | 17 |
| 3630 | 3612 | 30815 | 77.1 | GTGCCGTTCTGTAATCGTGCAGCC | 33 | 12 | 14 | 4 | 33 | 36 |
| 3631 | 3613 | 40952 | 78.6 | GTGCCGTTCCATTTGACACGTCCC | 33 | 12 | 15 | 1 | 30 | 28 |
| 3632 | 3614 | 30816 | 77.5 | GTGCCGTTGGTAGACCCGTTTCGT | 33 | 12 | 18 | 32 | 12 | 10 |
| 3633 | 3615 | 40953 | 76.8 | GTGCCGTTGAGTAGCCGCAACCTA | 33 | 12 | 20 | 36 | 21 | 26 |
| 3634 | 3616 | 30817 | 75.6 | GTGCCGTTGATGTCTGGCTTTCGT | 33 | 12 | 27 | 8 | 17 | 10 |
| 3635 | 3617 | 30818 | 78.3 | GTGCCGTTTCCCTTAGTCCCCAGC | 33 | 12 | 28 | 3 | 28 | 31 |
| 3636 | 3618 | 10869 | 80.5 | GTGCCGTTGGACGACCAATCGACC | 33 | 12 | 34 | 32 | 4 | 32 |
| 3637 | 3619 | 10870 | 77.6 | GTGCCTCATTGACACGGGTATGCG | 33 | 13 | 1 | 30 | 18 | 29 |
| 3638 | 3620 | 10874 | 75.6 | GTGCCTCACCATAGCCCGTTTGAT | 33 | 13 | 15 | 36 | 12 | 2 |
| 3639 | 3621 | 10877 | 80.8 | GTGCCTCAAGTGGGACCAGCCACG | 33 | 13 | 22 | 34 | 31 | 30 |
| 3640 | 3622 | 10880 | 75.1 | GTGCCTCACCTACTTGACGGGCTT | 33 | 13 | 26 | 11 | 35 | 17 |
| 3641 | 3623 | 10881 | 77.7 | GTGCCTCATCCCTGATGATGCACG | 33 | 13 | 28 | 2 | 27 | 30 |
| 3642 | 3624 | 30819 | 79 | GTGCCTCAAGCCTGATGGACGTGC | 33 | 13 | 36 | 2 | 34 | 33 |
| 3643 | 3625 | 10886 | 81.7 | GTGCCTGTTCTGTGCGTCCCGTGC | 33 | 14 | 8 | 29 | 28 | 33 |
| 3644 | 3626 | 10899 | 82.5 | GTGCCTGTGATGCACGGCTTTGCG | 33 | 14 | 27 | 30 | 17 | 29 |
| 3645 | 3627 | 30820 | 77.7 | GTGCCCATTTGACGAAGTGCATCG | 33 | 15 | 1 | 16 | 33 | 24 |
| 3646 | 3628 | 40960 | 79.5 | GTGCCCATTCTGATCGTCCCGCTT | 33 | 15 | 8 | 24 | 28 | 17 |
| 3647 | 3629 | 30821 | 78.6 | GTGCCCATTGTCTGTCCAGCGCTT | 33 | 15 | 9 | 9 | 31 | 17 |
| 3648 | 3630 | 16391 | 75.9 | GTGCCCATTCGTACGGGTCTTGTC | 33 | 15 | 10 | 35 | 19 | 9 |
| 3649 | 3631 | 16393 | 77.2 | GTGCCCATCTCAATACGGACGCAA | 33 | 15 | 13 | 5 | 34 | 21 |
| 3650 | 3632 | 40963 | 78.3 | GTGCCCATAGGAGTGCGATGCCAT | 33 | 15 | 25 | 33 | 27 | 15 |
| 3651 | 3633 | 40964 | 78.1 | GTGCCCATCCTACACGGACCGGTA | 33 | 15 | 26 | 30 | 32 | 18 |
| 3652 | 3634 | 10910 | 80.5 | GTGCCCATTGCGGAGTACGGATCG | 33 | 15 | 29 | 20 | 35 | 24 |
| 3653 | 3635 | 10911 | 78.9 | GTGCCCATCAGCCTGTACCTTGCG | 33 | 15 | 31 | 14 | 23 | 29 |
| 3654 | 3636 | 40967 | 77.7 | GTGCCGAATTGAGATGGATGCACG | 33 | 16 | 1 | 27 | 27 | 30 |
| 3655 | 3637 | 30822 | 75.5 | GTGCCGAATGATAATCCAGCCCAT | 33 | 16 | 2 | 4 | 31 | 15 |
| 3656 | 3638 | 10914 | 75.3 | GTGCCGAAAATCAATCGAGTTCCC | 33 | 16 | 4 | 4 | 20 | 28 |
| 3657 | 3639 | 16396 | 77 | GTGCCGAAAAGGGTATCCCATCG | 33 | 16 | 6 | 18 | 28 | 24 |
| 3658 | 3640 | 22045 | 78.5 | GTGCCGAATGTCGATGTGATTGCG | 33 | 16 | 9 | 27 | 2 | 29 |
| 3659 | 3641 | 10918 | 77.2 | GTGCCGAACGTTTGATGACCGGTA | 33 | 16 | 12 | 2 | 32 | 18 |
| 3660 | 3642 | 30823 | 78.6 | GTGCCGAACCATTCGTCAGCGTCT | 33 | 16 | 15 | 10 | 31 | 19 |
| 3661 | 3643 | 30824 | 77.8 | GTGCCGAAAGTGAATCGCAACACG | 33 | 16 | 22 | 4 | 21 | 30 |
| 3662 | 3644 | 10926 | 79.7 | GTGCCGAACACGCGTTGAGTACGG | 33 | 16 | 30 | 12 | 20 | 35 |
| 3663 | 3645 | 22050 | 76.3 | GTGCCGAAGGACCTGTAAAGCACG | 33 | 16 | 34 | 14 | 6 | 30 |
| 3664 | 3646 | 16401 | 80.6 | GTGCCGAAACGGCCATCGAACTTG | 33 | 16 | 35 | 15 | 16 | 11 |
| 3665 | 3647 | 30825 | 77.3 | GTGCGCTTTTAGTCGTGTGCCAGC | 33 | 17 | 3 | 10 | 33 | 31 |
| 3666 | 3648 | 10932 | 75.1 | GTGCGCTTAAAGAGTGCACGTCGT | 33 | 17 | 6 | 22 | 30 | 10 |
| 3667 | 3649 | 40971 | 77.2 | GTGCGCTTACAAAAGCACGACGG | 33 | 17 | 7 | 6 | 30 | 35 |
| 3668 | 3650 | 10936 | 77.3 | GTGCGCTTCTCACTCAGGACCACG | 33 | 17 | 13 | 13 | 34 | 30 |
| 3669 | 3651 | 22053 | 75.5 | GTGCGCTTGGTAGTCTACGGTCCC | 33 | 17 | 18 | 19 | 35 | 28 |
| 3670 | 3652 | 30826 | 75.6 | GTGCGCTTAGGACCATCGTTAGCC | 33 | 17 | 25 | 15 | 12 | 36 |
| 3671 | 3654 | 10943 | 77.5 | GTGCGCTTGATGCTTGGGTACGAA | 33 | 17 | 27 | 11 | 18 | 16 |
| 3672 | 3655 | 10944 | 79.1 | GTGCGCTTTCCCCGAATTGAGACC | 33 | 17 | 28 | 16 | 1 | 32 |

FIG. 25UUU

| SEQ ID NO: | 4,633 ID# | HEX ID# | Tm | ZIPCODE (5'-3') | TETRAMER NUMBERS | | | | |
|---|---|---|---|---|---|---|---|---|---|
| 3673 | 3656 | 10946 | 75.1 | GTGCGCTTGACCTCTGGGTAACCT | 33 | 17 | 32 | 8 | 18 | 23 |
| 3674 | 3657 | 10948 | 78.5 | GTGCGCTTGGACTGTCGATGCTCA | 33 | 17 | 34 | 9 | 27 | 13 |
| 3675 | 3658 | 30828 | 77.5 | GTGCGGTAAAAGGACCGGACGGTA | 33 | 18 | 6 | 32 | 34 | 18 |
| 3676 | 3659 | 30829 | 77.7 | GTGCGGTACGTTTCTGGACCGCTT | 33 | 18 | 12 | 8 | 32 | 17 |
| 3677 | 3660 | 22057 | 80 | GTGCGGTACGAATGCGAGGAAGCC | 33 | 18 | 16 | 29 | 25 | 36 |
| 3678 | 3661 | 30830 | 77.7 | GTGCGGTAGCAAAGGACAGCCCAT | 33 | 18 | 21 | 25 | 31 | 15 |
| 3679 | 3662 | 16408 | 79.8 | GTGCGGTACCTAACGGGTGCCAGC | 33 | 18 | 26 | 35 | 33 | 31 |
| 3680 | 3663 | 16409 | 80.1 | GTGCGGTAAGCCGGACTCTGGTGC | 33 | 18 | 36 | 34 | 8 | 33 |
| 3681 | 3664 | 10961 | 76.2 | GTGCGTCTTTGACCTATGCGTCCC | 33 | 19 | 1 | 26 | 29 | 28 |
| 3682 | 3665 | 10963 | 79.8 | GTGCGTCTTGTCGCAACGAAACGG | 33 | 19 | 9 | 21 | 16 | 35 |
| 3683 | 3666 | 10966 | 78.2 | GTGCGTCTGGTAATCGGTGCCCAT | 33 | 19 | 18 | 24 | 33 | 15 |
| 3684 | 3667 | 10967 | 77.3 | GTGCGTCTATCGGCTTACGGTCCC | 33 | 19 | 24 | 17 | 35 | 28 |
| 3685 | 3668 | 10969 | 80.7 | GTGCGTCTGATGCTTGGTGCCACG | 33 | 19 | 27 | 11 | 33 | 30 |
| 3686 | 3669 | 10970 | 78.3 | GTGCGTCTTCCCGTCTGCTTACGG | 33 | 19 | 28 | 19 | 17 | 35 |
| 3687 | 3670 | 10983 | 76.8 | GTGCGAGTAGGAGCAATGCGGGTA | 33 | 20 | 25 | 21 | 29 | 18 |
| 3688 | 3671 | 10984 | 82.7 | GTGCGAGTGATGCAGCCAGCACGG | 33 | 20 | 27 | 31 | 31 | 35 |
| 3689 | 3672 | 10985 | 80.2 | GTGCGAGTTCCCGTCTCAGCGACC | 33 | 20 | 28 | 19 | 31 | 32 |
| 3690 | 3673 | 16417 | 77.1 | GTGCGAGTTGCGAATCCGTTATCG | 33 | 20 | 29 | 4 | 12 | 24 |
| 3691 | 3674 | 40979 | 76.4 | GTGCGCAATTGATTAGAGCCAGCC | 33 | 21 | 1 | 3 | 36 | 36 |
| 3692 | 3675 | 30831 | 78 | GTGCGCAAATACCAGCAAAGTGCG | 33 | 21 | 5 | 31 | 6 | 29 |
| 3693 | 3676 | 40981 | 79.7 | GTGCGCAATACAAGCCCTGTTGCG | 33 | 21 | 7 | 36 | 14 | 29 |
| 3694 | 3677 | 40982 | 79.7 | GTGCGCAATGTCTCTGGGACCACG | 33 | 21 | 9 | 8 | 34 | 30 |
| 3695 | 3679 | 10993 | 77.6 | GTGCGCAACTCAGGACATCGCTGT | 33 | 21 | 13 | 34 | 24 | 14 |
| 3696 | 3680 | 40983 | 80 | GTGCGCAACTGTGATGGACCCGAA | 33 | 21 | 14 | 27 | 32 | 16 |
| 3697 | 3681 | 16419 | 75.2 | GTGCGCAAGGTATACAGCAAACGG | 33 | 21 | 18 | 7 | 21 | 35 |
| 3698 | 3682 | 10998 | 76 | GTGCGCAAAGTGATACAGGATGCG | 33 | 21 | 22 | 5 | 25 | 29 |
| 3699 | 3683 | 30833 | 78.6 | GTGCGCAAACCTTCGTGACCGAGT | 33 | 21 | 23 | 10 | 32 | 20 |
| 3700 | 3684 | 10999 | 77.6 | GTGCGCAAATCGTACACACGGACC | 33 | 21 | 24 | 7 | 30 | 32 |
| 3701 | 3685 | 16421 | 78.9 | GTGCGCAAGATGAGTGACGGTCCC | 33 | 21 | 27 | 22 | 35 | 28 |
| 3702 | 3686 | 11003 | 82.5 | GTGCGCAATGCGGCTTGGACAGTG | 33 | 21 | 29 | 17 | 34 | 22 |
| 3703 | 3687 | 11006 | 78.4 | GTGCGCAAGTGCAGGACGTTTTGA | 33 | 21 | 33 | 25 | 12 | 1 |
| 3704 | 3688 | 40985 | 76 | GTGCAGTGGCTTACGGCCTAAGGA | 33 | 22 | 17 | 35 | 26 | 25 |
| 3705 | 3689 | 11016 | 81.8 | GTGCAGTGGATGGCAATGCGCCAT | 33 | 22 | 27 | 21 | 29 | 15 |
| 3706 | 3690 | 16425 | 80.9 | GTGCAGTGTGCGGCTTTGTCTGCG | 33 | 22 | 29 | 17 | 9 | 29 |
| 3707 | 3691 | 22072 | 78.6 | GTGCAGTGGGACATCGGATGTCCC | 33 | 22 | 34 | 24 | 27 | 28 |
| 3708 | 3692 | 11020 | 81 | GTGCAGTGACGGCAGCGTCTCACG | 33 | 22 | 35 | 31 | 19 | 30 |
| 3709 | 3693 | 30834 | 78.9 | GTGCAGTGAGCCAATCGACCGACC | 33 | 22 | 36 | 4 | 32 | 32 |
| 3710 | 3694 | 11029 | 82.5 | GTGCACCTGATGACGGGTGCGTGC | 33 | 23 | 27 | 35 | 33 | 33 |
| 3711 | 3695 | 11031 | 80.1 | GTGCACCTCACGCACGAATCCGAA | 33 | 23 | 30 | 30 | 4 | 16 |
| 3712 | 3696 | 11034 | 77.6 | GTGCACCTACGGCCATTTGATCCC | 33 | 23 | 35 | 15 | 1 | 28 |
| 3713 | 3697 | 11037 | 81 | GTGCATCGTGATCAGCACGGGCAA | 33 | 24 | 2 | 31 | 35 | 21 |
| 3714 | 3698 | 30835 | 80.8 | GTGCATCGCTTGCTCAACGGGGAC | 33 | 24 | 11 | 13 | 35 | 34 |
| 3715 | 3699 | 30836 | 77.4 | GTGCATCGCTGTTTAGAGCCTGCG | 33 | 24 | 14 | 3 | 36 | 29 |
| 3716 | 3700 | 40991 | 80.5 | GTGCATCGGTCTGTGCGACCGATG | 33 | 24 | 19 | 33 | 32 | 27 |
| 3717 | 3701 | 40992 | 81.3 | GTGCATCGACCTTGCGCACGGAGT | 33 | 24 | 23 | 29 | 30 | 20 |
| 3718 | 3702 | 40993 | 76.9 | GTGCATCGATCGTGATAGCCGACC | 33 | 24 | 24 | 2 | 36 | 32 |
| 3719 | 3703 | 30837 | 80.7 | GTGCATCGTCCCCTTGTCCCTCCC | 33 | 24 | 28 | 11 | 28 | 28 |
| 3720 | 3704 | 16431 | 79.7 | GTGCATCGCACGCACGGCTTAATC | 33 | 24 | 30 | 30 | 17 | 4 |
| 3721 | 3705 | 11050 | 79.4 | GTGCATCGCAGCCGTTTCGTAGGA | 33 | 24 | 31 | 12 | 10 | 25 |
| 3722 | 3706 | 11051 | 79.4 | GTGCATCGACGGGCAATGATGACC | 33 | 24 | 35 | 21 | 2 | 32 |
| 3723 | 3707 | 30838 | 79.3 | GTGCAGGATCGTTGTCTCCCGCAA | 33 | 25 | 10 | 9 | 28 | 21 |

FIG. 25VVV

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 3724 | 3708 | 11052 | 78.3 | GTGCAGGACTTGCGAAATCGAGCC | 33 | 25 | 11 | 16 | 24 | 36 |
| 3725 | 3709 | 22086 | 76.6 | GTGCAGGAGCTTGCTTCGTTACGG | 33 | 25 | 17 | 17 | 12 | 35 |
| 3726 | 3710 | 30839 | 77.6 | GTGCAGGAAGGAAATCGACCCGAA | 33 | 25 | 25 | 4 | 32 | 16 |
| 3727 | 3712 | 16435 | 78.3 | GTGCAGGACACGTGTCGCAACGTT | 33 | 25 | 30 | 9 | 21 | 12 |
| 3728 | 3713 | 11063 | 78.1 | GTGCAGGACAGCCGAACGAAGCTT | 33 | 25 | 31 | 16 | 16 | 17 |
| 3729 | 3714 | 11064 | 80 | GTGCAGGAGACCCGAAGACCACGG | 33 | 25 | 32 | 16 | 32 | 35 |
| 3730 | 3715 | 11065 | 77.9 | GTGCAGGAGTGCCGTTAGCCACCT | 33 | 25 | 33 | 12 | 36 | 23 |
| 3731 | 3716 | 11067 | 78.3 | GTGCAGGAACGGCTGTCGTTAGCC | 33 | 25 | 35 | 14 | 12 | 36 |
| 3732 | 3717 | 11071 | 76.4 | GTGCCCTAAAAGGACCTCCCGATG | 33 | 26 | 6 | 32 | 28 | 27 |
| 3733 | 3718 | 11072 | 78.7 | GTGCCCTATGTCCGAAATCGCACG | 33 | 26 | 9 | 16 | 24 | 30 |
| 3734 | 3719 | 40995 | 76.4 | GTGCCCTACGTTGGTAGCTTTGCG | 33 | 26 | 12 | 18 | 17 | 29 |
| 3735 | 3720 | 40996 | 79.3 | GTGCCCTACCATTCTGCACGCGAA | 33 | 26 | 15 | 8 | 30 | 16 |
| 3736 | 3721 | 41000 | 78.2 | GTGCCCTAGACCTGTCGCAAACGG | 33 | 26 | 32 | 9 | 21 | 35 |
| 3737 | 3722 | 30840 | 76.6 | GTGCCCTAAGCCTCGTCTGTTCCC | 33 | 26 | 36 | 10 | 14 | 28 |
| 3738 | 3723 | 11084 | 75.8 | GTGCGATGTGATATCGCGAAATCG | 33 | 27 | 2 | 24 | 16 | 24 |
| 3739 | 3724 | 11086 | 81.8 | GTGCGATGTCTGTGCGAGCCGACC | 33 | 27 | 8 | 29 | 36 | 32 |
| 3740 | 3725 | 16441 | 77.5 | GTGCGATGCTTGGCAATTAGGCAA | 33 | 27 | 11 | 21 | 3 | 21 |
| 3741 | 3726 | 11092 | 80.7 | GTGCGATGATCGCTGTGTGCGACC | 33 | 27 | 24 | 14 | 33 | 32 |
| 3742 | 3727 | 30841 | 80.5 | GTGCGATGTCCCGGACGCAAAATC | 33 | 27 | 28 | 34 | 21 | 4 |
| 3743 | 3728 | 11099 | 78.5 | GTGCTCCCTTAGCTTGGTGCTGCG | 33 | 28 | 3 | 11 | 33 | 29 |
| 3744 | 3729 | 11104 | 78.1 | GTGCTCCCCTTGGAGTTGATTGCG | 33 | 28 | 11 | 20 | 2 | 29 |
| 3745 | 3730 | 16449 | 79.1 | GTGCTCCCCGTTCTGTCTGTTGCG | 33 | 28 | 12 | 14 | 14 | 29 |
| 3746 | 3731 | 11111 | 77.1 | GTGCTCCCGAGTTACAGTGCCACG | 33 | 28 | 20 | 7 | 33 | 30 |
| 3747 | 3732 | 16451 | 78.1 | GTGCTCCCACCTGACCCCTATCCC | 33 | 28 | 23 | 32 | 26 | 28 |
| 3748 | 3733 | 22097 | 78.5 | GTGCTCCCATCGATCGCGTTAGGA | 33 | 28 | 24 | 24 | 12 | 25 |
| 3749 | 3734 | 41006 | 81.1 | GTGCTCCCGTGCAGTGTCCCGGTA | 33 | 28 | 33 | 22 | 28 | 18 |
| 3750 | 3735 | 11116 | 78 | GTGCTCCCGGACTTGAGTGCGAGT | 33 | 28 | 34 | 1 | 33 | 20 |
| 3751 | 3736 | 11118 | 81.1 | GTGCTCCCAGCCGTCTTCTGCACG | 33 | 28 | 36 | 19 | 8 | 30 |
| 3752 | 3737 | 41007 | 78.7 | GTGCTGCGTCTGTCTGCACGAGGA | 33 | 29 | 8 | 8 | 30 | 25 |
| 3753 | 3738 | 11125 | 77.6 | GTGCTGCGCTGTGCAAAATCCCTA | 33 | 29 | 14 | 21 | 4 | 26 |
| 3754 | 3739 | 41008 | 75.4 | GTGCTGCGGAGTAAAGAGCCCCTA | 33 | 29 | 20 | 6 | 36 | 26 |
| 3755 | 3740 | 11132 | 78.3 | GTGCTGCGTCCCTACACAGCTCCC | 33 | 29 | 28 | 7 | 31 | 28 |
| 3756 | 3741 | 11133 | 82.9 | GTGCTGCGCACGGCTTGTCTGTGC | 33 | 29 | 30 | 17 | 19 | 33 |
| 3757 | 3742 | 11134 | 81 | GTGCTGCGCAGCAAAGCACGTGTC | 33 | 29 | 31 | 6 | 30 | 9 |
| 3758 | 3743 | 11135 | 80.1 | GTGCTGCGGACCTCTGAGTGTGCG | 33 | 29 | 32 | 8 | 22 | 29 |
| 3759 | 3744 | 16457 | 82 | GTGCTGCGAGCCGCAAGATGCTTG | 33 | 29 | 36 | 21 | 27 | 11 |
| 3760 | 3745 | 16458 | 80.9 | GTGCCACGTTAGGTGCGTGCCCAT | 33 | 30 | 3 | 33 | 33 | 15 |
| 3761 | 3746 | 11144 | 78.3 | GTGCCACGTCTGAGTGGACCCCAT | 33 | 30 | 8 | 22 | 32 | 15 |
| 3762 | 3747 | 16460 | 76.2 | GTGCCACGGGTAACCTAGGATCCC | 33 | 30 | 18 | 23 | 25 | 28 |
| 3763 | 3748 | 30842 | 77.9 | GTGCCACGGAGTACGGGAGTGACC | 33 | 30 | 20 | 35 | 20 | 32 |
| 3764 | 3749 | 11152 | 77.6 | GTGCCACGAGTGTGTCATCGGGAC | 33 | 30 | 22 | 9 | 24 | 34 |
| 3765 | 3750 | 11158 | 79.7 | GTGCCACGAGCCAATCCTCACACG | 33 | 30 | 36 | 4 | 13 | 30 |
| 3766 | 3751 | 30843 | 75.4 | GTGCCAGCTGATAGCCAAAGGCTT | 33 | 31 | 2 | 36 | 6 | 17 |
| 3767 | 3752 | 41012 | 76.1 | GTGCCAGCAATCAAAGGGTAACGG | 33 | 31 | 4 | 6 | 18 | 35 |
| 3768 | 3753 | 11162 | 79.3 | GTGCCAGCATACCAGCGATGCTT | 33 | 31 | 5 | 31 | 27 | 12 |
| 3769 | 3754 | 22115 | 77.6 | GTGCCAGCAAAGGTCTGTGCAGGA | 33 | 31 | 6 | 19 | 33 | 25 |
| 3770 | 3755 | 30844 | 79 | GTGCCAGCCGAATTAGTGCGATCG | 33 | 31 | 16 | 3 | 29 | 24 |
| 3771 | 3756 | 11171 | 78.6 | GTGCCAGCGTCTTGTCGTGCTTGA | 33 | 31 | 19 | 9 | 33 | 1 |
| 3772 | 3757 | 41014 | 78.4 | GTGCCAGCGAGTTTAGGTGCAGCC | 33 | 31 | 20 | 3 | 33 | 36 |
| 3773 | 3758 | 30845 | 76.8 | GTGCCAGCCCTAAATCGGACCCTA | 33 | 31 | 26 | 4 | 34 | 26 |
| 3774 | 3759 | 11176 | 79.6 | GTGCCAGCTCCCCTCACTTGCCAT | 33 | 31 | 28 | 13 | 11 | 15 |

FIG. 25WWW

| SEQ ID NO: | 4,633 ID# | HEX ID# | Tm | ZIPCODE (5'-3') | TETRAMER NUMBERS | | | | |
|---|---|---|---|---|---|---|---|---|---|
| 3775 | 3760 | 11178 | 80.8 | GTGCCAGCGTGCAGTGGCAACTTG | 33 | 31 | 33 | 22 | 21 | 11 |
| 3776 | 3761 | 11179 | 78.9 | GTGCCAGCACGGAAAGATCGGATG | 33 | 31 | 35 | 6 | 24 | 27 |
| 3777 | 3762 | 16466 | 78.9 | GTGCGACCTTAGGTGCGGTATGCG | 33 | 32 | 3 | 33 | 18 | 29 |
| 3778 | 3763 | 11183 | 81 | GTGCGACCATACAGCCGGACCGAA | 33 | 32 | 5 | 36 | 34 | 16 |
| 3779 | 3764 | 11186 | 76.1 | GTGCGACCCTGTTTAGCAGCGAGT | 33 | 32 | 14 | 3 | 31 | 20 |
| 3780 | 3765 | 16468 | 79.7 | GTGCGACCCGAAAGCCTGTCACCT | 33 | 32 | 16 | 36 | 9 | 23 |
| 3781 | 3766 | 41018 | 78.3 | GTGCGACCGCTTATACCAGCAGCC | 33 | 32 | 17 | 5 | 31 | 36 |
| 3782 | 3767 | 30847 | 77 | GTGCGACCGGTAGGACGGTAGCTT | 33 | 32 | 18 | 34 | 18 | 17 |
| 3783 | 3768 | 11191 | 81.2 | GTGCGACCAGTGGATGCACGCTCA | 33 | 32 | 22 | 27 | 30 | 13 |
| 3784 | 3769 | 16469 | 77.8 | GTGCGACCAGGAAGCCACCTGAGT | 33 | 32 | 25 | 36 | 23 | 20 |
| 3785 | 3770 | 11196 | 80.2 | GTGCGACCCAGCGAGTAGCCCTTG | 33 | 32 | 31 | 20 | 36 | 11 |
| 3786 | 3771 | 11197 | 81.2 | GTGCGACCACGGCTCAATCGTCGT | 33 | 32 | 35 | 13 | 24 | 10 |
| 3787 | 3772 | 41020 | 79.2 | GTGCGTGCTTGACGAAGGACAGCC | 33 | 33 | 1 | 16 | 34 | 36 |
| 3788 | 3773 | 11198 | 76.7 | GTGCGTGCTGATTCCCAAAGAGGA | 33 | 33 | 2 | 28 | 6 | 25 |
| 3789 | 3774 | 22127 | 77.6 | GTGCGTGCTACATGCGAGGACGTT | 33 | 33 | 7 | 29 | 25 | 12 |
| 3790 | 3775 | 11205 | 76.5 | GTGCGTGCCTGTACCTGACCACCT | 33 | 33 | 14 | 23 | 32 | 23 |
| 3791 | 3776 | 11208 | 79.2 | GTGCGTGCGTCTCCATGCAACTCA | 33 | 33 | 19 | 15 | 21 | 13 |
| 3792 | 3777 | 11209 | 79.4 | GTGCGTGCGAGTCTGTGTGCCTCA | 33 | 33 | 20 | 14 | 33 | 13 |
| 3793 | 3778 | 11210 | 79.8 | GTGCGTGCATCGCCATAGCCTGTC | 33 | 33 | 24 | 15 | 36 | 9 |
| 3794 | 3779 | 11212 | 82.6 | GTGCGTGCCACGGCTTCACGTCTG | 33 | 33 | 30 | 17 | 30 | 8 |
| 3795 | 3780 | 11216 | 80.7 | GTGCGGACATACGCAAAGCCGACC | 33 | 34 | 5 | 21 | 36 | 32 |
| 3796 | 3781 | 30848 | 78.2 | GTGCGGACGTCTCGTTGGTAAGCC | 33 | 34 | 19 | 12 | 18 | 36 |
| 3797 | 3782 | 11226 | 78.9 | GTGCGGACTCCCCAGCGTCTACCT | 33 | 34 | 28 | 31 | 19 | 23 |
| 3798 | 3783 | 11227 | 81.3 | GTGCGGACTGCGAGTGTGTCGCAA | 33 | 34 | 29 | 22 | 9 | 21 |
| 3799 | 3784 | 11228 | 78.4 | GTGCGGACGACCTCGTTTGACCAT | 33 | 34 | 32 | 10 | 1 | 15 |
| 3800 | 3785 | 41026 | 82.5 | GTGCACGGAATCGCTTTGCGGGAC | 33 | 35 | 4 | 17 | 29 | 34 |
| 3801 | 3786 | 41027 | 82.9 | GTGCACGGTCTGTCCCCACGCCAT | 33 | 35 | 8 | 28 | 30 | 15 |
| 3802 | 3787 | 30849 | 79.3 | GTGCACGGCTCAACCTTCTGCAGC | 33 | 35 | 13 | 23 | 8 | 31 |
| 3803 | 3788 | 11239 | 78.6 | GTGCACGGCCATCTTGACCTGCTT | 33 | 35 | 15 | 11 | 23 | 17 |
| 3804 | 3789 | 22145 | 79.8 | GTGCACGGGTCTTGCGATCGTCTG | 33 | 35 | 19 | 29 | 24 | 8 |
| 3805 | 3790 | 41028 | 78.8 | GTGCACGGGAGTCCATCGAAATCG | 33 | 35 | 20 | 15 | 16 | 24 |
| 3806 | 3791 | 41029 | 82.7 | GTGCACGGAGTGGACCAGCCGGAC | 33 | 35 | 22 | 32 | 36 | 34 |
| 3807 | 3792 | 41030 | 80.2 | GTGCACGGATCGGATGAGCCCCTA | 33 | 35 | 24 | 27 | 36 | 26 |
| 3808 | 3793 | 11243 | 77.7 | GTGCACGGAGGATCCCTGTCTCGT | 33 | 35 | 25 | 28 | 9 | 10 |
| 3809 | 3794 | 11246 | 83.4 | GTGCACGGGTGCGAGTGTGCGATG | 33 | 35 | 33 | 20 | 33 | 27 |
| 3810 | 3795 | 22147 | 78.1 | GTGCACGGGACCCATTCTGTGAT | 33 | 35 | 34 | 15 | 8 | 2 |
| 3811 | 3796 | 11248 | 79.8 | GTGCACGGACGGAGTGGTGCAAAG | 33 | 35 | 35 | 22 | 33 | 6 |
| 3812 | 3797 | 16475 | 79.1 | GTGCAGCCAAAGCAGCCGTTTGTC | 33 | 36 | 6 | 31 | 12 | 9 |
| 3813 | 3798 | 11250 | 77 | GTGCAGCCTCGTTACAACGGGATG | 33 | 36 | 10 | 7 | 35 | 27 |
| 3814 | 3799 | 16478 | 77.3 | GTGCAGCCATCGAATCGCAATGAT | 33 | 36 | 24 | 4 | 21 | 2 |
| 3815 | 3800 | 16479 | 81.5 | GTGCAGCCTCCCGACCACCTCGTT | 33 | 36 | 28 | 32 | 23 | 12 |
| 3816 | 3801 | 11261 | 81.5 | GTGCAGCCTGCGCCATCTTGAGGA | 33 | 36 | 29 | 15 | 11 | 25 |
| 3817 | 3802 | 11264 | 82.4 | GTGCAGCCGACCCCATGTGCAGTG | 33 | 36 | 32 | 15 | 33 | 22 |
| 3818 | 3803 | 11265 | 80.9 | GTGCAGCCGTGCAGTGCGAATCTG | 33 | 36 | 33 | 22 | 16 | 8 |
| 3819 | 3804 | 11266 | 82.6 | GTGCAGCCACGGGATGCTGTGTGC | 33 | 36 | 35 | 27 | 14 | 33 |
| 3820 | 3805 | 41034 | 78 | GGACTTGAAGCCAATCCCATTGCG | 34 | 1 | 36 | 4 | 15 | 29 |
| 3821 | 3806 | 11275 | 81.8 | GGACTTAGCAGCCACGCACGTGCG | 34 | 3 | 31 | 30 | 30 | 29 |
| 3822 | 3807 | 11276 | 78 | GGACAATCCTTGACGGCCATCAGC | 34 | 4 | 11 | 35 | 15 | 31 |
| 3823 | 3808 | 30850 | 75.8 | GGACAATCTGCGTACAAGCCCGTT | 34 | 4 | 29 | 7 | 36 | 12 |
| 3824 | 3809 | 11295 | 80.5 | GGACAAAGGATGACGGGCAATGCG | 34 | 6 | 27 | 35 | 21 | 29 |
| 3825 | 3810 | 30851 | 76.8 | GGACAAAGCACGAGCCTTGACGAA | 34 | 6 | 30 | 36 | 1 | 16 |

FIG. 25XXX

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 3826 | 3811 | 11300 | 77.2 | GGACTCTGCGTTTCGTTCGTGTGC | 34 | 8 | 12 | 10 | 10 | 33 |
| 3827 | 3812 | 11303 | 79.4 | GGACTCTGCCTAACGGCTTTGCG | 34 | 8 | 26 | 35 | 17 | 29 |
| 3828 | 3813 | 11305 | 78 | GGACTCTGCACGGCAAACCTGCTT | 34 | 8 | 30 | 21 | 23 | 17 |
| 3829 | 3814 | 30852 | 76.8 | GGACTCGTCGTTATCGCAGCAGGA | 34 | 10 | 12 | 24 | 31 | 25 |
| 3830 | 3815 | 16494 | 78.8 | GGACTCGTCCATGATGGGACTGCG | 34 | 10 | 15 | 27 | 34 | 29 |
| 3831 | 3816 | 11321 | 78.3 | GGACTCGTACGGCTTGGTCTTGCG | 34 | 10 | 35 | 11 | 19 | 29 |
| 3832 | 3817 | 30853 | 77.2 | GGACCTTGCTTGTGCGTTAGCACG | 34 | 11 | 11 | 29 | 3 | 30 |
| 3833 | 3818 | 30854 | 75.8 | GGACCTTGCGTTACGGCCTATTGA | 34 | 11 | 12 | 35 | 26 | 1 |
| 3834 | 3819 | 41042 | 77.7 | GGACCTTGCTCAAAAGCAGCAGCC | 34 | 11 | 13 | 6 | 31 | 36 |
| 3835 | 3820 | 11328 | 78.1 | GGACCTTGGAGTCACGAGCCATCG | 34 | 11 | 20 | 30 | 36 | 24 |
| 3836 | 3821 | 30855 | 77.1 | GGACCTTGGCAAGGACGCAAGAGT | 34 | 11 | 21 | 34 | 21 | 20 |
| 3837 | 3823 | 11332 | 79.2 | GGACCTTGCAGCGCTTGCAAAGTG | 34 | 11 | 31 | 17 | 21 | 22 |
| 3838 | 3824 | 16502 | 79.7 | GGACCTTGGTGCCGAATCGTGGAC | 34 | 11 | 33 | 16 | 10 | 34 |
| 3839 | 3825 | 11335 | 79.1 | GGACCTTGGGACGCAACGAAGACC | 34 | 11 | 34 | 21 | 16 | 32 |
| 3840 | 3826 | 30856 | 76.3 | GGACCGTTCGTTATACACGGGCAA | 34 | 12 | 12 | 5 | 35 | 21 |
| 3841 | 3827 | 16508 | 77.2 | GGACCGTTACCTGAGTTGCGGGAC | 34 | 12 | 23 | 20 | 29 | 34 |
| 3842 | 3828 | 22167 | 76.5 | GGACCGTTTGCGGAGTATCGTTGA | 34 | 12 | 29 | 20 | 24 | 1 |
| 3843 | 3829 | 11361 | 75.4 | GGACCTGTTTGATGCGGAGTAGCC | 34 | 14 | 1 | 29 | 20 | 36 |
| 3844 | 3830 | 11363 | 77.2 | GGACCTGTCCATCCATTCCCAGGA | 34 | 14 | 15 | 15 | 28 | 25 |
| 3845 | 3831 | 16519 | 79.1 | GGACCCATTGATCAGCGACCCCAT | 34 | 15 | 2 | 31 | 32 | 15 |
| 3846 | 3832 | 11374 | 77.1 | GGACCCATAAAGCTGTTCCCGTGC | 34 | 15 | 6 | 14 | 28 | 33 |
| 3847 | 3833 | 11378 | 77.9 | GGACCCATCTTGCTTGTCCCATCG | 34 | 15 | 11 | 11 | 28 | 24 |
| 3848 | 3834 | 16522 | 76.5 | GGACCCATGGTATGCGGTGCATAC | 34 | 15 | 18 | 29 | 33 | 5 |
| 3849 | 3835 | 11385 | 78.9 | GGACCCATCACGCTTGCGAACTTG | 34 | 15 | 30 | 11 | 16 | 11 |
| 3850 | 3836 | 22172 | 76.7 | GGACCCATGTGCATACGCAAGGAC | 34 | 15 | 33 | 5 | 21 | 34 |
| 3851 | 3837 | 30859 | 79.7 | GGACCGAATTGACTTGCACGCACG | 34 | 16 | 1 | 11 | 30 | 30 |
| 3852 | 3838 | 11392 | 77.4 | GGACCGAAATACACGGGTGCCCTA | 34 | 16 | 5 | 35 | 33 | 26 |
| 3853 | 3839 | 41053 | 76 | GGACCGAAAAAGTCTGCTTGGCAA | 34 | 16 | 6 | 8 | 11 | 21 |
| 3854 | 3840 | 30860 | 78.7 | GGACCGAACTTGACGGTCCCTCGT | 34 | 16 | 11 | 35 | 28 | 10 |
| 3855 | 3841 | 11397 | 75.6 | GGACCGAAGCTTTCGTAGGACACG | 34 | 16 | 17 | 10 | 25 | 30 |
| 3856 | 3842 | 41055 | 77.4 | GGACCGAAACCTGCTTGCTTGACC | 34 | 16 | 23 | 17 | 17 | 32 |
| 3857 | 3843 | 41056 | 77.1 | GGACCGAAAGGAATACCAGCCACG | 34 | 16 | 25 | 5 | 31 | 30 |
| 3858 | 3844 | 11402 | 77.4 | GGACCGAAGACCCAGCGCAATTAG | 34 | 16 | 32 | 31 | 21 | 3 |
| 3859 | 3845 | 16533 | 77 | GGACGCTTTTAGGGACCGAACGAA | 34 | 17 | 3 | 34 | 16 | 16 |
| 3860 | 3846 | 16534 | 79.3 | GGACGCTTAAAGGTGCGTGCTCCC | 34 | 17 | 6 | 33 | 33 | 28 |
| 3861 | 3847 | 41058 | 80 | GGACGCTTTGTCACCTTCCCTGCG | 34 | 17 | 9 | 23 | 28 | 29 |
| 3862 | 3848 | 41059 | 75.2 | GGACGCTTGGTAAATCGCTTTCGT | 34 | 17 | 18 | 4 | 17 | 10 |
| 3863 | 3849 | 11413 | 75.8 | GGACGCTTACCTGCAACGAACCAT | 34 | 17 | 23 | 21 | 16 | 15 |
| 3864 | 3850 | 30862 | 76.6 | GGACGCTTCCTATGTCATCGGCAA | 34 | 17 | 26 | 9 | 24 | 21 |
| 3865 | 3851 | 30863 | 79.9 | GGACGCTTTGCGTTGAATCGGACC | 34 | 17 | 29 | 1 | 24 | 32 |
| 3866 | 3852 | 41061 | 79.5 | GGACGGTACGTTTCGTTGCGGCTT | 34 | 18 | 12 | 10 | 29 | 17 |
| 3867 | 3853 | 16537 | 75.9 | GGACGGTACCATTGTCGCAAGGAC | 34 | 18 | 15 | 9 | 21 | 34 |
| 3868 | 3854 | 16539 | 79.1 | GGACGGTAGTGCAGTGCAGCGACC | 34 | 18 | 33 | 22 | 31 | 32 |
| 3869 | 3855 | 11431 | 78.5 | GGACGGTAGGACGCAATCCCACCT | 34 | 18 | 34 | 21 | 28 | 23 |
| 3870 | 3856 | 16540 | 80.7 | GGACGGTAAGCCGTGCACCTGTGC | 34 | 18 | 36 | 33 | 23 | 33 |
| 3871 | 3857 | 11433 | 80.2 | GGACGTCTTTGATCCCACGCGAA | 34 | 19 | 1 | 28 | 30 | 16 |
| 3872 | 3858 | 11434 | 76.8 | GGACGTCTTCGTGCAAGCAAAGGA | 34 | 19 | 10 | 21 | 21 | 25 |
| 3873 | 3859 | 16541 | 79.9 | GGACGTCTCCATGGACCAGCGACC | 34 | 19 | 15 | 34 | 31 | 32 |
| 3874 | 3860 | 11437 | 77.3 | GGACGTCTGCAAGACCTCTGTGCG | 34 | 19 | 21 | 32 | 8 | 29 |
| 3875 | 3861 | 16543 | 79.3 | GGACGTCTCACGCACGAAAGCAGC | 34 | 19 | 30 | 30 | 6 | 31 |
| 3876 | 3862 | 11449 | 77.1 | GGACGAGTATCGGGACCCTATGCG | 34 | 20 | 24 | 34 | 26 | 29 |

FIG. 25YYY

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 3877 | 3863 | 11452 | 82.4 | GGACGAGTCAGCGTGCGTGCAGGA | 34 | 20 | 31 | 33 | 33 | 25 |
| 3878 | 3864 | 11455 | 75 | GGACGAGTACGGTTGAATCGGCTT | 34 | 20 | 35 | 1 | 24 | 17 |
| 3879 | 3865 | 30864 | 79 | GGACGCAATTGAACGGAGTGCAGC | 34 | 21 | 1 | 35 | 22 | 31 |
| 3880 | 3866 | 11458 | 78.5 | GGACGCAAATACGTGCCCATGGAC | 34 | 21 | 5 | 33 | 15 | 34 |
| 3881 | 3867 | 22187 | 75.8 | GGACGCAATGTCCCATGGTAGGAC | 34 | 21 | 9 | 15 | 18 | 34 |
| 3882 | 3868 | 11460 | 77.1 | GGACGCAATCGTTCTGGTGCAAAG | 34 | 21 | 10 | 8 | 33 | 6 |
| 3883 | 3869 | 30865 | 77.1 | GGACGCAACCTAATACTGCGTGCG | 34 | 21 | 26 | 5 | 29 | 29 |
| 3884 | 3870 | 11468 | 78.4 | GGACGCAATGCGTTGAAGGATCGT | 34 | 21 | 29 | 1 | 25 | 10 |
| 3885 | 3871 | 11469 | 78.2 | GGACGCAAGTGCAGTGGTCTTCCC | 34 | 21 | 33 | 22 | 19 | 28 |
| 3886 | 3872 | 30866 | 76.6 | GGACGCAAGGACTCCCGGTAAAAG | 34 | 21 | 34 | 28 | 18 | 6 |
| 3887 | 3873 | 22189 | 78.9 | GGACGCAAACGGTGATCAGCCTTG | 34 | 21 | 35 | 2 | 31 | 11 |
| 3888 | 3874 | 16552 | 79.8 | GGACAGTGTGCGACGGACCTGTGC | 34 | 22 | 29 | 35 | 23 | 33 |
| 3889 | 3875 | 16556 | 78.8 | GGACACCTCACGGGACTGATTGCG | 34 | 23 | 30 | 34 | 2 | 29 |
| 3890 | 3876 | 16557 | 81.1 | GGACACCTGACCGTGCACGGCCTA | 34 | 23 | 32 | 33 | 35 | 26 |
| 3891 | 3877 | 30867 | 75.8 | GGACACCTAGCCTTAGCGTTTGCG | 34 | 23 | 36 | 3 | 12 | 29 |
| 3892 | 3878 | 11490 | 80.6 | GGACATCGAAAGACGGGTGCCACG | 34 | 24 | 6 | 35 | 33 | 30 |
| 3893 | 3879 | 41069 | 78.2 | GGACATCGGCTTCTTGCTTGACGG | 34 | 24 | 17 | 11 | 11 | 35 |
| 3894 | 3880 | 11496 | 78.9 | GGACATCGCACGGTCTAGCCATCG | 34 | 24 | 30 | 19 | 36 | 24 |
| 3895 | 3881 | 11499 | 79.3 | GGACATCGACGGGGACCTGTCGTT | 34 | 24 | 35 | 34 | 14 | 12 |
| 3896 | 3882 | 22199 | 78.9 | GGACAGGACGAAATCGTCCCGGAC | 34 | 25 | 16 | 24 | 28 | 34 |
| 3897 | 3883 | 16564 | 76.7 | GGACAGGAATCGACGGCCTACCAT | 34 | 25 | 24 | 35 | 26 | 15 |
| 3898 | 3884 | 11505 | 75.3 | GGACAGGAAGGATTGAGGACGTGC | 34 | 25 | 25 | 1 | 34 | 33 |
| 3899 | 3885 | 41072 | 77.3 | GGACCCTACGAAAGGATCGTTGCG | 34 | 26 | 16 | 25 | 10 | 29 |
| 3900 | 3886 | 11511 | 75.4 | GGACCCTAGCTTGCAAGTGCGTCT | 34 | 26 | 17 | 21 | 33 | 19 |
| 3901 | 3887 | 30869 | 78.7 | GGACCCTAGCAACAGCGATGCGAA | 34 | 26 | 21 | 31 | 27 | 16 |
| 3902 | 3888 | 11516 | 76.4 | GGACCCTACCTAGACCAGCCACGG | 34 | 26 | 26 | 32 | 36 | 35 |
| 3903 | 3889 | 41076 | 78.9 | GGACGATGCTCACTGTTGCGGACC | 34 | 27 | 13 | 14 | 29 | 32 |
| 3904 | 3890 | 30870 | 76.3 | GGACGATGGGTAACGGGGTACCAT | 34 | 27 | 18 | 35 | 18 | 15 |
| 3905 | 3891 | 11527 | 75.4 | GGACGATGGTCTAGCCCGAAAGTG | 34 | 27 | 19 | 36 | 16 | 22 |
| 3906 | 3892 | 41077 | 79.7 | GGACGATGATCGCGAAAGCCGTCT | 34 | 27 | 24 | 16 | 36 | 19 |
| 3907 | 3893 | 11535 | 78.6 | GGACTCCCTGTCCGTTGCTTGCAA | 34 | 28 | 9 | 12 | 17 | 21 |
| 3908 | 3894 | 11537 | 75.4 | GGACTCCCCTGTTACAGACCTGCG | 34 | 28 | 14 | 7 | 32 | 29 |
| 3909 | 3895 | 16576 | 77 | GGACTCCCCATTTAGCACGGATG | 34 | 28 | 15 | 3 | 30 | 27 |
| 3910 | 3896 | 30872 | 76.6 | GGACTCCCACCTAGCCCAGCTGTC | 34 | 28 | 23 | 36 | 31 | 9 |
| 3911 | 3897 | 16578 | 78.4 | GGACTCCCATCGCGAAAGGAGGAC | 34 | 28 | 24 | 16 | 25 | 34 |
| 3912 | 3898 | 41080 | 79.6 | GGACTCCCCACGCTTGCGTTAGGA | 34 | 28 | 30 | 11 | 12 | 25 |
| 3913 | 3899 | 11548 | 79.5 | GGACTCCCGGACGCTTCACGTGAT | 34 | 28 | 34 | 17 | 30 | 2 |
| 3914 | 3900 | 11551 | 78.9 | GGACTGCGTTAGCCATCACGACGG | 34 | 29 | 3 | 15 | 30 | 35 |
| 3915 | 3901 | 11555 | 78.1 | GGACTGCGTCGTCGTTCAGCAGTG | 34 | 29 | 10 | 12 | 31 | 22 |
| 3916 | 3902 | 16583 | 78 | GGACTGCGCTTGACCTCACGACCT | 34 | 29 | 11 | 23 | 30 | 23 |
| 3917 | 3903 | 11557 | 77.6 | GGACTGCGCTCATCGTCGTTTTGA | 34 | 29 | 13 | 10 | 12 | 1 |
| 3918 | 3904 | 30874 | 77.7 | GGACTGCGGCTTAGGAGCTTCACG | 34 | 29 | 17 | 25 | 17 | 30 |
| 3919 | 3905 | 16587 | 76.8 | GGACTGCGACCTTTGAGCAACGAA | 34 | 29 | 23 | 1 | 21 | 16 |
| 3920 | 3906 | 11563 | 78 | GGACTGCGATCGACCTCCATGGAC | 34 | 29 | 24 | 23 | 15 | 34 |
| 3921 | 3907 | 11565 | 77.5 | GGACTGCGGATGGAGTATCGCCAT | 34 | 29 | 27 | 20 | 24 | 15 |
| 3922 | 3908 | 11567 | 79.5 | GGACTGCGCACGATACCAGCAGGA | 34 | 29 | 30 | 5 | 31 | 25 |
| 3923 | 3909 | 11568 | 79.9 | GGACTGCGGGACCCATCCATGGTA | 34 | 29 | 34 | 15 | 15 | 18 |
| 3924 | 3910 | 16588 | 80.1 | GGACCACGTGATGACCTCCCCGAA | 34 | 30 | 2 | 32 | 28 | 16 |
| 3925 | 3911 | 30875 | 77.4 | GGACCACGCTCATTGATCCCCTGT | 34 | 30 | 13 | 1 | 28 | 14 |
| 3926 | 3912 | 11578 | 79.1 | GGACCACGGCTTTCTGCACGAGTG | 34 | 30 | 17 | 8 | 30 | 22 |
| 3927 | 3913 | 41086 | 76.9 | GGACCACGGAGTATCGCTCACACG | 34 | 30 | 20 | 24 | 13 | 30 |

FIG. 25ZZZ

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 3928 | 3914 | 11584 | 81.3 | GGACCACGCACGCTCAGTGCCCTA | 34 | 30 | 30 | 13 | 33 | 26 |
| 3929 | 3915 | 11589 | 79.7 | GGACCACGACGGTCTGTGCGTGTC | 34 | 30 | 35 | 8 | 29 | 9 |
| 3930 | 3916 | 16594 | 79.8 | GGACCACGAGCCCGAACGTTTGTC | 34 | 30 | 36 | 16 | 12 | 9 |
| 3931 | 3917 | 41088 | 78.1 | GGACCAGCTTGATCGTCGAAACGG | 34 | 31 | 1 | 10 | 16 | 35 |
| 3932 | 3918 | 11595 | 78.7 | GGACCAGCTGTCCAGCAGGACGAA | 34 | 31 | 9 | 31 | 25 | 16 |
| 3933 | 3919 | 30876 | 78 | GGACCAGCCTTGTGCGACGGATAC | 34 | 31 | 11 | 29 | 35 | 5 |
| 3934 | 3921 | 11599 | 78.9 | GGACCAGCCTGTGGACTGTCCACG | 34 | 31 | 14 | 34 | 9 | 30 |
| 3935 | 3922 | 30877 | 77.9 | GGACCAGCGGTATGATGACCAGCC | 34 | 31 | 18 | 2 | 32 | 36 |
| 3936 | 3923 | 41094 | 78.8 | GGACCAGCAGTGACCTGTGCGCTT | 34 | 31 | 22 | 23 | 33 | 17 |
| 3937 | 3924 | 11607 | 81.2 | GGACCAGCTGCGGACCCTCAGGAC | 34 | 31 | 29 | 32 | 13 | 34 |
| 3938 | 3925 | 30879 | 79.6 | GGACGACCTTGAGTGCGCAAGCAA | 34 | 32 | 1 | 33 | 21 | 21 |
| 3939 | 3926 | 30880 | 76.6 | GGACGACCCTGTAGTGCGTTCGAA | 34 | 32 | 14 | 22 | 12 | 16 |
| 3940 | 3927 | 22225 | 78 | GGACGACCGGTAGTGCAGCCAATC | 34 | 32 | 18 | 33 | 36 | 4 |
| 3941 | 3928 | 22226 | 79.4 | GGACGACCGTCTGTGCACCTCGAA | 34 | 32 | 19 | 33 | 23 | 16 |
| 3942 | 3929 | 11615 | 76.9 | GGACGACCGAGTCTTGGGACGAGT | 34 | 32 | 20 | 11 | 34 | 20 |
| 3943 | 3930 | 41097 | 78.2 | GGACGACCAGTGAAAGGTGCAGCC | 34 | 32 | 22 | 6 | 33 | 36 |
| 3944 | 3931 | 16601 | 80.6 | GGACGACCGACCCCATCTCATCCC | 34 | 32 | 32 | 15 | 13 | 28 |
| 3945 | 3932 | 11626 | 76.4 | GGACGTGCTGATTGATTCCCAGGA | 34 | 33 | 2 | 2 | 28 | 25 |
| 3946 | 3933 | 16603 | 80.1 | GGACGTGCAATCGGACCGTTTCGT | 34 | 33 | 4 | 34 | 12 | 10 |
| 3947 | 3934 | 11629 | 76.9 | GGACGTGCTCTGTCGTCCATACGG | 34 | 33 | 8 | 10 | 15 | 35 |
| 3948 | 3935 | 11630 | 79.9 | GGACGTGCTGTCCAGCACGGAGTG | 34 | 33 | 9 | 31 | 35 | 22 |
| 3949 | 3936 | 30881 | 78 | GGACGTGCTCGTCGAAGCAAACCT | 34 | 33 | 10 | 16 | 21 | 23 |
| 3950 | 3937 | 11632 | 78.9 | GGACGTGCCGTTGCTTCGAATGTC | 34 | 33 | 12 | 17 | 16 | 9 |
| 3951 | 3938 | 30882 | 79.8 | GGACGTGCCGAAATACTCCCGTGC | 34 | 33 | 16 | 5 | 28 | 33 |
| 3952 | 3939 | 30883 | 79.1 | GGACGTGCGGTATGTCGGACAGGA | 34 | 33 | 18 | 9 | 34 | 25 |
| 3953 | 3940 | 16606 | 81.4 | GGACGTGCAGTGGTGCTGCGACCT | 34 | 33 | 22 | 33 | 29 | 23 |
| 3954 | 3941 | 30884 | 76.3 | GGACGTGCCCTACCTATCGTTCCC | 34 | 33 | 26 | 26 | 10 | 28 |
| 3955 | 3942 | 16609 | 80 | GGACGTGCTGCGTGTCCTTGCTTG | 34 | 33 | 29 | 9 | 11 | 11 |
| 3956 | 3943 | 11644 | 81.6 | GGACGTGCCACGGGACAGTGCTTG | 34 | 33 | 30 | 34 | 22 | 11 |
| 3957 | 3944 | 11646 | 79.5 | GGACGTGCACGGTGATTGTCGACC | 34 | 33 | 35 | 2 | 9 | 32 |
| 3958 | 3945 | 16610 | 78 | GGACGGACTCGTCTGTCACGGGAC | 34 | 34 | 10 | 14 | 30 | 34 |
| 3959 | 3946 | 30885 | 78.1 | GGACGGACCGTTTTAGGACCGACC | 34 | 34 | 12 | 3 | 32 | 32 |
| 3960 | 3947 | 16612 | 77.7 | GGACGGACCTGTTACATCCCCACG | 34 | 34 | 14 | 7 | 28 | 30 |
| 3961 | 3948 | 30886 | 79.6 | GGACGGACCGAAGATGCAGCCTGT | 34 | 34 | 16 | 27 | 31 | 14 |
| 3962 | 3949 | 41101 | 78.8 | GGACGGACGAGTTACATGCGACGG | 34 | 34 | 20 | 7 | 29 | 35 |
| 3963 | 3950 | 30887 | 79.3 | GGACGGACACCTGCAACTTGGCAA | 34 | 34 | 23 | 21 | 11 | 21 |
| 3964 | 3951 | 41103 | 77.2 | GGACGGACGATGTTAGACGGAGCC | 34 | 34 | 27 | 3 | 35 | 36 |
| 3965 | 3952 | 11662 | 79.5 | GGACGGACTCCCAGTGACGGTCGT | 34 | 34 | 28 | 22 | 35 | 10 |
| 3966 | 3953 | 22239 | 79.6 | GGACGGACTGCGAGGATCTGCCAT | 34 | 34 | 29 | 25 | 8 | 15 |
| 3967 | 3954 | 11664 | 77.3 | GGACGGACCAGCCCATGCTTAAAG | 34 | 34 | 31 | 15 | 17 | 6 |
| 3968 | 3955 | 11667 | 79.2 | GGACACGGTTAGGACCTGCGAGCC | 34 | 35 | 3 | 32 | 29 | 36 |
| 3969 | 3956 | 16616 | 79.1 | GGACACGGTCTGAGCCTCGTGTGC | 34 | 35 | 8 | 36 | 10 | 33 |
| 3970 | 3957 | 11670 | 77.1 | GGACACGGCGTTAATCTGCGAGTG | 34 | 35 | 12 | 4 | 29 | 22 |
| 3971 | 3958 | 11672 | 75.5 | GGACACGGCTGTTACAGCTTTCCC | 34 | 35 | 14 | 7 | 17 | 28 |
| 3972 | 3959 | 22240 | 78 | GGACACGGGAGTCGAAGGACATCG | 34 | 35 | 20 | 16 | 34 | 24 |
| 3973 | 3960 | 11674 | 77.4 | GGACACGGAGTGCGTTCCTAAGCC | 34 | 35 | 22 | 12 | 26 | 36 |
| 3974 | 3961 | 11681 | 77.3 | GGACAGCCCGTTCTTGAATCCAGC | 34 | 36 | 12 | 11 | 4 | 31 |
| 3975 | 3962 | 30889 | 76.6 | GGACAGCCTGTAAAGAGCCGACC | 34 | 36 | 14 | 6 | 36 | 32 |
| 3976 | 3963 | 11688 | 81.1 | GGACAGCCTGCGGCAACTCAGTGC | 34 | 36 | 29 | 21 | 13 | 33 |
| 3977 | 3964 | 16618 | 82.8 | GGACAGCCCACGCACGTGATGCAA | 34 | 36 | 30 | 30 | 2 | 21 |
| 3978 | 3965 | 11690 | 80.8 | GGACAGCCGACCCGTTCTGTCACG | 34 | 36 | 32 | 12 | 14 | 30 |

FIG. 25AAAA

| SEQ ID NO: | 4,633 ID# | BBX ID# | Tm | ZIPCODE (5'-3') | TETRAMER NUMBERS | | | | | |
|---|---|---|---|---|---|---|---|---|---|---|
| 3979 | 3966 | 11692 | 79.1 | GGACAGCCGGACCCTACTCAACGG | 34 | 36 | 34 | 26 | 13 | 35 |
| 3980 | 3968 | 30890 | 77.9 | ACGGTTGACCATTGATTGCGGCTT | 35 | 1 | 15 | 2 | 29 | 17 |
| 3981 | 3969 | 11704 | 79.8 | ACGGTTGACAGCCACGATCGCTCA | 35 | 1 | 31 | 30 | 24 | 13 |
| 3982 | 3970 | 11705 | 80.2 | ACGGTTGAGACCGGACGATGACGG | 35 | 1 | 32 | 34 | 27 | 35 |
| 3983 | 3971 | 41106 | 78.5 | ACGGTTGAGTGCTGCGTTGATCCC | 35 | 1 | 33 | 29 | 1 | 28 |
| 3984 | 3972 | 41107 | 78.7 | ACGGTGATCGAAGCAAATCGCAGC | 35 | 2 | 16 | 21 | 24 | 31 |
| 3985 | 3973 | 16624 | 77.2 | ACGGTGATGCAAACCTTCCCTCGT | 35 | 2 | 21 | 23 | 28 | 10 |
| 3986 | 3974 | 16625 | 79.1 | ACGGTGATGGACTCCCTGCGGTCT | 35 | 2 | 34 | 28 | 29 | 19 |
| 3987 | 3975 | 30891 | 77.4 | ACGGTTAGGCAACACGGATGGACC | 35 | 3 | 21 | 30 | 27 | 32 |
| 3988 | 3976 | 11723 | 75.2 | ACGGTTAGTCCCAAAGGGACTCCC | 35 | 3 | 28 | 6 | 34 | 28 |
| 3989 | 3977 | 41110 | 78.1 | ACGGTTAGCACGCAGCTTGAAGCC | 35 | 3 | 30 | 31 | 1 | 36 |
| 3990 | 3978 | 22253 | 78.5 | ACGGAATCCCATTCGTAGCCGACC | 35 | 4 | 15 | 10 | 36 | 32 |
| 3991 | 3979 | 16633 | 76.3 | ACGGAATCCGAAACCTGGACCCTA | 35 | 4 | 16 | 23 | 34 | 26 |
| 3992 | 3980 | 30892 | 78.6 | ACGGAATCATCGAGCCCAGCAGTG | 35 | 4 | 24 | 36 | 31 | 22 |
| 3993 | 3981 | 41116 | 79.4 | ACGGAATCCCACACGAGCCACGG | 35 | 4 | 26 | 30 | 36 | 35 |
| 3994 | 3982 | 11742 | 76.6 | ACGGAATCGATGTCTGGACCTCCC | 35 | 4 | 27 | 8 | 32 | 28 |
| 3995 | 3983 | 11743 | 77.3 | ACGGAATCTCCCGGTAGCAACGAA | 35 | 4 | 28 | 18 | 21 | 16 |
| 3996 | 3984 | 41117 | 77 | ACGGAATCGGACTGATACGGCCAT | 35 | 4 | 34 | 2 | 35 | 15 |
| 3997 | 3985 | 30893 | 76.1 | ACGGATACCGAACGTTCGAACGAA | 35 | 5 | 16 | 12 | 16 | 16 |
| 3998 | 3986 | 41119 | 75.7 | ACGGATACGCTTGACCCGTTATCG | 35 | 5 | 17 | 32 | 12 | 24 |
| 3999 | 3987 | 16644 | 77 | ACGGATACGGACTTGACACGCGAA | 35 | 5 | 34 | 1 | 30 | 16 |
| 4000 | 3988 | 41122 | 75.9 | ACGGAAAGCTCAGCAACAGCGTCT | 35 | 6 | 13 | 21 | 31 | 19 |
| 4001 | 3989 | 16647 | 75.2 | ACGGAAAGCTGTATCGCTTGGACC | 35 | 6 | 14 | 24 | 11 | 32 |
| 4002 | 3990 | 30894 | 76.1 | ACGGAAAGCGAATTAGACGGGGAC | 35 | 6 | 16 | 3 | 35 | 34 |
| 4003 | 3991 | 16650 | 75.4 | ACGGAAAGGAGTATCGTCCCCCAT | 35 | 6 | 20 | 24 | 28 | 15 |
| 4004 | 3992 | 30895 | 78.8 | ACGGAAAGAGGACACGTCCCCAGC | 35 | 6 | 25 | 30 | 28 | 31 |
| 4005 | 3993 | 11771 | 76.5 | ACGGAAAGCAGCTCGTGTGCTGAT | 35 | 6 | 31 | 10 | 33 | 2 |
| 4006 | 3994 | 16653 | 79.2 | ACGGAAAGGTGCGACCCCATATCG | 35 | 6 | 33 | 32 | 15 | 24 |
| 4007 | 3995 | 41125 | 78.8 | ACGGAAAGAGCCGGTAGCAAACGG | 35 | 6 | 36 | 18 | 21 | 35 |
| 4008 | 3996 | 11777 | 76.8 | ACGGTACAGCTTGATGGCTTTGCG | 35 | 7 | 17 | 27 | 17 | 29 |
| 4009 | 3997 | 30896 | 76.3 | ACGGTACATGCGTCCCTGATACGG | 35 | 7 | 29 | 28 | 2 | 35 |
| 4010 | 3998 | 11786 | 81.8 | ACGGTCTGAAAGCACGCACGCGAA | 35 | 8 | 6 | 30 | 30 | 16 |
| 4011 | 3999 | 16655 | 78.4 | ACGGTCTGCGTTGACCAGTGTCCC | 35 | 8 | 12 | 32 | 22 | 28 |
| 4012 | 4000 | 11789 | 77.3 | ACGGTCTGCTCACGTTCAGCAGGA | 35 | 8 | 13 | 12 | 31 | 25 |
| 4013 | 4001 | 11790 | 76.6 | ACGGTCTGCTGTCGAAATCGGATG | 35 | 8 | 14 | 16 | 24 | 27 |
| 4014 | 4002 | 16656 | 80 | ACGGTCTGCCATGTGCCACGTGTC | 35 | 8 | 15 | 33 | 30 | 9 |
| 4015 | 4003 | 41126 | 76.4 | ACGGTCTGGGTATTGAATCGTGCG | 35 | 8 | 18 | 1 | 24 | 29 |
| 4016 | 4004 | 16657 | 77.5 | ACGGTCTGAGGAACCTAGCCGCAA | 35 | 8 | 25 | 23 | 36 | 21 |
| 4017 | 4005 | 11800 | 78 | ACGGTCTGGGACCCATACGGGTCT | 35 | 8 | 34 | 15 | 35 | 19 |
| 4018 | 4006 | 30897 | 78.1 | ACGGTGTCCTCAGGACGTGCCTGT | 35 | 9 | 13 | 34 | 33 | 14 |
| 4019 | 4007 | 30898 | 75.2 | ACGGTGTCCCATATCGAATCGCTT | 35 | 9 | 15 | 24 | 4 | 17 |
| 4020 | 4008 | 11803 | 76.6 | ACGGTGTCGGTAAGTGGTCTTGCG | 35 | 9 | 18 | 22 | 19 | 29 |
| 4021 | 4009 | 16662 | 79.1 | ACGGTGTCCACGACCTGACCGATG | 35 | 9 | 30 | 23 | 32 | 27 |
| 4022 | 4010 | 30899 | 79.1 | ACGGTCGTTGATTTGAACGGCACG | 35 | 10 | 2 | 1 | 35 | 30 |
| 4023 | 4011 | 30900 | 77.9 | ACGGTCGTCGTTTAGACGGCAGC | 35 | 10 | 12 | 3 | 35 | 31 |
| 4024 | 4012 | 41130 | 77 | ACGGTCGTCTCATTAGCAGCTGCG | 35 | 10 | 13 | 3 | 31 | 29 |
| 4025 | 4013 | 30901 | 76.7 | ACGGTCGTGCTTAGGACGTTCACG | 35 | 10 | 17 | 25 | 12 | 30 |
| 4026 | 4014 | 16667 | 76 | ACGGTCGTACCTTCGTTGCGAAAG | 35 | 10 | 23 | 10 | 29 | 6 |
| 4027 | 4015 | 30902 | 78.5 | ACGGTCGTGATGAAAGGGACTGCG | 35 | 10 | 27 | 6 | 34 | 29 |
| 4028 | 4016 | 11823 | 80.9 | ACGGTCGTTGCGCTTGTCGTTCGT | 35 | 10 | 29 | 11 | 10 | 10 |
| 4029 | 4017 | 11824 | 80.4 | ACGGTCGTGTGCCCATGATGCTCA | 35 | 10 | 33 | 15 | 27 | 13 |

FIG. 25BBBB

| SEQ ID NO: | 4,633 ID# | HEX ID# | Tm | ZIPCODE (5'-3') | TETRAMER NUMBERS | | | | |
|---|---|---|---|---|---|---|---|---|---|
| 4030 | 4018 | 41133 | 77.5 | ACGGTCGTACGGATACTGCGGACC | 35 | 10 | 35 | 5 | 29 32 |
| 4031 | 4019 | 16668 | 78.8 | ACGGCTTGTCTGAGGAGTGCACGG | 35 | 11 | 8 | 25 | 33 35 |
| 4032 | 4020 | 16669 | 76 | ACGGCTTGTCGTGCTTAATCAGCC | 35 | 11 | 10 | 17 | 4 36 |
| 4033 | 4021 | 30903 | 78.4 | ACGGCTTGGGTACTCACACGGTGC | 35 | 11 | 18 | 13 | 30 33 |
| 4034 | 4022 | 30904 | 78.4 | ACGGCTTGGAGTCGTTCAGCCTCA | 35 | 11 | 20 | 12 | 31 13 |
| 4035 | 4023 | 30905 | 78.3 | ACGGCTTGAGTGTCCCTCTGGCAA | 35 | 11 | 22 | 28 | 8 21 |
| 4036 | 4024 | 41138 | 78.8 | ACGGCTTGACCTGACCCCATCCAT | 35 | 11 | 23 | 32 | 15 15 |
| 4037 | 4025 | 30906 | 77.8 | ACGGCTTGAGGAGGACTCCCGTCT | 35 | 11 | 25 | 34 | 28 19 |
| 4038 | 4026 | 11842 | 80.3 | ACGGCTTGCAGCCAGCTGATTCGT | 35 | 11 | 31 | 31 | 2 10 |
| 4039 | 4027 | 11844 | 80.9 | ACGGCTTGGTGCCCATTGATGTGC | 35 | 11 | 33 | 15 | 2 33 |
| 4040 | 4028 | 11845 | 79.7 | ACGGCTTGGGACCACGACCTGGTA | 35 | 11 | 34 | 30 | 23 18 |
| 4041 | 4029 | 16671 | 77.2 | ACGGCTTGACGGATACCGTTTCGT | 35 | 11 | 35 | 5 | 12 10 |
| 4042 | 4030 | 11847 | 78.2 | ACGGCGTTTGATGATGATCGGACC | 35 | 12 | 2 | 27 | 24 32 |
| 4043 | 4031 | 11849 | 75.7 | ACGGCGTTTACAGACCCTGTGGAC | 35 | 12 | 7 | 32 | 14 34 |
| 4044 | 4032 | 11850 | 79.2 | ACGGCGTTCTGGTCTCAGCCCAT | 35 | 12 | 8 | 19 | 31 15 |
| 4045 | 4033 | 11851 | 76 | ACGGCGTTTGTCTTGAAGGACAGC | 35 | 12 | 9 | 1 | 25 31 |
| 4046 | 4034 | 41141 | 76.4 | ACGGCGTTCTCATTGAAAAGCGAA | 35 | 12 | 13 | 1 | 6 16 |
| 4047 | 4035 | 41142 | 76.8 | ACGGCGTTCTGTACCTCTTGTGCG | 35 | 12 | 14 | 23 | 11 29 |
| 4048 | 4036 | 11856 | 78.1 | ACGGCGTTGCTTGCTTAGGAGTGC | 35 | 12 | 17 | 17 | 25 33 |
| 4049 | 4037 | 11857 | 75.3 | ACGGCGTTGGTATCGTAGGACGTT | 35 | 12 | 18 | 10 | 25 12 |
| 4050 | 4038 | 41143 | 75.5 | ACGGCGTTACCTAGTGACGGCTGT | 35 | 12 | 23 | 22 | 35 14 |
| 4051 | 4039 | 30907 | 76.6 | ACGGCGTTAGGAATCGGTCTCGTT | 35 | 12 | 25 | 24 | 19 12 |
| 4052 | 4040 | 11861 | 76.3 | ACGGCGTTCCTAAATCGTGCTTGA | 35 | 12 | 26 | 4 | 33 1 |
| 4053 | 4041 | 11862 | 80.5 | ACGGCGTTTGCGTTGAGATGAGCC | 35 | 12 | 29 | 1 | 27 36 |
| 4054 | 4042 | 11863 | 80 | ACGGCGTTCACGGTCTTCGTTCGT | 35 | 12 | 30 | 19 | 10 10 |
| 4055 | 4043 | 11864 | 80.1 | ACGGCGTTCAGCTGCGTGATCTCA | 35 | 12 | 31 | 29 | 2 13 |
| 4056 | 4044 | 11865 | 78.5 | ACGGCGTTGGACACCTGCTTTGTC | 35 | 12 | 34 | 23 | 17 9 |
| 4057 | 4045 | 41145 | 79.1 | ACGGCGTTACGGTACAATCGTGCG | 35 | 12 | 35 | 7 | 24 29 |
| 4058 | 4046 | 41146 | 79.4 | ACGGCTCATGATCACGACGGCTTG | 35 | 13 | 2 | 30 | 35 11 |
| 4059 | 4047 | 11867 | 76.3 | ACGGCTCATTAGGCAACGTTCGAA | 35 | 13 | 3 | 21 | 12 16 |
| 4060 | 4048 | 30908 | 77.8 | ACGGCTCAAAAGGTGCGCAAAATC | 35 | 13 | 6 | 33 | 21 4 |
| 4061 | 4049 | 16677 | 76.6 | ACGGCTCATCGTATCGAGTGACGG | 35 | 13 | 10 | 24 | 22 35 |
| 4062 | 4050 | 11874 | 76.3 | ACGGCTCACGTTCTGTCCATGCTT | 35 | 13 | 12 | 14 | 15 17 |
| 4063 | 4051 | 30909 | 78.8 | ACGGCTCAGCTTGCAATGCGAATC | 35 | 13 | 17 | 21 | 29 4 |
| 4064 | 4052 | 11878 | 75.8 | ACGGCTCAGGTAATACGGACGTGC | 35 | 13 | 18 | 5 | 34 33 |
| 4065 | 4053 | 11881 | 76 | ACGGCTCAGCAAAGGACTGTACGG | 35 | 13 | 21 | 25 | 14 35 |
| 4066 | 4054 | 41151 | 77.1 | ACGGCTCACCTACCTAAGCCGTGC | 35 | 13 | 26 | 26 | 36 33 |
| 4067 | 4055 | 11886 | 82.1 | ACGGCTCATGCGGATGAGTGTGCG | 35 | 13 | 29 | 27 | 22 29 |
| 4068 | 4056 | 11888 | 78.3 | ACGGCTCAGACCCTTGGTGCTTGA | 35 | 13 | 32 | 11 | 33 1 |
| 4069 | 4058 | 11890 | 75.9 | ACGGCTGTAATCTCTGTCCCGTGC | 35 | 14 | 4 | 8 | 28 33 |
| 4070 | 4059 | 41153 | 80.3 | ACGGCTGTTCTGGGACGACCGATG | 35 | 14 | 8 | 34 | 32 27 |
| 4071 | 4060 | 30911 | 78 | ACGGCTGTCGAAAGTGGACCGGTA | 35 | 14 | 16 | 22 | 32 18 |
| 4072 | 4061 | 11896 | 77.3 | ACGGCTGTGCTTCTGTGCAAAGGA | 35 | 14 | 17 | 14 | 21 25 |
| 4073 | 4063 | 30912 | 78.9 | ACGGCTGTGTCTTGCGGAGTCAGC | 35 | 14 | 19 | 29 | 20 31 |
| 4074 | 4064 | 41155 | 76.1 | ACGGCTGTGAGTAGTGAGCCCAGC | 35 | 14 | 20 | 22 | 36 31 |
| 4075 | 4065 | 30913 | 79 | ACGGCTGTACCTTGTCAGCCGCAA | 35 | 14 | 23 | 9 | 36 21 |
| 4076 | 4066 | 30914 | 77.7 | ACGGCTGTACGGTGATTCGTGCAA | 35 | 14 | 35 | 2 | 10 21 |
| 4077 | 4067 | 11907 | 78.1 | ACGGCCATTGTCCGTTTCTGCTGT | 35 | 15 | 9 | 12 | 8 14 |
| 4078 | 4068 | 11908 | 77.9 | ACGGCCATTCGTGTGCCCTAGGTA | 35 | 15 | 10 | 33 | 26 18 |
| 4079 | 4069 | 30916 | 77.2 | ACGGCCATCTCAACCTCTTGCCAT | 35 | 15 | 13 | 23 | 11 15 |
| 4080 | 4070 | 30917 | 78 | ACGGCCATAGTGCCATAGCCAGGA | 35 | 15 | 22 | 15 | 36 25 |

FIG. 25CCCC

| SEQ ID NO: | 4,633 ID# | HEX ID# | Tm | ZIPCODE (5'-3') | TETRAMER NUMBERS | | | | |
|---|---|---|---|---|---|---|---|---|---|
| 4081 | 4071 | 41157 | 76.2 | ACGGCCATCCTAGCTTTGTCTCCC | 35 | 15 | 26 | 17 | 9 | 28 |
| 4082 | 4072 | 11917 | 81.8 | ACGGCCATTCCCCCATCTGTCACG | 35 | 15 | 28 | 15 | 14 | 30 |
| 4083 | 4073 | 11918 | 82.5 | ACGGCCATTGCGCGTTGAGTCGTT | 35 | 15 | 29 | 12 | 28 | 12 |
| 4084 | 4074 | 11919 | 79.9 | ACGGCCATGACCCTGTCCATACGG | 35 | 15 | 32 | 14 | 15 | 35 |
| 4085 | 4075 | 41158 | 78.3 | ACGGCCATAGCCCCTAAAAGGCAA | 35 | 15 | 36 | 26 | 6 | 21 |
| 4086 | 4076 | 41159 | 77.4 | ACGGCGAATTGAAGTGATCGGCTT | 35 | 16 | 1 | 22 | 24 | 17 |
| 4087 | 4077 | 30918 | 76.6 | ACGGCGAATGATAGGACAGCGATG | 35 | 16 | 2 | 25 | 31 | 27 |
| 4088 | 4078 | 41160 | 77.7 | ACGGCGAATTAGGATGCTTGACGG | 35 | 16 | 3 | 27 | 11 | 35 |
| 4089 | 4079 | 11922 | 75.8 | ACGGCGAAAATCTACAATCGGTGC | 35 | 16 | 4 | 7 | 24 | 33 |
| 4090 | 4080 | 11924 | 75.3 | ACGGCGAATCTGTCTGGGTATCGT | 35 | 16 | 8 | 8 | 18 | 10 |
| 4091 | 4081 | 41161 | 79.3 | ACGGCGAATCGTTGATCGTTTCCC | 35 | 16 | 10 | 2 | 12 | 28 |
| 4092 | 4082 | 11926 | 79.4 | ACGGCGAACTTGGAGTGTGCATCG | 35 | 16 | 11 | 20 | 33 | 24 |
| 4093 | 4083 | 11927 | 79 | ACGGCGAACGTTTCGTCTGTCGAA | 35 | 16 | 12 | 10 | 14 | 16 |
| 4094 | 4084 | 11928 | 76.1 | ACGGCGAACTCATTGACCATCGTT | 35 | 16 | 13 | 1 | 15 | 12 |
| 4095 | 4085 | 11931 | 75.6 | ACGGCGAAGGTATCTGAGTGCGTT | 35 | 16 | 18 | 8 | 22 | 12 |
| 4096 | 4086 | 41162 | 79.4 | ACGGCGAAGAGTGATGGATGTGCG | 35 | 16 | 20 | 27 | 27 | 29 |
| 4097 | 4087 | 41163 | 80.4 | ACGGCGAAATCGAGGATGTCTGCG | 35 | 16 | 24 | 25 | 9 | 29 |
| 4098 | 4088 | 11935 | 79.8 | ACGGCGAATCCCACCTGCTTGGTA | 35 | 16 | 28 | 23 | 17 | 18 |
| 4099 | 4089 | 11937 | 80.1 | ACGGCGAACACGCTTGGAGTTCGT | 35 | 16 | 30 | 11 | 20 | 10 |
| 4100 | 4090 | 30919 | 80.8 | ACGGCGAAGTGCACGGTCGTCCTA | 35 | 16 | 33 | 35 | 10 | 26 |
| 4101 | 4091 | 11939 | 80.1 | ACGGCGAAGGACCTCACACGCTGT | 35 | 16 | 34 | 13 | 30 | 14 |
| 4102 | 4092 | 11940 | 79.5 | ACGGCGAAAGCCAATCCGAACTTG | 35 | 16 | 36 | 4 | 16 | 11 |
| 4103 | 4093 | 30920 | 75.2 | ACGGGCTTTTGACCTAATCGCTTG | 35 | 17 | 1 | 26 | 24 | 11 |
| 4104 | 4094 | 16691 | 76.5 | ACGGGCTTTGATTACATGCGATCG | 35 | 17 | 2 | 7 | 29 | 24 |
| 4105 | 4095 | 30921 | 77.4 | ACGGGCTTTTAGGTGCCGTTCTCA | 35 | 17 | 3 | 33 | 12 | 13 |
| 4106 | 4096 | 30922 | 77.3 | ACGGGCTTAAAGCCTATCCCCAGC | 35 | 17 | 6 | 26 | 28 | 31 |
| 4107 | 4097 | 16692 | 76.3 | ACGGGCTTTACATCGTCAGCAGGA | 35 | 17 | 7 | 10 | 31 | 25 |
| 4108 | 4098 | 30923 | 78.7 | ACGGGCTTCGTTCTCACGTTTCCC | 35 | 17 | 12 | 13 | 12 | 28 |
| 4109 | 4099 | 30924 | 76.3 | ACGGGCTTCTCATCGTCCTAAGCC | 35 | 17 | 13 | 10 | 26 | 36 |
| 4110 | 4100 | 41164 | 75.1 | ACGGGCTTCTGTAGGAGCTTCGAA | 35 | 17 | 14 | 25 | 17 | 16 |
| 4111 | 4101 | 11949 | 75.6 | ACGGGCTTGGTAAAAGCTGTCGAA | 35 | 17 | 18 | 6 | 14 | 16 |
| 4112 | 4102 | 30926 | 77.3 | ACGGGCTTGAGTGGTAGTGCCGTT | 35 | 17 | 20 | 18 | 33 | 12 |
| 4113 | 4103 | 11957 | 80.1 | ACGGGCTTTCCCGCTTCCATCCTA | 35 | 17 | 28 | 17 | 15 | 26 |
| 4114 | 4104 | 11958 | 75.9 | ACGGGCTTGACCTTGATTAGTGCG | 35 | 17 | 32 | 1 | 3 | 29 |
| 4115 | 4105 | 11960 | 75.8 | ACGGGTATGATCACGGATGCCTA | 35 | 18 | 2 | 30 | 27 | 26 |
| 4116 | 4106 | 16703 | 76.1 | ACGGGTATACAAGCCGTGCTTGA | 35 | 18 | 7 | 36 | 33 | 1 |
| 4117 | 4107 | 16704 | 76.6 | ACGGGTATCTGACGGAGTGTCCC | 35 | 18 | 8 | 35 | 22 | 28 |
| 4118 | 4108 | 22300 | 75.2 | ACGGGTACGTTCACGAATCTCGT | 35 | 18 | 12 | 30 | 4 | 10 |
| 4119 | 4109 | 30927 | 77.4 | ACGGGTACTGTGAGTTCCCCACG | 35 | 18 | 14 | 20 | 28 | 30 |
| 4120 | 4110 | 30928 | 77.3 | ACGGGTAGCTTGGTACAGCCGAA | 35 | 18 | 17 | 18 | 31 | 16 |
| 4121 | 4111 | 30929 | 76 | ACGGGTAGCAAAATCCGAAGACC | 35 | 18 | 21 | 4 | 16 | 32 |
| 4122 | 4112 | 11972 | 76.2 | ACGGGTAAGGAGTCTCACGAGCC | 35 | 18 | 25 | 19 | 30 | 36 |
| 4123 | 4113 | 16710 | 75.3 | ACGGGTACCTATCCCTCGTCCAT | 35 | 18 | 26 | 28 | 10 | 15 |
| 4124 | 4114 | 11975 | 78.6 | ACGGGTATGCGCGTTAGGAGACC | 35 | 18 | 29 | 12 | 25 | 32 |
| 4125 | 4115 | 11976 | 76.6 | ACGGGTAGTGCATACGAGTTGCG | 35 | 18 | 33 | 5 | 20 | 29 |
| 4126 | 4116 | 30930 | 76.3 | ACGGGTAGGACTCTGCTTGAGCC | 35 | 18 | 34 | 8 | 11 | 36 |
| 4127 | 4117 | 16711 | 78.4 | ACGGGTAACGGCCTAAATCCACG | 35 | 18 | 35 | 26 | 4 | 30 |
| 4128 | 4118 | 16712 | 78.5 | ACGGGTAAGCCCGAACTGTACGG | 35 | 18 | 36 | 16 | 14 | 35 |
| 4129 | 4119 | 11982 | 76.1 | ACGGGTCTAAAGCGAATCCCCTTG | 35 | 19 | 6 | 16 | 28 | 11 |
| 4130 | 4120 | 41170 | 78.5 | ACGGGTCTCGTTGCAAGATGGTGC | 35 | 19 | 12 | 21 | 27 | 33 |
| 4131 | 4121 | 11987 | 76.6 | ACGGGTCTCTCAAGCCACCTCGTT | 35 | 19 | 13 | 36 | 23 | 12 |

FIG. 25DDDD

| SEQ ID NO: | 4,633 ID# | HEX ID# | Tm | ZIPCODE (5'-3') | TETRAMER NUMBERS | | | | |
|---|---|---|---|---|---|---|---|---|---|
| 4132 | 4122 | 11990 | 76.9 | ACGGGTCTCGAAGGACGTCTGGAC | 35 | 19 | 16 | 34 | 19 | 34 |
| 4133 | 4123 | 30931 | 79.1 | ACGGGTCTATCGACGGGCTTCGAA | 35 | 19 | 24 | 35 | 17 | 16 |
| 4134 | 4124 | 11997 | 78.2 | ACGGGTCTGACCCTTGGGACTCGT | 35 | 19 | 32 | 11 | 34 | 10 |
| 4135 | 4125 | 11998 | 77.5 | ACGGGTCTGTGCAAAGGATGTCCC | 35 | 19 | 33 | 6 | 27 | 28 |
| 4136 | 4126 | 11999 | 78.6 | ACGGGTCTACGGGACCTCGTGGAC | 35 | 19 | 35 | 32 | 10 | 34 |
| 4137 | 4127 | 12000 | 76.1 | ACGGGAGTTGATCTGTTCCCCCAT | 35 | 20 | 2 | 14 | 28 | 15 |
| 4138 | 4128 | 16717 | 78.9 | ACGGGAGTCTTGCAGCACCTTCCC | 35 | 20 | 11 | 31 | 23 | 28 |
| 4139 | 4129 | 12004 | 76.6 | ACGGGAGTCTCAAGCCAAAGCCAT | 35 | 20 | 13 | 36 | 6 | 15 |
| 4140 | 4130 | 30932 | 78.8 | ACGGGAGTGGTAAGTGGTGCGCAA | 35 | 20 | 18 | 22 | 33 | 21 |
| 4141 | 4131 | 12011 | 78.9 | ACGGGAGTGATGGTGCTCTGGCAA | 35 | 20 | 27 | 33 | 8 | 21 |
| 4142 | 4132 | 12012 | 79.4 | ACGGGAGTTCCCCTGTCACGATCG | 35 | 20 | 28 | 14 | 30 | 24 |
| 4143 | 4133 | 30933 | 77.7 | ACGGGAGTCAGCTGATGACCGACC | 35 | 20 | 31 | 2 | 32 | 32 |
| 4144 | 4134 | 30934 | 77.8 | ACGGGCAAAATCAGTGCCATCCAT | 35 | 21 | 4 | 22 | 15 | 15 |
| 4145 | 4135 | 30935 | 76.8 | ACGGGCAAATACAGTGATCGGCAA | 35 | 21 | 5 | 22 | 24 | 21 |
| 4146 | 4136 | 41174 | 76.1 | ACGGGCAATACACTTGAGCCGGTA | 35 | 21 | 7 | 11 | 36 | 18 |
| 4147 | 4137 | 30936 | 76.4 | ACGGGCAACGTTTAGCCTAAGCC | 35 | 21 | 12 | 3 | 26 | 36 |
| 4148 | 4138 | 12024 | 78.2 | ACGGGCAAGCTTCGAACAGCTCTG | 35 | 21 | 17 | 16 | 31 | 8 |
| 4149 | 4139 | 12026 | 76.5 | ACGGGCAAGAGTCTCAGACCCCAT | 35 | 21 | 20 | 13 | 32 | 15 |
| 4150 | 4140 | 30937 | 80 | ACGGGCAAGCAAATCGCGTTGTCT | 35 | 21 | 21 | 24 | 12 | 19 |
| 4151 | 4141 | 16725 | 75.5 | ACGGGCAACCTACACGCCTAGGTA | 35 | 21 | 26 | 30 | 26 | 18 |
| 4152 | 4142 | 12033 | 82.4 | ACGGGCAAACGGCCATGTCTCGAA | 35 | 21 | 35 | 15 | 19 | 16 |
| 4153 | 4143 | 12034 | 79.1 | ACGGGCAAAGCCTCTGCCTAGTGC | 35 | 21 | 36 | 8 | 26 | 33 |
| 4154 | 4144 | 30938 | 77.6 | ACGGAGTGCGAATTGATCGTTCCC | 35 | 22 | 16 | 1 | 10 | 28 |
| 4155 | 4146 | 22312 | 77.6 | ACGGAGTGGGTACGAAGTGCGACC | 35 | 22 | 18 | 16 | 33 | 32 |
| 4156 | 4147 | 12044 | 76.9 | ACGGAGTGGAGTTGTCTCCCCAGC | 35 | 22 | 20 | 9 | 28 | 31 |
| 4157 | 4148 | 41178 | 77.4 | ACGGAGTGGCAACAGCCTTGACCT | 35 | 22 | 21 | 31 | 11 | 23 |
| 4158 | 4149 | 22313 | 76.6 | ACGGAGTGATCGTCGTCTCAACGG | 35 | 22 | 24 | 10 | 13 | 35 |
| 4159 | 4150 | 12047 | 75.4 | ACGGAGTGCCTACGTTTGTCCGTT | 35 | 22 | 26 | 12 | 9 | 12 |
| 4160 | 4151 | 12048 | 77.9 | ACGGAGTGTGCGTCGTGCAAGGTA | 35 | 22 | 29 | 10 | 21 | 18 |
| 4161 | 4152 | 16729 | 80.5 | ACGGAGTGGGACGCTTGCAACAGC | 35 | 22 | 34 | 17 | 21 | 31 |
| 4162 | 4153 | 12055 | 78.1 | ACGGACCTTGATGATGTCCCACGG | 35 | 23 | 2 | 27 | 28 | 35 |
| 4163 | 4154 | 12058 | 78.9 | ACGGACCTTGTCCGTTGACCCGTT | 35 | 23 | 9 | 12 | 32 | 12 |
| 4164 | 4155 | 12059 | 77.5 | ACGGACCTCTTGCACGCCTAAGGA | 35 | 23 | 11 | 30 | 26 | 25 |
| 4165 | 4156 | 30939 | 75.9 | ACGGACCTGCTTAAAGCCATCACG | 35 | 23 | 17 | 6 | 15 | 30 |
| 4166 | 4157 | 12063 | 77.9 | ACGGACCTGTCTGACCCCATCGAA | 35 | 23 | 19 | 32 | 15 | 16 |
| 4167 | 4158 | 12066 | 78.6 | ACGGACCTTCCCGAGTTTGAACGG | 35 | 23 | 28 | 20 | 1 | 35 |
| 4168 | 4159 | 30940 | 78.3 | ACGGACCTGACCAAAGACGGGCTT | 35 | 23 | 32 | 6 | 35 | 17 |
| 4169 | 4160 | 16731 | 78.1 | ACGGACCTAGCCGCTTTCTGTCCC | 35 | 23 | 36 | 17 | 8 | 28 |
| 4170 | 4161 | 41185 | 76.8 | ACGGATCGAAAGTCCCAAAGACGG | 35 | 24 | 6 | 28 | 6 | 35 |
| 4171 | 4163 | 12074 | 80.3 | ACGGATCGTGTCCGAACACGAGCC | 35 | 24 | 9 | 16 | 30 | 36 |
| 4172 | 4164 | 30942 | 77.8 | ACGGATCGCTCACGAATCCCTCTG | 35 | 24 | 13 | 16 | 28 | 8 |
| 4173 | 4165 | 12079 | 77.9 | ACGGATCGCTGTCTGTGATGCGAA | 35 | 24 | 14 | 14 | 27 | 16 |
| 4174 | 4166 | 41188 | 78.5 | ACGGATCGGAGTCGAACGAACACG | 35 | 24 | 20 | 16 | 16 | 30 |
| 4175 | 4167 | 41189 | 79.8 | ACGGATCGGCAACTTGGACCCTCA | 35 | 24 | 21 | 11 | 32 | 13 |
| 4176 | 4168 | 12083 | 77.4 | ACGGATCGAGTGTCTGCCATCACG | 35 | 24 | 22 | 8 | 15 | 30 |
| 4177 | 4169 | 30943 | 77.1 | ACGGATCGACCTCTTGACGGGGTA | 35 | 24 | 23 | 11 | 35 | 18 |
| 4178 | 4170 | 30945 | 79.4 | ACGGATCGCAGCTCCCTGATGCTT | 35 | 24 | 31 | 28 | 2 | 17 |
| 4179 | 4171 | 12088 | 78.2 | ACGGATCGGGACGGACTTAGCCAT | 35 | 24 | 34 | 34 | 3 | 15 |
| 4180 | 4172 | 12089 | 80.6 | ACGGATCGACGGCTCAGAGTTGCG | 35 | 24 | 35 | 13 | 20 | 29 |
| 4181 | 4173 | 22320 | 78.1 | ACGGATCGAGCCCCTAAGGAGTGC | 35 | 24 | 36 | 26 | 25 | 33 |
| 4182 | 4175 | 22321 | 75 | ACGGAGGATCTGGCAAACCTATCG | 35 | 25 | 8 | 21 | 23 | 24 |

FIG. 25EEEE

| SEQ ID NO: | 4,633 ID# | HEX ID# | Tm | ZIPCODE (5'-3') | TETRAMER NUMBERS | | | | |
|---|---|---|---|---|---|---|---|---|---|
| 4183 | 4176 | 12098 | 75.5 | ACGGAGGACCATAATCGATGACGG | 35 | 25 | 15 | 4 | 27 | 35 |
| 4184 | 4177 | 30946 | 76.7 | ACGGAGGAGCTTGTGCCGTTACCT | 35 | 25 | 17 | 33 | 12 | 23 |
| 4185 | 4178 | 41192 | 78.6 | ACGGAGGAGGTATCGTGTGCTGCG | 35 | 25 | 18 | 10 | 33 | 29 |
| 4186 | 4179 | 22323 | 79.8 | ACGGAGGAGTCTAGCCCACGTGCG | 35 | 25 | 19 | 36 | 30 | 29 |
| 4187 | 4180 | 16734 | 76.6 | ACGGAGGAGCAAAGCCAATCCTGT | 35 | 25 | 21 | 36 | 4 | 14 |
| 4188 | 4181 | 12106 | 79.6 | ACGGAGGATGCGCCTAACCTCACG | 35 | 25 | 29 | 26 | 23 | 30 |
| 4189 | 4182 | 12110 | 76.7 | ACGGCCTATCTGGAGTCAGCCGTT | 35 | 26 | 8 | 20 | 31 | 12 |
| 4190 | 4183 | 41199 | 78.5 | ACGGCCTACTGTGGACACGGCTTG | 35 | 26 | 14 | 34 | 35 | 11 |
| 4191 | 4184 | 30948 | 77.1 | ACGGCCTAGAGTTCGTGGACCAGC | 35 | 26 | 20 | 10 | 34 | 31 |
| 4192 | 4185 | 30950 | 76.7 | ACGGCCTACCTATCCCTGTCACGG | 35 | 26 | 26 | 28 | 9 | 35 |
| 4193 | 4186 | 22328 | 76.5 | ACGGGATGAATCCCATAGGAACGG | 35 | 27 | 4 | 15 | 25 | 35 |
| 4194 | 4187 | 12121 | 76.6 | ACGGGATGCCATCGAATTAGTCCC | 35 | 27 | 15 | 16 | 3 | 28 |
| 4195 | 4188 | 41207 | 80.2 | ACGGGATGATCGGAGTCGTTTGCG | 35 | 27 | 24 | 20 | 12 | 29 |
| 4196 | 4189 | 41208 | 76.8 | ACGGGATGCCTAAGTGCTTGTCCC | 35 | 27 | 26 | 22 | 11 | 28 |
| 4197 | 4190 | 12129 | 78.3 | ACGGGATGGGACCACGATACTCCC | 35 | 27 | 34 | 30 | 5 | 28 |
| 4198 | 4191 | 12131 | 80.1 | ACGGGATGAGCCGTGCACGGATAC | 35 | 27 | 36 | 33 | 35 | 5 |
| 4199 | 4192 | 16741 | 75.8 | ACGGTCCCTTGACGTTGCAAAAAG | 35 | 28 | 1 | 12 | 21 | 6 |
| 4200 | 4193 | 30952 | 79.2 | ACGGTCCCCTCAAATCACGGATCG | 35 | 28 | 13 | 4 | 35 | 24 |
| 4201 | 4194 | 41214 | 78.6 | ACGGTCCCCATACCTGACCGGTA | 35 | 28 | 15 | 23 | 32 | 18 |
| 4202 | 4195 | 30953 | 78.1 | ACGGTCCCAGTGTGTCTGCGACCT | 35 | 28 | 22 | 9 | 29 | 23 |
| 4203 | 4196 | 12142 | 79.6 | ACGGTCCCATCGGCTTGTCTCAGC | 35 | 28 | 24 | 17 | 19 | 31 |
| 4204 | 4197 | 12143 | 77 | ACGGTCCCCTATCGTGATGCTGT | 35 | 28 | 26 | 10 | 27 | 14 |
| 4205 | 4198 | 12144 | 76.4 | ACGGTCCCGATGTGATTTAGCACG | 35 | 28 | 27 | 2 | 3 | 30 |
| 4206 | 4199 | 30954 | 78.4 | ACGGTGCGTTGAATACAGCCGACC | 35 | 29 | 1 | 5 | 36 | 32 |
| 4207 | 4200 | 16745 | 75.4 | ACGGTGCGTGATAGGATCTGGCTT | 35 | 29 | 2 | 25 | 8 | 17 |
| 4208 | 4201 | 16746 | 79 | ACGGTGCGTTAGGGACGACCACCT | 35 | 29 | 3 | 34 | 32 | 23 |
| 4209 | 4202 | 41217 | 76.9 | ACGGTGCGATACAATCATCGCGTT | 35 | 29 | 5 | 4 | 24 | 12 |
| 4210 | 4203 | 41218 | 76.8 | ACGGTGCGTACACGTTGGACCCTA | 35 | 29 | 7 | 12 | 34 | 26 |
| 4211 | 4204 | 12150 | 80.5 | ACGGTGCGCTTGCCTAAGGACACG | 35 | 29 | 11 | 26 | 25 | 30 |
| 4212 | 4205 | 12152 | 78.7 | ACGGTGCGCCATATACGACCAGGA | 35 | 29 | 15 | 5 | 32 | 25 |
| 4213 | 4206 | 30955 | 81.7 | ACGGTGCGAGTGCTGTCAGCCAGC | 35 | 29 | 22 | 14 | 31 | 31 |
| 4214 | 4207 | 12153 | 78.9 | ACGGTGCGAGGACTCAGATGCAGC | 35 | 29 | 25 | 13 | 27 | 31 |
| 4215 | 4208 | 12154 | 83.4 | ACGGTGCGTGCGCACGAATCCTGT | 35 | 29 | 29 | 30 | 4 | 14 |
| 4216 | 4209 | 12155 | 83.4 | ACGGTGCGCACGGTGCCTGTCCTA | 35 | 29 | 30 | 33 | 14 | 26 |
| 4217 | 4210 | 30957 | 82.7 | ACGGTGCGCAGCACCTCCATGCTT | 35 | 29 | 31 | 23 | 15 | 17 |
| 4218 | 4211 | 12156 | 82.7 | ACGGTGCGGTGCGAGTGCTTCGTT | 35 | 29 | 33 | 20 | 17 | 12 |
| 4219 | 4212 | 12157 | 82.2 | ACGGTGCGGGACCAGCACCTCTTG | 35 | 29 | 34 | 31 | 23 | 11 |
| 4220 | 4213 | 12158 | 81.2 | ACGGTGCGAGCCCTTGGAGTGCTT | 35 | 29 | 36 | 11 | 20 | 17 |
| 4221 | 4214 | 12159 | 77.6 | ACGGCACGTTGAGGACTGATTCCC | 35 | 30 | 1 | 34 | 2 | 28 |
| 4222 | 4215 | 41220 | 76.7 | ACGGCACGTGATACGGTGATCGTT | 35 | 30 | 2 | 35 | 2 | 12 |
| 4223 | 4216 | 41221 | 77.2 | ACGGCACGTTAGAGTGATCGCGAA | 35 | 30 | 3 | 22 | 24 | 16 |
| 4224 | 4217 | 41222 | 80.5 | ACGGCACGAATCCAGCTCTGACGG | 35 | 30 | 4 | 31 | 8 | 35 |
| 4225 | 4218 | 30958 | 77.7 | ACGGCACGTACATGATTGCGCCTA | 35 | 30 | 7 | 2 | 29 | 26 |
| 4226 | 4219 | 12162 | 79.5 | ACGGCACGTCTGCTCAATCGATCG | 35 | 30 | 8 | 13 | 24 | 24 |
| 4227 | 4220 | 12164 | 79.5 | ACGGCACGTCGTGCTTCGAATCTG | 35 | 30 | 10 | 17 | 16 | 8 |
| 4228 | 4221 | 30959 | 80.6 | ACGGCACGGAGTCTCACAGCGGAC | 35 | 30 | 20 | 13 | 31 | 34 |
| 4229 | 4222 | 12168 | 78.2 | ACGGCACGACCTCGAATCTGAGGA | 35 | 30 | 23 | 16 | 8 | 25 |
| 4230 | 4223 | 16748 | 81.6 | ACGGCACGCAGCTGATGGACGGTA | 35 | 30 | 31 | 2 | 34 | 18 |
| 4231 | 4224 | 12172 | 81.9 | ACGGCACGGGACGGACGGTATCTG | 35 | 30 | 34 | 34 | 18 | 8 |
| 4232 | 4225 | 12173 | 81.7 | ACGGCACGACGGTCGTGAGTCGAA | 35 | 30 | 35 | 10 | 20 | 16 |
| 4233 | 4226 | 16749 | 75 | ACGGCAGCTTAGAAAGCCATTCGT | 35 | 31 | 3 | 6 | 15 | 10 |

FIG. 25FFFF

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 4234 | 4227 | 16750 | 78.5 | ACGGCAGCTGTCCGAAATACCACG | 35 | 31 | 9 | 16 | 5 | 30 |
| 4235 | 4228 | 12179 | 79.5 | ACGGCAGCCTTGCTCAGATGGCTT | 35 | 31 | 11 | 13 | 27 | 17 |
| 4236 | 4229 | 22350 | 80.1 | ACGGCAGCCTGTTTAGACGGCGAA | 35 | 31 | 14 | 3 | 35 | 16 |
| 4237 | 4230 | 12181 | 78.3 | ACGGCAGCCCATAATCCACGTCTG | 35 | 31 | 15 | 4 | 30 | 8 |
| 4238 | 4231 | 12182 | 81.3 | ACGGCAGCCGAACTGTTCGTGTGC | 35 | 31 | 16 | 14 | 10 | 33 |
| 4239 | 4232 | 12183 | 81.6 | ACGGCAGCGCTTGAGTGAGTTGCG | 35 | 31 | 17 | 20 | 20 | 29 |
| 4240 | 4233 | 22351 | 79 | ACGGCAGCGGTACACGTTAGCGAA | 35 | 31 | 18 | 30 | 3 | 16 |
| 4241 | 4234 | 12188 | 77.7 | ACGGCAGCAGGAGTCTACGGCTGT | 35 | 31 | 25 | 19 | 35 | 14 |
| 4242 | 4235 | 12190 | 80.9 | ACGGCAGCCACGAGGAGCAATTGA | 35 | 31 | 30 | 25 | 21 | 1 |
| 4243 | 4236 | 12191 | 82.5 | ACGGCAGCCAGCCTGTCGAACAGC | 35 | 31 | 31 | 14 | 16 | 31 |
| 4244 | 4237 | 12193 | 81.2 | ACGGCAGCGTGCCCTATCCCAATC | 35 | 31 | 33 | 26 | 28 | 4 |
| 4245 | 4238 | 12194 | 82.1 | ACGGCAGCACGGTCGTGACCAGTG | 35 | 31 | 35 | 10 | 32 | 22 |
| 4246 | 4239 | 12195 | 75.7 | ACGGGACCTTGATTGACGTTCAGC | 35 | 32 | 1 | 1 | 12 | 31 |
| 4247 | 4240 | 16752 | 78.1 | ACGGGACCAATCACCTGACCATCG | 35 | 32 | 4 | 23 | 32 | 24 |
| 4248 | 4241 | 16753 | 76.6 | ACGGGACCAAAGAATCGATGGACC | 35 | 32 | 6 | 4 | 27 | 32 |
| 4249 | 4242 | 12199 | 76.2 | ACGGGACCTACACAGCGCAACTGT | 35 | 32 | 7 | 31 | 21 | 14 |
| 4250 | 4243 | 12201 | 78.7 | ACGGGACCCGTTGTCTTCGTAGCC | 35 | 32 | 12 | 19 | 10 | 36 |
| 4251 | 4244 | 30960 | 79.1 | ACGGGACCCTCAGTGCGATGACCT | 35 | 32 | 13 | 33 | 27 | 23 |
| 4252 | 4245 | 30961 | 78.8 | ACGGGACCCCATACCTCGAACGAA | 35 | 32 | 15 | 23 | 16 | 16 |
| 4253 | 4246 | 12202 | 79.1 | ACGGGACCCGAACTCATGTCGCTT | 35 | 32 | 16 | 13 | 9 | 17 |
| 4254 | 4247 | 16754 | 76.6 | ACGGGACCGCTTAATCCCTAGCAA | 35 | 32 | 17 | 4 | 26 | 21 |
| 4255 | 4248 | 12206 | 76.5 | ACGGGACCATCGTCCCACCTAATC | 35 | 32 | 24 | 28 | 23 | 4 |
| 4256 | 4249 | 12208 | 80.3 | ACGGGACCGATGGATGCAGCTGTC | 35 | 32 | 27 | 27 | 31 | 9 |
| 4257 | 4250 | 12209 | 78.7 | ACGGGACCTCCCATCGGGTATTGA | 35 | 32 | 28 | 24 | 18 | 1 |
| 4258 | 4251 | 16755 | 80.3 | ACGGGACCCAGCCGAACCTAATCG | 35 | 32 | 31 | 16 | 26 | 24 |
| 4259 | 4252 | 12212 | 81.3 | ACGGGACCGTGCGGACTTAGGTGC | 35 | 32 | 33 | 34 | 3 | 33 |
| 4260 | 4253 | 41229 | 77.2 | ACGGGTGCTTGAGTCTAGCCCAGC | 35 | 33 | 1 | 19 | 36 | 31 |
| 4261 | 4254 | 30963 | 77.7 | ACGGGTGCTGATTTGAATCGAGCC | 35 | 33 | 2 | 1 | 24 | 36 |
| 4262 | 4255 | 30964 | 76.2 | ACGGGTGCTTAGTCTGGCTTTCCC | 35 | 33 | 3 | 8 | 17 | 28 |
| 4263 | 4256 | 41230 | 79.7 | ACGGGTGCAATCGCTTCTTGAGCC | 35 | 33 | 4 | 17 | 11 | 36 |
| 4264 | 4257 | 41231 | 77.7 | ACGGGTGCATACACCTGACCCGTT | 35 | 33 | 5 | 23 | 32 | 12 |
| 4265 | 4258 | 16757 | 80.7 | ACGGGTGCTGTCGGACTCTGCAGC | 35 | 33 | 9 | 34 | 8 | 31 |
| 4266 | 4259 | 12216 | 79.2 | ACGGGTGCCTCACTGTTGTCACGG | 35 | 33 | 13 | 14 | 9 | 35 |
| 4267 | 4260 | 12217 | 77.8 | ACGGGTGCCGAAGACCCCTAAATC | 35 | 33 | 16 | 32 | 26 | 4 |
| 4268 | 4261 | 12218 | 79.7 | ACGGGTGCGCTTGCTTTTGAGGAC | 35 | 33 | 17 | 17 | 1 | 34 |
| 4269 | 4262 | 30965 | 78.4 | ACGGGTGCGTCTCCTAACGGACCT | 35 | 33 | 19 | 26 | 35 | 23 |
| 4270 | 4263 | 12220 | 80.7 | ACGGGTGCGCAACAGCTGATCCAT | 35 | 33 | 21 | 31 | 2 | 15 |
| 4271 | 4264 | 12221 | 79.4 | ACGGGTGCAGTGGACCACGGTACA | 35 | 33 | 22 | 32 | 35 | 7 |
| 4272 | 4265 | 22367 | 77.4 | ACGGGTGCACCTGCAACTCATCTG | 35 | 33 | 23 | 21 | 13 | 8 |
| 4273 | 4266 | 12223 | 80.3 | ACGGGTGCTGCGAGGAATACCACG | 35 | 33 | 29 | 25 | 5 | 30 |
| 4274 | 4267 | 12224 | 80.5 | ACGGGTGCGACCATCGGGTACTCA | 35 | 33 | 32 | 24 | 18 | 13 |
| 4275 | 4268 | 12225 | 81.7 | ACGGGTGCGGACCACGGGTATGTC | 35 | 33 | 34 | 30 | 18 | 9 |
| 4276 | 4269 | 12226 | 75.8 | ACGGGACTTGAAAAGTTGATGCG | 35 | 34 | 1 | 6 | 1 | 29 |
| 4277 | 4270 | 41232 | 77.3 | ACGGGACTTAGTGCGGCAACCTA | 35 | 34 | 3 | 29 | 21 | 26 |
| 4278 | 4271 | 30966 | 78.9 | ACGGGACTACAACGGGGACCTCA | 35 | 34 | 7 | 35 | 34 | 13 |
| 4279 | 4272 | 30967 | 78.9 | ACGGGACCTTGACGGTTGATCGT | 35 | 34 | 11 | 35 | 1 | 10 |
| 4280 | 4273 | 41234 | 78.3 | ACGGGACCGTTATCGCGAAGAGT | 35 | 34 | 12 | 24 | 16 | 20 |
| 4281 | 4274 | 30968 | 77.5 | ACGGGACGGTAAGGAAATCGCTT | 35 | 34 | 18 | 25 | 4 | 17 |
| 4282 | 4275 | 12237 | 79.8 | ACGGGACGCAAAGTGCCATAGGA | 35 | 34 | 21 | 22 | 15 | 25 |
| 4283 | 4276 | 22374 | 77.5 | ACGGGACACCTGAGTTCCCAGTG | 35 | 34 | 23 | 20 | 28 | 22 |
| 4284 | 4277 | 12238 | 77.2 | ACGGGACATCGTCCCATCGATAC | 35 | 34 | 24 | 28 | 24 | 5 |

FIG. 25GGGG

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 4285 | 4278 | 12239 | 81.2 | ACGGGGACTCCCGATGCTCAATCG | 35 | 34 | 28 | 27 | 13 | 24 |
| 4286 | 4279 | 12240 | 82.3 | ACGGGGACTGCGCTGTGCTTGGAC | 35 | 34 | 29 | 14 | 17 | 34 |
| 4287 | 4280 | 12241 | 80.8 | ACGGGGACGTGCGCAACCTAACCT | 35 | 34 | 33 | 21 | 26 | 23 |
| 4288 | 4281 | 12243 | 76.1 | ACGGACGGTTGAGGTACACGAGGA | 35 | 35 | 1 | 18 | 30 | 25 |
| 4289 | 4282 | 41238 | 77 | ACGGACGGTACACGAACAGCCTCA | 35 | 35 | 7 | 16 | 31 | 13 |
| 4290 | 4283 | 41239 | 78.5 | ACGGACGGTCTGAATCACCTTGCG | 35 | 35 | 8 | 4 | 23 | 29 |
| 4291 | 4284 | 41241 | 79.1 | ACGGACGGTCGTGGTAGACCGCTT | 35 | 35 | 10 | 18 | 32 | 17 |
| 4292 | 4285 | 30970 | 79.2 | ACGGACGGCTCAGTCTTCCCGGTA | 35 | 35 | 13 | 19 | 28 | 18 |
| 4293 | 4286 | 30971 | 77.7 | ACGGACGGGAGTTCGTAATCTGCG | 35 | 35 | 20 | 10 | 4 | 29 |
| 4294 | 4287 | 12249 | 80 | ACGGACGGGCAATCGTCAGCTGAT | 35 | 35 | 21 | 10 | 31 | 2 |
| 4295 | 4288 | 12251 | 77.3 | ACGGACGGACCTGGTAGTGCTCGT | 35 | 35 | 23 | 18 | 33 | 10 |
| 4296 | 4289 | 12253 | 76.6 | ACGGACGGGATGTCCCAAAGAATC | 35 | 35 | 27 | 28 | 6 | 4 |
| 4297 | 4290 | 12254 | 78.7 | ACGGACGGTCCCTCTGGGTACAGC | 35 | 35 | 28 | 8 | 18 | 31 |
| 4298 | 4291 | 12256 | 80.1 | ACGGACGGCAGCTTGACGAATCGT | 35 | 35 | 31 | 1 | 16 | 10 |
| 4299 | 4292 | 12258 | 82.9 | ACGGACGGGTGCCTGTCGAACACG | 35 | 35 | 33 | 14 | 16 | 30 |
| 4300 | 4293 | 12259 | 80.8 | ACGGACGGAGCCGCTTGTCTAGCC | 35 | 35 | 36 | 17 | 19 | 36 |
| 4301 | 4294 | 16761 | 76.7 | ACGGAGCCTTAGCTTGGACCGGTA | 35 | 36 | 3 | 11 | 32 | 18 |
| 4302 | 4295 | 12262 | 78.1 | ACGGAGCCAATCGTCTATCGGCAA | 35 | 36 | 4 | 19 | 24 | 21 |
| 4303 | 4296 | 22383 | 77.5 | ACGGAGCCTGTCCGAAGCAACTGT | 35 | 36 | 9 | 16 | 21 | 14 |
| 4304 | 4297 | 12265 | 76.7 | ACGGAGCCTCGTGGTATGATTCCC | 35 | 36 | 10 | 18 | 2 | 28 |
| 4305 | 4298 | 12268 | 76.7 | ACGGAGCCCTGTTCCCAATCAATC | 35 | 36 | 14 | 28 | 4 | 4 |
| 4306 | 4299 | 41247 | 79.7 | ACGGAGCCCGAAGATGGGTAAGCC | 35 | 36 | 16 | 27 | 18 | 36 |
| 4307 | 4300 | 12270 | 79.6 | ACGGAGCCAGTGGGACTGTCGGAC | 35 | 36 | 22 | 34 | 9 | 34 |
| 4308 | 4301 | 41251 | 77.1 | ACGGAGCCCCTATACATCCCCCAT | 35 | 36 | 26 | 7 | 28 | 15 |
| 4309 | 4302 | 12274 | 77.6 | ACGGAGCCGATGAATCAGGAATCG | 35 | 36 | 27 | 4 | 25 | 24 |
| 4310 | 4303 | 12275 | 80.7 | ACGGAGCCTCCCGCAAGGTAGTGC | 35 | 36 | 28 | 21 | 18 | 33 |
| 4311 | 4304 | 12277 | 82.1 | ACGGAGCCCAGCGATGTTGAACGG | 35 | 36 | 31 | 27 | 1 | 35 |
| 4312 | 4305 | 12278 | 81.1 | ACGGAGCCGACCCCTATGTCCACG | 35 | 36 | 32 | 26 | 9 | 30 |
| 4313 | 4306 | 12279 | 83.1 | ACGGAGCCGGACGATGCTGTCACG | 35 | 36 | 34 | 27 | 14 | 30 |
| 4314 | 4307 | 12280 | 79.8 | ACGGAGCCACGGTTGACGTTCCAT | 35 | 36 | 35 | 1 | 12 | 15 |
| 4315 | 4308 | 22393 | 76.3 | AGCCTTGAAAAGTGCGCGAAAGTG | 36 | 1 | 6 | 29 | 16 | 22 |
| 4316 | 4309 | 41252 | 78 | AGCCTTGATCGTGCTTGCAAAGCC | 36 | 1 | 10 | 17 | 21 | 36 |
| 4317 | 4310 | 30972 | 77.9 | AGCCTTGACGTTCTCAAGCCCACG | 36 | 1 | 12 | 13 | 36 | 30 |
| 4318 | 4311 | 41253 | 79.8 | AGCCTTGAGCTTGTGCACGGGACC | 36 | 1 | 17 | 33 | 35 | 32 |
| 4319 | 4312 | 30973 | 77.3 | AGCCTTGAGCAATGTCGATGCGAA | 36 | 1 | 21 | 9 | 27 | 16 |
| 4320 | 4313 | 41254 | 76.6 | AGCCTTGAAGGAACCTGGACCGAA | 36 | 1 | 25 | 23 | 34 | 16 |
| 4321 | 4314 | 12288 | 80.2 | AGCCTTGAGATGTGCGACGGCGTT | 36 | 1 | 27 | 29 | 35 | 12 |
| 4322 | 4315 | 12293 | 78.8 | AGCCTTGAGGACGCAACTTGTGCG | 36 | 1 | 34 | 21 | 11 | 29 |
| 4323 | 4316 | 30974 | 76.9 | AGCCTGATGCTTACGGTGTCTGCG | 36 | 2 | 17 | 35 | 9 | 29 |
| 4324 | 4318 | 12308 | 75.4 | AGCCTTAGGCTTCAGCGATGGATG | 36 | 3 | 17 | 31 | 27 | 27 |
| 4325 | 4319 | 12315 | 75.2 | AGCCTTAGCAGCATCGCTTGGAGT | 36 | 3 | 31 | 24 | 11 | 20 |
| 4326 | 4320 | 30976 | 78.2 | AGCCAATCCGTTTGTCGTGCGAGT | 36 | 4 | 12 | 9 | 33 | 20 |
| 4327 | 4321 | 41261 | 77.8 | AGCCAATCGCAAGAGTACGGGTGC | 36 | 4 | 21 | 20 | 35 | 33 |
| 4328 | 4322 | 12327 | 79.5 | AGCCAATCAGTGAGCCACGGTCCC | 36 | 4 | 22 | 36 | 35 | 28 |
| 4329 | 4323 | 30977 | 75.3 | AGCCAATCAGGATGCGGCTTTTAG | 36 | 4 | 25 | 29 | 17 | 3 |
| 4330 | 4324 | 30978 | 76.7 | AGCCAATCCCTATGTCTCCCCACG | 36 | 4 | 26 | 9 | 28 | 30 |
| 4331 | 4325 | 12329 | 75.5 | AGCCAATCGATGAAAGTGCGGTCT | 36 | 4 | 27 | 6 | 29 | 19 |
| 4332 | 4326 | 22403 | 75.6 | AGCCAATCGGACTACACACGTCCC | 36 | 4 | 34 | 7 | 30 | 28 |
| 4333 | 4327 | 12332 | 78.2 | AGCCAATCAGCCCTGTACGGCTCA | 36 | 4 | 36 | 14 | 35 | 13 |
| 4334 | 4328 | 41263 | 75.7 | AGCCATACCGTTACGGTGTCCAGC | 36 | 5 | 12 | 35 | 9 | 31 |
| 4335 | 4329 | 16784 | 75 | AGCCATACGCTTCTCAATCGGCTT | 36 | 5 | 17 | 13 | 24 | 17 |

FIG. 25HHHH

| SEQ ID NO: | 4,633 ID# | HEX ID# | Tm | ZIPCODE (5'-3') | TETRAMER NUMBERS | | | | |
|---|---|---|---|---|---|---|---|---|---|
| 4336 | 4330 | 12342 | 76.5 | AGCCATACACCTGGACCCATTCCC | 36 | 5 | 23 | 34 | 15 | 28 |
| 4337 | 4331 | 12343 | 78.3 | AGCCATACAGGATCCCGTGCGATG | 36 | 5 | 25 | 28 | 33 | 27 |
| 4338 | 4332 | 12346 | 79.1 | AGCCATACCAGCGACCGGACACCT | 36 | 5 | 31 | 32 | 34 | 23 |
| 4339 | 4333 | 30979 | 79 | AGCCATACGTGCCTCATGCGCCTA | 36 | 5 | 33 | 13 | 29 | 26 |
| 4340 | 4334 | 12351 | 77.9 | AGCCAAAGTGATTCCCGACCTCCC | 36 | 6 | 2 | 28 | 32 | 28 |
| 4341 | 4335 | 22406 | 78.2 | AGCCAAAGTCTGGCAAGCTTTGCG | 36 | 6 | 8 | 21 | 17 | 29 |
| 4342 | 4336 | 16789 | 77.2 | AGCCAAAGGCAAGGACAGTGAGCC | 36 | 6 | 21 | 34 | 22 | 36 |
| 4343 | 4337 | 12357 | 81.3 | AGCCAAAGAGTGGTGCGTGCACGG | 36 | 6 | 22 | 33 | 33 | 35 |
| 4344 | 4338 | 12358 | 75.2 | AGCCAAAGAGGACTCACGAAACGG | 36 | 6 | 25 | 13 | 16 | 35 |
| 4345 | 4339 | 41267 | 75 | AGCCAAAGCCTATGATTCCCATCG | 36 | 6 | 26 | 2 | 28 | 24 |
| 4346 | 4340 | 30980 | 77.1 | AGCCAAAGGACCTTGACACGAGCC | 36 | 6 | 32 | 1 | 30 | 36 |
| 4347 | 4341 | 41271 | 76.3 | AGCCTACATGCGATACTGCGCCAT | 36 | 7 | 29 | 5 | 29 | 15 |
| 4348 | 4342 | 30981 | 77.8 | AGCCTCTGCTTGTTGACACGCACG | 36 | 8 | 11 | 1 | 30 | 30 |
| 4349 | 4343 | 41272 | 78.9 | AGCCTCTGCTCAGACCGGACGCTT | 36 | 8 | 13 | 32 | 34 | 17 |
| 4350 | 4344 | 12372 | 75.5 | AGCCTCTGCTGTATCGCGAAGGAC | 36 | 8 | 14 | 24 | 16 | 34 |
| 4351 | 4345 | 12374 | 77.5 | AGCCTCTGGAGTCACGCGAACCAT | 36 | 8 | 20 | 30 | 16 | 15 |
| 4352 | 4346 | 12378 | 75.5 | AGCCTCTGGATGAAAGGATGGCAA | 36 | 8 | 27 | 6 | 27 | 21 |
| 4353 | 4347 | 30982 | 77.1 | AGCCTCTGGGACATCGAGCCAAAG | 36 | 8 | 34 | 24 | 36 | 6 |
| 4354 | 4349 | 12392 | 77.8 | AGCCTGTCTGCGCGAATACATCCC | 36 | 9 | 29 | 16 | 7 | 28 |
| 4355 | 4350 | 16797 | 77.8 | AGCCTGTCCAGCAAAGCAGCACCT | 36 | 9 | 31 | 6 | 31 | 23 |
| 4356 | 4351 | 30983 | 75.4 | AGCCTCGTTTGATGTCGCTTAGCC | 36 | 10 | 1 | 9 | 17 | 36 |
| 4357 | 4353 | 12398 | 75.9 | AGCCTCGTTGTCTACATGCGGACC | 36 | 10 | 9 | 7 | 29 | 32 |
| 4358 | 4354 | 12403 | 78 | AGCCTCGTGAGTGGACAGCCCTTG | 36 | 10 | 20 | 34 | 36 | 11 |
| 4359 | 4355 | 30984 | 76.6 | AGCCTCGTGCAACGAAGCAAGGTA | 36 | 10 | 21 | 16 | 21 | 18 |
| 4360 | 4356 | 30985 | 76.2 | AGCCTCGTACCTCGAAAGCCGAGT | 36 | 10 | 23 | 16 | 36 | 20 |
| 4361 | 4357 | 16802 | 80.3 | AGCCTCGTTCCCGACCCTTGAGGA | 36 | 10 | 28 | 32 | 11 | 25 |
| 4362 | 4358 | 12406 | 77.1 | AGCCTCGTTGCGATACTCGTTCCC | 36 | 10 | 29 | 5 | 10 | 28 |
| 4363 | 4359 | 12410 | 75.2 | AGCCCTTGTTGAGCTTGCAAGCTT | 36 | 11 | 1 | 17 | 21 | 17 |
| 4364 | 4360 | 41284 | 76.4 | AGCCCTTGCTCAAGGATTGAAGCC | 36 | 11 | 13 | 25 | 1 | 36 |
| 4365 | 4361 | 30986 | 75 | AGCCCTTGCTGTACCTACGGCCTA | 36 | 11 | 14 | 23 | 35 | 26 |
| 4366 | 4362 | 41286 | 76.2 | AGCCCTTGGTCTATCGCTTGGGAC | 36 | 11 | 19 | 24 | 11 | 34 |
| 4367 | 4363 | 30987 | 78.5 | AGCCCTTGGCAAAGCCTGTCCCTA | 36 | 11 | 21 | 36 | 9 | 26 |
| 4368 | 4364 | 41287 | 78.3 | AGCCCTTGAGTGATCGCGTTCGAA | 36 | 11 | 22 | 24 | 12 | 16 |
| 4369 | 4365 | 30989 | 75.2 | AGCCCTTGCCTAGTCTAGCCCCAT | 36 | 11 | 26 | 19 | 36 | 15 |
| 4370 | 4366 | 30990 | 80.5 | AGCCCTTGGACCGAGTTCCCGATG | 36 | 11 | 32 | 20 | 28 | 27 |
| 4371 | 4367 | 12422 | 76.6 | AGCCCTTGGGACTGTCCTTGCTGT | 36 | 11 | 34 | 9 | 11 | 14 |
| 4372 | 4368 | 30991 | 78.2 | AGCCCTTGAGCCAAAGGATGAGCC | 36 | 11 | 36 | 6 | 27 | 36 |
| 4373 | 4369 | 30992 | 77.6 | AGCCCGTTAATCGTGCGGTAATCG | 36 | 12 | 4 | 33 | 18 | 24 |
| 4374 | 4370 | 41290 | 75.7 | AGCCCGTTTACAAATCCGTTCACG | 36 | 12 | 7 | 4 | 12 | 30 |
| 4375 | 4371 | 30994 | 75.6 | AGCCCGTTGGTACGAATACAACGG | 36 | 12 | 18 | 16 | 7 | 35 |
| 4376 | 4372 | 30995 | 75 | AGCCCGTTGAGTAAAGCGTTCGTT | 36 | 12 | 20 | 6 | 12 | 12 |
| 4377 | 4373 | 41293 | 76.4 | AGCCCGTTAGTGAAAGACGGAGCC | 36 | 12 | 22 | 6 | 35 | 36 |
| 4378 | 4374 | 12439 | 76.1 | AGCCCGTTATCGTGATTGCGTGAT | 36 | 12 | 24 | 2 | 29 | 2 |
| 4379 | 4375 | 12441 | 81.8 | AGCCCGTTTCCCGATGCCATGATG | 36 | 12 | 28 | 27 | 15 | 27 |
| 4380 | 4376 | 12442 | 83.1 | AGCCCGTTTGCGCGTTCTCACACG | 36 | 12 | 29 | 12 | 13 | 30 |
| 4381 | 4377 | 12444 | 77.3 | AGCCCGTTGACCATACTGCGACCT | 36 | 12 | 32 | 5 | 29 | 23 |
| 4382 | 4378 | 12445 | 77.6 | AGCCCGTTGTGCTACAATCGGACC | 36 | 12 | 33 | 7 | 24 | 32 |
| 4383 | 4379 | 41295 | 77.5 | AGCCCTCATTGATGTCTGCGGCTT | 36 | 13 | 1 | 9 | 29 | 17 |
| 4384 | 4380 | 12447 | 76.9 | AGCCCTCATGATCCATTGCGTTGA | 36 | 13 | 2 | 15 | 29 | 1 |
| 4385 | 4381 | 30996 | 78.9 | AGCCCTCAAAAGGCAAGCAAACGG | 36 | 13 | 6 | 21 | 21 | 35 |
| 4386 | 4382 | 41296 | 79.1 | AGCCCTCACTTGGAGTTGCGAGCC | 36 | 13 | 11 | 20 | 29 | 36 |

FIG. 25IIII

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 4387 | 4383 | 12453 | 77.4 | AGCCCTCACCATGGACGCTTCTGT | 36 | 13 | 15 | 34 | 17 | 14 |
| 4388 | 4384 | 30997 | 76.1 | AGCCCTGTTGATATCGGACCCCAT | 36 | 14 | 2 | 24 | 32 | 15 |
| 4389 | 4385 | 12467 | 77.3 | AGCCCTGTTGTCATACGTGCACGG | 36 | 14 | 9 | 5 | 33 | 35 |
| 4390 | 4386 | 30998 | 79 | AGCCCTGTCCATGCAAGTGCCTCA | 36 | 14 | 15 | 21 | 33 | 13 |
| 4391 | 4387 | 41303 | 78.2 | AGCCCTGTGCTTTCGTCACGGGTA | 36 | 14 | 17 | 10 | 30 | 18 |
| 4392 | 4388 | 41304 | 77.8 | AGCCCTGTGGTAGCAAAGCCGATG | 36 | 14 | 18 | 21 | 36 | 27 |
| 4393 | 4389 | 16828 | 77.6 | AGCCCTGTACCTCAGCGCAACGTT | 36 | 14 | 23 | 31 | 21 | 12 |
| 4394 | 4390 | 12474 | 75.9 | AGCCCTGTATCGCCTAACGGGAGT | 36 | 14 | 24 | 26 | 35 | 20 |
| 4395 | 4391 | 41306 | 80 | AGCCCTGTCACGGTGCCGTTCCTA | 36 | 14 | 30 | 33 | 12 | 26 |
| 4396 | 4392 | 31000 | 77.9 | AGCCCTGTAGCCCTTGGGTAACGG | 36 | 14 | 36 | 11 | 18 | 35 |
| 4397 | 4393 | 41308 | 75.8 | AGCCCCATTTGATTAGCGTTCACG | 36 | 15 | 1 | 3 | 12 | 30 |
| 4398 | 4394 | 41310 | 78.4 | AGCCCCATAATCCGAAGTGCGCTT | 36 | 15 | 4 | 16 | 33 | 17 |
| 4399 | 4395 | 31001 | 75.6 | AGCCCCATAAAGTCCCGATGACCT | 36 | 15 | 6 | 28 | 27 | 23 |
| 4400 | 4396 | 16834 | 76.2 | AGCCCCATTACATCGTGACCGATG | 36 | 15 | 7 | 10 | 32 | 27 |
| 4401 | 4397 | 16835 | 78.3 | AGCCCCATTGTCGTCTACGGGCTT | 36 | 15 | 9 | 19 | 35 | 17 |
| 4402 | 4398 | 12485 | 78.6 | AGCCCCATTCGTCTCAGATGCACG | 36 | 15 | 10 | 13 | 27 | 30 |
| 4403 | 4399 | 12486 | 76.3 | AGCCCCATCTCAGATGGGACCTGT | 36 | 15 | 13 | 27 | 34 | 14 |
| 4404 | 4400 | 16836 | 77.6 | AGCCCCATCGAACACGGTCTATCG | 36 | 15 | 16 | 30 | 19 | 24 |
| 4405 | 4401 | 31002 | 79.4 | AGCCCCATCAGCCCATAAAGCACG | 36 | 15 | 31 | 15 | 6 | 30 |
| 4406 | 4402 | 31004 | 79.1 | AGCCCCATACGGCCTACGAAGCAA | 36 | 15 | 35 | 26 | 16 | 21 |
| 4407 | 4403 | 41314 | 77.1 | AGCCCGAATTGAACCTCGTTCAGC | 36 | 16 | 1 | 23 | 12 | 31 |
| 4408 | 4404 | 12497 | 76 | AGCCCGAAATACCGAACTTGGGAC | 36 | 16 | 5 | 16 | 11 | 34 |
| 4409 | 4405 | 16840 | 75.4 | AGCCCGAAAAGATACGTCTTGCG | 36 | 16 | 6 | 5 | 19 | 29 |
| 4410 | 4406 | 41315 | 76.8 | AGCCCGAATACACTTGGGACCAGC | 36 | 16 | 7 | 11 | 34 | 31 |
| 4411 | 4407 | 12501 | 78.4 | AGCCCGAATCGTGTGCATCGAATC | 36 | 16 | 10 | 33 | 24 | 4 |
| 4412 | 4408 | 31005 | 78.3 | AGCCCGAACTTGGGTATGCGGTCT | 36 | 16 | 11 | 18 | 29 | 19 |
| 4413 | 4409 | 31006 | 78 | AGCCCGAACTCAGTCTACGGCACG | 36 | 16 | 13 | 19 | 35 | 30 |
| 4414 | 4410 | 12503 | 78.1 | AGCCCGAACGAACTGTTCTGCAGC | 36 | 16 | 16 | 14 | 8 | 31 |
| 4415 | 4411 | 41317 | 77.1 | AGCCCGAAGCTTACGGAGTGGATG | 36 | 16 | 17 | 35 | 22 | 27 |
| 4416 | 4412 | 31007 | 77.9 | AGCCCGAAGAGTGTCTGCAAACGG | 36 | 16 | 20 | 19 | 21 | 35 |
| 4417 | 4413 | 12509 | 79.3 | AGCCCGAAATCGCTGTAGCCCTCA | 36 | 16 | 24 | 14 | 36 | 13 |
| 4418 | 4414 | 31008 | 78.8 | AGCCCGAAAGGATCTGACGGATCG | 36 | 16 | 25 | 8 | 35 | 24 |
| 4419 | 4415 | 16843 | 80.9 | AGCCCGAATGCGCGTTACCTTCGT | 36 | 16 | 29 | 12 | 23 | 10 |
| 4420 | 4416 | 12513 | 78 | AGCCCGAACACGTCCCAAAGTTGA | 36 | 16 | 30 | 28 | 6 | 1 |
| 4421 | 4417 | 12515 | 79 | AGCCCGAAGGACGGTATGTCCGAA | 36 | 16 | 34 | 18 | 9 | 16 |
| 4422 | 4418 | 12516 | 81.5 | AGCCCGAAACGGGACTCTGGGAC | 36 | 16 | 35 | 34 | 8 | 34 |
| 4423 | 4419 | 41319 | 75.3 | AGCCGCTTTGATAGGAAGTGACGG | 36 | 17 | 2 | 25 | 22 | 35 |
| 4424 | 4420 | 31009 | 76.4 | AGCCGCTTTTAGGGTACGAAACGG | 36 | 17 | 3 | 18 | 16 | 35 |
| 4425 | 4421 | 16846 | 75 | AGCCGCTTATACTGTCAGCCCGTT | 36 | 17 | 5 | 9 | 36 | 12 |
| 4426 | 4422 | 12523 | 77.6 | AGCCGCTTTGTCGCTTGGTACGTT | 36 | 17 | 9 | 17 | 18 | 12 |
| 4427 | 4423 | 31010 | 77.3 | AGCCGCTTCTTGTGATGCAACGAA | 36 | 17 | 11 | 2 | 21 | 16 |
| 4428 | 4424 | 31011 | 78.7 | AGCCGCTTCTGTTCGTGATGACGG | 36 | 17 | 14 | 10 | 27 | 35 |
| 4429 | 4425 | 31012 | 78.8 | AGCCGCTTCCATTTGAGACCGACC | 36 | 17 | 15 | 1 | 32 | 32 |
| 4430 | 4426 | 31013 | 78 | AGCCGCTTGGTAGGACGTCTGTGC | 36 | 17 | 18 | 34 | 19 | 33 |
| 4431 | 4427 | 12533 | 82.8 | AGCCGCTTTGCGCTCAACGGTTGA | 36 | 17 | 29 | 13 | 35 | 1 |
| 4432 | 4428 | 12534 | 79.8 | AGCCGCTTCAGCGAGTACGGGATG | 36 | 17 | 31 | 20 | 35 | 27 |
| 4433 | 4429 | 12536 | 80.3 | AGCCGCTTGTGCCACGTCCCATAC | 36 | 17 | 33 | 30 | 28 | 5 |
| 4434 | 4430 | 41324 | 76.4 | AGCCGGTATTGATCCCCTCAAGGA | 36 | 18 | 1 | 28 | 13 | 25 |
| 4435 | 4431 | 31014 | 77.2 | AGCCGGTAAATCACCTGTGCCGTT | 36 | 18 | 4 | 23 | 33 | 12 |
| 4436 | 4432 | 41325 | 76.8 | AGCCGGTAAAAGGTCTTGCGCTGT | 36 | 18 | 6 | 19 | 29 | 14 |
| 4437 | 4433 | 16852 | 76.6 | AGCCGGTATCTGCCATCTTGGCTT | 36 | 18 | 8 | 15 | 11 | 17 |

FIG. 25JJJJ

| SEQ ID NO: | 4,633 ID# | HBX ID# | TR | ZIPCODE (5'-3') | TETRAMER NUMBERS | | | | | |
|---|---|---|---|---|---|---|---|---|---|---|
| 4438 | 4434 | 12542 | 76.2 | AGCCGGTATCGTTTGACGTTCGAA | 36 | 18 | 10 | 1 | 12 | 16 |
| 4439 | 4435 | 22438 | 81.7 | AGCCGGTACTGTTCCCAGCCGCAA | 36 | 18 | 14 | 28 | 36 | 21 |
| 4440 | 4436 | 22439 | 75 | AGCCGGTAGGTACCATAGGATGCG | 36 | 18 | 18 | 15 | 25 | 29 |
| 4441 | 4437 | 31015 | 77.1 | AGCCGGTAGAGTCAGCATCGGGAC | 36 | 18 | 20 | 31 | 24 | 34 |
| 4442 | 4438 | 16861 | 78.5 | AGCCGGTATCCCCTTGTCGTACGG | 36 | 18 | 28 | 11 | 10 | 35 |
| 4443 | 4439 | 12559 | 79.4 | AGCCGTCTAATCGGACCCATTGCG | 36 | 19 | 4 | 34 | 15 | 29 |
| 4444 | 4440 | 12561 | 75.5 | AGCCGTCTTACAATCGATCGCCAT | 36 | 19 | 7 | 24 | 24 | 15 |
| 4445 | 4441 | 16866 | 75 | AGCCGTCTACCTTCGTAGCCCTCA | 36 | 19 | 23 | 10 | 36 | 13 |
| 4446 | 4442 | 12572 | 76.4 | AGCCGTCTGATGTCGTGCTTTCGT | 36 | 19 | 27 | 10 | 17 | 10 |
| 4447 | 4443 | 12574 | 78.6 | AGCCGTCTCACGATCGTGTCGGAC | 36 | 19 | 30 | 24 | 9 | 34 |
| 4448 | 4444 | 31017 | 79.3 | AGCCGTCTCAGCACGGCTTGTTGA | 36 | 19 | 31 | 35 | 11 | 1 |
| 4449 | 4445 | 12576 | 79.7 | AGCCGTCTGACCGAGTGACCGGAC | 36 | 19 | 32 | 20 | 32 | 34 |
| 4450 | 4447 | 31018 | 77 | AGCCGTCTAGCCAATCGCTTGCTT | 36 | 19 | 36 | 4 | 17 | 17 |
| 4451 | 4449 | 41333 | 80.3 | AGCCGAGTTGTCCACGCCATGGAC | 36 | 20 | 9 | 30 | 15 | 34 |
| 4452 | 4450 | 12582 | 76.4 | AGCCGAGTTCGTGAGTAGCCTCCC | 36 | 20 | 10 | 20 | 36 | 28 |
| 4453 | 4451 | 12586 | 77.7 | AGCCGAGTGTCTTACATGCGCACG | 36 | 20 | 19 | 7 | 29 | 30 |
| 4454 | 4452 | 31019 | 79.2 | AGCCGAGTATCGCAGCCTGTGCAA | 36 | 20 | 24 | 31 | 14 | 21 |
| 4455 | 4453 | 31020 | 75.7 | AGCCGAGTCCTATTGATCCCCGTT | 36 | 20 | 26 | 1 | 28 | 12 |
| 4456 | 4454 | 41335 | 77.4 | AGCCGAGTGATGTCCCGAGTCGTT | 36 | 20 | 27 | 28 | 20 | 12 |
| 4457 | 4455 | 22446 | 76.7 | AGCCGAGTTGCGTTGACTGTGGAC | 36 | 20 | 29 | 1 | 14 | 34 |
| 4458 | 4456 | 16874 | 79.2 | AGCCGAGTAGCCCAGCCTCACAGC | 36 | 20 | 36 | 31 | 13 | 31 |
| 4459 | 4457 | 41337 | 78 | AGCCGCAATTGAAGGAGCAACAGC | 36 | 21 | 1 | 25 | 21 | 31 |
| 4460 | 4458 | 31021 | 76.7 | AGCCGCAATGATAGCCTGATCACG | 36 | 21 | 2 | 36 | 2 | 30 |
| 4461 | 4459 | 12596 | 76.1 | AGCCGCAATTAGCGAATGCGATAC | 36 | 21 | 3 | 16 | 29 | 5 |
| 4462 | 4460 | 31022 | 76.8 | AGCCGCAATACAAGTGTCCCTCCC | 36 | 21 | 7 | 22 | 28 | 28 |
| 4463 | 4461 | 41338 | 78.3 | AGCCGCAATCTGGGTAGGACCGTT | 36 | 21 | 8 | 18 | 34 | 12 |
| 4464 | 4462 | 41339 | 79.3 | AGCCGCAACGTTTGCGTGATATCG | 36 | 21 | 12 | 29 | 2 | 24 |
| 4465 | 4463 | 31023 | 77.4 | AGCCGCAACTCAAGGAAGCCTCTG | 36 | 21 | 13 | 25 | 36 | 8 |
| 4466 | 4464 | 12602 | 77.4 | AGCCGCAACGAAGGTAATCGTCGT | 36 | 21 | 16 | 18 | 24 | 10 |
| 4467 | 4465 | 12603 | 79.5 | AGCCGCAAGCTTGAGTCACGCTCA | 36 | 21 | 17 | 20 | 30 | 13 |
| 4468 | 4466 | 41340 | 78.8 | AGCCGCAAGCAATCCCCTTGAATC | 36 | 21 | 21 | 28 | 11 | 4 |
| 4469 | 4467 | 12608 | 79.3 | AGCCGCAAATCGGCAAACCTCTGT | 36 | 21 | 24 | 21 | 23 | 14 |
| 4470 | 4468 | 12609 | 77.7 | AGCCGCAAAGGAGCAACGTTGAGT | 36 | 21 | 25 | 21 | 12 | 20 |
| 4471 | 4469 | 12610 | 81.4 | AGCCGCAATCCCGGTAAGTGCAGC | 36 | 21 | 28 | 18 | 22 | 31 |
| 4472 | 4470 | 12611 | 81.7 | AGCCGCAATGCGATCGCTCATTGA | 36 | 21 | 29 | 24 | 13 | 1 |
| 4473 | 4471 | 31024 | 83.2 | AGCCGCAACACGCTGTGTGCTCCC | 36 | 21 | 30 | 14 | 33 | 28 |
| 4474 | 4472 | 41342 | 80.3 | AGCCGCAAGTGCATACACGGGACC | 36 | 21 | 33 | 5 | 35 | 32 |
| 4475 | 4473 | 12615 | 80.7 | AGCCGCAAACGGCCTAGCTTGGAC | 36 | 21 | 35 | 26 | 17 | 34 |
| 4476 | 4474 | 12616 | 81.5 | AGCCGCAAAGCCCTGTCTTGACGG | 36 | 21 | 36 | 14 | 11 | 35 |
| 4477 | 4475 | 41343 | 77.2 | AGCCAGTGTCGTATCGCACGAGGA | 36 | 22 | 10 | 24 | 30 | 25 |
| 4478 | 4476 | 16878 | 77.8 | AGCCAGTGCTTGAGTGGGACGACC | 36 | 22 | 11 | 22 | 34 | 32 |
| 4479 | 4477 | 31025 | 78.7 | AGCCAGTGCTGTGATGACGGAGCC | 36 | 22 | 14 | 27 | 35 | 36 |
| 4480 | 4478 | 41345 | 79.8 | AGCCAGTGGGTACAGCAGCCAGCC | 36 | 22 | 18 | 31 | 36 | 36 |
| 4481 | 4479 | 12622 | 76.8 | AGCCAGTGACCTGCTTTCCCGTCT | 36 | 22 | 23 | 17 | 28 | 19 |
| 4482 | 4480 | 12623 | 77.9 | AGCCAGTGATCGGAGTACGGCAGC | 36 | 22 | 24 | 20 | 35 | 31 |
| 4483 | 4481 | 16881 | 78 | AGCCAGTGTGCGATACCACGCTCA | 36 | 22 | 29 | 5 | 30 | 13 |
| 4484 | 4482 | 12629 | 78.6 | AGCCAGTGGACCAGGAGCAACACG | 36 | 22 | 32 | 25 | 21 | 30 |
| 4485 | 4483 | 31027 | 78.9 | AGCCACCTTGTCAGGACACGGCAA | 36 | 23 | 9 | 25 | 30 | 21 |
| 4486 | 4484 | 41346 | 75.6 | AGCCACCTTCGTAAAGCCATCGAA | 36 | 23 | 10 | 6 | 15 | 16 |
| 4487 | 4485 | 31028 | 78.2 | AGCCACCTCGAATGTCCTTGCGAA | 36 | 23 | 16 | 9 | 11 | 16 |
| 4488 | 4486 | 12643 | 76.1 | AGCCACCTATCGACCTGATGGCAA | 36 | 23 | 24 | 23 | 27 | 21 |

FIG. 25KKKK

| SEQ ID NO: | 4,633 ID# | HEX ID# | Tm | ZIPCODE (5'-3') | TETRAMER NUMBERS | | | | |
|---|---|---|---|---|---|---|---|---|---|
| 4489 | 4487 | 12644 | 76.1 | AGCCACCTAGGAAGTGCTCATGCG | 36 | 23 | 25 | 22 | 13 | 29 |
| 4490 | 4488 | 12646 | 77.3 | AGCCACCTCACGAATCTCCAGGA | 36 | 23 | 30 | 4 | 28 | 25 |
| 4491 | 4489 | 12656 | 77.3 | AGCCATCGCGAATTGAGGACCCTA | 36 | 24 | 16 | 1 | 34 | 26 |
| 4492 | 4490 | 12661 | 77.6 | AGCCATCGGCAAAATCCAGCAATC | 36 | 24 | 21 | 4 | 31 | 4 |
| 4493 | 4491 | 31030 | 75.9 | AGCCATCGCCTAATACCCATTCCC | 36 | 24 | 26 | 5 | 15 | 28 |
| 4494 | 4492 | 12667 | 76.9 | AGCCAGGAATACGGTATCCCTGCG | 36 | 25 | 5 | 18 | 28 | 29 |
| 4495 | 4493 | 16892 | 76.8 | AGCCAGGAAAAGTTGACACGTGCG | 36 | 25 | 6 | 1 | 30 | 29 |
| 4496 | 4494 | 12669 | 77.5 | AGCCAGGATACATGCGCTCACACG | 36 | 25 | 7 | 29 | 13 | 30 |
| 4497 | 4495 | 12670 | 78.5 | AGCCAGGATCTGCACGCTGTGCTT | 36 | 25 | 8 | 30 | 14 | 17 |
| 4498 | 4496 | 41354 | 77.3 | AGCCAGGACGTTTGTCTCCCGGTA | 36 | 25 | 12 | 9 | 28 | 18 |
| 4499 | 4497 | 12671 | 76.7 | AGCCAGGACTCAAGCCGAGTCCAT | 36 | 25 | 13 | 36 | 20 | 15 |
| 4500 | 4498 | 16893 | 77.8 | AGCCAGGACCATTTGAGTGCCAGC | 36 | 25 | 15 | 1 | 33 | 31 |
| 4501 | 4499 | 12677 | 75.5 | AGCCAGGAGCAAATACGATGCCAT | 36 | 25 | 21 | 5 | 27 | 15 |
| 4502 | 4500 | 16895 | 79.8 | AGCCAGGATGCGCGAAGGTAGTGC | 36 | 25 | 29 | 16 | 18 | 33 |
| 4503 | 4501 | 12681 | 77.8 | AGCCAGGACAGCCTTGAATCACGG | 36 | 25 | 31 | 11 | 4 | 35 |
| 4504 | 4502 | 12682 | 76.2 | AGCCAGGAGACCTCGTCTCATCCC | 36 | 25 | 32 | 10 | 13 | 28 |
| 4505 | 4503 | 31031 | 78.1 | AGCCAGGAGGACAAAGGTGCTCCC | 36 | 25 | 34 | 6 | 33 | 28 |
| 4506 | 4504 | 31032 | 79.8 | AGCCAGGAACGGCCATAATCGCAA | 36 | 25 | 35 | 15 | 4 | 21 |
| 4507 | 4505 | 31033 | 75.2 | AGCCCCTATGATAGCCGATGCTTG | 36 | 26 | 2 | 36 | 27 | 11 |
| 4508 | 4506 | 31034 | 79.2 | AGCCCCTATGTCAGCCCACGCTGT | 36 | 26 | 9 | 36 | 30 | 14 |
| 4509 | 4507 | 41356 | 76.4 | AGCCCCTACTTGAGGACAGCCAGC | 36 | 26 | 11 | 25 | 31 | 31 |
| 4510 | 4508 | 41357 | 76 | AGCCCCTACTCACTCAATCGCACG | 36 | 26 | 13 | 13 | 24 | 30 |
| 4511 | 4509 | 16902 | 77.6 | AGCCCCTAGAGTGCAATGCGAGGA | 36 | 26 | 20 | 21 | 29 | 25 |
| 4512 | 4510 | 41358 | 77.4 | AGCCCCTAGCAACCATGTGCGAGT | 36 | 26 | 21 | 15 | 33 | 20 |
| 4513 | 4511 | 31035 | 75 | AGCCCCTAACCTTCTGGCTTAGCC | 36 | 26 | 23 | 8 | 17 | 36 |
| 4514 | 4512 | 12695 | 77.7 | AGCCCCTAGATGGCAATCGTGTGC | 36 | 26 | 27 | 21 | 10 | 33 |
| 4515 | 4513 | 12697 | 75.6 | AGCCCCTACACGAATCAATCACGG | 36 | 26 | 30 | 4 | 4 | 35 |
| 4516 | 4514 | 12699 | 79.6 | AGCCCCTAACGGCACGCTGTTGTC | 36 | 26 | 35 | 30 | 14 | 9 |
| 4517 | 4515 | 12700 | 76.8 | AGCCGATGTGATCTTGATCGCAGC | 36 | 27 | 2 | 11 | 24 | 31 |
| 4518 | 4516 | 12701 | 75.3 | AGCCGATGTTAGTTGATGCGCTCA | 36 | 27 | 3 | 1 | 29 | 13 |
| 4519 | 4517 | 12703 | 77.2 | AGCCGATGTACATGTCGACCCACG | 36 | 27 | 7 | 9 | 32 | 30 |
| 4520 | 4518 | 12704 | 75.9 | AGCCGATGTCTGAATCGCAAGGAC | 36 | 27 | 8 | 4 | 21 | 34 |
| 4521 | 4519 | 31036 | 82.3 | AGCCGATGTGTCAGCCTGCGGGAC | 36 | 27 | 9 | 36 | 29 | 34 |
| 4522 | 4520 | 41363 | 78.8 | AGCCGATGCTCAACCTGCTTCACG | 36 | 27 | 13 | 23 | 17 | 30 |
| 4523 | 4521 | 22465 | 77.3 | AGCCGATGGCTTAGCCTTAGTGCG | 36 | 27 | 17 | 36 | 3 | 29 |
| 4524 | 4522 | 16908 | 76.3 | AGCCGATGACCTCAGCCCTAGACC | 36 | 27 | 23 | 31 | 26 | 32 |
| 4525 | 4523 | 41364 | 78.2 | AGCCGATGCCTACCATGTGCGTCT | 36 | 27 | 26 | 15 | 33 | 19 |
| 4526 | 4524 | 31038 | 77.6 | AGCCTCCCTTGAACCTTCCCAGGA | 36 | 28 | 1 | 23 | 28 | 25 |
| 4527 | 4525 | 31039 | 77 | AGCCTCCCATACTGCGCTCAGCTT | 36 | 28 | 5 | 29 | 13 | 17 |
| 4528 | 4526 | 41367 | 77 | AGCCTCCCTACAACCTTGCGGATG | 36 | 28 | 7 | 23 | 29 | 27 |
| 4529 | 4527 | 16911 | 76.8 | AGCCTCCCTGTCAAAGGTGCGAGT | 36 | 28 | 9 | 6 | 33 | 20 |
| 4530 | 4528 | 12724 | 75.1 | AGCCTCCCTCGTACGGGGTAGAGT | 36 | 28 | 10 | 35 | 18 | 20 |
| 4531 | 4529 | 12725 | 76.9 | AGCCTCCCCTTGTTGAAGTGACGG | 36 | 28 | 11 | 1 | 22 | 35 |
| 4532 | 4530 | 22467 | 76.7 | AGCCTCCCCATCCTAGGACCTGT | 36 | 28 | 15 | 26 | 34 | 14 |
| 4533 | 4531 | 31040 | 80.2 | AGCCTCCCCGAATCTGGTGCCTGT | 36 | 28 | 16 | 8 | 33 | 14 |
| 4534 | 4532 | 41368 | 77.8 | AGCCTCCCGTCTGGTAGGACGCTT | 36 | 28 | 19 | 18 | 34 | 17 |
| 4535 | 4533 | 31041 | 76.9 | AGCCTCCCGAGTCCTATCCCGAGT | 36 | 28 | 20 | 26 | 28 | 20 |
| 4536 | 4534 | 16914 | 79 | AGCCTCCCAGTGCTTGCTTGGACC | 36 | 28 | 22 | 11 | 11 | 32 |
| 4537 | 4535 | 12733 | 76.8 | AGCCTCCCATCGTTGAAATCGGAC | 36 | 28 | 24 | 1 | 4 | 34 |
| 4538 | 4536 | 22471 | 76.6 | AGCCTCCCAGGACCTATCGTCGAA | 36 | 28 | 25 | 26 | 10 | 16 |
| 4539 | 4537 | 22472 | 75.3 | AGCCTCCCCCTACTGTCTCATCCC | 36 | 28 | 26 | 14 | 13 | 28 |

FIG. 25LLLL

| SEQ ID NO: | 4,633 ID# | HEX ID# | Tm | ZIPCODE (5'-3') | TETRAMER NUMBERS | | | | |
|---|---|---|---|---|---|---|---|---|---|
| 4540 | 4538 | 12734 | 78.9 | AGCCTCCCGATGGATGGCAATGAT | 36 | 28 | 27 | 27 | 21 | 2 |
| 4541 | 4539 | 12735 | 80.6 | AGCCTCCCTCCCGCAAACCTGATG | 36 | 28 | 28 | 21 | 23 | 27 |
| 4542 | 4540 | 12736 | 80.5 | AGCCTCCCGTGCATCGTTGACAGC | 36 | 28 | 33 | 24 | 1 | 31 |
| 4543 | 4541 | 12737 | 81.8 | AGCCTCCCACGGCCATGAGTCGAA | 36 | 28 | 35 | 15 | 20 | 16 |
| 4544 | 4542 | 12738 | 78.6 | AGCCTCCCAGCCAAAGTCGTTCGT | 36 | 28 | 36 | 6 | 10 | 10 |
| 4545 | 4543 | 12739 | 77.5 | AGCCTGCGAATCGGTAAGTGCGTT | 36 | 29 | 4 | 18 | 22 | 12 |
| 4546 | 4544 | 31042 | 76.7 | AGCCTGCGAAAGTCTGTCCCCCTA | 36 | 29 | 6 | 8 | 28 | 26 |
| 4547 | 4546 | 22477 | 81.2 | AGCCTGCGCTCACTTGGCAAGCAA | 36 | 29 | 13 | 11 | 21 | 21 |
| 4548 | 4547 | 12745 | 79.3 | AGCCTGCGCTGTGTCTTGTCCGAA | 36 | 29 | 14 | 19 | 9 | 16 |
| 4549 | 4548 | 12748 | 78.5 | AGCCTGCGGAGTGATGCTGTGCTT | 36 | 29 | 20 | 27 | 14 | 17 |
| 4550 | 4549 | 31043 | 79.7 | AGCCTGCGAGTGGAGTTCCCATCG | 36 | 29 | 22 | 20 | 28 | 24 |
| 4551 | 4550 | 31044 | 77.6 | AGCCTGCGAGGAGCTTCCTATCCC | 36 | 29 | 25 | 17 | 26 | 28 |
| 4552 | 4551 | 12751 | 79.5 | AGCCTGCGTGCGAAAGCCTATCGT | 36 | 29 | 29 | 6 | 26 | 10 |
| 4553 | 4552 | 12752 | 83.6 | AGCCTGCGCACGCTCATCTGCAGC | 36 | 29 | 30 | 13 | 8 | 31 |
| 4554 | 4553 | 12753 | 82.9 | AGCCTGCGGTGCGATGAGCCTTGA | 36 | 29 | 33 | 27 | 36 | 1 |
| 4555 | 4554 | 31045 | 80.1 | AGCCCACGAATCGACCGGTACACG | 36 | 30 | 4 | 32 | 18 | 30 |
| 4556 | 4555 | 41379 | 77.4 | AGCCCACGTACACTCAATCGTGCG | 36 | 30 | 7 | 13 | 24 | 29 |
| 4557 | 4556 | 12760 | 79.2 | AGCCCACGCTTGGCAAGGTATCGT | 36 | 30 | 11 | 21 | 18 | 10 |
| 4558 | 4557 | 22487 | 76.2 | AGCCCACGGTCTAGGAGGTAACGG | 36 | 30 | 19 | 25 | 18 | 35 |
| 4559 | 4558 | 16921 | 78.6 | AGCCCACGACCTTCCCCTCATGTC | 36 | 30 | 23 | 28 | 13 | 9 |
| 4560 | 4559 | 31047 | 78.3 | AGCCCACGCCTACGTTGCTTTTGA | 36 | 30 | 26 | 12 | 17 | 1 |
| 4561 | 4560 | 12769 | 82.9 | AGCCCACGCAGCGGACTTGAGCAA | 36 | 30 | 31 | 34 | 1 | 21 |
| 4562 | 4561 | 12770 | 81.8 | AGCCCACGGACCGCTTGCAACTGT | 36 | 30 | 32 | 17 | 21 | 14 |
| 4563 | 4562 | 12772 | 82 | AGCCCACGACGGCTCAAGGAGCAA | 36 | 30 | 35 | 13 | 25 | 21 |
| 4564 | 4563 | 41381 | 77.6 | AGCCCAGCTGATCCTAGACCGCAA | 36 | 31 | 2 | 26 | 32 | 21 |
| 4565 | 4564 | 22490 | 77.8 | AGCCCAGCTTAGAGTGCAGCCGAA | 36 | 31 | 3 | 22 | 31 | 16 |
| 4566 | 4565 | 31048 | 79.6 | AGCCCAGCAAAGGACCAGTGACGG | 36 | 31 | 6 | 32 | 22 | 35 |
| 4567 | 4566 | 31049 | 77.7 | AGCCCAGCTACAGATGTCCCCACG | 36 | 31 | 7 | 27 | 28 | 30 |
| 4568 | 4567 | 16923 | 78.5 | AGCCCAGCTCGTGCTTGCTTGGTA | 36 | 31 | 10 | 17 | 17 | 18 |
| 4569 | 4568 | 12780 | 78.8 | AGCCCAGCCCATTTGAAGGAGTGC | 36 | 31 | 15 | 1 | 25 | 33 |
| 4570 | 4569 | 12781 | 77.7 | AGCCCAGCGCTTACCTATCGCTCA | 36 | 31 | 17 | 23 | 24 | 13 |
| 4571 | 4570 | 31050 | 76.3 | AGCCCAGCGTCTATACCAGCTCCC | 36 | 31 | 19 | 5 | 31 | 28 |
| 4572 | 4571 | 31051 | 79.3 | AGCCCAGCAGGACTGTTCCCCTCA | 36 | 31 | 25 | 14 | 28 | 13 |
| 4573 | 4572 | 12787 | 81.5 | AGCCCAGCGACCCTCAACCTCACG | 36 | 31 | 32 | 13 | 23 | 30 |
| 4574 | 4573 | 12789 | 80 | AGCCCAGCAGCCCCATCCTACCAT | 36 | 31 | 36 | 15 | 26 | 15 |
| 4575 | 4574 | 22495 | 75.2 | AGCCGACCTTGAGGTACGAAATCG | 36 | 32 | 1 | 18 | 16 | 24 |
| 4576 | 4575 | 41384 | 79 | AGCCGACCTGATGGACGCAACTCA | 36 | 32 | 2 | 34 | 21 | 13 |
| 4577 | 4576 | 12794 | 79.1 | AGCCGACCAAAGCAGCTCCCTGTC | 36 | 32 | 6 | 31 | 28 | 9 |
| 4578 | 4577 | 12796 | 76.8 | AGCCGACCCTTGAAAGCTGTCGTT | 36 | 32 | 11 | 6 | 14 | 12 |
| 4579 | 4578 | 12798 | 76.2 | AGCCGACCCTCACCTAGGACCTTG | 36 | 32 | 13 | 26 | 34 | 11 |
| 4580 | 4579 | 41385 | 80.3 | AGCCGACCGTCTGATGTCCCATCG | 36 | 32 | 19 | 27 | 28 | 24 |
| 4581 | 4580 | 12801 | 79.7 | AGCCGACCGCAACTCAAATCCAGC | 36 | 32 | 21 | 13 | 4 | 31 |
| 4582 | 4581 | 12802 | 75.5 | AGCCGACCAGTGTTAGGTGCCCTA | 36 | 32 | 22 | 3 | 33 | 26 |
| 4583 | 4582 | 31052 | 79.8 | AGCCGACCATCGTCTGGCAACCAT | 36 | 32 | 24 | 8 | 21 | 15 |
| 4584 | 4583 | 16926 | 77.8 | AGCCGACCAGGAAGTGCGTTATCG | 36 | 32 | 25 | 22 | 12 | 24 |
| 4585 | 4584 | 12807 | 81.4 | AGCCGACCCACGAGTGCTGTCACG | 36 | 32 | 30 | 22 | 14 | 30 |
| 4586 | 4585 | 12809 | 80.4 | AGCCGACCGTGCATCGAAAGATCG | 36 | 32 | 33 | 24 | 6 | 24 |
| 4587 | 4587 | 31053 | 77.4 | AGCCGTGCAATCTCGTTCCCTGAT | 36 | 33 | 4 | 10 | 28 | 2 |
| 4588 | 4588 | 31054 | 78.5 | AGCCGTGCATACCCTACAGCACGG | 36 | 33 | 5 | 26 | 31 | 35 |
| 4589 | 4589 | 12814 | 77.6 | AGCCGTGCTCTGAGTGCCATGATG | 36 | 33 | 8 | 22 | 15 | 27 |
| 4590 | 4590 | 12816 | 78.1 | AGCCGTGCTCGTTCGTGTCTAGCC | 36 | 33 | 10 | 10 | 19 | 36 |

FIG. 25MMMM

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 4591 | 4591 | 12817 | 79.3 | AGCCGTGCCTTGGAGTGCAAACCT | 36 | 33 | 11 | 20 | 21 | 23 |
| 4592 | 4592 | 12818 | 80.9 | AGCCGTGCCGAAGCAATGTCAGGA | 36 | 33 | 16 | 21 | 9 | 25 |
| 4593 | 4593 | 12819 | 81.8 | AGCCGTGCGCTTGTGCTCGTGGTA | 36 | 33 | 17 | 33 | 10 | 18 |
| 4594 | 4594 | 31055 | 79.9 | AGCCGTGCGTCTGCTTTCCCTGTC | 36 | 33 | 19 | 17 | 28 | 9 |
| 4595 | 4595 | 12821 | 82.1 | AGCCGTGCATCGGCAACTGTCACG | 36 | 33 | 24 | 21 | 14 | 30 |
| 4596 | 4596 | 12824 | 82.4 | AGCCGTGCGGACCTTGTCGTCAGC | 36 | 33 | 34 | 11 | 10 | 31 |
| 4597 | 4597 | 31056 | 75.5 | AGCCGGACTTAGTACAAGCCTGCG | 36 | 34 | 3 | 7 | 36 | 29 |
| 4598 | 4598 | 12830 | 75.9 | AGCCGGACTGTCTCGTGGTAATCG | 36 | 34 | 9 | 10 | 18 | 24 |
| 4599 | 4599 | 12831 | 79.9 | AGCCGGACCGTTTGTCGACCTTGA | 36 | 34 | 12 | 9 | 32 | 1 |
| 4600 | 4600 | 12833 | 79.6 | AGCCGGACCCATCAGCGAGTTGTC | 36 | 34 | 15 | 31 | 20 | 9 |
| 4601 | 4601 | 16931 | 79.5 | AGCCGGACGCTTCTTGCTCACGTT | 36 | 34 | 17 | 11 | 13 | 12 |
| 4602 | 4602 | 12836 | 76.6 | AGCCGGACACCTCTTGACCTTCGT | 36 | 34 | 23 | 11 | 23 | 10 |
| 4603 | 4603 | 12837 | 79.3 | AGCCGGACATCGCGTTTCTGACCT | 36 | 34 | 24 | 12 | 8 | 23 |
| 4604 | 4604 | 22502 | 75.1 | AGCCGGACAGGACCTACAGCAATC | 36 | 34 | 25 | 26 | 31 | 4 |
| 4605 | 4605 | 12840 | 78.7 | AGCCGGACTCCCTACACACGGGAC | 36 | 34 | 28 | 7 | 30 | 34 |
| 4606 | 4606 | 12842 | 82.6 | AGCCGGACGTGCGAGTGACCGGTA | 36 | 34 | 33 | 20 | 32 | 18 |
| 4607 | 4607 | 12843 | 80.7 | AGCCGGACGGACGACCCAGCTTAG | 36 | 34 | 34 | 32 | 31 | 3 |
| 4608 | 4608 | 12846 | 76.7 | AGCCACGGAATCTGATGCTTCACG | 36 | 35 | 4 | 2 | 17 | 30 |
| 4609 | 4609 | 12847 | 77.7 | AGCCACGGATACCAGCTCGTACGG | 36 | 35 | 5 | 31 | 10 | 35 |
| 4610 | 4610 | 41393 | 76.9 | AGCCACGGAAAGAAAGGATGGTGC | 36 | 35 | 6 | 6 | 27 | 33 |
| 4611 | 4611 | 31057 | 75.5 | AGCCACGGTACACCTATCCCGATG | 36 | 35 | 7 | 26 | 28 | 27 |
| 4612 | 4612 | 12849 | 78.9 | AGCCACGGTCTGGATGCGTTTTGA | 36 | 35 | 8 | 27 | 12 | 1 |
| 4613 | 4613 | 31058 | 81.2 | AGCCACGGTGTCGGACATCGCTTG | 36 | 35 | 9 | 34 | 24 | 11 |
| 4614 | 4614 | 31059 | 81.2 | AGCCACGGGCTTGCTTCACGACCT | 36 | 35 | 17 | 17 | 30 | 23 |
| 4615 | 4615 | 31060 | 81.3 | AGCCACGGGTCTGTCTGTGCCACG | 36 | 35 | 19 | 19 | 33 | 30 |
| 4616 | 4616 | 12856 | 79.3 | AGCCACGGATCGGCTTTCGTGAGT | 36 | 35 | 24 | 17 | 10 | 20 |
| 4617 | 4617 | 12859 | 80.9 | AGCCACGGGACCAGTGGACCCTGT | 36 | 35 | 32 | 22 | 32 | 14 |
| 4618 | 4618 | 12860 | 80.5 | AGCCACGGGTGCTACAGGACGTGC | 36 | 35 | 33 | 7 | 34 | 33 |
| 4619 | 4619 | 16934 | 81 | AGCCACGGACGGCCTAAGTGCGTT | 36 | 35 | 35 | 26 | 22 | 12 |
| 4620 | 4620 | 31061 | 75.3 | AGCCAGCCTGATACCTAGCCATCG | 36 | 36 | 2 | 23 | 36 | 24 |
| 4621 | 4621 | 41394 | 76.8 | AGCCAGCCAAAGACCTACGGCTGT | 36 | 36 | 6 | 23 | 35 | 14 |
| 4622 | 4622 | 12866 | 78.6 | AGCCAGCCTCTGGACCAGGATCGT | 36 | 36 | 8 | 32 | 25 | 10 |
| 4623 | 4623 | 41395 | 77 | AGCCAGCCTCGTAGTGGGTAACGG | 36 | 36 | 10 | 22 | 18 | 35 |
| 4624 | 4624 | 12867 | 77.8 | AGCCAGCCCTTGTGTCCGAACTTG | 36 | 36 | 11 | 9 | 16 | 11 |
| 4625 | 4625 | 12868 | 78.1 | AGCCAGCCCGTTCGTTTCGTTACA | 36 | 36 | 12 | 12 | 10 | 7 |
| 4626 | 4626 | 16936 | 76.9 | AGCCAGCCCTCAGCTTCTTGGGTA | 36 | 36 | 13 | 17 | 11 | 18 |
| 4627 | 4627 | 12870 | 79.1 | AGCCAGCCGCTTAGTGCAGCAGTG | 36 | 36 | 17 | 22 | 31 | 22 |
| 4628 | 4628 | 12872 | 77.2 | AGCCAGCCGTCTTTGAGGACCTTG | 36 | 36 | 19 | 1 | 34 | 11 |
| 4629 | 4629 | 12874 | 78.5 | AGCCAGCCATCGTGATGATGAGCC | 36 | 36 | 24 | 2 | 27 | 36 |
| 4630 | 4630 | 12876 | 81.1 | AGCCAGCCTCCCCAGCGATGTGAT | 36 | 36 | 28 | 31 | 27 | 2 |
| 4631 | 4631 | 12878 | 82.6 | AGCCAGCCCACGCCATGCAACTGT | 36 | 36 | 30 | 15 | 21 | 14 |
| 4632 | 4632 | 12879 | 81.6 | AGCCAGCCGACCCAGCAGGAGATG | 36 | 36 | 32 | 31 | 25 | 27 |
| 4633 | 4633 | 12880 | 80.2 | AGCCAGCCGGACGGTAATCGGTCT | 36 | 36 | 34 | 18 | 24 | 19 |

FIG. 26A

| SEQ ID NO: | 4,633 ID# | HEX ID# | Tm | ZIPCODE (5'-3') | TETRAMER NUMBERS | | | | |
|---|---|---|---|---|---|---|---|---|---|
| 1 | 3 | 8 | 77.6 | TTGAAATCCAGCGCAAAATCTGCG | 1 | 4 | 31 | 21 | 4 | 29 |
| 2 | 5 | 15 | 77.2 | TTGAAAAGCCTACACGACGGCGAA | 1 | 6 | 26 | 30 | 35 | 16 |
| 3 | 7 | 22 | 76.5 | TTGATCTGCCATACGGGCTTACGG | 1 | 8 | 15 | 35 | 17 | 35 |
| 4 | 15 | 45 | 80.6 | TTGACTTGTCCCAGCACGGCCAT | 1 | 11 | 28 | 31 | 35 | 15 |
| 5 | 17 | 56 | 80.4 | TTGACGTTGACCAGCCCGTTGCAA | 1 | 12 | 32 | 36 | 12 | 21 |
| 6 | 20 | 72 | 76.4 | TTGACGAAGCTTTCCCCCATGATG | 1 | 16 | 17 | 28 | 15 | 27 |
| 7 | 24 | 90 | 81.2 | TTGAGCAAGGACGACCGCAAACGG | 1 | 21 | 34 | 32 | 21 | 35 |
| 8 | 30 | 126 | 82.4 | TTGAGATGACGGACGGTGCGGCAA | 1 | 27 | 35 | 35 | 29 | 21 |
| 9 | 33 | 140 | 76.3 | TTGATCCCATCGAAAGGGACGATG | 1 | 28 | 24 | 6 | 34 | 27 |
| 10 | 36 | 150 | 80.1 | TTGATGCGTCTGGGACGTGCCTTG | 1 | 29 | 8 | 34 | 33 | 11 |
| 11 | 44 | 166 | 80.3 | TTGACACGTCGTCAGCTCCCGTGC | 1 | 30 | 10 | 31 | 28 | 33 |
| 12 | 48 | 180 | 80 | TTGACAGCCTGTTGCGGTGCGTCT | 1 | 31 | 14 | 29 | 33 | 19 |
| 13 | 52 | 202 | 76.5 | TTGAGTGCGGTACTTGCAGCGATG | 1 | 33 | 18 | 11 | 31 | 27 |
| 14 | 55 | 222 | 81.2 | TTGAACGGTCTGCACGTCCCAGCC | 1 | 35 | 8 | 30 | 28 | 36 |
| 15 | 67 | 269 | 82.2 | TGATTCTGGTGCGTGCCAGCCAGC | 2 | 8 | 33 | 33 | 31 | 31 |
| 16 | 69 | 274 | 76.8 | TGATTGTCGCTTTCTGACGGAGCC | 2 | 9 | 17 | 8 | 35 | 36 |
| 17 | 73 | 294 | 77.9 | TGATCGTTTGCGGGTATCCCTCGT | 2 | 12 | 29 | 18 | 28 | 10 |
| 18 | 75 | 310 | 77.9 | TGATCGAAAGGACAGCAGCCTCCC | 2 | 16 | 25 | 31 | 36 | 28 |
| 19 | 79 | 328 | 76.9 | TGATGCAAGCAACGAACACGCTGT | 2 | 21 | 21 | 16 | 30 | 14 |
| 20 | 92 | 372 | 79.5 | TGATTGCGAGTGGACCATCGCCAT | 2 | 29 | 22 | 32 | 24 | 15 |
| 21 | 94 | 379 | 80 | TGATCACGCTTGCCATGGACGGAC | 2 | 30 | 11 | 15 | 34 | 34 |
| 22 | 104 | 418 | 82 | TGATGTGCCTCAACGGGTGCAGCC | 2 | 33 | 13 | 35 | 33 | 36 |
| 23 | 111 | 431 | 75.6 | TGATGGACCGTTAGCCGATGTTGA | 2 | 34 | 12 | 36 | 27 | 1 |
| 24 | 118 | 444 | 79.5 | TGATACGGAGGAGGACTGCGTGCG | 2 | 35 | 25 | 34 | 29 | 29 |
| 25 | 129 | 555 | 79.9 | TTAGGATGAGCCAGCCTGCGAGCC | 3 | 27 | 36 | 36 | 29 | 36 |
| 26 | 151 | 690 | 77.7 | AATCTCGTCGTTTCCCCTCATGCG | 4 | 10 | 12 | 28 | 13 | 29 |
| 27 | 166 | 805 | 77.4 | AATCGCAACTGTCGTTCACGGTGC | 4 | 21 | 14 | 12 | 30 | 33 |
| 28 | 167 | 842 | 81.4 | AATCAGGACACGCAGCGACCTGCG | 4 | 25 | 30 | 31 | 32 | 29 |
| 29 | 183 | 926 | 76.7 | AATCGACCCTGTGTCTGCTTTGCG | 4 | 32 | 14 | 19 | 17 | 29 |
| 30 | 197 | 983 | 76.9 | AATCAGCCAAAGCGAAGTGCGATG | 4 | 36 | 6 | 16 | 33 | 27 |
| 31 | 216 | 1111 | 76.2 | ATACGACCTCGTGAGTTCCCGCAA | 5 | 32 | 10 | 20 | 28 | 21 |
| 32 | 226 | 1207 | 75.4 | AAAGCTTGACCTATCGAGCCGTGC | 6 | 11 | 23 | 24 | 36 | 33 |
| 33 | 268 | 1503 | 75.5 | AAAGAGCCGCTTGAGTCGAAATCG | 6 | 36 | 17 | 20 | 16 | 24 |
| 34 | 297 | 1649 | 75.7 | TCTGCTTGCTCACCTACCATTGCG | 8 | 11 | 13 | 26 | 15 | 29 |
| 35 | 332 | 1771 | 75 | TCTGATCGCCTAGGTAACGGGGAC | 8 | 24 | 26 | 18 | 35 | 34 |
| 36 | 358 | 1847 | 76.9 | TCTGCAGCGGTACTGTGGACCCAT | 8 | 31 | 18 | 14 | 34 | 15 |
| 37 | 375 | 1912 | 75.8 | TCTGAGCCACCTAATCTCCCACGG | 8 | 36 | 23 | 4 | 28 | 35 |
| 38 | 385 | 1941 | 77.4 | TGTCTCGTTCCCACCTCCATTCCC | 9 | 10 | 28 | 23 | 15 | 28 |
| 39 | 442 | 2093 | 81.4 | TGTCATCGCAGCGAGTCAGCCACG | 9 | 24 | 31 | 20 | 31 | 30 |
| 40 | 445 | 2103 | 77.7 | TGTCCCTAACCTGATGGTGCGCAA | 9 | 26 | 23 | 27 | 33 | 21 |
| 41 | 461 | 2143 | 77.3 | TGTCTGCGGTCTCCATATCGGTGC | 9 | 29 | 19 | 15 | 24 | 33 |
| 42 | 469 | 2154 | 76.2 | TGTCCACGCGTTACCTTGTCGATG | 9 | 30 | 12 | 23 | 9 | 27 |
| 43 | 487 | 2196 | 79.1 | TGTCGTGCTCTGACCTTGCGCTCA | 9 | 33 | 8 | 23 | 29 | 13 |
| 44 | 508 | 2231 | 81.7 | TGTCACGGAATCGTGCTGCGGCTT | 9 | 35 | 4 | 33 | 29 | 17 |
| 45 | 527 | 2307 | 77.4 | TCGTTCTGGCTTGGACGCTTCTCA | 10 | 8 | 17 | 34 | 17 | 13 |
| 46 | 602 | 2543 | 80 | TCGTTGCGTGTCGGACCTTGGATG | 10 | 29 | 9 | 34 | 11 | 27 |
| 47 | 686 | 2755 | 78.3 | CTTGCGTTGATGCGAATCGTCGAA | 11 | 12 | 27 | 16 | 10 | 16 |
| 48 | 973 | 3831 | 77.7 | CTGTCACGCTCAACCTTCCCCGTT | 14 | 30 | 13 | 23 | 28 | 12 |
| 49 | 987 | 3866 | 77.6 | CTGTGTGCCGTTTCGTGTGCAGTG | 14 | 33 | 12 | 10 | 33 | 22 |
| 50 | 1053 | 4127 | 77 | CCATGCAATCCCAGGATGTCGGTA | 15 | 21 | 28 | 25 | 9 | 18 |
| 51 | 1093 | 4232 | 78.7 | CCATCAGCTCTGGCAATGCGGAGT | 15 | 31 | 8 | 21 | 29 | 20 |

FIG. 26B

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 52 | 1142 | 4394 | 75.4 | CGAATCTGGGTAAGGAAGCCATCG | 16 | 8 | 18 | 25 | 36 | 24 |
| 53 | 1145 | 20638 | 77.7 | CGAATGTCCTGTCCATCGAATGCG | 16 | 9 | 14 | 15 | 16 | 29 |
| 54 | 1159 | 4453 | 75.2 | CGAACGTTTACATGCGTCGTAGCC | 16 | 12 | 7 | 29 | 10 | 36 |
| 55 | 1193 | 4568 | 78.3 | CGAAAGTGAGCCGCAACTTGGGAC | 16 | 22 | 36 | 21 | 11 | 34 |
| 56 | 1246 | 4751 | 78.9 | CGAAGGACAGTGAGTGTGCGCACG | 16 | 34 | 22 | 22 | 29 | 30 |
| 57 | 1560 | 6171 | 75.4 | GCAAAGCCATACCTTGGCTTGCTT | 21 | 36 | 5 | 11 | 17 | 17 |
| 58 | 1641 | 6531 | 75.7 | ACCTCTTGCCTACGAACAGCCAA | 23 | 11 | 26 | 16 | 31 | 16 |
| 59 | 1655 | 6599 | 78.8 | ACCTGCAAGTGCCCATGTGCCCTA | 23 | 21 | 33 | 15 | 33 | 26 |
| 60 | 1919 | 7289 | 80.1 | AGGATCTGGACCGGACTCCCCGAA | 25 | 8 | 32 | 34 | 28 | 16 |
| 61 | 1982 | 7538 | 78 | AGGAACGGCAGCTACACACGAGCC | 25 | 35 | 31 | 7 | 30 | 36 |
| 62 | 2081 | 8056 | 78.1 | GATGGACCACCTCAGCGCTTGACC | 27 | 32 | 23 | 31 | 17 | 32 |
| 63 | 2105 | 8145 | 77.8 | TCCCTTAGGACCCAGCGTCTGTGC | 28 | 3 | 32 | 31 | 19 | 33 |
| 64 | 2623 | 8944 | 75.5 | TGCGCCATAAAGGACCTTAGCCAT | 29 | 15 | 6 | 32 | 3 | 15 |
| 65 | 2755 | 9114 | 75.8 | TGCGAGGACCATGGTAGGTAAGCC | 29 | 25 | 15 | 18 | 18 | 36 |
| 66 | 12 | 42 | 81.5 | TTGATCGTGGACACGGCACGCTCA | 1 | 10 | 34 | 35 | 30 | 13 |
| 67 | 26 | 94 | 78.2 | TTGAAGTGCAGCCACGAAAGCGAA | 1 | 22 | 31 | 30 | 6 | 16 |
| 68 | 29 | 112 | 79.3 | TTGAATCGGAGTTGCGCGTTGGAC | 1 | 24 | 20 | 29 | 12 | 34 |
| 69 | 82 | 346 | 80.9 | TGATGATGGCTTCAGCTGCGCGAA | 2 | 27 | 17 | 31 | 29 | 16 |
| 70 | 86 | 351 | 79.2 | TGATTCCCTTGAACGGTCCCGGAC | 2 | 28 | 1 | 35 | 28 | 34 |
| 71 | 124 | 521 | 78.3 | TTAGGCAATTGATCCCGACCGTGC | 3 | 21 | 1 | 28 | 32 | 33 |
| 72 | 132 | 567 | 78.2 | TTAGTCCCACGGGATGCGTTGACC | 3 | 28 | 35 | 27 | 12 | 32 |
| 73 | 191 | 962 | 77.5 | AATCGGACATCGAGTGTCCCCAGC | 4 | 34 | 24 | 22 | 28 | 31 |
| 74 | 210 | 1078 | 75.8 | ATACTGCGCGTTCTGTGAGTTGCG | 5 | 29 | 12 | 14 | 20 | 29 |
| 75 | 325 | 1744 | 78.5 | TCTGGTCTGCAATCGTCACGCAGC | 8 | 19 | 21 | 10 | 30 | 31 |
| 76 | 436 | 2073 | 79.4 | TGTCAGTGCACGGCTTCTGTTGCC | 9 | 22 | 30 | 17 | 14 | 29 |
| 77 | 551 | 2365 | 77.2 | TCGTCTCAGCTTGACCGCTTCAGC | 10 | 13 | 17 | 32 | 17 | 31 |
| 78 | 629 | 2593 | 76.7 | TCGTCAGCCCTAATCGACCTGTGC | 10 | 31 | 26 | 24 | 23 | 33 |
| 79 | 644 | 2624 | 75.5 | TCGTGTGCGCTTAATCACGGAATC | 10 | 33 | 17 | 4 | 35 | 4 |
| 80 | 804 | 3213 | 76.4 | CGTTCGAAGTCTCTTGACGGACGG | 12 | 16 | 19 | 11 | 35 | 35 |
| 81 | 836 | 3345 | 75.7 | CGTTTCCCAATCATCGGCAAGTCT | 12 | 28 | 4 | 24 | 21 | 19 |
| 82 | 872 | 3431 | 77.5 | CGTTGTGCTGATGCAAATCGGCTT | 12 | 33 | 2 | 21 | 24 | 17 |
| 83 | 949 | 3748 | 79.9 | CTGTCTTGGTGCGCAAAGGATGCG | 14 | 11 | 33 | 21 | 25 | 29 |
| 84 | 1148 | 4415 | 77.1 | CGAATCGTTTGAGCAAGACCCACG | 16 | 10 | 1 | 21 | 32 | 30 |
| 85 | 1235 | 4695 | 76.7 | CGAACAGCTGCGAATCGTCTAGCC | 16 | 31 | 29 | 4 | 19 | 36 |
| 86 | 1406 | 5575 | 75.8 | GAGTTCGTGCTTACGGCTTGAGCC | 20 | 10 | 17 | 35 | 11 | 36 |
| 87 | 1603 | 6332 | 75.6 | AGTGTCCCGAGTACCTGGACACGG | 22 | 28 | 20 | 23 | 34 | 35 |
| 88 | 2216 | 8362 | 76.3 | TCCCGCTTTGATTCTGTCGTTCGT | 28 | 17 | 2 | 8 | 10 | 10 |
| 89 | 2286 | 8468 | 75 | TCCCACCTGTCTACCTAGCCGACC | 28 | 23 | 19 | 23 | 36 | 32 |
| 90 | 2364 | 8591 | 77.1 | TCCCCACGATACACCTTTGATGCG | 28 | 30 | 5 | 23 | 1 | 29 |
| 91 | 2556 | 30603 | 76.3 | TGCGCTTGATACTGTCGCTTCGAA | 29 | 11 | 5 | 9 | 17 | 16 |
| 92 | 2587 | 8909 | 75.8 | TGCGCTCAATACAGCCTCGTATCG | 29 | 13 | 5 | 36 | 10 | 24 |
| 93 | 2741 | 9095 | 79.8 | TGCGATCGCGAAGCAATGATCGTT | 29 | 24 | 16 | 21 | 2 | 12 |
| 94 | 2793 | 9168 | 77.9 | TGCGTCCCTCTGTGATCACGAGGA | 29 | 28 | 8 | 2 | 30 | 25 |
| 95 | 2821 | 9200 | 80.5 | TGCGCACGAGGAATCGCTTGAGTG | 29 | 30 | 25 | 24 | 11 | 22 |
| 96 | 3120 | 9759 | 76.9 | CACGGTGCTACAGTGCAAAGCACG | 30 | 33 | 7 | 33 | 6 | 30 |
| 97 | 6 | 18 | 79.1 | TTGAAAAGGGACGTGCGCTTCGAA | 1 | 6 | 34 | 33 | 17 | 16 |
| 98 | 8 | 25 | 79.5 | TTGATCTGCACGCGTTGTGCGGTA | 1 | 8 | 30 | 12 | 33 | 18 |
| 99 | 9 | 29 | 80.3 | TTGATGTCCCATTCCCCACGCGTT | 1 | 9 | 15 | 28 | 30 | 12 |
| 100 | 13 | 43 | 79.2 | TTGATCGTAGCCGGTATGCGACGG | 1 | 10 | 36 | 18 | 29 | 35 |
| 101 | 18 | 64 | 79.7 | TTGACCATGCTTCGAAACGGCGAA | 1 | 15 | 17 | 16 | 35 | 16 |
| 102 | 21 | 75 | 77.4 | TTGACGAAATCGGCAACCTATGCG | 1 | 16 | 34 | 21 | 26 | 29 |

*FIG. 26C*

| SEQ ID NO: | 4,633 ID# | HXX ID# | Tm | ZIPCODE (5'-3') | TETRAMER NUMBERS | | | | | |
|---|---|---|---|---|---|---|---|---|---|---|
| 103 | 32 | 12925 | 75.7 | TTGATCCCGGTATTAGAGCCCACG | 1 | 28 | 18 | 3 | 36 | 30 |
| 104 | 42 | 161 | 80.7 | TTGATGCGTGCGCTCAATCGAGGA | 1 | 29 | 29 | 13 | 24 | 25 |
| 105 | 43 | 165 | 80.1 | TTGATGCGAGCCGATGCCATCTTG | 1 | 29 | 36 | 27 | 15 | 11 |
| 106 | 49 | 186 | 79.1 | TTGACAGCACGGGACCCCTACACG | 1 | 31 | 35 | 32 | 26 | 30 |
| 107 | 53 | 208 | 80.3 | TTGAGTGCTCCCGCAACGTTGTGC | 1 | 33 | 28 | 21 | 12 | 33 |
| 108 | 58 | 230 | 76.8 | TTGAACGGGCAAACCTCTTGCTTG | 1 | 35 | 21 | 23 | 11 | 11 |
| 109 | 59 | 232 | 78.7 | TTGAACGGGATGGCAAGGACCTCA | 1 | 35 | 27 | 21 | 34 | 13 |
| 110 | 60 | 238 | 81.2 | TTGAAGCCTGTCCGTTTGCGACGG | 1 | 36 | 9 | 12 | 29 | 35 |
| 111 | 62 | 12961 | 75.5 | TTGAAGCCAGGATCCCAAAGCCTA | 1 | 36 | 25 | 28 | 6 | 26 |
| 112 | 68 | 270 | 78.4 | TGATTCTGACGGTCCCGCTTACGG | 2 | 8 | 35 | 28 | 17 | 35 |
| 113 | 70 | 275 | 82.6 | TGATTGTCCACGTGCGGGACACGG | 2 | 9 | 30 | 29 | 34 | 35 |
| 114 | 76 | 311 | 82.5 | TGATCGAAGTGCCACGCACGCGTT | 2 | 16 | 33 | 30 | 30 | 12 |
| 115 | 78 | 322 | 78.2 | TGATGGTAACGGCTCAAGCCGCTT | 2 | 18 | 35 | 13 | 36 | 17 |
| 116 | 81 | 335 | 80.5 | TGATGCAAAGCCGTGCAGCCTCTG | 2 | 21 | 36 | 33 | 36 | 8 |
| 117 | 84 | 349 | 80.6 | TGATGATGGTGCGCTTAGCCGCAA | 2 | 27 | 33 | 17 | 36 | 21 |
| 118 | 88 | 361 | 77.3 | TGATTCCCTCCCGGTATCGTACGG | 2 | 28 | 28 | 18 | 10 | 35 |
| 119 | 89 | 362 | 80.2 | TGATTCCCCACGGAGTGGACCAGC | 2 | 28 | 30 | 20 | 34 | 31 |
| 120 | 95 | 386 | 80.8 | TGATCACGATCGGGACGCAACACG | 2 | 30 | 24 | 34 | 21 | 30 |
| 121 | 96 | 388 | 77.8 | TGATCACGTCCCTTGAGACCGCAA | 2 | 30 | 28 | 1 | 32 | 21 |
| 122 | 98 | 404 | 80.2 | TGATCAGCCACGGGACAGCCAGTG | 2 | 31 | 30 | 34 | 36 | 22 |
| 123 | 99 | 405 | 76.7 | TGATCAGCGGACTTAGTCCCGTGC | 2 | 31 | 34 | 3 | 28 | 33 |
| 124 | 100 | 409 | 76.4 | TGATGACCCGAATGATTGTCGCAA | 2 | 32 | 15 | 2 | 9 | 21 |
| 125 | 101 | 411 | 79.7 | TGATGACCATCGAGCCCACGAGGA | 2 | 32 | 24 | 36 | 30 | 25 |
| 126 | 105 | 420 | 77.3 | TGATGTGCCGAAGAGTCACGGGAC | 2 | 33 | 16 | 20 | 30 | 34 |
| 127 | 106 | 421 | 80.4 | TGATGTGCGTCTACGGAGCCTGCG | 2 | 33 | 19 | 35 | 36 | 29 |
| 128 | 107 | 422 | 79.7 | TGATGTGCGAGTACGGACGGCGTT | 2 | 33 | 20 | 35 | 35 | 12 |
| 129 | 109 | 426 | 76.6 | TGATGTGCTGCGAAAGAGGATCCC | 2 | 33 | 29 | 6 | 25 | 28 |
| 130 | 112 | 435 | 78.3 | TGATGGACGACCCGAAGGACCTTG | 2 | 34 | 32 | 16 | 34 | 11 |
| 131 | 114 | 437 | 80.1 | TGATGGACAGCCGCTTGACCGATG | 2 | 34 | 36 | 17 | 32 | 27 |
| 132 | 125 | 532 | 76.8 | TTAGGCAATGCGCTGTCCTAACGG | 3 | 21 | 29 | 14 | 26 | 35 |
| 133 | 126 | 539 | 75.3 | TTAGATCGCACGTCTGCTTGCCAT | 3 | 24 | 30 | 8 | 11 | 15 |
| 134 | 135 | 599 | 75.7 | TTAGCAGCGCAATACAGGACCACG | 3 | 31 | 21 | 7 | 34 | 30 |
| 135 | 140 | 627 | 76.2 | TTAGGGACCTGTGTGCCTTGCGTT | 3 | 34 | 14 | 33 | 11 | 12 |
| 136 | 145 | 636 | 77.2 | TTAGGGACGGACAATCGATGCACG | 3 | 34 | 34 | 4 | 27 | 30 |
| 137 | 150 | 683 | 76.5 | AATCTCTGCGTTCCTATGCGCAA | 4 | 8 | 12 | 26 | 29 | 16 |
| 138 | 153 | 714 | 76 | AATCCGTTTCCCATACGATGCGAA | 4 | 12 | 28 | 5 | 27 | 16 |
| 139 | 157 | 743 | 77.7 | AATCCGAATCTGTCCCTCCCGGAC | 4 | 16 | 8 | 28 | 28 | 34 |
| 140 | 159 | 748 | 76.5 | AATCCGAAGCAAACGGTGTCGATG | 4 | 16 | 21 | 35 | 9 | 27 |
| 141 | 161 | 756 | 78.2 | AATCCGAACACGGACCGGACAGTG | 4 | 16 | 30 | 32 | 34 | 22 |
| 142 | 162 | 762 | 76 | AATCGCTTTAGGATGCAGCACGG | 4 | 17 | 3 | 27 | 31 | 35 |
| 143 | 163 | 768 | 75.4 | AATCGCTTCCATCGAAGACCGGTA | 4 | 17 | 15 | 16 | 32 | 18 |
| 144 | 165 | 793 | 79.6 | AATCGAGTCGAATGCGTCCCAGCC | 4 | 20 | 16 | 29 | 28 | 36 |
| 145 | 168 | 843 | 76.7 | AATCAGGAACGGCGTTCTTGGCTT | 4 | 25 | 35 | 12 | 11 | 17 |
| 146 | 171 | 877 | 76.6 | AATCTGCGTCGTTCTGTCCCGATG | 4 | 29 | 10 | 8 | 28 | 27 |
| 147 | 179 | 919 | 77.2 | AATCCAGCGATGGGACGAGTCGTT | 4 | 31 | 27 | 34 | 20 | 12 |
| 148 | 189 | 949 | 76.8 | AATCGTGCAGGACTCAGGACTGCG | 4 | 33 | 25 | 13 | 34 | 29 |
| 149 | 192 | 966 | 78.9 | AATCGGACTGCGCCATACCTGCAA | 4 | 34 | 29 | 15 | 23 | 21 |
| 150 | 201 | 993 | 78 | AATCAGCCATCGCTGTGCTTGCAA | 4 | 36 | 24 | 14 | 17 | 21 |
| 151 | 203 | 999 | 79.5 | AATCAGCCGTGCGGTAGACCGGAC | 4 | 36 | 33 | 18 | 32 | 34 |
| 152 | 205 | 1040 | 79 | ATACGCTTGGACGAGTTGCGGCAA | 5 | 17 | 34 | 20 | 29 | 21 |
| 153 | 206 | 1047 | 79.6 | ATACGCAAGACCATCGCACGGCAA | 5 | 21 | 32 | 24 | 30 | 21 |

FIG. 26D

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 154 | 214 | 1104 | 77.1 | ATACCAGCCTCAAGCCCGAAGTGC | 5 | 31 | 13 | 36 | 16 | 33 |
| 155 | 218 | 1122 | 80.3 | ATACGTGCTCGTGCTTTGCGTGCG | 5 | 33 | 10 | 17 | 29 | 29 |
| 156 | 228 | 1217 | 76.3 | AAAGCGTTTGTCCTTGGATGCGAA | 6 | 12 | 9 | 11 | 27 | 16 |
| 157 | 231 | 1229 | 77.1 | AAAGCTCATCGTGGACCGAAAGCC | 6 | 13 | 10 | 34 | 16 | 36 |
| 158 | 234 | 1271 | 75.1 | AAAGCGAACTGTAGTGCAGCACGG | 6 | 16 | 14 | 22 | 31 | 35 |
| 159 | 242 | 1333 | 76.6 | AAAGATCGCTTGCTGTACGGCGAA | 6 | 24 | 11 | 14 | 35 | 16 |
| 160 | 243 | 1337 | 76.5 | AAAGATCGGGTATGCGCACGTGTC | 6 | 24 | 18 | 29 | 30 | 9 |
| 161 | 248 | 1393 | 76 | AAAGTGCGATCGAGGACTCAACGG | 6 | 29 | 24 | 25 | 13 | 35 |
| 162 | 255 | 1441 | 75.6 | AAAGGACCGCAACTGTTCGTGCTT | 6 | 32 | 21 | 14 | 10 | 17 |
| 163 | 264 | 1474 | 76.7 | AAAGGGACCGAAAGTGCCATGGAC | 6 | 34 | 16 | 22 | 15 | 34 |
| 164 | 271 | 1519 | 80.5 | TACACCATTCCCTCCCCAGCGCAA | 7 | 15 | 28 | 28 | 31 | 21 |
| 165 | 272 | 1533 | 81.8 | TACATCCCCTTGCGAATGCGTGCG | 7 | 28 | 11 | 16 | 29 | 29 |
| 166 | 281 | 1587 | 76.8 | TACAACGGCTGTTCGTTGTCGCAA | 7 | 35 | 14 | 10 | 9 | 21 |
| 167 | 282 | 1590 | 76.1 | TACAACGGGCTTTGTCCACGGAGT | 7 | 35 | 17 | 9 | 30 | 20 |
| 168 | 286 | 1602 | 78.6 | TACAACGGACGGCCATCCATGCTT | 7 | 35 | 35 | 15 | 15 | 17 |
| 169 | 289 | 1620 | 78.5 | TCTGTTGAAGCCCGTTCGAAACGG | 8 | 1 | 36 | 12 | 16 | 35 |
| 170 | 290 | 1621 | 78.2 | TCTGTGATTGCGCTTGGGACGATG | 8 | 2 | 29 | 11 | 34 | 27 |
| 171 | 291 | 1624 | 78.6 | TCTGAATCTGCGCGAATGTCTGCG | 8 | 4 | 29 | 16 | 9 | 29 |
| 172 | 292 | 1625 | 76.4 | TCTGAATCCACGTTAGTGCGCACG | 8 | 4 | 30 | 3 | 29 | 30 |
| 173 | 298 | 1650 | 76.5 | TCTGCTTGCTGTGCTTTCCCCCTA | 8 | 11 | 14 | 17 | 28 | 26 |
| 174 | 299 | 1651 | 75.1 | TCTGCTTGGCTTAGTGGCTTCACG | 8 | 11 | 17 | 22 | 17 | 30 |
| 175 | 300 | 1653 | 80.1 | TCTGCTTGGATGCCATACGGTGCG | 8 | 11 | 27 | 15 | 35 | 29 |
| 176 | 301 | 1656 | 79.8 | TCTGCTTGGACCCTGTCACGGCAA | 8 | 11 | 32 | 14 | 30 | 21 |
| 177 | 304 | 1670 | 78.8 | TCTGCGTTATCGCACGGAGTGCAA | 8 | 12 | 24 | 30 | 20 | 21 |
| 178 | 306 | 1678 | 79.5 | TCTGCGTTAGCCGGACCTGTCACG | 8 | 12 | 36 | 34 | 14 | 30 |
| 179 | 313 | 1698 | 80.3 | TCTGCCATGACCGACCTCCCCTTG | 8 | 15 | 32 | 32 | 28 | 11 |
| 180 | 317 | 1722 | 80.4 | TCTGGCTTTGTCCAGCGCAATCCC | 8 | 17 | 9 | 31 | 21 | 28 |
| 181 | 321 | 1733 | 80 | TCTGGCTTGTGCGTCTGTGCCGTT | 8 | 17 | 33 | 19 | 33 | 12 |
| 182 | 322 | 1735 | 76.9 | TCTGGGTACGTTCGAATCCCCCAT | 8 | 18 | 12 | 16 | 28 | 15 |
| 183 | 324 | 1740 | 76.5 | TCTGGGTAGTGCATCGCGAAGCTT | 8 | 18 | 33 | 24 | 16 | 17 |
| 184 | 331 | 1765 | 79.3 | TCTGACCTACGGGTGCCGTTGTGC | 8 | 23 | 35 | 33 | 12 | 33 |
| 185 | 333 | 1772 | 79.4 | TCTGATCGTGCGGTCTACGGGTGC | 8 | 24 | 29 | 19 | 35 | 33 |
| 186 | 335 | 1776 | 80.3 | TCTGATCGGGACCAGCATCGGACC | 8 | 24 | 34 | 31 | 24 | 32 |
| 187 | 340 | 1800 | 79.3 | TCTGTCCCCTGTGACCAGCCGATG | 8 | 28 | 14 | 32 | 36 | 27 |
| 188 | 346 | 1811 | 79.1 | TCTGTGCGAAAGGGACCAGCAGGA | 8 | 29 | 6 | 34 | 31 | 25 |
| 189 | 353 | 1833 | 77.3 | TCTGCACGACCTTTGATCCCGATG | 8 | 30 | 23 | 1 | 28 | 27 |
| 190 | 363 | 1865 | 82.1 | TCTGGTGCAATCGACCCACGCAGC | 8 | 33 | 4 | 32 | 30 | 31 |
| 191 | 376 | 1917 | 77.7 | TCTGAGCCGACCTCGTGATGCTTG | 8 | 36 | 32 | 10 | 27 | 11 |
| 192 | 387 | 1945 | 79.7 | TGTCTCGTGTGCTCGTGACCGCAA | 9 | 10 | 33 | 10 | 32 | 21 |
| 193 | 392 | 1960 | 77.2 | TGTCCGTTTTGAGGACGACCATCG | 9 | 12 | 1 | 34 | 32 | 24 |
| 194 | 393 | 1961 | 78.6 | TGTCCGTTTGATTCCCCTTGGCAA | 9 | 12 | 2 | 28 | 11 | 21 |
| 195 | 395 | 1974 | 79.8 | TGTCCGTTGTGCCGTTCAGCCTGT | 9 | 12 | 33 | 12 | 31 | 14 |
| 196 | 399 | 1983 | 77.6 | TGTCCCATTTGAAAAGCAGCTGCG | 9 | 15 | 1 | 6 | 31 | 29 |
| 197 | 418 | 2028 | 75.5 | TGTCGCTTACGGATACAGCCGATG | 9 | 17 | 35 | 5 | 36 | 27 |
| 198 | 422 | 2035 | 79 | TGTCGGTAGGACATCGGGACCACG | 9 | 18 | 34 | 24 | 34 | 30 |
| 199 | 425 | 2049 | 81.3 | TGTCGAGTGCTTGTGCGTGCGACC | 9 | 20 | 17 | 33 | 33 | 32 |
| 200 | 430 | 2057 | 79.5 | TGTCGCAACTTGCTTGGTGCTCCC | 9 | 21 | 11 | 11 | 33 | 28 |
| 201 | 431 | 2058 | 77.8 | TGTCGCAACCATCACGGTCTGCTT | 9 | 21 | 15 | 30 | 19 | 17 |
| 202 | 432 | 2061 | 76.6 | TGTCGCAAGGTAAATCTGCGTCCC | 9 | 21 | 18 | 4 | 29 | 28 |
| 203 | 443 | 2094 | 78.4 | TGTCATCGGACCAATCATCGCGAA | 9 | 24 | 32 | 4 | 24 | 16 |
| 204 | 444 | 2097 | 79.5 | TGTCAGGACGAATCCCATCGGCAA | 9 | 25 | 16 | 28 | 24 | 21 |

FIG. 26E

| SEQ ID NO: | 4,633 ID# | HEX ID# | Tm | ZIPCODE (5'-3') | TETRAMER NUMBERS | | | | |
|---|---|---|---|---|---|---|---|---|---|
| 205 | 448 | 2109 | 76.6 | TGTCGATGCTTGTACATCCCGCAA | 9 | 27 | 11 | 7 | 28 | 21 |
| 206 | 449 | 2114 | 81.9 | TGTCGATGGATGGACCTGCGACGG | 9 | 27 | 27 | 32 | 29 | 35 |
| 207 | 450 | 2115 | 78.3 | TGTCGATGTCCCTCGTGCTTGTGC | 9 | 27 | 28 | 18 | 17 | 33 |
| 208 | 451 | 2116 | 79.2 | TGTCGATGTGCGCCTACAGCATCG | 9 | 27 | 29 | 26 | 31 | 24 |
| 209 | 452 | 2117 | 76.1 | TGTCGATGCACGACCTTTAGCGAA | 9 | 27 | 30 | 23 | 3 | 16 |
| 210 | 464 | 2147 | 75.8 | TGTCTGCGCCTATGATCTTGCAGC | 9 | 29 | 26 | 2 | 11 | 31 |
| 211 | 472 | 2158 | 75.9 | TGTCCACGGCAAAAAGCCTAGACC | 9 | 30 | 21 | 6 | 26 | 32 |
| 212 | 473 | 2163 | 78.8 | TGTCCACGCAGCAATCAGCCTTGA | 9 | 30 | 31 | 4 | 36 | 1 |
| 213 | 476 | 2174 | 79.6 | TGTCCAGCATCGCCATGATGGCTT | 9 | 31 | 24 | 15 | 27 | 17 |
| 214 | 477 | 2176 | 79.2 | TGTCCAGCCAGCCTTGCGAACTGT | 9 | 31 | 31 | 11 | 16 | 14 |
| 215 | 480 | 2181 | 80.9 | TGTCGACCAAAGAGCCAGCCCGAA | 9 | 32 | 6 | 36 | 36 | 16 |
| 216 | 481 | 2185 | 76.4 | TGTCGACCGGTAAGCCGACCATAC | 9 | 32 | 18 | 36 | 32 | 5 |
| 217 | 482 | 2186 | 81.6 | TGTCGACCAGTGCAGCGATGGCAA | 9 | 32 | 22 | 31 | 27 | 21 |
| 218 | 484 | 2189 | 80.6 | TGTCGACCTCCCGACCTCGTCAGC | 9 | 32 | 28 | 32 | 10 | 31 |
| 219 | 485 | 2191 | 79 | TGTCGACCGTGCTGTCAATCCACG | 9 | 32 | 33 | 9 | 4 | 30 |
| 220 | 488 | 2197 | 78.1 | TGTCGTGCTGTCTCGTAGCCCGAA | 9 | 33 | 9 | 10 | 36 | 16 |
| 221 | 495 | 2208 | 77.1 | TGTCGTGCCCTATCTGTGCGGTCT | 9 | 33 | 26 | 8 | 29 | 19 |
| 222 | 497 | 2212 | 79.2 | TGTCGTGCCAGCCCATAGGAATCG | 9 | 33 | 31 | 15 | 25 | 24 |
| 223 | 498 | 2215 | 80.1 | TGTCGGACAAAGTGCGACGGATCG | 9 | 34 | 6 | 29 | 35 | 24 |
| 224 | 499 | 2217 | 77.4 | TGTCGGACCTCAATACGTGCCAGC | 9 | 34 | 13 | 5 | 33 | 31 |
| 225 | 501 | 2219 | 78.4 | TGTCGGACCCATGACCCTCACCAT | 9 | 34 | 15 | 32 | 13 | 15 |
| 226 | 510 | 2234 | 75.9 | TGTCACGGCGTTAAAGTGTCCGAA | 9 | 35 | 12 | 6 | 9 | 16 |
| 227 | 515 | 2247 | 77.9 | TGTCAGCCCTTGCAGCAAAGCTTG | 9 | 36 | 11 | 31 | 6 | 11 |
| 228 | 525 | 2301 | 76.3 | TCGTAAAGACGGTGTCGCAACACG | 10 | 6 | 35 | 9 | 21 | 30 |
| 229 | 537 | 2336 | 77.2 | TCGTCTTGCTTGCGTTATCGCCAT | 10 | 11 | 11 | 12 | 24 | 15 |
| 230 | 545 | 2353 | 76.4 | TCGTCGTTGCAACTCAGGTATGCG | 10 | 12 | 21 | 13 | 18 | 29 |
| 231 | 547 | 2355 | 76.3 | TCGTCGTTAGGAACCTACGGCGAA | 10 | 12 | 25 | 23 | 35 | 16 |
| 232 | 548 | 2359 | 77.1 | TCGTCGTTCACGTACATCGTTGCG | 10 | 12 | 30 | 7 | 10 | 29 |
| 233 | 554 | 2371 | 81 | TCGTCTGTTCGTGACCACGGTGCG | 10 | 14 | 10 | 32 | 35 | 29 |
| 234 | 557 | 2382 | 79.3 | TCGTCCATATCGCAGCCCATCAGC | 10 | 15 | 24 | 31 | 15 | 31 |
| 235 | 560 | 2390 | 78.4 | TCGTCCATGGACCGAAGCAAGACC | 10 | 15 | 34 | 16 | 21 | 32 |
| 236 | 581 | 2470 | 82 | TCGTACCTGTGCCAGCCACGGTGC | 10 | 23 | 33 | 31 | 30 | 33 |
| 237 | 582 | 2475 | 75.7 | TCGTATCGCTGTACCTCGTTTGCG | 10 | 24 | 14 | 23 | 12 | 29 |
| 238 | 588 | 2502 | 75.9 | TCGTCCTAACGGATCGTTGAAGCC | 10 | 26 | 35 | 24 | 1 | 36 |
| 239 | 589 | 2509 | 81.8 | TCGTGATGATCGGTGCACGGTCCC | 10 | 27 | 24 | 33 | 35 | 28 |
| 240 | 591 | 2523 | 77.1 | TCGTTCCCCTCAAGTGGACCACCT | 10 | 28 | 13 | 22 | 32 | 23 |
| 241 | 596 | 2531 | 79.5 | TCGTTCCCAGTGGATGGGACCCAT | 10 | 28 | 22 | 27 | 34 | 15 |
| 242 | 597 | 2534 | 77.9 | TCGTTCCCGATGAGGAACGGTGAT | 10 | 28 | 27 | 25 | 35 | 2 |
| 243 | 599 | 2536 | 80.5 | TCGTTCCCAGCCGTTGTCTCAGC | 10 | 28 | 31 | 12 | 19 | 31 |
| 244 | 606 | 2549 | 80.7 | TCGTTGCGGCAATGATCCATCACG | 10 | 29 | 21 | 2 | 15 | 30 |
| 245 | 609 | 2555 | 81.8 | TCGTTGCGTCCCCTCAGTGCCTCA | 10 | 29 | 28 | 13 | 33 | 13 |
| 246 | 610 | 2557 | 80.5 | TCGTTGCGCACGTGATCGTTCCAT | 10 | 29 | 30 | 2 | 12 | 15 |
| 247 | 613 | 2560 | 80.9 | TCGTTGCGGTGCTGATGGACATCG | 10 | 29 | 33 | 2 | 34 | 24 |
| 248 | 638 | 2611 | 81.5 | TCGTGACCGACCGATGTCCCAGGA | 10 | 32 | 32 | 27 | 28 | 25 |
| 249 | 649 | 2631 | 80.4 | TCGTGTGCGATGGAGTGTGCCCAT | 10 | 33 | 27 | 20 | 33 | 15 |
| 250 | 650 | 2633 | 78.1 | TCGTGTGCGACCTGATATCGGTGC | 10 | 33 | 32 | 2 | 24 | 33 |
| 251 | 657 | 2649 | 77.5 | TCGTGGACAGGAGATGGCTTGTGC | 10 | 34 | 25 | 27 | 17 | 33 |
| 252 | 663 | 2659 | 81 | TCGTACGGTGATCACGCAGCACGG | 10 | 35 | 2 | 30 | 31 | 35 |
| 253 | 667 | 2674 | 76.2 | TCGTACGGGACAAAGCGTTGTCT | 10 | 35 | 34 | 6 | 12 | 19 |
| 254 | 678 | 2722 | 81.6 | CTTGTGTCGTGCACGGCTGTTGCG | 11 | 9 | 33 | 35 | 14 | 29 |
| 255 | 679 | 2725 | 75.8 | CTTGTCGTCCATAGCCTCCCGGTA | 11 | 10 | 15 | 36 | 28 | 18 |

FIG. 26F

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 256 | 692 | 2779 | 79 | CTTGCCATGTCTTGCGGCTTACGG | 11 | 15 | 19 | 29 | 17 | 35 |
| 257 | 695 | 2808 | 76.3 | CTTGGCTTTCGTCCATCTTGGTGC | 11 | 17 | 10 | 15 | 11 | 33 |
| 258 | 711 | 2878 | 79.6 | CTTGAGGAGCTTTGCGCCATGCAA | 11 | 25 | 17 | 29 | 15 | 21 |
| 259 | 721 | 2907 | 77.2 | CTTGTCCCAAAGGCTTGCAATCCC | 11 | 28 | 6 | 17 | 21 | 28 |
| 260 | 726 | 2928 | 75.6 | CTTGTGCGCTTGAAAGCGAATCTG | 11 | 29 | 11 | 6 | 16 | 8 |
| 261 | 727 | 2931 | 77.5 | CTTGTGCGGAGTTGTCAGCCGGTA | 11 | 29 | 20 | 9 | 36 | 18 |
| 262 | 731 | 2945 | 80.3 | CTTGCACGTGTCTCCCAGCCCCAT | 11 | 30 | 9 | 28 | 36 | 15 |
| 263 | 733 | 2948 | 75.6 | CTTGCACGCTGTCGAATTAGCAGC | 11 | 30 | 14 | 16 | 3 | 31 |
| 264 | 749 | 3014 | 78.3 | CTTGGGACACCTCTGTGTGCGCAA | 11 | 34 | 23 | 14 | 33 | 21 |
| 265 | 753 | 3027 | 79.5 | CTTGACGGAGTGACGGCGAACGAA | 11 | 35 | 22 | 35 | 16 | 16 |
| 266 | 759 | 3038 | 78.5 | CTTGAGCCAATCTGCGGCAACCAT | 11 | 36 | 4 | 29 | 21 | 15 |
| 267 | 760 | 3045 | 75 | CTTGAGCCGTCTCCTAATCGAGCC | 11 | 36 | 19 | 26 | 24 | 36 |
| 268 | 762 | 3048 | 78.2 | CTTGAGCCAGTGAAAGTGCGCACG | 11 | 36 | 22 | 6 | 29 | 30 |
| 269 | 773 | 3108 | 80.7 | CGTTTCTGTCGTTCCCGTGCGGAC | 12 | 8 | 10 | 28 | 33 | 34 |
| 270 | 784 | 3142 | 78.7 | CGTTTCGTGTCTGGACCACGTCCC | 12 | 10 | 19 | 34 | 30 | 28 |
| 271 | 809 | 3232 | 79.6 | CGTTGCTTTGCGGATGTCGTACGG | 12 | 17 | 29 | 27 | 10 | 35 |
| 272 | 810 | 3238 | 75.4 | CGTTGGTAAAAGTCGTTCCCAGCC | 12 | 18 | 6 | 10 | 28 | 36 |
| 273 | 811 | 3245 | 80.4 | CGTTGGTACACGCCATCAGCCACG | 12 | 18 | 30 | 15 | 31 | 30 |
| 274 | 832 | 3321 | 78.9 | CGTTCCTACACGCTTGTGCGGACC | 12 | 26 | 30 | 11 | 29 | 32 |
| 275 | 837 | 3349 | 76.4 | CGTTTCCCCGTTGGTAAATCCCAT | 12 | 28 | 12 | 18 | 4 | 15 |
| 276 | 838 | 3351 | 77.5 | CGTTTCCCCATTGTCGAGTCGTT | 12 | 28 | 15 | 9 | 20 | 12 |
| 277 | 843 | 3364 | 79.4 | CGTTTCCCGTGCTGCGAGTGTGAT | 12 | 28 | 33 | 29 | 22 | 2 |
| 278 | 844 | 3366 | 76.1 | CGTTTGCGTTAGAGTGCACGATCG | 12 | 29 | 3 | 22 | 30 | 24 |
| 279 | 857 | 3398 | 77.8 | CGTTCACGCACGTGTCAAAGTCCC | 12 | 30 | 30 | 9 | 6 | 28 |
| 280 | 867 | 3420 | 76.8 | CGTTGACCCTTGGCAATACAACGG | 12 | 32 | 11 | 21 | 7 | 35 |
| 281 | 878 | 3451 | 80.1 | CGTTGTGCACGGCTTGTGTCCGTT | 12 | 33 | 35 | 11 | 9 | 12 |
| 282 | 898 | 3516 | 76.1 | CTCAAAAGTGCGTCGTTGATTGCG | 13 | 6 | 29 | 10 | 2 | 29 |
| 283 | 899 | 3518 | 75.4 | CTCAAAAGGACCTCTGCAGCCGTT | 13 | 6 | 32 | 8 | 31 | 12 |
| 284 | 901 | 3530 | 78.5 | CTCATCGTGCAACGTTGACCACGG | 13 | 10 | 21 | 12 | 32 | 35 |
| 285 | 923 | 3620 | 77.7 | CTCATCCCGGACAGGAGTGCACCT | 13 | 28 | 34 | 25 | 33 | 23 |
| 286 | 961 | 3798 | 80 | CTGTGATGCAGCCGAAATCGCAGC | 14 | 27 | 31 | 16 | 24 | 31 |
| 287 | 965 | 3809 | 77.1 | CTGTTCCCTGCGTTGAGGTATGCG | 14 | 28 | 29 | 1 | 18 | 29 |
| 288 | 972 | 3829 | 79.1 | CTGTTGCGACGGGCAACCATTGAT | 14 | 29 | 35 | 21 | 15 | 2 |
| 289 | 982 | 3856 | 77.2 | CTGTGACCCATCTTGATCGGCAA | 14 | 32 | 15 | 11 | 24 | 21 |
| 290 | 989 | 3872 | 80.5 | CTGTGTGCATCGGACCACCTTGCG | 14 | 33 | 24 | 32 | 23 | 29 |
| 291 | 991 | 3873 | 77.2 | CTGTGTGCCACGATACGGACCGTT | 14 | 33 | 30 | 5 | 34 | 12 |
| 292 | 993 | 3878 | 77 | CTGTGGACCCTACCATTCCCAGCC | 14 | 34 | 26 | 15 | 28 | 36 |
| 293 | 994 | 3882 | 81 | CTGTGGACCACGGTGCGATGCTCA | 14 | 34 | 30 | 33 | 27 | 13 |
| 294 | 1016 | 3987 | 76.6 | CCATTGTCCAGCTTGAACGGCTGT | 15 | 9 | 31 | 1 | 35 | 14 |
| 295 | 1018 | 3993 | 75.1 | CCATTCGTTCGTCGTTGCTTATCG | 15 | 10 | 10 | 12 | 17 | 24 |
| 296 | 1020 | 3999 | 80.8 | CCATTCGTGAGTCACGTGCGCAGC | 15 | 10 | 20 | 30 | 29 | 31 |
| 297 | 1074 | 4202 | 79.8 | CCATTGCGATACGGACATCGGCAA | 15 | 29 | 5 | 34 | 24 | 21 |
| 298 | 1077 | 4209 | 80 | CCATTGCGCGAAGATGCTCACAGC | 15 | 29 | 16 | 27 | 13 | 31 |
| 299 | 1085 | 4220 | 79.4 | CCATCACGAATCGCTTGTGCGCTT | 15 | 30 | 4 | 17 | 33 | 17 |
| 300 | 1099 | 4243 | 77.3 | CCATCAGCAGCCAAAGGTCTTCCC | 15 | 31 | 36 | 6 | 19 | 28 |
| 301 | 1126 | 14325 | 76.8 | CGAATTGATCCCAATCCGAATCCC | 16 | 1 | 28 | 4 | 16 | 28 |
| 302 | 1129 | 4341 | 77 | CGAATTAGCACGGGTACAGCACGG | 16 | 3 | 30 | 18 | 31 | 35 |
| 303 | 1147 | 30238 | 79.8 | CGAATGTCTCCCGTGCCCATAGCC | 16 | 9 | 28 | 33 | 15 | 36 |
| 304 | 1151 | 4428 | 75.9 | CGAATCGTACCTTGCGGGTCTCGTT | 16 | 10 | 23 | 29 | 19 | 12 |
| 305 | 1152 | 14366 | 76.5 | CGAATCGTCCTAAGGATCCCAGCC | 16 | 10 | 26 | 25 | 28 | 36 |
| 306 | 1162 | 4467 | 80.7 | CGAACTCACGTTCACGCGTTTGCG | 16 | 13 | 12 | 30 | 12 | 29 |

FIG. 26G

| SEQ ID NO: | 4,633 ID# | HEX ID# | Tm | ZIPCODE (5'-3') | TETRAMER NUMBERS | | | | |
|---|---|---|---|---|---|---|---|---|---|
| 307 | 1167 | 4480 | 77.4 | CGAACCATTGATCTTGCACGCGTT | 16 | 15 | 2 | 11 | 30 | 12 |
| 308 | 1172 | 4490 | 78.2 | CGAACCATCAGCGACCGTCTAGCC | 16 | 15 | 31 | 32 | 19 | 36 |
| 309 | 1179 | 4518 | 78.4 | CGAAGCTTCTGTTCCCCGTTTCCC | 16 | 17 | 14 | 28 | 12 | 28 |
| 310 | 1200 | 4598 | 76.4 | CGAAATCGACCTTCTGGATGCAGC | 16 | 24 | 23 | 8 | 27 | 31 |
| 311 | 1201 | 4604 | 79 | CGAAATCGACGGGAGTTGTCTGCG | 16 | 24 | 35 | 20 | 9 | 29 |
| 312 | 1221 | 4659 | 76.6 | CGAATGCGGCTTCGTTAAAGCTTG | 16 | 29 | 17 | 12 | 6 | 11 |
| 313 | 1222 | 4660 | 76.6 | CGAATGCGGGTAATACTGCGTCGT | 16 | 29 | 18 | 5 | 29 | 10 |
| 314 | 1249 | 4759 | 76.7 | CGAAGGACGTGCACCTCCTACGAA | 16 | 34 | 33 | 23 | 26 | 16 |
| 315 | 1251 | 4761 | 77.2 | CGAAACGGTTAGCTGTCAGCACGG | 16 | 35 | 3 | 14 | 31 | 35 |
| 316 | 1259 | 4782 | 79.8 | CGAAACGGAGCCGTCTCGTTGCTT | 16 | 35 | 36 | 19 | 12 | 17 |
| 317 | 1263 | 4793 | 79.1 | CGAAAGCCGCAAAGTGAATCGTGC | 16 | 36 | 21 | 22 | 4 | 33 |
| 318 | 1284 | 4872 | 76.1 | GCTTTCGTCGAAGTCTCACGCCAT | 17 | 10 | 16 | 19 | 30 | 15 |
| 319 | 1290 | 4896 | 76.5 | GCTTCTTGACGGAGCCTTGACACG | 17 | 11 | 35 | 36 | 1 | 30 |
| 320 | 1375 | 5432 | 77.1 | GTCTCTTGCGTTTGCGCCTAGCAA | 19 | 11 | 12 | 29 | 26 | 21 |
| 321 | 1398 | 5534 | 78.6 | GTCTGTGCGGACCCTAACGGCTCA | 19 | 33 | 34 | 26 | 35 | 13 |
| 322 | 1424 | 5680 | 79 | GAGTGACCCAGCTGTCGGACCACG | 20 | 32 | 31 | 9 | 34 | 30 |
| 323 | 1427 | 5684 | 79.5 | GAGTGTGCCTTGTGCGCGAACGTT | 20 | 33 | 11 | 29 | 16 | 12 |
| 324 | 1439 | 5787 | 80.7 | GCAATACATCCCGGACACGGGCAA | 21 | 7 | 28 | 34 | 35 | 21 |
| 325 | 1454 | 5821 | 78.8 | GCAATCGTGATGGTCTTGCGTCCC | 21 | 10 | 27 | 19 | 29 | 28 |
| 326 | 1462 | 5855 | 78 | GCAACGTTGGACCTTGCTGTTCCC | 21 | 12 | 34 | 11 | 14 | 28 |
| 327 | 1463 | 5859 | 75.3 | GCAACTCAACCTCCATTCGTTCCC | 21 | 13 | 23 | 15 | 10 | 28 |
| 328 | 1465 | 5862 | 80.8 | GCAACTCATGCGCACGTCTGGTGC | 21 | 13 | 29 | 30 | 8 | 33 |
| 329 | 1479 | 5941 | 77.6 | GCAAGCAATTAGCACGCCATCGAA | 21 | 21 | 3 | 30 | 15 | 16 |
| 330 | 1485 | 5962 | 76.9 | GCAAAGTGTCGTTTGATGCGGGAC | 21 | 22 | 10 | 1 | 29 | 34 |
| 331 | 1489 | 5980 | 77.9 | GCAAACCTCTCATGCGTGATTGCG | 21 | 23 | 13 | 29 | 2 | 29 |
| 332 | 1496 | 14968 | 78.2 | GCAAATCGATCGCGAACGAAGGAC | 21 | 24 | 24 | 16 | 16 | 34 |
| 333 | 1499 | 6008 | 75.1 | GCAAATCGAGCCAATCGGTAACCT | 21 | 24 | 36 | 4 | 18 | 23 |
| 334 | 1550 | 6148 | 77.1 | GCAAGGACGTCTTGTCCGTTCACG | 21 | 34 | 19 | 9 | 12 | 30 |
| 335 | 1561 | 6173 | 78.4 | GCAAAGCCCGTTCAGCACCTTCTG | 21 | 36 | 12 | 31 | 23 | 8 |
| 336 | 1580 | 6250 | 76.9 | AGTGCGAACTTGTCTGGGACTGCG | 22 | 16 | 11 | 8 | 34 | 29 |
| 337 | 1632 | 6471 | 75.2 | ACCTTTAGCGTTTGTCTGCGTCCC | 23 | 3 | 12 | 9 | 29 | 28 |
| 338 | 1647 | 6557 | 75.4 | ACCTCGAACCATTACATGCGGCTT | 23 | 16 | 15 | 7 | 29 | 17 |
| 339 | 1650 | 6572 | 76.2 | ACCTGCTTCGAAGTGCCTGTCAGC | 23 | 17 | 16 | 33 | 14 | 31 |
| 340 | 1675 | 6706 | 78.3 | ACCTGTGCTTGACACGATCGCACG | 23 | 33 | 1 | 30 | 24 | 30 |
| 341 | 1700 | 6802 | 76.1 | ATCGAAAGCTCAGTGCGCAAGCTT | 24 | 6 | 13 | 33 | 21 | 17 |
| 342 | 1710 | 6845 | 77.1 | ATCGCTTGTGTCTGCGAGCCTCTG | 24 | 11 | 9 | 29 | 36 | 8 |
| 343 | 1712 | 6850 | 75.7 | ATCGCTTGCGAAAAGCTGTCCAT | 24 | 11 | 16 | 6 | 14 | 15 |
| 344 | 1724 | 6870 | 75.1 | ATCGCGTTGAGTAGGAGGACGGAC | 24 | 12 | 20 | 25 | 34 | 34 |
| 345 | 1730 | 6882 | 81.7 | ATCGCTCATCTGGTGCGGACGCAA | 24 | 13 | 8 | 33 | 34 | 21 |
| 346 | 1737 | 6903 | 80.1 | ATCGCTGTGATGCGTTACGGCACG | 24 | 14 | 27 | 12 | 35 | 30 |
| 347 | 1743 | 6911 | 77.2 | ATCGCCATAATCCAGCCAGCACCT | 24 | 15 | 4 | 31 | 31 | 23 |
| 348 | 1766 | 6956 | 75.7 | ATCGGCTTCAGCAAAGTCTGCCAT | 24 | 17 | 31 | 6 | 8 | 15 |
| 349 | 1781 | 6994 | 79.4 | ATCGGAGTGGACCACGCTTGGGAC | 24 | 20 | 34 | 30 | 11 | 34 |
| 350 | 1794 | 7018 | 76.4 | ATCGAGTGCTCAAGGAATCGGCAA | 24 | 22 | 13 | 25 | 24 | 21 |
| 351 | 1813 | 7068 | 76.9 | ATCGCCTAGATGTGCGAGGATCCC | 24 | 26 | 27 | 29 | 25 | 28 |
| 352 | 1831 | 7104 | 80.2 | ATCGTCCCAGCCCTGTGATGGTGC | 24 | 28 | 36 | 14 | 27 | 33 |
| 353 | 1877 | 7191 | 76.6 | ATCGGGACTACAATCGCAGCGATG | 24 | 34 | 7 | 24 | 31 | 27 |
| 354 | 1889 | 7213 | 79.4 | ATCGACGGTGTCCGAACCATGCAA | 24 | 35 | 9 | 16 | 15 | 21 |
| 355 | 1904 | 7235 | 76.7 | ATCGAGCCGAGTTGACGAACACG | 24 | 36 | 20 | 1 | 16 | 30 |
| 356 | 1923 | 7302 | 78.5 | AGGATCGTGACCAGGACAGCACGG | 25 | 10 | 32 | 25 | 31 | 35 |
| 357 | 1940 | 7357 | 78.7 | AGGAGCTTGATGTCCCGCAATCCC | 25 | 17 | 27 | 28 | 21 | 28 |

*FIG. 26H*

| SEQ ID NO: | 4,633 ID# | HEX ID# | Tm | ZIPCODE (5'-3') | TETRAMER NUMBERS | | | | |
|---|---|---|---|---|---|---|---|---|---|
| 358 | 1944 | 7388 | 76.7 | AGGAAGTGGGTAGCAATCCCCACG | 25 | 22 | 18 | 21 | 28 | 30 |
| 359 | 1975 | 7510 | 79.3 | AGGAGTGCGTGCCTTGGACCACCT | 25 | 33 | 33 | 11 | 32 | 23 |
| 360 | 2007 | 7750 | 78.7 | CCTACAGCAGGAGACCGACCGCAA | 26 | 31 | 25 | 32 | 32 | 21 |
| 361 | 2029 | 7882 | 77.9 | GATGCCATGCAACAGCAGGACAGC | 27 | 15 | 21 | 31 | 25 | 31 |
| 362 | 2083 | 8075 | 79.2 | GATGGGACCTTGCACGTCGTCGAA | 27 | 34 | 11 | 30 | 10 | 16 |
| 363 | 2098 | 8128 | 78.2 | TCCCTGATTCCCCGAACGTTGATG | 28 | 2 | 28 | 16 | 12 | 27 |
| 364 | 2128 | 15756 | 76.4 | TCCCTACATGCGTTAGGACCCACG | 28 | 7 | 29 | 3 | 32 | 30 |
| 365 | 2134 | 8207 | 79.3 | TCCCTCTGGATGCACGAATCGTGC | 28 | 8 | 27 | 30 | 4 | 33 |
| 366 | 2158 | 8259 | 79.9 | TCCCCTTGTGCGATCGCTGTCTCA | 28 | 11 | 29 | 24 | 14 | 13 |
| 367 | 2174 | 8284 | 78.8 | TCCCCGTTACGGAGTGGTCTGCAA | 28 | 12 | 35 | 22 | 19 | 21 |
| 368 | 2177 | 8289 | 79.4 | TCCCCTCATACAACGGCCATGCAA | 28 | 13 | 7 | 35 | 15 | 21 |
| 369 | 2179 | 8294 | 76.8 | TCCCCTCACTGTCCTATCCCAGCC | 28 | 13 | 14 | 26 | 28 | 36 |
| 370 | 2183 | 8299 | 75.3 | TCCCCTCACCTAATACACGGCGTT | 28 | 13 | 26 | 5 | 35 | 12 |
| 371 | 2197 | 8327 | 78.3 | TCCCCCATATACGCAACAGCAGCC | 28 | 15 | 5 | 21 | 31 | 36 |
| 372 | 2207 | 8344 | 76.9 | TCCCGAATGATGCTTCGTTTTGA | 28 | 16 | 2 | 17 | 12 | 1 |
| 373 | 2237 | 8396 | 78.7 | TCCCGGTAGACCCCATGACCACCT | 28 | 18 | 32 | 15 | 32 | 23 |
| 374 | 2243 | 8403 | 78.1 | TCCCGTCTCTGTGATGAGCCCGTT | 28 | 19 | 14 | 27 | 36 | 12 |
| 375 | 2254 | 40508 | 82.8 | TCCCGAGTTGTCGACCCCATTGCG | 28 | 20 | 9 | 32 | 15 | 29 |
| 376 | 2271 | 8440 | 79.1 | TCCCGCAAAGGAGAGTGATGCGAA | 28 | 21 | 25 | 20 | 27 | 16 |
| 377 | 2293 | 8479 | 76.5 | TCCCATCGTGTCTGATAGCCAGCC | 28 | 24 | 9 | 2 | 36 | 36 |
| 378 | 2304 | 8502 | 77.7 | TCCCAGGACTGTTTGACACGGCAA | 28 | 25 | 14 | 1 | 30 | 21 |
| 379 | 2365 | 8592 | 76.3 | TCCCACGTACAGGACAATCAGCC | 28 | 30 | 7 | 34 | 4 | 36 |
| 380 | 2369 | 8597 | 80 | TCCCACGGCTTCTTGACCTCGAA | 28 | 30 | 17 | 11 | 23 | 16 |
| 381 | 2403 | 8640 | 80.9 | TCCCGACCGCTTGGTACCATGTGC | 28 | 32 | 17 | 18 | 15 | 33 |
| 382 | 2421 | 8665 | 77.3 | TCCCGGACTGATCGTTGATGCTTG | 28 | 34 | 2 | 12 | 27 | 11 |
| 383 | 2422 | 8666 | 76.9 | TCCCGGACTTAGCGAACTTGTCCC | 28 | 34 | 3 | 16 | 11 | 28 |
| 384 | 2440 | 8695 | 79.7 | TCCCACGGCGAATGTCCCTACGTT | 28 | 35 | 16 | 9 | 26 | 12 |
| 385 | 2444 | 8703 | 81.8 | TCCCACGGTCCCGAGTGGTAACGG | 28 | 35 | 28 | 20 | 18 | 35 |
| 386 | 2452 | 8710 | 77.1 | TCCCAGCCTACATGTCACGGGATG | 28 | 36 | 7 | 9 | 35 | 27 |
| 387 | 2461 | 8720 | 80.4 | TCCCAGCCGATGGATGATCGGGTA | 28 | 36 | 27 | 27 | 24 | 18 |
| 388 | 2468 | 8728 | 79.2 | TGCGTTGACTTGAGTGACGGCACG | 29 | 1 | 11 | 22 | 35 | 30 |
| 389 | 2471 | 15876 | 76.1 | TGCGTTGAACCTACGGGGACTGAT | 29 | 1 | 23 | 35 | 34 | 2 |
| 390 | 2477 | 40574 | 78.8 | TGCGTGATCGTTCTCACAGCCGAA | 29 | 2 | 12 | 13 | 31 | 16 |
| 391 | 2479 | 8749 | 79.4 | TGCGTGATGTCTCACGCGAACAGC | 29 | 2 | 19 | 30 | 16 | 31 |
| 392 | 2482 | 8752 | 77 | TGCGTGATGATGTGTCCGAAGTGC | 29 | 2 | 27 | 9 | 16 | 33 |
| 393 | 2497 | 8775 | 77.2 | TGCGAATCCTGTTGTCCAGCGTCT | 29 | 4 | 14 | 9 | 31 | 19 |
| 394 | 2503 | 8788 | 75.3 | TGCGATACGTCTGAGTAGCCCGAA | 29 | 5 | 19 | 20 | 36 | 16 |
| 395 | 2507 | 8796 | 76.1 | TGCGAAAGTGATAGCCAGTGGCAA | 29 | 6 | 2 | 36 | 22 | 21 |
| 396 | 2515 | 8808 | 77.9 | TGCGAAAGGTGCAGGAGAGTTCCC | 29 | 6 | 33 | 25 | 20 | 28 |
| 397 | 2517 | 15901 | 77.1 | TGCGTACATCGTACGGCTCACACG | 29 | 7 | 10 | 35 | 13 | 30 |
| 398 | 2520 | 8817 | 78.5 | TGCGTACAGGACTGCGAAAGTGCG | 29 | 7 | 34 | 29 | 6 | 29 |
| 399 | 2546 | 8864 | 75.1 | TGCGTCGTGGTACCTATGTCGCTT | 29 | 10 | 18 | 26 | 9 | 17 |
| 400 | 2578 | 8901 | 76.5 | TGCGCGTTCCTAAAAGCCATCTGT | 29 | 12 | 26 | 6 | 15 | 14 |
| 401 | 2592 | 15912 | 78.2 | TGCGCTCACTCAGACCAAAGGCAA | 29 | 13 | 13 | 32 | 6 | 21 |
| 402 | 2594 | 15913 | 78.7 | TGCGCTCACGAACCATCGTTTTGA | 29 | 13 | 16 | 15 | 12 | 1 |
| 403 | 2595 | 30609 | 77.9 | TGCGCTCAGAGTTTAGCACGACGG | 29 | 13 | 20 | 3 | 30 | 35 |
| 404 | 2599 | 8923 | 79.3 | TGCGCTCAAGCCAGGAGCTTGGTA | 29 | 13 | 36 | 25 | 17 | 18 |
| 405 | 2600 | 8924 | 76.6 | TGCGCTGTTTGAGTGCTCGTATCG | 29 | 14 | 1 | 33 | 10 | 24 |
| 406 | 2608 | 21521 | 76.7 | TGCGCTGTCGTTAGGATCTGTCCC | 29 | 14 | 12 | 25 | 8 | 28 |
| 407 | 2614 | 30613 | 77.9 | TGCGCTGTGAGTCTGTCGAAAGCC | 29 | 14 | 20 | 14 | 16 | 36 |
| 408 | 2624 | 40623 | 77.7 | TGCGCCATCTGTAGCCTGATCAGC | 29 | 15 | 14 | 36 | 2 | 31 |

FIG. 26I

| SEQ ID NO: | 4,633 ID# | BEX ID# | Tm | ZIPCODE (5'-3') | TETRAMER NUMBERS | | | | | |
|---|---|---|---|---|---|---|---|---|---|---|
| 409 | 2641 | 8968 | 79.5 | TGCGCGAAGACCACCTCTGTACGG | 29 | 16 | 32 | 23 | 14 | 35 |
| 410 | 2642 | 8970 | 80.4 | TGCGCGAAGGACGCAATTAGTCCC | 29 | 16 | 34 | 21 | 3 | 28 |
| 411 | 2643 | 8973 | 77.3 | TGCGGCTTAATCCTCAGCAACGAA | 29 | 17 | 4 | 13 | 21 | 16 |
| 412 | 2655 | 8991 | 79.4 | TGCGGGTATCTGCTGTGACCCAGC | 29 | 18 | 8 | 14 | 32 | 31 |
| 413 | 2663 | 9004 | 77.7 | TGCGGGTAGATGCCTAGACCGACC | 29 | 18 | 27 | 26 | 32 | 32 |
| 414 | 2687 | 21565 | 80.5 | TGCGGAGTGAGTGCTTCAGCACGG | 29 | 20 | 20 | 17 | 31 | 35 |
| 415 | 2690 | 9040 | 80.1 | TGCGGAGTTGCGAGTGCGAACTGT | 29 | 20 | 29 | 22 | 16 | 14 |
| 416 | 2691 | 30634 | 78.6 | TGCGGAGTCACGTCCCTACAAGCC | 29 | 20 | 30 | 28 | 7 | 36 |
| 417 | 2708 | 9054 | 82.1 | TGCGAGTGAATCGGACGGACGTGC | 29 | 22 | 4 | 34 | 34 | 33 |
| 418 | 2721 | 9070 | 76.7 | TGCGACCTTCTGTACAGTGCTGCG | 29 | 23 | 8 | 7 | 33 | 29 |
| 419 | 2748 | 9104 | 81.3 | TGCGATCGGTGCGAGTTTGAAGCC | 29 | 24 | 33 | 20 | 1 | 36 |
| 420 | 2762 | 40657 | 78.4 | TGCGCCTATTAGAGCCGTGCCTGT | 29 | 26 | 3 | 36 | 33 | 14 |
| 421 | 2763 | 9128 | 77.3 | TGCGCCTAAATCCTGTCTTGCGAA | 29 | 26 | 4 | 14 | 11 | 16 |
| 422 | 2770 | 9139 | 77.3 | TGCGCCTAAGTGCGAAACCTTTGA | 29 | 26 | 22 | 16 | 23 | 1 |
| 423 | 2784 | 9156 | 76.9 | TGCGGATGAGGATTGATCGTTCGT | 29 | 27 | 25 | 1 | 10 | 10 |
| 424 | 2791 | 30649 | 78.8 | TGCGTCCCATACTGATGTGCCACG | 29 | 28 | 5 | 2 | 33 | 30 |
| 425 | 2802 | 9177 | 78 | TGCGTCCCAGGAGTGCTTAGAGCC | 29 | 28 | 25 | 33 | 3 | 36 |
| 426 | 2843 | 9222 | 77.7 | TGCGGACCTTAGCTCACCATTCCC | 29 | 32 | 3 | 13 | 15 | 28 |
| 427 | 2861 | 9247 | 78.9 | TGCGGTGCAGTGGGTATCTGGCTT | 29 | 33 | 22 | 18 | 8 | 17 |
| 428 | 2876 | 9264 | 78.6 | TGCGGACGGTAACGGTGATCCTA | 29 | 34 | 18 | 35 | 2 | 26 |
| 429 | 2886 | 9275 | 79.1 | TGCGACGGAAAGGGTATGTCACGG | 29 | 35 | 6 | 18 | 9 | 35 |
| 430 | 2904 | 9292 | 77.7 | TGCGAGCCCTGTTTAGGATGTCCC | 29 | 36 | 14 | 3 | 27 | 28 |
| 431 | 3018 | 9551 | 79.4 | CACGGAGTGATGAGCCCTTGCGAA | 30 | 20 | 27 | 36 | 11 | 16 |
| 432 | 3021 | 9556 | 75.2 | CACGGCAAATACTCTGGAGTTGCG | 30 | 21 | 5 | 8 | 20 | 29 |
| 433 | 3045 | 9608 | 77.8 | CACGATCGGCAAATCGTCGTCTTG | 30 | 24 | 21 | 24 | 10 | 11 |
| 434 | 3053 | 9626 | 80 | CACGAGGAAGTGGCAACACGCAGC | 30 | 25 | 22 | 21 | 30 | 31 |
| 435 | 3057 | 9633 | 79 | CACGAGGAGACCCTCACGAATGCG | 30 | 25 | 32 | 13 | 16 | 29 |
| 436 | 3103 | 9728 | 79.9 | CACGCAGCGCTTGCTTTCTGAGGA | 30 | 31 | 17 | 17 | 8 | 25 |
| 437 | 3153 | 9818 | 76.1 | CACGAGCCGGTACGTTGGTAGGAC | 30 | 36 | 18 | 12 | 18 | 34 |
| 438 | 3171 | 9864 | 77.6 | CAGCATACGTGCTCCCAGGAGCAA | 31 | 5 | 33 | 28 | 25 | 21 |
| 439 | 3256 | 10059 | 78.4 | CAGCGAGTCCATGGACAGTGCGAA | 31 | 20 | 15 | 34 | 22 | 16 |
| 440 | 3258 | 10060 | 76.6 | CAGCGAGTGGTAATCGTCCCCTCA | 31 | 20 | 18 | 24 | 28 | 13 |
| 441 | 3273 | 10091 | 80.3 | CAGCAGTGATCGCTTGAGCCTGCG | 31 | 22 | 24 | 11 | 36 | 29 |
| 442 | 3342 | 10220 | 76.4 | CAGCCAGCAAAGCCTAAGGAGCAA | 31 | 31 | 6 | 26 | 25 | 21 |
| 443 | 3343 | 10221 | 77 | CAGCCAGCTACAAGCCAGGACGAA | 31 | 31 | 7 | 36 | 25 | 16 |
| 444 | 3473 | 10530 | 76.7 | GACCGCAAACCTGTCTATCGCGAA | 32 | 21 | 23 | 19 | 24 | 16 |
| 445 | 3492 | 16297 | 76.5 | GACCGATGCGAATACAGACCCGAA | 32 | 27 | 16 | 7 | 32 | 16 |
| 446 | 3493 | 10589 | 78.5 | GACCGATGGAGTGATGGACCACGG | 32 | 27 | 20 | 27 | 32 | 35 |
| 447 | 3501 | 30792 | 79.6 | GACCTCCCGCAAGTCTGGACCGAA | 32 | 28 | 21 | 19 | 34 | 16 |
| 448 | 3653 | 10942 | 75.6 | GTGCGCTTCCTAACGGGATGAAAG | 33 | 17 | 26 | 35 | 27 | 6 |
| 449 | 3678 | 30832 | 77 | GTGCGCAACGTTGCTTTTAGCGTT | 33 | 21 | 12 | 17 | 3 | 12 |
| 450 | 3711 | 11060 | 78.1 | GTGCAGGACCTAAGCCATCGACGG | 33 | 25 | 26 | 36 | 24 | 35 |
| 451 | 3822 | 11330 | 76.4 | GGACCTTGAGGATGTCGATGGCAA | 34 | 11 | 25 | 9 | 27 | 21 |
| 452 | 3920 | 11597 | 77.6 | GGACCAGCCGTTTGAGATGCCAT | 34 | 31 | 12 | 1 | 27 | 15 |
| 453 | 3967 | 11693 | 79.2 | ACGGTTGATTGAATCGCGTTTGCG | 35 | 1 | 1 | 24 | 12 | 29 |
| 454 | 4057 | 41152 | 78.3 | ACGGCTCAGGACATACCCATTGCG | 35 | 13 | 34 | 5 | 15 | 29 |
| 455 | 4062 | 11897 | 75.6 | ACGGCTGTGGTACTCATCGTTCCC | 35 | 14 | 18 | 13 | 10 | 28 |
| 456 | 4145 | 12041 | 77.8 | ACGGAGTGGCTTGTCTGACCAGCC | 35 | 22 | 17 | 19 | 32 | 36 |
| 457 | 4162 | 30941 | 78 | ACGGATCGTCTGTCTGGACCCGAA | 35 | 24 | 8 | 8 | 32 | 16 |
| 458 | 4174 | 12091 | 75.6 | ACGGAGGATGATACCTCACGGTGC | 35 | 25 | 2 | 23 | 30 | 33 |
| 459 | 4317 | 16775 | 75.8 | AGCCTTAGCCATTCTGCGAACGAA | 36 | 3 | 15 | 8 | 16 | 16 |

FIG. 26J

| SEQ ID NO: | 4,633 ID# | REX ID# | Tm | ZIPCODE (5'-3') | TETRAMER NUMBERS | | | | | |
|---|---|---|---|---|---|---|---|---|---|---|
| 460 | 4348 | 12389 | 75.5 | AGCCTGTCGCAAATACCGTTCGTT | 36 | 9 | 21 | 5 | 12 | 12 |
| 461 | 4352 | 12396 | 75 | AGCCTCGTTTAGTCGTTGCGGTCT | 36 | 10 | 3 | 18 | 29 | 19 |
| 462 | 4446 | 12578 | 76.8 | AGCCGTCTGGACTGATTCTGCACG | 36 | 19 | 34 | 2 | 8 | 30 |
| 463 | 4448 | 12580 | 76.2 | AGCCGAGTTTAGCCTACACGTGCG | 36 | 20 | 3 | 26 | 30 | 29 |
| 464 | 4545 | 12741 | 75.7 | AGCCTGCGTACACTGTCCATTCCC | 36 | 29 | 7 | 14 | 15 | 28 |
| 465 | 4586 | 12811 | 77.8 | AGCCGACCAGCCTTAGGGACGAGT | 36 | 32 | 36 | 3 | 34 | 20 |

FIG. 27A

| SEQ ID NO: | 4,633 ID# | HEX ID# | Tm | ZIPCODE (5'-3') | TETRAMER NUMBERS | | | | |
|---|---|---|---|---|---|---|---|---|---|
| 1 | 3 | 8 | 77.6 | TTGAAATCCAGCGCAAAATCTGCG | 1 | 4 | 31 | 21 | 4 | 29 |
| 2 | 5 | 15 | 77.2 | TTGAAAGCCTACACGACGGCGAA | 1 | 6 | 26 | 30 | 35 | 16 |
| 3 | 7 | 22 | 76.5 | TTGATCTGCCATACGGGCTTACGG | 1 | 8 | 15 | 35 | 17 | 35 |
| 4 | 15 | 45 | 80.6 | TTGACTTGTCCCCAGCACGGCCAT | 1 | 11 | 28 | 31 | 35 | 15 |
| 5 | 17 | 56 | 80.4 | TTGACGTTGACCAGCCCGTTGCAA | 1 | 12 | 32 | 36 | 12 | 21 |
| 6 | 20 | 72 | 76.4 | TTGACGAAGCTTTCCCCCATGATG | 1 | 16 | 17 | 28 | 15 | 27 |
| 7 | 24 | 90 | 81.2 | TTGAGCAAGGACGACCGCAAACGG | 1 | 21 | 34 | 32 | 21 | 35 |
| 8 | 30 | 126 | 82.4 | TTGAGATGACGGACGGTGCGGCAA | 1 | 27 | 35 | 35 | 29 | 21 |
| 9 | 33 | 140 | 76.3 | TTGATCCCATCGAAAGGGACGATG | 1 | 28 | 24 | 6 | 34 | 27 |
| 10 | 36 | 150 | 80.1 | TTGATGCGTCTGGGACGTGCCTTG | 1 | 29 | 8 | 34 | 33 | 11 |
| 11 | 44 | 166 | 80.3 | TTGACACGTCGTCAGCTCCCGTGC | 1 | 30 | 10 | 31 | 28 | 33 |
| 12 | 48 | 180 | 80 | TTGACAGCCTGTTGCGGTGCGTCT | 1 | 31 | 14 | 29 | 33 | 19 |
| 13 | 52 | 202 | 76.5 | TTGAGTGCGGTACTTGCAGCGATG | 1 | 33 | 18 | 11 | 31 | 27 |
| 14 | 55 | 222 | 81.2 | TTGAACGGTCTGCACGTCCCAGCC | 1 | 35 | 8 | 30 | 28 | 36 |
| 15 | 67 | 269 | 82.2 | TGATTCTGGTGCGTGCCAGCCAGC | 2 | 8 | 33 | 33 | 31 | 31 |
| 16 | 69 | 274 | 76.8 | TGATTGTCGCTTTCTGACGGAGCC | 2 | 9 | 17 | 8 | 35 | 36 |
| 17 | 73 | 294 | 77.9 | TGATCGTTTGCGGGTATCCCTCGT | 2 | 12 | 29 | 18 | 28 | 10 |
| 18 | 75 | 310 | 77.9 | TGATCGAAAGGACAGCAGCCTCCC | 2 | 16 | 25 | 31 | 36 | 28 |
| 19 | 79 | 328 | 76.9 | TGATGCAAGCAACGAACACGCTGT | 2 | 21 | 21 | 16 | 30 | 14 |
| 20 | 92 | 372 | 79.5 | TGATTGCGAGTGGACCATCGCCAT | 2 | 29 | 22 | 32 | 24 | 15 |
| 21 | 94 | 379 | 80 | TGATCACGCTTGCCATGGACGGAC | 2 | 30 | 11 | 15 | 34 | 34 |
| 22 | 104 | 418 | 82 | TGATGTGCCTCAACGGGTGCAGCC | 2 | 33 | 13 | 35 | 33 | 36 |
| 23 | 111 | 431 | 75.6 | TGATGGACCGTTAGCCGATGTTGA | 2 | 34 | 12 | 36 | 27 | 1 |
| 24 | 118 | 444 | 79.5 | TGATACGGAGGAGGACTGCGTGCG | 2 | 35 | 25 | 34 | 29 | 29 |
| 25 | 129 | 555 | 79.9 | TTAGGATGAGCCAGCCTGCGAGCC | 3 | 27 | 36 | 36 | 29 | 36 |
| 26 | 151 | 690 | 77.7 | AATCTCGTCGTTTCCCCTCATGCG | 4 | 10 | 12 | 28 | 13 | 29 |
| 27 | 166 | 805 | 77.4 | AATCGCAACTGTCGTTCACGGTGC | 4 | 21 | 14 | 12 | 30 | 33 |
| 28 | 167 | 842 | 81.4 | AATCAGGACACGCAGCGACCTGCG | 4 | 25 | 30 | 31 | 32 | 29 |
| 29 | 183 | 926 | 76.7 | AATCGACCCTGTGTCTGCTTTGCG | 4 | 32 | 14 | 19 | 17 | 29 |
| 30 | 197 | 983 | 76.9 | AATCAGCCAAAGCGAAGTGCGATG | 4 | 36 | 6 | 16 | 33 | 27 |
| 31 | 216 | 1111 | 76.2 | ATACGACCTCGTGAGTTCCCGCAA | 5 | 32 | 10 | 20 | 28 | 21 |
| 32 | 226 | 1207 | 75.4 | AAAGCTTGACCTATCGAGCCGTGC | 6 | 11 | 23 | 24 | 36 | 33 |
| 33 | 268 | 1503 | 75.5 | AAAGAGCCGCTTGAGTCGAAATCG | 6 | 36 | 17 | 20 | 16 | 24 |
| 34 | 297 | 1649 | 75.7 | TCTGCTTGCTCACCTACCATTGCG | 8 | 11 | 13 | 26 | 15 | 29 |
| 35 | 332 | 1771 | 75 | TCTGATCGCCTAGGTAACGGGGAC | 8 | 24 | 26 | 18 | 35 | 34 |
| 36 | 358 | 1847 | 76.9 | TCTGCAGCGGTACTGTGGACCCAT | 8 | 31 | 18 | 14 | 34 | 15 |
| 37 | 375 | 1912 | 75.8 | TCTGAGCCACCTAATCTCCCACGG | 8 | 36 | 23 | 4 | 28 | 35 |
| 38 | 385 | 1941 | 77.4 | TGTCTCGTTCCCACCTCCATTCCC | 9 | 10 | 28 | 23 | 15 | 28 |
| 39 | 442 | 2093 | 81.4 | TGTCATCGCAGCGAGTCAGCCACG | 9 | 24 | 31 | 20 | 31 | 30 |
| 40 | 445 | 2103 | 77.7 | TGTCCCTAACCTGATGGTGCGCAA | 9 | 26 | 23 | 27 | 33 | 21 |
| 41 | 461 | 2143 | 77.3 | TGTCTGCGGTCTCCATATCGGTGC | 9 | 29 | 19 | 15 | 24 | 33 |
| 42 | 469 | 2154 | 76.2 | TGTCCACGCGTTACCTTGTCGATG | 9 | 30 | 12 | 23 | 9 | 27 |
| 43 | 487 | 2196 | 79.1 | TGTCGTGCTCTGACCTTGCGCTCA | 9 | 33 | 8 | 23 | 29 | 13 |
| 44 | 508 | 2231 | 81.7 | TGTCACGGAATCGTGCTGCGGCTT | 9 | 35 | 4 | 33 | 29 | 17 |
| 45 | 527 | 2307 | 77.4 | TCGTTCTGGCTTGGACGCTTCTCA | 10 | 8 | 17 | 34 | 17 | 13 |
| 46 | 602 | 2543 | 80 | TCGTTGCGTGTCGGACCTTGGATG | 10 | 29 | 9 | 34 | 11 | 27 |
| 47 | 686 | 2755 | 78.3 | CTTGCGTTGATGCGAATCGTCGAA | 11 | 12 | 27 | 16 | 10 | 16 |
| 48 | 973 | 3831 | 77.7 | CTGTCACGCTCAACCTTCCCCGTT | 14 | 30 | 13 | 23 | 28 | 12 |
| 49 | 987 | 3866 | 77.6 | CTGTGTGCCGTTTCGTGTGCAGTG | 14 | 33 | 12 | 10 | 33 | 22 |
| 50 | 1053 | 4127 | 77 | CCATGCAATCCCAGGATGTCGGTA | 15 | 21 | 28 | 25 | 9 | 18 |
| 51 | 1093 | 4232 | 78.7 | CCATCAGCTCTGGCAATGCGGAGT | 15 | 31 | 8 | 21 | 29 | 20 |

*FIG. 27B*

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 52 | 1142 | 4394 | 75.4 | CGAATCTGGGTAAGGAAGCCATCG | 16 | 8 | 18 | 25 | 36 | 24 |
| 53 | 1145 | 20638 | 77.7 | CGAATGTCCTGTCCATCGAATGCG | 16 | 9 | 14 | 15 | 16 | 29 |
| 54 | 1159 | 4453 | 75.2 | CGAACGTTTACATGCGTCGTAGCC | 16 | 12 | 7 | 29 | 10 | 36 |
| 55 | 1193 | 4568 | 78.3 | CGAAAGTGAGCCGCAACTTGGGAC | 16 | 22 | 36 | 21 | 11 | 34 |
| 56 | 1246 | 4751 | 78.9 | CGAAGGACAGTGAGTGTGCGCACG | 16 | 34 | 22 | 22 | 29 | 30 |
| 57 | 1560 | 6171 | 75.4 | GCAAAGCCATACCTTGGCTTGCTT | 21 | 36 | 5 | 11 | 17 | 17 |
| 58 | 1641 | 6531 | 75.7 | ACCTCTTGCCTACGAACAGCCGAA | 23 | 11 | 26 | 16 | 31 | 16 |
| 59 | 1655 | 6599 | 78.8 | ACCTGCAAGTGCCCATGTGCCCTA | 23 | 21 | 33 | 15 | 33 | 26 |
| 60 | 1919 | 7289 | 80.1 | AGGATCTGGACCGGACTCCCCGAA | 25 | 8 | 32 | 34 | 28 | 16 |
| 61 | 1982 | 7538 | 78 | AGGAACGGCAGCTACACACGAGCC | 25 | 35 | 31 | 7 | 30 | 36 |
| 62 | 2081 | 8056 | 78.1 | GATGGACCACCTCAGCGCTTGACC | 27 | 32 | 23 | 31 | 17 | 32 |
| 63 | 2105 | 8145 | 77.8 | TCCCTTAGGACCCAGCGTCTGTGC | 28 | 3 | 32 | 31 | 19 | 33 |
| 64 | 2623 | 8944 | 75.5 | TGCGCCATAAAGGACCTTAGCCAT | 29 | 15 | 6 | 32 | 3 | 15 |
| 65 | 2755 | 9114 | 75.8 | TGCGAGGACCATGGTAGGTAAGCC | 29 | 25 | 15 | 18 | 18 | 36 |
| 66 | 12 | 42 | 81.5 | TTGATCGTGGACACGGCACGCTCA | 1 | 10 | 34 | 35 | 30 | 13 |
| 67 | 26 | 94 | 78.2 | TTGAAGTGCAGCCACGAAAGCGAA | 1 | 22 | 31 | 30 | 6 | 16 |
| 68 | 29 | 112 | 79.3 | TTGAATCGGAGTTGCGCGTTGGAC | 1 | 24 | 20 | 29 | 12 | 34 |
| 69 | 82 | 346 | 80.9 | TGATGATGGCTTCAGCTGCGCGAA | 2 | 27 | 17 | 31 | 29 | 16 |
| 70 | 86 | 351 | 79.2 | TGATTCCCTTGAACGGTCCCGGAC | 2 | 28 | 1 | 35 | 28 | 34 |
| 71 | 124 | 521 | 78.3 | TTAGGCAATTGATCCCGACCGTGC | 3 | 21 | 1 | 28 | 32 | 33 |
| 72 | 132 | 567 | 78.2 | TTAGTCCCACGGGATGCGTTGACC | 3 | 28 | 35 | 27 | 12 | 32 |
| 73 | 191 | 962 | 77.5 | AATCGGACATCGAGTGTCCCCAGC | 4 | 34 | 24 | 22 | 28 | 31 |
| 74 | 210 | 1078 | 75.8 | ATACTGCGCGTTCTGTGAGTTGCG | 5 | 29 | 12 | 14 | 20 | 29 |
| 75 | 325 | 1744 | 78.5 | TCTGGTCTGCAATCGTCACGCAGC | 8 | 19 | 21 | 10 | 30 | 31 |
| 76 | 436 | 2073 | 79.4 | TGTCAGTGCACGGCTTCTGTTGCG | 9 | 22 | 30 | 17 | 14 | 29 |
| 77 | 551 | 2365 | 77.2 | TCGTCTCAGCTTGACCGCTTCAGC | 10 | 13 | 17 | 32 | 17 | 31 |
| 78 | 629 | 2593 | 76.7 | TCGTCAGCCCTAATCGACCTGTGC | 10 | 31 | 26 | 24 | 23 | 33 |
| 79 | 644 | 2624 | 75.5 | TCGTGTGCGCTTAATCACGGAATC | 10 | 33 | 17 | 4 | 35 | 4 |
| 80 | 804 | 3213 | 76.4 | CGTTCGAAGTCTCTTGACGGACGG | 12 | 16 | 19 | 11 | 35 | 35 |
| 81 | 836 | 3345 | 75.7 | CGTTTCCCAATCATCGGCAAGTCT | 12 | 28 | 4 | 24 | 21 | 19 |
| 82 | 872 | 3431 | 77.5 | CGTTGTGCTGATGCAAATCGGCTT | 12 | 33 | 2 | 21 | 24 | 17 |
| 83 | 949 | 3748 | 79.9 | CTGTCTTGGTGCGCAAAGGATGCG | 14 | 11 | 33 | 21 | 25 | 29 |
| 84 | 1148 | 4415 | 77.1 | CGAATCGTTTGAGCAAGACCCACG | 16 | 10 | 1 | 21 | 32 | 30 |
| 85 | 1235 | 4695 | 76.7 | CGAACAGCTGCGAATCGTCTAGCC | 16 | 31 | 29 | 4 | 19 | 36 |
| 86 | 1406 | 5575 | 75.8 | GAGTTCGTGCTTACGGCTTGAGCC | 20 | 10 | 17 | 35 | 11 | 36 |
| 87 | 1603 | 6332 | 75.6 | AGTGTCCCGAGTACCTGGACACGG | 22 | 28 | 20 | 23 | 34 | 35 |
| 88 | 2216 | 8362 | 76.3 | TCCCGCTTTGATTCTGTCGTTCGT | 28 | 17 | 2 | 8 | 10 | 10 |
| 89 | 2286 | 8468 | 75 | TCCCACCTGTCTACCTAGCCGACC | 28 | 23 | 19 | 23 | 36 | 32 |
| 90 | 2364 | 8591 | 77.1 | TCCCCACGATACACCTTTGATGCG | 28 | 30 | 5 | 23 | 1 | 29 |
| 91 | 2556 | 30603 | 76.3 | TGCGCTTGATACTGTCGCTTCGAA | 29 | 11 | 5 | 9 | 17 | 16 |
| 92 | 2587 | 8909 | 75.8 | TGCGCTCAATACAGCCTCGTATCG | 29 | 13 | 5 | 36 | 10 | 24 |
| 93 | 2741 | 9095 | 79.8 | TGCGATCGCGAAGCAATGATCGTT | 29 | 24 | 16 | 21 | 2 | 12 |
| 94 | 2793 | 9168 | 77.9 | TGCGTCCCTCTGTGATCACGAGGA | 29 | 28 | 8 | 2 | 30 | 25 |
| 95 | 2821 | 9200 | 80.5 | TGCGCACGAGGAATCGCTTGAGTG | 29 | 30 | 25 | 24 | 11 | 22 |
| 96 | 3120 | 9759 | 76.9 | CACGGTGCTACAGTGCAAAGCACG | 30 | 33 | 7 | 33 | 6 | 30 |

FIG. 28A

| SEQ ID NO: | 4,633 ID# | HEX ID# | Tm | ZIPCODE (5'-3') | TETRAMER NUMBERS | | | | |
|---|---|---|---|---|---|---|---|---|---|
| 1 | 3 | 8 | 77.6 | TTGAAATCCAGCGCAAAATCTGCG | 1 | 4 | 31 | 21 | 4 29 |
| 2 | 5 | 15 | 77.2 | TTGAAAAGCCTACACGACGGCGAA | 1 | 6 | 26 | 30 | 35 16 |
| 3 | 7 | 22 | 76.5 | TTGATCTGCCATACGGGCTTACGG | 1 | 8 | 15 | 35 | 17 35 |
| 4 | 15 | 45 | 80.6 | TTGACTTGTCCCCAGCACGGCCAT | 1 | 11 | 28 | 31 | 35 15 |
| 5 | 17 | 56 | 80.4 | TTGACGTTGACCAGCCCGTTGCAA | 1 | 12 | 32 | 36 | 12 21 |
| 6 | 20 | 72 | 76.4 | TTGACGAAGCTTTCCCCATGATG | 1 | 16 | 17 | 28 | 15 27 |
| 7 | 24 | 90 | 81.2 | TTGAGCAAGGACGACCGCAAACGG | 1 | 21 | 34 | 32 | 21 35 |
| 8 | 30 | 126 | 82.4 | TTGAGATGACGGACGGTGCGGCAA | 1 | 27 | 35 | 35 | 29 21 |
| 9 | 33 | 140 | 76.3 | TTGATCCCATCGAAAGGGACGATG | 1 | 28 | 24 | 6 | 34 27 |
| 10 | 36 | 150 | 80.1 | TTGATGCGTCTGGGACGTGCCTTG | 1 | 29 | 8 | 34 | 33 11 |
| 11 | 44 | 166 | 80.3 | TTGACACGTCGTCAGCTCCCGTGC | 1 | 30 | 10 | 31 | 28 33 |
| 12 | 48 | 180 | 80 | TTGACAGCCTGTTGCGGTGCGTCT | 1 | 31 | 14 | 29 | 33 19 |
| 13 | 52 | 202 | 76.5 | TTGAGTGCGGTACTTGCAGCGATG | 1 | 33 | 10 | 11 | 31 27 |
| 14 | 55 | 222 | 81.2 | TTGAACGGTCTGCACGTCCCAGCC | 1 | 35 | 8 | 30 | 28 36 |
| 15 | 67 | 269 | 82.2 | TGATTCTGGTGCGTGCCAGCCAGC | 2 | 8 | 33 | 33 | 31 31 |
| 16 | 69 | 274 | 76.8 | TGATTGTCGCTTTCTGACGGAGCC | 2 | 9 | 17 | 8 | 35 36 |
| 17 | 73 | 294 | 77.9 | TGATCGTTTGCGGGTATCCCTCGT | 2 | 12 | 29 | 18 | 28 10 |
| 18 | 75 | 310 | 77.9 | TGATCGAAAGGACAGCAGCCTCCC | 2 | 16 | 25 | 31 | 36 28 |
| 19 | 79 | 328 | 76.9 | TGATGCAAGCAACGAACACGCTGT | 2 | 21 | 21 | 16 | 30 14 |
| 20 | 92 | 372 | 79.5 | TGATTGCGAGTGGACCATCGCCAT | 2 | 29 | 22 | 32 | 24 15 |
| 21 | 94 | 379 | 80 | TGATCACGCTTGCCATGGACGGAC | 2 | 30 | 11 | 15 | 34 34 |
| 22 | 104 | 418 | 82 | TGATGTGCCTCAACGGGTGCAGCC | 2 | 33 | 13 | 35 | 33 36 |
| 23 | 111 | 431 | 75.6 | TGATGGACCGTTAGCCGATGTTGA | 2 | 34 | 12 | 36 | 27 1 |
| 24 | 118 | 444 | 79.5 | TGATACGGAGGAGGACTGCGTGCG | 2 | 35 | 25 | 34 | 29 29 |
| 25 | 129 | 555 | 79.9 | TTAGGATGAGCCAGCCTGCGAGCC | 3 | 27 | 36 | 36 | 29 36 |
| 26 | 151 | 690 | 77.7 | AATCTCGTCGTTTCCCCTCATGCG | 4 | 10 | 12 | 28 | 13 29 |
| 27 | 166 | 805 | 77.4 | AATCGCAACTGTCGTTCACGGTGC | 4 | 21 | 14 | 12 | 30 33 |
| 28 | 167 | 842 | 81.4 | AATCAGGACACGCAGCGACCTGCG | 4 | 25 | 30 | 31 | 32 29 |
| 29 | 183 | 926 | 76.7 | AATCGACCCTGTGTCTGCTTTGCG | 4 | 32 | 14 | 19 | 17 29 |
| 30 | 197 | 983 | 76.9 | AATCAGCCAAAGCGAAGTGCGATG | 4 | 36 | 6 | 16 | 33 27 |
| 31 | 216 | 1111 | 76.2 | ATACGACCTCGTGAGTTCCCGCAA | 5 | 32 | 10 | 20 | 28 21 |
| 32 | 226 | 1207 | 75.4 | AAAGCTTGACCTATCGAGCCGTGC | 6 | 11 | 23 | 24 | 36 33 |
| 33 | 268 | 1503 | 75.5 | AAAGAGCCGCTTGAGTCGAAATCG | 6 | 36 | 17 | 20 | 16 24 |
| 34 | 297 | 1649 | 75.7 | TCTGCTTGCTCACCTACCATTGCG | 8 | 11 | 13 | 26 | 15 29 |
| 35 | 332 | 1771 | 75 | TCTGATCGCCTAGGTAACGGGAC | 8 | 24 | 26 | 18 | 35 34 |
| 36 | 358 | 1847 | 76.9 | TCTGCAGCGGTACTGTGGACCCAT | 8 | 31 | 18 | 14 | 34 15 |
| 37 | 375 | 1912 | 75.8 | TCTGAGCCACCTAATCTCCCACGG | 8 | 36 | 23 | 4 | 28 35 |
| 38 | 385 | 1941 | 77.4 | TGTCTCGTTCCCACCTCCATTCCC | 9 | 10 | 28 | 23 | 15 28 |
| 39 | 442 | 2093 | 81.4 | TGTCATCGCAGCGAGTCAGCCACG | 9 | 24 | 31 | 20 | 31 30 |
| 40 | 445 | 2103 | 77.7 | TGTCCCTAACCTGATGGTGCGCAA | 9 | 26 | 23 | 27 | 33 21 |
| 41 | 461 | 2143 | 77.3 | TGTCTGCGGTCTCCATATCGGTGC | 9 | 29 | 19 | 15 | 24 33 |
| 42 | 469 | 2154 | 76.2 | TGTCCACGCGTTACCTTGTCGATG | 9 | 30 | 12 | 23 | 9 27 |
| 43 | 487 | 2196 | 79.1 | TGTCGTGCTCTGACCTTGCGCTCA | 9 | 33 | 8 | 23 | 29 13 |
| 44 | 508 | 2231 | 81.7 | TGTCACGGAATCGTGCTGCGGCTT | 9 | 35 | 4 | 33 | 29 17 |
| 45 | 527 | 2307 | 77.4 | TCGTTCTGGCTTGGACGCTTCTCA | 10 | 8 | 17 | 34 | 17 13 |
| 46 | 602 | 2543 | 80 | TCGTTGCGTGTCGGACCTTGGATG | 10 | 29 | 9 | 34 | 11 27 |
| 47 | 686 | 2755 | 78.3 | CTTGCGTTGATGCGAATCGTCGAA | 11 | 12 | 27 | 16 | 10 16 |
| 48 | 973 | 3831 | 77.7 | CTGTCACGCTCAACCTTCCCCGTT | 14 | 30 | 13 | 23 | 28 12 |
| 49 | 987 | 3866 | 77.6 | CTGTGTGCCGTTTCGTGTGCAGTG | 14 | 33 | 12 | 10 | 33 22 |
| 50 | 1053 | 4127 | 77 | CCATGCAATCCCAGGATGTCGGTA | 15 | 21 | 28 | 25 | 9 18 |
| 51 | 1093 | 4232 | 78.7 | CCATCAGCTCTGGCAATGCGGAGT | 15 | 31 | 8 | 21 | 29 20 |

*FIG. 28B*

| SEQ ID NO: | 4,633 ID# | HEX ID# | Tm | ZIPCODE (5'-3') | TETRAMER NUMBERS | | | | | |
|---|---|---|---|---|---|---|---|---|---|---|
| 52 | 1142 | 4394 | 75.4 | CGAATCTGGGTAAGGAAGCCATCG | 16 | 8 | 18 | 25 | 36 | 24 |
| 53 | 1145 | 20638 | 77.7 | CGAATGTCCTGTCCATCGAATGCG | 16 | 9 | 14 | 15 | 16 | 29 |
| 54 | 1159 | 4453 | 75.2 | CGAACGTTTACATGCGTCGTAGCC | 16 | 12 | 7 | 29 | 10 | 36 |
| 55 | 1193 | 4568 | 78.3 | CGAAAGTGAGCCGCAACTTGGGAC | 16 | 22 | 36 | 21 | 11 | 34 |
| 56 | 1246 | 4751 | 78.9 | CGAAGGACAGTGAGTGTGCGCACG | 16 | 34 | 22 | 22 | 29 | 30 |
| 57 | 1560 | 6171 | 75.4 | GCAAAGCCATACCTTGGCTTGCTT | 21 | 36 | 5 | 11 | 17 | 17 |
| 58 | 1641 | 6531 | 75.7 | ACCTCTTGCCTACGAACAGCCGAA | 23 | 11 | 26 | 16 | 31 | 16 |
| 59 | 1655 | 6599 | 78.8 | ACCTGCAAGTGCCCATGTGCCCTA | 23 | 21 | 33 | 15 | 33 | 26 |
| 60 | 1919 | 7289 | 80.1 | AGGATCTGGACCGGACTCCCCGAA | 25 | 8 | 32 | 34 | 28 | 16 |
| 61 | 1982 | 7538 | 78 | AGGAACGGCAGCTACACACGAGCC | 25 | 35 | 31 | 7 | 30 | 36 |
| 62 | 2081 | 8056 | 78.1 | GATGGACCACCTCAGCGCTTGACC | 27 | 32 | 23 | 31 | 17 | 32 |
| 63 | 2105 | 8145 | 77.8 | TCCCTTAGGACCCAGCGTCTGTGC | 28 | 3 | 32 | 31 | 19 | 33 |
| 64 | 2623 | 8944 | 75.5 | TGCGCCATAAAGGACCTTAGCCAT | 29 | 15 | 6 | 32 | 3 | 15 |
| 65 | 2755 | 9114 | 75.8 | TGCGAGGACCATGGTAGGTAAGCC | 29 | 25 | 15 | 18 | 18 | 36 |

FIG. 29A

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 4634 | 1 | 3 | 8 | 70.8 | AATCCAGCGCAAAATCTGCG | 4 | 31 | 21 | 4 | 29 | 0 |
| 4635 | 2 | 5 | 15 | 70.4 | AAAGCCTACACGACGGCGAA | 6 | 26 | 30 | 35 | 16 | 0 |
| 4636 | 3 | 7 | 22 | 70.6 | TCTGCCATACGGGCTTACGG | 8 | 15 | 35 | 17 | 35 | 0 |
| 4637 | 4 | 15 | 45 | 74.6 | CTTGTCCCCAGCACGGCCAT | 11 | 28 | 31 | 35 | 15 | 1 |
| 4638 | 5 | 17 | 56 | 74.4 | CGTTGACCAGCCCGTTGCAA | 12 | 32 | 36 | 12 | 21 | 0 |
| 4639 | 6 | 20 | 72 | 69.8 | CGAAGCTTTCCCCCATGATG | 16 | 17 | 28 | 15 | 27 | 0 |
| 4640 | 7 | 24 | 90 | 75.3 | GCAAGGACGACCGCAAACGG | 21 | 34 | 32 | 21 | 35 | 0 |
| 4641 | 8 | 30 | 126 | 76.5 | GATGACGGACGGTGCGGCAA | 27 | 35 | 35 | 29 | 21 | 0 |
| 4642 | 9 | 33 | 140 | 70 | TCCCATCGAAAGGGACGATG | 28 | 24 | 6 | 34 | 27 | 0 |
| 4643 | 10 | 36 | 150 | 74.4 | TGCGTCTGGGACGTGCCTTG | 29 | 8 | 34 | 33 | 11 | 0 |
| 4644 | 11 | 44 | 166 | 74 | CACGTCGTCAGCTCCCGTGC | 30 | 10 | 31 | 28 | 33 | 0 |
| 4645 | 12 | 48 | 180 | 73.8 | CAGCCTGTTGCGGTGCGTCT | 31 | 14 | 29 | 33 | 19 | 0 |
| 4646 | 13 | 52 | 202 | 69.6 | GTGCGGTACTTGCAGCGATG | 33 | 18 | 11 | 31 | 27 | 0 |
| 4647 | 14 | 55 | 222 | 74.7 | ACGGTCTGCACGTCCCAGCC | 35 | 8 | 30 | 28 | 36 | 0 |
| 4648 | 15 | 67 | 269 | 76.9 | TCTGGTGCGTGCCAGCCAGC | 8 | 33 | 33 | 31 | 31 | 0 |
| 4649 | 16 | 69 | 274 | 70.6 | TGTCGCTTTCTGACGGAGCC | 9 | 17 | 8 | 35 | 36 | 0 |
| 4650 | 17 | 73 | 294 | 71.7 | CGTTTGCGGGTATCCCTCGT | 12 | 29 | 18 | 28 | 10 | 0 |
| 4651 | 18 | 75 | 310 | 71.5 | CGAAAGGACAGCAGCCTCCC | 16 | 25 | 31 | 36 | 28 | 0 |
| 4652 | 19 | 79 | 328 | 69.2 | GCAAGCAACGAACACGCTGT | 21 | 21 | 16 | 30 | 14 | 0 |
| 4653 | 20 | 92 | 372 | 73.7 | TGCGAGTGGACCATCGCCAT | 29 | 22 | 32 | 24 | 15 | 0 |
| 4654 | 21 | 94 | 379 | 73.8 | CACGCTTGCCATGGACGGAC | 30 | 11 | 15 | 34 | 34 | 0 |
| 4655 | 22 | 104 | 418 | 75.2 | GTGCCTCAACGGGTGCAGCC | 33 | 13 | 35 | 33 | 36 | 0 |
| 4656 | 23 | 111 | 431 | 68.7 | TGATGGACCGTTAGCCGATG | 2 | 34 | 12 | 36 | 27 | 0 |
| 4657 | 24 | 118 | 444 | 75 | ACGGAGGAGGACTGCGTGCG | 35 | 25 | 34 | 29 | 29 | 0 |
| 4658 | 25 | 129 | 555 | 74.7 | GATGAGCCAGCCTGCGAGCC | 27 | 36 | 36 | 29 | 36 | 0 |
| 4659 | 26 | 151 | 690 | 73.4 | TCGTCGTTTCCCCTCATGCG | 10 | 12 | 28 | 13 | 29 | 1 |
| 4660 | 27 | 166 | 805 | 69.1 | GCAACTGTCGTTCACGGTGC | 21 | 14 | 12 | 30 | 33 | 0 |
| 4661 | 28 | 167 | 842 | 76 | AGGACACGCAGCGACCTGCG | 25 | 30 | 31 | 32 | 29 | 0 |
| 4662 | 29 | 183 | 926 | 68.4 | GACCCTGTGTCTGCTTTGCG | 32 | 14 | 19 | 17 | 29 | 0 |
| 4663 | 30 | 197 | 983 | 70.8 | AGCCAAAGCGAAGTGCGATG | 36 | 6 | 16 | 33 | 27 | 0 |
| 4664 | 31 | 216 | 1111 | 70.2 | GACCTCGTGAGTTCCCGCAA | 32 | 10 | 20 | 28 | 21 | 0 |
| 4665 | 32 | 226 | 1207 | 67.8 | CTTGACCTATCGAGCCGTGC | 11 | 23 | 24 | 36 | 33 | 0 |
| 4666 | 33 | 268 | 1503 | 70 | AGCCGCTTGAGTCGAAATCG | 36 | 17 | 20 | 16 | 24 | 0 |
| 4667 | 34 | 297 | 1649 | 66.3 | CTTGCTCACCTACCATTGCG | 11 | 13 | 26 | 15 | 29 | 0 |
| 4668 | 35 | 332 | 1771 | 67.9 | ATCGCCTAGGTAACGGGGAC | 24 | 26 | 18 | 35 | 34 | 0 |
| 4669 | 36 | 358 | 1847 | 67.5 | CAGCGGTACTGTGGACCCAT | 31 | 18 | 14 | 34 | 15 | 0 |
| 4670 | 37 | 375 | 1912 | 68.5 | AGCCACCTAATCTCCCACGG | 36 | 23 | 4 | 28 | 35 | 0 |
| 4671 | 38 | 385 | 1941 | 71.2 | TCGTTCCCACCTCCATTCCC | 10 | 28 | 23 | 15 | 28 | 0 |
| 4672 | 39 | 442 | 2093 | 73.8 | ATCGCAGCGAGTCAGCCACG | 24 | 31 | 20 | 31 | 30 | 0 |
| 4673 | 40 | 445 | 2103 | 69 | CCTAACCTGATGGTGCGCAA | 26 | 23 | 27 | 33 | 21 | 0 |
| 4674 | 41 | 461 | 2143 | 71 | TGCGGTCTCCATATCGGTGC | 29 | 19 | 15 | 24 | 33 | 0 |
| 4675 | 42 | 469 | 2154 | 67 | CACGCGTTACCTTGTCGATG | 30 | 12 | 23 | 9 | 27 | 0 |
| 4676 | 43 | 487 | 2196 | 69.9 | TGTCGTGCTCTGACCTTGCG | 9 | 33 | 8 | 23 | 29 | 0 |
| 4677 | 44 | 508 | 2231 | 74.6 | ACGGAATCGTGCTGCGGCTT | 35 | 4 | 33 | 29 | 17 | 0 |
| 4678 | 45 | 527 | 2307 | 70.2 | TCGTTCTGGCTTGGACGCTT | 10 | 8 | 17 | 34 | 17 | 0 |
| 4679 | 46 | 602 | 2543 | 72 | TCGTTGCGTGTCGGACCTTG | 10 | 29 | 9 | 34 | 11 | 0 |
| 4680 | 47 | 686 | 2755 | 69.9 | CGTTGATGCGAATCGTCGAA | 12 | 27 | 16 | 10 | 16 | 0 |
| 4681 | 48 | 973 | 3831 | 71.7 | CACGCTCAACCTTCCCCGTT | 30 | 13 | 23 | 28 | 12 | 1 |

FIG. 29B

| SEQ ID NO: | ZIP ID# | 4,633 ID# | HEX ID# | Tm | ZIPCODE (NH2 -> CONE2) | TETRAMER NUMBERS | | | | | "UNALLOWED DIMERS" |
|---|---|---|---|---|---|---|---|---|---|---|---|
| 4682 | 49 | 987 | 3866 | 70.1 | CTGTGTGCCGTTTCGTGTGC | 14 | 33 | 12 | 10 | 33 | 0 |
| 4683 | 50 | 1053 | 4127 | 67.7 | CCATGCAATCCCAGGATGTC | 15 | 21 | 28 | 25 | 9 | 0 |
| 4684 | 51 | 1093 | 4232 | 71.8 | CCATCAGCTCTGGCAATGCG | 15 | 31 | 8 | 21 | 29 | 0 |
| 4685 | 52 | 1142 | 4394 | 67.2 | TCTGGGTAAGGAAGCCATCG | 8 | 18 | 25 | 36 | 24 | 0 |
| 4686 | 53 | 1145 | 20638 | 69.4 | TGTCCTGTCCATCGAATGCG | 9 | 14 | 15 | 16 | 29 | 0 |
| 4687 | 54 | 1159 | 4453 | 66.7 | CGAACGTTTACATGCGTCGT | 16 | 12 | 7 | 29 | 10 | 0 |
| 4688 | 55 | 1193 | 4568 | 69.5 | AGTGAGCCGCAACTTGGGAC | 22 | 36 | 21 | 11 | 34 | 0 |
| 4689 | 56 | 1246 | 4751 | 70 | GGACAGTGAGTGTGCGCACG | 34 | 22 | 22 | 29 | 30 | 0 |
| 4690 | 57 | 1560 | 6171 | 66.9 | GCAAAGCCATACCTTGGCTT | 21 | 36 | 5 | 11 | 17 | 0 |
| 4691 | 58 | 1641 | 6531 | 68.6 | CTTGCCTACGAACAGCCGAA | 11 | 26 | 16 | 31 | 16 | 0 |
| 4692 | 59 | 1655 | 6599 | 71.1 | GCAAGTGCCCATGTGCCCTA | 21 | 33 | 15 | 33 | 26 | 0 |
| 4693 | 60 | 1919 | 7289 | 74.1 | TCTGGACCGGACTCCCCGAA | 8 | 32 | 34 | 28 | 16 | 0 |
| 4694 | 61 | 1982 | 7538 | 70.5 | ACGGCAGCTACACACGAGCC | 35 | 31 | 7 | 30 | 36 | 0 |
| 4695 | 62 | 2081 | 8056 | 69.8 | GACCACCTCAGCGCTTGACC | 32 | 23 | 31 | 17 | 32 | 0 |
| 4696 | 63 | 2105 | 8145 | 68.2 | TCCCTTAGGACCCAGCGTCT | 28 | 3 | 32 | 31 | 19 | 0 |
| 4697 | 64 | 2623 | 8944 | 65.5 | TGCGCCATAAAGGACCTTAG | 29 | 15 | 6 | 32 | 3 | 0 |
| 4698 | 65 | 2755 | 9114 | 65.8 | TGCGAGGACCATGGTAGGTA | 29 | 25 | 15 | 18 | 18 | 0 |
| 4699 | 66 | 12 | 42 | 75.8 | TCGTGGACACGGCACGCTCA | 10 | 34 | 35 | 30 | 13 | 0 |
| 4700 | 67 | 26 | 94 | 71.3 | AGTGCAGCCACGAAAGCGAA | 22 | 31 | 30 | 6 | 16 | 0 |
| 4701 | 68 | 29 | 112 | 72.6 | ATCGGAGTTGCGCGTTGGAC | 24 | 20 | 29 | 12 | 34 | 0 |
| 4702 | 69 | 82 | 346 | 74 | GATGGCTTCAGCTGCGCGAA | 27 | 17 | 31 | 29 | 16 | 0 |
| 4703 | 70 | 86 | 351 | 73.6 | TCCCTTGAACGGTCCCGGAC | 28 | 1 | 35 | 28 | 34 | 1 |
| 4704 | 71 | 124 | 521 | 72.8 | GCAATTGATCCCGACCGTGC | 21 | 1 | 28 | 32 | 33 | 0 |
| 4705 | 72 | 132 | 567 | 75.3 | TCCCACGGGATGCGTTGACC | 28 | 35 | 27 | 12 | 32 | 0 |
| 4706 | 73 | 191 | 962 | 69.3 | GGACATGAGTGTCCCCAGC | 34 | 24 | 22 | 28 | 31 | 1 |
| 4707 | 74 | 210 | 1078 | 73.4 | TGCGCGTTCTGTGAGTTGCG | 29 | 12 | 14 | 20 | 29 | 0 |
| 4708 | 75 | 325 | 1744 | 69.4 | GTCTGCAATCGTCACGCAGC | 19 | 21 | 10 | 30 | 31 | 0 |
| 4709 | 76 | 436 | 2073 | 71.6 | AGTGCACGGCTTCTGTTGCG | 22 | 30 | 17 | 14 | 29 | 0 |
| 4700 | 77 | 551 | 2365 | 68.1 | CTCAGCTTGACCGCTTCAGC | 13 | 17 | 32 | 17 | 31 | 0 |
| 4711 | 78 | 629 | 2593 | 67.6 | CAGCCCTAATCGACCTGTGC | 31 | 26 | 24 | 23 | 33 | 0 |
| 4712 | 79 | 644 | 2624 | 70 | TCGTGTGCGCTTAATCACGG | 19 | 33 | 17 | 4 | 35 | 0 |
| 4713 | 80 | 804 | 3213 | 67.6 | CGAAGTCTCTTGACGGACGG | 16 | 19 | 11 | 35 | 35 | 0 |
| 4714 | 81 | 836 | 3345 | 71.1 | CGTTTCCCAATCATCGGCAA | 12 | 28 | 4 | 24 | 21 | 1 |
| 4715 | 82 | 872 | 3431 | 68.2 | GTGCTGATGCAAATCGGCTT | 33 | 2 | 21 | 24 | 17 | 0 |
| 4716 | 83 | 949 | 3748 | 74.2 | CTTGGTGCGCAAAGGATGCG | 11 | 33 | 21 | 25 | 29 | 0 |
| 4717 | 84 | 1148 | 4415 | 68.9 | TCGTTTGAGCAAGACCCACG | 10 | 1 | 21 | 32 | 30 | 0 |
| 4718 | 85 | 1235 | 4695 | 68.4 | CGAACAGCTGCGAATCGTCT | 16 | 31 | 29 | 4 | 19 | 0 |
| 4719 | 86 | 1406 | 5575 | 70.8 | TCGTGCTTACGGCTTGAGCC | 10 | 17 | 35 | 11 | 36 | 0 |
| 4720 | 87 | 1603 | 6332 | 69.9 | TCCCGAGTACCTGGACACGG | 28 | 20 | 23 | 34 | 35 | 0 |
| 4721 | 88 | 2216 | 8362 | 67.6 | TCCCGCTTTGATTCTGTCGT | 28 | 17 | 2 | 8 | 10 | 0 |
| 4722 | 89 | 2286 | 8468 | 63.7 | TCCCACCTGTCTACCTAGCC | 28 | 23 | 19 | 23 | 36 | 0 |
| 4723 | 90 | 2364 | 8591 | 65.6 | TCCCACGATACACCTTTGA | 28 | 30 | 5 | 23 | 1 | 1 |
| 4724 | 91 | 2556 | 30603 | 66.6 | TGCGCTTGATACTGTCGCTT | 29 | 11 | 5 | 9 | 17 | 0 |
| 4725 | 92 | 2587 | 8909 | 68.9 | TGCGCTCAATACAGCCTCGT | 29 | 13 | 5 | 36 | 10 | 0 |
| 4726 | 93 | 2741 | 9095 | 71.9 | TGCGATCGCGAAGCAATGAT | 29 | 24 | 16 | 21 | 2 | 0 |
| 4727 | 94 | 2793 | 9168 | 69.4 | TGCGTCCCTCTGTGATCACG | 29 | 28 | 8 | 2 | 30 | 0 |
| 4728 | 95 | 2821 | 9200 | 74.8 | TGCGCACGAGGAATCGCTTG | 29 | 30 | 25 | 24 | 11 | 0 |
| 4729 | 96 | 3120 | 9759 | 64.8 | GTGCTACAGTGCAAAGCACG | 33 | 7 | 33 | 6 | 30 | 0 |

FIG. 29C

| SEQ ID NO: | ZIP ID# | 4,633 ID# | HEX ID# Tm | ZIPCODE (NH2 -> CONH2) | TETRAMER NUMBERS | | | | "UNALLOWED DIMERS" |
|---|---|---|---|---|---|---|---|---|---|
| 4730 | 97 | 6 | 18 72.6 | AAAGGGACGTGCGCTTCGAA | 6 34 33 17 16 | | | | 0 |
| 4731 | 98 | 8 | 25 73.7 | TCTGCACGCGTTGTGCGGTA | 8 30 12 33 18 | | | | 0 |
| 4732 | 99 | 9 | 29 74.9 | TGTCCCATTCCCCACGCGTT | 9 15 28 30 12 | | | | 0 |
| 4733 | 100 | 13 | 43 73.6 | TCGTAGCCGGTATGCGACGG | 10 36 18 29 35 | | | | 0 |
| 4734 | 101 | 18 | 64 73.7 | CCATGCTTCGAAACGGCGAA | 15 17 16 35 16 | | | | 0 |
| 4735 | 102 | 21 | 75 71.1 | CGAAATCGGCAACCTATGCG | 16 24 21 26 29 | | | | 0 |
| 4736 | 103 | 32 | 12925 69.6 | TCCCGGTATTAGAGCCCACG | 28 18 3 36 30 | | | | 0 |
| 4737 | 104 | 42 | 161 75.2 | TGCGTGCGCTCAATCGAGGA | 29 29 13 24 25 | | | | 0 |
| 4738 | 105 | 43 | 165 74.5 | TGCGAGCCGATGCCATCTTG | 29 36 27 15 11 | | | | 0 |
| 4739 | 106 | 49 | 186 72.8 | CAGCACGGGACCCCTACACG | 31 35 32 26 30 | | | | 0 |
| 4740 | 107 | 53 | 208 74 | GTGCTCCCGCAACGTTGTGC | 33 28 21 12 33 | | | | 0 |
| 4741 | 108 | 58 | 230 69.8 | ACGGGCAAACCTCTTGCTTG | 35 21 23 11 11 | | | | 0 |
| 4742 | 109 | 59 | 232 71.8 | ACGGGATGGCAAGGACCTCA | 35 27 21 34 13 | | | | 0 |
| 4743 | 110 | 60 | 238 75 | AGCCTGTCCGTTTGCGACGG | 36 9 12 29 35 | | | | 0 |
| 4744 | 111 | 62 | 12961 68.4 | AGCCAGGATCCCAAAGCCTA | 36 25 28 6 26 | | | | 0 |
| 4745 | 112 | 68 | 270 72.7 | TCTGACGGTCCCGCTTACGG | 8 35 28 17 35 | | | | 1 |
| 4746 | 113 | 70 | 275 77.2 | TGTCCACGTGCGGGACACGG | 9 30 29 34 35 | | | | 0 |
| 4747 | 114 | 76 | 311 76.8 | CGAAGTGCCACGCACGCGTT | 16 33 30 30 12 | | | | 0 |
| 4748 | 115 | 78 | 322 71.4 | GGTAACGGCTCAAGCCGCTT | 18 35 13 36 17 | | | | 0 |
| 4749 | 116 | 81 | 335 74.6 | TGATGCAAAGCCGTGCAGCC | 2 21 36 33 36 | | | | 0 |
| 4750 | 117 | 84 | 349 73.9 | GATGGTGCGCTTAGCCGCAA | 27 33 17 36 21 | | | | 0 |
| 4751 | 118 | 88 | 361 71.5 | TCCCTCCCGGTATCGTACGG | 28 28 18 10 35 | | | | 0 |
| 4752 | 119 | 89 | 362 74.5 | TCCCCACGGAGTGGACCAGC | 28 30 20 34 31 | | | | 0 |
| 4753 | 120 | 95 | 386 74.7 | CACGATCGGGACGCAACACG | 30 24 34 21 30 | | | | 0 |
| 4754 | 121 | 96 | 388 71.1 | CACGTCCCTTGAGACCGCAA | 30 28 1 32 21 | | | | 0 |
| 4755 | 122 | 98 | 404 73.9 | CAGCCACGGGACAGCCAGTG | 31 30 34 36 22 | | | | 0 |
| 4756 | 123 | 99 | 405 70.1 | CAGCGGACTTAGTCCCGTGC | 31 34 3 28 33 | | | | 0 |
| 4757 | 124 | 100 | 409 68.6 | GACCCGAATGATTGTCGCAA | 32 16 2 9 21 | | | | 0 |
| 4758 | 125 | 101 | 411 72.4 | GACCATCGAGCCCACGAGGA | 32 24 36 30 25 | | | | 0 |
| 4759 | 126 | 105 | 420 69.6 | GTGCCGAAGAGTCACGGGAC | 33 16 20 30 34 | | | | 0 |
| 4760 | 127 | 106 | 421 73.4 | GTGCGTCTACGGAGCCTGCG | 33 19 35 36 29 | | | | 0 |
| 4761 | 128 | 107 | 422 72.8 | GTGCGAGTACGGACGGCGTT | 33 20 35 35 12 | | | | 0 |
| 4762 | 129 | 109 | 426 69.1 | GTGCTGCGAAAGAGGATCCC | 33 29 6 25 28 | | | | 0 |
| 4763 | 130 | 112 | 435 71 | GGACGACCCGAAGGACCTTG | 34 32 16 34 11 | | | | 0 |
| 4764 | 131 | 114 | 437 73 | GGACAGCCGCTTGACCGATG | 34 36 17 32 27 | | | | 0 |
| 4765 | 132 | 125 | 532 71.1 | GCAATGCGCTGTCCTAACGG | 21 29 14 26 35 | | | | 0 |
| 4766 | 133 | 126 | 539 70.9 | ATCGCACGTCTGCTTGCCAT | 24 30 8 11 15 | | | | 0 |
| 4767 | 134 | 135 | 599 69.4 | CAGCGCAATACAGGACCACG | 31 21 7 34 30 | | | | 0 |
| 4768 | 135 | 140 | 627 70.2 | GGACCTGTGTGCCTTGCGTT | 34 14 33 11 12 | | | | 0 |
| 4769 | 136 | 145 | 636 71.3 | GGACGGACAATCGATGCACG | 34 34 4 27 30 | | | | 0 |
| 4770 | 137 | 150 | 683 72.2 | TCTGCGTTCCTATGCGCGAA | 8 12 26 29 16 | | | | 0 |
| 4771 | 138 | 153 | 714 69 | CGTTTCCCATACGATGCGAA | 12 28 5 27 16 | | | | 1 |
| 4772 | 139 | 157 | 743 71 | CGAATCTGTCCCTCCCGGAC | 16 8 28 28 34 | | | | 0 |
| 4773 | 140 | 159 | 748 69.4 | CGAAGCAAACGGTGTCGATG | 16 21 35 9 27 | | | | 0 |
| 4774 | 141 | 161 | 756 71.3 | AATCCGAACACGGACCGGAC | 4 16 30 32 34 | | | | 0 |
| 4775 | 142 | 162 | 762 68.1 | GCTTTTAGGATGCAGCACGG | 17 3 27 31 35 | | | | 0 |
| 4776 | 143 | 163 | 768 67.2 | GCTTCCATCGAAGACCGGTA | 17 15 16 32 18 | | | | 0 |
| 4777 | 144 | 165 | 793 72.1 | GAGTCGAATGCGTCCCAGCC | 20 16 29 28 36 | | | | 0 |

FIG. 29D

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 4778 | 145 | 168 | 843 | 70.8 | AGGAACGGCGTTCTTGGCTT | 25 | 35 | 12 | 11 | 17 | 0 |
| 4779 | 146 | 171 | 877 | 72 | TGCGTCGTTCTGTCCCGATG | 29 | 10 | 8 | 28 | 27 | 0 |
| 4780 | 147 | 179 | 919 | 70.3 | CAGCGATGGGACGAGTCGTT | 31 | 27 | 34 | 20 | 12 | 0 |
| 4781 | 148 | 189 | 949 | 68.3 | GTGCAGGACTCAGGACTGCG | 33 | 25 | 13 | 34 | 29 | 0 |
| 4782 | 149 | 192 | 966 | 71.3 | GGACTGCGCCATACCTGCAA | 34 | 29 | 15 | 23 | 21 | 0 |
| 4783 | 150 | 201 | 993 | 72.1 | AGCCATCGCTGTGCTTGCAA | 36 | 24 | 14 | 17 | 21 | 0 |
| 4784 | 151 | 203 | 999 | 74 | AGCCGTGCGGTAGACCGGAC | 36 | 33 | 18 | 32 | 34 | 0 |
| 4785 | 152 | 205 | 1040 | 73.8 | GCTTGGACGAGTTGCGGCAA | 17 | 34 | 20 | 29 | 21 | 0 |
| 4786 | 153 | 206 | 1047 | 74.5 | GCAAGACCATCGCACGGCAA | 21 | 32 | 24 | 30 | 21 | 0 |
| 4787 | 154 | 214 | 1104 | 72.5 | CAGCCTCAAGCCCGAAGTGC | 31 | 13 | 36 | 16 | 33 | 0 |
| 4788 | 155 | 218 | 1122 | 75.3 | GTGCTCGTGCTTTGCGTGCG | 33 | 10 | 17 | 29 | 29 | 0 |
| 4789 | 156 | 228 | 1217 | 68.9 | CGTTTGTCCTTGGATGCGAA | 12 | 9 | 11 | 27 | 16 | 0 |
| 4790 | 157 | 231 | 1229 | 69.8 | CTCATCGTGGACCGAAAGCC | 13 | 10 | 34 | 16 | 36 | 0 |
| 4791 | 158 | 234 | 1271 | 67.1 | CGAACTGTAGTGCAGCACGG | 16 | 14 | 22 | 31 | 35 | 0 |
| 4792 | 159 | 242 | 1333 | 71.3 | ATCGCTTGCTGTACGGCGAA | 24 | 11 | 14 | 35 | 16 | 0 |
| 4793 | 160 | 243 | 1337 | 71 | ATCGGGTATGCGCACGTGTC | 24 | 18 | 29 | 30 | 9 | 0 |
| 4794 | 161 | 248 | 1393 | 71.2 | TGCGATCGAGGACTCAACGG | 29 | 24 | 25 | 13 | 35 | 0 |
| 4795 | 162 | 255 | 1441 | 68.1 | GACCGCAACTGTTCGTGCTT | 32 | 21 | 14 | 10 | 17 | 0 |
| 4796 | 163 | 264 | 1474 | 69.4 | GGACCGAAAGTGCCATGGAC | 34 | 16 | 22 | 15 | 34 | 0 |
| 4797 | 164 | 271 | 1519 | 76.8 | CCATTCCCTCCCCAGCGCAA | 15 | 28 | 28 | 31 | 21 | 0 |
| 4798 | 165 | 272 | 1533 | 78.8 | TCCCCTTGCGAATGCGTGCG | 28 | 11 | 16 | 29 | 29 | 0 |
| 4799 | 166 | 281 | 1587 | 71.8 | ACGGCTGTTCGTTGTCGCAA | 35 | 14 | 10 | 9 | 21 | 0 |
| 4800 | 167 | 282 | 1590 | 71.2 | ACGGGCTTTGTCCACGGAGT | 35 | 17 | 9 | 30 | 20 | 0 |
| 4801 | 168 | 286 | 1602 | 74.2 | ACGGACGGCCATCCATGCTT | 35 | 35 | 15 | 15 | 17 | 0 |
| 4802 | 169 | 289 | 1620 | 72.8 | TTGAAGCCCGTTCGAAACGG | 1 | 36 | 12 | 16 | 35 | 0 |
| 4803 | 170 | 290 | 1621 | 72.1 | TGATTGCGCTTGGGACGATG | 2 | 29 | 11 | 34 | 27 | 0 |
| 4804 | 171 | 291 | 1624 | 71.6 | AATCTGCGCGAATGTCTGCG | 4 | 29 | 16 | 9 | 29 | 0 |
| 4805 | 172 | 292 | 1625 | 69.1 | AATCCACGTTAGTGCGCACG | 4 | 30 | 3 | 29 | 30 | 0 |
| 4806 | 173 | 298 | 1650 | 68.3 | TCTGCTTGCTGTGCTTTCCC | 8 | 11 | 14 | 17 | 28 | 0 |
| 4807 | 174 | 299 | 1651 | 65.8 | CTTGGCTTAGTGGCTTCACG | 11 | 17 | 22 | 17 | 30 | 0 |
| 4808 | 175 | 300 | 1653 | 71.6 | CTTGGATGCCATACGGTGCG | 11 | 27 | 15 | 35 | 29 | 0 |
| 4809 | 176 | 301 | 1656 | 71 | CTTGGACCCTGTCACGGCAA | 11 | 32 | 14 | 30 | 21 | 0 |
| 4810 | 177 | 304 | 1670 | 70 | CGTTATCGCACGGAGTGCAA | 12 | 24 | 30 | 20 | 21 | 0 |
| 4811 | 178 | 306 | 1678 | 70.8 | CGTTAGCCGGACCTGTCACG | 12 | 36 | 34 | 14 | 30 | 0 |
| 4812 | 179 | 313 | 1698 | 72.2 | TCTGCCATGACCGACCTCCC | 8 | 15 | 32 | 32 | 28 | 0 |
| 4813 | 180 | 317 | 1722 | 72.3 | GCTTTGTCCAGCGCAATCCC | 17 | 9 | 31 | 21 | 28 | 0 |
| 4814 | 181 | 321 | 1733 | 71.4 | GCTTGTGCGTCTGTGCCGTT | 17 | 33 | 19 | 33 | 12 | 0 |
| 4815 | 182 | 322 | 1735 | 68.2 | GGTACGTTCGAATCCCCCAT | 18 | 12 | 16 | 28 | 15 | 0 |
| 4816 | 183 | 324 | 1740 | 69.4 | TCTGGGTAGTGCATCGCGAA | 8 | 18 | 33 | 24 | 16 | 0 |
| 4817 | 184 | 331 | 1765 | 72.5 | ACCTACGGGTGCCGTTGTGC | 23 | 35 | 33 | 12 | 33 | 0 |
| 4818 | 185 | 333 | 1772 | 72.5 | ATCGTGCGGTCTACGGGTGC | 24 | 29 | 19 | 35 | 33 | 0 |
| 4819 | 186 | 335 | 1776 | 73.5 | ATCGGGACCAGCATCGGACC | 24 | 34 | 31 | 24 | 32 | 0 |
| 4820 | 187 | 340 | 1800 | 73.1 | TCCCCTGTGACCAGCCGATG | 28 | 14 | 32 | 36 | 27 | 0 |
| 4821 | 188 | 346 | 1811 | 73.2 | TGCGAAAGGGACCAGCAGGA | 29 | 6 | 34 | 31 | 25 | 0 |
| 4822 | 189 | 353 | 1833 | 68 | CACGACCTTTGATCCCGATG | 30 | 23 | 1 | 28 | 27 | 1 |
| 4823 | 190 | 363 | 1865 | 73.9 | GTGCAATCGACCCACGCAGC | 33 | 4 | 32 | 30 | 31 | 0 |
| 4824 | 191 | 376 | 1917 | 70.4 | AGCCGACCTCGTGATGCTTG | 36 | 32 | 10 | 27 | 11 | 0 |
| 4825 | 192 | 387 | 1945 | 73.5 | TCGTGTGCTCGTGACCGCAA | 10 | 33 | 10 | 32 | 21 | 0 |

*FIG. 29E*

| SEQ ID NO: | ZIP ID# | 4,633 ID# | HEX ID# Tm | ZIPCODE (NH2 -> CONH2) | TETRAMER NUMBERS | | | | | "UNALLOWED DIMERS" |
|---|---|---|---|---|---|---|---|---|---|---|
| 4826 | 193 | 392 | 1960 | 68.3 | CGTTTTGAGGACGACCATCG | 12 | 1 | 34 | 32 | 24 | 1 |
| 4827 | 194 | 393 | 1961 | 70.3 | CGTTTGATTCCCCTTGGCAA | 12 | 2 | 28 | 11 | 21 | 0 |
| 4828 | 195 | 395 | 1974 | 72 | TGTCCGTTGTGCCGTTCAGC | 9 | 12 | 33 | 12 | 31 | 0 |
| 4829 | 196 | 399 | 1983 | 69.1 | CCATTTGAAAAGCAGCTGCG | 15 | 1 | 6 | 31 | 29 | 0 |
| 4830 | 197 | 418 | 2028 | 65.9 | TGTCGCTTACGGATACAGCC | 9 | 17 | 35 | 5 | 36 | 0 |
| 4831 | 198 | 422 | 2035 | 69.3 | GGTAGGACATCGGGACCACG | 18 | 34 | 24 | 34 | 30 | 0 |
| 4832 | 199 | 425 | 2049 | 71.8 | GAGTGCTTGTGCGTGCGACC | 20 | 17 | 33 | 33 | 32 | 0 |
| 4833 | 200 | 430 | 2057 | 70 | GCAACTTGCTTGGTGCTCCC | 21 | 11 | 11 | 33 | 28 | 0 |
| 4834 | 201 | 431 | 2058 | 68.9 | TGTCGCAACCATCACGGTCT | 9 | 21 | 15 | 30 | 19 | 0 |
| 4835 | 202 | 432 | 2061 | 66.9 | TGTCGCAAGGTAAATCTGCG | 9 | 21 | 18 | 4 | 29 | 0 |
| 4836 | 203 | 443 | 2094 | 70.6 | ATCGGACCAATCATCGCGAA | 24 | 32 | 4 | 24 | 16 | 0 |
| 4837 | 204 | 444 | 2097 | 71.9 | AGGACGAATCCCATCGGCAA | 25 | 16 | 28 | 24 | 21 | 0 |
| 4838 | 205 | 448 | 2109 | 66.4 | GATGCTTGTACATCCCGCAA | 27 | 11 | 7 | 28 | 21 | 0 |
| 4839 | 206 | 449 | 2114 | 72.6 | GATGGATGGACCTGCGACGG | 27 | 27 | 32 | 29 | 35 | 0 |
| 4840 | 207 | 450 | 2115 | 68.1 | TGTCGATGTCCCTCGTGCTT | 9 | 27 | 28 | 10 | 17 | 0 |
| 4841 | 208 | 451 | 2116 | 69.9 | TGTCGATGTGCGCCTACAGC | 9 | 27 | 29 | 26 | 31 | 0 |
| 4842 | 209 | 452 | 2117 | 66 | GATGCACGACCTTTAGCGAA | 27 | 30 | 23 | 3 | 16 | 0 |
| 4843 | 210 | 464 | 2147 | 69.3 | TGCGCCTATGATCTTGCAGC | 29 | 26 | 2 | 11 | 31 | 0 |
| 4844 | 211 | 472 | 2158 | 68.8 | TGTCCACGGCAAAAGCCTA | 9 | 30 | 21 | 6 | 26 | 0 |
| 4845 | 212 | 473 | 2163 | 72.1 | TGTCCACGCAGCAATCAGCC | 9 | 30 | 31 | 4 | 36 | 0 |
| 4846 | 213 | 476 | 2174 | 71.2 | CAGCATCGCCATGATGGCTT | 31 | 24 | 15 | 27 | 17 | 0 |
| 4847 | 214 | 477 | 2176 | 74.2 | TGTCCAGCCAGCCTTGCGAA | 9 | 31 | 31 | 11 | 16 | 0 |
| 4848 | 215 | 480 | 2181 | 71.9 | GACCAAAGAGCCAGCCCGAA | 32 | 6 | 36 | 36 | 16 | 0 |
| 4849 | 216 | 481 | 2185 | 72.5 | TGTCGACCGGTAAGCCGACC | 9 | 32 | 18 | 36 | 32 | 0 |
| 4850 | 217 | 482 | 2186 | 72.1 | GACCAGTGCAGCGATGGCAA | 32 | 22 | 31 | 27 | 21 | 0 |
| 4851 | 218 | 484 | 2189 | 71.9 | TGTCGACCTCCCGACCTCGT | 9 | 32 | 28 | 32 | 10 | 0 |
| 4852 | 219 | 485 | 2191 | 68.9 | GACCGTGCTGTCAATCCACG | 32 | 33 | 9 | 4 | 30 | 0 |
| 4853 | 220 | 488 | 2197 | 68.2 | GTGCTGTCTCGTAGCCCGAA | 33 | 9 | 10 | 36 | 16 | 0 |
| 4854 | 221 | 495 | 2208 | 69.7 | TGTCGTGCCCTATCTGTGCG | 9 | 33 | 26 | 8 | 29 | 0 |
| 4855 | 222 | 497 | 2212 | 71.5 | TGTCGTGCCAGCCCATAGGA | 9 | 33 | 31 | 15 | 25 | 0 |
| 4856 | 223 | 498 | 2215 | 72 | TGTCGGACAAAGTGCGACGG | 9 | 34 | 6 | 29 | 35 | 0 |
| 4857 | 224 | 499 | 2217 | 67.4 | GGACCTCAATACGTGCCAGC | 34 | 13 | 5 | 33 | 31 | 0 |
| 4858 | 225 | 501 | 2219 | 70.9 | TGTCGGACCCATGACCCTCA | 9 | 34 | 15 | 32 | 13 | 0 |
| 4859 | 226 | 510 | 2234 | 67.9 | ACGGCGTTAAAGTGTCCGAA | 35 | 12 | 6 | 9 | 16 | 0 |
| 4860 | 227 | 515 | 2247 | 70.2 | AGCCCTTGCAGCAAAGCTTG | 36 | 11 | 31 | 6 | 11 | 0 |
| 4861 | 228 | 525 | 2301 | 68.9 | AAAGACGGTGTCGCAACACG | 6 | 35 | 9 | 21 | 30 | 0 |
| 4862 | 229 | 537 | 2336 | 68.6 | CTTGCTTGCGTTATCGCCAT | 11 | 11 | 12 | 24 | 15 | 0 |
| 4863 | 230 | 545 | 2353 | 67.2 | CGTTGCAACTCAGGTATGCG | 12 | 21 | 13 | 18 | 29 | 0 |
| 4864 | 231 | 547 | 2355 | 67.7 | CGTTAGGAACCTACGGCGAA | 12 | 25 | 23 | 35 | 16 | 0 |
| 4865 | 232 | 548 | 2359 | 67.9 | CGTTCACGTACATCGTTGCG | 12 | 30 | 7 | 10 | 29 | 0 |
| 4866 | 233 | 554 | 2371 | 72.4 | CTGTTCGTGACCACGGTGCG | 14 | 10 | 32 | 35 | 29 | 0 |
| 4867 | 234 | 557 | 2382 | 70.8 | CCATATCGCAGCCCATCAGC | 15 | 24 | 31 | 15 | 31 | 0 |
| 4868 | 235 | 560 | 2390 | 71.5 | TCGTCCATGGACCGAAGCAA | 10 | 15 | 34 | 16 | 21 | 0 |
| 4869 | 236 | 581 | 2470 | 75.6 | ACCGTGCCAGCCACGGTGC | 23 | 33 | 31 | 30 | 33 | 0 |
| 4870 | 237 | 582 | 2475 | 68.4 | ATCGCTGTACCTCGTTTGCG | 24 | 14 | 23 | 12 | 29 | 0 |
| 4871 | 238 | 588 | 2502 | 67 | CCTAACGGATCGTTGAAGCC | 26 | 35 | 24 | 1 | 36 | 0 |
| 4872 | 239 | 589 | 2509 | 72.6 | TCGTGATGATCGGTGCACGG | 10 | 27 | 24 | 33 | 35 | 0 |
| 4873 | 240 | 591 | 2523 | 69 | TCGTTCCCCTCAAGTGGACC | 10 | 28 | 13 | 22 | 32 | 0 |

FIG. 29F

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 4874 | 241 | 596 | 2531 | 71.3 | TCCCAGTGGATGGGACCCAT | 28 | 22 | 27 | 34 | 15 | 0 |
| 4875 | 242 | 597 | 2534 | 72.4 | TCGTTCCCGATGAGGAACGG | 10 | 28 | 27 | 25 | 35 | 0 |
| 4876 | 243 | 599 | 2536 | 72.6 | TCCCCAGCCGTTGTCTCAGC | 28 | 31 | 12 | 19 | 31 | 0 |
| 4877 | 244 | 606 | 2549 | 72.7 | TGCGGCAATGATCCATCACG | 29 | 21 | 2 | 15 | 30 | 0 |
| 4878 | 245 | 609 | 2555 | 73.9 | TGCGTCCCTCAGTGCCTCA | 29 | 28 | 13 | 33 | 13 | 0 |
| 4879 | 246 | 610 | 2557 | 72.6 | TCGTTGCGCACGTGATCGTT | 10 | 29 | 30 | 2 | 12 | 0 |
| 4880 | 247 | 613 | 2560 | 72.8 | TGCGGTGCTGATGGACATCG | 29 | 33 | 2 | 34 | 24 | 0 |
| 4881 | 248 | 638 | 2611 | 73 | TCGTGACCGACCGATGTCCC | 10 | 32 | 32 | 27 | 28 | 0 |
| 4882 | 249 | 649 | 2631 | 70.7 | GTGCGATGGAGTGTGCCCAT | 33 | 27 | 20 | 33 | 15 | 0 |
| 4883 | 250 | 650 | 2633 | 68.2 | GTGCGACCTGATATCGGTGC | 33 | 32 | 2 | 24 | 33 | 0 |
| 4884 | 251 | 657 | 2649 | 67.2 | TCGTGGACAGGAGATGGCTT | 10 | 34 | 25 | 27 | 17 | 0 |
| 4885 | 252 | 663 | 2659 | 74.3 | ACGGTGATCACGCAGCACGG | 35 | 2 | 30 | 31 | 35 | 0 |
| 4886 | 253 | 667 | 2674 | 70 | TCGTACGGGACAAAGCGTT | 10 | 35 | 34 | 6 | 12 | 0 |
| 4887 | 254 | 678 | 2722 | 76.4 | TGTCGTGCACGGCTGTTGCG | 9 | 33 | 35 | 14 | 29 | 0 |
| 4888 | 255 | 679 | 2725 | 69.9 | TCGTCCATAGCCTCCCGGTA | 10 | 15 | 36 | 28 | 18 | 0 |
| 4889 | 256 | 692 | 2779 | 71 | CCATGTCTTGCGGCTTACGG | 15 | 19 | 29 | 17 | 35 | 0 |
| 4890 | 257 | 695 | 2808 | 67.6 | GCTTTCGTCCATCTTGGTGC | 17 | 10 | 15 | 11 | 33 | 0 |
| 4891 | 258 | 711 | 2878 | 73.5 | AGGAGCTTTGCGCCATGCAA | 25 | 17 | 29 | 15 | 21 | 0 |
| 4892 | 259 | 721 | 2907 | 71.7 | TCCCAAAGGCTTGCAATCCC | 28 | 6 | 17 | 21 | 28 | 0 |
| 4893 | 260 | 726 | 2928 | 69.7 | CTTGTGCGCTTGAAAGCGAA | 11 | 29 | 11 | 6 | 16 | 0 |
| 4894 | 261 | 727 | 2931 | 71.7 | TGCGGAGTTGTCAGCCGGTA | 29 | 20 | 9 | 36 | 18 | 0 |
| 4895 | 262 | 731 | 2945 | 72.2 | CACGTGTCTCCCAGCCCCAT | 30 | 9 | 28 | 36 | 15 | 0 |
| 4896 | 263 | 733 | 2948 | 66.6 | CACGCTGTCGAATTAGCAGC | 30 | 14 | 16 | 3 | 31 | 0 |
| 4897 | 264 | 749 | 3014 | 69.5 | GGACACCTCTGTGTGCGCAA | 34 | 23 | 14 | 33 | 21 | 0 |
| 4898 | 265 | 753 | 3027 | 73.1 | ACGGAGTGACGGCGAACGAA | 35 | 22 | 35 | 16 | 16 | 0 |
| 4899 | 266 | 759 | 3038 | 72.2 | AGCCAATCTGCGGCAACCAT | 36 | 4 | 29 | 21 | 15 | 0 |
| 4900 | 267 | 760 | 3045 | 68.2 | AGCCGTCTCCTAATCGAGCC | 36 | 19 | 26 | 24 | 36 | 0 |
| 4901 | 268 | 762 | 3048 | 71.6 | AGCCAGTGAAAGTGCGCACG | 36 | 22 | 6 | 29 | 30 | 0 |
| 4902 | 269 | 773 | 3108 | 73.3 | TCTGTCGTTCCCGTGCGGAC | 8 | 10 | 28 | 33 | 34 | 0 |
| 4903 | 270 | 784 | 3142 | 70.5 | TCGTGTCTGGACCACGTCCC | 10 | 19 | 34 | 30 | 28 | 0 |
| 4904 | 271 | 809 | 3232 | 71.4 | CGTTGCTTTGCGGATGTCGT | 12 | 17 | 29 | 27 | 10 | 0 |
| 4905 | 272 | 810 | 3238 | 66.1 | GGTAAAAGTCGTTCCCAGCC | 18 | 6 | 10 | 28 | 36 | 0 |
| 4906 | 273 | 811 | 3245 | 71.4 | GGTACACGCCATCAGCCACG | 18 | 30 | 15 | 31 | 30 | 0 |
| 4907 | 274 | 832 | 3321 | 70.8 | CCTACACGCTTGTGCGGACC | 26 | 30 | 11 | 29 | 32 | 0 |
| 4908 | 275 | 837 | 3349 | 68.6 | TCCCCGTTGGTAAATCCCAT | 28 | 12 | 18 | 4 | 15 | 0 |
| 4909 | 276 | 838 | 3351 | 69.5 | TCCCCCATTGTCGAGTCGTT | 28 | 15 | 9 | 20 | 12 | 0 |
| 4910 | 277 | 843 | 3364 | 74.1 | CGTTCCCGTGCTGCGAGTG | 12 | 28 | 33 | 29 | 22 | 1 |
| 4911 | 278 | 844 | 3366 | 67.6 | TGCGTTAGAGTGCACGATCG | 29 | 3 | 22 | 30 | 24 | 0 |
| 4912 | 279 | 857 | 3398 | 69 | CACGCACGTGTCAAAGTCCC | 30 | 30 | 9 | 6 | 28 | 1 |
| 4913 | 280 | 867 | 3420 | 67.5 | GACCCTTGGCAATACAACGG | 32 | 11 | 21 | 7 | 35 | 0 |
| 4914 | 281 | 878 | 3451 | 71.1 | GTGCACGGCTTGTGTCCGTT | 33 | 35 | 11 | 9 | 12 | 0 |
| 4915 | 282 | 898 | 3516 | 69.2 | AAAGTGCGTCGTTGATTGCG | 6 | 29 | 10 | 2 | 29 | 0 |
| 4916 | 283 | 899 | 3518 | 68.5 | AAAGGACCTCTGCAGCCGTT | 6 | 32 | 8 | 31 | 12 | 0 |
| 4917 | 284 | 901 | 3530 | 72.8 | TCGTGCAACGTTGACCACGG | 10 | 21 | 12 | 32 | 35 | 0 |
| 4918 | 285 | 923 | 3620 | 71.9 | TCCCGGACAGGAGTGCACCT | 28 | 34 | 25 | 33 | 23 | 0 |
| 4919 | 286 | 961 | 3798 | 73.4 | GATGCAGCCGAAATCGCAGC | 27 | 31 | 16 | 24 | 31 | 0 |
| 4920 | 287 | 965 | 3809 | 71.3 | TCCCTGCGTTGAGGTATGCG | 28 | 29 | 1 | 18 | 29 | 0 |
| 4921 | 288 | 972 | 3829 | 73.7 | TGCGACGGGCAACCATTGAT | 29 | 35 | 21 | 15 | 2 | 0 |

*FIG. 29G*

| SEQ ID NO: | ZIP ID# | 4,633 ID# | HEX ID# | Ta | ZIPCODE (NH2 -> CONH2) | TETRAMER NUMBERS | | | | | "UNALLOWED DIMERS" |
|---|---|---|---|---|---|---|---|---|---|---|---|
| 4922 | 289 | 982 | 3856 | 69.9 | GACCCCATCTTGATCGGCAA | 32 | 15 | 11 | 24 | 21 | 0 |
| 4923 | 290 | 989 | 3872 | 73.8 | GTGCATCGGACCACCTTGCG | 33 | 24 | 32 | 23 | 29 | 0 |
| 4924 | 291 | 991 | 3873 | 70 | GTGCCACGATACGGACCGTT | 33 | 30 | 5 | 34 | 12 | 0 |
| 4925 | 292 | 993 | 3878 | 70 | GGACCCTACCATTCCCAGCC | 34 | 26 | 15 | 28 | 36 | 0 |
| 4926 | 293 | 994 | 3882 | 74.2 | GGACCACGGTGCGATGCTCA | 34 | 30 | 33 | 27 | 13 | 0 |
| 4927 | 294 | 1016 | 3987 | 68.4 | TGTCCAGCTTGAACGGCTGT | 9 | 31 | 1 | 35 | 14 | 0 |
| 4928 | 295 | 1018 | 3993 | 68.2 | CCATTCGTTCGTCGTTGCTT | 15 | 10 | 10 | 12 | 17 | 0 |
| 4929 | 296 | 1020 | 3999 | 73.3 | TCGTGAGTCACGTGCGCAGC | 10 | 20 | 30 | 29 | 31 | 0 |
| 4930 | 297 | 1074 | 4202 | 72.5 | TGCGATACGGACATCGGCAA | 29 | 5 | 34 | 24 | 21 | 0 |
| 4931 | 298 | 1077 | 4209 | 72.6 | TGCGCGAAGATGCTCACAGC | 29 | 16 | 27 | 13 | 31 | 0 |
| 4932 | 299 | 1085 | 4220 | 71.7 | CACGAATCGCTTGTGCGCTT | 30 | 4 | 17 | 33 | 17 | 0 |
| 4933 | 300 | 1099 | 4243 | 69.2 | CAGCAGCCAAAGGTCTTCCC | 31 | 36 | 6 | 19 | 28 | 0 |
| 4934 | 301 | 1126 | 14325 | 68.9 | TTGATCCCAATCCGAATCCC | 1 | 28 | 4 | 16 | 28 | 0 |
| 4935 | 302 | 1129 | 4341 | 69.1 | TTAGCACGGGTACAGCACGG | 3 | 30 | 18 | 31 | 35 | 0 |
| 4936 | 303 | 1147 | 30238 | 72.4 | TGTCTCCCGTGCCCATAGCC | 9 | 28 | 33 | 15 | 36 | 0 |
| 4937 | 304 | 1151 | 4428 | 67.8 | TCGTACCTTGCGGTCTCGTT | 10 | 23 | 29 | 19 | 12 | 0 |
| 4938 | 305 | 1152 | 14366 | 68.5 | TCGTCCTAAGGATCCCAGCC | 10 | 26 | 25 | 28 | 36 | 0 |
| 4939 | 306 | 1162 | 4467 | 72.9 | CTCACGTTCACGCGTTTGCG | 13 | 12 | 30 | 12 | 29 | 0 |
| 4940 | 307 | 1167 | 4480 | 68.9 | CCATTGATCTTGCACGCGTT | 15 | 2 | 11 | 30 | 12 | 0 |
| 4941 | 308 | 1172 | 4490 | 70.3 | CGAACCATCAGCGACCGTCT | 16 | 15 | 31 | 32 | 19 | 0 |
| 4942 | 309 | 1179 | 4518 | 70.4 | GCTTCTGTTCCCCGTTTCCC | 17 | 14 | 28 | 12 | 28 | 1 |
| 4943 | 310 | 1200 | 4598 | 67 | ATCGACCTTCTGGATGCAGC | 24 | 23 | 8 | 27 | 31 | 0 |
| 4944 | 311 | 1201 | 4604 | 70.3 | ATCGACGGGAGTTGTCTGCG | 24 | 35 | 20 | 9 | 29 | 0 |
| 4945 | 312 | 1221 | 4659 | 69 | TGCGGCTTCGTTAAAGCTTG | 29 | 17 | 12 | 6 | 11 | 0 |
| 4946 | 313 | 1222 | 4660 | 68.9 | CGAATGCGGGTAATACTGCG | 16 | 29 | 18 | 5 | 29 | 0 |
| 4947 | 314 | 1249 | 4759 | 68.1 | CGAAGGACGTGCACCTCCTA | 16 | 34 | 33 | 23 | 26 | 0 |
| 4948 | 315 | 1251 | 4761 | 68.2 | ACGGTTAGCTGTCAGCACGG | 35 | 3 | 14 | 31 | 35 | 0 |
| 4949 | 316 | 1259 | 4782 | 72 | CGAAACGGAGCCGTCTCGTT | 16 | 35 | 36 | 19 | 12 | 0 |
| 4950 | 317 | 1263 | 4793 | 70.7 | AGCCGCAAAGTGAATCGTGC | 36 | 21 | 22 | 4 | 33 | 0 |
| 4951 | 318 | 1284 | 4872 | 68.3 | TCGTCGAAGTCTCACGCCAT | 10 | 16 | 19 | 30 | 15 | 0 |
| 4952 | 319 | 1298 | 4896 | 68.5 | CTTGACGGAGCCTTGACACG | 11 | 35 | 36 | 1 | 30 | 0 |
| 4953 | 320 | 1375 | 5432 | 72.1 | CTTGCGTTTGCGCCTAGCAA | 11 | 12 | 29 | 26 | 21 | 0 |
| 4954 | 321 | 1398 | 5534 | 72.7 | GTGCGGACCCTAACGGCTCA | 33 | 34 | 26 | 35 | 13 | 0 |
| 4955 | 322 | 1424 | 5680 | 72.8 | GACCCAGCTGTCGGACCACG | 32 | 31 | 9 | 34 | 30 | 0 |
| 4956 | 323 | 1427 | 5684 | 73.7 | GTGCCTTGTGCGCGAACGTT | 33 | 11 | 29 | 16 | 12 | 0 |
| 4957 | 324 | 1439 | 5787 | 73.6 | TACATCCCGGACACGGGCAA | 7 | 28 | 34 | 35 | 21 | 0 |
| 4958 | 325 | 1454 | 5821 | 70.9 | TCGTGATGGTCTTGCGTCCC | 10 | 27 | 19 | 29 | 28 | 0 |
| 4959 | 326 | 1462 | 5855 | 69.7 | CGTTGGACCTTGCTGTTCCC | 12 | 34 | 11 | 14 | 28 | 0 |
| 4960 | 327 | 1463 | 5859 | 66.4 | CTCAACCTCCATTCGTTCCC | 13 | 23 | 15 | 10 | 28 | 0 |
| 4961 | 328 | 1465 | 5862 | 72.6 | CTCATGCGCACGTCTGGTGC | 13 | 29 | 30 | 8 | 33 | 0 |
| 4962 | 329 | 1479 | 5941 | 69.3 | GCAATTAGCACGCATCGAA | 21 | 3 | 30 | 15 | 16 | 0 |
| 4963 | 330 | 1485 | 5962 | 67.6 | AGTGTCGTTTGATGCGGGAC | 22 | 10 | 1 | 29 | 34 | 0 |
| 4964 | 331 | 1489 | 5980 | 68.8 | ACCTCTCATGCGTGATTGCC | 23 | 13 | 29 | 2 | 29 | 0 |
| 4965 | 332 | 1496 | 14968 | 71.5 | GCAAATCGATCGCGAACGAA | 21 | 24 | 24 | 16 | 16 | 0 |
| 4966 | 333 | 1499 | 6008 | 68.3 | GCAAATCGAGCCAATCGGTA | 21 | 24 | 36 | 4 | 18 | 0 |
| 4967 | 334 | 1550 | 6148 | 68.1 | GGACGTCTTGTCCGTTCACG | 34 | 19 | 9 | 12 | 30 | 0 |
| 4968 | 335 | 1561 | 6173 | 72 | GCAAAGCCCGTTCAGCACCT | 21 | 36 | 12 | 31 | 23 | 0 |
| 4969 | 336 | 1580 | 6250 | 68.5 | CGAACTTGTCTGGGACTGCG | 16 | 11 | 8 | 34 | 29 | 0 |

FIG. 29H

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 4970 | 337 | 1632 | 6471 | 68.4 | TTAGCGTTTGTCTGCGTCCC | 3 | 12 | 9 | 29 | 28 | 0 |
| 4971 | 338 | 1647 | 6557 | 68.3 | CGAACCATTACATGCGGCTT | 16 | 15 | 7 | 29 | 17 | 0 |
| 4972 | 339 | 1650 | 6572 | 67.9 | GCTTCGAAGTGCCTGTCAGC | 17 | 16 | 33 | 14 | 31 | 0 |
| 4973 | 340 | 1675 | 6706 | 70.1 | GTGCTTGACACGATCGCACG | 33 | 1 | 30 | 24 | 30 | 0 |
| 4974 | 341 | 1700 | 6802 | 69 | ATCGAAAGCTCAGTGCGCAA | 24 | 6 | 13 | 33 | 21 | 0 |
| 4975 | 342 | 1710 | 6845 | 70.6 | ATCGCTTGTGTCTGCGAGCC | 24 | 11 | 9 | 29 | 36 | 0 |
| 4976 | 343 | 1712 | 6850 | 67.6 | ATCGCTTGCGAAAAAGCTGT | 24 | 11 | 16 | 6 | 14 | 0 |
| 4977 | 344 | 1724 | 6870 | 64 | CGTTGAGTAGGAGGACGGAC | 12 | 20 | 25 | 34 | 34 | 0 |
| 4978 | 345 | 1730 | 6882 | 72.1 | CTCATCTGGTGCGGACGCAA | 13 | 8 | 33 | 34 | 21 | 0 |
| 4979 | 346 | 1737 | 6903 | 70.3 | CTGTGATGCGTTACGGCACG | 14 | 27 | 12 | 35 | 30 | 0 |
| 4980 | 347 | 1743 | 6911 | 69.6 | ATCGCCATAATCCAGCCAGC | 24 | 15 | 4 | 31 | 31 | 0 |
| 4981 | 348 | 1766 | 6956 | 65.1 | ATCGGCTTCAGCAAAGTCTG | 24 | 17 | 31 | 6 | 8 | 0 |
| 4982 | 349 | 1781 | 6994 | 70.1 | ATCGGAGTGGACCACGCTTG | 24 | 20 | 34 | 30 | 11 | 0 |
| 4983 | 350 | 1794 | 7018 | 67.8 | AGTGCTCAAGGAATCGGCAA | 22 | 13 | 25 | 24 | 21 | 0 |
| 4984 | 351 | 1813 | 7068 | 67.7 | ATCGCCTAGATGTGCGAGGA | 24 | 26 | 27 | 29 | 25 | 0 |
| 4985 | 352 | 1831 | 7104 | 73.1 | TCCCAGCCCTGTGATGGTGC | 28 | 36 | 14 | 27 | 33 | 0 |
| 4986 | 353 | 1877 | 7191 | 67.2 | ATCGGACTACAATCGCAGC | 24 | 34 | 7 | 24 | 31 | 0 |
| 4987 | 354 | 1889 | 7213 | 71.2 | ACGGTGTCCGAACCATGCAA | 35 | 9 | 16 | 15 | 21 | 0 |
| 4988 | 355 | 1904 | 7235 | 68.1 | AGCCGAGTTTGACGAACACG | 36 | 20 | 1 | 16 | 30 | 0 |
| 4989 | 356 | 1923 | 7302 | 71.8 | TCGTGACCAGGACAGCACGG | 10 | 32 | 25 | 31 | 35 | 0 |
| 4990 | 357 | 1940 | 7357 | 71.9 | GCTTGATGTCCCGCAATCCC | 17 | 27 | 28 | 21 | 28 | 0 |
| 4991 | 358 | 1944 | 7388 | 69.2 | AGTGGGTAGCAATCCCCACG | 22 | 18 | 21 | 28 | 30 | 0 |
| 4992 | 359 | 1975 | 7510 | 72.4 | GTGCGTGCCTTGGACCACCT | 33 | 33 | 11 | 32 | 23 | 0 |
| 4993 | 360 | 2007 | 7750 | 73.7 | CAGCAGGAGACCGACCGCAA | 31 | 25 | 32 | 32 | 21 | 0 |
| 4994 | 361 | 2029 | 7882 | 69.5 | GATGCCATGCAACAGCAGGA | 27 | 15 | 21 | 31 | 25 | 0 |
| 4995 | 362 | 2083 | 8075 | 71.1 | GGACCTTGCACGTCGTCGAA | 34 | 11 | 30 | 10 | 16 | 0 |
| 4996 | 363 | 2098 | 8128 | 71 | TCCCTGATTCCCCGAACGTT | 28 | 2 | 28 | 16 | 12 | 0 |
| 4997 | 364 | 2128 | 15756 | 66.4 | TACATGCGTTAGGACCCACG | 7 | 29 | 3 | 32 | 30 | 0 |
| 4998 | 365 | 2134 | 8207 | 69.5 | TCTGGATGCACGAATCGTGC | 8 | 27 | 30 | 4 | 33 | 0 |
| 4999 | 366 | 2158 | 8259 | 73 | TCCCCTTGTGCGATCGCTGT | 28 | 11 | 29 | 24 | 14 | 0 |
| 5000 | 367 | 2174 | 8284 | 68.7 | TCCCCGTTACGGAGTGGTCT | 28 | 12 | 35 | 22 | 19 | 0 |
| 5001 | 368 | 2177 | 8289 | 69.5 | TCCCCTCATACAACGGCCAT | 28 | 13 | 7 | 35 | 15 | 0 |
| 5002 | 369 | 2179 | 8294 | 65.6 | TCCCCTCACTGTCCTATCCC | 28 | 13 | 14 | 26 | 28 | 0 |
| 5003 | 370 | 2183 | 8299 | 64.5 | TCCCCTCACCTAATACACGG | 28 | 13 | 26 | 5 | 35 | 0 |
| 5004 | 371 | 2197 | 8327 | 68 | TCCCCATATACGCAACAGC | 28 | 15 | 5 | 21 | 31 | 0 |
| 5005 | 372 | 2207 | 8344 | 69.8 | TCCCGAATGATGCTTCGTT | 28 | 16 | 2 | 17 | 12 | 0 |
| 5006 | 373 | 2237 | 8396 | 71.1 | TCCCGGTAGACCCCATGACC | 28 | 18 | 32 | 15 | 32 | 0 |
| 5007 | 374 | 2243 | 8403 | 67.5 | TCCCGTCTCTGTGATGAGCC | 28 | 19 | 14 | 27 | 36 | 0 |
| 5008 | 375 | 2254 | 40508 | 71.7 | TCCCGAGTTGTCGACCCCAT | 28 | 20 | 9 | 32 | 15 | 0 |
| 5009 | 376 | 2271 | 8440 | 67.9 | TCCCGCAAAGGAGAGTGATG | 28 | 21 | 25 | 20 | 27 | 0 |
| 5010 | 377 | 2293 | 8479 | 65.1 | TCCCATCGTGTCTGATAGCC | 28 | 24 | 9 | 2 | 36 | 0 |
| 5011 | 378 | 2304 | 8502 | 65.8 | TCCCAGGACTGTTTGACACG | 28 | 25 | 14 | 1 | 30 | 0 |
| 5012 | 379 | 2365 | 8592 | 64.8 | TCCCCACGTACAGGACAATC | 28 | 30 | 7 | 34 | 4 | 0 |
| 5013 | 380 | 2369 | 8597 | 71.2 | TCCCCACGGCTTCTTGACCT | 28 | 30 | 17 | 11 | 23 | 0 |
| 5014 | 381 | 2403 | 8640 | 71.9 | TCCCGACCGCTTGGTACCAT | 28 | 32 | 17 | 18 | 15 | 0 |
| 5015 | 382 | 2421 | 8665 | 68.3 | TCCCGGACTGATCGTTGATG | 28 | 34 | 2 | 12 | 27 | 0 |
| 5016 | 383 | 2422 | 8666 | 67.5 | TCCCGGACTTAGCGAACTTG | 28 | 34 | 3 | 16 | 11 | 0 |
| 5017 | 384 | 2440 | 8695 | 72.8 | TCCCACGGCGAATGTCCCTA | 28 | 35 | 16 | 9 | 26 | 0 |

FIG. 291

| SEQ ID NO: | ZIP ID# | 4,633 ID# | HEX ID# | Tm | ZIPCODE (NH2 -> CONH2) | TETRAMER NUMBERS | | | | "UNALLOWED DIMERS" |
|---|---|---|---|---|---|---|---|---|---|---|
| 5018 | 385 | 2444 | 8703 | 72.6 | TCCCACGGTCCCGAGTGGTA | 28 | 35 | 28 | 20 | 18 | 1 |
| 5019 | 386 | 2452 | 8710 | 68.5 | TCCCAGCCTACATGTCACGG | 28 | 36 | 7 | 9 | 35 | 0 |
| 5020 | 387 | 2461 | 8720 | 73.1 | TCCCAGCCGATGGATGATCG | 28 | 36 | 27 | 27 | 24 | 0 |
| 5021 | 388 | 2468 | 8728 | 67.1 | TGCGTTGACTTGAGTGACGG | 29 | 1 | 11 | 22 | 35 | 0 |
| 5022 | 389 | 2471 | 15876 | 70.2 | TGCGTTGAACCTACGGGAC | 29 | 1 | 23 | 35 | 34 | 0 |
| 5023 | 390 | 2477 | 40574 | 67.2 | TGCGTGATCGTTCTCACAGC | 29 | 2 | 12 | 13 | 31 | 0 |
| 5024 | 391 | 2479 | 8749 | 71.1 | TGCGTGATGTCTCACGCGAA | 29 | 2 | 19 | 30 | 16 | 0 |
| 5025 | 392 | 2482 | 8752 | 68.1 | TGCGTGATGATGTGTCCGAA | 29 | 2 | 27 | 9 | 16 | 0 |
| 5026 | 393 | 2497 | 8775 | 68.8 | TGCGAATCCTGTTGTCCAGC | 29 | 4 | 14 | 9 | 31 | 0 |
| 5027 | 394 | 2503 | 8788 | 63.4 | TGCGATACGTCTGAGTAGCC | 29 | 5 | 19 | 20 | 36 | 0 |
| 5028 | 395 | 2507 | 8796 | 64.2 | TGCGAAAGTGATAGCCAGTG | 29 | 6 | 2 | 36 | 22 | 0 |
| 5029 | 396 | 2515 | 8808 | 67.7 | TGCGAAAGGTGCAGGAGAGT | 29 | 6 | 33 | 25 | 20 | 0 |
| 5030 | 397 | 2517 | 15901 | 67.9 | TGCGTACATCGTACGGCTCA | 29 | 7 | 10 | 35 | 13 | 0 |
| 5031 | 398 | 2520 | 8817 | 66.9 | TGCGTACAGGACTGCGAAAG | 29 | 7 | 34 | 29 | 6 | 0 |
| 5032 | 399 | 2546 | 8864 | 63.6 | TGCGTCGTGGTACCTATGTC | 29 | 10 | 18 | 26 | 9 | 0 |
| 5033 | 400 | 2578 | 8901 | 70.5 | TGCGCGTTCCTAAAAGCCAT | 29 | 12 | 26 | 6 | 15 | 0 |
| 5034 | 401 | 2592 | 15912 | 66.6 | TGCGCTCACTCAGACCAAAG | 29 | 13 | 13 | 32 | 6 | 0 |
| 5035 | 402 | 2594 | 15913 | 71.7 | TGCGCTCACGAACCATCGTT | 29 | 13 | 16 | 15 | 12 | 0 |
| 5036 | 403 | 2595 | 30609 | 67.2 | TGCGCTCAGAGTTTAGCACG | 29 | 13 | 20 | 3 | 30 | 0 |
| 5037 | 404 | 2599 | 8923 | 72.8 | TGCGCTCAAGCCAGGAGCTT | 29 | 13 | 36 | 25 | 17 | 0 |
| 5038 | 405 | 2600 | 8924 | 69.7 | TGCGCTGTTTGAGTGCTCGT | 29 | 14 | 1 | 33 | 10 | 0 |
| 5039 | 406 | 2608 | 21521 | 66.7 | TGCGCTGTCGTTAGGATCTG | 29 | 14 | 12 | 25 | 8 | 0 |
| 5040 | 407 | 2614 | 30613 | 67.8 | TGCGCTGTGAGTCTGTCGAA | 29 | 14 | 20 | 14 | 16 | 0 |
| 5041 | 408 | 2624 | 40623 | 68.6 | TGCGCCATCTGTAGCCTGAT | 29 | 15 | 14 | 36 | 2 | 0 |
| 5042 | 409 | 2641 | 8968 | 70.9 | TGCGCGAAGACCACCTCTGT | 29 | 16 | 32 | 23 | 14 | 0 |
| 5043 | 410 | 2642 | 8970 | 71.8 | TGCGCGAAGGACGCAATTAG | 29 | 16 | 34 | 21 | 3 | 0 |
| 5044 | 411 | 2643 | 8973 | 69 | TGCGGCTTAATCCTCAGCAA | 29 | 17 | 4 | 13 | 21 | 0 |
| 5045 | 412 | 2655 | 8991 | 68.6 | TGCGGGTATCTGCTGTGACC | 29 | 18 | 8 | 14 | 32 | 0 |
| 5046 | 413 | 2663 | 9004 | 67.3 | TGCGGGTAGATGCCTAGACC | 29 | 18 | 27 | 26 | 32 | 0 |
| 5047 | 414 | 2687 | 21565 | 69.1 | TGCGGAGTGAGTGCTTCAGC | 29 | 20 | 20 | 17 | 31 | 0 |
| 5048 | 415 | 2690 | 9040 | 75.2 | TGCGGAGTTGCGAGTGCGAA | 29 | 20 | 29 | 22 | 16 | 0 |
| 5049 | 416 | 2691 | 30634 | 69.1 | TGCGGAGTCACGTCCCTACA | 29 | 20 | 30 | 28 | 7 | 0 |
| 5050 | 417 | 2708 | 9054 | 71 | TGCGAGTGAATCGGACGGAC | 29 | 22 | 4 | 34 | 34 | 0 |
| 5051 | 418 | 2721 | 9070 | 63.8 | TGCGACCTTCTGTACAGTGC | 29 | 23 | 8 | 7 | 33 | 0 |
| 5052 | 419 | 2748 | 9104 | 72.7 | TGCGATCGGTGCGAGTTTGA | 29 | 24 | 33 | 20 | 1 | 0 |
| 5053 | 420 | 2762 | 40657 | 71 | TGCGCCTATTAGAGCCGTGC | 29 | 26 | 3 | 36 | 33 | 0 |
| 5054 | 421 | 2763 | 9128 | 66.1 | TGCGCCTAAATCCTGTCTTG | 29 | 26 | 4 | 14 | 11 | 0 |
| 5055 | 422 | 2770 | 9139 | 70.5 | TGCGCCTAAGTGCGAAACCT | 29 | 26 | 22 | 16 | 23 | 0 |
| 5056 | 423 | 2784 | 9156 | 68 | TGCGGATGAGGATTGATCGT | 29 | 27 | 25 | 1 | 10 | 0 |
| 5057 | 424 | 2791 | 30649 | 66.9 | TGCGTCCCATACTGATGTGC | 29 | 28 | 5 | 2 | 33 | 0 |
| 5058 | 425 | 2802 | 9177 | 68.2 | TGCGTCCCAGGAGTGCTTAG | 29 | 28 | 25 | 33 | 3 | 0 |
| 5059 | 426 | 2843 | 9222 | 67.6 | TGCGGACCTTAGCTCACCAT | 29 | 32 | 3 | 13 | 15 | 0 |
| 5060 | 427 | 2861 | 9247 | 69.6 | TGCGGTGCAGTGGGTATCTG | 29 | 33 | 22 | 18 | 8 | 0 |
| 5061 | 428 | 2876 | 9264 | 72.8 | TGCGGGACGGTAACGGTGAT | 29 | 34 | 18 | 35 | 2 | 0 |
| 5062 | 429 | 2886 | 9275 | 67.9 | TGCGACGGAAAGGGTATGTC | 29 | 35 | 6 | 18 | 9 | 0 |
| 5063 | 430 | 2904 | 9292 | 68.3 | TGCGAGCCCTGTTTAGGATG | 29 | 36 | 14 | 3 | 27 | 0 |
| 5064 | 431 | 3018 | 9551 | 68.2 | CACGGAGTGATGAGCCCTTG | 30 | 20 | 27 | 36 | 11 | 0 |
| 5065 | 432 | 3021 | 9556 | 63.1 | GCAAATACTCTGGAGTTGCG | 21 | 5 | 8 | 20 | 29 | 0 |

FIG. 29J

| SEQ ID NO: | ZIP ID# | 4,633 ID# | HEX ID# | Tm | ZIPCODE (NB2 -> CONB2) | TETRAMER NUMBERS | | | | | "UNALLOWED DIMERS" |
|---|---|---|---|---|---|---|---|---|---|---|---|
| 5066 | 433 | 3045 | 9608 | 71.1 | CACGATCGGCAAATCGTCGT | 30 | 24 | 21 | 24 | 10 | 0 |
| 5067 | 434 | 3053 | 9626 | 70.5 | AGGAAGTGGCAACACGCAGC | 25 | 22 | 21 | 30 | 31 | 0 |
| 5068 | 435 | 3057 | 9633 | 69.4 | AGGAGACCCTCACGAATGCG | 25 | 32 | 13 | 16 | 29 | 0 |
| 5069 | 436 | 3103 | 9728 | 72.5 | CACGCAGCGCTTGCTTTCTG | 30 | 31 | 17 | 17 | 8 | 0 |
| 5070 | 437 | 3153 | 9818 | 68.9 | CACGAGCCGGTACGTTGGTA | 30 | 36 | 18 | 12 | 18 | 0 |
| 5071 | 438 | 3171 | 9864 | 68.8 | CAGCATACGTGCTCCCAGGA | 31 | 5 | 33 | 28 | 25 | 0 |
| 5072 | 439 | 3256 | 10059 | 66.3 | CAGCGAGTCCATGGACAGTG | 31 | 20 | 15 | 34 | 22 | 0 |
| 5073 | 440 | 3258 | 10060 | 67.5 | CAGCGAGTGGTAATCGTCCC | 31 | 20 | 18 | 24 | 28 | 0 |
| 5074 | 441 | 3273 | 10091 | 70.8 | AGTGATCGCTTGAGCCTGCG | 22 | 24 | 11 | 36 | 29 | 0 |
| 5075 | 442 | 3342 | 10220 | 67.9 | CAGCCAGCAAAGCCTAAGGA | 31 | 31 | 6 | 26 | 25 | 0 |
| 5076 | 443 | 3343 | 10221 | 68.4 | CAGCCAGCTACAAGCCAGGA | 31 | 31 | 7 | 36 | 25 | 0 |
| 5077 | 444 | 3473 | 10530 | 66 | GCAAACCTGTCTATCGCGAA | 21 | 23 | 19 | 24 | 16 | 0 |
| 5078 | 445 | 3492 | 10297 | 65.5 | GATGCGAATACAGACCCGAA | 27 | 16 | 7 | 32 | 16 | 0 |
| 5079 | 446 | 3493 | 10589 | 67.4 | GATGGAGTGATGGACCACGG | 27 | 20 | 27 | 32 | 35 | 0 |
| 5080 | 447 | 3501 | 30792 | 73 | TCCCGCAAGTCTGGACCGAA | 28 | 21 | 19 | 34 | 16 | 0 |
| 5081 | 448 | 3653 | 10942 | 70.1 | GTGCGCTTCCTAACGGGATG | 33 | 17 | 26 | 35 | 27 | 0 |
| 5082 | 449 | 3678 | 30832 | 67 | GTGCGCAACGTTGCTTTTAG | 33 | 21 | 12 | 17 | 3 | 0 |
| 5083 | 450 | 3711 | 11060 | 68.7 | AGGACCTAAGCCATCGACGG | 25 | 26 | 36 | 24 | 35 | 0 |
| 5084 | 451 | 3822 | 11330 | 66.2 | CTTGAGGATGTCGATGGCAA | 11 | 25 | 9 | 27 | 21 | 0 |
| 5085 | 452 | 3920 | 11597 | 68.1 | CAGCCGTTTTGAGATGCCAT | 31 | 12 | 1 | 27 | 15 | 1 |
| 5086 | 453 | 3967 | 11693 | 70.1 | TTGATTGAATCGCGTTTGCG | 1 | 1 | 24 | 12 | 29 | 0 |
| 5087 | 454 | 4057 | 41152 | 66.2 | ACGGCTCAGGACATACCCAT | 35 | 13 | 34 | 5 | 15 | 0 |
| 5088 | 455 | 4062 | 11897 | 64.7 | ACGGCTGTGGTACTCATCGT | 35 | 14 | 18 | 13 | 10 | 0 |
| 5089 | 456 | 4145 | 12041 | 66.9 | AGTGGCTTGTCTGACCAGCC | 22 | 17 | 19 | 32 | 36 | 0 |
| 5090 | 457 | 4162 | 30941 | 67 | ATCGTCTGTCTGGACCCGAA | 24 | 8 | 8 | 32 | 16 | 0 |
| 5091 | 458 | 4174 | 12091 | 64.2 | ACGGAGGATGATACCTCACG | 35 | 25 | 2 | 23 | 30 | 0 |
| 5092 | 459 | 4317 | 16775 | 67.5 | AGCCTTAGCCATTCTGCGAA | 36 | 3 | 15 | 8 | 16 | 0 |
| 5093 | 460 | 4348 | 12389 | 67.1 | AGCCTGTCGCAAATACCGTT | 36 | 9 | 21 | 5 | 12 | 0 |
| 5094 | 461 | 4352 | 12396 | 67.8 | AGCCTCGTTTAGTCGTTGCG | 36 | 10 | 3 | 10 | 29 | 0 |
| 5095 | 462 | 4446 | 12578 | 64.4 | AGCCGTCTGGACTGATTCTG | 36 | 19 | 34 | 2 | 8 | 0 |
| 5096 | 463 | 4448 | 12580 | 64.7 | AGCCGAGTTTAGCCTACACG | 36 | 20 | 3 | 26 | 30 | 0 |
| 5097 | 464 | 4545 | 12741 | 65.9 | TGCGTACACTGTCCATTCCC | 29 | 7 | 14 | 15 | 28 | 0 |
| 5098 | 465 | 4586 | 12811 | 70.2 | AGCCGACCAGCCTTAGGGAC | 36 | 32 | 36 | 3 | 34 | 0 |
| 5099 | 466 | 1 | 20001 | 71.9 | TTGAAGCCATCGGCTTTCCC | 1 | 36 | 24 | 17 | 28 | 0 |
| 5100 | 467 | 2 | 12884 | 73.6 | AATCCACGTCCCCGAAACGG | 4 | 30 | 28 | 16 | 35 | 0 |
| 5101 | 468 | 4 | 30001 | 70.5 | AAAGCGTTCTCATGCGCGTT | 6 | 12 | 13 | 29 | 12 | 0 |
| 5102 | 469 | 10 | 39 | 76.6 | TCGTCAGCCACGACGGACGG | 10 | 31 | 30 | 35 | 35 | 0 |
| 5103 | 470 | 11 | 12889 | 76.2 | TCGTGTGCACGGTGCGATCG | 10 | 33 | 35 | 29 | 24 | 0 |
| 5104 | 471 | 14 | 40001 | 73.9 | CTTGCGAAGTGCGTGCCGTT | 11 | 16 | 33 | 33 | 12 | 0 |
| 5105 | 472 | 16 | 30002 | 72.6 | CGTTTCCCACGAGTGCGTT | 12 | 28 | 30 | 22 | 12 | 1 |
| 5106 | 473 | 19 | 68 | 77.2 | CCATGTGCACGGCACGCCAT | 15 | 33 | 35 | 30 | 15 | 0 |
| 5107 | 474 | 22 | 40002 | 74.1 | CGAAACGGCTCACAGCCACG | 16 | 35 | 13 | 31 | 30 | 0 |
| 5108 | 475 | 23 | 40003 | 72.5 | GCTTTCCCGGTATCCCGGAC | 17 | 28 | 18 | 28 | 34 | 0 |
| 5109 | 476 | 25 | 30003 | 69.9 | AGTGCGAAATCGGTGCACCT | 22 | 16 | 24 | 33 | 23 | 0 |
| 5110 | 477 | 27 | 100 | 72.2 | ACCTCAGCCACGAGCCAGGA | 23 | 31 | 30 | 36 | 25 | 0 |
| 5111 | 478 | 28 | 12908 | 73.1 | ACCTAGCCTGCGTCCCGACC | 23 | 36 | 29 | 28 | 32 | 0 |
| 5112 | 479 | 31 | 12921 | 72.7 | TCCCAAAGGCAAAGCCATCG | 28 | 6 | 21 | 36 | 24 | 0 |
| 5113 | 480 | 34 | 40004 | 73.4 | TCCCTCCCCCTACACGCGTT | 28 | 28 | 26 | 30 | 12 | 0 |

FIG. 29K

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 5114 | 481 | 35 | 40005 | 76 | TGCGTTGACAGCGGACGCAA | 29 | 1 | 31 | 34 | 21 | 0 |
| 5115 | 482 | 37 | 12931 | 72.5 | TGCGCGAACCTAGATGCACG | 29 | 16 | 26 | 27 | 30 | 0 |
| 5116 | 483 | 38 | 30005 | 70.4 | TGCGGGTATTAGCACGGACC | 29 | 18 | 3 | 30 | 32 | 0 |
| 5117 | 484 | 39 | 12933 | 75.7 | TGCGAGTGACGGGTGCTCCC | 29 | 22 | 35 | 33 | 28 | 0 |
| 5118 | 485 | 40 | 30006 | 71.6 | TGCGCCTATCTGACGGCTTG | 29 | 26 | 8 | 35 | 11 | 0 |
| 5119 | 486 | 41 | 12934 | 73.3 | TGCGGATGCAGCTACATGCG | 29 | 27 | 31 | 7 | 29 | 0 |
| 5120 | 487 | 45 | 12936 | 75 | CACGCTTGCACGATCGGTGC | 30 | 11 | 30 | 24 | 33 | 0 |
| 5121 | 488 | 46 | 12939 | 74.7 | CACGGTGCCCATCTGTTGCG | 30 | 33 | 15 | 14 | 29 | 0 |
| 5122 | 489 | 47 | 30007 | 70.9 | CACGACGGAAAGGCAAATCG | 30 | 35 | 6 | 21 | 24 | 0 |
| 5123 | 490 | 50 | 40008 | 73.1 | CAGCAGCCAGTGGTGCTCCC | 31 | 36 | 22 | 33 | 28 | 0 |
| 5124 | 491 | 51 | 12944 | 74.3 | TTGAGACCTGCGCAGCCGAA | 1 | 32 | 29 | 31 | 16 | 0 |
| 5125 | 492 | 54 | 40009 | 72.8 | GGACACGGTCCCTGTCTGCG | 34 | 35 | 28 | 9 | 29 | 1 |
| 5126 | 493 | 56 | 12951 | 71.1 | TTGAACGGCTTGCTTGCCAT | 1 | 35 | 11 | 11 | 15 | 0 |
| 5127 | 494 | 57 | 30014 | 72.8 | ACGGGAGTACGGCACGCTTG | 35 | 20 | 35 | 30 | 11 | 0 |
| 5128 | 495 | 61 | 40010 | 70.5 | AGCCCTTGAGGAACGGGGTA | 36 | 11 | 25 | 35 | 18 | 0 |
| 5129 | 496 | 63 | 12968 | 73.5 | TTGAAGCCCTCAAGCCGCAA | 1 | 36 | 13 | 36 | 21 | 0 |
| 5130 | 497 | 64 | 12969 | 73.2 | TGATTGCGGCAACTTGCACG | 2 | 29 | 21 | 11 | 30 | 0 |
| 5131 | 498 | 65 | 264 | 74 | TCTGCCATGGACACGGGTGC | 8 | 15 | 34 | 35 | 33 | 0 |
| 5132 | 499 | 66 | 12973 | 72.3 | TCTGCAGCAGGACCATTGCG | 8 | 31 | 25 | 15 | 29 | 0 |
| 5133 | 500 | 71 | 282 | 75.6 | TCGTCAGCCAGCGTGCGATG | 10 | 31 | 31 | 33 | 27 | 0 |
| 5134 | 501 | 72 | 286 | 74.3 | CTTGCCATTCCCGGACCAGC | 11 | 15 | 28 | 34 | 31 | 0 |
| 5135 | 502 | 74 | 308 | 69.9 | CGAAGCTTAGCCCCTATGCG | 16 | 17 | 36 | 26 | 29 | 0 |
| 5136 | 503 | 77 | 12989 | 69.8 | GGTATGCGTCGTTCGTTCCC | 18 | 29 | 10 | 10 | 28 | 0 |
| 5137 | 504 | 80 | 20049 | 69.5 | GCAAGATGGATGTCCCAGCC | 21 | 27 | 27 | 28 | 36 | 0 |
| 5138 | 505 | 83 | 12997 | 71.4 | GATGGCAACAGCTCCCCAT | 27 | 21 | 31 | 28 | 15 | 0 |
| 5139 | 506 | 85 | 350 | 75.8 | GATGACGGGACCCACGTGCG | 27 | 35 | 32 | 30 | 29 | 0 |
| 5140 | 507 | 87 | 40012 | 72.1 | TCCCGAGTAGCCCACGTCGT | 28 | 20 | 36 | 30 | 10 | 0 |
| 5141 | 508 | 90 | 13002 | 72.1 | TCCCGTGCAAAGACGGACCT | 28 | 33 | 6 | 35 | 23 | 0 |
| 5142 | 509 | 91 | 30016 | 72.4 | TGCGGAGTCTTGACGGGGAC | 29 | 20 | 11 | 35 | 34 | 0 |
| 5143 | 510 | 93 | 30017 | 72.9 | TGCGGATGAATCATCGTGCG | 29 | 27 | 4 | 24 | 29 | 0 |
| 5144 | 511 | 97 | 13012 | 74 | CAGCATCGTCCCGCAAATCG | 31 | 24 | 28 | 21 | 24 | 0 |
| 5145 | 512 | 102 | 413 | 76.5 | GACCGATGCACGACGGGCAA | 32 | 27 | 30 | 35 | 21 | 0 |
| 5146 | 513 | 103 | 13014 | 72.4 | TGATGACCGTGCAGCCGGTA | 2 | 32 | 33 | 36 | 18 | 0 |
| 5147 | 514 | 108 | 425 | 69.8 | GTGCTCCCTACATCCCTGCG | 33 | 28 | 7 | 28 | 29 | 0 |
| 5148 | 515 | 110 | 13017 | 73.5 | GTGCGGACGATGAGCCGGTA | 33 | 34 | 27 | 36 | 18 | 0 |
| 5149 | 516 | 113 | 40013 | 73.7 | GGACGGACATCGGACCGCTT | 34 | 34 | 24 | 32 | 17 | 0 |
| 5150 | 517 | 115 | 438 | 75.8 | ACGGTCGTCAGCCGTTTGCG | 35 | 10 | 31 | 12 | 29 | 0 |
| 5151 | 518 | 116 | 439 | 75.4 | ACGGCTTGCACGACGGAGGA | 35 | 11 | 30 | 35 | 25 | 0 |
| 5152 | 519 | 117 | 20065 | 73.9 | ACGGCGTTTAGCACGTGCG | 35 | 12 | 3 | 30 | 29 | 0 |
| 5153 | 520 | 119 | 30021 | 71.5 | ACGGCCTAGATGACGGCGTT | 35 | 26 | 27 | 35 | 12 | 0 |
| 5154 | 521 | 120 | 40015 | 70.1 | CTTGGCAACTCACAGCGCAA | 11 | 21 | 13 | 31 | 21 | 0 |
| 5155 | 522 | 121 | 30023 | 72 | CGTTAGCCTCTGCAGCGCAA | 12 | 36 | 8 | 31 | 21 | 0 |
| 5156 | 523 | 122 | 40016 | 69.3 | CCATAGCCTTGAAGCCGGAC | 15 | 36 | 1 | 36 | 34 | 0 |
| 5157 | 524 | 123 | 13046 | 69.2 | CGAAACCTAGCCAGCCCCTA | 16 | 23 | 36 | 36 | 26 | 0 |
| 5158 | 525 | 127 | 544 | 73.4 | AGGATGCGCTCATCCCGTT | 25 | 29 | 13 | 28 | 12 | 0 |
| 5159 | 526 | 128 | 30025 | 72.4 | GATGCGAACACGGATGTGCG | 27 | 16 | 30 | 27 | 29 | 0 |
| 5160 | 527 | 130 | 40017 | 73.1 | TCCCCGTTCGAAGATGCGAA | 28 | 12 | 16 | 27 | 16 | 0 |
| 5161 | 528 | 131 | 13070 | 75.8 | TCCCATCGACGGTGCGGGTA | 28 | 24 | 35 | 29 | 18 | 0 |

FIG. 29L

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 5162 | 529 | 133 | 30026 | 78.3 | TCCCAGCCCGAAAGCCCAGC | 28 | 36 | 16 | 36 | 31 | 0 |
| 5163 | 530 | 134 | 40018 | 78.7 | TGCGCTTGTGCGGTGCATCG | 29 | 11 | 29 | 33 | 24 | 0 |
| 5164 | 531 | 136 | 30028 | 70.2 | CAGCCCTATCTGCAGCGACC | 31 | 26 | 8 | 31 | 32 | 0 |
| 5165 | 532 | 137 | 603 | 68.9 | CAGCACGGTACACACGGCTT | 31 | 35 | 7 | 30 | 17 | 0 |
| 5166 | 533 | 138 | 13093 | 73.9 | GACCGATGGCTTCACGTGCG | 32 | 27 | 17 | 30 | 29 | 0 |
| 5167 | 534 | 139 | 30030 | 73.4 | GTGCGACCGTGCCGTTTGAT | 33 | 32 | 33 | 12 | 2 | 0 |
| 5168 | 535 | 141 | 13103 | 71.9 | GGACATCGCCTAAGCCCGAA | 34 | 24 | 26 | 36 | 16 | 0 |
| 5169 | 536 | 142 | 13104 | 71.3 | GGACCCTATCCCCGAATCCC | 34 | 26 | 28 | 16 | 28 | 0 |
| 5170 | 537 | 143 | 30031 | 71.3 | GGACTCCCTCTGACGGCAGC | 34 | 28 | 8 | 35 | 31 | 0 |
| 5171 | 538 | 144 | 13105 | 69.7 | GGACCACGTCGTATCGAGCC | 34 | 30 | 10 | 24 | 36 | 0 |
| 5172 | 539 | 146 | 13110 | 73.8 | ACGGATCGATCGAGCCGGAC | 35 | 24 | 24 | 36 | 34 | 0 |
| 5173 | 540 | 147 | 646 | 77.4 | ACGGAGGAACGGCACGGCAA | 35 | 25 | 35 | 30 | 21 | 0 |
| 5174 | 541 | 148 | 20075 | 73.8 | AGCCGCAAGAGTGTGCCACG | 36 | 21 | 20 | 33 | 30 | 0 |
| 5175 | 542 | 149 | 13129 | 71.2 | AAAGCGTTTCCCAGCCCTTG | 6 | 12 | 28 | 36 | 11 | 1 |
| 5176 | 543 | 152 | 30036 | 69.5 | CGTTGCAACTGTAGCCCACG | 12 | 21 | 14 | 36 | 30 | 0 |
| 5177 | 544 | 154 | 721 | 68 | CTCAACGGTCCCATACACGG | 13 | 35 | 28 | 5 | 35 | 1 |
| 5178 | 545 | 155 | 741 | 73.1 | CGAAAATCAGCCTGCGCGTT | 16 | 4 | 36 | 29 | 12 | 0 |
| 5179 | 546 | 156 | 13151 | 71.2 | CGAAAAGGATGCGAATGCG | 16 | 6 | 27 | 16 | 29 | 0 |
| 5180 | 547 | 158 | 745 | 70.9 | CGAACTCAACGGGCAAGTGC | 16 | 13 | 35 | 21 | 33 | 0 |
| 5181 | 548 | 160 | 749 | 75 | CGAAAGTGCACGCACGGTGC | 16 | 22 | 30 | 30 | 33 | 0 |
| 5182 | 549 | 164 | 779 | 67.7 | GGTAGCAAAAAGGGACGCAA | 18 | 21 | 6 | 34 | 21 | 0 |
| 5183 | 550 | 169 | 30039 | 68.1 | CCTATGCGTGTCATCGGCTT | 26 | 29 | 9 | 24 | 17 | 0 |
| 5184 | 551 | 170 | 867 | 72.1 | TCCCGTCTCGAAGACCCGAA | 28 | 19 | 16 | 32 | 16 | 0 |
| 5185 | 552 | 172 | 13204 | 70.5 | TGCGGCTTTACAGGACGCTT | 29 | 17 | 7 | 34 | 17 | 0 |
| 5186 | 553 | 173 | 40024 | 74.8 | TGCGAGGAGACCTCCCACGG | 29 | 25 | 32 | 28 | 35 | 0 |
| 5187 | 554 | 174 | 888 | 74 | TGCGGACCGGTATCCCACCT | 29 | 32 | 18 | 28 | 23 | 0 |
| 5188 | 555 | 175 | 40025 | 74 | TGCGGTGCTCTGACGGTCGT | 29 | 33 | 8 | 35 | 10 | 0 |
| 5189 | 556 | 176 | 20090 | 71.7 | CACGTCGTACGGGCAACAGC | 30 | 10 | 35 | 21 | 31 | 0 |
| 5190 | 557 | 177 | 13215 | 72.2 | CAGCCTTGCTTGGGACGGAC | 31 | 11 | 11 | 34 | 34 | 0 |
| 5191 | 558 | 178 | 13217 | 68.4 | CAGCCCTAAGGAGGACAGCC | 31 | 26 | 25 | 34 | 36 | 0 |
| 5192 | 559 | 180 | 20095 | 73.5 | AATCCAGCTGCGCGTTCGAA | 4 | 31 | 29 | 12 | 16 | 0 |
| 5193 | 560 | 181 | 921 | 70.9 | CAGCACGGGTCTAGCCGATG | 31 | 35 | 19 | 36 | 27 | 0 |
| 5194 | 561 | 182 | 923 | 71.3 | GACCAATCGCTTGACCGCAA | 32 | 4 | 17 | 32 | 21 | 0 |
| 5195 | 562 | 184 | 13219 | 68.2 | GACCCCATCGTTAGTGTGCG | 32 | 15 | 12 | 22 | 29 | 0 |
| 5196 | 563 | 185 | 30045 | 68.1 | GACCCCTAACGGAAAGCGTT | 32 | 26 | 35 | 6 | 12 | 0 |
| 5197 | 564 | 186 | 13223 | 71 | GACCGATGCCATTCGTCGAA | 32 | 27 | 15 | 10 | 16 | 0 |
| 5198 | 565 | 187 | 30046 | 70.4 | GACCGGACAGGATGATTGCG | 32 | 34 | 25 | 2 | 29 | 0 |
| 5199 | 566 | 188 | 13226 | 68.3 | GTGCCTCAATACCAGCACGG | 33 | 13 | 5 | 31 | 35 | 0 |
| 5200 | 567 | 190 | 40031 | 73.3 | GTGCGATGCAGCGTCTGCAA | 33 | 27 | 31 | 19 | 21 | 0 |
| 5201 | 568 | 193 | 20097 | 69.7 | GGACAGCCAGGAATCGATCG | 34 | 36 | 25 | 24 | 24 | 0 |
| 5202 | 569 | 194 | 973 | 69.5 | ACGGCTCACTCATCCCCTCA | 35 | 13 | 13 | 28 | 13 | 0 |
| 5203 | 570 | 195 | 977 | 70.8 | ACGGACCTCTCAAGCCGACC | 35 | 23 | 13 | 36 | 32 | 0 |
| 5204 | 571 | 196 | 978 | 72.6 | ACGGGATGCGAACGAAGTGC | 35 | 27 | 16 | 16 | 33 | 0 |
| 5205 | 572 | 198 | 40034 | 69.8 | AGCCCGTTAAAGTGCGGATG | 36 | 12 | 6 | 29 | 27 | 0 |
| 5206 | 573 | 199 | 40035 | 74.3 | AGCCCTCAATCGCAGCAGCC | 36 | 13 | 24 | 31 | 36 | 0 |
| 5207 | 574 | 200 | 20100 | 72.1 | AGCCGGTACCATAGCCTGCG | 36 | 18 | 15 | 36 | 29 | 0 |
| 5208 | 575 | 202 | 20101 | 69.4 | AGCCAGGATGTCCCTATGCG | 36 | 25 | 9 | 26 | 29 | 0 |
| 5209 | 576 | 204 | 1022 | 73.3 | CCATCGAAGGACTGCGCAGC | 15 | 16 | 34 | 29 | 31 | 0 |

FIG. 29M

| SEQ ID NO: | ZIP ID# | 4,633 ID# | HEX ID# | Tm | ZIPCODE (NH2 -> CONH2) | TETRAMER NUMBERS | | | | | 'UNALLOWED DIMERS' |
|---|---|---|---|---|---|---|---|---|---|---|---|
| 5210 | 577 | 207 | 40037 | 72.6 | GCAAACGGCTCATCCCGGTA | 21 | 35 | 13 | 28 | 18 | 0 |
| 5211 | 578 | 208 | 20103 | 73.2 | CCTAACGGCAGCTGCGCTGT | 26 | 35 | 31 | 29 | 14 | 0 |
| 5212 | 579 | 209 | 1063 | 75.8 | GATGACGGCAGCTCCCGCAA | 27 | 35 | 31 | 28 | 21 | 0 |
| 5213 | 580 | 211 | 13280 | 78 | TGCGCTGTTCCCCACGAGCC | 29 | 14 | 28 | 30 | 36 | 0 |
| 5214 | 581 | 212 | 20105 | 73.2 | TGCGCGAATTAGGCAAAGCC | 29 | 16 | 3 | 21 | 36 | 0 |
| 5215 | 582 | 213 | 1094 | 73.3 | CACGATCGTCCCGAACGAA | 30 | 24 | 28 | 16 | 16 | 0 |
| 5216 | 583 | 215 | 40038 | 73.8 | CAGCGGACCCTAAGCCAGCC | 31 | 34 | 26 | 36 | 36 | 0 |
| 5217 | 584 | 217 | 1117 | 72.9 | GACCGAGTTGCGTCCCGATG | 32 | 20 | 29 | 28 | 27 | 0 |
| 5218 | 585 | 219 | 20108 | 70.4 | GTGCTGCGGGTACCATGGAC | 33 | 29 | 18 | 15 | 34 | 0 |
| 5219 | 586 | 220 | 30048 | 72.9 | GTGCCACGATCGCTTGTCCC | 33 | 30 | 24 | 11 | 28 | 1 |
| 5220 | 587 | 221 | 40039 | 73.3 | GGACGACCTGTCGGACGCAA | 34 | 32 | 9 | 34 | 21 | 0 |
| 5221 | 588 | 222 | 1148 | 71.3 | ACGGCCTAACGGTGTCCGTT | 35 | 26 | 35 | 9 | 12 | 0 |
| 5222 | 589 | 223 | 30052 | 75.8 | ACGGTCCCCGTTGGACCAGC | 35 | 28 | 12 | 34 | 31 | 1 |
| 5223 | 590 | 224 | 30053 | 72.9 | AGCCCGAACAGCTCCCTCGT | 36 | 16 | 31 | 28 | 10 | 0 |
| 5224 | 591 | 225 | 1200 | 74.8 | TCGTAGCCATCGCACGCAGC | 10 | 36 | 24 | 30 | 31 | 0 |
| 5225 | 592 | 227 | 40040 | 69.1 | CGTTTTGACGTTAGCCTGCG | 12 | 1 | 12 | 36 | 29 | 1 |
| 5226 | 593 | 229 | 13343 | 68.8 | AAAGCGTTATCGTCCCGACC | 6 | 12 | 24 | 28 | 32 | 0 |
| 5227 | 594 | 230 | 40041 | 73.2 | CGTTGACCGATGACGGCCAT | 12 | 32 | 27 | 35 | 15 | 0 |
| 5228 | 595 | 232 | 30054 | 70.2 | AAAGCCATGCTTTCCCTCCC | 6 | 15 | 17 | 28 | 28 | 0 |
| 5229 | 596 | 233 | 40042 | 69.5 | CGAATCGTTCGTCTTGCACG | 16 | 10 | 10 | 11 | 30 | 0 |
| 5230 | 597 | 235 | 30055 | 68.5 | CGAACGAAGATGCCATCAGC | 16 | 16 | 27 | 15 | 31 | 0 |
| 5231 | 598 | 236 | 1277 | 70.1 | CGAACAGCGACCCCTACAGC | 16 | 31 | 32 | 26 | 31 | 0 |
| 5232 | 599 | 237 | 13376 | 68.5 | GCTTATCGTGCGTCGTGCTT | 17 | 24 | 29 | 10 | 17 | 0 |
| 5233 | 600 | 238 | 40043 | 67.7 | GCAAAAAGTGTCCAGCGGAC | 21 | 6 | 9 | 31 | 34 | 0 |
| 5234 | 601 | 239 | 30058 | 69.4 | GCAATCGTTGTCGGTATGCG | 21 | 10 | 9 | 18 | 29 | 0 |
| 5235 | 602 | 240 | 13388 | 72.4 | GCAAAGTGCGAACACGGCAA | 21 | 22 | 16 | 30 | 21 | 0 |
| 5236 | 603 | 241 | 30059 | 71.5 | AAAGGCAACAGCGCAAGCAA | 6 | 21 | 31 | 21 | 21 | 0 |
| 5237 | 604 | 244 | 40044 | 71.4 | ATCGGCAAAAGTCCCCGAA | 24 | 21 | 6 | 28 | 16 | 1 |
| 5238 | 605 | 245 | 30060 | 74.8 | ATCGCAGCGCTTGATGTGCG | 24 | 31 | 17 | 27 | 29 | 0 |
| 5239 | 606 | 246 | 1355 | 73.2 | GATGCTCAAGCCCAGCACGG | 27 | 13 | 36 | 31 | 35 | 0 |
| 5240 | 607 | 247 | 13417 | 72.9 | AAAGTCCCGAGTTGCGTGCG | 6 | 28 | 20 | 29 | 29 | 1 |
| 5241 | 608 | 249 | 30063 | 73.6 | TGCGAGCCATCGACCTACGG | 29 | 36 | 24 | 23 | 35 | 0 |
| 5242 | 609 | 250 | 40048 | 70.8 | CACGGCTTGGTAGTGCGACC | 30 | 17 | 18 | 33 | 32 | 0 |
| 5243 | 610 | 251 | 40049 | 71.2 | CACGGCAATGATCACGGACC | 30 | 21 | 2 | 30 | 32 | 0 |
| 5244 | 611 | 252 | 1413 | 72.3 | CACGAGTGGGACGTGCATCG | 30 | 22 | 34 | 33 | 24 | 0 |
| 5245 | 612 | 253 | 13443 | 68.5 | CAGCGCTTGGTAATCGGGTA | 31 | 17 | 18 | 24 | 18 | 0 |
| 5246 | 613 | 254 | 30067 | 67.8 | GACCGGTAAAAGCGAAGCAA | 32 | 18 | 6 | 16 | 21 | 0 |
| 5247 | 614 | 256 | 13456 | 69 | GTGCTCGTCAGCAGTGCGTT | 33 | 10 | 31 | 22 | 12 | 0 |
| 5248 | 615 | 257 | 13457 | 71.3 | GTGCCTTGGTGCGATGCCTA | 33 | 11 | 33 | 27 | 26 | 0 |
| 5249 | 616 | 258 | 30069 | 71.2 | GTGCCTCATGTCACGGGTGC | 33 | 13 | 9 | 35 | 33 | 0 |
| 5250 | 617 | 259 | 30070 | 70.8 | AAAGGTGCCGAAATCGGGAC | 6 | 33 | 16 | 24 | 34 | 0 |
| 5251 | 618 | 260 | 40052 | 72.2 | GTGCCAGCGGTAGGACCAGC | 33 | 31 | 18 | 34 | 31 | 0 |
| 5252 | 619 | 261 | 1467 | 70.5 | GGACTTGAACGGGCTTGCAA | 34 | 1 | 35 | 17 | 21 | 0 |
| 5253 | 620 | 262 | 40053 | 70.8 | GGACCTCAGCAAAGCCCCAT | 34 | 13 | 21 | 36 | 15 | 0 |
| 5254 | 621 | 263 | 30072 | 69.2 | GGACCCATGCTTCCATGACC | 34 | 15 | 17 | 15 | 32 | 0 |
| 5255 | 622 | 265 | 1483 | 71.7 | ACGGTCTGGCTTACGGGTGC | 35 | 8 | 17 | 35 | 33 | 0 |
| 5256 | 623 | 266 | 30073 | 72.6 | ACGGCGTTGTGCAAAGTCCC | 35 | 12 | 33 | 6 | 28 | 1 |
| 5257 | 624 | 267 | 13472 | 73.4 | ACGGATCGCACGCCTAGCAA | 35 | 24 | 30 | 26 | 21 | 0 |

FIG. 29N

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 5258 | 625 | 269 | 40054 | 73.5 | AGCCGAGTGGACATCGTGCG | 36 | 20 | 34 | 24 | 29 | 0 |
| 5259 | 626 | 270 | 20130 | 73.4 | AGCCAGTGACGGCCATCACG | 36 | 22 | 35 | 15 | 30 | 0 |
| 5260 | 627 | 273 | 20134 | 74 | TCCCCGAAGGTAACGGCAGC | 28 | 16 | 18 | 35 | 31 | 0 |
| 5261 | 628 | 274 | 1538 | 73.5 | TCCCATCGGAGTTCCCGACC | 28 | 24 | 20 | 28 | 32 | 0 |
| 5262 | 629 | 275 | 1555 | 76.5 | TGCGGGACGAGTGACCCACG | 29 | 34 | 20 | 32 | 30 | 0 |
| 5263 | 630 | 276 | 13501 | 72.4 | CAGCTGCGTACATGCGCCAT | 31 | 29 | 7 | 29 | 15 | 0 |
| 5264 | 631 | 277 | 13503 | 73.6 | GACCGCAACGAAAGCCTCCC | 32 | 21 | 16 | 36 | 28 | 0 |
| 5265 | 632 | 278 | 13505 | 76.1 | GTGCACGGGCAAGACCGTGC | 33 | 35 | 21 | 32 | 33 | 0 |
| 5266 | 633 | 279 | 13506 | 70 | ACGGTCGTATCGCTTGCCAT | 35 | 10 | 24 | 11 | 15 | 0 |
| 5267 | 634 | 280 | 1586 | 73.4 | ACGGCTTGCTCAGACCGCAA | 35 | 11 | 13 | 32 | 21 | 0 |
| 5268 | 635 | 283 | 1593 | 75.5 | ACGGAGTTGCGCAGCCTCA | 35 | 20 | 29 | 31 | 13 | 0 |
| 5269 | 636 | 284 | 1595 | 74.1 | ACGGACCTGATGCAGCGCAA | 35 | 23 | 27 | 31 | 21 | 0 |
| 5270 | 637 | 285 | 30077 | 71.7 | TACAACGGCACGTGCGACCT | 7 | 35 | 30 | 29 | 23 | 0 |
| 5271 | 638 | 287 | 13515 | 71.3 | AGCCGCAAGTCTTGCGTTGA | 36 | 21 | 19 | 29 | 1 | 0 |
| 5272 | 639 | 288 | 13516 | 75.6 | AGCCATCGCAGCCTTGGCAA | 36 | 24 | 31 | 11 | 21 | 0 |
| 5273 | 640 | 293 | 1633 | 76.1 | TCTGCGTTTGCGGCAAAGCC | 8 | 12 | 29 | 21 | 36 | 0 |
| 5274 | 641 | 294 | 13523 | 73.2 | TCTGCGAATGCGGACCGTCT | 8 | 16 | 29 | 32 | 19 | 0 |
| 5275 | 642 | 295 | 20141 | 68.7 | TCTGTCGTGCTTGACCAGCC | 8 | 10 | 17 | 32 | 36 | 0 |
| 5276 | 643 | 296 | 40058 | 68.5 | CTTGCGTTGCTTTGTCCGTT | 11 | 12 | 17 | 9 | 12 | 0 |
| 5277 | 644 | 302 | 40059 | 71.1 | CGTTTTGAGTGCAGCCCAGC | 12 | 1 | 33 | 36 | 31 | 1 |
| 5278 | 645 | 303 | 30080 | 69.8 | TCTGCGTTCGTTCTTGCGAA | 8 | 12 | 12 | 11 | 16 | 0 |
| 5279 | 646 | 305 | 13535 | 69.4 | CGTTGATGAGGACAGCTGCG | 12 | 27 | 25 | 31 | 29 | 0 |
| 5280 | 647 | 307 | 1679 | 69.4 | CTCAGCAAACCTGTGCACGG | 13 | 21 | 23 | 33 | 35 | 0 |
| 5281 | 648 | 308 | 1680 | 72.5 | CTCACAGCACGGGTGCGATG | 13 | 31 | 35 | 33 | 27 | 0 |
| 5282 | 649 | 309 | 1688 | 72.4 | CTGTCACGGACCCAGCCGTT | 14 | 30 | 32 | 31 | 12 | 0 |
| 5283 | 650 | 310 | 1693 | 68.8 | TCTGCCATCGAAAGTGGTGC | 8 | 15 | 16 | 22 | 33 | 0 |
| 5284 | 651 | 311 | 13539 | 70.5 | CCATGGTACGTTTGCGGACC | 15 | 18 | 12 | 29 | 32 | 0 |
| 5285 | 652 | 312 | 30083 | 71.3 | CCATTCCCATCGTCTGCACG | 15 | 28 | 24 | 8 | 30 | 0 |
| 5286 | 653 | 314 | 1703 | 69.7 | CGAATCTGCGTTTGATTGCG | 16 | 8 | 12 | 2 | 29 | 0 |
| 5287 | 654 | 315 | 13544 | 71.9 | CGAAAGTGACGGAGCCCGTT | 16 | 22 | 35 | 36 | 12 | 0 |
| 5288 | 655 | 316 | 1718 | 69.9 | CGAAGTGCCTTGTCGTTCCC | 16 | 33 | 11 | 10 | 28 | 0 |
| 5289 | 656 | 318 | 13550 | 68.7 | TCTGGCTTAGGAACGGGCTT | 8 | 17 | 25 | 35 | 17 | 0 |
| 5290 | 657 | 319 | 40061 | 69.2 | GCTTTGCGAATCCTTGGCTT | 17 | 29 | 4 | 11 | 17 | 0 |
| 5291 | 658 | 320 | 1732 | 73 | TCTGGCTTGACCGACCCGAA | 8 | 17 | 32 | 32 | 16 | 0 |
| 5292 | 659 | 323 | 1739 | 69.3 | GGTATCCCCGAATGTCCACG | 18 | 28 | 16 | 9 | 30 | 0 |
| 5293 | 660 | 326 | 1750 | 69.3 | GCAATGATATCGCACGGTGC | 21 | 2 | 24 | 30 | 33 | 0 |
| 5294 | 661 | 327 | 1751 | 69.1 | TCTGGCAAAAAGGCTTTCCC | 8 | 21 | 6 | 17 | 28 | 0 |
| 5295 | 662 | 328 | 1752 | 69.4 | GCAACTGTCAGCGCTTCGAA | 21 | 14 | 31 | 17 | 16 | 0 |
| 5296 | 663 | 329 | 13554 | 68 | GCAAGGTATCTGCAGCCAGC | 21 | 18 | 8 | 31 | 31 | 0 |
| 5297 | 664 | 330 | 1763 | 73.9 | AGTGGCAATCCCTCCCTGCG | 22 | 21 | 28 | 28 | 29 | 0 |
| 5298 | 665 | 334 | 30086 | 73.6 | ATCGGTGCTGCGAATCGTGC | 24 | 33 | 29 | 4 | 33 | 0 |
| 5299 | 666 | 336 | 1788 | 71.2 | CCTACAGCCGAATCCCGCTT | 26 | 31 | 16 | 28 | 17 | 0 |
| 5300 | 667 | 337 | 40062 | 72.3 | TCTGGATGCCATGTGCCGAA | 8 | 27 | 15 | 33 | 16 | 0 |
| 5301 | 668 | 338 | 30087 | 69.3 | TCTGGATGCGAAAAGTGCG | 8 | 27 | 16 | 6 | 29 | 0 |
| 5302 | 669 | 339 | 1797 | 70.9 | TCTGGATGGGACGGTATGCG | 8 | 27 | 34 | 18 | 29 | 0 |
| 5303 | 670 | 341 | 40063 | 72.9 | TCCCCATTCGTGATGGTGC | 28 | 15 | 10 | 27 | 33 | 0 |
| 5304 | 671 | 342 | 40064 | 73.6 | TCCCGCTTTCTGGATGTGCG | 28 | 17 | 8 | 27 | 29 | 0 |
| 5305 | 672 | 343 | 40065 | 70.7 | TCCCGGTACCATATCGCGAA | 28 | 18 | 15 | 24 | 16 | 0 |

FIG. 29O

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 5306 | 673 | 344 | 13566 | 72.7 | TCCCGAGTGGACGCAACCAT | 28 | 20 | 34 | 21 | 15 | 0 |
| 5307 | 674 | 345 | 13568 | 72.3 | TCCCAGCCCCTATCCCACCT | 28 | 36 | 26 | 28 | 23 | 0 |
| 5308 | 675 | 347 | 1812 | 74.1 | TGCGTCTGTCCCCGAAGCAA | 29 | 8 | 28 | 16 | 21 | 0 |
| 5309 | 676 | 348 | 1822 | 74.3 | TGCGTGCGGATGACCTACGG | 29 | 29 | 27 | 23 | 35 | 0 |
| 5310 | 677 | 349 | 1823 | 72 | TGCGGACCTCGTTGATCACG | 29 | 32 | 10 | 2 | 30 | 0 |
| 5311 | 678 | 350 | 1828 | 67.2 | TCTGCACGCTTGTTAGCAGC | 8 | 30 | 11 | 3 | 31 | 0 |
| 5312 | 679 | 351 | 1831 | 74.8 | TCTGCACGCCATGTGCCGTT | 8 | 30 | 15 | 33 | 12 | 0 |
| 5313 | 680 | 352 | 40067 | 71.4 | CACGGAGTTGTCGGACGTGC | 30 | 20 | 9 | 34 | 33 | 0 |
| 5314 | 681 | 354 | 30090 | 70.3 | TCTGCACGCCTAAGCCCTGT | 8 | 30 | 26 | 36 | 14 | 0 |
| 5315 | 682 | 355 | 40068 | 70.9 | CACGGATGACGGACCTCGAA | 30 | 27 | 35 | 23 | 16 | 0 |
| 5316 | 683 | 356 | 1845 | 68.9 | CAGCCTGTGGTACACGCGTT | 31 | 14 | 18 | 30 | 12 | 0 |
| 5317 | 684 | 357 | 20165 | 73.6 | CAGCCGAAGCTTGCAAACGG | 31 | 16 | 17 | 21 | 35 | 0 |
| 5318 | 685 | 359 | 13579 | 77.2 | TCTGCAGCGTGCGCAAAGCC | 8 | 31 | 33 | 21 | 36 | 0 |
| 5319 | 686 | 360 | 1860 | 71.6 | TCTGGACCTGCGCCATCTCA | 8 | 32 | 29 | 15 | 13 | 0 |
| 5320 | 687 | 361 | 1861 | 71.7 | GACCCACGGACCTGTCCAGC | 32 | 30 | 32 | 9 | 31 | 0 |
| 5321 | 688 | 362 | 13581 | 70.5 | TCTGGACCGACCAGTGCGTT | 8 | 32 | 32 | 22 | 12 | 0 |
| 5322 | 689 | 364 | 1867 | 70 | GTGCTCGTCTGTGTGCACGG | 33 | 10 | 14 | 33 | 35 | 0 |
| 5323 | 690 | 365 | 30091 | 69.2 | TCTGGTGCGGTACAGCCTCA | 8 | 33 | 18 | 31 | 13 | 0 |
| 5324 | 691 | 366 | 40071 | 73.5 | GTGCATCGGGACATCGGTGC | 33 | 24 | 34 | 24 | 33 | 0 |
| 5325 | 692 | 367 | 40072 | 68.6 | GGACCGTTGTCTAGCCCGTT | 34 | 12 | 19 | 36 | 12 | 0 |
| 5326 | 693 | 368 | 40073 | 70.9 | GGACCCTAATCGACGGCGTT | 34 | 26 | 24 | 35 | 12 | 0 |
| 5327 | 694 | 369 | 1898 | 72.2 | ACGGGAGTGCAACACGGACC | 35 | 20 | 21 | 30 | 32 | 0 |
| 5328 | 695 | 370 | 13593 | 70.8 | ACGGGCAACTTGATCGCTCA | 35 | 21 | 11 | 24 | 13 | 0 |
| 5329 | 696 | 371 | 1902 | 69.3 | ACGGGATGACCTAGCCGATG | 35 | 27 | 23 | 36 | 27 | 0 |
| 5330 | 697 | 372 | 1904 | 72.8 | ACGGACGGGCTTAGTGTGCG | 35 | 35 | 17 | 22 | 29 | 0 |
| 5331 | 698 | 373 | 1906 | 71.3 | AGCCAAAGGTGCCCATCGTT | 36 | 6 | 33 | 15 | 12 | 0 |
| 5332 | 699 | 374 | 40076 | 70.7 | TCTGAGCCGCAAGGTAACGG | 8 | 36 | 21 | 18 | 35 | 0 |
| 5333 | 700 | 377 | 1921 | 73.3 | TTGAAGCCCCATTGCGCCTA | 1 | 36 | 15 | 29 | 26 | 0 |
| 5334 | 701 | 378 | 1924 | 76.9 | AATCCAGCGTGCTGCGTGCG | 4 | 31 | 33 | 29 | 29 | 0 |
| 5335 | 702 | 379 | 1926 | 73.6 | AATCACGGAGCCCACGGGAC | 4 | 35 | 36 | 30 | 34 | 0 |
| 5336 | 703 | 380 | 1927 | 73.2 | AATCAGCCAGCCCAGCTCCC | 4 | 36 | 36 | 31 | 28 | 0 |
| 5337 | 704 | 381 | 1928 | 70.7 | AAAGCCATACGGCAGCGATG | 6 | 15 | 35 | 31 | 27 | 0 |
| 5338 | 705 | 382 | 1933 | 71.5 | AAAGCAGCCACGTGATTGCG | 6 | 31 | 30 | 2 | 29 | 0 |
| 5339 | 706 | 383 | 1936 | 71.5 | TGTCCGAAGGACCAGCTCCC | 9 | 16 | 34 | 31 | 28 | 0 |
| 5340 | 707 | 384 | 13599 | 70.5 | TGTCGCAAAGCCAAAGTCCC | 9 | 21 | 36 | 6 | 28 | 1 |
| 5341 | 708 | 386 | 1943 | 77.7 | TCGTCACGTGCGGACCTGCG | 10 | 30 | 29 | 32 | 29 | 0 |
| 5342 | 709 | 388 | 1946 | 72.4 | TCGTACGGCGTTTTGATGCG | 10 | 35 | 12 | 1 | 29 | 1 |
| 5343 | 710 | 389 | 1947 | 71.9 | CTTGCTCAATCGGTGCGTGC | 11 | 13 | 24 | 33 | 33 | 0 |
| 5344 | 711 | 390 | 30093 | 68.2 | CTTGCACGTTAGGACCCGAA | 11 | 30 | 3 | 32 | 16 | 0 |
| 5345 | 712 | 391 | 1957 | 70.1 | TGTCCTTGGACCCGAAGTGC | 9 | 11 | 32 | 16 | 33 | 0 |
| 5346 | 713 | 394 | 1969 | 71.1 | CGTTACCTTCCCGACCGACC | 12 | 23 | 28 | 32 | 32 | 1 |
| 5347 | 714 | 396 | 1978 | 68.3 | CTCAGCAATGTCGGACAGCC | 13 | 21 | 9 | 34 | 36 | 0 |
| 5348 | 715 | 397 | 20181 | 69.5 | CTCATCCCACCTCACGAGCC | 13 | 28 | 23 | 30 | 36 | 0 |
| 5349 | 716 | 398 | 20184 | 67.5 | CTGTACGGAATCAGCCGACC | 14 | 35 | 4 | 36 | 32 | 0 |
| 5350 | 717 | 400 | 1984 | 72.7 | CCATCTTGGACCCAGCACGG | 15 | 11 | 32 | 31 | 35 | 0 |
| 5351 | 718 | 401 | 1987 | 68.2 | TGTCCCATCGAAAATCCGAA | 9 | 15 | 16 | 4 | 16 | 0 |
| 5352 | 719 | 402 | 13609 | 68.2 | CCATGCAAAGGAAGGAGCAA | 15 | 21 | 25 | 25 | 21 | 0 |
| 5353 | 720 | 403 | 1992 | 69.8 | CCATCCTACGTTGTGCGCAA | 15 | 26 | 12 | 33 | 21 | 0 |

FIG. 29P

| SEQ ID NO: | ZIP ID# | 4,633 ID# | HEX ID# Tm | ZIPCODE (NH2 -> CONH2) | TETRAMER NUMBERS | | | | | "UNALLOWED DIMERS" |
|---|---|---|---|---|---|---|---|---|---|---|
| 5354 | 721 | 404 | 1993 71.5 | CCATGATGGCAAGTGCCAGC | 15 | 27 | 21 | 33 | 31 | 0 |
| 5355 | 722 | 405 | 13610 71.5 | TGTCCCATCAGCACGGGATG | 9 | 15 | 31 | 35 | 27 | 0 |
| 5356 | 723 | 406 | 13612 68.6 | CCATAGCCATACTGCGGTGC | 15 | 36 | 5 | 29 | 33 | 0 |
| 5357 | 724 | 407 | 30095 69.4 | CGAACGTTGCTTGGACGATG | 16 | 12 | 17 | 34 | 27 | 0 |
| 5358 | 725 | 408 | 30096 67.5 | CGAAGCTTCTTGGGACGGTA | 16 | 17 | 11 | 34 | 18 | 0 |
| 5359 | 726 | 409 | 13616 71.3 | TGTCCGAAACCTCGAATGCG | 9 | 16 | 23 | 16 | 29 | 0 |
| 5360 | 727 | 410 | 40878 69.8 | CGAAAGGAAGGAGGACGCAA | 16 | 25 | 25 | 34 | 21 | 0 |
| 5361 | 728 | 411 | 2007 67.3 | CGAACCTACTCATCCCCACG | 16 | 26 | 13 | 28 | 30 | 0 |
| 5362 | 729 | 412 | 2011 70.2 | CGAACAGCGGACAAAGAGCC | 16 | 31 | 34 | 6 | 36 | 0 |
| 5363 | 730 | 413 | 40880 68.6 | GCTTCGTTCGTTATCGGCAA | 17 | 12 | 12 | 24 | 21 | 0 |
| 5364 | 731 | 414 | 13620 68.2 | GCTTCCATCGTTGATGACGG | 17 | 15 | 12 | 27 | 35 | 0 |
| 5365 | 732 | 415 | 40881 67.6 | GCTTGCTTCCATTGTCGCTT | 17 | 17 | 15 | 9 | 17 | 0 |
| 5366 | 733 | 416 | 30098 67.3 | GCTTATCGACCTAGCCGTGC | 17 | 24 | 23 | 36 | 33 | 0 |
| 5367 | 734 | 417 | 13621 70.7 | TGTCGCTTAGGAAGCCACGG | 9 | 17 | 25 | 36 | 35 | 0 |
| 5368 | 735 | 419 | 2029 71 | GGTATCGTTCCCTCCCGTGC | 18 | 10 | 28 | 28 | 33 | 0 |
| 5369 | 736 | 420 | 2031 67.3 | GGTAGCAAACCTACGGCAGC | 18 | 21 | 23 | 35 | 31 | 0 |
| 5370 | 737 | 421 | 2034 72.8 | TGTCGGTACAGCCAGCGCAA | 9 | 18 | 31 | 31 | 21 | 0 |
| 5371 | 738 | 423 | 2037 68.7 | GTCTTCGTGGACCGTTTCCC | 19 | 10 | 34 | 12 | 28 | 1 |
| 5372 | 739 | 424 | 2039 71.8 | GTCTCGAATCCCGACCACGG | 19 | 16 | 28 | 32 | 35 | 0 |
| 5373 | 740 | 426 | 2050 71.8 | TGTCGAGTCAGCAGCCCGAA | 9 | 20 | 31 | 36 | 16 | 0 |
| 5374 | 741 | 427 | 30099 67.5 | GCAATTGACCATAGCCGACC | 21 | 1 | 15 | 36 | 32 | 0 |
| 5375 | 742 | 428 | 2054 67 | GCAAAATCTCGTGATGTGCG | 21 | 4 | 10 | 27 | 29 | 0 |
| 5376 | 743 | 429 | 40882 68.8 | GCAATCGTGCTTGATGCCAT | 21 | 10 | 17 | 27 | 15 | 0 |
| 5377 | 744 | 433 | 2062 73.4 | TGTCGCAAGAGTTGCGCACG | 9 | 21 | 20 | 29 | 30 | 0 |
| 5378 | 745 | 434 | 2063 68.9 | GCAAAGTGGTCTGTGCCGAA | 21 | 22 | 19 | 33 | 16 | 0 |
| 5379 | 746 | 435 | 13629 73.8 | TGTCGCAATGCGGACCCCTA | 9 | 21 | 29 | 32 | 26 | 0 |
| 5380 | 747 | 437 | 2074 76.2 | AGTGCAGCAGCCGGACTGCG | 22 | 31 | 36 | 34 | 29 | 0 |
| 5381 | 748 | 438 | 2079 74.6 | ACCTCACGCGAAACGGCGTT | 23 | 30 | 16 | 35 | 12 | 0 |
| 5382 | 749 | 439 | 2082 72.9 | ATCGTCGTCAGCGCAAAGCC | 24 | 10 | 31 | 21 | 36 | 0 |
| 5383 | 750 | 440 | 2090 74.5 | ATCGGATGGCAAACGGGTGC | 24 | 27 | 21 | 35 | 33 | 0 |
| 5384 | 751 | 441 | 30100 76.5 | TGTCATCGTGCGCAGCGTGC | 9 | 24 | 29 | 31 | 33 | 0 |
| 5385 | 752 | 446 | 2107 73.4 | CCTACAGCAGCCCAGCGTGC | 26 | 31 | 36 | 31 | 33 | 0 |
| 5386 | 753 | 447 | 40883 72.5 | TGTCCCTAACGGGACCTGCG | 9 | 26 | 35 | 32 | 29 | 0 |
| 5387 | 754 | 453 | 2119 69.8 | GATGGTGCCCATCTTGCCAT | 27 | 33 | 15 | 11 | 15 | 0 |
| 5388 | 755 | 454 | 40884 71.8 | GATGGGACGATGCGTTTCCC | 27 | 34 | 27 | 12 | 28 | 1 |
| 5389 | 756 | 455 | 40885 70.3 | TCCCCGTTAGGATTGATGCG | 28 | 12 | 25 | 1 | 29 | 0 |
| 5390 | 757 | 456 | 13642 73.5 | TCCCAGGAGGACGACCGCTT | 28 | 25 | 34 | 32 | 17 | 0 |
| 5391 | 758 | 457 | 2135 72.8 | TGCGTTGAACGGGACCACCT | 29 | 1 | 35 | 32 | 23 | 0 |
| 5392 | 759 | 458 | 2136 75.1 | TGCGAATCGACCCAGCCCAT | 29 | 4 | 32 | 31 | 15 | 0 |
| 5393 | 760 | 459 | 2137 72.9 | TGCGAAAGCAGCCTTGGCTT | 29 | 6 | 31 | 11 | 17 | 0 |
| 5394 | 761 | 460 | 40887 70.5 | TGCGGGTACGAACCTAACGG | 29 | 18 | 16 | 26 | 35 | 0 |
| 5395 | 762 | 462 | 2145 78.1 | TGCGAGTGGCAATGCGGCAA | 29 | 22 | 21 | 29 | 21 | 0 |
| 5396 | 763 | 463 | 2146 70.7 | TGCGAGGACGAACACGACCT | 29 | 25 | 16 | 30 | 23 | 0 |
| 5397 | 764 | 465 | 2149 75 | TGTCTGCGTGCGGTGCCCTA | 9 | 29 | 29 | 33 | 26 | 0 |
| 5398 | 765 | 466 | 30103 76.9 | TGCGGTGCCAGCTCTGGTGC | 29 | 33 | 31 | 8 | 33 | 0 |
| 5399 | 766 | 467 | 13646 70.8 | CACGTCGTGACCCTTGCCAT | 30 | 10 | 32 | 11 | 15 | 0 |
| 5400 | 767 | 468 | 2153 74.1 | TGTCCACGCTTGGACCCACG | 9 | 30 | 11 | 32 | 30 | 0 |
| 5401 | 768 | 470 | 30104 68.7 | TGTCCACGGCTTCCTAGCAA | 9 | 30 | 17 | 26 | 21 | 0 |

*FIG. 29Q*

| SEQ ID NO: | ZIP ID# | 4,633 ID# | HEX ID# | Tm | ZIPCODE (NH2 -> CONH2) | TETRAMER NUMBERS | "UNALLOWED DIMERS" |
|---|---|---|---|---|---|---|---|
| 5402 | 769 | 471 | 40088 | 68.9 | CACGGGTACTGTCACGACGG | 30 18 14 30 35 | 0 |
| 5403 | 770 | 474 | 2164 | 70.5 | TGTCCACGGACCTCGTGCTT | 9 30 32 10 17 | 0 |
| 5404 | 771 | 475 | 40090 | 69.8 | CAGCACCTTCGTACGGTCCC | 31 23 10 35 28 | 1 |
| 5405 | 772 | 478 | 40091 | 70 | CAGCGACCTTGAGGACCAGC | 31 32 1 34 31 | 0 |
| 5406 | 773 | 479 | 2180 | 70.9 | TGTCGACCAATCTCCCGTGC | 9 32 4 28 33 | 0 |
| 5407 | 774 | 483 | 30110 | 71 | GACCAGGACTCATGCGGCAA | 32 25 13 29 21 | 0 |
| 5408 | 775 | 486 | 13654 | 68.4 | GTGCAATCAATCCACGCCAT | 33 4 4 30 15 | 0 |
| 5409 | 776 | 489 | 2198 | 69.7 | TGTCGTGCTCGTGCAAGACC | 9 33 10 21 32 | 0 |
| 5410 | 777 | 490 | 30111 | 72.7 | GTGCCTTGCTGTCACGCACG | 33 11 14 30 30 | 0 |
| 5411 | 778 | 491 | 30112 | 70.2 | TGTCGTGCGGTATCTGGCAA | 9 33 18 8 21 | 0 |
| 5412 | 779 | 492 | 40092 | 69.6 | GTGCGTCTTCTGGGACGGAC | 33 19 8 34 34 | 0 |
| 5413 | 780 | 493 | 2205 | 67 | TGTCGTGCACCTACCTGTGC | 9 33 23 23 33 | 0 |
| 5414 | 781 | 494 | 40093 | 68.2 | GTGCAGGACTGTCGAAACGG | 33 25 14 16 35 | 0 |
| 5415 | 782 | 496 | 2210 | 70.2 | TGTCGTGCTCCCCGAAAATC | 9 33 28 16 4 | 0 |
| 5416 | 783 | 500 | 2218 | 68 | TGTCGACCTGTGCTTAGCC | 9 34 14 17 36 | 0 |
| 5417 | 784 | 502 | 40094 | 68.9 | GGACGTCTGGTAAGCCGCTT | 34 19 18 36 17 | 0 |
| 5418 | 785 | 503 | 13659 | 68.6 | TGTCGGACACCTCGTTACGG | 9 34 23 12 35 | 0 |
| 5419 | 786 | 504 | 13660 | 67 | TGTCGGACCCTAAATCGCTT | 9 34 26 4 17 | 0 |
| 5420 | 787 | 505 | 13661 | 66.7 | GGACGATGAGTGCCTAAGCC | 34 27 22 26 36 | 0 |
| 5421 | 788 | 506 | 2226 | 71.7 | GGACTCCGACCAGTGGTGC | 34 28 32 22 33 | 0 |
| 5422 | 789 | 507 | 2230 | 71.5 | TGTCACGGTTGATCCCACGG | 9 35 1 28 35 | 1 |
| 5423 | 790 | 509 | 2233 | 73.7 | TGTCACGGCTTGCGTTGCAA | 9 35 11 12 21 | 0 |
| 5424 | 791 | 511 | 40096 | 69 | ACGGGCTTACCTGATGCCAT | 35 17 23 27 15 | 0 |
| 5425 | 792 | 512 | 30115 | 69.6 | ACGGGAGTAGGACGTTTGCG | 35 20 25 12 29 | 0 |
| 5426 | 793 | 513 | 30116 | 71.9 | TGTCACGGGCAAAAAGCGAA | 9 35 21 6 16 | 0 |
| 5427 | 794 | 514 | 13665 | 73 | ACGGTCCCCTTGGGACAGGA | 35 28 11 34 25 | 1 |
| 5428 | 795 | 516 | 13667 | 67.5 | AGCCCTGTATACCGAATGCG | 36 14 5 16 29 | 0 |
| 5429 | 796 | 517 | 2249 | 69.6 | AGCCGCTTTTGACGTTTCGT | 36 17 1 12 10 | 0 |
| 5430 | 797 | 518 | 2252 | 69.2 | AGCCACCTGCAAGATGGCTT | 36 23 21 27 17 | 0 |
| 5431 | 798 | 519 | 40097 | 70 | AGCCATCGTTAGCAGCCAGC | 36 24 3 31 31 | 0 |
| 5432 | 799 | 520 | 13669 | 73.3 | TGTCAGCCGACCGCTTTCGT | 9 36 32 17 10 | 0 |
| 5433 | 800 | 521 | 13672 | 68.8 | TGATGCTTCTTGGTGCGCTT | 2 17 11 33 17 | 0 |
| 5434 | 801 | 522 | 2282 | 72.7 | TTAGGGACAGCCAGCCACGG | 3 34 36 36 35 | 0 |
| 5435 | 802 | 523 | 2287 | 70.3 | AATCCACGCGTTGGTAACGG | 4 30 12 18 35 | 0 |
| 5436 | 803 | 524 | 2300 | 70.8 | AAAGGGACAGGATCCCTGCG | 6 34 25 28 29 | 0 |
| 5437 | 804 | 526 | 13686 | 69.5 | AAAGAGCCAAAGCACGCCAT | 6 36 6 30 15 | 0 |
| 5438 | 805 | 528 | 2310 | 72.5 | TCGTTCTGTGCGCGAAGTGC | 10 8 29 16 33 | 0 |
| 5439 | 806 | 529 | 30120 | 68.7 | TCTGCACGATACGACCGCTT | 8 30 5 32 17 | 0 |
| 5440 | 807 | 530 | 2316 | 69.8 | TCGTTGTCCGTTGAGTTGCG | 10 9 12 20 29 | 0 |
| 5441 | 808 | 531 | 2317 | 73.1 | TGTCCTCAACGGTGCGGCTT | 9 13 35 29 17 | 0 |
| 5442 | 809 | 532 | 2321 | 71.3 | TGTCGAGTTGCGCTTGGACC | 9 20 29 11 32 | 0 |
| 5443 | 810 | 533 | 30121 | 73 | TCGTTGTCCACGAGCCCGTT | 10 9 30 36 12 | 0 |
| 5444 | 811 | 534 | 30122 | 70.9 | TCGTTGTCACGGTCGTGCAA | 10 9 35 10 21 | 0 |
| 5445 | 812 | 535 | 13693 | 69.6 | TCGTTCGTGGTATGCGCCTA | 10 10 18 29 26 | 0 |
| 5446 | 813 | 536 | 13694 | 70.8 | TCGTTGCGATCGTACATGCG | 10 29 24 7 29 | 0 |
| 5447 | 814 | 538 | 30123 | 69.3 | CTTGCGTTCTTGCTTGCAGC | 11 12 11 11 31 | 0 |
| 5448 | 815 | 539 | 2340 | 71.4 | TCGTCTTGTCCCGGACTCCC | 10 11 28 34 28 | 1 |
| 5449 | 816 | 540 | 13698 | 69.6 | TCGTCTTGGACCAGCCACCT | 10 11 32 36 23 | 0 |

FIG. 29R

| SEQ ID NO: | ZIP ID# | 4,633 ID# | HEX ID# | Tm | ZIPCODE (NB2 -> CONB2) | TETRAMER NUMBERS | | | | "UNALLOWED DIMERS" |
|---|---|---|---|---|---|---|---|---|---|---|
| 5450 | 817 | 541 | 2345 | 68.5 | CTTGAGCCAGCCATACACGG | 11 | 36 | 36 | 5 35 | 0 |
| 5451 | 818 | 542 | 2346 | 70.4 | CGTTTGATGCAACAGCGTGC | 12 | 2 | 21 | 31 33 | 0 |
| 5452 | 819 | 543 | 2347 | 70.2 | CGTTTGTCAATCGTGCGTGC | 12 | 9 | 4 | 33 33 | 0 |
| 5453 | 820 | 544 | 40099 | 69 | CGTTCGAAGGTAGCAATGCG | 12 | 16 | 18 | 21 29 | 0 |
| 5454 | 821 | 546 | 2354 | 68.8 | CGTTACCTCGTTCGAATGCG | 12 | 23 | 12 | 16 29 | 0 |
| 5455 | 822 | 549 | 13701 | 75.2 | TCGTCGTTGACCCACGCACG | 10 | 12 | 32 | 30 30 | 0 |
| 5456 | 823 | 550 | 2363 | 68.8 | TCGTCGTTAGCCAGCCTTGA | 10 | 12 | 36 | 36 1 | 0 |
| 5457 | 824 | 552 | 2367 | 71.8 | TCGTCTCACAGCGTGCCGTT | 10 | 13 | 31 | 33 12 | 0 |
| 5458 | 825 | 553 | 13703 | 68 | CTCAAGCCTTAGGTGCCACG | 13 | 36 | 3 | 33 30 | 0 |
| 5459 | 826 | 555 | 2375 | 72.4 | CTGTAGCCCAGCTGCGGCTT | 14 | 36 | 31 | 29 17 | 0 |
| 5460 | 827 | 556 | 2379 | 71 | CCATCTCAAGCCCCATGCAA | 15 | 13 | 36 | 15 21 | 0 |
| 5461 | 828 | 558 | 13705 | 71.9 | CCATCAGCGGTAACGGGACC | 15 | 31 | 18 | 35 32 | 0 |
| 5462 | 829 | 559 | 13706 | 71.8 | TCGTCCATGACCCACGCTTG | 10 | 15 | 32 | 30 11 | 0 |
| 5463 | 830 | 561 | 2393 | 68.2 | CGAAAATCACGGTGTCGCTT | 16 | 4 | 35 | 9 17 | 0 |
| 5464 | 831 | 562 | 2394 | 70.3 | TCGTCGAAAAGGACCACGG | 10 | 16 | 6 | 32 35 | 0 |
| 5465 | 832 | 563 | 2395 | 73.8 | CGAATCTGTGCGGGACCACG | 16 | 8 | 29 | 34 30 | 0 |
| 5466 | 833 | 564 | 40100 | 71.6 | TCGTCGAAACCTTCCCGGAC | 10 | 16 | 23 | 28 34 | 1 |
| 5467 | 834 | 565 | 13712 | 67.9 | TCGTCGAAAGGAATCGGATG | 10 | 16 | 25 | 24 27 | 0 |
| 5468 | 835 | 566 | 2407 | 73.6 | TCGTCGAAGTGCGCAATCCC | 10 | 16 | 33 | 21 28 | 0 |
| 5469 | 836 | 567 | 2413 | 69.1 | TCGTGCTTCTCAGACCTGCG | 10 | 17 | 13 | 32 29 | 0 |
| 5470 | 837 | 568 | 2429 | 69.8 | TCGTGGTAAGCCCACGGAGT | 10 | 18 | 36 | 30 20 | 0 |
| 5471 | 838 | 569 | 2431 | 71.2 | GTCTCGTTTCCCACGGAGCC | 19 | 12 | 28 | 35 36 | 1 |
| 5472 | 839 | 570 | 13723 | 73.4 | GTCTGCAAAGCCAGCCGTGC | 19 | 21 | 36 | 36 33 | 0 |
| 5473 | 840 | 571 | 2435 | 71.5 | TCGTGTCTGTGCATCGTGCG | 10 | 19 | 33 | 24 29 | 0 |
| 5474 | 841 | 572 | 2436 | 69.8 | GAGTTCGTCAGCGGACGACC | 20 | 10 | 31 | 34 32 | 0 |
| 5475 | 842 | 573 | 20241 | 68.7 | GAGTCCATTGCGGTCTTCCC | 20 | 15 | 29 | 19 28 | 0 |
| 5476 | 843 | 574 | 40102 | 68 | TCGTGCAATTGATGTCGTGC | 10 | 21 | 1 | 9 33 | 0 |
| 5477 | 844 | 575 | 2447 | 66.7 | TCGTGCAAGCTTCTTGGATG | 10 | 21 | 17 | 11 27 | 0 |
| 5478 | 845 | 576 | 2452 | 75 | TCGTGCAATGCGGTGCTCGT | 10 | 21 | 29 | 33 10 | 0 |
| 5479 | 846 | 577 | 2454 | 70.9 | TCGTGCAAGGACAGCCTCGT | 10 | 21 | 34 | 36 10 | 0 |
| 5480 | 847 | 578 | 2457 | 72.5 | AGTGTGCGGGTAACGGGTGC | 22 | 29 | 18 | 35 33 | 0 |
| 5481 | 848 | 579 | 2459 | 74.3 | AGTGGTGCGATGGTGCGTGC | 22 | 33 | 27 | 33 33 | 0 |
| 5482 | 849 | 580 | 2469 | 73.7 | ACCTCAGCACGGACGGGGAC | 23 | 31 | 35 | 35 34 | 0 |
| 5483 | 850 | 583 | 13733 | 69.4 | TCGTATCGGCTTATCGCACG | 10 | 24 | 17 | 24 30 | 0 |
| 5484 | 851 | 584 | 2485 | 73.1 | ATCGGGACGACCTCCCAGGA | 24 | 34 | 32 | 28 25 | 0 |
| 5485 | 852 | 585 | 20255 | 67.7 | AGGAGACCTCTGAGCCAGCC | 25 | 32 | 8 | 36 36 | 0 |
| 5486 | 853 | 586 | 2491 | 71.4 | AGGAAGCCCCATCCATGTGC | 25 | 36 | 15 | 15 33 | 0 |
| 5487 | 854 | 587 | 20256 | 70.5 | CCTAAAAGTGCGTGCGAGCC | 26 | 6 | 29 | 29 36 | 0 |
| 5488 | 855 | 590 | 2516 | 72.3 | TCGTGATGAGCCGCAACAGC | 10 | 27 | 36 | 21 31 | 0 |
| 5489 | 856 | 592 | 13744 | 68 | TCGTTCCCTGTTTAGCGAA | 10 | 28 | 14 | 3 16 | 0 |
| 5490 | 857 | 593 | 40104 | 69.3 | TCGTTCCCCATAAAGGTGC | 10 | 28 | 15 | 6 33 | 0 |
| 5491 | 858 | 594 | 2528 | 68.7 | TCCCGTCTGCAACCTAGCAA | 28 | 19 | 21 | 26 21 | 0 |
| 5492 | 859 | 595 | 40106 | 70.6 | TCCCGAGTCCATCTTGGCAA | 28 | 20 | 15 | 11 21 | 0 |
| 5493 | 860 | 598 | 13745 | 73.5 | TCGTTCCCTGCGTCGTACGG | 10 | 28 | 29 | 10 35 | 0 |
| 5494 | 861 | 600 | 30130 | 73.3 | TCGTTCCCGGACTGTCGTGC | 10 | 28 | 34 | 9 33 | 0 |
| 5495 | 862 | 601 | 13747 | 70.4 | TCGTTGCGAATCAATCGCAA | 10 | 29 | 4 | 4 21 | 0 |
| 5496 | 863 | 603 | 30132 | 70 | TGCGTCGTAGTGGAGTTGCG | 29 | 10 | 22 | 20 29 | 0 |
| 5497 | 864 | 604 | 13748 | 73.3 | TCGTTGCGCTCATTGATGCG | 10 | 29 | 13 | 1 29 | 0 |

FIG. 29S

| SEQ ID NO: | ZIP ID# | 4,633 ID# | HEX Tm | ZIPCODE (NH2 -> CONH2) | TETRAMER NUMBERS | | | | | "UNALLOWED DIMERS" |
|---|---|---|---|---|---|---|---|---|---|---|
| 5498 | 865 | 685 | 30133 71 | TGCGGAGTGGTAGACCCACG | 29 | 20 | 18 | 32 | 30 | 0 |
| 5499 | 866 | 687 | 2550 69.8 | TCGTTGCGAGTGAAAGCGAA | 10 | 29 | 22 | 6 | 16 | 0 |
| 5500 | 867 | 688 | 30134 72.4 | TGCGGATGGGTAGGACAGCC | 29 | 27 | 18 | 34 | 36 | 0 |
| 5501 | 868 | 611 | 2558 75.6 | TCGTTGCGCAGCTGTCCACG | 10 | 29 | 31 | 9 | 30 | 0 |
| 5502 | 869 | 612 | 2559 73.5 | TCGTTGCGGACCAAAGGTGC | 10 | 29 | 32 | 6 | 33 | 0 |
| 5503 | 870 | 614 | 2561 71 | TCGTTGCGAGCCAATCTCGT | 10 | 29 | 36 | 4 | 10 | 0 |
| 5504 | 871 | 615 | 20265 66.3 | CACGAAAGATACACGGCAGC | 30 | 6 | 5 | 35 | 31 | 0 |
| 5505 | 872 | 616 | 2564 73.1 | CACGTCTGTCCCTGCGAGCC | 30 | 8 | 28 | 29 | 36 | 0 |
| 5506 | 873 | 617 | 2565 71 | CACGCTTGCTCACAGCTCCC | 30 | 11 | 13 | 31 | 28 | 0 |
| 5507 | 874 | 618 | 13749 69.4 | TCGTCACGCGTTTCTGGGTA | 10 | 30 | 12 | 8 | 18 | 0 |
| 5508 | 875 | 619 | 30135 68.7 | TCGTCACGCTGTAGCCCCTA | 10 | 30 | 14 | 36 | 26 | 0 |
| 5509 | 876 | 620 | 2569 70 | TCGTCACGCCATGATGGATG | 10 | 30 | 15 | 27 | 27 | 0 |
| 5510 | 877 | 621 | 2574 68.2 | CACGGCAATACAGACCGGAC | 30 | 21 | 7 | 32 | 34 | 0 |
| 5511 | 878 | 622 | 20267 66.1 | CACGAGTGAAAGGCTTGTGC | 30 | 22 | 6 | 17 | 33 | 0 |
| 5512 | 879 | 623 | 13751 69.4 | TCGTCACGATCGTCTGACGG | 10 | 30 | 24 | 8 | 35 | 0 |
| 5513 | 880 | 624 | 2580 74 | TCGTCACGACGGGATGACGG | 10 | 30 | 35 | 27 | 35 | 0 |
| 5514 | 881 | 625 | 2585 68.6 | TCGTCAGCCTCATGTCAGCC | 10 | 31 | 13 | 9 | 36 | 0 |
| 5515 | 882 | 626 | 2587 70.4 | CAGCCCATGACCTGTCAGCC | 31 | 15 | 32 | 9 | 36 | 0 |
| 5516 | 883 | 627 | 40109 67.2 | CAGCGGTATTGAGGACCGTT | 31 | 18 | 1 | 34 | 12 | 0 |
| 5517 | 884 | 628 | 30137 69.9 | CAGCGAGTAGTGCAGCGTGC | 31 | 20 | 22 | 31 | 33 | 0 |
| 5518 | 885 | 630 | 13756 72.2 | CAGCGACCGAGTTCGTTCCC | 31 | 32 | 20 | 10 | 28 | 0 |
| 5519 | 886 | 631 | 2601 70.5 | GACCAATCCGTTGGACTGCG | 32 | 4 | 12 | 34 | 29 | 0 |
| 5520 | 887 | 632 | 2602 70.2 | GACCAAAGCTTGAGCCGTGC | 32 | 6 | 11 | 36 | 33 | 0 |
| 5521 | 888 | 633 | 40110 66.5 | GACCCGTTACCTTCTGACGG | 32 | 12 | 23 | 8 | 35 | 0 |
| 5522 | 889 | 634 | 40111 68.9 | GACCCTGTTTGAAGCCGCTT | 32 | 14 | 1 | 36 | 17 | 0 |
| 5523 | 890 | 635 | 30138 68.7 | GACCGCTTCCATGAGTTCCC | 32 | 17 | 15 | 20 | 28 | 0 |
| 5524 | 891 | 636 | 30139 72.8 | GACCGTCTGGACGTGCGACC | 32 | 19 | 34 | 33 | 32 | 0 |
| 5525 | 892 | 637 | 40112 68.2 | GACCATCGTCGTAGGATGCG | 32 | 24 | 10 | 25 | 29 | 0 |
| 5526 | 893 | 639 | 2614 66.6 | TCGTGTGCAATCTCTGCCAT | 10 | 33 | 4 | 8 | 15 | 0 |
| 5527 | 894 | 640 | 2615 71.6 | GTGCTCTGCCATAGCCGCAA | 33 | 8 | 15 | 36 | 21 | 0 |
| 5528 | 895 | 641 | 2616 71.9 | TCGTGTGCTGTCGCAATCCC | 10 | 33 | 9 | 21 | 28 | 0 |
| 5529 | 896 | 642 | 30141 68.5 | GTGCCTTGATACCACGCAGC | 33 | 11 | 5 | 30 | 31 | 0 |
| 5530 | 897 | 643 | 20269 69 | TCGTGTGCCTGTGCTTCCAT | 10 | 33 | 14 | 17 | 15 | 0 |
| 5531 | 898 | 645 | 20270 69.9 | GTGCGGTAACCTACGGACGG | 33 | 18 | 23 | 35 | 35 | 0 |
| 5532 | 899 | 646 | 2626 68.7 | GTGCGTCTGGACAGTGCGTT | 33 | 19 | 34 | 22 | 12 | 0 |
| 5533 | 900 | 647 | 2627 70 | TCGTGTGCGAGTCACGAGGA | 10 | 33 | 20 | 30 | 25 | 0 |
| 5534 | 901 | 648 | 2628 71.7 | TCGTGTGCGCAAAAGAGCC | 10 | 33 | 21 | 6 | 36 | 0 |
| 5535 | 902 | 651 | 2637 71.8 | GGACTTGATCCCTGCGCGTT | 34 | 1 | 28 | 29 | 12 | 0 |
| 5536 | 903 | 652 | 2638 71.5 | GGACAATCCAGCGACCCGTT | 34 | 4 | 31 | 32 | 12 | 0 |
| 5537 | 904 | 653 | 2639 70.5 | GGACAAAGGCAAGTGCCGAA | 34 | 6 | 21 | 33 | 16 | 0 |
| 5538 | 905 | 654 | 20272 69.5 | TCGTGGACCTTGGACCGTCT | 10 | 34 | 11 | 32 | 19 | 0 |
| 5539 | 906 | 655 | 40114 71.7 | TCGTGGACCTGTTGCGCCTA | 10 | 34 | 14 | 29 | 26 | 0 |
| 5540 | 907 | 656 | 40115 69.6 | GGACGAGTTCTGGTGCGACC | 34 | 20 | 8 | 33 | 32 | 0 |
| 5541 | 908 | 658 | 13764 69.2 | GGACGATGCCTACAGCCCAT | 34 | 27 | 26 | 31 | 15 | 0 |
| 5542 | 909 | 659 | 13765 67.7 | GGACTCCCTCCCATACAGCC | 34 | 28 | 28 | 5 | 36 | 0 |
| 5543 | 910 | 660 | 2653 74.8 | TCGTGGACTGCGGTGCCTCA | 10 | 34 | 29 | 33 | 13 | 0 |
| 5544 | 911 | 661 | 40117 67.9 | GGACCACGTTAGATCGGCAA | 34 | 30 | 3 | 24 | 21 | 0 |
| 5545 | 912 | 662 | 2658 70.3 | GGACAGCCCCATAGTGCGAA | 34 | 36 | 15 | 22 | 16 | 0 |

FIG. 29T

| SEQ ID NO: | ZIP ID# | 4,633 ID# | HEX ID# | Tm | ZIPCODE (NH2 -> CONH2) | TETRAMER NUMBERS | | | | | 'UNALLOWED DIMERS' |
|---|---|---|---|---|---|---|---|---|---|---|---|
| 5546 | 913 | 664 | 30143 | 69.9 | ACGGTCGTTCTGATCGCGTT | 35 | 10 | 8 | 24 | 12 | 0 |
| 5547 | 914 | 665 | 13771 | 71.4 | ACGGCCATGGTATCGTGCAA | 35 | 15 | 18 | 10 | 21 | 0 |
| 5548 | 915 | 666 | 40118 | 69.9 | ACGGCCTAATCGCTCAATCG | 35 | 26 | 24 | 13 | 24 | 0 |
| 5549 | 916 | 668 | 2677 | 69.9 | TCGTAGCCTTGACAGCGCAA | 10 | 36 | 1 | 31 | 21 | 0 |
| 5550 | 917 | 669 | 2681 | 72.2 | AGCCTGTCGGTAAGCCTGCG | 36 | 9 | 18 | 36 | 29 | 0 |
| 5551 | 918 | 670 | 13779 | 67.5 | AGCCTCGTAGGACTGTTGCG | 36 | 10 | 25 | 14 | 29 | 0 |
| 5552 | 919 | 671 | 13780 | 70.5 | AGCCCGTTCTGTTGATGCG | 36 | 12 | 8 | 1 | 29 | 0 |
| 5553 | 920 | 672 | 13781 | 70.6 | AGCCCCATGAGTGACCCAT | 36 | 15 | 20 | 32 | 15 | 0 |
| 5554 | 921 | 673 | 30148 | 71.8 | AGCCTGCGATACTCCCCACG | 36 | 29 | 5 | 28 | 30 | 0 |
| 5555 | 922 | 674 | 2696 | 72.7 | TTGAAGCCGACCGGTAACGG | 1 | 36 | 32 | 18 | 35 | 0 |
| 5556 | 923 | 675 | 2703 | 75.4 | AATCGACCACGGGTGCACGG | 4 | 32 | 35 | 33 | 35 | 0 |
| 5557 | 924 | 676 | 2709 | 73.9 | AAAGTCCCGGACCGAATGCG | 6 | 28 | 34 | 16 | 29 | 1 |
| 5558 | 925 | 677 | 2719 | 73.5 | TCTGCACGGACCCCTATGCG | 8 | 30 | 32 | 26 | 29 | 0 |
| 5559 | 926 | 680 | 20288 | 68.8 | CTTGCTTGACCTGCAAACGG | 11 | 11 | 23 | 21 | 35 | 0 |
| 5560 | 927 | 681 | 2735 | 66.3 | CTTGATCGTTAGTGCGACGG | 11 | 24 | 3 | 29 | 35 | 0 |
| 5561 | 928 | 682 | 40122 | 69.4 | CTTGCCTACTTGCACGGCAA | 11 | 26 | 11 | 30 | 21 | 0 |
| 5562 | 929 | 683 | 2737 | 71 | CTTGGATGGGACATCGCGAA | 11 | 27 | 34 | 24 | 16 | 0 |
| 5563 | 930 | 684 | 30149 | 70.3 | CGTTTTGAAGCCGGTAACGG | 12 | 1 | 36 | 18 | 35 | 1 |
| 5564 | 931 | 685 | 13804 | 70.2 | CTTGCGTTACCTTGCGGACC | 11 | 12 | 23 | 29 | 32 | 0 |
| 5565 | 932 | 687 | 2767 | 69.6 | CTCACACGGGACAGGAAGCC | 13 | 30 | 34 | 25 | 36 | 0 |
| 5566 | 933 | 688 | 2769 | 74 | CTCAGTGCCAGCGACCACGG | 13 | 33 | 31 | 32 | 35 | 0 |
| 5567 | 934 | 689 | 40125 | 69.5 | CTGTGCAAGTGCCGTTACGG | 14 | 21 | 33 | 12 | 35 | 0 |
| 5568 | 935 | 690 | 30151 | 71.9 | CTTGCCATCCATCACGGCAA | 11 | 15 | 15 | 30 | 21 | 0 |
| 5569 | 936 | 691 | 30152 | 68.5 | CCATGCTTAGTGGTGCAGCC | 15 | 17 | 22 | 33 | 36 | 0 |
| 5570 | 937 | 693 | 30153 | 68.7 | CTTGCGAATTGAATCGGTGC | 11 | 16 | 1 | 24 | 33 | 0 |
| 5571 | 938 | 694 | 40127 | 66.4 | CGAAGCTTCCTAGGACGCTT | 16 | 17 | 26 | 34 | 17 | 0 |
| 5572 | 939 | 696 | 2811 | 69.6 | CTTGGCTTCCATCACGTCCC | 11 | 17 | 15 | 30 | 28 | 0 |
| 5573 | 940 | 697 | 2813 | 71.2 | GCTTGTCTTCCCGACCGGAC | 17 | 19 | 28 | 32 | 34 | 0 |
| 5574 | 941 | 698 | 40128 | 71.3 | GCTTCAGCGGACCTGTTCCC | 17 | 31 | 34 | 14 | 28 | 0 |
| 5575 | 942 | 699 | 30155 | 70.1 | GCTTGTGCCTTGCTTGGCTT | 17 | 33 | 11 | 11 | 17 | 0 |
| 5576 | 943 | 700 | 40129 | 70.1 | GCTTACGGCGTTAGCCAGGA | 17 | 35 | 12 | 36 | 25 | 0 |
| 5577 | 944 | 701 | 2828 | 66.4 | GTCTTCGTCCTATCCCACGG | 19 | 10 | 26 | 28 | 35 | 0 |
| 5578 | 945 | 702 | 20300 | 69.8 | GTCTCACGGCAAGACCCAGC | 19 | 30 | 21 | 32 | 31 | 0 |
| 5579 | 946 | 703 | 40132 | 68.6 | GCAAGCTTTGATTCCCCAT | 21 | 17 | 2 | 28 | 15 | 0 |
| 5580 | 947 | 704 | 2847 | 68.3 | GCAAGAGTGGACAGGATGCG | 21 | 20 | 34 | 25 | 29 | 0 |
| 5581 | 948 | 705 | 30156 | 68 | GCAAACCTTTAGCACGCGTT | 21 | 23 | 3 | 30 | 12 | 0 |
| 5582 | 949 | 706 | 30157 | 66.7 | GCAAATCGAAAGGATGGCTT | 21 | 24 | 6 | 27 | 17 | 0 |
| 5583 | 950 | 707 | 40133 | 68.9 | CTTGGCAAAGGAAGCCCTGT | 11 | 21 | 25 | 36 | 14 | 0 |
| 5584 | 951 | 708 | 30158 | 75.4 | GCAAGACCAGCCGTGCGACC | 21 | 32 | 36 | 33 | 32 | 0 |
| 5585 | 952 | 709 | 2858 | 70.3 | AGTGCGAAGACCATCGACGG | 22 | 16 | 32 | 24 | 35 | 0 |
| 5586 | 953 | 710 | 2866 | 75.2 | ACCTGTGCGGACAGCCCGAA | 23 | 33 | 34 | 36 | 16 | 0 |
| 5587 | 954 | 712 | 30159 | 71.7 | AGGATGCGACCTCAGCGGAC | 25 | 29 | 23 | 31 | 34 | 0 |
| 5588 | 955 | 713 | 2881 | 74.5 | AGGACACGAGCCAGCCGAA | 25 | 30 | 36 | 31 | 16 | 0 |
| 5589 | 956 | 714 | 13849 | 68.1 | CTTGCCTAATCGAGGATGCG | 11 | 26 | 24 | 25 | 29 | 0 |
| 5590 | 957 | 715 | 13852 | 66.9 | CCTAACGGTCCCAATCCTCA | 26 | 35 | 28 | 4 | 13 | 1 |
| 5591 | 958 | 716 | 20309 | 67.9 | CTTGGATGTCGTGACCAGCC | 11 | 27 | 10 | 32 | 36 | 0 |
| 5592 | 959 | 717 | 13853 | 71.2 | CTTGGATGCTTGCAGCAGCC | 11 | 27 | 11 | 31 | 36 | 0 |
| 5593 | 960 | 718 | 2898 | 68.5 | CTTGGATGCGTTGCTTGACC | 11 | 27 | 12 | 17 | 32 | 0 |

FIG. 29U

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 5594 | 961 | 719 | 2899 | 68.9 | GATGCTGTTCGTCAGCCGAA | 27 | 14 | 10 | 31 | 16 | 0 |
| 5595 | 962 | 720 | 30160 | 69.8 | GATGGCAAAGCCGAGTGCTT | 27 | 21 | 36 | 20 | 17 | 0 |
| 5596 | 963 | 722 | 2910 | 71 | TCCCCTGTCTTGAGCCCAT | 28 | 14 | 11 | 36 | 15 | 0 |
| 5597 | 964 | 723 | 2921 | 73.2 | TCCCACGGGCAATTGAATCG | 28 | 35 | 21 | 1 | 24 | 0 |
| 5598 | 965 | 724 | 2926 | 76.7 | TGCGTGTCCAGCGTGCTCCC | 29 | 9 | 31 | 33 | 28 | 0 |
| 5599 | 966 | 725 | 13864 | 72.3 | TGCGTCGTTTGACAGCCAGC | 29 | 10 | 1 | 31 | 31 | 0 |
| 5600 | 967 | 728 | 2938 | 75.1 | TGCGTGCGCCATTCTGCTGT | 29 | 29 | 15 | 8 | 14 | 0 |
| 5601 | 968 | 729 | 2940 | 73.9 | CTTGTGCGCAGCAGTGCACG | 11 | 29 | 31 | 22 | 30 | 0 |
| 5602 | 969 | 730 | 13871 | 68.1 | CACGAATCTCTGGACCGTGC | 30 | 4 | 8 | 32 | 33 | 0 |
| 5603 | 970 | 732 | 2947 | 67.9 | CTTGCACGCTTGTTGAGCAA | 11 | 30 | 11 | 1 | 21 | 1 |
| 5604 | 971 | 734 | 2951 | 71.1 | CTTGCACGAGTGGCAAAGCC | 11 | 30 | 22 | 21 | 36 | 0 |
| 5605 | 972 | 735 | 40137 | 67.7 | CACGAGGACCTACACGCCAT | 30 | 25 | 26 | 30 | 15 | 0 |
| 5606 | 973 | 736 | 2959 | 69.3 | CTTGCAGCTGATACGGGCAA | 11 | 31 | 2 | 35 | 21 | 0 |
| 5607 | 974 | 737 | 2960 | 71.8 | CAGCAATCGTGCATCGAGCC | 31 | 4 | 33 | 24 | 36 | 0 |
| 5608 | 975 | 738 | 30162 | 68.2 | CAGCCTCAGGTATCCCCCAT | 31 | 13 | 18 | 28 | 15 | 0 |
| 5609 | 976 | 739 | 13879 | 72.1 | CTTGCAGCGGTAATCGTGCG | 11 | 31 | 18 | 24 | 29 | 0 |
| 5610 | 977 | 740 | 13880 | 66.2 | CAGCGTCTAAAGACGGCTCA | 31 | 19 | 6 | 35 | 13 | 0 |
| 5611 | 978 | 741 | 13883 | 68.7 | CAGCGACCTACAGTGCCAGC | 31 | 32 | 7 | 33 | 31 | 0 |
| 5612 | 979 | 742 | 2979 | 70.1 | GACCTTGAGACCACGGGCAA | 32 | 1 | 32 | 35 | 21 | 0 |
| 5613 | 980 | 743 | 40139 | 68.7 | GACCAGGACCTAACGGACGG | 32 | 25 | 26 | 35 | 35 | 0 |
| 5614 | 981 | 744 | 20324 | 68.2 | GACCGGACCCTAGATGCCAT | 32 | 34 | 26 | 27 | 15 | 0 |
| 5615 | 982 | 745 | 30163 | 67.8 | CTTGGTGCGGTACTCAAGCC | 11 | 33 | 18 | 13 | 36 | 0 |
| 5616 | 983 | 746 | 40140 | 72.2 | GTGCGTCTTCGTGTGCCGAA | 33 | 19 | 10 | 33 | 16 | 0 |
| 5617 | 984 | 747 | 13893 | 67.2 | GTGCGAGTAATCGACCCGTT | 33 | 20 | 4 | 32 | 12 | 0 |
| 5618 | 985 | 748 | 20327 | 71.8 | CTTGGTGCGGACTCTGTGCG | 11 | 33 | 34 | 8 | 29 | 0 |
| 5619 | 986 | 750 | 30165 | 68 | GGACATCGAGGAGCTTGCAA | 34 | 24 | 25 | 17 | 21 | 0 |
| 5620 | 987 | 751 | 3019 | 71.7 | CTTGGGACGACCCGTTGCTT | 11 | 34 | 32 | 12 | 17 | 0 |
| 5621 | 988 | 752 | 40142 | 71.2 | ACGGGAGTAGCCACGGGGTA | 35 | 20 | 36 | 35 | 18 | 0 |
| 5622 | 989 | 754 | 13905 | 70.8 | ACGGACCTCACGGACCCTGT | 35 | 23 | 30 | 32 | 14 | 0 |
| 5623 | 990 | 755 | 30166 | 70.8 | ACGGAGGATCGTAGCCGGAC | 35 | 25 | 10 | 36 | 34 | 0 |
| 5624 | 991 | 756 | 13906 | 71.5 | ACGGGATGGGTAAGGATGCG | 35 | 27 | 18 | 25 | 29 | 0 |
| 5625 | 992 | 757 | 3036 | 70 | AGCCTTGACTCATCCCGCAA | 36 | 1 | 13 | 28 | 21 | 0 |
| 5626 | 993 | 758 | 3037 | 72.1 | AGCCTGATAGCCTGCGACGG | 36 | 2 | 36 | 29 | 35 | 0 |
| 5627 | 994 | 761 | 13910 | 71.5 | AGCCGAGTGTGCTGATTGCG | 36 | 20 | 33 | 2 | 29 | 0 |
| 5628 | 995 | 763 | 3053 | 68.4 | AGCCTCCCTGATCCATACGG | 36 | 28 | 2 | 15 | 35 | 0 |
| 5629 | 996 | 764 | 13912 | 72.8 | AGCCCAGCGGACTACATGCG | 36 | 31 | 34 | 7 | 29 | 0 |
| 5630 | 997 | 765 | 20336 | 71.2 | AGCCGGACGAGTTCGTAGCC | 36 | 34 | 20 | 10 | 36 | 0 |
| 5631 | 998 | 766 | 30168 | 71.5 | TTGAATCGGGACGTGCAGGA | 1 | 24 | 34 | 33 | 25 | 0 |
| 5632 | 999 | 767 | 13918 | 73.3 | TGATCACGCTCATGCGCAGC | 2 | 30 | 13 | 29 | 31 | 0 |
| 5633 | 1000 | 768 | 13920 | 66.8 | TTAGGCAAGATGGGACCGTT | 3 | 21 | 27 | 34 | 12 | 0 |
| 5634 | 1001 | 769 | 40145 | 68.5 | AATCGCAAGCTTTGTCGTGC | 4 | 21 | 17 | 9 | 33 | 0 |
| 5635 | 1002 | 770 | 3086 | 73.6 | AATCTCCCACGTCCCGTGC | 4 | 28 | 30 | 28 | 33 | 0 |
| 5636 | 1003 | 771 | 40146 | 71.9 | AATCCACGCTCAAGCCAGCC | 4 | 30 | 13 | 36 | 36 | 0 |
| 5637 | 1004 | 772 | 30172 | 69.8 | AAAGCCATTCCCAAAGCACG | 6 | 15 | 28 | 6 | 30 | 0 |
| 5638 | 1005 | 774 | 3109 | 66.4 | TCTGCGTTGGTAAGGAGCAA | 8 | 12 | 18 | 25 | 21 | 0 |
| 5639 | 1006 | 775 | 13938 | 66.9 | TCTGGCAATTAGCTTGCGAA | 8 | 21 | 3 | 11 | 16 | 0 |
| 5640 | 1007 | 776 | 30174 | 69.9 | TCTGGGACAATCGCAATCCC | 8 | 34 | 4 | 21 | 28 | 0 |
| 5641 | 1008 | 777 | 3121 | 72.4 | CGTTTCTGAGCCGGACAGCC | 12 | 8 | 36 | 34 | 36 | 0 |

FIG. 29V

| SEQ ID NO: | ZIP ID# | 4,633 ID# | HEX ID# Tm | ZIPCODE (NH2 -> CONH2) | TETRAMER NUMBERS | | | | | "UNALLOWED DIMERS" |
|---|---|---|---|---|---|---|---|---|---|---|
| 5642 | 1009 | 778 | 40147 70.1 | TGTCCCATCACGTGTCTGCG | 9 | 15 | 30 | 9 | 29 | 0 |
| 5643 | 1010 | 779 | 3127 72.2 | TGTCGTCTTGCGGGTATGCG | 9 | 19 | 29 | 18 | 29 | 0 |
| 5644 | 1011 | 780 | 3129 71.8 | TGTCATCGCGTTCACGTCCC | 9 | 24 | 12 | 30 | 28 | 0 |
| 5645 | 1012 | 781 | 3131 69.7 | TGTCGATGCCATACCTTGCG | 9 | 27 | 15 | 23 | 29 | 0 |
| 5646 | 1013 | 782 | 20344 69.3 | CGTTTCGTAAAGCGAATGCG | 12 | 10 | 6 | 16 | 29 | 0 |
| 5647 | 1014 | 783 | 30177 70.6 | CGTTTCGTGGTAACGGCGTT | 12 | 10 | 18 | 35 | 12 | 0 |
| 5648 | 1015 | 785 | 40148 68 | TCGTACGGAAAGCTTGCCAT | 10 | 35 | 6 | 11 | 15 | 0 |
| 5649 | 1016 | 786 | 40149 72.3 | CTTGCAGCCGTTCCATGCAA | 11 | 31 | 12 | 15 | 21 | 0 |
| 5650 | 1017 | 787 | 30179 68.5 | CGTTTTGAGCAATCCCATCG | 12 | 1 | 21 | 28 | 24 | 1 |
| 5651 | 1018 | 788 | 3159 70 | CGTTAAAGACGGTCCCGTGC | 12 | 6 | 35 | 28 | 33 | 1 |
| 5652 | 1019 | 789 | 40151 68.1 | CGTTCGAAAAGAGGATGCG | 12 | 16 | 6 | 25 | 29 | 0 |
| 5653 | 1020 | 790 | 3165 72.9 | CGTTCGTTGTCTTGCGTGCG | 12 | 12 | 19 | 29 | 29 | 0 |
| 5654 | 1021 | 791 | 13963 73.4 | CTCAATCGGACCCACGCGAA | 13 | 24 | 32 | 30 | 16 | 0 |
| 5655 | 1022 | 792 | 3182 69.8 | CGTTCTCAACGGGACCCTTG | 12 | 13 | 35 | 32 | 11 | 0 |
| 5656 | 1023 | 793 | 3183 67.6 | CTGTTCGTAGGAACGGACGG | 14 | 10 | 25 | 35 | 35 | 0 |
| 5657 | 1024 | 794 | 3190 72.9 | CCATTGTCGACCAGCCCAGC | 15 | 9 | 32 | 36 | 31 | 0 |
| 5658 | 1025 | 795 | 13969 69.1 | CCATCCATCGAACTGTTGCG | 15 | 15 | 16 | 14 | 29 | 0 |
| 5659 | 1026 | 796 | 13970 71.7 | CGTTCCATATCGCCATTGCG | 12 | 15 | 24 | 15 | 29 | 0 |
| 5660 | 1027 | 797 | 3201 67.9 | CCATGATGTGATCAGCGCAA | 15 | 27 | 2 | 31 | 21 | 0 |
| 5661 | 1028 | 798 | 3202 69.4 | CCATGACCAATCGATGCGAA | 15 | 32 | 4 | 27 | 16 | 0 |
| 5662 | 1029 | 799 | 3203 70.2 | CGTTCCATGGACGCAAACCT | 12 | 15 | 34 | 21 | 23 | 0 |
| 5663 | 1030 | 800 | 20357 67.7 | CGTTCCATACGGAGCCTCTG | 12 | 15 | 35 | 36 | 8 | 0 |
| 5664 | 1031 | 801 | 30185 68.7 | CGTTCGAATCGTAGCCGATG | 12 | 16 | 10 | 36 | 27 | 0 |
| 5665 | 1032 | 802 | 13972 70.9 | CGAACTTGCACGGCTTGACC | 16 | 11 | 30 | 17 | 32 | 0 |
| 5666 | 1033 | 803 | 3210 68.1 | CGAACTCAGATGTCCCGTGC | 16 | 13 | 27 | 28 | 33 | 0 |
| 5667 | 1034 | 805 | 20361 70.1 | CGTTCGAAGAGTTGCGGCTT | 12 | 16 | 20 | 29 | 17 | 0 |
| 5668 | 1035 | 806 | 40152 67.8 | CGAAATCGTACAACGGAGCC | 16 | 24 | 7 | 35 | 36 | 0 |
| 5669 | 1036 | 807 | 13977 73 | CGTTCGAAGACCGACCCACG | 12 | 16 | 32 | 32 | 30 | 0 |
| 5670 | 1037 | 808 | 20363 68.9 | GCTTGTCTACGGGGACGACC | 17 | 19 | 35 | 34 | 32 | 0 |
| 5671 | 1038 | 812 | 3249 65.4 | GTCTCGTTATCGGTCTTGCG | 19 | 12 | 24 | 19 | 29 | 0 |
| 5672 | 1039 | 813 | 3257 71.3 | GAGTTCGTGCAAACGGGCAA | 20 | 10 | 21 | 35 | 21 | 0 |
| 5673 | 1040 | 814 | 3260 69 | GAGTCAGCCGAACGTTTCCC | 20 | 31 | 16 | 12 | 28 | 1 |
| 5674 | 1041 | 815 | 20369 69.2 | CGTTGAGTGGACGATGCAGC | 12 | 20 | 34 | 27 | 31 | 0 |
| 5675 | 1042 | 816 | 13992 70.6 | CGTTGCAATGATGCTTTGCG | 12 | 21 | 2 | 17 | 29 | 0 |
| 5676 | 1043 | 817 | 40155 67.7 | GCAACGAACGAAAATCGACC | 21 | 16 | 16 | 4 | 32 | 0 |
| 5677 | 1044 | 818 | 30191 69.1 | GCAAGGTAGACCTGCGGACC | 21 | 18 | 32 | 29 | 32 | 0 |
| 5678 | 1045 | 819 | 13994 65.7 | GCAAGAGTAAAGTGCGCGTT | 21 | 20 | 6 | 29 | 12 | 0 |
| 5679 | 1046 | 820 | 30192 67.3 | GCAAACCTCCTAGCAAACGG | 21 | 23 | 26 | 21 | 35 | 0 |
| 5680 | 1047 | 821 | 20374 66.4 | CGTTGCAACAGCACCTCTGT | 12 | 21 | 31 | 23 | 14 | 0 |
| 5681 | 1048 | 822 | 3277 69.7 | CGTTGCAAAGCCGCTTTACA | 12 | 21 | 36 | 17 | 7 | 0 |
| 5682 | 1049 | 823 | 3281 71.3 | AGTGCACGGGACACCTTCCC | 22 | 30 | 34 | 23 | 28 | 1 |
| 5683 | 1050 | 824 | 14083 74.9 | AGTGCAGCCAGCGGACGCTT | 22 | 31 | 31 | 34 | 17 | 0 |
| 5684 | 1051 | 825 | 14084 75 | AGTGGTGCCACGGACCCGAA | 22 | 33 | 30 | 32 | 16 | 0 |
| 5685 | 1052 | 826 | 3291 74.1 | ACCTGACCTGCGCGTTGCAA | 23 | 32 | 29 | 12 | 21 | 0 |
| 5686 | 1053 | 827 | 14013 73.1 | ATCGCTGTCAGCGTGCCCAT | 24 | 14 | 31 | 33 | 15 | 0 |
| 5687 | 1054 | 828 | 30193 69.5 | ATCGGGTATCGTGACCCGAA | 24 | 18 | 10 | 32 | 16 | 0 |
| 5688 | 1055 | 829 | 40156 70.4 | ATCGGACCTCTGGGACGCTT | 24 | 32 | 8 | 34 | 17 | 0 |
| 5689 | 1056 | 830 | 3309 68.9 | AGGATGCGTACAGTGCGTGC | 25 | 29 | 7 | 33 | 33 | 0 |

FIG. 29W

| SEQ ID NO: | ZIP ID# | 4,633 ID# | HEX ID# | Tm | ZIPCODE (SH2 -> CONH2) | TETRAMER NUMBERS | | | | | "UNALLOWED DIMERS" |
|---|---|---|---|---|---|---|---|---|---|---|---|
| 5690 | 1057 | 831 | 14021 | 71.2 | AGGAAGCCGGTAGGACTGCG | 25 | 36 | 18 | 34 | 29 | 0 |
| 5691 | 1058 | 833 | 30194 | 66.6 | GATGCGTTAATCGGACTCCC | 27 | 12 | 4 | 34 | 28 | 0 |
| 5692 | 1059 | 834 | 14032 | 71 | CGTTGATGGACCGTGCCCTA | 12 | 27 | 32 | 33 | 26 | 0 |
| 5693 | 1060 | 835 | 40157 | 73.5 | CGTTGATGGGACGACCCACG | 12 | 27 | 34 | 32 | 30 | 0 |
| 5694 | 1061 | 839 | 3356 | 70.7 | TCCCAGTGGGTACACGGTGC | 28 | 22 | 18 | 30 | 33 | 0 |
| 5695 | 1062 | 840 | 40160 | 68.4 | TCCCCCTAAATCCCATCAGC | 28 | 26 | 4 | 15 | 31 | 0 |
| 5696 | 1063 | 841 | 3361 | 71.8 | CGTTTCCCTCCCTCGTCGAA | 12 | 28 | 28 | 10 | 16 | 1 |
| 5697 | 1064 | 842 | 14040 | 73.8 | TCCCTGCGCCATGGTACGAA | 28 | 29 | 15 | 18 | 16 | 0 |
| 5698 | 1065 | 845 | 40162 | 70.8 | TGCGATACAGCCTCCCCTCA | 29 | 5 | 36 | 28 | 13 | 0 |
| 5699 | 1066 | 846 | 40164 | 72.8 | TGCGCGAATGCGTTAGCTTG | 29 | 16 | 29 | 3 | 11 | 0 |
| 5700 | 1067 | 847 | 20392 | 74.7 | CGTTGCGGCTTGTGCCTCA | 12 | 29 | 17 | 33 | 13 | 0 |
| 5701 | 1068 | 848 | 40165 | 70.4 | TGCGGTCTTACACACGCGAA | 29 | 19 | 7 | 30 | 16 | 0 |
| 5702 | 1069 | 849 | 14044 | 69 | TGCGAGGAATCGTTAGCGAA | 29 | 25 | 24 | 3 | 16 | 0 |
| 5703 | 1070 | 850 | 3381 | 73.6 | CGTTTGCGGATGCCATGCTT | 12 | 29 | 27 | 15 | 17 | 0 |
| 5704 | 1071 | 851 | 14045 | 70.7 | TGCGTCCCTTGAGCTTCAGC | 29 | 28 | 1 | 17 | 31 | 0 |
| 5705 | 1072 | 852 | 14046 | 77 | CGTTTGCGCACGCGTTGCTT | 12 | 29 | 30 | 12 | 17 | 0 |
| 5706 | 1073 | 853 | 40166 | 69.7 | CACGTCGTTGTCCAGCGGTA | 30 | 10 | 9 | 31 | 18 | 0 |
| 5707 | 1074 | 854 | 20396 | 67.1 | CACGCTTGTGATCCATCGAA | 30 | 11 | 2 | 15 | 16 | 0 |
| 5708 | 1075 | 855 | 40167 | 70.4 | CGTTCACGCTGTCTTGTGCG | 12 | 30 | 14 | 11 | 29 | 0 |
| 5709 | 1076 | 856 | 40171 | 67.5 | CACGGATGTTAGCGAATCCC | 30 | 27 | 3 | 16 | 28 | 0 |
| 5710 | 1077 | 858 | 14053 | 74.7 | CGTTCACGCAGCGCAATCGT | 12 | 30 | 31 | 21 | 10 | 0 |
| 5711 | 1078 | 859 | 20400 | 66.3 | CACGGACCAAAGTTAGTGCG | 30 | 32 | 6 | 3 | 29 | 0 |
| 5712 | 1079 | 860 | 3401 | 72 | CGTTCACGACGGGTCTGCAA | 12 | 30 | 35 | 19 | 21 | 0 |
| 5713 | 1080 | 861 | 20402 | 71.8 | CGTTCACGAGCCTCGTCACG | 12 | 30 | 36 | 10 | 30 | 0 |
| 5714 | 1081 | 862 | 20403 | 65.7 | CAGCTCTGGACCAAAGCTCA | 31 | 8 | 32 | 6 | 13 | 0 |
| 5715 | 1082 | 863 | 30197 | 69.1 | CGTTCAGCGCTTCGTTTCTG | 12 | 31 | 17 | 12 | 8 | 0 |
| 5716 | 1083 | 864 | 3411 | 74.7 | CGTTCAGCCACGCAGCAGGA | 12 | 31 | 30 | 31 | 25 | 0 |
| 5717 | 1084 | 865 | 14060 | 69.7 | CAGCGTGCTTGAAATCGTGC | 31 | 33 | 1 | 4 | 33 | 0 |
| 5718 | 1085 | 866 | 3418 | 69.6 | CGTTGACCTCTGTCCCCAGC | 12 | 32 | 8 | 28 | 31 | 0 |
| 5719 | 1086 | 868 | 40173 | 68.7 | CGTTGACCCTGTCGAACGAA | 12 | 32 | 14 | 16 | 16 | 0 |
| 5720 | 1087 | 869 | 3424 | 67 | CGTTGACCATCGTTAGCACG | 12 | 32 | 24 | 3 | 30 | 0 |
| 5721 | 1088 | 870 | 3426 | 69.4 | GACCTGCGCTCAGGTAAGCC | 32 | 29 | 13 | 18 | 36 | 0 |
| 5722 | 1089 | 871 | 40175 | 71.7 | CGTTGACCCAGCTCCCGTCT | 12 | 32 | 31 | 28 | 19 | 0 |
| 5723 | 1090 | 873 | 3435 | 72.1 | GTGCTGTCCTTGCAGCTGCG | 33 | 9 | 11 | 31 | 29 | 0 |
| 5724 | 1091 | 874 | 20413 | 65.8 | GTGCCTTGTACACAGCGACC | 33 | 11 | 7 | 31 | 32 | 0 |
| 5725 | 1092 | 875 | 30199 | 69 | GTGCCTCAAAAGTCCCCAGC | 33 | 13 | 6 | 28 | 31 | 1 |
| 5726 | 1093 | 876 | 40177 | 69.8 | CGTTGTGCGATGTGTCGCTT | 12 | 33 | 27 | 9 | 17 | 0 |
| 5727 | 1094 | 877 | 3450 | 71.8 | GTGCGACCGTCTATCGTGCG | 33 | 32 | 19 | 24 | 29 | 0 |
| 5728 | 1095 | 879 | 30200 | 73.2 | CGTTGGACCGTTGGACCGAA | 12 | 34 | 12 | 34 | 16 | 0 |
| 5729 | 1096 | 880 | 30202 | 67.8 | GGACGGTACGAAGCTTCACG | 34 | 18 | 16 | 17 | 30 | 0 |
| 5730 | 1097 | 881 | 40178 | 70.4 | GGACAGGATGTCACGGCAGC | 34 | 25 | 9 | 35 | 31 | 0 |
| 5731 | 1098 | 882 | 14078 | 68.2 | GGACGGACTTGAAGTGTGCG | 34 | 34 | 1 | 22 | 29 | 0 |
| 5732 | 1099 | 883 | 3463 | 71.8 | GGACACGGCCATCTGTGCAA | 34 | 35 | 15 | 14 | 21 | 0 |
| 5733 | 1100 | 884 | 14079 | 70 | ACGGTTGAACCTGGACGTGC | 35 | 1 | 23 | 34 | 33 | 1 |
| 5734 | 1101 | 885 | 3465 | 70.8 | ACGGAATCCTTGCACGCTCA | 35 | 4 | 11 | 30 | 13 | 0 |
| 5735 | 1102 | 886 | 14080 | 71.5 | ACGGAAAGGACCGACCATCG | 35 | 6 | 32 | 32 | 24 | 0 |
| 5736 | 1103 | 887 | 3468 | 71.5 | ACGGTCTGGACCGCAAGGAC | 35 | 8 | 32 | 21 | 34 | 0 |
| 5737 | 1104 | 888 | 30203 | 71.5 | ACGGCTGTCTTGTCCCGACC | 35 | 14 | 11 | 28 | 32 | 1 |

FIG. 29X

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 5738 | 1105 | 889 | 3472 | 67.9 | ACGGGAGTTTGATTGATGCG | 35 | 20 | 1 | 1 | 29 | 0 |
| 5739 | 1106 | 890 | 30204 | 74.1 | ACGGGATGCAGCAGTGCGAA | 35 | 27 | 31 | 22 | 16 | 0 |
| 5741 | 1107 | 891 | 30205 | 70.7 | AGCCTTGAGTGCCTTGCACG | 36 | 1 | 33 | 11 | 30 | 0 |
| 5741 | 1108 | 892 | 14087 | 73.1 | AGCCTGATTGCGCAGCCTTG | 36 | 2 | 29 | 31 | 11 | 0 |
| 5742 | 1109 | 893 | 14097 | 70.4 | AGCCGACCTGTCATCGCTTG | 36 | 32 | 9 | 24 | 11 | 0 |
| 5743 | 1110 | 894 | 3498 | 71.8 | AGCCACGGCTCAAATCGACC | 36 | 35 | 13 | 4 | 32 | 0 |
| 5744 | 1111 | 895 | 3502 | 71.6 | TTGAAGCCTCGTACGGTGCG | 1 | 36 | 10 | 35 | 29 | 0 |
| 5745 | 1112 | 896 | 14102 | 73.3 | AATCGCTTCAGCAGCCTGCG | 4 | 17 | 31 | 36 | 29 | 0 |
| 5746 | 1113 | 897 | 14106 | 73 | AAAGCGTTGTGCCAGCAGCC | 6 | 12 | 33 | 31 | 36 | 0 |
| 5747 | 1114 | 900 | 3525 | 74.5 | TGTCTGCGCAGCTGCGGTCT | 9 | 29 | 31 | 29 | 19 | 0 |
| 5748 | 1115 | 902 | 3532 | 77.1 | TCGTCACGGGACTGCGGCAA | 10 | 30 | 34 | 29 | 21 | 0 |
| 5749 | 1116 | 903 | 20437 | 71 | TCGTAGCCAGGAGTGCCGAA | 10 | 36 | 25 | 33 | 16 | 0 |
| 5750 | 1117 | 904 | 20439 | 69.8 | CTTGAGTGCGTTCGTTTGCG | 11 | 22 | 12 | 12 | 29 | 0 |
| 5751 | 1118 | 905 | 20441 | 69.4 | CGTTTCGTGACCTGTCTGCG | 12 | 10 | 32 | 9 | 29 | 0 |
| 5752 | 1119 | 906 | 14112 | 72.5 | CGTTACGGCGAAAGGAACGG | 12 | 35 | 16 | 25 | 35 | 0 |
| 5753 | 1120 | 907 | 3546 | 75.8 | CTCAACGGCGAATGCGCCAT | 13 | 35 | 16 | 29 | 15 | 0 |
| 5754 | 1121 | 908 | 3547 | 73.6 | CCATGCTTGGACGGACACGG | 15 | 17 | 34 | 34 | 35 | 0 |
| 5755 | 1122 | 909 | 3548 | 69.3 | CCATTGCGAAAGGACCCTGT | 15 | 29 | 6 | 32 | 14 | 0 |
| 5756 | 1123 | 910 | 14114 | 74.4 | CGAAATCGATCGCAGCTGCG | 16 | 24 | 24 | 31 | 29 | 0 |
| 5757 | 1124 | 911 | 3557 | 71.9 | CGAACACGAGGAACGGTCCC | 16 | 30 | 25 | 35 | 28 | 1 |
| 5758 | 1125 | 912 | 3558 | 77.2 | CGAACAGCACGGCACGGTGC | 16 | 31 | 35 | 30 | 33 | 0 |
| 5759 | 1126 | 913 | 30207 | 71.2 | GCAAACGGACGGAAAGGGAC | 21 | 35 | 35 | 6 | 34 | 0 |
| 5760 | 1127 | 914 | 3582 | 73.8 | AGTGGTGCCGAAGTGCTGCG | 22 | 33 | 16 | 33 | 29 | 0 |
| 5761 | 1128 | 915 | 3585 | 74.7 | ACCTACGGTGCGGACCGTGC | 23 | 35 | 29 | 32 | 33 | 0 |
| 5762 | 1129 | 916 | 20457 | 71.1 | CTCAATCGCTTGGCAAACGG | 13 | 24 | 11 | 21 | 35 | 0 |
| 5763 | 1130 | 917 | 30208 | 71.3 | CTCAATCGCCATCACGCGTT | 13 | 24 | 15 | 30 | 12 | 0 |
| 5764 | 1131 | 918 | 3591 | 69.8 | ATCGGGTAGCTTCAGCGTGC | 24 | 18 | 17 | 31 | 33 | 0 |
| 5765 | 1132 | 919 | 14129 | 72.2 | ATCGACGGGTCTGGACACGG | 24 | 35 | 19 | 34 | 35 | 0 |
| 5766 | 1133 | 920 | 3600 | 71.8 | AGGAGCTTCAGCCAGCCGAA | 25 | 17 | 31 | 31 | 16 | 0 |
| 5767 | 1134 | 921 | 3601 | 75.5 | AGGACACGGTGCCACGACGG | 25 | 30 | 33 | 30 | 35 | 0 |
| 5768 | 1135 | 922 | 14132 | 73.3 | TCCCGCTTGCAACCATGACC | 28 | 17 | 21 | 15 | 32 | 0 |
| 5769 | 1136 | 924 | 3624 | 75.4 | TGCGAATCATCGCAGCCACG | 29 | 4 | 24 | 31 | 30 | 0 |
| 5770 | 1137 | 925 | 3625 | 73.4 | TGCGTCTGAGCCTGCGGTCT | 29 | 8 | 36 | 29 | 19 | 0 |
| 5771 | 1138 | 926 | 3629 | 70.8 | TGCGCTCAGGACCGTTTGAT | 29 | 13 | 34 | 12 | 2 | 0 |
| 5772 | 1139 | 927 | 14135 | 70.1 | TGCGGTCTAGCCCTTGTCGT | 29 | 19 | 36 | 11 | 10 | 0 |
| 5773 | 1140 | 928 | 3637 | 71.7 | TGCGTCCCCTACCTAACGG | 29 | 28 | 26 | 26 | 35 | 0 |
| 5774 | 1141 | 929 | 40180 | 75.4 | TGCGGACCGCTTGACCTCGT | 29 | 32 | 17 | 32 | 10 | 0 |
| 5775 | 1142 | 930 | 14139 | 73.3 | CACGCCTAGGACACGGCAGC | 30 | 26 | 34 | 35 | 31 | 0 |
| 5776 | 1143 | 931 | 3649 | 76 | CACGCAGCGTGCCTCACACG | 30 | 31 | 33 | 13 | 30 | 0 |
| 5777 | 1144 | 932 | 3650 | 74.8 | CACGGACCGTCTGCAATGCG | 30 | 32 | 19 | 21 | 29 | 0 |
| 5778 | 1145 | 933 | 3658 | 76.9 | CAGCATCGAGCCACGGCGAA | 31 | 24 | 36 | 35 | 16 | 0 |
| 5779 | 1146 | 934 | 14144 | 73.8 | CAGCTGCGGGACAGGAGCAA | 31 | 29 | 34 | 25 | 21 | 0 |
| 5780 | 1147 | 935 | 20484 | 70.4 | GACCGATGGTCTCCATTGCG | 32 | 27 | 19 | 15 | 29 | 0 |
| 5781 | 1148 | 936 | 3672 | 73.4 | GACCGTGCGAGTAGCCTGCG | 32 | 33 | 20 | 36 | 29 | 0 |
| 5782 | 1149 | 937 | 3691 | 74.9 | GGACGATGCACGTCCCGGAC | 34 | 27 | 30 | 28 | 34 | 0 |
| 5783 | 1150 | 938 | 14153 | 72.6 | GGACGGACCCATAGCCCCAT | 34 | 34 | 15 | 36 | 15 | 0 |
| 5784 | 1151 | 939 | 30211 | 68.8 | ACGGCATAAAGGCAAGACC | 35 | 15 | 6 | 21 | 32 | 0 |
| 5785 | 1152 | 940 | 3701 | 68.5 | ACGGGTCTCCATTTGAAGCC | 35 | 19 | 15 | 1 | 36 | 0 |

FIG. 29Y

| SEQ ID NO: | ZIP ID# | 4,633 ID# | HEX ID# Tm | ZIPCODE (NH2 -> CONH2) | TETRAMER NUMBERS | | | | | "UNALLOWED DIMERS" |
|---|---|---|---|---|---|---|---|---|---|---|
| 5786 | 1153 | 941 | 3703 72.2 | ACGGATCGGACCTGTCCACG | 35 | 24 | 32 | 9 | 30 | 0 |
| 5787 | 1154 | 942 | 40182 72.4 | ACGGAGGAAAAGTGCGGCAA | 35 | 25 | 6 | 29 | 21 | 0 |
| 5788 | 1155 | 943 | 20493 71.5 | ACGGCCTAGGACGTGCGTCT | 35 | 26 | 34 | 33 | 19 | 0 |
| 5789 | 1156 | 944 | 3708 69.3 | AGCCTTGAAATCACGGCGTT | 36 | 1 | 4 | 35 | 12 | 0 |
| 5790 | 1157 | 945 | 3711 70.5 | AGCCTCTGAGCCCGTTCCAT | 36 | 8 | 36 | 12 | 15 | 0 |
| 5791 | 1158 | 946 | 30212 71.2 | CTCAAGCCCGTTGGACTCCC | 13 | 36 | 12 | 34 | 28 | 0 |
| 5792 | 1159 | 947 | 30213 68.8 | AGCCGGTACGAACCATAGCC | 36 | 18 | 16 | 15 | 36 | 0 |
| 5793 | 1160 | 948 | 30214 73.2 | CTCAAGCCGATGTCCCTGCG | 13 | 36 | 27 | 28 | 29 | 0 |
| 5794 | 1161 | 950 | 3749 73.3 | CGTTCGTTACGGCAGCGGAC | 12 | 12 | 35 | 31 | 34 | 0 |
| 5795 | 1162 | 951 | 3750 74.1 | CGTTCCATTCCCTGCGGGAC | 12 | 15 | 28 | 29 | 34 | 0 |
| 5796 | 1163 | 952 | 3757 73.5 | CGTTCAGCCCTATGCGCAGC | 12 | 31 | 26 | 29 | 31 | 0 |
| 5797 | 1164 | 953 | 3765 72.1 | CTGTCGAACGTTTGCGCAGC | 14 | 16 | 12 | 29 | 31 | 0 |
| 5798 | 1165 | 954 | 20509 71.5 | CGAATCCCCGTTGACCGAGT | 16 | 28 | 12 | 32 | 20 | 0 |
| 5799 | 1166 | 955 | 20511 69.2 | GCTTGTGCGAGTCCATCACG | 17 | 33 | 20 | 15 | 30 | 0 |
| 5800 | 1167 | 956 | 3781 73.6 | GCAACCATAGCCGGACGCAA | 21 | 15 | 36 | 34 | 21 | 0 |
| 5801 | 1168 | 957 | 3782 71.6 | GCAACGAATGTCAGCCACGG | 21 | 16 | 9 | 36 | 35 | 0 |
| 5802 | 1169 | 958 | 14170 69 | GCAAGCAATCTGCAGCCTTG | 21 | 21 | 8 | 31 | 11 | 0 |
| 5803 | 1170 | 959 | 3786 74.2 | GCAAGACCGCAAATCGTGCG | 21 | 32 | 21 | 24 | 29 | 0 |
| 5804 | 1171 | 960 | 14173 72.1 | GATGTGCGAATCGGACGCAA | 27 | 29 | 4 | 34 | 21 | 0 |
| 5805 | 1172 | 962 | 3800 69.8 | TCCCCTTGAGGACCATCACG | 28 | 11 | 25 | 15 | 30 | 0 |
| 5806 | 1173 | 963 | 30215 71.9 | TCCCGCTTCCTAGTGCGACC | 28 | 17 | 26 | 33 | 32 | 0 |
| 5807 | 1174 | 964 | 3805 74.5 | TCCCAGTGCGAATCCCGGAC | 28 | 22 | 16 | 28 | 34 | 0 |
| 5808 | 1175 | 966 | 3817 75.4 | TGCGTGTCCACGCCTATGCG | 29 | 9 | 30 | 26 | 29 | 0 |
| 5809 | 1176 | 967 | 14180 72.7 | TGCGCGAACTTGCCATGGTA | 29 | 16 | 11 | 15 | 18 | 0 |
| 5810 | 1177 | 968 | 40184 72.2 | TGCGGCTTTCGTGCTTTTGA | 29 | 17 | 10 | 17 | 1 | 0 |
| 5811 | 1178 | 969 | 40185 73.3 | TGCGGAGTCCATCAGCGCTT | 29 | 20 | 15 | 31 | 17 | 0 |
| 5812 | 1179 | 970 | 40186 71.8 | TGCGAGGAAAAGCTGTTGCG | 29 | 25 | 6 | 14 | 29 | 0 |
| 5813 | 1180 | 971 | 14181 74.8 | CTGTTGCGCAGCACGGCCTA | 14 | 29 | 31 | 35 | 26 | 0 |
| 5814 | 1181 | 974 | 3832 73.4 | CACGCTGTTCCCGACCAGGA | 30 | 14 | 28 | 32 | 25 | 0 |
| 5815 | 1182 | 975 | 20528 72.5 | CACGCCATAATCGTGCCACG | 30 | 15 | 4 | 33 | 30 | 0 |
| 5816 | 1183 | 976 | 14182 70.3 | CACGCGAAATACGCAACGAA | 30 | 16 | 5 | 21 | 16 | 0 |
| 5817 | 1184 | 977 | 3836 73.7 | CACGGGTAACGGCGAAGCAA | 30 | 18 | 35 | 16 | 21 | 0 |
| 5818 | 1185 | 978 | 3837 73.8 | CACGGATGGGACGCAACAGC | 30 | 27 | 34 | 21 | 31 | 0 |
| 5819 | 1186 | 979 | 3847 76 | CAGCATCGCGTTGCAATGCG | 31 | 24 | 12 | 21 | 29 | 0 |
| 5820 | 1187 | 980 | 3849 76.5 | CAGCGATGTGCGGTGCCCAT | 31 | 27 | 29 | 33 | 15 | 0 |
| 5821 | 1188 | 981 | 40187 74.5 | CAGCTGCGAGTGAGCCGTGC | 31 | 29 | 22 | 36 | 33 | 0 |
| 5822 | 1189 | 983 | 40188 70.8 | GACCGCAAATACGACCGTGC | 32 | 21 | 5 | 32 | 33 | 0 |
| 5823 | 1190 | 984 | 14187 74 | GACCTCCCCAGCTGCGTCGT | 32 | 28 | 31 | 29 | 10 | 0 |
| 5824 | 1191 | 985 | 14188 74.4 | CTGTGACCTGCGCACGCCAT | 14 | 32 | 29 | 30 | 15 | 0 |
| 5825 | 1192 | 986 | 20536 69.8 | GACCCACGACCTACGGCTTG | 32 | 30 | 23 | 35 | 11 | 0 |
| 5826 | 1193 | 988 | 3869 69.8 | GTGCGCTTCCATCTTGGGAC | 33 | 17 | 15 | 11 | 34 | 0 |
| 5827 | 1194 | 990 | 40189 74.4 | GTGCTGCGGATGATCGGCAA | 33 | 29 | 27 | 24 | 21 | 0 |
| 5828 | 1195 | 992 | 14190 72.4 | GTGCGGACTGATCACGTGCG | 33 | 34 | 2 | 30 | 29 | 0 |
| 5829 | 1196 | 995 | 3884 69.3 | GGACGGACATACGGACGCTT | 34 | 34 | 5 | 34 | 17 | 0 |
| 5830 | 1197 | 996 | 14193 73.9 | GGACAGCCCTCACACGTGCG | 34 | 36 | 13 | 30 | 29 | 0 |
| 5831 | 1198 | 997 | 3886 75.6 | ACGGCTTGGACCGTGCGATG | 35 | 11 | 32 | 33 | 27 | 0 |
| 5832 | 1199 | 998 | 3891 73.6 | ACGGACCTACGGGACCACGG | 35 | 23 | 35 | 32 | 35 | 0 |
| 5833 | 1200 | 999 | 3900 73.6 | AGCCTCGTGCTTCACGCGAA | 36 | 10 | 17 | 30 | 16 | 0 |

FIG. 29Z

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 5834 | 1201 | 1000 | 30218 | 70.9 | AGCCGCTTATCGTGTCTGCG | 36 | 17 | 24 | 9 | 29 | 0 |
| 5835 | 1202 | 1001 | 3905 | 77.2 | AGCCGTCTTGCGGGACGTGC | 36 | 19 | 29 | 34 | 33 | 0 |
| 5836 | 1203 | 1002 | 3912 | 71.2 | AGCCTCCAAAGCTCAACGG | 36 | 28 | 6 | 13 | 35 | 0 |
| 5837 | 1204 | 1003 | 3915 | 72.3 | AGCCGACCTCTGCTTGCAGC | 36 | 32 | 8 | 11 | 31 | 0 |
| 5838 | 1205 | 1004 | 3923 | 71 | TTGAGGACCGAACACGACGG | 1 | 34 | 16 | 30 | 35 | 0 |
| 5839 | 1206 | 1005 | 3927 | 74.4 | TGATGACCGGACCACGGCAA | 2 | 32 | 34 | 30 | 21 | 0 |
| 5840 | 1207 | 1006 | 20546 | 68.4 | TTAGGACCAAAGCCATTGCG | 3 | 32 | 6 | 15 | 29 | 0 |
| 5841 | 1208 | 1007 | 20548 | 69.8 | AATCCGTTGCTTGTGCCCAT | 4 | 12 | 17 | 33 | 15 | 0 |
| 5842 | 1209 | 1008 | 3942 | 71.9 | AATCTCCCCATCACGCGAA | 4 | 28 | 15 | 30 | 16 | 0 |
| 5843 | 1210 | 1009 | 14213 | 72 | AATCAGCCCGAATCCCTCCC | 4 | 36 | 16 | 28 | 28 | 0 |
| 5844 | 1211 | 1010 | 3948 | 71.4 | AAAGCTTGCAGCATCGGCAA | 6 | 11 | 31 | 24 | 21 | 0 |
| 5845 | 1212 | 1011 | 14216 | 70.7 | AAAGACGGCGAAGACCCGTT | 6 | 35 | 16 | 32 | 12 | 0 |
| 5846 | 1213 | 1012 | 3965 | 72.4 | TCTGAGGATGCGGGACGGAC | 8 | 25 | 29 | 34 | 34 | 0 |
| 5847 | 1214 | 1013 | 14222 | 69.4 | TCTGAGCCTGTCATCGCGAA | 8 | 36 | 9 | 24 | 16 | 0 |
| 5848 | 1215 | 1014 | 3982 | 72.6 | TGTCATCGCCATGACCGTGC | 9 | 24 | 15 | 32 | 33 | 0 |
| 5849 | 1216 | 1015 | 3985 | 71.9 | TGTCTGCGCCATCGTTGGAC | 9 | 29 | 15 | 12 | 34 | 0 |
| 5850 | 1217 | 1017 | 3990 | 71.3 | TGTCACGGCCATGATGGACC | 9 | 35 | 15 | 27 | 32 | 0 |
| 5851 | 1218 | 1019 | 30219 | 69.2 | TCGTGCTTTACAAGCCACGG | 10 | 17 | 7 | 36 | 35 | 0 |
| 5852 | 1219 | 1021 | 14233 | 67.1 | CTTGCGAATTAGGTGCTCCC | 11 | 16 | 3 | 33 | 28 | 0 |
| 5853 | 1220 | 1022 | 4021 | 74.1 | CGTTCTCATCCCTGCGTGCG | 12 | 13 | 28 | 29 | 29 | 0 |
| 5854 | 1221 | 1023 | 4025 | 68.1 | CGTTGCAAATACATCGTGCG | 12 | 21 | 5 | 24 | 29 | 0 |
| 5855 | 1222 | 1024 | 4026 | 68.2 | CGTTACCTAGCCACCTTGCG | 12 | 23 | 36 | 23 | 29 | 0 |
| 5856 | 1223 | 1025 | 4027 | 67.1 | CGTTATCGTGCGAAAGCTCA | 12 | 24 | 29 | 6 | 13 | 0 |
| 5857 | 1224 | 1026 | 4033 | 71.1 | CGTTGACCGCTTAGGATGCG | 12 | 32 | 17 | 25 | 29 | 0 |
| 5858 | 1225 | 1027 | 4034 | 69.8 | CGTTGTGCCCTAGGACGGAC | 12 | 33 | 26 | 34 | 34 | 0 |
| 5859 | 1226 | 1028 | 4040 | 73 | CCATCTCAACGGCACGAGCC | 15 | 13 | 35 | 30 | 36 | 0 |
| 5860 | 1227 | 1029 | 4042 | 70.4 | CTGTTCGTGCAATCGTTGCG | 14 | 10 | 21 | 10 | 29 | 0 |
| 5861 | 1228 | 1030 | 4045 | 69.4 | CTGTTCCCGGTACACGTCCC | 14 | 28 | 18 | 30 | 28 | 0 |
| 5862 | 1229 | 1031 | 4046 | 74.5 | CTGTGTGCGTGCGATGTGCG | 14 | 33 | 33 | 27 | 29 | 0 |
| 5863 | 1230 | 1032 | 4052 | 71.2 | CCATCCTACAGCTGCGCAGC | 15 | 26 | 31 | 29 | 31 | 0 |
| 5864 | 1231 | 1033 | 14242 | 73.6 | CCATCCATGGACGACCTGCG | 15 | 15 | 34 | 32 | 29 | 0 |
| 5865 | 1232 | 1034 | 14243 | 69.7 | CGAATCGTCGTTGATGGCAA | 16 | 10 | 12 | 27 | 21 | 0 |
| 5866 | 1233 | 1035 | 14244 | 69.5 | CGAACGTTCACGAGTGCAGC | 16 | 12 | 30 | 22 | 31 | 0 |
| 5867 | 1234 | 1036 | 40192 | 68.8 | CGAACGAACCTACGAATGCG | 16 | 16 | 26 | 16 | 29 | 0 |
| 5868 | 1235 | 1037 | 40193 | 70.6 | CGAAACCTTGTCGACCACGG | 16 | 23 | 9 | 32 | 35 | 0 |
| 5869 | 1236 | 1038 | 30222 | 71.6 | CGAACAGCCCATTCGTCACG | 16 | 31 | 15 | 10 | 30 | 0 |
| 5870 | 1237 | 1039 | 4076 | 71.2 | GCTTCTCAACGGCAGCATCG | 17 | 13 | 35 | 31 | 24 | 0 |
| 5871 | 1238 | 1040 | 14253 | 66.2 | GCTTAGGAAGGAATCGCGTT | 17 | 25 | 25 | 24 | 12 | 0 |
| 5872 | 1239 | 1041 | 14255 | 67.8 | GCTTCAGCTACATCCCGTGC | 17 | 31 | 7 | 28 | 33 | 0 |
| 5873 | 1240 | 1042 | 4087 | 69.7 | CCATGCTTGACCCGAAGCTT | 15 | 17 | 32 | 16 | 17 | 0 |
| 5874 | 1241 | 1043 | 4088 | 73.8 | CCATGCTTGTGCGACCGACC | 15 | 17 | 33 | 32 | 32 | 0 |
| 5875 | 1242 | 1044 | 4093 | 68.7 | GGTAGCTTGCAAATCGCGAA | 18 | 17 | 21 | 24 | 16 | 0 |
| 5876 | 1243 | 1045 | 4099 | 71.6 | CCATGTACAGCTGCGACGG | 15 | 18 | 31 | 29 | 35 | 0 |
| 5877 | 1244 | 1046 | 4100 | 73.1 | GGTAGTGCACGGAGCCGTGC | 18 | 33 | 35 | 36 | 33 | 0 |
| 5878 | 1245 | 1047 | 4104 | 70.7 | GTCTCACGTGCGCTTGTCCC | 19 | 30 | 29 | 11 | 28 | 1 |
| 5879 | 1246 | 1048 | 14264 | 70.2 | CCATGCAATCGTGCAAATCG | 15 | 21 | 10 | 21 | 24 | 0 |
| 5880 | 1247 | 1049 | 40195 | 68 | CCATGCAACGAATCCCAATC | 15 | 21 | 16 | 28 | 4 | 0 |
| 5881 | 1248 | 1050 | 4121 | 71.3 | GCAAGTCTTCCCAGCCGGAC | 21 | 19 | 28 | 36 | 34 | 0 |

FIG. 29AA

| SEQ ID NO: | ZIP ID# | 4,633 BBX ID# | Tm | ZIPCODE (NH2 -> CONH2) | TETRAMER NUMBERS | | | | | "UNALLOWED DIMERS" |
|---|---|---|---|---|---|---|---|---|---|---|
| 5882 | 1249 | 1051 | 4122 | 72.2 | GCAAGAGTTCCCCAGCCACG | 21 | 20 | 28 | 31 | 30 | 0 |
| 5883 | 1250 | 1052 | 40196 | 67.8 | GCAAATCGTTAGGGACGTGC | 21 | 24 | 3 | 34 | 33 | 0 |
| 5884 | 1251 | 1054 | 14269 | 69.9 | CCATGCAACACGATCGATCG | 15 | 21 | 30 | 24 | 24 | 0 |
| 5885 | 1252 | 1055 | 14270 | 69.9 | CCATGCAAGACCCGTTAGCC | 15 | 21 | 32 | 12 | 36 | 0 |
| 5886 | 1253 | 1056 | 20576 | 69.6 | CCATGCAAGGACGAGTTCCC | 15 | 21 | 34 | 20 | 28 | 0 |
| 5887 | 1254 | 1057 | 4132 | 71.4 | CCATGCAAAGCCCTCAGCAA | 15 | 21 | 36 | 13 | 21 | 0 |
| 5888 | 1255 | 1058 | 20578 | 70.4 | AGTGGACCCTTGCTGTTGCG | 22 | 32 | 11 | 14 | 29 | 0 |
| 5889 | 1256 | 1059 | 4140 | 69.5 | ACCTTCCCATACCAGCTGCG | 23 | 28 | 5 | 31 | 29 | 1 |
| 5890 | 1257 | 1060 | 4147 | 68.9 | ATCGGGTATCTGGACCACGG | 24 | 18 | 8 | 32 | 35 | 0 |
| 5891 | 1258 | 1061 | 20580 | 69.8 | ATCGGAGTGATGTGCGGGAC | 24 | 20 | 27 | 29 | 34 | 0 |
| 5892 | 1259 | 1062 | 4150 | 71.8 | ATCGTCCCCGTTCACGAGGA | 24 | 28 | 12 | 30 | 25 | 0 |
| 5893 | 1260 | 1063 | 4158 | 73.8 | AGGAAGGATCCCCACGCACG | 25 | 25 | 28 | 30 | 30 | 0 |
| 5894 | 1261 | 1064 | 14279 | 68.8 | CCATGATGCGTTCAGCGTCT | 15 | 27 | 12 | 31 | 19 | 0 |
| 5895 | 1262 | 1065 | 4178 | 71.1 | GATGATCGGATGGTGCACGG | 27 | 24 | 27 | 33 | 35 | 0 |
| 5896 | 1263 | 1066 | 4179 | 67.1 | CCATGATGCCTAGGACGACC | 15 | 27 | 26 | 34 | 32 | 0 |
| 5897 | 1264 | 1067 | 4181 | 71.7 | CCATGATGTCCCGATGCGAA | 15 | 27 | 28 | 27 | 16 | 0 |
| 5898 | 1265 | 1068 | 4182 | 74.1 | CCATGATGCAGCCACGCCAT | 15 | 27 | 31 | 30 | 15 | 0 |
| 5899 | 1266 | 1069 | 14281 | 69.3 | TCCCTTAGCGTTCAGCCCAT | 28 | 3 | 12 | 31 | 15 | 0 |
| 5900 | 1267 | 1070 | 14283 | 71.7 | CCATTCCCCTCAACGGGATG | 15 | 28 | 13 | 35 | 27 | 0 |
| 5901 | 1268 | 1071 | 20589 | 70.6 | TCCCACCTAGTGCACGCCAT | 28 | 23 | 22 | 30 | 15 | 0 |
| 5902 | 1269 | 1072 | 40260 | 67.1 | TGCTGATAATCCTTGGCAA | 29 | 2 | 4 | 11 | 21 | 0 |
| 5903 | 1270 | 1073 | 40261 | 71.2 | TGCGTTAGCGTTTCCCGGTA | 29 | 3 | 12 | 28 | 18 | 1 |
| 5904 | 1271 | 1075 | 14287 | 70.1 | TGCGTGTCGGTAAAAGTGCG | 29 | 9 | 18 | 6 | 29 | 0 |
| 5905 | 1272 | 1076 | 40262 | 69 | TGCGTCGTAAAGTCCCATCG | 29 | 10 | 6 | 28 | 24 | 1 |
| 5906 | 1273 | 1078 | 40263 | 72 | TGCGAGGACACGGAGTGTGC | 29 | 25 | 30 | 20 | 33 | 0 |
| 5907 | 1274 | 1079 | 4213 | 74 | CCATTGCGTGCGAATCCAGC | 15 | 29 | 29 | 4 | 31 | 0 |
| 5908 | 1275 | 1080 | 4214 | 75.2 | TGCGCACGGCAAGAGTCGAA | 29 | 30 | 21 | 20 | 16 | 0 |
| 5909 | 1276 | 1081 | 4215 | 74 | TGCGGACCCACGTCTGGATG | 29 | 32 | 30 | 8 | 27 | 0 |
| 5910 | 1277 | 1082 | 4216 | 77.6 | CCATTGCGGTGCGGACCGTT | 15 | 29 | 33 | 34 | 12 | 0 |
| 5911 | 1278 | 1083 | 4217 | 73.8 | CCATTGCGACGGCCATATCG | 15 | 29 | 35 | 15 | 24 | 0 |
| 5912 | 1279 | 1084 | 4218 | 73 | CACGTTGAAGCCTGCGGCTT | 30 | 1 | 36 | 29 | 17 | 0 |
| 5913 | 1280 | 1086 | 4221 | 72.9 | CACGTCTGGCAATCCCAGCC | 30 | 8 | 21 | 28 | 36 | 0 |
| 5914 | 1281 | 1087 | 4224 | 68.9 | CACGAGTGACCTTCCCCCAT | 30 | 22 | 23 | 28 | 15 | 1 |
| 5915 | 1282 | 1088 | 40284 | 71.9 | CACGATCGGCTTTTGATGCG | 30 | 24 | 17 | 1 | 29 | 0 |
| 5916 | 1283 | 1089 | 40285 | 71 | CACGTGCGAAAGATCGAGCC | 30 | 29 | 6 | 24 | 36 | 0 |
| 5917 | 1284 | 1090 | 40286 | 74.1 | CACGGACCGAGTGCTTTGCG | 30 | 32 | 20 | 17 | 29 | 0 |
| 5918 | 1285 | 1091 | 4230 | 72.6 | CACGAGCCGATGAGTGCACG | 30 | 36 | 27 | 22 | 30 | 0 |
| 5919 | 1286 | 1092 | 4231 | 69.7 | CAGCTTGATCCCCCATCAGC | 31 | 1 | 28 | 15 | 31 | 0 |
| 5920 | 1287 | 1094 | 4233 | 71.5 | CCATCAGCCTTGGGACCGTT | 15 | 31 | 11 | 34 | 12 | 0 |
| 5921 | 1288 | 1095 | 20601 | 68.7 | CAGCCGTTTTAGTCCCCCAT | 31 | 12 | 3 | 28 | 15 | 0 |
| 5922 | 1289 | 1096 | 4236 | 71.9 | CAGCAGTGGCAAGTGCAGCC | 31 | 22 | 21 | 33 | 36 | 0 |
| 5923 | 1290 | 1097 | 4237 | 67.8 | CAGCACCTTTAGTGCGGACC | 31 | 23 | 3 | 29 | 32 | 0 |
| 5924 | 1291 | 1098 | 4238 | 68.6 | CCATCAGCTCCCAGGAGACC | 15 | 31 | 28 | 25 | 32 | 0 |
| 5925 | 1292 | 1100 | 30226 | 69.9 | GACCGAGTAGGAACGGTGCG | 32 | 20 | 25 | 35 | 29 | 0 |
| 5926 | 1293 | 1101 | 4253 | 67.7 | GACCAGGAAATCTCCCGACC | 32 | 25 | 4 | 28 | 32 | 0 |
| 5927 | 1294 | 1102 | 40269 | 70.5 | GACCGATGCTTGGCTTCGAA | 32 | 27 | 11 | 17 | 16 | 0 |
| 5928 | 1295 | 1103 | 4256 | 69.1 | GACCTCCCGGTAGTCTTGCG | 32 | 28 | 18 | 19 | 29 | 0 |
| 5929 | 1296 | 1104 | 14299 | 72 | CCATGACCAGCCGAGTGCAA | 15 | 32 | 36 | 20 | 21 | 0 |

FIG. 29BB

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 5930 | 1297 | 1105 | 4261 | 67.4 | GTGCTGATACCTGTGCGCAA | 33 | 2 | 23 | 33 | 21 | 0 |
| 5931 | 1298 | 1106 | 4262 | 72.9 | GTGCAATCTGCGACGGGACC | 33 | 4 | 29 | 35 | 32 | 0 |
| 5932 | 1299 | 1107 | 4264 | 70.7 | GTGCTCTGCGTTGGACGCTT | 33 | 8 | 12 | 34 | 17 | 0 |
| 5933 | 1300 | 1108 | 4268 | 69 | GTGCCTGTCGTTTGTCACGG | 33 | 14 | 12 | 9 | 35 | 0 |
| 5934 | 1301 | 1109 | 14301 | 67.4 | GTGCGCTTCGTTAATCCCAT | 33 | 17 | 12 | 4 | 15 | 0 |
| 5935 | 1302 | 1110 | 4273 | 68.7 | GTGCATCGGGTAACCTTCCC | 33 | 24 | 18 | 23 | 28 | 1 |
| 5936 | 1303 | 1111 | 4274 | 66.1 | GTGCAGGAATACTCCCCGTT | 33 | 25 | 5 | 28 | 12 | 0 |
| 5937 | 1304 | 1112 | 4275 | 72 | GTGCTGCGGGACTCTGGACC | 33 | 29 | 34 | 8 | 32 | 0 |
| 5938 | 1305 | 1113 | 14305 | 70 | GTGCGACCCCTACCTATGCG | 33 | 32 | 26 | 26 | 29 | 0 |
| 5939 | 1306 | 1114 | 4278 | 71.6 | CCATGTGCAGCCCACGAAAG | 15 | 33 | 36 | 30 | 6 | 0 |
| 5940 | 1307 | 1115 | 40211 | 69 | CCATGGACGGTACTCATGCG | 15 | 34 | 18 | 13 | 29 | 0 |
| 5941 | 1308 | 1116 | 4288 | 68.1 | CCATGGACAGGACACGAGGA | 15 | 34 | 25 | 30 | 25 | 0 |
| 5942 | 1309 | 1117 | 4292 | 71.5 | GGACCACGGTCTCACGGGAC | 34 | 30 | 19 | 30 | 34 | 0 |
| 5943 | 1310 | 1118 | 14310 | 72 | CCATGGACGTGCCAGCTTGA | 15 | 34 | 33 | 31 | 1 | 0 |
| 5944 | 1311 | 1119 | 4297 | 74.9 | ACGGAATCGCAATGCGAGCC | 35 | 4 | 21 | 29 | 36 | 0 |
| 5945 | 1312 | 1120 | 4298 | 75.5 | ACGGTCTGGCAAAGCCGCAA | 35 | 8 | 21 | 36 | 21 | 0 |
| 5946 | 1313 | 1121 | 40213 | 71.5 | ACGGCTTGCCTATCCCGGTA | 35 | 11 | 26 | 28 | 18 | 0 |
| 5947 | 1314 | 1122 | 4304 | 71.2 | ACGGGCAATCTGAGTGCACG | 35 | 21 | 8 | 22 | 30 | 0 |
| 5948 | 1315 | 1123 | 4309 | 71.2 | ACGGGACCCTGTAGCCGGTA | 35 | 32 | 14 | 36 | 18 | 0 |
| 5949 | 1316 | 1124 | 30227 | 71.9 | ACGGGTGCTCGTCCATCGTT | 35 | 33 | 10 | 15 | 12 | 0 |
| 5950 | 1317 | 1125 | 14321 | 74.6 | CCATAGCCGTGCGCAACGAA | 15 | 36 | 33 | 21 | 16 | 0 |
| 5951 | 1318 | 1127 | 4335 | 71.1 | TGATTGCGCCATTGATGCAA | 2 | 29 | 15 | 2 | 21 | 0 |
| 5952 | 1319 | 1128 | 20626 | 70.2 | TGATCACGCTGTACGGGCAA | 2 | 30 | 14 | 35 | 21 | 0 |
| 5953 | 1320 | 1130 | 40217 | 68.7 | CGAAAATCCACGACGGTTGA | 16 | 4 | 30 | 35 | 1 | 1 |
| 5954 | 1321 | 1131 | 30232 | 72 | CGAAAATCGTGCCTGTTGCG | 16 | 4 | 33 | 14 | 29 | 0 |
| 5955 | 1322 | 1132 | 40218 | 68.7 | CGAAAATCGGACTTGATGCG | 16 | 4 | 34 | 1 | 29 | 0 |
| 5956 | 1323 | 1133 | 20631 | 72.9 | ATACGCTTTCCCGCAATGCG | 5 | 17 | 28 | 21 | 29 | 0 |
| 5957 | 1324 | 1134 | 30233 | 68.6 | AAAGCGAAATCGTTGATGCG | 6 | 16 | 24 | 1 | 29 | 0 |
| 5958 | 1325 | 1135 | 30234 | 68.9 | CGAAAAGTCCCTGCGGAGT | 16 | 6 | 28 | 29 | 20 | 1 |
| 5959 | 1326 | 1136 | 30235 | 67.8 | CGAAAAGCACGAAAGCCAT | 16 | 6 | 30 | 6 | 15 | 0 |
| 5960 | 1327 | 1137 | 4381 | 70.8 | CGAAAAGCAGCGGACCTCA | 16 | 6 | 31 | 34 | 13 | 0 |
| 5961 | 1328 | 1138 | 14350 | 73.4 | CGAAAAGGTGCCACGCAGC | 16 | 6 | 33 | 30 | 31 | 0 |
| 5962 | 1329 | 1139 | 4385 | 70.8 | CGAAAAGAGCCGTGCCTCA | 16 | 6 | 36 | 33 | 13 | 0 |
| 5963 | 1330 | 1140 | 4388 | 73.9 | TCTGTCGTTGCGCGAAAGCC | 8 | 10 | 29 | 16 | 36 | 0 |
| 5964 | 1331 | 1141 | 30236 | 67.8 | TCTGCCATAGGAGACCACGG | 8 | 15 | 25 | 32 | 35 | 0 |
| 5965 | 1332 | 1143 | 4399 | 68.1 | TCTGCACGTACACAGCCACG | 8 | 30 | 7 | 31 | 30 | 0 |
| 5966 | 1333 | 1144 | 4403 | 72.9 | TGTCCTCAAGCCGTGCCCAT | 9 | 13 | 36 | 33 | 15 | 0 |
| 5967 | 1334 | 1146 | 20640 | 68.9 | TGTCGTCTCTGTTGCGAGCC | 9 | 19 | 14 | 29 | 36 | 0 |
| 5968 | 1335 | 1149 | 4421 | 70 | CGAATCGTCTGTCAGCGCAA | 16 | 10 | 14 | 31 | 21 | 0 |
| 5969 | 1336 | 1150 | 14364 | 69 | TCGTGCTTCCATAGCCATCG | 10 | 17 | 15 | 36 | 24 | 0 |
| 5970 | 1337 | 1153 | 4437 | 71.5 | CTTGTCGTGACCCAGCCACG | 11 | 10 | 32 | 31 | 30 | 0 |
| 5971 | 1338 | 1154 | 40222 | 70.8 | CGAACTTGGCTTGACCCACG | 16 | 11 | 17 | 32 | 30 | 0 |
| 5972 | 1339 | 1155 | 30240 | 70 | CTTGCAGCAGTGGATGCGAA | 11 | 31 | 22 | 27 | 16 | 0 |
| 5973 | 1340 | 1156 | 4448 | 70.8 | CGAACTTGGACCCTTGTGCG | 16 | 11 | 32 | 11 | 29 | 0 |
| 5974 | 1341 | 1157 | 14373 | 72.7 | CGAACTTGGTGCCAGCCGTT | 16 | 11 | 33 | 31 | 12 | 0 |
| 5975 | 1342 | 1158 | 20649 | 68.3 | CTTGAGCCGATGGAGTCACG | 11 | 36 | 27 | 20 | 30 | 0 |
| 5976 | 1343 | 1160 | 20650 | 66.9 | CGAACGTTGAGTCGAACACG | 16 | 12 | 20 | 16 | 30 | 0 |
| 5977 | 1344 | 1161 | 4464 | 69.7 | CGAACGTTGTGCTCTGCAGC | 16 | 12 | 33 | 8 | 31 | 0 |

FIG. 29CC

| SEQ ID NO: | ZIP ID# | 4,633 ID# | HEK ID# | Tm | ZIPCODE (NH2 -> CONH2) | TETRAMER NUMBERS | | | | | "UNALLOWED DIMERS" |
|---|---|---|---|---|---|---|---|---|---|---|---|
| 5978 | 1345 | 1163 | 4468 | 71.2 | CTCACCATGCAAACGGCGTT | 13 | 15 | 21 | 35 | 12 | 0 |
| 5979 | 1346 | 1164 | 4469 | 71.3 | CTCAGCTTTGCGAGGATGCG | 13 | 17 | 29 | 25 | 29 | 0 |
| 5980 | 1347 | 1165 | 4471 | 66.6 | CTCATCCCATACGCAAGCAA | 13 | 28 | 5 | 21 | 21 | 0 |
| 5981 | 1348 | 1166 | 4473 | 72.1 | CTCACAGCCAGCGCTTGTGC | 13 | 31 | 31 | 17 | 33 | 0 |
| 5982 | 1349 | 1168 | 40224 | 70.1 | CCATCGAACCATGACCGGAC | 15 | 16 | 15 | 32 | 34 | 0 |
| 5983 | 1350 | 1169 | 4487 | 68.4 | CCATATCGAGTGCAGCGGAC | 15 | 24 | 22 | 31 | 34 | 0 |
| 5984 | 1351 | 1170 | 14385 | 67.9 | CCATCCTAAATCCGTTTGCG | 15 | 26 | 4 | 12 | 29 | 0 |
| 5985 | 1352 | 1171 | 20658 | 66.7 | CCATCACGTTAGGCAAGCAA | 15 | 30 | 3 | 21 | 21 | 0 |
| 5986 | 1353 | 1173 | 4493 | 70.5 | CCATGGACCTCATCCCTCCC | 15 | 34 | 13 | 28 | 28 | 0 |
| 5987 | 1354 | 1174 | 30244 | 70.9 | CGAAAAAGACCTTGCGGCAA | 16 | 6 | 23 | 29 | 21 | 0 |
| 5988 | 1355 | 1175 | 14389 | 67.3 | CGAATCGTTTAGCGTTGCAA | 16 | 10 | 3 | 12 | 21 | 0 |
| 5989 | 1356 | 1176 | 14395 | 68.5 | CGAAGCTTTGATCACGCGTT | 16 | 17 | 2 | 30 | 12 | 0 |
| 5990 | 1357 | 1177 | 4513 | 67.4 | GCTTTACATGCGTTGATGCG | 17 | 7 | 29 | 1 | 29 | 0 |
| 5991 | 1358 | 1178 | 4517 | 67.3 | GCTTCGTTCGAAGGACAGGA | 17 | 12 | 16 | 34 | 25 | 0 |
| 5992 | 1359 | 1180 | 30245 | 69.4 | CGAAGCTTCGAATCGTGCAA | 16 | 17 | 16 | 10 | 21 | 0 |
| 5993 | 1360 | 1181 | 20663 | 68.9 | CGAAGCTTGTGCGGACAAAG | 16 | 17 | 33 | 34 | 6 | 0 |
| 5994 | 1361 | 1182 | 20668 | 68.6 | GAGTCCATACGGTCCCAGCC | 20 | 15 | 35 | 28 | 36 | 1 |
| 5995 | 1362 | 1183 | 20670 | 69.9 | GCAATTGAACCTTGCGGGAC | 21 | 1 | 23 | 29 | 34 | 0 |
| 5996 | 1363 | 1184 | 4548 | 67.8 | GCAAAATCAGCCACCTACGG | 21 | 4 | 36 | 23 | 35 | 0 |
| 5997 | 1364 | 1185 | 40225 | 71.3 | GCAAAAGCCATCGTTTGCG | 21 | 6 | 15 | 12 | 29 | 0 |
| 5998 | 1365 | 1186 | 30248 | 70.6 | CGAAGCAACCATACGGCGTT | 16 | 21 | 15 | 35 | 12 | 0 |
| 5999 | 1366 | 1187 | 20673 | 68.3 | GCAAGATGAGCCTGTCCACG | 21 | 27 | 36 | 9 | 30 | 0 |
| 6000 | 1367 | 1188 | 4557 | 69 | AGTGCTTGGCAACGTTCACG | 22 | 11 | 21 | 12 | 30 | 0 |
| 6001 | 1368 | 1189 | 20675 | 71.4 | AGTGCGTTTGCGTCTGGTGC | 22 | 12 | 29 | 8 | 33 | 0 |
| 6002 | 1369 | 1190 | 4558 | 66.9 | AGTGCGAATGTCAGTGCGAA | 22 | 16 | 9 | 22 | 16 | 0 |
| 6003 | 1370 | 1191 | 14414 | 68.4 | AGTGGCTTGGACTCGTTCCC | 22 | 17 | 34 | 10 | 28 | 0 |
| 6004 | 1371 | 1192 | 14416 | 72.5 | AGTGGATGGACCCAGCTGCG | 22 | 27 | 32 | 31 | 29 | 0 |
| 6005 | 1372 | 1194 | 4578 | 70.1 | ACCTGAGTACGGTGCGCGTT | 23 | 20 | 35 | 29 | 12 | 0 |
| 6006 | 1373 | 1195 | 4579 | 66.3 | ACCTGCAACTGTGGTATGCG | 23 | 21 | 14 | 18 | 29 | 0 |
| 6007 | 1374 | 1196 | 4584 | 69.2 | ACCTTGCGGGTAACCTCGAA | 23 | 29 | 18 | 23 | 16 | 0 |
| 6008 | 1375 | 1197 | 30249 | 70.4 | ACCTGACCTTGATGCGCAGC | 23 | 32 | 1 | 29 | 31 | 0 |
| 6009 | 1376 | 1198 | 4585 | 69.9 | ACCTGTGCGTCTGACCGGAC | 23 | 33 | 19 | 32 | 34 | 0 |
| 6010 | 1377 | 1199 | 30250 | 70.4 | ATCGGAGTTCTGCCATTGCG | 24 | 20 | 8 | 15 | 29 | 0 |
| 6011 | 1378 | 1202 | 14431 | 69.4 | AGGAAGTGCACGGATGAGCC | 25 | 22 | 30 | 27 | 36 | 0 |
| 6012 | 1379 | 1203 | 4616 | 69.5 | AGGATCCCGGTAGGACGACC | 25 | 28 | 18 | 34 | 32 | 0 |
| 6013 | 1380 | 1204 | 40232 | 69.5 | AGGAAGCCAGCCTGTCGATG | 25 | 36 | 36 | 9 | 27 | 0 |
| 6014 | 1381 | 1205 | 14434 | 67.1 | CCTAGCAATGTCGCAAGCAA | 26 | 21 | 9 | 21 | 21 | 0 |
| 6015 | 1382 | 1206 | 14435 | 67.7 | CCTAGTGCAATCAGCCGCTT | 26 | 33 | 4 | 36 | 17 | 0 |
| 6016 | 1383 | 1207 | 4628 | 72.7 | GATGTCGTTGCGACGGTCCC | 27 | 10 | 29 | 35 | 28 | 1 |
| 6017 | 1384 | 1208 | 20694 | 67.1 | GATGGTCTATCGAGCCCGAA | 27 | 19 | 24 | 36 | 16 | 0 |
| 6018 | 1385 | 1209 | 4633 | 69.5 | GATGTCCCCTCAAGCCATCG | 27 | 28 | 13 | 36 | 24 | 0 |
| 601 | 1386 | 1210 | 4634 | 70.9 | CGAAGATGCACGCTGTGCAA | 16 | 27 | 30 | 14 | 21 | 0 |
| 6020 | 1387 | 1211 | 40233 | 71.8 | CGAAGATGGGACTCCCACGG | 16 | 27 | 34 | 28 | 35 | 0 |
| 6021 | 1388 | 1212 | 30252 | 69.7 | GATGAGCCTGATGTGCGCAA | 27 | 36 | 2 | 33 | 21 | 0 |
| 6022 | 1389 | 1213 | 4640 | 70 | TCCCTGTCCAGCAATCGCTT | 28 | 9 | 31 | 4 | 17 | 0 |
| 6023 | 1390 | 1214 | 30254 | 69.8 | TCCCGATGATACGACCGGAC | 28 | 27 | 5 | 32 | 34 | 0 |
| 6024 | 1391 | 1215 | 4649 | 71.8 | TCCCCACGAATCAGTGTGCG | 28 | 30 | 4 | 22 | 29 | 0 |
| 6025 | 1392 | 1216 | 4650 | 74 | TCCCCAGCGTGCTGATCGAA | 28 | 31 | 33 | 2 | 16 | 0 |

FIG. 29DD

| SEQ ID NO: | ZIP ID# | 4,633 ID# | HEX ID# Tm | ZIPCODE (NH2 -> CONH2) | TETRAMER NUMBERS | | | | "UNALLOWED DIMERS" |
|---|---|---|---|---|---|---|---|---|---|
| 6026 | 1393 | 1217 | 4652 72.3 | CGAATCCCACGGATCGTCGT | 16 | 28 | 35 | 24 10 | 0 |
| 6027 | 1394 | 1218 | 14444 68.8 | TGCGTGATCAGCAAAGGCTT | 29 | 2 | 31 | 6 17 | 0 |
| 6028 | 1395 | 1219 | 40235 73.3 | TGCGTACACAGCGTGCCAGC | 29 | 7 | 31 | 33 31 | 0 |
| 6029 | 1396 | 1220 | 4658 74.8 | CGAATGCGCGAACAGCAGGA | 16 | 29 | 16 | 31 25 | 0 |
| 6030 | 1397 | 1223 | 4665 72.4 | TGCGCAGCTACAGACCCACG | 29 | 31 | 7 | 32 30 | 0 |
| 6031 | 1398 | 1224 | 4668 69.5 | CACGTCTGTCTGGTGCCGAA | 30 | 8 | 8 | 33 16 | 0 |
| 6032 | 1399 | 1225 | 20704 72.1 | CACGCCATTCCCAATCCCAT | 30 | 15 | 28 | 4 15 | 0 |
| 6033 | 1400 | 1226 | 4671 67.8 | CACGGAGTTTAGTCCCTGCG | 30 | 20 | 3 | 28 29 | 0 |
| 6034 | 1401 | 1227 | 4674 72.9 | CACGTGCGGATGGTCTGCAA | 30 | 29 | 27 | 19 21 | 0 |
| 6035 | 1402 | 1228 | 14449 72 | CACGCACGCACGTTAGAGCC | 30 | 30 | 30 | 3 36 | 0 |
| 6036 | 1403 | 1229 | 14453 71.6 | CGAACAGCAATCACGGACGG | 16 | 31 | 4 | 35 35 | 0 |
| 6037 | 1404 | 1230 | 30255 67.5 | CAGCTCGTAGTGCTGTTGCG | 31 | 10 | 22 | 14 29 | 0 |
| 6038 | 1405 | 1231 | 40236 72.5 | CAGCCTTGCCATGCAAGCAA | 31 | 11 | 15 | 21 21 | 0 |
| 6039 | 1406 | 1232 | 4689 67.6 | CGAACAGCGAGTTTGATCCC | 16 | 31 | 20 | 1 28 | 0 |
| 6040 | 1407 | 1233 | 4690 66.6 | CAGCAGTGTTAGCAGCAGCC | 31 | 22 | 3 | 31 36 | 0 |
| 6041 | 1408 | 1234 | 40238 69.4 | CAGCGATGAAAGGTGCGATG | 31 | 27 | 6 | 33 27 | 0 |
| 6042 | 1409 | 1236 | 4696 73.7 | CGAACAGCCAGCGACCGGTA | 16 | 31 | 31 | 32 18 | 0 |
| 6043 | 1410 | 1237 | 4704 68.1 | GACCCTGTCTCAGTGCGTGC | 32 | 14 | 13 | 33 33 | 0 |
| 6044 | 1411 | 1238 | 14466 65.8 | GACCGTCTAGGATCCCCTCA | 32 | 19 | 25 | 28 13 | 0 |
| 6045 | 1412 | 1239 | 4713 68.3 | CGAAGACCTCCCCCTAATCG | 16 | 32 | 28 | 26 24 | 0 |
| 6046 | 1413 | 1240 | 14470 67.2 | GACCTGCGTTAGCTCAAGCC | 32 | 29 | 3 | 13 36 | 0 |
| 6047 | 1414 | 1241 | 40239 68.8 | GTGCGGTAAATCTCGTTGCG | 33 | 18 | 4 | 10 29 | 0 |
| 6048 | 1415 | 1242 | 14481 69.8 | CGAAGTGCAGGAAGCCTCGT | 16 | 33 | 25 | 36 10 | 0 |
| 6049 | 1416 | 1243 | 4734 69.6 | GTGCTCCCCCTAGATGCGAA | 33 | 28 | 26 | 27 16 | 0 |
| 6050 | 1417 | 1244 | 14485 73 | CGAAGTGCAGCCGATGGGAC | 16 | 33 | 36 | 27 34 | 0 |
| 6051 | 1418 | 1245 | 4747 68.8 | GGACGCTTGACCTGATGCAA | 34 | 17 | 32 | 2 21 | 0 |
| 6052 | 1419 | 1247 | 14491 69.3 | GGACACCTTCTGTCCCACGG | 34 | 23 | 8 | 28 35 | 0 |
| 6053 | 1420 | 1248 | 4755 68.5 | GGACGATGGAGTACGGGCTT | 34 | 27 | 20 | 35 17 | 0 |
| 6054 | 1421 | 1250 | 30260 68.8 | ACGGTGATTCCCTGTCGACC | 35 | 2 | 28 | 9 32 | 0 |
| 6055 | 1422 | 1252 | 14498 69.5 | ACGGTCTGCAGCAAAGTCCC | 35 | 8 | 31 | 6 28 | 1 |
| 6056 | 1423 | 1253 | 30262 70.2 | CGAAACGGGAGTGGACGGTA | 16 | 35 | 20 | 34 18 | 0 |
| 6057 | 1424 | 1254 | 20723 66.5 | CGAAACGGACCTAGGACGTT | 16 | 35 | 23 | 25 12 | 0 |
| 6058 | 1425 | 1255 | 40241 68.5 | ACGGAGGACTTGATCGAGCC | 35 | 25 | 11 | 24 36 | 0 |
| 6059 | 1426 | 1256 | 4775 71.5 | CGAACGGCCTATCGTGCAA | 16 | 35 | 26 | 10 21 | 0 |
| 6060 | 1427 | 1257 | 4778 73.7 | CGAACGGTGCGCTGTTCGT | 16 | 35 | 29 | 14 10 | 0 |
| 6061 | 1428 | 1258 | 4781 76.1 | CGAACGGACGGCACGATCG | 16 | 35 | 35 | 30 24 | 0 |
| 6062 | 1429 | 1260 | 30263 67.5 | AGCCTGATCCTATCCCGGAC | 36 | 2 | 26 | 28 34 | 0 |
| 6063 | 1430 | 1261 | 4786 70.8 | CGAAAGCCTCTGGCAACGAA | 16 | 36 | 8 | 21 16 | 0 |
| 6064 | 1431 | 1262 | 40243 68.3 | AGCCCTCAAATCGATGGGAC | 36 | 13 | 4 | 27 34 | 0 |
| 6065 | 1432 | 1264 | 14508 67.6 | CGAAAGCCACCTTTAGCAGC | 16 | 36 | 23 | 3 31 | 0 |
| 6066 | 1433 | 1265 | 4795 70.7 | AGCCATCGGTCTGATGCGAA | 36 | 24 | 19 | 27 16 | 0 |
| 6067 | 1434 | 1266 | 30266 68.2 | AGCCAGGAAGTGGATGGCTT | 36 | 25 | 22 | 27 17 | 0 |
| 6068 | 1435 | 1267 | 14510 70.6 | CGAAAGCCGATGCGAATGAT | 16 | 36 | 27 | 16 2 | 0 |
| 6069 | 1436 | 1268 | 14511 75.3 | CGAAAGCCGTGCGATGGGAC | 16 | 36 | 33 | 27 34 | 0 |
| 6070 | 1437 | 1269 | 20732 67.8 | TGATATCGCTTGACGGGACC | 2 | 24 | 11 | 35 32 | 0 |
| 6071 | 1438 | 1270 | 4811 73.6 | TGATCAGCTCCCGACCTGCG | 2 | 31 | 28 | 32 29 | 0 |
| 6072 | 1439 | 1271 | 4812 71.8 | TGATGACCCATTCCCGACC | 2 | 32 | 15 | 28 32 | 0 |
| 6073 | 1440 | 1272 | 4829 71.5 | AATCCAGCGGTATCCCCACG | 4 | 31 | 18 | 28 30 | 0 |

FIG. 29EE

| SEQ ID NO: | ZIP ID# | 4,633 ID# | HEX ID# | Tm | ZIPCODE (NH2 -> CONH2) | TETRAMER NUMBERS | | | | | 'UNALLOWED DIMERS' |
|---|---|---|---|---|---|---|---|---|---|---|---|
| 6074 | 1441 | 1273 | 30268 | 73.8 | AAAGCGTTTGCGCCATGTGC | 6 | 12 | 29 | 15 | 33 | 0 |
| 6075 | 1442 | 1274 | 30269 | 72 | AAAGCAGCGACCGCTTCGTT | 6 | 31 | 32 | 17 | 12 | 0 |
| 6076 | 1443 | 1275 | 14530 | 72 | TCTGCTTGACGGCTTGGCAA | 8 | 11 | 35 | 11 | 21 | 0 |
| 6077 | 1444 | 1276 | 14532 | 67.9 | TCTGCTCAGGACGCTTTCGT | 8 | 13 | 34 | 17 | 10 | 0 |
| 6078 | 1445 | 1277 | 4845 | 70.7 | TCTGCTGTTCCCCAGCCTCA | 8 | 14 | 28 | 31 | 13 | 0 |
| 6079 | 1446 | 1278 | 14535 | 68.3 | TCTGCCTAAGGATGCGATCG | 8 | 26 | 25 | 29 | 24 | 0 |
| 6080 | 1447 | 1279 | 14536 | 71 | TCTGGGACGCAAATCGCCTA | 8 | 34 | 21 | 24 | 26 | 0 |
| 6081 | 1448 | 1280 | 20744 | 68.8 | TGTCGAGTGTCTTCCCTGCG | 9 | 20 | 19 | 28 | 29 | 0 |
| 6082 | 1449 | 1281 | 14544 | 72 | TGTCGACCGCTTCGAAGCAA | 9 | 32 | 17 | 16 | 21 | 0 |
| 6083 | 1450 | 1282 | 4867 | 73.8 | TCGTTGTCGTGCTGCGCTCA | 10 | 9 | 33 | 29 | 13 | 0 |
| 6084 | 1451 | 1283 | 14548 | 70.3 | TCGTCGTTGTGCAGGAGCAA | 10 | 12 | 33 | 25 | 21 | 0 |
| 6085 | 1452 | 1285 | 14552 | 71.2 | TCGTGATGCCTATCCCTGCG | 10 | 27 | 26 | 28 | 29 | 0 |
| 6086 | 1453 | 1286 | 30272 | 68.2 | TCGTAGCCTTAGTCCCGCAA | 10 | 36 | 3 | 28 | 21 | 0 |
| 6087 | 1454 | 1287 | 30273 | 69.3 | CTTGCCATCTTGGATGTGCG | 11 | 15 | 11 | 27 | 29 | 0 |
| 6088 | 1455 | 1288 | 30274 | 69 | CTTGGCAAAGTGCGTTACGG | 11 | 21 | 22 | 12 | 35 | 0 |
| 6089 | 1456 | 1289 | 4887 | 72.7 | CTTGATCGACGGTCCCACGG | 11 | 24 | 35 | 28 | 35 | 1 |
| 6090 | 1457 | 1291 | 4907 | 71.1 | CGTTCAGCCGTTGACCAGGA | 12 | 31 | 12 | 32 | 25 | 0 |
| 6091 | 1458 | 1292 | 30275 | 73.8 | GCTTCGTTGTGCAGCCCGAA | 17 | 12 | 33 | 36 | 16 | 0 |
| 6092 | 1459 | 1293 | 4917 | 74.2 | CTCAGTGCGCTTTGCGCGTT | 13 | 33 | 17 | 29 | 12 | 0 |
| 6093 | 1460 | 1294 | 14568 | 73 | CTGTACGGGACCGACCTGCG | 14 | 35 | 32 | 32 | 29 | 0 |
| 6094 | 1461 | 1295 | 30276 | 72.9 | CCATTCCCGATGTCCCTCCC | 15 | 28 | 27 | 28 | 28 | 0 |
| 6095 | 1462 | 1296 | 14575 | 73 | CGAACTTGGCAATCCCGTGC | 16 | 11 | 21 | 28 | 33 | 0 |
| 6096 | 1463 | 1297 | 4950 | 71.1 | CGAACTGTGCAAAGCCCAGC | 16 | 14 | 21 | 36 | 31 | 0 |
| 6097 | 1464 | 1298 | 4953 | 70.8 | CGAAAGTGGCAAACGGGATG | 16 | 22 | 21 | 35 | 27 | 0 |
| 6098 | 1465 | 1299 | 30277 | 70 | GCTTCGAAAGGATGCGCTGT | 17 | 16 | 25 | 29 | 14 | 0 |
| 6099 | 1466 | 1300 | 20755 | 66.2 | GCTTCTTGATACAGCCGCAA | 17 | 11 | 5 | 36 | 21 | 0 |
| 6100 | 1467 | 1301 | 40247 | 68.7 | GCTTGCTTTCCCTCTGAGCC | 17 | 17 | 28 | 8 | 36 | 0 |
| 6101 | 1468 | 1302 | 4982 | 67.9 | GCTTGGTAGCAAGTGCGGAC | 17 | 18 | 21 | 33 | 34 | 0 |
| 6102 | 1469 | 1303 | 4991 | 71.2 | GAGTCGTTTCCCGACCAGCC | 20 | 12 | 28 | 32 | 36 | 1 |
| 6103 | 1470 | 1304 | 4994 | 73 | GAGTGTGCTGCGCTTGCACG | 20 | 33 | 29 | 11 | 30 | 0 |
| 6104 | 1471 | 1305 | 14589 | 72 | GCTTGCAAAAGCACGCGAA | 17 | 21 | 6 | 30 | 16 | 0 |
| 6105 | 1472 | 1306 | 30279 | 69.6 | GCAATCGTCTCAGCAATGCG | 21 | 18 | 13 | 21 | 29 | 0 |
| 6106 | 1473 | 1307 | 30280 | 69.4 | GCAACGAAGTCTCAGCGCAA | 21 | 16 | 19 | 31 | 21 | 0 |
| 6107 | 1474 | 1308 | 30281 | 70.5 | GCTTGCAAACCTCACGCCAT | 17 | 21 | 23 | 30 | 15 | 0 |
| 6108 | 1475 | 1309 | 5005 | 70.3 | GCTTGCAAGATGCAGCTCCC | 17 | 21 | 27 | 31 | 28 | 0 |
| 6109 | 1476 | 1310 | 5022 | 73.2 | ACCTCAGCTCCCAGCCAGCC | 23 | 31 | 28 | 36 | 36 | 0 |
| 6110 | 1477 | 1311 | 40248 | 69.4 | ATCGCTTGTCTGGTGCTCCC | 24 | 11 | 8 | 33 | 28 | 0 |
| 6111 | 1478 | 1312 | 30283 | 69.4 | ATCGCCTATTGAACGGCGTT | 24 | 26 | 1 | 35 | 12 | 0 |
| 6112 | 1479 | 1313 | 14603 | 73.4 | ATCGGACCGACCCTTGCGTT | 24 | 32 | 32 | 11 | 12 | 0 |
| 6113 | 1480 | 1314 | 5045 | 71.9 | CCTACGTTTGCGCTTGCGAA | 26 | 12 | 29 | 11 | 16 | 0 |
| 6114 | 1481 | 1315 | 30284 | 70.5 | GATGGCAAAGGACACGACGG | 27 | 21 | 25 | 30 | 35 | 0 |
| 6115 | 1482 | 1316 | 30285 | 68.5 | GCTTGATGCACGAAAGCGTT | 17 | 27 | 30 | 6 | 12 | 0 |
| 6116 | 1483 | 1317 | 20770 | 67.1 | GATGGTGCATACCGTTTCCC | 27 | 33 | 5 | 12 | 28 | 1 |
| 6117 | 1484 | 1318 | 5072 | 71.1 | TCCCATCGGTCTGACCTCCC | 28 | 24 | 19 | 32 | 28 | 0 |
| 6118 | 1485 | 1319 | 14622 | 73.7 | TCCCGACCGGTATGTCGCAA | 28 | 32 | 18 | 9 | 21 | 0 |
| 6119 | 1486 | 1320 | 30289 | 73.3 | TGCGTACAACGGGCAATCCC | 29 | 7 | 35 | 21 | 28 | 0 |
| 6120 | 1487 | 1321 | 14629 | 72.2 | TGCGCGAAGAGTATCGGCAA | 29 | 16 | 20 | 24 | 21 | 0 |
| 6121 | 1488 | 1322 | 5087 | 68.3 | TGCGGGTAAATCGAGTACGG | 29 | 18 | 4 | 20 | 35 | 0 |

FIG. 29FF

| SEQ ID NO: | ZIP ID# | 4,633 ID# | HEX ID# Tm | ZIPCODE (NH2 -> CONH2) | TETRAMER NUMBERS | | | | | "UNALLOWED DIMERS" |
|---|---|---|---|---|---|---|---|---|---|---|
| 6122 | 1489 | 1323 | 30290 72.6 | TGCGAGTGGGACCTTGAGCC | 29 | 22 | 34 | 11 | 36 | 0 |
| 6123 | 1490 | 1324 | 14631 74.5 | GCTTTGCGATCGGCAATCCC | 17 | 29 | 24 | 21 | 28 | 0 |
| 6124 | 1491 | 1325 | 14632 72.6 | TGCGACGGTGTCAAAGGCAA | 29 | 35 | 9 | 6 | 21 | 0 |
| 6125 | 1492 | 1326 | 5097 74.3 | CACGTGTCCACGTCCCCACG | 30 | 9 | 30 | 28 | 30 | 0 |
| 6126 | 1493 | 1327 | 40252 68.7 | CACGCTTGAAAGCAGCGAGT | 30 | 11 | 6 | 31 | 20 | 0 |
| 6127 | 1494 | 1328 | 5100 67.6 | CACGCTGTTACAATCGGCAA | 30 | 14 | 7 | 24 | 21 | 0 |
| 6128 | 1495 | 1329 | 14636 72.7 | CACGTCCCGATGCTTGGACC | 30 | 28 | 27 | 11 | 32 | 0 |
| 6129 | 1496 | 1330 | 30293 73.2 | CACGGACCCACGGAGTCGAA | 30 | 32 | 30 | 20 | 16 | 0 |
| 6130 | 1497 | 1331 | 5108 71.5 | CAGCAATCTCCCCGAAAGCC | 31 | 4 | 28 | 16 | 36 | 0 |
| 6131 | 1498 | 1332 | 5109 72.4 | CAGCTCTGAGCCTCCCCACG | 31 | 8 | 36 | 28 | 30 | 0 |
| 6132 | 1499 | 1333 | 30294 66.9 | CAGCTCGTAATCTCCCCAGC | 31 | 10 | 4 | 28 | 31 | 0 |
| 6133 | 1500 | 1334 | 5117 68.1 | CAGCGCAAAAAGAATCGACC | 31 | 21 | 6 | 4 | 32 | 0 |
| 6134 | 1501 | 1335 | 40256 70.8 | CAGCACCTGGTAAGCCACGG | 31 | 23 | 18 | 36 | 35 | 0 |
| 6135 | 1502 | 1336 | 5123 72.4 | CAGCCACGGCAACTCAGCAA | 31 | 30 | 21 | 13 | 21 | 0 |
| 6136 | 1503 | 1337 | 5128 72.9 | GACCAATCCACGTGCGAGCC | 32 | 4 | 30 | 29 | 36 | 0 |
| 6137 | 1504 | 1338 | 30296 69.6 | GCTTGACCCCATGCTTGCTT | 17 | 32 | 15 | 17 | 17 | 0 |
| 6138 | 1505 | 1339 | 40258 71.8 | GACCCCTAAGCCCACGCTCA | 32 | 26 | 36 | 30 | 13 | 0 |
| 6139 | 1506 | 1340 | 14653 75.4 | GCTTGACCCAGCGACCGTGC | 17 | 32 | 31 | 32 | 33 | 0 |
| 6140 | 1507 | 1341 | 14656 71.7 | GCTTGTGCATCGGTGCCTTG | 17 | 33 | 24 | 33 | 11 | 0 |
| 6141 | 1508 | 1342 | 5148 71 | GCTTGTGCTCCCAATCTGCG | 17 | 33 | 28 | 4 | 29 | 0 |
| 6142 | 1509 | 1343 | 20786 71.3 | GGACCGTTTCTGGTGCCCAT | 34 | 12 | 8 | 33 | 15 | 0 |
| 6143 | 1510 | 1344 | 5158 70.4 | GCTTGGACCGAATCTGGCAA | 17 | 34 | 16 | 8 | 21 | 0 |
| 6144 | 1511 | 1345 | 5161 70.1 | GGACTCCCCTTGTGTCGCAA | 34 | 28 | 11 | 9 | 21 | 0 |
| 6145 | 1512 | 1346 | 40259 69.3 | GGACCACGTACATCCCAGCC | 34 | 30 | 7 | 28 | 36 | 0 |
| 6146 | 1513 | 1347 | 14668 72.9 | ACGGTCTGACGGTGCGTCGT | 35 | 8 | 35 | 29 | 10 | 0 |
| 6147 | 1514 | 1348 | 30301 69.9 | AGCCCTGTAATCACGGGCAA | 36 | 14 | 4 | 35 | 21 | 0 |
| 6148 | 1515 | 1349 | 5192 70.5 | AGCCATCGCTCAAAAGCGAA | 36 | 24 | 13 | 6 | 16 | 0 |
| 6149 | 1516 | 1350 | 5216 72.1 | TCTGGTGCAGGACGAATGCG | 8 | 33 | 25 | 16 | 29 | 0 |
| 6150 | 1517 | 1351 | 5219 76.2 | TGTCGCTTTGCGCAGCTCCC | 9 | 17 | 29 | 31 | 28 | 0 |
| 6151 | 1518 | 1352 | 5252 74 | CGAACAGCGGTAAGCCGCAA | 16 | 31 | 18 | 36 | 21 | 0 |
| 6152 | 1519 | 1353 | 30304 70.1 | CGAAAGCCTACAAGCCCGAA | 16 | 36 | 7 | 36 | 16 | 0 |
| 6153 | 1520 | 1354 | 5266 75.5 | GCAACAGCGACCCAGCCAGC | 21 | 31 | 32 | 31 | 31 | 0 |
| 6154 | 1521 | 1355 | 5268 71.9 | GCAAGGACTGCGTCTGTGCG | 21 | 34 | 29 | 8 | 29 | 0 |
| 6155 | 1522 | 1356 | 5277 74.7 | ACCTCACGTGCGCTGTTGCG | 23 | 30 | 29 | 14 | 29 | 0 |
| 6156 | 1523 | 1357 | 40264 70.4 | ATCGGCAACGTTCTTGACGG | 24 | 21 | 12 | 11 | 35 | 0 |
| 6157 | 1524 | 1358 | 5296 71.3 | GATGGCTTCGTTTCCCCAGC | 27 | 17 | 12 | 28 | 31 | 1 |
| 6158 | 1525 | 1359 | 14728 72.2 | TGCGGCAACTGTATCGGTGC | 29 | 21 | 14 | 24 | 33 | 0 |
| 6159 | 1526 | 1360 | 5328 72.2 | TGCGAGTGGTGCGGTAGTGC | 29 | 22 | 33 | 18 | 33 | 0 |
| 6160 | 1527 | 1361 | 30306 71.1 | CACGGCAACGTTCCATTCGT | 30 | 21 | 12 | 15 | 10 | 0 |
| 6161 | 1528 | 1362 | 5341 73.7 | CACGATCGGACCAGGATGCG | 30 | 24 | 32 | 25 | 29 | 0 |
| 6162 | 1529 | 1363 | 5344 73.2 | CACGAGCCGAGTCAGCGCTT | 30 | 36 | 20 | 31 | 17 | 0 |
| 6163 | 1530 | 1364 | 30307 70.4 | CAGCGCTTAGGAGGACGTGC | 31 | 17 | 25 | 34 | 33 | 0 |
| 6164 | 1531 | 1365 | 5355 73.3 | CAGCGACCCTGTTCCCTCCC | 31 | 32 | 14 | 28 | 28 | 0 |
| 6165 | 1532 | 1366 | 5360 71.3 | GACCGGTACAGCATCGCGAA | 32 | 18 | 31 | 24 | 16 | 0 |
| 6166 | 1533 | 1367 | 5362 74.9 | GACCATCGCAGCGTGCATCG | 32 | 24 | 31 | 33 | 24 | 0 |
| 6167 | 1534 | 1368 | 40267 75.8 | GACCGTGCCCATCCATTGCG | 32 | 33 | 15 | 15 | 29 | 0 |
| 6168 | 1535 | 1369 | 5368 69.9 | GACCACGGTTAGTGCGAGCC | 32 | 35 | 3 | 29 | 36 | 0 |
| 6169 | 1536 | 1370 | 30308 70.5 | ACGGTCGTTTAGACGGTGCG | 35 | 10 | 3 | 35 | 29 | 0 |

FIG. 29GG

| SEQ ID NO: | ZIP ID# | 4,633 ID# | HEX ID# | Tm | ZIPCODE (NB2 -> CONH2) | TETRAMER NUMBERS | | | | | 'UNALLOWED DIMERS' |
|---|---|---|---|---|---|---|---|---|---|---|---|
| 6170 | 1537 | 1371 | 30309 | 71.8 | ACGGCTGTGTGCGATGGATG | 35 | 14 | 33 | 27 | 27 | 0 |
| 6171 | 1538 | 1372 | 30310 | 69.5 | AGCCGAGTACCTTGCGCTGT | 36 | 20 | 23 | 29 | 14 | 0 |
| 6172 | 1539 | 1373 | 5420 | 72.6 | TTGATGCGCGTTTGCGAAAG | 1 | 29 | 12 | 29 | 6 | 0 |
| 6173 | 1540 | 1374 | 5425 | 74.5 | TCTGCAGCTGCGCTTGCCAT | 8 | 31 | 29 | 11 | 15 | 0 |
| 6174 | 1541 | 1376 | 5437 | 76.4 | CTTGCAGCACGGTCCCTGCG | 11 | 31 | 35 | 28 | 29 | 1 |
| 6175 | 1542 | 1377 | 5440 | 73.2 | CGTTCGAACAGCAGCCGCTT | 12 | 16 | 31 | 36 | 17 | 0 |
| 6176 | 1543 | 1378 | 5444 | 75.8 | CGTTGTGCCACGTCGTTGCG | 12 | 33 | 30 | 10 | 29 | 0 |
| 6177 | 1544 | 1379 | 5449 | 72.1 | CCATTCCCACGGCTGTAGCC | 15 | 28 | 35 | 14 | 36 | 0 |
| 6178 | 1545 | 1380 | 5450 | 72.9 | CGAACGAACAGCGCAACACG | 16 | 16 | 31 | 21 | 30 | 0 |
| 6179 | 1546 | 1381 | 5453 | 74.4 | CGAAATCGCGAAACGGGACC | 16 | 24 | 16 | 35 | 32 | 0 |
| 6180 | 1547 | 1382 | 20836 | 68.6 | GCAAATCGAATCTCCCCGTT | 21 | 24 | 4 | 28 | 12 | 0 |
| 6181 | 1548 | 1383 | 5481 | 75.4 | GATGCAGCATCGTGCGGCAA | 27 | 31 | 24 | 29 | 21 | 0 |
| 6182 | 1549 | 1384 | 30311 | 76.1 | TCCCCTTGACGGCGTTGCAA | 28 | 11 | 35 | 12 | 21 | 0 |
| 6183 | 1550 | 1385 | 30312 | 71.7 | TCCCCCATTCTGACGGGGTA | 28 | 15 | 8 | 35 | 18 | 0 |
| 6184 | 1551 | 1386 | 40269 | 74 | TCCCACGGAGTGCCATGTGC | 28 | 35 | 22 | 15 | 33 | 0 |
| 6185 | 1552 | 1387 | 5498 | 73.7 | TGCGAGTGATCGAGCCAGCC | 29 | 22 | 24 | 36 | 36 | 0 |
| 6186 | 1553 | 1388 | 30313 | 72.5 | TGCGGACCTCCCTACAACGG | 29 | 32 | 28 | 7 | 35 | 0 |
| 6187 | 1554 | 1389 | 5507 | 73.7 | CACGCTCAACGGCTTGCCAT | 30 | 13 | 35 | 11 | 15 | 0 |
| 6188 | 1555 | 1390 | 30314 | 74.1 | CACGGCTTTGTCAGCCGTGC | 30 | 17 | 9 | 36 | 33 | 0 |
| 6189 | 1556 | 1391 | 5509 | 73.8 | CACGCCTAGACCTGCGGCAA | 30 | 26 | 32 | 29 | 21 | 0 |
| 6190 | 1557 | 1392 | 5510 | 74 | CACGTCCCCTGTGCTTTGCG | 30 | 28 | 14 | 17 | 29 | 0 |
| 6191 | 1558 | 1393 | 14801 | 74.9 | CACGACGGCGTTCGTTGTGC | 30 | 35 | 12 | 12 | 33 | 0 |
| 6192 | 1559 | 1394 | 5519 | 71.6 | CAGCCAGCTCGTTCGTCGAA | 31 | 31 | 10 | 10 | 16 | 0 |
| 6193 | 1560 | 1395 | 5520 | 74.8 | CAGCGGACGGACGGACCCTA | 31 | 34 | 34 | 34 | 26 | 0 |
| 6194 | 1561 | 1396 | 40271 | 72.8 | GTGCGCTTCACGTTGATGCG | 33 | 17 | 30 | 1 | 29 | 0 |
| 6195 | 1562 | 1397 | 40272 | 72.5 | GTGCGCAAGGACCGTTCCAT | 33 | 21 | 34 | 12 | 15 | 0 |
| 6196 | 1563 | 1399 | 40273 | 75 | GTGCAGCCGCTTTCCCAGGA | 33 | 36 | 17 | 28 | 25 | 0 |
| 6197 | 1564 | 1400 | 30315 | 70.7 | GTCTGGACGCTTACGGCGAA | 19 | 34 | 17 | 35 | 16 | 0 |
| 6198 | 1565 | 1401 | 5540 | 76.1 | GGACTCCCGCAACACGTGCG | 34 | 28 | 21 | 30 | 29 | 0 |
| 6199 | 1566 | 1402 | 5545 | 73.9 | GGACAGCCATCGATCGTGCG | 34 | 36 | 24 | 24 | 29 | 0 |
| 6200 | 1567 | 1403 | 14814 | 71.8 | AGCCGGTACAGCTCCCATCG | 36 | 18 | 31 | 28 | 24 | 0 |
| 6201 | 1568 | 1404 | 5568 | 79.2 | TCTGTGCGCACGCACGGCAA | 8 | 29 | 30 | 30 | 21 | 0 |
| 6202 | 1569 | 1405 | 5569 | 76.6 | TCTGCACGACGGCACGTCCC | 8 | 30 | 35 | 30 | 28 | 0 |
| 6203 | 1570 | 1407 | 5577 | 74.1 | CTTGCACGCCATAGCCCACG | 11 | 30 | 15 | 36 | 30 | 0 |
| 6204 | 1571 | 1408 | 5580 | 72 | CGTTCGTTAGCCATCGTGCG | 12 | 12 | 36 | 24 | 29 | 0 |
| 6205 | 1572 | 1409 | 20857 | 72.3 | CTGTCACGCAGCAGCCAGGA | 14 | 30 | 31 | 36 | 25 | 0 |
| 6206 | 1573 | 1410 | 30317 | 72.8 | CGAAAGCCTGCGTCGTCCAT | 16 | 36 | 29 | 10 | 15 | 0 |
| 6207 | 1574 | 1411 | 5597 | 71.4 | GCTTGCAACACGCACGACCT | 17 | 21 | 30 | 30 | 23 | 0 |
| 6208 | 1575 | 1412 | 5599 | 76.4 | GCTTCACGGTGCGTGCAGCC | 17 | 30 | 33 | 33 | 36 | 0 |
| 6209 | 1576 | 1413 | 5612 | 72.8 | ATCGTGCGATCGGACCCTCA | 24 | 29 | 24 | 32 | 13 | 0 |
| 6210 | 1577 | 1414 | 20866 | 72.8 | CCTACAGCTCCCGCTTTGCG | 26 | 31 | 28 | 17 | 29 | 0 |
| 6211 | 1578 | 1415 | 5633 | 73.3 | TCCCGTGCCCTATCGTGTGC | 28 | 33 | 26 | 10 | 33 | 0 |
| 6212 | 1579 | 1416 | 14828 | 76.8 | TGCGAAAGCACGGGACGTGC | 29 | 6 | 30 | 34 | 33 | 0 |
| 6213 | 1580 | 1417 | 5645 | 71.6 | TGCGCCATTACATCCCGGTA | 29 | 15 | 7 | 28 | 18 | 0 |
| 6214 | 1581 | 1418 | 40276 | 72.3 | TGCGGGTAGCAATCTGCACG | 29 | 18 | 21 | 8 | 30 | 0 |
| 6215 | 1582 | 1419 | 40277 | 75.2 | TGCGACCTAGCCTCCCTGCG | 29 | 23 | 36 | 28 | 29 | 0 |
| 6216 | 1583 | 1420 | 5671 | 77 | CAGCGATGGTGCGGACACGG | 31 | 27 | 33 | 34 | 35 | 0 |
| 6217 | 1584 | 1421 | 20874 | 70.8 | CAGCTCCCTCTGGACCCGTT | 31 | 28 | 8 | 32 | 12 | 0 |

FIG. 29HH

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 6218 | 1585 | 1422 | 5673 | 74.2 | CAGCGGACAGCCGAGTCACG | 31 | 34 | 36 | 20 | 30 | 0 |
| 6219 | 1586 | 1423 | 5676 | 71.4 | GAGTGACCCGTTTCCCCGAA | 20 | 32 | 12 | 28 | 16 | 1 |
| 6220 | 1587 | 1425 | 14843 | 75.2 | GACCGTGCGACCAGCCCTTG | 32 | 33 | 32 | 36 | 11 | 0 |
| 6221 | 1588 | 1426 | 20876 | 69.8 | GTGCTTGAGGACTCCCGTGC | 33 | 1 | 34 | 28 | 33 | 0 |
| 6222 | 1589 | 1428 | 5693 | 71.5 | GGACCCATTGTCGGACGGAC | 34 | 15 | 9 | 34 | 34 | 0 |
| 6223 | 1590 | 1429 | 5699 | 71.3 | GGACGGACTGTCATCGCACG | 34 | 34 | 9 | 24 | 30 | 0 |
| 6224 | 1591 | 1430 | 14849 | 71.7 | ACGGCCATTTAGTGCGGCTT | 35 | 15 | 3 | 29 | 17 | 0 |
| 6225 | 1592 | 1431 | 5716 | 76.9 | AGCCATCGGACCAGCCCACG | 36 | 24 | 32 | 36 | 30 | 0 |
| 6226 | 1593 | 1432 | 5730 | 71.3 | GCAATTGAGTGCGGACCGAA | 21 | 1 | 33 | 34 | 16 | 0 |
| 6227 | 1594 | 1433 | 5732 | 71.1 | TGATTCGTTCCCCTTGCACG | 2 | 10 | 28 | 11 | 30 | 0 |
| 6228 | 1595 | 1434 | 5737 | 72.8 | TGATCAGCGCTTTCCCAGCC | 2 | 31 | 17 | 28 | 36 | 0 |
| 6229 | 1596 | 1435 | 5752 | 71.2 | GCAAAATCATCGGTGCCGAA | 21 | 4 | 24 | 33 | 16 | 0 |
| 6230 | 1597 | 1436 | 40281 | 68.2 | AATCTCCCATCGCTCATCCC | 4 | 28 | 24 | 13 | 28 | 0 |
| 6231 | 1598 | 1437 | 14874 | 70.5 | GCAAAATCCACGCAGCCTGT | 21 | 4 | 30 | 31 | 14 | 0 |
| 6232 | 1599 | 1438 | 5778 | 66.6 | AAAGACCTAGGAAGCCGCAA | 6 | 23 | 25 | 36 | 21 | 0 |
| 6233 | 1600 | 1440 | 30319 | 68.2 | TCTGCGTTTTAGGGACACGG | 8 | 12 | 3 | 34 | 35 | 0 |
| 6234 | 1601 | 1441 | 30320 | 68.8 | TCTGGCAACGTTATCGCGTT | 8 | 21 | 12 | 24 | 12 | 0 |
| 6235 | 1602 | 1442 | 5792 | 70.4 | TCTGTCCCGCAACTCAAGCC | 8 | 28 | 21 | 13 | 36 | 0 |
| 6236 | 1603 | 1443 | 5793 | 73.1 | TCTGTGCGCTGTGGACGTGC | 8 | 29 | 14 | 34 | 33 | 0 |
| 6237 | 1604 | 1444 | 30321 | 69.4 | TCTGGACCAATCAGCCCCAT | 8 | 32 | 4 | 36 | 15 | 0 |
| 6238 | 1605 | 1445 | 40284 | 75.8 | TCTGGGACAGCCGTGCCAGC | 8 | 34 | 36 | 33 | 31 | 0 |
| 6239 | 1606 | 1446 | 5796 | 72.7 | TGTCTCGTGACCTGCGCGAA | 9 | 10 | 32 | 29 | 16 | 0 |
| 6240 | 1607 | 1447 | 30323 | 70.3 | TGTCGCTTTCGTGTGCCTCA | 9 | 17 | 10 | 33 | 13 | 0 |
| 6241 | 1608 | 1448 | 20893 | 69.1 | TGTCGGTAGACCTCCCGCTT | 9 | 18 | 32 | 28 | 17 | 0 |
| 6242 | 1609 | 1449 | 14901 | 73 | TGTCATCGTCCCTCCCACG | 9 | 24 | 28 | 28 | 30 | 0 |
| 6243 | 1610 | 1450 | 5804 | 72.2 | GCAATGTCTGCGGATGCGAA | 21 | 9 | 29 | 27 | 16 | 0 |
| 6244 | 1611 | 1451 | 14902 | 71.7 | GCAATGTCCACGCGAAATCG | 21 | 9 | 30 | 16 | 24 | 0 |
| 6245 | 1612 | 1452 | 5812 | 69.4 | TCGTCTGTTGCGAATCCGAA | 10 | 14 | 29 | 4 | 16 | 0 |
| 6246 | 1613 | 1453 | 5818 | 69.5 | TCGTACCTGCTTGTGCCGAA | 10 | 23 | 17 | 33 | 16 | 0 |
| 6247 | 1614 | 1455 | 30324 | 69.6 | TCGTAGCCTGATTCCCCAGC | 10 | 36 | 2 | 28 | 31 | 0 |
| 6248 | 1615 | 1456 | 5835 | 73.6 | CTTGGATGAGCCCACGCGAA | 11 | 27 | 36 | 30 | 16 | 0 |
| 6249 | 1616 | 1457 | 14911 | 71.8 | GCAACTTGCAGCCGAAGCAA | 21 | 11 | 31 | 16 | 21 | 0 |
| 6250 | 1617 | 1458 | 40286 | 68.5 | CGTTTTGATCGTCACGAGCC | 12 | 1 | 10 | 30 | 36 | 1 |
| 6251 | 1618 | 1459 | 5842 | 72.6 | CGTTTACAACGGCAGCGCAA | 12 | 7 | 35 | 31 | 21 | 0 |
| 6252 | 1619 | 1460 | 14919 | 73.9 | CGTTGATGGTGCTCCCTGCG | 12 | 27 | 33 | 28 | 29 | 0 |
| 6253 | 1620 | 1461 | 30326 | 69.2 | CGTTTCCCACCTTTGAAGCC | 12 | 28 | 23 | 1 | 36 | 2 |
| 6254 | 1621 | 1464 | 5860 | 70.4 | CTCAATCGCGAAGTGCCCAT | 13 | 24 | 16 | 33 | 15 | 0 |
| 6255 | 1622 | 1466 | 5863 | 71.8 | CTCACACGACGGGTGCAGGA | 13 | 30 | 35 | 33 | 25 | 0 |
| 6256 | 1623 | 1467 | 5864 | 70.2 | CTCAACGGGCTTGGACAGGA | 13 | 35 | 17 | 34 | 25 | 0 |
| 6257 | 1624 | 1468 | 30327 | 72.5 | GCAACTGTTGCGGCAAGCAA | 21 | 14 | 29 | 21 | 21 | 0 |
| 6258 | 1625 | 1469 | 5875 | 71.2 | CCATCTCAGGACCAGCGCAA | 15 | 13 | 34 | 31 | 21 | 0 |
| 6259 | 1626 | 1470 | 20911 | 68.9 | GCAACCATCGAATGTCACGG | 21 | 15 | 16 | 9 | 35 | 0 |
| 6260 | 1627 | 1471 | 5881 | 70.4 | CCATGATGACGGTCCCAGGA | 15 | 27 | 35 | 28 | 25 | 1 |
| 6261 | 1628 | 1472 | 5882 | 67.8 | GCAACCATTGCGTCCCTTAG | 21 | 15 | 29 | 28 | 3 | 0 |
| 6262 | 1629 | 1473 | 5885 | 71.9 | GCAACCATGGACGATGCGAA | 21 | 15 | 34 | 27 | 16 | 0 |
| 6263 | 1630 | 1474 | 20915 | 67.6 | CGAAGCTTGACCTGTCGCTT | 16 | 17 | 32 | 9 | 17 | 0 |
| 6264 | 1631 | 1475 | 40288 | 68.5 | GCTTGCTTTGTCCTTGGCAA | 17 | 17 | 9 | 11 | 21 | 0 |
| 6265 | 1632 | 1476 | 5912 | 70.5 | GCAAGCTTCACGGCTTCAGC | 21 | 17 | 30 | 17 | 31 | 0 |

FIG. 29II

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 6266 | 1633 | 1477 | 5914 | 70.6 | GCTTAGCCGATGGTGCCTCA | 17 | 36 | 27 | 33 | 13 | 0 |
| 6267 | 1634 | 1478 | 5924 | 66 | GTCTGCTTAATCGACCGCAA | 19 | 17 | 4 | 32 | 21 | 0 |
| 6268 | 1635 | 1480 | 14946 | 70 | GCAAAATCGCAATCGTTCCC | 21 | 4 | 21 | 10 | 28 | 0 |
| 6269 | 1636 | 1481 | 5946 | 71.2 | GCAACTTGCTCATGCGAGCC | 21 | 11 | 13 | 29 | 36 | 0 |
| 6270 | 1637 | 1482 | 5948 | 68.4 | GCAAGCAACTCAGACCCACG | 21 | 21 | 13 | 32 | 30 | 0 |
| 6271 | 1638 | 1483 | 5952 | 70.4 | GCAAGCAAGCTTTCCCGATG | 21 | 21 | 17 | 28 | 27 | 0 |
| 6272 | 1639 | 1484 | 40290 | 70 | GCAACAGCATACGACCGCAA | 21 | 31 | 5 | 32 | 21 | 0 |
| 6273 | 1640 | 1486 | 14955 | 68.5 | GCAAAGTGGGTACCATTGCG | 21 | 22 | 18 | 15 | 29 | 0 |
| 6274 | 1641 | 1487 | 20929 | 69.7 | ACCTTCTGAGCCCTTGCACG | 23 | 8 | 36 | 11 | 30 | 0 |
| 6275 | 1642 | 1488 | 5978 | 70.6 | ACCTTGTCCAGCTCCGGAC | 23 | 9 | 31 | 28 | 34 | 0 |
| 6276 | 1643 | 1490 | 20930 | 72 | GCAAACCTCCATTGCGGGAC | 21 | 23 | 15 | 29 | 34 | 0 |
| 6277 | 1644 | 1491 | 30333 | 68 | GCAAACCTGCAAGACCCTCA | 21 | 23 | 21 | 32 | 13 | 0 |
| 6278 | 1645 | 1492 | 40294 | 72.4 | GCAAACCTGACCGCAAAGCC | 21 | 23 | 32 | 21 | 36 | 0 |
| 6279 | 1646 | 1493 | 14961 | 71.5 | ACCTGGACGCAAGACCGACC | 23 | 34 | 21 | 32 | 32 | 0 |
| 6280 | 1647 | 1494 | 40295 | 67.3 | GCAAATCGCTCACCTAAGCC | 21 | 24 | 13 | 26 | 36 | 0 |
| 6281 | 1648 | 1495 | 30334 | 69.4 | ATCGGAGTTGTCCAGCAGCC | 24 | 20 | 9 | 31 | 36 | 0 |
| 6282 | 1649 | 1497 | 40297 | 70.8 | ATCGTCCCCAGCTGTCCCAT | 24 | 28 | 31 | 9 | 15 | 0 |
| 6283 | 1650 | 1498 | 6006 | 68.3 | GCAAATCGGACCATACGTGC | 21 | 24 | 32 | 5 | 33 | 0 |
| 6284 | 1651 | 1500 | 6010 | 71.4 | GCAAAGGATCTGTGCGGCAA | 21 | 25 | 8 | 29 | 21 | 0 |
| 6285 | 1652 | 1501 | 14971 | 72.4 | AGGACTTGGGACACGGTGCG | 25 | 11 | 34 | 35 | 29 | 0 |
| 6286 | 1653 | 1502 | 6012 | 71 | AGGACTCAGTGCAGCCGCAA | 25 | 13 | 33 | 36 | 21 | 0 |
| 6287 | 1654 | 1503 | 40298 | 66 | AGGAACCTATCGGATGCGTT | 25 | 23 | 24 | 27 | 12 | 0 |
| 6288 | 1655 | 1504 | 14972 | 70.5 | GCAAAGGAATCGCACGGGTA | 21 | 25 | 24 | 30 | 18 | 0 |
| 6289 | 1656 | 1505 | 6024 | 71.5 | CCTAGACCGCTTTCCCACGG | 26 | 32 | 17 | 28 | 35 | 0 |
| 6290 | 1657 | 1506 | 14975 | 68.3 | CCTAAGCCAGGATCGTTCCC | 26 | 36 | 25 | 10 | 28 | 0 |
| 6291 | 1658 | 1507 | 30336 | 67.4 | GATGCGTTAGTGGGACAGCC | 27 | 12 | 22 | 34 | 36 | 0 |
| 6292 | 1659 | 1508 | 14978 | 70.2 | GATGCCTACACGCGAAAGCC | 27 | 26 | 30 | 16 | 36 | 0 |
| 6293 | 1660 | 1509 | 6038 | 68.1 | GATGTGCGTTGAGACCCAGC | 27 | 29 | 1 | 32 | 31 | 0 |
| 6294 | 1661 | 1510 | 14982 | 73.4 | GCAATCCCAATCACGGCGAA | 21 | 28 | 4 | 35 | 16 | 0 |
| 6295 | 1662 | 1511 | 14983 | 70.3 | TCCCTCTGCAGCGAGTGCTT | 28 | 8 | 31 | 20 | 17 | 0 |
| 6296 | 1663 | 1512 | 30342 | 75.3 | TCCCACGGGGACAATCGTGC | 28 | 35 | 34 | 4 | 33 | 0 |
| 6297 | 1664 | 1513 | 40304 | 72.3 | TGCGTTAGGATGCCATTGCG | 29 | 3 | 27 | 15 | 29 | 0 |
| 6298 | 1665 | 1514 | 40305 | 72 | TGCGAAAGGATGCGTTCGAA | 29 | 6 | 27 | 12 | 16 | 0 |
| 6299 | 1666 | 1515 | 6065 | 71.3 | GCAATGCGTCGTCGAATCGT | 21 | 29 | 10 | 16 | 10 | 0 |
| 6300 | 1667 | 1516 | 6067 | 74.5 | GCAATGCGCGTTGTGCCTGT | 21 | 29 | 12 | 33 | 14 | 0 |
| 6301 | 1668 | 1517 | 30344 | 72.3 | TGCGCTCAACCTCGTTGTGC | 29 | 13 | 23 | 12 | 33 | 0 |
| 6302 | 1669 | 1518 | 6069 | 72.1 | TGCGCGAATCTGGATGATCG | 29 | 16 | 8 | 27 | 24 | 0 |
| 6303 | 1670 | 1519 | 6071 | 75 | TGCGCAGCGCTTTCTGATCG | 29 | 31 | 17 | 8 | 24 | 0 |
| 6304 | 1671 | 1520 | 6072 | 68.6 | TGCGGGACTTAGACCTTCCC | 29 | 34 | 3 | 23 | 28 | 1 |
| 6305 | 1672 | 1521 | 6075 | 71.6 | CACGAATCGATGCAGCGGAC | 30 | 4 | 27 | 31 | 34 | 0 |
| 6306 | 1673 | 1522 | 6077 | 71.3 | CACGTCTGCCTATGCGCCAT | 30 | 8 | 26 | 29 | 15 | 0 |
| 6307 | 1674 | 1523 | 14994 | 69.4 | CACGCGTTCTGTGGTAACGG | 30 | 12 | 14 | 18 | 35 | 0 |
| 6308 | 1675 | 1524 | 40306 | 68.8 | CACGCTCAGCAAAAAGCGTT | 30 | 13 | 21 | 6 | 12 | 0 |
| 6309 | 1676 | 1525 | 6091 | 71.9 | GCAACACGTCCCGTCTTCCC | 21 | 30 | 28 | 19 | 28 | 0 |
| 6310 | 1677 | 1526 | 15001 | 73.6 | GCAACACGGGACCACGATCG | 21 | 30 | 34 | 30 | 24 | 0 |
| 6311 | 1678 | 1527 | 15002 | 72.7 | CAGCTTGATGCGCCATCACG | 31 | 1 | 29 | 15 | 30 | 0 |
| 6312 | 1679 | 1528 | 40308 | 66.9 | CAGCTCGTAGGAATCGGCTT | 31 | 10 | 25 | 24 | 17 | 0 |
| 6313 | 1680 | 1529 | 20970 | 69.3 | CAGCCCATAGTGATCGCACG | 31 | 15 | 22 | 24 | 30 | 0 |

FIG. 29JJ

| SEQ ID NO: | ZIP ID# | 4,633 ID# | HEX ID# Tm | ZIPCODE (NH2 -> CONH2) | TETRAMER NUMBERS | | | | | "UNALLOWED DIMERS" |
|---|---|---|---|---|---|---|---|---|---|---|
| 6314 | 1681 | 1530 | 30346 67.6 | CAGCGGTAAAAGGCTTCAGC | 31 | 18 | 6 | 17 | 31 | 0 |
| 6315 | 1682 | 1531 | 30347 68.7 | CAGCGAGTAGGAGTGCCACG | 31 | 20 | 25 | 33 | 30 | 0 |
| 6316 | 1683 | 1532 | 15007 66.8 | CAGCCCTAATACAGCCCGTT | 31 | 26 | 5 | 36 | 12 | 0 |
| 6317 | 1684 | 1533 | 15008 74.4 | GCAACAGCCACGCTTGCAGC | 21 | 31 | 30 | 11 | 31 | 0 |
| 6318 | 1685 | 1534 | 40312 69.3 | GCAAGACCCCATTCGTCGTT | 21 | 32 | 15 | 10 | 12 | 0 |
| 6319 | 1686 | 1535 | 30348 67.1 | GACCACCTAATCGGACACGG | 32 | 23 | 4 | 34 | 35 | 0 |
| 6320 | 1687 | 1536 | 40313 75.1 | GCAAGACCGGACGGACCACG | 21 | 32 | 34 | 34 | 30 | 0 |
| 6321 | 1688 | 1537 | 30349 69.8 | GTGCCTTGAATCTGCGGGAC | 33 | 11 | 4 | 29 | 34 | 0 |
| 6322 | 1689 | 1538 | 30350 70.4 | GTGCCTGTCTGTTCCCACGG | 33 | 14 | 14 | 28 | 35 | 0 |
| 6323 | 1690 | 1539 | 20980 69.5 | GCAAGTGCGGTATCCCGAGT | 21 | 33 | 18 | 28 | 20 | 0 |
| 6324 | 1691 | 1540 | 40314 69.7 | GTGCGCAATTAGATCGTGCG | 33 | 21 | 3 | 24 | 29 | 0 |
| 6325 | 1692 | 1541 | 40315 72.6 | GTGCACCTGACCTCCCCACG | 33 | 23 | 32 | 28 | 30 | 0 |
| 6326 | 1693 | 1542 | 6133 70 | GTGCATCGCCTAGTGCTCCC | 33 | 24 | 26 | 33 | 28 | 0 |
| 6327 | 1694 | 1543 | 15018 71.1 | GCAAGTGCCCTAGTGCGTGC | 21 | 33 | 26 | 33 | 33 | 0 |
| 6328 | 1695 | 1544 | 6137 72.3 | GTGCTCCCGTCTGTGCCCAT | 33 | 28 | 19 | 33 | 15 | 0 |
| 6329 | 1696 | 1545 | 15020 70.9 | GCAAGTGCGTGCAAAGGCTT | 21 | 33 | 33 | 6 | 17 | 0 |
| 6330 | 1697 | 1546 | 15021 70.3 | GCAAGTGCACGGACCTTCGT | 21 | 33 | 35 | 23 | 10 | 0 |
| 6331 | 1698 | 1547 | 6142 73.4 | GGACAATCCGAATGCGGCAA | 34 | 4 | 16 | 29 | 21 | 0 |
| 6332 | 1699 | 1548 | 40316 73.8 | GGACTCGTGGACGTGCGTGC | 34 | 10 | 34 | 33 | 33 | 0 |
| 6333 | 1700 | 1549 | 30351 69.7 | GGACCTGTTCTGGCAAACGG | 34 | 14 | 8 | 21 | 35 | 0 |
| 6334 | 1701 | 1551 | 6151 71.9 | GCAAGGACATCGCCATTCCC | 21 | 34 | 24 | 15 | 28 | 0 |
| 6335 | 1702 | 1552 | 40317 69.2 | GGACCAGCTTAGGGACTGCG | 34 | 31 | 3 | 34 | 29 | 0 |
| 6336 | 1703 | 1553 | 6156 68.8 | GCAAGGACGGACAGGAGCTT | 21 | 34 | 34 | 25 | 17 | 0 |
| 6337 | 1704 | 1554 | 6159 69 | ACGGCTGTCACGTGATCGAA | 35 | 14 | 30 | 2 | 16 | 0 |
| 6338 | 1705 | 1555 | 6160 72.8 | GCAAACGGGCTTGTGCCCTA | 21 | 35 | 17 | 33 | 26 | 0 |
| 6339 | 1706 | 1556 | 40318 71 | ACGGGTCTGAGTCACGCACG | 35 | 19 | 20 | 30 | 30 | 0 |
| 6340 | 1707 | 1557 | 15029 69.9 | ACGGAGTGCTCACAGCCGTT | 35 | 22 | 13 | 31 | 12 | 0 |
| 6341 | 1708 | 1558 | 6164 73.7 | ACGGTGCGCGAAGTCTGTGC | 35 | 29 | 16 | 19 | 33 | 0 |
| 6342 | 1709 | 1559 | 6167 72.9 | ACGGGGACGATGTCTGCGAA | 35 | 34 | 27 | 8 | 16 | 0 |
| 6343 | 1710 | 1562 | 6175 69.2 | GCAAAGCCGTCTGTCTGCAA | 21 | 36 | 19 | 19 | 21 | 0 |
| 6344 | 1711 | 1563 | 6176 70.4 | GCAAAGCCACCTCCATCGAA | 21 | 36 | 23 | 15 | 16 | 0 |
| 6345 | 1712 | 1564 | 20998 66.4 | AGCCAGGAACCTAAAGGCAA | 36 | 25 | 23 | 6 | 21 | 0 |
| 6346 | 1713 | 1565 | 30357 72.1 | GCAAAGCCCCTAGTGCCGAA | 21 | 36 | 26 | 33 | 16 | 0 |
| 6347 | 1714 | 1566 | 6178 70 | AGCCTCCCTGTGGTAAGCC | 36 | 28 | 14 | 18 | 36 | 0 |
| 6348 | 1715 | 1567 | 6183 69.8 | AATCCGAAAGGAGTGCTGCG | 4 | 16 | 25 | 33 | 29 | 0 |
| 6349 | 1716 | 1568 | 6187 75.8 | AATCACGGCAGCAGCCACGG | 4 | 35 | 31 | 36 | 35 | 0 |
| 6350 | 1717 | 1569 | 6195 76.7 | TCTGCACGCAGCCACGGACC | 8 | 30 | 31 | 30 | 32 | 0 |
| 6351 | 1718 | 1570 | 6200 74.6 | TCGTACGGACCTTGCGTGCG | 10 | 35 | 23 | 29 | 29 | 0 |
| 6352 | 1719 | 1571 | 40320 69.8 | AGTGCTTGCCATAGCCAGCC | 22 | 11 | 15 | 36 | 36 | 0 |
| 6353 | 1720 | 1572 | 6205 68.4 | CTTGGGTAGGACGTGCGATG | 11 | 18 | 34 | 33 | 27 | 0 |
| 6354 | 1721 | 1573 | 15037 67.6 | CTTGCCTACCATAGCCCGAA | 11 | 26 | 15 | 36 | 16 | 0 |
| 6355 | 1722 | 1574 | 30358 69.9 | AGTGCTTGGGACTGCGGGTA | 22 | 11 | 34 | 29 | 18 | 0 |
| 6356 | 1723 | 1575 | 30359 68.6 | CGTTTCGTAGTGGGACTGCG | 12 | 10 | 22 | 34 | 29 | 0 |
| 6357 | 1724 | 1576 | 6219 70.4 | CGTTGTCTGATGCGTTTGCG | 12 | 19 | 27 | 12 | 29 | 0 |
| 6358 | 1725 | 1577 | 6230 71 | CTCATCCCGAAGGACGACC | 13 | 28 | 16 | 34 | 32 | 0 |
| 6359 | 1726 | 1578 | 30360 72.9 | CTGTTCCCATCGGTGCCAGC | 14 | 28 | 24 | 33 | 31 | 0 |
| 6360 | 1727 | 1579 | 6238 70.7 | CCATCTTGACGGCTCAACGG | 15 | 11 | 35 | 13 | 35 | 0 |
| 6361 | 1728 | 1581 | 6258 68.1 | CGAATGCGAAAGTTGAAGCC | 16 | 29 | 6 | 1 | 36 | 1 |

FIG. 29KK

| SEQ ID NO: | ZIP ID# | 4,633 ID# | HEX ID# | Tm | ZIPCODE (NH2 -> CONH2) | TETRAMER NUMBERS | | | | | 'UNALLOWED DIMERS' |
|---|---|---|---|---|---|---|---|---|---|---|---|
| 6362 | 1729 | 1582 | 40323 | 70   | GCTTCGTTCTTGCACGTCCC | 17 | 12 | 11 | 30 | 28 | 0 |
| 6363 | 1730 | 1583 | 40324 | 71.3 | GCTTTCCCGGACCCTACACG | 17 | 28 | 34 | 26 | 30 | 0 |
| 6364 | 1731 | 1584 | 6269  | 69.4 | GCTTTGCGCCTAGATGGCTT | 17 | 29 | 26 | 27 | 17 | 0 |
| 6365 | 1732 | 1585 | 6270  | 70.1 | GCTTGACCCTGTACGGCAGC | 17 | 32 | 14 | 35 | 31 | 0 |
| 6366 | 1733 | 1586 | 30364 | 70.1 | GCTTAGCCTCGTGACCCACG | 17 | 36 | 18 | 32 | 30 | 0 |
| 6367 | 1734 | 1587 | 6273  | 69.2 | GGTACGTTACGGGTGCCCAT | 18 | 12 | 35 | 33 | 15 | 0 |
| 6368 | 1735 | 1588 | 6278  | 70.3 | GGTATGCGGCTTGACCCTCA | 18 | 29 | 17 | 32 | 13 | 0 |
| 6369 | 1736 | 1589 | 6283  | 66.7 | GCAAAAGTCTGCTGTTGCG  | 21 | 6  | 8  | 14 | 29 | 0 |
| 6370 | 1737 | 1590 | 6290  | 73.7 | GCAAAGTGAGCCTGCGCAGC | 21 | 22 | 36 | 29 | 31 | 0 |
| 6371 | 1738 | 1591 | 40325 | 71.8 | GCAAGACCTCGTGTGCGTGC | 21 | 32 | 10 | 33 | 33 | 0 |
| 6372 | 1739 | 1592 | 6300  | 72.4 | ATCGCTCAACGGAGCCGGTA | 24 | 13 | 35 | 36 | 18 | 0 |
| 6373 | 1740 | 1593 | 15068 | 71   | ATCGTGCGACCTTGTCACGG | 24 | 29 | 23 | 9  | 35 | 0 |
| 6374 | 1741 | 1594 | 15069 | 72.4 | ATCGCAGCACCTTGCGGAGT | 24 | 31 | 23 | 29 | 20 | 0 |
| 6375 | 1742 | 1595 | 40327 | 74   | ATCGGTGCATCGGCTTGCAA | 24 | 33 | 24 | 17 | 21 | 0 |
| 6376 | 1743 | 1596 | 15071 | 73.4 | ATCGACGGGGTATCCCACGG | 24 | 35 | 18 | 28 | 35 | 0 |
| 6377 | 1744 | 1597 | 6313  | 68   | CCTATCCCCTTGGCTTCGTT | 26 | 28 | 11 | 17 | 12 | 0 |
| 6378 | 1745 | 1598 | 6316  | 75.2 | CCTACAGCGCAATGCGCACG | 26 | 31 | 21 | 29 | 30 | 0 |
| 6379 | 1746 | 1599 | 21014 | 71   | CCTAGTGCGCTTACGGGCAA | 26 | 33 | 17 | 35 | 21 | 0 |
| 6380 | 1747 | 1600 | 6325  | 72.6 | GATGAGCCGGACACGGCCTA | 27 | 36 | 34 | 35 | 26 | 0 |
| 6381 | 1748 | 1601 | 15080 | 72.3 | TCCCTCGTAGCCAGCCAGGA | 28 | 10 | 36 | 36 | 25 | 0 |
| 6382 | 1749 | 1602 | 6329  | 74.7 | TCCCCTGTTCCCGATGCAGC | 28 | 14 | 28 | 27 | 31 | 0 |
| 6383 | 1750 | 1604 | 6337  | 71.1 | TCCCGTGCATACCGAAATCG | 28 | 33 | 5  | 16 | 24 | 0 |
| 6384 | 1751 | 1605 | 6341  | 75.3 | TGCGAATCTGCGCAGCAGGA | 29 | 4  | 29 | 31 | 25 | 0 |
| 6385 | 1752 | 1606 | 6343  | 74.4 | TGCGCTTGGTCTGACCACGG | 29 | 11 | 19 | 32 | 35 | 0 |
| 6386 | 1753 | 1607 | 6347  | 72.5 | TGCGCGAACTGTGATGCCAT | 29 | 16 | 14 | 27 | 15 | 0 |
| 6387 | 1754 | 1608 | 30366 | 70   | TGCGCCTAGAGTAGCCGCTT | 29 | 26 | 20 | 36 | 17 | 0 |
| 6388 | 1755 | 1609 | 15086 | 73.4 | TGCGTGCGTACACACGCCAT | 29 | 29 | 7  | 30 | 15 | 0 |
| 6389 | 1756 | 1610 | 40331 | 67.8 | AGTGCACGCGTTAAAGAGCC | 22 | 30 | 12 | 6  | 36 | 0 |
| 6390 | 1757 | 1611 | 15088 | 70.3 | CACGCGAATACACAGCACGG | 30 | 16 | 7  | 31 | 35 | 0 |
| 6391 | 1758 | 1612 | 40332 | 72.1 | CACGTGCGCGTTTACAAGCC | 30 | 29 | 12 | 7  | 36 | 0 |
| 6392 | 1759 | 1613 | 30369 | 68.5 | CACGGACCTTAGAGCCCCAT | 30 | 32 | 3  | 36 | 15 | 0 |
| 6393 | 1760 | 1614 | 15093 | 67.6 | CAGCGCTTCCTAAAAGGTGC | 31 | 17 | 26 | 6  | 33 | 0 |
| 6394 | 1761 | 1615 | 6392  | 68.5 | GACCGCAACCTAGTGCATCG | 32 | 21 | 26 | 33 | 24 | 0 |
| 6395 | 1762 | 1616 | 40333 | 70.8 | GACCGGACTCTGTCCCGACC | 32 | 34 | 8  | 28 | 32 | 0 |
| 6396 | 1763 | 1617 | 21032 | 67.2 | GTGCAATCCTCAGTGCTCCC | 33 | 4  | 13 | 33 | 28 | 0 |
| 6397 | 1764 | 1618 | 30374 | 69.8 | GTGCCCATCGAAGCTTGGAC | 33 | 15 | 16 | 17 | 34 | 0 |
| 6398 | 1765 | 1619 | 15105 | 66.6 | GTGCGTCTATACTGCGCAGC | 33 | 19 | 5  | 29 | 31 | 0 |
| 6399 | 1766 | 1620 | 40334 | 69.8 | GTGCGAGTCCTATGCGGACC | 33 | 20 | 26 | 29 | 32 | 0 |
| 6400 | 1767 | 1621 | 6416  | 68.3 | GGACTCGTCTTGATCGTGCG | 34 | 10 | 11 | 24 | 29 | 0 |
| 6401 | 1768 | 1622 | 40335 | 67.3 | GGACCCATAATCCTTGTGCG | 34 | 15 | 4  | 11 | 29 | 0 |
| 6402 | 1769 | 1623 | 30377 | 75.6 | ACGGCTCAGTGCTGCGCCAT | 35 | 13 | 33 | 29 | 15 | 0 |
| 6403 | 1770 | 1624 | 30378 | 71.4 | ACGGGTACTTGGGACGTGC  | 35 | 18 | 11 | 34 | 33 | 0 |
| 6404 | 1771 | 1625 | 30379 | 70.7 | ACGGGATGTGATTCCCCGTT | 35 | 27 | 2  | 28 | 12 | 0 |
| 6405 | 1772 | 1626 | 6444  | 73.2 | ACGGGGACGTCTTCCCAGGA | 35 | 34 | 19 | 28 | 25 | 0 |
| 6406 | 1773 | 1627 | 15116 | 70.3 | AGCCCTTGATACCAGCGCAA | 36 | 11 | 5  | 31 | 21 | 0 |
| 6407 | 1774 | 1628 | 15118 | 70.4 | AGCCATCGAAAGCGTTCGAA | 36 | 24 | 6  | 12 | 16 | 0 |
| 6408 | 1775 | 1629 | 15120 | 74.1 | AGCCGGACGTCTAGCCACGG | 36 | 34 | 19 | 36 | 35 | 0 |
| 6409 | 1776 | 1630 | 6461  | 71.6 | TTGACGAATGCGACGGTCGT | 1  | 16 | 29 | 35 | 10 | 0 |

FIG. 29LL

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 6410 | 1777 | 1631 | 30380 | 69.9 | ACCTTGATTGCGTGCGGTCT | 23 | 2 | 29 | 29 | 19 | 0 |
| 6411 | 1778 | 1633 | 6493 | 69.5 | ACCTTCTGCTTGTGCGGCTT | 23 | 8 | 11 | 29 | 17 | 0 |
| 6412 | 1779 | 1634 | 40339 | 73.8 | TCTGTGCGCAGCGTCTTCCC | 8 | 29 | 31 | 19 | 28 | 0 |
| 6413 | 1780 | 1635 | 6505 | 72.3 | TGTCCCATGTGCCCATCACG | 9 | 15 | 33 | 15 | 30 | 0 |
| 6414 | 1781 | 1636 | 30382 | 71.5 | TCGTTCGTATCGTGCGAGCC | 10 | 10 | 24 | 29 | 36 | 0 |
| 6415 | 1782 | 1637 | 40340 | 71.3 | TCGTCGTTACGGCCATACGG | 10 | 12 | 35 | 15 | 35 | 0 |
| 6416 | 1783 | 1638 | 6521 | 68.1 | TCGTTCCCTTAGGATGTGCG | 10 | 28 | 3 | 27 | 29 | 0 |
| 6417 | 1784 | 1639 | 40341 | 76.1 | TCGTCAGCACGGTGCGCTCA | 10 | 31 | 35 | 29 | 13 | 0 |
| 6418 | 1785 | 1640 | 30383 | 71.3 | CTTGGCTTCCTATGCGTGCG | 11 | 17 | 26 | 29 | 29 | 0 |
| 6419 | 1786 | 1642 | 6539 | 71.5 | CGTTCTTGCCATACGGCGAA | 12 | 11 | 15 | 35 | 16 | 0 |
| 6420 | 1787 | 1643 | 6540 | 68.3 | CGTTCCATAGCCCTGTGTGC | 12 | 15 | 36 | 14 | 33 | 0 |
| 6421 | 1788 | 1644 | 6549 | 71.7 | CCATCACGGCTTGAGTTGCG | 15 | 30 | 17 | 20 | 29 | 0 |
| 6422 | 1789 | 1645 | 6551 | 71.2 | CCATACGGGATGCACGCCTA | 15 | 35 | 27 | 30 | 26 | 0 |
| 6423 | 1790 | 1646 | 30384 | 70 | CGAACGTTAGCCCAGCGAGT | 16 | 12 | 36 | 31 | 20 | 0 |
| 6424 | 1791 | 1648 | 6558 | 72.1 | CGAAGGTATGCGCTCATGCG | 16 | 18 | 29 | 13 | 29 | 0 |
| 6425 | 1792 | 1649 | 6569 | 69.3 | ACCTGCTTCTTGTCCCCACG | 23 | 17 | 11 | 28 | 30 | 1 |
| 6426 | 1793 | 1651 | 6575 | 70.3 | ACCTGCTTTGCGGAGTCGAA | 23 | 17 | 29 | 20 | 16 | 0 |
| 6427 | 1794 | 1652 | 40344 | 74.4 | GCTTCAGCCTTGCACGTGCG | 17 | 31 | 11 | 30 | 29 | 0 |
| 6428 | 1795 | 1653 | 6589 | 73.5 | GCAATGATGCAATGCGTGCG | 21 | 2 | 21 | 29 | 29 | 0 |
| 6429 | 1796 | 1654 | 21067 | 67.7 | GCAAGAGTCTTGGTGCAGCC | 21 | 20 | 11 | 33 | 36 | 0 |
| 6430 | 1797 | 1656 | 6602 | 70.4 | AGTGCCATTCTGCAGCGCTT | 22 | 15 | 8 | 31 | 17 | 0 |
| 6431 | 1798 | 1657 | 6638 | 71.7 | TCCCAATCGATGGTGCATCG | 28 | 4 | 27 | 33 | 24 | 0 |
| 6432 | 1799 | 1658 | 40349 | 71.1 | TCCCAAAGTGATTGCGGTGC | 28 | 6 | 2 | 29 | 33 | 0 |
| 6433 | 1800 | 1659 | 30387 | 69.8 | TCCCCTGTCAGCGAGTTCGT | 28 | 14 | 31 | 20 | 10 | 0 |
| 6434 | 1801 | 1660 | 30388 | 70.7 | TCCCACCTCGAACACGCCTA | 28 | 23 | 16 | 30 | 26 | 0 |
| 6435 | 1802 | 1661 | 15188 | 71.2 | TCCCATCGTCGTCACGTCGT | 28 | 24 | 10 | 30 | 10 | 0 |
| 6436 | 1803 | 1662 | 21077 | 70.5 | ACCTTCCCCCTAAGCCTCCC | 23 | 28 | 26 | 36 | 28 | 1 |
| 6437 | 1804 | 1663 | 6652 | 73.3 | TCCCACGGCTCAGATGACGG | 28 | 35 | 13 | 27 | 35 | 0 |
| 6438 | 1805 | 1664 | 30389 | 70.1 | TGCGTTGATGATTGCGTCGT | 29 | 1 | 2 | 29 | 10 | 0 |
| 6439 | 1806 | 1665 | 6665 | 71.3 | TGCGCGAAAAAGTCGTCGTT | 29 | 16 | 6 | 10 | 12 | 0 |
| 6440 | 1807 | 1666 | 6666 | 72.2 | TGCGGCTTGCTTTCGTCTCA | 29 | 17 | 17 | 10 | 13 | 0 |
| 6441 | 1808 | 1667 | 6671 | 75.1 | TGCGACGGCAGCACCTCTCA | 29 | 35 | 31 | 23 | 13 | 0 |
| 6442 | 1809 | 1668 | 6672 | 73 | CACGAAAGTCCCAGCCACGG | 30 | 6 | 28 | 36 | 35 | 1 |
| 6443 | 1810 | 1669 | 15189 | 71 | ACCTCACGGTCTTCCCCGAA | 23 | 30 | 19 | 28 | 16 | 0 |
| 6444 | 1811 | 1670 | 6678 | 69.2 | CACGGAGTCTGTACGGTGCG | 30 | 28 | 14 | 35 | 29 | 0 |
| 6445 | 1812 | 1671 | 15190 | 73.2 | CACGTCCCCATACGGCTCA | 30 | 28 | 15 | 35 | 13 | 0 |
| 6446 | 1813 | 1672 | 40354 | 69.4 | GACCCGAACTGTGGACCAGC | 32 | 16 | 14 | 34 | 31 | 0 |
| 6447 | 1814 | 1673 | 30390 | 69.7 | ACCTGACCCACGAAAGGCAA | 23 | 32 | 30 | 6 | 21 | 0 |
| 6448 | 1815 | 1674 | 21097 | 70.8 | ACCTGACCACGGTTGATGCG | 23 | 32 | 35 | 1 | 29 | 1 |
| 6449 | 1816 | 1676 | 6711 | 68.3 | GTGCCTCAGCAAGATGACGG | 33 | 13 | 21 | 27 | 35 | 0 |
| 6450 | 1817 | 1677 | 30391 | 73.1 | GTGCGAGTCGAAACGGGTGC | 33 | 20 | 16 | 35 | 33 | 0 |
| 6451 | 1818 | 1678 | 15203 | 71.8 | GTGCACCTCAGCGATGCAGC | 33 | 23 | 31 | 27 | 31 | 0 |
| 6452 | 1819 | 1679 | 15205 | 72.2 | ACCTGTGCAGGATCCCACGG | 23 | 33 | 25 | 28 | 35 | 0 |
| 6453 | 1820 | 1680 | 30392 | 70.4 | GTGCCCTACACGGGACATCG | 33 | 26 | 30 | 34 | 24 | 0 |
| 6454 | 1821 | 1681 | 15207 | 69.6 | GGACCTTGCGAATCGCTT | 34 | 11 | 29 | 4 | 17 | 0 |
| 6455 | 1822 | 1682 | 15212 | 70.5 | ACCTGGACGATGTGCGCTGT | 23 | 34 | 27 | 29 | 14 | 0 |
| 6456 | 1823 | 1683 | 15213 | 69.7 | GGACTCCCTCGTCAGCGATG | 34 | 28 | 10 | 31 | 27 | 0 |
| 6457 | 1824 | 1684 | 30393 | 72 | GGACAGCCAATCCACGAGCC | 34 | 36 | 4 | 30 | 36 | 0 |

FIG. 29MM

| SEQ ID NO: | ZIP ID# | 4,633 ID# | HEX ID# | Tm | ZIPCODE (NH2 -> CONH2) | TETRAMER NUMBERS | | | | "UNALLOWED DIMERS" |
|---|---|---|---|---|---|---|---|---|---|---|
| 6458 | 1825 | 1685 | 6736 | 71.4 | ACGGTTGACGAAGCAATGCG | 35 | 1 | 16 | 21 29 | 1 |
| 6459 | 1826 | 1686 | 30394 | 70.4 | ACGGCGTTCGAAGCTTGGTA | 35 | 12 | 16 | 17 18 | 0 |
| 6460 | 1827 | 1687 | 6766 | 74.3 | TTGACGAAAGCCAGCCGCAA | 1 | 16 | 36 | 36 21 | 0 |
| 6461 | 1828 | 1688 | 6770 | 71 | TTGAAGGATGCGGACCATCG | 1 | 25 | 29 | 32 24 | 0 |
| 6462 | 1829 | 1689 | 30398 | 69.5 | TTGAACGGTGCGTCTGGATG | 1 | 35 | 29 | 8 27 | 0 |
| 6463 | 1830 | 1690 | 6773 | 75.7 | TGATCACGGTGCACGGCGAA | 2 | 30 | 33 | 35 16 | 0 |
| 6464 | 1831 | 1691 | 6779 | 69 | TTAGGTGCACCTTGCGCCTA | 3 | 33 | 23 | 29 26 | 0 |
| 6465 | 1832 | 1692 | 30399 | 70.4 | ATCGAATCCGTTACGGTGCG | 24 | 4 | 12 | 35 29 | 0 |
| 6466 | 1833 | 1693 | 6781 | 67.9 | AATCCTCAATCGGCAACACG | 4 | 13 | 24 | 21 30 | 0 |
| 6467 | 1834 | 1694 | 6783 | 72.3 | AATCATCGGGACAGCCACGG | 4 | 24 | 34 | 36 35 | 0 |
| 6468 | 1835 | 1695 | 40358 | 72.4 | AATCGACCTGCGTCCCATCG | 4 | 32 | 29 | 28 24 | 0 |
| 6469 | 1836 | 1696 | 6789 | 69.2 | AATCGGACCTTGATCGGTGC | 4 | 34 | 11 | 24 33 | 0 |
| 6470 | 1837 | 1697 | 6793 | 68.2 | ATCGATACGCTTTGCGCTGT | 24 | 5 | 17 | 29 14 | 0 |
| 6471 | 1838 | 1698 | 6796 | 73 | ATACCAGCCCATTGCGGCAA | 5 | 31 | 15 | 29 21 | 0 |
| 6472 | 1839 | 1699 | 6797 | 68.5 | ATACACGGTTGAACGGCGAA | 5 | 35 | 1 | 35 16 | 1 |
| 6473 | 1840 | 1701 | 40360 | 72.1 | TCTGCCATGCTTCACGACGG | 8 | 15 | 17 | 30 35 | 0 |
| 6474 | 1841 | 1702 | 6814 | 70.6 | TCTGCCTAAGCCGATGACGG | 8 | 26 | 36 | 27 35 | 0 |
| 6475 | 1842 | 1703 | 6815 | 72.7 | TCTGCAGCGGACAGTGGCAA | 8 | 31 | 34 | 22 21 | 0 |
| 6476 | 1843 | 1704 | 6820 | 70.3 | TGTCCCATTCGTGCAACACG | 9 | 15 | 10 | 21 30 | 0 |
| 6477 | 1844 | 1705 | 21109 | 76.2 | TGTCGTGCGATGACGGTGCG | 9 | 33 | 27 | 35 29 | 0 |
| 6478 | 1845 | 1706 | 6828 | 72.4 | TCGTTTGACACGGGACGCAA | 10 | 1 | 30 | 34 21 | 0 |
| 6479 | 1846 | 1707 | 6837 | 72.4 | TCGTGATGGGACGCTTTCCC | 10 | 27 | 34 | 17 28 | 0 |
| 6480 | 1847 | 1708 | 21110 | 68.3 | TCGTGTGCTTGACTGTTGCG | 10 | 33 | 1 | 14 29 | 0 |
| 6481 | 1848 | 1709 | 6841 | 71.3 | TCGTAGCCCAGCTCTGCGAA | 10 | 36 | 31 | 8 16 | 0 |
| 6482 | 1849 | 1711 | 15250 | 71.5 | ATCGCTTGCTTGCGAAGCAA | 24 | 11 | 11 | 16 21 | 0 |
| 6483 | 1850 | 1713 | 30401 | 70.5 | ATCGCTTGGGTATCGTTGCG | 24 | 11 | 18 | 19 29 | 0 |
| 6484 | 1851 | 1714 | 30402 | 67 | ATCGCTTGACCTTGTCGCTT | 24 | 11 | 23 | 9 17 | 0 |
| 6485 | 1852 | 1715 | 40364 | 65.4 | CTTGCCTATGATCAGCAGCC | 11 | 26 | 2 | 31 36 | 0 |
| 6486 | 1853 | 1716 | 15254 | 71.8 | ATCGCTTGCACGGAGTTCCC | 24 | 11 | 30 | 20 28 | 0 |
| 6487 | 1854 | 1717 | 30403 | 65.9 | CGTTTGATACGGTCTGGTGC | 12 | 2 | 35 | 8 33 | 0 |
| 6488 | 1855 | 1718 | 30404 | 66.9 | CGTTTTAGGCTTAGCCGCTT | 12 | 3 | 17 | 36 17 | 0 |
| 6489 | 1856 | 1719 | 6860 | 67.3 | ATCGCGTTAAAGCACGGTCT | 24 | 12 | 6 | 30 19 | 0 |
| 6490 | 1857 | 1720 | 6865 | 69 | ATCGCGTTCTTGGGTAAGCC | 24 | 12 | 11 | 18 36 | 0 |
| 6491 | 1858 | 1721 | 30405 | 71.5 | ATCGCGTTCGTTCAGCATCG | 24 | 12 | 12 | 31 24 | 0 |
| 6492 | 1859 | 1722 | 30406 | 72.2 | ATCGCGTTCTGTTCCCCGAA | 24 | 12 | 14 | 28 16 | 0 |
| 6493 | 1860 | 1723 | 40366 | 67.9 | ATCGCGTTGGTATGTCCAGC | 24 | 12 | 18 | 9 31 | 0 |
| 6494 | 1861 | 1725 | 6871 | 66.9 | CGTTAGTGTCTGACGGCACG | 12 | 22 | 8 | 35 30 | 0 |
| 6495 | 1862 | 1726 | 6873 | 66.7 | CGTTATCGGCTTAGTGCACG | 12 | 24 | 17 | 22 30 | 0 |
| 6496 | 1863 | 1727 | 6874 | 65.1 | CGTTGATGTACACCATTGCG | 12 | 27 | 7 | 15 29 | 0 |
| 6497 | 1864 | 1728 | 6877 | 67.3 | ATCGCGTTGGACTACAAGCC | 24 | 12 | 34 | 7 36 | 0 |
| 6498 | 1865 | 1729 | 6880 | 67.9 | CTCATGATACGGTCCCCACG | 13 | 2 | 35 | 28 30 | 1 |
| 6499 | 1866 | 1731 | 30407 | 70.1 | ATCGCTCACGTTTGCGACCT | 24 | 13 | 12 | 29 23 | 0 |
| 6500 | 1867 | 1732 | 6886 | 68.5 | CTCAGATGGCAAGACCTGCG | 13 | 27 | 21 | 32 29 | 0 |
| 6501 | 1868 | 1733 | 6894 | 70.9 | CTGTTGATTCCCAGCCTGCG | 14 | 2 | 28 | 36 29 | 0 |
| 6502 | 1869 | 1734 | 6895 | 72.1 | ATCGCTGTTGTCCACGCACG | 24 | 14 | 9 | 30 30 | 0 |
| 6503 | 1870 | 1735 | 6896 | 72.1 | CTGTCTTGCCATTGCGCAGC | 14 | 11 | 15 | 29 31 | 0 |
| 6504 | 1871 | 1736 | 15268 | 69.7 | ATCGCTGTGCAATGCGTGTC | 24 | 14 | 21 | 29 9 | 0 |
| 6505 | 1872 | 1738 | 15270 | 71.1 | ATCGCTGTTGCGCGTTTGAT | 24 | 14 | 29 | 12 2 | 0 |

FIG. 29NN

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 6506 | 1873 | 1739 | 30408 | 69 | ATCGCTGTCACGAATCTGCG | 24 | 14 | 30 | 4 | 29 | 0 |
| 6507 | 1874 | 1740 | 30409 | 71.4 | CTGTGACCGACCCTCATGCG | 14 | 32 | 32 | 13 | 29 | 0 |
| 6508 | 1875 | 1741 | 30410 | 68.2 | ATCGCCATTTGATGCGTGAT | 24 | 15 | 1 | 29 | 2 | 0 |
| 6509 | 1876 | 1742 | 15272 | 66.6 | CCATTGATCGAACTTGCAA | 15 | 2 | 16 | 11 | 16 | 0 |
| 6510 | 1877 | 1744 | 30411 | 66.9 | ATCGCCATTCGTAATCCGTT | 24 | 15 | 10 | 4 | 12 | 0 |
| 6511 | 1878 | 1745 | 30412 | 65.2 | ATCGCCATCTTGAAAGCTTG | 24 | 15 | 11 | 6 | 11 | 0 |
| 6512 | 1879 | 1746 | 30413 | 68.5 | ATCGCCATCTCACTTGCAA | 24 | 15 | 13 | 11 | 16 | 0 |
| 6513 | 1880 | 1747 | 6918 | 68.8 | ATCGCCATGCTTCTGTGTGC | 24 | 15 | 17 | 14 | 33 | 0 |
| 6514 | 1881 | 1748 | 30414 | 70.6 | ATCGCCATAGGAAGCCCGTT | 24 | 15 | 25 | 36 | 12 | 0 |
| 6515 | 1882 | 1749 | 40369 | 68.7 | ATCGCCATCCTAAGGAACGG | 24 | 15 | 26 | 25 | 35 | 0 |
| 6516 | 1883 | 1750 | 30415 | 68.7 | ATCGCCATGTGCTTAGGCAA | 24 | 15 | 33 | 3 | 21 | 0 |
| 6517 | 1884 | 1751 | 6929 | 67.4 | CGAAATACCTCATCCCACGG | 16 | 5 | 13 | 28 | 35 | 0 |
| 6518 | 1885 | 1752 | 6932 | 71.5 | ATCGCGAATCTGCTCATGCG | 24 | 16 | 8 | 13 | 29 | 0 |
| 6519 | 1886 | 1753 | 21122 | 66.2 | CGAATCGTGGTAAATCGTGC | 16 | 10 | 18 | 4 | 33 | 0 |
| 6520 | 1887 | 1754 | 40370 | 69.1 | ATCGCGAACTGTCTTGCACG | 24 | 16 | 14 | 11 | 30 | 0 |
| 6521 | 1888 | 1755 | 6936 | 64.4 | CGAAGGTATTGAGACCAGCC | 16 | 18 | 1 | 32 | 36 | 0 |
| 6522 | 1889 | 1756 | 6937 | 68.1 | ATCGCGAAGTCTCGAAGCAA | 24 | 16 | 19 | 16 | 21 | 0 |
| 6523 | 1890 | 1757 | 30416 | 67.5 | ATCGCGAAACCTCCATGGTA | 24 | 16 | 23 | 15 | 18 | 0 |
| 6524 | 1891 | 1758 | 15285 | 67.1 | ATCGCGAACCTACAGCTCGT | 24 | 16 | 26 | 31 | 10 | 0 |
| 6525 | 1892 | 1759 | 6943 | 75 | ATCGCGAATGCGTGTCGCAA | 24 | 16 | 29 | 9 | 21 | 0 |
| 6526 | 1893 | 1760 | 30417 | 68.2 | CGAAGACCATACCACGACGG | 16 | 32 | 5 | 30 | 35 | 0 |
| 6527 | 1894 | 1761 | 21125 | 68.5 | GCTTTTAGCCATCAGCTGCG | 17 | 3 | 15 | 31 | 29 | 0 |
| 6528 | 1895 | 1762 | 6947 | 65.9 | GCTTTACACCATGTGCGGAC | 17 | 7 | 15 | 33 | 34 | 0 |
| 6529 | 1896 | 1763 | 40373 | 65.2 | GCTTTCTGTTGACAGCGACC | 17 | 8 | 1 | 31 | 32 | 0 |
| 6530 | 1897 | 1764 | 6950 | 68.9 | ATCGGCTTCGTTGACCACCT | 24 | 17 | 12 | 32 | 23 | 0 |
| 6531 | 1898 | 1765 | 30418 | 66.7 | GCTTCTGTATCGGACCCAGC | 17 | 14 | 24 | 32 | 31 | 0 |
| 6532 | 1899 | 1767 | 6958 | 67.9 | ATCGGCTTGTGCTTAGCAGC | 24 | 17 | 33 | 3 | 31 | 0 |
| 6533 | 1900 | 1768 | 40375 | 65 | GGTACGTTAGGACACGCGTT | 18 | 12 | 25 | 30 | 12 | 0 |
| 6534 | 1901 | 1769 | 15292 | 65.4 | GGTAGCAAGTCTCAGCGTGC | 18 | 21 | 19 | 31 | 33 | 0 |
| 6535 | 1902 | 1770 | 6968 | 66.8 | ATCGGGTAAGGAACCTGCAA | 24 | 18 | 25 | 23 | 21 | 0 |
| 6536 | 1903 | 1771 | 15294 | 67.5 | ATCGGGTATCCCAGGACCAT | 24 | 18 | 28 | 25 | 15 | 0 |
| 6537 | 1904 | 1772 | 6974 | 65.3 | ATCGGGTAACGGTACAGCAA | 24 | 18 | 35 | 7 | 21 | 0 |
| 6538 | 1905 | 1773 | 30421 | 66.5 | ATCGGGTAAGCCTGATACGG | 24 | 18 | 36 | 2 | 35 | 0 |
| 6539 | 1906 | 1774 | 15298 | 67.8 | ATCGGTCTCGAAAATCGCAA | 24 | 19 | 16 | 4 | 21 | 0 |
| 6540 | 1907 | 1775 | 40376 | 67.2 | ATCGGTCTGCTTAGCCGGTA | 24 | 19 | 17 | 36 | 18 | 0 |
| 6541 | 1908 | 1776 | 6981 | 69.8 | GTCTATCGCACGGGACCAGC | 19 | 24 | 30 | 34 | 31 | 0 |
| 6542 | 1909 | 1777 | 6986 | 69.1 | ATCGGTCTACGGCCATGGAC | 24 | 19 | 35 | 15 | 34 | 0 |
| 6543 | 1910 | 1778 | 40377 | 67.5 | GAGTGCAAGCTTGACCGGAC | 20 | 21 | 17 | 32 | 34 | 0 |
| 6544 | 1911 | 1779 | 6990 | 69.6 | GAGTATCGCTTGCAGCGCAA | 20 | 24 | 11 | 31 | 21 | 0 |
| 6545 | 1912 | 1780 | 6992 | 65.5 | GAGTCAGCTTAGACGGCACG | 20 | 31 | 3 | 35 | 30 | 0 |
| 6546 | 1913 | 1782 | 40378 | 69.8 | ATCGGCAATGATTGCGACCT | 24 | 21 | 2 | 29 | 23 | 0 |
| 6547 | 1914 | 1783 | 15303 | 66.4 | ATCGGCAATACAAATCGCAA | 24 | 21 | 7 | 4 | 21 | 0 |
| 6548 | 1915 | 1784 | 30422 | 68.3 | GCAATGTCTCCCTCTGCACG | 21 | 9 | 28 | 8 | 30 | 0 |
| 6549 | 1916 | 1785 | 40379 | 67.5 | GCAACTCAAAAGGGACCACG | 21 | 13 | 6 | 34 | 30 | 0 |
| 6550 | 1917 | 1786 | 40380 | 65.7 | GCAACCATACCTTCTGGCAA | 21 | 15 | 23 | 8 | 21 | 0 |
| 6551 | 1918 | 1787 | 40381 | 65.9 | GCAAGCTTTTAGATCGCGAA | 21 | 17 | 3 | 24 | 16 | 0 |
| 6552 | 1919 | 1788 | 40382 | 66.2 | ATCGGCAAGAGTAGCCGTCT | 24 | 21 | 20 | 36 | 19 | 0 |
| 6553 | 1920 | 1789 | 15309 | 66.9 | GCAAGCAATCGTAGTGGCAA | 21 | 21 | 10 | 22 | 21 | 0 |

FIG. 29OO

| SEQ ID NO: | ZIP ID# | 4,633 ID# | BBX ID# | Tm | ZIPCODE (NH2 -> CONH2) | TETRAMER NUMBERS | | | | "UNALLOWED DIMERS" |
|---|---|---|---|---|---|---|---|---|---|---|
| 6554 | 1921 | 1790 | 7008 | 68.2 | ATCGGCAAAGTGCTTGATCG | 24 21 22 11 24 | | | | 0 |
| 6555 | 1922 | 1791 | 30423 | 69.5 | ATCGGCAAAGGAAGTGGTGC | 24 21 25 22 33 | | | | 0 |
| 6556 | 1923 | 1792 | 7013 | 68.4 | ATCGGCAACAGCAGTGCTGT | 24 21 31 22 14 | | | | 0 |
| 6557 | 1924 | 1793 | 7015 | 67.5 | ATCGGCAAGGACTGTCGGTA | 24 21 34 9 18 | | | | 0 |
| 6558 | 1925 | 1795 | 7019 | 68.4 | AGTGCGAATGATGGACCACG | 22 16 2 34 30 | | | | 0 |
| 6559 | 1926 | 1796 | 7022 | 68.7 | ATCGAGTGCCTATGCGCTCA | 24 22 26 29 13 | | | | 0 |
| 6560 | 1927 | 1797 | 30424 | 69.5 | AGTGGTGCTTGAACGGAGCC | 22 33 1 35 36 | | | | 0 |
| 6561 | 1928 | 1798 | 7026 | 71.4 | ACCTGGTAACGGCACGGACC | 23 18 35 30 32 | | | | 0 |
| 6562 | 1929 | 1799 | 7027 | 67 | ACCTGCAATCTGAGGAACGG | 23 21 8 25 35 | | | | 0 |
| 6563 | 1930 | 1800 | 7032 | 73.2 | ATCGACCTGGACCACGTGCG | 24 23 34 30 29 | | | | 0 |
| 6564 | 1931 | 1801 | 30425 | 71.2 | ATCGCTGTATCGCAGCCGAA | 24 14 24 31 16 | | | | 0 |
| 6565 | 1932 | 1802 | 30426 | 67.6 | ATCGGCTTAGGAGACCCGTT | 24 17 25 32 12 | | | | 0 |
| 6566 | 1933 | 1803 | 15317 | 70.8 | ATCGATCGAGGAAGCCGGAC | 24 24 25 36 34 | | | | 0 |
| 6567 | 1934 | 1804 | 30427 | 72.5 | ATCGGTGCCGTTTGTCAGCC | 24 33 12 9 36 | | | | 0 |
| 6568 | 1935 | 1805 | 21139 | 69 | AGGAACCTGCTTAGCCCACG | 25 23 17 36 30 | | | | 0 |
| 6569 | 1936 | 1806 | 7049 | 70.7 | AGGAATCGGTGCCTGTGCAA | 25 24 33 14 21 | | | | 0 |
| 6570 | 1937 | 1807 | 7056 | 67.5 | ATCGCCTATGATACGGCAGC | 24 26 2 35 31 | | | | 0 |
| 6571 | 1938 | 1808 | 15323 | 67.5 | CCTAAAAGCTCAAGCCACGG | 26 6 13 36 35 | | | | 0 |
| 6572 | 1939 | 1809 | 7059 | 70.3 | ATCGCCTATGTCCCATTGCG | 24 26 9 15 29 | | | | 0 |
| 6573 | 1940 | 1810 | 30428 | 66.8 | ATCGCCTACGTTTCGTCCAT | 24 26 12 10 15 | | | | 0 |
| 6574 | 1941 | 1811 | 30429 | 68.6 | ATCGCCTAGCTTTCCCCTCA | 24 26 17 28 13 | | | | 0 |
| 6575 | 1942 | 1812 | 30430 | 65.5 | CCTAAGGAATACACGGCACG | 26 25 5 35 30 | | | | 0 |
| 6576 | 1943 | 1814 | 21141 | 69.2 | ATCGCCTATGCGGGTATCGT | 24 26 29 18 10 | | | | 0 |
| 6577 | 1944 | 1815 | 15327 | 69.4 | ATCGCCTACACGGCTTCGTT | 24 26 30 17 12 | | | | 0 |
| 6578 | 1945 | 1816 | 7073 | 68.8 | GATGTTGAGCAAAGCCTGCG | 27 1 21 36 29 | | | | 0 |
| 6579 | 1946 | 1817 | 40389 | 70.2 | GATGTCGTGGACGACCAGCC | 27 10 34 32 36 | | | | 0 |
| 6580 | 1947 | 1818 | 30432 | 67 | GATGCTCAACGGAATCCGTT | 27 13 35 4 12 | | | | 0 |
| 6581 | 1948 | 1819 | 15330 | 67.9 | ATCGGATGCTGTCGTTACGG | 24 27 14 12 35 | | | | 0 |
| 6582 | 1949 | 1820 | 15331 | 70.4 | GATGGTCTGTGCCAGCGGAC | 27 19 33 31 34 | | | | 0 |
| 6583 | 1950 | 1821 | 40390 | 69.1 | ATCGGATGATCGAGGAACGG | 24 27 24 25 35 | | | | 0 |
| 6584 | 1951 | 1822 | 30433 | 66.6 | GATGCCTAGTCTTCCCCACG | 27 26 19 28 30 | | | | 0 |
| 6585 | 1952 | 1823 | 7082 | 70.3 | GATGTGCGCTTGTGATTGCG | 27 29 11 2 29 | | | | 0 |
| 6586 | 1953 | 1824 | 30434 | 72.4 | ATCGGATGCACGCTTGGCTT | 24 27 30 11 17 | | | | 0 |
| 6587 | 1954 | 1825 | 7083 | 68.5 | ATCGGATGCAGCTTAGTGCG | 24 27 31 3 29 | | | | 0 |
| 6578 | 1955 | 1826 | 30435 | 68.5 | ATCGGATGGGACAGCCTGAT | 24 27 34 36 2 | | | | 0 |
| 6589 | 1956 | 1827 | 40391 | 71.4 | ATCGGATGACGGCTTGTCCC | 24 27 35 11 28 | | | | 1 |
| 6590 | 1957 | 1828 | 15335 | 76.6 | TCCCTGTCCGAATGCGCACG | 28 9 16 29 30 | | | | 0 |
| 6591 | 1958 | 1829 | 30437 | 69.6 | TCCCAGGATCGTGCTTAGCC | 28 25 10 17 36 | | | | 0 |
| 6592 | 1959 | 1830 | 30438 | 71.6 | TCCCGATGCCTACGTTTCCC | 28 27 26 12 28 | | | | 1 |
| 6593 | 1960 | 1832 | 40393 | 68.9 | TGCGTTGATGTCCGTTAGCC | 29 1 9 12 36 | | | | 0 |
| 6594 | 1961 | 1833 | 15343 | 71.3 | TGCGTTAGTCCCTCCCCGTT | 29 3 28 28 12 | | | | 0 |
| 6595 | 1962 | 1834 | 7108 | 74.8 | ATCGTGCGCTTGCTTGCACG | 24 29 11 11 30 | | | | 0 |
| 6596 | 1963 | 1835 | 7109 | 70.1 | ATCGTGCGCTCATGTCTCCC | 24 29 13 9 28 | | | | 0 |
| 6597 | 1964 | 1836 | 30439 | 71.6 | TGCGCATCCTAGCAAATCG | 29 15 26 21 24 | | | | 0 |
| 6598 | 1965 | 1837 | 7110 | 70.4 | TGCGGCTTCCATAATCGACC | 29 17 15 4 32 | | | | 0 |
| 6599 | 1966 | 1838 | 15345 | 71.3 | TGCGGAGTGCTTTCGTGACC | 29 20 17 10 32 | | | | 0 |
| 6600 | 1967 | 1839 | 7116 | 73.2 | TGCGTCCCAGCAAAGAGGA | 29 28 31 6 25 | | | | 0 |
| 6601 | 1968 | 1840 | 7117 | 71.9 | TGCGCACGTACAAGCCACCT | 29 30 7 36 23 | | | | 0 |

FIG. 29PP

| SEQ ID NO: | ZIP ID# | 4,633 ID# | HEX ID# Tm | ZIPCODE (NH2 -> CONH2) | TETRAMER NUMBERS | | | | | "UNALLOWED DIMERS" |
|---|---|---|---|---|---|---|---|---|---|---|
| 6602 | 1969 | 1841 | 7119 73.8 | TGCGGTGCGGTACCATTCGT | 29 | 33 | 18 | 15 | 10 | 0 |
| 6603 | 1970 | 1842 | 30440 71.6 | ATCGCACGAAAGGACCGCTT | 24 | 30 | 6 | 32 | 17 | 0 |
| 6604 | 1971 | 1843 | 30441 70.8 | CACGCTTGGTCTACGGACGG | 30 | 11 | 19 | 35 | 35 | 0 |
| 6605 | 1972 | 1844 | 7127 70.3 | ATCGCACGCGAAGAGTCGTT | 24 | 30 | 16 | 20 | 12 | 0 |
| 6606 | 1973 | 1845 | 40394 70.6 | ATCGCACGGCTTACCTCACG | 24 | 30 | 17 | 23 | 30 | 0 |
| 6607 | 1974 | 1846 | 21150 66.8 | CACGAGTGTTAGTGCGCGTT | 30 | 22 | 3 | 29 | 12 | 0 |
| 6608 | 1975 | 1847 | 40395 70.8 | ATCGCACGACCTGCAAAGGA | 24 | 30 | 23 | 21 | 25 | 0 |
| 6609 | 1976 | 1848 | 7133 72.9 | ATCGCACGTCCCTCACGAA | 24 | 30 | 28 | 13 | 16 | 0 |
| 6610 | 1977 | 1849 | 7134 74.7 | ATCGCACGTGCGCTCAGTGC | 24 | 30 | 29 | 13 | 33 | 0 |
| 6611 | 1978 | 1850 | 7137 75 | ATCGCACGACGGCTGTGCAA | 24 | 30 | 35 | 14 | 21 | 0 |
| 6612 | 1979 | 1851 | 7138 70.3 | ATCGCACGAGCCATACGACC | 24 | 30 | 36 | 5 | 32 | 0 |
| 6613 | 1980 | 1852 | 7141 68.6 | ATCGCAGCTTAGCGAAGCAA | 24 | 31 | 3 | 16 | 21 | 0 |
| 6614 | 1981 | 1853 | 15350 66.1 | CAGCTCTGTTGAGGACTGCG | 31 | 8 | 1 | 34 | 29 | 0 |
| 6615 | 1982 | 1854 | 7146 71 | CAGCTGTCGAGTGTGCGCAA | 31 | 9 | 20 | 33 | 21 | 0 |
| 6616 | 1983 | 1855 | 30443 67.8 | CAGCTCGTCCTACAGCGGAC | 31 | 10 | 26 | 31 | 34 | 0 |
| 6617 | 1984 | 1856 | 30444 69.5 | ATCGCAGCGTCTCTTGGGAC | 24 | 31 | 19 | 11 | 34 | 0 |
| 6618 | 1985 | 1857 | 40397 68.3 | ATCGCAGCAGTGTGTCCGTT | 24 | 31 | 22 | 9 | 12 | 0 |
| 6619 | 1986 | 1858 | 7153 69 | ATCGCAGCATCGATACGTGC | 24 | 31 | 24 | 5 | 33 | 0 |
| 6620 | 1987 | 1859 | 7155 71.5 | ATCGCAGCGGACATACTGCG | 24 | 31 | 34 | 5 | 29 | 0 |
| 6621 | 1988 | 1860 | 7156 74.2 | ATCGCAGCACGGCTCACGAA | 24 | 31 | 35 | 13 | 16 | 0 |
| 6622 | 1989 | 1861 | 7159 68.5 | ATCGGACCTACAAGCCGACC | 24 | 32 | 7 | 36 | 32 | 0 |
| 6623 | 1990 | 1862 | 30446 69.4 | GACCCGTTCCATTCTGGTGC | 32 | 12 | 15 | 8 | 33 | 0 |
| 6624 | 1991 | 1863 | 7166 69 | GACCGCAAGATGTGTCGTGC | 32 | 21 | 27 | 9 | 33 | 0 |
| 6625 | 1992 | 1864 | 30447 68.8 | ATCGGACCATCGAGTGGCTT | 24 | 32 | 24 | 22 | 17 | 0 |
| 6626 | 1993 | 1865 | 7171 67.5 | ATCGGACCTGCGTGTCAATC | 24 | 32 | 29 | 9 | 4 | 0 |
| 6627 | 1994 | 1866 | 21160 68.7 | ATCGGACCGGACTTGACGTT | 24 | 32 | 34 | 1 | 12 | 0 |
| 6628 | 1995 | 1867 | 15358 71.8 | ATCGGACCACGGCCATAGGA | 24 | 32 | 35 | 15 | 25 | 0 |
| 6629 | 1996 | 1868 | 40399 66.3 | GTGCTTGATGATCAGCCGAA | 33 | 1 | 2 | 31 | 16 | 0 |
| 6630 | 1997 | 1869 | 40400 68.7 | GTGCTGTCACCTACGGGCAA | 33 | 9 | 23 | 35 | 21 | 0 |
| 6631 | 1998 | 1870 | 15361 67.5 | ATCGGTGCCTCACGAACCTA | 24 | 33 | 13 | 16 | 26 | 0 |
| 6632 | 1999 | 1871 | 7181 66.8 | ATCGGTGCGGTAGTCTGACC | 24 | 33 | 18 | 19 | 32 | 0 |
| 6633 | 2000 | 1872 | 7185 68.5 | ATCGGTGCGATGTTAGGCAA | 24 | 33 | 27 | 3 | 21 | 0 |
| 6634 | 2001 | 1873 | 30449 73.6 | GTGCCACGCTGTGGACGCTT | 33 | 30 | 14 | 34 | 17 | 0 |
| 6635 | 2002 | 1874 | 21166 74.3 | ATCGGTGCGGACAGTGCACG | 24 | 33 | 34 | 22 | 30 | 0 |
| 6636 | 2003 | 1875 | 7188 72.2 | ATCGGTGCAGCCGAGTCGTT | 24 | 33 | 36 | 20 | 12 | 0 |
| 6637 | 2004 | 1876 | 40402 68.9 | ATCGGGACAAAGACGGCTGT | 24 | 34 | 6 | 35 | 14 | 0 |
| 6638 | 2005 | 1878 | 7193 69.6 | ATCGGGACCGTTCCTATCCC | 24 | 34 | 12 | 26 | 28 | 0 |
| 6639 | 2006 | 1879 | 15366 68.5 | ATCGGGACCGAAGAGTACGG | 24 | 34 | 16 | 20 | 35 | 0 |
| 6640 | 2007 | 1880 | 7197 69.7 | ATCGGGACGCTTGATGTCGT | 24 | 34 | 17 | 27 | 10 | 0 |
| 6641 | 2008 | 1881 | 30450 64.8 | GGACGGTAGGTAAAAGCACG | 34 | 18 | 18 | 6 | 30 | 0 |
| 6642 | 2009 | 1882 | 40404 66.5 | GGACGAGTAAAGTCCCCACG | 34 | 20 | 6 | 28 | 30 | 1 |
| 6643 | 2010 | 1883 | 40405 68 | GGACACCTGGTATCCCCGTT | 34 | 23 | 18 | 28 | 12 | 0 |
| 6644 | 2011 | 1884 | 7203 66.9 | GGACTCCCTTGACTTGGCAA | 34 | 28 | 1 | 11 | 21 | 0 |
| 6645 | 2012 | 1885 | 7206 70.9 | ATCGGGACACGGAGGACGTT | 24 | 34 | 35 | 25 | 12 | 0 |
| 6646 | 2013 | 1886 | 30452 71.2 | ACGGTTGATCTGGTGCTGCG | 35 | 1 | 8 | 33 | 29 | 1 |
| 6647 | 2014 | 1887 | 7210 73.1 | ACGGATACACGGAGCCGCAA | 35 | 5 | 35 | 36 | 21 | 0 |
| 6648 | 2015 | 1888 | 7211 71.3 | ACGGTACAACGGGACCGGAC | 35 | 7 | 35 | 32 | 34 | 0 |
| 6649 | 2016 | 1890 | 40406 68.7 | ACGGCTTGTTAGCTTGCACG | 35 | 11 | 3 | 11 | 30 | 0 |

FIG. 29QQ

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 6650 | 2017 | 1891 | 15370 | 69.3 | ACGGCTGTTGATCGTTGCAA | 35 | 14 | 2 | 12 | 21 | 0 |
| 6651 | 2018 | 1892 | 21169 | 68.1 | ACGGCCATTACAGGTATGCG | 35 | 15 | 7 | 18 | 29 | 0 |
| 6652 | 2019 | 1893 | 7219 | 69.7 | ATCGACGGATCGGGTACGAA | 24 | 35 | 24 | 18 | 16 | 0 |
| 6653 | 2020 | 1894 | 15371 | 69.8 | ATCGACGGAGGACGAACGAA | 24 | 35 | 25 | 16 | 16 | 0 |
| 6654 | 2021 | 1895 | 30454 | 71.1 | ACGGGATGAGTGTCCCGGAC | 35 | 27 | 22 | 28 | 34 | 1 |
| 6655 | 2022 | 1896 | 21173 | 74.3 | ACGGACGGAATCCAGCCGAA | 35 | 35 | 4 | 31 | 16 | 0 |
| 6656 | 2023 | 1897 | 7225 | 71.5 | ACGGAGCCCCATACCTCACG | 35 | 36 | 15 | 23 | 30 | 0 |
| 6657 | 2024 | 1898 | 30455 | 68.4 | AGCCTGATGGTAAGCCCGTT | 36 | 2 | 18 | 36 | 12 | 0 |
| 6658 | 2025 | 1899 | 7227 | 69.1 | AGCCTTAGGACCGCTTCACG | 36 | 3 | 32 | 17 | 30 | 0 |
| 6659 | 2026 | 1900 | 15375 | 70.5 | AGCCTGTCTCCCATCGTCCC | 36 | 9 | 28 | 24 | 28 | 0 |
| 6660 | 2027 | 1901 | 15376 | 68.2 | AGCCCTTGATCGACCTCGTT | 36 | 11 | 24 | 23 | 12 | 0 |
| 6661 | 2028 | 1902 | 40407 | 69.2 | AGCCCTGTGTCTACGGCGTT | 36 | 14 | 19 | 35 | 12 | 0 |
| 6662 | 2029 | 1903 | 40408 | 70.1 | ATCGAGCCGGTAACCTGCAA | 24 | 36 | 18 | 23 | 21 | 0 |
| 6663 | 2030 | 1905 | 7236 | 71.2 | AGCCGCAATGTCCTGTCACG | 36 | 21 | 9 | 14 | 30 | 0 |
| 6664 | 2031 | 1906 | 21178 | 66.9 | AGCCAGGAGGTATCTGCGAA | 36 | 25 | 18 | 8 | 16 | 0 |
| 6665 | 2032 | 1907 | 40409 | 71.3 | AGCCTCCCCGTTTTAGTGCG | 36 | 28 | 12 | 3 | 29 | 0 |
| 6666 | 2033 | 1908 | 7241 | 67.8 | ATCGAGCCGACCTTAGGACC | 24 | 36 | 32 | 3 | 32 | 0 |
| 6667 | 2034 | 1909 | 7245 | 69.8 | TGATCGAACCATTCCCGCTT | 2 | 16 | 15 | 28 | 17 | 0 |
| 6668 | 2035 | 1910 | 15383 | 69.3 | AGGATTAGGCAATCCCGCAA | 25 | 3 | 21 | 28 | 21 | 0 |
| 6669 | 2036 | 1911 | 30457 | 69.2 | AATCGCAATCTGACGGGCTT | 4 | 21 | 8 | 35 | 17 | 0 |
| 6670 | 2037 | 1912 | 30458 | 69.4 | AATCGGACTCGTCAGCGCTT | 4 | 34 | 10 | 31 | 17 | 0 |
| 6671 | 2038 | 1913 | 7271 | 68.6 | AAAGCCATCCATGATGCACG | 6 | 15 | 15 | 27 | 30 | 0 |
| 6672 | 2039 | 1914 | 15390 | 69.5 | AGGAAAAGGCTTTGCGCTTG | 25 | 6 | 17 | 29 | 11 | 0 |
| 6673 | 2040 | 1915 | 21182 | 67.8 | AAAGTCCCTGATGTGCGTGC | 6 | 28 | 2 | 33 | 33 | 1 |
| 6674 | 2041 | 1916 | 30459 | 68.1 | AAAGCACGATCGAAAGGCAA | 6 | 30 | 24 | 6 | 21 | 0 |
| 6675 | 2042 | 1917 | 40411 | 70.1 | TCTGCGTTCTGTCGTTTGCG | 8 | 12 | 14 | 12 | 29 | 0 |
| 6676 | 2043 | 1918 | 21184 | 71.3 | TCTGCGAAACCTCACGACGG | 8 | 16 | 23 | 30 | 35 | 0 |
| 6677 | 2044 | 1920 | 15398 | 73 | TCTGAGCCACGGCCATCGTT | 8 | 36 | 35 | 15 | 12 | 0 |
| 6678 | 2045 | 1921 | 21188 | 75.6 | TGTCCAGCTCGTTGCGTGCG | 9 | 31 | 10 | 29 | 29 | 0 |
| 6679 | 2046 | 1922 | 30460 | 70.8 | TCGTCGAAAGCCCTTGCTTG | 10 | 16 | 36 | 11 | 11 | 0 |
| 6680 | 2047 | 1924 | 30461 | 74.5 | TCGTACGGCAGCGACCGATG | 10 | 35 | 31 | 32 | 27 | 0 |
| 6681 | 2048 | 1925 | 15408 | 68.1 | AGGACTTGGCTTAGCCGGAC | 25 | 11 | 17 | 36 | 34 | 0 |
| 6682 | 2049 | 1926 | 7309 | 67.9 | CTTGGGTATGTCGTGCCGTT | 11 | 18 | 9 | 33 | 12 | 0 |
| 6683 | 2050 | 1927 | 40412 | 69.6 | CTTGGCAATGATTCCCGGAC | 11 | 21 | 2 | 28 | 34 | 0 |
| 6684 | 2051 | 1928 | 7318 | 70.7 | CGTTATCGATCGTCCCGTGC | 12 | 24 | 24 | 28 | 33 | 0 |
| 6685 | 2052 | 1929 | 7321 | 71.9 | CGTTCAGCGAGTTGCGCCTA | 12 | 31 | 20 | 29 | 26 | 0 |
| 6686 | 2053 | 1930 | 40413 | 72.5 | CGTTGTGCATCGCGTTGACC | 12 | 33 | 24 | 12 | 32 | 0 |
| 6687 | 2054 | 1931 | 7324 | 74.2 | CGTTGGACGTGCTCCCTCCC | 12 | 34 | 33 | 28 | 28 | 0 |
| 6688 | 2055 | 1932 | 40414 | 71.3 | CCATGCAATGTCAGCCGGAC | 15 | 21 | 9 | 36 | 34 | 0 |
| 6689 | 2056 | 1933 | 21197 | 68.2 | CCATAGTGGCAAGGACACGG | 15 | 22 | 21 | 34 | 35 | 0 |
| 6690 | 2057 | 1934 | 7333 | 69.9 | CCATCAGCAAAGCCATGCAA | 15 | 31 | 6 | 15 | 21 | 0 |
| 6691 | 2058 | 1935 | 15417 | 75.5 | CCATGTGCTCCCACGGCGTT | 15 | 33 | 28 | 35 | 12 | 0 |
| 6692 | 2059 | 1936 | 7339 | 68.3 | CGAACGTTTAGCAGCGACC | 16 | 12 | 3 | 31 | 32 | 0 |
| 6693 | 2060 | 1937 | 7343 | 69.1 | CGAAACCTTCTGCCATGCAA | 16 | 23 | 8 | 15 | 21 | 0 |
| 6694 | 2061 | 1938 | 15422 | 68.9 | CGAAACGGGGTAAAGCCAT | 16 | 35 | 18 | 6 | 15 | 0 |
| 6695 | 2062 | 1939 | 7352 | 70.1 | GCTTTCTGAGCCACGATCG | 17 | 8 | 36 | 30 | 24 | 0 |
| 6696 | 2063 | 1941 | 15438 | 73 | GCAAGGACCGAACCATTGCG | 21 | 34 | 16 | 15 | 29 | 0 |
| 6697 | 2064 | 1942 | 30463 | 70.5 | GCAAACGGACCTCAGCGGTA | 21 | 35 | 23 | 31 | 18 | 0 |

FIG. 29RR

| SEQ ID NO: | ZIP ID# | 4,633 ID# | HEX ID# | Tm | ZIPCODE (NH2 -> CONH2) | TETRAMER NUMBERS | | | | "UNALLOWED DIMERS" |
|---|---|---|---|---|---|---|---|---|---|---|
| 6698 | 2065 | 1943 | 40415 | 70.1 | AGTGCCATCGTTTCCCATCG | 22 | 15 | 12 | 28 24 | 1 |
| 6699 | 2066 | 1945 | 7390 | 70.5 | AGTGCCTACACGCACGAGCC | 22 | 26 | 30 | 30 36 | 0 |
| 6700 | 2067 | 1946 | 7393 | 69.7 | AGTGCAGCATCGCTCAGCAA | 22 | 31 | 24 | 13 21 | 0 |
| 6701 | 2068 | 1947 | 7396 | 71.1 | AGTGAGCCCCTAAGCCACGG | 22 | 36 | 26 | 36 35 | 0 |
| 6702 | 2069 | 1948 | 15443 | 70.8 | ACCTCAGCCCATAGCCGCTT | 23 | 31 | 15 | 36 17 | 0 |
| 6703 | 2070 | 1949 | 7404 | 72.5 | ACCTGACCGCTTGGACGTGC | 23 | 32 | 17 | 34 33 | 0 |
| 6704 | 2071 | 1950 | 7408 | 68.5 | ATCGCCATCTGTGCTTCGAA | 24 | 15 | 14 | 17 16 | 0 |
| 6705 | 2072 | 1951 | 15446 | 73.7 | ATCGACCTTCCCGTGCGCTT | 24 | 23 | 28 | 33 17 | 1 |
| 6706 | 2073 | 1952 | 30465 | 72.2 | ATCGCAGCGGTAGTGCCCAT | 24 | 31 | 18 | 33 15 | 0 |
| 6707 | 2074 | 1953 | 40419 | 72.6 | AGGACACGATCGACGGCAGC | 25 | 30 | 24 | 35 31 | 0 |
| 6708 | 2075 | 1954 | 40420 | 73.4 | GATGGCAAATCGCACGCCAT | 27 | 21 | 24 | 30 15 | 0 |
| 6709 | 2076 | 1955 | 30466 | 72.3 | TCCCCTTGGTCTAGCCGCAA | 28 | 11 | 19 | 36 21 | 0 |
| 6710 | 2077 | 1956 | 15460 | 69.8 | TCCCGAGTTCGTGATGGCTT | 28 | 20 | 10 | 27 17 | 0 |
| 6711 | 2078 | 1957 | 7449 | 72.3 | TGCGCGTTCTTGCTGTGGAC | 29 | 12 | 11 | 14 34 | 0 |
| 6712 | 2079 | 1958 | 15467 | 74.2 | TGCGAGTGCGTTGCAACACG | 29 | 22 | 12 | 21 30 | 0 |
| 6713 | 2080 | 1959 | 7455 | 72.6 | TGCGTGCGACGGTACACGTT | 29 | 29 | 35 | 7 12 | 0 |
| 6714 | 2081 | 1960 | 15469 | 72.2 | TGCGGTGCTACACAGCGCTT | 29 | 33 | 7 | 31 17 | 0 |
| 6715 | 2082 | 1961 | 21221 | 70.5 | CACGATACGATGCAGCTGCG | 30 | 5 | 27 | 31 29 | 0 |
| 6716 | 2083 | 1962 | 21224 | 70.5 | CACGGGTATTGAACGGACGG | 30 | 18 | 1 | 35 35 | 0 |
| 6717 | 2084 | 1963 | 7463 | 68.7 | CACGACCTAGCCTCTGTGCG | 30 | 23 | 36 | 8 29 | 0 |
| 6718 | 2085 | 1964 | 30468 | 69.2 | CACGCCTAAAAGGGACGCTT | 30 | 26 | 6 | 34 17 | 0 |
| 6719 | 2086 | 1965 | 7470 | 73.5 | CACGGGACGTCTTGCGTCGT | 30 | 34 | 19 | 29 10 | 0 |
| 6720 | 2087 | 1966 | 7479 | 73.5 | CAGCATCGGTGCAGTGCACG | 31 | 24 | 33 | 22 30 | 0 |
| 6721 | 2088 | 1967 | 15479 | 72.8 | CAGCAGGATGCGGATGTCCC | 31 | 25 | 29 | 27 28 | 0 |
| 6722 | 2089 | 1968 | 40425 | 70.4 | CAGCCCTATGTCCAGCCGAA | 31 | 26 | 9 | 31 16 | 0 |
| 6723 | 2090 | 1969 | 30470 | 70.4 | CAGCCACGTTAGTCCCCGAA | 31 | 30 | 3 | 28 16 | 0 |
| 6724 | 2091 | 1970 | 21235 | 69.5 | GTGCATACGACCATCGGCAA | 33 | 5 | 32 | 24 21 | 0 |
| 6725 | 2092 | 1971 | 7498 | 74 | GTGCAAAGTGCGGTGCGACC | 33 | 6 | 29 | 33 32 | 0 |
| 6726 | 2093 | 1972 | 15487 | 69.1 | GTGCGTCTAAAGCAGCGTGC | 33 | 19 | 6 | 31 33 | 0 |
| 6727 | 2094 | 1973 | 7506 | 68.3 | GTGCCCTACAGCAGTGGTGC | 33 | 26 | 31 | 22 33 | 0 |
| 6728 | 2095 | 1974 | 15491 | 70.5 | GTGCGACCTCGTTGTCGGAC | 33 | 32 | 10 | 9 34 | 0 |
| 6729 | 2096 | 1976 | 15493 | 74.2 | GGACCTTGTCCCGCAAACGG | 34 | 11 | 28 | 21 35 | 1 |
| 6730 | 2097 | 1977 | 15495 | 71 | GGACCCATGGACTCCCCTCA | 34 | 15 | 34 | 28 13 | 0 |
| 6731 | 2098 | 1978 | 7522 | 70.1 | GGACGATGACCTCACGCGTT | 34 | 27 | 23 | 30 12 | 0 |
| 6732 | 2099 | 1979 | 7533 | 70.7 | ACGGATCGCCTACCATGCAA | 35 | 24 | 26 | 15 21 | 0 |
| 6733 | 2100 | 1980 | 15502 | 69.9 | ACGGAGGACACGCTGTGACC | 35 | 25 | 30 | 14 32 | 0 |
| 6734 | 2101 | 1981 | 7535 | 70.5 | ACGGGATGGTCTCAGCTCCC | 35 | 27 | 19 | 31 28 | 0 |
| 6735 | 2102 | 1983 | 7539 | 69.5 | AGCCAAAGGAGTTCCCCCAT | 36 | 6 | 20 | 28 15 | 0 |
| 6736 | 2103 | 1984 | 40427 | 69 | AGCCCTCAATACCACGCCAT | 36 | 13 | 5 | 30 15 | 0 |
| 6737 | 2104 | 1985 | 15506 | 72 | AGCCAGTGCAGCCCATCCAT | 36 | 22 | 31 | 15 15 | 0 |
| 6738 | 2105 | 1986 | 15508 | 72 | AGCCCACGGCTTTTGACAGC | 36 | 30 | 17 | 1 31 | 0 |
| 6739 | 2106 | 1987 | 7553 | 73.7 | AGGAAGCCCAGCCACGCTGT | 25 | 36 | 31 | 30 14 | 0 |
| 6740 | 2107 | 1988 | 7554 | 71.2 | AGCCGTGCTGTCCTCACACG | 36 | 33 | 9 | 13 30 | 0 |
| 6741 | 2108 | 1989 | 7558 | 71.7 | TTGATGCGGCAATCGTCGTT | 1 | 29 | 21 | 10 12 | 0 |
| 6742 | 2109 | 1990 | 15532 | 72.8 | TGTCGCAATGTCGTGCGCTT | 9 | 21 | 9 | 33 17 | 0 |
| 6743 | 2110 | 1991 | 7587 | 77.4 | TGTCACGGGACCGCAATGCG | 9 | 35 | 32 | 21 29 | 0 |
| 6744 | 2111 | 1992 | 7589 | 73.3 | TCGTTCGTTGTCTGCGCACG | 10 | 18 | 9 | 29 30 | 0 |
| 6745 | 2112 | 1993 | 15526 | 77.8 | TCGTCACGGTGCCAGCTGCG | 10 | 30 | 33 | 31 29 | 0 |

FIG. 29SS

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 6746 | 2113 | 1994 | 7611 | 76.1 | CGTTGACCGACCGGACTGCG | 12 | 32 | 32 | 34 | 29 | 0 |
| 6747 | 2114 | 1995 | 15536 | 76.1 | CTGTTGCGCACGACGGGACC | 14 | 29 | 30 | 35 | 32 | 0 |
| 6748 | 2115 | 1996 | 7640 | 75.2 | GCTTGACCTCCCGTGCCACG | 17 | 32 | 28 | 33 | 30 | 0 |
| 6749 | 2116 | 1997 | 40430 | 69.7 | GCAAGCAACACGCCTACACG | 21 | 21 | 30 | 26 | 30 | 0 |
| 6750 | 2117 | 1998 | 30474 | 70 | ATCGCCATAGTGTCCCCACG | 24 | 15 | 22 | 28 | 30 | 1 |
| 6751 | 2118 | 1999 | 7700 | 72.2 | TCCCTTGAAGCCACGGCTGT | 28 | 1 | 36 | 35 | 14 | 0 |
| 6752 | 2119 | 2000 | 30475 | 75.2 | TCCCCTCAGACCACGGCGAA | 28 | 13 | 32 | 35 | 16 | 0 |
| 6753 | 2120 | 2001 | 30476 | 70.6 | TCCCCACGTGATAGCCGGTA | 28 | 30 | 2 | 36 | 18 | 0 |
| 6754 | 2121 | 2002 | 7731 | 73.6 | CACGTCGTAGCCCACGCGTT | 30 | 10 | 36 | 30 | 12 | 0 |
| 6755 | 2122 | 2003 | 7733 | 73.6 | CACGCTGTCGTTGTGCGTGC | 30 | 14 | 12 | 33 | 33 | 0 |
| 6756 | 2123 | 2004 | 7740 | 72.3 | CACGCAGCAGTGTGCGACCT | 30 | 31 | 22 | 29 | 23 | 0 |
| 6757 | 2124 | 2005 | 21261 | 72.3 | CAGCGTCTTCGTCAGCTGCG | 31 | 19 | 10 | 31 | 29 | 0 |
| 6758 | 2125 | 2006 | 7747 | 73.4 | CAGCGAGTCACGGCAAAGCC | 31 | 20 | 30 | 21 | 36 | 0 |
| 6759 | 2126 | 2008 | 30477 | 69.3 | GACCCGAACCATCCATACGG | 32 | 16 | 15 | 15 | 35 | 0 |
| 6760 | 2127 | 2009 | 21266 | 69.8 | GTGCGTCTCGTTACGGGACC | 33 | 19 | 12 | 35 | 32 | 0 |
| 6761 | 2128 | 2010 | 7780 | 69.3 | GTGCACGGTTGAGCAAATCG | 33 | 35 | 1 | 21 | 24 | 1 |
| 6762 | 2129 | 2011 | 15616 | 74.6 | GGACCACGCAGCTCGTGCAA | 34 | 30 | 31 | 10 | 21 | 0 |
| 6763 | 2130 | 2012 | 40433 | 69.5 | AGCCGAGTAGTGGTGCGACC | 36 | 20 | 22 | 33 | 32 | 0 |
| 6764 | 2131 | 2013 | 40434 | 71.8 | AGCCACCTCTTGTCCCTGCG | 36 | 23 | 11 | 28 | 29 | 1 |
| 6765 | 2132 | 2014 | 7825 | 75.1 | TTGAAGCCGTGCGTGCGGTA | 1 | 36 | 33 | 33 | 18 | 0 |
| 6766 | 2133 | 2015 | 7831 | 74.7 | AATCGTGCACGGCGTTTCCC | 4 | 33 | 35 | 12 | 28 | 1 |
| 6767 | 2134 | 2016 | 7832 | 72.2 | AATCACGGTCGTTCCCCACG | 4 | 35 | 10 | 28 | 30 | 0 |
| 6768 | 2135 | 2017 | 7834 | 72.8 | AAAGCCATCAGCGGACGTGC | 6 | 15 | 31 | 34 | 33 | 0 |
| 6769 | 2136 | 2018 | 15632 | 70.8 | AAAGCGAAAGCCCCATCGTT | 6 | 16 | 36 | 15 | 12 | 0 |
| 6770 | 2137 | 2019 | 15633 | 77.2 | AAAGCACGCAGCTGCGTGCG | 6 | 30 | 31 | 29 | 29 | 0 |
| 6771 | 2138 | 2020 | 7845 | 69.2 | GATGCTTGCGTTCCATGTGC | 27 | 11 | 12 | 15 | 33 | 0 |
| 6772 | 2139 | 2021 | 7854 | 73.1 | CGTTTGTCCGAAAGCCACGG | 12 | 9 | 16 | 36 | 35 | 0 |
| 6773 | 2140 | 2022 | 15643 | 70.3 | GATGCGTTGGACAGCCCCTA | 27 | 12 | 34 | 36 | 26 | 0 |
| 6774 | 2141 | 2023 | 7867 | 72.5 | CTCACACGCGAACACGGTGC | 13 | 30 | 16 | 30 | 33 | 0 |
| 6775 | 2142 | 2024 | 7870 | 68.5 | CTGTCGAACCTATGCGGTGC | 14 | 16 | 26 | 29 | 33 | 0 |
| 6776 | 2143 | 2025 | 7873 | 71.8 | CTGTCAGCCACGGCTTGTGC | 14 | 31 | 30 | 17 | 33 | 0 |
| 6777 | 2144 | 2026 | 7875 | 71.7 | CTGTAGCCACGGGCAACACG | 14 | 36 | 35 | 21 | 30 | 0 |
| 6778 | 2145 | 2027 | 7879 | 68.3 | CCATCGTTTCGTGCTTGGAC | 15 | 12 | 10 | 17 | 34 | 0 |
| 6779 | 2146 | 2028 | 30480 | 70.9 | GATGCCATCCATCAGCCGAA | 27 | 15 | 15 | 31 | 16 | 0 |
| 6780 | 2147 | 2030 | 7883 | 69.4 | CCATAGGAGGACCAGCCGAA | 15 | 25 | 34 | 31 | 16 | 0 |
| 6781 | 2148 | 2031 | 7884 | 69.1 | CCATCCTACGAAAGCCGACC | 15 | 26 | 16 | 36 | 32 | 0 |
| 6782 | 2149 | 2032 | 15648 | 71.3 | CCATTCCCGGTACAGCCCAT | 15 | 28 | 18 | 31 | 15 | 0 |
| 6783 | 2150 | 2033 | 7895 | 72 | CGAACTCATGCGGGACTCCC | 16 | 13 | 29 | 34 | 28 | 0 |
| 6784 | 2151 | 2034 | 30483 | 70.3 | CGAAATCGCCTACAGCGCTT | 16 | 24 | 26 | 31 | 17 | 0 |
| 6785 | 2152 | 2035 | 7908 | 70.8 | CGAAACGGGCAATGTCCTTG | 16 | 35 | 21 | 9 | 11 | 0 |
| 6786 | 2153 | 2036 | 15657 | 74 | GATGCGAAAGCCGCTTGCAA | 27 | 16 | 36 | 17 | 21 | 0 |
| 6787 | 2154 | 2037 | 7913 | 73.2 | GCTTCTTGCACGGACCGTGC | 17 | 11 | 30 | 32 | 33 | 0 |
| 6788 | 2155 | 2038 | 30484 | 69.2 | GCTTGCAAAGGATCGTGCAA | 17 | 21 | 25 | 10 | 21 | 0 |
| 6789 | 2156 | 2039 | 7923 | 71.2 | GCTTGACCGTCTCAGCTGCG | 17 | 32 | 19 | 31 | 29 | 0 |
| 6790 | 2157 | 2040 | 15665 | 71.5 | GATGGGTATGCGATCGCACG | 27 | 18 | 29 | 24 | 30 | 0 |
| 6791 | 2158 | 2041 | 7931 | 74.9 | GGTAGTGCCACGTGCGCACG | 18 | 33 | 30 | 29 | 30 | 0 |
| 6792 | 2159 | 2042 | 7933 | 70.5 | GAGTTCCGGTAGTGCGCAA | 20 | 28 | 18 | 33 | 21 | 0 |
| 6793 | 2160 | 2043 | 7938 | 72.2 | GCAATCTGCGAATCCCAGCC | 21 | 8 | 16 | 28 | 36 | 0 |

*FIG. 29TT*

| SEQ ID NO: | ZIP ID# | 4,633 ID# | HEX Tm | ZIPCODE (NH2 -> CONH2) | TETRAMER NUMBERS | | | | | "UNALLOWED DIMERS" |
|---|---|---|---|---|---|---|---|---|---|---|
| 6794 | 2161 | 2044 | 40438 | 67.6 | GCAACGTTATACGCAATGCG | 21 | 12 | 5 | 21 | 29 | 0 |
| 6795 | 2162 | 2045 | 39485 | 67.6 | GATGGCAAGCTTCAGCCCTA | 27 | 21 | 17 | 31 | 26 | 0 |
| 6796 | 2163 | 2046 | 39486 | 68 | GCAAACCTAAAGCAGCCGAA | 21 | 23 | 6 | 31 | 16 | 0 |
| 6797 | 2164 | 2047 | 7947 | 72.5 | GCAAGATGGACCAGCCCGAA | 21 | 27 | 32 | 36 | 16 | 0 |
| 6798 | 2165 | 2048 | 7954 | 69.4 | AGTGGCAACGTTCGTTTCCC | 22 | 21 | 12 | 12 | 28 | 1 |
| 6799 | 2166 | 2049 | 40439 | 72.7 | ACCTTGCGCGTTGCTTCGTT | 23 | 29 | 12 | 17 | 12 | 0 |
| 6800 | 2167 | 2050 | 30487 | 70.5 | ATCGCGTTCCATGCTTACGG | 24 | 12 | 15 | 17 | 35 | 0 |
| 6801 | 2168 | 2051 | 7959 | 71.5 | ATCGCCATTGTCCACGCTCA | 24 | 15 | 9 | 30 | 13 | 0 |
| 6802 | 2169 | 2052 | 40440 | 72.6 | ATCGGCTTCCATGGACTGCG | 24 | 17 | 15 | 34 | 29 | 0 |
| 6803 | 2170 | 2053 | 30488 | 74.3 | ATCGCACGGATGCGTTCACG | 24 | 30 | 27 | 12 | 30 | 0 |
| 6804 | 2171 | 2054 | 7980 | 69.4 | CCTAAGCCGGTAGTGCGGAC | 26 | 36 | 18 | 33 | 34 | 0 |
| 6805 | 2172 | 2055 | 7981 | 67.9 | GATGCTCAGACCCGTTCGAA | 27 | 13 | 32 | 12 | 16 | 0 |
| 6806 | 2173 | 2056 | 7985 | 73.4 | GATGCCTATGCGAGCCTGCG | 27 | 26 | 29 | 36 | 29 | 0 |
| 6807 | 2174 | 2057 | 15679 | 69.5 | GATGGTGCTGATCACGCGAA | 27 | 33 | 2 | 30 | 16 | 0 |
| 6808 | 2175 | 2058 | 7988 | 68.8 | GATGAGCCAATCCAGCTCCC | 27 | 36 | 4 | 31 | 28 | 0 |
| 6809 | 2176 | 2059 | 30489 | 69.5 | TCCCGCTTAATCCTTGCGTT | 28 | 17 | 4 | 11 | 12 | 0 |
| 6810 | 2177 | 2060 | 7993 | 71.7 | TCCCGTCTCGTTGACCCCAT | 28 | 19 | 12 | 32 | 15 | 0 |
| 6811 | 2178 | 2061 | 15686 | 74.5 | TCCCCAGCGCTTCACGGTCT | 28 | 31 | 17 | 30 | 19 | 0 |
| 6812 | 2179 | 2062 | 15687 | 72.8 | TCCCGACCATACTCCCGCAA | 28 | 32 | 5 | 28 | 21 | 0 |
| 6813 | 2180 | 2063 | 21306 | 70.2 | TGCGTTAGCAGCGATGATCG | 29 | 3 | 31 | 27 | 24 | 0 |
| 6814 | 2181 | 2064 | 15692 | 71.3 | TGCGGGTAATCGGCTTGATG | 29 | 18 | 24 | 17 | 27 | 0 |
| 6815 | 2182 | 2065 | 15696 | 75.2 | TGCGCACGCGAATCGTAGGA | 29 | 30 | 16 | 10 | 25 | 0 |
| 6816 | 2183 | 2066 | 30492 | 76.6 | TGCGCAGCGCAAATCGACCT | 29 | 31 | 21 | 24 | 23 | 0 |
| 6817 | 2184 | 2067 | 8021 | 74.8 | CACGTGTCGTGCAGCCGGAC | 30 | 9 | 33 | 36 | 34 | 0 |
| 6818 | 2185 | 2068 | 8024 | 71.1 | GATGCACGCCATCGTTCGTT | 27 | 30 | 15 | 12 | 12 | 0 |
| 6819 | 2186 | 2069 | 8028 | 71.3 | CACGAGTGACGGATCGGTGC | 30 | 22 | 35 | 24 | 33 | 0 |
| 6820 | 2187 | 2070 | 15699 | 73.9 | CACGTGCGGTCTGACCCAGC | 30 | 29 | 19 | 32 | 31 | 0 |
| 6821 | 2188 | 2071 | 15700 | 72.7 | GATGCACGCACGCTTGATCG | 27 | 30 | 30 | 11 | 24 | 0 |
| 6822 | 2189 | 2072 | 30494 | 73.8 | CACGAGCCGACCAATCACGG | 30 | 36 | 32 | 4 | 35 | 0 |
| 6823 | 2190 | 2073 | 8036 | 70.7 | CAGCTGATTGCGATCGGGAC | 31 | 2 | 29 | 24 | 34 | 0 |
| 6824 | 2191 | 2074 | 30495 | 71.5 | CAGCTCGTCACGTCCCATCG | 31 | 10 | 30 | 28 | 24 | 0 |
| 6825 | 2192 | 2075 | 15704 | 71.5 | GATGCAGCCTTGATCGCGAA | 27 | 31 | 11 | 24 | 16 | 0 |
| 6826 | 2193 | 2076 | 40443 | 67.9 | CAGCCTCATGATGACCGCTT | 31 | 13 | 2 | 32 | 17 | 0 |
| 6827 | 2194 | 2077 | 39496 | 67.8 | GATGCAGCGGTAGGTAACGG | 27 | 31 | 18 | 18 | 35 | 0 |
| 6828 | 2195 | 2078 | 8048 | 73 | CAGCGTGCGCTTGTCTCACG | 31 | 33 | 17 | 19 | 30 | 0 |
| 6829 | 2196 | 2079 | 15708 | 72 | GATGCAGCAGCCCTCATCCC | 27 | 31 | 36 | 13 | 28 | 0 |
| 6830 | 2197 | 2080 | 40444 | 70.3 | GACCCGTTGGACAAAGCGAA | 32 | 12 | 34 | 6 | 16 | 0 |
| 6831 | 2198 | 2082 | 15712 | 72 | GATGGACCCACGACGGGGTA | 27 | 32 | 30 | 35 | 18 | 0 |
| 6832 | 2199 | 2084 | 8088 | 73.4 | ACGGTTGAGCTTTGCGGCAA | 35 | 1 | 17 | 29 | 21 | 1 |
| 6833 | 2200 | 2085 | 30499 | 71.3 | ACGGGGTAGACCCGAAGCAA | 35 | 18 | 32 | 16 | 21 | 0 |
| 6834 | 2201 | 2086 | 40447 | 72.1 | AGCCCTCACTCAAGCCTGCG | 36 | 13 | 13 | 36 | 29 | 0 |
| 6835 | 2202 | 2087 | 21328 | 70.2 | GATGAGCCGTCTACGGCAGC | 27 | 36 | 19 | 35 | 31 | 0 |
| 6836 | 2203 | 2088 | 15729 | 71.5 | AGCCATCGTCGTCCATGCAA | 36 | 24 | 10 | 15 | 21 | 0 |
| 6837 | 2204 | 2089 | 8108 | 70.2 | AGCCCAGCATACGCAACGTT | 36 | 31 | 5 | 21 | 12 | 0 |
| 6838 | 2205 | 2090 | 8112 | 70.2 | TTGAAATCTGCGAGCCCGTT | 1 | 4 | 29 | 36 | 12 | 0 |
| 6839 | 2206 | 2091 | 21331 | 68.8 | TCCCTTGAAGGAAGCCCTTG | 28 | 1 | 25 | 36 | 11 | 0 |
| 6840 | 2207 | 2092 | 30500 | 66.9 | TTGATGCGTTAGGGTATGCG | 1 | 29 | 3 | 18 | 29 | 0 |
| 6841 | 2208 | 2093 | 8118 | 67.6 | TTGACAGCAAAGATCGCACG | 1 | 31 | 6 | 24 | 30 | 0 |

FIG. 29UU

| SEQ ID NO: | ZIP ID# | 4,633 ID# | HEX ID# | Tm | ZIPCODE (NH2 -> CONH2) | TETRAMER NUMBERS | | | | "UNALLOWED DIMERS" |
|---|---|---|---|---|---|---|---|---|---|---|
| 6842 | 2209 | 2094 | 15734 | 71.8 | TTGAGGACCACGGATGCACG | 1 | 34 | 30 | 27 30 | 0 |
| 6843 | 2210 | 2095 | 8122 | 70.1 | TGATTCTGGGACCAGCAGCC | 2 | 8 | 34 | 31 36 | 0 |
| 6844 | 2211 | 2096 | 21332 | 67.3 | TGATTCGTAATCACGGCACG | 2 | 10 | 4 | 35 30 | 0 |
| 6845 | 2212 | 2097 | 40453 | 68.1 | TGATCGAATTGAAGCCAGCC | 2 | 16 | 1 | 36 36 | 0 |
| 6846 | 2213 | 2099 | 15737 | 67.5 | TCCCTGATTGCGAGGACCTA | 28 | 2 | 29 | 25 26 | 0 |
| 6847 | 2214 | 2100 | 8131 | 69 | TGATGACCTGTCACGGACGG | 2 | 32 | 9 | 35 35 | 0 |
| 6848 | 2215 | 2101 | 8136 | 67.8 | TTAGCTGTATCGTGCGCGAA | 3 | 14 | 24 | 29 16 | 0 |
| 6849 | 2216 | 2102 | 30501 | 68.3 | TCCCTTAGGCAAGCTTGCAA | 28 | 3 | 21 | 17 21 | 0 |
| 6850 | 2217 | 2103 | 8140 | 66.3 | TTAGAGGAAATCTGCGTGCG | 3 | 25 | 4 | 29 29 | 0 |
| 6851 | 2218 | 2104 | 8143 | 68 | TCCCTTAGCACGCTTGAGGA | 28 | 3 | 30 | 11 25 | 0 |
| 6852 | 2219 | 2106 | 30502 | 68.7 | TCCCAATCCTGTGGACTCCC | 28 | 4 | 14 | 34 28 | 0 |
| 6853 | 2220 | 2107 | 30503 | 66.4 | TCCCAATCGCTTCCTAGACC | 28 | 4 | 17 | 26 32 | 0 |
| 6854 | 2221 | 2108 | 8155 | 64.2 | TCCCAATCGAGTACCTGACC | 28 | 4 | 20 | 23 32 | 0 |
| 6855 | 2222 | 2109 | 8157 | 69.6 | TCCCAATCAGTGGACCGACC | 28 | 4 | 22 | 32 32 | 0 |
| 6856 | 2223 | 2110 | 30504 | 66.8 | TCCCAATCACCTCTTGAGCC | 28 | 4 | 23 | 11 36 | 0 |
| 6857 | 2224 | 2111 | 15748 | 70.9 | TCCCAATCTCCCAGTGTGCG | 28 | 4 | 28 | 22 29 | 0 |
| 6858 | 2225 | 2112 | 8162 | 71 | TCCCAATCGACCTCTGCACG | 28 | 4 | 32 | 8 30 | 0 |
| 6859 | 2226 | 2113 | 8164 | 73 | TCCCAATCAGCCGATGCGTT | 28 | 4 | 36 | 27 12 | 0 |
| 6860 | 2227 | 2114 | 8166 | 70.8 | TCCCATACCTTGGTGCACGG | 28 | 5 | 11 | 33 35 | 0 |
| 6861 | 2228 | 2115 | 30506 | 70 | TCCCATACCCATCAGCCAGC | 28 | 5 | 15 | 31 31 | 0 |
| 6862 | 2229 | 2116 | 30507 | 65.6 | TCCCATACCGAAATACGTGC | 28 | 5 | 16 | 5 33 | 0 |
| 6863 | 2230 | 2117 | 15753 | 69.1 | TCCCATACGTGCCGAACTCA | 28 | 5 | 33 | 16 13 | 0 |
| 6864 | 2231 | 2118 | 30510 | 70.2 | TCCCAAAGCGTTTCGTCGTT | 28 | 6 | 12 | 10 12 | 0 |
| 6865 | 2232 | 2119 | 40458 | 66.4 | TCCCAAAGGGTACCATCGTT | 28 | 6 | 18 | 15 12 | 0 |
| 6866 | 2233 | 2120 | 40459 | 67.8 | TCCCAAAGGTCTCGTTCACG | 28 | 6 | 19 | 12 30 | 0 |
| 6867 | 2234 | 2121 | 30511 | 67.7 | TCCCAAAGACCTCACGATCG | 28 | 6 | 23 | 30 24 | 0 |
| 6868 | 2235 | 2122 | 8183 | 65.4 | AAAGATCGCGAATTAGCGAA | 6 | 24 | 16 | 3 16 | 0 |
| 6869 | 2236 | 2123 | 8184 | 64.5 | AAAGGATGACCTCTTGCGAA | 6 | 27 | 23 | 11 16 | 0 |
| 6870 | 2237 | 2124 | 8186 | 68 | TCCCAAAGTGCGTGATCCAT | 28 | 6 | 29 | 2 15 | 0 |
| 6871 | 2238 | 2125 | 8188 | 65.9 | AAAGCAGCAATCTGTCGTGC | 6 | 31 | 4 | 9 33 | 0 |
| 6872 | 2239 | 2126 | 8189 | 68.9 | TCCCAAAGGACCTCGTTCGT | 28 | 6 | 32 | 10 10 | 0 |
| 6873 | 2240 | 2127 | 30512 | 71.8 | TCCCAAAGAGCCCTTGACGG | 28 | 6 | 36 | 11 35 | 0 |
| 6874 | 2241 | 2129 | 15757 | 71.4 | TCCCTCTGCGTTTCCCTCGT | 28 | 8 | 12 | 28 10 | 1 |
| 6875 | 2242 | 2130 | 40460 | 67.9 | TCTGCTCACCTAACGGCGTT | 8 | 13 | 26 | 35 12 | 0 |
| 6876 | 2243 | 2131 | 15759 | 69.5 | TCCCTCTGGTCTGACCCGAA | 28 | 8 | 19 | 32 16 | 0 |
| 6877 | 2244 | 2132 | 30515 | 74.3 | TCCCTCTGATCGCAGCGCAA | 28 | 8 | 24 | 31 21 | 0 |
| 6878 | 2245 | 2133 | 8206 | 66.4 | TCTGAGGACGTTCTGTTGCG | 8 | 25 | 12 | 14 29 | 0 |
| 6879 | 2246 | 2135 | 8208 | 66.5 | TCTGTCCCTTGATGTCGCAA | 8 | 28 | 1 | 9 21 | 0 |
| 6880 | 2247 | 2136 | 40461 | 68.9 | TCCCTCTGGGACTGTCGACC | 28 | 8 | 34 | 9 32 | 0 |
| 6881 | 2248 | 2137 | 8213 | 68.9 | TGTCCTTGCGTTTCTGACGG | 9 | 11 | 12 | 8 35 | 0 |
| 6882 | 2249 | 2138 | 40462 | 69.4 | TGTCATCGAATCGTGCGGAC | 9 | 24 | 4 | 33 34 | 0 |
| 6883 | 2250 | 2139 | 15761 | 69.4 | TGTCAGGATGTCGACCTGCC | 9 | 25 | 9 | 32 29 | 0 |
| 6884 | 2251 | 2140 | 40463 | 67.1 | TGTCGGACTACATCCCCGTT | 9 | 34 | 7 | 28 12 | 0 |
| 6885 | 2252 | 2141 | 15766 | 68.7 | TCGTTGTCACCTCAGCAGCC | 10 | 9 | 23 | 31 36 | 0 |
| 6886 | 2253 | 2142 | 30518 | 70.1 | TCGTCTCAGACCCAGCGCTT | 10 | 13 | 32 | 31 17 | 0 |
| 6887 | 2254 | 2143 | 40464 | 67.5 | TCGTGGTATACATGCGCAGC | 10 | 18 | 7 | 29 31 | 0 |
| 6888 | 2255 | 2144 | 8234 | 67.6 | TCCCTCGTGTCTTGTCAGCC | 28 | 10 | 19 | 9 36 | 0 |
| 6889 | 2256 | 2145 | 40465 | 71.1 | TCCCTCGTGCAAAGTGGTGC | 28 | 10 | 21 | 22 33 | 0 |

FIG. 29VV

| SEQ ID NO: | ZIP ID# | 4,633 ID# | HEX ID# | Tm | ZIPCODE (NH2 -> CONH2) | TETRAMER NUMBERS | | | | "UNALLOWED DIMERS" |
|---|---|---|---|---|---|---|---|---|---|---|
| 6890 | 2257 | 2146 | 40466 | 66 | TCGTACCTCCTAGTGCTGCG | 10 | 23 | 26 | 33 29 | 0 |
| 6891 | 2258 | 2147 | 8237 | 71.9 | TCCCTCGTGATGCACGATCG | 28 | 10 | 27 | 30 24 | 0 |
| 6892 | 2259 | 2148 | 8238 | 73.1 | TCCCTCGTTGCGCCATAGGA | 28 | 10 | 29 | 15 25 | 0 |
| 6893 | 2260 | 2149 | 8240 | 71.5 | TCCCTCGTGACCTCGTGCAA | 28 | 10 | 32 | 10 21 | 0 |
| 6894 | 2261 | 2150 | 15769 | 67.6 | TCCCTCGTGTGCTTAGCCAT | 28 | 10 | 33 | 3 15 | 0 |
| 6895 | 2262 | 2151 | 21356 | 69.7 | TCGTGGACGCTTAGTGCGAA | 10 | 34 | 17 | 22 16 | 0 |
| 6896 | 2263 | 2152 | 30519 | 71.1 | TCCCCTTGTGATTCGTTGCG | 28 | 11 | 2 | 10 29 | 0 |
| 6897 | 2264 | 2153 | 21357 | 65.1 | TCCCCTTGAAAGGGTAACCT | 28 | 11 | 6 | 18 23 | 0 |
| 6898 | 2265 | 2154 | 30520 | 66.1 | TCCCCTTGTCTGACCTAGCC | 28 | 11 | 8 | 23 36 | 0 |
| 6899 | 2266 | 2155 | 40469 | 66.9 | TCCCCTTGCTCAGGACTCTG | 28 | 11 | 13 | 34 8 | 0 |
| 6900 | 2267 | 2156 | 30521 | 70.2 | TCCCCTTGGGTAAGTGTGCG | 28 | 11 | 18 | 22 29 | 0 |
| 6901 | 2268 | 2157 | 40470 | 68.9 | TCCCCTTGATCGTCTGTCCC | 28 | 11 | 24 | 8 28 | 0 |
| 6902 | 2269 | 2159 | 15779 | 69.7 | TCCCCTTGAGCCAGGATTGA | 28 | 11 | 36 | 25 1 | 0 |
| 6903 | 2270 | 2160 | 30522 | 64.8 | TCCCCGTTTGATATCGTGAT | 28 | 12 | 2 | 24 2 | 0 |
| 6904 | 2271 | 2161 | 8266 | 68.9 | TCCCCGTTATACGTGCGATG | 28 | 12 | 5 | 33 27 | 0 |
| 6905 | 2272 | 2162 | 40473 | 66.2 | TCCCCGTTTACATTGACACG | 28 | 12 | 7 | 1 30 | 0 |
| 6906 | 2273 | 2163 | 40474 | 69.9 | TCCCCGTTTGTCTGTCGACC | 28 | 12 | 9 | 9 32 | 0 |
| 6907 | 2274 | 2164 | 8267 | 73.4 | TCCCCGTTTCGTCAGCATCG | 28 | 12 | 10 | 31 24 | 0 |
| 6908 | 2275 | 2165 | 8268 | 67.3 | TCCCCGTTCTTGGAGTGGTA | 28 | 12 | 11 | 20 18 | 0 |
| 6909 | 2276 | 2166 | 8270 | 67.7 | TCCCCGTCTCAGGTACACG | 28 | 12 | 13 | 18 30 | 0 |
| 6910 | 2277 | 2167 | 8272 | 72.9 | TCCCCGTTCCATCACGGATG | 28 | 12 | 15 | 30 27 | 0 |
| 6911 | 2278 | 2168 | 8274 | 73.3 | TCCCCGTTGCTTTCCCCTGT | 28 | 12 | 17 | 28 14 | 0 |
| 6912 | 2279 | 2169 | 8276 | 69.6 | TCCCCGTTGCAATCTGACCT | 28 | 12 | 21 | 8 23 | 0 |
| 6913 | 2280 | 2170 | 30523 | 67.1 | TCCCCGTTACCTTGATACGG | 28 | 12 | 23 | 2 35 | 0 |
| 6914 | 2281 | 2171 | 8277 | 70.8 | TCCCCGTTATCGCCTATCCC | 28 | 12 | 24 | 26 28 | 0 |
| 6915 | 2282 | 2172 | 8281 | 73.1 | TCCCCGTTTGCGTCGTAGGA | 28 | 12 | 29 | 10 25 | 0 |
| 6916 | 2283 | 2173 | 8283 | 73.8 | TCCCCGTTGTGCAGTGCGTT | 28 | 12 | 33 | 22 12 | 0 |
| 6917 | 2284 | 2175 | 15780 | 73.2 | TCCCCTCATGATTGCGACGG | 28 | 13 | 2 | 29 35 | 0 |
| 6918 | 2285 | 2176 | 8287 | 68.3 | TCCCCTCATTAGCTTGTGCG | 28 | 13 | 3 | 11 29 | 0 |
| 6919 | 2286 | 2178 | 8290 | 64.2 | TCCCCTCATCTGGCTTTTAG | 28 | 13 | 8 | 17 3 | 0 |
| 6920 | 2287 | 2180 | 8295 | 68.4 | TCCCCTCACCATCCTAAGCC | 28 | 13 | 15 | 26 36 | 0 |
| 6921 | 2288 | 2181 | 30525 | 66.9 | TCCCCTCAGCTTAGGACGAA | 28 | 13 | 17 | 25 16 | 0 |
| 6922 | 2289 | 2182 | 8298 | 66.8 | TCCCCTCAACCTCCTACACG | 28 | 13 | 23 | 26 30 | 0 |
| 6923 | 2290 | 2184 | 8302 | 70.3 | TCCCCTCACACGATCGTCGT | 28 | 13 | 30 | 24 10 | 0 |
| 6924 | 2291 | 2185 | 8303 | 71.4 | TCCCCTCACAGCCTGTTCCC | 28 | 13 | 31 | 14 28 | 0 |
| 6925 | 2292 | 2186 | 30527 | 67.5 | TCCCCTGTTGATGCTTGACC | 28 | 14 | 2 | 17 32 | 0 |
| 6926 | 2293 | 2187 | 8308 | 68.3 | TCCCCTGTTCTGCCATGATG | 28 | 14 | 8 | 15 27 | 0 |
| 6927 | 2294 | 2188 | 40477 | 70.1 | TCCCCTGTTGTCGCAAGACC | 28 | 14 | 9 | 21 32 | 0 |
| 6928 | 2295 | 2189 | 30528 | 64.7 | TCCCCTGTTCGTACCTATCG | 28 | 14 | 10 | 23 24 | 0 |
| 6929 | 2296 | 2190 | 15784 | 69.3 | TCCCCTGTCGAAAAGCGTT | 28 | 14 | 16 | 6 12 | 0 |
| 6930 | 2297 | 2191 | 8315 | 69.9 | TCCCCTGTGCAAAGTGGACC | 28 | 14 | 21 | 22 32 | 0 |
| 6931 | 2298 | 2192 | 30529 | 72 | TCCCCTGTAGGATCCCGCAA | 28 | 14 | 25 | 28 21 | 0 |
| 6932 | 2299 | 2193 | 40479 | 72 | TCCCCTGTCCTAAGCCTGCG | 28 | 14 | 26 | 36 29 | 0 |
| 6933 | 2300 | 2194 | 30530 | 72.8 | TCCCCTGTGATGGGACACGG | 28 | 14 | 27 | 34 35 | 0 |
| 6934 | 2301 | 2195 | 8320 | 71.1 | TCCCCTGTTGCGCTTGTGTC | 28 | 14 | 29 | 11 9 | 0 |
| 6935 | 2302 | 2196 | 8325 | 65.2 | TCCCCCATTTGATCGTAGTG | 28 | 15 | 1 | 10 22 | 0 |
| 6936 | 2303 | 2198 | 8330 | 73.1 | TCCCCCATCTTGTGCGGATG | 28 | 15 | 11 | 29 27 | 0 |
| 6937 | 2304 | 2199 | 8331 | 70.4 | TCCCCCATCGTTGTCTCGAA | 28 | 15 | 12 | 19 16 | 0 |

FIG. 29WW

| SEQ ID NO: | ZIP ID# | 4,633 ID# | HEX ID# Tm | ZIPCODE (NH2 -> CONH2) | TETRAMER NUMBERS | | | | | "UNALLOWED DIMERS" |
|---|---|---|---|---|---|---|---|---|---|---|
| 6938 | 2305 | 2200 | 30532 | 69.7 | TCCCCCATCTCAGACCATCG | 28 | 15 | 13 | 32 | 24 | 0 |
| 6939 | 2306 | 2201 | 30533 | 73.1 | TCCCCCATGCTTCTTGCGAA | 28 | 15 | 17 | 11 | 16 | 0 |
| 6940 | 2307 | 2202 | 40481 | 64.6 | TCCCCCATGGTATTGAAAAG | 28 | 15 | 18 | 1 | 6 | 0 |
| 6941 | 2308 | 2203 | 8335 | 67.3 | TCCCCCATAGTGAGTGCGTT | 28 | 15 | 22 | 22 | 12 | 0 |
| 6942 | 2309 | 2204 | 8336 | 74.6 | TCCCCCATTGCGAATCAGCC | 28 | 15 | 29 | 4 | 36 | 0 |
| 6943 | 2310 | 2205 | 15792 | 70.3 | TCCCCCATGTGCCAGCTTAG | 28 | 15 | 33 | 31 | 3 | 0 |
| 6944 | 2311 | 2206 | 21375 | 63.9 | TCCCCCATGGACACCTATAC | 28 | 15 | 34 | 23 | 5 | 0 |
| 6945 | 2312 | 2208 | 40485 | 66.1 | TCCCCGAAATACAATCTCCC | 28 | 16 | 5 | 4 | 28 | 0 |
| 6946 | 2313 | 2209 | 8346 | 69.4 | TCCCCGAAAAGGCAAGGTA | 28 | 16 | 6 | 21 | 18 | 0 |
| 6947 | 2314 | 2210 | 8347 | 68.1 | TCCCCGAATACAAGTGCAGC | 28 | 16 | 7 | 22 | 31 | 0 |
| 6948 | 2315 | 2211 | 8350 | 72.5 | TCCCCGAACTTGGATGCAGC | 28 | 16 | 11 | 27 | 31 | 0 |
| 6949 | 2316 | 2212 | 40486 | 69.1 | TCCCCGAAGCTTTTGACCAT | 28 | 16 | 17 | 1 | 15 | 0 |
| 6950 | 2317 | 2213 | 40487 | 67 | TCCCCGAAGTCTGGTAGTGC | 28 | 16 | 19 | 18 | 33 | 0 |
| 6951 | 2318 | 2214 | 15795 | 73.6 | TCCCCGAAAGTGGGACGGAC | 28 | 16 | 22 | 34 | 34 | 0 |
| 6952 | 2319 | 2215 | 8359 | 70.4 | TCCCCGAATGCGATCGTTAG | 28 | 16 | 29 | 24 | 3 | 0 |
| 6953 | 2320 | 2217 | 40490 | 71 | TCCCGCTTTAGGACCGGAC | 28 | 17 | 3 | 32 | 34 | 0 |
| 6954 | 2321 | 2218 | 21380 | 65.9 | TCCCGCTTTACACTGTACGG | 28 | 17 | 7 | 14 | 35 | 0 |
| 6955 | 2322 | 2219 | 8367 | 70.6 | TCCCGCTTCGAAATCGTCTG | 28 | 17 | 16 | 24 | 8 | 0 |
| 6956 | 2323 | 2220 | 8368 | 74.2 | TCCCGCTTGCTTGTGCGGTA | 28 | 17 | 17 | 33 | 18 | 0 |
| 6957 | 2324 | 2221 | 30536 | 64.9 | TCCCGCTTGTCTAGGACTTG | 28 | 17 | 19 | 25 | 11 | 0 |
| 6958 | 2325 | 2222 | 40494 | 69.7 | TCCCGCTTAGTGCTTGGACC | 28 | 17 | 22 | 11 | 32 | 0 |
| 6959 | 2326 | 2223 | 8372 | 70.3 | TCCCGCTTATCGAGCCTTGA | 28 | 17 | 24 | 36 | 1 | 0 |
| 6960 | 2327 | 2224 | 8375 | 73.3 | TCCCGCTTCACGATCGCCTA | 28 | 17 | 30 | 24 | 26 | 0 |
| 6961 | 2328 | 2225 | 8376 | 70.5 | TCCCGCTTCAGCCTCAGATG | 28 | 17 | 31 | 13 | 27 | 0 |
| 6962 | 2329 | 2226 | 15801 | 71.1 | TCCCGCTTAGCCTCTGGCTT | 28 | 17 | 36 | 8 | 17 | 0 |
| 6963 | 2330 | 2227 | 15802 | 65.2 | TCCCGGTATGATCGAAGATG | 28 | 18 | 2 | 16 | 27 | 0 |
| 6964 | 2331 | 2228 | 30537 | 69.6 | TCCCGGTAAATCCACGGGTA | 28 | 18 | 4 | 30 | 18 | 0 |
| 6965 | 2332 | 2229 | 40498 | 68.9 | TCCCGGTATGTCCTTGGCTT | 28 | 18 | 9 | 11 | 17 | 0 |
| 6966 | 2333 | 2230 | 40499 | 68.1 | TCCCGGTACTCAAATCTGCG | 28 | 18 | 13 | 4 | 29 | 0 |
| 6967 | 2334 | 2231 | 30539 | 67.1 | TCCCGGTACTGTAGGAACGG | 28 | 18 | 14 | 25 | 35 | 0 |
| 6968 | 2335 | 2232 | 40500 | 64 | TCCCGGTAGGTACCTAGTGC | 28 | 18 | 18 | 26 | 33 | 0 |
| 6969 | 2336 | 2233 | 8391 | 68.5 | TCCCGGTAAGGAGCTTCGTT | 28 | 18 | 25 | 17 | 12 | 0 |
| 6970 | 2337 | 2234 | 40503 | 64.5 | TCCCGGTACCTATTAGCAGC | 28 | 18 | 26 | 3 | 31 | 0 |
| 6971 | 2338 | 2235 | 30541 | 65.3 | TCCCGGTAGATGTCGTTCTG | 28 | 18 | 27 | 10 | 8 | 0 |
| 6972 | 2339 | 2236 | 8393 | 72 | TCCCGGTATGCGGGTAAGGA | 28 | 18 | 29 | 18 | 25 | 0 |
| 6973 | 2340 | 2238 | 8398 | 71.1 | TCCCGGTAAGCCCCATCTGT | 28 | 18 | 36 | 15 | 14 | 0 |
| 6974 | 2341 | 2239 | 15810 | 67.1 | TCCCGTCTTTGAGCTTGACC | 28 | 19 | 1 | 17 | 32 | 0 |
| 6975 | 2342 | 2240 | 30542 | 74.3 | TCCCGTCTTGTCACGGTGCG | 28 | 19 | 9 | 35 | 29 | 0 |
| 6976 | 2343 | 2241 | 40504 | 65.8 | TCCCGTCTTCGTAGTGCTTG | 28 | 19 | 10 | 22 | 11 | 0 |
| 6977 | 2344 | 2242 | 40505 | 70.4 | TCCCGTCTCTCAACCTTGCG | 28 | 19 | 13 | 23 | 29 | 0 |
| 6978 | 2345 | 2244 | 8406 | 69.2 | TCCCGTCTAGTGTCCCAGCC | 28 | 19 | 22 | 28 | 36 | 1 |
| 6979 | 2346 | 2245 | 8407 | 67.3 | TCCCGTCTACCTCCTATGCG | 28 | 19 | 23 | 26 | 29 | 0 |
| 6980 | 2347 | 2246 | 30544 | 71.4 | TCCCGTCTATCGCTCATGCG | 28 | 19 | 24 | 13 | 29 | 0 |
| 6981 | 2348 | 2247 | 15812 | 65.2 | TCCCGTCTCCTAAGGAGACC | 28 | 19 | 26 | 25 | 32 | 0 |
| 6982 | 2349 | 2248 | 8409 | 73 | TCCCGTCTTGCGCCATGAGT | 28 | 19 | 29 | 15 | 20 | 0 |
| 6983 | 2350 | 2249 | 40506 | 67.4 | TCCCGTCTCACGACCTTGTC | 28 | 19 | 30 | 23 | 9 | 0 |
| 6984 | 2351 | 2250 | 40507 | 68.9 | TCCCGTCTGGACTCTGGCTT | 28 | 19 | 34 | 8 | 17 | 0 |
| 6985 | 2352 | 2251 | 15814 | 67.2 | TCCCGTCTACGGCTTGAATC | 28 | 19 | 35 | 11 | 4 | 0 |

FIG. 29XX

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 6986 | 2353 | 2252 | 30545 | 69.4 | TCCCGTCTAGCCGAGTGACC | 28 | 19 | 36 | 20 | 32 | 0 |
| 6987 | 2354 | 2253 | 8412 | 65.1 | TCCCGAGTTGATCCATCTTG | 28 | 20 | 2 | 15 | 11 | 0 |
| 6988 | 2355 | 2255 | 30546 | 69.1 | TCCCGAGTCTTGATCGGCTT | 28 | 20 | 11 | 24 | 17 | 0 |
| 6989 | 2356 | 2256 | 15816 | 69.7 | TCCCGAGTCGAAGACCCTCA | 28 | 20 | 16 | 32 | 13 | 0 |
| 6990 | 2357 | 2257 | 40510 | 65.3 | TCCCGAGTATCGTCTGATCG | 28 | 20 | 24 | 8 | 24 | 0 |
| 6991 | 2358 | 2258 | 8420 | 72 | TCCCGAGTCAGCGACCACCT | 28 | 20 | 31 | 32 | 23 | 0 |
| 6992 | 2359 | 2259 | 30548 | 74.2 | TCCCGAGTGACCACGGGCTT | 28 | 20 | 32 | 35 | 17 | 0 |
| 6993 | 2360 | 2260 | 40511 | 69.4 | TCCCGAGTGTGCTGTCGATG | 28 | 20 | 33 | 9 | 27 | 0 |
| 6994 | 2361 | 2261 | 8424 | 72.2 | TCCCGAGTACGGCAAAGGA | 28 | 20 | 35 | 21 | 25 | 0 |
| 6995 | 2362 | 2262 | 40512 | 66.1 | TCCCGCAATTGACGTTAAAG | 28 | 21 | 1 | 12 | 6 | 0 |
| 6996 | 2363 | 2263 | 40513 | 67.9 | TCCCGCAATTAGCCATCCTA | 28 | 21 | 3 | 15 | 26 | 0 |
| 6997 | 2364 | 2264 | 40514 | 70.2 | TCCCGCAAAATCGGACAATC | 28 | 21 | 4 | 34 | 4 | 0 |
| 6998 | 2365 | 2265 | 8429 | 66.4 | TCCCGCAATACAATCGAGTG | 28 | 21 | 7 | 24 | 22 | 0 |
| 6999 | 2366 | 2266 | 8431 | 68.2 | TCCCGCAACTTGAAAGATCG | 28 | 21 | 11 | 6 | 24 | 0 |
| 7000 | 2367 | 2267 | 8436 | 70.8 | TCCCGCAACGAAGTGCTGAT | 28 | 21 | 16 | 33 | 2 | 0 |
| 7001 | 2368 | 2268 | 8437 | 72.9 | TCCCGCAAGCTTTCTGGTGC | 28 | 21 | 17 | 8 | 33 | 0 |
| 7002 | 2369 | 2269 | 30549 | 71.6 | TCCCGCAAGAGTCCATGCAA | 28 | 21 | 20 | 15 | 21 | 0 |
| 7003 | 2370 | 2270 | 40515 | 68.6 | TCCCGCAAAGTGAGTGGATG | 28 | 21 | 22 | 22 | 27 | 0 |
| 7004 | 2371 | 2272 | 8442 | 76.2 | TCCCGCAACAGCGGACAGGA | 28 | 21 | 31 | 34 | 25 | 0 |
| 7005 | 2372 | 2273 | 8444 | 69.5 | TCCCGCAAGGACCCTACTTG | 28 | 21 | 34 | 26 | 11 | 0 |
| 7006 | 2373 | 2274 | 8445 | 72.6 | TCCCGCAAAGCCGGACATAC | 28 | 21 | 36 | 34 | 5 | 0 |
| 7007 | 2374 | 2275 | 8447 | 71.7 | TCCCAGTGCTCAGTGCCGAA | 28 | 22 | 13 | 33 | 16 | 0 |
| 7008 | 2375 | 2276 | 8448 | 69.7 | TCCCAGTGCTGTATCGCACG | 28 | 22 | 14 | 24 | 30 | 0 |
| 7009 | 2376 | 2277 | 8449 | 71.8 | TCCCAGTGCCATTCCCGAGT | 28 | 22 | 15 | 28 | 20 | 0 |
| 7010 | 2377 | 2278 | 40518 | 71.5 | TCCCAGTGGCAATCGTCGAA | 28 | 22 | 21 | 10 | 16 | 0 |
| 7011 | 2378 | 2279 | 8454 | 66.5 | TCCCAGTGCCTAGGACGTCT | 28 | 22 | 26 | 34 | 19 | 0 |
| 7012 | 2379 | 2280 | 40519 | 69 | TCCCAGTGTCCCCCTAGTGC | 28 | 22 | 28 | 26 | 33 | 1 |
| 7013 | 2380 | 2281 | 8457 | 70.9 | TCCCAGTGCAGCGTCTCGTT | 28 | 22 | 31 | 19 | 12 | 0 |
| 7014 | 2381 | 2282 | 15826 | 69.5 | TCCCAGTGGGACAGTGGCTT | 28 | 22 | 34 | 22 | 17 | 0 |
| 7015 | 2382 | 2283 | 8459 | 72.1 | TCCCAGTGAGCCCGTTTCGT | 28 | 22 | 36 | 12 | 10 | 0 |
| 7016 | 2383 | 2284 | 21397 | 66.3 | ACCTTCTGAATCTCCCTGCG | 23 | 8 | 4 | 28 | 29 | 0 |
| 7017 | 2384 | 2285 | 8463 | 70.7 | TCCCACCTTGTCATCGGTGC | 28 | 23 | 9 | 24 | 33 | 0 |
| 7018 | 2385 | 2287 | 8470 | 69.1 | TCCCACCTGCAACACGTGTC | 28 | 23 | 21 | 30 | 9 | 0 |
| 7019 | 2386 | 2288 | 8471 | 64.8 | ACCTAGGACAGCTCTGCACG | 23 | 25 | 31 | 8 | 30 | 0 |
| 7020 | 2387 | 2289 | 15831 | 68.9 | ACCTGATGCTTGTCGTTGCG | 23 | 27 | 11 | 10 | 29 | 0 |
| 7021 | 2388 | 2290 | 8474 | 75 | TCCCACCTTCCCCACGCTCA | 28 | 23 | 28 | 30 | 13 | 1 |
| 7022 | 2389 | 2291 | 21400 | 68.7 | TCCCACCTCAGCCTTGGAGT | 28 | 23 | 31 | 11 | 20 | 0 |
| 7023 | 2390 | 2292 | 8476 | 70.5 | TCCCACCTACGGTCGTCGAA | 28 | 23 | 35 | 10 | 16 | 0 |
| 7024 | 2391 | 2294 | 40523 | 68.6 | TCCCATCGCGTTGCTTAAAG | 28 | 24 | 12 | 17 | 6 | 0 |
| 7025 | 2392 | 2295 | 8483 | 73.8 | TCCCATCGCCATCAGCCTCA | 28 | 24 | 15 | 31 | 13 | 0 |
| 7026 | 2393 | 2296 | 30553 | 64.9 | ATCGGATGTTAGACCTTGCG | 24 | 27 | 3 | 23 | 29 | 0 |
| 7027 | 2394 | 2297 | 8489 | 70.6 | TCCCATCGTGCGAGGAGGTA | 28 | 24 | 29 | 25 | 18 | 0 |
| 7028 | 2395 | 2298 | 8490 | 75.4 | TCCCATCGCACGTCGTTCCC | 28 | 24 | 30 | 10 | 28 | 0 |
| 7029 | 2396 | 2299 | 8491 | 73.5 | TCCCATCGCAGCCAGCAATC | 28 | 24 | 31 | 31 | 4 | 0 |
| 7030 | 2397 | 2300 | 15834 | 69.9 | TCCCATCGGACCTTGACAGC | 28 | 24 | 32 | 1 | 31 | 0 |
| 7031 | 2398 | 2301 | 8493 | 72.2 | TCCCATCGGGACCTCAATCG | 28 | 24 | 34 | 13 | 24 | 0 |
| 7032 | 2399 | 2302 | 30554 | 75 | TCCCATCGAGCCATCGCCAT | 28 | 24 | 36 | 24 | 15 | 0 |
| 7033 | 2400 | 2303 | 40528 | 73.3 | TCCCAGGACTTGGTGCGTGC | 28 | 25 | 11 | 33 | 33 | 0 |

FIG. 29YY

| SEQ ID NO: | ZIP ID# | 4,633 ID# | HEX ID# Tm | ZIPCODE (RE2 -> COMB2) | TETRAMER NUMBERS | | | | | "UNALLOWED DIMERS" |
|---|---|---|---|---|---|---|---|---|---|---|
| 7034 | 2401 | 2305 | 15836 71.1 | TCCCAGGAGCTTACGGAGCC | 28 | 25 | 17 | 35 | 36 | 0 |
| 7035 | 2402 | 2306 | 40529 65.2 | AGGAGGTATTAGTGCGTGCG | 25 | 18 | 3 | 29 | 29 | 0 |
| 7036 | 2403 | 2307 | 8506 67.9 | TCCCAGGAGAGTGGACTCCC | 28 | 25 | 20 | 34 | 28 | 0 |
| 7037 | 2404 | 2308 | 15837 69.9 | TCCCAGGAACCTCGAAGCAA | 28 | 25 | 23 | 16 | 21 | 0 |
| 7038 | 2405 | 2309 | 40531 74.3 | TCCCAGGAGATGTGCGTGCG | 28 | 25 | 27 | 29 | 29 | 0 |
| 7039 | 2406 | 2310 | 8510 70.1 | TCCCAGGATCCCCCTAAGGA | 28 | 25 | 28 | 26 | 25 | 0 |
| 7040 | 2407 | 2311 | 8511 73.9 | TCCCAGGATGCGAATCGCAA | 28 | 25 | 29 | 4 | 21 | 0 |
| 7041 | 2408 | 2312 | 30559 68.6 | TCCCCCTATGATCGAAAGCC | 28 | 26 | 2 | 16 | 36 | 0 |
| 7042 | 2409 | 2313 | 30560 66.5 | TCCCCCTACGTTCCTAATCG | 28 | 26 | 12 | 26 | 24 | 0 |
| 7043 | 2410 | 2314 | 40535 70.1 | TCCCCCTACTCAGTGCACGG | 28 | 26 | 13 | 33 | 35 | 0 |
| 7044 | 2411 | 2315 | 30561 69.1 | TCCCCCTAGCTTCACGGGTA | 28 | 26 | 17 | 30 | 18 | 0 |
| 7045 | 2412 | 2316 | 30562 66.6 | TCCCCCTAGGTAGAGTTGCG | 28 | 26 | 18 | 20 | 29 | 0 |
| 7046 | 2413 | 2317 | 8528 75.5 | TCCCCCTATGCGGATGTGCG | 28 | 26 | 29 | 27 | 29 | 0 |
| 7047 | 2414 | 2318 | 8531 66.8 | TCCCCCTAGACCATACACGG | 28 | 26 | 32 | 5 | 35 | 0 |
| 7048 | 2415 | 2319 | 40538 66.3 | TCCCCCTAGGACAATCCTCA | 28 | 26 | 34 | 4 | 13 | 0 |
| 7049 | 2416 | 2320 | 8532 71.5 | TCCCCCTAACGGCTGTGGAC | 28 | 26 | 35 | 14 | 34 | 0 |
| 7050 | 2417 | 2321 | 30563 69.4 | TCCCGATGTTGATCCCCCTA | 28 | 27 | 1 | 28 | 26 | 0 |
| 7051 | 2418 | 2322 | 21415 65 | TCCCGATGTTAGCTGTAGCC | 28 | 27 | 3 | 14 | 36 | 0 |
| 7052 | 2419 | 2323 | 15848 68.8 | TCCCGATGTGTCACGGTGTC | 28 | 27 | 9 | 35 | 9 | 0 |
| 7053 | 2420 | 2324 | 8539 67 | TCCCGATGCTGTAAAGGGAC | 28 | 27 | 14 | 6 | 34 | 0 |
| 7054 | 2421 | 2325 | 8541 68.9 | TCCCGATGGGTAAGTGTCCC | 28 | 27 | 18 | 22 | 28 | 1 |
| 7055 | 2422 | 2326 | 15849 67.5 | TCCCGATGGAGTTGTCCTTG | 28 | 27 | 20 | 9 | 11 | 0 |
| 7056 | 2423 | 2327 | 30564 70.6 | TCCCGATGGCAAGCAAAAAG | 28 | 27 | 21 | 21 | 6 | 0 |
| 7057 | 2424 | 2328 | 8545 70.6 | TCCCGATGATCGGGACAGTG | 28 | 27 | 24 | 34 | 22 | 0 |
| 7058 | 2425 | 2329 | 8548 70.3 | TCCCGATGTGCGATACCCAT | 28 | 27 | 29 | 5 | 15 | 0 |
| 7059 | 2426 | 2330 | 8549 75.4 | TCCCGATGCACGGGACCTTG | 28 | 27 | 30 | 34 | 11 | 0 |
| 7060 | 2427 | 2331 | 15852 75 | TCCCGATGGACCGCAACGTT | 28 | 27 | 32 | 21 | 12 | 0 |
| 7061 | 2428 | 2332 | 8552 71.4 | TCCCGATGGGACCCTACAGC | 28 | 27 | 34 | 26 | 31 | 0 |
| 7062 | 2429 | 2333 | 8553 71 | TCCCGATGACGGCTCACTTG | 28 | 27 | 35 | 13 | 11 | 0 |
| 7063 | 2430 | 2334 | 15853 70.6 | TCCCGATGAGCCTGCGTTAG | 28 | 27 | 36 | 29 | 3 | 0 |
| 7064 | 2431 | 2335 | 40540 67.9 | TCCCTGATACCTCAGCGTGC | 28 | 2 | 23 | 31 | 33 | 0 |
| 7065 | 2432 | 2336 | 30565 71.4 | TCCCTACAGTGCGCAAACGG | 28 | 7 | 33 | 21 | 35 | 0 |
| 7066 | 2433 | 2337 | 8558 68.8 | TCCCTCCCTGTCCCTACGAA | 28 | 28 | 9 | 26 | 16 | 0 |
| 7067 | 2434 | 2338 | 40541 67.8 | TCCCCTTGTTAGGGACCCAT | 28 | 11 | 3 | 34 | 15 | 0 |
| 7068 | 2435 | 2339 | 8560 70.8 | TCCCTCCCCTCACGTTCCAT | 28 | 28 | 13 | 12 | 15 | 0 |
| 7069 | 2436 | 2340 | 8561 71.9 | TCCCTCCCCTGTGTGCGAGT | 28 | 28 | 14 | 33 | 20 | 0 |
| 7070 | 2437 | 2341 | 30566 70.7 | TCCCCGAATTAGCTGTTGCG | 28 | 16 | 3 | 14 | 29 | 0 |
| 7071 | 2438 | 2342 | 8566 71.7 | TCCCTCCCATCGCCTAATCG | 28 | 28 | 24 | 26 | 24 | 0 |
| 7072 | 2439 | 2343 | 30567 71.4 | TCCCTCCCAGGATTGAACGG | 28 | 28 | 25 | 1 | 35 | 0 |
| 7073 | 2440 | 2344 | 8568 67.9 | TCCCTCCCGATGAAAGACCT | 28 | 28 | 27 | 6 | 23 | 0 |
| 7074 | 2441 | 2345 | 21423 71.7 | TCCCTCCCACGGAATCAGGA | 28 | 28 | 35 | 4 | 25 | 0 |
| 7075 | 2442 | 2346 | 40543 69.3 | TCCCTGCGTGATAGTGGCAA | 28 | 29 | 2 | 22 | 21 | 0 |
| 7076 | 2443 | 2347 | 30568 71.4 | TGCGATACGTGCAATCGCAA | 29 | 5 | 33 | 4 | 21 | 0 |
| 7077 | 2444 | 2348 | 30569 71.1 | TCCCTGCGAAAGAGTGCGAA | 28 | 29 | 6 | 22 | 16 | 0 |
| 7078 | 2445 | 2349 | 40544 68.2 | TGCGTACACCATATCGTGCG | 29 | 7 | 15 | 24 | 29 | 0 |
| 7079 | 2446 | 2350 | 40545 70.6 | TGCGTGTCAGTGCTTGGTGC | 29 | 9 | 22 | 11 | 33 | 0 |
| 7080 | 2447 | 2351 | 8575 68 | TGCGCTTGAGGAATACCGTT | 29 | 11 | 25 | 5 | 12 | 0 |
| 7081 | 2448 | 2352 | 8578 74 | TGCGCGAACACGTGATCACG | 29 | 16 | 30 | 2 | 30 | 0 |

FIG. 29ZZ

| SEQ ID NO: | ZIP ID# | 4,633 ID# | HEX ID# | Tm | ZIPCODE (NH2 -> CONH2) | TETRAMER NUMBERS | | | | "UNALLOWED DIMERS" |
|---|---|---|---|---|---|---|---|---|---|---|
| 7082 | 2449 | 2353 | 8579 | 70.8 | TGCGGCTTTTGAAGTGAGCC | 29 17 1 22 36 | | | | 0 |
| 7083 | 2450 | 2354 | 8581 | 73.1 | TCCCTGCGGCAACGTTGTCT | 28 29 21 12 19 | | | | 0 |
| 7084 | 2451 | 2355 | 8582 | 73.6 | TCCCTGCGACCTGCAAATCG | 28 29 23 21 24 | | | | 0 |
| 7085 | 2452 | 2356 | 40547 | 71.2 | TGCGAGGAGAGTGTGCGGAC | 29 25 20 33 34 | | | | 0 |
| 7086 | 2453 | 2357 | 15859 | 76.2 | TCCCTGCGTCCCGAGTGCAA | 28 29 28 20 21 | | | | 0 |
| 7087 | 2454 | 2358 | 8585 | 75.2 | TCCCTGCGCACGGGTACGTT | 28 29 30 18 12 | | | | 0 |
| 7088 | 2455 | 2359 | 8586 | 73.3 | TCCCTGCGCAGCCTGTAGGA | 28 29 31 14 25 | | | | 0 |
| 7089 | 2456 | 2360 | 8587 | 74.8 | TCCCTGCGGACCCTGTCAGC | 28 29 32 14 31 | | | | 0 |
| 7090 | 2457 | 2361 | 8588 | 79.4 | TCCCTGCGGTGCGCTTGCAA | 28 29 33 17 21 | | | | 0 |
| 7091 | 2458 | 2362 | 30570 | 72.3 | TCCCCACGTTGACAGCTCCC | 28 30 1 31 28 | | | | 0 |
| 7092 | 2459 | 2363 | 30571 | 65.4 | TCCCCACGTTAGTCGTCTTG | 28 30 3 10 11 | | | | 0 |
| 7093 | 2460 | 2366 | 8593 | 75.3 | TCCCCACGTCTGGGACACGG | 28 30 8 34 35 | | | | 0 |
| 7094 | 2461 | 2367 | 8594 | 69.2 | TCCCCACGTCGTGTGCATAC | 28 30 10 33 5 | | | | 0 |
| 7095 | 2462 | 2368 | 8596 | 72.6 | TCCCCACGCTGTTCTGAGCC | 28 30 14 8 36 | | | | 0 |
| 7096 | 2463 | 2370 | 21430 | 72.9 | TCCCCACGGGTATCCCCTGT | 28 30 18 28 14 | | | | 0 |
| 7097 | 2464 | 2371 | 8598 | 73.3 | TCCCCACGGTCTCAGCATCG | 28 30 19 31 24 | | | | 0 |
| 7098 | 2465 | 2372 | 8599 | 75.5 | TCCCCACGGCAAAATCGTGC | 28 30 21 4 33 | | | | 0 |
| 7099 | 2466 | 2373 | 8600 | 67.6 | TCCCCACGACCTAATCGATG | 28 30 23 4 27 | | | | 0 |
| 7100 | 2467 | 2374 | 8601 | 72.7 | TCCCCACGATCGCGAATGAT | 28 30 24 16 2 | | | | 0 |
| 7101 | 2468 | 2375 | 8602 | 74.9 | TCCCCACGCCTAGTGCAGCC | 28 30 26 33 36 | | | | 0 |
| 7102 | 2469 | 2376 | 8604 | 73.6 | TCCCCACGTGCGTGATTCGT | 28 30 29 2 10 | | | | 0 |
| 7103 | 2470 | 2377 | 8605 | 75.8 | TCCCCACGCAGCCGTTCTTG | 28 30 31 12 11 | | | | 0 |
| 7104 | 2471 | 2378 | 8606 | 72.7 | TCCCCACGGACCAGCCTACA | 28 30 32 36 7 | | | | 0 |
| 7105 | 2472 | 2379 | 8607 | 76.6 | TCCCCACGGTGCTGTCTGCG | 28 30 33 9 29 | | | | 0 |
| 7106 | 2473 | 2380 | 8608 | 75.9 | TCCCCACGGGACCCATCGTT | 28 30 34 15 12 | | | | 0 |
| 7107 | 2474 | 2381 | 30572 | 68.6 | TCCCCAGCTTGAAAAGGACC | 28 31 1 6 32 | | | | 0 |
| 7108 | 2475 | 2382 | 8611 | 72.8 | TCCCCAGCAATCGGACGGTA | 28 31 4 34 18 | | | | 0 |
| 7109 | 2476 | 2383 | 30573 | 65.4 | TCCCCAGCTACAGCAAAAAG | 28 31 7 21 6 | | | | 0 |
| 7110 | 2477 | 2384 | 8615 | 68.8 | TCCCCAGCTCTGATCGGTCT | 28 31 8 24 19 | | | | 0 |
| 7111 | 2478 | 2385 | 8616 | 68.4 | TCCCCAGCTCGTCTGTGATG | 28 31 10 14 27 | | | | 0 |
| 7112 | 2479 | 2386 | 8617 | 70.4 | TCCCCAGCCTTGCTGTATCG | 28 31 11 14 24 | | | | 0 |
| 7113 | 2480 | 2387 | 8619 | 75.3 | TCCCCAGCCGAAGTGCCTCA | 28 31 16 33 13 | | | | 0 |
| 7114 | 2481 | 2388 | 8621 | 71.8 | TCCCCAGCGGTAAGGACAGC | 28 31 18 25 31 | | | | 0 |
| 7115 | 2482 | 2389 | 15863 | 70.1 | TCCCCAGCACCTAATCACGG | 28 31 23 4 35 | | | | 0 |
| 7116 | 2483 | 2390 | 8623 | 73.4 | TCCCCAGCATCGGATGCTTG | 28 31 24 27 11 | | | | 0 |
| 7117 | 2484 | 2391 | 30574 | 68.7 | TCCCCAGCAGGAGAGTAGCC | 28 31 25 20 36 | | | | 0 |
| 7118 | 2485 | 2392 | 8627 | 70.1 | TCCCCAGCCAGCTCTGTGTC | 28 31 31 8 9 | | | | 0 |
| 7119 | 2486 | 2393 | 21442 | 74.5 | TCCCCAGCGGACCGAATGTC | 28 31 34 16 9 | | | | 0 |
| 7120 | 2487 | 2394 | 8629 | 73.8 | TCCCCAGCAGCCGGTAGCTT | 28 31 36 18 17 | | | | 0 |
| 7121 | 2488 | 2395 | 8631 | 64.8 | TCCCGACCTGATTGATTGTC | 28 32 2 2 9 | | | | 0 |
| 7122 | 2489 | 2396 | 15865 | 67.2 | TCCCGACCTTAGAATCGTGC | 28 32 3 4 33 | | | | 0 |
| 7123 | 2490 | 2397 | 40549 | 66.6 | TCCCGACCAATCTTGAGACC | 28 32 4 1 32 | | | | 0 |
| 7124 | 2491 | 2398 | 8634 | 67.7 | TCCCGACCTACATTGAACGG | 28 32 7 1 35 | | | | 0 |
| 7125 | 2492 | 2399 | 8635 | 71 | TCCCGACCTGTCTCCCGAGT | 28 32 9 28 20 | | | | 0 |
| 7126 | 2493 | 2400 | 40550 | 71.5 | TCCCGACCCGTTTTAGCGTT | 28 32 12 3 12 | | | | 0 |
| 7127 | 2494 | 2401 | 21445 | 69.8 | TCCCGACCCTCAGGTAGCAA | 28 32 13 18 21 | | | | 0 |
| 7128 | 2495 | 2402 | 15866 | 66.8 | TCCCGACCCGTAGGACTTG | 28 32 14 25 11 | | | | 0 |
| 7129 | 2496 | 2404 | 40551 | 68.5 | TCCCGACCGTCTAAAGGACC | 28 32 19 6 32 | | | | 0 |

FIG. 29AAA

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 7130 | 2497 | 2405 | 8641 | 73.5 | TCCCGACCGAGTGTCTTGCG | 28 | 32 | 20 | 19 | 29 | 0 |
| 7131 | 2498 | 2406 | 8642 | 72.6 | TCCCGACCGCAAAGGAGATG | 28 | 32 | 21 | 25 | 27 | 0 |
| 7132 | 2499 | 2407 | 8646 | 67 | TCCCGACCCCTAATACGATG | 28 | 32 | 26 | 5 | 27 | 0 |
| 7133 | 2500 | 2408 | 15867 | 79.8 | TCCCGACCCACGGTGCAGCC | 28 | 32 | 30 | 33 | 36 | 0 |
| 7134 | 2501 | 2409 | 8648 | 66.1 | TCCCGTGCTTGATCTGAGTG | 28 | 33 | 1 | 8 | 22 | 0 |
| 7135 | 2502 | 2410 | 40555 | 65 | TCCCGTGCTTAGTGATAGCC | 28 | 33 | 3 | 2 | 36 | 0 |
| 7136 | 2503 | 2411 | 30576 | 72.7 | TCCCGTGCTGTCCCATCGTT | 28 | 33 | 9 | 15 | 12 | 0 |
| 7137 | 2504 | 2412 | 8651 | 73.4 | TCCCGTGCCTCAAATCGTGC | 28 | 33 | 13 | 4 | 33 | 0 |
| 7138 | 2505 | 2413 | 8652 | 73.9 | TCCCGTGCCGAACGAACTCA | 28 | 33 | 16 | 16 | 13 | 0 |
| 7139 | 2506 | 2414 | 40558 | 71.2 | TCCCGTGCGTCTCTGTACGG | 28 | 33 | 19 | 14 | 35 | 0 |
| 7140 | 2507 | 2415 | 8655 | 69.2 | TCCCGTGCACCTGTCTGATG | 28 | 33 | 23 | 19 | 27 | 0 |
| 7141 | 2508 | 2416 | 8659 | 78 | TCCCGTGCTCCCGCTTGTGC | 28 | 33 | 28 | 17 | 33 | 0 |
| 7142 | 2509 | 2417 | 8661 | 71.1 | TCCCGTGCGACCTTGAAGTG | 28 | 33 | 32 | 1 | 22 | 0 |
| 7143 | 2510 | 2418 | 15868 | 73.7 | TCCCGTGCGTGCTTAGGTGC | 28 | 33 | 33 | 3 | 33 | 0 |
| 7144 | 2511 | 2419 | 8663 | 73.2 | TCCCGTGCACGGAAAGCCTA | 28 | 33 | 35 | 6 | 26 | 0 |
| 7145 | 2512 | 2420 | 8664 | 70.4 | TCCCGTGCAGCCAGGATTAG | 28 | 33 | 36 | 25 | 3 | 0 |
| 7146 | 2513 | 2423 | 8667 | 70.3 | TCCCGGACAATCATCGAGGA | 28 | 34 | 4 | 24 | 25 | 0 |
| 7147 | 2514 | 2424 | 30577 | 67.4 | TCCCGGACATACTGTCGGAC | 28 | 34 | 5 | 9 | 34 | 0 |
| 7148 | 2515 | 2425 | 21453 | 66.3 | TCCCGGACAAAGTCCCTTAG | 28 | 34 | 6 | 28 | 3 | 1 |
| 7149 | 2516 | 2426 | 8669 | 67.7 | TCCCGGACTACACTTGACGG | 28 | 34 | 7 | 11 | 35 | 0 |
| 7150 | 2517 | 2427 | 40559 | 71.5 | TCCCGGACTCGTCGAAGACC | 28 | 34 | 10 | 16 | 32 | 0 |
| 7151 | 2518 | 2428 | 8672 | 72.8 | TCCCGGACCTTGCCATCTCA | 28 | 34 | 11 | 15 | 13 | 0 |
| 7152 | 2519 | 2429 | 8673 | 76.1 | TCCCGGACCGTTCACGCTCA | 28 | 34 | 12 | 30 | 13 | 0 |
| 7153 | 2520 | 2430 | 40561 | 66 | TCCCGGACGTCTATACTCCC | 28 | 34 | 19 | 5 | 28 | 0 |
| 7154 | 2521 | 2431 | 8678 | 70.3 | TCCCGGACATCGGAGTCTCA | 28 | 34 | 24 | 20 | 13 | 0 |
| 7155 | 2522 | 2432 | 30578 | 73.2 | TCCCGGACGATGCCATATCG | 28 | 34 | 27 | 15 | 24 | 0 |
| 7156 | 2523 | 2433 | 8682 | 72.1 | TCCCGGACTGCGAATCCCTA | 28 | 34 | 29 | 4 | 26 | 0 |
| 7157 | 2524 | 2434 | 8683 | 73.6 | TCCCGGACCACGTTGACGAA | 28 | 34 | 30 | 1 | 16 | 0 |
| 7158 | 2525 | 2435 | 8684 | 74.6 | TCCCGGACGACCGGACAAAG | 28 | 34 | 32 | 34 | 6 | 0 |
| 7159 | 2526 | 2436 | 8685 | 71.1 | TCCCGGACGTGCAAAGTCTG | 28 | 34 | 33 | 6 | 8 | 0 |
| 7160 | 2527 | 2437 | 8686 | 77.3 | TCCCGGACGGACGCAAAGGA | 28 | 34 | 34 | 21 | 25 | 0 |
| 7161 | 2528 | 2438 | 8687 | 73.9 | TCCCGGACAGCCACCTAGCC | 28 | 34 | 36 | 23 | 36 | 0 |
| 7162 | 2529 | 2439 | 15871 | 65.4 | TCCCACGGTTGACTGTAGGA | 28 | 35 | 1 | 14 | 25 | 1 |
| 7163 | 2530 | 2441 | 8696 | 74.5 | TCCCACGGGCTTTCTGCGTT | 28 | 35 | 17 | 8 | 12 | 0 |
| 7164 | 2531 | 2442 | 8697 | 68.9 | TCCCACGGGTCTGGTAGCTT | 28 | 35 | 19 | 18 | 17 | 0 |
| 7165 | 2532 | 2443 | 40565 | 69.1 | TCCCACGGCCTATCCCATAC | 28 | 35 | 26 | 28 | 5 | 0 |
| 7166 | 2533 | 2445 | 8704 | 71.2 | ACGGTGCGCCTAATACGCAA | 35 | 29 | 26 | 5 | 21 | 0 |
| 7167 | 2534 | 2446 | 21461 | 70.1 | ACGGGACCATACCTGTTGCG | 35 | 32 | 5 | 14 | 29 | 0 |
| 7168 | 2535 | 2447 | 8708 | 71 | TCCCACGGGTGCATCGTTAG | 28 | 35 | 33 | 24 | 3 | 0 |
| 7169 | 2536 | 2448 | 40566 | 67.8 | TCCCAGCCTTGATCTGATCG | 28 | 36 | 1 | 8 | 24 | 0 |
| 7170 | 2537 | 2449 | 30579 | 71.9 | TCCCAGCCTGATGATGTGCG | 28 | 36 | 2 | 27 | 29 | 0 |
| 7171 | 2538 | 2450 | 8709 | 65.1 | TCCCAGCCTTAGAGTGCTTG | 28 | 36 | 3 | 32 | 11 | 0 |
| 7172 | 2539 | 2451 | 40567 | 68.5 | TCCCAGCCATACAATCACGG | 28 | 36 | 5 | 4 | 35 | 0 |
| 7173 | 2540 | 2453 | 30580 | 67.8 | TCCCAGCCTCTGTTGAGTGC | 28 | 36 | 8 | 1 | 33 | 0 |
| 7174 | 2541 | 2454 | 8711 | 70.3 | TCCCAGCCTCGTGTCTACGG | 28 | 36 | 10 | 19 | 35 | 0 |
| 7175 | 2542 | 2455 | 15874 | 68.4 | TCCCAGCCCTCATTAGTCCC | 28 | 36 | 13 | 3 | 28 | 0 |
| 7176 | 2543 | 2456 | 8716 | 70.8 | TCCCAGCCGCTTCCTAACCT | 28 | 36 | 17 | 26 | 23 | 0 |
| 7177 | 2544 | 2457 | 30581 | 68.6 | TCCCAGCCGGTATTAGGACC | 28 | 36 | 18 | 3 | 32 | 0 |

FIG. 29BBB

| SEQ ID NO: | ZIP ID# | 4,633 ID# | HEX ID# | TM | ZIPCODE (NH2 -> CONH2) | TETRAMER NUMBERS | | | | | "UNALLOWED DIMERS" |
|---|---|---|---|---|---|---|---|---|---|---|---|
| 7178 | 2545 | 2458 | 30583 | 65.4 | TCCCAGCCAGTGTTAGCCTA | 28 | 36 | 22 | 3 | 26 | 0 |
| 7179 | 2546 | 2459 | 8718 | 68.1 | TCCCAGCCACCTATACTGCG | 28 | 36 | 23 | 5 | 29 | 0 |
| 7180 | 2547 | 2460 | 8719 | 72.8 | TCCCAGCCATCGGTGCTGAT | 28 | 36 | 24 | 33 | 2 | 0 |
| 7181 | 2548 | 2462 | 8721 | 71 | TCCCAGCCTCCCACCTTGAT | 28 | 36 | 28 | 23 | 2 | 0 |
| 7182 | 2549 | 2463 | 8722 | 75.9 | TCCCAGCCCACGGGTAAGCC | 28 | 36 | 30 | 18 | 36 | 0 |
| 7183 | 2550 | 2464 | 8723 | 74.7 | TCCCAGCCCAGCCTTGGATG | 28 | 36 | 31 | 11 | 27 | 0 |
| 7184 | 2551 | 2465 | 8724 | 73.2 | TCCCAGCCGTGCAAAGAGGA | 28 | 36 | 33 | 6 | 25 | 0 |
| 7185 | 2552 | 2466 | 21468 | 64 | TGCGTTGATTGAGAGTACGG | 29 | 1 | 1 | 20 | 35 | 0 |
| 7186 | 2553 | 2467 | 40569 | 70.1 | TGCGTTGAAAAGATCGTGCG | 29 | 1 | 6 | 24 | 29 | 0 |
| 7187 | 2554 | 2469 | 8729 | 64.4 | TGCGTTGACGTTCTGTCCTA | 29 | 1 | 12 | 14 | 26 | 0 |
| 7188 | 2555 | 2470 | 40571 | 67.3 | TGCGTTGACCATTCGTATCG | 29 | 1 | 15 | 10 | 24 | 0 |
| 7189 | 2556 | 2472 | 15879 | 71.3 | TGCGTTGACACGCGTTTTGA | 29 | 1 | 30 | 12 | 1 | 1 |
| 7190 | 2557 | 2473 | 15881 | 70.9 | TGCGTTGAGGACGATGTCCC | 29 | 1 | 34 | 27 | 28 | 0 |
| 7191 | 2558 | 2474 | 8740 | 72.9 | TGCGTTGAAGCCAGTGCGAA | 29 | 1 | 36 | 22 | 16 | 0 |
| 7192 | 2559 | 2475 | 15882 | 69.7 | TGCGTGATTGTCCAGCCTTG | 29 | 2 | 9 | 31 | 11 | 0 |
| 7193 | 2560 | 2476 | 15883 | 69.9 | TGCGTGATCTTGGGACTCCC | 29 | 2 | 11 | 34 | 28 | 0 |
| 7194 | 2561 | 2478 | 30585 | 70.7 | TGCGTGATGCTTTCCCACCT | 29 | 2 | 17 | 28 | 23 | 0 |
| 7195 | 2562 | 2480 | 8759 | 69.7 | TGCGTGATGAGTCAGCCAGC | 29 | 2 | 20 | 31 | 31 | 0 |
| 7196 | 2563 | 2481 | 40575 | 68 | TGATGCAACTGTCCATTGCG | 2 | 21 | 14 | 15 | 29 | 0 |
| 7197 | 2564 | 2483 | 30586 | 68.6 | TGCGTGATTCCCACCTCTTG | 29 | 2 | 28 | 23 | 11 | 0 |
| 7198 | 2565 | 2484 | 40576 | 69.3 | TGCGTGATGGACCCATATCG | 29 | 2 | 34 | 15 | 24 | 0 |
| 7199 | 2566 | 2485 | 40577 | 69.6 | TGATAGCCCAGCAATCGCAA | 2 | 36 | 31 | 4 | 21 | 0 |
| 7200 | 2567 | 2486 | 21481 | 65.7 | TGCGTTAGTTGAGACCGCTT | 29 | 3 | 1 | 32 | 17 | 0 |
| 7201 | 2568 | 2487 | 8756 | 68.2 | TGCGTTAGAAAGGACCCACG | 29 | 3 | 6 | 32 | 30 | 0 |
| 7202 | 2569 | 2488 | 8758 | 69.1 | TGCGTTAGCGAATGTCGGAC | 29 | 3 | 16 | 9 | 34 | 0 |
| 7203 | 2570 | 2489 | 40578 | 68.4 | TGCGTTAGGCTTTCCCAGTG | 29 | 3 | 17 | 28 | 22 | 0 |
| 7204 | 2571 | 2490 | 30588 | 67.5 | TTAGTGCGCGAAATACTGCG | 3 | 29 | 16 | 5 | 29 | 0 |
| 7205 | 2572 | 2491 | 8765 | 67.5 | TGCGTTAGGTGCTTGAGCAA | 29 | 3 | 33 | 1 | 21 | 0 |
| 7206 | 2573 | 2492 | 30589 | 72.2 | TGCGTTAGACGGGATGTGCG | 29 | 3 | 35 | 27 | 29 | 0 |
| 7207 | 2574 | 2493 | 8768 | 69.5 | TGCGTTAGAGCCGCTTGATG | 29 | 3 | 36 | 17 | 27 | 0 |
| 7208 | 2575 | 2494 | 30590 | 67.9 | TGCGAATCAAAGATCGTCCC | 29 | 4 | 6 | 24 | 28 | 0 |
| 7209 | 2576 | 2495 | 30591 | 69.9 | TGCGAATCTCGTTCGTCACG | 29 | 4 | 10 | 10 | 30 | 0 |
| 7210 | 2577 | 2496 | 40581 | 70.7 | TGCGAATCCTCAGACCCGAA | 29 | 4 | 13 | 32 | 16 | 0 |
| 7211 | 2578 | 2498 | 30592 | 71.9 | TGCGAATCCATTCCCGTCT | 29 | 4 | 15 | 28 | 19 | 0 |
| 7212 | 2579 | 2499 | 40582 | 71.6 | TGCGAATCGAGTAGCCGTGC | 29 | 4 | 20 | 36 | 33 | 0 |
| 7213 | 2580 | 2500 | 8789 | 73.5 | TGCGAATCAGTGCAGCTGCG | 29 | 4 | 22 | 31 | 29 | 0 |
| 7214 | 2581 | 2501 | 8782 | 72.7 | TGCGAATCCACGCGAACTCA | 29 | 4 | 30 | 16 | 13 | 0 |
| 7215 | 2582 | 2502 | 40583 | 63.5 | TGCGATACGGTATGATAGCC | 29 | 5 | 18 | 2 | 36 | 0 |
| 7216 | 2583 | 2504 | 30593 | 69 | TGCGATACGCAACTGTGCAA | 29 | 5 | 21 | 14 | 21 | 0 |
| 7217 | 2584 | 2505 | 40584 | 66.1 | TGCGATACCCTAGCTTGTGC | 29 | 5 | 26 | 17 | 33 | 0 |
| 7218 | 2585 | 2506 | 8794 | 70.4 | TGCGATACGATGGCTTTCCC | 29 | 5 | 27 | 17 | 28 | 0 |
| 7219 | 2586 | 2508 | 30594 | 69.6 | TGCGAAAGAAAGTCCCGCTT | 29 | 6 | 6 | 28 | 17 | 1 |
| 7220 | 2587 | 2509 | 40586 | 70.1 | TGCGAAAGTCGTCTTGTGCG | 29 | 6 | 10 | 11 | 29 | 0 |
| 7221 | 2588 | 2510 | 15896 | 72.3 | TGCGAAAGCGTTGGACATCG | 29 | 6 | 12 | 34 | 24 | 0 |
| 7222 | 2589 | 2511 | 40587 | 69 | TGCGAAAGGGTATCGTCACG | 29 | 6 | 18 | 10 | 30 | 0 |
| 7223 | 2590 | 2512 | 30595 | 69.9 | TGCGAAAGGAGTGATGCACG | 29 | 6 | 20 | 27 | 30 | 0 |
| 7224 | 2591 | 2513 | 40588 | 65.4 | TGCGAAAGACCTTTAGACGG | 29 | 6 | 23 | 3 | 35 | 0 |
| 7225 | 2592 | 2514 | 8806 | 69.9 | TGCGAAAGTCCCCGTTGAGT | 29 | 6 | 28 | 12 | 20 | 1 |

FIG. 29CCC

| SEQ ID NO: | ZIP ID# | 4,633 ID# | HEX ID# | Tm | ZIPCODE (NH2 -> CONH2) | TETRAMER NUMBERS | | | | "UNALLOWED DIMERS" |
|---|---|---|---|---|---|---|---|---|---|---|
| 7226 | 2593 | 2516 | 8809 | 68.1 | TGCGTACAAAAGTGCGCTTG | 29 | 7 | 6 | 29 | 11 | 0 |
| 7227 | 2594 | 2518 | 8811 | 67.9 | TGCGTACAACCTACGGTCCC | 29 | 7 | 23 | 35 | 28 | 1 |
| 7228 | 2595 | 2519 | 8816 | 71.9 | TGCGTACAGACCACGGACGG | 29 | 7 | 32 | 35 | 35 | 0 |
| 7229 | 2596 | 2521 | 8819 | 68.1 | TGCGTCTGTTGATCCCGAGT | 29 | 8 | 1 | 28 | 20 | 0 |
| 7230 | 2597 | 2522 | 8820 | 71.3 | TGCGTCTGTGATGTGCACGG | 29 | 8 | 2 | 33 | 35 | 0 |
| 7231 | 2598 | 2523 | 8824 | 70.7 | TGCGTCTGTGTCTGCGATCG | 29 | 8 | 9 | 29 | 24 | 0 |
| 7232 | 2599 | 2524 | 40589 | 67.2 | TGCGTCTGTCGTCCTACACG | 29 | 8 | 10 | 26 | 30 | 0 |
| 7233 | 2600 | 2525 | 40590 | 69.2 | TGCGTCTGCTTGAAAGGTGC | 29 | 8 | 11 | 6 | 33 | 0 |
| 7234 | 2601 | 2526 | 30597 | 72.4 | TGCGTCTGCTCAAGGATGCC | 29 | 8 | 13 | 25 | 29 | 0 |
| 7235 | 2602 | 2527 | 8828 | 66.5 | TGCGTCTGGCTTCACGATAC | 29 | 8 | 17 | 30 | 5 | 0 |
| 7236 | 2603 | 2528 | 40591 | 66.3 | TGCGTCTGGTCTAGTGACGG | 29 | 8 | 19 | 22 | 35 | 0 |
| 7237 | 2604 | 2529 | 8831 | 70.3 | TGCGTCTGGCAAATCGTTGA | 29 | 8 | 21 | 24 | 1 | 0 |
| 7238 | 2605 | 2530 | 8832 | 72.2 | TGCGTCTGAGTGTCCCTGCG | 29 | 8 | 22 | 28 | 29 | 1 |
| 7239 | 2606 | 2531 | 40594 | 69.3 | TGCGTCTGATCGAAAGCAGC | 29 | 8 | 24 | 6 | 31 | 0 |
| 7240 | 2607 | 2532 | 40595 | 67.4 | TGCGTCTGCCTATTGACACG | 29 | 8 | 26 | 1 | 30 | 0 |
| 7241 | 2608 | 2533 | 8837 | 69.3 | TGCGTCTGCAGCTTAGCGTT | 29 | 8 | 31 | 3 | 12 | 0 |
| 7242 | 2609 | 2534 | 8841 | 71.9 | TGCGTGTCTGATTGCGTCCC | 29 | 9 | 2 | 29 | 28 | 0 |
| 7243 | 2610 | 2535 | 8843 | 73.1 | TGCGTGTCTCTGCACGGTGC | 29 | 9 | 8 | 30 | 33 | 0 |
| 7244 | 2611 | 2536 | 8844 | 72.9 | TGCGTGTCTGTCGTGCGGAC | 29 | 9 | 9 | 33 | 34 | 0 |
| 7245 | 2612 | 2537 | 40596 | 66.9 | TGCGTGTCGCTTATACAGCC | 29 | 9 | 17 | 5 | 36 | 0 |
| 7246 | 2613 | 2538 | 40597 | 73.5 | TGCGTGTCGAGTTCCCAGCC | 29 | 9 | 20 | 28 | 36 | 0 |
| 7247 | 2614 | 2539 | 8852 | 67.1 | TGCGTGTCACCTATCGATCG | 29 | 9 | 23 | 24 | 24 | 0 |
| 7248 | 2615 | 2540 | 30599 | 67.5 | TGCGTGTCAGGAGGTATCCC | 29 | 9 | 25 | 18 | 28 | 0 |
| 7249 | 2616 | 2541 | 8853 | 71.2 | TGCGTGTCGATGGACCCTGT | 29 | 9 | 27 | 32 | 14 | 0 |
| 7250 | 2617 | 2542 | 40599 | 72.9 | TGCGTGTCTCCCCGAATCGT | 29 | 9 | 28 | 16 | 10 | 0 |
| 7251 | 2618 | 2543 | 8856 | 71.6 | TGCGTGTCGACCTCGTCGTT | 29 | 9 | 32 | 10 | 12 | 0 |
| 7252 | 2619 | 2544 | 8862 | 68.4 | TGCGTCGTCTCAACCTTCGT | 29 | 10 | 13 | 23 | 10 | 0 |
| 7253 | 2620 | 2545 | 15908 | 63.5 | TCGTCTGTTTAGGTCTTGCG | 10 | 14 | 3 | 19 | 29 | 0 |
| 7254 | 2621 | 2547 | 40601 | 66.4 | TGCGTCGTGTCTAGTGAGCC | 29 | 10 | 19 | 22 | 36 | 0 |
| 7255 | 2622 | 2548 | 30602 | 71.8 | TGCGTCGTCCTATGCGAGGA | 29 | 10 | 26 | 29 | 25 | 0 |
| 7256 | 2623 | 2549 | 8866 | 70.1 | TGCGTCGTGATGCGTTCTGT | 29 | 10 | 27 | 12 | 14 | 0 |
| 7257 | 2624 | 2550 | 8867 | 67.5 | TGCGTCGTTCCCCCTATTAG | 29 | 10 | 28 | 26 | 3 | 0 |
| 7258 | 2625 | 2551 | 8868 | 76.3 | TGCGTCGTTGCGGGACTCGT | 29 | 10 | 29 | 34 | 10 | 0 |
| 7259 | 2626 | 2552 | 8869 | 76 | TGCGTCGTCACGCACGCTGT | 29 | 10 | 30 | 30 | 14 | 0 |
| 7260 | 2627 | 2553 | 8870 | 70.1 | TGCGTCGTGACCCCTAGACC | 29 | 10 | 32 | 26 | 32 | 0 |
| 7261 | 2628 | 2554 | 8872 | 72.9 | TGCGTCGTGGACTCGTCACG | 29 | 10 | 34 | 10 | 30 | 0 |
| 7262 | 2629 | 2555 | 8873 | 66.8 | TGCGCTTGTTAGAGCCTTGA | 29 | 11 | 3 | 36 | 1 | 0 |
| 7263 | 2630 | 2557 | 8874 | 64.5 | TGCGCTTGTACAATACCAGC | 29 | 11 | 7 | 5 | 31 | 0 |
| 7264 | 2631 | 2558 | 8875 | 72.1 | TGCGCTTGTCTGCGAACGTT | 29 | 11 | 8 | 16 | 12 | 0 |
| 7265 | 2632 | 2559 | 8877 | 72.1 | TGCGCTTGCGTTTCGTTGAT | 29 | 11 | 12 | 10 | 2 | 0 |
| 7266 | 2633 | 2560 | 8878 | 69.9 | TGCGCTTGCTCAATACCGAA | 29 | 11 | 13 | 5 | 16 | 0 |
| 7267 | 2634 | 2561 | 15909 | 71.9 | TGCGCTTGCTGTCGAACCAT | 29 | 11 | 14 | 16 | 15 | 0 |
| 7268 | 2635 | 2562 | 30604 | 65.9 | TGCGCTTGGAGTATCGAATC | 29 | 11 | 20 | 24 | 4 | 0 |
| 7269 | 2636 | 2563 | 40604 | 66.7 | TGCGCTTGAGTGAATCCTTG | 29 | 11 | 22 | 4 | 11 | 0 |
| 7270 | 2637 | 2564 | 8885 | 69.9 | TGCGCTTGATCGATCGAGTG | 29 | 11 | 24 | 24 | 22 | 0 |
| 7271 | 2638 | 2565 | 8887 | 73 | TGCGCTTGGATGACGGGAGT | 29 | 11 | 27 | 35 | 20 | 0 |
| 7272 | 2639 | 2566 | 8888 | 76.6 | TGCGCTTGCAGCCACGGAGT | 29 | 11 | 31 | 30 | 20 | 0 |
| 7273 | 2640 | 2567 | 40605 | 74.1 | TGCGCTTGGTGCACCTCGTT | 29 | 11 | 33 | 23 | 12 | 0 |

FIG. 29DDD

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 7273 | 2641 | 2568 | 8890 | 75.5 | TGCGCTTGAGCCGACCACCT | 29 | 11 | 36 | 32 | 23 | 0 |
| 7274 | 2642 | 2569 | 21509 | 67.9 | TGCGCGTTAATCCCTACCAT | 29 | 12 | 4 | 26 | 15 | 0 |
| 7275 | 2643 | 2570 | 40607 | 66.3 | TGCGCGTTATACTCTGAGCC | 29 | 12 | 5 | 8 | 36 | 0 |
| 7276 | 2644 | 2571 | 30606 | 70.1 | TGCGCGTTAAAGAATCGCAA | 29 | 12 | 6 | 4 | 21 | 0 |
| 7277 | 2645 | 2572 | 8893 | 72.6 | TGCGCGTTTCTGCTTGATCG | 29 | 12 | 8 | 11 | 24 | 0 |
| 7278 | 2646 | 2573 | 8894 | 75.2 | TGCGCGTTTCGTCGAACGAA | 29 | 12 | 10 | 16 | 16 | 0 |
| 7279 | 2647 | 2574 | 8895 | 70.4 | TGCGCGTCGTTAGTGCTTG | 29 | 12 | 12 | 22 | 11 | 0 |
| 7280 | 2648 | 2575 | 30607 | 67 | TGCGCGTTGGTACCATTTAG | 29 | 12 | 18 | 15 | 3 | 0 |
| 7281 | 2649 | 2576 | 8899 | 68.9 | TGCGCGTTGTCTGGTAGACC | 29 | 12 | 19 | 18 | 32 | 0 |
| 7282 | 2650 | 2577 | 21511 | 68.1 | TGCGCGTTATCGTTGATTGA | 29 | 12 | 24 | 1 | 1 | 0 |
| 7283 | 2651 | 2579 | 8902 | 72.5 | TGCGCGTTGATGTCCCTTGA | 29 | 12 | 27 | 28 | 1 | 0 |
| 7284 | 2652 | 2580 | 8903 | 74.7 | TGCGCGTTTCCCGCTTACCT | 29 | 12 | 28 | 17 | 23 | 1 |
| 7286 | 2653 | 2581 | 8904 | 75.5 | TGCGCGTTCACGGAGTCACG | 29 | 12 | 30 | 20 | 30 | 0 |
| 7287 | 2654 | 2582 | 40609 | 71.2 | TGCGCGTTCAGCTTAGAGCC | 29 | 12 | 31 | 3 | 36 | 0 |
| 7288 | 2655 | 2583 | 8906 | 71.1 | TGCGCGTTGACCTCCCATAC | 29 | 12 | 32 | 28 | 5 | 0 |
| 7289 | 2656 | 2584 | 8908 | 71.4 | TGCGCGTTACGGGGTAGATG | 29 | 12 | 35 | 18 | 27 | 0 |
| 7290 | 2657 | 2585 | 40611 | 66.6 | TGCGCTCATGATAATCAGCC | 29 | 13 | 2 | 4 | 36 | 0 |
| 7291 | 2658 | 2586 | 40612 | 73.5 | TGCGCTCATTAGCACGCACG | 29 | 13 | 3 | 30 | 30 | 0 |
| 7292 | 2659 | 2588 | 40614 | 69.6 | TGCGCTCAAAAGCTCAATCG | 29 | 13 | 6 | 13 | 24 | 0 |
| 7293 | 2660 | 2589 | 8910 | 70.4 | TGCGCTCATACATGCGGGTA | 29 | 13 | 7 | 29 | 18 | 0 |
| 7294 | 2661 | 2590 | 8911 | 67 | TGCGCTCATCTGATCGTGTC | 29 | 13 | 8 | 24 | 9 | 0 |
| 7295 | 2662 | 2591 | 40615 | 70.3 | TGCGCTCACGTTATCGCTTG | 29 | 13 | 12 | 24 | 11 | 0 |
| 7296 | 2663 | 2593 | 8915 | 70.9 | TGCGCTCACTGTTCCCGTCT | 29 | 13 | 14 | 28 | 19 | 0 |
| 7297 | 2664 | 2596 | 8918 | 70.8 | TGCGCTCAGCAAAGTGCTCA | 29 | 13 | 21 | 22 | 13 | 0 |
| 7298 | 2665 | 2597 | 30610 | 66.4 | TGCGCTCACCTACGAAAAAG | 29 | 13 | 26 | 16 | 6 | 0 |
| 7299 | 2666 | 2598 | 8921 | 71.8 | TGCGCTCAGATGGTGCGAGT | 29 | 13 | 27 | 33 | 20 | 0 |
| 7300 | 2667 | 2601 | 40617 | 68 | TGCGCTGTTGATAAAGTGCG | 29 | 14 | 2 | 6 | 29 | 0 |
| 7301 | 2668 | 2602 | 8925 | 66.6 | TGCGCTGTAATCGCTTGTCT | 29 | 14 | 4 | 17 | 19 | 0 |
| 7302 | 2669 | 2603 | 8926 | 69.9 | TGCGCTGTATACGACCACGG | 29 | 14 | 5 | 32 | 35 | 0 |
| 7303 | 2670 | 2604 | 8928 | 66.9 | TGCGCTGTTACACCTAACGG | 29 | 14 | 7 | 26 | 35 | 0 |
| 7304 | 2671 | 2605 | 40618 | 66.7 | TGCGCTGTTCTGTGATAGCC | 29 | 14 | 8 | 2 | 36 | 0 |
| 7305 | 2672 | 2606 | 8929 | 71.4 | TGCGCTGTTGTCAATCGCAA | 29 | 14 | 9 | 4 | 21 | 0 |
| 7306 | 2673 | 2607 | 8931 | 69.7 | TGCGCTGTCTTGGACCAGTG | 29 | 14 | 11 | 32 | 22 | 0 |
| 7307 | 2674 | 2609 | 40619 | 67.2 | TGCGCTGTCTCACCATTCTG | 29 | 14 | 13 | 15 | 8 | 0 |
| 7308 | 2675 | 2610 | 40620 | 70.6 | TGCGCTGTCTGTTCTGCGAA | 29 | 14 | 14 | 8 | 16 | 0 |
| 7309 | 2676 | 2611 | 30611 | 66.1 | TGCGCTGTCCATCCTAAAAG | 29 | 14 | 15 | 26 | 6 | 0 |
| 7310 | 2677 | 2612 | 8933 | 70.8 | TGCGCTGTCGAAAATCCCAT | 29 | 14 | 16 | 4 | 15 | 0 |
| 7311 | 2678 | 2613 | 30612 | 68 | TGCGCTGTGGTAGAGTTCCC | 29 | 14 | 18 | 20 | 28 | 0 |
| 7312 | 2679 | 2615 | 15915 | 70.8 | TGCGCTGTAGTGGGACCGTT | 29 | 14 | 22 | 34 | 12 | 0 |
| 7313 | 2680 | 2616 | 30614 | 67.7 | TGCGCTGTCAGCTTAGCTCA | 29 | 14 | 31 | 3 | 13 | 0 |
| 7314 | 2681 | 2617 | 8938 | 75.9 | TGCGCTGTGACCGGACCCAT | 29 | 14 | 32 | 34 | 15 | 0 |
| 7315 | 2682 | 2618 | 8940 | 72.4 | TGCGCTGTACGGGTGCTCTG | 29 | 14 | 35 | 33 | 8 | 0 |
| 7316 | 2683 | 2619 | 8941 | 69.5 | TGCGCTGTAGCCGAGTCTTG | 29 | 14 | 36 | 20 | 11 | 0 |
| 7317 | 2684 | 2620 | 40621 | 69.1 | TGCGCCATTTGAACCTATCG | 29 | 15 | 1 | 23 | 24 | 0 |
| 7318 | 2685 | 2621 | 8943 | 68 | TGCGCCATTTAGGAGTCGTT | 29 | 15 | 3 | 20 | 12 | 0 |
| 7319 | 2686 | 2622 | 40622 | 70.1 | TGCGCCATAATCTCTGTGCG | 29 | 15 | 4 | 8 | 29 | 0 |
| 7320 | 2687 | 2625 | 8946 | 69.6 | TGCGCCATCGAAGTCTTTGA | 29 | 15 | 16 | 19 | 1 | 0 |
| 7321 | 2688 | 2626 | 8947 | 71.7 | TGCGCCATGTCTGATGGACC | 29 | 15 | 19 | 27 | 32 | 0 |

FIG. 29EEE

| SEQ ID NO: | ZIP ID# | 4,633 ID# | HEX ID# | Tm | ZIPCODE (NB2 -> CONB2) | TETRAMER NUMBERS | | | | | "UNALLOWED DIMERS" |
|---|---|---|---|---|---|---|---|---|---|---|---|
| 7322 | 2689 | 2627 | 30616 | 71.4 | TGCGCCATATCGGTCTCAGC | 29 | 15 | 24 | 19 | 31 | 0 |
| 7323 | 2690 | 2628 | 8951 | 71.7 | TGCGCCATTCCCTCGTTACA | 29 | 15 | 28 | 10 | 7 | 0 |
| 7324 | 2691 | 2629 | 8952 | 69.6 | TGCGCCATGACCCTGATCTTG | 29 | 15 | 32 | 2 | 11 | 0 |
| 7325 | 2692 | 2630 | 8954 | 76.8 | TGCGCCATGGACCCATCGAA | 29 | 15 | 34 | 15 | 16 | 0 |
| 7326 | 2693 | 2631 | 8955 | 72.7 | TGCGCCATACGGCTGTCTCA | 29 | 15 | 35 | 14 | 13 | 0 |
| 7327 | 2694 | 2632 | 40624 | 70 | TGCGCGAATGATCGTTCTTG | 29 | 16 | 2 | 12 | 11 | 0 |
| 7328 | 2695 | 2633 | 8956 | 71.9 | TGCGCGAAAATCAAAGCAGC | 29 | 16 | 4 | 6 | 31 | 0 |
| 7329 | 2696 | 2634 | 21535 | 71.8 | TGCGCGAACTCAGACCAGGA | 29 | 16 | 13 | 32 | 25 | 0 |
| 7330 | 2697 | 2635 | 8959 | 69.7 | TGCGCGAACCATCTGTTGTC | 29 | 16 | 15 | 14 | 9 | 0 |
| 7331 | 2698 | 2636 | 8960 | 74.1 | TGCGCGAACGAAAGCCAAAG | 29 | 16 | 16 | 36 | 6 | 0 |
| 7332 | 2699 | 2637 | 8962 | 71.9 | TGCGCGAAGCAACTCACCAT | 29 | 16 | 21 | 13 | 15 | 0 |
| 7333 | 2700 | 2638 | 8963 | 71.6 | TGCGCGAAATCGTGATCCAT | 29 | 16 | 24 | 2 | 15 | 0 |
| 7334 | 2701 | 2639 | 30619 | 73.7 | TGCGCGAAAGGAGATGGTGC | 29 | 16 | 25 | 27 | 33 | 0 |
| 7335 | 2702 | 2640 | 15917 | 74.9 | TGCGCGAATCCCCCTACAGC | 29 | 16 | 28 | 26 | 31 | 0 |
| 7336 | 2703 | 2644 | 40625 | 66.1 | TGCGGCTTATACAATCGCTT | 29 | 17 | 5 | 4 | 17 | 0 |
| 7337 | 2704 | 2645 | 30628 | 73.7 | TGCGGCTTTCTGCAGCTCGT | 29 | 17 | 8 | 31 | 10 | 0 |
| 7338 | 2705 | 2646 | 8975 | 71.4 | TGCGGCTTCTTGCTGTGACC | 29 | 17 | 11 | 14 | 32 | 0 |
| 7339 | 2706 | 2647 | 8976 | 66.6 | TGCGGCTTCTCAAGTGAGTG | 29 | 17 | 13 | 22 | 22 | 0 |
| 7340 | 2707 | 2648 | 8978 | 69.1 | TGCGGCTTCGAATTGATCTG | 29 | 17 | 16 | 1 | 8 | 0 |
| 7341 | 2708 | 2649 | 8980 | 69.4 | TGCGGCTTGCAATCTGAAAG | 29 | 17 | 21 | 8 | 6 | 0 |
| 7342 | 2709 | 2650 | 8984 | 76.6 | TGCGGCTTTCCCCAGCCCTA | 29 | 17 | 28 | 31 | 26 | 0 |
| 7343 | 2710 | 2651 | 30622 | 78.3 | TGCGGCTTCACGGGACCGAA | 29 | 17 | 30 | 34 | 16 | 0 |
| 7344 | 2711 | 2652 | 8988 | 77.6 | TGCGGCTTAGCCGACCCGAA | 29 | 17 | 36 | 32 | 16 | 0 |
| 7345 | 2712 | 2653 | 30623 | 66.5 | TGCGGGTAAAAGAGGAGGAC | 29 | 18 | 6 | 25 | 34 | 0 |
| 7346 | 2713 | 2654 | 8990 | 66.4 | TGCGGGTATACACCATACGG | 29 | 18 | 7 | 15 | 35 | 0 |
| 7347 | 2714 | 2656 | 30624 | 68.8 | TGCGGGTATGTCCACGAAAG | 29 | 18 | 9 | 30 | 6 | 0 |
| 7348 | 2715 | 2657 | 30625 | 71.4 | TGCGGGTACGTTCAGCCTTG | 29 | 18 | 12 | 31 | 11 | 0 |
| 7349 | 2716 | 2658 | 21547 | 68.6 | TGCGGGTACTCAGCAACGTT | 29 | 18 | 13 | 21 | 12 | 0 |
| 7350 | 2717 | 2659 | 8994 | 67.4 | TGCGGGTACTGTGCAACTTG | 29 | 18 | 14 | 21 | 11 | 0 |
| 7351 | 2718 | 2660 | 30626 | 69.7 | TGCGGGTAGCTTAGCCGAGT | 29 | 18 | 17 | 36 | 20 | 0 |
| 7352 | 2719 | 2661 | 8998 | 67.9 | TGCGGGTAGAGTGGACCTTG | 29 | 18 | 20 | 34 | 11 | 0 |
| 7353 | 2720 | 2662 | 9003 | 69.5 | TGCGGGTACCTAGACCCAGC | 29 | 18 | 26 | 32 | 31 | 0 |
| 7354 | 2721 | 2664 | 9005 | 72.7 | TGCGGGTACACGTGTCACGG | 29 | 18 | 30 | 9 | 35 | 0 |
| 7355 | 2722 | 2665 | 9008 | 66.2 | TGCGGGTAGTGCTGTCTGTC | 29 | 18 | 33 | 9 | 9 | 0 |
| 7356 | 2723 | 2666 | 9009 | 65.9 | TGCGGGTAGGACCCTAGAGT | 29 | 18 | 34 | 26 | 20 | 0 |
| 7357 | 2724 | 2667 | 9010 | 74.2 | TGCGGGTAAGCCGTCTGCAA | 29 | 18 | 36 | 19 | 21 | 0 |
| 7358 | 2725 | 2668 | 30627 | 68.3 | TGCGGTCTTGATCGAATCGT | 29 | 19 | 2 | 16 | 10 | 0 |
| 7359 | 2726 | 2669 | 21553 | 65.7 | TGCGGTCTTTAGCTGTTCGT | 29 | 19 | 3 | 14 | 10 | 0 |
| 7360 | 2727 | 2670 | 40630 | 68.4 | TGCGGTCTAAAGGATGCAGC | 29 | 19 | 6 | 27 | 31 | 0 |
| 7361 | 2728 | 2671 | 40631 | 64.9 | TGCGGTCTTCTGTCCCTTAG | 29 | 19 | 8 | 28 | 3 | 0 |
| 7362 | 2729 | 2672 | 9014 | 73.1 | TGCGGTCTTGTCCAGCCGTT | 29 | 19 | 9 | 31 | 12 | 0 |
| 7363 | 2730 | 2673 | 40632 | 69.2 | TGCGGTCTCTTGGGTATCCC | 29 | 19 | 11 | 18 | 28 | 0 |
| 7364 | 2731 | 2674 | 9017 | 66.5 | TGCGGTCTCTGTTTGAATCG | 29 | 19 | 14 | 1 | 24 | 0 |
| 7365 | 2732 | 2675 | 40634 | 71.1 | TGCGGTCTCGAAAGGAGCAA | 29 | 19 | 16 | 25 | 21 | 0 |
| 7366 | 2733 | 2676 | 21556 | 72.3 | TGCGGTCTGGTATCCCGACC | 29 | 19 | 18 | 28 | 32 | 0 |
| 7367 | 2734 | 2677 | 40635 | 67.4 | TGCGGTCTGAGTAGTGTGCG | 29 | 19 | 20 | 22 | 29 | 0 |
| 7368 | 2735 | 2678 | 30629 | 66.2 | TGCGGTCTACCTGCAAAAG | 29 | 19 | 23 | 21 | 6 | 0 |
| 7369 | 2736 | 2679 | 30630 | 71.1 | TGCGGTCTATCGGACCGATG | 29 | 19 | 24 | 32 | 27 | 0 |

FIG. 29FFF

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 7370 | 2737 | 2680 | 30631 | 66.5 | TGCGGTCTAGGAAAAGGACC | 29 | 19 | 25 | 6 | 32 | 0 |
| 7371 | 2738 | 2681 | 30632 | 66.7 | TGCGGTCTGATGAAAGCTTG | 29 | 19 | 27 | 6 | 11 | 0 |
| 7372 | 2739 | 2682 | 9025 | 71.5 | TGCGGTCTCAGCCGAACTTG | 29 | 19 | 31 | 16 | 11 | 0 |
| 7373 | 2740 | 2683 | 30633 | 63.1 | TGCGGAGTTGATAGCCTTAG | 29 | 20 | 2 | 36 | 3 | 0 |
| 7374 | 2741 | 2684 | 21559 | 67.3 | TGCGGAGTATACGTGCGGTA | 29 | 20 | 5 | 33 | 18 | 0 |
| 7375 | 2742 | 2685 | 21560 | 67.2 | TGCGGAGTTCTGATACGCAA | 29 | 20 | 8 | 5 | 21 | 0 |
| 7376 | 2743 | 2686 | 40636 | 70.2 | TGCGGAGTTCGTTCTGGACC | 29 | 20 | 10 | 8 | 32 | 0 |
| 7377 | 2744 | 2688 | 9036 | 74.1 | TGCGGAGTGCAAGACCCGAA | 29 | 20 | 21 | 32 | 16 | 0 |
| 7378 | 2745 | 2689 | 9039 | 71 | TGCGGAGTTCCCTGTCGATG | 29 | 20 | 28 | 9 | 27 | 0 |
| 7379 | 2746 | 2692 | 9041 | 74.9 | TGCGGAGTGTGCGTGCACCT | 29 | 20 | 33 | 33 | 23 | 0 |
| 7380 | 2747 | 2693 | 40638 | 70.5 | TGCGGAGTGGACCGTTGAGT | 29 | 20 | 34 | 12 | 20 | 0 |
| 7381 | 2748 | 2694 | 9042 | 71.9 | TGCGGCAATTGAGATGCGTT | 29 | 21 | 1 | 27 | 12 | 0 |
| 7382 | 2749 | 2695 | 15926 | 68.3 | TGCGGCAATTAGCGTTACCT | 29 | 21 | 3 | 12 | 23 | 0 |
| 7383 | 2750 | 2696 | 30635 | 68.9 | TGCGGCAAAATCTTAGCAGC | 29 | 21 | 4 | 3 | 31 | 0 |
| 7384 | 2751 | 2697 | 30636 | 67.7 | TGCGGCAAAAAGTTAGGGAC | 29 | 21 | 6 | 3 | 34 | 0 |
| 7385 | 2752 | 2698 | 9045 | 66.6 | TGCGGCAATCTGATACCTTG | 29 | 21 | 8 | 5 | 11 | 0 |
| 7386 | 2753 | 2699 | 9046 | 73.4 | TGCGGCAACGAATGATTCCC | 29 | 21 | 16 | 2 | 28 | 0 |
| 7387 | 2754 | 2700 | 9047 | 67.6 | TGCGGCAAGCTTAAAGGAGT | 29 | 21 | 17 | 6 | 20 | 0 |
| 7388 | 2755 | 2701 | 21570 | 74.4 | TGCGGCAAGTCTGACCCACG | 29 | 21 | 19 | 32 | 30 | 0 |
| 7389 | 2756 | 2702 | 9048 | 69.2 | TGCGGCAAGAGTATCGATCG | 29 | 21 | 20 | 24 | 24 | 0 |
| 7390 | 2757 | 2703 | 40641 | 68.4 | TGCGGCAAGATGAGGAAAAG | 29 | 21 | 27 | 25 | 6 | 0 |
| 7391 | 2758 | 2704 | 9049 | 70.7 | TGCGGCAATCCCGCTTATAC | 29 | 21 | 28 | 17 | 5 | 0 |
| 7392 | 2759 | 2705 | 9050 | 71.1 | TGCGGCAACAGCAAAGACCT | 29 | 21 | 31 | 6 | 23 | 0 |
| 7393 | 2760 | 2706 | 9051 | 71.5 | TGCGGCAAGACCCCTAACCT | 29 | 21 | 32 | 26 | 23 | 0 |
| 7394 | 2761 | 2707 | 15927 | 75.3 | TGCGGCAAGTGCAAAGCGAA | 29 | 21 | 33 | 6 | 16 | 0 |
| 7395 | 2762 | 2709 | 9056 | 71.4 | TGCGAGTGTCTGAGCCCAGC | 29 | 22 | 8 | 36 | 31 | 0 |
| 7396 | 2763 | 2710 | 40642 | 72.7 | TGCGAGTGTCGTTGCGAGGA | 29 | 22 | 10 | 29 | 25 | 0 |
| 7397 | 2764 | 2711 | 9058 | 67.8 | TGCGAGTGCTTGCAGCATAC | 29 | 22 | 11 | 31 | 5 | 0 |
| 7398 | 2765 | 2712 | 15928 | 68.3 | TGCGAGTGGCTTCCATTGAT | 29 | 22 | 17 | 15 | 2 | 0 |
| 7399 | 2766 | 2713 | 30637 | 67.7 | TGCGAGTGGGTACTTGTCCC | 29 | 22 | 18 | 11 | 28 | 1 |
| 7400 | 2767 | 2714 | 40643 | 70.1 | TGCGAGTGACCTCGAATCCC | 29 | 22 | 23 | 16 | 28 | 0 |
| 7401 | 2768 | 2715 | 9063 | 68.5 | TGCGAGTGAGGAGATGCGTT | 29 | 22 | 25 | 27 | 12 | 0 |
| 7402 | 2769 | 2716 | 9066 | 75.5 | TGCGAGTGTGCGGTGCCTTG | 29 | 22 | 29 | 33 | 11 | 0 |
| 7403 | 2770 | 2717 | 9067 | 67.6 | TGCGAGTGCAGCACCTAGTG | 29 | 22 | 31 | 23 | 22 | 0 |
| 7404 | 2771 | 2718 | 30638 | 72.3 | TGCGACCTTGATCAGCGTGC | 29 | 23 | 2 | 31 | 33 | 0 |
| 7405 | 2772 | 2719 | 30639 | 71.7 | TGCGACCTAAAGGTGCTGCG | 29 | 23 | 6 | 33 | 29 | 0 |
| 7406 | 2773 | 2720 | 9069 | 65.8 | TGCGACCTTACAGGACAGGA | 29 | 23 | 7 | 34 | 25 | 0 |
| 7407 | 2774 | 2722 | 40645 | 68.5 | TGCGACCTTCGTGTCTGACC | 29 | 23 | 10 | 19 | 32 | 0 |
| 7408 | 2775 | 2723 | 40646 | 72.8 | TGCGACCTCTTGCGTTTCCC | 29 | 23 | 11 | 12 | 28 | 1 |
| 7409 | 2776 | 2724 | 9071 | 64.5 | TGCGACCTCTCATTAGGACC | 29 | 23 | 13 | 3 | 32 | 0 |
| 7410 | 2777 | 2725 | 21582 | 70.6 | TGCGACCTCTGTCAGCCCAT | 29 | 23 | 14 | 31 | 15 | 0 |
| 7411 | 2778 | 2726 | 9072 | 69.7 | TGCGACCTCCATGCAACTTG | 29 | 23 | 15 | 21 | 11 | 0 |
| 7412 | 2779 | 2727 | 30640 | 65.7 | TGCGACCTCGAAGCTTAAAG | 29 | 23 | 16 | 17 | 6 | 0 |
| 7413 | 2780 | 2728 | 9074 | 66.2 | TGCGACCTGGTAAAAGCTTG | 29 | 23 | 18 | 6 | 11 | 0 |
| 7414 | 2781 | 2729 | 9077 | 69.1 | TGCGACCTAGTGACCTTGCG | 29 | 23 | 22 | 23 | 29 | 0 |
| 7415 | 2782 | 2730 | 9078 | 67.4 | TGCGACCTACCTCCTAACGG | 29 | 23 | 23 | 26 | 35 | 0 |
| 7416 | 2783 | 2731 | 9079 | 66.8 | TGCGACCTATCGCAGCATAC | 29 | 23 | 24 | 31 | 5 | 0 |
| 7417 | 2784 | 2732 | 9081 | 75.6 | TGCGACCTTCCCCGAACACG | 29 | 23 | 28 | 16 | 30 | 1 |

FIG. 29GGG

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 7418 | 2785 | 2733 | 9082 | 77.2 | TGCGACCTTGCGGTGCAGGA | 29 | 23 | 29 | 33 | 25 | 0 |
| 7419 | 2786 | 2734 | 30642 | 70.4 | TGCGACCTCACGTTGACACG | 29 | 23 | 30 | 1 | 30 | 0 |
| 7420 | 2787 | 2735 | 9085 | 73.9 | TGCGACCTGGACCGTTCGAA | 29 | 23 | 34 | 12 | 16 | 0 |
| 7421 | 2788 | 2736 | 30643 | 73.3 | TGCGATCGTTGATCCCCAGC | 29 | 24 | 1 | 28 | 31 | 0 |
| 7422 | 2789 | 2737 | 9087 | 64.7 | TGCGATCGTGATAATCGATG | 29 | 24 | 2 | 4 | 27 | 0 |
| 7423 | 2790 | 2738 | 9091 | 73.2 | TGCGATCGTGTCGCTTCACG | 29 | 24 | 9 | 17 | 30 | 0 |
| 7424 | 2791 | 2739 | 21588 | 72.1 | TGCGATCGCTTGTCGTGGAC | 29 | 24 | 11 | 10 | 34 | 0 |
| 7425 | 2792 | 2740 | 9094 | 72.8 | TGCGATCGCCATGGTACACG | 29 | 24 | 15 | 18 | 30 | 0 |
| 7426 | 2793 | 2742 | 9097 | 68.1 | TGCGATCGGGTAAATCCTTG | 29 | 24 | 18 | 4 | 11 | 0 |
| 7427 | 2794 | 2743 | 9099 | 71.5 | TGCGATCGAGTGGCAACCAT | 29 | 24 | 22 | 21 | 15 | 0 |
| 7428 | 2795 | 2744 | 40650 | 69.6 | TGCGATCGATCGTGTCCTTG | 29 | 24 | 24 | 9 | 11 | 0 |
| 7429 | 2796 | 2745 | 9100 | 68.9 | TGCGATCGCCTACCTACGAA | 29 | 24 | 26 | 26 | 16 | 0 |
| 7430 | 2797 | 2746 | 9101 | 72.8 | TGCGATCGTCCCGTCTCCAT | 29 | 24 | 28 | 19 | 15 | 0 |
| 7431 | 2798 | 2747 | 9103 | 70 | TGCGATCGCAGCAAAGTGTC | 29 | 24 | 31 | 6 | 9 | 0 |
| 7432 | 2799 | 2749 | 9105 | 74.9 | TGCGATCGACGGACCTGCAA | 29 | 24 | 35 | 23 | 21 | 0 |
| 7433 | 2800 | 2750 | 9106 | 71.4 | TGCGATCGAGCCATACAGCC | 29 | 24 | 36 | 5 | 36 | 0 |
| 7434 | 2801 | 2751 | 9107 | 69.2 | TGCGAGGATTAGCACGATCG | 29 | 25 | 3 | 30 | 24 | 0 |
| 7435 | 2802 | 2752 | 15931 | 71.5 | TGCGAGGATGTCTCCCTCCC | 29 | 25 | 9 | 28 | 28 | 0 |
| 7436 | 2803 | 2753 | 9111 | 67.8 | TGCGAGGACTTGCACGTACA | 29 | 25 | 11 | 30 | 7 | 0 |
| 7437 | 2804 | 2754 | 40652 | 69.8 | TGCGAGGACTGTAGCCCCAT | 29 | 25 | 14 | 36 | 15 | 0 |
| 7438 | 2805 | 2756 | 15933 | 69.8 | TGCGAGGAGCAAAAAGGACC | 29 | 25 | 21 | 6 | 32 | 0 |
| 7439 | 2806 | 2757 | 40654 | 67.6 | TGCGAGGAAGTGAGTGGGAC | 29 | 25 | 22 | 22 | 34 | 0 |
| 7440 | 2807 | 2758 | 9119 | 68.4 | TGCGAGGAAGGATGCGTTAG | 29 | 25 | 25 | 29 | 3 | 0 |
| 7441 | 2808 | 2759 | 9122 | 73.8 | TGCGAGGACAGCCGTTCAGC | 29 | 25 | 31 | 12 | 31 | 0 |
| 7442 | 2809 | 2760 | 9125 | 73.5 | TGCGAGGAACGGGAGTCACG | 29 | 25 | 35 | 20 | 30 | 0 |
| 7443 | 2810 | 2761 | 40656 | 66.6 | TGCGCCTATTGACGAATGTC | 29 | 26 | 1 | 16 | 9 | 0 |
| 7444 | 2811 | 2764 | 30646 | 70.7 | TGCGCCTATACAAGCCGGAC | 29 | 26 | 7 | 36 | 34 | 0 |
| 7445 | 2812 | 2765 | 15936 | 70.6 | TGCGCCTATGTCAGGAAGCC | 29 | 26 | 9 | 25 | 36 | 0 |
| 7446 | 2813 | 2766 | 9133 | 70.6 | TGCGCCTACTTGTGCGTTGA | 29 | 26 | 11 | 29 | 1 | 0 |
| 7447 | 2814 | 2767 | 9136 | 68.6 | TGCGCCTACGAAATACCAGC | 29 | 26 | 16 | 5 | 31 | 0 |
| 7448 | 2815 | 2768 | 40661 | 67.4 | TGCGCCTAGGTAAATCCGTT | 29 | 26 | 18 | 4 | 12 | 0 |
| 7449 | 2816 | 2769 | 9137 | 71.8 | TGCGCCTAGTCTCACGCAGC | 29 | 26 | 19 | 30 | 31 | 0 |
| 7450 | 2817 | 2771 | 9141 | 73.5 | TGCGCCTATCCCGCAATGTC | 29 | 26 | 28 | 21 | 9 | 0 |
| 7451 | 2818 | 2772 | 9142 | 72.2 | TGCGCCTATGCGAGTGCCTA | 29 | 26 | 29 | 22 | 26 | 0 |
| 7452 | 2819 | 2773 | 9143 | 69.1 | TGCGCCTACACGGATGAAAG | 29 | 26 | 30 | 27 | 6 | 0 |
| 7453 | 2820 | 2774 | 15937 | 73.8 | TGCGCCTAGGACACCTTGCG | 29 | 26 | 34 | 23 | 29 | 0 |
| 7454 | 2821 | 2775 | 9146 | 71.8 | TGCGCCTAACGGCCTAACCT | 29 | 26 | 35 | 26 | 23 | 0 |
| 7455 | 2822 | 2776 | 9147 | 72.6 | TGCGCCTAAGCCCTCAAGGA | 29 | 26 | 36 | 13 | 25 | 0 |
| 7456 | 2823 | 2777 | 40663 | 71.9 | TGCGGATGTTGAGTGCGCTT | 29 | 27 | 1 | 33 | 17 | 0 |
| 7457 | 2824 | 2778 | 30647 | 68.9 | TGCGGATGTGATGCTTCCAT | 29 | 27 | 2 | 17 | 15 | 0 |
| 7458 | 2825 | 2779 | 40666 | 66.6 | TGCGGATGTGTCCGTTAAAG | 29 | 27 | 9 | 12 | 6 | 0 |
| 7459 | 2826 | 2780 | 9150 | 75.4 | TGCGGATGCGTTGATGCAGC | 29 | 27 | 12 | 27 | 31 | 0 |
| 7460 | 2827 | 2781 | 9151 | 66.1 | TGCGGATGCTCAATACGTCT | 29 | 27 | 13 | 5 | 19 | 0 |
| 7461 | 2828 | 2782 | 9152 | 73.4 | TGCGGATGCTGTGATGGCAA | 29 | 27 | 14 | 27 | 21 | 0 |
| 7462 | 2829 | 2783 | 30648 | 71.6 | TGCGGATGGCAAAGTGAGGA | 29 | 27 | 21 | 22 | 25 | 0 |
| 7463 | 2830 | 2785 | 40667 | 70.9 | TGCGGATGCCTATCGTCGTT | 29 | 27 | 26 | 10 | 12 | 0 |
| 7464 | 2831 | 2786 | 9158 | 77.5 | TGCGGATGCACGCGTTGGAC | 29 | 27 | 30 | 12 | 34 | 0 |
| 7465 | 2832 | 2787 | 9160 | 74.3 | TGCGGATGGTGCCGAACTTG | 29 | 27 | 33 | 16 | 11 | 0 |

FIG. 29HHH

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 7466 | 2833 | 2788 | 40668 | 71 | TGCGGATGGGACTTGACAGC | 29 | 27 | 34 | 1 | 31 | 0 |
| 7467 | 2834 | 2789 | 15940 | 69.2 | TGCGGATGACGGTGTCAATC | 29 | 27 | 35 | 9 | 4 | 0 |
| 7468 | 2835 | 2790 | 9165 | 67.2 | TGCGTCCCAATCTCTGACCT | 29 | 28 | 4 | 8 | 23 | 0 |
| 7469 | 2836 | 2792 | 9167 | 74.2 | TGCGTCCCAAAGCTTGGCAA | 29 | 28 | 6 | 11 | 21 | 0 |
| 7470 | 2837 | 2794 | 9169 | 66.9 | TGCGTCCCTCGTAAAGGTCT | 29 | 28 | 10 | 6 | 19 | 0 |
| 7471 | 2838 | 2795 | 9170 | 70.4 | TGCGTCCCCTTGCTTGAATC | 29 | 28 | 11 | 11 | 4 | 0 |
| 7472 | 2839 | 2796 | 30650 | 75.1 | TGCGTCCCCGTTGATGGCTT | 29 | 28 | 12 | 27 | 17 | 0 |
| 7473 | 2840 | 2797 | 9171 | 67.6 | TGCGTCCCCATAATCAATC | 29 | 28 | 15 | 4 | 4 | 0 |
| 7474 | 2841 | 2798 | 9172 | 71.9 | TGCGTCCCCGAACCATACCT | 29 | 28 | 16 | 15 | 23 | 0 |
| 7475 | 2842 | 2799 | 21616 | 68.4 | TGCGTCCCGGTAATACAGGA | 29 | 28 | 18 | 5 | 25 | 0 |
| 7476 | 2843 | 2800 | 9173 | 68.5 | TGCGTCCCGTCTGAGTTGTC | 29 | 28 | 19 | 20 | 9 | 0 |
| 7477 | 2844 | 2801 | 40670 | 70.7 | TGCGTCCCACCTATCGCTGT | 29 | 28 | 23 | 24 | 14 | 0 |
| 7478 | 2845 | 2803 | 40671 | 74.6 | TGCGTCCCTCCCTCCCAGTG | 29 | 28 | 28 | 28 | 22 | 0 |
| 7479 | 2846 | 2804 | 9178 | 73.4 | TGCGTCCCGGACCTCAAGTG | 29 | 28 | 34 | 13 | 22 | 0 |
| 7480 | 2847 | 2805 | 9179 | 72.4 | TGCGTCCCACGGAGGAAATC | 29 | 28 | 35 | 25 | 4 | 0 |
| 7481 | 2848 | 2806 | 9181 | 69.8 | TGCGTGCGATACCTTGCCTA | 29 | 29 | 5 | 11 | 26 | 0 |
| 7482 | 2849 | 2807 | 40672 | 69.7 | TGCGTGCGTCTGATACGGAC | 29 | 29 | 8 | 5 | 34 | 0 |
| 7483 | 2850 | 2808 | 9183 | 73.1 | TGCGTGCGTGTCCTCACAGC | 29 | 29 | 9 | 13 | 31 | 0 |
| 7484 | 2851 | 2809 | 9184 | 73.3 | TGCGTGCGTCGTCAGCTGTC | 29 | 29 | 10 | 31 | 9 | 0 |
| 7485 | 2852 | 2810 | 30651 | 75.2 | TGCGTGCGGCTTAGTGGCAA | 29 | 29 | 17 | 22 | 21 | 0 |
| 7486 | 2853 | 2811 | 9186 | 71 | TGCGTGCGGAGTCCTACGTT | 29 | 29 | 20 | 26 | 12 | 0 |
| 7487 | 2854 | 2812 | 9187 | 75.5 | TGCGTGCGATCGCGTTTGTC | 29 | 29 | 24 | 12 | 9 | 0 |
| 7488 | 2855 | 2813 | 9188 | 72.3 | TGCGTGCGCCTACCATCTTG | 29 | 29 | 26 | 15 | 11 | 0 |
| 7489 | 2856 | 2814 | 9189 | 76.8 | TGCGTGCGTCCCGCTTTGTC | 29 | 29 | 28 | 17 | 9 | 0 |
| 7490 | 2857 | 2815 | 21629 | 69.7 | TGCGCACGTTGAAAAGAGGA | 29 | 30 | 1 | 6 | 25 | 0 |
| 7491 | 2858 | 2816 | 9191 | 72.6 | TGCGCACGTTAGCGTTACGG | 29 | 30 | 3 | 12 | 35 | 0 |
| 7492 | 2859 | 2817 | 40673 | 70.8 | TGCGCACGAAAGACCTAGCC | 29 | 30 | 6 | 23 | 36 | 0 |
| 7493 | 2860 | 2818 | 9193 | 77.5 | TGCGCACGTCGTCACGGACC | 29 | 30 | 10 | 30 | 32 | 0 |
| 7494 | 2861 | 2819 | 40674 | 76.3 | TGCGCACGCTGTCCATCACG | 29 | 30 | 14 | 15 | 30 | 0 |
| 7495 | 2862 | 2820 | 9198 | 72.3 | TGCGCACGGTCTAATCGTGC | 29 | 30 | 19 | 4 | 33 | 0 |
| 7496 | 2863 | 2822 | 21632 | 68.2 | TGCGCACGCCTATTAGGAGT | 29 | 30 | 26 | 3 | 20 | 0 |
| 7497 | 2864 | 2823 | 9201 | 73.2 | TGCGCACGGATGCTGTTCTG | 29 | 30 | 27 | 14 | 8 | 0 |
| 7498 | 2865 | 2824 | 9202 | 76.1 | TGCGCACGTCCCACCTTCGT | 29 | 30 | 28 | 23 | 10 | 0 |
| 7499 | 2866 | 2825 | 9203 | 74.8 | TGCGCACGGACCAGTGTCGT | 29 | 30 | 32 | 22 | 10 | 0 |
| 7500 | 2867 | 2826 | 9204 | 74.8 | TGCGCACGGGACTCGTGGTA | 29 | 30 | 34 | 10 | 18 | 0 |
| 7501 | 2868 | 2827 | 9205 | 74.4 | TGCGCACGAGCCGTCTAGGA | 29 | 30 | 36 | 19 | 25 | 0 |
| 7502 | 2869 | 2828 | 40675 | 73.1 | TGCGCAGCTTGACAGCAGGA | 29 | 31 | 1 | 31 | 25 | 0 |
| 7503 | 2870 | 2829 | 40676 | 70.2 | TGCGCAGCTGATTTAGCGAA | 29 | 31 | 2 | 3 | 16 | 0 |
| 7504 | 2871 | 2830 | 40677 | 66 | TGCGCAGCTTAGGCTTAATC | 29 | 31 | 3 | 17 | 4 | 0 |
| 7505 | 2872 | 2831 | 30652 | 70.4 | TGCGCAGCATACTCTGCAGC | 29 | 31 | 5 | 8 | 31 | 0 |
| 7506 | 2873 | 2832 | 9210 | 72.6 | TGCGCAGCTCGTGTCTCAGC | 29 | 31 | 10 | 19 | 31 | 0 |
| 7507 | 2874 | 2833 | 9211 | 72.7 | TGCGCAGCCCATTTAGGCTT | 29 | 31 | 15 | 3 | 17 | 0 |
| 7508 | 2875 | 2834 | 9212 | 74.7 | TGCGCAGCGGTACTCAACGG | 29 | 31 | 18 | 13 | 35 | 0 |
| 7509 | 2876 | 2835 | 30653 | 70.3 | TGCGCAGCGAGTGCAAATAC | 29 | 31 | 20 | 21 | 5 | 0 |
| 7510 | 2877 | 2836 | 9214 | 69.8 | TGCGCAGCATCGTTAGGGTA | 29 | 31 | 24 | 3 | 18 | 0 |
| 7511 | 2878 | 2837 | 9215 | 71 | TGCGCAGCCCTAGATGTCGT | 29 | 31 | 26 | 27 | 10 | 0 |
| 7512 | 2879 | 2838 | 9216 | 73.2 | TGCGCAGCGATGATACCACG | 29 | 31 | 27 | 5 | 30 | 0 |
| 7513 | 2880 | 2839 | 9217 | 78.7 | TGCGCAGCCAGCCAGCCCTA | 29 | 31 | 31 | 31 | 26 | 0 |

FIG. 29III

| SEQ ID NO: | ZIP ID# | 4,633 ID# | HEX ID# | Tm | ZIPCODE (NH2 -> CONH2) | TETRAMER NUMBERS | | | | "UNALLOWED DIMERS" |
|---|---|---|---|---|---|---|---|---|---|---|
| 7514 | 2881 | 2840 | 15942 | 71.8 | TGCGCAGCGACCAAAGAAAG | 29 | 31 | 32 | 6 6 | 0 |
| 7515 | 2882 | 2841 | 9219 | 75 | TGCGCAGCAGCCTCGTTCTG | 29 | 31 | 36 | 10 8 | 0 |
| 7516 | 2883 | 2842 | 15943 | 68.5 | TGCGGACCTGATCGAATGTC | 29 | 32 | 2 | 16 9 | 0 |
| 7517 | 2884 | 2844 | 9223 | 69.9 | TGCGGACCAATCAGGAGACC | 29 | 32 | 4 | 25 32 | 0 |
| 7518 | 2885 | 2845 | 9224 | 69.7 | TGCGGACCATACAATCTGCG | 29 | 32 | 5 | 4 29 | 0 |
| 7519 | 2886 | 2846 | 21640 | 67.7 | TGCGGACCTACACTGTTCCC | 29 | 32 | 7 | 14 28 | 0 |
| 7520 | 2887 | 2847 | 40680 | 68.6 | TGCGGACCTGTCTGATACGG | 29 | 32 | 9 | 2 35 | 0 |
| 7521 | 2888 | 2848 | 9226 | 71.4 | TGCGGACCCGTTGCAATTAG | 29 | 32 | 12 | 21 3 | 0 |
| 7522 | 2889 | 2849 | 9229 | 70.9 | TGCGGACCCCATCTGTTCTG | 29 | 32 | 15 | 14 8 | 0 |
| 7523 | 2890 | 2850 | 9230 | 73.4 | TGCGGACCCGAACTTGATCG | 29 | 32 | 16 | 11 24 | 0 |
| 7524 | 2891 | 2851 | 9231 | 74.2 | TGCGGACCGAGTCCATGTGC | 29 | 32 | 20 | 15 33 | 0 |
| 7525 | 2892 | 2852 | 9232 | 69 | TGCGGACCAGGAAAAGGTCT | 29 | 32 | 25 | 6 19 | 0 |
| 7526 | 2893 | 2853 | 9234 | 70.1 | TGCGGACCGATGTGTCAGTG | 29 | 32 | 27 | 9 22 | 0 |
| 7527 | 2894 | 2854 | 9235 | 73.7 | TGCGGACCCAGCTCGTCTTG | 29 | 32 | 31 | 10 11 | 0 |
| 7528 | 2895 | 2855 | 9236 | 76.1 | TGCGGACCGACCGGTAGCAA | 29 | 32 | 32 | 18 21 | 0 |
| 7529 | 2896 | 2856 | 9237 | 75.1 | TGCGGACCACGGAAAGCCAT | 29 | 32 | 35 | 6 15 | 0 |
| 7530 | 2897 | 2857 | 30654 | 74.9 | TGCGGTGCAATCACGGCCTA | 29 | 33 | 4 | 35 26 | 0 |
| 7531 | 2898 | 2858 | 9240 | 75.6 | TGCGGTGCAAAGCGTTCACG | 29 | 33 | 6 | 12 30 | 0 |
| 7532 | 2899 | 2859 | 40685 | 72.4 | TGCGGTGCTGTCCCTATCCC | 29 | 33 | 9 | 26 28 | 0 |
| 7533 | 2900 | 2860 | 21649 | 71.5 | TGCGGTGCCGTTATCGAAAG | 29 | 33 | 12 | 24 6 | 0 |
| 7534 | 2901 | 2862 | 9248 | 73.5 | TGCGGTGCACCTCCATCCAT | 29 | 33 | 23 | 15 15 | 0 |
| 7535 | 2902 | 2863 | 9251 | 75.6 | TGCGGTGCTCCCCTGTACGG | 29 | 33 | 28 | 14 35 | 0 |
| 7536 | 2903 | 2864 | 9252 | 75.2 | TGCGGTGCAGCCCCTACCAT | 29 | 33 | 36 | 26 15 | 0 |
| 7537 | 2904 | 2865 | 9253 | 68.7 | TGCGGGACTTGAGTCTGTGC | 29 | 34 | 1 | 19 33 | 0 |
| 7538 | 2905 | 2866 | 9254 | 68.8 | TGCGGGACTGATTTGACAGC | 29 | 34 | 2 | 1 31 | 0 |
| 7539 | 2906 | 2867 | 40686 | 70.7 | TGCGGGACATACGCTTAGCC | 29 | 34 | 5 | 17 36 | 0 |
| 7540 | 2907 | 2868 | 30655 | 68.1 | TGCGGGACAAAGTTAGCGTT | 29 | 34 | 6 | 3 12 | 0 |
| 7541 | 2908 | 2869 | 30656 | 70.3 | TGCGGGACTGTCTCTGAGCC | 29 | 34 | 9 | 8 36 | 0 |
| 7542 | 2909 | 2870 | 30657 | 66.7 | TGCGGGACCTTGTTAGGAGT | 29 | 34 | 11 | 3 20 | 0 |
| 7543 | 2910 | 2871 | 9259 | 74.4 | TGCGGGACCGTTGGTATCCC | 29 | 34 | 12 | 18 28 | 0 |
| 7544 | 2911 | 2872 | 40688 | 71.9 | TGCGGGACCCTCAGACCACCT | 29 | 34 | 13 | 32 23 | 0 |
| 7545 | 2912 | 2873 | 30658 | 69.8 | TGCGGGACCTGTAATCCGTT | 29 | 34 | 14 | 4 12 | 0 |
| 7546 | 2913 | 2874 | 9262 | 73.9 | TGCGGGACCGAACGTTCTCA | 29 | 34 | 16 | 12 13 | 0 |
| 7547 | 2914 | 2875 | 9263 | 68.6 | TGCGGGACGCTTGCTTATAC | 29 | 34 | 17 | 17 5 | 0 |
| 7548 | 2915 | 2877 | 9265 | 70.1 | TGCGGGACGTCTACCTGCTT | 29 | 34 | 19 | 23 17 | 0 |
| 7549 | 2916 | 2878 | 9266 | 72.8 | TGCGGGACAGTGACGGACCT | 29 | 34 | 22 | 35 23 | 0 |
| 7550 | 2917 | 2879 | 9267 | 73.9 | TGCGGGACATCGCTCATCGT | 29 | 34 | 24 | 13 10 | 0 |
| 7551 | 2918 | 2880 | 15946 | 68.6 | TGCGGGACCCTATACAGCAA | 29 | 34 | 26 | 7 21 | 0 |
| 7552 | 2919 | 2881 | 9270 | 77.3 | TGCGGGACGATGGTGCGATG | 29 | 34 | 27 | 33 27 | 0 |
| 7553 | 2920 | 2882 | 9271 | 75.9 | TGCGGGACTGCGTGTCCCAT | 29 | 34 | 29 | 9 15 | 0 |
| 7554 | 2921 | 2883 | 15947 | 74.9 | TGCGGGACAGCCATACGCAA | 29 | 34 | 36 | 5 21 | 0 |
| 7555 | 2922 | 2884 | 30659 | 68.6 | TGCGACGGTTAGGCTTTCTG | 29 | 35 | 3 | 17 8 | 0 |
| 7556 | 2923 | 2885 | 30660 | 69.6 | TGCGACGGAATCAATCATCG | 29 | 35 | 4 | 4 24 | 0 |
| 7557 | 2924 | 2887 | 40691 | 69.3 | TGCGACGGTCTGCGAATTAG | 29 | 35 | 8 | 16 3 | 0 |
| 7558 | 2925 | 2888 | 9277 | 69.9 | TGCGACGGCTCATTGAAGTG | 29 | 35 | 13 | 1 22 | 0 |
| 7559 | 2926 | 2889 | 9278 | 70.7 | TGCGACGGCTGTCCATACCT | 29 | 35 | 14 | 15 23 | 0 |
| 7560 | 2927 | 2890 | 9279 | 69.8 | TGCGACGGGTCTCTTGGAGT | 29 | 35 | 19 | 11 20 | 0 |
| 7561 | 2928 | 2891 | 30661 | 68.4 | TGCGACGGGAGTCGTTAAAG | 29 | 35 | 20 | 12 6 | 0 |

FIG. 29JJJ

| SEQ ID NO: | ZIP ID# | 4,633 ID# | HEX ID# | Tm | ZIPCODE (NB2 -> CONB2) | TETRAMER NUMBERS | | | | | "UNALLOWED DIMERS" |
|---|---|---|---|---|---|---|---|---|---|---|---|
| 7562 | 2929 | 2892 | 40692 | 72 | TGCGACGGAGTGACCTCACG | 29 | 35 | 22 | 23 | 30 | 0 |
| 7563 | 2930 | 2893 | 40693 | 73.3 | TGCGACGGAGGATGTCGGAC | 29 | 35 | 25 | 9 | 34 | 0 |
| 7564 | 2931 | 2894 | 9282 | 74.2 | TGCGACGGGATGGTGCTGTC | 29 | 35 | 27 | 33 | 9 | 0 |
| 7565 | 2932 | 2895 | 9284 | 76.1 | TGCGACGGGTGCGGTAAGGA | 29 | 35 | 33 | 18 | 25 | 0 |
| 7566 | 2933 | 2896 | 9285 | 77.1 | TGCGACGGGGACGCTTAGCC | 29 | 35 | 34 | 17 | 36 | 0 |
| 7567 | 2934 | 2897 | 9286 | 66.5 | TGCGAGCCTTGATGTCTCTG | 29 | 36 | 1 | 9 | 8 | 0 |
| 7568 | 2935 | 2898 | 40694 | 71.9 | TGCGAGCCTGATTCTGGCAA | 29 | 36 | 2 | 8 | 21 | 0 |
| 7569 | 2936 | 2899 | 9288 | 68.6 | TGCGAGCCTTAGGCAATCTG | 29 | 36 | 3 | 21 | 8 | 0 |
| 7570 | 2937 | 2900 | 9289 | 68.1 | TGCGAGCCCAAAGGGACATAC | 29 | 36 | 6 | 34 | 5 | 0 |
| 7571 | 2938 | 2901 | 40696 | 68.5 | TGCGAGCCTACAAAAGGTGC | 29 | 36 | 7 | 6 | 33 | 0 |
| 7572 | 2939 | 2902 | 9290 | 69.4 | TGCGAGCCTGTCGACCTACA | 29 | 36 | 9 | 32 | 7 | 0 |
| 7573 | 2940 | 2903 | 40697 | 69.5 | TGCGAGCCCTCAGGTAGGAC | 29 | 36 | 13 | 18 | 34 | 0 |
| 7574 | 2941 | 2905 | 9293 | 74.8 | TGCGAGCCCCATGGTAAGCC | 29 | 36 | 15 | 18 | 36 | 0 |
| 7575 | 2942 | 2906 | 21669 | 73.6 | TGCGAGCCGGTATGTCAGCC | 29 | 36 | 18 | 9 | 36 | 0 |
| 7576 | 2943 | 2907 | 40701 | 74.3 | TGCGAGCCAGGAGATGCGAA | 29 | 36 | 25 | 27 | 16 | 0 |
| 7577 | 2944 | 2908 | 9296 | 72 | TGCGAGCCCCTATCTGAGCC | 29 | 36 | 26 | 8 | 36 | 0 |
| 7578 | 2945 | 2909 | 9297 | 76 | TGCGAGCCTCCCGCTTGATG | 29 | 36 | 28 | 17 | 27 | 0 |
| 7579 | 2946 | 2910 | 9298 | 76.4 | TGCGAGCCCACGTGTCGCTT | 29 | 36 | 30 | 9 | 17 | 0 |
| 7580 | 2947 | 2911 | 15948 | 77.9 | TGCGAGCCCAGCCAGCGTCT | 29 | 36 | 31 | 31 | 19 | 0 |
| 7581 | 2948 | 2912 | 9300 | 75.7 | TGCGAGCCGGACTCGTGCTT | 29 | 36 | 34 | 10 | 17 | 0 |
| 7582 | 2949 | 2913 | 9301 | 76.5 | TGCGAGCCACGGCAGCTGAT | 29 | 36 | 35 | 31 | 2 | 0 |
| 7583 | 2950 | 2914 | 9302 | 76.2 | TGCGAGCCAGCCGATGGGTA | 29 | 36 | 36 | 27 | 18 | 0 |
| 7584 | 2951 | 2915 | 9304 | 71.9 | CACGTTGACCATTGCGCCAT | 30 | 1 | 15 | 29 | 15 | 0 |
| 7585 | 2952 | 2916 | 9305 | 69.4 | TTGAGCAAACGGAAAGTGCG | 1 | 21 | 35 | 6 | 29 | 0 |
| 7586 | 2953 | 2917 | 9307 | 71.5 | TTGAATCGCACGGACCCTCA | 1 | 24 | 30 | 32 | 13 | 0 |
| 7587 | 2954 | 2918 | 9311 | 70.1 | TGATTCGTGTGCCGTTCGAA | 2 | 10 | 33 | 12 | 16 | 0 |
| 7588 | 2955 | 2919 | 30662 | 69.5 | CACGTGATTCCCAATCGCAA | 30 | 2 | 28 | 4 | 21 | 0 |
| 7589 | 2956 | 2920 | 9314 | 73.4 | TGATGTGCCCATTCCCCGAA | 2 | 33 | 15 | 28 | 16 | 0 |
| 7590 | 2957 | 2921 | 15953 | 68.3 | TTAGCACGGCAAAGTGGCTT | 3 | 30 | 21 | 22 | 17 | 0 |
| 7591 | 2958 | 2922 | 9332 | 73.5 | CACGAATCCACGGACCACGG | 30 | 4 | 30 | 32 | 35 | 0 |
| 7592 | 2959 | 2923 | 30663 | 68.1 | ATACGCAAAAAGACGGGCAA | 5 | 21 | 6 | 35 | 21 | 0 |
| 7593 | 2960 | 2924 | 40704 | 68.7 | ATACTGCGTCTGACGGCGAA | 5 | 29 | 8 | 35 | 16 | 0 |
| 7594 | 2961 | 2925 | 15961 | 68.5 | CACGATACACGGACGGAGGA | 30 | 5 | 35 | 35 | 25 | 0 |
| 7595 | 2962 | 2926 | 9345 | 68.9 | CACGAAAGCTGTGGACCGAA | 30 | 6 | 14 | 34 | 16 | 0 |
| 7596 | 2963 | 2927 | 15965 | 67.7 | AAAGGGTAATCGCTTGTGCG | 6 | 18 | 24 | 11 | 29 | 0 |
| 7597 | 2964 | 2928 | 30664 | 68 | AAAGCCTAAGTGCACGCAGC | 6 | 26 | 22 | 30 | 31 | 0 |
| 7598 | 2965 | 2929 | 9354 | 66 | AAAGTGCGATACACCTTGCG | 6 | 29 | 5 | 23 | 29 | 0 |
| 7599 | 2966 | 2930 | 9355 | 67.9 | CACGAAAGGTGCAAAGAGCC | 30 | 6 | 33 | 6 | 36 | 0 |
| 7600 | 2967 | 2931 | 30665 | 70.4 | AAAGGGACACCTGTGCTGCG | 6 | 34 | 23 | 33 | 29 | 0 |
| 7601 | 2968 | 2932 | 30666 | 66 | TCTGCGTTATACTGCGGCTT | 8 | 12 | 5 | 29 | 17 | 0 |
| 7602 | 2969 | 2933 | 15972 | 69.5 | TCTGTGCGTGATACGGGTGC | 8 | 29 | 2 | 35 | 33 | 0 |
| 7603 | 2970 | 2934 | 9366 | 69.6 | TCTGCACGGCTTAAAGCACG | 8 | 30 | 17 | 6 | 30 | 0 |
| 7604 | 2971 | 2935 | 9367 | 68.8 | CACGTCTGCAGCATCGACCT | 30 | 8 | 31 | 24 | 23 | 0 |
| 7605 | 2972 | 2936 | 40705 | 72.5 | TCTGGACCCTTGGACCTGCG | 8 | 32 | 11 | 32 | 29 | 0 |
| 7606 | 2973 | 2937 | 30667 | 67 | TGTCCGTTAGGAGCAATCCC | 9 | 12 | 25 | 21 | 28 | 0 |
| 7607 | 2974 | 2938 | 9376 | 73 | TGTCGACCGATGGACCGGAC | 9 | 32 | 27 | 32 | 34 | 0 |
| 7608 | 2975 | 2939 | 9379 | 72.9 | CACGTGTCAGCCGATGGCAA | 30 | 9 | 36 | 27 | 21 | 0 |
| 7609 | 2976 | 2940 | 9382 | 71.4 | TCGTTCTGCGTTACGGACGG | 10 | 8 | 12 | 35 | 35 | 0 |

FIG. 29KKK

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 7610 | 2977 | 2941 | 15975 | 69.5 | CACGTCGTTCGTCCATCGAA | 30 | 10 | 10 | 15 | 16 | 0 |
| 7611 | 2978 | 2942 | 40706 | 68.1 | TCGTCCATAAAGAGCCCACG | 10 | 15 | 6 | 36 | 30 | 0 |
| 7612 | 2979 | 2943 | 9387 | 68.2 | TCGTACCTGTCTTGCGAGCC | 10 | 23 | 19 | 29 | 36 | 0 |
| 7613 | 2980 | 2944 | 9394 | 73 | TCGTGGACGCAAGATGCACG | 10 | 34 | 21 | 27 | 30 | 0 |
| 7614 | 2981 | 2945 | 9397 | 72 | CACGCTTGTGTCGGACCGAA | 30 | 11 | 9 | 34 | 16 | 0 |
| 7615 | 2982 | 2946 | 9404 | 66.6 | CACGCTTGAGTGAGTGGTGC | 30 | 11 | 22 | 22 | 33 | 0 |
| 7616 | 2983 | 2947 | 30668 | 67.9 | CACGCTTGACCTCGTTAGCC | 30 | 11 | 23 | 12 | 36 | 0 |
| 7617 | 2984 | 2948 | 21698 | 67.8 | CACGCTTGTCCCTCGTTGAT | 30 | 11 | 28 | 10 | 2 | 1 |
| 7618 | 2985 | 2949 | 9409 | 67.3 | CACGCTTGAGCCTCTGACCT | 30 | 11 | 36 | 8 | 23 | 0 |
| 7619 | 2986 | 2950 | 30669 | 67.1 | CACGCGTTACAAGGACACG | 30 | 12 | 7 | 25 | 30 | 0 |
| 7620 | 2987 | 2951 | 9414 | 66.7 | CACGCGTTTGTCGCTTAATC | 30 | 12 | 9 | 17 | 4 | 0 |
| 7621 | 2988 | 2952 | 15981 | 73.2 | CACGCGTTTCGTGATGCGAA | 30 | 12 | 10 | 27 | 16 | 0 |
| 7622 | 2989 | 2953 | 9416 | 71.6 | CACGCGTTCTTGCGTTCGTT | 30 | 12 | 11 | 12 | 12 | 0 |
| 7623 | 2990 | 2954 | 9418 | 71.6 | CACGCGTTCGAAGTGCGTCT | 30 | 12 | 16 | 33 | 19 | 0 |
| 7624 | 2991 | 2955 | 9420 | 67.5 | CACGCGTTGTCTTTAGTGCG | 30 | 12 | 19 | 3 | 29 | 0 |
| 7625 | 2992 | 2956 | 9421 | 70.4 | CACGCGTTGCAAGCAATGTC | 30 | 12 | 21 | 21 | 9 | 0 |
| 7626 | 2993 | 2957 | 40710 | 65.8 | CACGCGTTCCTATGATGACC | 30 | 12 | 26 | 2 | 32 | 0 |
| 7627 | 2994 | 2958 | 9425 | 69.9 | CACGCGTTGATGCTCAAGGA | 30 | 12 | 27 | 13 | 25 | 0 |
| 7628 | 2995 | 2959 | 15985 | 70.1 | CACGCGTTTCCCTGATAGCC | 30 | 12 | 28 | 2 | 36 | 1 |
| 7629 | 2996 | 2960 | 30670 | 75.2 | CACGCGTTAGCCCACGTCCC | 30 | 12 | 36 | 30 | 28 | 0 |
| 7630 | 2997 | 2961 | 21702 | 71.7 | CACGCTCAAATCAGCCCACG | 30 | 13 | 4 | 36 | 30 | 0 |
| 7631 | 2998 | 2962 | 40712 | 68.4 | CACGCTCACGAAAAAGCCAT | 30 | 13 | 16 | 6 | 15 | 0 |
| 7632 | 2999 | 2963 | 9436 | 66.2 | CACGCTCAGGTAATCGATCG | 30 | 13 | 18 | 24 | 24 | 0 |
| 7633 | 3000 | 2964 | 9439 | 72 | CACGCTCATCCCCCATCCAT | 30 | 13 | 28 | 15 | 15 | 0 |
| 7634 | 3001 | 2965 | 40714 | 66 | CACGCTGTATCGACCTCAGC | 30 | 14 | 24 | 23 | 31 | 0 |
| 7635 | 3002 | 2966 | 9454 | 72.5 | CACGCTGTTGCGCTCAAGGA | 30 | 14 | 29 | 13 | 25 | 0 |
| 7636 | 3003 | 2967 | 30672 | 66.3 | CCATTACAACCTCAGCTGCG | 15 | 7 | 23 | 31 | 29 | 0 |
| 7637 | 3004 | 2968 | 30673 | 71.7 | CACGCCATTCTGCTTGGTGC | 30 | 15 | 8 | 11 | 33 | 0 |
| 7638 | 3005 | 2969 | 9462 | 70.5 | CACGCCATTCGTTCTGGGAC | 30 | 15 | 10 | 8 | 34 | 0 |
| 7639 | 3006 | 2970 | 15993 | 69.1 | CACGCCATCTTGAATCCACG | 30 | 15 | 11 | 4 | 30 | 0 |
| 7640 | 3007 | 2971 | 15994 | 69.4 | CACGCCATCCATCGTTGGTA | 30 | 15 | 15 | 12 | 18 | 0 |
| 7641 | 3008 | 2972 | 30674 | 70.7 | CACGCCATGGTAAGGAACGG | 30 | 15 | 18 | 25 | 35 | 0 |
| 7642 | 3009 | 2973 | 15996 | 67.2 | CCATGTCTCAGCTGTCGCAA | 15 | 19 | 31 | 9 | 21 | 0 |
| 7643 | 3010 | 2974 | 9468 | 72.2 | CACGCCATGAGTGTGCGCTT | 30 | 15 | 20 | 33 | 17 | 0 |
| 7644 | 3011 | 2975 | 9469 | 65.5 | CACGCCATAGTGTGTCTCCC | 30 | 15 | 22 | 9 | 28 | 0 |
| 7645 | 3012 | 2976 | 15997 | 68.6 | CACGCCATAGGACGTTACGG | 30 | 15 | 25 | 12 | 35 | 0 |
| 7646 | 3013 | 2977 | 9473 | 76.4 | CACGCCATTGCGGCTTCAGC | 30 | 15 | 29 | 17 | 31 | 0 |
| 7647 | 3014 | 2978 | 15999 | 71.5 | CACGCCATCACGCTCAGGAC | 30 | 15 | 30 | 13 | 34 | 0 |
| 7648 | 3015 | 2979 | 30675 | 70 | CACGCCATGACCTACATGCG | 30 | 15 | 32 | 7 | 29 | 0 |
| 7649 | 3016 | 2980 | 9477 | 70.7 | CACGCCATACGGAGTGAGCC | 30 | 15 | 35 | 22 | 36 | 0 |
| 7650 | 3017 | 2981 | 40717 | 69.2 | CACGCGAATTGACGTTGCTT | 30 | 16 | 1 | 12 | 17 | 0 |
| 7651 | 3018 | 2982 | 16001 | 69.5 | CACGCGAAAATCGAGTCACG | 30 | 16 | 4 | 20 | 30 | 0 |
| 7652 | 3019 | 2983 | 40720 | 66.1 | CACGCGAATCTGAATCCTTG | 30 | 16 | 8 | 4 | 11 | 0 |
| 7653 | 3020 | 2984 | 40722 | 65.9 | CACGCGAACTTGTTGAGGAC | 30 | 16 | 11 | 1 | 34 | 1 |
| 7654 | 3021 | 2985 | 30677 | 69.1 | CACGCGAACTGTCAGCCCTA | 30 | 16 | 14 | 31 | 26 | 0 |
| 7655 | 3022 | 2986 | 9483 | 70.7 | CACGCGAAGCTTCCATTCGT | 30 | 16 | 17 | 15 | 10 | 0 |
| 7656 | 3023 | 2987 | 9484 | 67.5 | CACGCGAAGGTACTCATCCC | 30 | 16 | 18 | 13 | 28 | 0 |
| 7657 | 3024 | 2988 | 9485 | 70.9 | CACGCGAAGTCTTCCCGATG | 30 | 16 | 19 | 28 | 27 | 0 |

FIG. 29LLL

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 7658 | 3025 | 2989 | 16803 | 66.7 | CACGCGAAGCAACGAAATAC | 30 | 16 | 21 | 16 | 5 | 0 |
| 7659 | 3026 | 2990 | 40723 | 65.6 | CACGCGAAGATGTTAGAGCC | 30 | 16 | 27 | 3 | 36 | 0 |
| 7660 | 3027 | 2991 | 9490 | 73.5 | CACGCGAATCCCGGTACGAA | 30 | 16 | 28 | 18 | 16 | 0 |
| 7661 | 3028 | 2992 | 9491 | 75 | CACGCGAATGCGGATGCTTG | 30 | 16 | 29 | 27 | 11 | 0 |
| 7662 | 3029 | 2993 | 9495 | 63.1 | GCTTTTAGTGATGGACTGCG | 17 | 3 | 2 | 34 | 29 | 0 |
| 7663 | 3030 | 2994 | 9498 | 68.3 | CACGGCTTTCGTGTCTGCTT | 30 | 17 | 10 | 19 | 17 | 0 |
| 7664 | 3031 | 2995 | 9503 | 69.2 | CACGGCTTGCAAGCAACTGT | 30 | 17 | 21 | 21 | 14 | 0 |
| 7665 | 3032 | 2996 | 40725 | 73 | CACGGCTTATCGGTGCGCTT | 30 | 17 | 24 | 33 | 17 | 0 |
| 7666 | 3033 | 2997 | 9510 | 74.8 | CACGGCTTTCCCGTGCCTGT | 30 | 17 | 28 | 33 | 14 | 0 |
| 7667 | 3034 | 2998 | 9513 | 68.1 | CACGGCTTGGACCTGTTGTC | 30 | 17 | 34 | 14 | 9 | 0 |
| 7668 | 3035 | 2999 | 40726 | 69.7 | CACGGCTTAGCCCCATAGGA | 30 | 17 | 36 | 15 | 25 | 0 |
| 7669 | 3036 | 3000 | 9516 | 66.7 | GGTATGATCAGCGATGCACG | 18 | 2 | 31 | 27 | 30 | 0 |
| 7670 | 3037 | 3001 | 40727 | 68.5 | CACGGGTATCGTGCTTCAGC | 30 | 18 | 10 | 17 | 31 | 0 |
| 7671 | 3038 | 3002 | 16011 | 66.3 | GGTACCATGTCTGTGCGTGC | 18 | 15 | 19 | 33 | 33 | 0 |
| 7672 | 3039 | 3003 | 40728 | 64.1 | GGTAGCTTAAAGTCCCGTGC | 18 | 17 | 6 | 28 | 33 | 1 |
| 7673 | 3040 | 3004 | 9527 | 66.1 | CACGGGTAGCAAAGTGATCG | 30 | 18 | 21 | 22 | 24 | 0 |
| 7674 | 3041 | 3005 | 30679 | 67.7 | CACGGGTAAGGACACGTCGT | 30 | 18 | 25 | 30 | 10 | 0 |
| 7675 | 3042 | 3006 | 9530 | 70.7 | GGTAGATGTGCGTCCCTGCG | 18 | 27 | 29 | 28 | 29 | 0 |
| 7676 | 3043 | 3007 | 30680 | 73.5 | CACGGGTAGACCAGCCGCAA | 30 | 18 | 32 | 36 | 21 | 0 |
| 7677 | 3044 | 3008 | 9532 | 66.4 | CACGGGTAGGACAAAGGGAC | 30 | 18 | 34 | 6 | 34 | 0 |
| 7678 | 3045 | 3009 | 9533 | 69.5 | CACGGTCTTGATCACGGCAA | 30 | 19 | 2 | 30 | 21 | 0 |
| 7679 | 3046 | 3010 | 9534 | 71.2 | CACGGTCTTCTGTGCGCCAT | 30 | 19 | 8 | 29 | 15 | 0 |
| 7680 | 3047 | 3011 | 30681 | 67.3 | CACGGTCTGCAAGGTATCCC | 30 | 19 | 21 | 18 | 28 | 0 |
| 7681 | 3048 | 3012 | 9540 | 73.6 | CACGGTCTTGCGCACGACCT | 30 | 19 | 29 | 30 | 23 | 0 |
| 7682 | 3049 | 3013 | 9542 | 67.6 | CACGGTCTACGGTTGAAGCC | 30 | 19 | 35 | 1 | 36 | 1 |
| 7683 | 3050 | 3014 | 9545 | 69.4 | CACGGAGTTGATCAGCTGCG | 30 | 20 | 2 | 31 | 29 | 0 |
| 7684 | 3051 | 3015 | 9546 | 65.7 | CACGGAGTTCGTTTAGCAGC | 30 | 20 | 10 | 3 | 31 | 0 |
| 7685 | 3052 | 3016 | 9549 | 71.9 | CACGGAGTGCTTACGGCACG | 30 | 20 | 17 | 35 | 30 | 0 |
| 7686 | 3053 | 3017 | 9550 | 67.4 | CACGGAGTAGGAGACCGTGC | 30 | 20 | 25 | 32 | 33 | 0 |
| 7687 | 3054 | 3019 | 21741 | 72.3 | CACGGAGTAGCCGGACCAGC | 30 | 20 | 36 | 34 | 31 | 0 |
| 7688 | 3055 | 3020 | 9554 | 66.6 | CACGGCAATTGATCTGCCTA | 30 | 21 | 1 | 8 | 26 | 0 |
| 7689 | 3056 | 3022 | 21742 | 69.2 | CACGGCAATGTCACGGAAAG | 30 | 21 | 9 | 35 | 6 | 0 |
| 7690 | 3057 | 3023 | 16021 | 66.8 | CACGGCAACTTGAATCATCG | 30 | 21 | 11 | 4 | 24 | 0 |
| 7691 | 3058 | 3024 | 9561 | 64.9 | CACGGCAAGGTACTCAGACC | 30 | 21 | 18 | 13 | 32 | 0 |
| 7692 | 3059 | 3025 | 30684 | 67.8 | CACGGCAACCTAAGGAATCG | 30 | 21 | 26 | 25 | 24 | 0 |
| 7693 | 3060 | 3026 | 40732 | 65.6 | CACGGCAAGATGTTGAGACC | 30 | 21 | 27 | 1 | 32 | 0 |
| 7694 | 3061 | 3027 | 9568 | 72.5 | CACGGCAATCCCCTACGAA | 30 | 21 | 28 | 26 | 16 | 0 |
| 7695 | 3062 | 3028 | 9569 | 75.9 | CACGGCAATGCGTCTGCACG | 30 | 21 | 29 | 8 | 30 | 0 |
| 7696 | 3063 | 3029 | 9570 | 75.6 | CACGGCAACACGGTGCATCG | 30 | 21 | 30 | 33 | 24 | 0 |
| 7697 | 3064 | 3030 | 30685 | 68.4 | CACGAGTGGCTTATCGCGTT | 30 | 22 | 17 | 24 | 12 | 0 |
| 7698 | 3065 | 3031 | 9578 | 70.3 | AGTGGATGAGGATGCGCAGC | 22 | 27 | 25 | 29 | 31 | 0 |
| 7699 | 3066 | 3032 | 16024 | 71.3 | AGTGTCCCGCAACCATTCCC | 22 | 28 | 21 | 15 | 28 | 1 |
| 7700 | 3067 | 3033 | 40735 | 69.9 | AGTGGACCAATCCAGCCACG | 22 | 32 | 4 | 31 | 30 | 0 |
| 7701 | 3068 | 3034 | 9585 | 68.4 | CACGACCTTGATGGACCGAA | 30 | 23 | 2 | 34 | 16 | 0 |
| 7702 | 3069 | 3035 | 9586 | 72.2 | ACCTTCTGCGAAACGGCAGC | 23 | 8 | 16 | 35 | 31 | 0 |
| 7703 | 3070 | 3036 | 9587 | 70.9 | CACGACCTTCGTGCAAAGCC | 30 | 23 | 10 | 21 | 36 | 0 |
| 7704 | 3071 | 3037 | 30686 | 69.1 | ACCTCCATATCGGACCGTGC | 23 | 15 | 24 | 32 | 33 | 0 |
| 7705 | 3072 | 3038 | 16026 | 72.7 | CACGACCTATCGTGCGTGCG | 30 | 23 | 24 | 29 | 29 | 0 |

FIG. 29MMM

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 7706 | 3073 | 3039 | 9593 | 71.2 | CACGACCTGATGTGCGGACC | 30 | 23 | 27 | 29 | 32 | 0 |
| 7707 | 3074 | 3040 | 9597 | 70.2 | ACCTGGACGGTACACGCAGC | 23 | 34 | 18 | 30 | 31 | 0 |
| 7708 | 3075 | 3041 | 9600 | 70.2 | CACGATCGAATCACGGGACC | 30 | 24 | 4 | 35 | 32 | 0 |
| 7709 | 3076 | 3042 | 9604 | 65.1 | ATCGCTGTAGTGATCGCCAT | 24 | 14 | 22 | 24 | 15 | 0 |
| 7710 | 3077 | 3043 | 30687 | 65.9 | CACGATCGGGTATACAACGG | 30 | 24 | 18 | 7 | 35 | 0 |
| 7711 | 3078 | 3044 | 40739 | 68.8 | ATCGGTCTCTTGTCCCCGAA | 24 | 19 | 11 | 28 | 16 | 1 |
| 7712 | 3079 | 3046 | 9609 | 71.8 | ATCGAGTGCCATCAGCGCAA | 24 | 22 | 15 | 31 | 21 | 0 |
| 7713 | 3080 | 3047 | 9610 | 70.7 | CACGATCGACCTCGAAACGG | 30 | 24 | 23 | 16 | 35 | 0 |
| 7714 | 3081 | 3048 | 16031 | 73.1 | CACGATCGAGCCGATGAGCC | 30 | 24 | 36 | 27 | 36 | 0 |
| 7715 | 3082 | 3049 | 9619 | 69.1 | CACGAGGAAAAGGCAATCCC | 30 | 25 | 6 | 21 | 28 | 0 |
| 7716 | 3083 | 3050 | 9620 | 68.2 | CACGAGGATCGTCTTGACGG | 30 | 25 | 10 | 11 | 35 | 0 |
| 7717 | 3084 | 3051 | 9621 | 69.9 | CACGAGGACTTGTGCGCTCA | 30 | 25 | 11 | 29 | 13 | 0 |
| 7718 | 3085 | 3052 | 30688 | 72.7 | AGGACCATTCCCCAGCGACC | 25 | 15 | 28 | 31 | 32 | 0 |
| 7719 | 3086 | 3054 | 9627 | 67.9 | CACGAGGAACCTTGCGAAAG | 30 | 25 | 23 | 29 | 6 | 0 |
| 7720 | 3087 | 3055 | 9631 | 68.8 | CACGAGGACACGGCTTCTCA | 30 | 25 | 30 | 17 | 13 | 0 |
| 7721 | 3088 | 3056 | 16035 | 71.3 | AGGACAGCGCTTCAGCTCCC | 25 | 31 | 17 | 31 | 28 | 0 |
| 7722 | 3089 | 3058 | 9634 | 67.6 | AGGAGGACAGTGGACCCGTT | 25 | 34 | 22 | 32 | 12 | 0 |
| 7723 | 3090 | 3059 | 30689 | 70.1 | CACGAGGAAGCCTTGAACGG | 30 | 25 | 36 | 1 | 35 | 0 |
| 7724 | 3091 | 3060 | 9640 | 68.6 | CACGCCTAAATCGACCATCG | 30 | 26 | 4 | 32 | 24 | 0 |
| 7725 | 3092 | 3061 | 30691 | 67.6 | CACGCCTAGCTTCGTTAGCC | 30 | 26 | 17 | 12 | 36 | 0 |
| 7726 | 3093 | 3062 | 30692 | 69.6 | CACGCCTAATCGTGCGTCTG | 30 | 26 | 24 | 29 | 8 | 0 |
| 7727 | 3094 | 3063 | 9650 | 65.3 | CACGCCTAGATGGGTACAGC | 30 | 26 | 27 | 18 | 31 | 0 |
| 7728 | 3095 | 3064 | 30693 | 67.8 | CACGGATGTCGTCTTGGGAC | 30 | 27 | 10 | 11 | 34 | 0 |
| 7729 | 3096 | 3065 | 40744 | 72.1 | CACGGATGCTTGTCCCCAT | 30 | 27 | 11 | 28 | 15 | 1 |
| 7730 | 3097 | 3066 | 9660 | 66 | CACGGATGCTCAGCTTTGTC | 30 | 27 | 13 | 17 | 9 | 0 |
| 7731 | 3098 | 3067 | 9663 | 67.4 | CACGGATGGGTATCGTAGCC | 30 | 27 | 18 | 10 | 36 | 0 |
| 7732 | 3099 | 3068 | 30694 | 67.8 | CACGGATGGAGTCAGCCCTA | 30 | 27 | 20 | 31 | 26 | 0 |
| 7733 | 3100 | 3069 | 9671 | 72.5 | CACGGATGCAGCGACCAGTG | 30 | 27 | 31 | 32 | 22 | 0 |
| 7734 | 3101 | 3070 | 9672 | 74.5 | CACGGATGGTGCCGTTCACG | 30 | 27 | 33 | 12 | 30 | 0 |
| 7735 | 3102 | 3071 | 9676 | 75.2 | CACGTCCCAATCGTGCGCAA | 30 | 28 | 4 | 33 | 21 | 0 |
| 7736 | 3103 | 3072 | 16048 | 72.9 | CACGTCCCTCTGGTGCAGCC | 30 | 28 | 8 | 33 | 36 | 0 |
| 7737 | 3104 | 3073 | 21776 | 68.1 | CACGTCCCGCTTGGTAGGTA | 30 | 28 | 17 | 18 | 18 | 0 |
| 7738 | 3105 | 3074 | 30695 | 69.2 | TCCCGGTAGCTTGATGGGAC | 28 | 18 | 17 | 27 | 34 | 0 |
| 7739 | 3106 | 3075 | 9686 | 72.1 | TCCCTGCGGGTACTTGCCAT | 28 | 29 | 18 | 11 | 15 | 0 |
| 7740 | 3107 | 3076 | 21783 | 69 | CACGTCCCACGGTGATCTCA | 30 | 28 | 35 | 2 | 13 | 0 |
| 7741 | 3108 | 3077 | 21785 | 69.9 | CACGTGCGTTGAAGTGCGTT | 30 | 29 | 1 | 22 | 12 | 0 |
| 7742 | 3109 | 3078 | 16052 | 71.3 | CACGTGCGATACACGGGGAC | 30 | 29 | 5 | 35 | 34 | 0 |
| 7743 | 3110 | 3079 | 30696 | 69.4 | CACGTGCGTACATCCCAGGA | 30 | 29 | 7 | 28 | 25 | 0 |
| 7744 | 3111 | 3080 | 30697 | 72.7 | TGCGTCTGCGTTCTGCAGC | 29 | 8 | 12 | 8 | 31 | 0 |
| 7745 | 3112 | 3081 | 21787 | 69.6 | CACGTGCGTGTCTCGTTCGT | 30 | 29 | 9 | 10 | 10 | 0 |
| 7746 | 3113 | 3082 | 21789 | 70.6 | TGCGGCTTCCTATCTGGTGC | 29 | 17 | 26 | 8 | 33 | 0 |
| 7747 | 3114 | 3083 | 9697 | 72.6 | CACGTGCGGGTAAGTGCACG | 30 | 29 | 18 | 22 | 30 | 0 |
| 7748 | 3115 | 3084 | 9699 | 69.7 | TGCGGAGTCGTTGAGTCACG | 29 | 20 | 12 | 20 | 30 | 0 |
| 7749 | 3116 | 3085 | 9700 | 71.9 | CACGTGCGGCAAGGTACAGC | 30 | 29 | 21 | 18 | 31 | 0 |
| 7750 | 3117 | 3086 | 9701 | 72.3 | CACGTGCGAGTGCCATGACC | 30 | 29 | 22 | 15 | 32 | 0 |
| 7751 | 3118 | 3087 | 30698 | 71 | CACGTGCGATCGAAAGAGCC | 30 | 29 | 24 | 6 | 36 | 0 |
| 7752 | 3119 | 3088 | 40756 | 72.1 | TGCGCCTACTGTGACCACGG | 29 | 26 | 14 | 32 | 35 | 0 |
| 7753 | 3120 | 3089 | 30700 | 76.3 | TGCGTGCGGCAATACATGCG | 29 | 29 | 21 | 7 | 29 | 0 |

*FIG. 29NNN*

| SEQ ID NO: | ZIP ID# | 4,633 ID# | HEX ID# | Tm | ZIPCODE (NH2 -> CONH2) | TETRAMER NUMBERS | | | | "UNALLOWED DIMERS" |
|---|---|---|---|---|---|---|---|---|---|---|
| 7754 | 3121 | 3090 | 9705 | 72 | TGCGACGGCCTAAAAGTCCC | 29 35 26 6 28 | | | | 1 |
| 7755 | 3122 | 3091 | 9706 | 68.3 | CACGCACGTTGAAATCTCCC | 30 30 1 4 28 | | | | 0 |
| 7756 | 3123 | 3092 | 9709 | 71.9 | CACGCACGTCTGGCTTCAGC | 30 30 8 17 31 | | | | 0 |
| 7757 | 3124 | 3093 | 40757 | 73.5 | CACGCACGTCGTCTCATGCG | 30 30 10 13 29 | | | | 0 |
| 7758 | 3125 | 3094 | 9713 | 66.7 | CACGCACGCCATAAAGAAAG | 30 30 15 6 6 | | | | 0 |
| 7759 | 3126 | 3095 | 40759 | 67.1 | CACGGTCTTACACGTTTGCG | 30 19 7 12 29 | | | | 0 |
| 7760 | 3127 | 3096 | 9716 | 72.7 | CACGCACGATCGCAGCAATC | 30 30 24 31 4 | | | | 0 |
| 7761 | 3128 | 3097 | 9718 | 73.9 | CACGCACGCAGCCGAAGAGT | 30 30 31 16 20 | | | | 0 |
| 7762 | 3129 | 3098 | 9719 | 75.6 | CACGCACGGACCGACCGTCT | 30 30 32 32 19 | | | | 0 |
| 7763 | 3130 | 3099 | 30701 | 72.2 | CACGCAGCTTAGCACGGTGC | 30 31 3 30 33 | | | | 0 |
| 7764 | 3131 | 3100 | 16054 | 73.8 | CACGCAGCTCTGCAGCCCAT | 30 31 8 31 15 | | | | 0 |
| 7765 | 3132 | 3101 | 9724 | 68.1 | CACGCAGCCTTGGGTAAAAG | 30 31 11 18 6 | | | | 0 |
| 7766 | 3133 | 3102 | 40763 | 76.3 | CACGCAGCCCTCAACGGACGG | 30 31 13 35 35 | | | | 0 |
| 7767 | 3134 | 3104 | 30702 | 69.7 | CACGCAGCGGTACGTTATCG | 30 31 18 12 24 | | | | 0 |
| 7768 | 3135 | 3105 | 9729 | 70.9 | CACGCAGCGTCTGAGTTCCC | 30 31 19 20 28 | | | | 0 |
| 7769 | 3136 | 3106 | 9732 | 68.9 | CACGCAGCACCTTTGATCGT | 30 31 23 1 10 | | | | 1 |
| 7770 | 3137 | 3107 | 9733 | 71 | CACGCAGCATCGCCTAGACC | 30 31 24 26 32 | | | | 0 |
| 7771 | 3138 | 3108 | 9734 | 70.7 | CACGCAGCGATGGGTAGACC | 30 31 27 18 32 | | | | 0 |
| 7772 | 3139 | 3109 | 9735 | 75.4 | CACGCAGCTCCCCTTGGTGC | 30 31 28 11 33 | | | | 0 |
| 7773 | 3140 | 3110 | 40766 | 70.1 | CACGGACCAATCTGCGACCT | 30 32 4 29 23 | | | | 0 |
| 7774 | 3141 | 3111 | 16056 | 71.6 | CACGGACCTCTGCGTTCACG | 30 32 8 12 30 | | | | 0 |
| 7775 | 3142 | 3112 | 30703 | 73.2 | CACGGACCCCATGATGGTGC | 30 32 15 27 33 | | | | 0 |
| 7776 | 3143 | 3113 | 9749 | 71.6 | CACGGACCGCAATCGTCTTG | 30 32 21 10 11 | | | | 0 |
| 7777 | 3144 | 3114 | 9750 | 70.9 | CACGGACCATCGAATCCGAA | 30 32 24 4 16 | | | | 0 |
| 7778 | 3145 | 3115 | 9751 | 64.8 | GACCAGGAGGTATGTCTGCG | 32 25 18 9 29 | | | | 0 |
| 7779 | 3146 | 3116 | 40770 | 67.8 | CACGGACCGATGTTAGCCAT | 30 32 27 3 15 | | | | 0 |
| 7780 | 3147 | 3117 | 16058 | 70.8 | CACGGTGCTTAGACGGGTGC | 30 33 3 35 33 | | | | 0 |
| 7781 | 3148 | 3118 | 9758 | 72.1 | CACGGTGCAATCCCATCACG | 30 33 4 15 30 | | | | 0 |
| 7782 | 3149 | 3119 | 40772 | 68.9 | CACGGTGCAAAGAAAGCAGC | 30 33 6 6 31 | | | | 0 |
| 7783 | 3150 | 3121 | 30704 | 72.5 | CACGGTGCTCTGCTTGCGAA | 30 33 8 11 16 | | | | 0 |
| 7784 | 3151 | 3122 | 9760 | 72.2 | CACGGTGCCTTGCGAACTCA | 30 33 11 16 13 | | | | 0 |
| 7785 | 3152 | 3123 | 40773 | 68.6 | CACGGTGCCTCAACCTCTCA | 30 33 13 23 13 | | | | 0 |
| 7786 | 3153 | 3124 | 9764 | 72.1 | CACGGTGCCGAAAGGAGACC | 30 33 16 25 32 | | | | 0 |
| 7787 | 3154 | 3125 | 9766 | 74.1 | CACGGTGCGAGTGCAAAGCC | 30 33 20 21 36 | | | | 0 |
| 7788 | 3155 | 3126 | 40775 | 68.9 | CACGGTGCACCTAGGAGCAA | 30 33 23 25 21 | | | | 0 |
| 7789 | 3156 | 3127 | 9770 | 71 | CACGGTGCAGGAATCGAGGA | 30 33 25 24 25 | | | | 0 |
| 7790 | 3157 | 3128 | 9771 | 67.2 | CACGGTGCCCTAACCTCCTA | 30 33 26 23 26 | | | | 0 |
| 7791 | 3158 | 3129 | 9772 | 74.7 | CACGGTGCTCCCCAGCCTGT | 30 33 28 31 14 | | | | 0 |
| 7792 | 3159 | 3130 | 9773 | 73.4 | CACGGTGCTGCGTGATGTGC | 30 33 29 2 33 | | | | 0 |
| 7793 | 3160 | 3131 | 30705 | 79.3 | CACGGTGCGGACGTGCAGCC | 30 33 34 33 36 | | | | 0 |
| 7794 | 3161 | 3132 | 40776 | 68.1 | GGACTTGAGCTTCGTTTGCG | 34 1 17 12 29 | | | | 0 |
| 7795 | 3162 | 3133 | 9778 | 67.4 | CACGGGACAATCTTGAAGCC | 30 34 4 1 36 | | | | 0 |
| 7796 | 3163 | 3134 | 9779 | 67.5 | CACGGGACATACAGCCACCT | 30 34 5 36 23 | | | | 0 |
| 7797 | 3164 | 3135 | 21811 | 66.9 | CACGGGACCTCACTCAGCTT | 30 34 13 13 17 | | | | 0 |
| 7798 | 3165 | 3136 | 9783 | 65.5 | GGACCTGTCTTGAGTGCACG | 34 14 11 22 30 | | | | 0 |
| 7799 | 3166 | 3137 | 9789 | 68.3 | CACGGGACGAGTTTGAATCG | 30 34 20 1 24 | | | | 0 |
| 7800 | 3167 | 3138 | 30706 | 72 | CACGGGACCCTAGTGCGGAC | 30 34 26 33 34 | | | | 0 |
| 7801 | 3168 | 3139 | 9793 | 72.9 | CACGGGACGACCACGGTGAT | 30 34 32 35 2 | | | | 0 |

FIG. 29000

| SEQ ID NO: | ZIP ID# | 4,633 ID# | HEX ID# Tm | ZIPCODE (NH2 -> CONH2) | TETRAMER NUMBERS | | | | | "UNALLOWED DIMERS" |
|---|---|---|---|---|---|---|---|---|---|---|
| 7802 | 3169 | 3140 | 9796 | 66 | ACGGAATCTCGTTGATTCCC | 35 | 4 | 10 | 2 | 28 | 0 |
| 7803 | 3170 | 3141 | 16062 | 70.8 | CACGACGGTACAAGCCCAGC | 30 | 35 | 7 | 36 | 31 | 0 |
| 7804 | 3171 | 3142 | 9799 | 75.7 | CACGACGGTGTCGTGCGTGC | 30 | 35 | 9 | 33 | 33 | 0 |
| 7805 | 3172 | 3143 | 21817 | 68.9 | ACGGAGTGCTTGTTGATGCG | 35 | 22 | 11 | 1 | 29 | 1 |
| 7806 | 3173 | 3144 | 16063 | 73.5 | CACGACGGATCGCGTTTCGT | 30 | 35 | 24 | 12 | 10 | 0 |
| 7807 | 3174 | 3145 | 9806 | 73 | CACGACGGCAGCTCTGGCTT | 30 | 35 | 31 | 8 | 17 | 0 |
| 7808 | 3175 | 3146 | 9807 | 69.5 | CACGACGGGACAGGAAATC | 30 | 35 | 34 | 25 | 4 | 0 |
| 7809 | 3176 | 3147 | 9810 | 70.5 | CACGAGCCAAAGTGCGGAGT | 30 | 36 | 6 | 29 | 20 | 0 |
| 7810 | 3177 | 3148 | 9811 | 71.9 | CACGAGCCTACAACGGTGCG | 30 | 36 | 7 | 35 | 29 | 0 |
| 7811 | 3178 | 3149 | 9812 | 67.5 | CACGAGCCTCTGAATCGCTT | 30 | 36 | 8 | 4 | 17 | 0 |
| 7812 | 3179 | 3150 | 9813 | 70.5 | CACGAGCCTGTCAGCCCCTA | 30 | 36 | 9 | 36 | 26 | 0 |
| 7813 | 3180 | 3151 | 40781 | 70.5 | CACGAGCCCTCACGTTGGAC | 30 | 36 | 13 | 12 | 34 | 0 |
| 7814 | 3181 | 3152 | 9817 | 67.8 | CACGAGCCGCTTACCTAGGA | 30 | 36 | 17 | 23 | 25 | 0 |
| 7815 | 3182 | 3154 | 30707 | 71.1 | CACGAGCCAGTGCGTTAGCC | 30 | 36 | 22 | 12 | 36 | 0 |
| 7816 | 3183 | 3155 | 30708 | 70.6 | AGCCACCTCAGCAGTGCAGC | 36 | 23 | 31 | 22 | 31 | 0 |
| 7817 | 3184 | 3156 | 16069 | 77.5 | CACGAGCCTGCGGACCGGAC | 30 | 36 | 29 | 32 | 34 | 0 |
| 7818 | 3185 | 3157 | 9827 | 76.3 | CACGAGCCCACGGCAACAGC | 30 | 36 | 30 | 21 | 31 | 0 |
| 7819 | 3186 | 3158 | 9830 | 73.9 | AGCCGTGCGAGTCTTGTGCG | 36 | 33 | 20 | 11 | 29 | 0 |
| 7820 | 3187 | 3159 | 9831 | 72.5 | CACGAGCCGGACCTCATCGT | 30 | 36 | 34 | 13 | 10 | 0 |
| 7821 | 3188 | 3160 | 9837 | 72.8 | TTGAGTGCCGAAAGCCGGAC | 1 | 33 | 16 | 36 | 34 | 0 |
| 7822 | 3189 | 3161 | 9839 | 71.2 | TGATGCTTGGACAGCCCAGC | 2 | 17 | 34 | 36 | 31 | 0 |
| 7823 | 3190 | 3162 | 16071 | 70.6 | TGATGCAACACGCTTGGTGC | 2 | 21 | 30 | 11 | 33 | 0 |
| 7824 | 3191 | 3163 | 40784 | 71.8 | TGATTCCCAGTGCACGGTGC | 2 | 28 | 22 | 30 | 33 | 0 |
| 7825 | 3192 | 3164 | 9848 | 70.2 | AATCTCGTACGGCACGCGTT | 4 | 10 | 35 | 30 | 12 | 0 |
| 7826 | 3193 | 3165 | 9849 | 67.3 | AATCCTCACGTTAGCCGTGC | 4 | 13 | 12 | 36 | 33 | 0 |
| 7827 | 3194 | 3166 | 9851 | 68.8 | CAGCAATCGGTAACGGCTTG | 31 | 4 | 18 | 35 | 11 | 0 |
| 7828 | 3195 | 3167 | 9852 | 70 | CAGCAATCGTCTTCCCCAGC | 31 | 4 | 19 | 28 | 31 | 0 |
| 7829 | 3196 | 3168 | 9854 | 67.2 | CAGCAATCATCGAAAGCACG | 31 | 4 | 24 | 6 | 30 | 0 |
| 7830 | 3197 | 3169 | 9861 | 72.1 | ATACTCCCACGGACGGCGAA | 5 | 28 | 35 | 35 | 16 | 0 |
| 7831 | 3198 | 3170 | 40787 | 73.9 | CAGCATACTGCGCACGTGCG | 31 | 5 | 29 | 30 | 29 | 0 |
| 7832 | 3199 | 3172 | 9874 | 69.1 | AAAGGTGCGTCTAGCCAGCC | 6 | 33 | 19 | 36 | 36 | 0 |
| 7833 | 3200 | 3173 | 9875 | 69.6 | AAAGACGGCACGAGTGAGCC | 6 | 35 | 30 | 22 | 36 | 0 |
| 7834 | 3201 | 3174 | 9880 | 74.3 | TCTGGATGAGCCACGGCACG | 8 | 27 | 36 | 35 | 30 | 0 |
| 7835 | 3202 | 3175 | 9886 | 71.6 | TGTCCTTGTCCCGCTTTCCC | 9 | 11 | 28 | 17 | 28 | 1 |
| 7836 | 3203 | 3176 | 9887 | 74.2 | TGTCCTCATGCGTGCGGACC | 9 | 13 | 29 | 29 | 32 | 0 |
| 7837 | 3204 | 3177 | 9894 | 73 | CAGCTGTCGTGCCCATGCAA | 31 | 9 | 33 | 15 | 21 | 0 |
| 7838 | 3205 | 3178 | 9896 | 70.4 | TGTCAGCCCGAAACCTACGG | 9 | 36 | 16 | 23 | 35 | 0 |
| 7839 | 3206 | 3179 | 9902 | 72.4 | CAGCTCGTTCCCGCTTGGAC | 31 | 10 | 28 | 17 | 34 | 0 |
| 7840 | 3207 | 3180 | 40795 | 70 | TCGTCAGCTCGTGAGTTGCG | 10 | 31 | 10 | 20 | 29 | 0 |
| 7841 | 3208 | 3181 | 16096 | 67.8 | CTTGAAAGGCTTAGCCTGCG | 11 | 6 | 17 | 36 | 29 | 0 |
| 7842 | 3209 | 3182 | 21838 | 69.8 | CAGCCTTGTCTGGACCAGCC | 31 | 11 | 8 | 32 | 36 | 0 |
| 7843 | 3210 | 3183 | 9910 | 63.9 | CAGCCTTGTCGTATACGTGC | 31 | 11 | 10 | 5 | 33 | 0 |
| 7844 | 3211 | 3184 | 9915 | 70.9 | CAGCCTTGAGTGGACCTGCG | 31 | 11 | 22 | 32 | 29 | 0 |
| 7845 | 3212 | 3185 | 40798 | 67.6 | CTTGAGGAGCAAGACCACGG | 11 | 25 | 21 | 32 | 35 | 0 |
| 7846 | 3213 | 3186 | 16097 | 69.8 | CAGCCTTGTCCCCTCAATCG | 31 | 11 | 28 | 13 | 24 | 1 |
| 7847 | 3214 | 3187 | 9921 | 71.7 | CAGCCTTGGACCCGTTCGTT | 31 | 11 | 32 | 12 | 12 | 0 |
| 7848 | 3215 | 3188 | 9922 | 69.7 | CAGCCTTGACGGGCAAGTCT | 31 | 11 | 35 | 21 | 19 | 0 |
| 7849 | 3216 | 3189 | 16099 | 65 | CAGCCGTTTACATCTGTCCC | 31 | 12 | 7 | 8 | 28 | 0 |

FIG. 29PPP

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 7850 | 3217 | 3190 | 30714 | 68.2 | CAGCCGTTTCTGAAAGCAGC | 31 | 12 | 8 | 6 | 31 | 0 |
| 7851 | 3218 | 3191 | 30715 | 70.9 | CAGCCGTTGCTTAGCCCTCA | 31 | 12 | 17 | 36 | 13 | 0 |
| 7852 | 3219 | 3192 | 9931 | 67.4 | CAGCCGTTGGTAACCTGACC | 31 | 12 | 18 | 23 | 32 | 0 |
| 7853 | 3220 | 3193 | 16101 | 70.5 | CAGCCGTTGCAAATCGGTCT | 31 | 12 | 21 | 24 | 19 | 0 |
| 7854 | 3221 | 3194 | 9933 | 67.1 | CAGCCGTTATCGGATGACCT | 31 | 12 | 24 | 27 | 23 | 0 |
| 7855 | 3222 | 3195 | 16102 | 65.4 | CGTTCCTAACGGATACCACG | 12 | 26 | 35 | 5 | 30 | 0 |
| 7856 | 3223 | 3196 | 30717 | 67.1 | CGTTGTGCTCGTAAAGGCAA | 12 | 33 | 10 | 6 | 21 | 0 |
| 7857 | 3224 | 3197 | 9939 | 72.7 | CAGCCGTTGGACGATGGCTT | 31 | 12 | 34 | 27 | 17 | 0 |
| 7858 | 3225 | 3198 | 16104 | 72.1 | CAGCCGTTAGCCGCTTAGCC | 31 | 12 | 36 | 17 | 36 | 0 |
| 7859 | 3226 | 3199 | 30718 | 65.4 | CAGCCTCATCGTAAAGGTGC | 31 | 13 | 10 | 6 | 33 | 0 |
| 7860 | 3227 | 3200 | 30719 | 71.7 | CAGCCTCACCATCAGCGTGC | 31 | 13 | 15 | 31 | 33 | 0 |
| 7861 | 3228 | 3201 | 40805 | 68.1 | CAGCCTCACGAACGAACGTT | 31 | 13 | 16 | 16 | 12 | 0 |
| 7862 | 3229 | 3202 | 40806 | 69.4 | CAGCCTCAGCTTTCGTGCAA | 31 | 13 | 17 | 10 | 21 | 0 |
| 7863 | 3230 | 3203 | 9945 | 67.3 | CAGCCTCAGCAAGACCGAGT | 31 | 13 | 21 | 32 | 20 | 0 |
| 7864 | 3231 | 3204 | 40807 | 64.4 | CAGCCTCAACCTAATCGACC | 31 | 13 | 23 | 4 | 32 | 0 |
| 7865 | 3232 | 3205 | 9947 | 69.8 | CAGCCTCATCCCGACCAAAG | 31 | 13 | 28 | 32 | 6 | 0 |
| 7866 | 3233 | 3206 | 9950 | 67.4 | CTCAGACCTGATTCCCTGCG | 13 | 32 | 2 | 28 | 29 | 0 |
| 7867 | 3234 | 3207 | 9954 | 64 | CAGCCTGTTGATCGTTTGA | 31 | 14 | 1 | 10 | 1 | 0 |
| 7868 | 3235 | 3208 | 9955 | 68.2 | CTGTTGATCGAATCCCGTGC | 14 | 2 | 16 | 28 | 33 | 0 |
| 7869 | 3236 | 3209 | 9956 | 70.1 | CAGCCTGTTCTGCGTTGCAA | 31 | 14 | 8 | 12 | 21 | 0 |
| 7870 | 3237 | 3210 | 9959 | 70 | CAGCCTGTCTCAAGCCGGAC | 31 | 14 | 13 | 36 | 34 | 0 |
| 7871 | 3238 | 3211 | 40810 | 69.1 | CAGCCTGTCCATCTCATGCG | 31 | 14 | 15 | 13 | 29 | 0 |
| 7872 | 3239 | 3212 | 9961 | 67.4 | CAGCCTGTGCTTCTCATCCC | 31 | 14 | 17 | 13 | 28 | 0 |
| 7873 | 3240 | 3213 | 21844 | 70.7 | CAGCCTGTGTGCCGAAGCTT | 31 | 14 | 33 | 16 | 17 | 0 |
| 7874 | 3241 | 3214 | 16113 | 70.1 | CAGCCCATTACACACGCACG | 31 | 15 | 7 | 30 | 30 | 0 |
| 7875 | 3242 | 3215 | 16114 | 70 | CAGCCCATTCTGCCATCCAT | 31 | 15 | 8 | 15 | 15 | 0 |
| 7876 | 3243 | 3216 | 30720 | 66.4 | CAGCCCATCTTGTGATCACG | 31 | 15 | 11 | 2 | 30 | 0 |
| 7877 | 3244 | 3217 | 30721 | 70.3 | CAGCCCATCGTTGCTTCCAT | 31 | 15 | 12 | 17 | 15 | 0 |
| 7878 | 3245 | 3218 | 40813 | 68.4 | CCATGTCTCCATGACCACGG | 15 | 19 | 15 | 32 | 35 | 0 |
| 7879 | 3246 | 3219 | 40814 | 68.5 | CCATGAGTGCTTAGCCACGG | 15 | 20 | 17 | 36 | 35 | 0 |
| 7880 | 3247 | 3220 | 9977 | 69.7 | CAGCCCATGCAATCTGCTCA | 31 | 15 | 21 | 8 | 13 | 0 |
| 7881 | 3248 | 3221 | 40815 | 71.6 | CAGCCCATCCTAACGGCCAT | 31 | 15 | 26 | 35 | 15 | 0 |
| 7882 | 3249 | 3222 | 30722 | 69.7 | CAGCCCATCACGAAAGGCTT | 31 | 15 | 30 | 6 | 17 | 0 |
| 7883 | 3250 | 3223 | 9988 | 70.6 | CAGCCCATACGGGAGTGTGC | 31 | 15 | 35 | 20 | 33 | 0 |
| 7884 | 3251 | 3224 | 40818 | 68.6 | CAGCCGAATCTGAAAGCGAA | 31 | 16 | 8 | 6 | 16 | 0 |
| 7885 | 3252 | 3225 | 9994 | 68.5 | CAGCCGAATGTCCGTTCTTG | 31 | 16 | 9 | 12 | 11 | 0 |
| 7886 | 3253 | 3226 | 16124 | 67.9 | CAGCCGAAGTCTTGCGAATC | 31 | 16 | 19 | 29 | 4 | 0 |
| 7887 | 3254 | 3227 | 40821 | 67.8 | CGAAAGTGATACGTGCGCAA | 16 | 22 | 5 | 33 | 21 | 0 |
| 7888 | 3255 | 3228 | 40822 | 68.4 | CAGCCGAAAGGATGTCATCG | 31 | 16 | 25 | 9 | 24 | 0 |
| 7889 | 3256 | 3229 | 10006 | 76.9 | CAGCCGAATGCGCTTGGCAA | 31 | 16 | 29 | 11 | 21 | 0 |
| 7890 | 3257 | 3230 | 16127 | 73 | CAGCCGAACACGGCTTGCTT | 31 | 16 | 30 | 17 | 17 | 0 |
| 7891 | 3258 | 3231 | 10009 | 68.3 | CGAAGACCCACGATACGTGC | 16 | 32 | 30 | 5 | 33 | 0 |
| 7892 | 3259 | 3232 | 10010 | 74 | CAGCCGAAACGGCACGTGTC | 31 | 16 | 35 | 30 | 9 | 0 |
| 7893 | 3260 | 3233 | 10011 | 70.3 | CAGCCGAAAGCCGGTAGATG | 31 | 16 | 36 | 18 | 27 | 0 |
| 7894 | 3261 | 3234 | 30724 | 66.8 | CAGCCGCTTAATCTGCGTCTG | 31 | 17 | 4 | 29 | 8 | 0 |
| 7895 | 3262 | 3235 | 10015 | 64.2 | CAGCCGCTTTACACGTTTGTC | 31 | 17 | 7 | 12 | 9 | 0 |
| 7896 | 3263 | 3236 | 30725 | 68.4 | CAGCCGCTTTGTCCGAAAAG | 31 | 17 | 9 | 16 | 6 | 0 |
| 7897 | 3264 | 3237 | 16128 | 69.5 | CAGCGCTTTCGTTCGTTTGA | 31 | 17 | 10 | 10 | 1 | 0 |

FIG. 29QQQ

| SEQ ID NO: | ZIP ID# | 4,633 ID# | HEX Tm | ZIPCODE (NH2 -> CONH2) | TETRAMER NUMBERS | | | | | "UNALLOWED DIMERS" |
|---|---|---|---|---|---|---|---|---|---|---|
| 7898 | 3265 | 3238 | 10019 69.5 | CAGCGCTTCTCAGGACCCAT | 31 | 17 | 13 | 34 | 15 | 0 |
| 7899 | 3266 | 3239 | 21856 69 | CAGCGCTTCTGTCGAAGTGC | 31 | 17 | 14 | 16 | 33 | 0 |
| 7900 | 3267 | 3240 | 10024 68.5 | CAGCGCTTATCGCGAAAATC | 31 | 17 | 24 | 16 | 4 | 0 |
| 7901 | 3268 | 3241 | 10026 73.3 | CAGCGCTTTGCGGCTTGAGT | 31 | 17 | 29 | 17 | 20 | 0 |
| 7902 | 3269 | 3242 | 10029 66.1 | CAGCGCTTAGCCTTGACTTG | 31 | 17 | 36 | 1 | 11 | 0 |
| 7903 | 3270 | 3243 | 30726 67.9 | CAGCGGTACCATCCATGACC | 31 | 18 | 15 | 15 | 32 | 0 |
| 7904 | 3271 | 3244 | 10036 66.4 | CAGCGGTACGAACGAACTTG | 31 | 18 | 16 | 16 | 11 | 0 |
| 7905 | 3272 | 3245 | 30727 68.4 | CAGCGGTACAGCACCTGCTT | 31 | 18 | 31 | 23 | 17 | 0 |
| 7906 | 3273 | 3246 | 10046 68.3 | CAGCGTCTTGATGGACCAGC | 31 | 19 | 2 | 34 | 31 | 0 |
| 7907 | 3274 | 3247 | 30728 65.6 | GTCTCCATCTCATCGTTGCG | 19 | 15 | 13 | 10 | 29 | 0 |
| 7908 | 3275 | 3248 | 30729 70 | CAGCGTCTCGAATCGTTCCC | 31 | 19 | 16 | 10 | 28 | 0 |
| 7909 | 3276 | 3249 | 21861 67.8 | CAGCGTCTGCTTATCGTCCC | 31 | 19 | 17 | 24 | 28 | 0 |
| 7910 | 3277 | 3250 | 10050 68.7 | CAGCGTCTTGCGAGGAGATG | 31 | 19 | 29 | 25 | 27 | 0 |
| 7911 | 3278 | 3251 | 30730 66 | CAGCGTCTGGACTTGAATCG | 31 | 19 | 34 | 1 | 24 | 0 |
| 7912 | 3279 | 3252 | 40828 68.5 | CAGCGTCTACGGAATCACGG | 31 | 19 | 35 | 4 | 35 | 0 |
| 7913 | 3280 | 3253 | 10056 69.8 | CAGCGAGTTCTGCAGCGATG | 31 | 20 | 8 | 31 | 27 | 0 |
| 7914 | 3281 | 3254 | 10057 69.5 | CAGCGAGTCTTGGCAACACG | 31 | 20 | 11 | 21 | 30 | 0 |
| 7915 | 3282 | 3255 | 10058 63.5 | CAGCGAGTCGTTATCGTGTC | 31 | 20 | 12 | 24 | 9 | 0 |
| 7916 | 3283 | 3257 | 30731 68.4 | CAGCGAGTCGAAAGGACGAA | 31 | 20 | 16 | 25 | 16 | 0 |
| 7917 | 3284 | 3259 | 16142 75.2 | CAGCGAGTGTGCGACCTGCG | 31 | 20 | 33 | 32 | 29 | 0 |
| 7918 | 3285 | 3260 | 40831 69.6 | CAGCGCAATGATCGAAATCG | 31 | 21 | 2 | 16 | 24 | 0 |
| 7919 | 3286 | 3261 | 16143 66.5 | CAGCGCAAATACAATCCAGC | 31 | 21 | 5 | 4 | 31 | 0 |
| 7920 | 3287 | 3262 | 16144 69.6 | CAGCGCAATCTGGCTTGATG | 31 | 21 | 8 | 17 | 27 | 0 |
| 7921 | 3288 | 3263 | 10076 71.6 | CAGCGCAATGTCCGTTGGAC | 31 | 21 | 9 | 12 | 34 | 0 |
| 7922 | 3289 | 3264 | 10078 69.4 | CAGCGCAACCATGGTAATCG | 31 | 21 | 15 | 18 | 24 | 0 |
| 7923 | 3290 | 3265 | 10079 69.7 | CAGCGCAACGAATCGTCTTG | 31 | 21 | 16 | 10 | 11 | 0 |
| 7924 | 3291 | 3266 | 30732 68.1 | CAGCGCAAGGTAGCAAGACC | 31 | 21 | 18 | 21 | 32 | 0 |
| 7925 | 3292 | 3267 | 10081 66.5 | CAGCGCAAGAGTCGTTCTTG | 31 | 21 | 20 | 12 | 11 | 0 |
| 7926 | 3293 | 3268 | 40833 68.5 | CAGCGCAAAGTGTGATTCCC | 31 | 21 | 22 | 2 | 28 | 0 |
| 7927 | 3294 | 3269 | 10084 73 | CAGCGCAAGGACGATGGACC | 31 | 21 | 34 | 27 | 32 | 0 |
| 7928 | 3295 | 3270 | 10085 75 | CAGCGCAAACGGTCGTCACG | 31 | 21 | 35 | 10 | 30 | 0 |
| 7929 | 3296 | 3271 | 10086 70.8 | AGTGTCGTGTGCTCCCCACG | 22 | 10 | 33 | 28 | 30 | 0 |
| 7930 | 3297 | 3272 | 30733 69.3 | AGTGGCTTGTGCCTGTTCCC | 22 | 17 | 33 | 14 | 28 | 0 |
| 7931 | 3298 | 3274 | 10093 69.8 | CAGCAGTGCCTAATCGCACG | 31 | 22 | 26 | 24 | 30 | 0 |
| 7932 | 3299 | 3275 | 16147 70.1 | CAGCAGTGTCCCCTTGCCAT | 31 | 22 | 28 | 11 | 15 | 1 |
| 7933 | 3300 | 3276 | 10097 70.2 | AGTGGGACGTCTACGGTGCG | 22 | 34 | 19 | 35 | 29 | 0 |
| 7934 | 3301 | 3277 | 16148 68.8 | CAGCACCTCGAAAATCTGCG | 31 | 23 | 16 | 4 | 29 | 0 |
| 7935 | 3302 | 3278 | 30734 69.9 | CAGCACCTCACGTCTGCGAA | 31 | 23 | 30 | 8 | 16 | 0 |
| 7936 | 3303 | 3279 | 10108 70.5 | ACCTGTGCGACCTGTCCGAA | 23 | 33 | 32 | 9 | 16 | 0 |
| 7937 | 3304 | 3280 | 10109 71.8 | CAGCACCTGGACGCTTGTGC | 31 | 23 | 34 | 17 | 33 | 0 |
| 7938 | 3305 | 3281 | 30735 68.7 | CAGCATCGGCTTACCTGTGC | 31 | 24 | 17 | 23 | 33 | 0 |
| 7939 | 3306 | 3282 | 30736 68.6 | ATCGGGTAAGTGAGCCGCTT | 24 | 18 | 22 | 36 | 17 | 0 |
| 7940 | 3307 | 3283 | 16154 70.1 | ATCGATCGGCAATCTGGTGC | 24 | 24 | 21 | 8 | 33 | 0 |
| 7941 | 3308 | 3284 | 10125 74.3 | CAGCATCGACGGCACGGGTA | 31 | 24 | 35 | 30 | 18 | 0 |
| 7942 | 3309 | 3285 | 10128 69.6 | CAGCAGGAAATCACGGTCCC | 31 | 25 | 4 | 35 | 28 | 1 |
| 7943 | 3310 | 3286 | 10130 67.9 | AGGATCGTGTCTCGAATGCG | 25 | 10 | 19 | 16 | 29 | 0 |
| 7944 | 3311 | 3287 | 10131 71.8 | CAGCAGGACTTGACGGCACG | 31 | 25 | 11 | 35 | 30 | 0 |
| 7945 | 3312 | 3288 | 30737 71 | CAGCAGGAGCAAATCGGTGC | 31 | 25 | 21 | 24 | 33 | 0 |

FIG. 29RRR

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 7946 | 3313 | 3289 | 10133 | 69.1 | CAGCAGGAAGTGTGCGCTGT | 31 | 25 | 22 | 29 | 14 | 0 |
| 7947 | 3314 | 3290 | 16157 | 70.3 | CAGCAGGACACGGATGGCTT | 31 | 25 | 30 | 27 | 17 | 0 |
| 7948 | 3315 | 3291 | 10135 | 67.4 | AGGAGTGCTCTGGGACTCCC | 25 | 33 | 8 | 34 | 28 | 0 |
| 7949 | 3316 | 3292 | 10136 | 67.6 | CAGCAGGAAGCCATACGGAC | 31 | 25 | 36 | 5 | 34 | 0 |
| 7950 | 3317 | 3293 | 30738 | 66.9 | CCTATCGTGCTTTGTCGCAA | 26 | 10 | 17 | 9 | 21 | 0 |
| 7951 | 3318 | 3294 | 30739 | 68 | CAGCCCTACGAATCTGCAGC | 31 | 26 | 16 | 8 | 31 | 0 |
| 7952 | 3319 | 3295 | 30740 | 65.1 | CCTAGCAAATACTCCCTGCG | 26 | 21 | 5 | 28 | 29 | 0 |
| 7953 | 3320 | 3296 | 16161 | 66.6 | CAGCCCTAAGTGAGCCGTCT | 31 | 26 | 22 | 36 | 19 | 0 |
| 7954 | 3321 | 3297 | 40839 | 70.6 | CAGCCCTAACCTTCCCAGCC | 31 | 26 | 23 | 28 | 36 | 1 |
| 7955 | 3322 | 3298 | 10148 | 67.1 | CAGCCCTAACGGTCGTCTGT | 31 | 26 | 35 | 10 | 14 | 0 |
| 7956 | 3323 | 3299 | 10151 | 70.4 | CAGCGATGAATCCACGGGAC | 31 | 27 | 4 | 30 | 34 | 0 |
| 7957 | 3324 | 3300 | 21879 | 63.4 | CAGCGATGTCTGACCTATCG | 31 | 27 | 8 | 23 | 24 | 0 |
| 7958 | 3325 | 3301 | 10152 | 69.1 | GATGTGTCCCATGCTTTGCG | 27 | 9 | 15 | 17 | 29 | 0 |
| 7959 | 3326 | 3302 | 10154 | 67.3 | CAGCGATGCTTGCTGTCTTG | 31 | 27 | 11 | 14 | 11 | 0 |
| 7960 | 3327 | 3303 | 10166 | 67.1 | CAGCGATGCTCAGTGCTCTG | 31 | 27 | 13 | 33 | 8 | 0 |
| 7961 | 3328 | 3304 | 40841 | 67.7 | GATGGTCTTGATTCCCGCAA | 27 | 19 | 2 | 28 | 21 | 0 |
| 7962 | 3329 | 3305 | 16169 | 67.9 | CAGCGATGAGGATCGTTCGT | 31 | 27 | 25 | 10 | 10 | 0 |
| 7963 | 3330 | 3306 | 30741 | 66.3 | CAGCGATGCCTAGCAACCTA | 31 | 27 | 26 | 21 | 26 | 0 |
| 7964 | 3331 | 3307 | 16170 | 70.4 | CAGCGATGTCCCCTTGCCTA | 31 | 27 | 28 | 11 | 26 | 0 |
| 7965 | 3332 | 3308 | 10164 | 68.9 | CAGCGATGGACCGATGAGTG | 31 | 27 | 32 | 27 | 22 | 0 |
| 7966 | 3333 | 3309 | 10167 | 70.9 | CAGCGATGACGGGATGTCGT | 31 | 27 | 35 | 27 | 10 | 0 |
| 7967 | 3334 | 3310 | 10168 | 72.3 | CAGCGATGAGCCCTGTGCAA | 31 | 27 | 36 | 14 | 21 | 0 |
| 7968 | 3335 | 3311 | 30742 | 68.5 | TCCCAAAGTCCCCTGTAGCC | 28 | 6 | 28 | 14 | 36 | 1 |
| 7969 | 3336 | 3312 | 30743 | 68.5 | TCCCCGTTAAAGATCGGACC | 28 | 12 | 6 | 24 | 32 | 0 |
| 7970 | 3337 | 3313 | 30744 | 69.7 | CAGCTCCCCTGTATCGCGTT | 31 | 28 | 14 | 24 | 12 | 0 |
| 7971 | 3338 | 3314 | 10175 | 70.9 | TCCCCGAAATCGTGTCGATG | 28 | 16 | 24 | 9 | 27 | 0 |
| 7972 | 3339 | 3315 | 30745 | 69.8 | TCCCGAGTGCTTTTGAAGCC | 28 | 20 | 17 | 1 | 36 | 0 |
| 7973 | 3340 | 3316 | 10178 | 67.3 | TCCCAGTGTTAGACGGCCAT | 28 | 22 | 3 | 35 | 15 | 0 |
| 7974 | 3341 | 3317 | 10179 | 66.3 | CAGCTCCCACCTACCTGGAC | 31 | 28 | 23 | 23 | 34 | 0 |
| 7975 | 3342 | 3318 | 10180 | 69.6 | TCCCGATGGTCTTCGTCGTT | 28 | 27 | 19 | 10 | 12 | 0 |
| 7976 | 3343 | 3319 | 16176 | 72.6 | CAGCTCCCTCCCGAGTTCCC | 31 | 28 | 28 | 20 | 28 | 0 |
| 7977 | 3344 | 3320 | 10182 | 70.7 | TCCCTGCGAATCAGGACGAA | 28 | 29 | 4 | 25 | 16 | 0 |
| 7978 | 3345 | 3321 | 10183 | 73 | TCCCCACGGATGATCGATCG | 28 | 30 | 27 | 24 | 24 | 0 |
| 7979 | 3346 | 3322 | 10186 | 70.8 | TCCCACGGTCGTTGTCCTTG | 28 | 35 | 10 | 9 | 11 | 0 |
| 7980 | 3347 | 3323 | 16177 | 71.6 | CAGCTGCGTTGAGTGCCGTT | 31 | 29 | 1 | 33 | 12 | 0 |
| 7981 | 3348 | 3324 | 40843 | 68.5 | TGCGTTAGTCTGGGACCGAA | 29 | 3 | 8 | 34 | 16 | 0 |
| 7982 | 3349 | 3325 | 16179 | 72.4 | TGCGATACCGAAAGCCCGTT | 29 | 5 | 16 | 36 | 12 | 0 |
| 7983 | 3350 | 3326 | 16180 | 73.3 | CAGCTGCGTCTGGACCCAGC | 31 | 29 | 8 | 32 | 31 | 0 |
| 7984 | 3351 | 3327 | 30746 | 68 | CAGCTGCGACCTAATCAGCC | 31 | 29 | 23 | 4 | 36 | 0 |
| 7985 | 3352 | 3328 | 40845 | 72.8 | TGCGATCGGCTTTGATGCAA | 29 | 24 | 17 | 2 | 21 | 0 |
| 7986 | 3353 | 3329 | 10195 | 71.4 | TGCGGATGGCTTGAGTCAGC | 29 | 27 | 17 | 20 | 31 | 0 |
| 7987 | 3354 | 3330 | 10196 | 74 | CAGCTGCGTCCCTGTCCACG | 31 | 29 | 28 | 9 | 30 | 0 |
| 7988 | 3355 | 3331 | 10197 | 77.6 | CAGCTGCGCACGCTTGACGG | 31 | 29 | 30 | 11 | 35 | 0 |
| 7989 | 3356 | 3332 | 40848 | 66.6 | CACGTTGATTAGGACCGCAA | 30 | 1 | 3 | 32 | 21 | 0 |
| 7990 | 3357 | 3333 | 10203 | 71.9 | CAGCCACGAATCGAGTTGCG | 31 | 30 | 4 | 20 | 29 | 0 |
| 7991 | 3358 | 3334 | 10204 | 67.5 | CAGCCACGATACCGAAGGAC | 31 | 30 | 5 | 16 | 34 | 0 |
| 7992 | 3359 | 3335 | 30747 | 68.7 | CACGTCTGTGTCTCCCACGG | 30 | 8 | 9 | 28 | 35 | 0 |
| 7993 | 3360 | 3336 | 21894 | 68.9 | CAGCCACGTCGTGCAAGTCT | 31 | 30 | 10 | 21 | 19 | 0 |

FIG. 29SSS

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 7993 | 3361 | 3337 | 10208 | 73.5 | CAGCCACGCGTTCGTTCCAT | 31 | 30 | 12 | 12 | 15 | 0 |
| 7994 | 3362 | 3338 | 10210 | 71.9 | CAGCCACGCGAAGTGCAATC | 31 | 30 | 16 | 33 | 4 | 0 |
| 7995 | 3363 | 3339 | 40850 | 71.8 | CAGCCACGCCTATCCCCCTA | 31 | 30 | 26 | 28 | 26 | 0 |
| 7996 | 3364 | 3340 | 30748 | 68.2 | CAGCCAGCTTGAGGACGGTA | 31 | 31 | 1 | 34 | 18 | 0 |
| 7997 | 3365 | 3341 | 16183 | 70.3 | CAGCCAGCTTAGGACCGTGC | 31 | 31 | 3 | 32 | 33 | 0 |
| 7998 | 3366 | 3344 | 16184 | 71.2 | CAGCCAGCTGTCACGGAGGA | 31 | 31 | 9 | 35 | 25 | 0 |
| 7999 | 3367 | 3345 | 30749 | 66.4 | CAGCCTCAATACGGTATGCG | 31 | 13 | 5 | 18 | 29 | 0 |
| 8001 | 3368 | 3346 | 16186 | 66.3 | CAGCCCATATCGATACTGCG | 31 | 15 | 24 | 5 | 29 | 0 |
| 8002 | 3369 | 3347 | 10228 | 71.5 | CAGCCAGCAGGACGTTCGAA | 31 | 31 | 25 | 12 | 16 | 0 |
| 8003 | 3370 | 3348 | 10229 | 67.6 | CAGCCAGCGATGTTAGGGAC | 31 | 31 | 27 | 3 | 34 | 0 |
| 8004 | 3371 | 3349 | 10230 | 70.1 | CAGCCAGCTCCCGGTACTTG | 31 | 31 | 28 | 18 | 11 | 0 |
| 8005 | 3372 | 3350 | 10233 | 73.2 | CAGCCAGCAGCCCTTGGATG | 31 | 31 | 36 | 11 | 27 | 0 |
| 8006 | 3373 | 3351 | 30750 | 65.9 | CAGCGACCAATCATACAGCC | 31 | 32 | 4 | 5 | 36 | 0 |
| 8007 | 3374 | 3352 | 40857 | 68.4 | CAGCGACCTCGTAGGAGCAA | 31 | 32 | 10 | 25 | 21 | 0 |
| 8008 | 3375 | 3353 | 40858 | 69.2 | CAGCGACCCTTGCCTAGACC | 31 | 32 | 11 | 26 | 32 | 0 |
| 8009 | 3376 | 3354 | 10239 | 73.6 | CAGCGACCGCAACACGGTCT | 31 | 32 | 21 | 30 | 19 | 0 |
| 8010 | 3377 | 3355 | 10241 | 66.8 | CAGCGACCATCGTACACAGC | 31 | 32 | 24 | 7 | 31 | 0 |
| 8011 | 3378 | 3356 | 30751 | 72 | CAGCGACCTCCCAATCGGAC | 31 | 32 | 28 | 4 | 34 | 0 |
| 8012 | 3379 | 3357 | 10242 | 71.4 | CAGCGACCCACGGCTTTACA | 31 | 32 | 30 | 17 | 7 | 0 |
| 8013 | 3380 | 3358 | 10244 | 70.3 | CAGCGACCGACCTCGTCTGT | 31 | 32 | 32 | 10 | 14 | 0 |
| 8014 | 3381 | 3359 | 30752 | 70 | CAGCGACCAGCCAGGAAATC | 31 | 32 | 36 | 25 | 4 | 0 |
| 8015 | 3382 | 3360 | 10249 | 67.5 | CAGCGTGCATACTGCGAAAG | 31 | 33 | 5 | 29 | 6 | 0 |
| 8016 | 3383 | 3361 | 10251 | 68.2 | CAGCGTGCTACAAGTGCACG | 31 | 33 | 7 | 22 | 30 | 0 |
| 8017 | 3384 | 3362 | 30753 | 72.3 | CAGCGTGCTCTGGATGGCAA | 31 | 33 | 8 | 27 | 21 | 0 |
| 8018 | 3385 | 3363 | 30754 | 69.6 | CAGCGTGCTCGTAGTGACGG | 31 | 33 | 10 | 22 | 35 | 0 |
| 8019 | 3386 | 3364 | 10253 | 69.8 | CAGCGTGCCTGTAATCTGCG | 31 | 33 | 14 | 4 | 29 | 0 |
| 8020 | 3387 | 3365 | 10254 | 71.6 | CAGCGTGCCGAACTGTGCTT | 31 | 33 | 16 | 14 | 17 | 0 |
| 8021 | 3388 | 3366 | 10256 | 69.9 | CAGCGTGCGTCTCTTGCTTG | 31 | 33 | 19 | 11 | 11 | 0 |
| 8022 | 3389 | 3367 | 30755 | 72.7 | CAGCGTGCACCTTCGTCACG | 31 | 33 | 23 | 10 | 30 | 0 |
| 8023 | 3390 | 3368 | 10259 | 74.7 | CAGCGTGCCACGCTTGTCGT | 31 | 33 | 30 | 11 | 10 | 0 |
| 8024 | 3391 | 3369 | 10260 | 77 | CAGCGTGCGACCCACGGATG | 31 | 33 | 32 | 30 | 27 | 0 |
| 8025 | 3392 | 3370 | 10262 | 72 | CAGCGTGCGGACATCGTGAT | 31 | 33 | 34 | 24 | 2 | 0 |
| 8026 | 3393 | 3371 | 10263 | 77.1 | CAGCGTGCACGGCAGCGAGT | 31 | 33 | 35 | 31 | 20 | 0 |
| 8027 | 3394 | 3372 | 10264 | 76.4 | CAGCGTGCAGCCCTCAACGG | 31 | 33 | 36 | 13 | 35 | 0 |
| 8028 | 3395 | 3373 | 40861 | 68.1 | CAGCGGACTGATAGCCAGGA | 31 | 34 | 2 | 36 | 25 | 0 |
| 8029 | 3396 | 3374 | 10265 | 69.1 | CAGCGGACAATCAAAGGCAA | 31 | 34 | 4 | 6 | 21 | 0 |
| 8030 | 3397 | 3375 | 30757 | 68.8 | CAGCGGACTGTCAATCCGAA | 31 | 34 | 9 | 4 | 16 | 0 |
| 8031 | 3398 | 3376 | 10273 | 70 | CAGCGGACGAGTCGAAGCTT | 31 | 34 | 20 | 16 | 17 | 0 |
| 8032 | 3399 | 3377 | 40864 | 67.8 | CAGCGGACACCTTACAAGCC | 31 | 34 | 23 | 7 | 36 | 0 |
| 8033 | 3400 | 3378 | 30758 | 72.3 | CAGCGGACGATGGGACACCT | 31 | 34 | 27 | 34 | 23 | 0 |
| 8034 | 3401 | 3379 | 16192 | 73.1 | CAGCGGACTGCGGTCTGGAC | 31 | 34 | 29 | 19 | 34 | 0 |
| 8035 | 3402 | 3380 | 10278 | 75.8 | CAGCGGACCACGCCATGCTT | 31 | 34 | 30 | 15 | 17 | 0 |
| 8036 | 3403 | 3381 | 10279 | 71.7 | CAGCGGACCAGCCCTACCAT | 31 | 34 | 31 | 26 | 15 | 0 |
| 8037 | 3404 | 3382 | 10280 | 73.6 | CAGCGGACACGGCGAACTGT | 31 | 34 | 35 | 16 | 14 | 0 |
| 8038 | 3405 | 3383 | 40866 | 66.4 | ACGGTTGAAATCCCTAACGG | 35 | 1 | 4 | 26 | 35 | 1 |
| 8039 | 3406 | 3384 | 10283 | 69.5 | CAGCACGGTGATGATGCGTT | 31 | 35 | 2 | 27 | 12 | 0 |
| 8040 | 3407 | 3385 | 40867 | 67.1 | ACGGAATCTCTGGGTATGCG | 35 | 4 | 8 | 18 | 29 | 0 |
| 8041 | 3408 | 3386 | 10285 | 67.2 | CAGCACGGATACAAAGCACG | 31 | 35 | 5 | 6 | 30 | 0 |

FIG. 29TTT

| SEQ ID NO: | ZIP ID# | 4,633 ID# | HEX ID# | Tm | ZIPCODE (5H2 -> CONH2) | TETRAMER NUMBERS | | | | | "UNALLOWED DIMERS" |
|---|---|---|---|---|---|---|---|---|---|---|---|
| 8042 | 3409 | 3387 | 21913 | 73.8 | CAGCACGGCTGTGACCGCTT | 31 | 35 | 14 | 32 | 17 | 0 |
| 8043 | 3410 | 3388 | 10291 | 72.1 | CAGCACGGCGAAGCTTGATG | 31 | 35 | 16 | 17 | 27 | 0 |
| 8044 | 3411 | 3389 | 10292 | 69.7 | ACGGGCTTGTCTCCTATGCG | 35 | 17 | 19 | 26 | 29 | 0 |
| 8045 | 3412 | 3390 | 10293 | 71.9 | CAGCACGGGGTACGAATCCC | 31 | 35 | 18 | 16 | 28 | 0 |
| 8046 | 3413 | 3391 | 21915 | 66.1 | ACGGGAGTATCGAGTGAGCC | 35 | 20 | 24 | 22 | 36 | 0 |
| 8047 | 3414 | 3392 | 30759 | 70.5 | CAGCACGGACCTTCTGCGTT | 31 | 35 | 23 | 8 | 12 | 0 |
| 8048 | 3415 | 3393 | 10295 | 71.4 | CAGCACGGATCGTCCCAGTG | 31 | 35 | 24 | 28 | 22 | 0 |
| 8049 | 3416 | 3394 | 10296 | 67.4 | ACGGAGGAACCTGAGTGCAA | 35 | 25 | 23 | 20 | 21 | 0 |
| 8050 | 3417 | 3395 | 16194 | 74 | CAGCACGGAGCCACCTGTGC | 31 | 35 | 36 | 23 | 33 | 0 |
| 8051 | 3418 | 3396 | 30760 | 66.7 | AGCCTGATAAAGAGCCACGG | 36 | 2 | 6 | 36 | 35 | 0 |
| 8052 | 3419 | 3397 | 16195 | 70.8 | CAGCAGCCAATCCTTGGTGC | 31 | 36 | 4 | 11 | 33 | 0 |
| 8053 | 3420 | 3398 | 30761 | 68.3 | CAGCAGCCTCTGTCGTGGAC | 31 | 36 | 8 | 10 | 34 | 0 |
| 8054 | 3421 | 3399 | 40870 | 75.8 | CAGCAGCCTGTCGTGCGCAA | 31 | 36 | 9 | 33 | 21 | 0 |
| 8055 | 3422 | 3400 | 10310 | 69.8 | CAGCAGCCCGTTCCTAAGGA | 31 | 36 | 12 | 26 | 25 | 0 |
| 8056 | 3423 | 3401 | 10315 | 69.3 | CAGCAGCCGTCTCTTGCTCA | 31 | 36 | 19 | 11 | 13 | 0 |
| 8057 | 3424 | 3402 | 30762 | 70.1 | AGCCGAGTGAGTCACGCGTT | 36 | 20 | 20 | 30 | 12 | 0 |
| 8058 | 3425 | 3403 | 10319 | 69 | AGCCACCTGATGTGTCGCAA | 36 | 23 | 27 | 9 | 21 | 0 |
| 8059 | 3426 | 3404 | 30763 | 72.4 | CAGCAGCCGATGATCGCTCA | 31 | 36 | 27 | 24 | 13 | 0 |
| 8060 | 3427 | 3405 | 10322 | 69.8 | CAGCAGCCGACCTACATCCC | 31 | 36 | 32 | 7 | 28 | 0 |
| 8061 | 3428 | 3406 | 16203 | 74.3 | TTAGGCAAACGGCACGCGAA | 3 | 21 | 35 | 30 | 16 | 0 |
| 8062 | 3429 | 3407 | 30764 | 69.6 | AATCCGAACGAACGAAACGG | 4 | 16 | 16 | 16 | 35 | 0 |
| 8063 | 3430 | 3408 | 10346 | 72.7 | GACCAATCGGACGTGCGGAC | 32 | 4 | 34 | 33 | 34 | 0 |
| 8064 | 3431 | 3409 | 30765 | 67 | AAAGCGTTAGCCCTGTCAGC | 6 | 12 | 36 | 14 | 31 | 0 |
| 8065 | 3432 | 3410 | 10356 | 71.7 | AAAGATCGCGTTGTGCTGCG | 6 | 24 | 12 | 33 | 29 | 0 |
| 8066 | 3433 | 3411 | 10357 | 72.7 | AAAGGATGCACGGACCTGCG | 6 | 27 | 30 | 32 | 29 | 0 |
| 8067 | 3434 | 3412 | 10360 | 70.7 | AAAGGGACGACCAGGAACGG | 6 | 34 | 32 | 25 | 35 | 0 |
| 8068 | 3435 | 3413 | 16210 | 73.7 | TCTGGTGCCAGCGCTTGGAC | 8 | 33 | 31 | 17 | 34 | 0 |
| 8069 | 3436 | 3414 | 10372 | 72.6 | TCTGACGGCGTTTCGTTCCC | 8 | 35 | 12 | 10 | 28 | 0 |
| 8070 | 3437 | 3415 | 10375 | 69.5 | TGTCGTGCAAAGCCATGACC | 9 | 33 | 6 | 15 | 32 | 0 |
| 8071 | 3438 | 3416 | 30766 | 72.1 | TCGTCGAATGCGGTCTGTGC | 10 | 16 | 29 | 19 | 33 | 0 |
| 8072 | 3439 | 3417 | 10378 | 70.6 | TCGTGGTATCCCGTGCGAGT | 10 | 18 | 28 | 33 | 20 | 0 |
| 8073 | 3440 | 3418 | 10379 | 71 | TCGTCACGGCTTACGGCTGT | 10 | 30 | 17 | 35 | 14 | 0 |
| 8074 | 3441 | 3419 | 30767 | 67.4 | CTTGCGAATCGTTACATGCG | 11 | 16 | 10 | 7 | 29 | 0 |
| 8075 | 3442 | 3420 | 30768 | 67.6 | GACCCTTGGGTACCATTCCC | 32 | 11 | 18 | 15 | 28 | 0 |
| 8076 | 3443 | 3421 | 30769 | 70.4 | CTTGCAGCCCTACAGCCAGC | 11 | 31 | 26 | 31 | 31 | 0 |
| 8077 | 3444 | 3422 | 16219 | 67.4 | GACCCGTTTACAGTGCGGAC | 32 | 12 | 7 | 33 | 34 | 0 |
| 8078 | 3445 | 3423 | 10396 | 69.3 | GACCCGTTTCTGCACGGTCT | 32 | 12 | 8 | 30 | 19 | 0 |
| 8079 | 3446 | 3424 | 30770 | 68.2 | GACCCGTTCTCAGCTTTCCC | 32 | 12 | 13 | 17 | 28 | 0 |
| 8080 | 3447 | 3425 | 30771 | 67.2 | CGTTGGTACAGCAATCTGCG | 12 | 18 | 31 | 4 | 29 | 0 |
| 8081 | 3448 | 3426 | 10402 | 68.1 | CGTTAGTGTTGATGCGCACG | 12 | 22 | 1 | 29 | 30 | 1 |
| 8082 | 3449 | 3427 | 30772 | 69.5 | GACCCGTTAGGATCCCCCAT | 32 | 12 | 25 | 28 | 15 | 0 |
| 8083 | 3450 | 3428 | 40880 | 70.6 | GACCCGTTGATGATCGCAGC | 32 | 12 | 27 | 24 | 31 | 0 |
| 8084 | 3451 | 3429 | 10404 | 68.5 | CGTTTGCGAATCTGTCGCTT | 12 | 29 | 4 | 9 | 17 | 0 |
| 8085 | 3452 | 3430 | 21938 | 67.6 | GACCCGTTCACGTGATGCTT | 32 | 12 | 30 | 2 | 17 | 0 |
| 8086 | 3453 | 3431 | 10405 | 69.6 | CGTTCAGCGGTATCTGTGCG | 12 | 31 | 18 | 8 | 29 | 0 |
| 8087 | 3454 | 3432 | 10406 | 72.2 | GACCCGTTGTGCGGACACCT | 32 | 12 | 33 | 34 | 23 | 0 |
| 8088 | 3455 | 3433 | 10422 | 68.3 | GACCTGTGCAAGGTATGCG | 32 | 14 | 21 | 18 | 29 | 0 |
| 8089 | 3456 | 3434 | 40883 | 68.5 | CCATTTGAGCAAGTGCGACC | 15 | 1 | 21 | 33 | 32 | 0 |

FIG. 29UUU

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 8090 | 3457 | 3435 | 40885 | 70.1 | CCATGGTACTTGTGCGCACG | 15 | 18 | 11 | 29 | 30 | 0 |
| 8091 | 3458 | 3436 | 16237 | 71.4 | CCATCACGGAGTGACCTGCG | 15 | 30 | 20 | 32 | 29 | 0 |
| 8092 | 3459 | 3437 | 16239 | 69.3 | GACCCCATACGGGTACACG | 32 | 15 | 35 | 18 | 30 | 0 |
| 8093 | 3460 | 3438 | 30773 | 68.5 | CGAATTGAAGGATCCCCGTT | 16 | 1 | 25 | 28 | 12 | 0 |
| 8094 | 3461 | 3439 | 40890 | 67 | CGAAGGTACCATCGAAAGCC | 16 | 18 | 15 | 16 | 36 | 0 |
| 8095 | 3462 | 3440 | 10453 | 69.5 | GACCCGAAATCGGCTTCTCA | 32 | 16 | 24 | 17 | 13 | 0 |
| 8096 | 3463 | 3441 | 16250 | 71 | GACCCGAAACGGGCTTAGGA | 32 | 16 | 35 | 17 | 25 | 0 |
| 8097 | 3464 | 3442 | 10460 | 65.3 | GACCGCTTTGATGGTAATCG | 32 | 17 | 2 | 18 | 24 | 0 |
| 8098 | 3465 | 3443 | 30775 | 73.2 | GCTTTGTCGGACCAGCGTGC | 17 | 9 | 34 | 31 | 33 | 0 |
| 8099 | 3466 | 3444 | 16254 | 66 | GCTTCTGTCCATGAGTTGCG | 17 | 14 | 15 | 20 | 29 | 0 |
| 8100 | 3467 | 3445 | 30776 | 67.4 | GACCGCTTGCTTACGGAAAG | 32 | 17 | 17 | 35 | 6 | 0 |
| 8101 | 3468 | 3446 | 40894 | 65.8 | GCTTATCGAATCGGTATGCG | 17 | 24 | 4 | 18 | 29 | 0 |
| 8102 | 3469 | 3447 | 30777 | 67.9 | GACCGCTTCCTAAGGAAGCC | 32 | 17 | 26 | 25 | 36 | 0 |
| 8103 | 3470 | 3448 | 30778 | 74.1 | GACCGCTTTGCGTCGTGTGC | 32 | 17 | 29 | 10 | 33 | 0 |
| 8104 | 3471 | 3449 | 16256 | 70.3 | GACCGCTTGTGCAATCCGTT | 32 | 17 | 33 | 4 | 12 | 0 |
| 8105 | 3472 | 3450 | 10478 | 70.5 | GACCGGTATTGATGCGACGG | 32 | 18 | 1 | 29 | 35 | 0 |
| 8106 | 3473 | 3451 | 30779 | 68.2 | GGTACGTTGGACCTCATGCG | 18 | 12 | 34 | 13 | 29 | 0 |
| 8107 | 3474 | 3452 | 16261 | 68.7 | GACCGGTACGAAGACCGGAC | 32 | 18 | 16 | 32 | 34 | 0 |
| 8108 | 3475 | 3453 | 40896 | 66 | GGTAGCTTCACGAATCGCAA | 18 | 17 | 30 | 4 | 21 | 0 |
| 8109 | 3476 | 3454 | 10487 | 66.1 | GGTAGGTAGCTTTCCCCACG | 18 | 18 | 17 | 28 | 30 | 0 |
| 8110 | 3477 | 3455 | 30780 | 68.2 | GACCGGTAAGGAAGGAACGG | 32 | 18 | 25 | 25 | 35 | 0 |
| 8111 | 3478 | 3456 | 10491 | 71 | GACCGGTATGCGTGCGTGAT | 32 | 18 | 29 | 29 | 2 | 0 |
| 8112 | 3479 | 3457 | 40898 | 68.5 | GTCTTCGTTTGAAGCCGCAA | 19 | 10 | 1 | 36 | 21 | 0 |
| 8113 | 3480 | 3458 | 10498 | 68.3 | GACCGTCTCGAACAGCATCG | 32 | 19 | 16 | 31 | 24 | 0 |
| 8114 | 3481 | 3459 | 16265 | 64.8 | GTCTGCTTTGATGGACGCTT | 19 | 17 | 2 | 34 | 17 | 0 |
| 8115 | 3482 | 3460 | 10503 | 70.5 | GACCGTCTGACCGTGCCTTG | 32 | 19 | 32 | 33 | 11 | 0 |
| 8116 | 3483 | 3461 | 10509 | 64.6 | GAGTGGTAAAAGACGGCAGC | 20 | 18 | 6 | 35 | 31 | 0 |
| 8117 | 3484 | 3462 | 10512 | 72 | GACCGAGTGTGCCGTTGCAA | 32 | 20 | 33 | 12 | 21 | 0 |
| 8118 | 3485 | 3463 | 10513 | 69.7 | GACCGAGTGGACACGGTCGT | 32 | 20 | 34 | 35 | 10 | 0 |
| 8119 | 3486 | 3464 | 10514 | 70.2 | GACCGAGTAGCCGATGCAGC | 32 | 20 | 36 | 27 | 31 | 0 |
| 8120 | 3487 | 3465 | 30781 | 71.3 | GACCGCAATGATACGGCGAA | 32 | 21 | 2 | 35 | 16 | 0 |
| 8121 | 3488 | 3466 | 21954 | 66.2 | GCAAAATCTGTCCTGTTGCG | 21 | 4 | 9 | 14 | 29 | 0 |
| 8122 | 3489 | 3467 | 40904 | 67.1 | GACCGCAATCTGTGATTCCC | 32 | 21 | 8 | 2 | 28 | 0 |
| 8123 | 3490 | 3468 | 30782 | 66.5 | GACCGCAACTTGTGATGTGC | 32 | 21 | 11 | 2 | 33 | 0 |
| 8124 | 3491 | 3469 | 30783 | 69.2 | GACCGCAAGCTTTTGATCCC | 32 | 21 | 17 | 1 | 28 | 0 |
| 8125 | 3492 | 3470 | 30784 | 70.5 | GACCGCAAGTCTCACGCGTT | 32 | 21 | 19 | 30 | 12 | 0 |
| 8126 | 3493 | 3471 | 10528 | 65.6 | GCAAGAGTTGATGGACACGG | 21 | 20 | 2 | 34 | 35 | 0 |
| 8127 | 3494 | 3472 | 10529 | 68 | GACCGCAAAGTGGATGGATG | 32 | 21 | 22 | 27 | 27 | 0 |
| 8128 | 3495 | 3474 | 30785 | 75.1 | GACCGCAATCCCCCATTCCC | 32 | 21 | 28 | 15 | 28 | 0 |
| 8129 | 3496 | 3475 | 10537 | 71.6 | AGTGTGCGGAGTGACCGCAA | 22 | 29 | 20 | 32 | 21 | 0 |
| 8130 | 3497 | 3476 | 10538 | 72.7 | AGTGCACGCTCACACGGCAA | 22 | 30 | 13 | 30 | 21 | 0 |
| 8131 | 3498 | 3477 | 16277 | 73.4 | AGTGAGCCGACCGACCCGTT | 22 | 36 | 32 | 32 | 12 | 0 |
| 8132 | 3499 | 3478 | 10545 | 70.7 | ACCTCACGGATGCCATCACG | 23 | 30 | 27 | 15 | 30 | 0 |
| 8133 | 3500 | 3479 | 40906 | 70.9 | ACCTACGGGCTTAGCCCGAA | 23 | 35 | 17 | 36 | 16 | 0 |
| 8134 | 3501 | 3480 | 10550 | 70.3 | GACCATCGCTCAAGCCCTCA | 32 | 24 | 13 | 36 | 13 | 0 |
| 8135 | 3502 | 3481 | 30786 | 71.4 | GACCATCGCGAATCCCCTGT | 32 | 24 | 16 | 28 | 14 | 0 |
| 8136 | 3503 | 3482 | 16287 | 68.9 | GACCAGGACCATACGGCCAT | 32 | 25 | 15 | 35 | 15 | 0 |
| 8137 | 3504 | 3483 | 10566 | 68.5 | AGGAATCGCGAAGATGGACC | 25 | 24 | 16 | 27 | 32 | 0 |

FIG. 29VVV

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 8138 | 3505 | 3484 | 16289 | 69.9 | AGGATCCCGCTTGAGTTCCC | 25 | 28 | 17 | 20 | 28 | 0 |
| 8139 | 3506 | 3485 | 10570 | 70.2 | AGGAGTGCCTTGGCTTGCAA | 25 | 33 | 11 | 17 | 21 | 0 |
| 8140 | 3507 | 3486 | 10573 | 68.3 | CCTACTTGCCATCACGGTGC | 26 | 11 | 15 | 30 | 33 | 0 |
| 8141 | 3508 | 3487 | 40909 | 66 | GACCCCTACGTTAGGAACGG | 32 | 26 | 12 | 25 | 35 | 0 |
| 8142 | 3509 | 3488 | 30787 | 66.5 | CCTACGAAGGTAAGCCCAGC | 26 | 16 | 18 | 36 | 31 | 0 |
| 8143 | 3510 | 3489 | 30788 | 70.1 | CCTAGCAACACGACGGAGCC | 26 | 21 | 30 | 35 | 36 | 0 |
| 8144 | 3511 | 3490 | 10581 | 66.1 | CCTAGTGCTGTCAGGATGCG | 26 | 33 | 9 | 25 | 29 | 0 |
| 8145 | 3512 | 3491 | 16294 | 71.8 | GACCCCTAGGACAGCCGCAA | 32 | 26 | 34 | 36 | 21 | 0 |
| 8146 | 3513 | 3494 | 40915 | 71.2 | GACCGATGATCGTGCGCCTA | 32 | 27 | 24 | 29 | 26 | 0 |
| 8147 | 3514 | 3495 | 16299 | 68.4 | GACCGATGAGGAATCGGGAC | 32 | 27 | 25 | 24 | 34 | 0 |
| 8148 | 3515 | 3496 | 10595 | 69.1 | GACCGATGTGCGTCGTATCG | 32 | 27 | 29 | 10 | 24 | 0 |
| 8149 | 3516 | 3497 | 16302 | 70.7 | GACCGATGCAGCCCTACACG | 32 | 27 | 31 | 26 | 30 | 0 |
| 8150 | 3517 | 3498 | 16303 | 73.3 | GACCGATGGTGCCAGCAGGA | 32 | 27 | 33 | 31 | 25 | 0 |
| 8151 | 3518 | 3499 | 30791 | 66.8 | GACCGATGAGCCTCTGGGTA | 32 | 27 | 36 | 8 | 18 | 0 |
| 8152 | 3519 | 3500 | 10602 | 70.2 | TCCCAAAGCGAAGATGCGTT | 28 | 6 | 16 | 27 | 12 | 0 |
| 8153 | 3520 | 3502 | 10611 | 73.1 | TCCCAGTGGTGCGCTTTCGT | 28 | 22 | 33 | 17 | 10 | 0 |
| 8154 | 3521 | 3503 | 10612 | 68.8 | TCCCACCTTACACGAATGCG | 28 | 23 | 7 | 16 | 29 | 0 |
| 8155 | 3522 | 3504 | 10619 | 71.7 | GACCTCCCGGACTCTGCGAA | 32 | 28 | 34 | 8 | 16 | 0 |
| 8156 | 3523 | 3505 | 10621 | 73.1 | GACCTCCCAGCCCGTTGCTT | 32 | 28 | 36 | 12 | 17 | 0 |
| 8157 | 3524 | 3506 | 30793 | 69.7 | TGCGTTGAGTCTACGGCGAA | 29 | 1 | 19 | 35 | 16 | 0 |
| 8158 | 3525 | 3507 | 10626 | 68.4 | TGCGTCGTACCTGATGGACC | 29 | 10 | 23 | 27 | 32 | 0 |
| 8159 | 3526 | 3508 | 10629 | 68.8 | TGCGGAGTCTGTATCGACGG | 29 | 20 | 14 | 24 | 35 | 0 |
| 8160 | 3527 | 3509 | 10631 | 71.5 | TGCGATCGGTCTACCTTGCG | 29 | 24 | 19 | 23 | 29 | 0 |
| 8161 | 3528 | 3510 | 30794 | 69.4 | TGCGCCTAAGGAAAAGAGCC | 29 | 26 | 25 | 6 | 36 | 0 |
| 8162 | 3529 | 3511 | 10634 | 76 | TGCGTGCGCGTTTGTCAGGA | 29 | 29 | 12 | 9 | 25 | 0 |
| 8163 | 3530 | 3512 | 10637 | 75.7 | GACCTGCGGTGCCACGAGGA | 32 | 29 | 33 | 30 | 25 | 0 |
| 8164 | 3531 | 3513 | 10638 | 68.8 | CACGTTAGGGACGATGGCAA | 30 | 3 | 34 | 27 | 21 | 0 |
| 8165 | 3532 | 3514 | 10639 | 71 | CACGTGTCCCATGACCCAGC | 30 | 9 | 15 | 32 | 31 | 0 |
| 8166 | 3533 | 3515 | 10640 | 70.2 | GACCCACGCTGTCAGCGTCT | 32 | 30 | 14 | 31 | 19 | 0 |
| 8167 | 3534 | 3516 | 10644 | 67.7 | GACCCACGCCTATCGTCTCA | 32 | 30 | 26 | 10 | 13 | 0 |
| 8168 | 3535 | 3517 | 10651 | 74.4 | GACCCACGAGCCGCAAGACC | 32 | 30 | 36 | 21 | 32 | 0 |
| 8169 | 3536 | 3518 | 40923 | 67.8 | CAGCTTGATACATGCGCGAA | 31 | 1 | 7 | 29 | 16 | 0 |
| 8170 | 3537 | 3519 | 10654 | 69.6 | CAGCATACCTTGGCAATGCG | 31 | 5 | 11 | 21 | 29 | 0 |
| 8171 | 3538 | 3520 | 10655 | 65.8 | CAGCTACACTTGGTGCCGTT | 31 | 7 | 11 | 33 | 12 | 0 |
| 8172 | 3539 | 3521 | 16324 | 66.9 | GACCCAGCGGTAGCTTTGTC | 32 | 31 | 18 | 17 | 9 | 0 |
| 8173 | 3540 | 3522 | 10662 | 69.1 | CAGCAGTGGACCAAAGCGAA | 31 | 22 | 32 | 6 | 16 | 0 |
| 8174 | 3541 | 3523 | 40926 | 70.9 | CAGCGATGCCATTGTCCCAT | 31 | 27 | 15 | 9 | 15 | 0 |
| 8175 | 3542 | 3524 | 30796 | 72.6 | CAGCGTGCAGGATGTCGTGC | 31 | 33 | 25 | 9 | 33 | 0 |
| 8176 | 3543 | 3525 | 10665 | 72.3 | GACCCAGCAGCCGCAAAATC | 32 | 31 | 36 | 21 | 4 | 0 |
| 8177 | 3544 | 3526 | 16328 | 68.2 | GACCGACCTGATAGCCCCAT | 32 | 32 | 2 | 36 | 15 | 0 |
| 8178 | 3545 | 3527 | 10668 | 67.8 | GACCAAAGGTCTGACCGCAA | 32 | 6 | 19 | 32 | 21 | 0 |
| 8179 | 3546 | 3528 | 10670 | 68.9 | GACCGACCTCTGCGAAGGAC | 32 | 32 | 8 | 16 | 34 | 0 |
| 8180 | 3547 | 3529 | 16329 | 66.9 | GACCGACCCTGTAAAGCAGC | 32 | 32 | 14 | 6 | 31 | 0 |
| 8181 | 3548 | 3530 | 30797 | 70 | GACCGACCACCTGCAACGTT | 32 | 32 | 23 | 21 | 12 | 0 |
| 8182 | 3549 | 3531 | 10680 | 71.5 | GACCGTGCCTCATCTGCACG | 32 | 33 | 13 | 8 | 30 | 0 |
| 8183 | 3550 | 3532 | 16333 | 67.3 | GACCGTGCTTAGGCTTACGG | 32 | 33 | 3 | 17 | 35 | 0 |
| 8184 | 3551 | 3533 | 21989 | 63.7 | GTGCATACTCGTCTTGCAGC | 33 | 5 | 10 | 11 | 31 | 0 |
| 8185 | 3552 | 3534 | 10690 | 67.6 | GACCGTGCCGAAGGTAAGTG | 32 | 33 | 16 | 18 | 22 | 0 |

FIG. 29WWW

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 8186 | 3553 | 3535 | 10691 | 65.2 | GACCGTGCGTCTCTCAAAAG | 32 | 33 | 19 | 13 | 6 | 0 |
| 8187 | 3554 | 3536 | 10693 | 71.1 | GACCGTGCGCAATCGTGTCT | 32 | 33 | 21 | 10 | 19 | 0 |
| 8188 | 3555 | 3537 | 40932 | 70 | GACCGTGCAGTGTCTGTGCG | 32 | 33 | 22 | 8 | 29 | 0 |
| 8189 | 3556 | 3538 | 30798 | 68.5 | GACCGTGCACCTCTCACGAA | 32 | 33 | 23 | 13 | 16 | 0 |
| 8190 | 3557 | 3539 | 30799 | 70.1 | GACCGTGCAGGACCATGGAC | 32 | 33 | 25 | 15 | 34 | 0 |
| 8191 | 3558 | 3540 | 10697 | 74.6 | GACCGTGCTGCGGTCTGCAA | 32 | 33 | 29 | 19 | 21 | 0 |
| 8192 | 3559 | 3541 | 10698 | 71.6 | GACCGTGCCACGCTCACTTG | 32 | 33 | 30 | 13 | 11 | 0 |
| 8193 | 3560 | 3542 | 10699 | 70.6 | GACCGTGCCAGCCTCATCTG | 32 | 33 | 31 | 13 | 8 | 0 |
| 8194 | 3561 | 3543 | 21992 | 73.7 | GACCGTGCGTGCGCTTGAGT | 32 | 33 | 33 | 17 | 20 | 0 |
| 8195 | 3562 | 3544 | 10706 | 72.9 | GACCGGACCGTTCAGCGATG | 32 | 34 | 12 | 31 | 27 | 0 |
| 8196 | 3563 | 3545 | 40935 | 71.2 | GACCGGACCTGTGGACCGTT | 32 | 34 | 14 | 34 | 12 | 0 |
| 8197 | 3564 | 3546 | 10709 | 67.2 | GGACCGAAAATCTGTCACGG | 34 | 16 | 4 | 9 | 35 | 0 |
| 8198 | 3565 | 3547 | 30800 | 73.8 | GACCGGACGCAAGCAAGCAA | 32 | 34 | 21 | 21 | 21 | 0 |
| 8199 | 3566 | 3548 | 10713 | 70.3 | GACCGGACATCGATCGATCG | 32 | 34 | 24 | 24 | 24 | 0 |
| 8200 | 3567 | 3549 | 40937 | 72.3 | GGACCAGCGTCTCAGCAGCC | 34 | 31 | 19 | 31 | 36 | 0 |
| 8201 | 3568 | 3550 | 30801 | 72.6 | GACCGGACGACCCTCACACG | 32 | 34 | 32 | 13 | 30 | 0 |
| 8202 | 3569 | 3551 | 10715 | 72.9 | GACCGGACGTGCCTCAATCG | 32 | 34 | 33 | 13 | 24 | 0 |
| 8203 | 3570 | 3552 | 10716 | 71.5 | GACCGGACACGGGTCTGCTT | 32 | 34 | 35 | 19 | 17 | 0 |
| 8204 | 3571 | 3553 | 16341 | 66.7 | ACGGTCGTAATCGATGTCCC | 35 | 10 | 4 | 27 | 28 | 0 |
| 8205 | 3572 | 3554 | 10722 | 67.6 | ACGGCTTGATCGTGATGCTT | 35 | 11 | 24 | 2 | 17 | 0 |
| 8206 | 3573 | 3555 | 10723 | 71.4 | GACCACGCGTTGTCTGTGC | 32 | 35 | 12 | 19 | 33 | 0 |
| 8207 | 3574 | 3556 | 30802 | 69 | ACGGCTGTATACCACGTGCG | 35 | 14 | 5 | 30 | 29 | 0 |
| 8208 | 3575 | 3557 | 16342 | 66.6 | ACGGGGTATTAGACGGCTTG | 35 | 18 | 3 | 35 | 11 | 0 |
| 8209 | 3576 | 3558 | 10726 | 65.9 | ACGGGTCTAGGATGTCGCTT | 35 | 19 | 25 | 9 | 17 | 0 |
| 8210 | 3577 | 3559 | 40939 | 67.2 | ACGGGAGTATACAGCCGTGC | 35 | 20 | 5 | 36 | 33 | 0 |
| 8211 | 3578 | 3560 | 16343 | 69.3 | ACGGCAGCTCGTTTAGAGCC | 35 | 31 | 10 | 3 | 36 | 0 |
| 8212 | 3579 | 3561 | 30804 | 73.8 | GACCACGGAGCCAGCCACCT | 32 | 35 | 36 | 36 | 23 | 0 |
| 8213 | 3580 | 3562 | 10735 | 70.1 | GACCAGCCAATCACGGCTGT | 32 | 36 | 4 | 35 | 14 | 0 |
| 8214 | 3581 | 3563 | 10736 | 71.5 | GACCAGCCAAAGCGTTGCAA | 32 | 36 | 6 | 12 | 21 | 0 |
| 8215 | 3582 | 3564 | 10738 | 67.1 | AGCCTCGTCCATAATCACGG | 36 | 10 | 15 | 4 | 35 | 0 |
| 8216 | 3583 | 3565 | 10741 | 71.6 | GACCAGCCCCATGCTTCGTT | 32 | 36 | 15 | 17 | 12 | 0 |
| 8217 | 3584 | 3566 | 10742 | 70.6 | GACCAGCCGCTTCGAACTCA | 32 | 36 | 17 | 16 | 13 | 0 |
| 8218 | 3585 | 3567 | 30805 | 73.5 | AGCCAGTGAGCCAGCCCCAT | 36 | 22 | 36 | 36 | 15 | 0 |
| 8219 | 3586 | 3568 | 30806 | 67.8 | AGCCATCGTACAATCGCGTT | 36 | 24 | 7 | 24 | 12 | 0 |
| 8220 | 3587 | 3569 | 30807 | 69.3 | GACCAGCCCCTAAATCTGCG | 32 | 36 | 26 | 4 | 29 | 0 |
| 8221 | 3588 | 3570 | 10748 | 73.4 | AGCCTCCCGGACAGTGCCAT | 36 | 28 | 34 | 22 | 15 | 0 |
| 8222 | 3589 | 3571 | 10749 | 72.5 | GACCAGCCTGCGTGTCCGTT | 32 | 36 | 29 | 9 | 12 | 0 |
| 8223 | 3590 | 3572 | 10750 | 73.4 | GACCAGCCGACCGATGCTCA | 32 | 36 | 32 | 27 | 13 | 0 |
| 8224 | 3591 | 3573 | 10753 | 69.5 | TTGAGCTTATCGGCAATGCG | 1 | 17 | 24 | 21 | 29 | 0 |
| 8225 | 3592 | 3574 | 10758 | 76.3 | TTGAGTGCGTGCTGCGCGAA | 1 | 33 | 33 | 29 | 16 | 0 |
| 8226 | 3593 | 3575 | 22007 | 69.2 | TGATCCATGTGCCTTGACGG | 2 | 15 | 33 | 11 | 35 | 0 |
| 8227 | 3594 | 3576 | 10763 | 74.2 | TGATGTGCCGTTTGCGGGAC | 2 | 33 | 12 | 29 | 34 | 0 |
| 8228 | 3595 | 3577 | 10775 | 68.1 | GTGCAATCCGAACGTTGGAC | 33 | 4 | 16 | 12 | 34 | 0 |
| 8229 | 3596 | 3578 | 10776 | 66.4 | GTGCAATCGGTATCGTCGAA | 33 | 4 | 18 | 10 | 16 | 0 |
| 8230 | 3597 | 3579 | 10780 | 70 | GTGCAATCGATGAGCCCAT | 33 | 4 | 27 | 36 | 15 | 0 |
| 8231 | 3598 | 3580 | 10781 | 67.6 | AATCTCCCGCAAATACTGCG | 4 | 28 | 21 | 5 | 29 | 0 |
| 8232 | 3599 | 3581 | 22013 | 66.2 | GTGCAATCCACGGATGTCTG | 33 | 4 | 30 | 27 | 8 | 0 |
| 8233 | 3600 | 3582 | 30809 | 73.9 | GTGCAATCCAGCAGCCCACG | 33 | 4 | 31 | 36 | 30 | 0 |

FIG. 29XXX

| SEQ ID NO: | ZIP ID# | 4,633 ID# | REX ID# Tm | ZIPCODE (NH2 -> CONH2) | TETRAMER NUMBERS | | | | | 'UNALLOWED DIMERS' |
|---|---|---|---|---|---|---|---|---|---|---|
| 8234 | 3601 | 3583 | 16358 69.2 | GTGCATACCACGGCAAATCG | 33 | 5 | 36 | 21 | 24 | 0 |
| 8235 | 3602 | 3584 | 10792 72.5 | GTGCATACAGCCACGGTGCG | 33 | 5 | 36 | 35 | 29 | 0 |
| 8236 | 3603 | 3585 | 10793 68.7 | AAAGTCGTCGAACACGCGAA | 6 | 10 | 16 | 30 | 16 | 0 |
| 8237 | 3604 | 3586 | 10799 68.6 | GTGCAAAGCCTAATCGGCAA | 33 | 6 | 26 | 24 | 21 | 0 |
| 8238 | 3605 | 3587 | 16360 70 | AAAGCAGCCAGCAGTGAGCC | 6 | 31 | 31 | 22 | 36 | 0 |
| 8239 | 3606 | 3588 | 30810 69.5 | GTGCAAAGGACCATCGGCTT | 33 | 6 | 32 | 24 | 17 | 0 |
| 8240 | 3607 | 3589 | 10808 70.3 | TCTGGGTAATCGGGACTGCG | 8 | 18 | 24 | 34 | 29 | 0 |
| 8241 | 3608 | 3590 | 10809 72 | TCTGCCTAGCTTTGCGCACG | 8 | 26 | 17 | 29 | 30 | 0 |
| 8242 | 3609 | 3591 | 10810 70.8 | TCTGTGCGCGTTAGTGCGAA | 8 | 29 | 12 | 22 | 16 | 0 |
| 8243 | 3610 | 3592 | 16367 70.3 | GTGCTGTCCGAAACGGCTGT | 33 | 9 | 16 | 35 | 14 | 0 |
| 8244 | 3611 | 3593 | 16368 73.5 | GTGCTGTCCACGGGACACGG | 33 | 9 | 30 | 34 | 35 | 0 |
| 8245 | 3612 | 3594 | 16369 73.8 | TGTCGACCGACCCAGCCTCA | 9 | 32 | 32 | 31 | 13 | 0 |
| 8246 | 3613 | 3595 | 10823 72.1 | TGTCACGGGTCTTCCCGGAC | 9 | 35 | 19 | 28 | 34 | 0 |
| 8247 | 3614 | 3596 | 10825 69.3 | TCGTTGATAGCCGCTTCACG | 10 | 2 | 36 | 17 | 30 | 0 |
| 8248 | 3615 | 3597 | 10828 70.1 | TCGTCTTGTGTCACGGCGAA | 10 | 11 | 9 | 35 | 16 | 0 |
| 8249 | 3616 | 3598 | 10834 68.9 | TCGTAGGAAATCAGCCGCAA | 10 | 25 | 4 | 36 | 21 | 0 |
| 8250 | 3617 | 3599 | 10836 71 | TCGTTCCCCGTTTTGACACG | 10 | 28 | 12 | 1 | 30 | 1 |
| 8251 | 3618 | 3600 | 16374 72.9 | TCGTGGACGGACGCTTCCAT | 10 | 34 | 34 | 17 | 15 | 0 |
| 8252 | 3619 | 3601 | 22025 69.4 | TCGTAGCCTCTGACGGGGAC | 10 | 36 | 8 | 35 | 34 | 0 |
| 8253 | 3620 | 3602 | 10843 70.5 | GTGCCTTGTTGATCCCGTGC | 33 | 11 | 1 | 28 | 33 | 1 |
| 8254 | 3621 | 3603 | 10844 66.3 | CTTGAAAGGCAACTTGCGAA | 11 | 6 | 21 | 11 | 16 | 0 |
| 8255 | 3622 | 3604 | 30811 70.7 | GTGCCTTGGTCTGGACTGCG | 33 | 11 | 19 | 34 | 29 | 0 |
| 8256 | 3623 | 3605 | 40950 68.9 | GTGCCTTGAGGAGTGCTCCC | 33 | 11 | 25 | 33 | 28 | 0 |
| 8257 | 3624 | 3606 | 10852 65.5 | GTGCCTTGCCTATCGTATCG | 33 | 11 | 26 | 10 | 24 | 0 |
| 8258 | 3625 | 3607 | 10853 70.4 | GTGCCTTGGATGGCTTCGAA | 33 | 11 | 27 | 17 | 16 | 0 |
| 8259 | 3626 | 3608 | 10855 66.8 | GTGCCTTGCAGCTGTCAGTG | 33 | 11 | 31 | 9 | 22 | 0 |
| 8260 | 3627 | 3609 | 30812 67.9 | CGTTTTGAAGGAGACCTGCG | 12 | 1 | 25 | 32 | 29 | 1 |
| 8261 | 3628 | 3610 | 30813 66.2 | CGTTTAGATCGGATGCGAA | 12 | 3 | 24 | 27 | 16 | 0 |
| 8262 | 3629 | 3611 | 30814 66.2 | CGTTCTGTGCGATACGCTT | 12 | 8 | 29 | 5 | 17 | 0 |
| 8263 | 3630 | 3612 | 30815 66.3 | CGTTCTGTAATCGTGCAGCC | 12 | 14 | 4 | 33 | 36 | 0 |
| 8264 | 3631 | 3613 | 40952 69 | GTGCCGTTCCATTTGACACG | 33 | 12 | 15 | 1 | 30 | 0 |
| 8265 | 3632 | 3614 | 30816 69.3 | GTGCCGTTGGTAGACCCGTT | 33 | 12 | 18 | 32 | 12 | 0 |
| 8266 | 3633 | 3615 | 40953 71.5 | GTGCCGTTGAGTAGCCGCAA | 33 | 12 | 20 | 36 | 21 | 0 |
| 8267 | 3634 | 3616 | 30817 67.8 | GTGCCGTTGATGTCTGGCTT | 33 | 12 | 27 | 8 | 17 | 0 |
| 8268 | 3635 | 3617 | 30818 68.4 | CGTTTCCCTTAGTCCCCAGC | 12 | 28 | 3 | 28 | 31 | 1 |
| 8269 | 3636 | 3618 | 10869 70.3 | GTGCCGTTGGACGACCAATC | 33 | 12 | 34 | 32 | 4 | 0 |
| 8270 | 3637 | 3619 | 10870 66.7 | CTCATTGACACGGGTATGCG | 13 | 1 | 30 | 18 | 29 | 0 |
| 8271 | 3638 | 3620 | 10874 69.3 | GTGCCTCACCATAGCCCGTT | 33 | 13 | 15 | 36 | 12 | 0 |
| 8272 | 3639 | 3621 | 10877 70.5 | CTCAAGTGGGACCAGCCACG | 13 | 22 | 34 | 31 | 30 | 0 |
| 8273 | 3640 | 3622 | 10880 64.9 | GTGCCTCACCTACTTGACGG | 33 | 13 | 26 | 11 | 35 | 0 |
| 8274 | 3641 | 3623 | 10881 66.3 | CTCATCCCTGATGATGCACG | 13 | 28 | 2 | 27 | 30 | 0 |
| 8275 | 3642 | 3624 | 30819 68.3 | CTCAAGCCTGATGGACGTGC | 13 | 36 | 2 | 34 | 33 | 0 |
| 8276 | 3643 | 3625 | 10886 71.6 | CTGTTCTGTGCGTCCCGTGC | 14 | 8 | 29 | 28 | 33 | 0 |
| 8277 | 3644 | 3626 | 10890 72.8 | CTGTGATGCACGGCTTTGCG | 14 | 27 | 30 | 17 | 29 | 0 |
| 8278 | 3645 | 3627 | 30820 68.3 | GTGCCCATTTGACGAAGTGC | 33 | 15 | 1 | 16 | 33 | 0 |
| 8279 | 3646 | 3628 | 40960 69.4 | CCATTCTGATCGTCCCGCTT | 15 | 8 | 24 | 28 | 17 | 0 |
| 8280 | 3647 | 3629 | 30821 68 | CCATTGTCTGTCCAGCGCTT | 15 | 9 | 9 | 31 | 17 | 0 |
| 8281 | 3648 | 3630 | 16391 69.2 | GTGCCCATTCGTACGGGTCT | 33 | 15 | 10 | 35 | 19 | 0 |

FIG. 29YYY

| SEQ ID NO: | ZIP ID# | 4,633 ID# | SEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 8282 | 3649 | 3631 | 16393 | 66.4 | CCATCTCAATACGGACGCAA | 15 | 13 | 5 | 34 | 21 | 0 |
| 8283 | 3650 | 3632 | 40963 | 68.2 | GTGCCCATAGGAGTGCGATG | 33 | 15 | 25 | 33 | 27 | 0 |
| 8284 | 3651 | 3633 | 40964 | 69.3 | GTGCCCATCCTACACGGACC | 33 | 15 | 26 | 30 | 32 | 0 |
| 8285 | 3652 | 3634 | 10910 | 72.9 | GTGCCCATTGCGGAGTACGG | 33 | 15 | 29 | 20 | 35 | 0 |
| 8286 | 3653 | 3635 | 10911 | 68.5 | CCATCAGCCTGTACCTTGCG | 15 | 31 | 14 | 23 | 29 | 0 |
| 8287 | 3654 | 3636 | 40967 | 66.7 | CGAATTGAGATGGATGCACG | 16 | 1 | 27 | 27 | 30 | 0 |
| 8288 | 3655 | 3637 | 30822 | 65.1 | GTGCCGAATGATAATCCAGC | 33 | 16 | 2 | 4 | 31 | 0 |
| 8289 | 3656 | 3638 | 10914 | 64.8 | GTGCCGAAAATCAATCGAGT | 33 | 16 | 4 | 4 | 20 | 0 |
| 8290 | 3657 | 3639 | 16396 | 68.2 | GTGCCGAAAAGGGTATCCC | 33 | 16 | 6 | 18 | 28 | 0 |
| 8291 | 3658 | 3640 | 22045 | 67.6 | CGAATGTCGATGTGATTGCG | 16 | 9 | 27 | 2 | 29 | 0 |
| 8292 | 3659 | 3641 | 10918 | 68.1 | GTGCCGAACGTTTGATGACC | 33 | 16 | 12 | 2 | 32 | 0 |
| 8293 | 3660 | 3642 | 30823 | 70.7 | GTGCCGAACCATTCGTCAGC | 33 | 16 | 15 | 10 | 31 | 0 |
| 8294 | 3661 | 3643 | 30824 | 69.1 | GTGCCGAAAGTGAATCGCAA | 33 | 16 | 22 | 4 | 21 | 0 |
| 8295 | 3662 | 3644 | 10926 | 71.2 | GTGCCGAACACGCGTTGAGT | 33 | 16 | 30 | 12 | 20 | 0 |
| 8296 | 3663 | 3645 | 22050 | 65.6 | CGAAGGACCTGTAAAGCACG | 16 | 34 | 14 | 6 | 30 | 0 |
| 8297 | 3664 | 3646 | 16401 | 75.6 | GTGCCGAAACGGCCATCGAA | 33 | 16 | 35 | 15 | 16 | 0 |
| 8298 | 3665 | 3647 | 30825 | 66.5 | GTGCGCTTTTAGTCGTGTGC | 33 | 17 | 3 | 10 | 33 | 0 |
| 8299 | 3666 | 3648 | 10932 | 66.8 | GTGCGCTTAAAGAGTGCACG | 33 | 17 | 6 | 22 | 30 | 0 |
| 8300 | 3667 | 3649 | 40971 | 67 | GTGCGCTTTACAAAAGCACG | 33 | 17 | 7 | 6 | 30 | 0 |
| 8301 | 3668 | 3650 | 10936 | 64.9 | GTGCGCTTCTCACTCAGGAC | 33 | 17 | 13 | 13 | 34 | 0 |
| 8302 | 3669 | 3651 | 22053 | 65.6 | GTGCGCTTGGTAGTCTACGG | 33 | 17 | 18 | 19 | 35 | 0 |
| 8303 | 3670 | 3652 | 30826 | 67.3 | GTGCGCTTAGGACCATCGTT | 33 | 17 | 25 | 15 | 12 | 0 |
| 8304 | 3671 | 3654 | 10943 | 69.1 | GTGCGCTTGATGCTTGGGTA | 33 | 17 | 27 | 11 | 18 | 0 |
| 8305 | 3672 | 3655 | 10944 | 72.7 | GTGCGCTTTCCCGAATTGA | 33 | 17 | 28 | 16 | 1 | 0 |
| 8306 | 3673 | 3656 | 10946 | 68 | GTGCGCTTGACCTCTGGGTA | 33 | 17 | 32 | 8 | 18 | 0 |
| 8307 | 3674 | 3657 | 10948 | 69.2 | GTGCGCTTGGACTGTCGATG | 33 | 17 | 34 | 9 | 27 | 0 |
| 8308 | 3675 | 3658 | 30828 | 69 | GTGCGGTAAAAGGACCGGAC | 33 | 18 | 6 | 32 | 34 | 0 |
| 8309 | 3676 | 3659 | 30829 | 67.4 | GTGCGGTACGTTTCTGGACC | 33 | 18 | 12 | 8 | 32 | 0 |
| 8310 | 3677 | 3660 | 22057 | 71.3 | GTGCGGTACGAATGCGACGA | 33 | 18 | 16 | 29 | 25 | 0 |
| 8311 | 3678 | 3661 | 30830 | 67.9 | GTGCGGTAGCAAAGGACAGC | 33 | 18 | 21 | 25 | 31 | 0 |
| 8312 | 3679 | 3662 | 16408 | 69.9 | GTGCGGTACCTAACGGGTGC | 33 | 18 | 26 | 35 | 33 | 0 |
| 8313 | 3680 | 3663 | 16409 | 70.1 | GTGCGGTAAGCCGGACTCTG | 33 | 18 | 36 | 34 | 8 | 0 |
| 8314 | 3681 | 3664 | 10961 | 66.3 | GTGCGTCTTTGACCTATGCG | 33 | 19 | 1 | 26 | 29 | 0 |
| 8315 | 3682 | 3665 | 10963 | 69.9 | GTGCGTCTTGTCGCAACGAA | 33 | 19 | 9 | 21 | 16 | 0 |
| 8316 | 3683 | 3666 | 10966 | 68.3 | GTGCGTCTGGTAATCGGTGC | 33 | 19 | 18 | 24 | 33 | 0 |
| 8317 | 3684 | 3667 | 10967 | 68 | GTGCGTCTATCGGCTTACGG | 33 | 19 | 24 | 17 | 35 | 0 |
| 8318 | 3685 | 3668 | 10969 | 69.2 | GTGCGTCTGATGCTTGGTGC | 33 | 19 | 27 | 11 | 33 | 0 |
| 8319 | 3686 | 3669 | 10970 | 69.6 | GTGCGTCTTCCCGTCTGCTT | 33 | 19 | 28 | 19 | 17 | 0 |
| 8320 | 3687 | 3670 | 10983 | 68.9 | GTGCGAGTAGGAGCAATGCG | 33 | 20 | 25 | 21 | 29 | 0 |
| 8321 | 3688 | 3671 | 10984 | 71.8 | GTGCGAGTGATGCAGCCAGC | 33 | 20 | 27 | 31 | 31 | 0 |
| 8322 | 3689 | 3672 | 10985 | 69.9 | GTGCGAGTTCCCGTCTCAGC | 33 | 20 | 28 | 19 | 31 | 0 |
| 8323 | 3690 | 3673 | 16417 | 70.5 | GTGCGAGTTGCGAATCCGTT | 33 | 20 | 29 | 4 | 12 | 0 |
| 8324 | 3691 | 3674 | 40979 | 65.6 | GTGCGCAATTGATTAGAGCC | 33 | 21 | 1 | 3 | 36 | 0 |
| 8325 | 3692 | 3675 | 30831 | 66.7 | GTGCGCAAATACCAGCAAAG | 33 | 21 | 5 | 31 | 6 | 0 |
| 8326 | 3693 | 3676 | 40981 | 68.8 | GCAATACAAGCCCTGTTGCG | 21 | 7 | 36 | 14 | 29 | 0 |
| 8327 | 3694 | 3677 | 40982 | 68.1 | GTGCGCAATGTCTCTGGGAC | 33 | 21 | 9 | 8 | 34 | 0 |
| 8328 | 3695 | 3679 | 10993 | 69.2 | GTGCGCAACTCAGGACATCG | 33 | 21 | 13 | 34 | 24 | 0 |
| 8329 | 3696 | 3680 | 40983 | 68.8 | GTGCGCAACTGTGATGGACC | 33 | 21 | 14 | 27 | 32 | 0 |

FIG. 29ZZZ

| SEQ ID NO: | ZIP ID# | 4,633 ID# | HEX ID# | Tm | ZIPCODE (NH2 -> CONH2) | TETRAMER NUMBERS | | | | | 'UNALLOWED DIMERS' |
|---|---|---|---|---|---|---|---|---|---|---|---|
| 8330 | 3697 | 3681 | 16419 | 64.5 | GTGCGCAAGGTATACAGCAA | 33 | 21 | 18 | 7 | 21 | 0 |
| 8331 | 3698 | 3682 | 10998 | 64 | GTGCGCAAAGTGATACAGGA | 33 | 21 | 22 | 5 | 25 | 0 |
| 8332 | 3699 | 3683 | 30833 | 70.8 | GTGCGCAAACCTTCGTGACC | 33 | 21 | 23 | 10 | 32 | 0 |
| 8333 | 3700 | 3684 | 10999 | 67.8 | GTGCGCAAATCGTACACACG | 33 | 21 | 24 | 7 | 30 | 0 |
| 8334 | 3701 | 3685 | 16421 | 69.2 | GTGCGCAAGATGAGTGACGG | 33 | 21 | 27 | 22 | 35 | 0 |
| 8335 | 3702 | 3686 | 11003 | 76.3 | GTGCGCAATGCGGCTTGGAC | 33 | 21 | 29 | 17 | 34 | 0 |
| 8336 | 3703 | 3687 | 11006 | 71.4 | GTGCGCAAGTGCAGGACGTT | 33 | 21 | 33 | 25 | 12 | 0 |
| 8337 | 3704 | 3688 | 40985 | 68.4 | GTGCAGTGGCTTACGGCCTA | 33 | 22 | 17 | 35 | 26 | 0 |
| 8338 | 3705 | 3689 | 11016 | 72.8 | AGTGGATGGCAATGCGCCAT | 22 | 27 | 21 | 29 | 15 | 0 |
| 8339 | 3706 | 3690 | 16425 | 71.6 | AGTGTGCGGCTTTGTCTGCG | 22 | 29 | 17 | 9 | 29 | 0 |
| 8340 | 3707 | 3691 | 22072 | 68.6 | GTGCAGTGGGACATCGGATG | 33 | 22 | 34 | 24 | 27 | 0 |
| 8341 | 3708 | 3692 | 11020 | 71.4 | AGTGACGGCAGCGTCTCACG | 22 | 35 | 31 | 19 | 30 | 0 |
| 8342 | 3709 | 3693 | 30834 | 69.2 | AGTGAGCCAATCGACCGACC | 22 | 36 | 4 | 32 | 32 | 0 |
| 8343 | 3710 | 3694 | 11029 | 73.2 | ACCTGATGACGGGTGCGTGC | 23 | 27 | 35 | 33 | 33 | 0 |
| 8344 | 3711 | 3695 | 11031 | 70.7 | ACCTCACGCACGAATCCGAA | 23 | 30 | 30 | 4 | 16 | 0 |
| 8345 | 3712 | 3696 | 11034 | 68.8 | GTGCACCTACGGCCATTTGA | 33 | 23 | 35 | 15 | 1 | 0 |
| 8346 | 3713 | 3697 | 11037 | 71.5 | ATCGTGATCAGCACGGGCAA | 24 | 2 | 31 | 35 | 21 | 0 |
| 8347 | 3714 | 3698 | 30835 | 71.9 | GTGCATCGCTTGCTCAACGG | 33 | 24 | 11 | 13 | 35 | 0 |
| 8348 | 3715 | 3699 | 30836 | 67.9 | ATCGCTGTTTAGAGCCTGCG | 24 | 14 | 3 | 36 | 29 | 0 |
| 8349 | 3716 | 3700 | 40991 | 71.3 | GTGCATCGGTCTGTGCGACC | 33 | 24 | 19 | 33 | 32 | 0 |
| 8350 | 3717 | 3701 | 40992 | 75 | GTGCATCGACCTTGCGCACG | 33 | 24 | 23 | 29 | 30 | 0 |
| 8351 | 3718 | 3702 | 40993 | 66.9 | ATCGATCGTGATAGCCGACC | 24 | 24 | 2 | 36 | 32 | 0 |
| 8352 | 3719 | 3703 | 30837 | 71.7 | GTGCATCGTCCCCTTGTCCC | 33 | 24 | 28 | 11 | 28 | 1 |
| 8353 | 3720 | 3704 | 16431 | 76.8 | GTGCATCGCACGCACGGCTT | 33 | 24 | 30 | 30 | 17 | 0 |
| 8354 | 3721 | 3705 | 11050 | 73.7 | GTGCATCGCAGCCGTTTCGT | 33 | 24 | 31 | 12 | 10 | 0 |
| 8355 | 3722 | 3706 | 11051 | 70.9 | GTGCATCGACGGGCAATGAT | 33 | 24 | 35 | 21 | 2 | 0 |
| 8356 | 3723 | 3707 | 30838 | 69.8 | AGGATCGTTGTCTCCCGCAA | 25 | 10 | 9 | 28 | 21 | 0 |
| 8357 | 3724 | 3708 | 11052 | 69 | AGGACTTGCGAAATCGAGCC | 25 | 11 | 16 | 24 | 36 | 0 |
| 8358 | 3725 | 3709 | 22086 | 67.6 | GTGCAGGAGCTTGCTTCGTT | 33 | 25 | 17 | 17 | 12 | 0 |
| 8359 | 3726 | 3710 | 30839 | 68.2 | AGGAAGGAAATCGACCCGAA | 25 | 25 | 4 | 32 | 16 | 0 |
| 8360 | 3727 | 3712 | 16435 | 70.4 | GTGCAGGACACGTGTCGCAA | 33 | 25 | 30 | 9 | 21 | 0 |
| 8361 | 3728 | 3713 | 11063 | 71.3 | GTGCAGGACAGCCGAACGAA | 33 | 25 | 31 | 16 | 16 | 0 |
| 8362 | 3729 | 3714 | 11064 | 70.6 | AGGAGACCCGAAGACCACGG | 25 | 32 | 16 | 32 | 35 | 0 |
| 8363 | 3730 | 3715 | 11065 | 70.1 | GTGCAGGAGTGCCGTTAGCC | 33 | 25 | 33 | 12 | 36 | 0 |
| 8364 | 3731 | 3716 | 11067 | 70.3 | GTGCAGGAACGGCTGTCGTT | 33 | 25 | 35 | 14 | 12 | 0 |
| 8365 | 3732 | 3717 | 11071 | 67.4 | GTGCCCTAAAAGGACCTCCC | 33 | 26 | 6 | 32 | 28 | 0 |
| 8366 | 3733 | 3718 | 11072 | 68.6 | CCTATGTCCGAAATCGCACG | 26 | 9 | 16 | 24 | 30 | 0 |
| 8367 | 3734 | 3719 | 40995 | 66 | CCTACGTTGGTAGCTTTGCG | 26 | 12 | 18 | 17 | 29 | 0 |
| 8368 | 3735 | 3720 | 40996 | 69.1 | CCTACCATTCTGCACGCGAA | 26 | 15 | 8 | 30 | 16 | 0 |
| 8369 | 3736 | 3721 | 41000 | 68 | GTGCCCTAGACCTGTCGCAA | 33 | 26 | 32 | 9 | 21 | 0 |
| 8370 | 3737 | 3722 | 30840 | 66.4 | GTGCCCTAAGCCTCGTCTGT | 33 | 26 | 36 | 10 | 14 | 0 |
| 8371 | 3738 | 3723 | 11084 | 67.3 | GTGCGATGTGATATCGCAA | 33 | 27 | 2 | 24 | 16 | 0 |
| 8372 | 3739 | 3724 | 11086 | 71.7 | GTGCGATGTCTGTGCGAGCC | 33 | 27 | 8 | 29 | 36 | 0 |
| 8373 | 3740 | 3725 | 16441 | 66.5 | GTGCGATGCTTGGCAATTAG | 33 | 27 | 11 | 21 | 3 | 0 |
| 8374 | 3741 | 3726 | 11092 | 70 | GTGCGATGATCGCTGTGTGC | 33 | 27 | 24 | 14 | 33 | 0 |
| 8375 | 3742 | 3727 | 30841 | 76.5 | GTGCGATGTCCCGGACGCAA | 33 | 27 | 28 | 34 | 21 | 0 |
| 8376 | 3743 | 3728 | 11099 | 70.9 | TCCCTTAGCTTGGTGCTGCG | 28 | 3 | 11 | 33 | 29 | 0 |
| 8377 | 3744 | 3729 | 11104 | 70.2 | TCCCCTTGGAGTTGATTGCG | 28 | 11 | 20 | 2 | 29 | 0 |

FIG. 29AAAA

| SEQ ID NO: | ZIP ID# | 4,633 ID# | HEX ID# | Tm | ZIPCODE (NH2 -> CONH2) | TETRAMER NUMBERS | | | | | *UNALLOWED DIMERS* |
|---|---|---|---|---|---|---|---|---|---|---|---|
| 8378 | 3745 | 3730 | 16449 | 71.1 | TCCCCGTTCTGTCTGTTGCG | 28 | 12 | 14 | 14 | 29 | 0 |
| 8379 | 3746 | 3731 | 11111 | 68.8 | TCCCGAGTTACAGTGCCACG | 28 | 20 | 7 | 33 | 30 | 0 |
| 8380 | 3747 | 3732 | 16451 | 70.2 | TCCCACCTGACCCCTATCCC | 28 | 23 | 32 | 26 | 28 | 0 |
| 8381 | 3748 | 3733 | 22097 | 72.6 | GTGCTCCCATCGATCGCGTT | 33 | 28 | 24 | 24 | 12 | 0 |
| 8382 | 3749 | 3734 | 41006 | 73.6 | TCCCGTGCAGTGTCCCGGTA | 28 | 33 | 22 | 28 | 18 | 1 |
| 8383 | 3750 | 3735 | 11116 | 69.8 | GTGCTCCCGGACTTGAGTGC | 33 | 28 | 34 | 1 | 33 | 0 |
| 8384 | 3751 | 3736 | 11118 | 73.7 | TCCCAGCCGTCTTCTGCACG | 28 | 36 | 19 | 8 | 30 | 0 |
| 8385 | 3752 | 3737 | 41007 | 70.3 | GTGCTGCGTCTGTCTGCACG | 33 | 29 | 8 | 8 | 30 | 0 |
| 8386 | 3753 | 3738 | 11125 | 69.7 | GTGCTGCGCTGTGCAAAATC | 33 | 29 | 14 | 21 | 4 | 0 |
| 8387 | 3754 | 3739 | 41008 | 67.3 | TGCGGAGTAAAGAGCCCCTA | 29 | 20 | 6 | 36 | 26 | 0 |
| 8388 | 3755 | 3740 | 11132 | 70.3 | TGCGTCCCTACACAGCTCCC | 29 | 28 | 7 | 31 | 28 | 0 |
| 8389 | 3756 | 3741 | 11133 | 75.6 | TGCGCACGGCTTGTCTGTGC | 29 | 30 | 17 | 19 | 33 | 0 |
| 8390 | 3757 | 3742 | 11134 | 75.5 | GTGCTGCGCAGCAAAGCACG | 33 | 29 | 31 | 6 | 30 | 0 |
| 8391 | 3758 | 3743 | 11135 | 72.2 | TGCGGACCTCTGAGTGTGCG | 29 | 32 | 8 | 22 | 29 | 0 |
| 8392 | 3759 | 3744 | 16457 | 74.9 | TGCGAGCCGCAAGATGCTTG | 29 | 36 | 21 | 27 | 11 | 0 |
| 8393 | 3760 | 3745 | 16458 | 71.7 | GTGCCACGTTAGGTGCGTGC | 33 | 30 | 3 | 33 | 33 | 0 |
| 8394 | 3761 | 3746 | 11144 | 67.7 | GTGCCACGTCTGAGTGGACC | 33 | 30 | 8 | 22 | 32 | 0 |
| 8395 | 3762 | 3747 | 16460 | 67 | GTGCCACGGGTAACCTAGGA | 33 | 30 | 18 | 23 | 25 | 0 |
| 8396 | 3763 | 3748 | 30842 | 69.2 | GTGCCACGGAGTACGGGAGT | 33 | 30 | 20 | 35 | 28 | 0 |
| 8397 | 3764 | 3749 | 11152 | 67 | GTGCCACGAGTGTGTCATCG | 33 | 30 | 22 | 9 | 24 | 0 |
| 8398 | 3765 | 3750 | 11158 | 71 | GTGCCACGAGCCAATCCTCA | 33 | 30 | 36 | 4 | 13 | 0 |
| 8399 | 3766 | 3751 | 30843 | 65.6 | GTGCCAGCTGATAGCCAAAG | 33 | 31 | 2 | 36 | 6 | 0 |
| 8400 | 3767 | 3752 | 41012 | 65.7 | GTGCCAGCAATCAAAGGGTA | 33 | 31 | 4 | 6 | 18 | 0 |
| 8401 | 3768 | 3753 | 11162 | 69.3 | GTGCCAGCATACCAGCGATG | 33 | 31 | 5 | 31 | 27 | 0 |
| 8402 | 3769 | 3754 | 22115 | 68.4 | GTGCCAGCAAAGGTCTGTGC | 33 | 31 | 6 | 19 | 33 | 0 |
| 8403 | 3770 | 3755 | 30844 | 71.1 | GTGCCAGCCGAATTAGTGCG | 33 | 31 | 16 | 3 | 29 | 0 |
| 8404 | 3771 | 3756 | 11171 | 71.8 | GTGCCAGCGTCTTGTCGTGC | 33 | 31 | 19 | 9 | 33 | 0 |
| 8405 | 3772 | 3757 | 41014 | 68.1 | CAGCGAGTTTAGGTGCAGCC | 31 | 20 | 3 | 33 | 36 | 0 |
| 8406 | 3773 | 3758 | 30845 | 69.1 | GTGCCAGCCCTAAATCGGAC | 33 | 31 | 26 | 4 | 34 | 0 |
| 8407 | 3774 | 3759 | 11176 | 69.8 | GTGCCAGCTCCCCTCACTTG | 33 | 31 | 28 | 13 | 11 | 0 |
| 8408 | 3775 | 3760 | 11178 | 75.5 | GTGCCAGCGTGCAGTGGCAA | 33 | 31 | 33 | 22 | 21 | 0 |
| 8409 | 3776 | 3761 | 11179 | 70.8 | GTGCCAGCACGGAAAGATCG | 33 | 31 | 35 | 6 | 24 | 0 |
| 8410 | 3777 | 3762 | 16466 | 68.2 | GTGCGACCTTAGGTGCGGTA | 33 | 32 | 3 | 33 | 18 | 0 |
| 8411 | 3778 | 3763 | 11183 | 70.5 | GTGCGACCATACAGCCGGAC | 33 | 32 | 5 | 36 | 34 | 0 |
| 8412 | 3779 | 3764 | 11186 | 67.9 | GTGCGACCCTGTTTAGCAGC | 33 | 32 | 14 | 3 | 31 | 0 |
| 8413 | 3780 | 3765 | 16468 | 72.2 | GTGCGACCCGAAAGCCTGTC | 33 | 32 | 16 | 36 | 9 | 0 |
| 8414 | 3781 | 3766 | 41018 | 68 | GTGCGACCGCTTATACCAGC | 33 | 32 | 17 | 5 | 31 | 0 |
| 8415 | 3782 | 3767 | 30847 | 70.2 | GTGCGACCGGTAGGACGGTA | 33 | 32 | 18 | 34 | 18 | 0 |
| 8416 | 3783 | 3768 | 11191 | 72.3 | GTGCGACCAGTGGATGCACG | 33 | 32 | 22 | 27 | 30 | 0 |
| 8417 | 3784 | 3769 | 16469 | 71.7 | GTGCGACCAGGAAGCCACCT | 33 | 32 | 25 | 36 | 23 | 0 |
| 8418 | 3785 | 3770 | 11196 | 72.4 | GTGCGACCCAGCGAGTAGCC | 33 | 32 | 31 | 20 | 36 | 0 |
| 8419 | 3786 | 3771 | 11197 | 73.9 | GTGCGACCACGGCTCAATCG | 33 | 32 | 35 | 13 | 24 | 0 |
| 8420 | 3787 | 3772 | 41020 | 68.4 | GTGCGTGCTTGACGAAGGAC | 33 | 33 | 1 | 16 | 34 | 0 |
| 8421 | 3788 | 3773 | 11198 | 68.5 | GTGCGTGCTGATTCCCAAAG | 33 | 33 | 2 | 28 | 6 | 0 |
| 8422 | 3789 | 3774 | 22127 | 69.9 | GTGCGTGCTACATGCGAGGA | 33 | 33 | 7 | 29 | 25 | 0 |
| 8423 | 3790 | 3775 | 11205 | 68.1 | GTGCGTGCCTGTACCTGACC | 33 | 33 | 14 | 23 | 32 | 0 |
| 8424 | 3791 | 3776 | 11208 | 73 | GTGCGTGCGCTCTCCATGCAA | 33 | 33 | 19 | 15 | 21 | 0 |
| 8425 | 3792 | 3777 | 11209 | 70.1 | GTGCGTGCGAGTCTGTGTGC | 33 | 33 | 20 | 14 | 33 | 0 |

FIG. 29BBBB

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 8426 | 3793 | 3778 | 11210 | 74 | GTGCGTGCATCGCCATAGCC | 33 | 33 | 24 | 15 | 36 | 0 |
| 8427 | 3794 | 3779 | 11212 | 77.2 | GTGCGTGCCACGGCTTCACG | 33 | 33 | 30 | 17 | 30 | 0 |
| 8428 | 3795 | 3780 | 11216 | 70.9 | GTGCGGACATACGCAAAGCC | 33 | 34 | 5 | 21 | 36 | 0 |
| 8429 | 3796 | 3781 | 30848 | 68.7 | GTGCGGACGTCTCGTTGGTA | 33 | 34 | 19 | 12 | 18 | 0 |
| 8430 | 3797 | 3782 | 11226 | 74 | GTGCGGACTCCCCAGCGTCT | 33 | 34 | 28 | 31 | 19 | 0 |
| 8431 | 3798 | 3783 | 11227 | 69.7 | GGACTGCGAGTGTGTCGCAA | 34 | 29 | 22 | 9 | 21 | 0 |
| 8432 | 3799 | 3784 | 11228 | 71.1 | GTGCGGACGACCTCGTTTGA | 33 | 34 | 32 | 10 | 1 | 0 |
| 8433 | 3800 | 3785 | 41026 | 74.2 | GTGCACGGAATCGCTTTGCG | 33 | 35 | 4 | 17 | 29 | 0 |
| 8434 | 3801 | 3786 | 41027 | 73.9 | ACGGTCTGTCCCCACGCCAT | 35 | 8 | 28 | 30 | 15 | 0 |
| 8435 | 3802 | 3787 | 30849 | 69.8 | ACGGCTCAACCTTCTGCAGC | 35 | 13 | 23 | 8 | 31 | 0 |
| 8436 | 3803 | 3788 | 11239 | 70.1 | GTGCACGGCCATCTTGACCT | 33 | 35 | 15 | 11 | 23 | 0 |
| 8437 | 3804 | 3789 | 22145 | 73.9 | GTGCACGGGTCTTGCGATCG | 33 | 35 | 19 | 29 | 24 | 0 |
| 8438 | 3805 | 3790 | 41028 | 70.9 | GTGCACGGGAGTCCATCGAA | 33 | 35 | 20 | 15 | 16 | 0 |
| 8439 | 3806 | 3791 | 41029 | 73.7 | ACGGAGTGGACCAGCCGGAC | 35 | 22 | 32 | 36 | 34 | 0 |
| 8440 | 3807 | 3792 | 41030 | 72.8 | GTGCACGGATCGGATGAGCC | 33 | 35 | 24 | 27 | 36 | 0 |
| 8441 | 3808 | 3793 | 11243 | 69.3 | GTGCACGGAGGATCCCTGTC | 33 | 35 | 25 | 28 | 9 | 0 |
| 8442 | 3809 | 3794 | 11246 | 74.8 | GTGCACGGGTGCAGTGTGC | 33 | 35 | 33 | 20 | 33 | 0 |
| 8443 | 3810 | 3795 | 22147 | 72.6 | GTGCACGGGGACCCATTCTG | 33 | 35 | 34 | 15 | 8 | 0 |
| 8444 | 3811 | 3796 | 11248 | 73.7 | GTGCACGGACGGAGTGGTGC | 33 | 35 | 35 | 22 | 33 | 0 |
| 8445 | 3812 | 3797 | 16475 | 73 | GTGCAGCCAAAGCAGCCGTT | 33 | 36 | 6 | 31 | 12 | 0 |
| 8446 | 3813 | 3798 | 11250 | 68.6 | GTGCAGCCTCGTTACAACGG | 33 | 36 | 10 | 7 | 35 | 0 |
| 8447 | 3814 | 3799 | 16478 | 72.2 | GTGCAGCCATCGAATCGCAA | 33 | 36 | 24 | 4 | 21 | 0 |
| 8448 | 3815 | 3800 | 16479 | 73.8 | GTGCAGCCTCCCGACCACCT | 33 | 36 | 28 | 32 | 23 | 0 |
| 8449 | 3816 | 3801 | 11261 | 74.2 | GTGCAGCCTGCGCCATCTTG | 33 | 36 | 29 | 15 | 11 | 0 |
| 8450 | 3817 | 3802 | 11264 | 75.9 | GTGCAGCCGACCCCATGTGC | 33 | 36 | 32 | 15 | 33 | 0 |
| 8451 | 3818 | 3803 | 11265 | 75.6 | GTGCAGCCGTGCAGTGCGAA | 33 | 36 | 33 | 22 | 16 | 0 |
| 8452 | 3819 | 3804 | 11266 | 73.4 | GTGCAGCCACGGGATGCTGT | 33 | 36 | 35 | 27 | 14 | 0 |
| 8453 | 3820 | 3805 | 41034 | 71.2 | TTGAAGCCAATCCCATTGCG | 1 | 36 | 4 | 15 | 29 | 0 |
| 8454 | 3821 | 3806 | 11275 | 75.7 | TTAGCAGCCACGCACGTGCG | 3 | 31 | 30 | 30 | 29 | 0 |
| 8455 | 3822 | 3807 | 11276 | 69.4 | AATCCTTGACGGCCATCAGC | 4 | 11 | 35 | 15 | 31 | 0 |
| 8456 | 3823 | 3808 | 30850 | 67.1 | AATCTGCGTACAAGCCCGTT | 4 | 29 | 7 | 36 | 12 | 0 |
| 8457 | 3824 | 3809 | 11295 | 72.6 | AAAGGATGACGGGCAATGCG | 6 | 27 | 35 | 21 | 29 | 0 |
| 8458 | 3825 | 3810 | 30851 | 68.2 | GGACAAAGCACGAGCCTTGA | 34 | 6 | 30 | 36 | 1 | 0 |
| 8459 | 3826 | 3811 | 11300 | 69.9 | TCTGCGTTTCGTTCGTGTGC | 8 | 12 | 10 | 10 | 33 | 0 |
| 8460 | 3827 | 3812 | 11303 | 73.1 | TCTGCCTAACGGGCTTTGCG | 8 | 26 | 35 | 17 | 29 | 0 |
| 8461 | 3828 | 3813 | 11305 | 71.1 | TCTGCACGGCAAACCTGCTT | 8 | 30 | 21 | 23 | 17 | 0 |
| 8462 | 3829 | 3814 | 30852 | 69.6 | TCGTCGTTATCGCAGCAGGA | 10 | 12 | 24 | 31 | 25 | 0 |
| 8463 | 3830 | 3815 | 16494 | 71.7 | TCGTCCATGATGGGACTGCG | 10 | 15 | 27 | 34 | 29 | 0 |
| 8464 | 3831 | 3816 | 11321 | 71.6 | TCGTACGGCTTGGTCTTGCG | 10 | 35 | 11 | 19 | 29 | 0 |
| 8465 | 3832 | 3817 | 30853 | 67.7 | CTTGCTTGTGCGTTAGCACG | 11 | 11 | 29 | 3 | 30 | 0 |
| 8466 | 3833 | 3818 | 30854 | 69.8 | GGACCTTGCGTTACGGCCTA | 34 | 11 | 12 | 35 | 26 | 0 |
| 8467 | 3834 | 3819 | 41042 | 68.4 | CTTGCTCAAAAGCAGCAGCC | 11 | 13 | 6 | 31 | 36 | 0 |
| 8468 | 3835 | 3820 | 11328 | 68.7 | GGACCTTGGAGTCACGAGCC | 34 | 11 | 20 | 30 | 36 | 0 |
| 8469 | 3836 | 3821 | 30855 | 72.6 | GGACCTTGGCAAGGACGCAA | 34 | 11 | 21 | 34 | 21 | 0 |
| 8470 | 3837 | 3823 | 11332 | 73.9 | GGACCTTGCAGCGCTTGCAA | 34 | 11 | 31 | 17 | 21 | 0 |
| 8471 | 3838 | 3824 | 16502 | 71.5 | GGACCTTGGTGCCGAATCGT | 34 | 11 | 33 | 16 | 10 | 0 |
| 8472 | 3839 | 3825 | 11335 | 72.5 | GGACCTTGGGACGCAACGAA | 34 | 11 | 34 | 21 | 16 | 0 |
| 8473 | 3840 | 3826 | 30856 | 66.8 | CGTTCGTTATACACGGGCAA | 12 | 12 | 5 | 35 | 21 | 0 |

FIG. 29CCCC

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 8474 | 3841 | 3827 | 16508 | 67.6 | GGACCGTTACCTGAGTTGCG | 34 | 12 | 23 | 20 | 29 | 0 |
| 8475 | 3842 | 3828 | 22167 | 69.9 | GGACCGTTTGCGGAGTATCG | 34 | 12 | 29 | 20 | 24 | 0 |
| 8476 | 3843 | 3829 | 11361 | 66.7 | GGACCTGTTTGATGCGGAGT | 34 | 14 | 1 | 29 | 20 | 0 |
| 8477 | 3844 | 3830 | 11363 | 68.1 | GGACCTGTCCATCCATTCCC | 34 | 14 | 15 | 15 | 28 | 0 |
| 8478 | 3845 | 3831 | 16519 | 69.8 | CCATTGATCAGCGACCCCAT | 15 | 2 | 31 | 32 | 15 | 0 |
| 8479 | 3846 | 3832 | 11374 | 67.8 | CCATAAAGCTGTTCCCGTGC | 15 | 6 | 14 | 28 | 33 | 0 |
| 8480 | 3847 | 3833 | 11378 | 68.6 | GGACCCATCTTGCTTGTCCC | 34 | 15 | 11 | 11 | 28 | 1 |
| 8481 | 3848 | 3834 | 16522 | 72.5 | GGACCCATGGTATGCGGTGC | 34 | 15 | 18 | 29 | 33 | 0 |
| 8482 | 3849 | 3835 | 11385 | 73.4 | GGACCCATCACGCTTGCGAA | 34 | 15 | 30 | 11 | 16 | 0 |
| 8483 | 3850 | 3836 | 22172 | 69.4 | GGACCCATGTGCATACGCAA | 34 | 15 | 33 | 5 | 21 | 0 |
| 8484 | 3851 | 3837 | 30859 | 70.4 | CGAATTGACTTGCACGCACG | 16 | 1 | 11 | 30 | 30 | 0 |
| 8485 | 3852 | 3838 | 11392 | 69.6 | GGACCGAAATACACGGGTGC | 34 | 16 | 5 | 35 | 33 | 0 |
| 8486 | 3853 | 3839 | 41053 | 66.3 | CGAAAAAGTCTGCTTGGCAA | 16 | 6 | 8 | 11 | 21 | 0 |
| 8487 | 3854 | 3840 | 30860 | 70.9 | GGACCGAACTTGACGGTCCC | 34 | 16 | 11 | 35 | 28 | 1 |
| 8488 | 3855 | 3841 | 11397 | 66.7 | GGACCGAAGCTTTCGTAGGA | 34 | 16 | 17 | 10 | 25 | 0 |
| 8489 | 3856 | 3842 | 41055 | 68.9 | GGACCGAAACCTGCTTGCTT | 34 | 16 | 23 | 17 | 17 | 0 |
| 8490 | 3857 | 3843 | 41056 | 67.8 | CGAAAGGAATACCAGCCACG | 16 | 25 | 5 | 31 | 30 | 0 |
| 8491 | 3858 | 3844 | 11402 | 74.9 | GGACCGAAGACCCAGCGCAA | 34 | 16 | 32 | 31 | 21 | 0 |
| 8492 | 3859 | 3845 | 16533 | 68.9 | GGACGCTTTTAGGGACCGAA | 34 | 17 | 3 | 34 | 16 | 0 |
| 8493 | 3860 | 3846 | 16534 | 70.3 | GGACGCTTAAAGGTGCGTGC | 34 | 17 | 6 | 33 | 33 | 0 |
| 8494 | 3861 | 3847 | 41058 | 70.1 | GCTTTGTCACCTTCCCTGCG | 17 | 9 | 23 | 28 | 29 | 1 |
| 8495 | 3862 | 3848 | 41059 | 66.9 | GGACGCTTGGTAAATCGCTT | 34 | 17 | 18 | 4 | 17 | 0 |
| 8496 | 3863 | 3849 | 11413 | 68.4 | GGACGCTTACCTGCAACGAA | 34 | 17 | 23 | 21 | 16 | 0 |
| 8497 | 3864 | 3850 | 30862 | 65.7 | GCTTCCTATGTCATCGGCAA | 17 | 26 | 9 | 24 | 21 | 0 |
| 8498 | 3865 | 3851 | 30863 | 71.1 | GGACGCTTTGCGTTGAATCG | 34 | 17 | 29 | 1 | 24 | 0 |
| 8499 | 3866 | 3852 | 41061 | 70.9 | GGACGGTACGTTTCGTTGCG | 34 | 18 | 12 | 10 | 29 | 0 |
| 8500 | 3867 | 3853 | 16537 | 68.6 | GGACGGTACCATTGTCGCAA | 34 | 18 | 15 | 9 | 21 | 0 |
| 8501 | 3868 | 3854 | 16539 | 68.4 | GGACGGTAGTGCAGTGCAGC | 34 | 18 | 33 | 22 | 31 | 0 |
| 8502 | 3869 | 3855 | 11431 | 71 | GGACGGTAGGACGCAATCCC | 34 | 18 | 34 | 21 | 28 | 0 |
| 8503 | 3870 | 3856 | 16540 | 71.7 | GGACGGTAAGCCGTGCACCT | 34 | 18 | 36 | 33 | 23 | 0 |
| 8504 | 3871 | 3857 | 11433 | 70.2 | GTCTTTGATCCCCACGCGAA | 19 | 1 | 28 | 30 | 16 | 0 |
| 8505 | 3872 | 3858 | 11434 | 69 | GGACGTCTTCGTGCAAGCAA | 34 | 19 | 10 | 21 | 21 | 0 |
| 8506 | 3873 | 3859 | 16541 | 69.3 | GGACGTCTCCATGGACCAGC | 34 | 19 | 15 | 34 | 31 | 0 |
| 8507 | 3874 | 3860 | 11437 | 55.9 | GTCTGCAAGACCTCTGTGCG | 19 | 21 | 32 | 8 | 29 | 0 |
| 8508 | 3875 | 3861 | 16543 | 68.8 | GTCTCACGCACGAAAGCAGC | 19 | 30 | 30 | 6 | 31 | 0 |
| 8509 | 3876 | 3862 | 11449 | 66.7 | GAGTATCGGGACCCTATGCG | 20 | 24 | 34 | 26 | 29 | 0 |
| 8510 | 3877 | 3863 | 11452 | 74.2 | GGACGAGTCAGCGTGCGTGC | 34 | 20 | 31 | 33 | 33 | 0 |
| 8511 | 3878 | 3864 | 11455 | 65 | GGACGAGTACGGTTGAATCG | 34 | 20 | 35 | 1 | 24 | 1 |
| 8512 | 3879 | 3865 | 30864 | 68.6 | GCAATTGAACGGAGTGCAGC | 21 | 1 | 35 | 22 | 31 | 0 |
| 8513 | 3880 | 3866 | 11458 | 70.2 | GGACGCAAATACGTGCCCAT | 34 | 21 | 5 | 33 | 15 | 0 |
| 8514 | 3881 | 3867 | 22187 | 68.3 | GGACGCAATGTCCCATGGTA | 34 | 21 | 9 | 15 | 18 | 0 |
| 8515 | 3882 | 3868 | 11460 | 70.7 | GGACGCAATCGTTCTGGTGC | 34 | 21 | 10 | 8 | 33 | 0 |
| 8516 | 3883 | 3869 | 30865 | 66.7 | GCAACCTAATACTGCGTGCG | 21 | 26 | 5 | 29 | 29 | 0 |
| 8517 | 3884 | 3870 | 11468 | 71.3 | GGACGCAATGCGTTGAAGGA | 34 | 21 | 29 | 1 | 25 | 0 |
| 8518 | 3885 | 3871 | 11469 | 67.8 | GGACGCAAGTGCAGTGGTCT | 34 | 21 | 33 | 22 | 19 | 0 |
| 8519 | 3886 | 3872 | 30866 | 71.6 | GGACGCAAGGACTCCCGGTA | 34 | 21 | 34 | 28 | 18 | 0 |
| 8520 | 3887 | 3873 | 22189 | 70.7 | GGACGCAAACGGTGATCAGC | 34 | 21 | 35 | 2 | 31 | 0 |
| 8521 | 3888 | 3874 | 16552 | 71 | AGTGTGCGACGGACCTGTGC | 22 | 29 | 35 | 23 | 33 | 0 |

FIG. 29DDDD

| SEQ ID NO: | ZIP ID# | 4,633 BEX ID# | Tm | ZIPCODE (NH2 -> CONH2) | TETRAMER NUMBERS | | | | | 'UNALLOWED DIMERS' |
|---|---|---|---|---|---|---|---|---|---|---|
| 8522 | 3889 | 3875 | 16556 | 70.1 | ACCTCACGGGACTGATTGCG | 23 | 30 | 34 | 2 | 29 | 0 |
| 8523 | 3890 | 3876 | 16557 | 73.5 | GGACACCTGACCGTGCACGG | 34 | 23 | 32 | 33 | 35 | 0 |
| 8524 | 3891 | 3877 | 30867 | 67.4 | ACCTAGCCTTAGCGTTTGCG | 23 | 36 | 3 | 12 | 29 | 0 |
| 8525 | 3892 | 3878 | 11490 | 72.5 | ATCGAAAGACGGGTGCCACG | 24 | 6 | 35 | 33 | 30 | 0 |
| 8526 | 3893 | 3879 | 41069 | 69.8 | ATCGGCTTCTTGCTTGACGG | 24 | 17 | 11 | 11 | 35 | 0 |
| 8527 | 3894 | 3880 | 11496 | 70.5 | ATCGCACGGTCTAGCCATCG | 24 | 30 | 19 | 36 | 24 | 0 |
| 8528 | 3895 | 3881 | 11499 | 71.1 | GGACATCGACGGGGACCTGT | 34 | 24 | 35 | 34 | 14 | 0 |
| 8529 | 3896 | 3882 | 22199 | 70.6 | AGGACGAAATCGTCCCGGAC | 25 | 16 | 24 | 28 | 34 | 0 |
| 8530 | 3897 | 3883 | 16564 | 69.4 | GGACAGGAATCGACGGCCTA | 34 | 25 | 24 | 35 | 26 | 0 |
| 8531 | 3898 | 3884 | 11505 | 66.1 | AGGAAGGATTGAGGACGTGC | 25 | 25 | 1 | 34 | 33 | 0 |
| 8532 | 3899 | 3885 | 41072 | 68 | CCTACGAAAGGATCGTTGCG | 26 | 16 | 25 | 10 | 29 | 0 |
| 8533 | 3900 | 3886 | 11511 | 67 | GGACCCTAGCTTGCAAGTGC | 34 | 26 | 17 | 21 | 33 | 0 |
| 8534 | 3901 | 3887 | 30869 | 69.5 | CCTAGCAACAGCGATGCGAA | 26 | 21 | 31 | 27 | 16 | 0 |
| 8535 | 3902 | 3888 | 11516 | 66.8 | CCTACCTAGACCAGCCACGG | 26 | 26 | 32 | 36 | 35 | 0 |
| 8536 | 3903 | 3889 | 41076 | 69.2 | GGACGATGCTCACTGTTGCG | 34 | 27 | 13 | 14 | 29 | 0 |
| 8537 | 3904 | 3890 | 30870 | 69.1 | GGACGATGGGTAACGGGGTA | 34 | 27 | 18 | 35 | 18 | 0 |
| 8538 | 3905 | 3891 | 11527 | 69.4 | GGACGATGGTCTAGCCCGAA | 34 | 27 | 19 | 36 | 16 | 0 |
| 8539 | 3906 | 3892 | 41077 | 72.2 | GGACGATGATCGCGAAAGCC | 34 | 27 | 24 | 16 | 36 | 0 |
| 8540 | 3907 | 3893 | 11535 | 71.7 | TCCCTGTCCGTTGCTTGCAA | 28 | 9 | 12 | 17 | 21 | 0 |
| 8541 | 3908 | 3894 | 11537 | 67.9 | TCCCTGTTACAGACCTGCG | 28 | 14 | 7 | 32 | 29 | 0 |
| 8542 | 3909 | 3895 | 16576 | 70.1 | TCCCCATTTAGCACGGATG | 28 | 15 | 3 | 30 | 27 | 0 |
| 8543 | 3910 | 3896 | 30872 | 70.4 | GGACTCCCACCTAGCCCAGC | 34 | 28 | 23 | 36 | 31 | 0 |
| 8544 | 3911 | 3897 | 16578 | 71.7 | GGACTCCCATCGCGAAAGGA | 34 | 28 | 24 | 16 | 25 | 0 |
| 8545 | 3912 | 3898 | 41080 | 74 | GGACTCCCCACGCTTGCGTT | 34 | 28 | 30 | 11 | 12 | 0 |
| 8546 | 3913 | 3899 | 11548 | 74.4 | GGACTCCCGACGCTTCACG | 34 | 28 | 34 | 17 | 30 | 0 |
| 8547 | 3914 | 3900 | 11551 | 72.2 | TGCGTTAGCCATCACGACGG | 29 | 3 | 15 | 30 | 35 | 0 |
| 8548 | 3915 | 3901 | 11555 | 70.8 | GGACTGCGTCGTCGTTCAGC | 34 | 29 | 10 | 12 | 31 | 0 |
| 8549 | 3916 | 3902 | 16583 | 70.9 | GGACTGCGCTTGACCTCACG | 34 | 29 | 11 | 23 | 30 | 0 |
| 8550 | 3917 | 3903 | 11557 | 70.5 | TGCGCTCATCGTCGTTTTGA | 29 | 13 | 10 | 12 | 1 | 1 |
| 8551 | 3918 | 3904 | 30874 | 71 | TGCGGCTTAGGAGCTTCACG | 29 | 17 | 25 | 17 | 30 | 0 |
| 8552 | 3919 | 3905 | 16587 | 69.7 | TGCGACCTTTGAGCAACGAA | 29 | 23 | 1 | 21 | 16 | 1 |
| 8553 | 3920 | 3906 | 11563 | 70.8 | TGCGATCGACCTCCATGGAC | 29 | 24 | 23 | 15 | 34 | 0 |
| 8554 | 3921 | 3907 | 11565 | 70.6 | TGCGGATGGAGTATCGCCAT | 29 | 27 | 20 | 24 | 15 | 0 |
| 8555 | 3922 | 3908 | 11567 | 72.7 | TGCGCACGATACCAGCAGGA | 29 | 30 | 5 | 31 | 25 | 0 |
| 8556 | 3923 | 3909 | 11568 | 73.4 | GGACTGCGGGACCCATCCAT | 34 | 29 | 34 | 15 | 15 | 0 |
| 8557 | 3924 | 3910 | 16588 | 70.7 | CACGTGATGACCTCCCCGAA | 30 | 2 | 32 | 28 | 16 | 0 |
| 8558 | 3925 | 3911 | 30875 | 69.3 | GGACCACGCTCATTGATCCC | 34 | 30 | 13 | 1 | 28 | 0 |
| 8559 | 3926 | 3912 | 11578 | 73.1 | GGACCACGGCTTTCTGCACG | 34 | 30 | 17 | 8 | 30 | 0 |
| 8560 | 3927 | 3913 | 41086 | 67.7 | GGACCACGGAGTATCGCTCA | 34 | 30 | 20 | 24 | 13 | 0 |
| 8561 | 3928 | 3914 | 11584 | 74 | GGACCACGCACGCTCAGTGC | 34 | 30 | 30 | 13 | 33 | 0 |
| 8562 | 3929 | 3915 | 11589 | 73.7 | GGACCACGACGGTCTGTGCG | 34 | 30 | 35 | 8 | 29 | 0 |
| 8563 | 3930 | 3916 | 16594 | 73.8 | GGACCACGAGCCCGAACGTT | 34 | 30 | 36 | 16 | 12 | 0 |
| 8564 | 3931 | 3917 | 41088 | 68.7 | CAGCTTGATCGTCGAAAACGG | 31 | 1 | 10 | 16 | 35 | 0 |
| 8565 | 3932 | 3918 | 11595 | 70.1 | GGACCAGCTGTCCAGCAGGA | 34 | 31 | 9 | 31 | 25 | 0 |
| 8566 | 3933 | 3919 | 30876 | 75.2 | GGACCAGCCTTGTCGACGG | 34 | 31 | 11 | 29 | 35 | 0 |
| 8567 | 3934 | 3921 | 11599 | 68.9 | CAGCCTGTGGACTGTCCACG | 31 | 14 | 34 | 9 | 30 | 0 |
| 8568 | 3935 | 3922 | 30877 | 68.2 | CAGCGGTATGATGACCAGCC | 31 | 18 | 2 | 32 | 36 | 0 |
| 8569 | 3936 | 3923 | 41094 | 69.1 | CAGCAGTGACCTGTGCGCTT | 31 | 22 | 23 | 33 | 17 | 0 |

FIG. 29EEEE

| SEQ ID NO: | ZIP ID# | 4,633 ID# | HEX Tm | ZIPCODE (NH2 -> CONH2) | TETRAMER NUMBERS | | | | | "UNALLOWED DIMERS" |
|---|---|---|---|---|---|---|---|---|---|---|
| 8570 | 3937 | 3924 | 11607 74.8 | GGACCAGCTGCGGACCCTCA | 34 | 31 | 29 | 32 | 13 | 0 |
| 8571 | 3938 | 3925 | 30879 71.3 | GGACGACCTTGAGTGCGCAA | 34 | 32 | 1 | 33 | 21 | 0 |
| 8572 | 3939 | 3926 | 30880 66.9 | GGACGACCCTGTAGTGCGTT | 34 | 32 | 14 | 22 | 12 | 0 |
| 8573 | 3940 | 3927 | 22225 72.1 | GGACGACCGGTAGTGCAGCC | 34 | 32 | 18 | 33 | 36 | 0 |
| 8574 | 3941 | 3928 | 22226 69.9 | GGACGACCGTCTGTGCACCT | 34 | 32 | 19 | 33 | 23 | 0 |
| 8575 | 3942 | 3929 | 11615 68.5 | GGACGACCGAGTCTTGGGAC | 34 | 32 | 20 | 11 | 34 | 0 |
| 8576 | 3943 | 3930 | 41097 67.3 | GACCAGTGAAAGGTGCAGCC | 32 | 22 | 6 | 33 | 36 | 0 |
| 8577 | 3944 | 3931 | 16601 72 | GGACGACCGACCCCATCTCA | 34 | 32 | 32 | 15 | 13 | 0 |
| 8578 | 3945 | 3932 | 11626 67.1 | GGACGTGCTGATTGATTCCC | 34 | 33 | 2 | 2 | 28 | 0 |
| 8579 | 3946 | 3933 | 16603 72.3 | GGACGTGCAATCGGACCGTT | 34 | 33 | 4 | 34 | 12 | 0 |
| 8580 | 3947 | 3934 | 11629 67.5 | GGACGTGCTCTGTCGTCCAT | 34 | 33 | 8 | 10 | 15 | 0 |
| 8581 | 3948 | 3935 | 11630 73.9 | GGACGTGCTGTCCAGCACGG | 34 | 33 | 9 | 31 | 35 | 0 |
| 8582 | 3949 | 3936 | 30881 71.4 | GGACGTGCTCGTCGAAGCAA | 34 | 33 | 10 | 16 | 21 | 0 |
| 8583 | 3950 | 3937 | 11632 73.6 | GGACGTGCCGTTGCTTCGAA | 34 | 33 | 12 | 17 | 16 | 0 |
| 8584 | 3951 | 3938 | 30882 69.9 | GTGCCGAAATACTCCCGTGC | 33 | 16 | 5 | 28 | 33 | 0 |
| 8585 | 3952 | 3939 | 30883 70.4 | GGACGTGCGGTATGTCGGAC | 34 | 33 | 18 | 9 | 34 | 0 |
| 8586 | 3953 | 3940 | 16606 74.9 | GGACGTGCAGTGGTGCTGCG | 34 | 33 | 22 | 33 | 29 | 0 |
| 8587 | 3954 | 3941 | 30884 66.2 | GGACGTGCCCTACCTATCGT | 34 | 33 | 26 | 26 | 10 | 0 |
| 8588 | 3955 | 3942 | 16609 71.6 | GGACGTGCTGCGTGTCCTTG | 34 | 33 | 29 | 9 | 11 | 0 |
| 8589 | 3956 | 3943 | 11644 73.5 | GGACGTGCCACGGGACAGTG | 34 | 33 | 30 | 34 | 22 | 0 |
| 8590 | 3957 | 3944 | 11646 68.6 | GGACGTGCACGGTGATTGTC | 34 | 33 | 35 | 2 | 9 | 0 |
| 8591 | 3958 | 3945 | 16610 67.9 | GGACGGACTCGTCTGTCACG | 34 | 34 | 10 | 14 | 30 | 0 |
| 8592 | 3959 | 3946 | 30885 68 | GGACGGACCGTTTTAGGACC | 34 | 34 | 12 | 3 | 32 | 0 |
| 8593 | 3960 | 3947 | 16612 66.9 | GGACCTGTTACATCCCCACG | 34 | 14 | 7 | 28 | 30 | 0 |
| 8594 | 3961 | 3948 | 30886 72.1 | GGACGGACCGAAGATGCAGC | 34 | 34 | 16 | 27 | 31 | 0 |
| 8595 | 3962 | 3949 | 41101 68.3 | GGACGGACGAGTTACATGCG | 34 | 34 | 20 | 7 | 29 | 0 |
| 8596 | 3963 | 3950 | 30887 68.7 | GGACACCTGCAACTTGGCAA | 34 | 23 | 21 | 11 | 21 | 0 |
| 8597 | 3964 | 3951 | 41103 67.3 | GGACGGACGATGTTAGACGG | 34 | 34 | 27 | 3 | 35 | 0 |
| 8598 | 3965 | 3952 | 11662 71.7 | GGACGGACTCCCAGTGACGG | 34 | 34 | 28 | 22 | 35 | 0 |
| 8599 | 3966 | 3953 | 22239 69.7 | GGACGGACTGCGAGGATCTG | 34 | 34 | 29 | 25 | 8 | 0 |
| 8600 | 3967 | 3954 | 11664 73.7 | GGACGGACCAGCCCATGCTT | 34 | 34 | 31 | 15 | 17 | 0 |
| 8601 | 3968 | 3955 | 11667 71 | ACGGTTAGGACCTGCGAGCC | 35 | 3 | 32 | 29 | 36 | 0 |
| 8602 | 3969 | 3956 | 16616 70.2 | ACGGTCTGAGCCTCGTGTGC | 35 | 8 | 36 | 10 | 33 | 0 |
| 8603 | 3970 | 3957 | 11670 71 | GGACACGGCGTTAATCTGCG | 34 | 35 | 12 | 4 | 29 | 0 |
| 8604 | 3971 | 3958 | 11672 66.6 | ACGGCTGTTACAGCTTTCCC | 35 | 14 | 7 | 17 | 28 | 0 |
| 8605 | 3972 | 3959 | 22240 69.2 | ACGGGAGTCGAAGGACATCG | 35 | 20 | 16 | 34 | 24 | 0 |
| 8606 | 3973 | 3960 | 11674 68.9 | ACGGAGTGCGTTCCTAAGCC | 35 | 22 | 12 | 26 | 36 | 0 |
| 8607 | 3974 | 3961 | 11681 68.8 | AGCCGTTCTTGAATCCAGC | 36 | 12 | 11 | 4 | 31 | 0 |
| 8608 | 3975 | 3962 | 30889 68.1 | AGCCCTGTAAAGAGCCGACC | 36 | 14 | 6 | 36 | 32 | 0 |
| 8609 | 3976 | 3963 | 11688 73.7 | GGACAGCCTGCGGCAACTCA | 34 | 36 | 29 | 21 | 13 | 0 |
| 8610 | 3977 | 3964 | 16618 74.8 | AGCCCACGCACGTGATGCAA | 36 | 30 | 30 | 2 | 21 | 0 |
| 8611 | 3978 | 3965 | 11690 72.6 | AGCCGACCCGTTCTGTCACG | 36 | 32 | 12 | 14 | 30 | 0 |
| 8612 | 3979 | 3966 | 11692 70.9 | AGCCGGACCCTACTCAACGG | 36 | 34 | 26 | 13 | 35 | 0 |
| 8613 | 3980 | 3968 | 30890 68.6 | ACGGTTGACCATTGATTGCG | 35 | 1 | 15 | 2 | 29 | 1 |
| 8614 | 3981 | 3969 | 11704 71 | ACGGTTGACAGCCACGATCG | 35 | 1 | 31 | 30 | 24 | 1 |
| 8615 | 3982 | 3970 | 11705 70.9 | TTGAGACCGGACGATGACGG | 1 | 32 | 34 | 27 | 35 | 0 |
| 8616 | 3983 | 3971 | 41106 69.3 | ACGGTTGAGTGCTGCGTTGA | 35 | 1 | 33 | 29 | 1 | 1 |
| 8617 | 3984 | 3972 | 41107 69.3 | TGATCGAAGCAAATCGCAGC | 2 | 16 | 21 | 24 | 31 | 0 |

FIG. 29FFFF

| SEQ ID NO: | ZIP ID# | 4,633 ID# | HEX ID# | Tm | ZIPCODE (NH2 -> CONH2) | TETRAMER NUMBERS | | | | "UNALLOWED DIMERS" |
|---|---|---|---|---|---|---|---|---|---|---|
| 8618 | 3985 | 3973 | 16624 | 69.1 | ACGGTGATGCAAACCTTCCC | 35 | 2 | 21 | 23 28 | 1 |
| 8619 | 3986 | 3974 | 16625 | 72.3 | ACGGTGATGGACTCCCTGCG | 35 | 2 | 34 | 28 29 | 0 |
| 8620 | 3987 | 3975 | 30891 | 67.9 | ACGGTTAGGCAACACGGATG | 35 | 3 | 21 | 30 27 | 0 |
| 8621 | 3988 | 3976 | 11723 | 65.3 | ACGGTTAGTCCCAAAGGGAC | 35 | 3 | 28 | 6 34 | 0 |
| 8622 | 3989 | 3977 | 41110 | 69 | ACGGTTAGCACGCAGCTTGA | 35 | 3 | 30 | 31 1 | 0 |
| 8623 | 3990 | 3978 | 22253 | 68.5 | ACGGAATCCCATTCGTAGCC | 35 | 4 | 15 | 10 36 | 0 |
| 8624 | 3991 | 3979 | 16633 | 68.3 | ACGGAATCCGAAACCTGGAC | 35 | 4 | 16 | 23 34 | 0 |
| 8625 | 3992 | 3980 | 30892 | 71.7 | ACGGAATCATCGAGCCCAGC | 35 | 4 | 24 | 36 31 | 0 |
| 8626 | 3993 | 3981 | 41116 | 69.4 | AATCCCTACACGAGCCACGG | 4 | 26 | 30 | 36 35 | 0 |
| 8627 | 3994 | 3982 | 11742 | 66.4 | ACGGAATCGATGTCTGGACC | 35 | 4 | 27 | 8 32 | 0 |
| 8628 | 3995 | 3983 | 11743 | 69.1 | ACGGAATCTCCCGGTAGCAA | 35 | 4 | 28 | 18 21 | 0 |
| 8629 | 3996 | 3984 | 41117 | 66.9 | ACGGAATCGGACTGATACGG | 35 | 4 | 34 | 2 35 | 0 |
| 8630 | 3997 | 3985 | 30893 | 67.6 | ACGGATACCGAACGTTCGAA | 35 | 5 | 16 | 12 16 | 0 |
| 8631 | 3998 | 3986 | 41119 | 69.1 | ACGGATACGCTTGACCCGTT | 35 | 5 | 17 | 32 12 | 0 |
| 8632 | 3999 | 3987 | 16644 | 66.1 | ATACGGACTTGACACGCGAA | 5 | 34 | 1 | 30 16 | 0 |
| 8633 | 4000 | 3988 | 41122 | 67.6 | ACGGAAAGCTCAGCAACAGC | 35 | 6 | 13 | 21 31 | 0 |
| 8634 | 4001 | 3989 | 16647 | 65.4 | ACGGAAAGCTGTATCGCTTG | 35 | 6 | 14 | 24 11 | 0 |
| 8635 | 4002 | 3990 | 30894 | 66.9 | ACGGAAAGCGAATTAGACGG | 35 | 6 | 16 | 3 35 | 0 |
| 8636 | 4003 | 3991 | 16650 | 65.3 | ACGGAAAGGAGTATCGTCCC | 35 | 6 | 20 | 24 28 | 0 |
| 8637 | 4004 | 3992 | 30895 | 68.4 | AAAGAGGACACGTCCCAGC | 6 | 25 | 30 | 28 31 | 0 |
| 8638 | 4005 | 3993 | 11771 | 70.7 | ACGGAAAGCAGCTCGTGTGC | 35 | 6 | 31 | 10 33 | 0 |
| 8639 | 4006 | 3994 | 16653 | 73.2 | ACGGAAAGGTGCGACCCCAT | 35 | 6 | 33 | 32 15 | 0 |
| 8640 | 4007 | 3995 | 41125 | 69.5 | ACGGAAAGAGCCGGTAGCAA | 35 | 6 | 36 | 18 21 | 0 |
| 8641 | 4008 | 3996 | 11777 | 67.1 | TACAGCTTGATGGCTTTGCG | 7 | 17 | 27 | 17 29 | 0 |
| 8642 | 4009 | 3997 | 30896 | 67.1 | ACGGTACATGCGTCCCTGAT | 35 | 7 | 29 | 28 2 | 0 |
| 8643 | 4010 | 3998 | 11786 | 73.1 | TCTGAAAGCACGCACGCGAA | 8 | 6 | 30 | 30 16 | 0 |
| 8644 | 4011 | 3999 | 16655 | 68.5 | ACGGTCTGCGTTGACCAGTG | 35 | 8 | 12 | 32 22 | 0 |
| 8645 | 4012 | 4000 | 11789 | 67.9 | ACGGTCTGCTCACGTTCAGC | 35 | 8 | 13 | 12 31 | 0 |
| 8646 | 4013 | 4001 | 11790 | 68 | ACGGTCTGCTGTCGAAATCG | 35 | 8 | 14 | 16 24 | 0 |
| 8647 | 4014 | 4002 | 16656 | 74.1 | ACGGTCTGCCATGTGCCACG | 35 | 8 | 15 | 33 30 | 0 |
| 8648 | 4015 | 4003 | 41126 | 66.4 | TCTGGGTATTGAATCGTGCG | 8 | 18 | 1 | 24 29 | 0 |
| 8649 | 4016 | 4004 | 16657 | 68 | TCTGAGGAACCTAGCCGCAA | 8 | 25 | 23 | 36 21 | 0 |
| 8650 | 4017 | 4005 | 11800 | 71.2 | ACGGTCTGGGACCCATACGG | 35 | 8 | 34 | 15 35 | 0 |
| 8651 | 4018 | 4006 | 30897 | 69.9 | ACGGTGTCCTCAGGACGTGC | 35 | 9 | 13 | 34 33 | 0 |
| 8652 | 4019 | 4007 | 30898 | 65.2 | TGTCCCATATCGAATCGCTT | 9 | 15 | 24 | 4 17 | 0 |
| 8653 | 4020 | 4008 | 11803 | 66.5 | TGTCGGTAAGTGGTCTTGCG | 9 | 18 | 22 | 19 29 | 0 |
| 8654 | 4021 | 4009 | 16662 | 69.5 | ACGGTGTCCACGACCTGACC | 35 | 9 | 30 | 23 32 | 0 |
| 8655 | 4022 | 4010 | 30899 | 69.8 | TCGTTGATTTGAACGGCACG | 10 | 2 | 1 | 35 30 | 0 |
| 8656 | 4023 | 4011 | 30900 | 68.5 | TCGTCGTTTTAGACGGCAGC | 10 | 12 | 3 | 35 31 | 0 |
| 8657 | 4024 | 4012 | 41130 | 67.1 | TCGTCTCATTAGCAGCTGCG | 10 | 13 | 3 | 31 29 | 0 |
| 8658 | 4025 | 4013 | 30901 | 66.9 | ACGGTCGTGCTTAGGACGTT | 35 | 10 | 17 | 25 12 | 0 |
| 8659 | 4026 | 4014 | 16667 | 70.5 | ACGGTCGTACCTTCGTTGCG | 35 | 10 | 23 | 10 29 | 0 |
| 8660 | 4027 | 4015 | 30902 | 68.8 | TCGTGATGAAAGGGACTGCG | 10 | 27 | 6 | 34 29 | 0 |
| 8661 | 4028 | 4016 | 11823 | 73.2 | ACGGTCGTTGCGCTTGTCGT | 35 | 10 | 29 | 11 10 | 0 |
| 8662 | 4029 | 4017 | 11824 | 71.5 | ACGGTCGTGTGCCCATGATG | 35 | 10 | 33 | 15 27 | 0 |
| 8663 | 4030 | 4018 | 41133 | 68.1 | ACGGTCGTACGGATACTGCG | 35 | 10 | 35 | 5 29 | 0 |
| 8664 | 4031 | 4019 | 16668 | 67 | ACGGTTGTCTGAGGAGTGC | 35 | 11 | 8 | 25 33 | 0 |
| 8665 | 4032 | 4020 | 16669 | 65.2 | ACGGCTTGTCGTGCTTAATC | 35 | 11 | 10 | 17 4 | 0 |

FIG. 29GGGG

| SEQ ID NO: | ZIP ID# | 4,633 ID# | HEX ID# | Tm | ZIPCODE (NH2 -> COEH2) | TETRAMER NUMBERS | | | | "UNALLOWED DIMERS" |
|---|---|---|---|---|---|---|---|---|---|---|
| 8666 | 4033 | 4021 | 30903 | 67.8 | ACGGCTTGGGTACTCACACG | 35 | 11 | 18 | 13 | 30 | 0 |
| 8667 | 4034 | 4022 | 30904 | 69.6 | ACGGCTTGGAGTCGTTCAGC | 35 | 11 | 20 | 12 | 31 | 0 |
| 8668 | 4035 | 4023 | 30905 | 66.9 | ACGGCTTGAGTGTCCCTCTG | 35 | 11 | 22 | 28 | 8 | 1 |
| 8669 | 4036 | 4024 | 41138 | 70.9 | ACGGCTTGACCTGACCCCAT | 35 | 11 | 23 | 32 | 15 | 0 |
| 8670 | 4037 | 4025 | 30906 | 69.9 | ACGGCTTGAGGAGGACTCCC | 35 | 11 | 25 | 34 | 28 | 0 |
| 8671 | 4038 | 4026 | 11842 | 72.6 | ACGGCTTGCAGCCAGCTGAT | 35 | 11 | 31 | 31 | 2 | 0 |
| 8672 | 4039 | 4027 | 11844 | 71.9 | ACGGCTTGGTGCCCATTGAT | 35 | 11 | 33 | 15 | 2 | 0 |
| 8673 | 4040 | 4028 | 11845 | 73.3 | ACGGCTTGGGACCACGACCT | 35 | 11 | 34 | 30 | 23 | 0 |
| 8674 | 4041 | 4029 | 16671 | 69.1 | ACGGCTTGACGGATACCGTT | 35 | 11 | 35 | 5 | 12 | 0 |
| 8675 | 4042 | 4030 | 11847 | 68.6 | ACGGCGTTTGATGATGATCG | 35 | 12 | 2 | 27 | 24 | 0 |
| 8676 | 4043 | 4031 | 11849 | 66.7 | ACGGCGTTTACAGACCCTGT | 35 | 12 | 7 | 32 | 14 | 0 |
| 8677 | 4044 | 4032 | 11850 | 69.6 | ACGGCGTTTCTGGTCTCAGC | 35 | 12 | 8 | 19 | 31 | 0 |
| 8678 | 4045 | 4033 | 11851 | 67.7 | ACGGCGTTTGTCTTGAAGGA | 35 | 12 | 9 | 1 | 25 | 0 |
| 8679 | 4046 | 4034 | 41141 | 65.1 | ACGGCGTTCTCATTGAAAAG | 35 | 12 | 13 | 1 | 6 | 0 |
| 8680 | 4047 | 4035 | 41142 | 64.9 | ACGGCGTTCTGTACCTCTTG | 35 | 12 | 14 | 23 | 11 | 0 |
| 8681 | 4048 | 4036 | 11856 | 70.5 | ACGGCGTTGCTTGCTTAGGA | 35 | 12 | 17 | 17 | 25 | 0 |
| 8682 | 4049 | 4037 | 11857 | 67.7 | ACGGCGTTGGTATCGTAGGA | 35 | 12 | 18 | 10 | 25 | 0 |
| 8683 | 4050 | 4038 | 41143 | 67.4 | ACGGCGTTACCTAGTGACGG | 35 | 12 | 23 | 22 | 35 | 0 |
| 8684 | 4051 | 4039 | 30907 | 68.4 | ACGGCGTTAGGAATCGGTCT | 35 | 12 | 25 | 24 | 19 | 0 |
| 8685 | 4052 | 4040 | 11861 | 69.8 | ACGGCGTTCCTAAATCGTGC | 35 | 12 | 26 | 4 | 33 | 0 |
| 8686 | 4053 | 4041 | 11862 | 71.4 | ACGGCGTTTGCGTTGAGATG | 35 | 12 | 29 | 1 | 27 | 0 |
| 8687 | 4054 | 4042 | 11863 | 72.2 | ACGGCGTTCACGGTCTTCGT | 35 | 12 | 30 | 19 | 10 | 0 |
| 8688 | 4055 | 4043 | 11864 | 73.3 | ACGGCGTTCAGCTGCGTGAT | 35 | 12 | 31 | 29 | 2 | 0 |
| 8689 | 4056 | 4044 | 11865 | 72.2 | ACGGCGTTGGACACCTGCTT | 35 | 12 | 34 | 23 | 17 | 0 |
| 8690 | 4057 | 4045 | 41145 | 68.3 | ACGGCGTTACGGTACAATCG | 35 | 12 | 35 | 7 | 24 | 0 |
| 8691 | 4058 | 4046 | 41146 | 70.9 | ACGGCTCATGATCACGACGG | 35 | 13 | 2 | 30 | 35 | 0 |
| 8692 | 4059 | 4047 | 11867 | 67.1 | ACGGCTCATTAGGCAACGTT | 35 | 13 | 3 | 21 | 12 | 0 |
| 8693 | 4060 | 4048 | 30908 | 73.4 | ACGGCTCAAAAGGTGCGCAA | 35 | 13 | 6 | 33 | 21 | 0 |
| 8694 | 4061 | 4049 | 16677 | 65.5 | ACGGCTCATCGTATCGAGTG | 35 | 13 | 10 | 24 | 22 | 0 |
| 8695 | 4062 | 4050 | 11874 | 67.2 | ACGGCTCACGTTCTGTCCAT | 35 | 13 | 12 | 14 | 15 | 0 |
| 8696 | 4063 | 4051 | 30909 | 74 | ACGGCTCAGCTTGCAATGCG | 35 | 13 | 17 | 21 | 29 | 0 |
| 8697 | 4064 | 4052 | 11878 | 64 | ACGGCTCAGGTAATACGGAC | 35 | 13 | 18 | 5 | 34 | 0 |
| 8698 | 4065 | 4053 | 11881 | 66.8 | ACGGCTCAGCAAAGGACTGT | 35 | 13 | 21 | 25 | 14 | 0 |
| 8699 | 4066 | 4054 | 41151 | 65.8 | ACGGCTCACCTACCTAAGCC | 35 | 13 | 26 | 26 | 36 | 0 |
| 8700 | 4067 | 4055 | 11886 | 71.1 | ACGGCTCATGCGGATGAGTG | 35 | 13 | 29 | 27 | 22 | 0 |
| 8701 | 4068 | 4056 | 11888 | 71.7 | ACGGCTCAGACCCTTGGTGC | 35 | 13 | 32 | 11 | 33 | 0 |
| 8702 | 4069 | 4058 | 11890 | 63.6 | ACGGCTGTAATCTCTGTCCC | 35 | 14 | 4 | 8 | 28 | 0 |
| 8703 | 4070 | 4059 | 41153 | 71.5 | ACGGCTGTTCTGGGACGACC | 35 | 14 | 8 | 34 | 32 | 0 |
| 8704 | 4071 | 4060 | 30911 | 69.3 | ACGGCTGTCGAAAGTGGACC | 35 | 14 | 16 | 22 | 32 | 0 |
| 8705 | 4072 | 4061 | 11896 | 69.5 | ACGGCTGTGCTTCTGTGCAA | 35 | 14 | 17 | 14 | 21 | 0 |
| 8706 | 4073 | 4063 | 30912 | 69.9 | ACGGCTGTGTCTTGCGGAGT | 35 | 14 | 19 | 29 | 20 | 0 |
| 8707 | 4074 | 4064 | 41155 | 64.6 | ACGGCTGTGAGTAGTGAGCC | 35 | 14 | 20 | 22 | 36 | 0 |
| 8708 | 4075 | 4065 | 30913 | 67.1 | ACGGCTGTACCTTGTCAGCC | 35 | 14 | 23 | 9 | 36 | 0 |
| 8709 | 4076 | 4066 | 30914 | 67.4 | ACGGCTGTACGGTGATTCGT | 35 | 14 | 35 | 2 | 10 | 0 |
| 8710 | 4077 | 4067 | 11907 | 70.2 | ACGGCCATTGTCCGTTTCTG | 35 | 15 | 9 | 12 | 8 | 0 |
| 8711 | 4078 | 4068 | 11908 | 72.9 | ACGGCCATTCGTGTGCCCTA | 35 | 15 | 10 | 33 | 26 | 0 |
| 8712 | 4079 | 4069 | 30916 | 67 | ACGGCCATCTCAACCTCTTG | 35 | 15 | 13 | 23 | 11 | 0 |

FIG. 29HHHH

| SEQ ID NO: | ZIP ID# | 4,633 ID# | HEX Tm | ZIPCODE (NH2 -> CONH2) | TETRAMER NUMBERS | | | | "UNALLOWED DIMERS" |
|---|---|---|---|---|---|---|---|---|---|
| 8714 | 4081 | 4071 | 41157 66.5 | ACGGCCATCCTAGCTTTGTC | 35 | 15 | 26 17 | 9 | 0 |
| 8715 | 4082 | 4072 | 11917 73 | ACGGCCATTCCCCATCTGT | 35 | 15 | 28 15 | 14 | 0 |
| 8716 | 4083 | 4073 | 11918 75.4 | ACGGCCATTGCGCGTTGAGT | 35 | 15 | 29 12 | 20 | 0 |
| 8717 | 4084 | 4074 | 11919 71.5 | ACGGCCATGACCCTGTCCAT | 35 | 15 | 32 14 | 15 | 0 |
| 8718 | 4085 | 4075 | 41158 68.4 | ACGGCCATAGCCCCTAAAAG | 35 | 15 | 36 26 | 6 | 0 |
| 8719 | 4086 | 4076 | 41159 68.1 | ACGGCGAATTGAAGTGATCG | 35 | 16 | 1 22 | 24 | 0 |
| 8720 | 4087 | 4077 | 30918 67.2 | ACGGCGAATGATAGGACAGC | 35 | 16 | 2 25 | 31 | 0 |
| 8721 | 4088 | 4078 | 41160 67.6 | ACGGCGAATTAGGATGCTTG | 35 | 16 | 3 27 | 11 | 0 |
| 8722 | 4089 | 4079 | 11922 65.3 | ACGGCGAAAATCTACAATCG | 35 | 16 | 4 7 | 24 | 0 |
| 8723 | 4090 | 4080 | 11924 67.5 | ACGGCGAATCTGTCTGGGTA | 35 | 16 | 8 8 | 18 | 0 |
| 8724 | 4091 | 4081 | 41161 69.9 | ACGGCGAATCGTTGATCGTT | 35 | 16 | 10 2 | 12 | 0 |
| 8725 | 4092 | 4082 | 11926 70.3 | ACGGCGAACTTGGAGTGTGC | 35 | 16 | 11 20 | 33 | 0 |
| 8726 | 4093 | 4083 | 11927 70 | ACGGCGAACGTTTCGTCTGT | 35 | 16 | 12 10 | 14 | 0 |
| 8727 | 4094 | 4084 | 11928 67.2 | ACGGCGAACTCATTGACCAT | 35 | 16 | 13 1 | 15 | 0 |
| 8728 | 4095 | 4085 | 11931 64.8 | ACGGCGAAGGTATCTGAGTG | 35 | 16 | 18 8 | 22 | 0 |
| 8729 | 4096 | 4086 | 41162 67.7 | ACGGCGAAGAGTGATGGATG | 35 | 16 | 20 27 | 27 | 0 |
| 8730 | 4097 | 4087 | 41163 69.4 | ACGGCGAAATCGAGGATGTC | 35 | 16 | 24 25 | 9 | 0 |
| 8731 | 4098 | 4088 | 11935 73.5 | ACGGCGAATCCCACCTGCTT | 35 | 16 | 28 23 | 17 | 0 |
| 8732 | 4099 | 4089 | 11937 72.3 | ACGGCGAACACGCTTGGAGT | 35 | 16 | 30 11 | 20 | 0 |
| 8733 | 4100 | 4090 | 30919 75.3 | ACGGCGAAGTGCACGGTCGT | 35 | 16 | 33 35 | 10 | 0 |
| 8734 | 4101 | 4091 | 11939 72.6 | ACGGCGAAGGACCTCACACG | 35 | 16 | 34 13 | 30 | 0 |
| 8735 | 4102 | 4092 | 11940 74.5 | ACGGCGAAAGCCAATCCGAA | 35 | 16 | 36 4 | 16 | 0 |
| 8736 | 4103 | 4093 | 30920 66.7 | ACGGCTTTTGACCTAATCG | 35 | 17 | 1 26 | 24 | 0 |
| 8737 | 4104 | 4094 | 16691 68.3 | ACGGCTTTGATTACATGCG | 35 | 17 | 2 7 | 29 | 0 |
| 8738 | 4105 | 4095 | 30921 70.8 | ACGGCTTTTAGGTGCCGTT | 35 | 17 | 3 33 | 12 | 0 |
| 8739 | 4106 | 4096 | 30922 67.5 | ACGGCTTAAAGCCTATCCC | 35 | 17 | 6 26 | 28 | 0 |
| 8740 | 4107 | 4097 | 16692 67.3 | ACGGCTTTACATCGTCAGC | 35 | 17 | 7 10 | 31 | 0 |
| 8741 | 4108 | 4098 | 30923 69.2 | ACGGCTTCGTTCTCACGTT | 35 | 17 | 12 13 | 12 | 0 |
| 8742 | 4109 | 4099 | 30924 66.8 | ACGGCTTCTCATCGTCCTA | 35 | 17 | 13 10 | 26 | 0 |
| 8743 | 4110 | 4100 | 41164 65.5 | ACGGCTTCTGTAGGAGCTT | 35 | 17 | 14 25 | 17 | 0 |
| 8744 | 4111 | 4101 | 11949 66.4 | ACGGCTTGGTAAAAGCTGT | 35 | 17 | 18 6 | 14 | 0 |
| 8745 | 4112 | 4102 | 30926 67.1 | ACGGCTTGAGTGGTAGTGC | 35 | 17 | 20 18 | 33 | 0 |
| 8746 | 4113 | 4103 | 11957 74.8 | ACGGCTTTCCCGCTTCCAT | 35 | 17 | 28 17 | 15 | 0 |
| 8747 | 4114 | 4104 | 11958 64.2 | ACGGCTTGACCTTGATTAG | 35 | 17 | 32 1 | 3 | 0 |
| 8748 | 4115 | 4105 | 11960 67.3 | ACGGGTATGATCACGGATG | 35 | 18 | 2 30 | 27 | 0 |
| 8749 | 4116 | 4106 | 16703 69.5 | ACGGGTATACAAGCCGTGC | 35 | 18 | 7 36 | 33 | 0 |
| 8750 | 4117 | 4107 | 16704 66.6 | ACGGGTATCTGACGGAGTG | 35 | 18 | 8 35 | 22 | 0 |
| 8751 | 4118 | 4108 | 22300 66.8 | ACGGGTACGTTCACGAATC | 35 | 18 | 12 30 | 4 | 0 |
| 8752 | 4119 | 4109 | 30927 65.7 | ACGGGTACTGTGAGTTCCC | 35 | 18 | 14 20 | 28 | 0 |
| 8753 | 4120 | 4110 | 30928 66.5 | ACGGGTAGCTTGGTACAGC | 35 | 18 | 17 18 | 31 | 0 |
| 8754 | 4121 | 4111 | 30929 69.2 | ACGGGTAGCAAAATCCGAA | 35 | 18 | 21 4 | 16 | 0 |
| 8755 | 4122 | 4112 | 11972 66.1 | ACGGGTAAGGAGTCTCACG | 35 | 18 | 25 19 | 30 | 0 |
| 8756 | 4123 | 4113 | 16710 67.1 | ACGGGTACCTATCCCTCGT | 35 | 18 | 26 28 | 10 | 0 |
| 8757 | 4124 | 4114 | 11975 72.3 | ACGGGTATGCGCGTTAGGA | 35 | 18 | 29 12 | 25 | 0 |
| 8758 | 4125 | 4115 | 11976 64.2 | ACGGGTAGTGCATACGAGT | 35 | 18 | 33 5 | 20 | 0 |
| 8759 | 4126 | 4116 | 30930 66.3 | ACGGGTAGGACTCTGCTTG | 35 | 18 | 34 8 | 11 | 0 |
| 8760 | 4127 | 4117 | 16711 68 | ACGGGTAACGGCCTAAATC | 35 | 18 | 35 26 | 4 | 0 |
| 8761 | 4128 | 4118 | 16712 70.4 | ACGGGTAAGCCCGAACTGT | 35 | 18 | 36 16 | 14 | 0 |

FIG. 29IIII

| SEQ ID NO: | ZIP ID# | 4,633 ID# | HEX Tm | ZIPCODE (NH2 -> CONH2) | TETRAMER NUMBERS | | | | "UNALLOWED DIMERS" |
|---|---|---|---|---|---|---|---|---|---|
| 8762 | 4129 | 4119 | 11982 | 68 | ACGGGTCTAAAGCGAATCCC | 35 | 19 | 6 | 16 | 28 | 0 |
| 8763 | 4130 | 4120 | 41170 | 67.8 | ACGGGTCTCGTTGCAAGATG | 35 | 19 | 12 | 21 | 27 | 0 |
| 8764 | 4131 | 4121 | 11987 | 68 | ACGGGTCTCTCAAGCCACCT | 35 | 19 | 13 | 36 | 23 | 0 |
| 8765 | 4132 | 4122 | 11990 | 68 | ACGGGTCTCGAAGGACGTCT | 35 | 19 | 16 | 34 | 19 | 0 |
| 8766 | 4133 | 4123 | 30931 | 70.5 | ACGGGTCTATCGACGGGCTT | 35 | 19 | 24 | 35 | 17 | 0 |
| 8767 | 4134 | 4124 | 11997 | 70.3 | ACGGGTCTGACCCTTGGGAC | 35 | 19 | 32 | 11 | 34 | 0 |
| 8768 | 4135 | 4125 | 11998 | 67.7 | ACGGGTCTGTGCAAAGGATG | 35 | 19 | 33 | 6 | 27 | 0 |
| 8769 | 4136 | 4126 | 11999 | 70.2 | ACGGGTCTACGGGACCTCGT | 35 | 19 | 35 | 32 | 10 | 0 |
| 8770 | 4137 | 4127 | 12000 | 65.7 | ACGGGAGTTGATCTGTTCCC | 35 | 20 | 2 | 14 | 28 | 0 |
| 8771 | 4138 | 4128 | 16717 | 69 | ACGGGAGTCTTGCAGCACCT | 35 | 20 | 11 | 31 | 23 | 0 |
| 8772 | 4139 | 4129 | 12004 | 66.4 | ACGGGAGTCTCAAGCCAAAG | 35 | 20 | 13 | 36 | 6 | 0 |
| 8773 | 4140 | 4130 | 30932 | 66.7 | ACGGGAGTGGTAAGTGGTGC | 35 | 20 | 18 | 22 | 33 | 0 |
| 8774 | 4141 | 4131 | 12011 | 67.5 | ACGGGAGTGATGGTGCTCTG | 35 | 20 | 27 | 33 | 8 | 0 |
| 8775 | 4142 | 4132 | 12012 | 71.4 | ACGGGAGTTCCCTGTCACG | 35 | 20 | 28 | 14 | 30 | 0 |
| 8776 | 4143 | 4133 | 30933 | 66.5 | ACGGGAGTCAGCTGATGACC | 35 | 20 | 31 | 2 | 32 | 0 |
| 8777 | 4144 | 4134 | 30934 | 69.8 | ACGGGCAAAATCAGTGCCAT | 35 | 21 | 4 | 22 | 15 | 0 |
| 8778 | 4145 | 4135 | 30935 | 65.5 | ACGGGCAAATACAGTGATCG | 35 | 21 | 5 | 22 | 24 | 0 |
| 8779 | 4146 | 4136 | 41174 | 67.2 | ACGGGCAATACACTTGAGCC | 35 | 21 | 7 | 11 | 36 | 0 |
| 8780 | 4147 | 4137 | 30936 | 67.5 | ACGGGCAACGTTTTAGCCTA | 35 | 21 | 12 | 3 | 26 | 0 |
| 8781 | 4148 | 4138 | 12024 | 72.2 | ACGGGCAAGCTTCGAACAGC | 35 | 21 | 17 | 16 | 31 | 0 |
| 8782 | 4149 | 4139 | 12026 | 66 | ACGGGCAAGAGTCTCAGACC | 35 | 21 | 20 | 13 | 32 | 0 |
| 8783 | 4150 | 4140 | 30937 | 74.6 | ACGGGCAAGCAAATCGCGTT | 35 | 21 | 21 | 24 | 12 | 0 |
| 8784 | 4151 | 4141 | 16725 | 70.1 | ACGGGCAACCTACACGCCTA | 35 | 21 | 26 | 30 | 26 | 0 |
| 8785 | 4152 | 4142 | 12033 | 74.2 | ACGGGCAAACGGCCATGTCT | 35 | 21 | 35 | 15 | 19 | 0 |
| 8786 | 4153 | 4143 | 12034 | 71.8 | ACGGGCAAAGCCTCTGCCTA | 35 | 21 | 36 | 8 | 26 | 0 |
| 8787 | 4154 | 4144 | 30938 | 67.4 | ACGGAGTGCGAATTGATCGT | 35 | 22 | 16 | 1 | 10 | 0 |
| 8788 | 4155 | 4146 | 22312 | 66.9 | ACGGAGTGGGTACGAAGTGC | 35 | 22 | 18 | 16 | 33 | 0 |
| 8789 | 4156 | 4147 | 12044 | 65.8 | AGTGGAGTTGTCTCCCCAGC | 22 | 20 | 9 | 28 | 31 | 0 |
| 8790 | 4157 | 4148 | 41178 | 70.4 | ACGGAGTGGCAACAGCCTTG | 35 | 22 | 21 | 31 | 11 | 0 |
| 8791 | 4158 | 4149 | 22313 | 65.3 | ACGGAGTGATCGTCGTCTCA | 35 | 22 | 24 | 10 | 13 | 0 |
| 8792 | 4159 | 4150 | 12047 | 64.7 | ACGGAGTGCCTACGTTGTC | 35 | 22 | 26 | 12 | 9 | 0 |
| 8793 | 4160 | 4151 | 12048 | 72.5 | ACGGAGTGTGCGTCGTGCAA | 35 | 22 | 29 | 10 | 21 | 0 |
| 8794 | 4161 | 4152 | 16729 | 73.1 | ACGGAGTGGGACGCTTGCAA | 35 | 22 | 34 | 17 | 21 | 0 |
| 8795 | 4162 | 4153 | 12055 | 67.2 | ACCTTGATGATGTCCCACGG | 23 | 2 | 27 | 28 | 35 | 0 |
| 8796 | 4163 | 4154 | 12058 | 68.9 | ACGGACCTTGTCCGTTGACC | 35 | 23 | 9 | 12 | 32 | 0 |
| 8797 | 4164 | 4155 | 12059 | 70.1 | ACGGACCTCTTGCACGCCTA | 35 | 23 | 11 | 30 | 26 | 0 |
| 8798 | 4165 | 4156 | 30939 | 66.3 | ACGGACCTGCTTAAAGCCAT | 35 | 23 | 17 | 6 | 15 | 0 |
| 8799 | 4166 | 4157 | 12063 | 68.2 | ACGGACCTGTCTGACCCAT | 35 | 23 | 19 | 32 | 15 | 0 |
| 8800 | 4167 | 4158 | 12066 | 68.9 | ACGGACCTTCCCGAGTTTGA | 35 | 23 | 28 | 20 | 1 | 1 |
| 8801 | 4168 | 4159 | 30940 | 69.1 | ACGGACCTGACCAAAGACGG | 35 | 23 | 32 | 6 | 35 | 0 |
| 8802 | 4169 | 4160 | 16731 | 69.1 | ACGGACCTAGCCGCTTTCTG | 35 | 23 | 36 | 17 | 8 | 0 |
| 8803 | 4170 | 4161 | 41185 | 66.3 | ACGGATCGAAAGTCCCAAAG | 35 | 24 | 6 | 28 | 6 | 1 |
| 8804 | 4171 | 4163 | 12074 | 70.8 | ACGGATCGTGTCCGAACACG | 35 | 24 | 9 | 16 | 30 | 0 |
| 8805 | 4172 | 4164 | 30942 | 71.5 | ACGGATCGCTCACGAATCCC | 35 | 24 | 13 | 16 | 28 | 0 |
| 8806 | 4173 | 4165 | 12079 | 66.8 | ATCGCTGTCTGTGATGCGAA | 24 | 14 | 14 | 27 | 16 | 0 |
| 8807 | 4174 | 4166 | 41188 | 69.8 | ACGGATCGGAGTCGAACGAA | 35 | 24 | 20 | 16 | 16 | 0 |
| 8808 | 4175 | 4167 | 41189 | 71.5 | ACGGATCGCAACTTGGACC | 35 | 24 | 21 | 11 | 32 | 0 |
| 8809 | 4176 | 4168 | 12083 | 67.1 | ACGGATCGAGTGTCTGCCAT | 35 | 24 | 22 | 8 | 15 | 0 |

FIG. 29JJJJ

| SEQ ID NO: | ZIP ID# | 4,633 ID# | HEX ID# | Tm | ZIPCODE (NH2 -> CONH2) | TETRAMER NUMBERS | | | | 'UNALLOWED DIMERS' |
|---|---|---|---|---|---|---|---|---|---|---|
| 8810 | 4177 | 4169 | 30943 | 69.2 | ACGGATCGACCTCTTGACGG | 35 24 23 11 35 | | | | 0 |
| 8811 | 4178 | 4170 | 30945 | 71.3 | ACGGATCGCAGCTCCCTGAT | 35 24 31 28 2 | | | | 0 |
| 8812 | 4179 | 4171 | 12088 | 68.5 | ACGGATCGGGACGGACTTAG | 35 24 34 34 3 | | | | 0 |
| 8813 | 4180 | 4172 | 12089 | 70.6 | ATCGACGGCTCAGAGTTGCG | 24 35 13 20 29 | | | | 0 |
| 8814 | 4181 | 4173 | 22320 | 70.5 | ACGGATCGAGCCCCTAAGGA | 35 24 36 26 25 | | | | 0 |
| 8815 | 4182 | 4175 | 22321 | 68 | ACGGAGGATCTGGCAAACCT | 35 25 8 21 23 | | | | 0 |
| 8816 | 4183 | 4176 | 12098 | 64.3 | ACGGAGGACCATAATCGATG | 35 25 15 4 27 | | | | 0 |
| 8817 | 4184 | 4177 | 30946 | 71.5 | ACGGAGGAGCTTGTGCCGTT | 35 25 17 33 12 | | | | 0 |
| 8818 | 4185 | 4178 | 41192 | 68.1 | AGGAGGTATCGTGTGCTGCG | 25 18 10 33 29 | | | | 0 |
| 8819 | 4186 | 4179 | 22323 | 69.7 | AGGAGTCTAGCCCACGTGCG | 25 19 36 30 29 | | | | 0 |
| 8820 | 4187 | 4180 | 16734 | 68.8 | ACGGAGGAGCAAAGCCAATC | 35 25 21 36 4 | | | | 0 |
| 8821 | 4188 | 4181 | 12106 | 70.6 | ACGGAGGATGCGCCTAACCT | 35 25 29 26 23 | | | | 0 |
| 8822 | 4189 | 4182 | 12110 | 66.3 | ACGCCTATCTGGAGTCAGC | 35 26 8 20 31 | | | | 0 |
| 8823 | 4190 | 4183 | 41199 | 70.1 | ACGGCCTACTGTGGACACGG | 35 26 14 34 35 | | | | 0 |
| 8824 | 4191 | 4184 | 30948 | 66.2 | ACGGCCTAGAGTTCGTGGAC | 35 26 20 10 34 | | | | 0 |
| 8825 | 4192 | 4185 | 30950 | 65.4 | ACGGCCTACCTATCCCTGTC | 35 26 26 28 9 | | | | 0 |
| 8826 | 4193 | 4186 | 22328 | 66.2 | ACGGGATGAATCCCATAGGA | 35 27 4 15 25 | | | | 0 |
| 8827 | 4194 | 4187 | 12121 | 67.1 | ACGGGATGCCATCGAATTAG | 35 27 15 16 3 | | | | 0 |
| 8828 | 4195 | 4188 | 41207 | 68.6 | ACGGGATGATCGGAGTCGTT | 35 27 24 20 12 | | | | 0 |
| 8829 | 4196 | 4189 | 41208 | 67.4 | ACGGGATGCCTAAGTGCTTG | 35 27 26 22 11 | | | | 0 |
| 8830 | 4197 | 4190 | 12129 | 68.7 | ACGGGATGGGACCACGATAC | 35 27 34 30 5 | | | | 0 |
| 8831 | 4198 | 4191 | 12131 | 77.7 | ACGGGATGAGCCGTGCACGG | 35 27 36 33 35 | | | | 0 |
| 8832 | 4199 | 4192 | 16741 | 70.6 | ACGGTCCCTTGACGTTGCAA | 35 28 1 12 21 | | | | 1 |
| 8833 | 4200 | 4193 | 30952 | 71.3 | ACGGTCCCCTCAAATCACGG | 35 28 13 4 35 | | | | 1 |
| 8834 | 4201 | 4194 | 41214 | 70.2 | ACGGTCCCCCATACCTGACC | 35 28 15 23 32 | | | | 1 |
| 8835 | 4202 | 4195 | 30953 | 70.8 | ACGGTCCCAGTGTGTCTGCG | 35 28 22 9 29 | | | | 1 |
| 8836 | 4203 | 4196 | 12142 | 71.1 | ACGGTCCCATCGGCTTGTCT | 35 28 24 17 19 | | | | 1 |
| 8837 | 4204 | 4197 | 12143 | 68.9 | ACGGTCCCCCTATCGTGATG | 35 28 26 10 27 | | | | 1 |
| 8838 | 4205 | 4198 | 12144 | 66.4 | TCCCGATGTGATTTAGCACG | 28 27 2 3 30 | | | | 0 |
| 8839 | 4206 | 4199 | 30954 | 68.9 | TGCGTTGAATACAGCCGACC | 29 1 5 36 32 | | | | 0 |
| 8840 | 4207 | 4200 | 16745 | 65.3 | ACGGTGCGTGATAGGATCTG | 35 29 2 25 8 | | | | 0 |
| 8841 | 4208 | 4201 | 16746 | 71.6 | ACGGTGCGTTAGGGACGACC | 35 29 3 34 32 | | | | 0 |
| 8842 | 4209 | 4202 | 41217 | 67.1 | TGCGATACAATCATCGCGTT | 29 5 4 24 12 | | | | 0 |
| 8843 | 4210 | 4203 | 41218 | 68.5 | ACGGTGCGTACACGTTGGAC | 35 29 7 12 34 | | | | 0 |
| 8844 | 4211 | 4204 | 12150 | 72.6 | ACGGTGCGCTTGCCTAAGGA | 35 29 11 26 25 | | | | 0 |
| 8845 | 4212 | 4205 | 12152 | 70.2 | ACGGTGCGCCATATACGACC | 35 29 15 5 32 | | | | 0 |
| 8846 | 4213 | 4206 | 30955 | 72.5 | TGCGAGTGCTGTCAGCCAGC | 29 22 14 31 31 | | | | 0 |
| 8847 | 4214 | 4207 | 12153 | 69 | TGCGAGGACTCAGATGCAGC | 29 25 13 27 31 | | | | 0 |
| 8848 | 4215 | 4208 | 12154 | 76.7 | ACGGTGCGTGCGCACGAATC | 35 29 29 30 4 | | | | 0 |
| 8849 | 4216 | 4209 | 12155 | 78.3 | ACGGTGCGCACGGTGCCTGT | 35 29 30 33 14 | | | | 0 |
| 8850 | 4217 | 4210 | 30957 | 75.3 | ACGGTGCGCAGCACCTCCAT | 35 29 31 23 15 | | | | 0 |
| 8851 | 4218 | 4211 | 12156 | 75.5 | ACGGTGCGGTGCGAGTGCTT | 35 29 33 20 17 | | | | 0 |
| 8852 | 4219 | 4212 | 12157 | 76.4 | ACGGTGCGGGACCAGCACCT | 35 29 34 31 23 | | | | 0 |
| 8853 | 4220 | 4213 | 12158 | 73.6 | ACGGTGCGAGCCCTTGGAGT | 35 29 36 11 20 | | | | 0 |
| 8854 | 4221 | 4214 | 12159 | 67.2 | ACGGCACGTTGAGGACTGAT | 35 30 1 34 2 | | | | 0 |
| 8855 | 4222 | 4215 | 41220 | 68 | ACGGCACGTGATACGGTGAT | 35 30 2 35 2 | | | | 0 |
| 8856 | 4223 | 4216 | 41221 | 65.6 | ACGGCACGTTAGAGTGATCG | 35 30 3 22 24 | | | | 0 |
| 8857 | 4224 | 4217 | 41222 | 70.4 | ACGGCACGAATCCAGCTCTG | 35 30 4 31 8 | | | | 0 |

FIG. 29KKKK

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 8858 | 4225 | 4218 | 30958 | 69.7 | ACGGCACGTACATGATTGCG | 35 | 30 | 7 | 2 | 29 | 0 |
| 8859 | 4226 | 4219 | 12162 | 71.3 | ACGGCACGTCTGCTCAATCG | 35 | 30 | 8 | 13 | 24 | 0 |
| 8860 | 4227 | 4220 | 12164 | 74.1 | ACGGCACGTCGTGCTTCGAA | 35 | 30 | 10 | 17 | 16 | 0 |
| 8861 | 4228 | 4221 | 30959 | 70.2 | ACGGCACGGAGTCTCACAGC | 35 | 30 | 20 | 13 | 31 | 0 |
| 8862 | 4229 | 4222 | 12168 | 70.3 | ACGGCACGACCTCGAATCTG | 35 | 30 | 23 | 16 | 8 | 0 |
| 8863 | 4230 | 4223 | 16748 | 73.5 | ACGGCACGCAGCTGATGGAC | 35 | 30 | 31 | 2 | 34 | 0 |
| 8864 | 4231 | 4224 | 12172 | 77.1 | ACGGCACGGGACGGACGGTA | 35 | 30 | 34 | 34 | 18 | 0 |
| 8865 | 4232 | 4225 | 12173 | 72.9 | ACGGCACGACGGTCGTGAGT | 35 | 30 | 35 | 10 | 20 | 0 |
| 8866 | 4233 | 4226 | 16749 | 66.6 | ACGGCAGCTTAGAAAGCCAT | 35 | 31 | 3 | 6 | 15 | 0 |
| 8867 | 4234 | 4227 | 16750 | 67.3 | ACGGCAGCTGTCCGAAATAC | 35 | 31 | 9 | 16 | 5 | 0 |
| 8868 | 4235 | 4228 | 12179 | 70.6 | ACGGCAGCCTTGCTCAGATG | 35 | 31 | 11 | 13 | 27 | 0 |
| 8869 | 4236 | 4229 | 22350 | 69.8 | ACGGCAGCCTGTTTAGACGG | 35 | 31 | 14 | 3 | 35 | 0 |
| 8870 | 4237 | 4230 | 12181 | 72.5 | ACGGCAGCCCATAATCCACG | 35 | 31 | 15 | 4 | 30 | 0 |
| 8871 | 4238 | 4231 | 12182 | 72.3 | ACGGCAGCCGAACTGTTCGT | 35 | 31 | 16 | 14 | 10 | 0 |
| 8872 | 4239 | 4232 | 12183 | 70.3 | ACGGCAGCGCTTGAGTGAGT | 35 | 31 | 17 | 20 | 20 | 0 |
| 8873 | 4240 | 4233 | 22351 | 68.4 | ACGGCAGCGGTACACGTTAG | 35 | 31 | 18 | 30 | 3 | 0 |
| 8874 | 4241 | 4234 | 12188 | 69.7 | ACGGCAGCAGGAGTCTACGG | 35 | 31 | 25 | 19 | 35 | 0 |
| 8875 | 4242 | 4235 | 12190 | 75.5 | ACGGCAGCCACGAGGAGCAA | 35 | 31 | 30 | 25 | 21 | 0 |
| 8876 | 4243 | 4236 | 12191 | 75.5 | ACGGCAGCCAGCCTGTCGAA | 35 | 31 | 31 | 14 | 16 | 0 |
| 8877 | 4244 | 4237 | 12193 | 76.1 | ACGGCAGCGTGCCCTATCCC | 35 | 31 | 33 | 26 | 28 | 0 |
| 8878 | 4245 | 4238 | 12194 | 75.6 | ACGGCAGCACGGTCGTGACC | 35 | 31 | 35 | 10 | 32 | 0 |
| 8879 | 4246 | 4239 | 12195 | 66.3 | ACGGGACCTTGATTGACGTT | 35 | 32 | 1 | 1 | 12 | 0 |
| 8880 | 4247 | 4240 | 16752 | 68.7 | ACGGGACCAATCACCTGACC | 35 | 32 | 4 | 23 | 32 | 0 |
| 8881 | 4248 | 4241 | 16753 | 66.9 | ACGGGACCAAAGAATCGATG | 35 | 32 | 6 | 4 | 27 | 0 |
| 8882 | 4249 | 4242 | 12199 | 70.8 | ACGGGACCTACACAGCGCAA | 35 | 32 | 7 | 31 | 21 | 0 |
| 8883 | 4250 | 4243 | 12201 | 71 | ACGGGACCCGTTGTCTTCGT | 35 | 32 | 12 | 19 | 10 | 0 |
| 8884 | 4251 | 4244 | 30960 | 72.3 | ACGGGACCCTCAGTGCGATG | 35 | 32 | 13 | 33 | 27 | 0 |
| 8885 | 4252 | 4245 | 30961 | 70.9 | ACGGGACCCCATACCTCGAA | 35 | 32 | 15 | 23 | 16 | 0 |
| 8886 | 4253 | 4246 | 12202 | 68.8 | ACGGGACCCGAACTCATGTC | 35 | 32 | 16 | 13 | 9 | 0 |
| 8887 | 4254 | 4247 | 16754 | 68.4 | ACGGGACCGCTTAATCCCTA | 35 | 32 | 17 | 4 | 26 | 0 |
| 8888 | 4255 | 4248 | 12206 | 72.9 | ACGGGACCATCGTCCCACCT | 35 | 32 | 24 | 28 | 23 | 0 |
| 8889 | 4256 | 4249 | 12208 | 74.6 | ACGGGACCGATGGATGCAGC | 35 | 32 | 27 | 27 | 31 | 0 |
| 8890 | 4257 | 4250 | 12209 | 73 | ACGGGACCTCCATCGGGTA | 35 | 32 | 28 | 24 | 18 | 0 |
| 8891 | 4258 | 4251 | 16755 | 73.4 | ACGGGACCCAGCCGAACCTA | 35 | 32 | 31 | 16 | 26 | 0 |
| 8892 | 4259 | 4252 | 12212 | 71.8 | ACGGGACCGTGCGGACTTAG | 35 | 32 | 33 | 34 | 3 | 0 |
| 8893 | 4260 | 4253 | 41229 | 66.4 | ACGGGTGCTTGAGTCTAGCC | 35 | 33 | 1 | 19 | 36 | 0 |
| 8894 | 4261 | 4254 | 30963 | 67.9 | ACGGGTGCTGATTTGAATCG | 35 | 33 | 2 | 1 | 24 | 0 |
| 8895 | 4262 | 4255 | 30964 | 66.2 | ACGGGTGCTTAGTCTGGCTT | 35 | 33 | 3 | 8 | 17 | 0 |
| 8896 | 4263 | 4256 | 41230 | 70.5 | ACGGGTGCAATCGCTTCTTG | 35 | 33 | 4 | 17 | 11 | 0 |
| 8897 | 4264 | 4257 | 41231 | 67.3 | ACGGGTGCATACACCTGACC | 35 | 33 | 5 | 23 | 32 | 0 |
| 8898 | 4265 | 4258 | 16757 | 70.1 | ACGGGTGCTGTCGGACTCTG | 35 | 33 | 9 | 34 | 8 | 0 |
| 8899 | 4266 | 4259 | 12216 | 67.4 | ACGGGTGCCTCACTGTTGTC | 35 | 33 | 13 | 14 | 9 | 0 |
| 8900 | 4267 | 4260 | 12217 | 73.4 | ACGGGTGCCGAAGACCCCTA | 35 | 33 | 16 | 32 | 26 | 0 |
| 8901 | 4268 | 4261 | 12218 | 73.4 | ACGGGTGCGCTTGCTTTTGA | 35 | 33 | 17 | 17 | 1 | 0 |
| 8902 | 4269 | 4262 | 30965 | 71.8 | ACGGGTGCGTCTCCTAACGG | 35 | 33 | 19 | 26 | 35 | 0 |
| 8903 | 4270 | 4263 | 12220 | 73.1 | ACGGGTGCGCAACAGCTGAT | 35 | 33 | 21 | 31 | 2 | 0 |
| 8904 | 4271 | 4264 | 12221 | 75.3 | ACGGGTGCAGTGGACCACGG | 35 | 33 | 22 | 32 | 35 | 0 |
| 8905 | 4272 | 4265 | 22367 | 71.4 | ACGGGTGCACCTGCAACTCA | 35 | 33 | 23 | 21 | 13 | 0 |

FIG. 29LLLL

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 8906 | 4273 | 4266 | 12223 | 69.5 | ACGGGTGCTGCGAGGAATAC | 35 | 33 | 29 | 25 | 5 | 0 |
| 8907 | 4274 | 4267 | 12224 | 74.9 | ACGGGTGCGACCATCGGGTA | 35 | 33 | 32 | 24 | 18 | 0 |
| 8908 | 4275 | 4268 | 12225 | 77 | ACGGGTGCGGACCACGGGTA | 35 | 33 | 34 | 30 | 18 | 0 |
| 8909 | 4276 | 4269 | 12226 | 64.3 | ACGGGGACTTGAAAAGTTGA | 35 | 34 | 1 | 6 | 1 | 1 |
| 8910 | 4277 | 4270 | 41232 | 72.3 | ACGGGGACTTAGTGCGGCAA | 35 | 34 | 3 | 29 | 21 | 0 |
| 8911 | 4278 | 4271 | 30966 | 70.4 | ACGGGGACTACAACGGGGAC | 35 | 34 | 7 | 35 | 34 | 0 |
| 8912 | 4279 | 4272 | 30967 | 71.8 | ACGGGGACCTTGACGGTTGA | 35 | 34 | 11 | 35 | 1 | 1 |
| 8913 | 4280 | 4273 | 41234 | 74.3 | ACGGGGACCGTTATCGCGAA | 35 | 34 | 12 | 24 | 16 | 0 |
| 8914 | 4281 | 4274 | 30968 | 67.6 | ACGGGGACGGTAAGGAAATC | 35 | 34 | 18 | 25 | 4 | 0 |
| 8915 | 4282 | 4275 | 12237 | 74.2 | ACGGGGACGCAAAGTGCCAT | 35 | 34 | 21 | 22 | 15 | 0 |
| 8916 | 4283 | 4276 | 22374 | 70.3 | ACGGGGACACCTGAGTTCCC | 35 | 34 | 23 | 20 | 28 | 0 |
| 8917 | 4284 | 4277 | 12238 | 74.3 | ACGGGGACATCGTCCCATCG | 35 | 34 | 24 | 28 | 24 | 0 |
| 8918 | 4285 | 4278 | 12239 | 74.2 | ACGGGGACTCCCGATGCTCA | 35 | 34 | 28 | 27 | 13 | 0 |
| 8919 | 4286 | 4279 | 12240 | 74.6 | ACGGGGACTGCGCTGTGCTT | 35 | 34 | 29 | 14 | 17 | 0 |
| 8920 | 4287 | 4280 | 12241 | 75.2 | ACGGGGACGTGCGCAACCTA | 35 | 34 | 33 | 21 | 26 | 0 |
| 8921 | 4288 | 4281 | 12243 | 67.7 | ACGGACGGTTGAGGTACACG | 35 | 35 | 1 | 18 | 30 | 1 |
| 8922 | 4289 | 4282 | 41238 | 67.8 | ACGGACGGTACACGAACAGC | 35 | 35 | 7 | 16 | 31 | 0 |
| 8923 | 4290 | 4283 | 41239 | 67.8 | ACGGTCTGAATCACCTTGCG | 35 | 8 | 4 | 23 | 29 | 0 |
| 8924 | 4291 | 4284 | 41241 | 69 | ACGGACGGTCGTGGTAGACC | 35 | 35 | 10 | 18 | 32 | 0 |
| 8925 | 4292 | 4285 | 30970 | 70.8 | ACGGACGGCTCAGTCTTCCC | 35 | 35 | 13 | 19 | 28 | 0 |
| 8926 | 4293 | 4286 | 30971 | 67.4 | ACGGGAGTTCGTAATCTGCG | 35 | 20 | 10 | 4 | 29 | 0 |
| 8927 | 4294 | 4287 | 12249 | 74.8 | ACGGACGGGCAATCGTCAGC | 35 | 35 | 21 | 10 | 31 | 0 |
| 8928 | 4295 | 4288 | 12251 | 69.2 | ACGGACGGACCTGGTAGTGC | 35 | 35 | 23 | 18 | 33 | 0 |
| 8929 | 4296 | 4289 | 12253 | 71.3 | ACGGACGGGATGTCCCAAAG | 35 | 35 | 27 | 28 | 6 | 0 |
| 8930 | 4297 | 4290 | 12254 | 70.9 | ACGGACGGTCCCTCTGGGTA | 35 | 35 | 28 | 8 | 18 | 1 |
| 8931 | 4298 | 4291 | 12256 | 73.3 | ACGGACGGCAGCTTGACGAA | 35 | 35 | 31 | 1 | 16 | 0 |
| 8932 | 4299 | 4292 | 12258 | 75.1 | ACGGACGGGTGCCTGTCGAA | 35 | 35 | 33 | 14 | 16 | 0 |
| 8933 | 4300 | 4293 | 12259 | 73.7 | ACGGACGGAGCCGCTTGTCT | 35 | 35 | 36 | 17 | 19 | 0 |
| 8934 | 4301 | 4294 | 16761 | 68.1 | ACGGAGCCTTAGCTTGGACC | 35 | 36 | 3 | 11 | 32 | 0 |
| 8935 | 4302 | 4295 | 12262 | 67.9 | AGCCAATCGTCTATCGGCAA | 36 | 4 | 19 | 24 | 21 | 0 |
| 8936 | 4303 | 4296 | 22383 | 72.4 | ACGGAGCCTGTCCGAAGCAA | 35 | 36 | 9 | 16 | 21 | 0 |
| 8937 | 4304 | 4297 | 12265 | 66.4 | ACGGAGCCTCGTGGTATGAT | 35 | 36 | 10 | 18 | 2 | 0 |
| 8938 | 4305 | 4298 | 12268 | 70.6 | ACGGAGCCCTGTTCCCAATC | 35 | 36 | 14 | 28 | 4 | 0 |
| 8939 | 4306 | 4299 | 41247 | 71.2 | ACGGAGCCCGAAGATGGGTA | 35 | 36 | 16 | 27 | 18 | 0 |
| 8940 | 4307 | 4300 | 12270 | 69 | ACGGAGCCAGTGGGACTGTC | 35 | 36 | 22 | 34 | 9 | 0 |
| 8941 | 4308 | 4301 | 41251 | 67.6 | ACGGAGCCCCTATACATCCC | 35 | 36 | 26 | 7 | 28 | 0 |
| 8942 | 4309 | 4302 | 12274 | 69.7 | ACGGAGCCGATGAATCAGGA | 35 | 36 | 27 | 4 | 25 | 0 |
| 8943 | 4310 | 4303 | 12275 | 73.7 | ACGGAGCCTCCCGCAAGGTA | 35 | 36 | 28 | 21 | 18 | 0 |
| 8944 | 4311 | 4304 | 12277 | 73 | ACGGAGCCCAGCGATGTTGA | 35 | 36 | 31 | 27 | 1 | 0 |
| 8945 | 4312 | 4305 | 12278 | 71.5 | AGCCGACCCCTATGTCCACG | 36 | 32 | 26 | 9 | 30 | 0 |
| 8946 | 4313 | 4306 | 12279 | 74.4 | ACGGAGCCGGACGATGCTGT | 35 | 36 | 34 | 27 | 14 | 0 |
| 8947 | 4314 | 4307 | 12280 | 72 | ACGGAGCCACGGTTGACGTT | 35 | 36 | 35 | 1 | 12 | 1 |
| 8948 | 4315 | 4308 | 22393 | 70.6 | AGCCTTGAAAAGTGCGCGAA | 36 | 1 | 6 | 29 | 16 | 0 |
| 8949 | 4316 | 4309 | 41252 | 69.2 | TTGATCGTGCTTGCAAAGCC | 1 | 10 | 17 | 21 | 36 | 0 |
| 8950 | 4317 | 4310 | 30972 | 68.9 | TTGACGTTCTCAAGCCCACG | 1 | 12 | 13 | 36 | 30 | 0 |
| 8951 | 4318 | 4311 | 41253 | 71.1 | TTGAGCTTGTGCACGGGACC | 1 | 17 | 33 | 35 | 32 | 0 |
| 8952 | 4319 | 4312 | 30973 | 67.9 | TTGAGCAATGTCGATGCGAA | 1 | 21 | 9 | 27 | 16 | 0 |
| 8953 | 4320 | 4313 | 41254 | 67.4 | TTGAAGGAACCTGGACCGAA | 1 | 25 | 23 | 34 | 16 | 0 |

FIG. 29MMMM

| SEQ ID NO: | ZIP ID# | 4,633 ID# | HEX ID# | Tm | ZIPCODE (NH2 -> CONH2) | TETRAMER NUMBERS | | | | "UNALLOWED DIMERS" |
|---|---|---|---|---|---|---|---|---|---|---|
| 8954 | 4321 | 4314 | 12288 | 71.7 | TTGAGATGTGCGACGGCGTT | 1 | 27 | 29 | 35 12 | 0 |
| 8955 | 4322 | 4315 | 12293 | 70 | TTGAGGACGCAACTTGTGCG | 1 | 34 | 21 | 11 29 | 0 |
| 8956 | 4323 | 4316 | 30974 | 67.4 | TGATGCTTACGGTGTCTGCG | 2 | 17 | 35 | 9 29 | 0 |
| 8957 | 4324 | 4318 | 12308 | 67.1 | AGCCTTAGGCTTCAGCGATG | 36 | 3 | 17 | 31 27 | 0 |
| 8958 | 4325 | 4319 | 12315 | 68.1 | AGCCTTAGCAGCATCGCTTG | 36 | 3 | 31 | 24 11 | 0 |
| 8959 | 4326 | 4320 | 30976 | 70.3 | AGCCAATCCGTTTGTCGTGC | 36 | 4 | 12 | 9 33 | 0 |
| 8960 | 4327 | 4321 | 41261 | 67.5 | AGCCAATCGCAAGAGTACGG | 36 | 4 | 21 | 20 35 | 0 |
| 8961 | 4328 | 4322 | 12327 | 70.3 | AGCCAATCAGTGAGCCACGG | 36 | 4 | 22 | 36 35 | 0 |
| 8962 | 4329 | 4323 | 30977 | 71.5 | AGCCAATCAGGATGCGGCTT | 36 | 4 | 25 | 29 17 | 0 |
| 8963 | 4330 | 4324 | 30978 | 65.9 | AATCCCTATGTCTCCCCACG | 4 | 26 | 9 | 28 30 | 0 |
| 8964 | 4331 | 4325 | 12329 | 68.2 | AGCCAATCGATGAAAGTGCG | 36 | 4 | 27 | 6 29 | 0 |
| 8965 | 4332 | 4326 | 22403 | 65.4 | AGCCAATCGGACTACACACG | 36 | 4 | 34 | 7 30 | 0 |
| 8966 | 4333 | 4327 | 12332 | 69.5 | AGCCAATCAGCCCTGTACGG | 36 | 4 | 36 | 14 35 | 0 |
| 8967 | 4334 | 4328 | 41263 | 64.6 | AGCCATACCGTTACGGTGTC | 36 | 5 | 12 | 35 9 | 0 |
| 8968 | 4335 | 4329 | 16784 | 65.2 | AGCCATACGCTTCTCAATCG | 36 | 5 | 17 | 13 24 | 0 |
| 8969 | 4336 | 4330 | 12342 | 66.1 | AGCCATACACCTGGACCCAT | 36 | 5 | 23 | 34 15 | 0 |
| 8970 | 4337 | 4331 | 12343 | 69.2 | AGCCATACAGGATCCCGTGC | 36 | 5 | 25 | 28 33 | 0 |
| 8971 | 4338 | 4332 | 12346 | 71.7 | AGCCATACCAGCGACCGGAC | 36 | 5 | 31 | 32 34 | 0 |
| 8972 | 4339 | 4333 | 30979 | 71.3 | AGCCATACGTGCCTCATGCG | 36 | 5 | 33 | 13 29 | 0 |
| 8973 | 4340 | 4334 | 12351 | 68.5 | AGCCAAAGTGATTCCCGACC | 36 | 6 | 2 | 28 32 | 0 |
| 8974 | 4341 | 4335 | 22406 | 68 | AAAGTCTGGCAAGCTTTGCG | 6 | 8 | 21 | 17 29 | 0 |
| 8975 | 4342 | 4336 | 16789 | 67.3 | AGCCAAAGGCAAGGACAGTG | 36 | 6 | 21 | 34 22 | 0 |
| 8976 | 4343 | 4337 | 12357 | 71.3 | AAAGAGTGGTGCGTGCACGG | 6 | 22 | 33 | 33 35 | 0 |
| 8977 | 4344 | 4338 | 12358 | 64.4 | AGCCAAAGAGGACTCACGAA | 36 | 6 | 25 | 13 16 | 0 |
| 8978 | 4345 | 4339 | 41267 | 65.8 | AGCCAAAGCCTATGATTCCC | 36 | 6 | 26 | 2 28 | 0 |
| 8979 | 4346 | 4340 | 30980 | 67.1 | AGCCAAAGGACCTTGACACG | 36 | 6 | 32 | 1 30 | 0 |
| 8980 | 4347 | 4341 | 41271 | 67.1 | TACATGCGATACTGCGCCAT | 7 | 29 | 5 | 29 15 | 0 |
| 8981 | 4348 | 4342 | 30981 | 68.3 | TCTGCTTGTTGACACGCACG | 8 | 11 | 1 | 30 30 | 1 |
| 8982 | 4349 | 4343 | 41272 | 70.1 | TCTGCTCAGACCGGACGCTT | 8 | 13 | 32 | 34 17 | 0 |
| 8983 | 4350 | 4344 | 12372 | 68.2 | AGCCTCTGCTGTATCGCGAA | 36 | 8 | 14 | 24 16 | 0 |
| 8984 | 4351 | 4345 | 12374 | 70.1 | AGCCTCTGGAGTCACGCGAA | 36 | 8 | 20 | 30 16 | 0 |
| 8985 | 4352 | 4346 | 12378 | 65.7 | TCTGGATGAAAGGATGGCAA | 8 | 27 | 6 | 27 21 | 0 |
| 8986 | 4353 | 4347 | 30982 | 70.8 | AGCCTCTGGGACATCGAGCC | 36 | 8 | 34 | 24 36 | 0 |
| 8987 | 4354 | 4349 | 12392 | 68.9 | AGCCTGTCTGCGCGAATACA | 36 | 9 | 29 | 16 7 | 0 |
| 8988 | 4355 | 4350 | 16797 | 70 | AGCCTGTCCAGCAAAGCAGC | 36 | 9 | 31 | 6 31 | 0 |
| 8989 | 4356 | 4351 | 30983 | 67 | AGCCTCGTTTGATGTCGCTT | 36 | 10 | 1 | 9 17 | 0 |
| 8990 | 4357 | 4353 | 12398 | 66.1 | TCGTTGTCTACATGCGGACC | 10 | 9 | 7 | 29 32 | 0 |
| 8991 | 4358 | 4354 | 12403 | 69.3 | AGCCTCGTGAGTGGACAGCC | 36 | 10 | 20 | 34 36 | 0 |
| 8992 | 4359 | 4355 | 30984 | 71.3 | AGCCTCGTGCAACGAAGCAA | 36 | 10 | 21 | 16 21 | 0 |
| 8993 | 4360 | 4356 | 30985 | 68.3 | AGCCTCGTACCTCGAAAGCC | 36 | 10 | 23 | 16 36 | 0 |
| 8994 | 4361 | 4357 | 16802 | 73.1 | AGCCTCGTTCCCGACCCTTG | 36 | 10 | 28 | 32 11 | 0 |
| 8995 | 4362 | 4358 | 12406 | 68.1 | TCGTTGCGATACTCGTTCCC | 10 | 29 | 5 | 10 28 | 0 |
| 8996 | 4363 | 4359 | 12410 | 68.1 | AGCCCTTGTTGAGCTTGCAA | 36 | 11 | 1 | 17 21 | 1 |
| 8997 | 4364 | 4360 | 41284 | 66.9 | AGCCCTTGCTCAAGGATTGA | 36 | 11 | 13 | 25 1 | 0 |
| 8998 | 4365 | 4361 | 30986 | 66.7 | AGCCCTTGCTGTACCTACGG | 36 | 11 | 14 | 23 35 | 0 |
| 8999 | 4366 | 4362 | 41286 | 66.7 | AGCCCTTGGTCTATCGCTTG | 36 | 11 | 19 | 24 11 | 0 |
| 9000 | 4367 | 4363 | 30987 | 71.2 | AGCCCTTGGCAAAGCCTGTC | 36 | 11 | 21 | 36 9 | 0 |
| 9001 | 4368 | 4364 | 41287 | 69.2 | AGCCCTTGAGTGATCGCGTT | 36 | 11 | 22 | 24 12 | 0 |

FIG. 29NNNN

| SEQ ID NO: | ZIP ID# | 4,633 ID# | HEX ID# | Tm | ZIPCODE (N5'2 -> CON5'2) | TETRAMER NUMBERS | | | | | "UNALLOWED DIMERS" |
|---|---|---|---|---|---|---|---|---|---|---|---|
| 9002 | 4369 | 4365 | 30989 | 65.4 | AGCCCTTGCCTAGTCTAGCC | 36 | 11 | 26 | 19 | 36 | 0 |
| 9003 | 4370 | 4366 | 30990 | 72.1 | AGCCCTTGGACCGAGTTCCC | 36 | 11 | 32 | 20 | 28 | 0 |
| 9004 | 4371 | 4367 | 12422 | 68.4 | AGCCCTTGGGACTGTCCTTG | 36 | 11 | 34 | 9 | 11 | 0 |
| 9005 | 4372 | 4368 | 30991 | 68.8 | AGCCCTTGAGCCAAAGGATG | 36 | 11 | 36 | 6 | 27 | 0 |
| 9006 | 4373 | 4369 | 30992 | 70.2 | AGCCCGTTAATCGTGCGGTA | 36 | 12 | 4 | 33 | 18 | 0 |
| 9007 | 4374 | 4370 | 41290 | 66.3 | AGCCCGTTTACAAATCCGTT | 36 | 12 | 7 | 4 | 12 | 0 |
| 9008 | 4375 | 4371 | 30994 | 65.3 | AGCCCGTTGGTACGAATACA | 36 | 12 | 18 | 16 | 7 | 0 |
| 9009 | 4376 | 4372 | 30995 | 66.6 | AGCCCGTTGAGTAAAGCGTT | 36 | 12 | 20 | 6 | 12 | 0 |
| 9010 | 4377 | 4373 | 41293 | 66.7 | AGCCCGTTAGTGAAAGACGG | 36 | 12 | 22 | 6 | 35 | 0 |
| 9011 | 4378 | 4374 | 12439 | 70.5 | AGCCCGTTATCGTGATTGCG | 36 | 12 | 24 | 2 | 29 | 0 |
| 9012 | 4379 | 4375 | 12441 | 75.4 | AGCCCGTTTCCCGATGCCAT | 36 | 12 | 28 | 27 | 15 | 1 |
| 9013 | 4380 | 4376 | 12442 | 75.6 | AGCCCGTTTGCGCGTTCTCA | 36 | 12 | 29 | 12 | 13 | 0 |
| 9014 | 4381 | 4377 | 12444 | 70.4 | AGCCCGTTGACCATACTGCG | 36 | 12 | 32 | 5 | 29 | 0 |
| 9015 | 4382 | 4378 | 12445 | 68.2 | AGCCCGTTGTGCTACAATCG | 36 | 12 | 33 | 7 | 24 | 0 |
| 9016 | 4383 | 4379 | 41295 | 67.9 | AGCCCTCATTGATGTCTGCG | 36 | 13 | 1 | 9 | 29 | 0 |
| 9017 | 4384 | 4380 | 12447 | 70.2 | AGCCCTCATGATCCATTGCG | 36 | 13 | 2 | 15 | 29 | 0 |
| 9018 | 4385 | 4381 | 30996 | 69.6 | AGCCCTCAAAAGGCAAGCAA | 36 | 13 | 6 | 21 | 21 | 0 |
| 9019 | 4386 | 4382 | 41296 | 69.7 | AGCCCTCACTTGGAGTTGCG | 36 | 13 | 11 | 20 | 29 | 0 |
| 9020 | 4387 | 4383 | 12453 | 71.2 | AGCCCTCACCATGGACGCTT | 36 | 13 | 15 | 34 | 17 | 0 |
| 9021 | 4388 | 4384 | 30997 | 66 | AGCCCTGTTGATATCGGACC | 36 | 14 | 2 | 24 | 32 | 0 |
| 9022 | 4389 | 4385 | 12467 | 65.4 | AGCCCTGTTGTCATACGTGC | 36 | 14 | 9 | 5 | 33 | 0 |
| 9023 | 4390 | 4386 | 30998 | 70.2 | AGCCCTGTCCATGCAAGTGC | 36 | 14 | 15 | 21 | 33 | 0 |
| 9024 | 4391 | 4387 | 41303 | 70.5 | AGCCCTGTGCTTTCGTCACG | 36 | 14 | 17 | 10 | 30 | 0 |
| 9025 | 4392 | 4388 | 41304 | 68.9 | AGCCCTGTGGTAGCAAAGCC | 36 | 14 | 18 | 21 | 36 | 0 |
| 9026 | 4393 | 4389 | 16828 | 70.3 | AGCCCTGTACCTCAGCGCAA | 36 | 14 | 23 | 31 | 21 | 0 |
| 9027 | 4394 | 4390 | 12474 | 69 | AGCCCTGTATCGCCTAACGG | 36 | 14 | 24 | 26 | 35 | 0 |
| 9028 | 4395 | 4391 | 41306 | 74.3 | AGCCCTGTCACGGTGCCGTT | 36 | 14 | 30 | 33 | 12 | 0 |
| 9029 | 4396 | 4392 | 31000 | 68.4 | AGCCCTGTAGCCCTTGGGTA | 36 | 14 | 36 | 11 | 18 | 0 |
| 9030 | 4397 | 4393 | 41308 | 66.3 | AGCCCATTTGATTAGCGTT | 36 | 15 | 1 | 3 | 12 | 0 |
| 9031 | 4398 | 4394 | 41310 | 68.7 | AGCCCATAATCCGAAGTGC | 36 | 15 | 4 | 16 | 33 | 0 |
| 9032 | 4399 | 4395 | 31001 | 68.6 | AGCCCATAAAGTCCCGATG | 36 | 15 | 6 | 28 | 27 | 1 |
| 9033 | 4400 | 4396 | 16834 | 66.7 | AGCCCATTACATCGTGACC | 36 | 15 | 7 | 10 | 32 | 0 |
| 9034 | 4401 | 4397 | 16835 | 69.4 | AGCCCATTGTCGTCTACGG | 36 | 15 | 9 | 19 | 35 | 0 |
| 9035 | 4402 | 4398 | 12485 | 66.8 | AGCCCATTCGTCTCAGATG | 36 | 15 | 10 | 13 | 27 | 0 |
| 9036 | 4403 | 4399 | 12486 | 68 | AGCCCATCTCAGATGGGAC | 36 | 15 | 13 | 27 | 34 | 0 |
| 9037 | 4404 | 4400 | 16836 | 71.1 | AGCCCATCGAACACGGTCT | 36 | 15 | 16 | 30 | 19 | 0 |
| 9038 | 4405 | 4401 | 31002 | 68.7 | AGCCCATCAGCCCATAAAG | 36 | 15 | 31 | 15 | 6 | 0 |
| 9039 | 4406 | 4402 | 31004 | 71.5 | AGCCCATACGGCCTACGAA | 36 | 15 | 35 | 26 | 16 | 0 |
| 9040 | 4407 | 4403 | 41314 | 68.3 | AGCCCGAATTGAACCTCGTT | 36 | 16 | 1 | 23 | 12 | 0 |
| 9041 | 4408 | 4404 | 12497 | 66.7 | AGCCCGAAATACCGAACTTG | 36 | 16 | 5 | 16 | 11 | 0 |
| 9042 | 4409 | 4405 | 16840 | 63.7 | CGAAAAGATACGTCTTGCG | 16 | 6 | 5 | 19 | 29 | 0 |
| 9043 | 4410 | 4406 | 41315 | 66.1 | AGCCCGAATACACTTGGGAC | 36 | 16 | 7 | 11 | 34 | 0 |
| 9044 | 4411 | 4407 | 12501 | 73.5 | AGCCCGAATCGTGTGCATCG | 36 | 16 | 10 | 33 | 24 | 0 |
| 9045 | 4412 | 4408 | 31005 | 71.9 | AGCCCGAACTTGGGTATGCG | 36 | 16 | 11 | 18 | 29 | 0 |
| 9046 | 4413 | 4409 | 31006 | 66.5 | AGCCCGAACTCAGTCTACGG | 36 | 16 | 13 | 19 | 35 | 0 |
| 9047 | 4414 | 4410 | 12503 | 67.3 | AGCCCGAACGAACTGTTCTG | 36 | 16 | 16 | 14 | 8 | 0 |
| 9048 | 4415 | 4411 | 41317 | 69.1 | AGCCCGAAGCTTACGGAGTG | 36 | 16 | 17 | 35 | 22 | 0 |
| 9049 | 4416 | 4412 | 31007 | 67.7 | AGCCCGAAGAGTGTCTGCAA | 36 | 16 | 20 | 19 | 21 | 0 |

FIG. 290000

| SEQ ID NO: | ZIP ID# | 4,633 HEX ID# | ID# | Tm | ZIPCODE (NH2 -> CONH2) | TETRAMER NUMBERS | | | | "UNALLOWED DIMERS" |
|---|---|---|---|---|---|---|---|---|---|---|
| 9050 | 4417 | 4413 | 12509 | 71.3 | AGCCCGAAATCGCTGTAGCC | 36 | 16 | 24 | 14 36 | 0 |
| 9051 | 4418 | 4414 | 31008 | 70.9 | AGCCCGAAAGGATCTGACGG | 36 | 16 | 25 | 8 35 | 0 |
| 9052 | 4419 | 4415 | 16843 | 73.8 | AGCCCGAATGCGCGTTACCT | 36 | 16 | 29 | 12 23 | 0 |
| 9053 | 4420 | 4416 | 12513 | 71.7 | AGCCCGAACACGTCCCAAAG | 36 | 16 | 30 | 28 6 | 0 |
| 9054 | 4421 | 4417 | 12515 | 68.5 | AGCCCGAAGGACGGTATGTC | 36 | 16 | 34 | 18 9 | 0 |
| 9055 | 4422 | 4418 | 12516 | 73.1 | AGCCCGAAACGGGGACTCTG | 36 | 16 | 35 | 34 8 | 0 |
| 9056 | 4423 | 4419 | 41319 | 64.5 | AGCCGCTTTGATAGGAAGTG | 36 | 17 | 2 | 25 22 | 0 |
| 9057 | 4424 | 4420 | 31009 | 66.8 | AGCCGCTTTTAGGGTACGAA | 36 | 17 | 3 | 18 16 | 0 |
| 9058 | 4425 | 4421 | 16846 | 64.6 | AGCCGCTTATACTGTCAGCC | 36 | 17 | 5 | 9 36 | 0 |
| 9059 | 4426 | 4422 | 12523 | 70.5 | AGCCGCTTTGTCGCTTGGTA | 36 | 17 | 9 | 17 18 | 0 |
| 9060 | 4427 | 4423 | 31010 | 68.8 | AGCCGCTTCTTGTGATGCAA | 36 | 17 | 11 | 2 21 | 0 |
| 9061 | 4428 | 4424 | 31011 | 68.2 | AGCCGCTTCTGTTCGTGATG | 36 | 17 | 14 | 10 27 | 0 |
| 9062 | 4429 | 4425 | 31012 | 68.8 | AGCCGCTTCCATTTGAGACC | 36 | 17 | 15 | 1 32 | 0 |
| 9063 | 4430 | 4426 | 31013 | 68.5 | AGCCGCTTGGTAGGACGTCT | 36 | 17 | 18 | 34 19 | 0 |
| 9064 | 4431 | 4427 | 12533 | 77.4 | AGCCGCTTTGCGCTCAACGG | 36 | 17 | 29 | 13 35 | 0 |
| 9065 | 4432 | 4428 | 12534 | 72.4 | AGCCGCTTCAGCGAGTACGG | 36 | 17 | 31 | 20 35 | 0 |
| 9066 | 4433 | 4429 | 12536 | 77 | AGCCGCTTGTGCCACGTCCC | 36 | 17 | 33 | 30 28 | 0 |
| 9067 | 4434 | 4430 | 41324 | 68.8 | AGCCGGTATTGATCCCCTCA | 36 | 18 | 1 | 28 13 | 0 |
| 9068 | 4435 | 4431 | 31014 | 67.2 | AGCCGGTAAATCACCTGTGC | 36 | 18 | 4 | 23 33 | 0 |
| 9069 | 4436 | 4432 | 41325 | 69.2 | AGCCGGTAAAAGGTCTTGCG | 36 | 18 | 6 | 19 29 | 0 |
| 9070 | 4437 | 4433 | 16852 | 67.3 | AGCCGGTATCTGCCATCTTG | 36 | 18 | 8 | 15 11 | 0 |
| 9071 | 4438 | 4434 | 12542 | 66.9 | AGCCGGTATCGTTTGACGTT | 36 | 18 | 10 | 1 12 | 0 |
| 9072 | 4439 | 4435 | 22438 | 70.9 | AGCCGGTACTGTTCCCAGCC | 36 | 18 | 14 | 28 36 | 0 |
| 9073 | 4440 | 4436 | 22439 | 63.7 | AGCCGGTAGGTACCATAGGA | 36 | 18 | 18 | 15 25 | 0 |
| 9074 | 4441 | 4437 | 31015 | 67.4 | AGCCGGTAGAGTCAGCATCG | 36 | 18 | 20 | 31 24 | 0 |
| 9075 | 4442 | 4438 | 16861 | 70.3 | AGCCGGTATCCCCTTGTCGT | 36 | 18 | 28 | 11 10 | 0 |
| 9076 | 4443 | 4439 | 12559 | 68.1 | AGCCGTCTAATCGGACCCAT | 36 | 19 | 4 | 34 15 | 0 |
| 9077 | 4444 | 4440 | 12561 | 65 | AGCCGTCTTACAATCGATCG | 36 | 19 | 7 | 24 24 | 0 |
| 9078 | 4445 | 4441 | 16866 | 66 | AGCCGTCTACCTTCGTAGCC | 36 | 19 | 23 | 10 36 | 0 |
| 9079 | 4446 | 4442 | 12572 | 67.5 | AGCCGTCTGATGTCGTGCTT | 36 | 19 | 27 | 10 17 | 0 |
| 9080 | 4447 | 4443 | 12574 | 67.6 | AGCCGTCTCACGATCGTGTC | 36 | 19 | 30 | 24 9 | 0 |
| 9081 | 4448 | 4444 | 31017 | 73 | AGCCGTCTCAGCACGGCTTG | 36 | 19 | 31 | 35 11 | 0 |
| 9082 | 4449 | 4445 | 12576 | 69.2 | AGCCGTCTGACCGAGTGACC | 36 | 19 | 32 | 20 32 | 0 |
| 9083 | 4450 | 4447 | 31018 | 68.9 | AGCCGTCTAGCCAATCGCTT | 36 | 19 | 36 | 4 17 | 0 |
| 9084 | 4451 | 4449 | 41333 | 72.1 | AGCCGAGTTGTCCACGCCAT | 36 | 20 | 9 | 30 15 | 0 |
| 9085 | 4452 | 4450 | 12582 | 66.6 | AGCCGAGTTCGTGAGTAGCC | 36 | 20 | 10 | 20 36 | 0 |
| 9086 | 4453 | 4451 | 12586 | 65.8 | AGCCGAGTGTCTTACATGCG | 36 | 20 | 19 | 7 29 | 0 |
| 9087 | 4454 | 4452 | 31019 | 69.4 | AGCCGAGTATCGCAGCCTGT | 36 | 20 | 24 | 31 14 | 0 |
| 9088 | 4455 | 4453 | 31020 | 65.3 | AGCCGAGTCCTATTGATCCC | 36 | 20 | 26 | 1 28 | 0 |
| 9089 | 4456 | 4454 | 41335 | 68.7 | AGCCGAGTGATGTCCCGAGT | 36 | 20 | 27 | 28 20 | 0 |
| 9090 | 4457 | 4455 | 22446 | 67.7 | AGCCGAGTTGCGTTGACTGT | 36 | 20 | 29 | 1 14 | 0 |
| 9091 | 4458 | 4456 | 16874 | 71.7 | AGCCGAGTAGCCCAGCCTCA | 36 | 20 | 36 | 31 13 | 0 |
| 9092 | 4459 | 4457 | 41337 | 70.4 | AGCCGCAATTGAAGGAGCAA | 36 | 21 | 1 | 25 21 | 0 |
| 9093 | 4460 | 4458 | 31021 | 67 | AGCCGCAATGATAGCCTGAT | 36 | 21 | 2 | 36 2 | 0 |
| 9094 | 4461 | 4459 | 12596 | 73.2 | AGCCGCAATTAGCGAATGCG | 36 | 21 | 3 | 16 29 | 0 |
| 9095 | 4462 | 4460 | 31022 | 67.2 | AGCCGCAATACAAGTGTCCC | 36 | 21 | 7 | 22 28 | 1 |
| 9096 | 4463 | 4461 | 41338 | 68.7 | AGCCGCAATCTGGGTAGGAC | 36 | 21 | 8 | 18 34 | 0 |
| 9097 | 4464 | 4462 | 41339 | 73.3 | AGCCGCAACGTTTGCGTGAT | 36 | 21 | 12 | 29 2 | 0 |

*FIG. 29PPPP*

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 9098 | 4465 | 4463 | 31023 | 71.3 | AGCCGCAACTCAAGGAAGCC | 36 | 21 | 13 | 25 | 36 | 0 |
| 9099 | 4466 | 4464 | 12602 | 70 | AGCCGCAACGAAGGTAATCG | 36 | 21 | 16 | 18 | 24 | 0 |
| 9100 | 4467 | 4465 | 12603 | 70.9 | AGCCGCAAGCTTGAGTCACG | 36 | 21 | 17 | 20 | 30 | 0 |
| 9101 | 4468 | 4466 | 41340 | 74.2 | AGCCGCAAGCAATCCCCTTG | 36 | 21 | 21 | 28 | 11 | 0 |
| 9102 | 4469 | 4467 | 12608 | 73.8 | AGCCGCAAATCGGCAAACCT | 36 | 21 | 24 | 21 | 23 | 0 |
| 9103 | 4470 | 4468 | 12609 | 71.8 | AGCCGCAAAGGAGCAACGTT | 36 | 21 | 25 | 21 | 12 | 0 |
| 9104 | 4471 | 4469 | 12610 | 71.9 | AGCCGCAATCCCGGTAAGTG | 36 | 21 | 28 | 18 | 22 | 0 |
| 9105 | 4472 | 4470 | 12611 | 76.5 | AGCCGCAATGCGATCGCTCA | 36 | 21 | 29 | 24 | 13 | 0 |
| 9106 | 4473 | 4471 | 31024 | 74.6 | AGCCGCAACACGCTGTGTGC | 36 | 21 | 30 | 14 | 33 | 0 |
| 9107 | 4474 | 4472 | 41342 | 71.4 | AGCCGCAAGTGCATACACGG | 36 | 21 | 33 | 5 | 35 | 0 |
| 9108 | 4475 | 4473 | 12615 | 73.3 | AGCCGCAAACGGCCTAGCTT | 36 | 21 | 35 | 26 | 17 | 0 |
| 9109 | 4476 | 4474 | 12616 | 72.2 | AGCCGCAAAGCCCTGTCTTG | 36 | 21 | 36 | 14 | 11 | 0 |
| 9110 | 4477 | 4475 | 41343 | 69 | AGCCAGTGTCGTATCGCACG | 36 | 22 | 10 | 24 | 30 | 0 |
| 9111 | 4478 | 4476 | 16878 | 66.9 | AGCCAGTGCTTGAGTGGGAC | 36 | 22 | 11 | 22 | 34 | 0 |
| 9112 | 4479 | 4477 | 31025 | 68.6 | AGCCAGTGCTGTGATGACGG | 36 | 22 | 14 | 27 | 35 | 0 |
| 9113 | 4480 | 4478 | 41345 | 69.5 | AGCCAGTGGGTACAGCAGCC | 36 | 22 | 18 | 31 | 36 | 0 |
| 9114 | 4481 | 4479 | 12622 | 68.6 | AGCCAGTGACCTGCTTTCCC | 36 | 22 | 23 | 17 | 28 | 0 |
| 9115 | 4482 | 4480 | 12623 | 67.2 | AGTGATCGGAGTACGGCAGC | 22 | 24 | 20 | 35 | 31 | 0 |
| 9116 | 4483 | 4481 | 16881 | 68.8 | AGCCAGTGTGCGATACCACG | 36 | 22 | 29 | 5 | 30 | 0 |
| 9117 | 4484 | 4482 | 12629 | 69.8 | AGCCAGTGGACCAGGAGCAA | 36 | 22 | 32 | 25 | 21 | 0 |
| 9118 | 4485 | 4483 | 31027 | 68.1 | ACCTTGTCAGGACACGGCAA | 23 | 9 | 25 | 30 | 21 | 0 |
| 9119 | 4486 | 4484 | 41346 | 66.3 | AGCCACCTTCGTAAAGCCAT | 36 | 23 | 10 | 6 | 15 | 0 |
| 9120 | 4487 | 4485 | 31028 | 67.6 | ACCTCGAATGTCCTTGCGAA | 23 | 16 | 9 | 11 | 16 | 0 |
| 9121 | 4488 | 4486 | 12643 | 64.9 | ACCTATCGACCTGATGGCAA | 23 | 24 | 23 | 27 | 21 | 0 |
| 9122 | 4489 | 4487 | 12644 | 64.9 | ACCTAGGAAGTGCTCATGCG | 23 | 25 | 22 | 13 | 29 | 0 |
| 9123 | 4490 | 4488 | 12646 | 68.3 | AGCCACCTCACGAATCTCCC | 36 | 23 | 30 | 4 | 28 | 0 |
| 9124 | 4491 | 4489 | 12656 | 69.5 | AGCCATCGCGAATTGAGGAC | 36 | 24 | 16 | 1 | 34 | 0 |
| 9125 | 4492 | 4490 | 12661 | 71.9 | AGCCATCGGCAAAATCCAGC | 36 | 24 | 21 | 4 | 31 | 0 |
| 9126 | 4493 | 4491 | 31030 | 66.1 | AGCCATCGCCTAATACCCAT | 36 | 24 | 26 | 5 | 15 | 0 |
| 9127 | 4494 | 4492 | 12667 | 66.5 | AGGAATACGGTATCCCTGCG | 25 | 5 | 18 | 28 | 29 | 0 |
| 9128 | 4495 | 4493 | 16892 | 65.7 | AGGAAAAGTTGACACGTGCG | 25 | 6 | 1 | 30 | 29 | 1 |
| 9129 | 4496 | 4494 | 12669 | 68.6 | AGCCAGGATACATGCGCTCA | 36 | 25 | 7 | 29 | 13 | 0 |
| 9130 | 4497 | 4495 | 12670 | 70 | AGCCAGGATCTGCACGCTGT | 36 | 25 | 8 | 30 | 14 | 0 |
| 9131 | 4498 | 4496 | 41354 | 68.4 | AGCCAGGACGTTTGTCTCCC | 36 | 25 | 12 | 9 | 28 | 0 |
| 9132 | 4499 | 4497 | 12671 | 68.3 | AGCCAGGACTCAAGCCGAGT | 36 | 25 | 13 | 36 | 20 | 0 |
| 9133 | 4500 | 4498 | 16893 | 66.9 | AGCCAGGACCATTTGAGTGC | 36 | 25 | 15 | 1 | 33 | 0 |
| 9134 | 4501 | 4499 | 12677 | 65 | AGCCAGGAGCAAATACGATG | 36 | 25 | 21 | 5 | 27 | 0 |
| 9135 | 4502 | 4500 | 16895 | 72.5 | AGCCAGGATGCGCGAAGGTA | 36 | 25 | 29 | 16 | 18 | 0 |
| 9136 | 4503 | 4501 | 12681 | 67 | AGGACAGCCTTGAATCACGG | 25 | 31 | 11 | 4 | 35 | 0 |
| 9137 | 4504 | 4502 | 12682 | 66.4 | AGCCAGGAGACCTCGTCTCA | 36 | 25 | 32 | 10 | 13 | 0 |
| 9138 | 4505 | 4503 | 31031 | 68.6 | AGCCAGGAGGACAAAGGTGC | 36 | 25 | 34 | 6 | 33 | 0 |
| 9139 | 4506 | 4504 | 31032 | 70.1 | AGGAACGGCCATAATCGCAA | 25 | 35 | 15 | 4 | 21 | 0 |
| 9140 | 4507 | 4505 | 31033 | 66.5 | AGCCCCTATGATAGCCGATG | 36 | 26 | 2 | 36 | 27 | 0 |
| 9141 | 4508 | 4506 | 31034 | 71.7 | AGCCCCTATGTCAGCCCACG | 36 | 26 | 9 | 36 | 30 | 0 |
| 9142 | 4509 | 4507 | 41356 | 65.6 | AGCCCCTACTTGAGGACAGC | 36 | 26 | 11 | 25 | 31 | 0 |
| 9143 | 4510 | 4508 | 41357 | 63.9 | AGCCCCTACTCACTCAATCG | 36 | 26 | 13 | 13 | 24 | 0 |
| 9144 | 4511 | 4509 | 16902 | 69.9 | AGCCCCTAGAGTGCAATGCG | 36 | 26 | 20 | 21 | 29 | 0 |
| 9145 | 4512 | 4510 | 41358 | 69.5 | AGCCCCTAGCAACCATGTGC | 36 | 26 | 21 | 15 | 33 | 0 |

FIG. 29QQQQ

| SEQ ID NO: | ZIP ID# | 4,633 ID# | HEX ID# | Tm | ZIPCODE (NH2 -> CONH2) | TETRAMER NUMBERS | | | | | 'UNALLOWED DIMERS' |
|---|---|---|---|---|---|---|---|---|---|---|---|
| 9146 | 4513 | 4511 | 31035 | 67 | AGCCCCTAACCTTCTGGCTT | 36 | 26 | 23 | 8 | 17 | 0 |
| 9147 | 4514 | 4512 | 12695 | 68.3 | AGCCCCTAGATGGCAATCGT | 36 | 26 | 27 | 21 | 10 | 0 |
| 9148 | 4515 | 4513 | 12697 | 63.8 | AGCCCCTACACGAATCAATC | 36 | 26 | 30 | 4 | 4 | 0 |
| 9149 | 4516 | 4514 | 12699 | 73.7 | AGCCCCTAACGGCACGCTGT | 36 | 26 | 35 | 30 | 14 | 0 |
| 9150 | 4517 | 4515 | 12700 | 65.3 | AGCCGATGTGATCTTGATCG | 36 | 27 | 2 | 11 | 24 | 0 |
| 9151 | 4518 | 4516 | 12701 | 65.9 | AGCCGATGTTAGTTGATGCG | 36 | 27 | 3 | 1 | 29 | 0 |
| 9152 | 4519 | 4517 | 12703 | 65.1 | AGCCGATGTACATGTCGACC | 36 | 27 | 7 | 9 | 32 | 0 |
| 9153 | 4520 | 4518 | 12704 | 68.5 | AGCCGATGTCTGAATCGCAA | 36 | 27 | 8 | 4 | 21 | 0 |
| 9154 | 4521 | 4519 | 31036 | 73.7 | AGCCGATGTGTCAGCCTGCG | 36 | 27 | 9 | 36 | 29 | 0 |
| 9155 | 4522 | 4520 | 41363 | 69.4 | AGCCGATGCTCAACCTGCTT | 36 | 27 | 13 | 23 | 17 | 0 |
| 9156 | 4523 | 4521 | 22465 | 66.5 | AGCCGATGGCTTAGCCTTAG | 36 | 27 | 17 | 36 | 3 | 0 |
| 9157 | 4524 | 4522 | 16908 | 69.1 | AGCCGATGACCTCAGCCCTA | 36 | 27 | 23 | 31 | 26 | 0 |
| 9158 | 4525 | 4523 | 41364 | 70.3 | AGCCGATGCCTACCATGTGC | 36 | 27 | 26 | 15 | 33 | 0 |
| 9159 | 4526 | 4524 | 31038 | 69.2 | AGCCTCCCTTGAACCTTCCC | 36 | 28 | 1 | 23 | 28 | 1 |
| 9160 | 4527 | 4525 | 31039 | 70.2 | AGCCTCCCATACTGCGCTCA | 36 | 28 | 5 | 29 | 13 | 0 |
| 9161 | 4528 | 4526 | 41367 | 69 | AGCCTCCCTACAACCTTGCG | 36 | 28 | 7 | 23 | 29 | 0 |
| 9162 | 4529 | 4527 | 16911 | 68.6 | AGCCTCCCTGTCAAAGGTGC | 36 | 28 | 9 | 6 | 33 | 0 |
| 9163 | 4530 | 4528 | 12724 | 70.5 | AGCCTCCCTCGTACGGGGTA | 36 | 28 | 10 | 35 | 18 | 0 |
| 9164 | 4531 | 4529 | 12725 | 67.7 | TCCCCTTGTTGAAGTGACGG | 28 | 11 | 1 | 22 | 35 | 1 |
| 9165 | 4532 | 4530 | 22467 | 68.9 | AGCCTCCCCCATCCTAGGAC | 36 | 28 | 15 | 26 | 34 | 0 |
| 9166 | 4533 | 4531 | 31040 | 73 | AGCCTCCCCGAATCTGGTGC | 36 | 28 | 16 | 8 | 33 | 0 |
| 9167 | 4534 | 4532 | 41368 | 69.1 | TCCCGTCTGGTAGGACGCTT | 28 | 19 | 18 | 34 | 17 | 0 |
| 9168 | 4535 | 4533 | 31041 | 69.1 | AGCCTCCCGAGTCCTATCCC | 36 | 28 | 20 | 26 | 28 | 0 |
| 9169 | 4536 | 4534 | 16914 | 70.2 | TCCCAGTGCTTGCTTGGACC | 28 | 22 | 11 | 11 | 32 | 0 |
| 9170 | 4537 | 4535 | 12733 | 67.5 | TCCCATCGTTGAAATCGGAC | 28 | 24 | 1 | 4 | 34 | 0 |
| 9171 | 4538 | 4536 | 22471 | 67.3 | TCCCAGGACCTATCGTCGAA | 28 | 25 | 26 | 10 | 16 | 0 |
| 9172 | 4539 | 4537 | 22472 | 65.6 | AGCCTCCCCCTACTGTCTCA | 36 | 28 | 26 | 14 | 13 | 0 |
| 9173 | 4540 | 4538 | 12734 | 74.2 | AGCCTCCCGATGGATGGCAA | 36 | 28 | 27 | 27 | 21 | 0 |
| 9174 | 4541 | 4539 | 12735 | 74.1 | AGCCTCCCTCCCGCAAACCT | 36 | 28 | 28 | 21 | 23 | 0 |
| 9175 | 4542 | 4540 | 12736 | 73 | AGCCTCCCGTGCATCGTTGA | 36 | 28 | 33 | 24 | 1 | 0 |
| 9176 | 4543 | 4541 | 12737 | 73.7 | TCCCACGGCCATGAGTCGAA | 28 | 35 | 15 | 20 | 16 | 0 |
| 9177 | 4544 | 4542 | 12738 | 70.6 | AGCCTCCCAGCCAAAGTCGT | 36 | 28 | 36 | 6 | 10 | 0 |
| 9178 | 4545 | 4543 | 12739 | 68.8 | TGCGAATCGGTAAGTGCGTT | 29 | 4 | 18 | 22 | 12 | 0 |
| 9179 | 4546 | 4544 | 31042 | 68.8 | AGCCTGCGAAAGTCTGTCCC | 36 | 29 | 6 | 8 | 28 | 0 |
| 9180 | 4547 | 4546 | 22477 | 73.6 | AGCCTGCGCTCACTTGGCAA | 36 | 29 | 13 | 11 | 21 | 0 |
| 9181 | 4548 | 4547 | 12745 | 70.3 | TGCGCTGTGTCTTGTCCGAA | 29 | 14 | 19 | 9 | 16 | 0 |
| 9182 | 4549 | 4548 | 12748 | 70 | AGCCTGCGGAGTGATGCTGT | 36 | 29 | 20 | 27 | 14 | 0 |
| 9183 | 4550 | 4549 | 31043 | 71 | TGCGAGTGGAGTTCCCATCG | 29 | 22 | 20 | 28 | 24 | 0 |
| 9184 | 4551 | 4550 | 31044 | 68.9 | AGCCTGCGAGGAGCTTCCTA | 36 | 29 | 25 | 17 | 26 | 0 |
| 9185 | 4552 | 4551 | 12751 | 72.9 | AGCCTGCGTGCGAAAGCCTA | 36 | 29 | 29 | 6 | 26 | 0 |
| 9186 | 4553 | 4552 | 12752 | 75.9 | TGCGCACGCTCATCTGCAGC | 29 | 30 | 13 | 8 | 31 | 0 |
| 9187 | 4554 | 4553 | 12753 | 77.3 | AGCCTGCGGGTGCGATGAGCC | 36 | 29 | 33 | 27 | 36 | 0 |
| 9188 | 4555 | 4554 | 31045 | 72.1 | AGCCCACGAATCGACCGGTA | 36 | 30 | 4 | 32 | 18 | 0 |
| 9189 | 4556 | 4555 | 41379 | 65.4 | AGCCCACGTACACTCAATCG | 36 | 30 | 7 | 13 | 24 | 0 |
| 9190 | 4557 | 4556 | 12760 | 72.4 | AGCCCACGCTTGGCAAGGTA | 36 | 30 | 11 | 21 | 18 | 0 |
| 9191 | 4558 | 4557 | 22487 | 65.9 | AGCCCACGGTCTAGGAGGTA | 36 | 30 | 19 | 25 | 18 | 0 |
| 9192 | 4559 | 4558 | 16921 | 73.3 | AGCCCACGACCTTCCCCTCA | 36 | 30 | 23 | 28 | 13 | 1 |
| 9193 | 4560 | 4559 | 31047 | 71.7 | AGCCCACGCCTACGTTGCTT | 36 | 30 | 26 | 12 | 17 | 0 |

FIG. 29RRRR

| SEQ ID NO: | ZIP ID# | 4,633 ID# | HEX ID# Tm | ZIPCODE (NH2 -> CONH2) | TETRAMER NUMBERS | | | | "UNALLOWED DIMERS" |
|---|---|---|---|---|---|---|---|---|---|
| 9194 | 4561 | 4560 | 12769 75.5 | AGCCCACGCAGCGGACTTGA | 36 30 | 31 | 34 | 1 | 0 |
| 9195 | 4562 | 4561 | 12770 77.5 | AGCCCACGGACCGCTTGCAA | 36 30 | 32 | 17 | 21 | 0 |
| 9196 | 4563 | 4562 | 12772 74.5 | AGCCCACGACGGCTCAAGGA | 36 30 | 35 | 13 | 25 | 0 |
| 9197 | 4564 | 4563 | 41381 65.8 | CAGCTGATCCTAGACCGCAA | 31 2 | 26 | 32 | 21 | 0 |
| 9198 | 4565 | 4564 | 22490 67 | AGCCCAGCTTAGAGTGCAGC | 36 31 | 3 | 22 | 31 | 0 |
| 9199 | 4566 | 4565 | 31048 69.5 | AGCCCAGCAAAGGACCAGTG | 36 31 | 6 | 32 | 22 | 0 |
| 9200 | 4567 | 4566 | 31049 66.1 | AGCCCAGCTACAGATGTCCC | 36 31 | 7 | 27 | 28 | 0 |
| 9201 | 4568 | 4567 | 16923 71.9 | AGCCCAGCTCGTGCTTGCTT | 36 31 | 10 | 17 | 17 | 0 |
| 9202 | 4569 | 4568 | 12780 71.3 | AGCCCAGCCCATTTGAAGGA | 36 31 | 15 | 1 | 25 | 0 |
| 9203 | 4570 | 4569 | 12781 69.3 | AGCCCAGCGCTTACCTATCG | 36 31 | 17 | 23 | 24 | 0 |
| 9204 | 4571 | 4570 | 31050 66.7 | AGCCCAGCGTCTATACCAGC | 36 31 | 19 | 5 | 31 | 0 |
| 9205 | 4572 | 4571 | 31051 70.8 | AGCCCAGCAGGACTGTTCCC | 36 31 | 25 | 14 | 28 | 0 |
| 9206 | 4573 | 4572 | 12787 72.7 | AGCCCAGCGACCCTCAACCT | 36 31 | 32 | 13 | 23 | 0 |
| 9207 | 4574 | 4573 | 12789 73.6 | AGCCCAGCAGCCCCATCCTA | 36 31 | 36 | 15 | 26 | 0 |
| 9208 | 4575 | 4574 | 22495 66.9 | AGCCGACCTTGAGGTACGAA | 36 32 | 1 | 18 | 16 | 0 |
| 9209 | 4576 | 4575 | 41384 73 | AGCCGACCTGATGGACGCAA | 36 32 | 2 | 34 | 21 | 0 |
| 9210 | 4577 | 4576 | 12794 73.4 | AGCCGACCAAAGCAGCTCCC | 36 32 | 6 | 31 | 28 | 0 |
| 9211 | 4578 | 4577 | 12796 68.5 | AGCCGACCCTTGAAAGCTGT | 36 32 | 11 | 6 | 14 | 0 |
| 9212 | 4579 | 4578 | 12798 67.6 | AGCCGACCCTCACCTAGGAC | 36 32 | 13 | 26 | 34 | 0 |
| 9213 | 4580 | 4579 | 41385 71.4 | AGCCGACCGTCTGATGTCCC | 36 32 | 19 | 27 | 28 | 0 |
| 9214 | 4581 | 4580 | 12801 69.6 | AGCCGACCGCAACTCAAATC | 36 32 | 21 | 13 | 4 | 0 |
| 9215 | 4582 | 4581 | 12802 67.1 | AGCCGACCAGTGTTAGGTGC | 36 32 | 22 | 3 | 33 | 0 |
| 9216 | 4583 | 4582 | 31052 73 | AGCCGACCATCGTCTGGCAA | 36 32 | 24 | 8 | 21 | 0 |
| 9217 | 4584 | 4583 | 16926 71.5 | AGCCGACCAGGAAGTGCGTT | 36 32 | 25 | 22 | 12 | 0 |
| 9218 | 4585 | 4584 | 12807 72.1 | AGCCGACCCACGAGTGCTGT | 36 32 | 30 | 22 | 14 | 0 |
| 9219 | 4586 | 4585 | 12809 72.8 | AGCCGACCGTGCATCGAAAG | 36 32 | 33 | 24 | 6 | 0 |
| 9220 | 4587 | 4587 | 31053 71.8 | AGCCGTGCAATCTCGTTCCC | 36 33 | 4 | 10 | 28 | 0 |
| 9221 | 4588 | 4588 | 31054 67.4 | AGCCGTGCATACCCTACAGC | 36 33 | 5 | 26 | 31 | 0 |
| 9222 | 4589 | 4589 | 12814 70 | AGCCGTGCTCTGAGTGCCAT | 36 33 | 8 | 22 | 15 | 0 |
| 9223 | 4590 | 4590 | 12816 70.1 | AGCCGTGCTCGTTCGTGTCT | 36 33 | 10 | 10 | 19 | 0 |
| 9224 | 4591 | 4591 | 12817 73.3 | AGCCGTGCCTTGGAGTGCAA | 36 33 | 11 | 20 | 21 | 0 |
| 9225 | 4592 | 4592 | 12818 72.8 | AGCCGTGCCGAAGCAATGTC | 36 33 | 16 | 21 | 9 | 0 |
| 9226 | 4593 | 4593 | 12819 75.7 | AGCCGTGCGCTTGTGCTCGT | 36 33 | 17 | 33 | 10 | 0 |
| 9227 | 4594 | 4594 | 31055 74.2 | AGCCGTGCGTCTGCTTTCCC | 36 33 | 19 | 17 | 28 | 0 |
| 9228 | 4595 | 4595 | 12821 73.1 | AGCCGTGCATCGGCAACTGT | 36 33 | 24 | 21 | 14 | 0 |
| 9229 | 4596 | 4596 | 12824 74.5 | AGCCGTGCGGACCTTGTCGT | 36 33 | 34 | 11 | 10 | 0 |
| 9230 | 4597 | 4597 | 31056 63.7 | AGCCGGACTTAGTACAAGCC | 36 34 | 3 | 7 | 36 | 0 |
| 9231 | 4598 | 4598 | 12830 67.4 | AGCCGGACTGTCTCGTGGTA | 36 34 | 9 | 10 | 18 | 0 |
| 9232 | 4599 | 4599 | 12831 73.8 | AGCCGGACCGTTTGTCGACC | 36 34 | 12 | 9 | 32 | 0 |
| 9233 | 4600 | 4600 | 12833 73.5 | AGCCGGACCCATCAGCGAGT | 36 34 | 15 | 31 | 20 | 0 |
| 9234 | 4601 | 4601 | 16931 72.7 | AGCCGGACGCTTCTTGCTCA | 36 34 | 17 | 11 | 13 | 0 |
| 9235 | 4602 | 4602 | 12836 68 | AGCCGGACACCTCTTGACCT | 36 34 | 23 | 11 | 23 | 0 |
| 9236 | 4603 | 4603 | 12837 72.8 | AGCCGGACATCGCGTTTCTG | 36 34 | 24 | 12 | 8 | 0 |
| 9237 | 4604 | 4604 | 22502 68.6 | AGCCGGACAGGACCTACAGC | 36 34 | 25 | 26 | 31 | 0 |
| 9238 | 4605 | 4605 | 12840 69.4 | AGCCGGACTCCCTACACACG | 36 34 | 28 | 7 | 30 | 0 |
| 9239 | 4606 | 4606 | 12842 74.9 | AGCCGGACGTGCGAGTGACC | 36 34 | 33 | 20 | 32 | 0 |
| 9240 | 4607 | 4607 | 12843 78.2 | AGCCGGACGGACGACCCAGC | 36 34 | 34 | 32 | 31 | 0 |
| 9241 | 4608 | 4608 | 12846 66.7 | AGCCACGGAATCTGATGCTT | 36 35 | 4 | 2 | 17 | 0 |

FIG. 29SSSS

| SEQ ID NO: | ZIP ID# | 4,633 ID# | HEX ID# | Tm | ZIPCODE (NH2 -> CONH2) | TETRAMER NUMBERS | | | | | "UNALLOWED DIMERS" |
|---|---|---|---|---|---|---|---|---|---|---|---|
| 9242 | 4609 | 4609 | 12847 | 69.1 | AGCCACGGATACCAGCTCGT | 36 | 35 | 5 | 31 | 10 | 0 |
| 9243 | 4610 | 4610 | 41393 | 66.5 | AGCCACGGAAAGAAAGGATG | 36 | 35 | 6 | 6 | 27 | 0 |
| 9244 | 4611 | 4611 | 31057 | 66 | AGCCACGGTACACCTATCCC | 36 | 35 | 7 | 26 | 28 | 0 |
| 9245 | 4612 | 4612 | 12849 | 72.1 | AGCCACGGTCTGGATGCGTT | 36 | 35 | 8 | 27 | 12 | 0 |
| 9246 | 4613 | 4613 | 31058 | 73.2 | AGCCACGGTGTCGGACATCG | 36 | 35 | 9 | 34 | 24 | 0 |
| 9247 | 4614 | 4614 | 31059 | 75.1 | AGCCACGGGCTTGCTTCACG | 36 | 35 | 17 | 17 | 30 | 0 |
| 9248 | 4615 | 4615 | 31060 | 70.8 | ACGGTCTGTCTGTGCCACG | 35 | 19 | 19 | 33 | 30 | 0 |
| 9249 | 4616 | 4616 | 12856 | 73.7 | AGCCACGGATCGGCTTTCGT | 36 | 35 | 24 | 17 | 10 | 0 |
| 9250 | 4617 | 4617 | 12859 | 73.5 | AGCCACGGGACCAGTGGACC | 36 | 35 | 32 | 22 | 32 | 0 |
| 9251 | 4618 | 4618 | 12860 | 70.2 | ACGGGTGCTACAGGACGTGC | 35 | 33 | 7 | 34 | 33 | 0 |
| 9252 | 4619 | 4619 | 16934 | 71.9 | AGCCACGGACGGCCTAAGTG | 36 | 35 | 35 | 26 | 22 | 0 |
| 9253 | 4620 | 4620 | 31061 | 65.9 | AGCCAGCCTGATACCTAGCC | 36 | 36 | 2 | 23 | 36 | 0 |
| 9254 | 4621 | 4621 | 41394 | 69 | AGCCAGCCAAAGACCTACGG | 36 | 36 | 6 | 23 | 35 | 0 |
| 9255 | 4622 | 4622 | 12866 | 71.3 | AGCCAGCCTCTGGACCAGGA | 36 | 36 | 8 | 32 | 25 | 0 |
| 9256 | 4623 | 4623 | 41395 | 66.9 | AGCCAGCCTCGTAGTGGGTA | 36 | 36 | 10 | 22 | 18 | 0 |
| 9257 | 4624 | 4624 | 12867 | 72.2 | AGCCAGCCCTTGTGTCCGAA | 36 | 36 | 11 | 9 | 16 | 0 |
| 9258 | 4625 | 4625 | 12868 | 73.7 | AGCCAGCCCGTTCGTTTCGT | 36 | 36 | 12 | 12 | 10 | 0 |
| 9259 | 4626 | 4626 | 16936 | 69.1 | AGCCAGCCCTCAGCTTCTTG | 36 | 36 | 13 | 17 | 11 | 0 |
| 9260 | 4627 | 4627 | 12870 | 72.5 | AGCCAGCCGCTTAGTGCAGC | 36 | 36 | 17 | 22 | 31 | 0 |
| 9261 | 4628 | 4628 | 12872 | 68.8 | AGCCAGCCGTCTTTGAGGAC | 36 | 36 | 19 | 1 | 34 | 0 |
| 9262 | 4629 | 4629 | 12874 | 68.5 | AGCCAGCCATCGTGATGATG | 36 | 36 | 24 | 2 | 27 | 0 |
| 9263 | 4630 | 4630 | 12876 | 76.3 | AGCCAGCCTCCCCAGCGATG | 36 | 36 | 28 | 31 | 27 | 0 |
| 9264 | 4631 | 4631 | 12878 | 78.3 | AGCCAGCCCACGCCATGCAA | 36 | 36 | 30 | 15 | 21 | 0 |
| 9265 | 4632 | 4632 | 12879 | 76.7 | AGCCAGCCGACCCAGCAGGA | 36 | 36 | 32 | 31 | 25 | 0 |
| 9266 | 4633 | 4633 | 12880 | 74.1 | AGCCAGCCGGACGGTAATCG | 36 | 36 | 34 | 18 | 24 | 0 |

FIG. 35A

```c
/* ANSI C code for ZIP-HYB3

The program compiled with this code must be copied
    into the same directory as the the input files.
    A minor inconvenience, but it avoids headaches.
    This is part of making the program "platform-
    independent." It should be possible to compile it
    with any ANSI C compiler.
*/ include <stdio.h>
include <stdlib.h>
#include <conio.h>
#include <ctype.h>
#include <math.h>
include <string.h> define FMax 60
define NMax 20
#define LMax 40
#define MisMax 10
/*
    FMax: maximum length of input and output file names
    NMax: maximum length of a sequence name (no spaces allowed)
    LMax: maximum length of a sequence (in nucleotides)
    MisMax: maximum number of mismatches allowed
*/

FILE *ifl1;   /* input file #1 (not the name!) */
FILE *ifl2;   /* input file #2 (not the name!) */
FILE *ofl;    /* output file (not the name!)   */

/* start global variables */
int badval;    /* general use for variable checking */
int check;     /* general use boolean character */
long tval;     /* general use for assignment of variable values */
char keychar;  /* general use for keyboard character checking */
```

FIG. 35B

```
char filechar;     /* general use for reading file characters */
char strng[10];    /* general use for variable checking */
char inm1[FMax];   /* input file #1 name; maximum of FMax characters */
char inm2[FMax];   /* input file #2 name; maximum of Fmax characters */
char onm[FMax];    /* output file name; maximum of Fmax characters */

/*
        Note: sequences (and their names) will not all be stored
        in memory. This allows for "unlimited" file sizes.
    */ char seqname[2][NMax];   /* name of current sequence from input files */
char sequence[2][LMax];  /* actual current sequence from input files */ int mmax=24;       /* Setting the maximum threshold for a match to 24 */
int Nmatch=6;      /* Number of sites that must match; default=6 */
long Totalcomp=0;  /* Number of comparisons made */
long Totalmatch=0; /* Number of comparisons meeting match criteria */
int nmax=NMax;     /* setting value of nmax for functions */
int lmax=Lmax;     /* setting value of lmax for functions */
int Nmisallow=0;   /* setting default value for number of misses allowed */
int mismax=MisMax; /* setting max number of mismatches allowed/*
int Nmatcharray[LMax][MisMax+1]; /* records number of matches of each
length */ char seqbase[16]={'A','G','C','T','U','R','Y','M',
                  'K','S','W','H','B','V','D','N'};
    /* array of allowable base characters
        (arranged in the most efficient order for basechecking loops):
        seqbase[0] = A
                1 = G
                2 = C
                3 = T
                4 = U
                5 = R (A or G)
                6 = Y (C, T or U)
                7 = M (A or C)
                8 = K (G, T or U)
```

/*A G C T U R Y M K S W H B V D N */
int basematch[16][16]={1,0,0,0,0,1,0,1,0,0,1,1,0,1,1,1,
                       0,1,0,0,0,1,0,0,1,1,0,0,1,1,1,1,
                       0,0,1,0,0,0,1,1,0,1,0,1,1,1,0,1,
                       0,0,0,1,1,0,1,0,1,0,1,1,1,0,1,1,
                       0,0,0,1,1,0,1,0,1,0,1,1,1,0,1,1,
                       1,1,0,0,0,1,0,1,1,1,1,1,1,1,1,1,
                       0,0,1,1,1,0,1,1,1,1,1,1,1,1,1,1,
                       1,0,1,0,0,1,1,1,0,1,1,1,1,1,1,1,
                       0,1,0,1,1,1,0,1,1,1,1,1,1,1,1,1,
                       0,1,1,0,0,1,1,1,1,1,0,1,1,1,1,1,
                       1,0,0,1,1,1,1,1,1,0,1,1,1,1,1,1,
                       1,0,1,1,1,1,1,1,1,1,1,1,1,1,1,1,
                       0,1,1,1,1,1,1,1,1,1,1,1,1,1,1,1,
                       1,1,1,0,0,1,1,1,1,1,1,1,1,1,1,1,
                       1,1,0,1,1,1,1,1,1,1,1,1,1,1,1,1,
                       1,1,1,1,1,1,1,1,1,1,1,1,1,1,1,1};
    /*
            This 16 x 16 array includes all possible comparisons.
            T and U are treated as if they are the same base
    */

/* end global variables */

/* start prototypes */
void GIVEUP(void);  /* called when user decides to quit */
void INTCHK(void);  /* called to see that keyboard input is a valid
integer */
void INFILE1(void); /* called to get name of input file #1 */
```

*FIG. 35D*

```
void INFILE2(void); /* called to get name of input file #2 */
void OUTFILE(void); /* called to get name of output file */
void NOTICE(void); /* provides some warning to the user */
void START(void);   /* first segment of program; user enters various stuff
*/
void COMPARE(void); /* second segment of program; compares the sequences
*/
void FINISH(void); /* final segment of program; doesn't do much */
/* end prototypes */ void GIVEUP(void)
{    printf("ZIP-HYB4 halted.\n"); exit(0); } void INTCHK(void)
{
     int i;
     badval=0;
     if(strng[0]!='\0')
     {
          for(i=0;strng[i]!='\0';i++)
               if(isdigit(strng[i])==0) { badval=1; break; }
     }
     else badval=1;
} void INFILE1(void)
{
     check=0;
     while(!check) /* loops until a valid file name is given or user
quits */
     {
          printf("Name of input file #1: ");
          gets(inm1);      /* gets file #1 name from keyboard */
          ifl1=fopen(inm1,"r"); /* attempts to open file #1 as "read-
only" */
          if(ifl1==NULL) /* means no file could be opened with that name
*/
          {
```

*FIG. 35E*

```
                printf("\aPROBLEM OPENING THE FILE %s.\n",inm1);
                printf("THE FILE MAY NOT EXIST.\n");
                printf("TYPE ""Q"" TO QUIT.\n");
                printf("OR TYPE ANY OTHER KEY TO CONTINUE");
                keychar=toupper(getch()); printf("\n\n");
                if(keychar=='Q') GIVEUP(); /* if 'Q' is typed, program
ends */
                check=0; /* loop not allowed to end if 'Q' is not typed */
            }
            else  /* means file #1 could be opened; loop can now end */
            {
                fclose(ifl1); check=1;
            }
        }
    } void INFILE2(void)  /* see INFILE1() above for notes */
    {
        check=0;
        while(!check)
        {
            printf("Name of input file #2: "); gets(inm2);
ifl2=fopen(inm2,"r");
            if(ifl2==NULL)
            {
                printf("\aPROBLEM OPENING THE FILE %s.\n",inm2);
                printf("THE FILE MAY NOT EXIST.\n");
                printf("TYPE ""Q"" TO QUIT.\n");
                printf("OR TYPE ANY OTHER KEY TO CONTINUE");
                keychar=toupper(getch()); printf("\n\n");
                if(keychar=='Q') GIVEUP(); check=0;
            }
            else { fclose(ifl2); check=1; }
        }
    } void OUTFILE(void)
    {
```

*FIG. 35F*

```
    check=0;
    while(!check) /* loops until an unused file name is given */
    {
        printf("Name of output file: ");
        gets(onm);      /* gets output file name from keyboard */
        ofl=fopen(onm,"r"); /* attempts to open output file as "read-
only" */
        if(ofl) /* means there was already a file with that name */
        {
            printf("\aTHE FILE %s ALREADY EXISTS. Try
again.\a\n\n",onm);
            fclose(ofl);
        }
        else check=1; /* means file name was not used, so loop can end
*/
    }
} void NOTICE(void)
{
    int noticecont=1;

printf("This program is used to compare sequences from one\n");
    printf("file to sequences from another. There are two
parameters:\n");
    printf("  (1) minimum number of matches (M) and\n");
    printf("  (2) maximum number of mismatches (X).\n\n");
    printf("The output shows all comparisons that satisfy the\n");
    printf("conditions of a positive match -- i.e., at least\n");
    printf("M out of M+X bases matching.\n\n");
    printf("This is an important warning!\n");
    printf("  If you set X to a value other than 0, you may\n");
    printf("  miss some \"perfect\" matches. For example, a\n");
    printf("  \"6 out of 6\" match may be reported as a \"7 out of
8\"\n");
    printf("  match if you allow 1 or more mismatches. For this
reason\n");
    printf("  it is suggested that analyses be performed with
```

*FIG. 35G*

```
varying\n");
      printf("   stringency.\n\n");
      printf("******************************************\n");
      printf("*  TYPE 'S' TO START THE ANALYSIS,  *\n");
      printf("*      TYPE 'Q' TO QUIT,            *\n");
      printf("* OR TYPE ANY OTHER KEY TO CONTINUE *\n");
      printf("*    WITH THE INTRODUCTION.         *\n");
      printf("******************************************\n");
      keychar=toupper(getch());
      if(keychar=='S') noticecont=0;
      if(keychar=='Q') GIVEUP();
      if(noticecont)
      {
           printf("\n\nThe input files should have the following
format:\n");
           printf("(1) There should be no empty lines;\n");
           printf("(2) Each line should begin with a sequence name;\n");
           printf("(3) Each sequence name should be followed by a\n");
           printf("    single space, followed immediately by the
sequence.\n");
           printf("    A \'*\' symbol should be typed at the end of
each\n");
           printf("    sequence, followed by a hard return.\n");
           printf("(4) The final line of each input file should be a\n");
           printf("    single \'#\' sign, followed ideally by a hard
return.\n\n");

printf("**********************************************\n");
           printf("*       TYPE 'Q' TO QUIT              *\n");
           printf("* OR TYPE ANY OTHER KEY TO START THE ANALYSIS. *\n");

printf("**********************************************\n");
           keychar=toupper(getch()); if(keychar=='Q') GIVEUP();
      }
} void START(void)
{
```

FIG. 35H

```
    int StepM=0;  /* boolean: change number of sites to match;
default=false */
    int StepX=0;  /* boolean: change number of mismatches allowed;
def=false*/
    int StepI1=1; /* boolean: change choice of input file #1;
default=true */
    int StepI2=1; /* boolean: change choice of input file #2;
default=true */
    int StepO=1;  /* boolean: change name of output file; default=true
*/
    char chng;    /* keyboard character read at prompt */

/*
        Entire function is a "do while" menu loop.  Loop ends when the
        user types 'G' for 'Go!'  Otherwise, some of the program
settings
        can be changed.
    */ printf("ZIP-HYB3 by RM Kliman and R Favis (1999)\n\n");
    do
    {
        if(StepI1) { StepI1=0; INFILE1(); } /* choose new input file #1
*/
        if(StepI2) { StepI2=0; INFILE2(); } /* choose new input file #2
*/
        if(StepO) { StepO=0; OUTFILE(); }  /* rename the output file
*/ while(StepM)   /* if this value is to be changed, loop
continues
                                    until a valid value is entered */
        {
            printf("\nNumber of sites that must match [2-%i]:
",MMax);
            gets(strng); /* gets keyboard input */
            INTCHK();    /* checks to see if keyboard input is an
integer */
```

FIG. 35I

```
            if(!badval)  /* if keyboard input is good, it is used
                                    and StepS is set to "false" */
            {
                    tval=atol(strng); /* conversion from string to
integer */
                    if(tval>1 && tval<MMax+1) /* makes sure value is in
range */
                    {
                            StepM=0;      /* if value is in range, loop
can end */
                            Nmatch=(int)tval; /* if value is in range,
assign value */
                    }
            }
            if(StepM) printf("\a\n\Bad value.  Try again.\n");
        } while(StepX)   /* if this value is to be changed, loop
continues
                                    until a valid value is entered */
        {
            printf("\nNumber of mismatches allowed [0-%i]:
",mismax);
            gets(strng);
            INTCHK();
            if(!badval)
            {
                    tval=atol(strng); /* conversion from string to
integer */
                    if(tval<mismax+1) /* makes sure value is in range
*/
                    {
                            StepX=0;      /* if value is in range, loop
can end */
                            Nmisallow=(int)tval; /* if value is in range,
assign value */
                    }
            }
```

*FIG. 35J*

```
            if(StepX) printf("\a\n\Bad value.  Try again.\n");
        } printf("\n1  Input file 1: %s\n",inm1);
        printf("2  Input file 2: %s\n",inm2);
        printf("O  Output file: %s\n",onm);
        printf("M  Number of sites that must match: %i\n",Nmatch);
        printf("X  Number of mismatches allowed:
%i\n\n",Nmisallow);
        printf("Type the letter or number associated with the\n");
        printf("menu item you wish to change.\n");
        printf("Type \'G\' to run the simulation.\n");
        check=0;
        while(!check) /* seeing if a valid menu choice is made */
        {
            chng=toupper(getch());
            switch(chng)
            {
                case '1': case '2': case 'O': case 'M': case 'X':
                case 'G':
                {check=1; break;}
                default:
                    printf("\a");
            }
        }

/*
            If one of the menu choices is made, loop repeats and the
            boolean value for the choice is set to 1 (i.e., true)
        */
        if(chng=='1') StepI1=1; if(chng=='2') StepI2=1;
        if(chng=='O') StepO=1;    if(chng=='M') StepM=1;
        if(chng=='X') StepX=1;
    }
    while(chng!='G');
} void COMPARE(void)
```

FIG. 35K

```
{
    int a,b,c,d,n;
    int compsize; /* size of region compared in a given loop */
    int mismatchcount; /* number of mismatches occuring in loop */
    int Nmismatch; /* number of mismatches in a comparison */
    int stopcompare=0; /* boolean: end compare loop when '#' found in
both */
    int endfile2; /* boolean: end inner loop when '#' found in file #2 */
    int spacepos; /* position of space b/n seqname and sequence */
    int file1cont,file2cont; /* boolean: keeps file reads going */
    int Matchcheck; /* boolean: did the comparison find a match? */
    int Matchsize; /* size of longest match */
    int Matchstart[2]; /* start of match in each sequence */
    int Matchdiff; /* difference in start positions of match */
    int foundmatch; /* boolean: 1 if at least 1 match is found */
    int seqsize[2]; /* lengths of two sequences being compared */
    int seqnamesize[2]; /* lengths of names of the sequences being
compared */
    int matcharray[LMax]; /* used to identify mismatches in matched
region */
    int nuc[2]; /* holds seqbase values of nucleotides being compared */
    char buffer[2][NMax+LMax+2]; /* allowed to read a line from each
input file */
    int thismismatch; /* used in summary output */ for(a=0;a<LMax;a++) for(b=0;b<MisMax;b++)
        Nmatcharray[a][b]=0; /* initializes array */
    foundmatch=0; /* initially no matches are found */
    ofl=fopen(onm,"w"); /* open output file as "read-write" */
    fprintf(ofl,"Output from ZIP-HYB3 Beta version (RM Kliman & R
Favis, 1999)\n\n");
    fprintf(ofl,"Input file 1: %s\n",inm1);
    fprintf(ofl,"Input file 2: %s\n",inm2);
    fprintf(ofl,"Minimum number of sites that must match:
%i\n",Nmatch);
    fprintf(ofl,"Maximum number of mismatches allowed:
%i\n\n",Nmisallow);
```

FIG. 35L

```
if11=fopen(inm1,"r"); /* open input file #1 as "read-only" */

/* start of comparison loop */
while(!stopcompare)
{
    file1cont=1;
    for(a=0;a<NMax;a++) seqname[0][a]=' ';
    for(a=0;a<LMax;a++) sequence[0][a]=' ';
    a=0;
    fgets(buffer[0],NMax+LMax+2,if11);
    if(buffer[0][0]=='#')
    {
        stopcompare=1;
        file1cont=0;
    }
    filechar='.'; /* just to make certain it's not a space */
    a=0;
    if(file1cont)
    {
        seqnamesize[0]=0;
        while(filechar!=' ') /* this is why filechar was set to '.' */
        {
            filechar=buffer[0][a];
            if(filechar!=' ')
            {
                seqname[0][a]=filechar;
                seqnamesize[0]++;
            }
            a++;
        }
        seqname[0][a-1]='\0';

spacepos=a; seqsize[0]=0;
        while(!isalpha(filechar))
        {
            filechar=buffer[0][a];
            if(!isalpha(filechar)) a++;
```

*FIG. 35M*

```
                    }
                    while(isalpha(filechar))
                    {
                        filechar=buffer[0][a];
                        if(isalpha(filechar))
                        {
                            sequence[0][a-spacepos]=filechar;
                            seqsize[0]++;
                            a++;
                        }
                    }
                    sequence[0][a-spacepos]='\0';

if12=fopen(inm2,"r"); /* re-open input file #2 as "read-
only" */
                    endfile2=0;
                    file2cont=1;
                    while(!endfile2)
                    {
                        for(b=0;b<NMax;b++) seqname[1][b]=' ';
                        for(b=0;b<LMax;b++) sequence[1][b]=' ';
                        b=0;
                        fgets(buffer[1],NMax+LMax+2,if12);
                        if(buffer[1][0]=='#')
                        {
                            endfile2=1;
                            file2cont=0;
                        }
                        if(file2cont==1)
                        {
                            seqnamesize[1]=0;
                            while(filechar!=' ')
                            {
                                filechar=buffer[1][b];
                                if(filechar!=' ')
                                {
                                    seqname[1][b]=filechar;
```

FIG. 35N

```
                seqnamesize[1]++;
            }
            b++;
        } spacepos=b; seqsize[1]=0;
        while(!isalpha(filechar))
        {
            filechar=buffer[1][b];
            if(filechar!= '*')
            {
                sequence[1][b-spacepos]=filechar;
                seqsize[1]++;
            }
            b++;
        }

/* start of comparison algorithm */
        Totalcomp++;
        Matchsize=0;

for(compsize=Nmatch+Nmisallow;compsize<=seqsize[1];compsize++)
        {
            for(b=0;b<1+seqsize[0]-compsize;b++)
            /* b is comparison start position in sequence[0] */
            {
                for(c=0;c<1+seqsize[1]-compsize;c++)
                /* c is comparison start position in sequence[1] */
                {
                    mismatchcount=0;
                    for(d=0;d<compsize;d++)
                    {
                        Matchcheck=1;

/* identify the
```

FIG. 35O

```
sequence characters */ if(toupper(sequence[1][c+d])
    ==seqbase[n])
break;

if(!basematch[nuc[0]][nuc[1]])

if(mismatchcount>Nmisallow | d==0)
mismatch is at the 5' end
sequence, the loop is
    automatically halted.

Matchcheck=0;

Nmismatch=mismatchcount;
Nmismatch;
```

```
        for(n=0;n<16;n++)
        {
            nuc[1]=n;
        }
        /* check for mismatch */
        {
            mismatchcount++;
            /*   if the
                of the
            */
            {
                break;
            }
        }
    }
    if(Matchcheck)
    {
            Matchsize=compsize-
```

*FIG. 35P*

```
                                        Matchstart[0]=b;
                                        Matchstart[1]=c;
                                    }
                                }
                            }
                            if(Matchsize+Nmismatch<compsize)
break;
                        }
                        if(Matchsize)
                        {
                            if(Nmismatch)
                            /*
                                this loop decreases the size of the
matched
                                region if the downstream bases do
not match.
                                Both the size of the matched region
and the
                                number of mismatches are
decremented.
                            */
                            {
                                check=1;
                                while(check)
                                {
                                    for(b=0;b<2;b++)
for(n=0;n<16;n++)
    if(toupper(sequence[b][Matchstart[b]
    +Matchsize+Nmismatch-1])
                                                ==seqbase[n])
                                        {
                                            nuc[b]=n; break;
                                        }
                                    if(Nmismatch &&
!basematch[nuc[0]][nuc[1]])
```

*FIG. 35Q*

```
                    Nmismatch--;
                else check=0;
            }
        }

Nmatcharray[Matchsize-1][Nmismatch]++;
        foundmatch=1;
        if(Matchstart[0]>Matchstart[1])
            Matchdiff=Matchstart[0]-
Matchstart[1];
        else Matchdiff=Matchstart[1]-
Matchstart[0];

for(b=0;b<Matchsize+Nmismatch;b++)
        {
            for(c=0;c<2;c++) for(n=0;n<16;n++)
    if(toupper(sequence[c][b+Matchstart[c]])
                            ==seqbase[n])
                    {
                        nuc[c]=n; break;
                    }
                if(basematch[nuc[0]][nuc[1]])
matcharray[b]=1;
                else matcharray[b]=0;
        }

/*if(Matchsize<10) fprintf(of1," ");*/
        fprintf(of1,"%2i out of ",Matchsize);
        /*if(Matchsize+Nmismatch<10)
fprintf(of1," ");*/
        fprintf(of1,"%2i
",Matchsize+Nmismatch);

for(b=0;b<2;b++)
        {
            if(b) fprintf(of1,"           ");
            for(c=0;c<seqnamesize[b];c++)
```

FIG. 35R

```c
            fprintf(ofl,"%c",seqname[b][c]);
                                        for(c=0;c<(nmax-
seqnamesize[b]);c++)
                                            fprintf(ofl," ");
                                        if(((Matchstart[0]>Matchstart[1]
&& b)
                                        ||
(Matchstart[1]>Matchstart[0] && !b))
                                            |
fprintf(ofl," ");
                                            for(c=0;c<Matchdiff;c++)
                                                fprintf(ofl," ");

for(c=0;c<seqsize[b];c++)
                                        {
                                            filechar=sequence[b][c];
                                            if(c==Matchstart[b])
fprintf(ofl,"(");

if(c>=Matchstart[b]
                                                &&
c<Matchstart[b]+Matchsize+Nmismatch
                                                && matcharray[c-
Matchstart[b]])

fprintf(ofl,"%c",toupper(filechar));
                                            else
fprintf(ofl,"%c",tolower(filechar));

if(c==Matchstart[b]+Matchsize+Nmismatch-1)
                                                fprintf(ofl,")");
                                        }
                                        fprintf(ofl,"\n");
                                    }
                                    fprintf(ofl,"\n");
                                }
                                /* end of comparison algorithm */
                            }
                        }
                        /* end of reading file #2 */
                        fclose(if12);
```

FIG. 35S

```
        }
    }
    /* end of comparison loop */
    fprintf(ofl,"SUMMARY OF ANALYSIS\n");
    printf    ("\nSUMMARY OF ANALYSIS\n");
    if(!foundmatch)
    {
        fprintf(ofl,"No matches found.");
        printf       ("No matches found.");
    }
    else
    {
        for(b=0;b<=Nmisallow;b++)
        {
            thismismatch=1;
            for(a=LMax-1;a>=0;a--) if(Nmatcharray[a][b])
            {
                Totalmatch+=Nmatcharray[a][b];
                if(thismismatch)
                {
                    thismismatch=0;
                    fprintf(ofl,"\nComparisons with %i ",b);
                    printf    ("\nComparisons with %i ",b);
                    if(b==1)
                    {
                        fprintf(ofl,"mismatch\n");
                        printf    ("mismatch\n");
                    }
                    else
                    {
                        fprintf(ofl,"mismatches\n");
                        printf    ("mismatches\n");
                    }
                }
                /*if(a<9) fprintf(ofl," ");*/
                fprintf(ofl," %2i out of ",a+1);
                printf    (" %2i out of ",a+1);
                /*if(a+b<9) fprintf(ofl," ");*/
```

*FIG. 35T*

```
                    fprintf(ofl,"%2i bases matching: %i\n",
                        a+1+b,Nmatcharray[a][b]);
                    printf    ("%2i bases matching: %i\n",
                        a+1+b,Nmatcharray[a][b]);
                }
            }
        }
        fprintf(ofl,"\nA total of %li out of ",Totalmatch);
        printf    ("\nA total of %li out of ",Totalmatch);
        fprintf(ofl,"%li sequence comparisons ",Totalcomp);
        printf    ("%li sequence comparisons ",Totalcomp);
        fprintf(ofl,"met the match criteria.");
        printf    ("met the match criteria.");
        fclose(ofl); fclose(ifl1); fclose(ifl2);
} void FINISH(void)
{
        printf("\n\nZIP-HYB3 done.\n"); /* writes to the screen that
program's done */
        printf("See file \"%s\" for details.\n",onm);
}

/* start main function */
int main()
{
        NOTICE();
        START();
        COMPARE();
        FINISH();
        return 0;
}
/* finish main function */
```

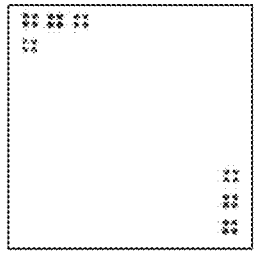
FIG. 36A
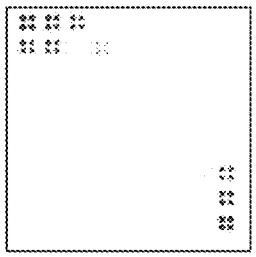 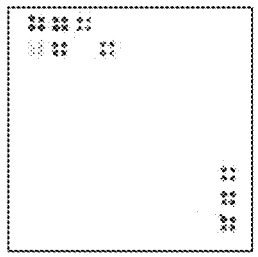 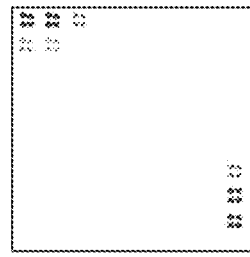
FIG. 36B    FIG. 36C    FIG. 36D
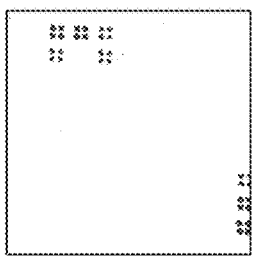 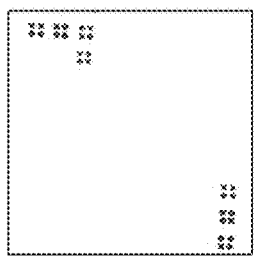 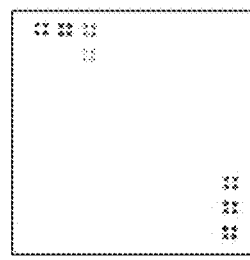
FIG. 36E    FIG. 36F    FIG. 36G
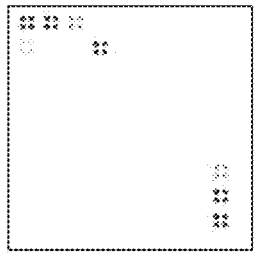
FIG. 36H

METHOD OF DESIGNING ADDRESSABLE ARRAY SUITABLE FOR DETECTION OF NUCLEIC ACID SEQUENCE DIFFERENCES USING LIGASE DETECTION REACTION

This application is a continuation of U.S. patent application Ser. No. 13/947,777, filed Jul. 22, 2013, which is a division of U.S. patent application Ser. No. 12/252,169, filed Oct. 15, 2008, now U.S. Pat. No. 8,492,085 issued on Jul. 23, 2013, which is a division of U.S. patent application Ser. No. 10/257,158, filed Apr. 1, 2004, now U.S. Pat. No. 7,455,965 issued on Nov. 25, 2008, which is a national stage application under 35 U.S.C. §371 PCT Application Serial No. PCT/US01/10958, filed Apr. 4, 2001, which claims the benefit of U.S. Provisional Patent Application Ser. No. 60/197,271, filed Apr. 14, 2000, each of which is hereby incorporated by reference in its entirety.

This invention was made with government support under grant numbers GM-41337-06, GM-43552-05, GM-42722-07, and GM-51628-02 awarded by National Institutes of Health. The government has certain rights in this invention

FIELD OF THE INVENTION

The present invention is directed to a method of designing a plurality of capture oligonucleotide probes for use on a support to which complementary oligonucleotide probes will hybridize with little mismatch, where the plural capture oligonucleotide probes have melting temperatures within a narrow range. Other aspects of the present invention relate to a support with the plurality of oligonucleotide probes immobilized on the support, a method of using the support to detect single-base changes, insertions, deletions, or translocations in a plurality of target nucleotide sequences, and a kit for such detection, which includes the support on which the oligonucleotides have been immobilized.

BACKGROUND OF THE INVENTION

Detection of Sequence Differences

Large-scale multiplex analysis of highly polymorphic loci is needed for practical identification of individuals, e.g., for paternity testing and in forensic science (Reynolds et al., *Anal. Chem.*, 63:2-15 (1991)), for organ-transplant donor-recipient matching (Buyse et al., *Tissue Antigens*, 41:1-14 (1993) and Gyllensten et al., *PCR Meth. Appl*, 1:91-98 (1991)), for genetic disease diagnosis, prognosis, and pre-natal counseling (Chamberlain et al., *Nucleic Acids Res.*, 16:11141-11156 (1988) and L. C. Tsui, *Human Mutat.*, 1:197-203 (1992)), and the study of oncogenic mutations (Hollstein et al., *Science*, 253:49-53 (1991)). In addition, the cost-effectiveness of infectious disease diagnosis by nucleic acid analysis varies directly with the multiplex scale in panel testing. Many of these applications depend on the discrimination of single-base differences at a multiplicity of sometimes closely space loci.

A variety of DNA hybridization techniques are available for detecting the presence of one or more selected polynucleotide sequences in a sample containing a large number of sequence regions. In a simple method, which relies on fragment capture and labeling, a fragment containing a selected sequence is captured by hybridization to an immobilized probe. The captured fragment can be labeled by hybridization to a second probe which contains a detectable reporter moiety.

Another widely used method is Southern blotting. In this method, a mixture of DNA fragments in a sample are fractionated by gel electrophoresis, then fixed on a nitrocellulose filter. By reacting the filter with one or more labeled probes under hybridization conditions, the presence of bands containing the probe sequence can be identified. The method is especially useful for identifying fragments in a restriction-enzyme DNA digest which contain a given probe sequence, and for analyzing restriction-fragment length polymorphisms ("RFLPs").

Another approach to detecting the presence of a given sequence or sequences in a polynucleotide sample involves selective amplification of the sequence(s) by polymerase chain reaction. U.S. Pat. No. 4,683,202 to Mullis, et al. and R. K. Saiki, et al., *Science* 230:1350 (1985). In this method, primers complementary to opposite end portions of the selected sequence(s) are used to promote, in conjunction with thermal cycling, successive rounds of primer-initiated replication. The amplified sequence may be readily identified by a variety of techniques. This approach is particularly useful for detecting the presence of low-copy sequences in a polynucleotide-containing sample, e.g., for detecting pathogen sequences in a body-fluid sample.

More recently, methods of identifying known target sequences by probe ligation methods have been reported. U.S. Pat. No. 4,883,750 to N. M. Whiteley, et al., D. Y. Wu, et al., *Genomics* 4:560 (1989), U. Landegren, et al., *Science* 241:1077 (1988), and E. Winn-Deen, et al., *Clin. Chem.* 37:1522 (1991). In one approach, known as oligonucleotide ligation assay ("OLA"), two probes or probe elements which span a target region of interest are hybridized with the target region. Where the probe elements match (basepair with) adjacent target bases at the confronting ends of the probe elements, the two elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, hybridization, and ligation in the presence of the two complementary pairs of probe elements, the target sequence is amplified exponentially, i.e., exponentially allowing very small amounts of target sequence to be detected and/or amplified. This approach is referred to as ligase chain reaction ("LCR"). F. Barany, "Genetic Disease Detection and DNA Amplification Using Cloned Thermostable Ligase," *Proc. Nat'l Acad. Sci. USA*, 88:189-93 (1991) and F. Barany, "The Ligase Chain Reaction (LCR) in a PCR World," PCR Methods and Applications, 1:5-16 (1991).

Another scheme for multiplex detection of nucleic acid sequence differences is disclosed in U.S. Pat. No. 5,470,705 to Grossman et. al. where sequence-specific probes, having a detectable label and a distinctive ratio of charge/translational frictional drag, can be hybridized to a target and ligated together. This technique was used in Grossman, et. al., "High-density Multiplex Detection of Nucleic Acid Sequences: Oligonucleotide Ligation Assay and Sequence-coded Separation," *Nucl. Acids Res.* 22(21):4527-34 (1994) for the large scale multiplex analysis of the cystic fibrosis transmembrane regulator gene.

Jou, et. al., "Deletion Detection in Dystrophin Gene by Multiplex Gap Ligase Chain Reaction and Immunochromatographic Strip Technology," *Human Mutation* 5:86-93 (1995) relates to the use of a so called "gap ligase chain reaction" process to amplify simultaneously selected regions of multiple exons with the amplified products being read on an immunochromatographic strip having antibodies specific to the different haptens on the probes for each exon.

There is a growing need, e.g., in the field of genetic screening, for methods useful in detecting the presence or absence of each of a large number of sequences in a target polynucleotide. For example, as many as 400 different mutations have been associated with cystic fibrosis. In screening for genetic predisposition to this disease, it is optimal to test all of the possible different gene sequence mutations in the subject's genomic DNA, in order to make a positive identification of "cystic fibrosis". It would be ideal to test for the presence or absence of all of the possible mutation sites in a single assay. However, the prior-art methods described above are not readily adaptable for use in detecting multiple selected sequences in a convenient, automated single-assay format.

Solid-phase hybridization assays require multiple liquid-handling steps, and some incubation and wash temperatures must be carefully controlled to keep the stringency needed for single-nucleotide mismatch discrimination. Multiplexing of this approach has proven difficult as optimal hybridization conditions vary greatly among probe sequences.

Allele-specific PCR products generally have the same size, and a given amplification tube is scored by the presence or absence of the product band in the gel lane associated with each reaction tube. Gibbs et al., *Nucleic Acids Res.,* 17:2437-2448 (1989). This approach requires splitting the test sample among multiple reaction tubes with different primer combinations, multiplying assay cost. PCR has also discriminated alleles by attaching different fluorescent dyes to competing allelic primers in a single reaction tube (F. F. Chehab, et al., *Proc. Natl. Acad. Sci. USA,* 86:9178-9182 (1989)), but this route to multiplex analysis is limited in scale by the relatively few dyes which can be spectrally resolved in an economical manner with existing instrumentation and dye chemistry. The incorporation of bases modified with bulky side chains can be used to differentiate allelic PCR products by their electrophoretic mobility, but this method is limited by the successful incorporation of these modified bases by polymerase, and by the ability of electrophoresis to resolve relatively large PCR products which differ in size by only one of these groups. Livak et al., *Nucleic Acids Res.,* 20:4831-4837 (1989). Each PCR product is used to look for only a single mutation, making multiplexing difficult.

Ligation of allele-specific probes generally has used solid-phase capture (U. Landegren et al., *Science,* 241:1077-1080 (1988); Nickerson et al., *Proc. Natl. Acad. Sci. USA,* 87:8923-8927 (1990)) or size-dependent separation (D. Y. Wu, et al., *Genomics,* 4:560-569 (1989) and F. Barany, *Proc. Natl. Acad. Sci.,* 88:189-193 (1991)) to resolve the allelic signals, the latter method being limited in multiplex scale by the narrow size range of ligation probes. The gap ligase chain reaction process requires an additional step—polymerase extension. The use of probes with distinctive ratios of charge/translational frictional drag technique to a more complex multiplex will either require longer electrophoresis times or the use of an alternate form of detection.

The need thus remains for a rapid single assay format to detect the presence or absence of multiple selected sequences in a polynucleotide sample.

Use of Oligonucleotide Arrays for Nucleic Acid Analysis

Ordered arrays of oligonucleotides immobilized on a solid support have been proposed for sequencing, sorting, isolating, and manipulating DNA. It has been recognized that hybridization of a cloned single-stranded DNA molecule to all possible oligonucleotide probes of a given length can theoretically identify the corresponding complementary DNA segments present in the molecule. In such an array, each oligonucleotide probe is immobilized on a solid support at a different predetermined position. All the oligonucleotide segments in a DNA molecule can be surveyed with such an array.

One example of a procedure for sequencing DNA molecules using arrays of oligonucleotides is disclosed in U.S. Pat. No. 5,202,231 to Drmanac, et. al. This involves application of target DNA to a solid support to which a plurality of oligonucleotides are attached. Sequences are read by hybridization of segments of the target DNA to the oligonucleotides and assembly of overlapping segments of hybridized oligonucleotides. The array utilizes all possible oligonucleotides of a certain length between 11 and 20 nucleotides, but there is little information about how this array is constructed. See also A. B. Chetverin, et. al., "Sequencing of Pools of Nucleic Acids on Oligonucleotide Arrays," *BioSystems* 30: 215-31 (1993); WO 92/16655 to Khrapko et. al.; Kuznetsova, et. al., "DNA Sequencing by Hybridization with Oligonucleotides Immobilized in Gel. Chemical Ligation as a Method of Expanding the Prospects for the Method," *Mol. Biol.* 28(20): 290-99(1994); M. A. Livits, et. al., "Dissociation of Duplexes Formed by Hybridization of DNA with Gel-Immobilized Oligonucleotides," *J. Biomolec. Struct. & Dynam.* 11(4): 783-812 (1994).

WO 89/10977 to Southern discloses the use of a support carrying an array of oligonucleotides capable of undergoing a hybridization reaction for use in analyzing a nucleic acid sample for known point mutations, genomic fingerprinting, linkage analysis, and sequence determination. The matrix is formed by laying nucleotide bases in a selected pattern on the support. This reference indicates that a hydroxyl linker group can be applied to the support with the oligonucleotides being assembled by a pen plotter or by masking.

WO 94/11530 to Cantor also relates to the use of an oligonucleotide array to carry out a process of sequencing by hybridization. The oligonucleotides are duplexes having overhanging ends to which target nucleic acids bind and are then ligated to the non-overhanging portion of the duplex. The array is constructed by using streptavidin-coated filter paper which captures biotinylated oligonucleotides assembled before attachment.

WO 93/17126 to Chetverin uses sectioned, binary oligonucleotide arrays to sort and survey nucleic acids. These arrays have a constant nucleotide sequence attached to an adjacent variable nucleotide sequence, both bound to a solid support by a covalent linking moiety. The constant nucleotide sequence has a priming region to permit amplification by PCR of hybridized strands. Sorting is then carried out by hybridization to the variable region. Sequencing, isolating, sorting, and manipulating fragmented nucleic acids on these binary arrays are also disclosed. In one embodiment with enhanced sensitivity, the immobilized oligonucleotide has a shorter complementary region hybridized to it, leaving part of the oligonucleotide uncovered. The array is then subjected to hybridization conditions so that a complementary nucleic acid anneals to the immobilized oligonucleotide. DNA ligase is then used to join the shorter complementary region and the complementary nucleic acid on the array. There is little disclosure of how to prepare the arrays of oligonucleotides.

WO 92/10588 to Fodor et. al., discloses a process for sequencing, fingerprinting, and mapping nucleic acids by hybridization to an array of oligonucleotides. The array of oligonucleotides is prepared by a very large scale immobilized polymer synthesis which permits the synthesis of large, different oligonucleotides. In this procedure, the substrate surface is functionalized and provided with a linker group by which oligonucleotides are assembled on the substrate. The regions where oligonucleotides are attached have protective groups (on the substrate or individual nucleotide subunits) which are selectively activated. Generally, this involves imaging the array with light using a mask of varying configuration so that areas exposed are deprotected. Areas which have been deprotected undergo a chemical reaction with a protected nucleotide to extend the oligonucleotide sequence where imaged. A binary masking strategy can be used to build two or more arrays at a given time. Detection involves positional localization of the region where hybridization has taken place. See also U.S. Pat. Nos. 5,324,633 and 5,424,186 to Fodor et. al., U.S. Pat. Nos. 5,143,854 and 5,405,783 to Pirrung, et. al., WO 90/15070 to Pirrung, et. al., A. C. Pease, et. al., "Light-generated Oligonucleotide Arrays for Rapid DNA Sequence Analysis", *Proc. Natl. Acad. Sci USA* 91: 5022-26 (1994). K. L. Beattie, et. al., "Advances in Genosensor Research," *Clin. Chem.* 41(5): 700-09 (1995) discloses attachment of previously assembled oligonucleotide probes to a solid support.

There are many drawbacks to the procedures for sequencing by hybridization to such arrays. Firstly, a very large number of oligonucleotides must be synthesized. Secondly, there is poor discrimination between correctly hybridized, properly matched duplexes and those which are mismatched. Finally, certain oligonucleotides will be difficult to hybridize to under standard conditions, with such oligonucleotides being capable of identification only through extensive hybridization studies.

The present invention is directed toward overcoming these deficiencies in the art.

SUMMARY OF THE INVENTION

The present invention is directed to a method of designing a plurality of capture oligonucleotide probes for use on a support to which complementary oligonucleotide probes will hybridize with little mismatch, where the plural capture oligonucleotide probes have melting temperatures within a narrow range. The first step of the method involves providing a first set of a plurality of tetramers of four nucleotides linked together, where (1) each tetramer within the set differs from all other tetramers in the set by at least two nucleotide bases, (2) no two tetramers within a set are complementary to one another, (3) no tetramers within a set are palindromic or dinucleotide repeats, and (4) no tetramer within a set has one or less or three or more G or C nucleotides. Groups of 2 to 4 of the tetramers from the first set are linked together to form a collection of multimer units. From the collection of multimer units, all multimer units formed from the same tetramer and all multimer units having a melting temperature in ° C. of less than 4 times the number of tetramers forming a multimer unit are removed to form a modified collection of multimer units. The modified collection of multimer units is arranged in a list in order of melting temperature. The order of the modified collection of multimer units is randomized in 2° C. increments of melting temperature. Alternating multimer units in the list are then divided into first and second subcollections, each arranged in order of melting temperature. After the order of the second subcollection is inverted, the first collection is linked in order to the inverted second collection to form a collection of double multimer units. From the collection of double multimer units those units (1) having a melting temperature in ° C. less than 11 times the number of tetramers and more than 15 times the number of tetramers, (2) double multimer units with the same 3 tetramers linked together, and (3) double multimer units with the same 4 tetramers linked together with or without interruption are removed, to form a modified collection of double multimer units.

Another aspect of the present invention relates to an oligonucleotide array which includes a support and a collection of double multimer unit oligonucleotides at different positions on the support so that complementary oligonucleotides to be immobilized on the solid support can be captured at the different positions. The complementary oligonucleotides will hybridize, within a narrow temperature range of greater than 24° C. with little mismatch, to members of the collection of double multimer unit oligonucleotides, the double multimer unit oligonucleotides are formed from sets of tetramers where (1) each tetramer within the set differs from all other tetramers in the set by at least two nucleotide bases, (2) no two tetramers within a set are complementary to one another, and (3) no tetramers within a set are palindromic or dinucleotide repeats, and the collection of double multimer unit oligonucleotides has had the following oligonucleotides removed from it: (1) oligonucleotides having a melting temperature in ° C. less than 12.5 times the number of tetramers and more than 14 times the number of tetramers, (2) double multimer units with the same 3 tetramers linked together, and (3) multimer units with the same 4 tetramers linked together with or without interruption.

Yet another aspect of the present invention relates to a method for identifying one or more of a plurality of sequences differing by one or more single-base changes, insertions, deletions, or translocations in a plurality of target nucleotide sequences. This method involves providing a sample potentially containing one or more target nucleotide sequences with a plurality of sequence differences. A plurality of oligonucleotide probe sets are also provided with each set characterized by (a) a first oligonucleotide probe, having a target-specific portion and an addressable array-specific portion, and (b) a second oligonucleotide probe, having a target-specific portion and a detectable reporter label. The oligonucleotide probes in a particular set are suitable for ligation together when hybridized adjacent to one another on a corresponding target nucleotide sequence, but have a mismatch which interferes with such ligation when hybridized to any other nucleotide sequence present in the sample. A ligase is also provided with the sample, the plurality of oligonucleotide probe sets, and the ligase being blended to form a mixture. The mixture is subjected to one or more ligase detection reaction cycles comprising a denaturation treatment, where any hybridized oligonucleotides are separated from the target nucleotide sequences, and a hybridization treatment, where the oligonucleotide probe sets hybridize at adjacent positions in a base-specific manner to their respective target nucleotide sequences, if present in the sample, and ligate to one another to form a ligated product sequence containing (a) the addressable array-specific portion, (b) the target-specific portions connected together, and (c) the detectable reporter label. The oligonucleotide probe sets may hybridize to nucleotide sequences in the sample other than their respective target nucleotide sequences but do not ligate together due to a presence of one or more mismatches and individually separate during the denaturation treatment. A support is provided with different capture oligonucleotides immobilized at different positions, where the capture oligonucleotides have nucleotide sequences complementary to the addressable array-specific portions and are formed from a collection of double multimer unit oligonucleotides. The oligonucleotide with addressable array-specific portions will hybridize, within a narrow temperature range of more than 4 times the number of tetramers in the multimer unit with little mismatch, to members of the capture oligonuncleotides. The double multimer unit oligonucleotides are formed from sets of tetramers where (1) each tetramer within the set differs from all other tetramers in the set by at least two nucleotide bases, (2) no two tetramers within a set are complementary to one another, and (3) no tetramers within a set are palindromic or dinucleotide repeats. The collection of double multimer unit oligonucleotides has had the following oligonucleotides removed from it: (1) oligonucleotides having a melting temperature in ° C. of less than 11 times the number of tetramers and more than 15 times the number of tetramers, (2) double multimer units with the same 3 tetramers linked together, and (3) double multimer units with the same 4 tetramers linked together with or without interruption, to form a modified collection of double multimer units. After subjecting the mixture to one or more ligase detection reaction cycles, the mixture is contacted with the support under conditions effective to hybridize the addressable array-specific portions to the capture oligonucleotides in a base-specific manner, thereby capturing the addressable array-specific portions on the support at the site with the complementary capture oligonucleotide. The reporter labels of ligated product sequences captured on the support at particular sites are detected, indicating the presence of one or more target nucleotide sequences in the sample.

Another aspect of the present invention is directed to a kit for identifying one or more of a plurality of sequences differing by single-base changes, insertions, deletions, or translocations in a plurality of target nucleotide sequences. In addition, to a ligase, the kit includes a plurality oligonucleotide probe sets, each characterized by (a) a first oligonucleotide probe, having a target sequence-specific portion and an addressable array-specific portion, and (b) a second oligonucleotide probe, having a target sequence-specific portion and detectable reporter label, wherein the oligonucleotide probes in a particular set are suitable for ligation together when hybridized adjacent to one another on a respective target nucleotide sequence, but have a mismatch which interferes with such ligation when hybridized to any other nucleotide sequence, present in the sample. Also found in the kit is a support with different capture oligonucleotides immobilized at different positions, where the capture oligonucleotides have nucleotide sequences complementary to the addressable array-specific portions and are formed from a collection of double multimer unit oligonucleotides. The oligonucleotide with addressable array-specific portions will hybridize, within a narrow temperature range of greater than 4 times the number of tetramers in the multimer unit with little mismatch, to members of the capture oligonuncleotides. The double multimer unit oligonucleotides are formed from sets of tetramers where (1) each tetramer within the set differs from all other tetramers in the set by at least two nucleotide bases, (2) no two tetramers within a set are complementary to one another, and (3) no tetramers within a set are palindromic or dinucleotide repeats. The collection of double multimer unit oligonucleotides has had the following oligonucleotides removed from it: (1) oligonucleotides having a melting temperature in ° C. of less than 11 times the number of tetramers and more than 15 times then number of tetramers, (2) double multimer units with the same 3 tetramers linked together, and (3) double multimer units with the same 4 tetramers linked together with or without interruption, where the capture oligonucleotides have nucleotide sequences complementary to the addressable array-specific portions.

Another aspect of the present invention relates to a method to avoid synthesizing ligase detection reaction oligonucleotides that will inappropriately cross-hybridize to capture oligonucleotides on a solid support. This method includes comparing the ligase detection reaction oligonucleotides with the capture oligonucleotides and identifying any capture oligonucleotides likely to cross-hybridize to the ligase detection reaction oligonucleotides.

BRIEF DESCRIPTION OF THE DRAWINGS

FIG. 5 is a schematic diagram depicting a PCR/LDR process, according to the present invention, using addresses on the allele-specific probes which distinguishes all possible bases at a given site.

FIG. 6 is a schematic diagram depicting a PCR/LDR process, according to the present invention, using addresses on the common probes which distinguishes all possible bases at a given site.

FIG. 7 is a schematic diagram depicting a PCR/LDR process, according to the present invention, using addresses on the allele-specific probes for detecting the presence of any possible base at two nearby sites.

FIG. 12 is a schematic diagram of a PCR/LDR process, in accordance with the present invention, using addresses on the common probes to detect a low abundance mutation (within a codon) in the presence of an excess of normal sequence.

FIG. 13 is a schematic diagram of a PCR/LDR process, in accordance with the present invention, where the address is placed on the common probe and the allele differences are distinguished by different fluorescent signals F1, F2, F3, and F4.

FIG. 14 is a schematic diagram of a PCR/LDR process, in accordance with the present invention, where both adjacent and nearby alleles are detected.

FIG. 15 is a schematic diagram of a PCR/LDR process, in accordance with the present invention, where all possible single-base mutations for a single codon are detected.

FIGS. 17A-C show two alternative formats for oligonucleotide probe capture. In FIG. 17B, the addressable array-specific portions are on the allele-specific probe. Alleles are distinguished by capture of fluorescent signals on addresses Z1 and Z2, respectively. In FIG. 17C, the addressable array-specific portions are on the common probe and alleles are distinguished by capture of fluorescent signals F1 and F2, which correspond to the two alleles, respectively.

FIG. 18 shows the chemical reactions for covalent modifications, grafting, oligomer attachments to solid supports.

FIG. 19 shows a design in accordance with the present invention using 36 tetramers differing by at least 2 bases, which can be used to create a series of unique 24-mers.

FIG. 20 shows an outline of the PCR/PCR/LDR method for detection of mutations in BRCA1 and BRCA2.

FIG. 22 shows an outline of multiplex LDR detection of 3 specific mutations in BRCA1 and BRCA2 using an universal DNA microarray.

FIG. 23A-H show the LDR detection of 3 specific mutations in BRCA1 and BRCA2 on an addressable universal microarray.

FIGS. 25A-25MMMM show a list of 4633 capture oligonucleotides (SEQ ID NOS: 1-4633) produced in accordance with the present invention. One of ordinary skill in the art can readily envision the complementary oligonucleotides corresponding to the capture oligonucleotides listed in FIGS. 25A-25MMMM.

FIGS. 26A-26J show a list of 465 capture oligonucleotides (SEQ ID NOS: 1-465) produced in accordance with the present invention. One of ordinary skill in the art can readily envision the complementary oligonucleotides corresponding to the capture oligonucleotides listed in FIGS. 26A-26J.

FIGS. 27A-27B show a list of 96 capture oligonucleotides (SEQ ID NOS: 1-96) produced in accordance with the present invention. One of ordinary skill in the art can readily envision the complementary oligonucleotides corresponding to the capture oligonucleotides listed in FIGS. 27A-27B.

FIGS. 28A-28B show a list of 65 capture oligonucleotides (SEQ ID NOS: 1-65) produced in accordance with the present invention. One of ordinary skill in the art can readily envision the complementary oligonucleotides corresponding to the capture oligonucleotides listed in FIGS. 28A-28B.

FIGS. 29A-29SSSS show a list of 4633 capture oligonucleotides (SEQ ID NOS: 4634-9266) (in the form of 20 mer PNAs) produced in accordance with the present invention.

FIGS. 35A-T set forth a computer program for comparing a target sequence with an array capture probe to insure that the latter will be designed not to hybridize to the former.

FIGS. 36A-H show the LDR detection of 7 specific mutations in K-ras on an addressable universal microarray.

DETAILED DESCRIPTION OF THE INVENTION AND DRAWINGS

Figure 1:
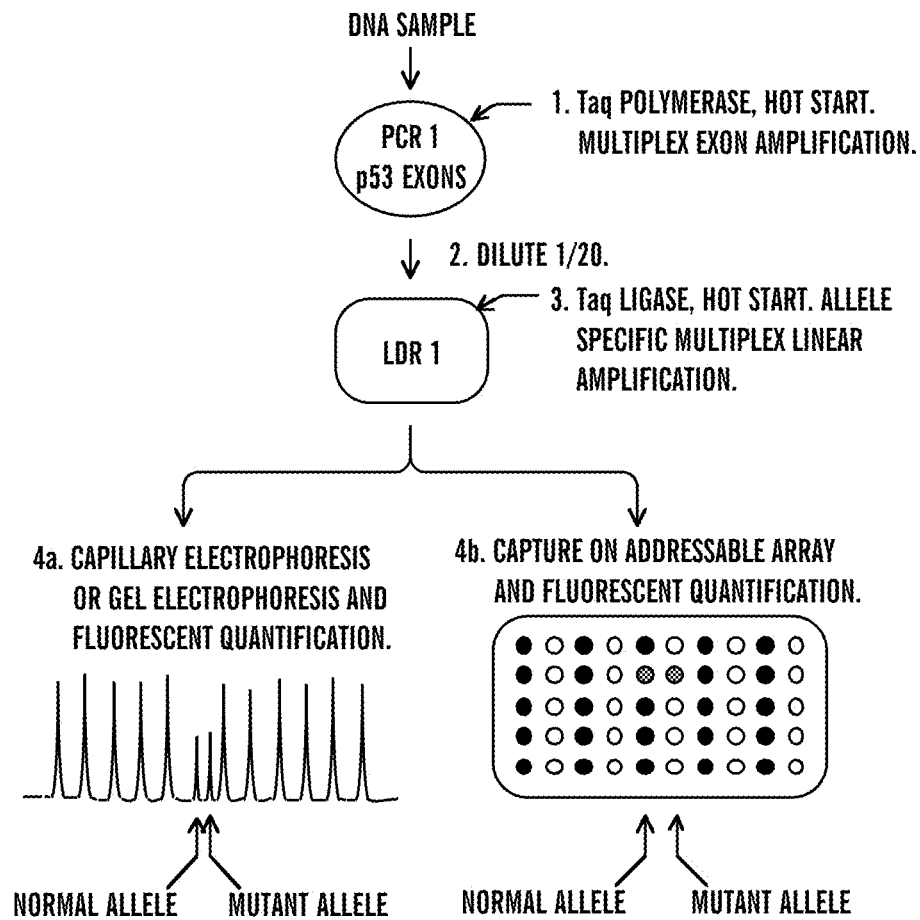
FIG. 1 is a flow diagram depicting polymerase chain reaction ("PCR")/ligase detection reaction ("LDR") processes, according to the prior art and the present invention, for detection of germline mutations, such as point mutations.

The present invention is directed to a method of designing a plurality of capture oligonucleotide probes for use on a support to which complementary oligonucleotide probes will hybridize with little mismatch, where the plural capture oligonucleotide probes have melting temperatures within a narrow range. The first step of the method involves providing a first set of a plurality of tetramers of four nucleotides linked together, where (1) each tetramer within the set differs from all other tetramers in the set by at least two nucleotide bases, (2) no two tetramers within a set are complementary to one another, (3) no tetramers within a set are palindromic or dinucleotide repeats, and (4) no tetramer within a set has one or less or three or more G or C nucleotides. Groups of 2 to 4 of the tetramers from the first set are linked together to form a collection of multimer units. From the collection of multimer units, all multimer units formed from the same tetramer and all multimer units having a melting temperature in ° C. of less than 4 times the number of tetramers forming a multimer unit are removed to form a modified collection of multimer units. The modified collection of multimer units is arranged in a list in order of melting temperature. The order of the modified collection of multimer units is randomized in 2° C. increments of melting temperature. Alternating multimer units in the list are then divided into first and second subcollections, each arranged in order of melting temperature. After the order of the second subcollection is inverted, the first collection is linked in order to the inverted second collection to form a collection of double multimer units. From the collection of double multimer units, those units (1) having a melting temperature in ° C. less than 11 times the number of tetramers and more than 15 times the number of tetramers, (2) double multimer units with the same 3 tetramers linked together, and (3) double multimer units with the same 4 tetramers linked together with or without interruption are removed, to form a modified collection of double multimer units.

Another aspect of the present invention relates to an oligonucleotide array which includes a support and a collection of double multimer unit oligonucleotides at different positions on the support so that complementary oligonucleotides to be immobilized on the solid support can be captured at the different positions. The complementary oligonucleotides will hybridize, within a narrow temperature range of greater than 24° C. with little mismatch, to members of the collection of double multimer unit oligonucleotides, the double multimer unit oligonucleotides are formed from sets of tetramers where (1) each tetramer within the set differs from all other tetramers in the set by at least two nucleotide bases, (2) no two tetramers within a set are complementary to one another, and (3) no tetramers within a set are palindromic or dinucleotide repeats, and the collection of double multimer unit oligonucleotides has had the following oligonucleotides removed from it: (1) oligonucleotides having a melting temperature in ° C. less than 12.5 times the number of tetramers and more than 14 times the number of tetramers, (2) double multimer units with the same 3 tetramers linked together, and (3) multimer units with the same 4 tetramers linked together with or without interruption.

Yet another aspect of the present invention relates to a method for identifying one or more of a plurality of sequences differing by one or more single-base changes, insertions, deletions, or translocations in a plurality of target nucleotide sequences. This method involves providing a sample potentially containing one or more target nucleotide sequences with a plurality of sequence differences. A plurality of oligonucleotide probe sets are also provided with each set characterized by (a) a first oligonucleotide probe, having a target-specific portion and an addressable array-specific portion, and (b) a second oligonucleotide probe, having a target-specific portion and a detectable reporter label. The oligonucleotide probes in a particular set are suitable for ligation together when hybridized adjacent to one another on a corresponding target nucleotide sequence, but have a mismatch which interferes with such ligation when hybridized to any other nucleotide sequence present in the sample. A ligase is also provided with the sample, the plurality of oligonucleotide probe sets, and the ligase being blended to form a mixture. The mixture is subjected to one or more ligase detection reaction cycles comprising a denaturation treatment, where any hybridized oligonucleotides are separated from the target nucleotide sequences, and a hybridization treatment, where the oligonucleotide probe sets hybridize at adjacent positions in a base-specific manner to their respective target nucleotide sequences, if present in the sample, and ligate to one another to form a ligated product sequence containing (a) the addressable array-specific portion, (b) the target-specific portions connected together, and (c) the detectable reporter label. The oligonucleotide probe sets may hybridize to nucleotide sequences in the sample other than their respective target nucleotide sequences but do not ligate together due to a presence of one or more mismatches and individually separate during the denaturation treatment. A support is provided with capture oligonucleotides immobilized at different positions, where the capture oligonucleotides have nucleotide sequences complementary to the addressable array-specific portions and are formed from a collection of double multimer unit oligonucleotides. The oligonucleotide with addressable array-specific portions will hybridize, within a narrow temperature range of more than 4 times the number of tetramers in the multimer unit with little mismatch, to members of the capture oligonuncleotides. The double multimer unit oligonucleotides are formed from sets of tetramers where (1) each tetramer within the set differs from all other tetramers in the set by at least two nucleotide bases, (2) no two tetramers within a set are complementary to one another, and (3) no tetramers within a set are palindromic or dinucleotide repeats. The collection of double multimer unit oligonucleotides has had the following oligonucleotides removed from it: (1) oligonucleotides having a melting temperature in ° C. of less than 11 times the number of tetramers and more than 15 times the number of tetramers, (2) double multimer units with the same 3 tetramers linked together, and (3) double multimer units with the same 4 tetramers linked together with or without interruption, to form a modified collection of double multimer units. After subjecting the mixture to one or more ligase detection reaction cycles, the mixture is contacted with the support under conditions effective to hybridize the addressable array-specific portions to the capture oligonucleotides in a base-specific manner, thereby capturing the addressable array-specific portions on the support at the site with the complementary capture oligonucleotide. The reporter labels of ligated product sequences captured on the support at particular sites are detected, indicating the presence of one or more target nucleotide sequences in the sample.

Another aspect of the present invention is directed to a kit for identifying one or more of a plurality of sequences differing by single-base changes, insertions, deletions, or translocations in a plurality of target nucleotide sequences. In addition, to a ligase, the kit includes a plurality oligonucleotide probe sets, each characterized by (a) a first oligonucleotide probe, having a target sequence-specific portion and an addressable array-specific portion, and (b) a second oligonucleotide probe, having a target sequence-specific portion and detectable reporter label, wherein the oligonucleotide probes in a particular set are suitable for ligation together when hybridized adjacent to one another on a respective target nucleotide sequence, but have a mismatch which interferes with such ligation when hybridized to any other nucleotide sequence, present in the sample. Also found in the kit is a support with different capture oligonucleotides immobilized at different positions, where the capture oligonucleotides have nucleotide sequences complementary to the addressable array-specific portions and are formed from a collection of double multimer unit oligonucleotides. The oligonucleotide with addressable array-specific portions will hybridize, within a narrow temperature range of greater than 4 times the number of tetramers in the multimer unit with little mismatch, to members of the capture oligonuncleotides. The double multimer unit oligonucleotides are formed from sets of tetramers where (1) each tetramer within the set differs from all other tetramers in the set by at least two nucleotide bases, (2) no two tetramers within a set are complementary to one another, and (3) no tetramers within a set are palindromic or dinucleotide repeats. The collection of double multimer unit oligonucleotides has had the following oligonucleotides removed from it: (1) oligonucleotides having a melting temperature in ° C. of less than 11 times the number of tetramers and more than 15 times then number of tetramers, (2) double multimer units with the same 3 tetramers linked together, and (3) double multimer units with the same 4 tetramers linked together with or without interruption, where the capture oligonucleotides have nucleotide sequences complementary to the addressable array-specific portions.

Often, a number of different single-base mutations, insertions, or deletions may occur at the same nucleotide position of the sequence of interest. The method provides for having an oligonucleotide set, where the second oligonucleotide probe is common and contains the detectable label, and the first oligonucleotide probe has different addressable array-specific portions and target-specific portions. The first oligonucleotide probe is suitable for ligation to a second adjacent oligonucleotide probe at a first ligation junction, when hybridized without mismatch, to the sequence in question. Different first adjacent oligonucleotide probes would contain different discriminating base(s) at the junction where only a hybridization without mismatch at the junction would allow for ligation. Each first adjacent oligonucleotide would contain a different addressable array-specific portion, and, thus, specific base changes would be distinguished by capture at different addresses. In this scheme, a plurality of different capture oligonucleotides are attached at different locations on the solid support for multiplex detection of additional nucleic acid sequences differing from other nucleic acids by at least a single base. Alternatively, the first oligonucleotide probe contains common addressable array-specific portions, and the second oligonucleotide probes have different detectable labels and target-specific portions.

Such arrangements permit multiplex detection of additional nucleic acid sequences differing from other nucleic acids by at least a single base. The nucleic acids sequences can be on the same or different alleles when carrying out such multiplex detection.

The present invention also relates to a kit for carrying out the method of the present invention which includes the ligase, the plurality of different oligonucleotide probe sets, and the solid support with immobilized capture oligonucleotides. Primers for preliminary amplification of the target nucleotide sequences may also be included in the kit. If amplification is by polymerase chain reaction, polymerase may also be included in the kit.

Figure 2:
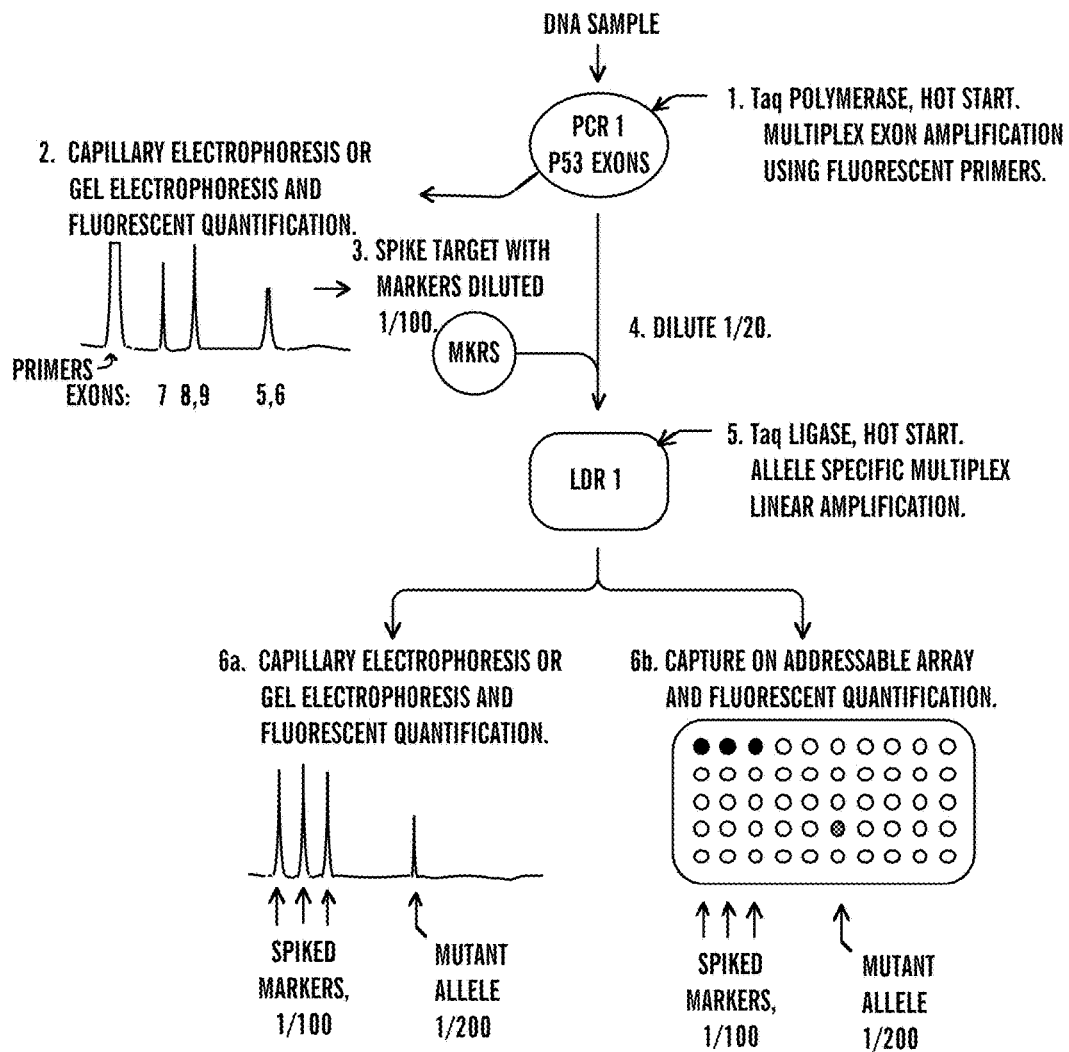
FIG. 2 is a flow diagram depicting PCR/LDR processes, according to the prior art and the present invention, for detection of cancer-associated mutations.

FIGS. 1 and 2 show flow diagrams of the process of the present invention compared to a prior art ligase detection reaction utilizing capillary or gel electrophoresis/fluorescent quantification. FIG. 1 relates to detection of a germline mutation detection, while FIG. 2 shows the detection of cancer.

FIG. 1 depicts the detection of a germline point mutation, such as the p53 mutations responsible for Li-Fraumeni syndrome. In step 1, after DNA sample preparation, exons 5-8 are PCR amplified using Taq (i.e. *Thermus aquaticus*) polymerase under hot start conditions. At the end of the reaction, Taq polymerase is degraded by treatment with Proteinase K. Products are diluted 20-fold in step 2 into fresh LDR buffer containing allele-specific and common LDR probes. A tube generally contains about 500 fmoles of each primer. In step 3, the ligase detection reaction is initiated by addition of Taq ligase under hot start conditions. The LDR probes ligate to their adjacent probes only in the presence of target sequence which gives perfect complementarity at the junction site. The products may be detected in two different formats. In the first format 4a., used in the prior art, fluorescently-labeled LDR probes contain different length poly A or hexaethylene oxide tails. Thus, each LDR product, resulting from ligation to normal DNA with a slightly different mobility, yields a ladder of peaks. A germline mutation would generate a new peak on the electrophorogram. The size of the new peak will approximate the amount of the mutation present in the original sample; 0% for homozygous normal, 50% for heterozygous carrier, or 100% for homozygous mutant. In the second format 4b., in accordance with the present invention, each allele-specific probe contains e.g., 24 additional nucleotide bases on their 5' ends. These sequences are unique addressable sequences which will specifically hybridize to their complementary address sequences on an addressable array. In the LDR reaction, each allele-specific probe can ligate to its adjacent fluorescently labeled common probe in the presence of the corresponding target sequence. Wild type and mutant alleles are captured on adjacent addresses on the array. Unreacted probes are washed away. The black dots indicate 100% signal for the wild type allele. The white dots indicate 0% signal for the mutant alleles. The shaded dots indicate the one position of germline mutation, 50% signal for each allele.

FIG. 2 depicts detection of somatic cell mutations in the p53 tumor suppressor gene but is general for all low sensitivity mutation detection. In step 1, DNA samples are prepared and exons 5-9 are PCR amplified as three fragments using fluorescent PCR primers. This allows for fluorescent quantification of PCR products in step 2 using capillary or gel electrophoresis. In step 3, the products are spiked with a 1/100 dilution of marker DNA (for each of the three fragments). This DNA is homologous to wild type DNA, except it contains a mutation which is not observed in cancer cells, but which may be readily detected with the appropriate LDR probes. The mixed DNA products in step 4 are diluted 20-fold into buffer containing all the LDR probes which are specific only to mutant or marker alleles. In step 5, the ligase detection reaction is initiated by addition of Taq ligase under hot start conditions. The LDR probes ligate to their adjacent probes only in the presence of target sequences which give perfect complementarity at the junction site. The products may be detected in the same two formats described in FIG. 1. In the format of step 6a, which is used in the prior art, products are separated by capillary or gel electrophoresis, and fluorescent signals are quantified. Ratios of mutant peaks to marker peaks give approximate amount of cancer mutations present in the original sample divided by 100. In the format of step 6b, in accordance with the present invention, products are detected by specific hybridization to complementary sequences on an addressable array. Ratios of fluorescent signals in mutant dots to marker dots give the approximate amount of cancer mutations present in the original sample divided by 100.

The ligase detection reaction process, in accordance with the present invention, is best understood by referring to FIGS. 3-15. It is described generally in WO 90/17239 to Barany et al., F. Barany et al., "Cloning, Overexpression and Nucleotide Sequence of a Thermostable DNA Ligase-encoding Gene," *Gene,* 109:1-11 (1991), and F. Barany, "Genetic Disease Detection and DNA Amplification Using Cloned Thermostable Ligase," *Proc. Natl. Acad. Sci. USA,* 88:189-193 (1991), the disclosures of which are hereby incorporated by reference. In accordance with the present invention, the ligase detection reaction can use 2 sets of complementary oligonucleotides. This is known as the ligase chain reaction which is described in the 3 immediately preceding references, which are hereby incorporated by reference. Alternatively, the ligase detection reaction can involve a single cycle which is known as the oligonucleotide ligation assay. See Landegren, et al., "A Ligase-Mediated Gene Detection Technique," *Science* 241:1077-80 (1988); Landegren, et al., "DNA Diagnostics—Molecular Techniques and Automation," *Science* 242:229-37 (1988); and U.S. Pat. No. 4,988,617 to Landegren, et al.

During the ligase detection reaction phase of the process, the denaturation treatment is carried out at a temperature of 80-105° C., while hybridization takes place at 50-85° C. Each cycle comprises a denaturation treatment and a thermal hybridization treatment which in total is from about one to five minutes long. Typically, the ligation detection reaction involves repeatedly denaturing and hybridizing for 2 to 50 cycles. The total time for the ligase detection reaction phase of the process is 1 to 250 minutes.

The oligonucleotide probe sets can be in the form of ribonucleotides, deoxynucleotides, modified ribonucleotides, modified deoxyribonucleotides, peptide nucleotide analogues, modified peptide nucleotide analogues, modified phosphate-sugar-backbone oligonucleotides, nucleotide analogs, and mixtures thereof.

In one variation, the oligonucleotides of the oligonucleotide probe sets each have a hybridization or melting temperature (i.e. $T_m$) of 66-70° C. These oligonucleotides are 20-28 nucleotides long.

It may be desirable to destroy chemically or enzymatically unconverted LDR oligonucleotide probes that contain addressable nucleotide array-specific portions prior to capture of the ligation products on a DNA array. Such unconverted probes will otherwise compete with ligation products for binding at the addresses on the array of the solid support which contain complementary sequences. Destruction can be accomplished by utilizing an exonuclease, such as exonuclease III (L-H Guo and R. Wu, *Methods in Enzymology* 100:60-96 (1985), which is hereby incorporated by reference) in combination with LDR probes that are blocked at the ends and not involved with ligation of probes to one another. The blocking moiety could be a reporter group or a phosphorothioate group. T. T. Nikiforow, et al., "The Use of Phosphorothioate Primers and Exonuclease Hydrolysis for the Preparation of Single-stranded PCR Products and their Detection by Solid-phase Hybridization," *PCR Methods and Applications,* 3:p. 285-291 (1994), which is hereby incorporated by reference. After the LDR process, unligated probes are selectively destroyed by incubation of the reaction mixture with the exonuclease. The ligated probes are protected due to the elimination of free 3' ends which are required for initiation of the exonuclease reaction. This approach results in an increase in the signal-to-noise ratio, especially where the LDR reaction forms only a small amount of product. Since unligated oligonucleotides compete for capture by the capture oligonucleotide, such competition with the ligated oligonucleotides lowers the signal. An additional advantage of this approach is that unhybridized label-containing sequences are degraded and, therefore, are less able to cause a target-independent background signal, because they can be removed more easily from the DNA array by washing.

The oligonucleotide probe sets, as noted above, have a reporter label suitable for detection. Useful labels include chromophores, fluorescent moieties, enzymes, antigens, heavy metals, magnetic probes, dyes, phosphorescent groups, radioactive materials, chemiluminescent moieties, and electrochemical detecting moieties. The capture oligonucleotides can be in the form of ribonucleotides, deoxyribonucleotides, modified ribonucleotides, modified deoxyribonucleotides, peptide nucleotide analogues, modified peptide nucleotide analogues, modified phosphate-sugar backbone oligonucleotides, nucleotide analogues, and mixtures thereof. Where the process of the present invention involves use of a plurality of oligonucleotide sets, the second oligonucleotide probes can be the same, while the addressable array-specific portions of the first oligonucleotide probes differ. Alternatively, the addressable array-specific portions of the first oligonucleotide probes may be the same, while the reporter labels of the second oligonucleotide probes are different.

Prior to the ligation detection reaction phase of the present invention, the sample is preferably amplified by an initial target nucleic acid amplification procedure. This increases the quantity of the target nucleotide sequence in the sample. For example, the initial target nucleic acid amplification may be accomplished using the polymerase chain reaction process, self-sustained sequence replication, or Q-β replicase-mediated RNA amplification. The polymerase chain reaction process is the preferred amplification procedure and is fully described in H. Erlich, et. al., "Recent Advances in the Polymerase Chain Reaction," *Science* 252: 1643-50 (1991); M. Innis, et. al., *PCR Protocols: A Guide to Methods and Applications, Academic Press: New York* (1990); and R. Saiki, et. al., "Primer-directed Enzymatic Amplification of DNA with a Thermostable DNA Polymerase," *Science* 239: 487-91 (1988), which are hereby incorporated by reference. J. Guatelli, et. al., "Isothermal, in vitro Amplification of Nucleic Acids by a Multienzyme Reaction Modeled After Retroviral Replication," *Proc. Natl. Acad. Sci. USA* 87: 1874-78 (1990), which is hereby incorporated by reference, describes the self-sustained sequence replication process. The Q-β replicase-mediated RNA amplification is disclosed in F. Kramer, et. al., "Replicatable RNA Reporters," *Nature* 339: 401-02 (1989), which is hereby incorporated by reference.

Figure 3:
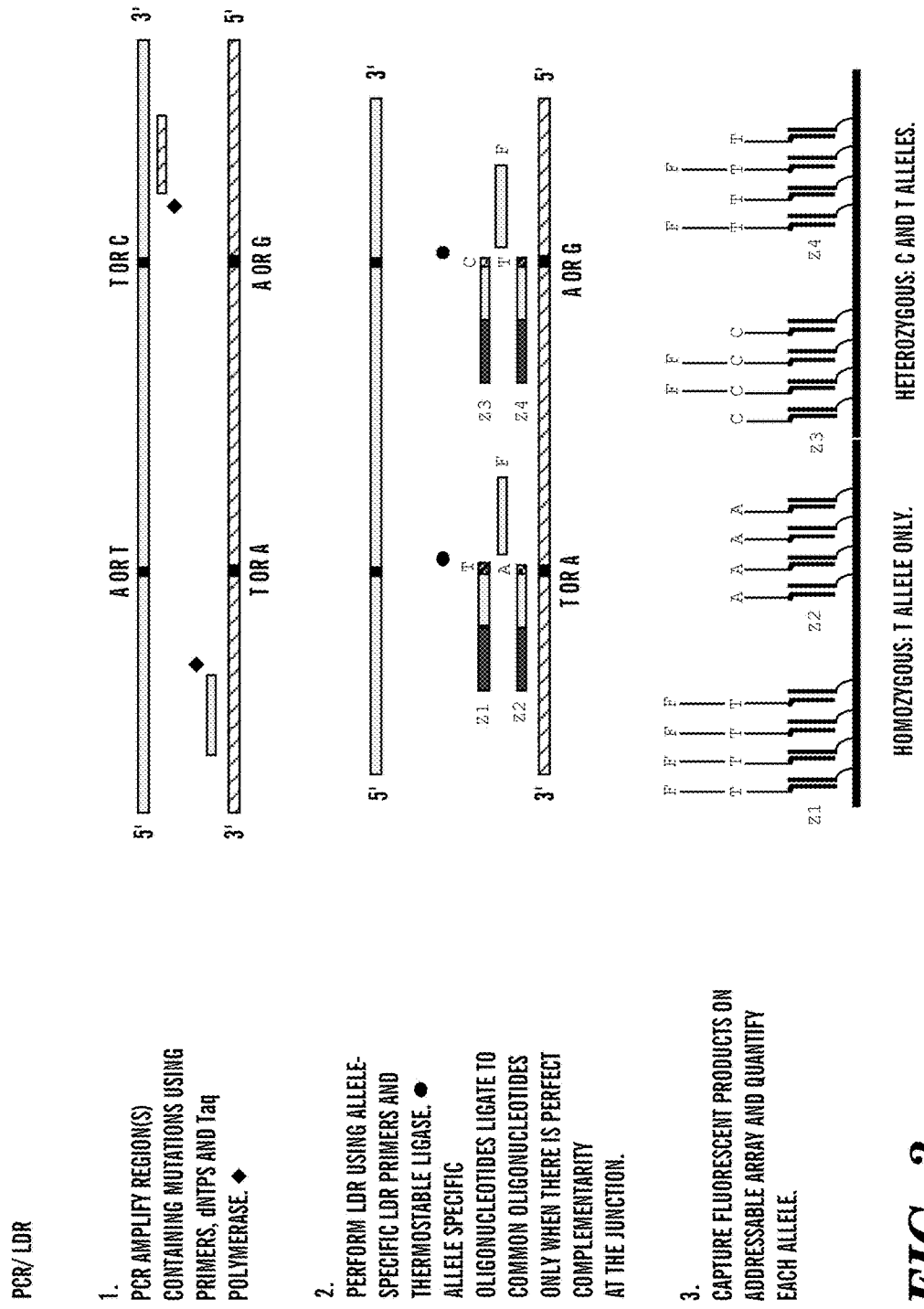
FIG. 3 is a schematic diagram depicting a PCR/LDR process, according to the present invention, using addresses on the allele-specific probes for detecting homo- or heterozygosity at two polymorphisms (i.e. allele differences) on the same gene.

The use of the polymerase chain reaction process and then the ligase detection process, in accordance with the present invention, is shown in FIG. 3. Here, homo- or heterozygosity at two polymorphisms (i.e. allele differences) are on the same gene. Such allele differences can alternatively be on different genes.

As shown in FIG. 3, the target nucleic acid, when present in the form of a double stranded DNA molecule is denatured to separate the strands. This is achieved by heating to a temperature of 80-105° C. Polymerase chain reaction primers are then added and allowed to hybridize to the strands, typically at a temperature of 20-85° C. A thermostable polymerase (e.g., *Thermus aquaticus* polymerase) is also added, and the temperature is then adjusted to 50-85° C. to extend the primer along the length of the nucleic acid to which the primer is hybridized. After the extension phase of the polymerase chain reaction, the resulting double stranded molecule is heated to a temperature of 80-105° C. to denature the molecule and to separate the strands. These hybridization, extension, and denaturation steps may be repeated a number of times to amplify the target to an appropriate level.

Once the polymerase chain reaction phase of the process is completed, the ligation detection reaction phase begins, as shown in FIG. 3. After denaturation of the target nucleic acid, if present as a double stranded DNA molecule, at a temperature of 80-105° C., preferably 94° C., ligation detection reaction oligonucleotide probes for one strand of the target nucleotide sequence are added along with a ligase (for example, as shown in FIG. 3, a thermostable ligase like *Thermus aquaticus* ligase). The oligonucleotide probes are then allowed to hybridize to the target nucleic acid molecule and ligate together, typically, at a temperature of 45-85° C., preferably, 65° C. When there is perfect complementarity at the ligation junction, the oligonucleotides can be ligated together. Where the variable nucleotide is T or A, the presence of T in the target nucleotide sequence will cause the oligonucleotide probe with the addressable array-specific portion Z1 to ligate to the oligonucleotide probe with the reporter label F, and the presence of A in the target nucleotide sequence will cause the oligonucleotide probe with the addressable array-specific portion Z2 to ligate to the oligonucleotide probe with reporter label F. Similarly, where the variable nucleotide is A or G, the presence of T in the target nucleotide sequence will cause the oligonucleotide probe with addressable array-specific portion Z4 to ligate to the oligonucleotide probe with the reporter label F, and the presence of C in the target nucleotide sequence will cause the oligonucleotide probe with the addressable array-specific portion Z3 to ligate to the oligonucleotide probe with reporter label F. Following ligation, the material is again subjected to denaturation to separate the hybridized strands. The hybridization/ligation and denaturation steps can be carried through one or more cycles (e.g., 1 to 50 cycles) to amplify the target signal. Fluorescent ligation products (as well as unligated oligonucleotide probes having an addressable array-specific portion) are captured by hybridization to capture probes complementary to portions Z1, Z2, Z3, and Z4 at particular addresses on the addressable arrays. The presence of ligated oligonucleotides is then detected by virtue of the label F originally on one of the oligonucleotides. In FIG. 3, ligated product sequences hybridize to the array at addresses with capture oligonucleotides complementary to addressable array-specific portions Z1 and Z3, while unligated oligonucleotide probes with addressable array-specific portions Z2 and Z4 hybridize to their complementary capture oligonucleotides. However, since only the ligated product sequences have label F, only their presence is detected.

Figure 4:
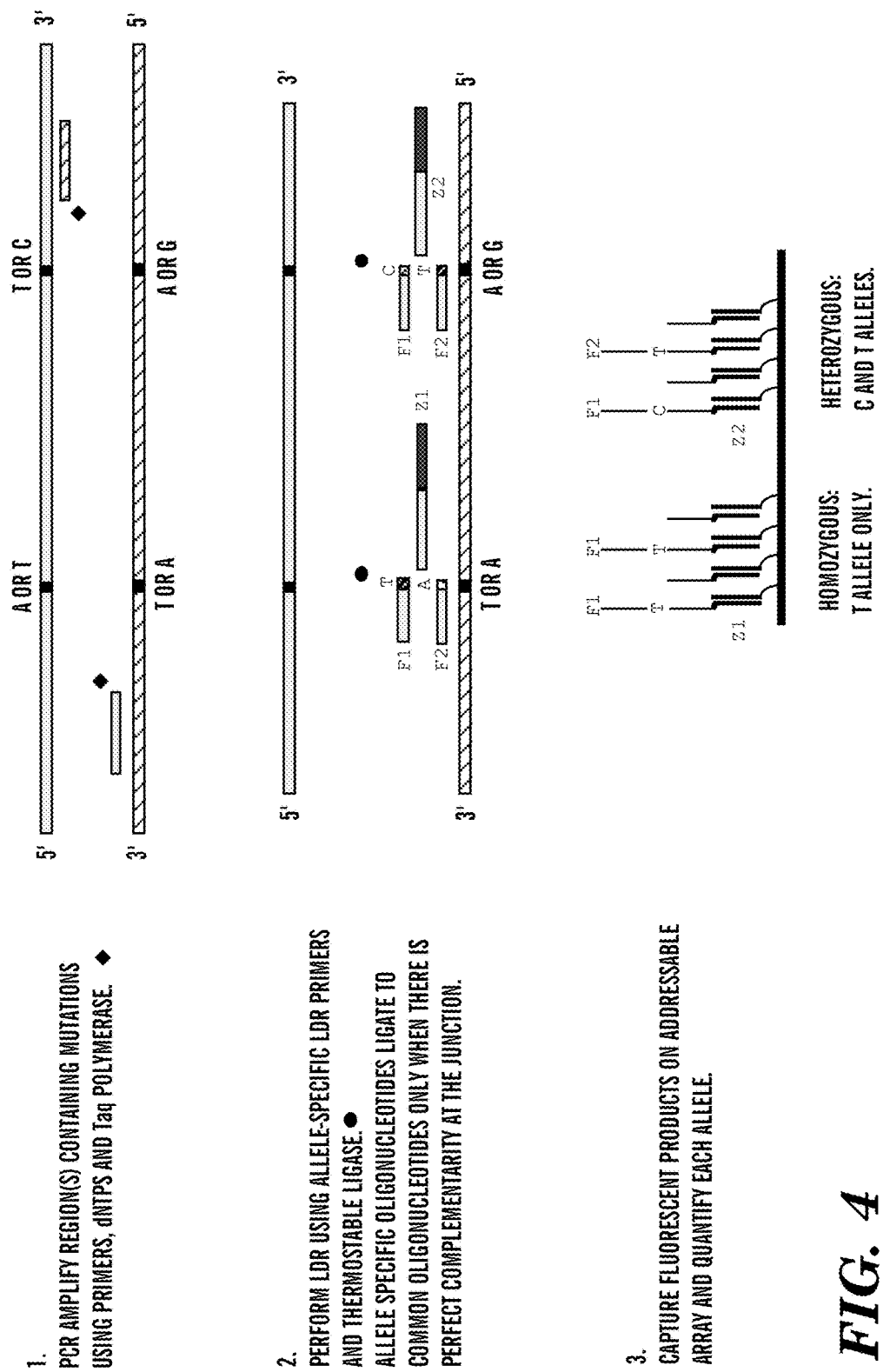
FIG. 4 is a schematic diagram depicting a PCR/LDR process according to the present invention, using addresses on common probes for detecting homo- or heterozygosity at two polymorphisms (i.e. allele differences) on the same gene.

FIG. 4 is similar to FIG. 3 except that in FIG. 4, the common oligonucleotide probe has an address-specific portion, while the allele-specific probes have different labels.

FIG. 5 is a flow diagram of a PCR/LDR process, in accordance with the present invention, which distinguishes any possible base at a given site. Appearance of fluorescent signal at the addresses complementary to addressable array-specific portions Z1, Z2, Z3, and Z4 indicates the presence of A, G, C, and T alleles in the target nucleotide sequence, respectively. Here, the presence of the A and C alleles in the target nucleotide sequences is indicated due to the fluorescence at the addresses on the solid support with capture oligonucleotide probes complementary to portions Z1 and Z3, respectively. Note that in FIG. 5 the addressable array-specific portions are on the discriminating oligonucleotide probes, and the discriminating base is on the 3' end of these probes.

FIG. 6 is similar to FIG. 5, except that in FIG. 6, the common oligonucleotide probe has the address-specific portion, while the allele-specific probes have different labels.

FIG. 7 is a flow diagram of a PCR/LDR process, in accordance with the present invention, for detecting the presence of any possible base at two nearby sites. Here, the LDR probes are able to overlap, yet are still capable of ligating provided there is perfect complementarity at the junction. This distinguishes LDR from other approaches, such as allele-specific PCR where overlapping primers would interfere with one another. In FIG. 7, the first nucleotide position is heterozygous at the A and C alleles, while the second nucleotide position is heterozygous to the G, C, and T alleles. As in FIG. 5, the addressable array-specific portions are on the discriminating oligonucleotide probes, and the discriminating base is on the 3' end of these probes. The reporter group (e.g., the fluorescent label) is on the 3' end of the common oligonucleotide probes. This is possible for example with the 21 hydroxylase gene, where each individual has 2 normal and 2 pseudogenes, and, at the intron 2 splice site (nucleotide 656), there are 3 possible single bases (G, A, and C). Also, this can be used to detect low abundance mutations in HIV infections which might indicate emergence of drug resistant (e.g., to AZT) strains. Returning to FIG. 7, appearance of fluorescent signal at the addresses complementary to addressable array-specific portions Z1, Z2, Z3, Z4, Z5, Z6, Z7, and Z8 indicates the presence of the A, G, C, and T, respectively, in the site heterozygous at the A and C alleles, and A, G, C, and T, respectively, in the site heterozygous at the G, C, and T alleles.

Figure 8:
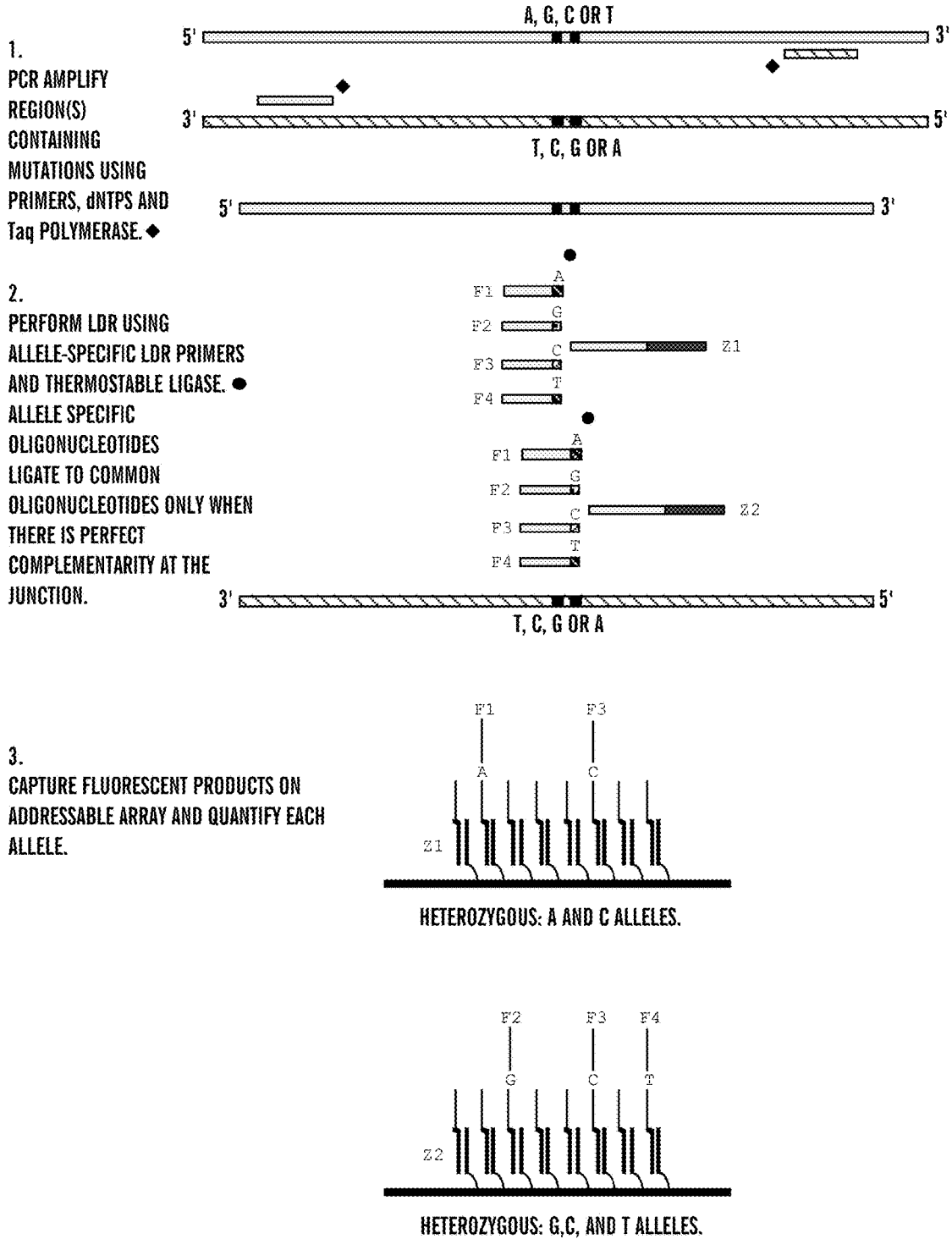
FIG. 8 is a schematic diagram depicting a PCR/LDR process, according to the present invention, using addresses on the common probes for detecting the presence of any possible base at two nearby sites.

FIG. 8 is similar to FIG. 7, except that in FIG. 8, the common oligonucleotide probes have the address-specific portions, while the allele specific probes have different labels.

Figure 9:
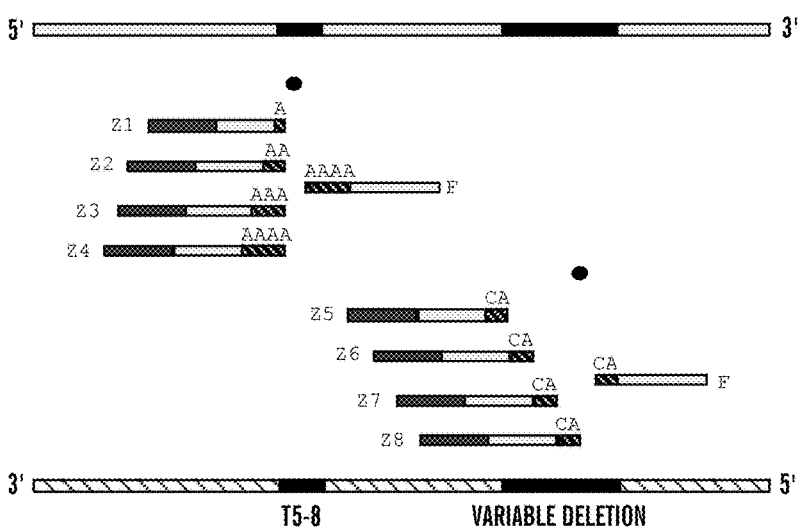
FIG. 9 is a schematic diagram of a PCR/LDR process, according to the present invention, using addresses on the allele-specific probes for distinguishing insertions and deletions.

FIG. 9 is a flow diagram of a PCR/LDR process, in accordance with the present invention, where insertions (top left set of probes) and deletions (bottom right set of probes) are distinguished. On the left, the normal sequence contains 5 A's in a polyA tract. The mutant sequence has an additional 2As inserted into the tract. Therefore, the LDR products with addressable array-specific portions Z1 (representing the normal sequence) and Z3 (representing a 2 base pair insertion) would be fluorescently labeled by ligation to the common probe. While the LDR process (e.g., using a thermostable ligase enzyme) has no difficulty distinguishing single base insertions or deletions in mononucleotide repeats, allele-specific PCR is unable to distinguish such differences, because the 3' base remains the same for both alleles. On the right, the normal sequence is a (CA)5 repeat (i.e. CACACACACA (SEQ ID NO: 9267)). The mutant contains two less CA bases than the normal sequence (i.e. CACACA). These would be detected as fluorescent LDR products at the addressable array-specific portions Z8 (representing the normal sequence) and Z6 (representing the 2 CA deletion) addresses. The resistance of various infectious agents to drugs can also be determined using the present invention. In FIG. 9, the presence of ligated product sequences, as indicated by fluorescent label F, at the address having capture oligonucleotides complementary to Z1 and Z3 demonstrates the presence of both the normal and mutant poly A sequences. Similarly, the presence of ligated product sequences, as indicated by fluorescent label F, at the address having capture oligonucleotides complementary to Z6 and Z8 demonstrates the presence of both the normal CA repeat and a sequence with one repeat unit deleted.

Figure 10:
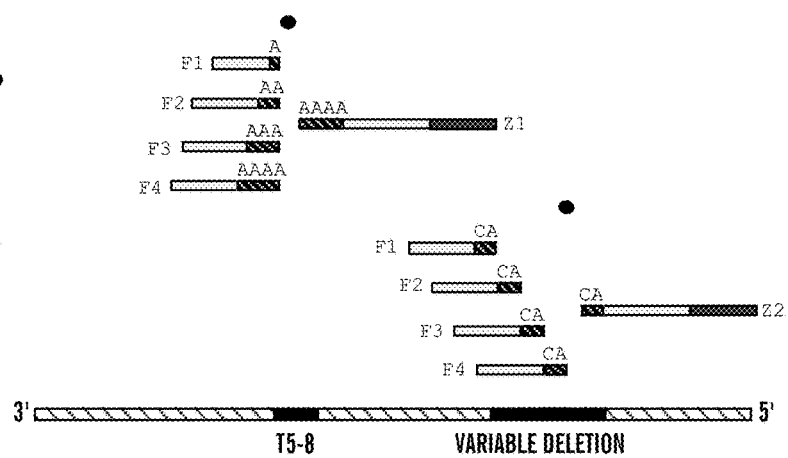
FIG. 10 is a schematic diagram of a PCR/LDR process, according to the present invention, using addresses on the common probes for distinguishing insertions and deletions.

FIG. 10 is similar to FIG. 9, except that in FIG. 10, the common oligonucleotide probes have the address-specific portions, while the allele-specific probes have different labels.

Figure 11:
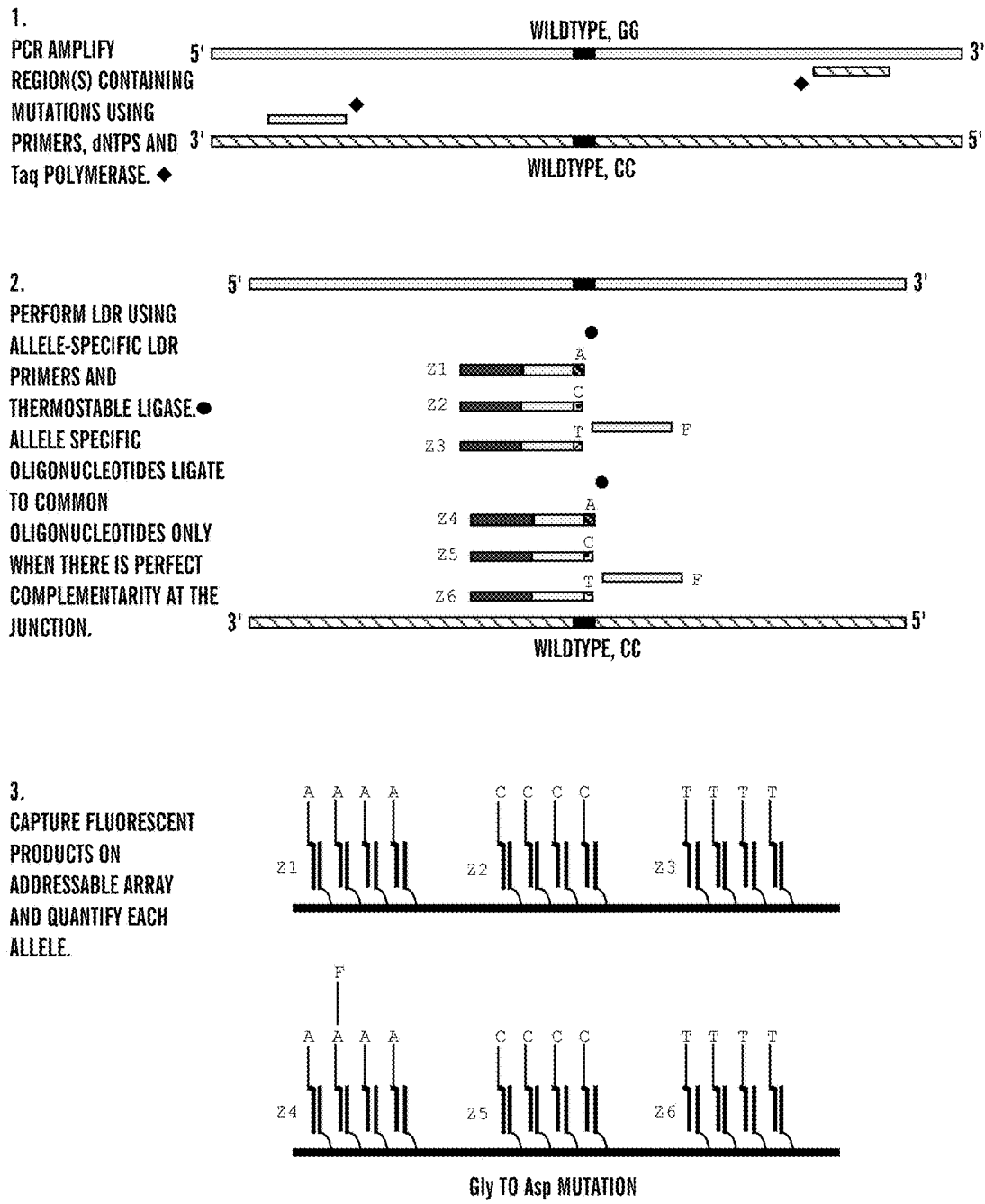
FIG. 11 is a schematic diagram of a PCR/LDR process, in accordance with the present invention, using addresses on the allele-specific probes to detect a low abundance mutation (within a codon) in the presence of an excess of normal sequence.

FIG. 11 is a flow diagram of a PCR/LDR process, in accordance with the present invention, using addressable array-specific portions to detect a low abundance mutation in the presence of an excess of normal sequence. FIG. 11 shows codon 12 of the K-ras gene, sequence GGT, which codes for glycine ("Gly"). A small percentage of the cells contain the G to A mutation in GAT, which codes for aspartic acid ("Asp"). The LDR probes for wild-type (i.e. normal sequences) are missing from the reaction. If the normal LDR probes (with the discriminating base=G) were included, they would ligate to the common probes and overwhelm any signal coming from the mutant target. Instead, as shown in FIG. 11, the existence of a ligated product sequence with fluorescent label F at the address with a capture oligonucleotide complementary to addressable array-specific portion Z4 indicates the presence of the aspartic acid encoding mutant.

FIG. 12 is similar to FIG. 11, except that in FIG. 12, the common oligonucleotide probes have address-specific portions, while the allele-specific probes have different labels.

FIG. 13 is a flow diagram of a PCR/LDR process, in accordance with the present invention, where the addressable array-specific portion is placed on the common oligonucleotide probe, while the discriminating oligonucleotide probe has the reporter label. Allele differences are distinguished by different fluorescent signals, F1, F2, F3, and F4. This mode allows for a more dense use of the arrays, because each position is predicted to light up with some group. It has the disadvantage of requiring fluorescent groups which have minimal overlap in their emission spectra and will require multiple scans. It is not ideally suitable for detection of low abundance alleles (e.g., cancer associated mutations).

FIG. 14 is a flow diagram of a PCR/LDR process, in accordance with the present invention, where both adjacent and nearby alleles are detected. The adjacent mutations are right next to each other, and one set of oligonucleotide probes discriminates the bases on the 3' end of the junction (by use of different addressable array-specific portions Z1, Z2, Z3, and Z4), while the other set of oligonucleotide probes discriminates the bases on the 5' end of the junction (by use of different fluorescent reporter labels F1, F2, F3, and F4). In FIG. 14, codons in a disease gene (e.g. CFTR for cystic fibrosis) encoding Gly and arginine ("Arg"), respectively, are candidates for germline mutations. The detection results in FIG. 14 show the Gly (GGA; indicated by the ligated product sequence having portion Z2 and label F2) has been mutated to glutamic acid ("Glu") (GAA; indicated by the ligated product sequence having portion Z2 and label F1), and the Arg (CGG; indicated by the ligated product sequence having portion Z7 and label F2) has been mutated to tryptophan ("Trp") (TGG; indicated by the ligated product sequence with portion Z8 and label F2). Therefore, the patient is a compound heterozygous individual (i.e. with allele mutations in both genes) and will have the disease.

FIG. 15 is a flow diagram of a PCR/LDR process, in accordance with the present invention, where all possible single-base mutations for a single codon are detected. Most amino acid codons have a degeneracy in the third base, thus the first two positions can determine all the possible mutations at the protein level. These amino acids include arginine, leucine, serine, threonine, proline, alanine, glycine, and valine. However, some amino acids are determined by all three bases in the codon and, thus, require the oligonucleotide probes to distinguish mutations in 3 adjacent positions. By designing four oligonucleotide probes containing the four possible bases in the penultimate position to the 3' end, as well as designing an additional four capture oligonucleotides containing the four possible bases at the 3' end, as shown in FIG. 15, this problem has been solved. The common oligonucleotide probes with the reporter labels only have two fluorescent groups which correspond to the codon degeneracies and distinguish between different ligated product sequences which are captured at the same array address. For example, as shown in FIG. 15, the presence of a glutamine ("Gln") encoding codon (i.e., CAA and CAG) is indicated by the presence of a ligated product sequence containing portion Z1 and label F2. Likewise, the existence of a Gln to histidine ("His") encoding mutation (coded by the codon CAC) is indicated by the presence of ligated product sequences with portion Z1 and label F2 and with portion Z7 and label F2 There is an internal redundancy built into this assay due to the fact that primers Z1 and Z7 have the identical sequence.

A particularly important aspect of the present invention is its capability to quantify the amount of target nucleotide sequence in a sample. This can be achieved in a number of ways by establishing standards which can be internal (i.e. where the standard establishing material is amplified and detected with the sample) or external (i.e. where the standard establishing material is not amplified, and is detected with the sample).

In accordance with one quantification method, the signal generated by the reporter label, resulting from capture of ligated product sequences produced from the sample being analyzed, are detected. The strength of this signal is compared to a calibration curve produced from signals generated by capture of ligated product sequences in samples with known amounts of target nucleotide sequence. As a result, the amount of target nucleotide sequence in the sample being analyzed can be determined. This technique involves use of an external standard.

Another quantification method, in accordance with the present invention, relates to an internal standard. Here, a known amount of one or more marker target nucleotide sequences are added to the sample. In addition, a plurality of marker-specific oligonucleotide probe sets are added along with the ligase, the previously-discussed oligonucleotide probe sets, and the sample to a mixture. The marker-specific oligonucleotide probe sets have (1) a first oligonucleotide probe with a target-specific portion complementary to the marker target nucleotide sequence and an addressable array-specific portion complementary to capture oligonucleotides on the support and (2) a second oligonucleotide probe with a target-specific portion complementary to the marker target nucleotide sequence and a detectable reporter label. The oligonucleotide probes in a particular marker-specific oligonucleotide set are suitable for ligation together when hybridized adjacent to one another on a corresponding marker target nucleotide sequence. However, there is a mismatch which interferes with such ligation when hybridized to any other nucleotide sequence present in the sample or added marker sequences. The presence of ligated product sequences captured on the support is identified by detection of reporter labels. The amount of target nucleotide sequences in the sample is then determined by comparing the amount of captured ligated product generated from known amounts of marker target nucleotide sequences with the amount of other ligated product sequences captured.

Another quantification method in accordance with the present invention involves analysis of a sample containing two or more of a plurality of target nucleotide sequences with a plurality of sequence differences. Here, ligated product sequences corresponding to the target nucleotide sequences are detected and distinguished by any of the previously-discussed techniques. The relative amounts of the target nucleotide sequences in the sample are then quantified by comparing the relative amounts of captured ligated product sequences generated. This provides a quantitative measure of the relative level of the target nucleotide sequences in the sample.

The ligase detection reaction process phase of the present invention can be preceded by the ligase chain reaction process to achieve oligonucleotide product amplification. This process is fully described in F. Barany, et. al., "Cloning, Overexpression and Nucleotide Sequence of a Thermostable DNA Ligase-encoding Gene," *Gene* 109: 1-11 (1991) and F. Barany, "Genetic Disease Detection and DNA Amplification Using Cloned Thermostable Ligase," *Proc. Natl. Acad. Sci. USA* 88: 189-93 (1991), which are hereby incorporated by reference. Instead of using the ligase chain reaction to achieve amplification, a transcription-based amplifying procedure can be used.

The preferred thermostable ligase is that derived from *Thermus aquaticus*. This enzyme can be isolated from that organism. M. Takahashi, et al., "Thermophillic DNA Ligase," *J. Biol. Chem.* 259:10041-47 (1984), which is hereby incorporated by reference. Alternatively, it can be prepared recombinantly. Procedures for such isolation as well as the recombinant production of *Thermus aquaticus* ligase (and *Thermus themophilus* ligase) are disclosed in WO 90/17239 to Barany, et. al., and F. Barany, et al., "Cloning, Overexpression and Nucleotide Sequence of a Thermostable DNA-Ligase Encoding Gene," *Gene* 109:1-11 (1991), which are hereby incorporated by reference. These references contain complete sequence information for this ligase as well as the encoding DNA. Other suitable ligases include *E. coli* ligase, T4 ligase, *Thermus* sp. AK16 ligase, *Aquifex aeolicus* ligase, *Thermotoga maritima* ligase, and *Pyrococcus* ligase.

The ligation amplification mixture may include a carrier DNA, such as salmon sperm DNA.

The hybridization step, which is preferably a thermal hybridization treatment, discriminates between nucleotide sequences based on a distinguishing nucleotide at the ligation junctions. The difference between the target nucleotide sequences can be, for example, a single nucleic acid base difference, a nucleic acid deletion, a nucleic acid insertion, or rearrangement. Such sequence differences involving more than one base can also be detected. Preferably, the oligonucleotide probe sets have substantially the same length so that they hybridize to target nucleotide sequences at substantially similar hybridization conditions. As a result, the process of the present invention is able to detect infectious diseases, genetic diseases, and cancer. It is also useful in environmental monitoring, forensics, and food science.

A wide variety of infectious diseases can be detected by the process of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli, Salmonella, Shigella, Klebsiella, Pseudomonas, Listeria monocytogenes, Mycobacterium tuberculosis, Mycobacterium avium-intracellulare, Yersinia, Francisella, Pasteurella, Brucella, Clostridia, Bordetella pertussis, Bacteroides, Staphylococcus aureus, Streptococcus pneumonia*, B-Hemolytic strep., *Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial* pathogens, *Nocardia*, and *Acitnomycetes*.

Fungal infectious agents which can be detected by the present invention include *Cryptococcus neoformans, Blastomyces dermatitidis, Histoplasma capsulatum, Coccidioides immitis, Paracoccicioides brasiliensis, Candida albicans, Aspergillus fumigautus, Phycomycetes (Rhizopus), Sporothrix schenckii, Chromomycosis*, and *Maduromycosis*.

Viral infectious agents which can be detected by the present invention include human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present invention include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis*, trematodes, *Diphyllobothrium latum, Taenia* spp., *Pneumocystis carinii*, and *Necator americanis*.

The present invention is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present invention.

Genetic diseases can also be detected by the process of the present invention. This can be carried out by prenatal screening for chromosomal and genetic aberrations or post natal screening for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Syndrome, thalassemia, Klinefelter's Syndrome, Huntington's Disease, autoimmune diseases, lipidosis, obesity defects, hemophilia, inborn errors in metabolism, and diabetes.

Cancers which can be detected by the process of the present invention generally involve oncogenes, tumor suppressor genes, or genes involved in DNA amplification, replication, recombination, or repair. Examples of these include: BRCA1 gene, p53 gene, *Familial polyposis coli*, Her2/Neu amplification, Bcr/Abl, K-ras gene, human papillomavirus Types 16 and 18, leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, ENT tumors, and loss of heterozygosity.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety or forensic areas, including for human identification for military personnel and criminal investigation, paternity testing and family relation analysis, HLA compatibility typing, and screening blood, sperm, or transplantation organs for contamination.

In the food and feed industry, the present invention has a wide variety of applications. For example, it can be used for identification and characterization of production organisms such as yeast for production of beer, wine, cheese, yogurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

Desirably, the oligonucleotide probes are suitable for ligation together at a ligation junction when hybridized adjacent to one another on a corresponding target nucleotide sequence due to perfect complementarity at the ligation junction. However, when the oligonucleotide probes in the set are hybridized to any other nucleotide sequence present in the sample, there is a mismatch at a base at the ligation junction which interferes with ligation. Most preferably, the mismatch is at the base adjacent the 3' base at the ligation junction. Alternatively, the mismatch can be at the bases adjacent to bases at the ligation junction.

The process of the present invention is able to detect the first and second nucleotide sequences in the sample in an amount of 100 attomoles to 250 femtomoles. By coupling the LDR step with a primary polymerase-directed amplification step, the entire process of the present invention is able to detect target nucleotide sequences in a sample containing as few as a single molecule. Furthermore, PCR amplified products, which often are in the picomole amounts, may easily be diluted within the above range. The ligase detection reaction achieves a rate of formation of mismatched ligated product sequences which is less than 0.005 of the rate of formation of matched ligated product sequences.

Once the ligation phase of the process is completed, the capture phase is initiated. During the capture phase of the process, the mixture is contacted with the solid support at a temperature of 25-90° C., preferably 60-80° C., and for a time period of 10-180 minutes, preferably up to 60 minutes. Hybridizations may be accelerated or improved by mixing the ligation mixture during hybridization, or by adding volume exclusion, chaotropic agents, tetramethylammonium chloride, or N,N,N, Trimethylglycine (Betaine monohydrate). When an array consists of dozens to hundreds of addresses, it is important that the correct ligation products have an opportunity to hybridize to the appropriate address. This may be achieved by the thermal motion of oligonucleotides at the high temperatures used, by mechanical movement of the fluid in contact with the array surface, or by moving the oligonucleotides across the array by electric fields. After hybridization, the array is washed with buffer to remove unhybridized probe and optimize detection of captured probe. Alternatively, the array is washed sequentially. The specificity of hybridization may be promoted by the addition of non-specific competitor DNA (e.g. herring sperm DNA) and/or the addition of formamide to the hybridization solution. The stringency of washing may also be augmented by elevating the washing temperature and/or adding formamide to the wash buffer. FIG. 16 shows the results of various combinations of the above alterations to standard hybridization and washing conditions.

Preferably, the solid support has a porous surface of a hydrophilic polymer composed of combinations of acrylamide with functional monomers containing carboxylate, aldehyde, or amino groups. This surface is formed by coating the support with a polyacrylamide based gel. Suitable formulations include mixtures of acrylamide/acrylic acid and N,N-dimethylacrylamide/glycerol monomethacrylate. A crosslinker, N, N'-methylenebisacryl-amide, is present at a level less than 50:1, preferably less than 500:1.

One embodiment of masking negative charges during the contacting of the solid support with the ligation mixture is achieved by using a divalent cation. The divalent cation can be $Mg^{2+}$, $Ca^{2+}$, $MN^{2+}$, or $Co^{2+}$. Typically, masking with the divalent cation is carried out by pre-hydridizing the solid support with hybridization buffer containing the cation at a minimum concentration of 10 mM for a period of 15 minutes at room temperature.

Another embodiment of masking negative charges during the contacting of the solid support with the ligation mixtures is achieved by carrying out the contacting at a pH at or below 6.0. This is effected by adding a buffer to the ligation mixtures before or during contact of it with the solid support. Suitable buffers include 2-(N-morpholino)ethanesulfonic acid (MES), sodium phosphate, and potassium phosphate.

Another embodiment of masking negative charges during the contacting of the solid support with the ligation mixture is achieved by capping free carboxylic acid groups with a neutralizing agent while preserving the hydrophillicity of the polymer. Suitable neutralizing agents include ethanolamine diethanolamine, propanolamine, dipropanolamine, isopropanolamine, and diisopropanolamine. Typically, masking with neutralizing agents is carried out by activating the carboxylic acid groups within the solid support with 1-[3-dimethylamino)propyl]-3-ethylcarbodiimide hydrochloride and N-hydroxysuccinimide followed by treatment with a solution of the neutralizing agent in a polar aprotic solvent such as chloroform, dichloromethane, or tetrahydrfuran.

By masking the negative charges in accordance with the present invention, an enhanced ability to detect the presence of ligated product in the presence of unligated oligonucleotide probes is achieved. In particular, the present invention is effective to detect the presence of ligated product in a ratio to unligated oligonucleotide probes of less than 1:300, preferably less than 1:900, more preferably less than 1:3000, and most preferably less than 1:9000.

In addition, by masking the negative charges in accordance with the present invention, an enhanced ability to detect the presence of a target nucleotide sequence from a non-target nucleotide sequence where the target nucleotide sequence differs from a non-target nucleotide sequence by a single base difference is achieved. In particular, the present invention is effective to detect target nucleotide sequence in a ratio of the target nucleotide sequence to non-target nucleotide sequence of less than 1:20, preferably less than 1:50, more preferably less than 1:100, most preferably less than 1:200.

It is important to select capture oligonucleotides and addressable nucleotide sequences which will hybridize in a stable fashion. This requires that the oligonucleotide sets and the capture oligonucleotides be configured so that the oligonucleotide sets hybridize to the target nucleotide sequences at a temperature less than that which the capture oligonucleotides hybridize to the addressable array-specific portions. Unless the oligonucleotides are designed in this fashion, false positive signals may result due to capture of adjacent unreacted oligonucleotides from the same oligonucleotide set which are hybridized to the target.

The detection phase of the process involves scanning and identifying if ligation of particular oligonucleotide sets occurred and correlating ligation to a presence or absence of the target nucleotide sequence in the test sample. Scanning can be carried out by scanning electron microscopy, confocal microscopy, charge-coupled device, scanning tunneling electron microscopy, infrared microscopy, atomic force microscopy, electrical conductance, and fluorescent or phosphor imaging. Correlating is carried out with a computer.

Another aspect of the present invention relates to a method of forming an array of oligonucleotides on a support. This method involves providing a support having an array of positions each suitable for attachment of an oligonucleotide. A linker or support (preferably non-hydrolyzable), suitable for coupling an oligonucleotide to the support at each of the array positions, is attached to the solid support. An array of oligonucleotides on a solid support is formed by a series of cycles of activating selected array positions for attachment of multimer nucleotides and attaching multimer nucleotides at the activated array positions.

Yet another aspect of the present invention relates to an array of oligonucleotides on a support per se. The support has an array of positions each suitable for an attachment of an oligonucleotide. A linker or support (preferably non-hydrolyzable), suitable for coupling an oligonucleotide to the support, is attached to the support at each of the array positions. An array of oligonucleotides are placed on a support with at least some of the array positions being occupied by oligonucleotides having greater than sixteen nucleotides.

In the method of forming arrays, multimer oligonucleotides from different multimer oligonucleotide sets are attached at different array positions on a support. As a result, the support has an array of positions with different groups of multimer oligonucleotides attached at different positions.

The 1,000 different addresses can be unique capture oligonucleotide sequences (e.g., 24-mer) linked covalently to the target-specific sequence (e.g., approximately 20- to 25-mer) of a LDR oligonucleotide probe. A capture oligonucleotide probe sequence does not have any homology to either the target sequence or to other sequences on genomes which may be present in the sample. This oligonucleotide probe is then captured by its addressable array-specific portion, a sequence complementary to the capture oligonucleotide on the addressable support array. The concept is shown in two possible formats, for example, for detection of the p53 R248 mutation (FIGS. 17A-C).

FIGS. 17A-C show two alternative formats for oligonucleotide probe design to identify the presence of a germ line mutation in codon 248 of the p53 tumor suppressor gene. The wild type sequence codes for arginine (R248), while the cancer mutation codes for tryptophan (R248W). The bottom part of the diagram is a schematic diagram of the capture oligonucleotide. The thick horizontal line depicts the membrane or surface containing the addressable array. The thin curved lines indicate a flexible linker arm. The thicker lines indicate a capture oligonucleotide sequence, attached to the solid surface in the C to N direction. For illustrative purposes, the capture oligonucleotides are drawn vertically, making the linker arm in section B appear "stretched". Since the arm is flexible, the capture oligonucleotide will be able to hybridize 5' to C and 3' to N in each case, as dictated by base pair complementarity. A similar orientation of oligonucleotide hybridization would be allowed if the oligonucleotides were attached to the membrane at the N-terminus. In this case, DNA/PNA hybridization would be in standard antiparallel 5' to 3' and 3' to 5'. Other modified sugar-phosphate backbones would be used in a similar fashion. FIG. 17B shows two LDR probes that are designed to discriminate wild type and mutant p53 by containing the discriminating base C or T at the 3' end. In the presence of the correct target DNA and Tth ligase, the discriminating probe is covalently attached to a common downstream oligonucleotide. The downstream oligonucleotide is fluorescently labeled. The discriminating oligonucleotides are distinguished by the presence of unique addressable array-specific portions, Z1 and Z2, at each of their 5' ends. A black dot indicates that target dependent ligation has taken place. After ligation, oligonucleotide probes may be captured by their complementary addressable array-specific portions at unique addresses on the array. Both ligated and unreacted oligonucleotide probes are captured by the oligonucleotide array. Unreacted fluorescently labeled common probes and target DNA are then washed away at a high temperature (approximately 65° C. to 80° C.) and low salt. Mutant signal is distinguished by detection of fluorescent signal at the capture oligonucleotide complementary to addressable array-specific portion Z1, while wild type signal appears at the capture oligonucleotide complementary to addressable array-specific portion Z2. Heterozygosity is indicated by equal signals at the capture oligonucleotides complementary to addressable array-specific portions Z1 and Z2. The signals may be quantified using a fluorescent imager. This format uses a unique address for each allele and may be preferred for achieving very accurate detection of low levels of signal (30 to 100 attomoles of LDR product). FIG. 17C shows the discriminating signals may be quantified using a fluorescent imager. This format uses a unique address where oligonucleotide probes are distinguished by having different fluorescent groups, F1 and F2, on their 5' end. Either oligonucleotide probe may be ligated to a common downstream oligonucleotide probe containing an addressable array-specific portion Z1 on its 3' end. In this format, both wild type and mutant LDR products are captured at the same address on the array, and are distinguished by their different fluorescence. This format allows for a more efficient use of the array and may be preferred when trying to detect hundreds of potential germline mutations.

The support can be made from a wide variety of materials. The substrate may be biological, nonbiological, organic, inorganic, or a combination of any of these, existing as particles, strands, precipitates, gels, sheets, tubing, spheres, containers, capillaries, pads, slices, films, plates, slides, discs, membranes, etc. The substrate may have any convenient shape, such as a disc, square, circle, etc. The substrate is preferably flat but may take on a variety of alternative surface configurations. For example, the substrate may contain raised or depressed regions on which the synthesis takes place. The substrate and its surface preferably form a rigid support on which to carry out the reactions described herein. The substrate and its surface is also chosen to provide appropriate light-absorbing characteristics. For instance, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polyethylene, polypropylene, polyvinyl chloride, poly(methyl acrylate), poly(methyl methacrylate), or combinations thereof. Other substrate materials will be readily apparent to those of ordinary skill in the art upon review of this disclosure. In a preferred embodiment, the substrate is flat glass or single-crystal silicon.

According to some embodiments, the surface of the substrate is etched using well known techniques to provide for desired surface features. For example, by way of the formation of trenches, v-grooves, mesa structures, raised platforms, or the like, the synthesis regions may be more closely placed within the focus point of impinging light, be provided with reflective "mirror" structures for maximization of light collection from fluorescent sources, or the like.

Surfaces on the substrate will usually, though not always, be composed of the same material as the substrate. Thus, the surface may be composed of any of a wide variety of materials, for example, polymers, plastics, ceramics, polysaccharides, silica or silica-based materials, carbon, metals, inorganic glasses, membranes, or composites thereof. The surface is functionalized with binding members which are attached firmly to the surface of the substrate. Preferably, the surface functionalities will be reactive groups such as silanol, olefin, amino, hydroxyl, aldehyde, keto, halo, acyl halide, or carboxyl groups. In some cases, such functionalities preexist on the substrate. For example, silica based materials have silanol groups, polysaccharides have hydroxyl groups, and synthetic polymers can contain a broad range of functional groups, depending on which monomers they are produced from. Alternatively, if the substrate does not contain the desired functional groups, such groups can be coupled onto the substrate in one or more steps.

A variety of commercially-available materials, which include suitably modified glass, plastic, or carbohydrate surfaces or a variety of membranes, can be used. Depending on the material, surface functional groups (e.g., silanol, hydroxyl, carboxyl, amino) may be present from the outset (perhaps as part of the coating polymer), or will require a separate procedure (e.g., plasma amination, chromic acid oxidation, treatment with a functionalized side chain alkyltrichlorosilane) for introduction of the functional group. Hydroxyl groups become incorporated into stable carbamate (urethane) linkages by several methods. Amino functions can be acylated directly, whereas carboxyl groups are activated, e.g., with N,N'-carbonyldiimidazole or water-soluble carbodiimides, and reacted with an amino-functionalized compound. As shown in FIG. 18, the supports can be membranes or surfaces with a starting functional group X. Functional group transformations can be carried out in a variety of ways (as needed) to provide group X* which represents one partner in the covalent linkage with group Y*. FIG. 18 shows specifically the grafting of PEG (i.e. polyethylene glycol), but the same repertoire of reactions can be used (however needed) to attach carbohydrates (with hydroxyl), linkers (with carboxyl), and/or oligonucleotides that have been extended by suitable functional groups (amino or carboxyl). In some cases, group X* or Y* is pre-activated (isolatable species from a separate reaction); alternatively, activation occurs in situ. Referring to PEG as drawn in FIG. 18, Y and Y* can be the same (homobifunctional) or different (heterobifunctional); in the latter case, Y can be protected for further control of the chemistry. Unreacted amino groups will be blocked by acetylation or succinylation, to ensure a neutral or negatively charged environment that "repels" excess unhybridized DNA. Loading levels can be determined by standard analytical methods. Fields, et al., "Principles and Practice of Solid-Phase Peptide Synthesis," *Synthetic Peptides: A User's Guide*, G. Grant, Editor, W.H. Freeman and Co.: New York. p. 77-183 (1992), which is hereby incorporated by reference.

One approach to applying functional groups on a silica-based support surface is to silanize with a molecule either having the desired functional group (e.g., olefin, amino, hydroxyl, aldehyde, keto, halo, acyl halide, or carboxyl) or a molecule A able to be coupled to another molecule B containing the desired functional group. In the former case, functionalizing of glass- or silica-based supports with, for example, an amino group is carried out by reacting with an amine compound such as 3-aminopropyl triethoxysilane, 3-aminopropylmethyldiethoxysilane, 3-aminopropyl dimethylethoxysilane, 3-aminopropyl trimethoxysilane, N-(2-aminoethyl)-3-aminopropylmethyl dimethoxysilane, N-(2-aminoethyl-3-aminopropyl) trimethoxysilane, aminophenyl trimethoxysilane, 4-aminobutyldimethyl methoxysilane, 4-aminobutyl triethoxysilane, aminoethylaminomethylphenethyl trimethoxysilane, or mixtures thereof. In the latter case, molecule A preferably contains olefinic groups, such as vinyl, acrylate, methacrylate, or allyl, while molecule B contains olefinic groups and the desired functional groups. In this case, molecules A and B are polymerized together. In some cases, it is desirable to modify the silanized surface to modify its properties (e.g., to impart biocompatibility and to increase mechanical stability). This can be achieved by addition of olefinic molecule C along with molecule B to produce a polymer network containing molecules A, B, and C.

Molecule A is defined by the following formula:

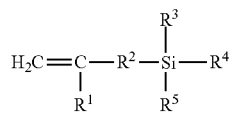

$R^1$ is H or $CH_3$ $R^2$ is (C=O)—O—$R^6$, aliphatic group with or without functional substituent(s), an aromatic group with or without functional substituent(s), or mixed aliphatic/aromatic groups with or without functional substituent(s);

$R^3$ is an O-alkyl, alkyl, or halogen group;

$R^4$ is an O-alkyl, alkyl, or halogen group;

$R^5$ is an O-alkyl, alkyl, or halogen group; and $R^6$ is an aliphatic group with or without functional substituent(s), an aromatic group with or without functional substituent(s), or mixed aliphatic/aromatic groups with or without functional substituent(s). Examples of Molecule A include 3-(trimethoxysilyl)propyl methacrylate, N-[3-(trimethoxysilyl)propyl]-N'-(4-vinylbenzyl)ethylenediamine, triethoxyvinylsilane, triethylvinylsilane, vinyltrichlorosilane, vinyltrimethoxysilane, and vinylytrimethylsilane.

Molecule B can be any monomer containing one or more of the functional groups described above. Molecule B is defined by the following formula:

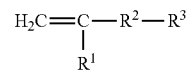

(i) $R^1$ is H or $CH_3$,
$R^2$ is (C=O), and
$R^3$ is OH or Cl.
or
(ii) $R^1$ is H or $CH_3$ and
$R^2$ is (C=O)—O—$R^4$, an aliphatic group with or without functional substituent(s), an aromatic group with or without functional substituent(s), and mixed aliphatic/aromatic groups with or without functional substituent(s); and
$R^3$ is a functional group, such as OH, COOH, $NH_2$, halogen, SH, COCl, or active ester; and
$R^4$ is an aliphatic group with or without functional substituent(s), an aromatic group with or without functional substituent(s), or mixed aliphatic/aromatic groups with or without functional substituent(s). Examples of molecule B include acrylic acid, acrylamide, methacrylic acid, vinylacetic acid, 4-vinylbenzoic acid, itaconic acid, allyl amine, allylethylamine, 4-aminostyrene, 2-aminoethyl methacrylate, acryloyl chloride, methacryloyl chloride, chlorostyrene, dichlorostyrene, 4-hydroxystyrene, hydroxymethyl styrene, vinylbenzyl alcohol, allyl alcohol, 2-hydroxyethyl methacrylate, or poly(ethylene glycol) methacrylate.

Molecule C can be any molecule capable of polymerizing to molecule A, molecule B, or both and may optionally contain one or more of the functional groups described above. Molecule C can be any monomer or cross-linker, such as acrylic acid, methacrylic acid, vinylacetic acid, 4-vinylbenzoic acid, itaconic acid, allyl amine, allylethylamine, 4-aminostyrene, 2-aminoethyl methacrylate, acryloyl chloride, methacryloyl chloride, chlorostyrene, dichlorostyrene, 4-hydroxystyrene, hydroxymethyl styrene, vinylbenzyl alcohol, allyl alcohol, 2-hydroxyethyl methacrylate, poly(ethylene glycol) methacrylate, methyl acrylate, methyl methacrylate, ethyl acrylate, ethyl methacrylate, styrene, 1-vinylimidazole, 2-vinylpyridine, 4-vinylpyridine, divinylbenzene, ethylene glycol dimethacryarylate, N,N'-methylenediacrylamide, N,N'-phenylenediacrylamide, 3,5-bis(acryloylamido)benzoic acid, pentaerythritol triacrylate, trimethylolpropane trimethacrylate, pentaerythritol tetraacrylate, trimethylolpropane ethoxylate (14/3 EO/OH) triacrylate, trimethylolpropane ethoxylate (7/3 EO/OH) triacrylate, triethylolpropane propoxylate (1 PO/OH) triacrylate, or trimethyolpropane propoxylate (2 PO/PH triacrylate).

Generally, the functional groups serve as starting points for oligonucleotides that will ultimately be coupled to the support. These functional groups can be reactive with an organic group that is to be attached to the support or it can be modified to be reactive with that group, as through the use of linkers or handles. The functional groups can also impart various desired properties to the support.

After functionalization (if necessary) of the support, tailor-made polymer networks containing activated functional groups that may serve as carrier sites for complementary oligonucleotide capture probes can be grafted to the support. The advantage of this approach is that the loading capacity of capture probes can thus be increased significantly, while physical properties of the intermediate solid-to-liquid phase can be controlled better. Parameters that are subject to optimization include the type and concentration of functional group-containing monomers, as well as the type and relative concentration of the crosslinkers that are used.

The surface of the functionalized substrate is preferably provided with a layer of linker molecules, although it will be understood that the linker molecules are not required elements of the invention. The linker molecules are preferably of sufficient length to permit polymers in a completed substrate to interact freely with molecules exposed to the substrate. The linker molecules should be 6-50 atoms long to provide sufficient exposure. The linker molecules may be, for example, aryl acetylene, ethylene glycol oligomers containing 2-10 monomer units, diamines, diacids, amino acids, or combinations thereof.

According to alternative embodiments, the linker molecules are selected based upon their hydrophilic/hydrophobic properties to improve presentation of synthesized polymers to certain receptors. For example, in the case of a hydrophilic receptor, hydrophilic linker molecules will be preferred to permit the receptor to approach more closely the synthesized polymer.

According to another alternative embodiment, linker molecules are also provided with a photocleavable group at any intermediate position. The photocleavable group is preferably cleavable at a wavelength different from the protective group. This enables removal of the various polymers following completion of the syntheses by way of exposure to the different wavelengths of light.

The linker molecules can be attached to the substrate via carbon-carbon bonds using, for example, (poly)tri-fluorochloroethylene surfaces or, preferably, by siloxane bonds (using, for example, glass or silicon oxide surfaces). Siloxane bonds with the surface of the substrate may be formed in one embodiment via reactions of linker molecules bearing trichlorosilyl groups. The linker molecules may optionally be attached in an ordered array, i.e., as parts of the head groups in a polymerized monolayer. In alternative embodiments, the linker molecules are adsorbed to the surface of the substrate.

As an example of assembling arrays with multimers, such assembly can be achieved with tetramers. Of the 256 ($4^4$) possible ways in which four bases can be arranged as tetramers, 36 that have unique sequences can be selected. Each of the chosen tetramers differs from all the others by at least two bases, and no two dimers are complementary to each other. Furthermore, tetramers that would result in self-pairing or hairpin formation of the addresses have been eliminated.

The final tetramers are listed in Table 1 and have been numbered arbitrarily from 1 to 36. This unique set of tetramers are used as design modules for the sometimes desired 24-mer capture oligonucleotide address sequences. The structures can be assembled by stepwise (one base at a time) or convergent (tetramer building blocks) synthetic strategies. Many other sets of tetramers may be designed which follow the above rules. The segment approach is not uniquely limited to tetramers, and other units, i.e. dimers, trimers, pentamers, or hexamers could also be used.

TABLE 1

List of tetramer PNA sequences and complementary DNA sequences, which differ from each other by at least 2 bases.

| Number | Sequence (N-C) | Complement (5'-3') | G + C |
|---|---|---|---|
| 1. | TCTG | CAGA | 2 |
| 2. | TGTC | GACA | 2 |
| 3. | TCCC | GGGA | 3 |
| 4. | TGCG | CGCA | 3 |
| 5. | TCGT | ACGA | 2 |
| 6. | TTGA | TCAA | 1 |
| 7. | TGAT | ATCA | 1 |
| 8. | TTAG | CTAA | 1 |
| 9. | CTTG | CAAG | 2 |
| 10. | CGTT | AACG | 2 |
| 11. | CTCA | TGAG | 2 |
| 12. | CACG | CGTG | 3 |
| 13. | CTGT | ACAG | 2 |
| 14. | CAGC | GCTG | 3 |
| 15. | CCAT | ATGG | 2 |
| 16. | CGAA | TTCG | 2 |
| 17. | GCTT | AAGC | 2 |
| 18. | GGTA | TACC | 2 |
| 19. | GTCT | AGAC | 2 |
| 20. | GACC | GGTC | 3 |
| 21. | GAGT | ACTC | 2 |
| 22. | GTGC | GCAC | 3 |
| 23. | GCAA | TTGC | 2 |
| 24. | GGAC | GTCC | 3 |
| 25. | AGTG | CACT | 2 |
| 26. | AATC | GATT | 1 |
| 27. | ACCT | AGGT | 2 |
| 28. | ATCG | CGAT | 2 |

TABLE 1-continued

List of tetramer PNA sequences and complementary DNA sequences, which differ from each other by at least 2 bases.

| Number | Sequence (N-C) | Complement (5'-3') | G + C |
|---|---|---|---|
| 29. | ACGG | CCGT | 3 |
| 30. | AGGA | TCCT | 2 |
| 31. | ATAC | GTAT | 1 |
| 32. | AAAG | CTTT | 1 |
| 33. | CCTA | TAGG | 2 |
| 34. | GATG | CATC | 2 |
| 35. | AGCC | GGCT | 3 |
| 36. | TACA | TGTA | 1 |

Note that the numbering scheme for tetramers permits abbreviation of each address as a string of six numbers (e.g., second column of Table 2 infra). The concept of a 24-mer address designed from a unique set of 36 tetramers (Table 1) allows a huge number of possible structures, $36^6 = 2,176,782,336$.

FIG. 19 shows one of the many possible designs of 36 tetramers which differ from each other by at least 2 bases. The checkerboard pattern shows all 256 possible tetramers. A given square represents the first two bases on the left followed by the two bases on the top of the checkerboard. Each tetramer must differ from each other by at least two bases, and should be non-complementary. The tetramers are shown in the white boxes, while their complements are listed as (number). Thus, the complementary sequences GACC (20) and GGTC (20') are mutually exclusive in this scheme. In addition, tetramers must be non-palindromic, e.g., TCGA (darker diagonal line boxes), and non-repetitive, e.g., CACA (darker diagonal line boxes from upper left to lower right). All other sequences which differ from the 36 tetramers by only 1 base are shaded in light gray. Four potential tetramers (white box) were not chosen as they are either all A•T or G•C bases. However, as shown below, the $T_m$ values of A•T bases can be raised to almost the level of G•C bases. Thus, all A•T or G•C base tetramers (including the ones in white boxes) could potentially be used in a tetramer design. In addition, thymine can be replaced by 5-propynyl uridine when used within capture oligonucleotide address sequences as well as in the oligonucleotide probe addressable array-specific portions. This would increase the $T_m$ of an A•T base pair by ~1.7° C. Thus, $T_m$ values of individual tetramers should be approximately 15.1° C. to 15.7° C. $T_m$ values for the full length 24-mers should be 95° C. or higher.

To illustrate the concept, a subset of six of the 36 tetramer sequences were used to construct arrays: 1=TGCG; 2=ATCG; 3=CAGC; 4=GGTA; 5=GACC; and 6=ACCT. This unique set of tetramers can be used as design modules for the required 24-mer addressable array-specific portion and 24-mer complementary capture oligonucleotide address sequences. This embodiment involves synthesis of five addressable array-specific portion (sequences listed in Table 2). Note that the numbering scheme for tetramers allows abbreviation of each portion (referred to as "Zip #") as a string of six numbers (referred to as "zip code").

TABLE 2

List of all 5 DNA/PNA oligonucleotide address sequences.

| Zip # | Zip code | Sequence (5' → 3' or NH2 → COOH) | G + C |
|---|---|---|---|
| Zip11 | 1-4-3-6-6-1 | TGCG-GGTA-CAGC-ACCT-ACCT-TGCG (SEQ ID NO: 9268) | 15 |
| Zip12 | 2-4-4-6-1-1 | ATCG-GGTA-GGTA-ACCT-TGCG-TGCG (SEQ ID NO: 9269) | 14 |
| Zip13 | 3-4-5-6-2-1 | CAGC-GGTA-GACC-ACCT-ATCG-TGCG (SEQ ID NO: 9270) | 15 |
| Zip14 | 4-4-6-6-3-1 | GGTA-GGTA-ACCT-ACCT-CAGC-TGCG (SEQ ID NO: 9271) | 14 |
| Zip15 | 5-4-1-6-4-1 | GACC-GGTA-TGCG-ACCT-GGTA-TGCG (SEQ ID NO: 9272) | 15 |

Each of these oligomers contains a hexaethylene oxide linker arm on their 5' termini [P. Grossman, et al., *Nucl. Acids Res.*, 22:4527-4534 (1994), which is hereby incorporated by reference], and ultimate amino-functions suitable for attachment onto the surfaces of glass slides, or alternative materials. Conjugation methods will depend on the free surface functional groups [Y. Zhang, et al., *Nucleic Acids Res.*, 19:3929-3933 (1991) and Z. Guo, et al., *Nucleic Acids Res.*, 34:5456-5465 (1994), which are hereby incorporated by reference].

Synthetic oligonucleotides (normal and complementary directions, either for capture hybridization or hybridization/ligation) are prepared as either DNA or PNA, with either natural bases or nucleotide analogues. Such analogues pair with perfect complementarity to the natural bases but increase $T_m$ values (e.g., 5-propynyl-uracil).

In accordance with the present invention, false hybridization signals from DNA synthesis errors are avoided. Addresses can be designed so there are very large differences in hybridization $T_m$ values to incorrect address. In contrast, the direct hybridization approaches depend on subtle differences. The present invention also eliminates problems of false data interpretation with gel electrophoresis or capillary electrophoresis resulting from either DNA synthesis errors, band broadening, or false band migration.

The use of a capture oligonucleotide to detect the presence of ligation products, eliminates the need to detect single-base differences in oligonucleotides using differential hybridization. Other existing methods in the prior art relying on allele-specific PCR, differential hybridization, or sequencing-by-hybridization methods must have hybridization conditions optimized individually for each new sequence being analyzed. When attempting to detect multiple mutations simultaneously, it becomes difficult or impossible to optimize hybridization conditions. In contrast, the present invention is a general method for high specificity detection of correct signal, independent of the target sequence, and under uniform hybridization conditions. The present invention yields a flexible method for discriminating between different oligonucleotide sequences with significantly greater fidelity than by any methods currently available within the prior art.

The array of the present invention will be universal, making it useful for detection of cancer mutations, inherited (germline) mutations, and infectious diseases. Further benefit is obtained from being able to reuse the array, lowering the cost per sample.

The present invention also affords great flexibility in the synthesis of oligonucleotides and their attachment to supports. Oligonucleotides can be synthesized off of the support and then attached to unique surfaces on the support. Segments of multimers of oligonucleotides, which do not require intermediate backbone protection (e.g., PNA), can be synthesized and linked onto to the solid support. Added benefit is achieved by being able to integrate these synthetic approaches with design of the capture oligonucleotide addresses. Such production of solid supports is amenable to automated manufacture, obviating the need for human intervention and resulting contamination concerns.

An important advantage of the array of the present invention is the ability to reuse it with the previously attached capture oligonucleotides. In order to prepare the solid support for such reuse, the captured oligonucleotides must be removed without removing the linking components connecting the captured oligonucleotides to the solid support. A variety of procedures can be used to achieve this objective. For example, the solid support can be treated in distilled water at 95-100° C., subjected to 0.01 N NaOH at room temperature, contacted with 50% dimethylformamide at 90-95° C., or treated with 50% formamide at 90-95° C. Generally, this procedure can be used to remove captured oligonucleotides in about 5 minutes. These conditions are suitable for disrupting DNA-DNA hybridizations; DNA-PNA hybridizations require other disrupting conditions.

The present invention is illustrated, but not limited, by the following examples.

EXAMPLES

Example 1

Materials and Methods

Oligonucleotide Synthesis and Purification. Oligonucleotides were obtained as custom synthesis products from IDT, Inc. (Coralville, Iowa), or synthesized in-house on an ABI 394 DNA Synthesizer (PE Biosystems Inc.; Foster City, Calf.) using standard phosphoramidite chemistry. Spacer phosphoramidite 18, 3'-amino-modifer C3 CPG, and 3'-fluorescein CPG were purchased from Glen Research (Sterling, Va). All other reagents were purchased from PE Biosystems. Both labeled and unlabeled oligonucleotides were purified by electrophoresis on 12% denaturing polyacrylamide gels. Bands were visualized by UV shadowing, excised from the gel, and eluted overnight in 0.5 M NaCl, 5 mM EDTA, pH 8.0 at 37° C. Oligonucleotide solutions were desalted on C18 Sep-Pak® separation columns (Waters Corporation; Milford, Mass.) according to the manufacturer's instructions, following which the oligonucleotides were concentrated to dryness (Speed-Vac) and stored at −20° C.

Cleaning of Microscope Slides. Glass microscope slides (VWR, precleaned, 3 in.×. 1 in.×1.2 mm) were incubated in boiling conc. $NH_4OH$-30% $H_2O_2$-$H_2O$ (1:1:5, v/v/v) for 10 min and rinsed in distilled water. A second incubation was performed in boiling conc. HCl-30% $H_2O_2$-$H_2O$ for 10 min. See U. Jonsson, et al., "Absorption Behavior of Fibronetin on Well Characterized Silica Surfaces," *J. Colloid Interface Sci.* 90:148-163 (1982), which is hereby incorporated by reference. The slides were rinsed thoroughly in distilled water, methanol, and acetone, and were air-dried at room temp.

Polymer Coated Slides. Immediately following cleaning, slides (Fisher Scientific, precleaned, 3 in.×1 in.×1.2 mm) were immersed in 2% methacryloxypropyltrimethoxysilane, 0.2% triethylamine in $CHCl_3$ for 30 min at 25° C., and then washed with $CHCl_3$ (2×15 min). A monomer solution [20 μL: 8% acrylamide, 2% acrylic acid, 0.02% N,N'-methylene-bisacrylamide (500:1 ratio of monomers:crosslinker), 0.8% ammonium persulfate radical polymerization initiator] was deposited on one end of the slides and spread out with the aid of a cover slip (24×50 mm) that had been previously silanized [5% $(CH_3)_2SiCl_2$ in $CHCl_3$]. Polymerization was achieved by heating the slides on a 70° C. hot plate for 4.5 min. Upon removal of the slides from the hot plate, the cover slips were immediately peeled off with aid of a single-edge razor blade. The coated slides were rinsed with deionized water, allowed to dry in an open atmosphere, and stored under ambient conditions.

Preparation of Zip-Code Arrays. Polymer-coated slides were pre-activated by immersing them for 30 min at 25° C. in a solution of 0.1 M 1-[3-(dimethylamino)propyl]-3-ethylcarbodiimide hydrochloride plus 20 mM N-hydroxysuccinimide in 0.1 M $K_2HPO_4$/$KH_2PO_4$, pH 6.0. The activated slides were rinsed with water, and then dried in a 65° C. oven; they were stable upon storage for 6 months or longer at 25° C. in a desiccator over Drierite.

Arrays were spotted on a Cartesian Technologies Pixsys 5500 robot at 25° C. and 70% relative humidity using 500 μM zip-code oligonucleotide solutions in 0.2 M $K_2HPO_4$/$KH_2PO_4$, pH 8.3. Each address was spotted in quadruplicate. Additionally, Cy3, Cy5, and fluorescein fiducials were printed along the top and down the right hand side of each array. Following spotting, uncoupled oligonucleotides were removed from the polymer surfaces by soaking the slides in 300 mM bicine, pH 8.0, 300 mM NaCl, 0.1% SDS, for 30 min at 65° C., rinsing with water, and drying. The arrays were stored at 25° C. in slide boxes until needed.

PCR Amplification of K-Ras DNA Samples. PCR amplifications were carried out under paraffin oil in 50 μL reaction mixtures containing 10 mM Tris.HCl, pH 8.3, 4 mM $MgCl_2$, 50 mM KCl, 800 μM dNTPs, 1 μM forward and reverse primers (50 pmol of each primer; K-rasEx1forward and K-rasEx1reverse (Table 3)), 1 U AmpliTaq Gold, and 100 ng of genomic DNA extracted from paraffin-embedded tumors or from cell lines. Reactions were preincubated for 10 min at 95° C. Amplification was achieved by thermally cycling for 40 rounds of 94° C. for 30 sec; 60° C. for 1 min; and 72° C. for 1 min, followed by a final elongation at 72° C. for 5 min. Following PCR, 1 μL of Proteinase K (18 mg/mL) was added, and reactions were heated to 70° C. for 10 min and then quenched at 95° C. for 15 min. Two μL of each PCR product was analyzed on a 3% agarose gel to verify the presence of amplification product of the expected size.

LDR of K-Ras DNA Samples. LDR was carried out under paraffin oil in 20 μL volumes containing 20 mM Tris.HCl, pH 8.5-5 mM $MgCl_2$-100 mM KCl, 10 mM DTT, 1 mM $NAD^+$, 10 pmol total LDR probes [500 fmol each of fluorescently-labeled discriminating probes (K-rasc32Wt, labeled with Cy3, Cy5, and fluorescein; K-rasc12.2D labeled with Cy3; K-rasc12.2A labeled with Cy5; K-rasc12.2V labeled with fluorescein; K-rasc12.1S labeled with Cy3; K-rasc12.1R, labeled with Cy5; K-rasc12.1C, labeled with fluorescein; and K-rasc13.4D labeled with Cy3)+5 pmol total common probes; (1500 fmol each of K-rascd32Com9cZip1, K-rascd12Com2cZip2, and K-rascd12Com1cZip3, and 500 fmol of K-rascd13Com4cZip4) (Table 3)], and 2 μL PCR products from the cell line or tumor samples. The reaction mixtures were pre-heated for 2 min at 94° C., and then 25 fmol of wild-type Tth DNA ligase was added. The LDR reaction mixtures were cycled for 20 rounds of 94° C. for 30 sec and 65° C. for 4 min.

mutation gave a Cy3 signal at address #4. The incorrect signals seen at Zip4 in the LS180 and SW1116 samples were due to contamination of the samples.

TABLE 3

Primers designed for mutation detection in K-ras by PCR/LDR/Array Hybridization.

| Primer | Sequence (5'→3') |
| --- | --- |
| K-rasEx1forward | AAC CTT ATG TGT GAC ATG TTC TAA TAT AGT CAC (SEQ ID NO: 9273) |
| K-rasEx1reverse | AAA ATG GTC AGA GAA ACC TTT ATC TGT ATC (SEQ ID NO: 9274) |
| K-rascd32Com9cZip1 | PTATGATCCAACAATAGAGGTAAATCTTGTCGCAGATTTTGCGCTGGAT TTCAA (SEQ ID NO: 9275) |
| K-rasc32Wt | Cy3-ATTCAGAATCATTTTGTGGACGAA (SEQ ID NO: 9276) |
| | Cy5-ATTCAGAATCATTTTGTGGACGAA (SEQ ID NO: 9276) |
| | Fam-ATTCAGAATCATTTTGTGGACGAA (SEQ ID NO: 9276) |
| K-rascd12Com2cZip2 | PTGGCGTAGGCAAGAGTGCCTTTCGCCGTCGTGTAGGCTTTTCAA (SEQ ID NO: 9277) |
| K-rasc12.2D | Cy3-AAACTTGTGGTAGTTGGAGCTGA (SEQ ID NO: 9278) |
| K-rasc12.2A | Cy5-AAACTTGTGGTAGTTGGAGCTGC (SEQ ID NO: 9279) |
| K-rasc12.2V | Fam-AAACTTGTGGTAGTTGGAGCTGT (SEQ ID NO: 9280) |
| K-rascd12Com1cZip3 | PGTGGCGTAGGCAAGAGTGCCCCGTAAGCCCGTATGGCAGATCAA (SEQ ID NO: 9281) |
| K-rasc12.1S | Cy3-ATATAAACTTGTGGTAGTTGGAGCTA (SEQ ID NO: 9282) |
| K-rasc12.1R | Cy5-ATATAAACTTGTGGTAGTTGGAGCTC (SEQ ID NO: 9283) |
| K-rasc12.1C | Fam-ATATAAACTTGTGGTAGTTGGAGCTT (SEQ ID NO: 9284) |
| K-rascd13Com4cZip4 | PCGTAGGCAAGAGTGCCTTGACATGGCCGTGCTGGGGACA AGTCAA (SEQ ID NO:9285) |
| K-rasc13.4D | Cy3-TGTGGTAGTTGGAGCTGGTGA (SEQ ID NO: 9286) |

Hybridization of K-Ras LDR Products to DNA Arrays. The LDR reaction mixtures were diluted with 20 μL of 2× hybridization buffer to produce a final buffer concentration of 300 mM MES, pH 6.0, 10 mM MgCl$_2$, 0.1% SDS, denatured at 94° C. for 3 min, and chilled on ice. Arrays were pre-incubated for 15 min at 25° C. in 1× hybridization buffer. Coverwells (Grace, Inc; Sunriver, Oreg.) were attached to the arrays and filled with 30 μL of the diluted LDR reaction mixtures. The arrays were placed in humidified culture tubes and incubated for 1 h at 65° C. and 20 rpm in a rotating hybridization oven. Following hybridization, the arrays were washed in 300 mM bicine, pH 8.0, 10 mM MgCl$_2$, 0.1% SDS for 10 min at 25° C. Fluorescent signals were measured using a Scanarray 5000 (GSI Lumonics).

LDR detection of 7 specific mutations in K-ras on an addressable universal microarray is shown in FIG. 36. The three signals along the top and those down the right hand side of each array are fiducials used for alignment. The next 4 addresses across in the second row correspond to addresses #1, #2, #3, and #4, complements of cZip1, cZip2, cZip3, and cZip4, respectively. The eight cell line (i.e. COL0205, LS180, SW1116, SW480, and DLD1) and tumor samples (G12S, G12R, and G12C) correctly identified the mutations present. Wild-type cell line COL0205 gave Cy3, Cy5, and fluorescein signal at address #1. The wild-type signal at address #1 was used as a control for all experiments. The LS180 cell line containing the Asp 12 mutation gave a Cy3 signal at address #2. The SW1116 cell line containing the Ala12 mutation gave a Cy5 signal at address #2. The SW480 cell line containing the Val12 mutation gave a fluorescein signal at address #2. The G12S tumor sample containing the Ser12 mutation gave a Cy3 signal at address #3. The G12R tumor sample containing the Arg12 mutation gave a Cy5 signal at address #3. The G12C tumor sample containing the Cys12 mutation gave a fluorescein signal at address #3. The DLD 1 cell line containing the Asp 13

Amplification was achieved by thermal cycling for 40 rounds of 94° C. for 15 sec and 60° C. for 2 min, followed by a final elongation step at 65° C. for 5 min. Following PCR, 1 μL of Proteinase K (18 mg/mL) was added, and reactions were heated to 70° C. for 10 min and then quenched at 95° C. for 15 min. One μL of each PCR product was analyzed on a 3% agarose gel to verify the presence of amplification product of the expected size.

LDR of K-Ras DNA Samples. LDR reactions were carried out under paraffin oil in 20 μL volumes containing 20 mM Tris.HCl, pH 8.5, 5 mM MgCl$_2$, 100 mM KCl, 10 mM DTT, 1 mM NAD$^+$, 8 pmol total LDR probes (500 fmol each of discriminating probes+4 pmol fluorescently-labeled common probes), and 1 pmol PCR products from cell line or tumor samples. Two probe mixes were prepared, each containing the seven mutation-specific probes, the three common probes, and either the wild-type discriminating probe for codon 12 or that for codon 13 (Table 3).

The reaction mixtures were pre-heated for 2 min at 94° C., and then 25 fmol of wild-type Tth DNA ligase was added. The LDR reactions were cycled for 20 rounds of 94° C. for 15 sec and 65° C. for 4 min. An aliquot of 2 μL of each reaction was mixed with 2 L of gel loading buffer [8% blue dextran, 50 mM EDTA, pH 8.0—formamide (1:5)], denatured at 94° C. for 2 min, and chilled on ice. One μL of each mixture was loaded on a 10% denaturing polyacrylamide gel and electrophoresed on an ABI 377 DNA sequencer at 1500 volts.

Hybridization of K-Ras LDR Products to DNA Arrays. The LDR reactions (17 μL) were diluted with 40 μL of 1.4× hybridization buffer to produce a final buffer concentration of 300 mM MES, pH 6.0, 10 mM MgCl$_2$, 0.1% SDS. Arrays were pre-incubated for 15 min at 25° C. in 1× hybridization buffer. Coverwells (Grace, Inc; Sunriver, Oreg.) were filled with the diluted LDR reactions and attached to the arrays.

The arrays were placed in humidified culture tubes and incubated for 1 h at 65° C. and 20 rpm in a rotating hybridization oven. Following hybridization, the arrays were washed in 300 mM bicine, pH 8.0, 10 mM $MgCl_2$, 0.1% SDS for 10 min at 25° C. Fluorescent signals were measured using a microscope/CCD, as described in the following paragraph.

Image Analysis. Arrays were imaged using a Molecular Dynamics FluorImager™595 dual-excitation, laser induced fluorescence scanner (Sunnyvale, Calif.) or an Olympus AX70 epifluorescence microscope (Melville, N.Y.) equipped with a Princeton Instruments TE/CCD-512 TKBM1 camera (Trenton, N.J.). For analysis of fluorescein-labeled probes on the FluorImager™595 dual-excitation, laser induced fluorescence scanner the 488 nm excitation was used with a 530/30 emission filter. The spatial resolution of scans was 100 μm per pixel. The resulting images were analyzed using ImageQuaNT™software provided with the instrument. The epifluorescence microscope was equipped with a 100 W mercury lamp, a FITC filter cube (excitation 480/40, dichroic beam splitter 505, emission 535/50), a Texas Red filter cube (excitation 560/55, dichroic beam splitter 595, emission 645/75), and a 100 mm macro objective. The macro objective allows illumination of an object field up to 15 mm in diameter and projects a 7×7 mm area of the array onto the 12.3×12.3 mm matrix of the CCD. Images were collected in 16-bit mode using the Winview32 software provided with the camera. Analysis was performed using Scion Image imaging software (Scion Corporation, Frederick, Md.).

Example 2

Amplification of BRCA1 and BRCA2 Exons for PCR/PCR/LDR Detection of Wild-Type and Mutant Alleles A multiplex assay was used to detect small insertions and deletions using a modified PCR to evenly amplify each amplicon (PCR/PCR) (Belgrader et al., "A Multiplex PCR-Ligase Detection Reaction Assay for Human Identity Testing," *Genome Science and Technology* 1:77-87 (1996), which is hereby incorporated by reference) followed by ligase detection reaction ("LDR") (Khanna, M. et al., "Multiplex PCR/LDR for Detection of K-ras Mutations in Primary Colon Tumors," *Oncogene* 18:27-38 (1999), which is hereby incorporated by reference). FIG. 20 shows how multiplex amplification of the relevant exons is carried out to ensure equal amplification of all products: a limited number of PCR cycles was performed using gene-specific primers, with further rounds of amplification primed from the universal sequences located at the extreme 5'-ends of the PCR primers. This approach minimizes amplification bias due to primer-specific effects. LDR was next used to detect both wild-type and mutant versions of the queried sequence. The ligation oligonucleotides probes hybridize to both wild-type and mutant products, but ligate only when both probes are perfectly matched with no gaps or overlaps. Products can be either eletrophoretically separated or hybridized to a microarray for identification.

PCR was carried out as a single-tube, multiplex reaction in order to simultaneously amplify BRCA1 exons 2 and 20 and BRCA2 exon 11. Genomic DNA was extracted from blood samples of Ashkenazi Jewish individuals and amplified in a 25 μl reaction mixture containing 100 ng of DNA, 400 μM of each dNTP, 1×PCR Buffer II (10 mM Tris-HCl pH 8.3 at 25° C., 50 mM KCl) supplemented with 4 mM $MgCl_2$, 1 U AmpliTaq Gold and 2 pmol of each gene-specific primer bearing either universal primer A or B on the 5' ends. Table 4 shows the primers and probes for detection of BRCA1 and BRCA2 mutations using PCR/LDR/array hybridization as follows:

TABLE 4

Primers and Probes designed for mutation detection in BRCA1 and BRCA2 by PCR/LDR/Array Hybridization.

| Primer | Sequence (5'→3') |
|---|---|
| *PCR primers:* | |
| Universal primer A (Uni A) | 5' ggagcacgctatcccgttagac 3' (SEQ ID NO:9287) |
| Universal primer B (Uni B) | 5' cgctgccaactaccgcacatg 3' (SEQ ID NO:9288) |
| BRCA1 exon 2 forward | 5' Uni A - TCATTGGAACAGAAAGAAATGGATTTATC 3' (SEQ ID NO: 9289) |
| BRCA1 exon 2 reverse | 5' Uni B - TCTTCCCTAGTATGTAAGGTCAATTCTGTTC 3' (SEQ ID NO :9290) |
| BRCA1 exon 20 forward | 5' Uni A - ACTTCCATTGAAGGAAGCTTCTCTTTC 3' (SEQ ID NO: 9291) |
| BRCA1 exon 20 reverse | 5' Uni B - ATCTCTGCAAAGGGGAGTGGAATAC 3' (SEQ ID NO: 9292) |
| BRCA2 exon 11 forward | 5' Uni A - CAAAATATGTCTGGATTGGAGAAAGTTTC 3' (SEQ ID NO: 9293) |
| BRCA2 exon 11 reverse | 5' Uni B - TTGGAAAAGACTTGCTTGGTACTATCTTC 3' (SEQ ID NO: 9294) |
| *LDR Gel-Based Assay:* *Discriminating Oligonucleotide Probes:* | |
| BRCA1 ex 2 wild-type position 185 | 5' Fam - aaCATTAATGCTATGCAGAAAATCTTAGAG 3' (SEQ ID NO: 9295) |
| BRCA1 ex 2 position 185 del AG mutation | 5' Tet - GTCATTAATGCTATGCAGAAAATCTTAG 3' (SEQ ID NO: 9296) |
| BRCA1 ex 20 wild-type position 5382 | 5' Fam - CCAAAGCGAGCAAGAGAATCC 3' (SEQ ID NO: 9297) |
| BRCA1 ex 20 position 5382 ins C mutation | 5' Tet - aaCAAAGCGAGCAAGAGAATCCC 3' (SEQ ID NO: 9298) |
| BRCA2 ex 11 wild-type position 6174 | 5' Fam - ca**CTTGTGGGATTTTTAGCACAGCAAGT 3' (SEQ ID NO: 9299) |
| BRCA2 ex 11 position 6174 del T mutation | 5' Tet - TACTTGTGGGATTTTTAGCACAGCAAG 3' (SEQ ID NO: 9300) |

TABLE 4-continued

Primers and Probes designed for mutation detection in BRCA1 and
BRCA2 by PCR/LDR/Array Hybridization.

| Primer | Sequence (5'→3') |
|---|---|
| LDR Common Oligonucleotide Probes: | |
| BRCA1 ex 2 position 185 | 5' P-TGTCCCATCTGGTAAGTCAGCACAAAC-B 3' (SEQ ID NO: 9301) |
| BRCA1 ex 20 position 5382 | 5' P-CAGGACAGAAAGGTAAAGCTCCCTC-B 3' (SEQ ID NO: 9302) |
| BRCA2 ex 11 position 6174 | 5' P-GGAAAATCTGTCCAGGTATCAGAT-B 3' (SEQ ID NO: 9303) |
| LDR Microarray Assay: Discriminating Oligonucleotide Probes: | |
| BRCA1 ex 2 control | 5' Cy3 - TGCATAGGAGATAATCATAGGAATCC 3' (SEQ ID NO: 9304) |
| BRCA1 ex 2 position 185 del AG mutation | 5' Cy3 - GTCATTAATGCTATGCAGAAAATCTTAG 3' (SEQ ID NO: 9305) |
| BRCA1 ex 20 control | 5' Cy3 - CCTCTGACTTCAAAATCATGCTG 3' (SEQ ID NO: 9306) |
| BRCA1 ex 20 position 5382 ins C mutation | 5' Cy3 - CAAAGCGAGCAAGAGAATCCC 3' (SEQ ID NO: 9307) |
| BRCA2 ex 11 control | 5' Cy3 - CTTCCCTATACTACATTTACATATATCTGAAG 3' (SEQ ID NO: 9308) |
| BRCA2 ex 11 position 6174 del T mutation | 5' Cy3 - TACTTGTGGGATTTTTAGCACAGCAAG 3' (SEQ ID NO: 9309) |
| Common Oligonucleotide Probes for Controls: | |
| BRCA1 exon 2 control + cZip 1 | ' P-CAAATTAATACACTCTTGTGCTGACTTACCA-cgcagattttgcgctggatttcaa-B 3' (SEQ ID NO: 9310) |
| BRCA1 exon 20 control + cZip 2 | 5' P-AAAGAAACCAAACACAACCCATCAG-ttcgccgtcgtgtaggcttttcaa-B 3' (SEQ ID NO: 9311) |
| BRCA2 exon 11 control + cZip 3 | 5' P-TTTCCAAACTAACATCACAAGGTGATATTT-ccgtaagcccgtatggcagatcaa-B 3' (SEQ ID NO: 9312) |
| Common Oligonucleotide Probes for Mutations: | |
| BRCA1 exon 2 position 185 +cZip 9 | 5' P-TGTCCCATCTGGTAAGTCAGCACAAAC-catcgtccctttcgatgggatcaa-B 3' (SEQ ID NO: 9313) |
| BRCA1 exon 20 position 5382 + cZip 10 | 5' P-CAGGACAGAAAGGTAAAGCTCCCTC-caaggcacgtcccagacgcatcaa-B 3' (SEQ ID NO: 9314) |
| BRCA2 exon 11 position 6174 + cZip 11 | 5' P-GGAAAATCTGTCCAGGTATCAGAT-gcacgggagctgacgacgtgtcaa-B 3' (SEQ ID NO: 9315) |

The reaction was overlaid with mineral oil and preincubated for 10 min at 95° C. Amplification was performed for 15 cycles as follows: 94° C. for 15 sec, 65° C. for 1 min. A second 25 µl aliquot of the reaction mixture was added through the mineral oil containing 25 pmol each of universal primers A and B. Cycling was repeated using 55° C. annealing temperature. The reaction was next digested with a 2 µl solution of 1 mg/ml Proteinase K/50 mM EDTA at 55° C. for 10 min. Proteinase K was eliminated by a final incubation at 90° C. for 15 min. For LDR, oligonucleotide synthesis and purification were carried out as previously described (Khanna et al., "Multiplex PCR/LDR for Detection of K-ras Mutations in Primary Colon Tumors," *Oncogene* 18:27-38 (1999), which is hereby incorporated by reference). Tth DNA ligase was overproduced and purified as described elsewhere (Luo et al., "Identification of Essential Residues in *Thermus thermophilus* DNA Ligase," *Nucleic Acids Research* 24: 3079-3085 (1996) and Barany et al., "Cloning, Overexpression, and Nucleotide Sequence of a Thermostable DNA Ligase Gene," *Gene* 109:1-11 (1991), which are hereby incorporated by reference). LDR was performed in a 20 µl reaction containing 500 fmol of each probe, 2 µl of amplified DNA and 20 mM Tris-HCl, pH 7.6; 10 mM $MgCl_2$; 100 mM KCl; 10 mM DTT; 1 mM $NAD^+$. The reaction was heated to 94° C. for 1.5 min prior to adding 25 fmol of Tth DNA ligase and then subjected to 20 cycles of 15 sec at 94° C. and 4 min at 65° C. (See Table 4).

Figure 21A:
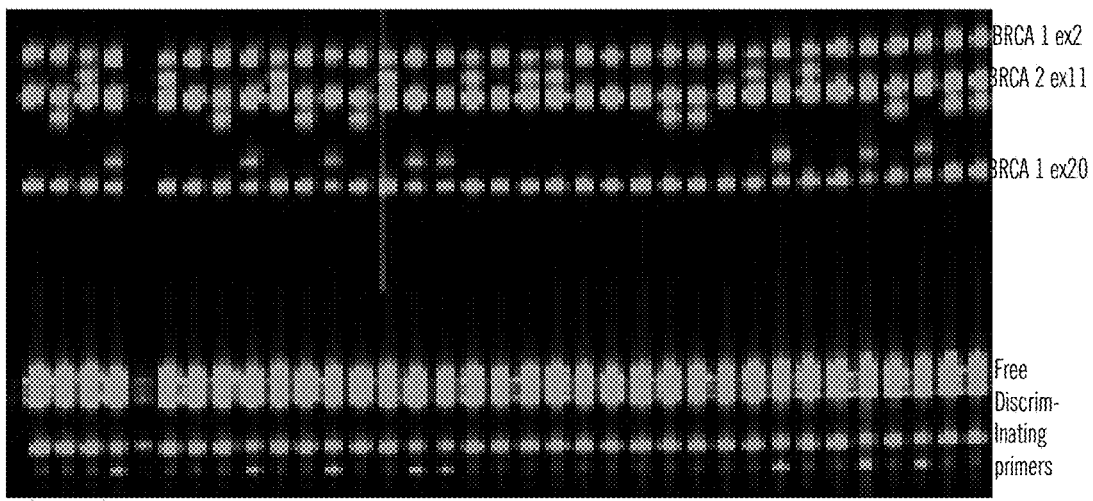
FIGS. 21A-B show the multiplex LDR detection of 3 specific mutations in BRCA1 and BRCA2 in a gel-based assay.

Using the three BRCA1 and BRCA2 founder mutations in the Ashkenazi Jewish population (BRCA1 185delAG; BRCA1 5382insC; BRCA2 6174delT) (Rahman et al., "The Genetics of Breast Cancer Susceptibility," *Annu. Rev. Genet.* 32:95-121 (1998), which is hereby incorporated by reference) as a model system, the assay readily detected these mutations in multiplexed reactions in over 80 DNA samples. FIG. 21A shows a representative LDR gel detecting the three BRCA mutations. By fluorescent end-labeling the discriminating upstream oligonucleotides with either FAM (for wild-type) or TET (for mutant), and by adding different length "tails" to LDR oligonucleotide probes, ligation products were easily distinguished based on label and migration on a polyacrylamide gel. Wild-type products are identified at the right side of the gel. Mutant products are identified at the top of the gel. Electrophoretic separation was performed at 1400 volts using 8 M urea-10% polyacrylamide gels and an ABI 373 DNA sequencer. Fluorescent ligation products were analyzed and quantified using the ABI Gene Scan 672 software.

Figure 21B:
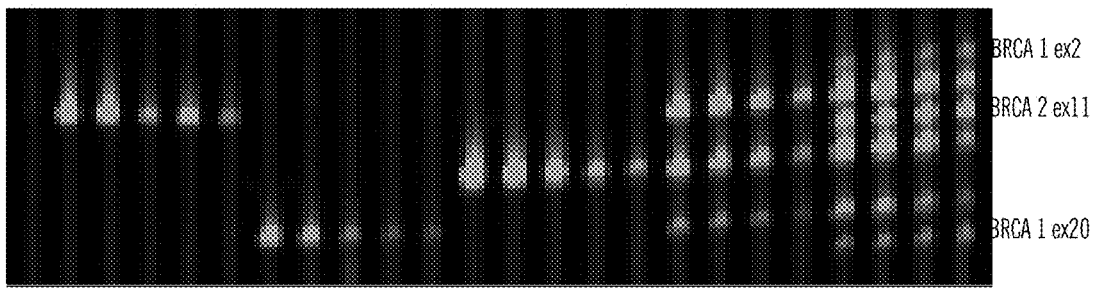

The analysis was next extended to detect the mutations in pooled samples of DNA. DNAs with known mutations were diluted 1:2, 1:5, 1:10, and 1:20 with wild-type DNA prior to PCR amplification and then subjected to LDR. These simulation experiments showed PCR/PCR/LDR could successfully detect the presence of all three mutations when known mutant DNA was diluted 1:20 in wild-type DNA prior to amplification. FIG. 21B shows BRCA1 and BRCA2 mutation detection on pooled samples of DNA. DNA samples with known mutations were diluted into wild-type DNA prior to amplification. Ligation products from multiplex LDR are shown for each dilution. BRCA1 del AG, BRCA1 ins C, and BRCA2 del T mean that only one mutation is present; multiplex LDR directed against only mutant sequences use 500 fmol of each LDR oligonucleotide probes. 3 mutations means that all three mutations are present; multiplex LDR directed against mutant sequences only use 500 fmol of each LDR oligonucleotide. 3 mutations+wild-type controls at 1:20 mean that all three mutations are present; multiplex LDR are directed against both mutant and wild-type sequences using 500 fmol and 25 fmol of each LDR oligonucleotide probes, respectively. The pooling experiment was repeated using 249 blinded Ashkenazi Jewish DNA samples. Tubes containing the blinded DNAs were assembled into a 9×9 gridded format and aliquots from each tube were combined across the rows and then down the columns to produce one tube of combined DNA for each row and each column. This was done to uniquely classify each sample using points of intersection on the gridded format. The pooled DNA was then subjected to amplification and LDR as described above. 248 of the 249 samples were correctly typed. The single sample that was incorrectly identified as wild-type proved to be too dilute and fell below the limits of detection when mixed with 9 other samples of higher concentration. The number of individual reactions carried out was reduced from 249 to 96 by this strategy (55 pooled samples and 41 individual samples used for confirmation).

In addition to gel-based detection, mutation identification was also accomplished by screening reaction products with a universal DNA microarray (Gerry et al., "Universal DNA Microarray Method for Multiplex Detection of Low Abundance Point Mutations," *J Mol Bio.* 292:251-262 (1999), which is hereby incorporated by reference). Microarrays were processed and spotted as previously described (Gerry et al., "Universal DNA Microarray Method for Multiplex Detection of Low Abundance Point Mutations," *J Mol Bio.* 292:251-262 (1999), which is hereby incorporated by reference) using a Pixsys5500 robot enclosed in a humidity chamber (Cartesian Technologies, Irvine, Calif.). Briefly, LDR reactions were hybridized in 32 µl containing 300 mM MES, pH 6.0, 10 mM $MgCl_2$, 0.1% SDS at 65° C. for 1 h in a rotating chamber. After washing in 300 mM bicine, pH 8.0, 10 mM $MgCl_2$, 0.1% SDS for 10 min at 25° C. The array was imaged on an Olympus Provis AX70 microscope using a 100 W mercury burner, a Texas Red filter cube, and a Princeton Instruments TEK512/CCD camera. The 16-bit greyscale images were captured using MetaMorph Imaging System (Universal Imaging Corporation, West Chester, Pa.) and rescaled to more narrowly bracket the LDR signal before conversion to 8-bit greyscale. The 8-bit images were colored using Adobe Photoshop to render the Cy3 signal red.

Preliminary microarray experiments using probes designed in the gel-based format (i.e., differentially labeled discriminating probes and identical common probes) demonstrated that wild-type and mutant versions of the three BRCA sequences were readily detected on the array (see WO 97/31256 to Barany et al., which is hereby incorporated by reference). In this version, both types of sequences were directed to the same addresses (e.g., BRCA1 185delAG and BRCA1 185 wild-type were both directed to zip-code 1). Although this format proved successful, PCR/PCR/LDR has the potential of detecting hundreds of mutations in a single-tube reaction and this design does not make optimal use of the array for such large-scale mutation detection experiments. In order to establish the experimental paradigm for future studies, the addressable format was expanded by choosing a sequence in each of the amplicons to use as a control an LDR ligation product. Thus, rather than require detection of wild-type sequences for each mutant LDR product, this format uses a single product to serve as a positive control for multiple different sequence variants within an amplicon (see FIG. 22). One advantage of this format is that it minimizes oligonucleotide synthesis; additionally, the use of each of the 64 positions is maximized. Since the number of LDR ligation products that can be detected at a single address is limited by the number of currently available spectrally separated fluorescent labels, confining the control to a specified region of the array permits one more sequence variant to be detected at each remaining address. In the experiments described below, control and mutant LDR ligation products for a queried position were directed to six separate addresses on a 64 position array.

All three frameshift mutations were detectable by hybridization to the universal array (FIG. 23). FIG. 23A shows the assignment of each control and mutant sequence to specific addresses on the array surface. Control signals are directed to the upper three addresses; mutant signals are assigned to the lower three. FIG. 23B shows signal produced by a wild-type DNA. FIGS. 23C, E, and G show representative hybridizations for individual DNA samples. FIGS. 23D, F, and H show representative hybridizations for each mutation using pooled samples of DNA from Ashkenazi individuals. The mutations are identified on the extreme right.

Only combinations of the six possible addresses were visible following hybridization and no additional signals were detected at any of the unused addresses. Thus, zip-code hybridization is very specific. Control and mutant signals were clearly present for each of the mutations derived from samples of DNA from single individuals (FIGS. 23C, E, and G). Pooled DNA used in analyzing the 249 DNA samples described above produced signals for mutations identical to those found in the gel-based assay (FIGS. 23D, F, and H). In each case, the array reproduced the result of the gel.

These results demonstrate that universal microarray analysis of PCR/PCR/LDR products permits rapid identification of small insertion and deletion mutations in the context of both clinical diagnosis and population studies.

Example 3 p53 Chip Hybridization and Washing Conditions

Figure 16A:
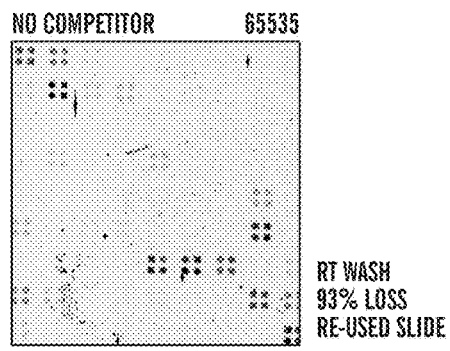
FIGS. 16A-P show the p53 chip hybridization and washing conditions.
Figure 16B:
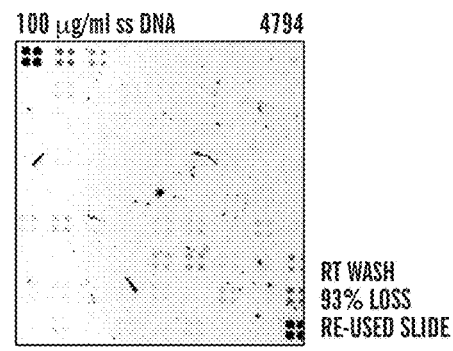
Figure 16C:
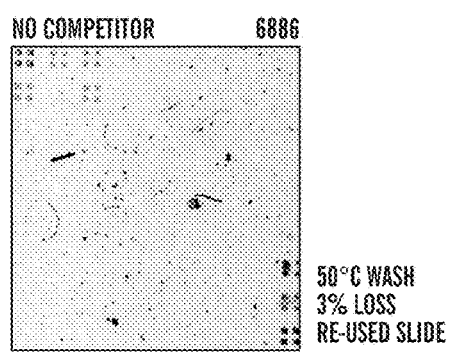
Figure 16D:
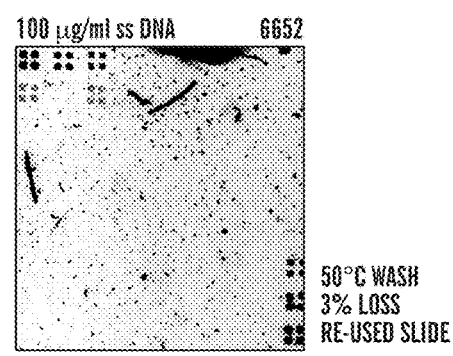
Figure 16E:
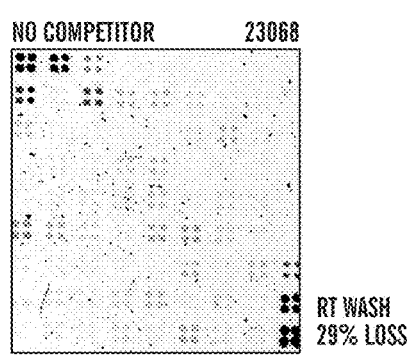
Figure 16F:
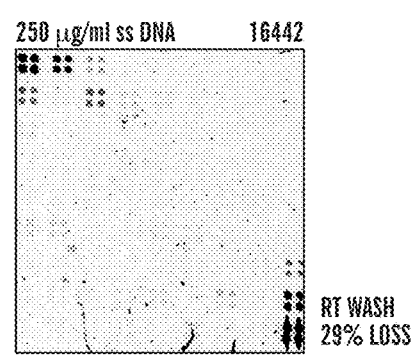
Figure 16G:
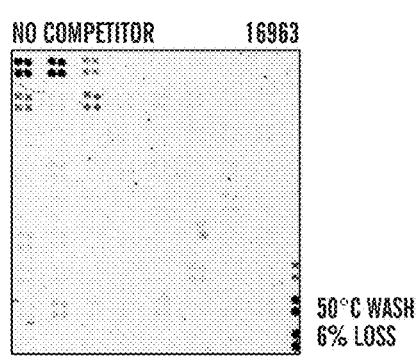
Figure 16H:
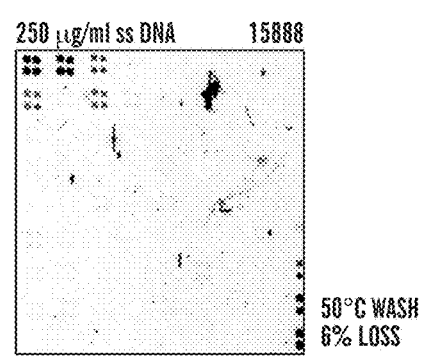
Figure 16I:
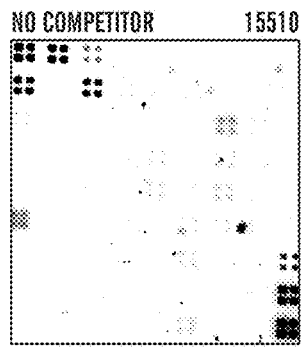
Figure 16J:
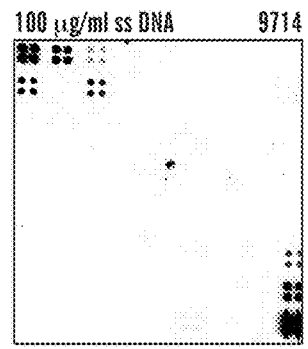
Figure 16K:
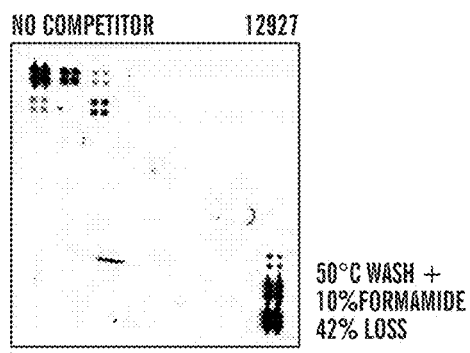
Figure 16L:
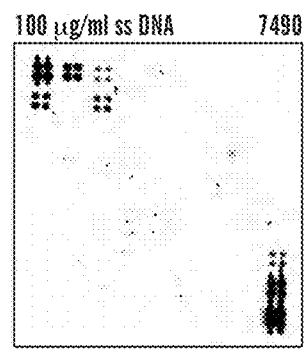
Figure 16M:
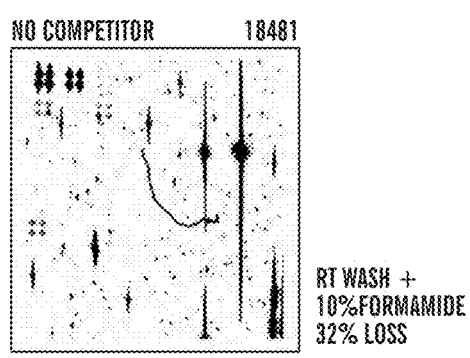
Figure 16N:
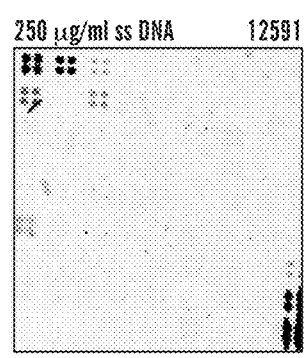
Figure 16O:
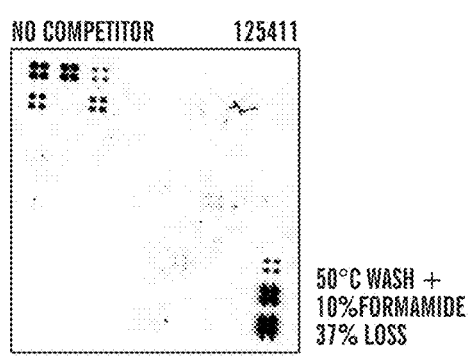
Figure 16P:
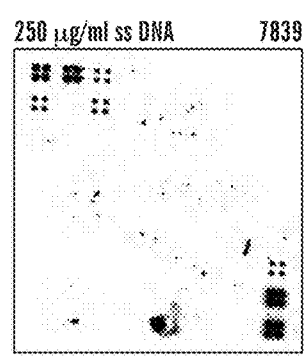

Three parameters (presence or absence of non-specific DNA competitor, temperature, and wash buffer composition) were varied in different combinations in order to determine which method would produce minimum background noise without significant loss of signal. Hybridization was performed with 100 µg/ml of sheared salmon sperm DNA (FIGS. 16B, D, J, and L), 250 µg/ml of sheared salmon sperm DNA (FIGS. 16F, H, N, and P), or no non-specific competitor DNA (FIGS. 16A, C, E, G, I, K, M, and O). Washing was performed for 10 min using four different conditions: room temperature in standard wash buffer (300 mM bicine, pH 8.0, 10 mM $MgCl_2$, 0.1% SDS) (FIGS. 16A, B, E, and F); room temperature in standard wash buffer supplemented with 10% formamide (FIGS. 16I, J, M, and N); 50° C. in standard wash buffer (FIGS. 16C, D, G, and H); or 50° C. in standard wash buffer supplemented with 10% formamide (FIGS. 16K, L, O, and P). The numbers on the upper right of each panel indicate the density of pixels for p53 exon 5 control (zip-code 1) for each condition. The percent of loss indicated on the right side of the figure compares the left and right panel directly adjacent to calculated percentage. Fiducials (Cy3, Cy5, and fluorescein) are spotted horizontally on the upper left and vertically on the lower right regions of the chips to give orientation. Zip-code 1 is located directly below the fiducial in the upper left area; subsequent zip-codes are spotted in numerical order in a left to right manner.

PCR was carried out as a single-tube, multiplex reaction in order to simultaneously amplify p53 exons 5 and 7. Commercially available genomic DNA from lymphocytes was amplified in a 25 µl reaction mixture containing 100 ng of DNA, 400 µM of each dNTP, 1×PCR Buffer II (10 mM Tris-HCl pH 8.3 at 25° C., 50 mM KCl) supplemented with 4 mM $MgCl_2$, 1 U AmpliTaq Gold and 2 pmol of each gene-specific primer bearing either universal primer A or B on the 5' ends (see Table 5). The reaction was overlaid with mineral oil and preincubated for 10 min at 95° C. Amplification was performed for 15 cycles as follows: 94° C. for 15 sec, 65° C. for 1 min. A second 25 µl aliquot of the reaction mixture was added through the mineral oil containing 25 pmol each of universal primers A and B. Cycling was repeated using 55° C. annealing temperature. The reaction was next digested with a 2 µl solution of 1 mg/ml Proteinase K/50 mM EDTA at 55° C. for 10 min. Proteinase K was eliminated by a final incubation at 90° C. for 15 min. For LDR, oligonucleotide synthesis and purification were carried out as previously described (Khanna et al., "Multiplex PCR/LDR for Detection of K-ras Mutations in Primary Colon Tumors," *Oncogene* 18:27-38 (1999), which is hereby incorporated by reference). Tth DNA ligase was overproduced and purified as described elsewhere (Luo et al., "Identification of Essential Residues in *Thermus thermophilus* DNA Ligase," *Nucleic Acids Research* 24:3079-3085 (1996) and Barany et al., "Cloning, Overexpression, and Nucleotide Sequence of a Thermostable DNA Ligase Gene," *Gene* 109:1-11 (1991), which are hereby incorporated by reference). LDR was performed in a 20 µl reaction containing 500 fmol of each probe, 2 µl of amplified DNA and 20 mM Tris-HCl, pH 7.6; 10 mM $MgCl_2$; 100 mM KCl; 10 mM DTT; 1 mM $NAD^+$. The reactants were heated to 94° C. for 1.5 min prior to adding 25 fmol of Tth DNA ligase and then subjected to 20 cycles of 15 sec at 94° C. and 4 min at 65° C. See Table 5 which shows the oligonucleotide primers and probes designed to detect mutations in p53 by PCR/LDR/array hybridization as follows:

TABLE 5

Primers and Probes Designed for Mutation Detection in p53 by PCR/LDR/Array Hybridization.

| Primer/Probe | Sequence (5'→3') |
|---|---|
| Uni A primer | GGAGCACGCTATCCCGTTAGAC (SEQ ID NO: 9316) |
| Uni B2 primer | CGCTGCCAACTACCGCACATC (SEQ ID NO: 9317) |
| p53X5FzipA | GGAGCACGCTATCCCGTTAGACCTGTTCACTTGTGCCCTGACTTTC (SEQ ID NO: 9318) |
| p53X5RzipB | CGCTGCCAACTACCGCACATCCCAGCTGCTCACCATCGCTATC (SEQ ID NO: 9319) |
| K132LA2G | Fam-aaaGCCAGTTGGCAAAACATCC (SEQ ID NO: 9320) |
| K132LA2G3 | Cy3-GCCAGTTGGCAAAACATCC (SEQ ID NO: 9321) |
| K132LA2GCOM | pTGTTGAGGGCAGGGGAGTACTGTAaaa-B (SEQ ID NO: 9322) |
| K132LA2Gzip9 | pTGTTGAGGGCAGGGGAGTACTGTA-catcgtcccUtcgatgggatcaa-B (SEQ ID NO: 9323) |
| C135UGA | Fam-CTGCCCTCAACAAGATGTTTTA (SEQ ID NO: 9324) |
| C135UGA3 | Cy3-CTGCCCTCAACAAGATGTTTTA (SEQ ID NO: 9325) |
| C135UGCom | pCCAACTGGCCAAGACCTGCCaaaa-B (SEQ ID NO: 9326) |
| C135UGT | Fam-CTGCCCTCAACAAGATGTTTTT (SEQ ID NO: 9327) |
| C135UGT5 | Cy5-CTGCCCTCAACAAGATGTTTTT (SEQ ID NO: 9328) |
| C135UGzip10 | pCCAACTGGCCAAGACCTGCC-caaggcacgtcccagacgcatcaa-B (SEQ ID NO: 9329) |
| C141UGA | Tet-GCCAACTGGCCAAGACCTA (SEQ ID NO: 9330) |
| C141UGA3 | Cy3-GCCAACTGGCCAAGACCTA (SEQ ID NO: 9331) |
| C141UGCom | pCCCTGTGCAGCTGTGGGTTGAaaaaa-B (SEQ ID NO: 9332) |
| C141UGzip11 | pCCCTGTGCAGCTGTGGGTTGA-gcacgggagctgacgacgtgtcaa-B (SEQ ID NO: 9333) |
| V143UGA | Fam-TGGCCAAGACCTGCCCTA (SEQ ID NO: 9334) |
| V143UGA3 | Cy3-TGGCCAAGACCTGCCCTA (SEQ ID NO: 9335) |
| V143UGACOM | pTGCAGCTGTGGGTTGATTCCAaaa-B (SEQ ID NO: 9336) |
| V143UGAzip12 | pTGCAGCTGTGGGTTGATTCCA-agacgcaccgcaacaggctgtcaa-B (SEQ ID NO: 9337) |

TABLE 5-continued

Primers and Probes Designed for Mutation Detection in p53 by PCR/LDR/Array Hybridization.

| Primer/Probe | Sequence (5'→3') |
| --- | --- |
| V143UTC | Fam-CCAAGACCTGCCCTGC (SEQ ID NO: 9338) |
| V143UTC3 | Cy3-CCAAGACCTGCCCTGC (SEQ ID NO: 9339) |
| V143UTCOM | pGCAGCTGTGGGTTGATTCCACAaaaa-B (SEQ ID NO: 9340) |
| V143UTzip13 | pGCAGCTGTGGGTTGATTCCACA-catcgctgcaagtaccgcactcaa-B (SEQ ID NO: 9341) |
| W146UG3A3 | Cy3-TGCCCTGTGCAGCTGTGA (SEQ ID NO: 9342) |
| W146UG3zip | pGTTGATTCCACACCCCCGCC-cgatggcttccttacccagattcg-B (SEQ ID NO: 9343) |
| P152LC2T2 | Tet-CGGGTGCCGGGCA (SEQ ID NO: 9344) |
| P152LC2T23 | Cy3-CGGGTGCCGGGCA (SEQ ID NO: 9344) |
| P152LC2T2COM | pGGGGTGTGGAATCAACCCACAaaaaaa-B (SEQ ID NO: 9345) |
| P152Lzip14 | pGGGGTGTGGAATCAACCCACA-ggctgggacgtgcagaccgttcaa-B (SEQ ID NO: 9346) |
| G154LG1A | Fam-atataaCACACCCCCGCCCA (SEQ ID NO: 9347) |
| G154LG1A3 | Cy3-CACACCCCCGCCCA (SEQ ID NO: 9348) |
| G154LG1ACom | pGCACCCGCGTCCGCatataa-B (SEQ ID NO: 9349) |
| G154LG1Azip15 | pGCACCCGCGTCCGCG-gctggctggcacgcaccagaatca-B (SEQ ID NO: 9350) |
| V157LGC | Tet-GCCATGGCGCGGAG (SEQ ID NO: 9351) |
| V157LGC5 | Cy5-GCCATGGCGCGGAG (SEQ ID NO: 9351) |
| V157LGCOM | pGCGGGTGCCGGGCGaaa-B (SEQ ID NO: 9352) |
| V157LGT | Tet-GCCATGGCGCGGAA (SEQ ID NO: 9353) |
| V157LGT3 | Cy3-GCCATGGCGCGGAA (SEQ ID NO: 9353) |
| V157LGzip16 | pGCGGGTGCCGGGCG-ggctccgtcagaaagcgacaatca-B (SEQ ID NO: 9354) |
| R158LC1A5 | Cy5-GATGGCCATGGCGCT (SEQ ID NO: 9355) |
| R158LC1zip | pGACGCGGGTGCCGGG-acgagggataccccgcaaacgatca-B (SEQ ID NO: 9356) |
| R158UGA | Tet-CGGCACCCGCGTCCA (SEQ ID NO: 9357) |
| R158UGA3 | Cy3-CGGCACCCGCGTCCA (SEQ ID NO: 9357) |
| R158UGACOM | pCGCCATGGCCATCTACAAGC-B (SEQ ID NO: 9358) |
| R158UGAzip17 | pCGCCATGGCCATCTACAAGC-acgagggataccccgcaaacgatca-B (SEQ ID NO: 9359) |
| A161LC2T5 | Cy5-GTGCTGTGACTGCTTGTAGATGA (SEQ ID NO: 9360) |
| A161LC2Tzip | pCCATGGCGCGGACGC-gggaggctgctgtcctttcgatca-B (SEQ ID NO: 9361) |
| A161UGA | Tet-aaaaaaaaGCGTCCGCGCCATGA (SEQ ID NO: 9362) |
| A161UGA3 | Cy3-GCGTCCGCGCCATGA (SEQ ID NO: 9363) |
| A161UGCOM | pCCATCTACAAGCAGTCACAGCACAaaaaaaaa-B (SEQ ID NO: 9364) |
| A161UGzip18 | pCCATCTACAAGCAGTCACAGCACA-gggaggctgctgtcctttcgatca-B (SEQ ID NO: 9365) |
| V173UGA | Fam-CACAGCACATGACGGAGGTTA (SEQ ID NO: 9366) |
| V173UGA3 | Cy3-CACAGCACATGACGGAGGTTA (SEQ ID NO: 9366) |
| V173UGCOM | pTGAGGCGCTGCCCCCAaaaaa-B (SEQ ID NO: 9367) |
| V173UGT | Fam-CACAGCACATGACGGAGGTTT (SEQ ID NO: 9368) |

TABLE 5-continued

Primers and Probes Designed for Mutation Detection in p53 by PCR/LDR/Array Hybridization.

| Primer/Probe | Sequence (5'→3') |
|---|---|
| V173UGT5 | Cy5-CACAGCACATGACGGAGGTTT (SEQ ID NO: 9368) |
| V173UGzip19 | pTGAGGCGCTGCCCCCA-acagcgtgttcgttgcttgcatca-B (SEQ ID NO: 9369) |
| R175LC1Com | pCCTCACAACCTCCGTCATGTGCT-B (SEQ ID NO: 9370) |
| R175LC1T | Fam-CATGGTGGGGGCAGCA (SEQ ID NO: 9371) |
| R175LC1T3 | Cy3-CATGGTGGGGGCAGCA (SEQ ID NO: 9371) |
| R175LC1zip20 | pCCTCACAACCTCCGTCATGTGCT-atggcgatggtccactcgcaatca-B (SEQ ID NO: 9372) |
| R175LG2T | Fam-CTCATGGTGGGGGCAGT (SEQ ID NO: 9373) |
| R175LG2T5 | Cy5-CTCATGGTGGGGGCAGT (SEQ ID NO: 9373) |
| R175LG2TCOM | pGCCTCACAACCTCCGTCATGTG-B (SEQ ID NO: 9374) |
| R175LG2Tzip21 | pGCCTCACAACCTCCGTCATGTG-gtccgtccatggcaagcgtgatca-B (SEQ ID NO: 9375) |
| R175UG2A | Tet-TGACGGAGGTTGTGAGGCA (SEQ ID NO: 9376) |
| R175UG2A3 | Cy3-TGACGGAGGTTGTGAGGCA (SEQ ID NO: 9376) |
| R175UG2ACom | pCTGCCCCCACCATGAGCGaaaaaaa-B (SEQ ID NO: 9377) |
| R175UG2Azip21 | pCTGCCCCCACCATGAGCG-gtccgtccatggcaagcgtgatca-B (SEQ ID NO: 9378) |
| C176UGA | Fam-CGGAGGTTGTGAGGCGCTA (SEQ ID NO: 9379) |
| C176UGA5 | Cy5-CGGAGGTTGTGAGGCGCTA (SEQ ID NO: 9379) |
| C176UGCom | pCCCCCACCATGAGCGCTGaaaaaaaa-B (SEQ ID NO: 9380) |
| C176UGT | Fam-CGGAGGTTGTGAGGCGCTT (SEQ ID NO: 9381) |
| C176UGT3 | Cy3-CGGAGGTTGTGAGGCGCTT (SEQ ID NO: 9381) |
| C176UGzip22 | pCCCCCACCATGAGCGCTG-ggctgcacccgttgaggcacatca-B (SEQ ID NO: 9382) |
| H179LACOM | pGGTGGGGGCAGCGCC-B (SEQ ID NO: 9383) |
| H179LAG | Fam-GCTATCTGAGCAGCGCTCAC (SEQ ID NO: 9384) |
| H179LAG3 | Cy3-GCTATCTGAGCAGCGCTCAC (SEQ ID NO: 9384) |
| H179LAT | Fam-GCTATCTGAGCAGCGCTCAA (SEQ ID NO: 9385) |
| H179LAT5 | Cy5-GCTATCTGAGCAGCGCTCAA (SEQ ID NO: 9385) |
| H179LAzip23 | pGGTGGGGGCAGCGCC-tcaacatcggctaacggtccatca-B (SEQ ID NO: 9386) |
| H179LCT | Fam-GCTATCTGAGCAGCGCTCATA (SEQ ID NO: 9387) |
| H179LCT3 | Cy3-GCTATCTGAGCAGCGCTCATA (SEQ ID NO: 9387) |
| H179LCTCOM | pGTGGGGGCAGCGCCTCAC-B (SEQ ID NO: 9388) |
| H179LCTzip24 | pGTGGGGGCAGCGCCTCAC-cgcacgcagtcctcctccgtatca-B (SEQ ID NO: 9389) |
| X5LCom | pCGGGGGTGTGGAATCAACCC-B (SEQ ID NO: 9390) |
| X5LWT | Fam-CGCGGGTGCCGGG (SEQ ID NO: 9391) |
| X5LWT3 | Cy3-CGCGGGTGCCGGG (SEQ ID NO: 9391) |
| X5LWT5 | Cy5-CGCGGGTGCCGGG (SEQ ID NO: 9391) |
| X5Lzip1 | pCGGGGGTGTGGAATCAACCC-cgcagatttgcgctggatttcaa-B (SEQ ID NO: 9392) |
| p53X6FzipA | GGAGCACGCTATCCCGTTAGACCCTCTGATTCCTCACTGATTGCTCTTA (SEQ ID NO: 9393) |

TABLE 5-continued

Primers and Probes Designed for Mutation Detection in p53 by PCR/LDR/Array Hybridization.

| Primer/Probe | Sequence (5'→3') |
|---|---|
| p53X6RzipB | CGCTGCCAACTACCGCACATCGGCCACTGACAACCACCCTTAAC (SEQ ID NO: 9394) |
| P190LCT | Tet-aaaaTCGGATAAGATGCTGAGGAGA (SEQ ID NO: 9395) |
| P190LCT3 | Cy3-TCGGATAAGATGCTGAGGAGA (SEQ ID NO: 9396) |
| P190LCTCOM | pGGCCAGACCCTAAGAGCAATCAGaaaa-B (SEQ ID NO: 9397) |
| P190LCTzip25 | pGGCCAGACCCTAAGAGCAATCAG-ggctcgcaggctggctcatcctaa-B (SEQ ID NO: 9398) |
| P190LTA5 | Cy5-CACTCGGATAAGATGCTGAGGT (SEQ ID NO: 9399) |
| P190LTAzip | pGGGGCCAGACCCTAAGAGCAA-ggctcgcaggctggctcatcctaa-B (SEQ ID NO: 9400) |
| H193LAG3 | Cy3-AATTTCCTTCCACTCGGATAAGAC (SEQ ID NO: 9401) |
| H193LAGzip | pGCTGAGGAGGGGCCAGACC-cgcattcgatggacaggacattcg-B (SEQ ID NO: 9402) |
| H193LTA5 | Cy5-AATTTCCTTCCACTCGGATAAGT (SEQ ID NO: 9403) |
| H193LTAzip | pTGCTGAGGAGGGGCCAGAC-cgcattcgatggacaggacattcg-B (SEQ ID NO: 9404) |
| R196LCCom | pGATAAGATGCTGAGGAGGGGCCA-B (SEQ ID NO: 9405) |
| R196LCT | Fam-CGCAAATTTCCTTCCACTCA (SEQ ID NO: 9406) |
| R196LCT3 | Cy3-CGCAAATTTCCTTCCACTCA (SEQ ID NO: 9406) |
| R196LCzip26 | pGATAAGATGCTGAGGAGGGGCCA-cgcatgaggggaaacgacgagatt-B (SEQ ID NO: 9407) |
| Y205LAC | Fam-AAAAGTGTTTCTGTCATCCAAAG (SEQ ID NO: 9408) |
| Y205LAC3 | Cy3-AAAAGTGTTTCTGTCATCCAAAG (SEQ ID NO: 9408) |
| Y205LACOM | pACTCCACACGCAAATTTCCTTCCAaaaaaa-B (SEQ ID NO: 9409) |
| Y205LAG | Fam-AAAAGTGTTTCTGTCATCCAAAC (SEQ ID NO: 9410) |
| Y205LAG5 | Cy5-AAAAGTGTTTCTGTCATCCAAAC (SEQ ID NO: 9410) |
| Y205LAzip27 | pACTCCACACGCAAATTTCCTTCCA-gcaccgtgaacgacagttgcgatt-B (SEQ ID NO: 9411) |
| T211LAG | Tet-CCACCACACTATGTCGAAAAGC (SEQ ID NO: 9412) |
| T211LAG3 | Cy3-CCACCACACTATGTCGAAAAGC (SEQ ID NO: 9412) |
| T211LAGCOM | pGTTTCTGTCATCCAAATACTCCACACGaaa-B (SEQ ID NO: 9413) |
| T211LAGzip28 | pGTTTCTGTCATCCAAATACTCCACACG-cgcaggtcgctgcgtgtcctgatt-B (SEQ ID NO: 9414) |
| T211LCT | Tet-ACCACCACACTATGTCGAAAAA (SEQ ID NO: 9415) |
| T211LCT3 | Cy3-ACCACCACACTATGTCGAAAAA (SEQ ID NO: 9415) |
| T211LCTCOM | pTGTTTCTGTCATCCAAATACTCCACACaaa-B (SEQ ID NO: 9416) |
| T211LCTzip29 | pTGTTTCTGTCATCCAAATACTCCACAC-cgcaaagcagacacagggtcgatt-B (SEQ ID NO: 9417) |
| R213LCCom | pAAAAGTGTTTCTGTCATCCAAATACTCCa-B (SEQ ID NO: 9418) |
| R213LCT | Tet-GGGCACCACCACACTATGTCA (SEQ ID NO: 9419) |
| R213LCT3 | Cy3-GGGCACCACCACACTATGTCA (SEQ ID NO: 9419) |
| R213LCzip30 | pAAAAGTGTTTCTGTCATCCAAATACTCC-catcgcacttcgctttggctgatt-B (SEQ ID NO: 9420) |

TABLE 5-continued

Primers and Probes Designed for Mutation Detection in p53 by PCR/LDR/Array Hybridization.

| Primer/Probe | Sequence (5'→3') |
|---|---|
| Y220LACom | pAGGGCACCACCACACTATGTCGA-B (SEQ ID NO: 9421) |
| Y220LAG | Tet-CAGACCTCAGGCGGCTCAC (SEQ ID NO: 9422) |
| Y220LAG3 | Cy3-CAGACCTCAGGCGGCTCAC (SEQ ID NO: 9422) |
| Y220LAzip31 | pAGGGCACCACCACACTATGTCGA-ttgcgggaactcacgaggtcgtat-B (SEQ ID NO: 9423) |
| X6UCOM | pCCTATGAGCCGCCTGAGGTCTaaaa-B (SEQ ID NO: 9424) |
| X6UWT | Fam-aaaTTCGACATAGTGTGGTGGTGC (SEQ ID NO: 9425) |
| X6UWT3 | Cy3-TTCGACATAGTGTGGTGGTGC (SEQ ID NO: 9545) |
| X6UWT5 | Cy5-TTCGACATAGTGTGGTGGTGC (SEQ ID NO: 9545) |
| X6Uzip2 | pCCTATGAGCCGCCTGAGGTCT-ttcgccgtcgtgtaggcttttcaa-B (SEQ ID NO: 9426) |
| p53X7FzipA | GGAGCACGCTATCCCGTTAGACGCCTCATCTTGGGCCTGTGTTATC (SEQ ID NO: 9427) |
| p53X7RzipB | CGCTGCCAACTACCGCACATCGTGGATGGGTAGTAGTATGGAAGAAATC (SEQ ID NO: 9428) |
| Y234UTA3 | Cy3-CTCTGACTGTACCACCATCCACA (SEQ ID NO: 9429) |
| Y234UTAzip | pACAACTACATGTGTAACAGTTCCTGCAT-ggctacgacgcatgtaaacgttcg-B (SEQ ID NO: 9430) |
| M237UGA | Fam-aaaaATAAGTACCACCATCCACTACAACTACATA (SEQ ID NO: 9431) |
| M237UGA3 | Cy3-ATAAGTACCACCATCCACTACAACTACATA (SEQ ID NO: 9432) |
| M237UGCOM | pTGTAACAGTTCCTGCATGGGCGaaaa-B (SEQ ID NO: 9433) |
| M237UGT | Fam-aaaaATAAGTACCACCATCCACTACAACTACATT (SEQ ID NO: 9434) |
| M237UGT5 | Cy5-ATAAGTACCACCATCCACTACAACTACATT (SEQ ID NO: 9435) |
| M237UGzip32 | pTGTAACAGTTCCTGCATGGGCG-gcacggctcgataggtcaagcttt-B (SEQ ID NO: 9436) |
| C238UGA | Tet-CCACCATCCACTACAACTACATGTA (SEQ ID NO: 9437) |
| C238UGA3 | Cy3-CCACCATCCACTACAACTACATGTA (SEQ ID NO: 9437) |
| C238UGCom | pTAACAGTTCCTGCATGGGCGGaaaaa-B (SEQ ID NO: 9438) |
| C238UGzip33 | pTAACAGTTCCTGCATGGGCGG-cgatttcgactcaagcggctcttt-B (SEQ ID NO: 9439) |
| S241LC2A6 | Fam-ATGCCGCCCATGCAGT (SEQ ID NO: 9440) |
| S241LC2Azip | pAACTGTTACACATGTAGTTGTAGTGGATGGT-cgcaatggtaggtgagcaagcaga-B (SEQ ID NO: 9441) |
| S241LCCom | pAACTGTTACACATGTAGTTGTAGTGGATGGTaaa-B (SEQ ID NO: 9442) |
| S241LCG | Fam-TGCCGCCCATGCAGC (SEQ ID NO: 9443) |
| S241LCG5 | Cy5-TGCCGCCCATGCAGC (SEQ ID NO: 9443) |
| S241LCT | Fam-TGCCGCCCATGCAGA (SEQ ID NO: 9444) |
| S241LCT3 | Cy3-TGCCGCCCATGCAGA (SEQ ID NO: 9444) |
| S241LCzip34 | pAACTGTTACACATGTAGTTGTAGTGGATGGT-cgcaatggtaggtgagcaagcaga-B (SEQ ID NO: 9445) |
| G244UG1T | Fam-aaaaaCATGTGTAACAGTTCCTGCATGT (SEQ ID NO: 9446) |
| G244UG1T3 | Cy3-CATGTGTAACAGTTCCTGCATGT (SEQ ID NO: 9447) |
| G244UG1TCOM | pGCGGCATGAACCGGAGGCaaaaaa-B (SEQ ID NO: 9448) |

TABLE 5-continued

Primers and Probes Designed for Mutation Detection in p53 by PCR/LDR/Array Hybridization.

| Primer/Probe | Sequence (5'→3') |
|---|---|
| G244UG1Tzip35 | pGCGGCATGAACCGGAGGC-gtccccgttacctaggcgatcaga-B (SEQ ID NO: 9449) |
| G244UG2A | Fam-aaaaaaTGTGTAACAGTTCCTGCATGGA (SEQ ID NO: 9450) |
| G244UG2A3 | Cy3-TGTGTAACAGTTCCTGCATGGA (SEQ ID NO: 9451) |
| G244UG2COM | pCGGCATGAACCGGAGGCCaaaaaa-B (SEQ ID NO: 9452) |
| G244UG2T | Fam-aaaaaaTGTGTAACAGTTCCTGCATGGT (SEQ ID NO: 9453) |
| G244UG2T5 | Cy5-TGTGTAACAGTTCCTGCATGGT (SEQ ID NO: 9454) |
| G244UG2zip36 | pCGGCATGAACCGGAGGCC-atgggtccacagtaccgctgcaga-B (SEQ ID NO: 9455) |
| G245UG1A | Tet-AACAGTTCCTGCATGGGCA (SEQ ID NO: 9456) |
| G245UG1A3 | Cy3-AACAGTTCCTGCATGGGCA (SEQ ID NO: 9456) |
| G245UG1ACom | pGCATGAACCGGAGGCCCAaaaa-B (SEQ ID NO: 9457) |
| G245UG1Azip37 | pGCATGAACCGGAGGCCCA-ccgtgggagattaggtggctcaga-B (SEQ ID NO: 9458) |
| G245UG2A | Fam-CAGTTCCTGCATGGGCGA (SEQ ID NO: 9459) |
| G245UG2A3 | Cy3-CAGTTCCTGCATGGGCGA (SEQ ID NO: 9459) |
| G245UG2ACom | pCATGAACCGGAGGCCCATCaaa-B (SEQ ID NO: 9460) |
| G245UG2Azip38 | pCATGAACCGGAGGCCCATC-gggaatggaggtgggaacgagaca-B (SEQ ID NO: 9461) |
| G245UG2T | Tet-aaaaaaaaAGTTCCTGCATGGGCGA (SEQ ID NO: 9462) |
| G245UG2T5 | Cy5-CAGTTCCTGCATGGGCGT (SEQ ID NO: 9463) |
| G245UG2TCOM | pCATGAACCGGAGGCCCATCaaaaaaaaa-B (SEQ ID NO: 9464) |
| R248LCCom | pGTTCATGCCGCCCATGCAaa-B (SEQ ID NO: 9465) |
| R248LCT | Tet-GGTGAGGATGGGCCTCCA (SEQ ID NO: 9466) |
| R248LCT3 | Cy3-GGTGAGGATGGGCCTCCA (SEQ ID NO: 9466) |
| R248LCzip39 | pGTTCATGCCGCCCATGCA-cgtggctgactcgctgcgatgaca-B (SEQ ID NO: 9467) |
| R248UGA | Tet-TGGGCGGCATGAACCA (SEQ ID NO: 9468) |
| R248UGA3 | Cy3-TGGGCGGCATGAACCA (SEQ ID NO: 9468) |
| R248UGCom | pGAGGCCCATCCTCACCATCATaa-B (SEQ ID NO: 9469) |
| R248UGzip40 | pGAGGCCCATCCTCACCATCAT-ttgcgcaccatcaggttagggaca-B (SEQ ID NO: 9470) |
| R249LACom | pCCGGTTCATGCCGCCCAa-B (SEQ ID NO: 9471) |
| R249LAG | Fam-TGATGGTGAGGATGGGCCC (SEQ ID NO: 9472) |
| R249LAG5 | Cy5-TGATGGTGAGGATGGGCCC (SEQ ID NO: 9472) |
| R249LAT | Fam-TGATGGTGAGGATGGGCCA (SEQ ID NO: 9473) |
| R249LAT3 | Cy3-TGATGGTGAGGATGGGCCA (SEQ ID NO: 9473) |
| R249LAzip41 | pCCGGTTCATGCCGCCCA-gcaccgatatggagaccgcagaca-B (SEQ ID NO: 9474) |
| R249LG3C | Tet-GATGATGGTGAGGATGGGG (SEQ ID NO: 9475) |
| R249LG3C3 | Cy3-GATGATGGTGAGGATGGGG (SEQ ID NO: 9475) |
| R249LG3Com | pCTCCGGTTCATGCCGCC-B (SEQ ID NO: 9476) |
| R249LG3zip42 | pCTCCGGTTCATGCCGCC-catcgacaaggtaacgcgtggaca-B (SEQ ID NO: 9477) |
| P250LC2T3 | Cy3-AGTGTGATGATGGTGAGGATGA (SEQ ID NO: 9478) |
| P250LC2Tzip | pGCCTCCGGTTCATGCCG-gtcccaagttgcggctcactttcg-B (SEQ ID NO: 9479) |

TABLE 5-continued

Primers and Probes Designed for Mutation Detection in p53 by PCR/LDR/Array Hybridization.

| Primer/Probe | Sequence (5'→3') |
|---|---|
| I254LAG | Fam-CTGGAGTCTTCCAGTGTGATGAC (SEQ ID NO: 9480) |
| I254LAG3 | Cy3-CTGGAGTCTTCCAGTGTGATGAC (SEQ ID NO: 9480) |
| I254LAGCOM | pGGTGAGGATGGGCCTCCG-B (SEQ ID NO: 9481) |
| I254LAGzip43 | pGGTGAGGATGGGCCTCCG-tgagcgcaaggtcagagcacgaca-B (SEQ ID NO: 9482) |
| X7LCom | pCATGCAGGAACTGTTACACATGTAGTTGTAa-B (SEQ ID NO: 9483) |
| X7LWT | Tet-TCCGGTTCATGCCGCC (SEQ ID NO: 9484) |
| X7LWT3 | Cy3-TCCGGTTCATGCCGCC (SEQ ID NO: 9484) |
| X7LWT5 | Cy5-TCCGGTTCATGCCGCC (SEQ ID NO: 9484) |
| X7Lzip3 | pCATGCAGGAACTGTTACACATGTAGTTGTA-ccgtaagcccgtatggcagatcaa-B (SEQ ID NO: 9485) |
| p53X8FzipA | GGAGCACGCTATCCCGTTAGACGGACAGGTAGGACCTGATTTCCTTAC (SEQ ID NO: 9486) |
| p53X8RzipB | CGCTGCCAACTACCGCACATCCGCTTCTTGTCCTGCTTGCTTAC (SEQ ID NO: 9487) |
| F270UTA | Tet-aaaaaATCTACTGGGACGGAACAGCA (SEQ ID NO: 9488) |
| F270UTA3 | Cy3-ATCTACTGGGACGGAACAGCA (SEQ ID NO: 9489) |
| F270UTCOM | pTTGAGGTGCGTGTTTGTGCCTaaaaaa-B (SEQ ID NO: 9490) |
| F270UTzip44 | pTTGAGGTGCGTGTTTGTGCCT-aagccgcagcacgattccgtgaca-B (SEQ ID NO: 9491) |
| V272UGA | Fam-aaaaaaGGACGGAACAGCTTTGAGA (SEQ ID NO: 9492) |
| V272UGA3 | Cy3-GGACGGAACAGCTTTGAGA (SEQ ID NO: 9493) |
| V272UGCOM | pTGCGTGTTTGTGCCTGTCCTGGaaaaaaa-B (SEQ ID NO: 9494) |
| V272UGT | Fam-aaaaaaGGACGGAACAGCTTTGAGT (SEQ ID NO: 9495) |
| V272UGT5 | Cy5-GGACGGAACAGCTTTGAGT (SEQ ID NO: 9496) |
| V272UGzip45 | pTGCGTGTTTGTGCCTGTCCTGG-tgagaagcgtccaagccagaacga-B (SEQ ID NO: 9497) |
| R273LCCom | pCACCTCAAAGCTGTTCCGTCCCaa-B (SEQ ID NO: 9498) |
| R273LCT | Tet-CCAGGACAGGCACAAACACA (SEQ ID NO: 9499) |
| R273LCT3 | Cy3-CCAGGACAGGCACAAACACA (SEQ ID NO: 9499) |
| R273LCzip46 | pCACCTCAAAGCTGTTCCGTCCC-catccaaggtccgacacgcaacga-B (SEQ ID NO: 9500) |
| R273UCA5 | Cy5-ACGGAACAGCTTTGAGGTGA (SEQ ID NO: 9501) |
| R273UCAzip | pGTGTTTGTGCCTGTCCTGGGAGA-catccaaggtccgacacgcaacga-B (SEQ ID NO: 9502) |
| R273UGA | Tet-CGGAACAGCTTTGAGGTGCA (SEQ ID NO: 9503) |
| R273UGA3 | Cy3-CGGAACAGCTTTGAGGTGCA (SEQ ID NO: 9503) |
| R273UGCom | pTGTTTGTGCCTGTCCTGGGAGaaaaaa-B (SEQ ID NO: 9504) |
| R273UGzip47 | pTGTTTGTGCCTGTCCTGGGAG-ttcgacgattcgcatcaacgcaag-B (SEQ ID NO: 9505) |
| C275UGA | Tet-aaaaaaaAGCTTTGAGGTGCGTGTTTA (SEQ ID NO: 9506) |
| C275UGA3 | Cy3-CAGCTTTGAGGTGCGTGTTTA (SEQ ID NO: 9507) |
| C275UGCOM | pTGCCTGTCCTGGGAGAGACCaaaaaaa-B (SEQ ID NO: 9508) |

TABLE 5-continued

Primers and Probes Designed for Mutation Detection in p53 by PCR/LDR/Array Hybridization.

| Primer/Probe | Sequence (5'→3') |
|---|---|
| C275UGT | Tet-aaaaaaaaCAGCTTTGAGGTGCGTGTTTT (SEQ ID NO: 9509) |
| C275UGT5 | Cy5-CAGCTTTGAGGTGCGTGTTTT (SEQ ID NO: 9510) |
| C275UGzip48 | pTGCCTGTCCTGGGAGAGACC-aacggggaaggttgagcgtgacag-B (SEQ ID NO: 9511) |
| R280UGA | Tet-TTTGTGCCTGTCCTGGGAA (SEQ ID NO: 9512) |
| R280UGA3 | Cy3-TTTGTGCCTGTCCTGGGAA (SEQ ID NO: 9512) |
| R280UGCOM | pAGACCGGCGCACAGAGGAAGaaaaaa-B (SEQ ID NO: 9513) |
| R280UGT | Tet-TTTGTGCCTGTCCTGGGAT (SEQ ID NO: 9514) |
| R280UGT5 | Cy5-TTTGTGCCTGTCCTGGGAT (SEQ ID NO: 9514) |
| R280UGzip49 | pAGACCGGCGCACAGAGGAAG-cactgcacacgaaacggcacacag-B (SEQ ID NO: 9515) |
| D281UCA3 | Cy3-GTGCCTGTCCTGGGAGAGAA (SEQ ID NO: 9516) |
| D281UCAGzip | pCGGCGCACAGAGGAAGAGAA-aagcaagccaaggtatggctttgc-B (SEQ ID NO: 9517) |
| D281UCG5 | Cy5-GTGCCTGTCCTGGGAGAGAG (SEQ ID NO: 9518) |
| D281UGA3 | Cy3-TTGTGCCTGTCCTGGGAGAA (SEQ ID NO: 9519) |
| D281UGACzip | pACCGGCGCACAGAGGAAGAG-cgtgcgcacactcactgtccttcg-B (SEQ ID NO: 9520) |
| D281UGC5 | Cy5-TTGTGCCTGTCCTGGGAGAC (SEQ ID NO: 9521) |
| R282LCCom | pGTCTCTCCCAGGACAGGCACAAAaaa-B (SEQ ID NO: 9522) |
| R282LCT | Fam-TCTCTTCCTCTGTGCGCCA (SEQ ID NO: 9523) |
| R282LCT3 | Cy3-TCTCTTCCTCTGTGCGCCA (SEQ ID NO: 9523) |
| R282LCzip50 | pGTCTCTCCCAGGACAGGCACAAA-taccgacatcctgggattgcatgg-B (SEQ ID NO: 9524) |
| R282UG2A5 | Cy5-CCTGTCCTGGGAGAGACCA (SEQ ID NO: 9525) |
| R282UG2Azip | pGCGCACAGAGGAAGAGAATCTCC-taccgacatcctgggattgcatgg-B (SEQ ID NO: 9526) |
| E286UGA3 | Cy3-AGACCGGCGCACAGAGA (SEQ ID NO: 9527) |
| E286UGAzip | pAAGAGAATCTCCGCAAGAAAGGG-ttcggctgttcgtaggcaagaggt-B (SEQ ID NO: 9528) |
| R306LCT | Cy3-TTGTCCTGCTTGCTTACCTCA (SEQ ID NO: 9529) |
| R306L CT | Fam-aaaaTTGTCCTGCTTGCTTACCTCA (SEQ ID NO: 9530) |
| R306L CT COM | pCTTAGTGCTCCCTGGGGGCAGaaaaa-B (SEQ ID NO: 9531) |
| R306LCTzip51 | pCTTAGTGCTCCCTGGGGGCAG-actccgcattgccagagctgatgg-B (SEQ ID NO: 9532) |
| X8UCOM | pCTCACCACGAGCTGCCCCC-B (SEQ ID NO: 9533) |
| X8UWT | Fam-TCCGCAAGAAAGGGGAGC (SEQ ID NO: 9534) |
| X8UWT3 | Cy3-TCCGCAAGAAAGGGGAGC (SEQ ID NO: 9534) |

TABLE 5-continued

Primers and Probes Designed for Mutation Detection in p53 by
PCR/LDR/Array Hybridization.

| Primer/Probe | Sequence (5'→3') |
|---|---|
| X8UWT5 | Cy5-TCCGCAAGAAAGGGGAGC (SEQ ID NO: 9534) |
| X8Uzip4 | pCTCACCACGAGCTGCCCCC-atggccgtgctggggacaagtcaa-B (SEQ ID NO: 9535) |

The PCR primers are specifically designed to amplify regions within and surrounding the p53 gene. After 15 rounds of amplification at high Tm's (i.e. 65° C.) using the longer gene-specific primers (at 1-2 pmoles per reaction), the two universal primers (bold upper case) are added at 50 pmoles in 50 µl and products cycled for an additional 20 rounds of amplification.
The allele-specific LDR probes contained fluorescent labels on the 5'-ends (Fam, Tet, Cy3 or Cy5) and the discriminating bases on their 3'-ends. Non-genomic sequence was added to the 5'-ends of some probes (designated by bold lower case) to control the final ligation product size for gel-based assays. The common LDR probes contained 5'-phosphates (p) and C-3 blocking (B) groups on their 3'-ends. Common LDR probes used in array-based detection have zipcode sequences (designated by lower case) on their 3'-ends.

LDR reactions were hybridized in 32 µl containing 300 mM MES, pH 6.0, 10 mM MgCl$_2$ 0.1% SDS with or without 100 µg/ml sheared salmon sperm DNA at 65° C. for 1 h in a rotating chamber. After washing in 300 mM bicine, pH 8.0, 10 mM MgCl$_2$, 0.1% SDS with or without 10% formamide for 10 min at 25° C. or for 10 min at 50° C. The array was imaged on an Olympus Provis AX70 microscope using a 100 W mercury burner, a Texas Red filter cube, and a Princeton Instruments TEK512/CCD camera. The 16-bit greyscale images were captured using MetaMorph Imaging System (Universal Imaging Corporation) and rescaled to more narrowly bracket the LDR signal before conversion to 8-bit greyscale. The 8-bit images were inverted using Adobe Photoshop to render the Cy3 signal black.

Figure 24A:
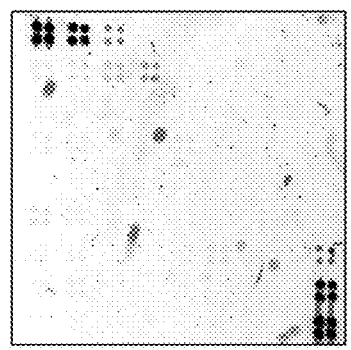
FIG. 24A-H show p53 chip hybridization indicating the presence of mutations in DNA from colon tumors.
Figure 24B:
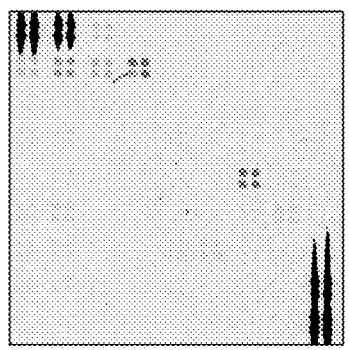
Figure 24C:
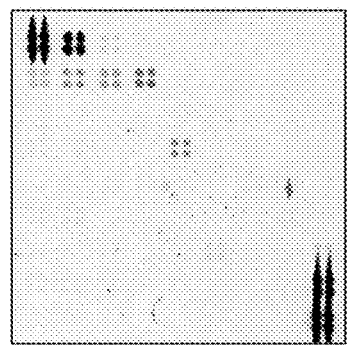
Figure 24D:
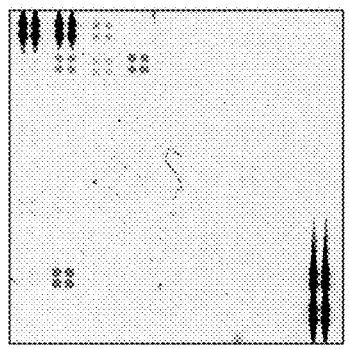
Figure 24E:
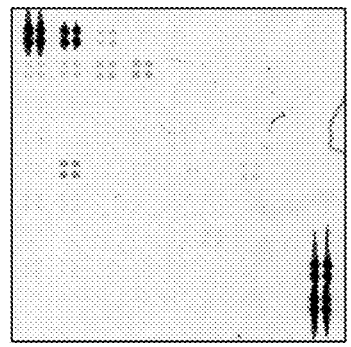
Figure 24F:
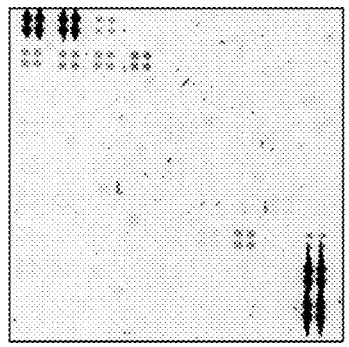
Figure 24G:
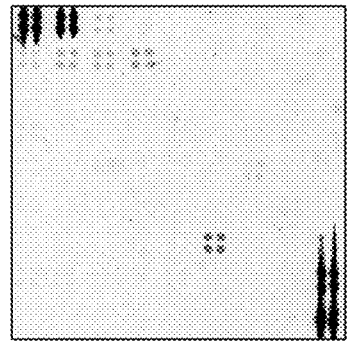
Figure 24H:
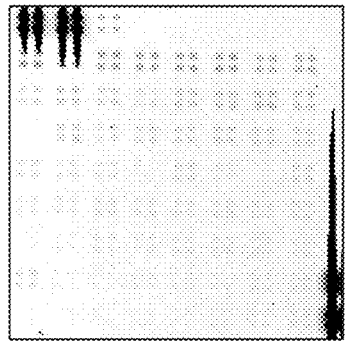

Example 4 p53 Chip Hybridization Showing the Presence of Mutations in DNA from Colon Tumors A p53 chip can detect the presence of 75 different mutations in exons 5, 6, 7 and 8 and uses 144 LDR oligonucleotides (see Table 5). FIG. 24 is an example of microarray-based p53 mutation detection using DNA derived from colon tumors. The mutation status of each sample and the zip-codes expected to capture signal are indicated to the right of each panel. The figure shows Cy3 background in the lowest panel on the right that is due to contaminating fluorescence in the spotted zip-codes (FIG. 24H). PCR was carried out as a single-tube, multiplex reaction in order to simultaneously amplify p53 exons 5, 6, 7, and 8. Genomic DNA extracted from colon tumors was amplified in a 25 µl reaction mixture containing 100 ng of DNA, 400 µM of each dNTP, 1×PCR Buffer II (10 mM Tris-HCl pH 8.3 at 25° C., 50 mM KCl) supplemented with 4 mM MgCl$_2$, 1 U AmpliTaq Gold and 2 pmol of each gene-specific primer bearing either universal primer A or B on the 5' ends (see Table 5). The reaction was overlaid with mineral oil and preincubated for 10 min at 95° C. Amplification was performed for 15 cycles as follows: 94° C. for 15 sec, 65° C. for 1 min. A second 25 µl aliquot of the reaction mixture was added through the mineral oil containing 25 pmol each of universal primers A and B. Cycling was repeated using 55° C. annealing temperature. The reaction was next digested with a 2 µl solution of 1 mg/ml Proteinase K/50 mM EDTA at 55° C. for 10 min. Proteinase K was eliminated by a final incubation at 90° C. for 15 min. For LDR, oligonucleotide synthesis and purification were carried out as previously described (Khanna et al., "Multiplex PCR/LDR for Detection of K-ras Mutations in Primary Colon Tumors," *Oncogene* 18:27-38 (1999), which is hereby incorporated by reference). Tth DNA ligase was overproduced and purified as described elsewhere (Luo et al., "Identification of Essential Residues in *Thermus thermophilus* DNA Ligase," *Nucleic Acids Research* 24:3079-3085 (1996) and Barany et al., "Cloning, Overexpression, and Nucleotide Sequence of a Thermostable DNA Ligase Gene," *Gene* 109:1-11(1991), which are hereby incorporated by reference). LDR was performed in a 20 µl reaction containing 500 fmol of each probe, 2 µl of amplified DNA and 20 mM Tris-HCl, pH 7.6; 10 mM MgCl$_2$; 100 mM KCl; 10 mM DTT; 1 mM NAD$^+$. Two reactions were performed for each sample containing LDR probes that were designed to hybridize to the upper strand or lower strand of p53 sequence. The reaction was heated to 94° C. for 1.5 min prior to adding 25 fmol of Tth DNA ligase and then subjected to 20 cycles of 15 sec at 94° C. and 4 min at 65° C. (See Table 5) LDR reactions were hybridized in 32 µl containing 100 µg/ml sheared salmon sperm DNA 300 mM MES, pH 6.0, 10 mM MgCl$_2$, 0.1% SDS at 65° C. for 1 h in a rotating chamber. After washing in 300 mM bicine, pH 8.0, 10 mM MgCl$_2$ 0.1% SDS for 10 min at 50° C. The array was imaged on an Olympus Provis AX70 microscope using a 100 W mercury burner, a Texas Red filter cube, and a Princeton Instruments TEK512/CCD camera. The 16-bit greyscale images were captured using MetaMorph Imaging System (Universal Imaging Corporation) and rescaled to more narrowly bracket the LDR signal before conversion to 8-bit greyscale. Using Adobe Photoshop, the 8-bit images were first inverted to render the Cy3 signal black and then the images for each sample derived from hybridization using LDR targeted to the upper strand and lower strand of the p53 sequence were overlaid and merged. The results of this procedure are shown in FIG. 24.

Example 5

Optimized Zipcode Sequence Construction Using Tetramers

The universal DNA array is designed on the concept of using divergent sequences to uniquely tag LDR products such that each one is captured at a unique site. The heart of the concept is the design of 36 tetramers, each of which differs from any other by at least 2 bases (See Table 6).

TABLE 6

| New tetramer designation | Original tetramer designation (See Table 1) | Tetramer sequence 5'-3' | Tetramer complement 5'-3' | G + C bases |
|---|---|---|---|---|
| 1 | 6 | TTGA | TCAA | 1 |
| 2 | 7 | TGAT | ATCA | 1 |
| 3 | 8 | TTAG | CTAA | 1 |
| 4 | 26 | AATC | GATT | 1 |
| 5 | 31 | ATAC | GTAT | 1 |
| 6 | 32 | AAAG | CTTT | 1 |
| 7 | 36 | TACA | TGTA | 1 |
| 8 | 1 | TCTG | CAGA | 2 |
| 9 | 2 | TGTC | GACA | 2 |
| 10 | 5 | TCGT | ACGA | 2 |
| 11 | 9 | CTTG | CAAG | 2 |
| 12 | 10 | CGTT | AACG | 2 |
| 13 | 11 | CTCA | TGAG | 2 |
| 14 | 13 | CTGT | ACAG | 2 |
| 15 | 15 | CCAT | ATGG | 2 |
| 16 | 16 | CGAA | TTCG | 2 |
| 17 | 17 | GCTT | AAGC | 2 |
| 18 | 18 | GGTA | TACC | 2 |
| 19 | 19 | GTCT | AGAC | 2 |
| 20 | 21 | GAGT | ACTC | 2 |
| 21 | 23 | GCAA | TTGC | 2 |
| 22 | 25 | AGTG | CACT | 2 |
| 23 | 27 | ACCT | AGGT | 2 |
| 24 | 28 | ATCG | CGAT | 2 |
| 25 | 30 | AGGA | TCCT | 2 |
| 26 | 33 | CCTA | TAGG | 2 |
| 27 | 34 | GATG | CATC | 2 |
| 28 | 3 | TCCC | GGGA | 3 |
| 29 | 4 | TGCG | CGCA | 3 |
| 30 | 12 | CACG | CGTG | 3 |
| 31 | 14 | CAGC | GCTG | 3 |
| 32 | 20 | GACC | GGTC | 3 |
| 33 | 22 | GTGC | GCAC | 3 |
| 34 | 24 | GGAC | GTCC | 3 |
| 35 | 29 | ACGG | CCGT | 3 |
| 36 | 35 | AGCC | GGCT | 3 |

By combining these 36 tetramers in sets of six, addresses that are 24 bases long can be constructed.

A 1296 array can be designed based on the concept of alternating tiling of given sets of tetramers. These capture oligonucleotides differed from their neighbors at three alternating positions, but were the same at the other three positions, i.e. (First=A, third=C, and fifth=E positions). Thus, each capture oligonucleotide differed from any other one by at least 6 out of 24 positions. Moreover, these differences were distributed across the length of the capture oligonucleotides. When aligning a correct capture oligonucleotide with an incorrect address, the Tm differences were predicted to be greater than 24° C. Nevertheless, one of the possibilities with this type of design is for three contiguous tetramers in a given set of positions (i.e. ABC) to match another capture oligonucleotide, but at a different set of positions (i.e. BCD).

Since optimal surfaces are three-dimensional porous surfaces, a given LDR product has numerous opportunity to be captured at the correct address. Even if an LDR product transiently dissociates from a given oligonucleotide within the correct address, it will rapidly find and hybridize to another oligonucleotide within the same address. In preliminary studies, it was found that changes which would be expected to alter Tm, (i.e. use of propynyl derivatives) did not markedly affect yield of correctly hybridized products. Thus, hybridization may be kinetically controlled. In order to minimize the possibility of even low levels of cross-hybridization between two closely related capture oligonucleotides, the sequences can be designed to maximize differences among the tetramer order with a 24 mer capture oligonucleotide.

The process for designing such sequences is outlined below:

1. Create three columns containing all 46,656 (=36×36×36) permutations of three sets of the 36 tetramers.

2. Compute the Tm of the 46,656 12-mers using the Oligo 6.0 program from Molecular Biology Insights, Inc. (Cascade, Colo.) and sort the list according to predicted Tm values.

3. Remove 12-mers that contain one GC base (Tetramers #1-7) in each tetramer or contain three GC bases in each tetramer (Tetramers #28-36). This process removes the extremes in Tm range. Remove 12-mers with Tm values less than 24° C. Remove the remaining 12-mers that have three repeated tetramers (i.e. 9-9-9)

4. Group the set of 12-mers by Tm with a new group for each 2 degrees increase in Tm. Values were set by dividing Tm by two and truncating to whole numbers.

5. Randomize list and split into odd and even 12-mers. Invert second list and append to the end of first list to form 6 tetramers=12,880 address candidates. Concatenate sequences and determine Tm values of 24-mers.

6. Select only hexa-tetramers with Tm values between 75 and 84. Reclaim unused trimers and make new hexa-tetramers with increased Tm and add back to list.

7. The lists were pruned using the 13 selection conditions as described in Table 7: A "1" indicates a match at that position, a "0" indicates no match. Anytime two candidate addresses matched at one of the conditions, it was removed from the candidate list and returned to the unused trimer list.

TABLE 7

| Condition | Tetramer 1 | Tetramer 2 | Tetramer 3 | Tetramer 4 | Tetramer 5 | Tetramer 6 |
|---|---|---|---|---|---|---|
| L Four in a row | 1 | 1 | 1 | 1 | 0 | 0 |
| M Four in a row | 0 | 1 | 1 | 1 | 1 | 0 |
| R Four in a row | 0 | 0 | 1 | 1 | 1 | 1 |
| L Three in a row | 1 | 1 | 1 | 0 | 0 | 0 |
| M Three in a row | 0 | 1 | 1 | 1 | 0 | 0 |
| M Three in a row | 0 | 0 | 1 | 1 | 1 | 0 |
| R Three in a row | 0 | 0 | 0 | 1 | 1 | 1 |
| Interrupted 4-1 | 1 | 1 | 0 | 1 | 1 | 0 |
| Interrupted 4-2 | 1 | 1 | 0 | 0 | 1 | 1 |
| Interrupted 4-3 | 0 | 1 | 1 | 0 | 1 | 1 |
| Interrupted 4-4 | 1 | 0 | 1 | 0 | 1 | 1 |
| Interrupted 4-5 | 1 | 1 | 0 | 1 | 0 | 1 |
| Interrupted 4-6 | 1 | 0 | 1 | 1 | 0 | 1 |

8. The above 13 selection conditions reduced the list to 9,650 address candidates.

9. The above 13 selection conditions remove matches of four in a row and three in a row which are in the same alignment as one another; however, they do not remove sequences which are similar but shifted over by one or two tetramer units. In order to eliminate those kinds of artifacts, the sequences were copied below the original 6 tetramers, offset by a tetramer or two as in Table 8 below:

TABLE 8

| Condition | Position A | Position B | Position C | Position D | Position E | Position F |
|---|---|---|---|---|---|---|
| Four in a row + 1 |  | Position A | Position B | Position C | Position D |  |
| Four in a row + 2 |  |  | Position A | Position B | Position C | Position D |
| Four in a row − 1 |  | Position C | Position D | Position E | Position F |  |
| Four split − 1 | Position B | Position C |  |  | Position E | Position F |

10. These three selections culled the list to 8,894 candidate capture oligonucleotides, 4,798 more than the target of 4,096 for a 64×64 address array. These capture oligonucleotide sequences have the following properties: (1) there are no cases of 4 tetramers in a row which are identical, either when capture oligonucleotide sequences are aligned with each other, or when they are offset with respect to each other or split with respect to each other; (2) there are no cases of 3 tetramers in a row which are identical, when capture oligonucleotide sequences are aligned with each other from one end; and (3) there are no cases where four out of six tetramers are in the same position.

11. For further selection, sequences of three in a row which were offset were eliminated as in Table 9 below.

TABLE 9

| Condition | Position A | Position B | Position C | Position D | Position E | Position F |
|---|---|---|---|---|---|---|
| Three in a row + 1 |  | Position A | Position B | Position C |  |  |
| Three in a row + 2 |  |  | Position A | Position B | Position C |  |
| Three in a row + 3 |  |  |  | Position A | Position B | Position C |
| Three in a row + 1 |  |  | Position B | Position C | Position D |  |
| Three in a row + 2 |  |  |  | Position B | Position C | Position D |
| Three in a row + 1 |  |  |  | Position C | Position D | Position E |

12. These six selections culled the list to 3,038 candidate capture oligonucleotides, more than a more selective target of 2,500 for a 50×50 address array. These capture oligonucleotide sequences have the following properties: (1) there are no cases of 4 tetramers in a row which are identical, either when capture oligonucleotide sequences are aligned with each other, or when they are offset with respect to each other; (2) there are no cases of 3 tetramers in a row which are identical, when capture oligonucleotides sequences are aligned with each other from one end, or when they are offset with respect to each other; and (3) there are no cases where four out of six tetramers are in the same position.

13. The order of tetramers were reversed and new Tm values were calculated, added back in (6,076), and then pruned as described in steps 7-11 above. The candidate list increased only marginally to 3,270. Therefore, an approach which enriched the unused trimers was needed.

14. A list of used trimers in all positions was used to determine available (unused) trimers and construct new sets of hexa-tetramers. To increase the percent of hexa-tetramers with Tm values in the 75-84° C. range, trimers with predicted Tm values of 34-50° C. were inverted with respect to each other and used (i.e. trimer ABC with Tm of 34 was fused to trimer DEF with Tm of 50, trimer ABC with Tm of 38 was fused to trimer DEF with Tm of 46, etc.).

15. Sets of hexa-tetramers were constructed and the trimers generated at the junction (i.e. positions BCD and CDE) were retested against the used trimer list, and those hexa-tetramers which conflicted were recycled. Those hexa-tetramers which did not conflict were added to the 3,270 candidate list and resorted and pruned as described in steps 7-11. The candidate list was expanded to 4,035.

16. The process was reiterated two more times to generate the final list of 4,633 capture oligonucleotides (SEQ ID NOS: 1-4633) (FIG. 25, which refers to the tetramers in Table 6), 537 sequences more than the target of 4,096 for a 64×64 address array. These capture oligonucleotide sequences have the following properties: (1) there are no cases of 4 tetramers in a row which are identical, either when capture oligonucleotide sequences are aligned with each other, or when they are offset with respect to each other; (2) there are no cases of 3 tetramers in a row which are identical, when capture oligonucleotide sequences are aligned with each other from one end, or when they are offset with respect to each other; and (3) there are no cases where four out of six tetramers are in the same position.

17. Using the 4,633 capture oligonucleotide list, smaller lists for an 8×8=64 address array, 8×12=96 address array, 16×24=384 address array, and 20×20=400 address array were created. As selection criteria, capture oligonucleotides which shared pairs of tetramers in common were selectively removed from the list. A culling of all dimer pairs which were the same in given positions (i.e. AB=AB) reduced the list to 465 capture oligonucleotide sequences (SEQ ID NOS: 1-465) (FIG. 26, which refers to the tetramers in Table 6). A second culling of dimer pairs similar among neighboring positions (i.e. AB=BC, BC=CD, etc.) and removal of all dimer pairs used more than twice reduced the set to 96 capture oligonucleotide sequences (SEQ ID NOS: 1-96) (FIG. 27, which refers to the tetramers in Table 6). Finally, ensuring that no dimer was used more than once generated a list of 65 capture oligonucleotide sequences (SEQ ID NOS: 1-65) (FIG. 28, which refers to the tetramers in Table 6).

18. The capture oligonucleotides can also be in the form of PNA (i.e. Peptide Nucleotide Analogues), as shown in FIG. 29 (which refers to the tetramers in Table 6), which contains a list of 4633 such capture oligonucleotides (SEQ ID NOS: 4634-9266). These PNA capture oligonucleotides are in the form of 20 mer units. PNA provides the advantage of increasing the Tm of the oligonucleotide, on average 1.0° C. to 1.5° C. per base, so the Tm values of the oligomers listed in FIG. 29 would be on average 20° C. (or more) higher when synthesized as the PNA form. Thus, the addresses would only need to be 20mers or less in the PNA form. These sequences are amenable to a more rapid synthesis by considering two alternative approaches. In the first approach, the 36 tetramers listed in Table 6 are initially synthesized, and then 5 tetramers linked in the correct order to form the sequences listed in FIG. 29. Alternatively, the PNA oligomers would be synthesized using a lithographic synthesis approach. A standard lithographic synthesis would use the 4 bases over and over again, i.e. A-C-G-T for the first position, A-C-G-T for the second position, etc., and would require 4×20=80 masks. The current sequences listed in FIG. 29 are amenable to synthesis in 62 masks, or less by altering the order of masks. The 62 masks would allow attachment of the PNA monomers in the following order:

(SEQ ID NO: 9536)
T-G-C-A-T-G-C-A-G-T-C-A-T-G-C-A-T-G-C-A-G-T-C-A-T-

G-C-A-T-G-C-A-G-T-C-A-T-G-C-A-T-G-C-A-G-T-C-A-T-G-

C-A-T-G-C-A-G-T-C-A-T-G

For a given sequence, the mask at the next base which allows that sequence is opened over that address. By way of example, if the nucleotide sequence of SEQ ID NO:9536 were shortened to be the first 20 nucleotides of SEQ ID NO:9536, it could be finished using just 20 masks. Different sequences will require more masks. Thus, the 20-mers are finished with different numbers of masks. Examples are provided below for synthesis of 5 different addresses Zip ID#s 1, 2, 3, 4, and 26 which require less than 62 masks. In these examples, use of a mask is designated by an underlining of that base to achieve the correct sequence.

Zip ID#1.
(SEQ ID NO:9545)
AATCCAGCGCAAAATCTGCG = 45 masks (SEQ ID NO: 9536)
T-G-C-A-T-G-C-A-G-T-C-A-T-G-C-A-T-G-C-A-G-T-C-A-T-

G-C-A-T-G-C-A-G-T-C-A-T-G-C-A-T-G-C-A-G-T-C-A-T-G-

C-A-T-G-C-A-G-T-C-A-T-G

Zip ID#2.
(SEQ ID NO: 9546)
AAAGCCTACACGACGGCGAA = 56 masks (SEQ ID NO: 9536)
T-G-C-A-T-G-C-A-G-T-C-A-T-G-C-A-T-G-C-A-G-T-C-A-T-

G-C-A-T-G-C-A-G-T-C-A-T-G-C-A-T-G-C-A-G-T-C-A-T-G-

C-A-T-G-C-A-G-T-C-A-T-G

Zip ID#3.
(SEQ ID NO: 9547)
TCTGCCATACGGGCTTACGG = 50 masks (SEQ ID NO: 9536)
T-G-C-A-T-G-C-A-G-T-C-A-T-G-C-A-T-G-C-A-G-T-C-A-T-

G-C-A-T-G-C-A-G-T-C-A-T-G-C-A-T-G-C-A-G-T-C-A-T-G-

C-A-T-G-C-A-G-T-C-A-T-G

Zip ID#4.
(SEQ ID NO: 9548)
CTTGTCCCCAGCACGGCCAT = 49 masks (SEQ ID NO: 9536)
T-G-C-A-T-G-C-A-G-T-C-A-T-G-C-A-T-G-C-A-G-T-C-A-T-

G-C-A-T-G-C-A-G-T-C-A-T-G-C-A-T-G-C-A-G-T-C-A-T-G-

C-A-T-G-C-A-G-T-C-A-T-G

Zip ID#26.
(SEQ ID NO: 9549)
TCGTCGTTTCCCCTCATGCG = 54 masks (SEQ ID NO: 9536)
T-G-C-A-T-G-C-A-G-T-C-A-T-G-C-A-T-G-C-A-G-T-C-A-T-

G-C-A-T-G-C-A-G-T-C-A-T-G-C-A-T-G-C-A-G-T-C-A-T-G-

C-A-T-G-C-A-G-T-C-A-T-G

This demonstrates that PNA addresses of 20 mers may be synthesized using a lithographic approach with no more than 62 masks, far less than the 80 masks required by the standard approach to synthesize a 20mer, and even less than the 64 masks required to make a standard PNA 16 mer.

Figure 30:
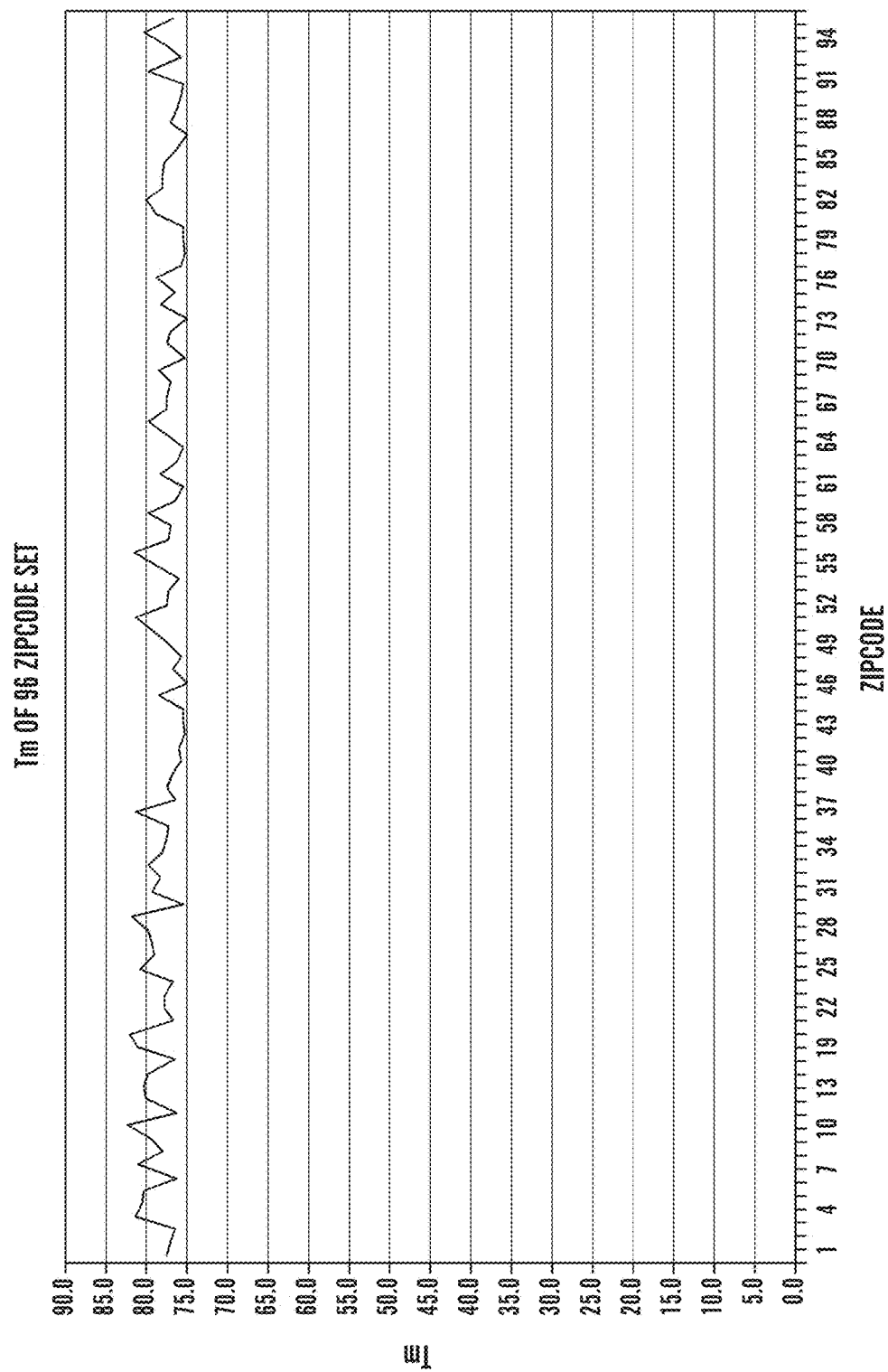
FIG. 30 shows a melting temperature (i.e. Tm) distribution for a list of 96 capture oligonucleotides produced in accordance with the present invention.
Figure 31:
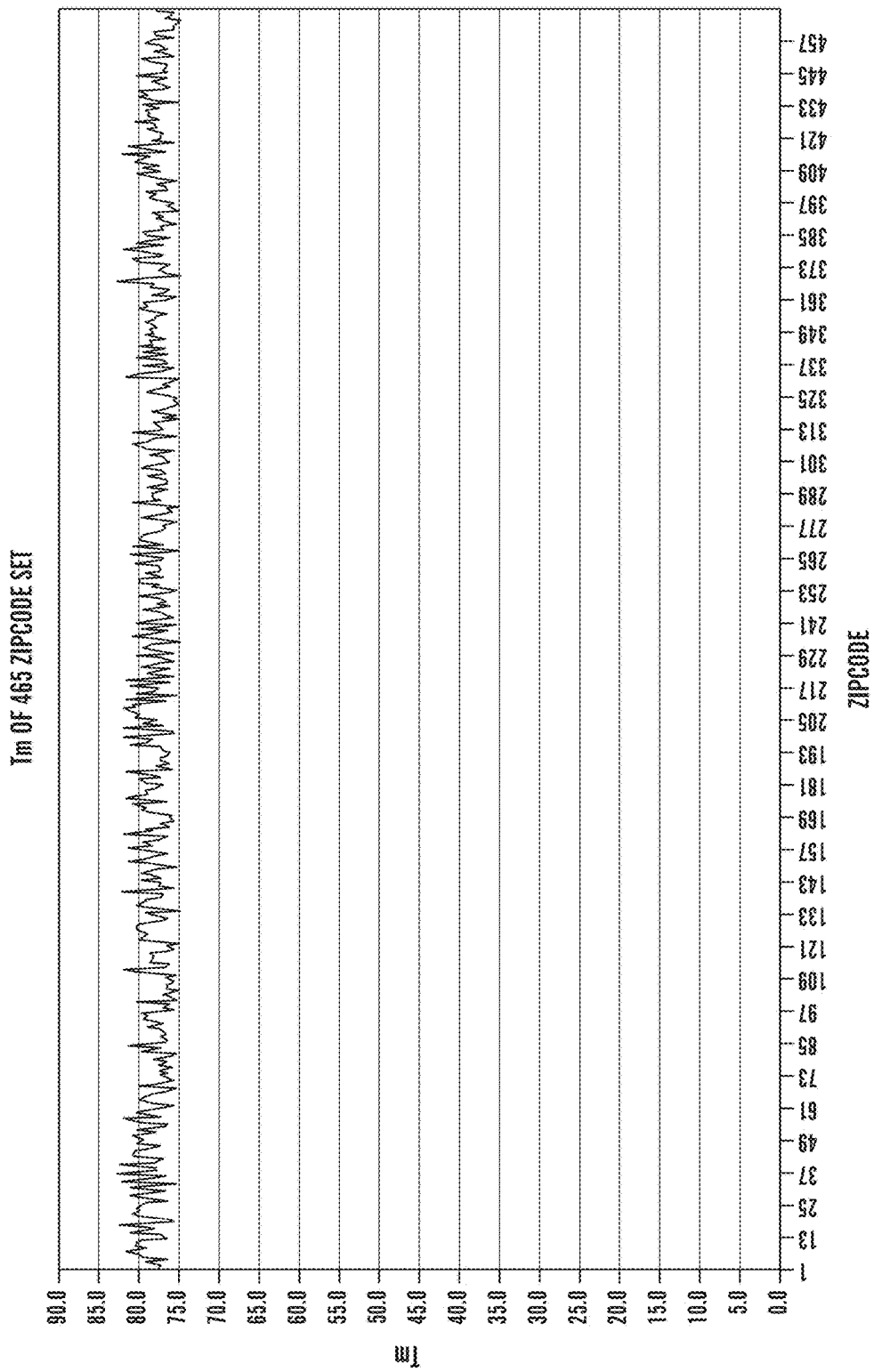
FIG. 31 shows a melting temperature (i.e. Tm) distribution for a list of 465 capture oligonucleotides produced in accordance with the present invention.
Figure 32:
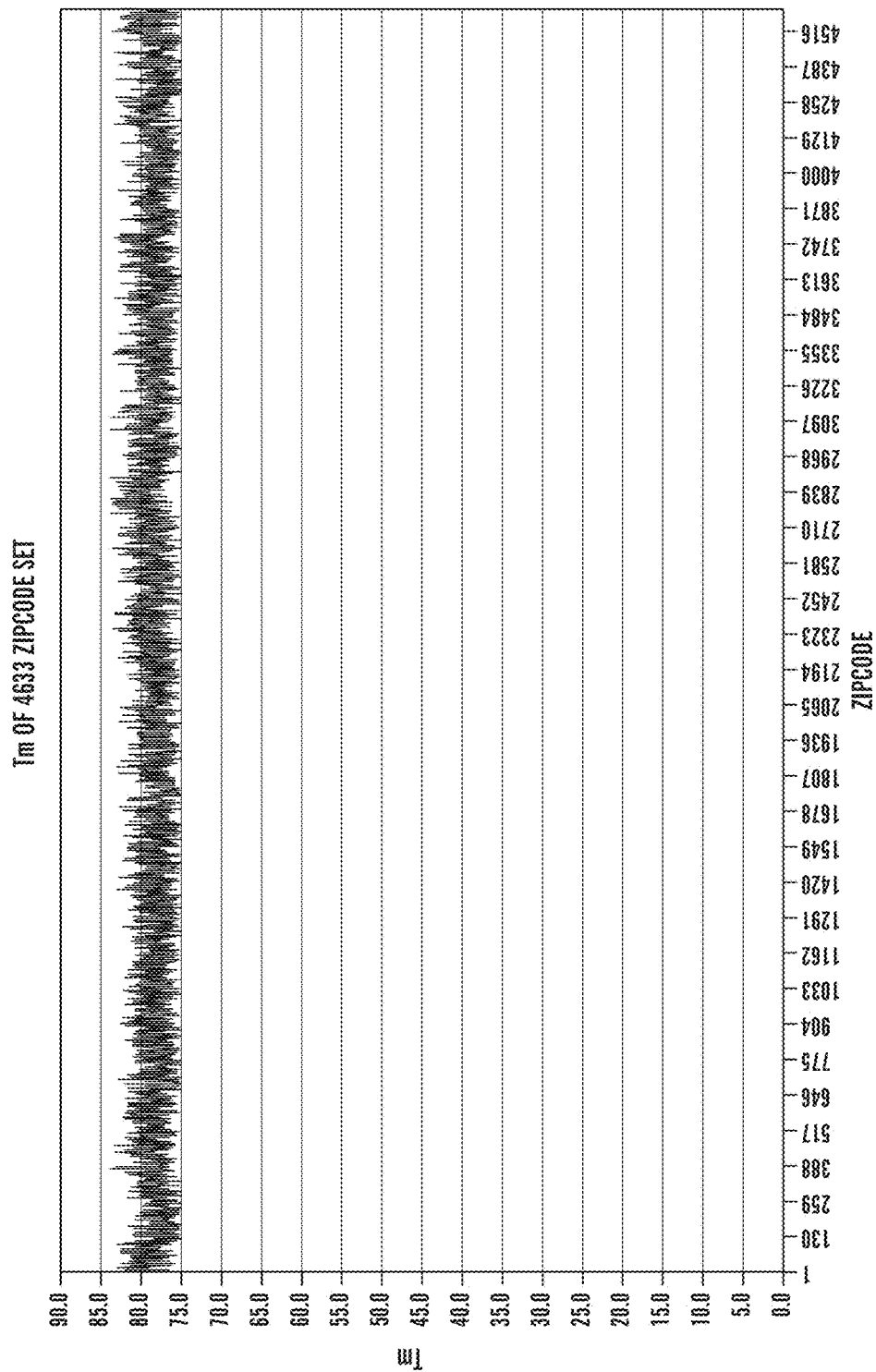
FIG. 32 shows a melting temperature (i.e. Tm) distribution for a list of 4633 capture oligonucleotides produced in accordance with the present invention.
Figure 33:
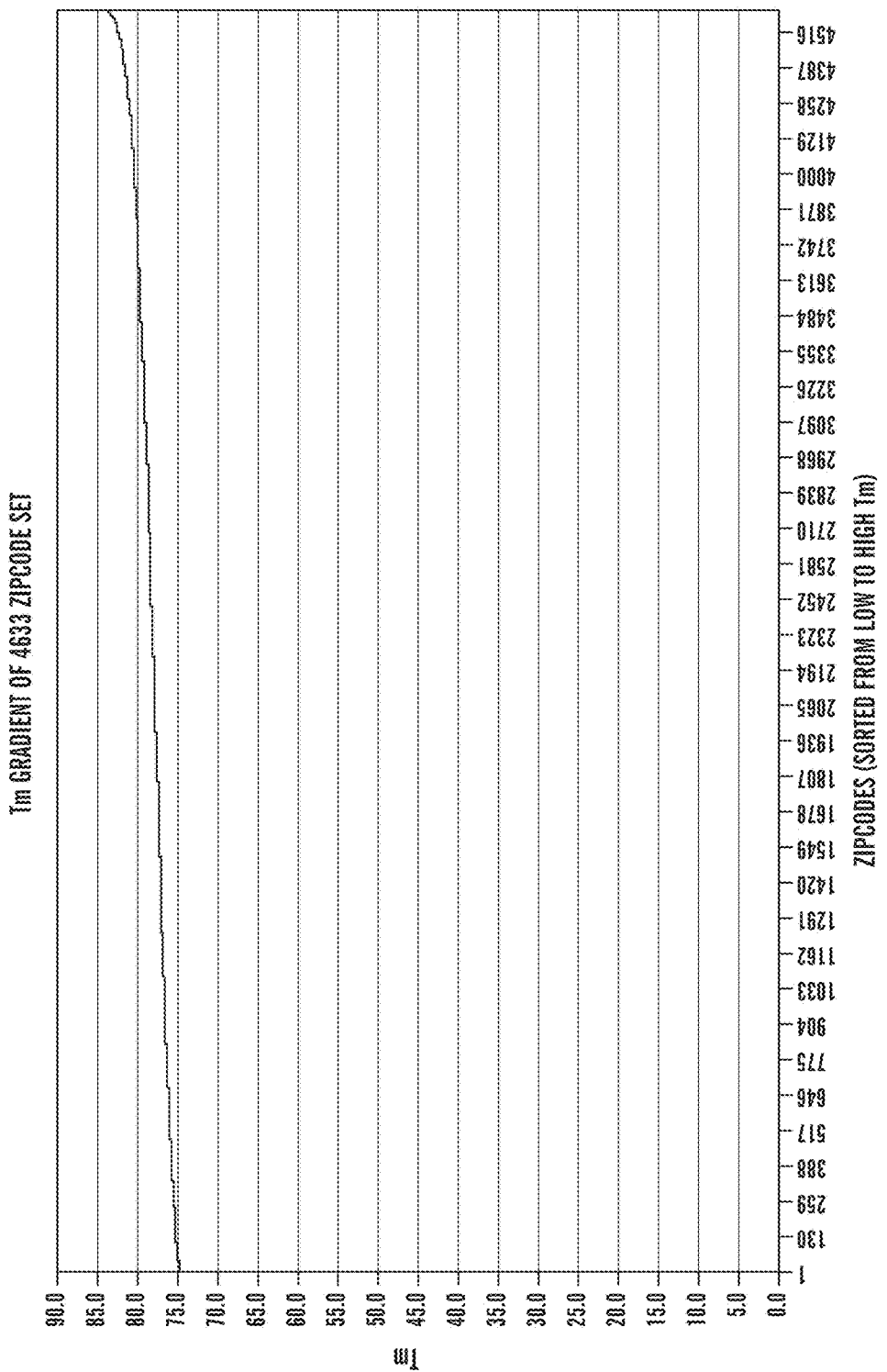
FIG. 33 shows a sorted melting temperature (i.e. Tm) distribution for a list of 4633 capture oligonucleotides produced in accordance with the present invention.
Figure 34:
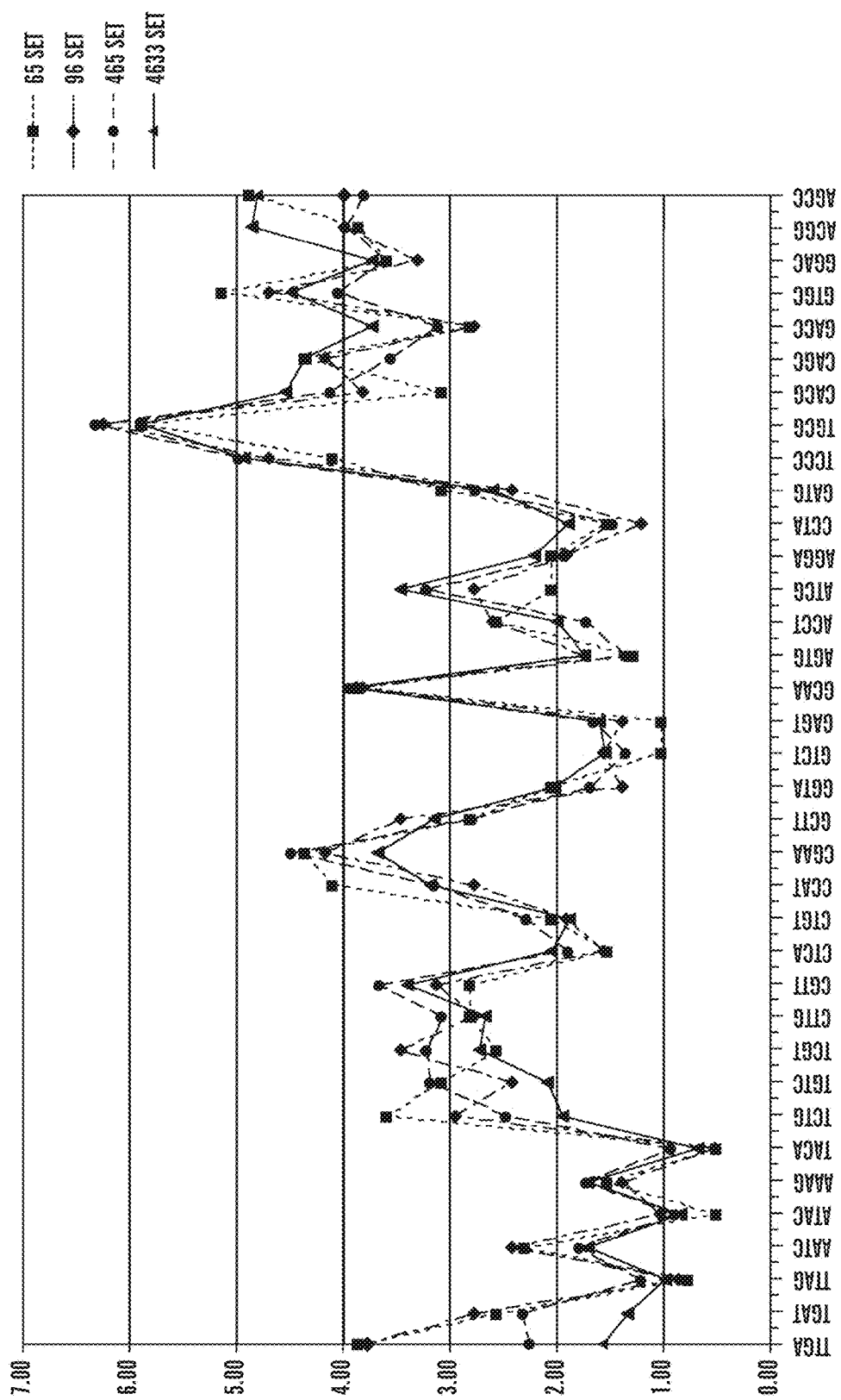
FIG. 34 shows the tetramer usage in the lists of 65, 96, 465, and 4633 capture oligonucleotides produced in accordance with the present invention.

All addresses were selected to have Tm values between 75 and 84° C. The distribution of Tm values is more or less independent of capture oligonucleotide number. While addresses with higher G+C content in general gave higher Tm values, the simple Tm=4(G+C)+2(A+T) rule was off by up to 10° C. in many cases. The values for the 96, 465, and 4633 capture oligonucleotides is shown in FIGS. 30, 31, and 32, respectively. Sorted Tm values of the 4633 list of capture oligonucleotide probes are shown in FIG. 33. The gradient of Tm values was relatively even, with the majority of capture oligonucleotides (80%) having Tm values from and including 75° C. to 80° C. FIG. 34 shows tetramer usage in the lists of 65, 96, 465, and 4633 capture oligonucleotides produced in accordance with the present invention. If tetramer distribution was completely random, each tetramer should be represented 2.7% of the time. However, selection was biased towards higher Tm capture oligonucleotide probes. Thus, tetramers which tend to increase the Tm values, i.e. #29=TGCG are over-represented, while tetramers which tend to decrease the Tm values, i.e. #7=TACA are under-represented.

The present approach to mutation detection has three orthogonal components: (i) primary PCR amplification; (ii) solution-phase LDR detection; and (iii) solid-phase hybridization capture. Therefore, background signal from each step can be minimized, and, consequently, the overall sensitivity and accuracy of the present method is significantly enhanced over those provided by other strategies. For example, "sequencing by hybridization" methods require: (i) multiple rounds of PCR or PCR/T7 transcription; (ii) processing of PCR amplified products to fragment them or render them single-stranded; and (iii) lengthy hybridization periods (10 h or more) which limit their throughput (Guo, et al., *Nucleic Acids Res* 22:5456-5465 (1994); Hacia, et. al., *Nat. Genet.*, 14441-447 (1996); Chee, et al., *Science,* 274:610-614 (1996); Cronin, et al., *Human Mutation,* 7:244-255 (1996); Wang, et al., *Science,* 280:1077-1082 (1998); Schena, et al., *Proc. Natl. Acad. Sci. USA,* 93:10614-10619 (1996); and Shalon, et al., *Genome Res.,* 6:639-645 (1996), which are hereby incorporated by reference). Additionally, since the immobilized probes on these arrays have a wide range of $T_m$'s, it is necessary to perform the hybridizations at temperatures from 0° C. to 44° C. The result is increased background noise and false signals due to mismatch hybridization and non-specific binding, for example on small insertions and deletions in repeat sequences (Hacia, et. al., *Nat. Genet.,* 14441-447 (1996); Cronin, et al., *Human Mutation,* 7:244-255 (1996); Wang, et al., *Science,* 280:1077-1082 (1998); and Southern, E. M., *Trends in Genet.,* 12:110-115 (1996), which are hereby incorporated by reference). In contrast, the approach of the present invention allows multiplexed PCR in a single reaction (Belgrader, et al., *Genome Sci. Technol.,* 1:77-87 (1996), which is hereby incorporated by reference), does not require an additional step to convert product into single-stranded form, and can readily distinguish all point mutations including slippage in repeat sequences (Day, et al., *Genomics,* 29:152-162 (1995), which is hereby incorporated by reference). Alternative DNA arrays suffer from differential hybridization efficiencies due to either sequence variation or to the amount of target present in the sample. By using the present approach of designing divergent address sequences with similar thermodynamic properties, hybridizations can be carried out at 65° C., resulting in a more stringent and rapid hybridization. The decoupling of the hybridization step from the mutation detection stage offers the prospect of quantification of LDR products, as has already been achieved using gel-based LDR detection.

Arrays spotted on polymer surfaces provide substantial improvements in signal capture, as compared with arrays spotted or synthesized in situ directly on glass surfaces (Drobyshev, et al., *Gene,* 188:45-52 (1997); Yershov, et al., *Proc. Natl. Acad. Sci. USA,* 93:4913-4918 (1996); and Parinov, et al., *Nucleic Acids Res.,* 24:2998-3004 (1996), which are hereby incorporated by reference). However, the polymers described by others are limited to using 8- to 10-mer addresses while the polymeric surface of the present invention readily allows 24-mer capture oligonucleotides to penetrate and couple covalently. Moreover, LDR products of length 60 to 75 nucleotide bases are also found to penetrate and subsequently hybridize to the correct address. As additional advantages, the polymer gives little or no background fluorescence and does not exhibit non-specific binding of fluorescently-labeled oligonucleotides. Finally, capture oligonucleotides spotted and coupled covalently at a discrete address do not "bleed over" to neighboring spots, hence obviating the need to physically segregate sites, e.g., by cutting gel pads.

The present invention relates to a strategy for high-throughput mutation detection which differs substantially from other array-based detection systems presented previously in the literature. In concert with a polymerase chain reaction/ligase detection reaction (PCR/LDR) assay carried out in solution, the array of the present invention allows for accurate detection of single base mutations, whether inherited and present as 50% of the sequence for that gene, or sporadic and present at 1% or less of the wild-type sequence. This sensitivity is achieved, because thermostable DNA ligase provides the specificity of mutation discrimination, while the divergent addressable array-specific portions of the LDR probes guide each LDR product to a designated address on the DNA array. Since the address sequences remain constant and their complements can be appended to any set of LDR probes, the addressable arrays of the present invention are universal. Thus, a single array design can be programmed to detect a wide range of genetic mutations.

Robust methods for the rapid detection of mutations at numerous potential sites in multiple genes hold great promise to improve the diagnosis and treatment of cancer patients. Noninvasive tests for mutational analysis of shed cells in saliva, sputum, urine, and stool could significantly simplify and improve the surveillance of high risk populations, reduce the cost and discomfort of endoscopic testing, and lead to more effective diagnosis of cancer in its early, curable stage. Although the feasibility of detecting shed mutations has been demonstrated clearly in patients with known and genetically characterized tumors (Sidransky, et al., *Science,* 256:102-105 (1992), Nollau, et al., *Int. J. Cancer,* 66:332-336 (1996); Calas, et al., *Cancer Res.* 54:3568-73 (1994); Hasegawa, et al., *Oncogene* 10:1413-16 (1995); and Wu et al., *Early Detection of Cancer Molecular Markers* (Lippman, et al. ed.) (1994), which are hereby incorporated by reference), effective presymptomatic screening will require that a myriad of potential low frequency mutations be identified with minimal false-positive and false-negative signals. Furthermore, the integration of technologies for determining the genetic changes within a tumor with clinical information about the likelihood of response to therapy could radically alter how patients with more advanced tumors are selected for treatment. Identification and validation of reliable genetic markers will require that many candidate genes be tested in large scale clinical trials. While costly microfabricated chips can be manufactured with over 100,000 addresses, none of them have demonstrated a capability to detect low abundance mutations (Hacia, et. al., *Nat. Genet.,* 14441-447 (1996); Chee, et al., *Science,* 274:610-614 (1996); Kozal, et al., *Nat. Med.,* 2:753-759 (1996); and Wang, et al., *Science,* 280:1077-1082 (1998), which are hereby incorporated by reference), as required to accurately score mutation profiles in such clinical trials. The universal addressable array approach of the present invention has the potential to allow rapid and reliable identification of low abundance mutations in multiple codons in numerous genes, as well as quantification of multiple gene deletions and amplifications associated with tumor progression. In addition, for mRNA expression profiling, the LDR-universal array can differentiate highly homologous genes, such as K-, N-, and H-ras. Moreover, as new therapies targeted to specific genes or specific mutant proteins are developed, the importance of rapid and accurate high-throughput genetic testing will undoubtedly increase.

Example 6

Computer Software for Designing Addressable Array to Avoid Binding to Target Sequence In designing an addressable array, it is important to insure that the target sequence does not hybridize to capture probes on the array. As described below, a computer program has been designed for this purpose. The program locates stretches of sequence that match any of the array sequences at N−x of N adjacent nucleotide positions. The parameters x and N are set by the user.

The program sends output to the screen and to a file. The screen output summarizes the number of sequences comparisons where the longest match was i of M bases, where M is greater than or equal to N, and where i is greater than or equal to M−x. The output file shows the actual match for each sequence pair, as well as giving the summary information provided on the screen. An example of the file output is shown below.

The area within the parentheses represents the longest identified match, with upper-case alleles representing the actual matched sites and lower-case alleles representing the allowed mismatches.

The program has been written in ANSI C for the purpose of portability across platforms. The precise software used is set forth in FIG. 35. The program accepts input files in straight text format. Sequences may include standard ambiguity codes (e.g., the code Y corresponds to either C or T).

Each of $F_1$ sequences in Input File #1 is compared to each of $F_2$ sequence in File #2, for a total of $F_1 \times F_2$ comparisons. For each pair, the two sequences are compared N consecutive sites at a time in all possible alignments. If a match of at least N−x out of N adjacent sites is detected, the number of sites compared is incremented by one (i.e., after i increments, the match criteria become N−x+i out of N+i sites). This process is repeated until no matches meeting the match criteria are found. The longest match for a sequence pair is defined as the match involving the longest value of N+i, as opposed to the longest value of N−x+i. Therefore, users are explicitly should repeat all analyses with different levels of stringency (i.e., x=0, x=1, x=2, . . . ). This is important if the user is concerned with the possibility that a perfect, or near-perfect, match might be masked by a less perfect match over a longer stretch. For example, 7 out of 7 matched sites would not be reported if (i) a pair of sequences matched at 8 out of 10 sites and (ii) if the match criterion allowed 2 mismatches.

Although the invention has been described in detail for the purpose of illustration, it is understood that such details are solely for that purpose and variations can be made therein by those skilled in the art without departing from the spirit and scope of the invention which is defined by the following claims.

```
Input file 1: kraspoly.dos
Input file 2: zip64.dos
Minimum number of sites that must match:     7
Maximum number of mismatches allowed:    2

7 out of 8  K-rasc32Wt       attcagaatc(ATTTTGtG)gacgaa (SEQ ID NO: 9537)
            ZIP1                       cgcag(ATTTTGcG)ctggatttcaa (SEQ ID
NO: 9538)

7 out of 9  K-rasc32Wt       attcagaatcattt(TGtGGACgA)a (SEQ ID NO: 9539)
            ZIP4                       atggccgtgc(TGgGGACaA)gtcaa (SEQ ID NO: 9540)

< . . . deleted output . . . >

7 out of 8  K-rasc13.4D      tgtggtagt(TGgAGCTG)gtga (SEQ ID NO: 9541)
            ZIP61                     ggctcgtg(TGtAGCTG)ccgttcct (SEQ ID NO: 9542)

7 out of 8  K-rasc13.4D      tgtggtagttg(GAGcTGGT)ga (SEQ ID NO: 9543)
            ZIP62                     ggtcaagcgct(GAGgTGGT)ccatc (SEQ ID NO: 9544)

SUMMARY OF ANALYSIS

Comparisons with 1 mismatch
    8 out of 9 bases matching:   10
    7 out of 8 bases matching:   9

Comparisons with 2 mismatches
    9 out of 11 bases matching:  2
    8 out of 10 bases matching:  27
    7 out of 9 bases matching:   36

A total of 84 out of 520 sequence comparisons met the match criteria.
```

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09725759B2). An electronic copy of the "Sequence Listing" will also be available from the USPTO upon request and payment of the fee set forth in 37 CFR 1.19(b)(3).

What is claimed:

1. A collection of oligonucleotides, wherein each type of oligonucleotide of the collection comprises a zip code sequence comprising two multimer unit sequences linked together, wherein each multimer unit sequence of the oligonucleotides in the collection (1) is comprised of three consecutive subunits linked together, each subunit independently selected from the group consisting of a trimer, tetramer, pentamer, or hexamer sequence, (2) differs from all other multimer unit sequences by at least two nucleotide bases, and (3) has a Tm value greater than 24° C., wherein the collection of oligonucleotides has at least 64 different types of oligonucleotides, and wherein the collection of oligonucleotides does not contain: (1) oligonucleotides having zip code sequences with a melting temperature in ° C. less than 11 times the number of subunits and more than 15 times the number of subunits, (2) oligonucleotides having zip code sequences comprised of two identical multimer unit sequences linked together and (3) two types of oligonucleotides with zip code sequences having the same four subunit sequences linked together in the same order without interruption.

2. The collection of claim 1, wherein each oligonucleotide in the collection comprises a zip code sequence of 20-24 bases.

3. The collection of claim 1, wherein one or more of the oligonucleotides in the collection is hybridized to a nucleic acid molecule comprising a complementary nucleotide sequence.

4. The collection of claim 1, wherein the collection of oligonucleotides does not contain oligonucleotides having a zip code sequence with a melting temperature in ° C. of more than 14 times the number of subunits.

5. The collection of claim 1, wherein the collection has greater than 4000 different types of oligonucleotides.

6. A group of spheres, wherein each sphere of the group has attached to it one or more types of oligonucleotides from the collection of claim 1, wherein the group of spheres comprises at least 64 different types of oligonucleotides from said collection.

7. The group of spheres of claim 6, wherein each oligonucleotide in the collection comprises a zip code sequence of 20-24 bases.

8. The group of spheres of claim 6, wherein one or more of the oligonucleotides in the collection is hybridized to a nucleic acid molecule comprising a complementary nucleotide sequence.

9. The group of spheres of claim 6, wherein the collection has greater than 4000 different types of oligonucleotides.

10. A device comprising:
a solid support having an array of positions each suitable for attachment of a oligonucleotide;
a collection of oligonucleotides on the solid support at the array of positions, wherein each type of oligonucleotide on the solid support comprises a zip code sequence comprising two multimer unit sequences linked together, wherein each multimer unit sequence is comprised of three consecutive subunits linked together, each subunit independently selected from the group consisting of a trimer, tetramer, pentamer, or hexamer sequence, wherein each multimer unit sequence has a Tm value of greater than 24° C., wherein each of the two multimer unit sequences differs from all other multimer unit sequences by at least two nucleotide bases when aligned, wherein the collection of oligonucleotides has at least 64 different types of oligonucleotides, wherein the collection of oligonucleotides on the solid support does not contain (1) oligonucleotides having zip code sequences with melting temperature in ° C. less than 11 times the number of subunits and more than 15 times the number of subunits, (2) oligonucleotides having zip code sequences comprised of two identical multimer unit sequences linked together and (3) two types of oligonucleotides with zip code sequences having the same four subunit sequences linked together in the same order without interruption; and
one or more target nucleic acid molecules hybridized to complementary portions of the oligonucleotides on the solid support.

11. The device of claim 10, wherein the collection has greater than 4000 different types of oligonucleotides.

12. The device according to claim 10, wherein each oligonucleotide comprises a zip code sequence of 20-24 bases.

13. The device according to claim 10, wherein different oligonucleotides are attached at different array positions on the solid support.

14. The device according to claim 10, wherein oligonucleotides having identical zip code sequences are attached at different positions on the support.

15. The device according to claim 10, wherein the solid support comprises particles, strands, precipitates, gels, sheets, tubing, spheres, containers, capillaries, pads, slices, films, plates, slides, discs, membranes, or any combination or composite thereof.

16. The device according to claim 10, wherein a linker couples the oligonucleotides to the solid support.

17. The device according to claim 16, wherein the linker comprises a silane on a surface of the solid support.

18. A collection of oligonucleotides, wherein each type of oligonucleotide of the collection comprises a zip code sequence having either five consecutive subunits linked together or six consecutive subunits linked together, each subunit independently selected from the group consisting of a trimer, tetramer, pentamer, or hexamer sequence, wherein (1) the sequence of any three consecutive subunits of the oligonucleotide sequence of one type of oligonucleotide in the collection differs from the sequence of any three consecutive subunits of the oligonucleotide sequence of any other type of oligonucleotide in the collection by at least two nucleotide bases and (2) the sequence of any three consecutive subunits of the oligonucleotide sequence in the collection of oligonucleotides has a Tm value greater than 24° C., wherein the collection of oligonucleotides has at least 64 different types of oligonucleotides, and wherein the collection of oligonucleotides does not contain: (1) oligonucleotides having zip code sequences with a melting temperature in ° C. less than 11 times the number of subunits and more than 15 times the number of subunits, (2) oligonucleotides having zip code sequences where the sequence of the first three consecutive subunits is identical to the sequence of the last three consecutive subunits of the same oligonucleotide sequence, and (3) two types of oligonucleotides with zip code sequences having the same four subunit sequences linked together in the same order with or without interruption.

19. The collection of claim 18, wherein the collection has greater than 4000 different types of oligonucleotides.

20. A device comprising:
   a solid support having an array of positions each suitable for attachment of a oligonucleotide;
   a collection of oligonucleotides on the solid support at the array of positions, wherein each type of oligonucleotide on the solid support comprises a zip code sequence having either five consecutive subunits linked together or six consecutive subunits linked together, each subunit independently selected from the group consisting of a trimer, tetramer, pentamer, or hexamer sequence, wherein (1) the sequence of any three consecutive subunits of the oligonucleotide sequence of one type of oligonucleotide in the collection differs from the sequence of any three consecutive subunits of the oligonucleotide sequence of any other type of oligonucleotide in the collection by at least two nucleotide bases and (2) the sequence of any three consecutive subunits of the oligonucleotide sequence in the collection of oligonucleotides has a Tm value greater than 24° C., wherein the collection of oligonucleotides has at least 64 different types of oligonucleotides, and wherein the collection of oligonucleotides does not contain: (1) oligonucleotides having zip code sequences with a melting temperature in ° C. less than 11 times the number of subunits and more than 15 times the number of subunits, (2) oligonucleotides having zip code sequences where the sequence of the first three consecutive subunits is identical to the sequence of the last three consecutive subunits of the same oligonucleotide sequence, and (3) two types of oligonucleotides with zip code sequences having the same four subunit sequences linked together in the same order with or without interruption; and
   one or more target nucleic acid molecules hybridized to complementary portions of the oligonucleotides on the solid support.

21. The device of claim 20, wherein the collection has greater than 4000 different types of oligonucleotides.

22. The device according to claim 20, each oligonucleotide comprises a zip code sequence of 20-24 bases.

23. The device according to claim 20, wherein different oligonucleotides are attached at different array positions on the solid support.

24. The device according to claim 20, wherein oligonucleotides having identical sequences are attached at different positions on the support.

25. The device according to claim 20, wherein the solid support comprises particles, strands, precipitates, gels, sheets, tubing, spheres, containers, capillaries, pads, slices, films, plates, slides, discs, membranes, or any combination or composite thereof.

* * * * *